US009212190B2

(12) United States Patent
Harriman et al.

(10) Patent No.: US 9,212,190 B2
(45) Date of Patent: Dec. 15, 2015

(54) IRAK INHIBITORS AND USES THEREOF

(71) Applicant: Nimbus Iris, Inc., Cambridge, MA (US)

(72) Inventors: Geraldine C. Harriman, Charlestown, RI (US); Ronald T. Wester, Ledyard, CT (US); Donna L. Romero, Chesterfield, MO (US); Shaughnessy Robinson, Westerly, RI (US); Mee Shelley, Tigard, OR (US); Matthew David Wessel, Sisters, OR (US); Jeremy Robert Greenwood, Brooklyn, NY (US); Craig E. Masse, Cambridge, MA (US); Rosana Kapeller-Libermann, Chestnut Hill, MA (US)

(73) Assignee: Nimbus Iris, Inc., Cambridge, MA (US)

( * ) Notice: Subject to any disclaimer, the term of this patent is extended or adjusted under 35 U.S.C. 154(b) by 0 days.

(21) Appl. No.: 13/738,410

(22) Filed: Jan. 10, 2013

(65) Prior Publication Data

US 2013/0231328 A1    Sep. 5, 2013

Related U.S. Application Data

(60) Provisional application No. 61/585,194, filed on Jan. 10, 2012, provisional application No. 61/663,227, filed on Jun. 22, 2012, provisional application No. 61/682,637, filed on Aug. 13, 2012, provisional application No. 61/724,695, filed on Nov. 9, 2012, provisional application No. 61/734,133, filed on Dec. 6, 2012.

(51) Int. Cl.
*A61K 31/4365* (2006.01)
*A61K 31/519* (2006.01)
*C07D 495/14* (2006.01)
*C07D 495/04* (2006.01)

(52) U.S. Cl.
CPC .......... *C07D 495/04* (2013.01); *A61K 31/4365* (2013.01); *A61K 31/519* (2013.01); *C07D 495/14* (2013.01)

(58) Field of Classification Search
CPC .. C07D 333/78; C07D 409/04; C07D 495/04; C07D 495/14; A61K 31/4365; A61K 31/519
See application file for complete search history.

(56) References Cited

U.S. PATENT DOCUMENTS

| 6,297,238 | B1 | 10/2001 | Doyle et al. |
| 6,482,948 | B1 | 11/2002 | Yamada et al. |
| 7,829,570 | B2 | 11/2010 | Hirst et al. |
| 8,058,285 | B2 | 11/2011 | Reichelt et al. |
| 8,703,941 | B2 | 4/2014 | Romero et al. |
| 2003/0119829 | A1 | 6/2003 | Stolle et al. |
| 2007/0155777 | A1 | 7/2007 | Burkitt et al. |
| 2008/0176871 | A1 | 7/2008 | Girardet et al. |
| 2010/0041676 | A1 | 2/2010 | Hirst et al. |
| 2010/0063047 | A1 | 3/2010 | Borchardt et al. |
| 2010/0143341 | A1 | 6/2010 | Taylor et al. |
| 2010/0227853 | A1* | 9/2010 | Hoffman et al. ......... 514/217.06 |
| 2012/0015962 | A1 | 1/2012 | Arora et al. |
| 2012/0283238 | A1 | 11/2012 | Romero et al. |
| 2013/0231328 | A1 | 9/2013 | Harriman et al. |
| 2014/0018343 | A1 | 1/2014 | Romero et al. |
| 2014/0018357 | A1 | 1/2014 | Harriman et al. |
| 2014/0018361 | A1 | 1/2014 | Harriman et al. |

FOREIGN PATENT DOCUMENTS

| WO | WO 02088138 A1 * | 11/2002 |
| WO | WO-03/057149 A2 | 7/2003 |
| WO | WO-2004/041285 A1 | 5/2004 |
| WO | WO-2011/029054 A1 | 3/2011 |
| WO | WO2013078126 * | 11/2011 |
| WO | WO-2012/007375 A1 | 1/2012 |
| WO | WO-2012/012712 A2 | 1/2012 |
| WO | WO 2012097013 A1 * | 7/2012 |

OTHER PUBLICATIONS

Patani et. al., Chemical Reviews, 1996, American Chemical Society, vol. 96, pp. 3147-3176.*
CAS STN abstract, pub. Mar. 14, 2008 & Sep. 16, 2009 for RN 1185175-64-7 & 1008036-50-7.*
International Search Report for PCT/2013/020981, (3 pages), Mar. 18, 2013.
International Search Report for PCT/US2012/020845, 3 pages (May 16, 2012).
International Search Report for PCT/US2013/050108, 3 pages (Dec. 16, 2013).
International Search Report for PCT/US2013/050113, 2 pages (Dec. 9, 2013).
International Search Report for PCT/US2014/010652, 3 pages (Apr. 30, 2014).
Ngo, VN et al., Oncogenically active MYD88 mutations in human lymphoma, Nature, 470(7332): 115-119 (2011).
Song, KW et al., The kinase activities of interleukin-1 receptor associated kinase (IRAK)-1 and 4 are redundant in the control of inflammatory cytokine expression in human cells, Molecular Immunology, 46(7): 1458-1466 (2009).
Wang, Z. et al., IRAK-4 inhibitors for inflammation, Current Topics in Medicinal Chemistry, 9(8): 724-737 (2009).
Written Opinion for PCT/US2012/020845, 7 pages (May 16, 2012).
Written Opinion for PCT/US2013/020981, 8 pages (Mar. 18, 2013).
Written Opinion for PCT/US2013/050108, 24 pages (Dec. 16, 2013).
Written Opinion for PCT/US2013/050113, 25 pages (Dec. 9, 2013).
Written Opinion for PCT/US2014/010652, 10 pages (Apr. 30, 2014).

* cited by examiner

*Primary Examiner* — Sarah Pihonak
(74) *Attorney, Agent, or Firm* — Dechert LLP; Andrea L. C. Reid

(57) ABSTRACT

The present invention provides compounds, compositions thereof, and methods of using the same.

11 Claims, 20 Drawing Sheets

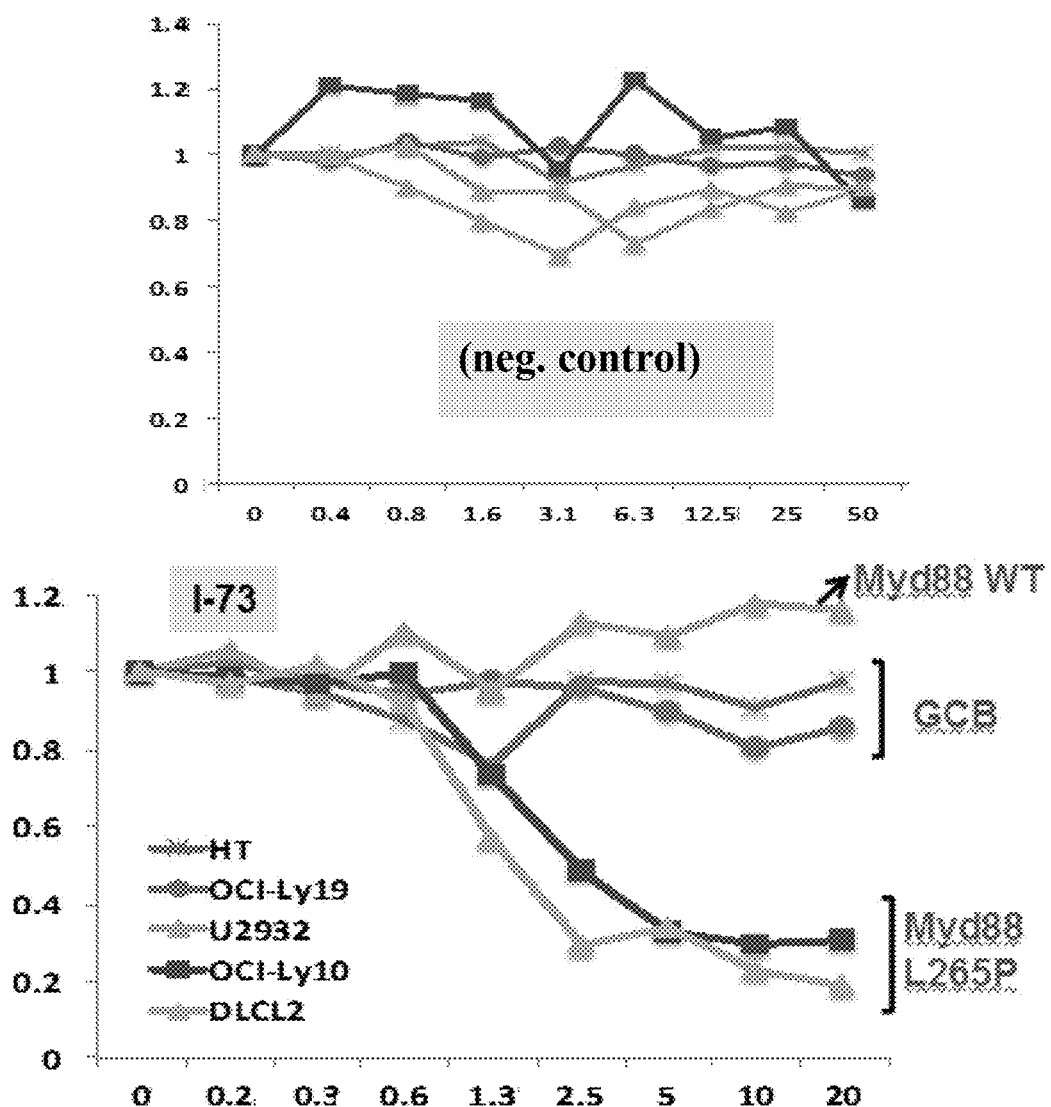
Figure 1A. DLBCL Cell proliferation inhibition

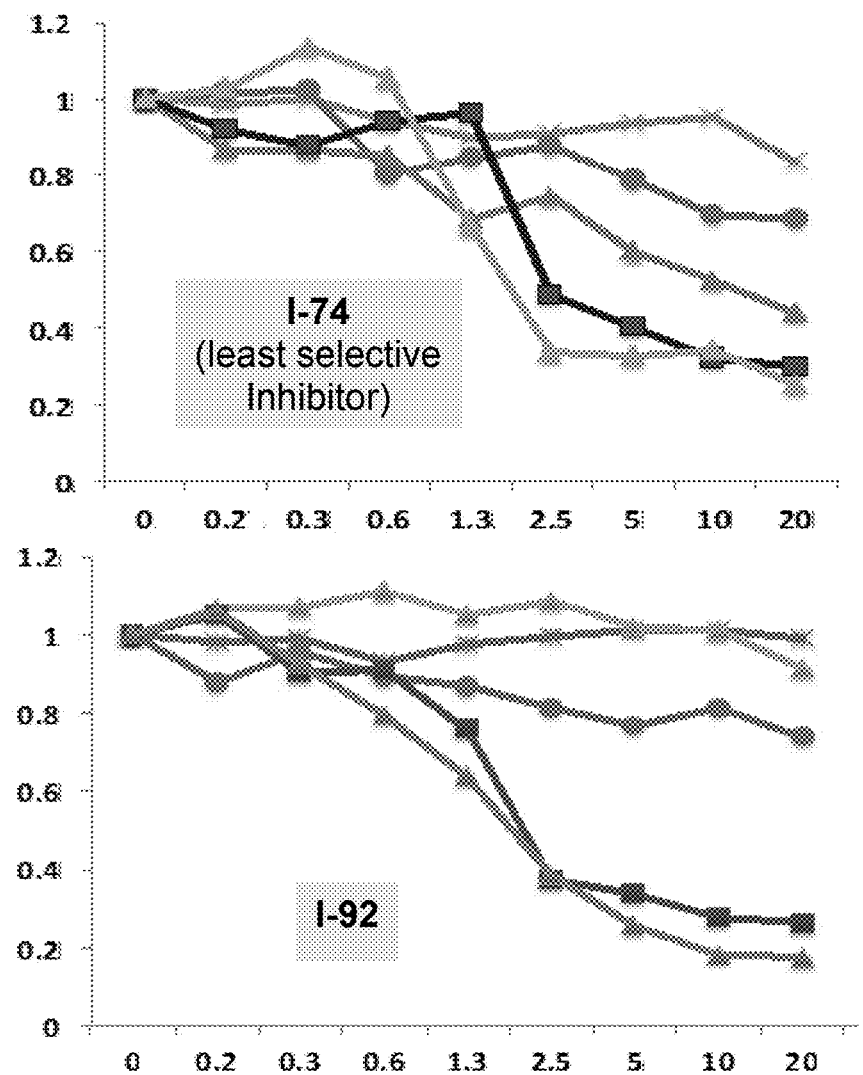
Figure 1B. Cell proliferation inhibition

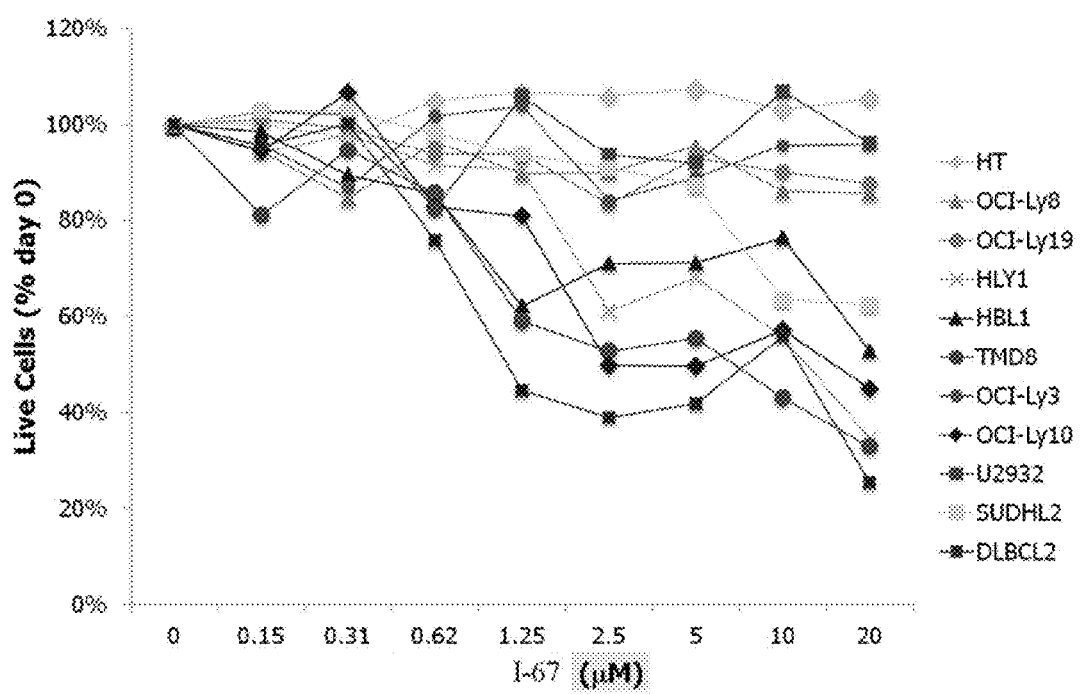
Figure 2. Cell proliferation inhibition by compound I-67

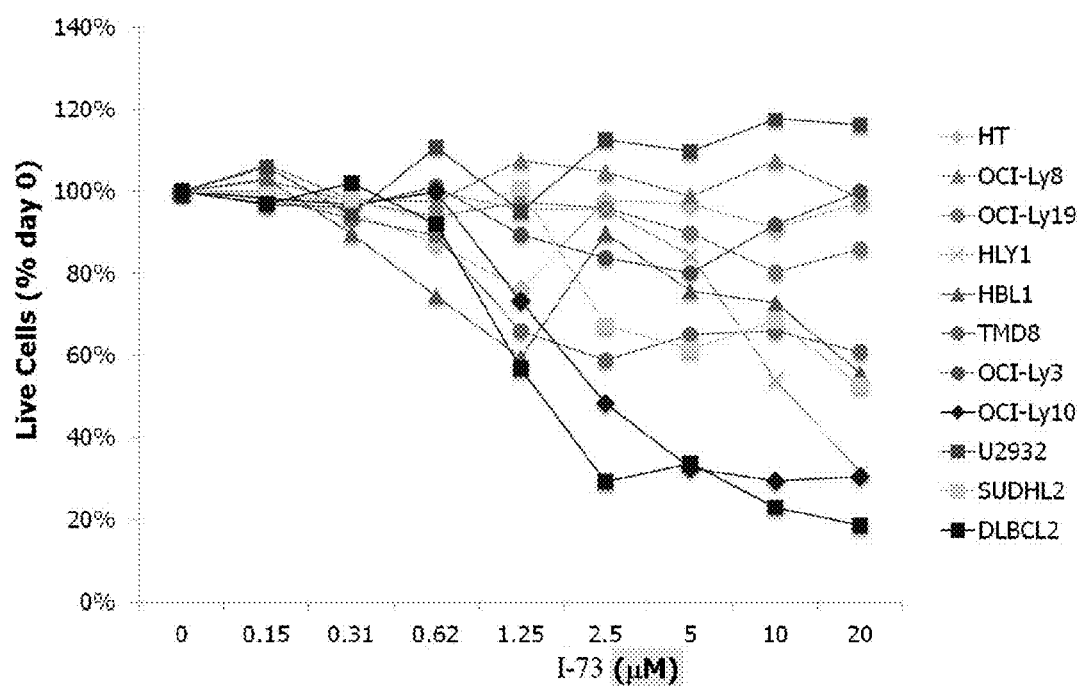
Figure 3. Cell proliferation inhibition by compound I-73

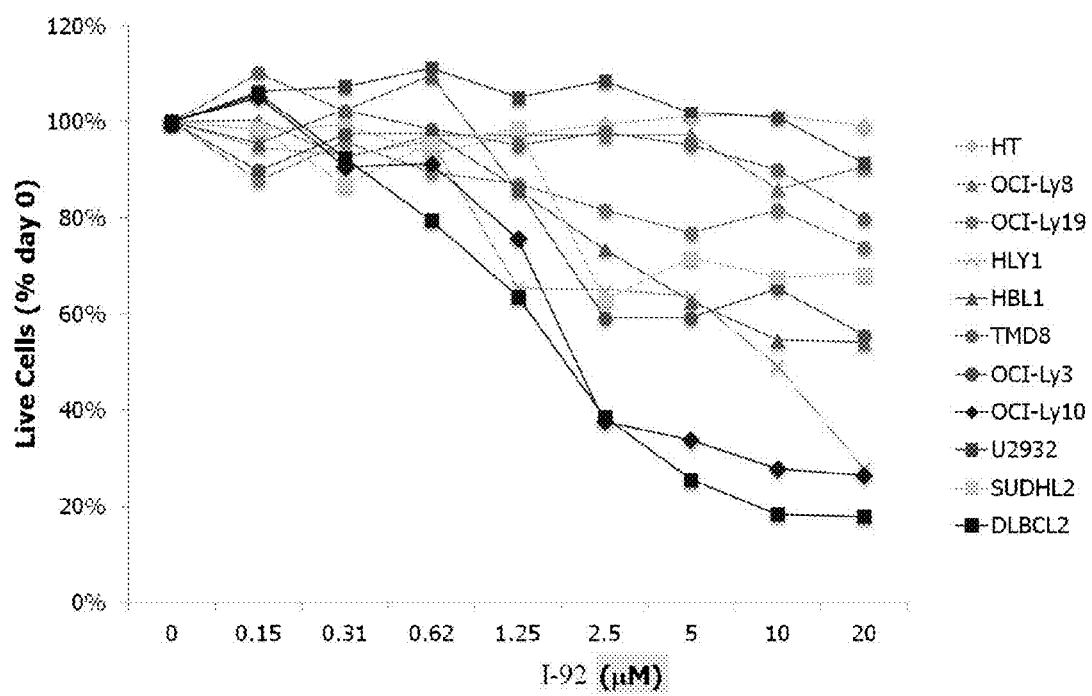
Figure 4. Cell proliferation inhibition by compound I-92

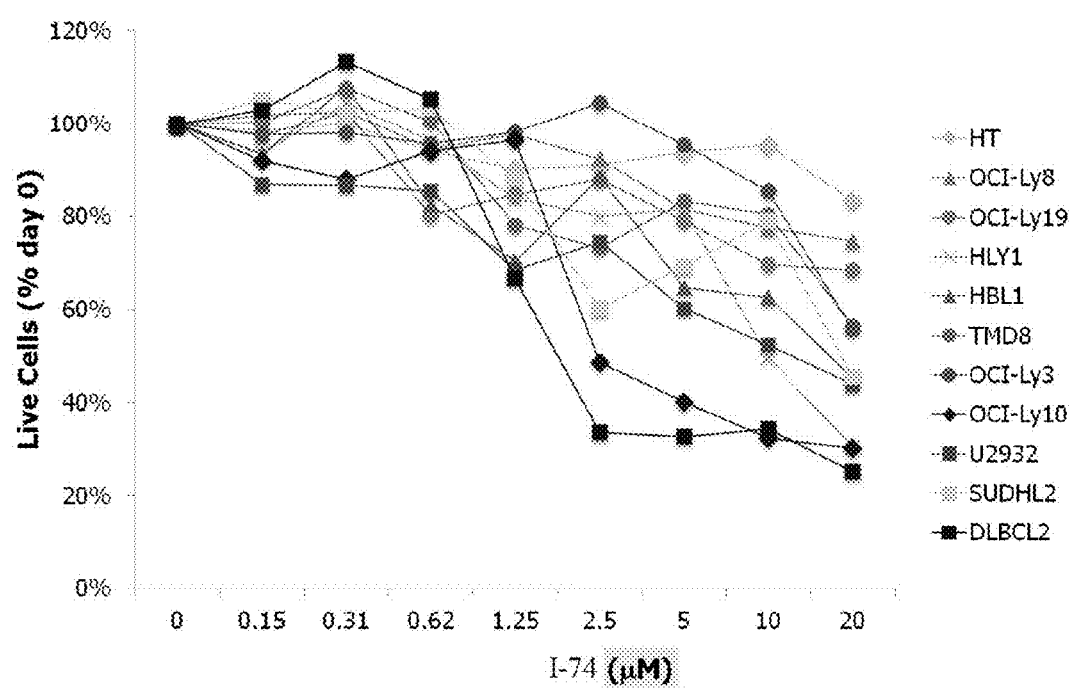
Figure 5. Cell proliferation inhibition by compound I-74

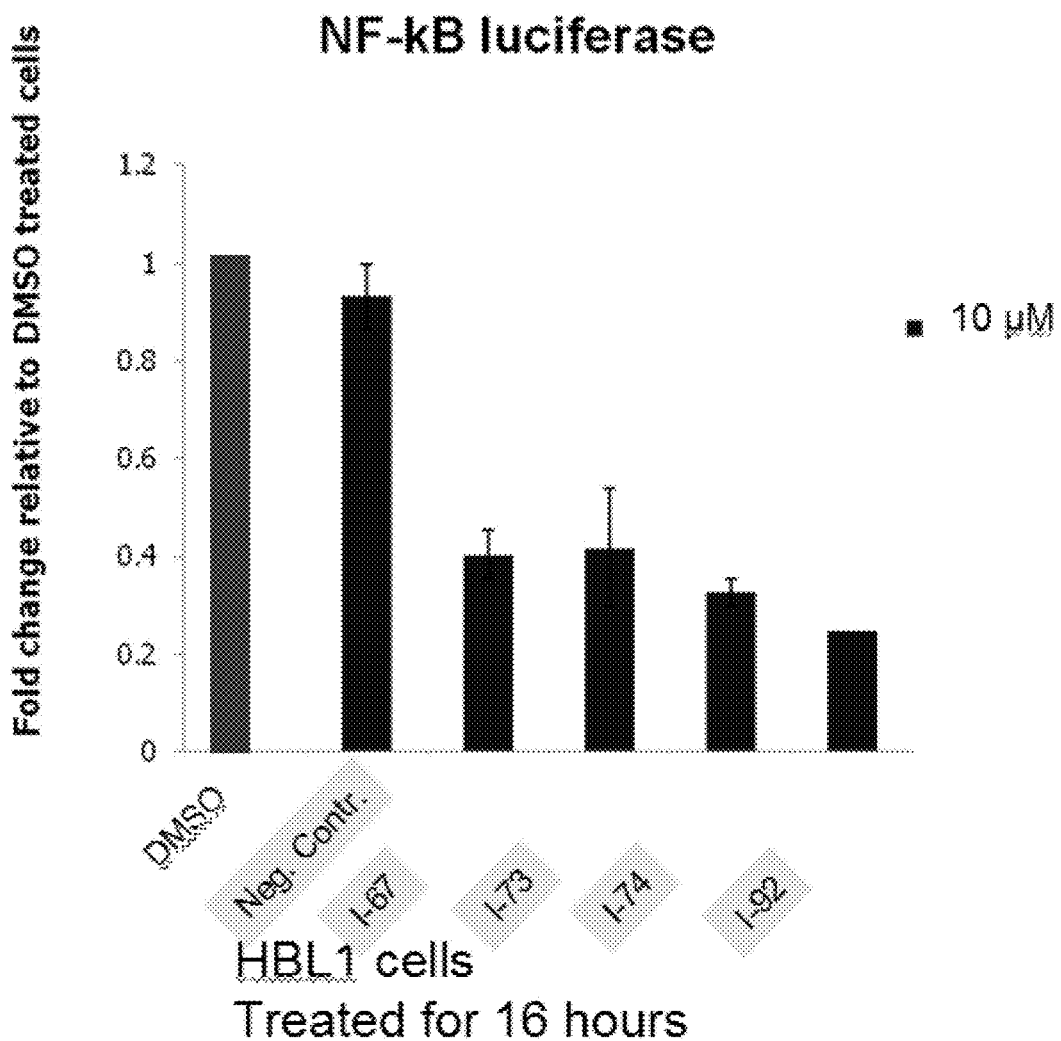
Figure 6. Inhibition of NFkB Activity

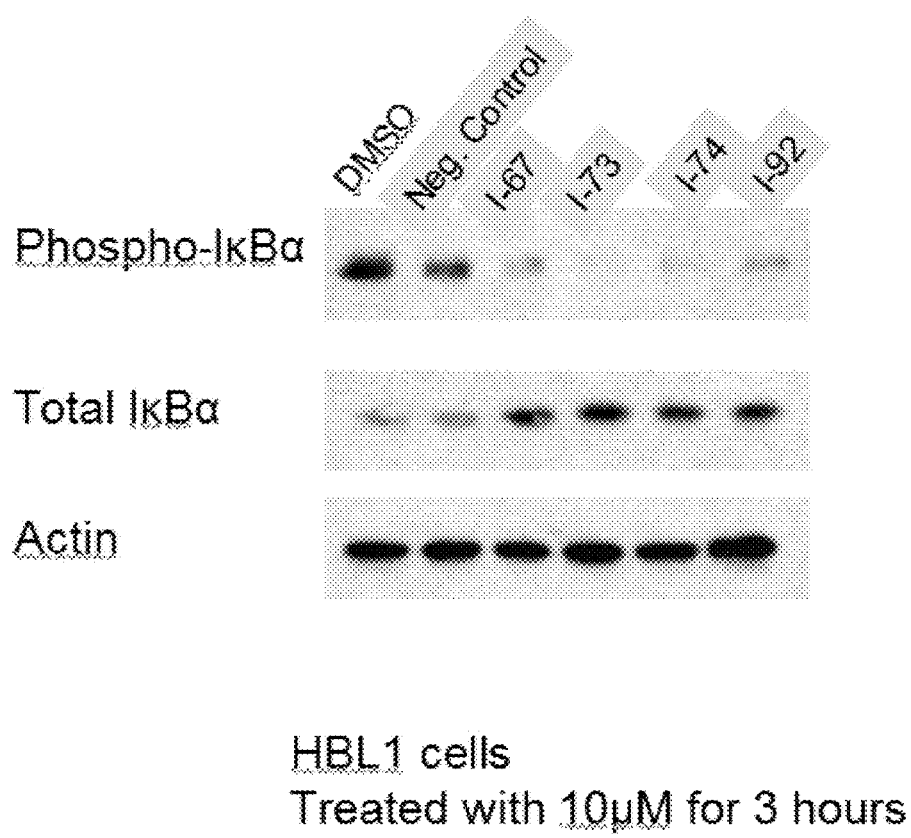
Figure 7. Inhibition of IκBα Phosphorylation and Degradation

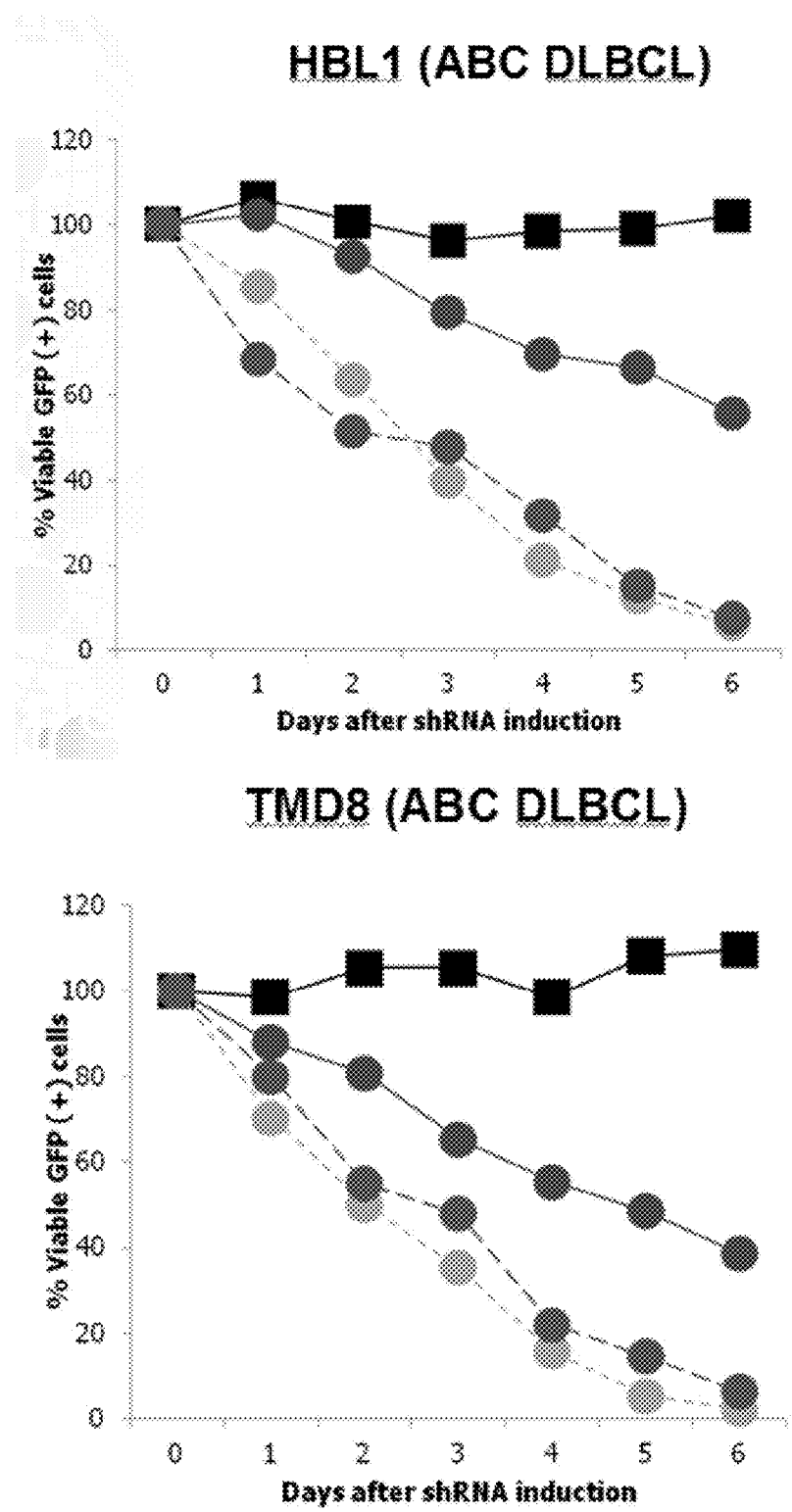
Figure 8. Sensitization of ABC DLBCL Cells to IRAK Inhibitors by BTK knockdown

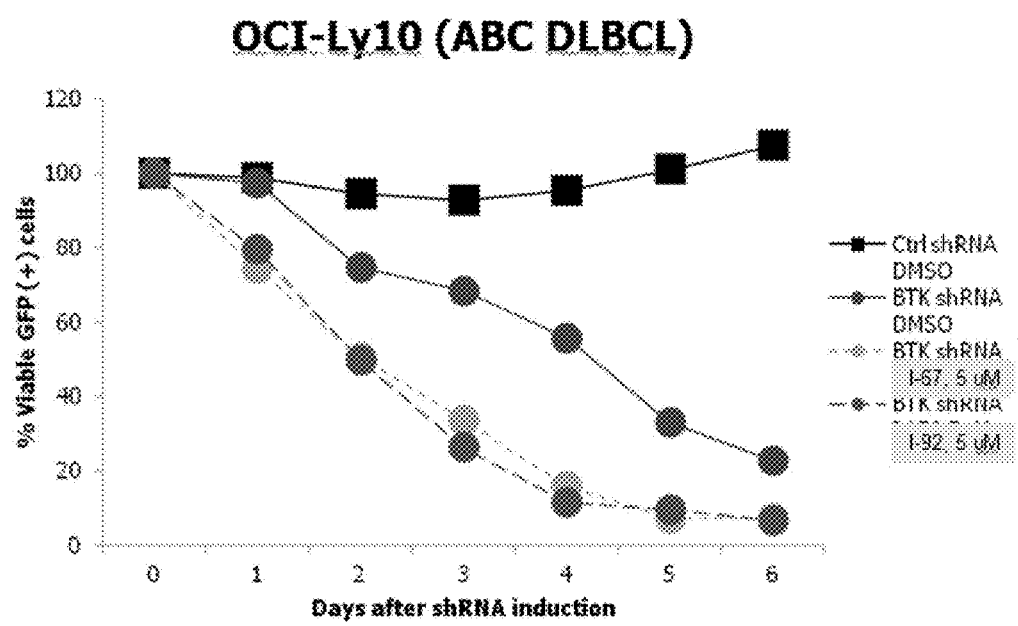
Figure 9. Sensitization of ABC DLBCL Cells to IRAK Inhibitors by BTK knockdown

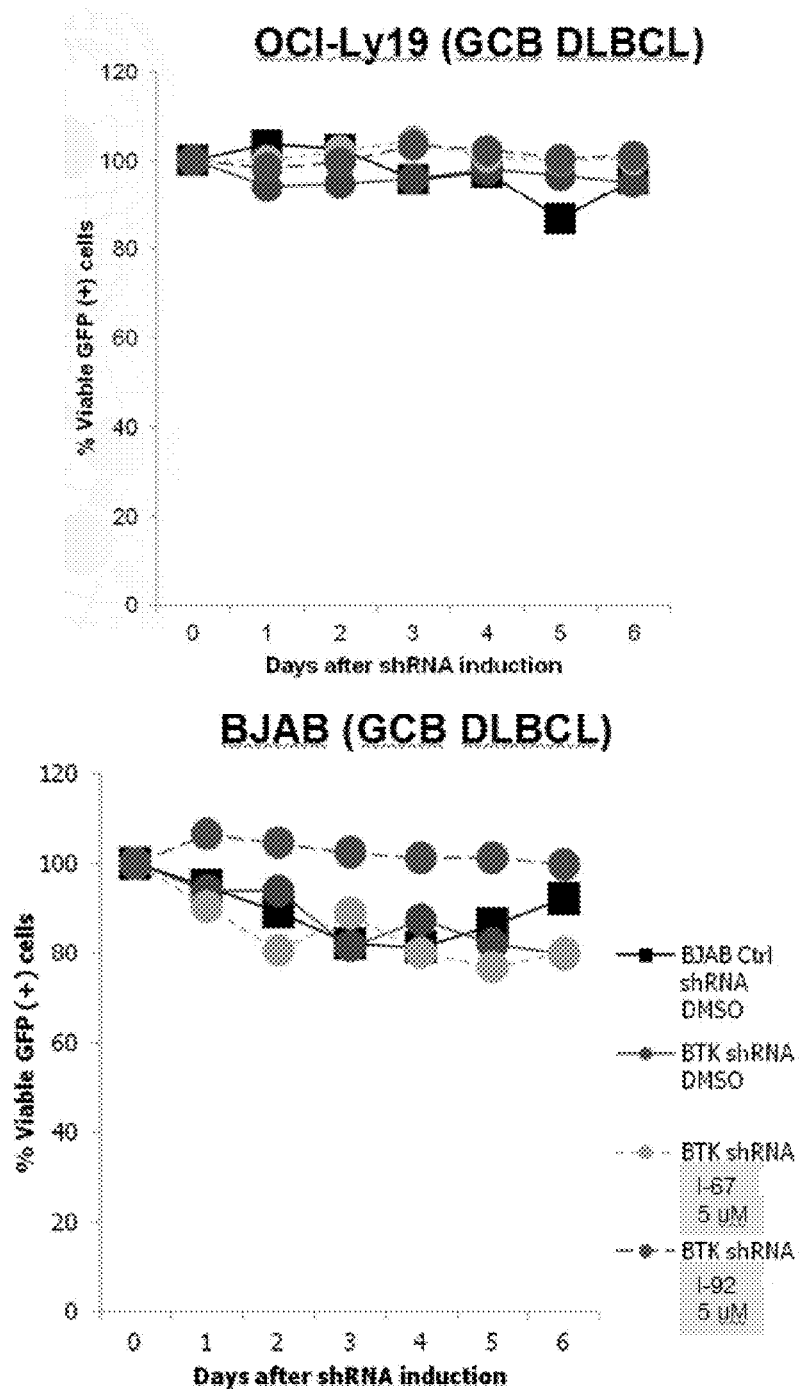
Figure 10. Non-sensitization of GCB DLBCL Cells to IRAK Inhibitors by BTK Knockdown

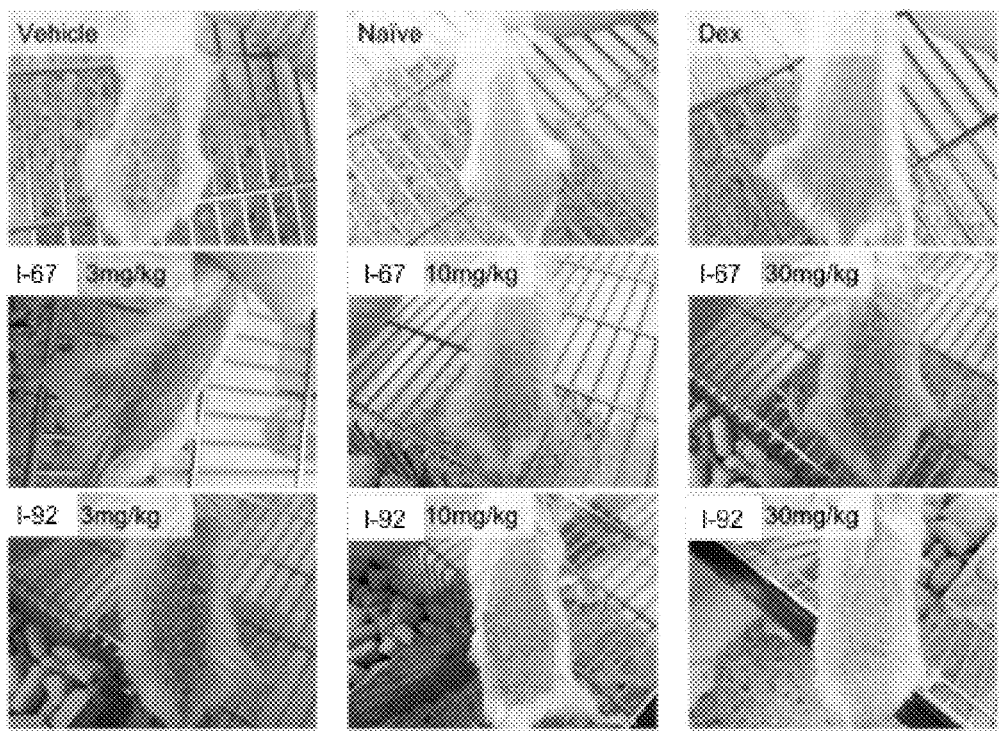
Figure 11 depicts results of an *in vivo* murine IMQ-induced psoriasis study. Representative mice were photographed to show the degree of skin scaling. Compounds I-67 or I-92 were administered at doses of 3, 10 and 30 mg/kg.

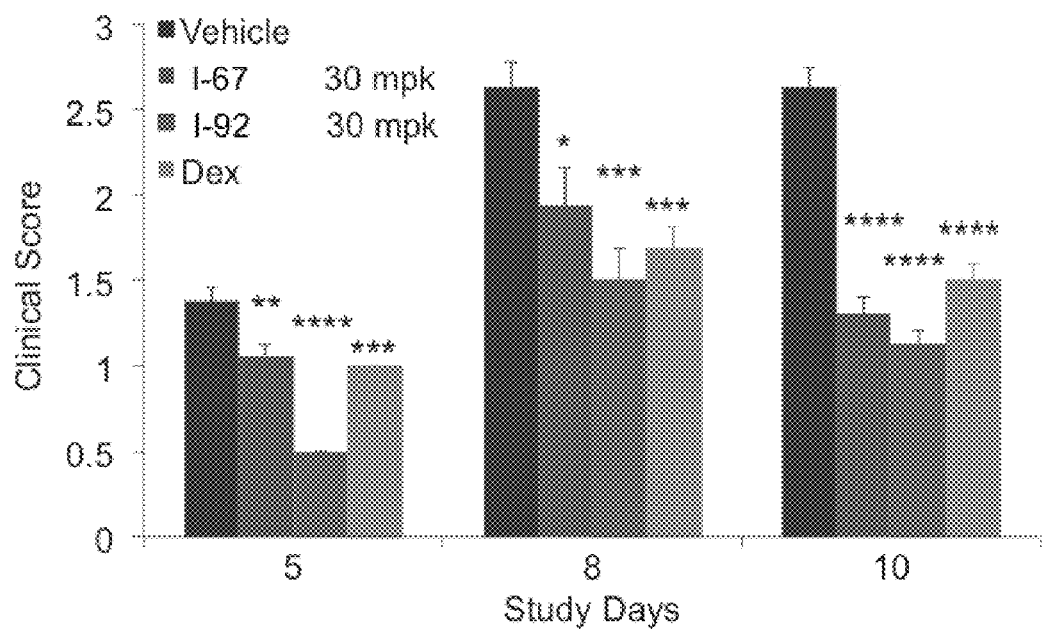
Figure 12 depicts results of an *in vivo* murine IMQ-induced psoriasis study. Mice were scored daily and the average scores of mice dosed at 30 mg/kg with either I-67 or I-92 are shown for days 5, 8 and 10.

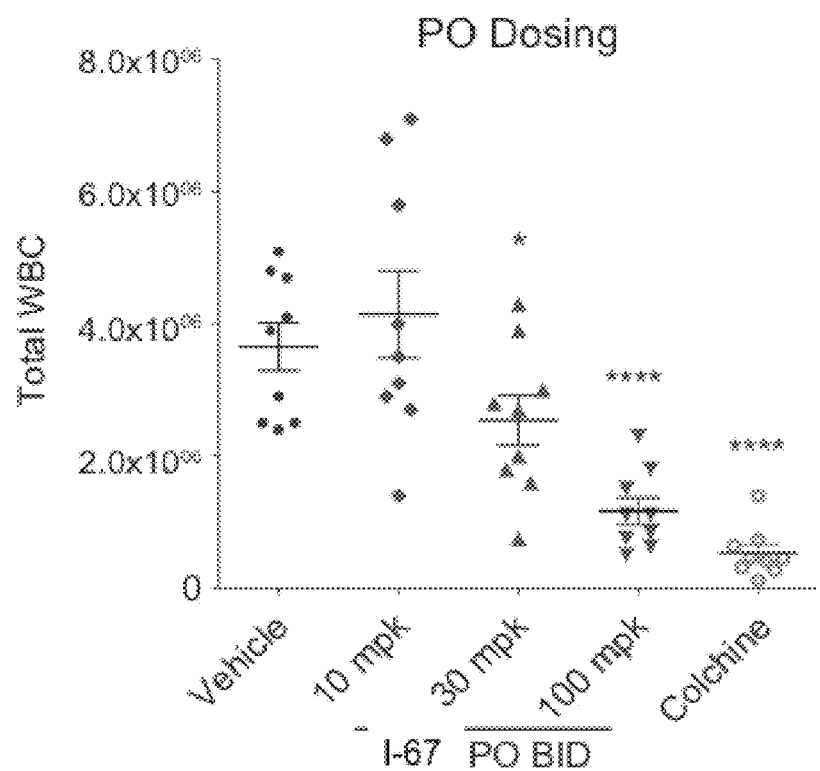
Figure 13 depicts results of an *in vivo* murine air pouch model of MSU-induced gout. The number of white blood cells in air pouch exudate were measured in rats treated with I-67 twice a day at doses of 10, 30 or 100 mg/kg for six days.

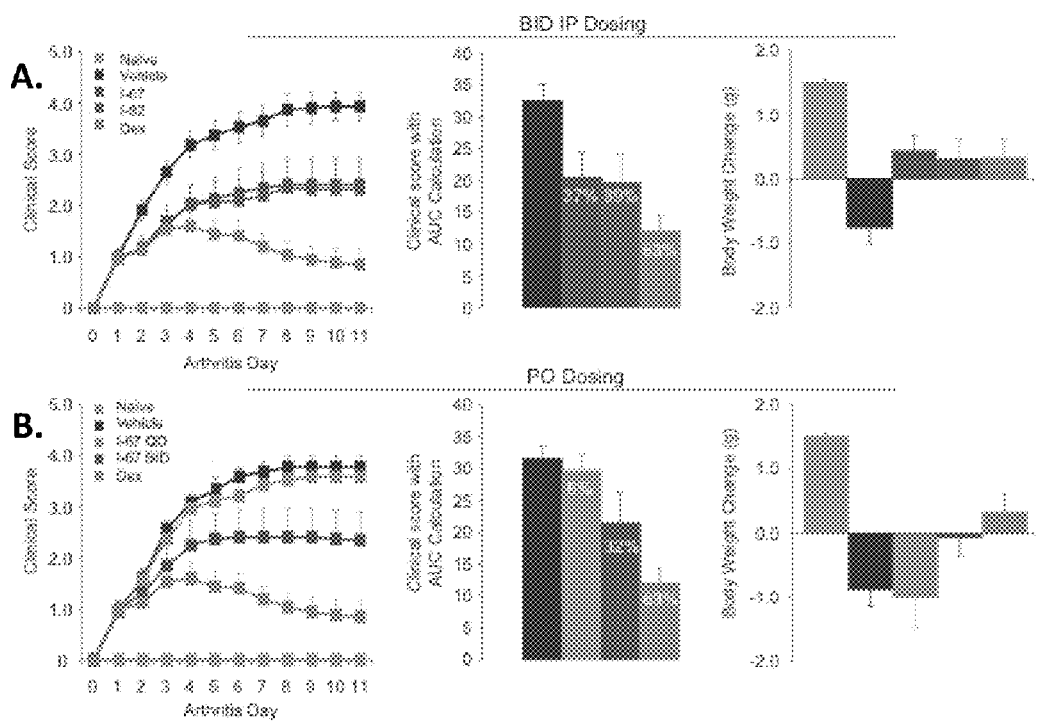

Figure 14 depicts results of an *in vivo* murine collagen-induced arthritis model. Figure 14A depicts the results for the groups dosed intraperitoneally (IP) with I-67 or I-92 at 30 mg/kg twice a day and the group dosed intraperitoneally with dexamethasone at 0.1 mg/kg twice a day. Figure 14B depicts the results for the groups dosed orally (PO) with I-67 at 30 mg/kg either once a day (QD) or twice a day (BID).

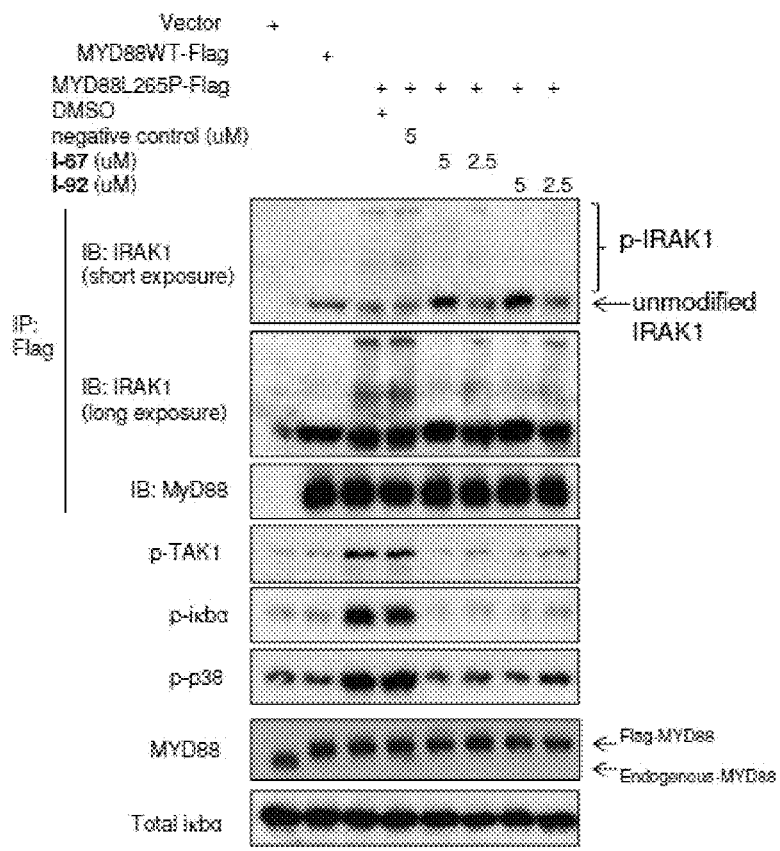
Figure 15 depicts a western blot of the indicated proteins in HBL1 cells treated with vector alone, wild-type MyD88, mutant MyD88-L265P with DMSO, mutant MyD88-L265P with a negative control (5 μm), mutant MyD88-L265P with either 5 μm or 2.5 μm I-67 and mutant MyD88-L265P with either 5 μm or 2.5 μm I-92.

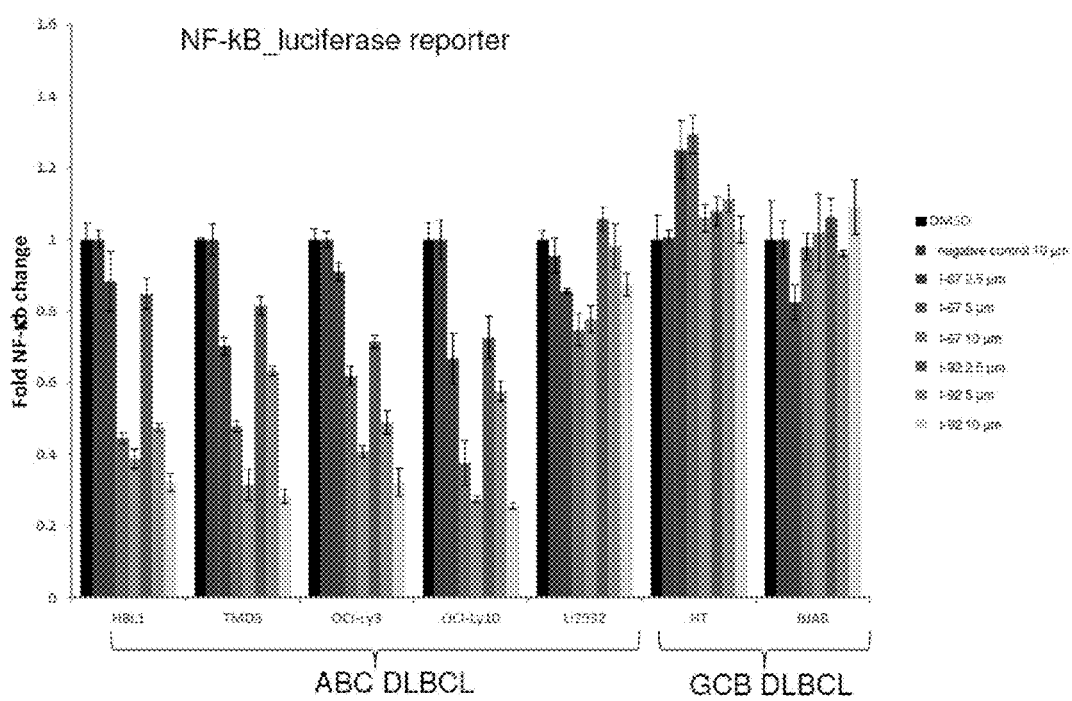
Figure 16 depicts results of an NF-κβ activity inhibition assay.

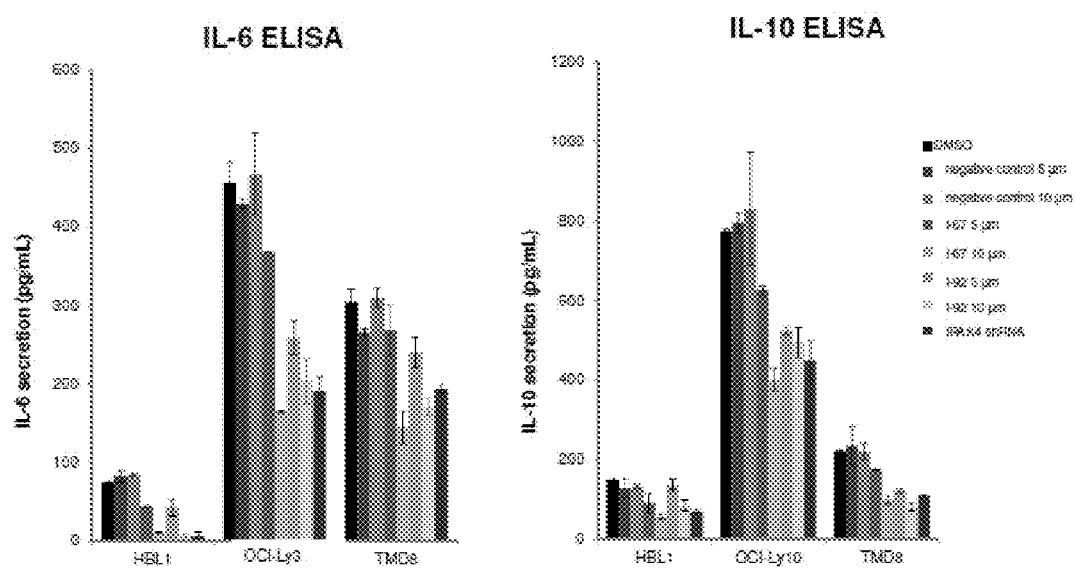
Figure 17 depicts results of a cytokine secretion inhibition assay.

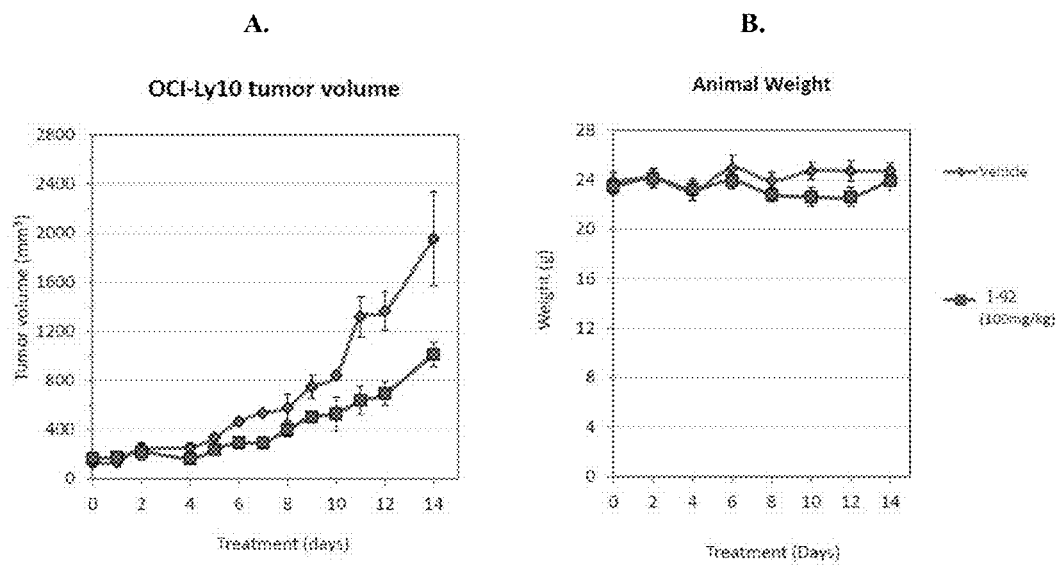
Figure 18 depicts results of an in vivo murine xenograft tumor model of human ABC DLBCL lymphoma. Figure 18A depicts the effects on tumor growth of treatment with either vehicle alone or I-92. Figure 18B depicts the effects on animal weight of treatment with either vehicle alone or I-92.

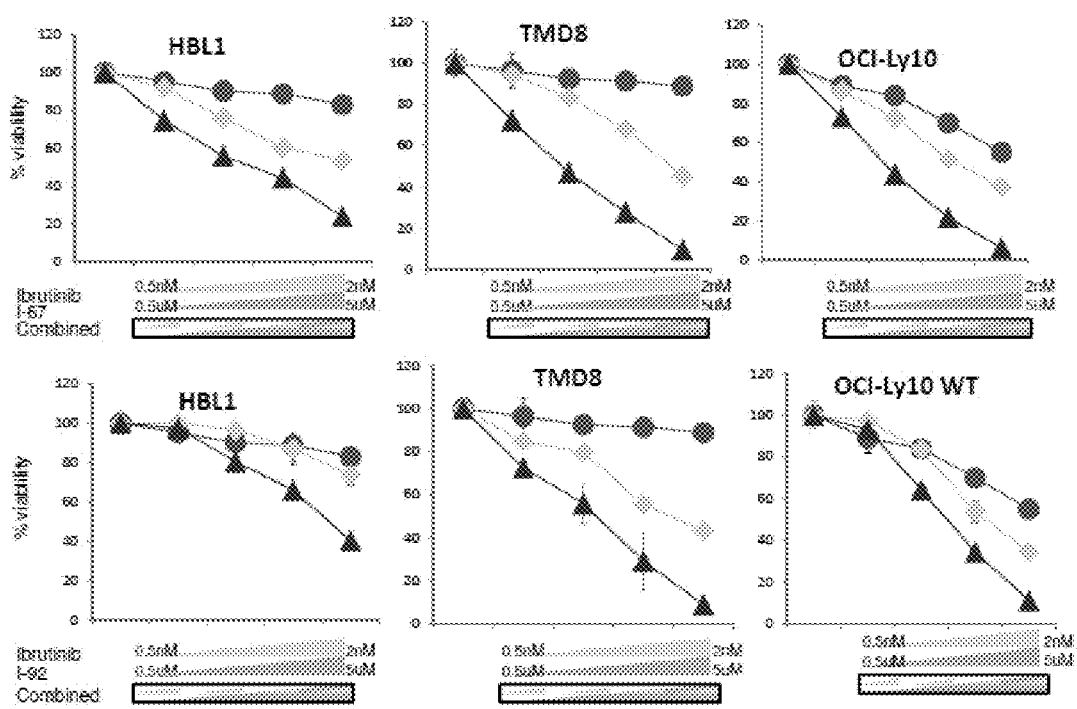

Figure 19 depicts the viability of ABC DLBCL cell lines treated at the concentrations indicated with ibrutinib, I-67, I-92 or a combination of ibrutinib with either I-67 or I-92. Assay conditions were as reported in Staudt et al. (2012). Ibrutinib is shown in closed circles; I-67 in upper panels is shown in closed squares; I-92 in lower panels is shown in closed squares; combined I-67 (upper panel) and I-92 (lower panel) treatments at a constant ibrutinib concentration of 0.5 nM are shown in closed triangles.

IRAK INHIBITORS AND USES THEREOF

TECHNICAL FIELD OF THE INVENTION

The present invention relates to compounds and methods useful for inhibiting one or more interleukin-1 receptor-associated kinases ("IRAK"). The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1), interleukin-8 (IL-8) and tumor necrosis factor $\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of IRAK kinases. Such compounds have the general formula I:

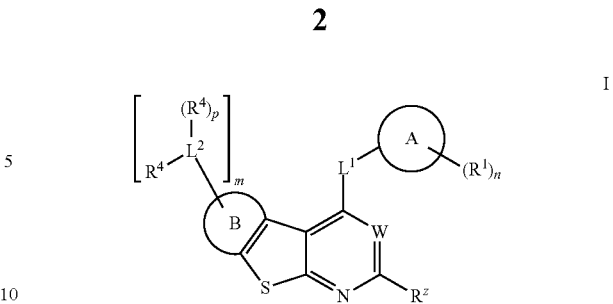

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating IRAK kinases. Such diseases, disorders, or conditions include those described herein.

Compounds provided by this invention are also useful for the study of IRAK enzymes in biological and pathological phenomena; the study of intracellular signal transduction pathways occurring in bodily tissues; and the comparative evaluation of new IRAK inhibitors or other regulators of kinases, signaling pathways, and cytokine levels in vitro or in vivo.

BRIEF DESCRIPTION OF THE DRAWINGS

FIG. 1A depicts the results of the cell proliferation assay for the negative control and compound I-73.

FIG. 1B depicts the results of the cell proliferation assay for compounds I-74 and I-92.

FIG. 2 depicts the results of the cell proliferation assay for compound I-67 against various DLBCL cell lines.

FIG. 3 depicts the results of the cell proliferation assay for compound I-73 against various DLBCL cell lines.

FIG. 4 depicts the results of the cell proliferation assay for compound I-92 against various DLBCL cell lines.

FIG. 5 depicts the results of the cell proliferation assay for compound I-74 against various DLBCL cell lines.

FIG. 6 depicts the results of the NFkB Inhibition Assay for compounds I-67, I-73, I-74, and I-92 in HBL[1] cells.

FIG. 7 depicts the results of the Inhibition of IκBα Phosphorylation and Degradation assay for compounds I-67, I-73, I-74, and I-92.

FIG. 8 depicts the sensitization of ABC DLBCL Cells to IRAK Inhibitors by BTK knockdown.

FIG. 9 depicts the sensitization of ABC DLBCL Cells to compounds I-67 and I-92 by BTK knockdown.

FIG. 10 depicts the lack of sensitization of GCB DLBCL Cells to compounds I-67 and I-92 by BTK Knockdown.

FIG. 11 depicts results of an in vivo murine IMQ-induced psoriasis study. Representative mice were photographed to show the degree of skin scaling. Compounds I-67 or I-92 were administered at doses of 3, 10 and 30 mg/kg.

FIG. 12 depicts results of an in vivo murine IMQ-induced psoriasis study. Mice were scored daily and the average scores of mice dosed at 30 mg/kg with either I-67 or I-92 are shown for days 5, 8 and 10.

FIG. 13 depicts results of an in vivo murine air pouch model of MSU-induced gout. The number of white blood cells in air pouch exudate were measured in rats treated with I-67 twice a day at doses of 10, 30 or 100 mg/kg for six days.

FIG. 14 depicts results of an in vivo murine collagen-induced arthritis model. The left panels show the average clinical scores for each group of mice up to day 11. The middle panels show the average clinical scores calculated as the area under the curve, and % inhibition relative to the vehicle is indicated in the bar graph. The right panels show the average body weight changes from day 1 to day 11.

FIG. 15 depicts a western blot of the indicated proteins in HBL[1] cells treated with vector alone, wild-type MyD88, mutant MyD88-L265P with DMSO, mutant MyD88-L265P with a negative control (5 μm), mutant MyD88-L265P with either 5 μm or 2.5 μm I-67 and mutant MyD88-L265P with either 5 μm or 2.5 μm I-92.

FIG. 16 depicts results of an NF-κβ activity inhibition assay. ABC DLBCL and GCB DLBCL cell lines were created with an NF-κβ transcriptional reporter by transduction with lentiviral particles containing an inducible NF-κβ-responsive luciferase reporter construct following the method of Staudt et al. (2012) and Ngo et al. (2011). Luciferase activity was then measured.

FIG. 17 depicts results of a cytokine secretion inhibition assay. Cells transduced with inducible shRNAs were placed in medium containing doxycycline and the concentrations of IL-6 and IL-10 were measured by ELISA, following the method of Ngo et al. (2011). Alternatively, unmanipulated lymphoma cells were placed into fresh media with the addition of I-67 or I-92 and assessed for cytokines as above.

FIG. 18A depicts the effects on tumor growth of treatment with either vehicle alone or I-92. Tumor growth was monitored by measuring tumor size in two orthogonal dimensions. The tumor volume was calculated by using the formula (½) (long dimension)×(short dimension)$^2$.

FIG. 18B depicts the effects on animal weight of treatment with either vehicle alone or I-92.

FIG. 19 depicts the viability of ABC DLBCL cell lines treated at the concentrations indicated with ibrutinib, I-67, I-92 or a combination of ibrutinib with either I-67 or I-92. Assay conditions were as reported in Staudt et al. (2012). Ibrutinib is shown in closed circles; I-67 in upper panels is shown in closed squares; I-92 in lower panels is shown in closed squares; combined I-67 (upper panel) and I-92 (lower panel) treatments at a constant ibrutinib concentration of 0.5 nM are shown in closed triangles.

DETAILED DESCRIPTION OF CERTAIN EMBODIMENTS

1. General Description of Certain Embodiments of the Invention

Compounds of the present invention, and compositions thereof, are useful as inhibitors of one or more IRAK protein kinases. In some embodiments, a provided compound inhibits IRAK-1 and IRAK-4.

The binding pocket of IRAK-4 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of IRAK-4.

Water molecules occupying hydration sites in the binding pocket of IRAK-4 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

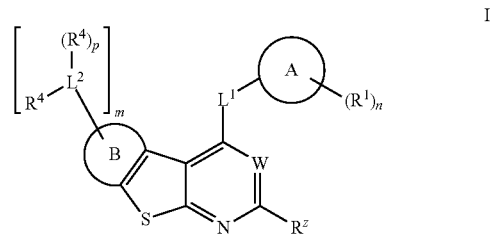

or a pharmaceutically acceptable salt thereof, wherein:
Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;
n is 0-4;
each $R^1$ is independently —R, halogen, —CN, —NO$_2$, —OR, —CH$_2$OR, —SR, —N(R)$_2$, —SO$_2$R, —SO$_2$N(R)$_2$, —SOR, —C(O)R, —CO$_2$R, —C(O)N(R)$_2$, —C(O)N(R)—OR, —NRC(O)OR, —NRC(O)N(R)$_2$, Cy, or —NRSO$_2$R; or $R^1$ is selected from one of the following formulas:

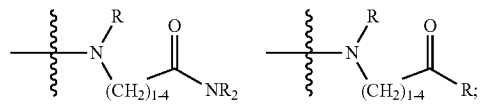

or
two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;
each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;
each R is independently hydrogen, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

Ring B is a 4-8 membered partially unsaturated carbocyclic fused ring; or a 4-7 membered partially unsaturated heterocyclic fused ring having 1-2 heteroatoms selected from nitrogen, oxygen, or sulfur; wherein said Ring B may be optionally substituted by one or more oxo, thiono, or imino groups;

m is 1-4;

p is 0-2;

W is N or —C($R^3$)—;

$R^z$ is R, CN, $NO^2$, halogen, —C(O)N(R)$_2$, —C(O)OR, —C(O)R, —N(R)$_2$, —NH-[Ar], —N(R)C(O)OR, —NRC(O)N(R)$_2$, —OR, or —$SO^2$N(R)$_2$;

$R^3$ is hydrogen, halogen, —CN, $C_{1-4}$ aliphatic, $C_{1-4}$ haloaliphatic, —OR, —C(O)R, or —C(O)N(R)$_2$;

[Ar] is an optionally substituted phenyl or heteroaromatic ring;

$L^1$ is a covalent bond or a $C_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—;

each $L^2$ is independently a covalent bond or a $C_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—;

each $R^4$ is independently halogen, —CN, —NO$_2$, —OR, —SR, —N(R)$_2$, —SO$_2$R, —SO$_2$N(R)$_2$, —SOR, —C(O)R, —CO$_2$R, —C(O)N(R)$_2$, —NRC(O)R, —NRC(O)N(R)$_2$, —C(O)N(R)OR, —N(R)C(O)OR, —N(R)S(O)$_2$N(R)$_2$, —NRSO$_2$R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two -L2($R^4$)$_p$—$R^4$ groups are taken together with their intervening atoms to form an optionally substituted 4-7 membered fused, spiro-fused, or bridged bicyclic ring having 0-2 heteroatoms independently selected from nitrogen, oxygen, or sulfur.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

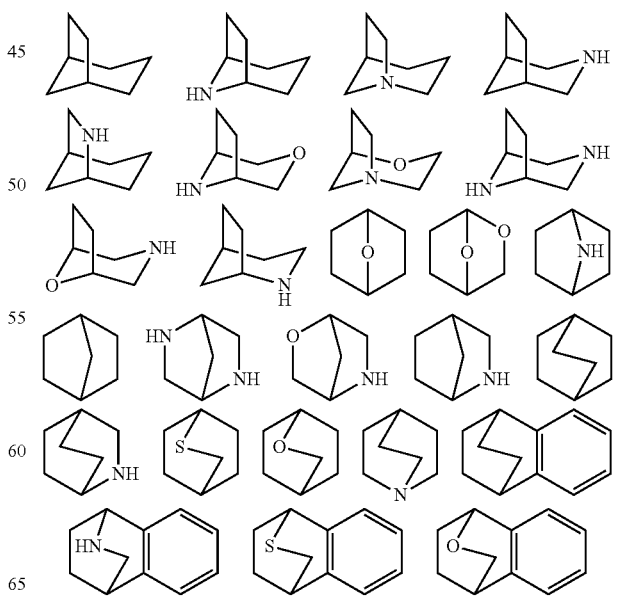

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

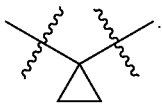 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$P(O)R°_2$; —$OP(O)(OR°)_2$; $SiR°_3$; —$(C_{1-4}$ straight or branched)alkylene)O—$N(R°)_2$; or —$(C_{1-4}$ straight or branched)alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)$C(O)OR^{\bullet}$, or —$SSR^{\bullet}$ wherein each $R^{\bullet}$ is unsubstituted or where preceded by "halo" is substituted only with one or more halogens, and is independently selected from $C_1$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits IRAK-4 with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof.

3. Description of Exemplary Embodiments

As described above, in certain embodiments, the present invention provides a compound of formula I:

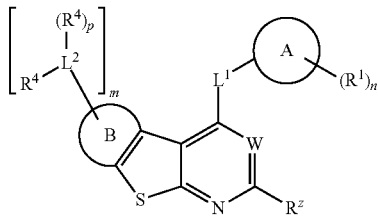

or a pharmaceutically acceptable salt thereof, wherein:
Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;
n is 0-4;
each $R^1$ is independently —R, halogen, —CN, —$NO_2$, —OR, —$CH_2$OR, —SR, —N(R)$_2$, —$SO_2$R, —$SO_2$N(R)$_2$, —SOR, —C(O)R, —$CO_2$R, —C(O)N(R)$_2$, —C(O)N(R)—OR, —NRC(O)OR, —NRC(O)N(R)$_2$, Cy, or —NRSO$_2$R, or $R^1$ is selected from one of the following formulas:

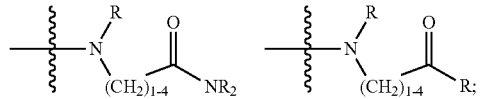

or
two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;
each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;
each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

Ring B is a 4-8 membered partially unsaturated carbocyclic fused ring; or a 4-7 membered partially unsaturated heterocyclic fused ring having 1-2 heteroatoms selected from nitrogen, oxygen, or sulfur; wherein said Ring B may be optionally substituted by one or more oxo, thiono, or imino groups;
m is 1-4;
p is 0-2;
W is N or —C($R^3$)—;
$R^z$ is R, CN, $NO^2$, halogen, —C(O)N(R)$_2$, —C(O)OR, —C(O)R, —N(R)$_2$, —NH—[Ar], —N(R)C(O)OR, —NRC(O)N(R)$_2$, —OR, or —$SO^2$N(R)$_2$;
[Ar] is an optionally substituted phenyl or heteroaromatic ring;
$R^3$ is hydrogen, halogen, —CN, $C_{1-4}$ aliphatic, $C_{1-4}$ haloaliphatic, —OR, —C(O)R, or —C(O)N(R)$_2$;
$L^1$ is a covalent bond or a $C_{1-6}$ bivalent hydrocarbon chain wherein one or two methylene units of the chain are optionally and independently replaced by —NR—, —N(R)C(O)—, —C(O)N(R)—, —N(R)$SO_2$—, —$SO_2$N(R)—, —O—, —C(O)—, —OC(O)—, —C(O)O—, —S—, —SO— or —$SO_2$—;
each $L^2$ is independently a covalent bond or a $C_{1-6}$ bivalent hydrocarbon chain wherein one or two methylene units of the chain are optionally and independently replaced by —NR—, —N(R)C(O)—, —C(O)N(R)—, —N(R)$SO_2$—, —$SO_2$N(R)—, —O—, —C(O)—, —OC(O)—, —C(O)O—, —S—, —SO— or —$SO_2$—;
each $R^4$ is independently halogen, —CN, —$NO_2$, —OR, —SR, —N(R)$_2$, —$SO_2$R, —$SO_2$N(R)$_2$, —SOR, —C(O)R, —$CO_2$R, —C(O)N(R)$_2$, —NRC(O)R, —NRC(O)N(R)$_2$, —C(O)N(R)OR, —N(R)C(O)OR, —N(R)S(O)$_2$N(R)$_2$, —NRSO$_2$R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:
two -L2($R^4$)$_p$—$R^4$ groups are taken together with their intervening atoms to form an optionally substituted 4-7 membered fused, spiro-fused, or bridged bicyclic ring having 0-2 heteroatoms independently selected from nitrogen, oxygen, or sulfur;

As defined generally above, the Ring A group of formula I is a 3-7 membered saturated or partially unsaturated carbocyclic ring or a 4-7 membered saturated or partially unsaturated heterocyclic ring having 1-3 heteroatoms independently selected from nitrogen, oxygen, or sulfur. In some embodiments, Ring A is a 3-7 membered saturated or partially unsaturated carbocyclic ring. In certain embodiments, Ring A is a 4-7 membered saturated or partially unsaturated heterocyclic ring having 1-3 heteroatoms independently selected from nitrogen, oxygen, or sulfur.

In some embodiments, Ring A is a 3-7 membered saturated carbocyclic ring. In certain embodiments, Ring A is cyclopentyl or cyclohexyl. In some embodiments, Ring A is cyclohexyl.

One of skill in the art will appreciate that a when Ring A is a disubstituted cycloalkyl ring, said ring can have cis or trans relative stereochemistry. In some embodiments, Ring A is a trans-1,4-disubstituted cycloalkyl ring. In some embodiments, Ring A a trans-1,4-disubstituted cyclohexyl ring.

In certain embodiments, Ring A is a 4-7 membered saturated heterocyclic ring having 1-3 heteroatoms independently selected from nitrogen, oxygen, or sulfur. In certain embodiments, Ring A is a 5-6 membered saturated heterocyclic ring having 1-3 heteroatoms independently selected from nitrogen, oxygen, or sulfur. In certain embodiments, Ring A is piperidinyl, piperazinyl, morpholinyl, thiomorpholinyl, tetrahydropyranyl, or tetrahydrofuranyl. In some embodiments, when Ring A is a 4-7 membered saturated heterocyclic ring, $L^1$ is a covalent bond. In some embodiments, when Ring A is a 4-7 membered saturated heterocyclic ring, $L^1$ is not a covalent bond.

As defined generally above, the n group of formula I is 0-4. In some embodiments, n is 0. In other embodiments, n is 1-4. In certain embodiments, n is 1 or 2.

As defined generally above, each $R^1$ group of formula I is independently —R, halogen, —CN, —NO$_2$, —OR, —CH$_2$OR, —SR, —N(R)$_2$, —SO$_2$R, —SO$_2$N(R)$_2$, —SOR, —C(O)R, —CO$_2$R, —C(O)N(R)$_2$, —C(O)N(R)—OR, —NRC(O)R, —NRC(O)N(R)$_2$, Cy, or —NRSO$_2$R; or $R^1$ is selected from one of the following formulas:

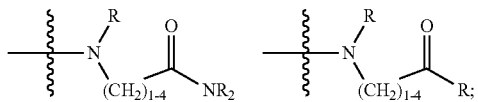

or
two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur.

In certain embodiments, $R^1$ is R, —OR, —N(R)$_2$, —CO$_2$R, —C(O)N(R)$_2$, —C(O)N(R)—OR, —SO$_2$N(R)$_2$, Cy, or —NRC(O)OR. In some embodiments, $R^1$ is —C(O)NH$_2$, —C(O)NHCH$_3$, —C(O)NH—OH, —CH$_3$, —CH$_2$CH$_3$, —SO$_2$t-butyl, —OH, —C(O)OH, —NH$_2$, —NHCH$_3$, —N(CH$_3$)$_2$, —N(CH$_2$CH$_3$)$_2$, —NHC(O)CH$_3$, or —CH$_2$-phenyl. In certain embodiments, $R^1$ is selected from one of the following formulas:

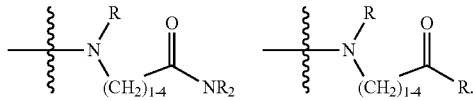

In certain embodiments, $R^1$ is Cy. In certain embodiments, $R^1$ is —N(R)$_2$. Exemplary $R^1$ groups include those depicted in Table 1.

In some embodiments, the present invention provides a compound of formula I wherein two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur. In certain embodiments, two $R^1$ groups on adjacent carbon atoms are taken together to form an optionally substituted 4-7 membered ring fused to Ring A. In other embodiments, two $R^1$ groups on the same carbon atom are taken together to form an optionally substituted 4-7 membered spiro-fused ring. In other embodiments, two $R^1$ groups on non-adjacent carbon atoms are taken together to form an optionally substituted bridged bicyclic ring with Ring A.

As defined generally above, Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur.

In some embodiments, Cy is a 3-7 membered saturated carbocyclic ring. In certain embodiments, Cy is a 4-7 membered saturated heterocyclic ring containing 1-2 heteroatoms independently selected from nitrogen, oxygen or sulfur. In certain embodiments Cy is a spirobicyclic 7-membered ring. In certain embodiments, Cy is morpholinyl, pyrrolidinyl, azetidinyl, piperidinyl or piperazinyl.

One of ordinary skill in the art will appreciate that an $R^1$ substituent on a saturated carbon of Ring A forms a chiral center. In some embodiments, that chiral center is in the (R) configuration. In other embodiments, that chiral center is in the (S) configuration.

As defined generally above, the $L^1$ group of formula I is a covalent bond or a $C_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—. In some embodiments, $L^1$ is a covalent bond. In other embodiments, $L^1$ is a $C_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—.

In some embodiments, $L^1$ is —NH— (i.e., a $C_1$ bivalent hydrocarbon chain wherein the methylene unit is replaced by —NH—), —O—, —CH$_2$O—, —OCH$_2$—, —NHC(O)—, —CH$_2$NH—, or —NHCH$_2$—. In some embodiments, $L^1$ is —O—. In some embodiments, $L^1$ is —NR—. In some embodiments, $L^1$ is —OCH$_2$—. In some embodiments, $L^1$ is —NRCH$_2$—. Exemplary $L^1$ groups include those depicted in Table 1.

As defined generally above, the Ring B group of formula I is a 4-8 membered partially unsaturated carbocyclic fused ring or a 4-7 membered partially unsaturated heterocyclic ring having 1-2 heteroatoms selected from nitrogen, oxygen or sulfur. In some embodiments, Ring B is a 4-8 membered partially unsaturated carbocyclic fused ring. In other embodiments, Ring B is a 4-7 membered partially unsaturated azacyclic fused ring having one or two nitrogens. In some embodiments, Ring B is a cyclohexo- or cyclopento-fused ring. In other embodiments, Ring B is a piperidino-fused ring. In some embodiments, Ring B is a tetrahydropyrano-fused ring. In some embodiments, Ring B is a pyrrolidino-fused ring.

One of ordinary skill in the art will appreciate that a substituent on a saturated carbon of Ring B forms a chiral center. In some embodiments, that chiral center is in the (R) configuration. In other embodiments, that chiral center is in the (S) configuration.

As defined generally above, the m group of formula I is 1-4. In other embodiments, m is 1-4. In certain embodiments, m is 1 or 2.

As defined generally above, each $L^2$ is independently a covalent bond or a $C_{1-6}$ bivalent hydrocarbon chain wherein one or two methylene units of the chain are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —SO— or —SO$_2$—.

In certain embodiments each $L^2$ is independently a covalent bond. In some embodiments each $L^2$ is a $C_{1-3}$ bivalent hydrocarbon chain wherein one or two methylene units of the chain are optionally and independently replaced by —C(O)N(R)—, —O—, —C(O)—, —S—, —SO— or —SO$_2$—. In certain embodiments, L$^2$ is methylene. In certain embodiments, L$^2$ is —CH$_2$—C(O)—. In certain embodiments, L$^2$ is a C$_2$ hydrocarbon chain substituted with a hydroxyl group (—CH$_2$CH(OH)—).

As defined generally above, each R$^4$ is independently halogen, —CN, —NO$_2$, —OR, —SR, —N(R)$_2$, —SO$_2$R, —SO$_2$N(R)$_2$, —SOR, —C(O)R, —CO$_2$R, —C(O)N(R)$_2$, —NRC(O)R, —NRC(O)N(R)$_2$, —C(O)N(R)OR, —N(R)C(O)OR, —N(R)S(O)$_2$N(R)$_2$, —NRSO$_2$R, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or: two -L2(R$^4$)$_p$—R$^4$ groups are taken together with their intervening atoms to form an optionally substituted 4-7 membered fused, spiro-fused, or bridged bicyclic ring having 0-2 heteroatoms independently selected from nitrogen, oxygen, or sulfur.

In some embodiments, each R$^4$ is independently —CN, —OR, —SR, —SOR, —SO$_2$R, —C(O)N(R)$_2$, —NRC(O)R, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur. In certain embodiments, each R$^4$ is independently —CN, —OR, —SR, —SOR, —SO$_2$R, —C(O)N(R)$_2$, or —NRC(O)R. In certain embodiments R$^4$ is an optionally substituted group selected from C$_{1-6}$ aliphatic, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur. In certain embodiments R$^4$ is hydroxyl. In certain embodiments R$^4$ is —C(O)N(R)$_2$.

In some embodiments, the present invention provides a compound of formula I wherein two -L2(R$^4$)$_p$—R$^4$ groups are taken together with their intervening atoms to form an optionally substituted 4-7 membered fused, spiro-fused, or bridged bicyclic ring having 0-2 heteroatoms independently selected from nitrogen, oxygen, or sulfur. In certain embodiments, two -L2-R$^4$ groups on adjacent carbon atoms are taken together to form an optionally substituted 4-7 membered ring fused to Ring B. In other embodiments, two -L2(R$^4$)$_p$—R$^4$ groups on the same carbon atom are taken together to form an optionally substituted 4-7 membered spiro-fused ring. In other embodiments, two -L2(R$^4$)$_p$—R$^4$ groups on non-adjacent carbon atoms are taken together to form an optionally substituted bridged bicyclic ring with Ring B.

In some embodiments, any one or more -L2(R$^4$)$_p$—R$^4$ groups are independently selected from deuterium, an unsubstituted alkyl group, a —CO$_2$R group, and an unsubstituted heterocyclyl group. In some embodiments, any one or more -L2(R$^4$)$_p$—R$^4$ groups are not independently selected from deuterium, an unsubstituted alkyl group a —CO$_2$R group, and an unsubstituted heterocyclyl group.

One of ordinary skill in the art will appreciate that an -L2(R$^4$)$_p$—R$^4$ substituent on a saturated carbon of Ring B forms a chiral center. In some embodiments, that chiral center is in the (R) configuration. In other embodiments, that chiral center is in the (S) configuration.

As defined generally above, the R$^z$ group of formula I is —R, —CN, —NO$_2$, halogen, —C(O)N(R)$_2$, —C(O)OR, —C(O)R, —N(R)$_2$, —NH-[Ar], —N(R)C(O)OR, —NRC(O)N(R)$_2$, —OR, or —SO$^2$N(R)$_2$. In some embodiments, R$^z$ is hydrogen. In other embodiments, R$^z$ is CN, halogen, —N(R)$_2$ or —C(O)N(R)$_2$. Exemplary R$^z$ groups include those depicted in Table 1.

As defined generally above, [Ar] is an optionally substituted phenyl or heteroaromatic ring. In some embodiments, [Ar] is an optionally substituted phenyl ring. In some embodiments, [Ar] is an optionally substituted heteroaromatic ring. In some embodiments, [Ar] is an optionally substituted 5-membered heteroaromatic ring. In some embodiments, [Ar] is an optionally substituted 6-membered heteroaromatic ring. In some embodiments, [Ar] is an optionally substituted pyrazole ring.

As defined generally above, p is 0-2. In some embodiments p is 0. In some embodiments p is 1. In certain embodiments, p is 2.

In some embodiments, the compound of formula I is not selected from the following compounds:

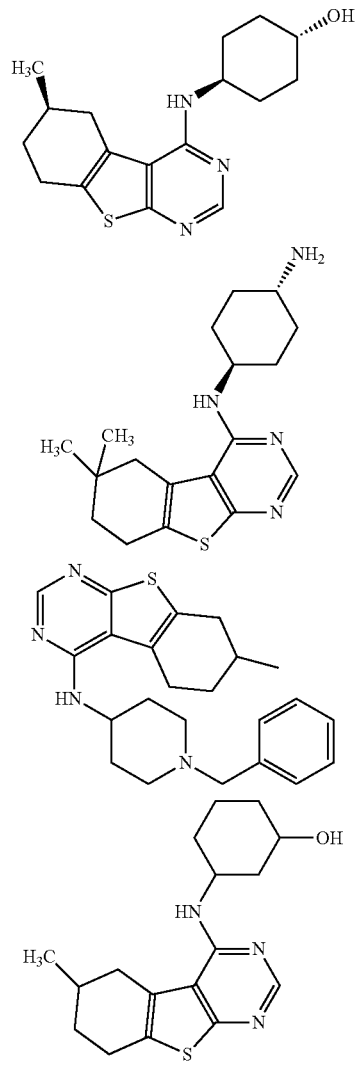

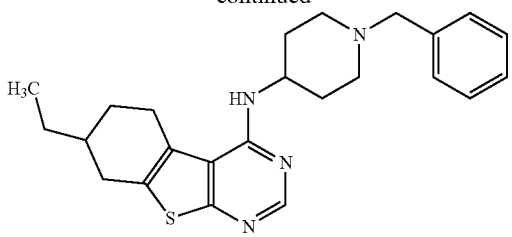
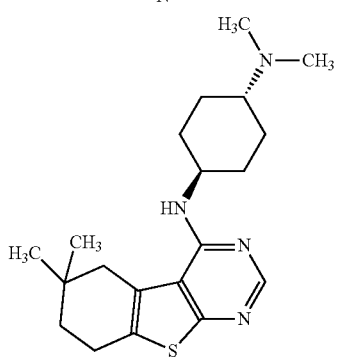
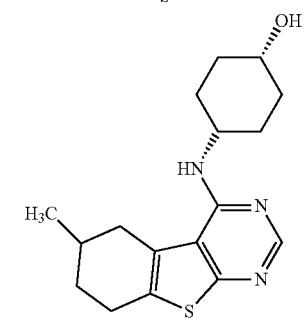
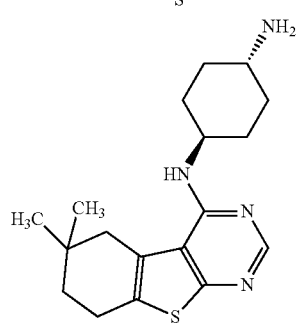
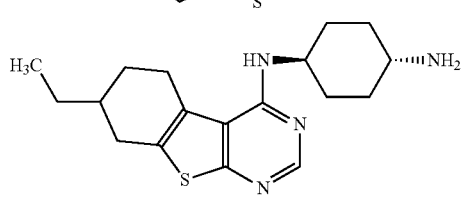
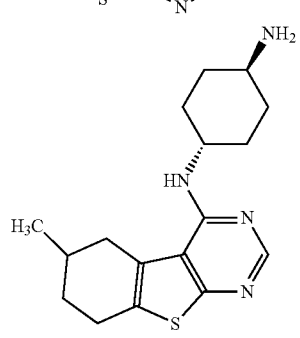
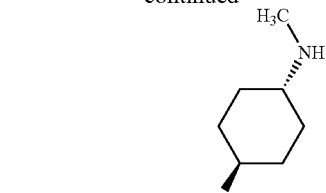
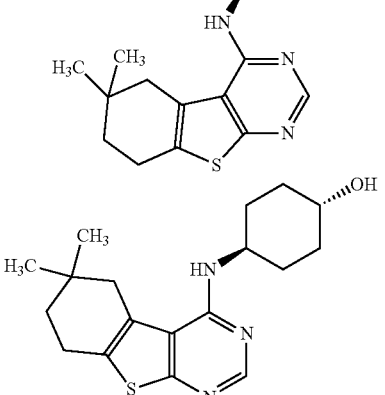
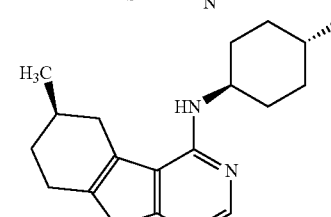
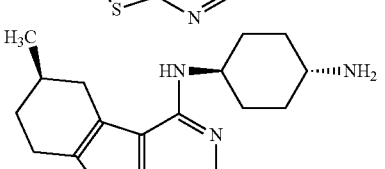
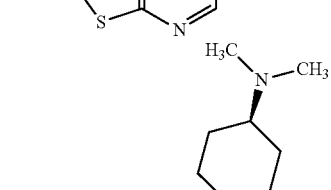
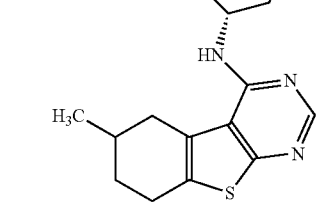
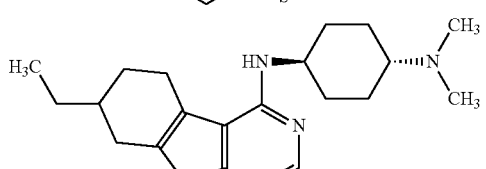
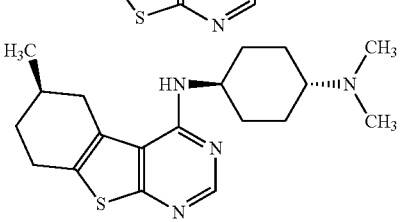

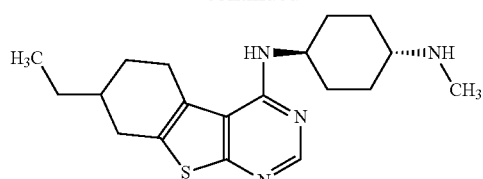
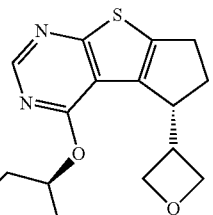
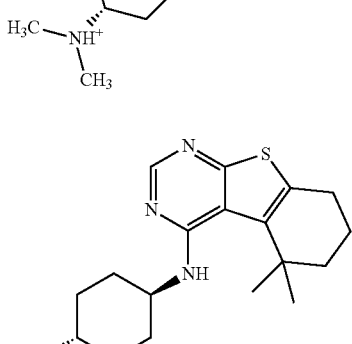
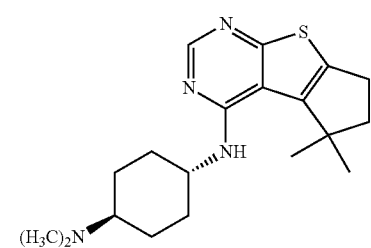
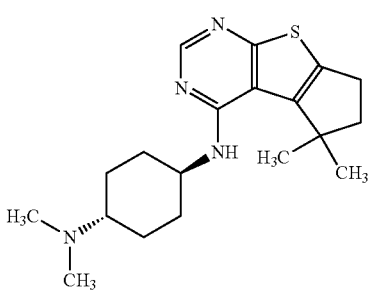
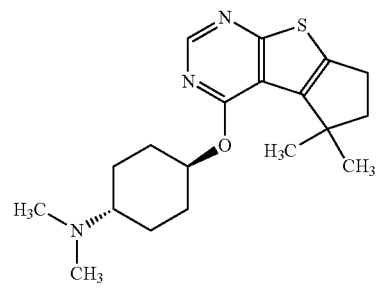
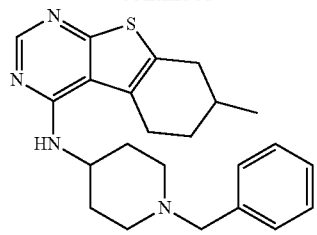
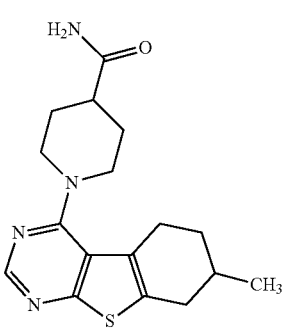
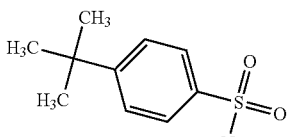
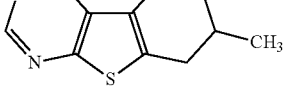
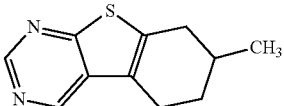
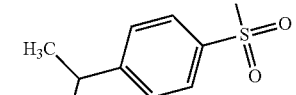
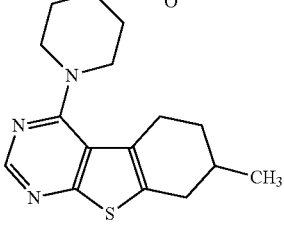

23
-continued
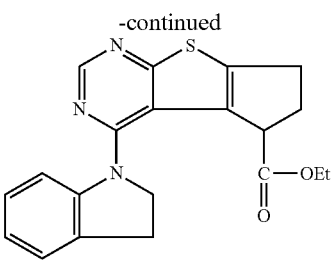
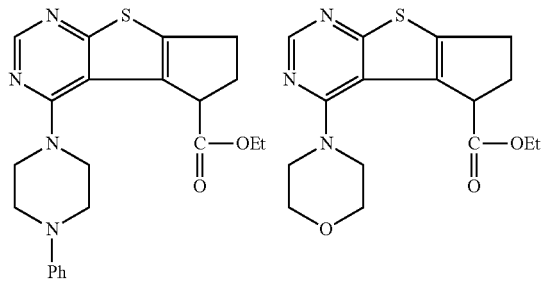
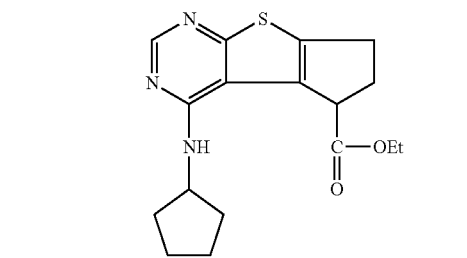
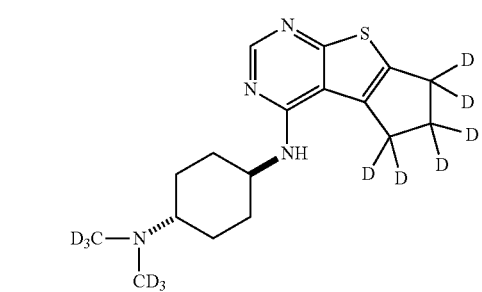
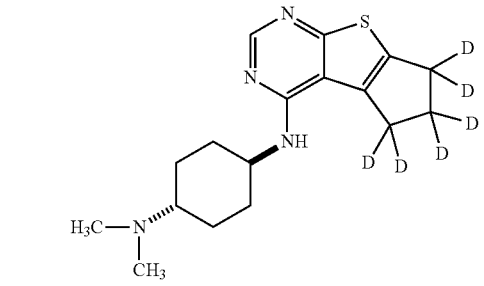
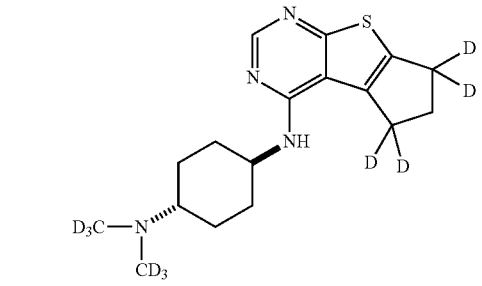
24
-continued
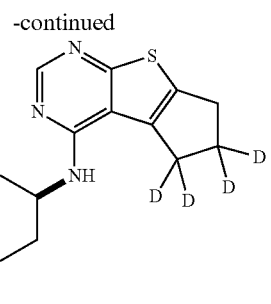
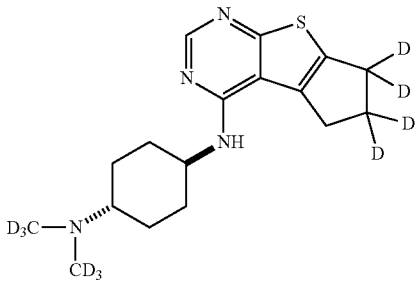
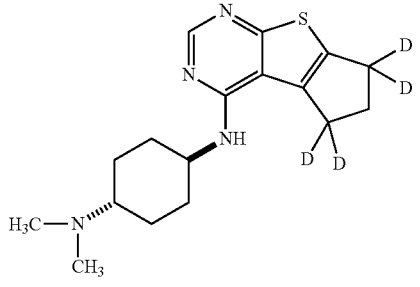
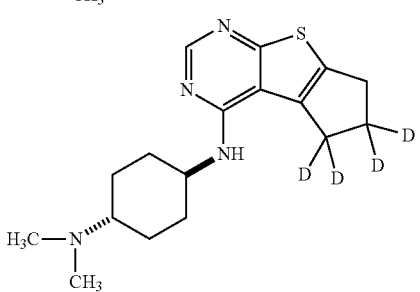
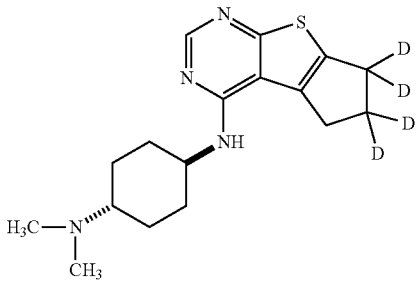
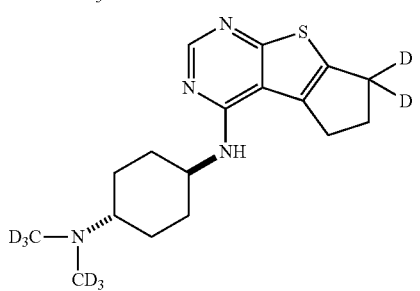

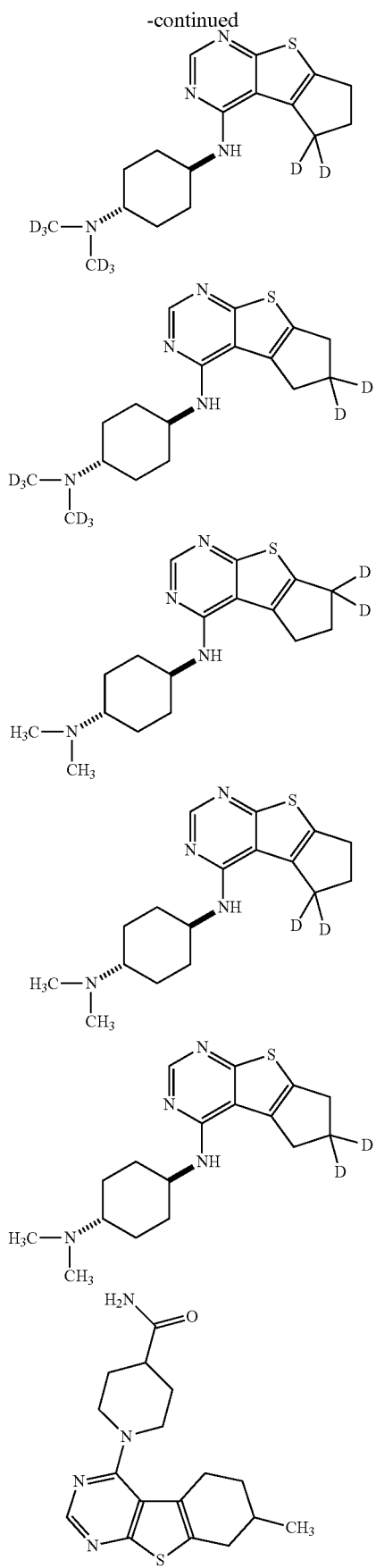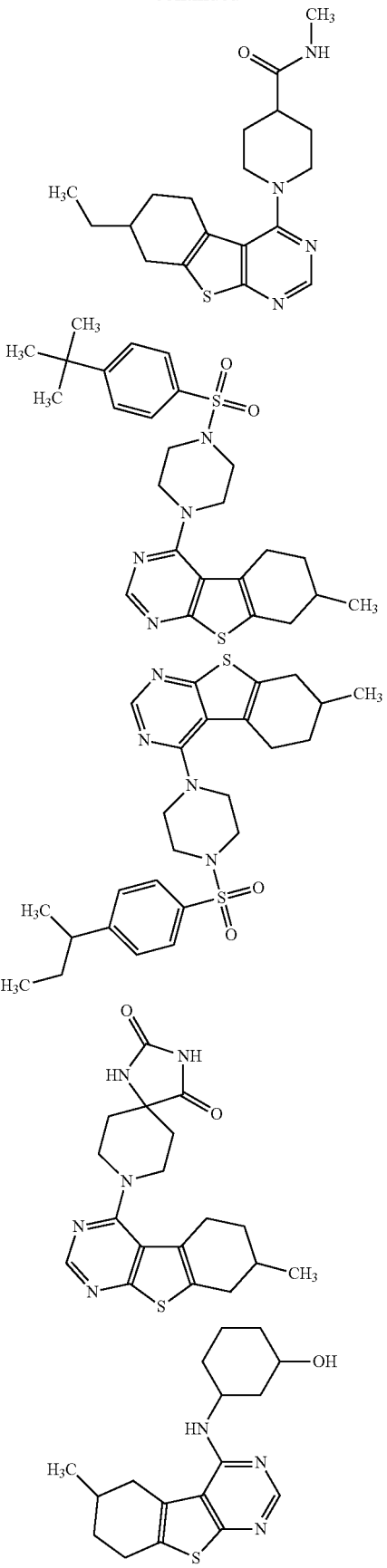

27
-continued
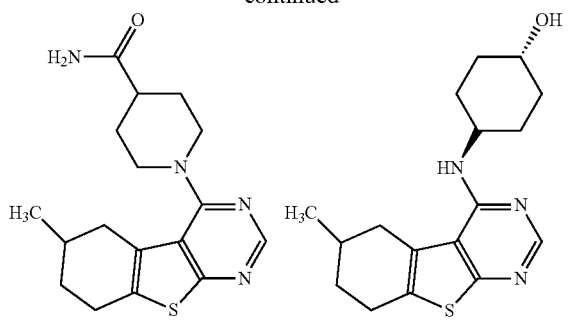
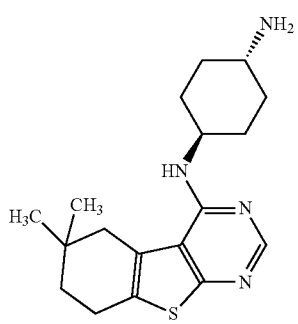
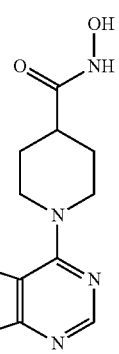
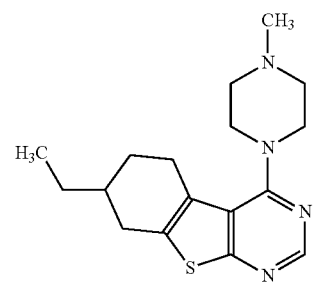
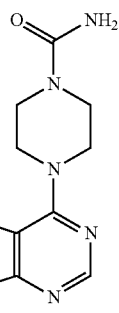
28
-continued
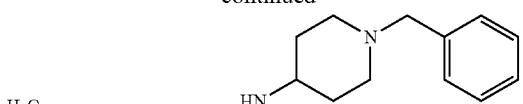
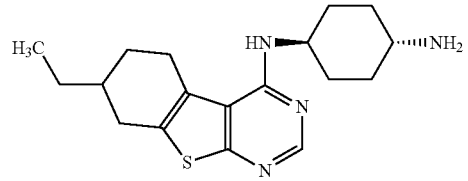
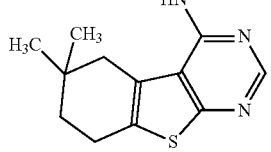
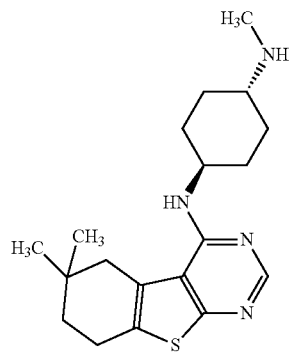
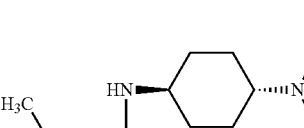
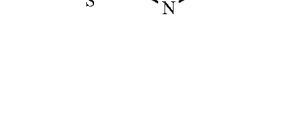

-continued

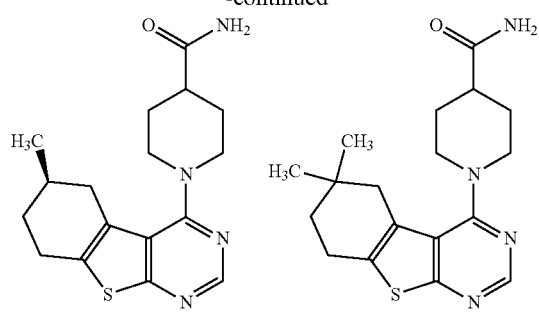

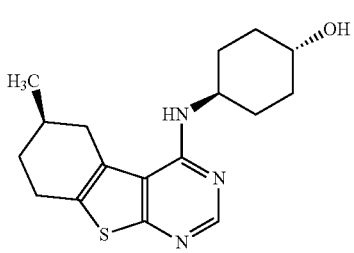

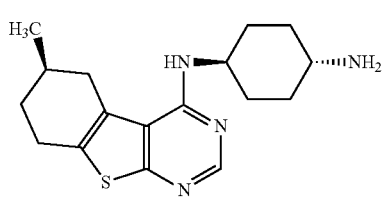

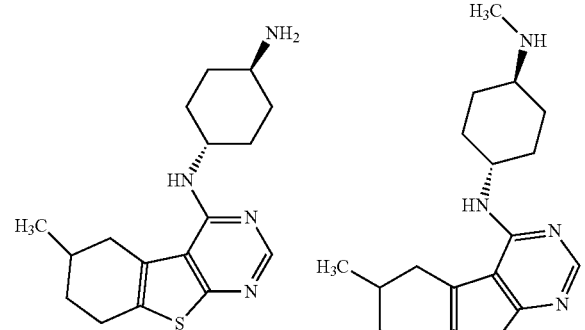

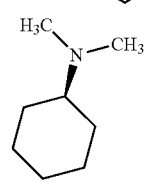

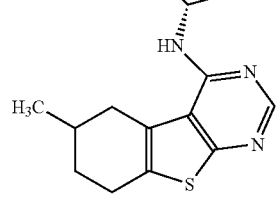

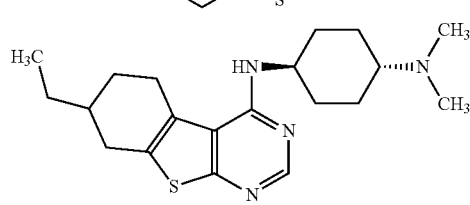

-continued

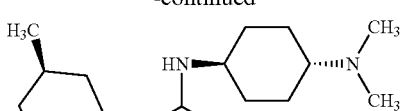

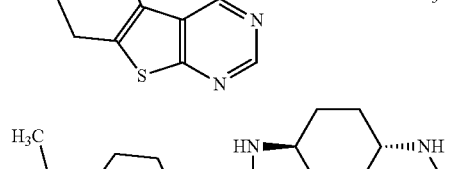

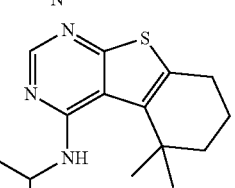

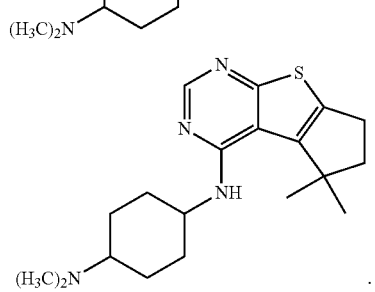

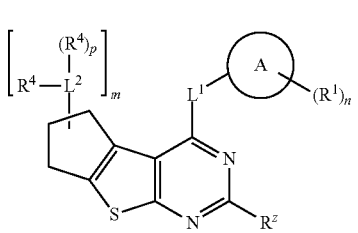

In certain embodiments, the present invention provides a compound of formula I, wherein Ring B is a cyclopento fused ring, and W is N, thereby forming a compound of formula II:

$$II$$

or a pharmaceutically acceptable salt thereof, wherein each of Ring A, $L^1$, $L^2$, $R^z$, $R^1$, $R^4$, m, n, and p is as defined above and described in embodiments herein, both singly and in combination.

In certain embodiments, the present invention provides a compound of formula II, wherein $R^1$ is one of the following formulas:

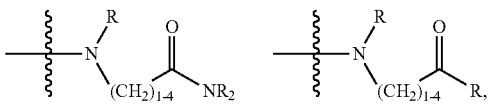

thereby forming a compound of formula II-a or II-b:

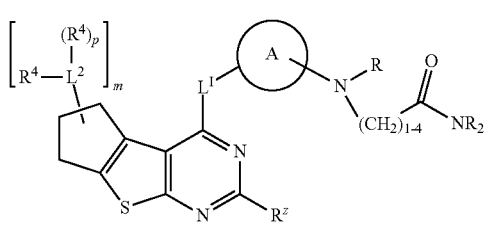

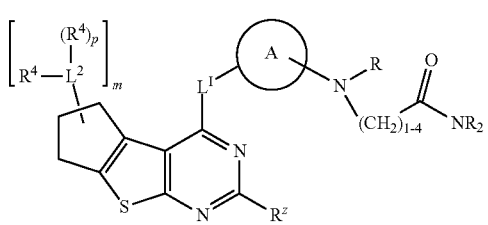

or a pharmaceutically acceptable salt thereof, wherein each of Ring A, $L^1$, $L^2$, R, $R^z$, $R^1$, $R^4$, m, n, and p is as defined above and described in embodiments herein, both singly and in combination.

In certain embodiments, the present invention provides a compound of formula II, wherein m is 1, thereby forming a compound of formula III:

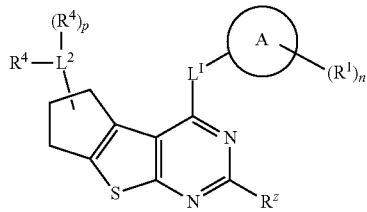

or a pharmaceutically acceptable salt thereof, wherein each of Ring A, $L^1$, $L^2$, $R^z$, $R^1$, $R^4$, n, and p is as defined above and described in embodiments herein, both singly and in combination.

In certain embodiments, the present invention provides a compound of formula III, wherein Ring A is cyclohexyl, thereby forming a compound of formula IV:

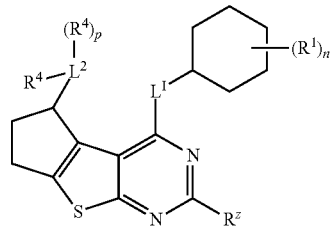

or a pharmaceutically acceptable salt thereof, wherein each of, $L^1$, $L^2$, $R^z$, $R^1$, $R^4$, n, and p is as defined above and described in embodiments herein, both singly and in combination.

In certain embodiments, the present invention provides a compound of formula III, wherein n is 1 and the cyclohexyl ring has trans stereochemistry, thereby forming a compound of formula V:

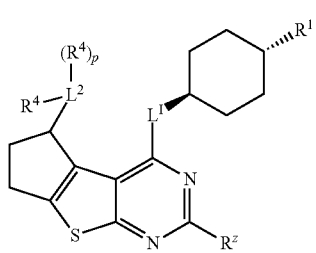

or a pharmaceutically acceptable salt thereof, wherein each of, $L^1$, $L^2$, $R^z$, $R^1$, $R^4$, and p is as defined above and described in embodiments herein, both singly and in combination.

In certain embodiments, the present invention provides a compound of formula V, wherein $R^z$ is $-N(R)_2$, thereby forming a compound of formula VI:

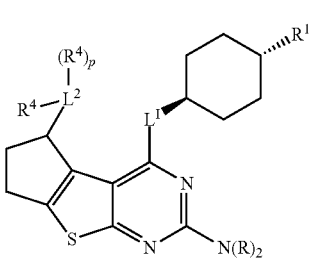

or a pharmaceutically acceptable salt thereof, wherein each of, $L^1$, $L^2$, R, $R^1$, $R^4$, and p is as defined above and described in embodiments herein, both singly and in combination.

In certain embodiments, the present invention provides a compound of formula VII, wherein $W^1$, $W^2$, $X^1$, $X^2$, $Y^1$, $Y^2$ and $Z^1$ are each independently hydrogen or deuterium:

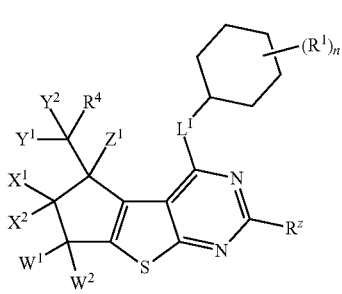

or a pharmaceutically acceptable salt thereof, wherein each of $L^1$, $L^2$, $R^1$, $R^z$, and $R^4$ is as defined above for formula I and described in embodiments herein, both singly and in combination.

In certain embodiments, the present invention provides a compound of formula VIII, wherein $W^1$, $W^2$, $X^1$, $X^2$, $Y^1$, $Y^2$, $Z^1$ and $Z^2$ are each independently hydrogen or deuterium:

VIII

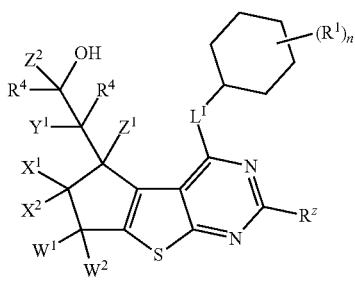

or a pharmaceutically acceptable salt thereof, wherein each of $L^1$, $L^2$, $R^1$, $R^z$, and $R^4$ are defined above for formula I and described in embodiments herein, both singly and in combination.

In certain embodiments, the present invention provides a compound of formula I, wherein Ring B is cyclohexo, W is N, and $R^z$ is hydrogen, thereby forming a compound of formula IX:

IX

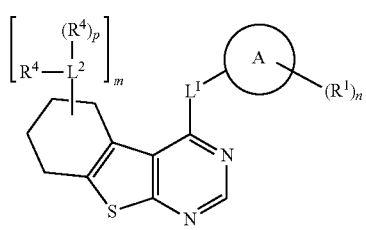

or a pharmaceutically acceptable salt thereof, wherein each of King A, $L^1$, $L^2$, $R^1$, $R^4$, m, n, and p is as defined above and described in embodiments herein, both singly and in combination.

In certain embodiments, the present invention provides a compound of formula IX, wherein m is 1, and $L^2$ is attached α to the thiophene ring, thereby forming a compound of formula X:

X

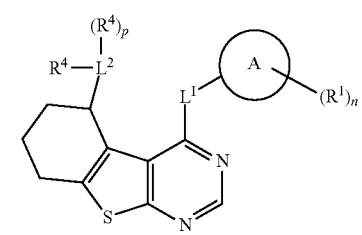

or a pharmaceutically acceptable salt thereof, wherein each of Ring A, $L^1$, $L^2$, $R^1$, $R^4$, n, and p is as defined above and described in embodiments herein, both singly and in combination.

In certain embodiments, the present invention provides a compound of formula IX, wherein m is 1, and $L^2$ is attached β to the thiophene ring, thereby forming a compound of formula XI:

XI

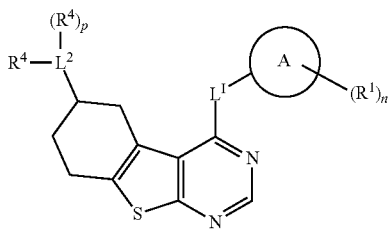

or a pharmaceutically acceptable salt thereof, wherein each of Ring A, $L^1$, $L^2$, $R^1$, $R^4$, n, and p is as defined above and described in embodiments herein, both singly and in combination.

In certain embodiments, the present invention provides a compound of formula III, wherein $R^z$ is hydrogen, and $L^2$ is $C_2$ alkylene, thereby forming a compound of formula XII:

XII

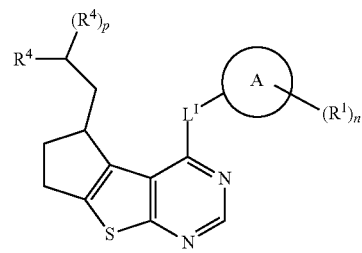

or a pharmaceutically acceptable salt thereof, wherein each of Ring A, $L^1$, $R^1$, $R^4$, n, and p is as defined above and described in embodiments herein, both singly and in combination.

In certain embodiments, the present invention provides a compound of formula XII, wherein one instance of $R^4$ is —C(O)$NR_2$, thereby forming a compound of formula XIII:

XIII

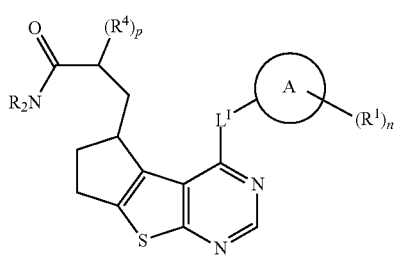

or a pharmaceutically acceptable salt thereof, wherein each of Ring A, $L^1$, R, $R^1$, $R^4$, n, and p is as defined above and described in embodiments herein, both singly and in combination.

In certain embodiments, the present invention provides a compound of formula XIII, wherein Ring A is 4-substituted cyclohexyl, thereby forming compound of formula XIV:

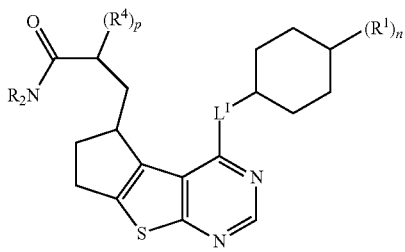

XIV or a pharmaceutically acceptable salt thereof, wherein each of $L^1$, R, $R^1$, $R^4$, n, and p is as defined above and described in embodiments herein, both singly and in combination.

In certain embodiments, the present invention provides a compound of formula XIV, wherein n is 1, and $R^1$ is —$NR_2$, thereby forming a compound of formula XV:

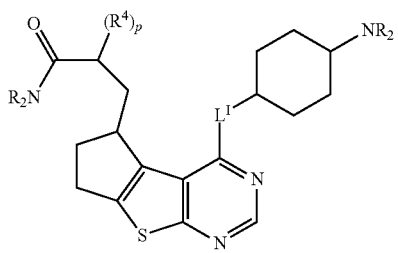

XV or a pharmaceutically acceptable salt thereof, wherein each of $L^1$, R, $R^4$, and p is as defined above and described in embodiments herein, both singly and in combination.

In certain embodiments, the present invention provides a compound of formula XV, wherein the stereochemistry of the substituent on the cyclopento ring is (R), and the relative stereochemistry on the cyclohexyl ring is trans thereby forming a compound of formula XVI:

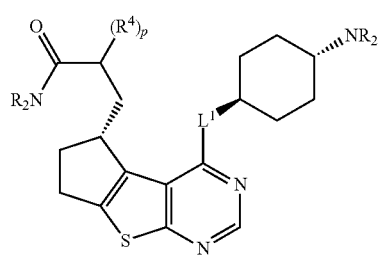

XVI or a pharmaceutically acceptable salt thereof, wherein each of $L^1$, R, $R^4$, and p is as defined above and described in embodiments herein, both singly and in combination.

In certain embodiments, the present invention provides a compound of formula XVI wherein each $R^4$ is independently hydrogen, fluoro or —OR.

In certain embodiments the present invention provides a compound of formula XVI wherein $L^1$ is —O—. In certain embodiments the present invention provides a compound of formula XVI wherein $L^1$ is —NH—.

In certain embodiments, the present invention provides a compound of formula III, wherein $R^z$ is hydrogen, and $L^2$ is $C_1$ alkylene, thereby forming a compound of formula XVII:

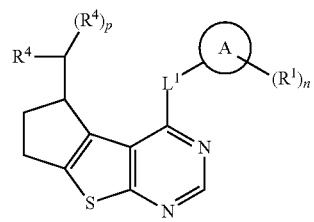

XVII or a pharmaceutically acceptable salt thereof, wherein each of Ring A, $L^1$, $R^1$, $R^4$, n, and p is as defined above and described in embodiments herein, both singly and in combination.

In certain embodiments, the present invention provides a compound of formula XVII, wherein one instance of $R_4$ is —$C(O)NR_2$, thereby forming a compound of formula XVIII:

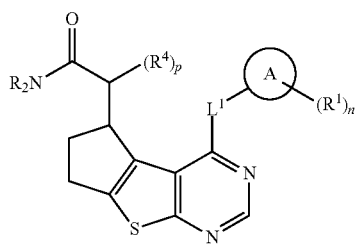

XVIII or a pharmaceutically acceptable salt thereof, wherein each of Ring A, $L^1$, R, $R^1$, $R^4$, n, and p is as defined above and described in embodiments herein, both singly and in combination.

In certain embodiments, the present invention provides a compound of formula XVIII, wherein Ring A is 4-substituted cyclohexyl, thereby forming a compound of formula XIX:

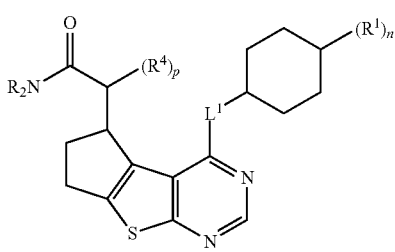

XIX or a pharmaceutically acceptable salt thereof, wherein each of $L^1$, R, $R^1$, $R^4$, n, and p is as defined above and described in embodiments herein, both singly and in combination.

In certain embodiments, the present invention provides a compound of formula XIX, wherein n is 1, and $R^1$ is —$NR_2$, thereby forming a compound of formula XX:

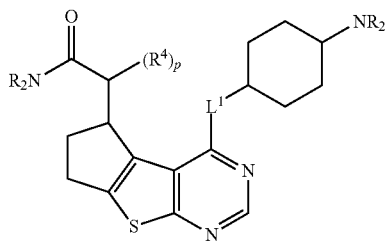

XX or a pharmaceutically acceptable salt thereof, wherein each of $L^1$, R, $R^4$, and p is as defined above and described in embodiments herein, both singly and in combination.

In certain embodiments, the present invention provides a compound of formula XX, wherein the stereochemistry of the substituent on the cyclopento ring is (R), and the relative stereochemistry on the cyclohexyl ring is trans thereby forming a compound of formula XXI:

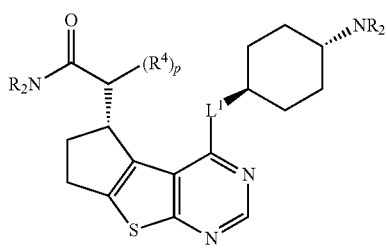

XXI or a pharmaceutically acceptable salt thereof, wherein each of $L^1$, R, $R^4$, and p is as defined above and described in embodiments herein, both singly and in combination.

In certain embodiments, the present invention provides a compound of formula XXI wherein each $R^4$ is independently hydrogen, fluoro or —OR.

In certain embodiments the present invention provides a compound of formula XXI wherein $L^1$ is —O—. In certain embodiments the present invention provides a compound of formula XXI wherein $L^1$ is —NH—.

In certain embodiments, the present invention provides a compound of formula I, wherein Ring B is piperidino, m is 1, and $R^z$ is hydrogen, thereby forming a compound of formula XXII:

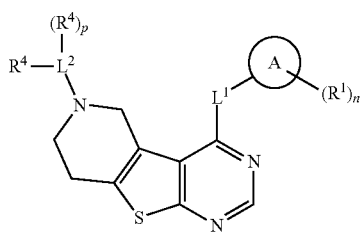

XXII or a pharmaceutically acceptable salt thereof, wherein each of Ring A, $L^1$, $L^2$, $R^1$, $R^4$, n, and p is as defined above and described in embodiments herein, both singly and in combination.

In certain embodiments, the present invention provides a compound of formula XXII, wherein $L^2$ is a bond and p is 0, thereby forming a compound of formula XXIII:

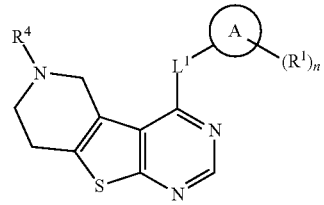

XXIII or a pharmaceutically acceptable salt thereof, wherein each of Ring A, $L^1$, $R^1$, $R^4$, n, and p is as defined above and described in embodiments herein, both singly and in combination.

In certain embodiments the present invention provides a compound of formula XXIII wherein $R^4$ is —S(O)$_2$R, —C(O)R, or —C(O)N(R)$_2$.

In certain embodiments, the present invention provides a compound of formula II, wherein $L^1$ is —O—, thereby forming a compound of formula XXIV:

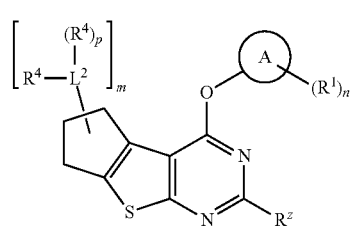

XXIV or a pharmaceutically acceptable salt thereof, wherein each of Ring A, $L^2$, $R^z$, $R^1$, $R^4$, m, n, and p is as defined above and described in embodiments herein, both singly and in combination.

In certain embodiments, the present invention provides a compound of formula XXIV, wherein m is 1, thereby forming a compound of formula XXV:

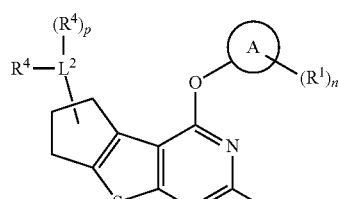

XXV or a pharmaceutically acceptable salt thereof, wherein each of Ring A, $L^2$, $R^z$, $R^1$, $R^4$, n, and p is as defined above and described in embodiments herein, both singly and in combination.

In certain embodiments, the present invention provides a compound of formula XXV, wherein Ring A is cyclohexyl, thereby forming a compound of formula XXVI:

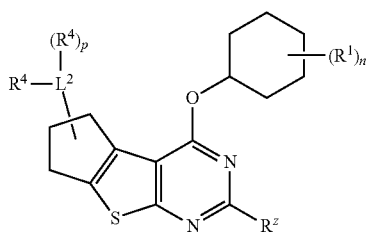

XXVI or a pharmaceutically acceptable salt thereof, wherein each of, $L^2$, $R^z$, $R^1$, $R^4$, n, and p is as defined above and described in embodiments herein, both singly and in combination.

In certain embodiments, the present invention provides a compound of formula I, wherein $R^z$ is —NH-[Ar], thereby forming a compound of formula XXVII:

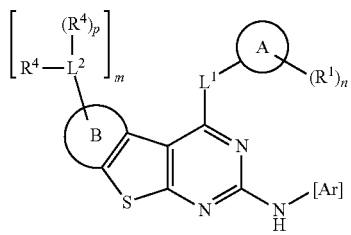

XXVII or a pharmaceutically acceptable salt thereof, wherein [Ar] is an optionally substituted phenyl or heteroaromatic ring, and each of Ring A, Ring B, $L^2$, $R^z$, $R^1$, $R^4$, m, n, and p is as defined above and described in embodiments herein, both singly and in combination.

In certain embodiments, the present invention provides a compound of formula XXVII, wherein n is 1 and Ring A is 1,4-trans-substituted cyclohexyl, thereby forming a compound of formula XXVIII:

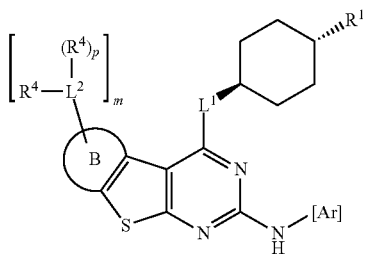

XXVIII or a pharmaceutically acceptable salt thereof, wherein [Ar] is an optionally substituted phenyl or heteroaromatic ring, and each of Ring A, Ring B, $L^1$, $L^2$, $R^1$, $R^4$, m, and p is as defined above and described in embodiments herein, both singly and in combination.

As described generally above, [Ar] is an optionally substituted phenyl or heteroaromatic ring. In some embodiments, [Ar] is optionally substituted phenyl. In some embodiments, [Ar] is an optionally substituted heteroaromatic ring. In some embodiments, [Ar] is an optionally substituted 5-membered heteroaromatic ring. In some embodiments, [Ar] is an optionally substituted 6-membered heteroaromatic ring. In some embodiments, [Ar] is an optionally substituted pyrazole ring.

In certain embodiments, the present invention provides a compound of formula XXVIII, wherein Ring B is cyclopento, thereby forming a compound of formula XXIX:

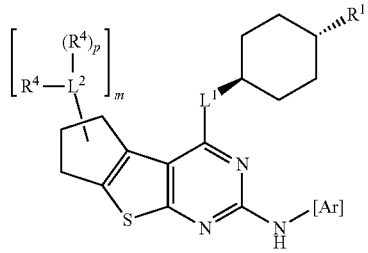

XXIX or a pharmaceutically acceptable salt thereof, wherein each of [Ar], $L^1$, $L^2$, $R^1$, $R^4$, m, and p is as defined above and described in embodiments herein, both singly and in combination.

In certain embodiments, the present invention provides a compound of formula XXVIII, wherein Ring B is cyclohexo, thereby forming a compound of formula XXIX:

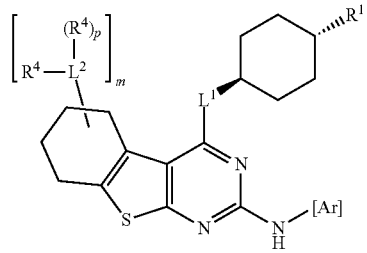

XXIX or a pharmaceutically acceptable salt thereof, wherein each of [Ar], $L^1$, $L^2$, $R^1$, $R^4$, m, and p is as defined above and described in embodiments herein, both singly and in combination.

In certain embodiments, the present invention provides a compound of formula XXVIII, wherein Ring B is a partially unsaturated tetrahydropyrano-fused ring, thereby forming a compound of one of formulae XXX-a, XXX-b, XXX-c, or XXX-d:

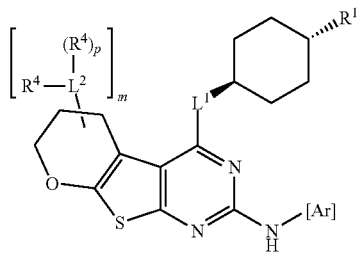

XXX-a

-continued

XXX-b
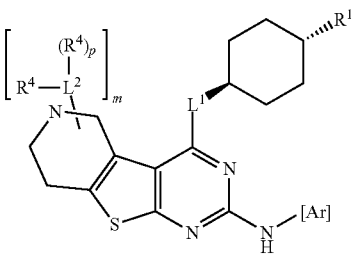

XXX-c
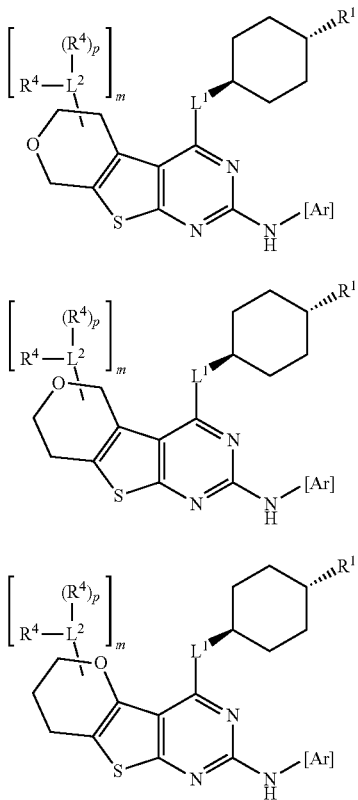

XXX-d or a pharmaceutically acceptable salt thereof, wherein each of [Ar], $L^1$, $L^2$, $R^1$, $R^4$, m, and p is as defined above and described in embodiments herein, both singly and in combination.

In certain embodiments, the present invention provides a compound of formula XXVIII, wherein Ring B is a partially unsaturated piperidino-fused ring, thereby forming a compound of one of formulae XXXI-a, XXXI-b, XXXI-c, or XXXI-d:

XXXI-a
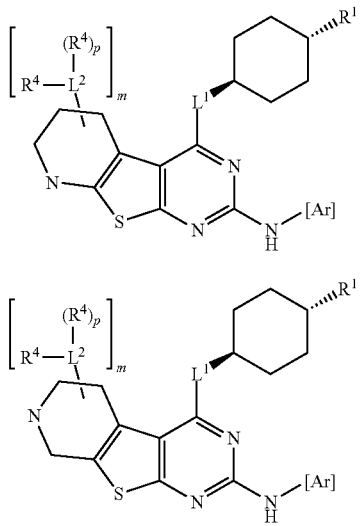

XXXI-b

-continued

XXXI-c
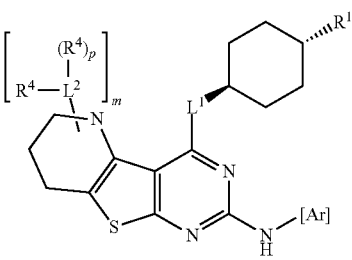

XXXI-d
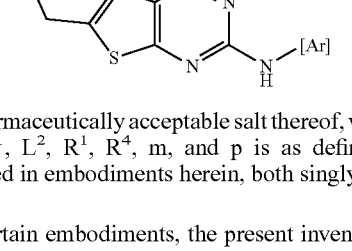

or a pharmaceutically acceptable salt thereof, wherein each of [Ar], $L^1$, $L^2$, $R^1$, $R^4$, m, and p is as defined above and described in embodiments herein, both singly and in combination.

In certain embodiments, the present invention provides a compound of formula XXVIII, wherein Ring B is a partially unsaturated pyrrolidino-fused ring, thereby forming a compound of one of formulae XXXII-a, XXXII-b, or XXXII-c:

XXXII-a
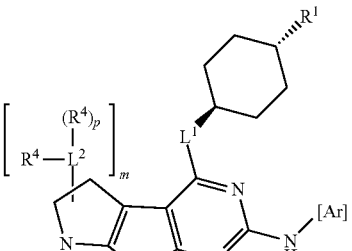

XXXII-b
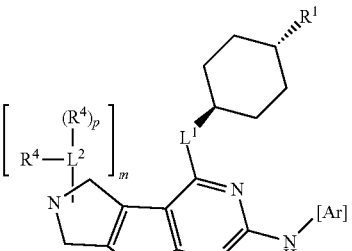

XXXII-c
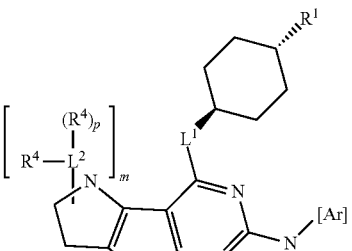

or a pharmaceutically acceptable salt thereof, wherein each of [Ar], L¹, L², R¹, R⁴, m, and p is as defined above and described in embodiments herein, both singly and in combination.

In certain embodiments, the present invention provides a compound of formula I, wherein n is 1, Ring A is trans-substituted cyclohexyl, and Ring B is a partially unsaturated tetrahydropyrano-fused ring, thereby forming a compound of one of formulae XXXIII-a, XXXIII-b, XXXIII-c, or XXXIII-d:

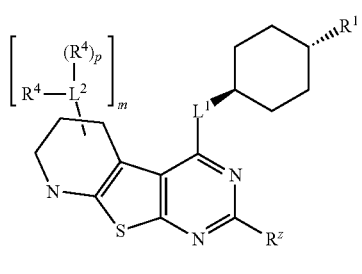

XXXIII-a

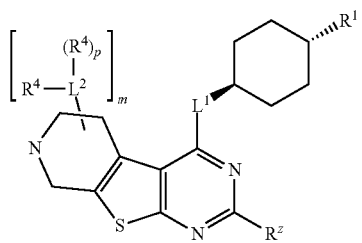

XXXIII-b

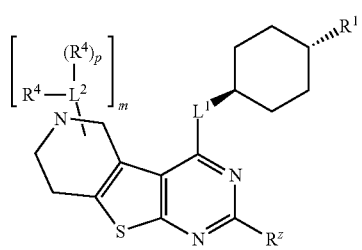

XXXIII-c

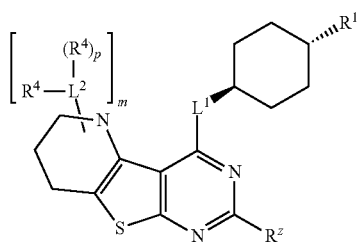

XXXIII-d or a pharmaceutically acceptable salt thereof, wherein each of L¹, L², R¹, R⁴, R^z, m, and p is as defined above and described in embodiments herein, both singly and in combination.

In certain embodiments, the present invention provides a compound of formula I, wherein n is 1, Ring A is trans-substituted cyclohexyl, and Ring B is a partially unsaturated piperidino-fused ring, thereby forming a compound of one of formulae XXXIV-a, XXXIV-b, XXXIV-c, or XXXIV-d:

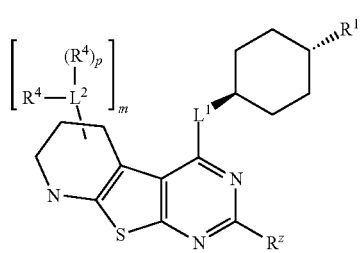

XXXIV-a

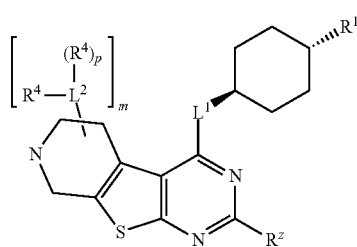

XXXIV-b

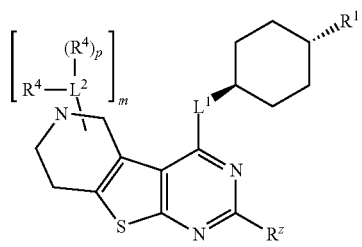

XXXIV-c

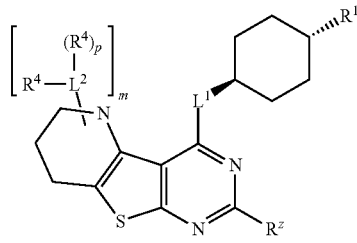

XXXIV-d or a pharmaceutically acceptable salt thereof, wherein each of L¹, L², R¹, R⁴, R^z, m, and p is as defined above and described in embodiments herein, both singly and in combination.

In certain embodiments, the present invention provides a compound of formula I, wherein n is 1, Ring A is trans-substituted cyclohexyl, and Ring B is a partially unsaturated pyrrolidino-fused ring, thereby forming a compound of one of formulae XXXV-a, XXXV-b, or XXXV-c:

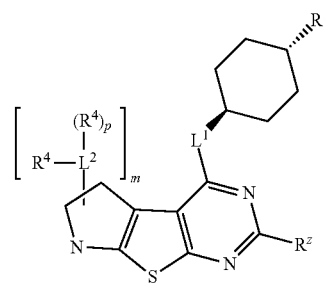

XXXV-a

XXXV-b
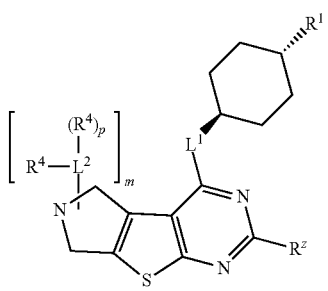

XXXV-c
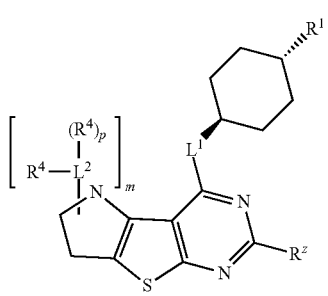

or a pharmaceutically acceptable salt thereof, wherein each of $L^1$, $L^2$, $R^1$, $R^4$, $R^z$, m, and p is as defined above and described in embodiments herein, both singly and in combination.

In certain embodiments, the present invention provides a compound of formula XXXIII-a, XXXIII-b, XXXIII-c, or XXXIII-d, wherein $R^z$ is hydrogen, thereby forming a compound of one of formulae XXXVI-a, XXXVI-b, XXXVI-c, or XXXVI-d:

XXXVI-a
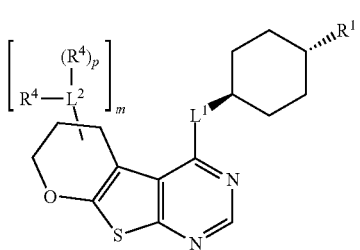

XXXVI-b
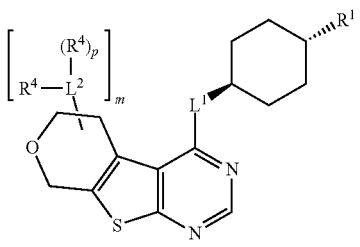

XXXVI-c
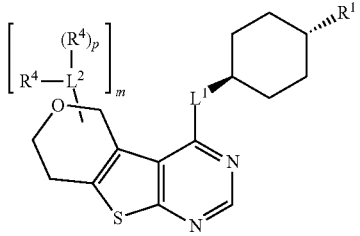

XXXVI-d
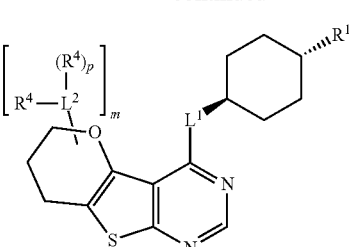

or a pharmaceutically acceptable salt thereof, wherein each of $L^1$, $L^2$, $R^1$, $R^4$, m, and p is as defined above and described in embodiments herein, both singly and in combination.

In certain embodiments, the present invention provides a compound of formula XXXIV-a, XXXIV-b, XXXIV-c, or XXXIV-d, wherein $R^z$ is hydrogen, thereby forming a compound of one of formulae XXXVII-a, XXXVII-b, XXXVII-c, or XXXVII-d:

XXXVII-a
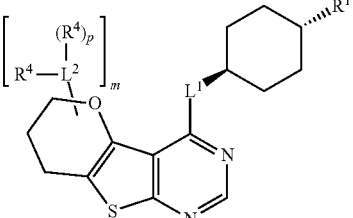

XXXVII-b
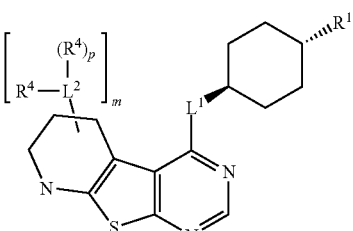

XXXVII-c
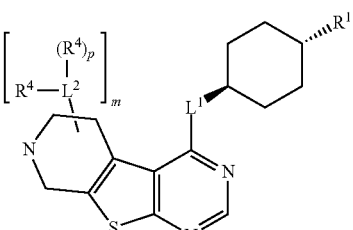

XXXVII-d
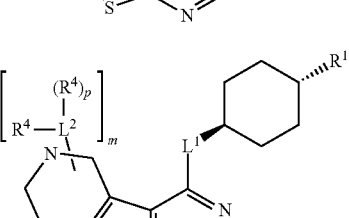

or a pharmaceutically acceptable salt thereof, wherein each of $L^1$, $L^2$, $R^1$, $R^4$, m, and p is as defined above and described in embodiments herein, both singly and in combination.

In certain embodiments, the present invention provides a compound of formula XXXV-a, XXXV-b, or XXXV-c, wherein R$^z$ is hydrogen, thereby forming a compound of one of formulae XXXVIII-a, XXXVIII-b, or XXXVIII-c:

XXXVIII-a

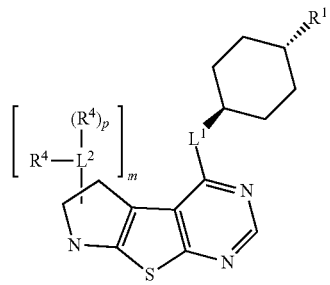

XXXVIII-b

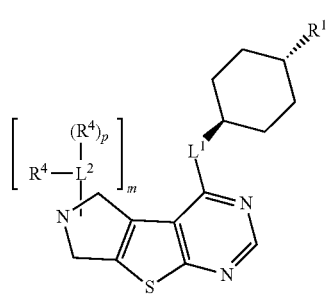

XXXVIII-c

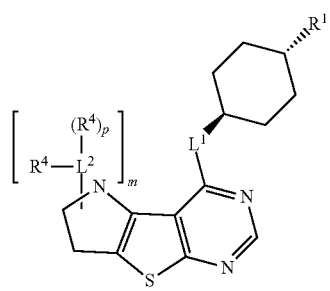

or a pharmaceutically acceptable salt thereof, wherein each of L$^1$, L$^2$, R$^1$, R$^4$, m, and p is as defined above and described in embodiments herein, both singly and in combination.

In certain embodiments, the present invention provides a compound of formula I, wherein W is N, and R$^z$ is hydrogen, thereby forming a compound of formula I-a:

I-a

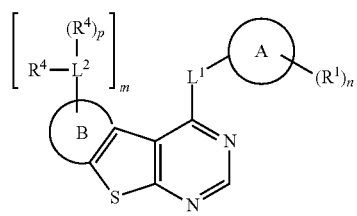

or a pharmaceutically acceptable salt thereof, wherein each of Ring A, Ring B, L$^1$, L$^2$, W, R$^z$, R$^1$, R$^4$, m, n, and p is as defined above and described in embodiments herein, both singly and in combination.

Exemplary compounds of the invention are set forth in Table 1, below.

TABLE 1

Exemplary Compounds

| Compound | Structure |
|---|---|
| I-1 | 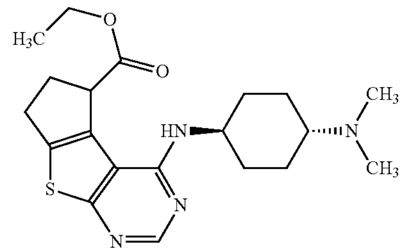 [SMILES: CCOC(=O)C1CCc2sc3ncnc(N[C@H]4CC[C@H](N(C)C)CC4)c3c21] |
| I-2 | 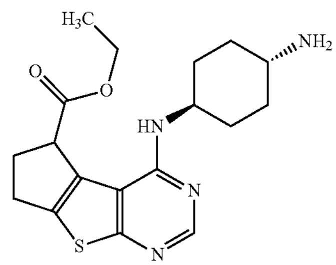 [SMILES: CCOC(=O)C1CCc2sc3ncnc(N[C@H]4CC[C@H](N)CC4)c3c21] |
| I-3 | 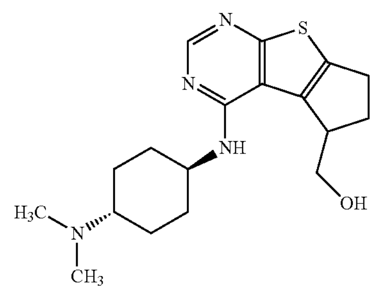 [SMILES: CN(C)[C@H]1CC[C@H](Nc2ncnc3sc4c(c23)C(CO)CC4)CC1] |
| I-4 | 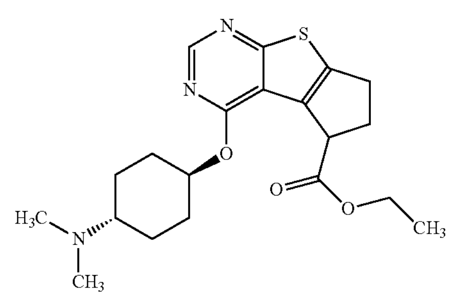 [SMILES: CCOC(=O)C1CCc2sc3ncnc(O[C@H]4CC[C@H](N(C)C)CC4)c3c21] |
| I-5 | 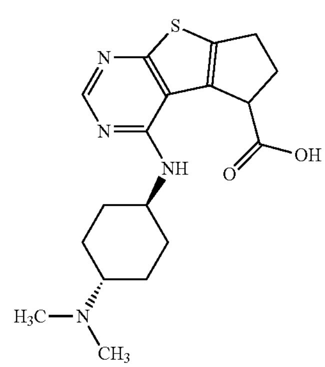 [SMILES: CN(C)[C@H]1CC[C@H](Nc2ncnc3sc4c(c23)C(C(=O)O)CC4)CC1] |

TABLE 1-continued

Exemplary Compounds

| Compound | Structure |
|---|---|
| I-6 | (structure) |
| I-7 | (structure) |
| I-8 | (structure) |
| I-9 | (structure) |
| I-10 | (structure) |
| I-11 | (structure) |
| I-12 | (structure) |
| I-13 | (structure) |

TABLE 1-continued

Exemplary Compounds

| Compound | Structure |
|---|---|
| I-14 | |
| I-15 | |
| I-16 | |
| I-17 | |
| I-18 | 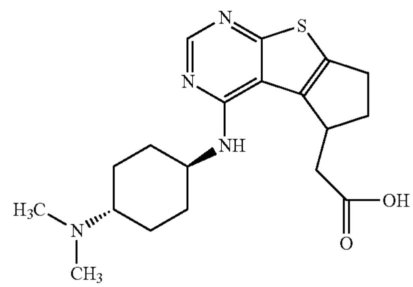 [SMILES: CN(C)[C@H]1CC[C@H](Nc2ncnc3sc4c(c23)C(CC(=O)O)CC4)CC1] |
| I-19 | 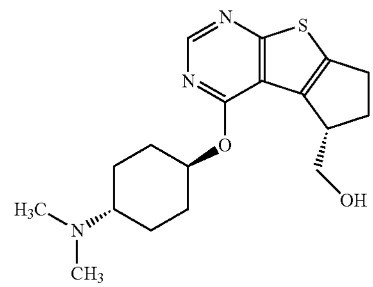 [SMILES: CN(C)[C@H]1CC[C@H](Oc2ncnc3sc4c(c23)[C@@H](CO)CC4)CC1] |
| I-20 | 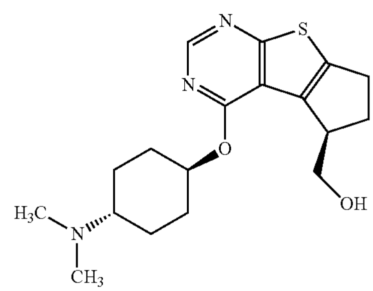 [SMILES: CN(C)[C@H]1CC[C@H](Oc2ncnc3sc4c(c23)[C@H](CO)CC4)CC1] |
| I-21 | 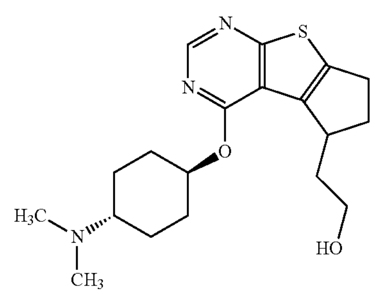 [SMILES: CN(C)[C@H]1CC[C@H](Oc2ncnc3sc4c(c23)C(CCO)CC4)CC1] |
| I-22 | 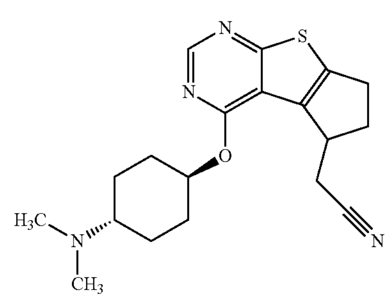 [SMILES: CN(C)[C@H]1CC[C@H](Oc2ncnc3sc4c(c23)C(CC#N)CC4)CC1] |

TABLE 1-continued

Exemplary Compounds

| Compound | Structure |
|---|---|
| I-23 | 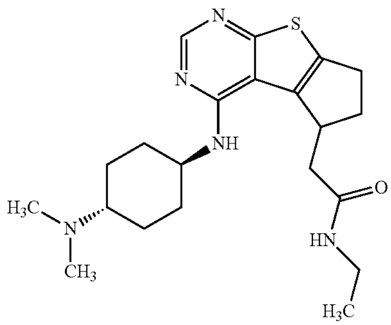 [SMILES: CCNC(=O)CC1CCc2sc3ncnc(N[C@H]4CC[C@H](N(C)C)CC4)c3c21] |
| I-24 | 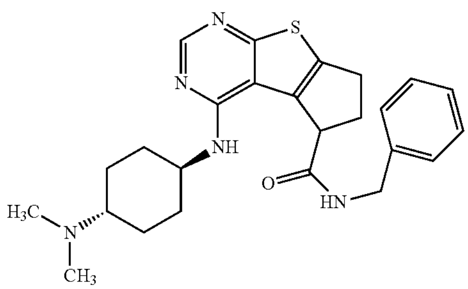 [SMILES: CN(C)[C@H]1CC[C@H](Nc2ncnc3sc4c(c23)C(C(=O)NCc2ccccc2)CC4)CC1] |
| I-25 | 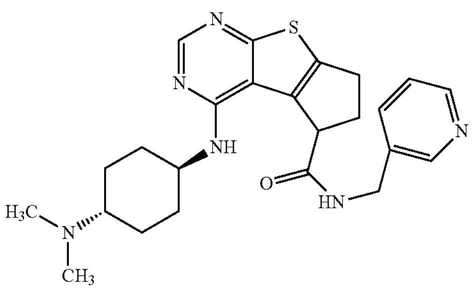 [SMILES: CN(C)[C@H]1CC[C@H](Nc2ncnc3sc4c(c23)C(C(=O)NCc2cccnc2)CC4)CC1] |
| I-26 | 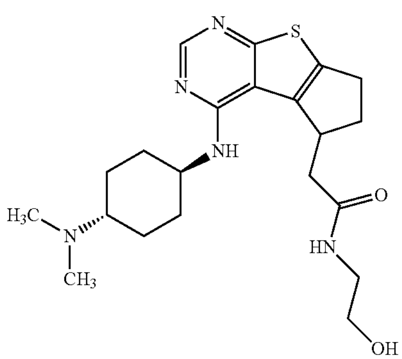 [SMILES: CN(C)[C@H]1CC[C@H](Nc2ncnc3sc4c(c23)C(CC(=O)NCCO)CC4)CC1] |
| I-27 | 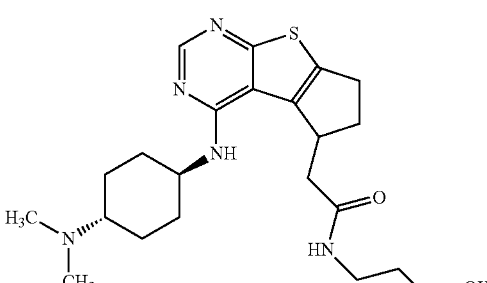 |
| I-28 | |
| I-29 | |
| I-30 | |
| I-31 | |
| I-32 | |

TABLE 1-continued

Exemplary Compounds

| Compound | Structure |
|---|---|
| I-33 | 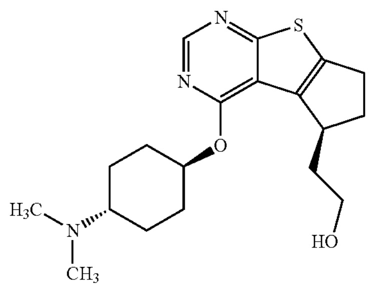 [SMILES: CN(C)[C@H]1CC[C@H](Oc2ncnc3sc4c(c23)[C@H](CCO)CC4)CC1] |
| I-34 | 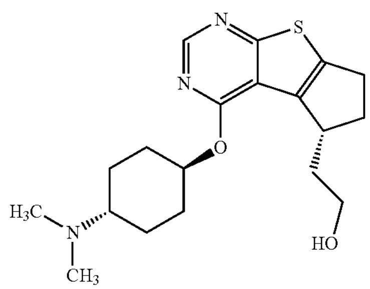 [SMILES: CN(C)[C@H]1CC[C@H](Oc2ncnc3sc4c(c23)[C@@H](CCO)CC4)CC1] |
| I-35 | 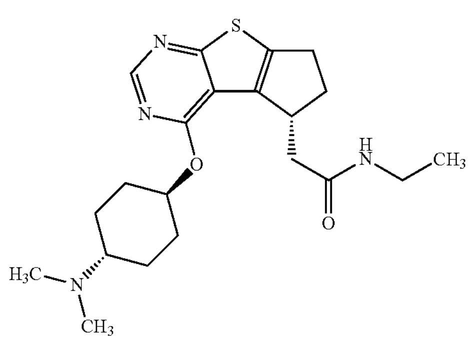 [SMILES: CCNC(=O)C[C@H]1CCc2sc3ncnc(O[C@H]4CC[C@H](N(C)C)CC4)c3c21] |
| I-36 | 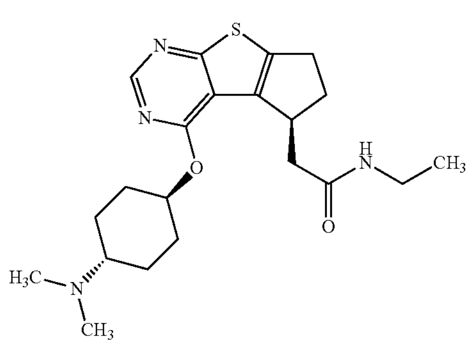 [SMILES: CCNC(=O)C[C@@H]1CCc2sc3ncnc(O[C@H]4CC[C@H](N(C)C)CC4)c3c21] |
| I-37 | |
| I-38 | |
| I-39 | |
| I-40 | |

TABLE 1-continued
Exemplary Compounds
| Compound | Structure |
|---|---|
| I-41 | 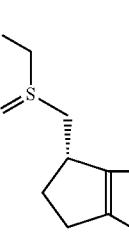 |
| I-42 | 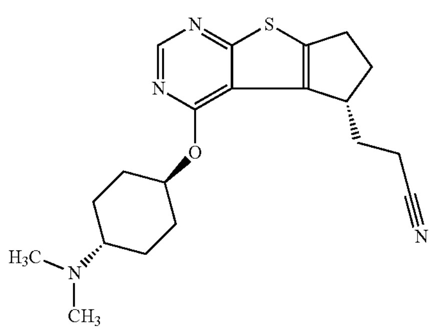 [SMILES: CN(C)[C@H]1CC[C@H](Oc2ncnc3sc4c(c23)[C@@H](CCC#N)CC4)CC1] |
| I-43 | 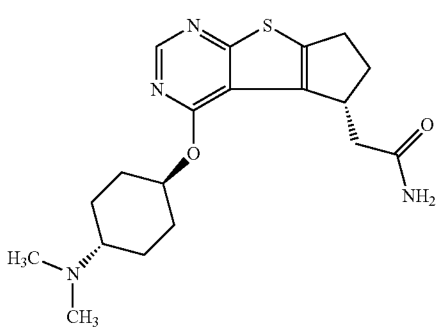 [SMILES: CN(C)[C@H]1CC[C@H](Oc2ncnc3sc4c(c23)[C@@H](CC(N)=O)CC4)CC1] |
| I-44 | 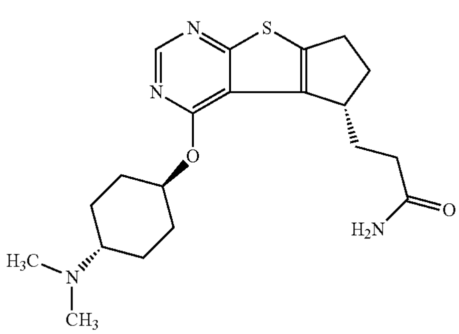 [SMILES: CN(C)[C@H]1CC[C@H](Oc2ncnc3sc4c(c23)[C@@H](CCC(N)=O)CC4)CC1] |
| I-45 | 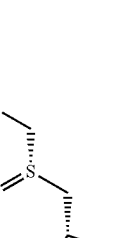 |
| I-46 | 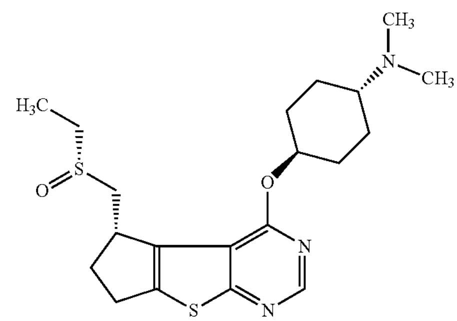 [SMILES: CCS(=O)C[C@H]1CCc2sc3ncnc(O[C@H]4CC[C@H](N(C)C)CC4)c3c21] |
| I-47 | 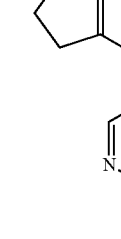 |
| I-48 | 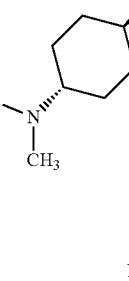 |
| I-49 | 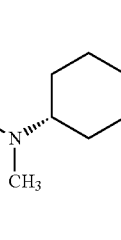 |

TABLE 1-continued
Exemplary Compounds
| Compound | Structure |
|---|---|
| I-50 | 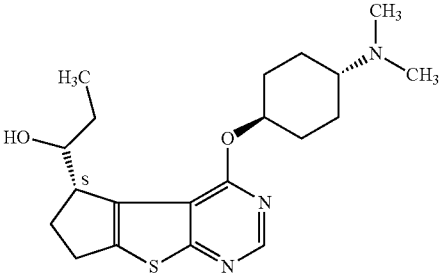 |
| I-51 | 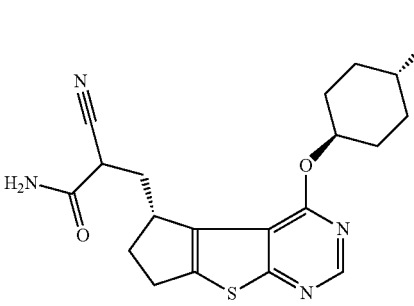 |
| I-52 | 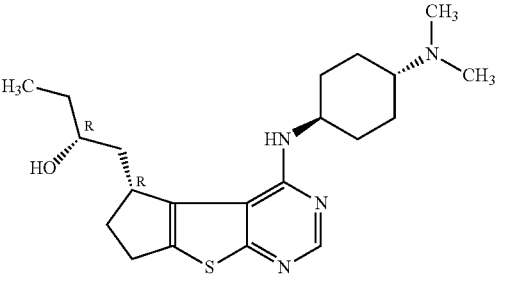 |
| I-53 | 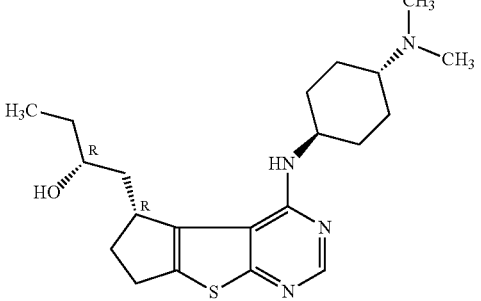 |
| I-54 | 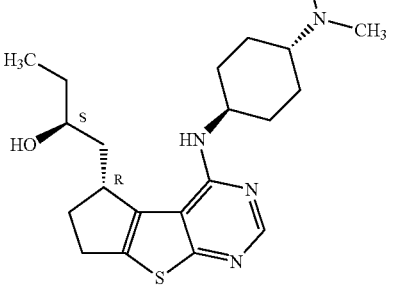 |
| I-55 | 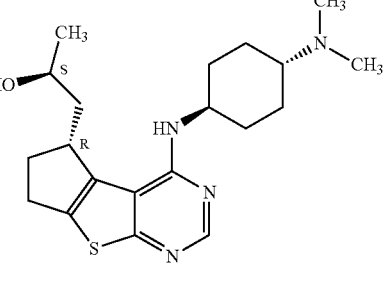 |
| I-56 | 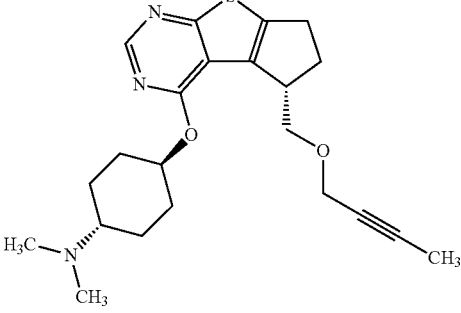 |
| I-57 | 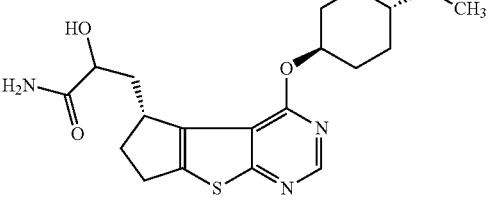 |
| I-58 | 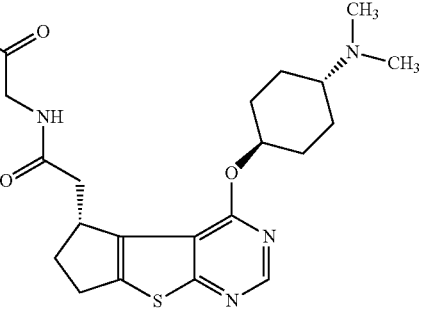 |

TABLE 1-continued
Exemplary Compounds
| Compound | Structure |
|---|---|
| I-59 | 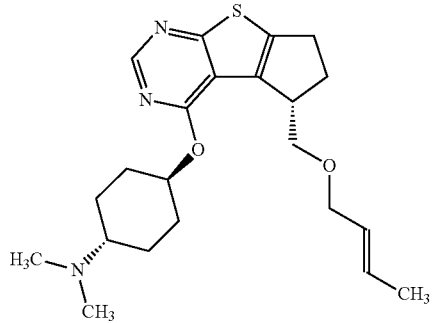 [SMILES: C/C=C/COC[C@H]1CCc2sc3ncnc(O[C@H]4CC[C@H](N(C)C)CC4)c3c21] |
| I-60 | 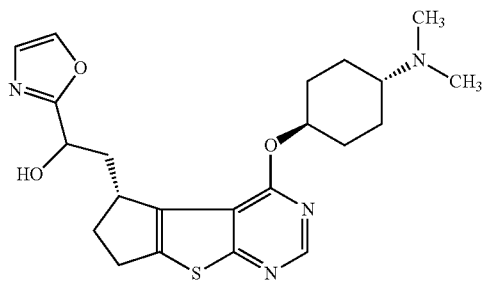 [SMILES: CN(C)[C@H]1CC[C@H](Oc2ncnc3sc4c(c23)[C@@H](CC(O)c2ncco2)CC4)CC1] |
| I-61 | 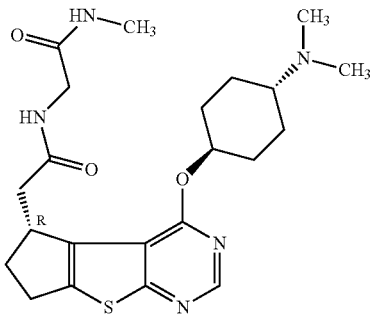 |
| I-62 | 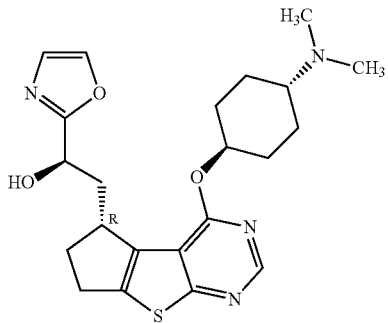 |
| I-63 | 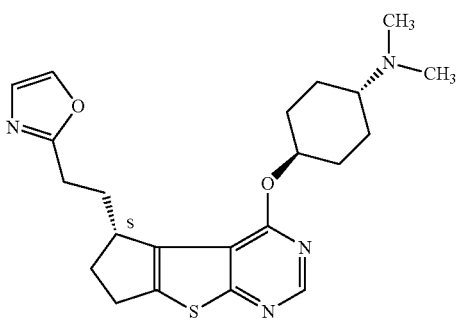 |
| I-64 | 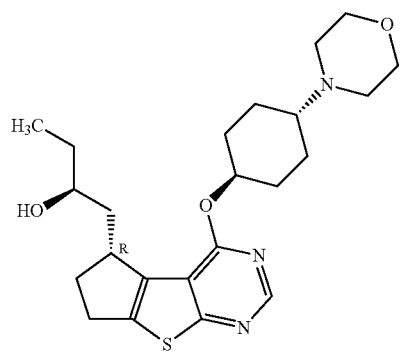 |
| I-65 | 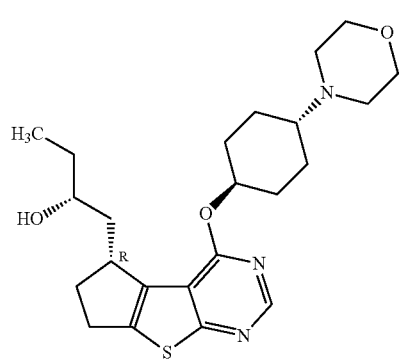 |
| I-66 | 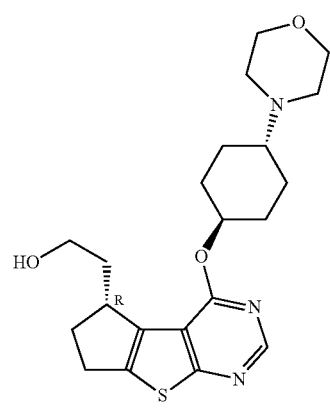 |

TABLE 1-continued

Exemplary Compounds

| Compound | Structure |
|---|---|
| I-67 | 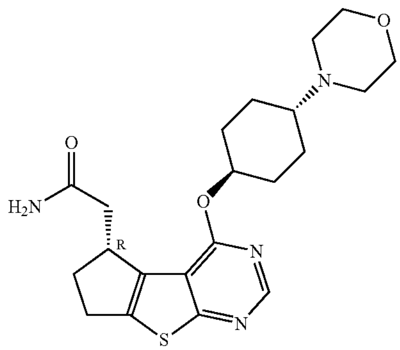 |
| I-68 | 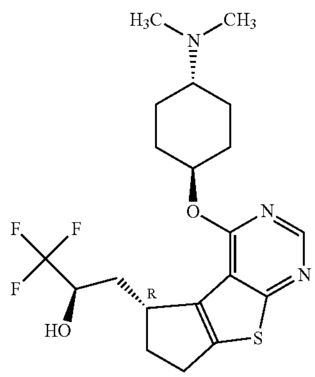 |
| I-69 | 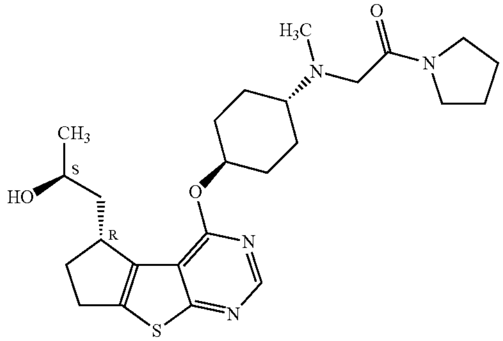 |
| I-70 | 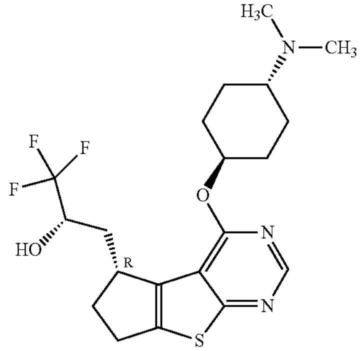 |
| I-71 | |
| I-72 | |
| I-73 | |
| I-74 | |

TABLE 1-continued
Exemplary Compounds
| Compound | Structure |
|---|---|
| I-75 | 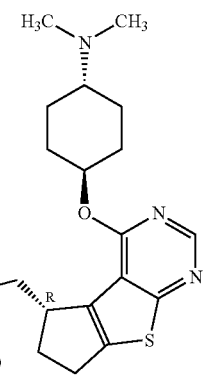 |
| I-76 | 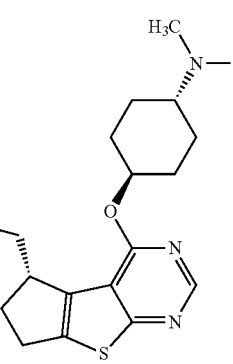 |
| I-77 | 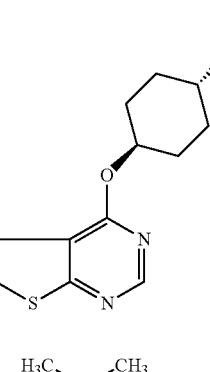 |
| I-78 | 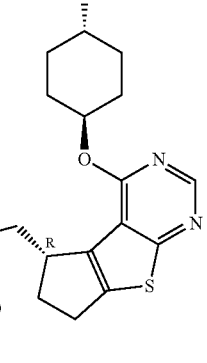 |
| I-79 | 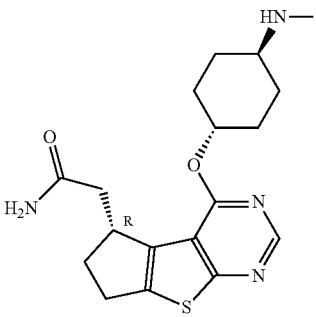 |
| I-80 | 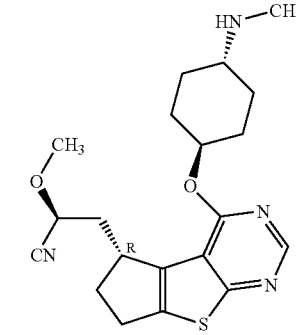 |
| I-81 | 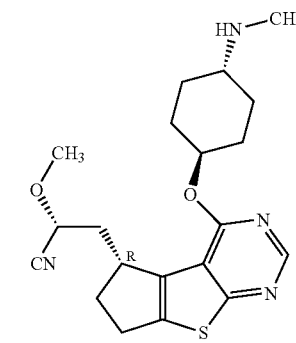 |
| I-82 | 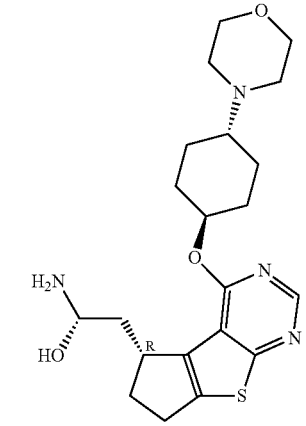 |

TABLE 1-continued

Exemplary Compounds

| Compound | Structure |
|---|---|
| I-83 | |
| I-84 | |
| I-85 | |
| I-86 | 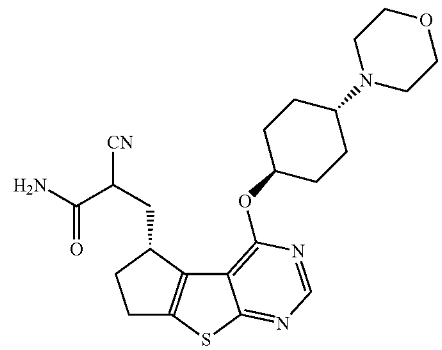 [SMILES: N#CC(C[C@H]1CCc2sc3ncnc(O[C@H]4CC[C@H](N5CCOCC5)CC4)c3c21)C(N)=O] |
| I-87 | 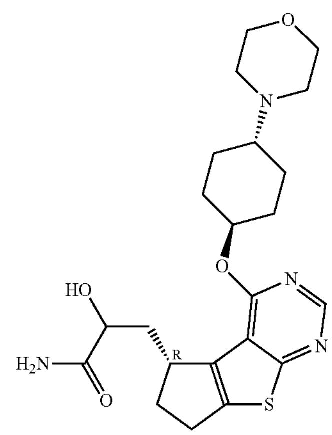 |
| I-88 | 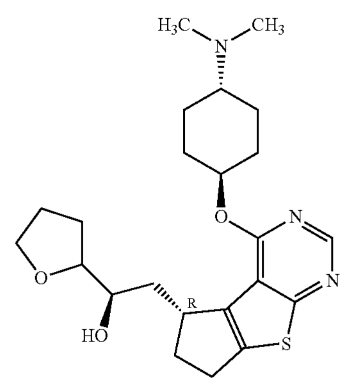 |
| I-89 | 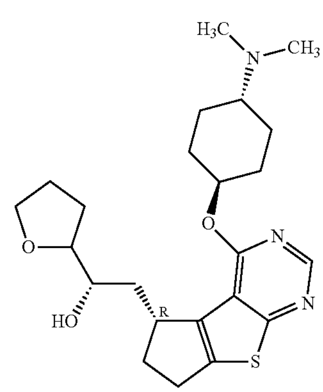 |

TABLE 1-continued
Exemplary Compounds
| Compound | Structure |
|---|---|
| I-90 | 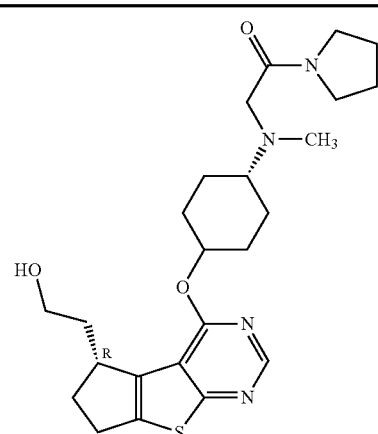 |
| I-91 | 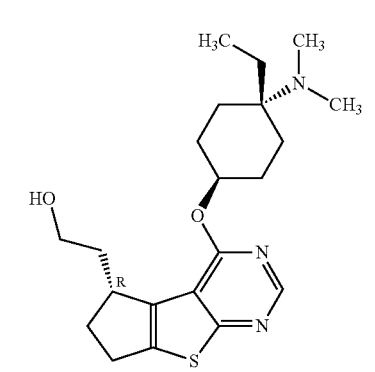 |
| I-92 | 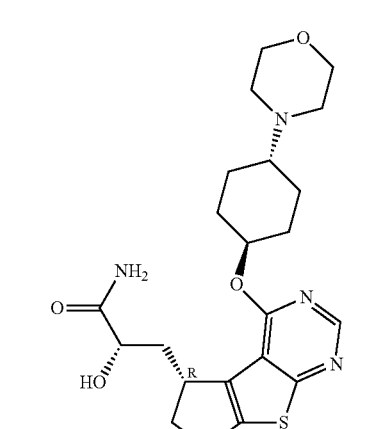 |
| I-93 | 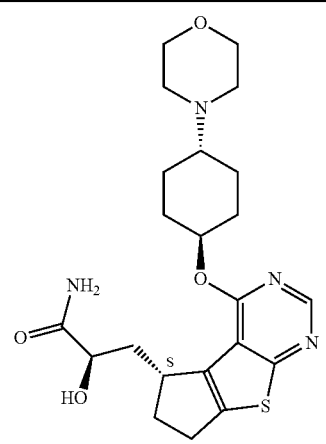 |
| I-94 | 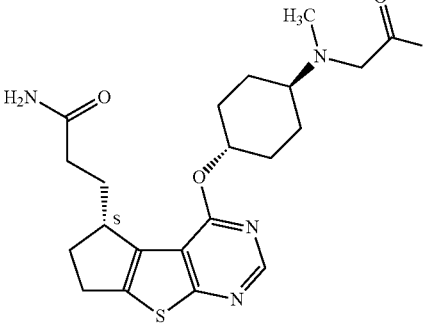 |
| I-95 | 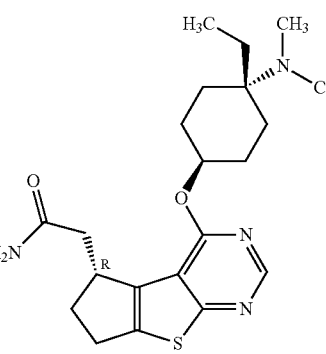 |
| I-96 | 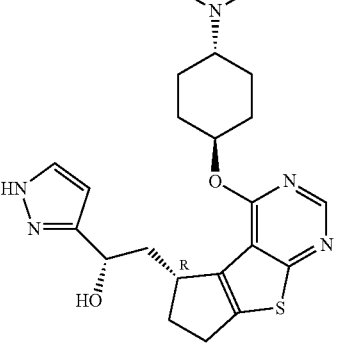 |

TABLE 1-continued
Exemplary Compounds
| Compound | Structure |
|---|---|
| I-97 | 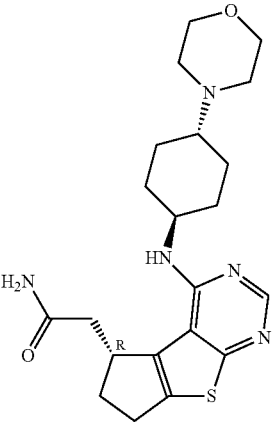 |
| I-98 | 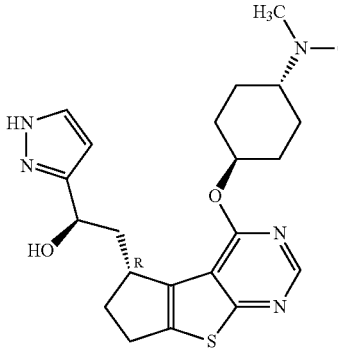 |
| I-99 | 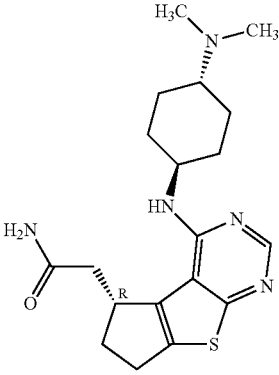 |
| I-100 | 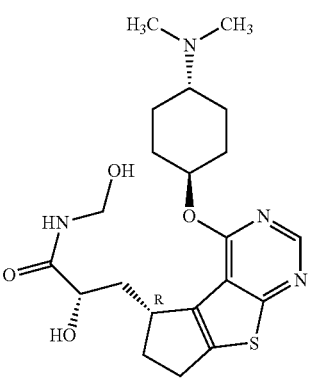 |
| I-101 | 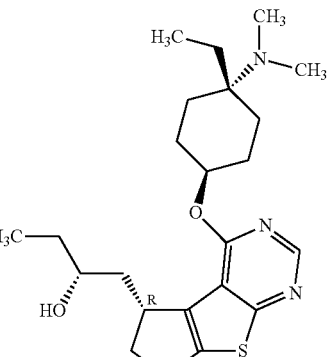 |
| I-102 | 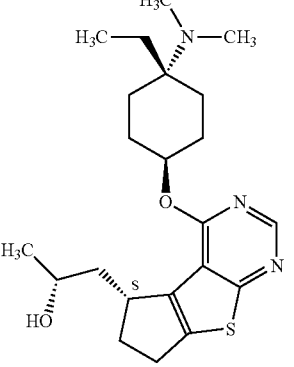 |
| I-103 | 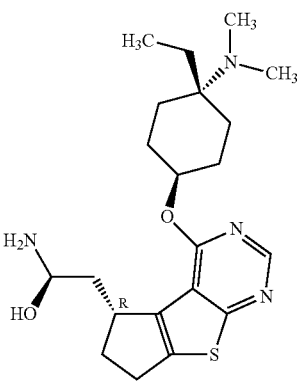 |
| I-104 | 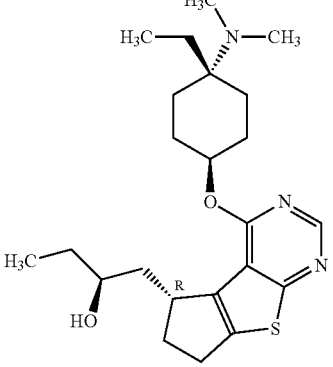 |

TABLE 1-continued

Exemplary Compounds

| Compound | Structure |
|---|---|
| I-105 | 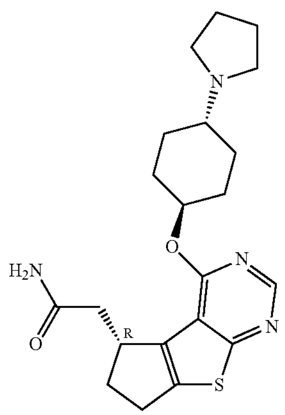 |
| I-106 | 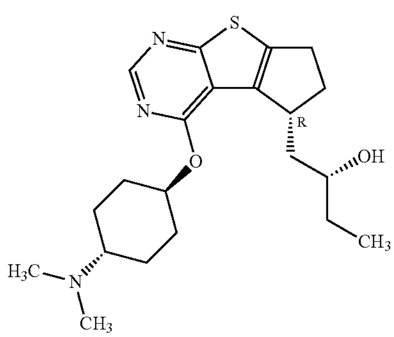 |
| I-107 | 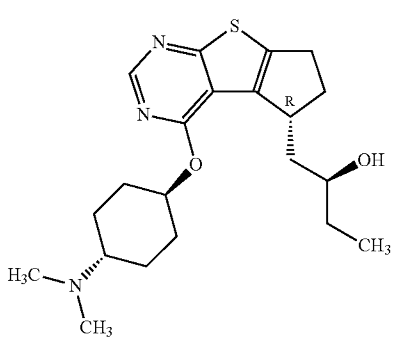 |
| I-108 | 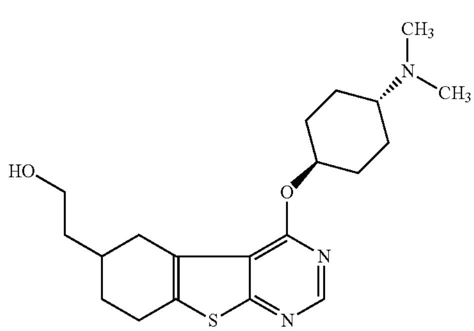 [SMILES: CN(C)[C@H]1CC[C@H](Oc2ncnc3sc4c(c23)CC(CCO)CC4)CC1] |
| I-109 | |
| I-110 | |
| I-111 | |
| I-112 | |

TABLE 1-continued

Exemplary Compounds

| Compound | Structure |
|---|---|
| I-113 | 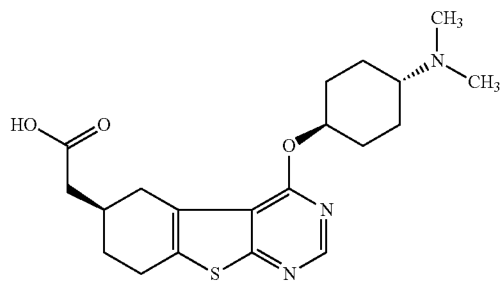 [SMILES: CN(C)[C@H]1CC[C@H](Oc2ncnc3sc4c(c23)C[C@H](CC(=O)O)CC4)CC1] |
| I-116 | 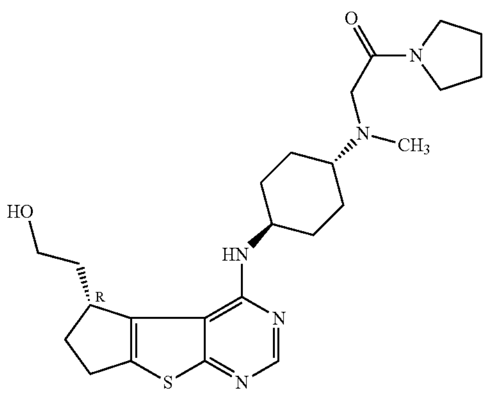 |
| I-117 | 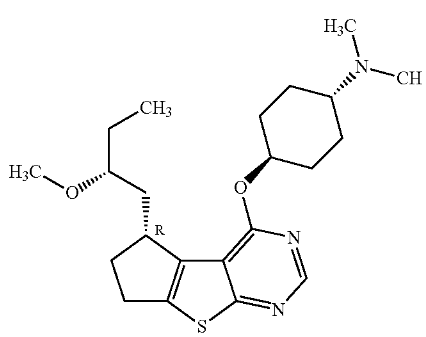 |
| I-118 | 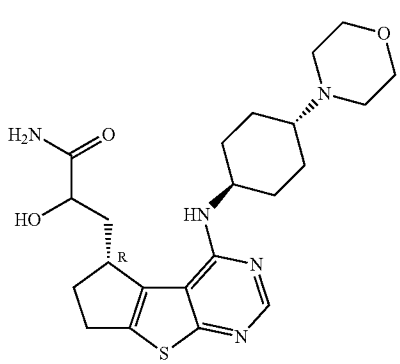 |
| I-119 | |
| I-120 | |
| I-121 | |
| I-122 | |

TABLE 1-continued

Exemplary Compounds

| Compound | Structure |
|---|---|
| I-123 | 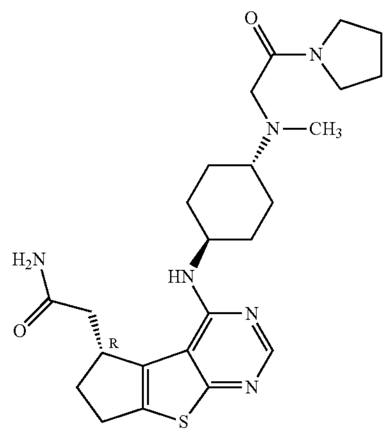 |
| I-124 | 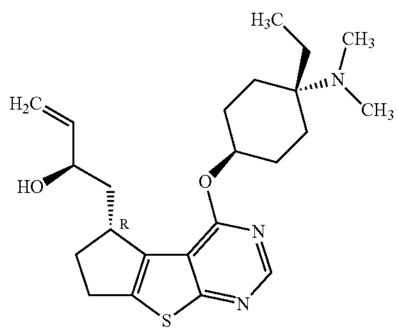 |
| I-125 | 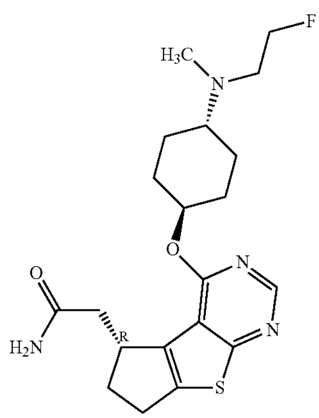 |
| I-126 | 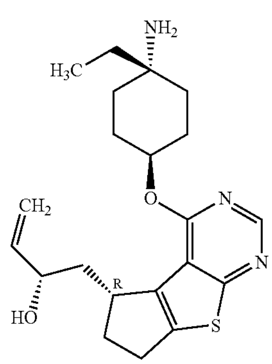 |
| I-127 | |
| I-128 | |
| I-129 | |
| I-130 | |

TABLE 1-continued
Exemplary Compounds
| Compound | Structure |
|---|---|
| I-131 | 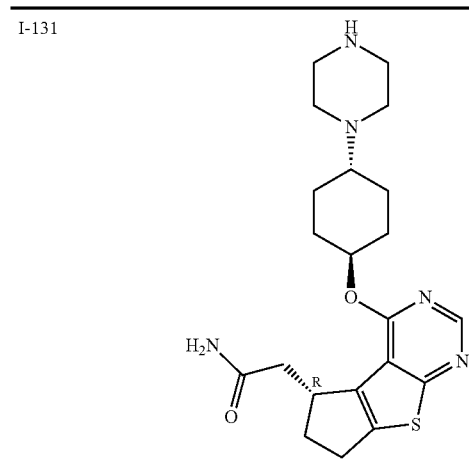 |
| I-132 | 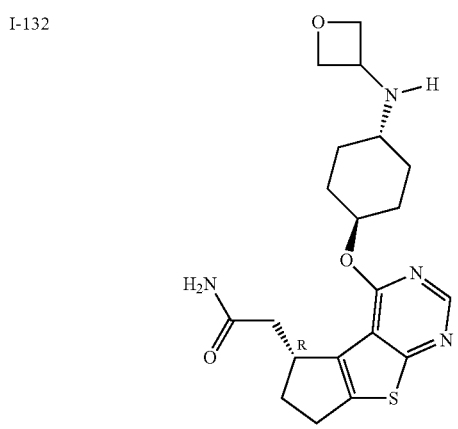 |
| I-133 | 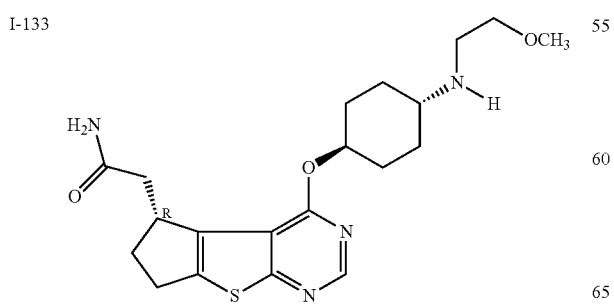 |
| I-134 | 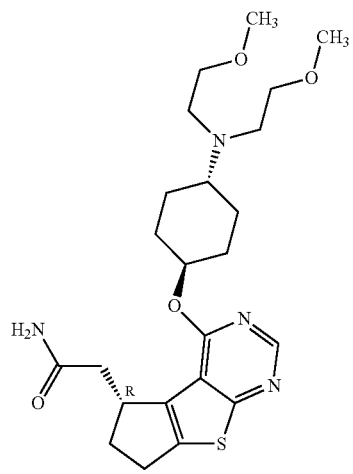 |
| I-135 | 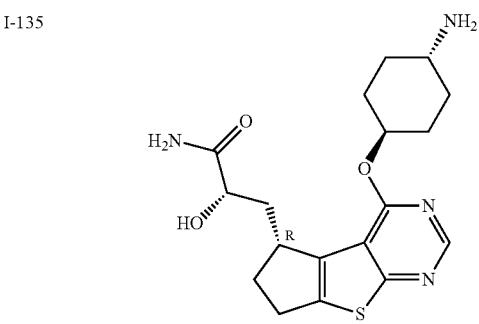 |
| I-136 | 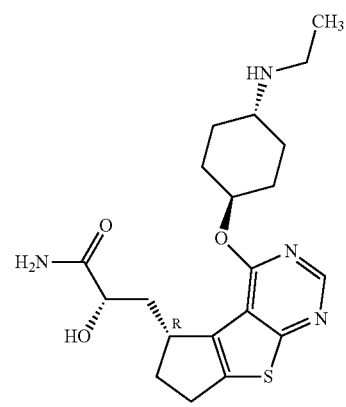 |

TABLE 1-continued

Exemplary Compounds

| Compound | Structure |
|---|---|
| I-137 | *(structure)* |
| I-138 | *(structure)* |
| I-139 | *(structure)* |
| I-140 | *(structure)* |
| I-141 | *(structure)* |
| I-142 | *(structure)* |
| I-143 | *(structure)* |
| I-144 | *(structure)* |

TABLE 1-continued
Exemplary Compounds
| Compound | Structure |
|---|---|
| I-145 | 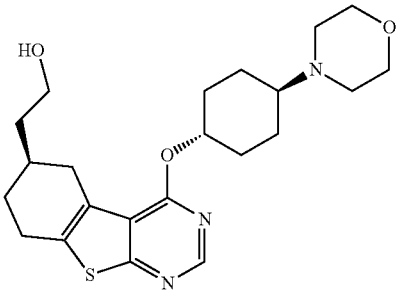 [SMILES: OCC[C@@H]1CCc2sc3ncnc(O[C@H]4CC[C@H](N5CCOCC5)CC4)c3c2C1] |
| I-146 | 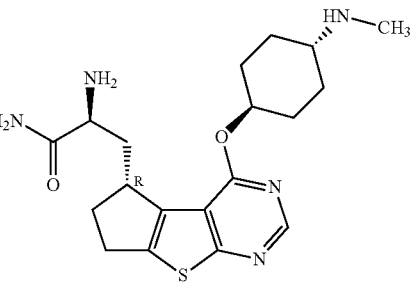 |
| I-147 | 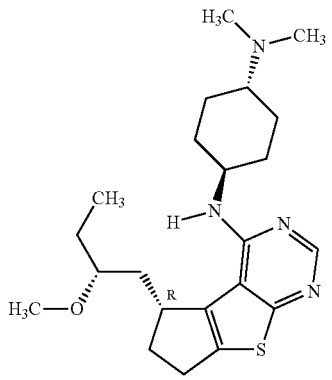 |
| I-148 | 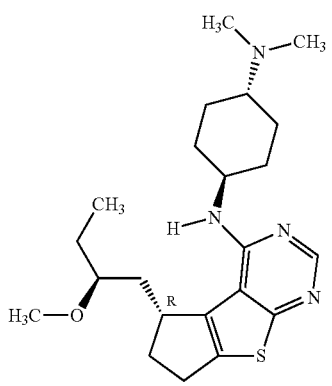 |
| I-149 | 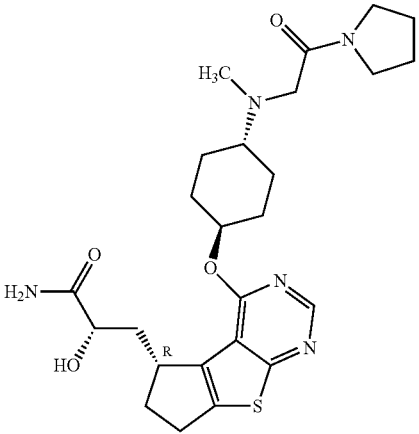 |
| I-150 | 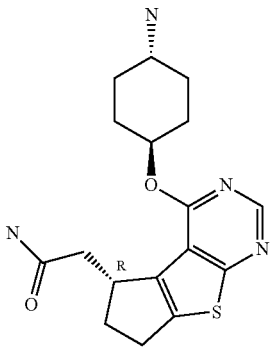 |
| I-151 | 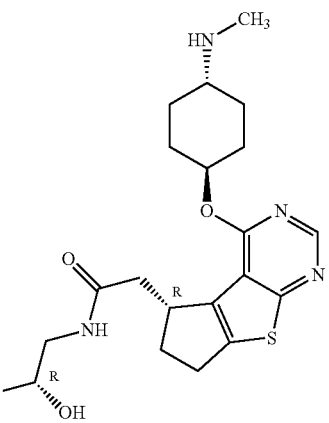 |
| I-152 | 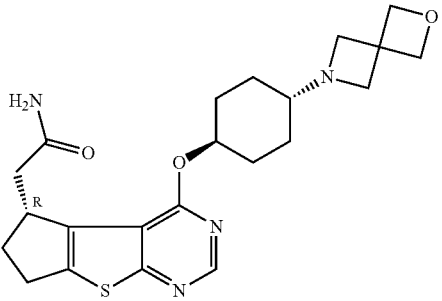 |

TABLE 1-continued

Exemplary Compounds

| Compound | Structure |
|---|---|
| I-153 | 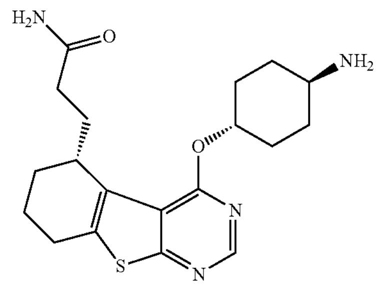 [SMILES: NC(=O)CC[C@H]1CCCc2sc3ncnc(O[C@H]4CC[C@H](N)CC4)c3c21] |
| I-154 | 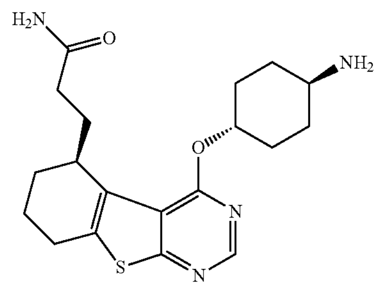 [SMILES: NC(=O)CC[C@@H]1CCCc2sc3ncnc(O[C@H]4CC[C@H](N)CC4)c3c21] |
| I-155 | 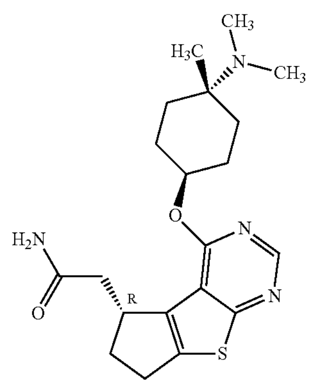 |
| I-156 | 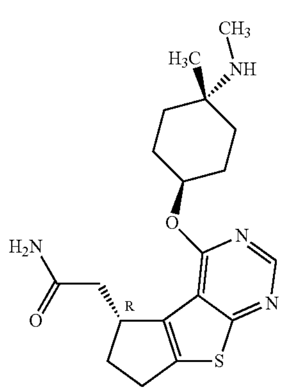 |
| I-157 | |
| I-158 | |
| I-159 | |

TABLE 1-continued

Exemplary Compounds

| Compound | Structure |
|---|---|
| I-160 | (structure) |
| I-161 | (structure) |
| I-162 | (structure) |
| I-163 | (structure) |
| I-167 | (structure) |
| I-168 | (structure) |
| I-169 | (structure) |
| I-170 | (structure) |
| I-171 | (structure) |

TABLE 1-continued

Exemplary Compounds

| Compound | Structure |
|---|---|
| I-172 | 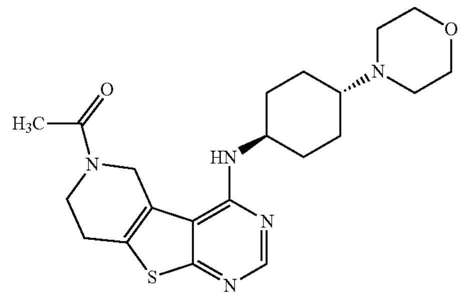 [SMILES: CC(=O)N1CCc2sc3ncnc(N[C@H]4CC[C@H](N5CCOCC5)CC4)c3c2C1] |
| I-173 | 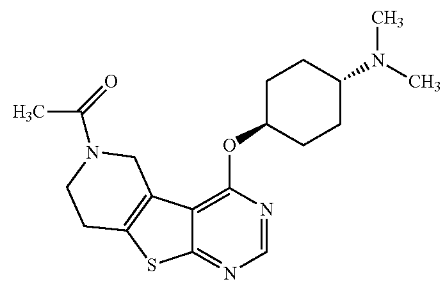 [SMILES: CC(=O)N1CCc2sc3ncnc(O[C@H]4CC[C@H](N(C)C)CC4)c3c2C1] |
| I-174 | 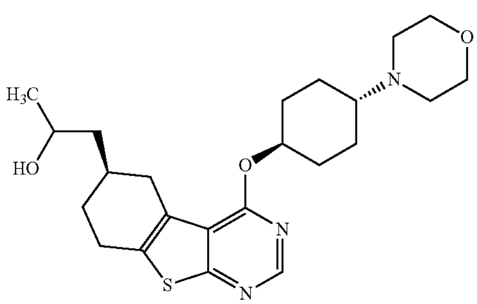 [SMILES: CC(O)C[C@@H]1CCc2sc3ncnc(O[C@H]4CC[C@H](N5CCOCC5)CC4)c3c2C1] |
| I-175 | 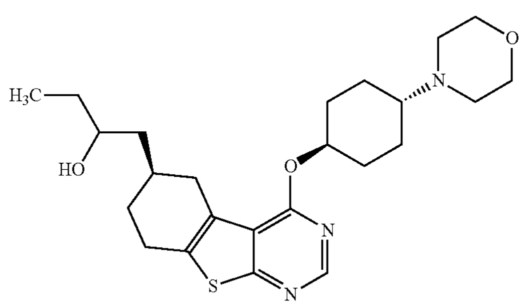 [SMILES: CCC(O)C[C@@H]1CCc2sc3ncnc(O[C@H]4CC[C@H](N5CCOCC5)CC4)c3c2C1] |
| I-176 | 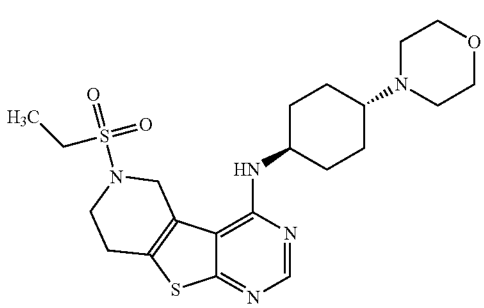 [SMILES: CCS(=O)(=O)N1CCc2sc3ncnc(N[C@H]4CC[C@H](N5CCOCC5)CC4)c3c2C1] |
| I-177 | 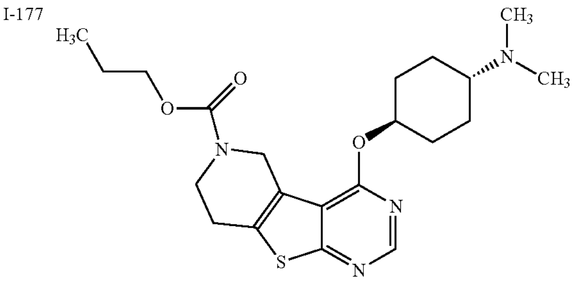 |
| I-178 | 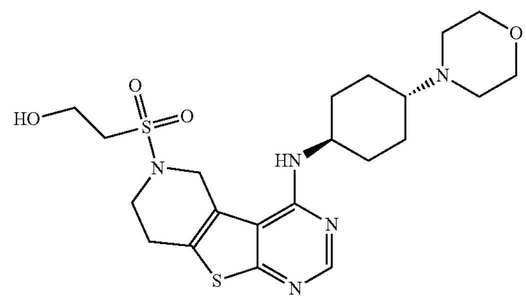 [SMILES: O=S(=O)(CCO)N1CCc2sc3ncnc(N[C@H]4CC[C@H](N5CCOCC5)CC4)c3c2C1] |
| I-179 | 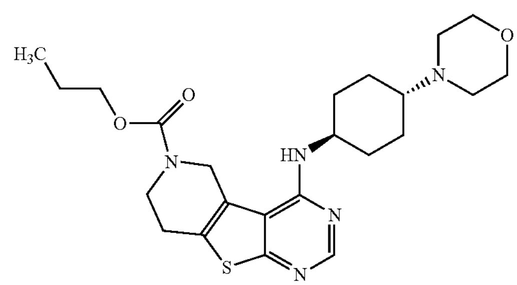 [SMILES: CCCOC(=O)N1CCc2sc3ncnc(N[C@H]4CC[C@H](N5CCOCC5)CC4)c3c2C1] |
| I-181 | 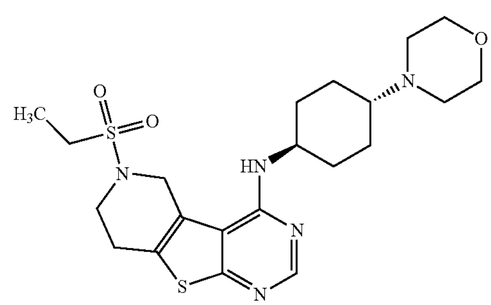 [SMILES: CCS(=O)(=O)N1CCc2sc3ncnc(N[C@H]4CC[C@H](N5CCOCC5)CC4)c3c2C1] |
| I-182 | 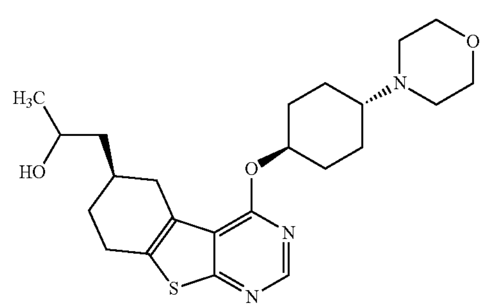 [SMILES: CC(O)C[C@@H]1CCc2sc3ncnc(O[C@H]4CC[C@H](N5CCOCC5)CC4)c3c2C1] |

TABLE 1-continued

Exemplary Compounds

| Compound | Structure |
|---|---|
| I-183 | 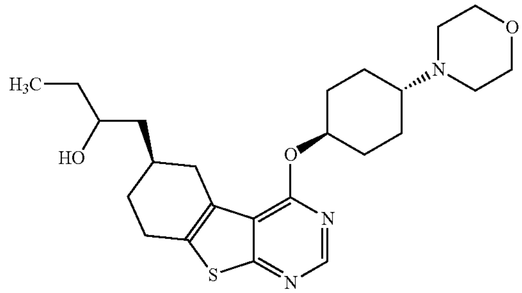 [SMILES: CCC(O)C[C@@H]1CCc2sc3ncnc(O[C@H]4CC[C@H](N5CCOCC5)CC4)c3c2C1] |
| I-184 | 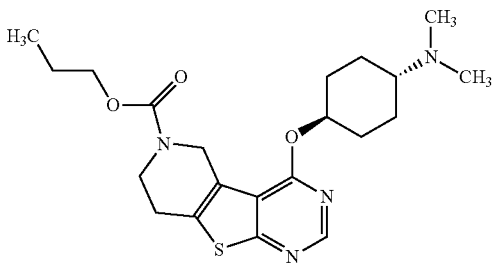 [SMILES: CCCOC(=O)N1CCc2sc3ncnc(O[C@H]4CC[C@H](N(C)C)CC4)c3c2C1] |
| I-185 | 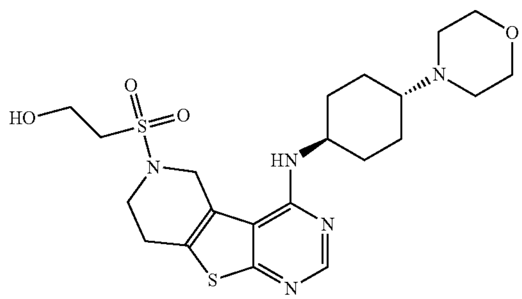 [SMILES: O=S(=O)(CCO)N1CCc2sc3ncnc(N[C@H]4CC[C@H](N5CCOCC5)CC4)c3c2C1] |
| I-186 | 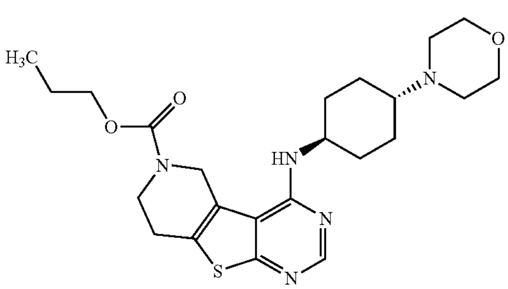 [SMILES: CCCOC(=O)N1CCc2sc3ncnc(N[C@H]4CC[C@H](N5CCOCC5)CC4)c3c2C1] |
| I-187 | 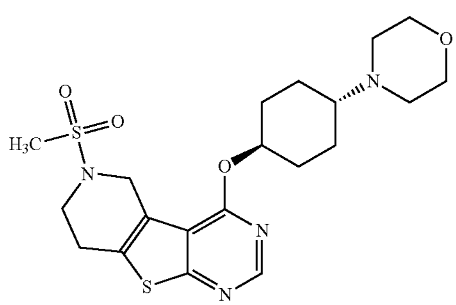 [SMILES: CS(=O)(=O)N1CCc2sc3ncnc(O[C@H]4CC[C@H](N5CCOCC5)CC4)c3c2C1] |
| I-188 | |
| I-190 | |
| I-192 | |
| I-193 | |

TABLE 1-continued

Exemplary Compounds

| Compound | Structure |
|---|---|
| I-194 | 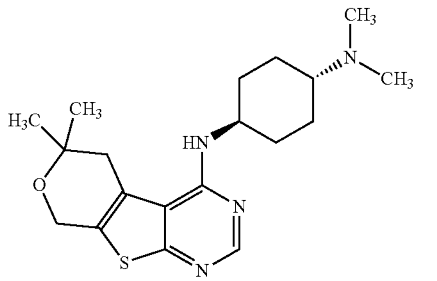 |
| I-195 | 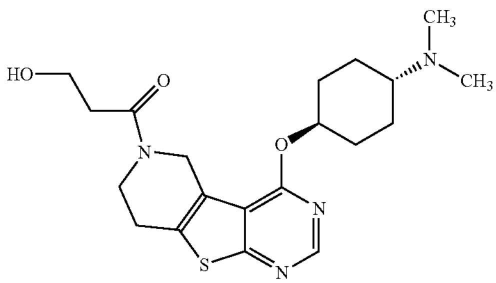 [SMILES: CN(C)[C@H]1CC[C@H](Oc2ncnc3sc4c(c23)CN(C(=O)CCO)CC4)CC1] |
| I-196 | 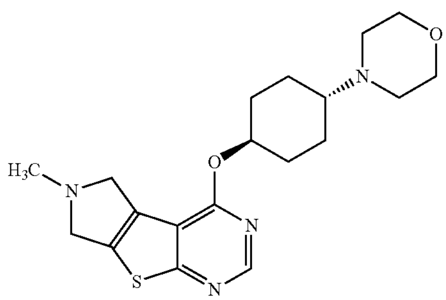 [SMILES: CN1Cc2sc3ncnc(O[C@H]4CC[C@H](N5CCOCC5)CC4)c3c2C1] |
| I-197 | 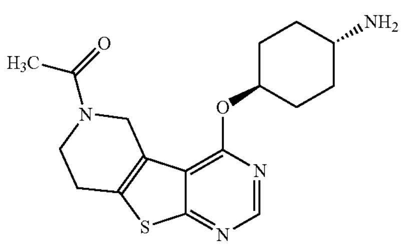 [SMILES: CC(=O)N1CCc2sc3ncnc(O[C@H]4CC[C@H](N)CC4)c3c2C1] |
| I-198 | 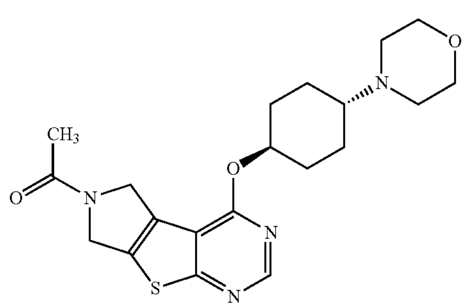 [SMILES: CC(=O)N1Cc2sc3ncnc(O[C@H]4CC[C@H](N5CCOCC5)CC4)c3c2C1] |
| I-199 | |
| I-200 | |
| I-201 | |
| I-202 | |
| I-203 | |

TABLE 1-continued

Exemplary Compounds

| Compound | Structure |
|---|---|
| I-204 | 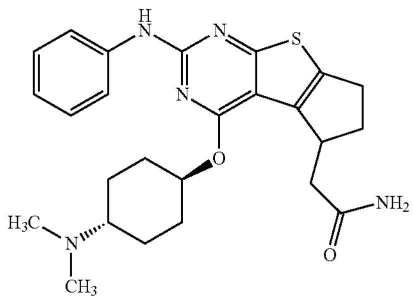 [SMILES: CN(C)[C@H]1CC[C@H](Oc2nc(Nc3ccccc3)nc3sc4c(c23)C(CC(N)=O)CC4)CC1] |
| I-205 | 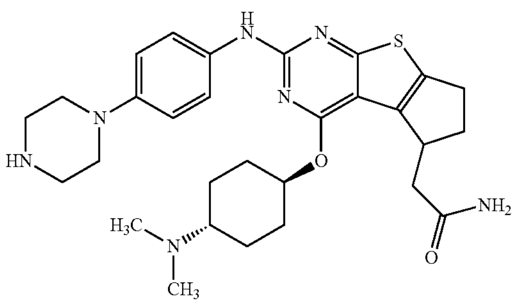 [SMILES: CN(C)[C@H]1CC[C@H](Oc2nc(Nc3ccc(N4CCNCC4)cc3)nc3sc4c(c23)C(CC(N)=O)CC4)CC1] |
| I-206 | 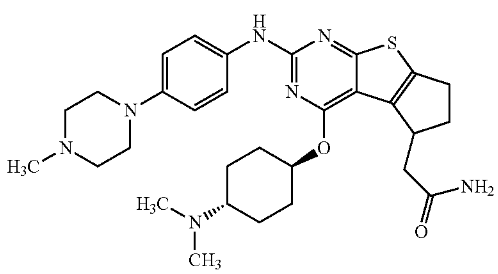 |
| I-207 | 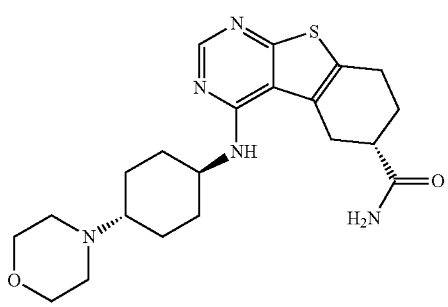 [SMILES: NC(=O)[C@H]1CCc2sc3ncnc(N[C@H]4CC[C@H](N5CCOCC5)CC4)c3c2C1] |
| I-208 | 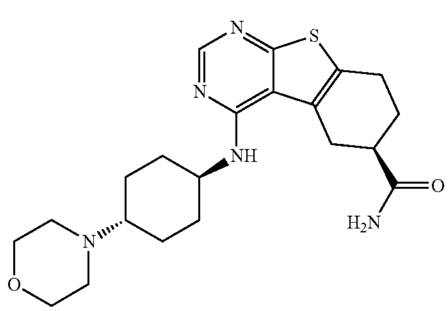 [SMILES: NC(=O)[C@@H]1CCc2sc3ncnc(N[C@H]4CC[C@H](N5CCOCC5)CC4)c3c2C1] |
| I-209 | |
| I-210 | |
| I-211 | |
| I-212 | |

TABLE 1-continued

Exemplary Compounds

| Compound | Structure |
|---|---|
| I-213 | 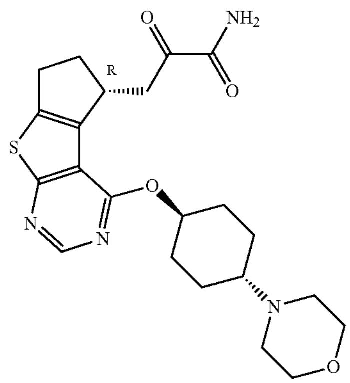 |
| I-214 | 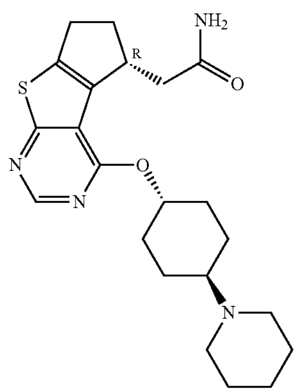 |
| I-215 | 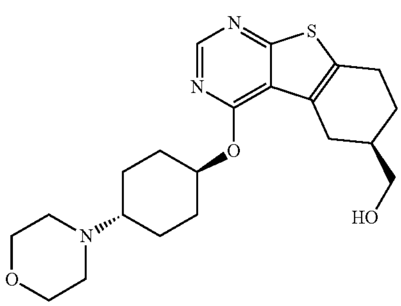 [SMILES: OC[C@@H]1CCc2sc3ncnc(O[C@H]4CC[C@H](N5CCOCC5)CC4)c3c2C1] |
| I-216 | 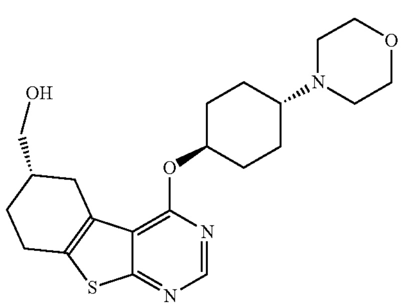 [SMILES: OC[C@H]1CCc2sc3ncnc(O[C@H]4CC[C@H](N5CCOCC5)CC4)c3c2C1] |
| I-217 | 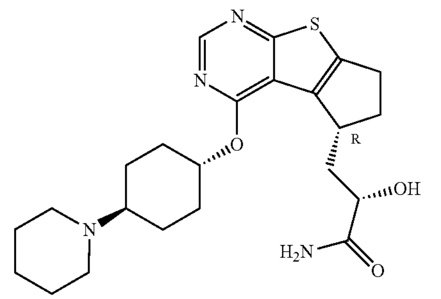 |
| I-218 | 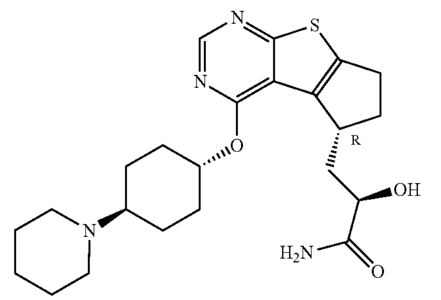 |
| I-219 | 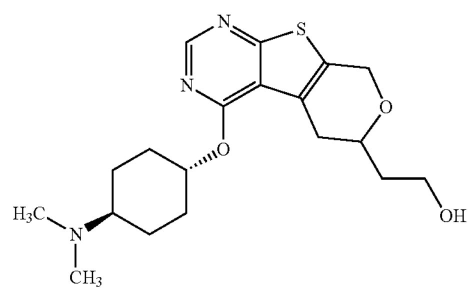 [SMILES: CN(C)[C@H]1CC[C@H](Oc2ncnc3sc4c(c23)CC(CCO)OC4)CC1] |
| I-220 | 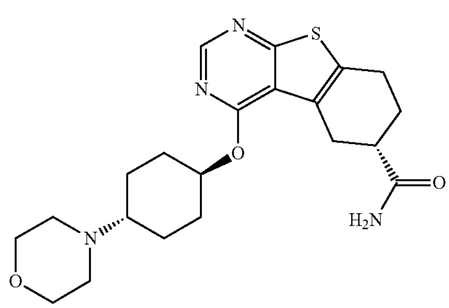 [SMILES: NC(=O)[C@H]1CCc2sc3ncnc(O[C@H]4CC[C@H](N5CCOCC5)CC4)c3c2C1] |
| I-221 | 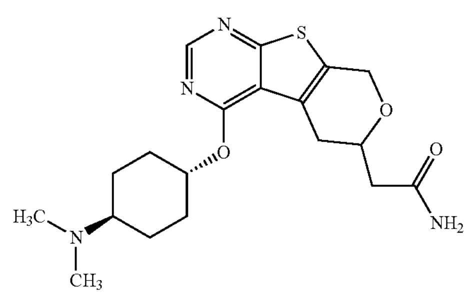 [SMILES: CN(C)[C@H]1CC[C@H](Oc2ncnc3sc4c(c23)CC(CC(N)=O)OC4)CC1] |

TABLE 1-continued

Exemplary Compounds

| Compound | Structure |
|---|---|
| I-222 | (structure) |
| I-224 | (structure) |
| I-226 | (structure) |
| I-227 | (structure) |
| I-228 | (structure) |
| I-229 | (structure) |
| I-230 | (structure) |
| I-231 | (structure) |

TABLE 1-continued

Exemplary Compounds

| Compound | Structure |
|---|---|
| I-232 | (structure) |
| I-233 | (structure) |
| I-234 | (structure) |
| I-235 | (structure) |
| I-236 | (structure) |
| I-237 | (structure) |
| I-238 | (structure) |
| I-240 | (structure) |
| I-241 | (structure) |
| I-242 | (structure) |

TABLE 1-continued
Exemplary Compounds
| Compound | Structure |
|---|---|
| I-242 | 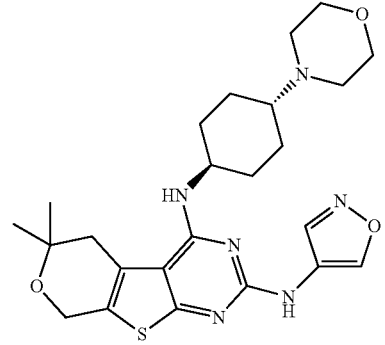 |
| I-243 | 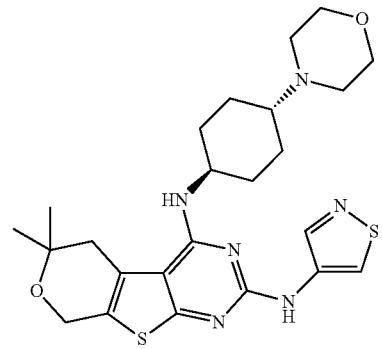 [SMILES: CC1(C)Cc2c(sc3nc(Nc4cnsc4)nc(N[C@H]4CC[C@H](N5CCOCC5)CC4)c23)CO1] |
| I-244 | 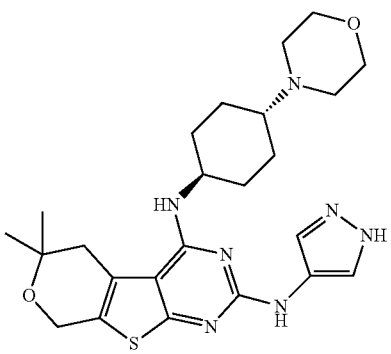 [SMILES: CC1(C)Cc2c(sc3nc(Nc4cn[nH]c4)nc(N[C@H]4CC[C@H](N5CCOCC5)CC4)c23)CO1] |
| I-245 | 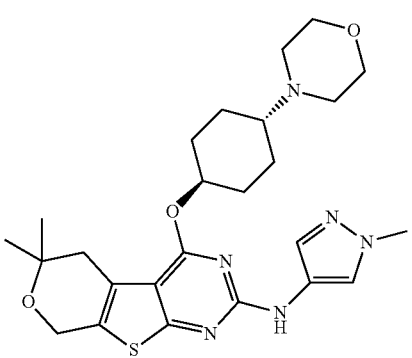 |
| I-246 | 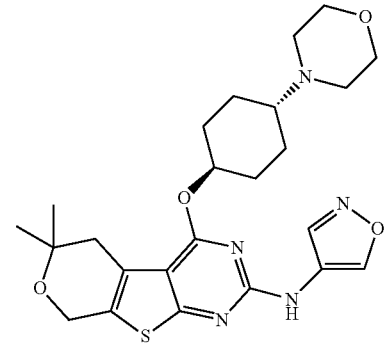 [SMILES: CC1(C)Cc2c(sc3nc(Nc4cnoc4)nc(O[C@H]4CC[C@H](N5CCOCC5)CC4)c23)CO1] |
| I-247 | 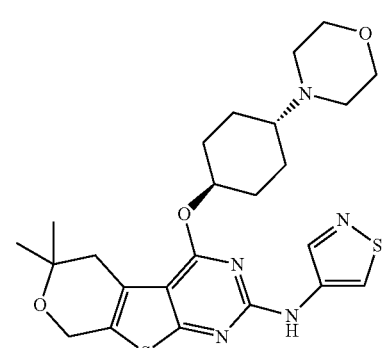 |
| I-248 | 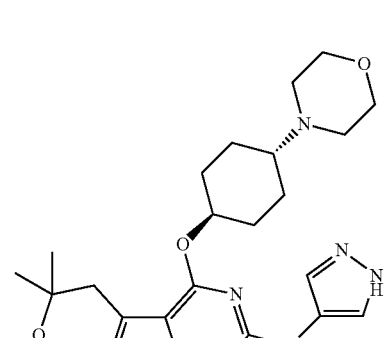 |
| I-249 | 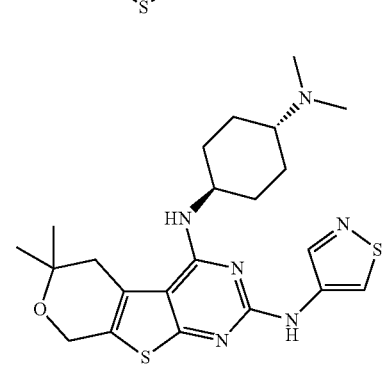 |

TABLE 1-continued
Exemplary Compounds
| Compound | Structure |
|---|---|
| I-250 | 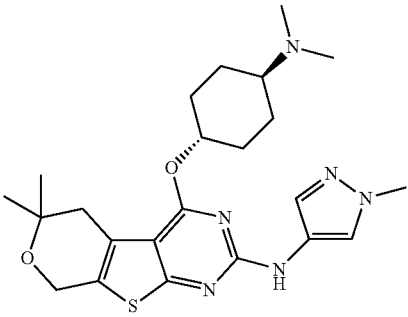 |
| I-251 | 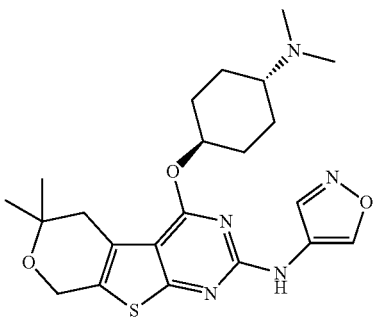 [SMILES: CN(C)[C@H]1CC[C@H](Oc2nc(Nc3cnoc3)nc3sc4c(c23)CC(C)(C)OC4)CC1] |
| I-252 | 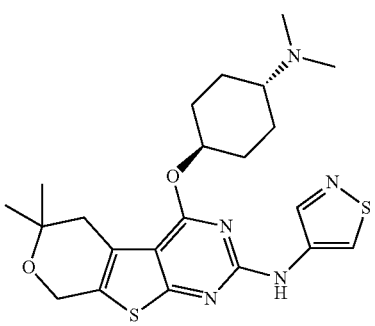 [SMILES: CN(C)[C@H]1CC[C@H](Oc2nc(Nc3cnsc3)nc3sc4c(c23)CC(C)(C)OC4)CC1] |
| I-253 | 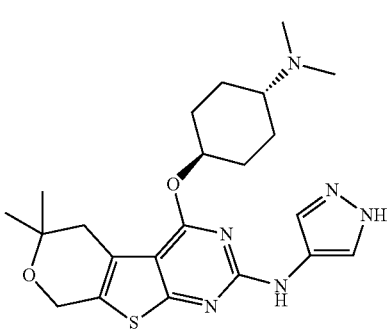 [SMILES: CN(C)[C@H]1CC[C@H](Oc2nc(Nc3cn[nH]c3)nc3sc4c(c23)CC(C)(C)OC4)CC1] |
| I-254 | 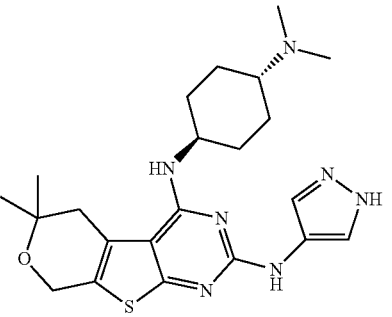 [SMILES: CN(C)[C@H]1CC[C@H](Nc2nc(Nc3cn[nH]c3)nc3sc4c(c23)CC(C)(C)OC4)CC1] |
| I-255 | 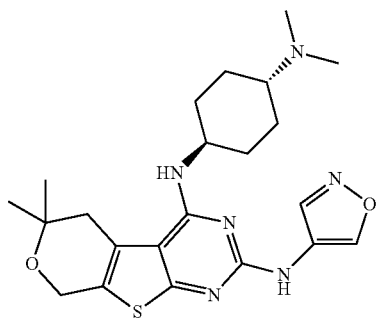 [SMILES: CN(C)[C@H]1CC[C@H](Nc2nc(Nc3cnoc3)nc3sc4c(c23)CC(C)(C)OC4)CC1] |
| I-256 | 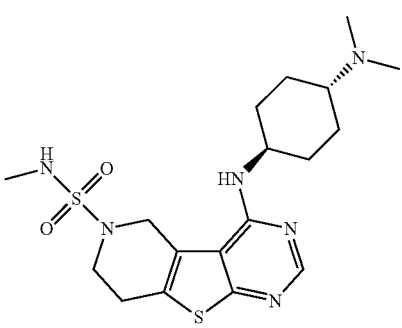 |
| I-257 | 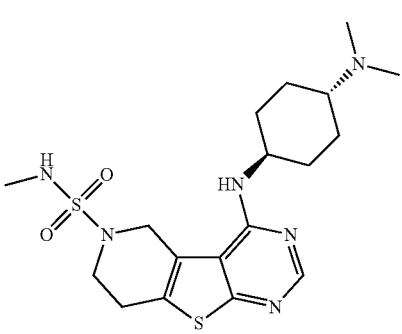 |

TABLE 1-continued
Exemplary Compounds
| Compound | Structure |
|---|---|
| I-258 | 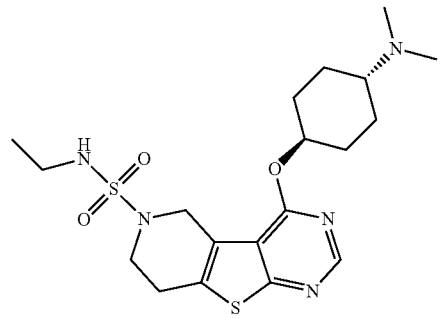 [SMILES: CCNS(=O)(=O)N1CCc2sc3ncnc(O[C@H]4CC[C@H](N(C)C)CC4)c3c2C1] |
| I-259 | 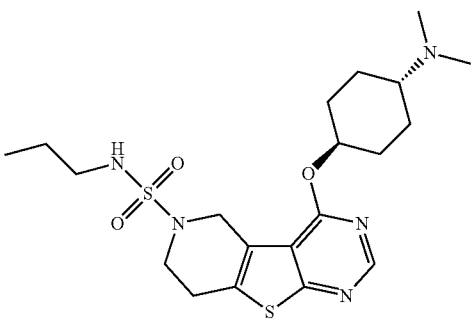 [SMILES: CCCNS(=O)(=O)N1CCc2sc3ncnc(O[C@H]4CC[C@H](N(C)C)CC4)c3c2C1] |
| I-260 | 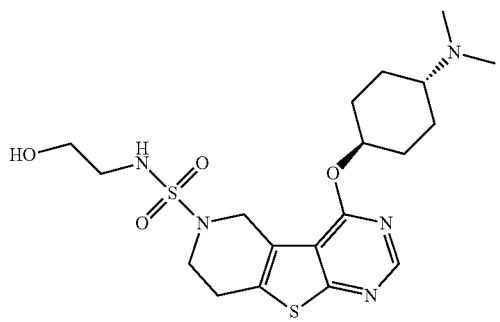 |
| I-261 | 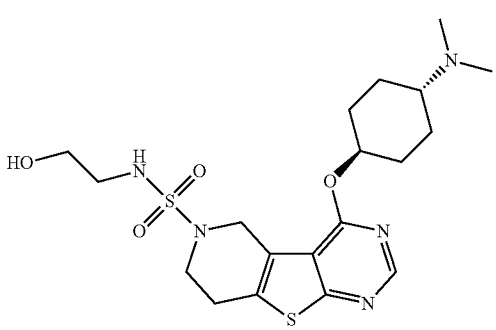 [SMILES: CN(C)[C@H]1CC[C@H](Oc2ncnc3sc4c(c23)CN(S(=O)(=O)NCCO)CC4)CC1] |
| I-262 | 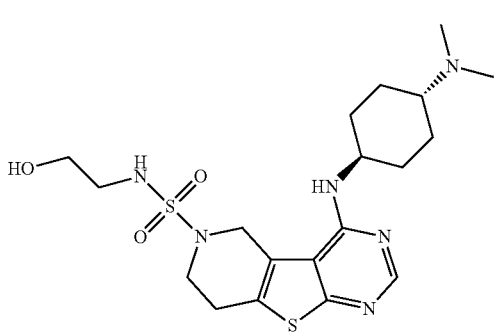 [SMILES: CN(C)[C@H]1CC[C@H](Nc2ncnc3sc4c(c23)CN(S(=O)(=O)NCCO)CC4)CC1] |
| I-263 | 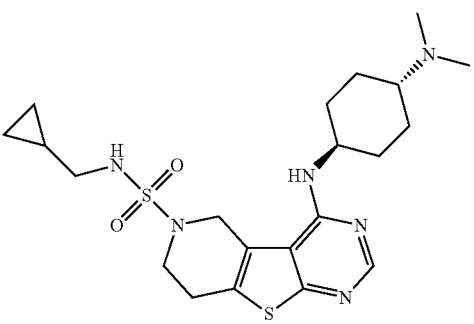 [SMILES: CN(C)[C@H]1CC[C@H](Nc2ncnc3sc4c(c23)CN(S(=O)(=O)NCC2CC2)CC4)CC1] |
| I-264 | |
| I-265 | 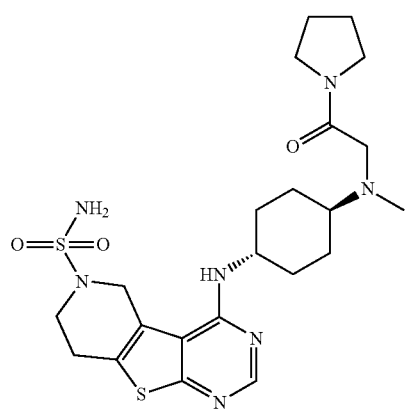 [SMILES: CN(CC(=O)N1CCCC1)[C@H]1CC[C@H](Nc2ncnc3sc4c(c23)CN(S(N)(=O)=O)CC4)CC1] |

TABLE 1-continued

Exemplary Compounds

| Compound | Structure |
|---|---|
| I-266 | 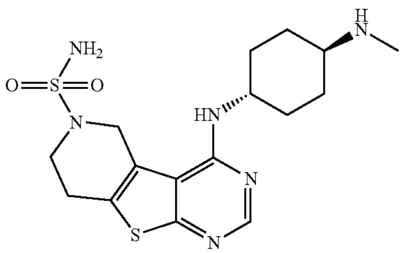 [SMILES: CN[C@H]1CC[C@H](Nc2ncnc3sc4c(c23)CN(S(N)(=O)=O)CC4)CC1] |
| I-267 | 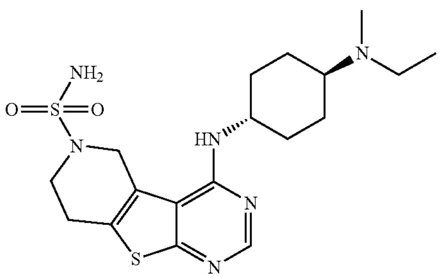 [SMILES: CCN(C)[C@H]1CC[C@H](Nc2ncnc3sc4c(c23)CN(S(N)(=O)=O)CC4)CC1] |
| I-268 | 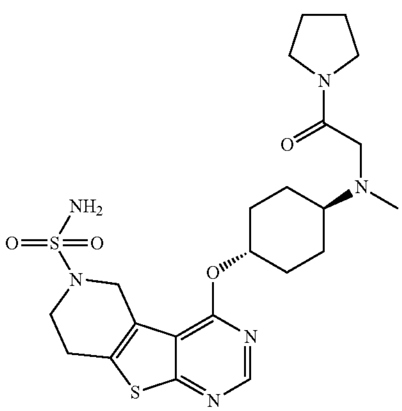 [SMILES: CN(CC(=O)N1CCCC1)[C@H]1CC[C@H](Oc2ncnc3sc4c(c23)CN(S(N)(=O)=O)CC4)CC1] |
| I-269 | 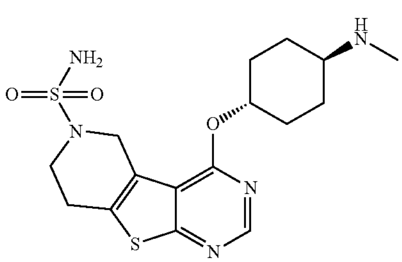 [SMILES: CN[C@H]1CC[C@H](Oc2ncnc3sc4c(c23)CN(S(N)(=O)=O)CC4)CC1] |
| I-270 | 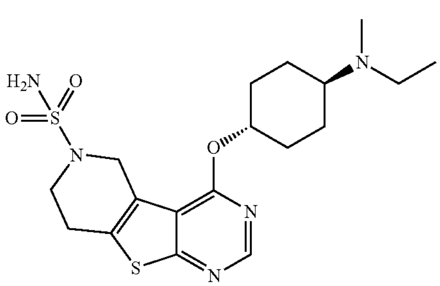 [SMILES: CCN(C)[C@H]1CC[C@H](Oc2ncnc3sc4c(c23)CN(S(N)(=O)=O)CC4)CC1] |
| I-271 | |
| I-272 | |
| I-273 | |
| I-274 | |

TABLE 1-continued
Exemplary Compounds
| Compound | Structure |
|---|---|
| I-275 | 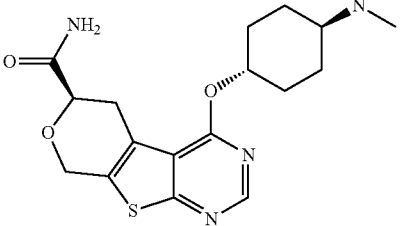 |
| I-276 | 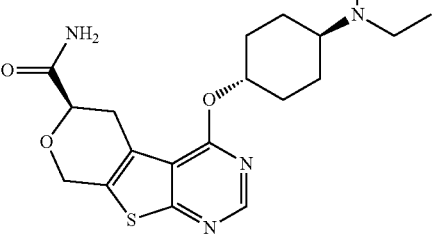 |
| I-277 | 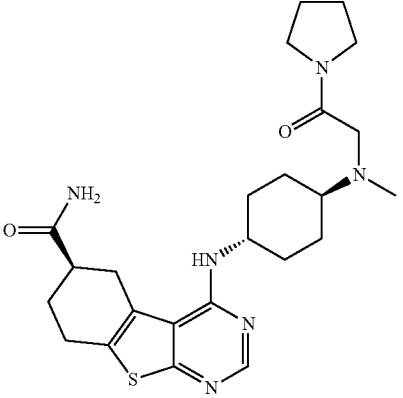 [SMILES: CN(CC(=O)N1CCCC1)[C@H]1CC[C@H](Nc2ncnc3sc4c(c23)C[C@H](C(N)=O)CC4)CC1] |
| I-278 | 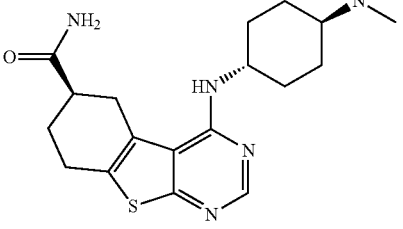 |
| I-279 | 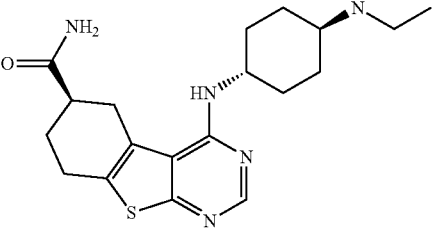 |
| I-280 | 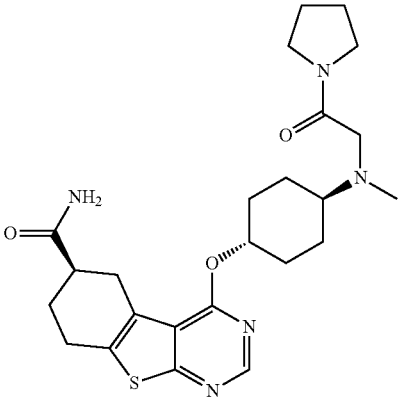 [SMILES: CN(CC(=O)N1CCCC1)[C@H]1CC[C@H](Oc2ncnc3sc4c(c23)C[C@H](C(N)=O)CC4)CC1] |
| I-281 | 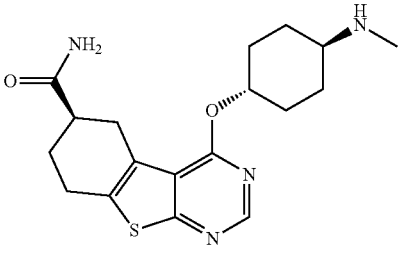 [SMILES: CN[C@H]1CC[C@H](Oc2ncnc3sc4c(c23)C[C@H](C(N)=O)CC4)CC1] |
| I-282 | 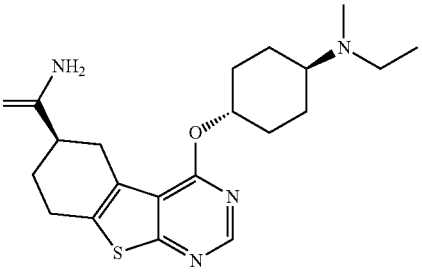 |
| I-283 | 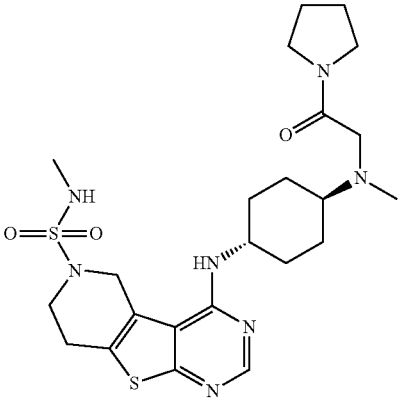 [SMILES: CNS(=O)(=O)N1CCc2sc3ncnc(N[C@H]4CC[C@H](N(C)CC(=O)N5CCCC5)CC4)c3c2C1] |

TABLE 1-continued

Exemplary Compounds

| Compound | Structure |
|---|---|
| I-284 | 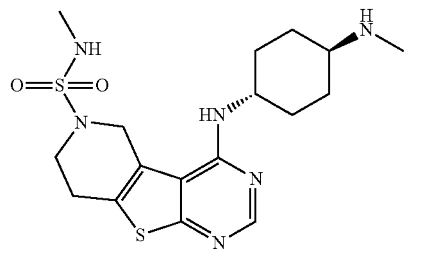 [SMILES: CNS(=O)(=O)N1CCc2sc3ncnc(N[C@H]4CC[C@H](NC)CC4)c3c2C1] |
| I-285 | 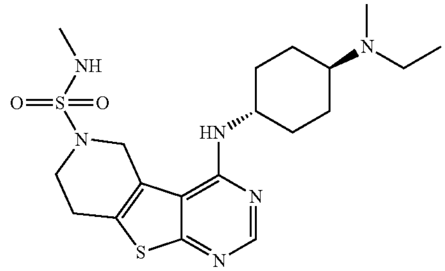 [SMILES: CCN(C)[C@H]1CC[C@H](Nc2ncnc3sc4c(c23)CN(S(=O)(=O)NC)CC4)CC1] |
| I-286 | 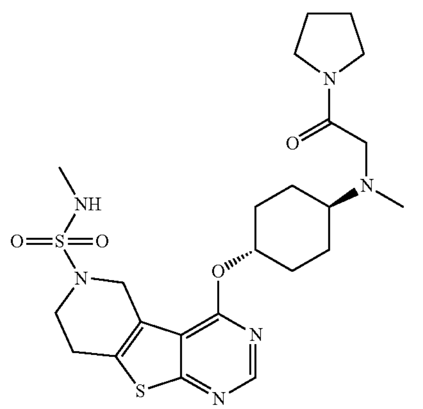 [SMILES: CNS(=O)(=O)N1CCc2sc3ncnc(O[C@H]4CC[C@H](N(C)CC(=O)N5CCCC5)CC4)c3c2C1] |
| I-287 | 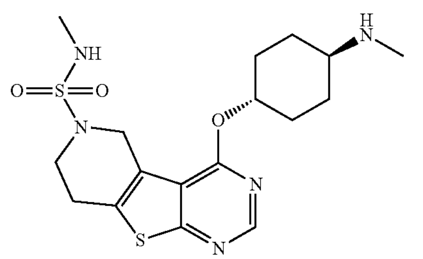 [SMILES: CNS(=O)(=O)N1CCc2sc3ncnc(O[C@H]4CC[C@H](NC)CC4)c3c2C1] |
| I-288 | 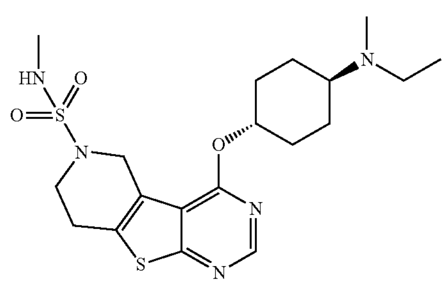 [SMILES: CCN(C)[C@H]1CC[C@H](Oc2ncnc3sc4c(c23)CN(S(=O)(=O)NC)CC4)CC1] |
| I-289 | |
| I-290 | |
| I-291 | |
| I-292 | |

TABLE 1-continued

Exemplary Compounds

| Compound | Structure |
|---|---|
| I-293 | (structure) |
| I-294 | (structure) |
| I-295 | (structure) |
| I-296 | (structure) |
| I-297 | (structure) |
| I-298 | (structure) |

In some embodiments, the present invention provides a compound set forth in Table 1, above, or a pharmaceutically acceptable salt thereof.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the present invention provides a complex comprising IRAK-4 and an inhibitor, wherein at least one unstable water of IRAK-4 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein. Methods and intermediates of the present invention are useful for preparing compounds as described in, e.g. U.S. patent application Ser. No. 61/734,133, filed Dec. 6, 2012, in the name of Harriman et al., the entirety of which is incorporated herein by reference.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "oxygen protecting group" includes, for example, carbonyl protecting groups, hydroxylprotecting groups, etc. Hydroxylprotecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like. In certain embodiments, the amino protecting group of the R$^{10}$ moiety is phthalimido. In still other embodiments, the amino protecting group of the R$^{10}$ moiety is a tert-butyloxycarbonyl (BOC) group. In certain embodiments, the amino protecting group is a sulphone (SO$_2$R).

In certain embodiments, compounds of the present invention are generally prepared according to Scheme I set forth below:

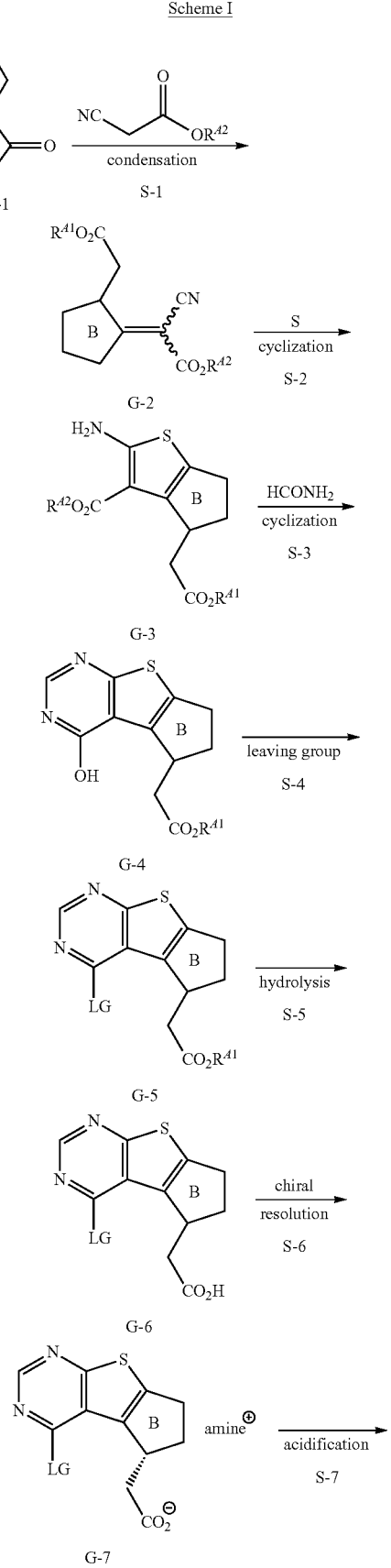

Scheme I

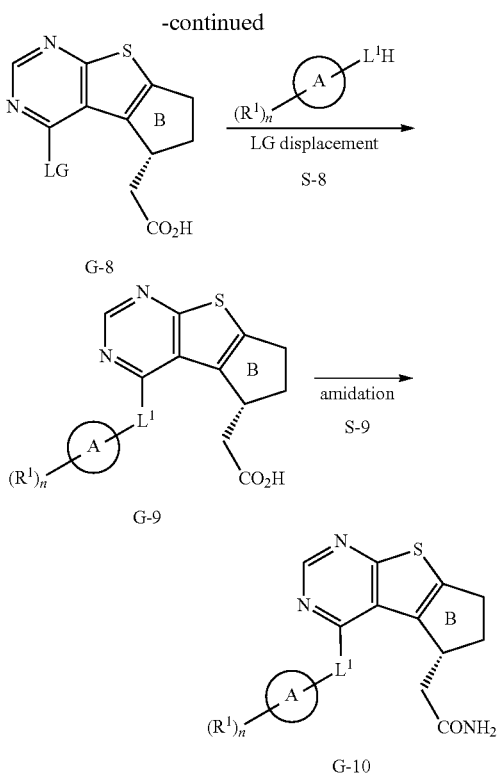

In Scheme I above, each of n, LG, $R^1$, $R^{A1}$, $R^{A2}$, $L^1$, Ring A, and Ring B is as defined above and below and in classes and subclasses as described herein.

In one aspect, the present invention provides methods for preparing chiral compounds of formula G-10 according to the steps depicted in Scheme 1, above. In some embodiments, at step S-1, a cyclic ketone of formula G-1 containing a Ring B is reacted with a cyanoacetic acid ester, or an equivalent thereof, to effect a condensation and dehydration reaction to form an olefin of formula G-2. In certain embodiments, the condensation reaction is performed in the presence of an amine and an acid. In some embodiments the base is HMDS (hexamethyldisilazane). In some embodiments the acid is acetic acid. In some embodiments, the S-1 reaction is performed without additional solvent. In some embodiments the cyclic ketone is cyclopentanone. In some embodiments the cyclic ketone is a cyclohexanone. In some embodiments, the cyclic ketone is a pyranone. In some embodiments $R^{A1}$ is a $C_{1-6}$ alkyl group. In some embodiments $R^{A1}$ is ethyl. In some embodiments $R^{A2}$ is a $C_{1-6}$ alkyl group. In some embodiments $R^{A2}$ is ethyl.

In some embodiments, step S-2 comprises contacting a compound of formula G-2 with elemental sulfur in the presence of an amine to form a compound of formula G-3. In some embodiments the amine is dimethylamine. In some embodiments step S-2 is performed with an alcohol as solvent. In some embodiments, the solvent is ethanol. In some embodiments steps S-1 and S-2 are performed without an intermediate purification of compound G-2.

In some embodiments, step S-3 comprises contacting the intermediate of formula G-3 with formamide to form a thienopyrimidine compound of formula G-4. In some embodiments the reaction further comprises contacting the reaction mixture with formamidine acetate.

In some embodiments, step S-4 comprises contacting the compound of formula G-4 with a reagent to convert the hydroxyl group into a leaving group LG. In some embodiments LG is a halogen. In some embodiments LG is chlorine. In some embodiments LG is a sulfonate. In some embodiments the reagent used to convert the hydroxyl group into LG is phosphorus oxychloride. In some embodiments step S-4 is performed in a solvent. In some embodiments the solvent is acetonitrile. In some embodiments step S-4 is performed without additional solvent.

In some embodiments step S-5 comprises contacting a compound of formula G-5 with a reagent to convert the ester group into a carboxylic acid, thereby forming a compound of formula G-6. In some embodiments the deesterification reagent is a base. In some embodiments the base is lithium hydroxide. In some embodiments the reagent is an acid. In some embodiments the reaction is performed in aqueous solvent. In some embodiments tetrahydrofuran is employed as a cosolvent. In some embodiments the reaction mixture further comprises TEAC (tetraethylammonium chloride) as a catalyst. In some embodiments the TEAC is present in substoichiometric amounts. In some embodiments step S-5 further comprises acidifying the crude reaction to obtain the free acid.

One of skill in the art will appreciate that compounds of formulae G-1, G-2, G-3, G-4, G-5, and G-6 contain a stereocenter, and are present as an racemic mixture. One of skill in the art will also appreciate that there are many methods known in the art for the separation of enantiomers to obtain enantioenriched or enantiopure isomers of those compounds, including but not limited to chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent. In some embodiments, the enantiomers of a compound of formula G-5 are resolved by the action of lipase enzymes.

In some embodiments step S-6 comprises contacting a racemic compound of formula G-6 with a chiral agent to form a mixture of diastereomeric salts. The resulting diastereomeric mixture is then separated by suitable means to obtain a compound of formula G-7. Such suitable means for separating diastereomeric mixtures are well known to one of ordinary skill in the art and include, but are not limited to, those methods described herein. It will be appreciated that, depending upon the chiral agent used, there may be one or more basic moieties present. In certain embodiments, the chiral base has two basic moieties as with, for example, 1,2-diphenylethane-1,2-diamine. In some embodiments the chiral agent is an enantioenriched monoamine. In some embodiments the chiral agent is selected from 1-phenethylamine, aminobutanol, phenylglycinol, p-methoxybenzyl-1-phenethylamine, cinchonine, p-dimethylaminobenzyl-1-phenethylamine, quinidine, cinchonidine, quinine, ephedrine, and norephedrine. In some embodiments the chiral agent is selected from cinchonine, cinchonidine, and ephedrine. In some embodiments the chiral agent is cinchonine. In some embodiments the chiral agent is cinchonidine. In some embodiments the chiral agent is ephedrine. In some embodiments the chiral agent is (−)-ephedrine.

Accordingly, one of ordinary skill in the art would appreciate that a compound of formula G-6 may form a hemi salt with said bi-functional chiral agent. As used herein, the term "hemi salt" refers to an adduct having two molecules of a compound of formula G-6 to each molecule of chiral acid. Alternatively, the resulting salt may have a one-to-one mixture chiral acid to a compound of formula G-6. In certain embodiments, the present invention provides a compound comprises equal molar amounts of the chiral agent to an acid of formula G-6. Furthermore, one of skill in the art that following resolution of the diastereomeric mixture of salts (e.g. by fractional crystallization), an enantioenriched salt is obtained from both the crystalline fraction and from the mother liquor. Accordingly, in some embodiments, the present invention provides a compound of formula G-7 wherein said compound comprises a molecule of a compound of formula G-8 in its salt form together with one or more molecules of the chiral agent. In some embodiments, the salt compound of formula G-7 comprises one molecule of a compound of formula G-8 together with one molecule of a chiral agent. In some embodiments, the salt compound of formula G-7 is a hemi salt comprising two molecules of a compound of formula G-8 together with one molecule of a dibasic chiral agent. In some embodiments, the compound of formula G-7 is a cinchonine salt, a cinchonidine salt, or an ephedrine salt.

In some embodiments the method of chiral resolution step S-6 comprises contacting a compound of formula G-6 with a chiral agent in a solvent. In some embodiments the chiral agent is selected from cinchonine, cinchonidine, and ephedrine. In some embodiments the solvent is an alcohol. In some embodiments the solvent is isopropanol. In some embodiments the mixture is heated. In some embodiments the solution is supersaturated. In some embodiments the reaction is seeded with a crystal. In some embodiments the resulting crystal mass is recrystallized from isopropanol.

When the chiral agent is a chiral amine, the compound of formula G-7, in step S-7, is treated with a suitable acid to form the enantioenriched free acid compound G-8. Free acids according to the invention are also prepared, for example, by contacting a compound of formula G-7 with a suitable acid in the presence of a solvent suitable for free acid formation. Such suitable acids include strong inorganic acids, i.e., those that completely dissociate in water. In certain embodiments, the acid is added in an amount of at least about 1 mol. eq. and, in other embodiments, in an amount of at least about 1 mol. eq. to about 2 mol. eq. relative to the compound of formula G-7. Examples of such acids include mineral acids, sulfonic acids, and combinations thereof. In some embodiments, the suitable acid is hydrochloric acid. In some embodiments, the solvent used to extract the free acid formed is an organic solvent.

Examples of solvents suitable for use during free base formation at step S-7 include polar solvents such as alkyl alcohols, such as $C_1$ to $C_4$ alcohols (e.g. ethanol, methanol, 2-propanol), water, dioxane, or THF (tetrahydrofuran) or combinations thereof. In certain embodiments, the suitable solvent is a $C_1$ to $C_4$ alcohol such as methanol, ethanol, 2-propanol, water, or combination thereof. According to one aspect of the present invention, aqueous hydrochloric acid is used at step S-7. According to another aspect of the present invention, the free base formation at step S-7 is performed in a bi-phasic mixture of solvents whereby the compound of formula G-8, as it is formed, is extracted into an organic layer. Thus, a suitable bi-phasic mixture of solvents includes an aqueous solvent and a non-miscible organic solvent. Such non-miscible organic solvents are well known to one of ordinary skill in the art and include halogenated hydrocarbon solvents (e.g. dichloromethane and chloroform), benzene and derivatives thereof (e.g. toluene), esters (e.g. ethyl acetate and isopropyl acetate), and ethers (e.g. MTBE, THF and derivatives thereof, glyme, and diglyme) and the like. In certain embodiments, the free acid formation at step S-7 is performed in a bi-phasic mixture comprising aqueous hydrochloric acid and dichloromethane. In some embodiments, the suitable acid is water soluble such that the reaction is performed in a mixture of dichloromethane and a suitable aqueous acid, such as aqueous hydrochloric acid.

At step S-8, displacement of LG of the chiral compound G-8 affords a compound of formula G-9. In certain embodiments, step S-8 comprises contacting a compound of formula G-8 with a compound of the formula

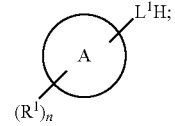

wherein
$L^1$, $R^1$, Ring A, and n are defined above and below and in classes and subclasses as described herein.

In some embodiments $L^1$ is selected from O— and —NH—, such that together with the hydrogen filling the open valence, $L^1H$ denotes an —OH or —$NH_2$ group. In some embodiments $L^1H$ is —OH. In some embodiments $L^1H$ is —$NH_2$.

In some embodiments n is 0-4. In some embodiments n is 1-4. In some embodiments n is 1.

In some embodiments $R^1$ is —$NR_2$. In some embodiments $R^1$ is dimethylamino. In some embodiments $R^1$ is morpholino. In some embodiments, Ring A is piperidine. In some embodiments Ring A is cyclohexyl. In some embodiments step S-8 comprises contacting a compound of formula G-8 having the structure:

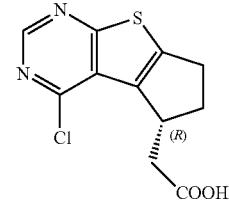

with a compound of the formula:

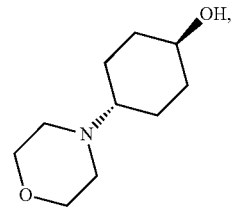 [SMILES: O[C@H]1CC[C@H](N2CCOCC2)CC1]

thereby forming a compound of formula G-9 having the structure:

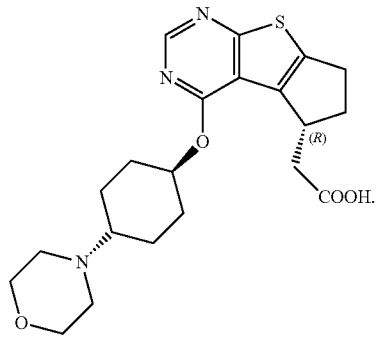

In some embodiments step S-8 further comprises contacting the reaction mixture with a base. In some embodiments the base is sodium bis(trimethylsilyl)amide. In some embodiments the reaction further comprises a solvent. In some embodiments the solvent is THF.

In some embodiments step S-9 comprises contacting a compound of formula G-9 with an amidating reagent system, thereby forming a compound of formula G-10. In some embodiments the amidating reagent system comprises thionyl chloride and ammonia. In some embodiments step S-9 further comprises use of a solvent. In some embodiments the solvent is methanol. In some embodiments step S-9 comprises contacting a compound of formula G-9 first with an activating reagent, and second with ammonia. In some embodiments the activating reagent is thionyl chloride.

As used herein, the term "diastereomeric salt" refers to the adduct of a chiral compound of formula G-6 with a chiral base.

As used herein, the term "enantiomeric salt" refers to the salt of the resolved chiral compound of formula G-8, wherein said compound of formula G-8 is enriched in one enantiomer. As used herein, the term "enantiomerically enriched", as used herein signifies that one enantiomer makes up at least 80% or 85% of the preparation. In certain embodiments, the term enantiomerically enriched signifies that at least 90% of the preparation is one of the enantiomers. In other embodiments, the term signifies that at least 95% of the preparation is one of the enantiomers. In other embodiments, the term signifies that at least 98% of the preparation is one of the enantiomers.

In certain embodiments, compounds of the present invention wherein $R^z$ is [Ar]—NH— are generally prepared according to Scheme II set forth below:

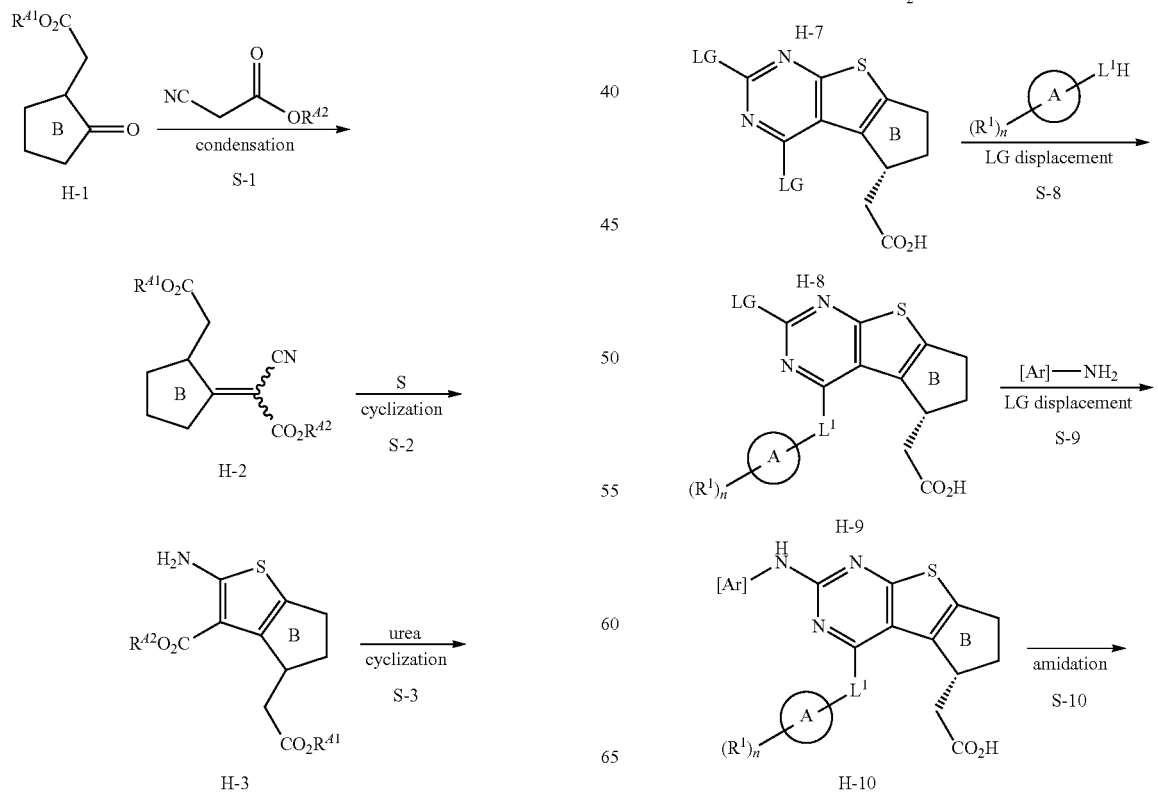

-continued

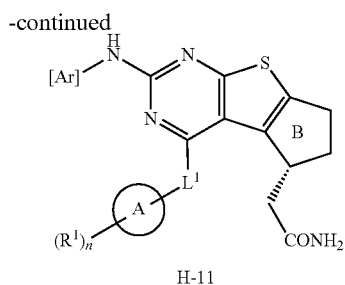

H-11

In Scheme I above, each of n, [Ar], LG, $R^1$, $R^{A1}$, $R^{A2}$, L1, Ring A, and Ring B is as defined above and below and in classes and subclasses as described herein.

In one aspect, the present invention provides methods for preparing chiral compounds of formula H-10 according to the steps depicted in Scheme 1, above. In some embodiments, at step S-1, a cyclic ketone of formula H-1 containing a Ring B is reacted with a cyanoacetic acid ester, or an equivalent thereof, to effect a condensation and dehydration reaction to form an olefin of formula H-2. In certain embodiments, the condensation reaction is performed in the presence of an amine and an acid. In some embodiments the base is HMDS (hexamethyldisilazane). In some embodiments the acid is acetic acid. In some embodiments, the S-1 reaction is performed without additional solvent. In some embodiments the cyclic ketone is cyclopentanone. In some embodiments the cyclic ketone is a cyclohexanone. In some embodiments, the cyclic ketone is a pyranone. In some embodiments $R^{A1}$ is a $C_{1-6}$ alkyl group. In some embodiments $R^{A1}$ is ethyl. In some embodiments $R^{A2}$ is a $C_{1-6}$ alkyl group. In some embodiments $R^{A2}$ is ethyl.

In some embodiments, step S-2 comprises contacting a compound of formula H-2 with elemental sulfur in the presence of an amine to form a compound of formula H-3. In some embodiments the amine is dimethylamine. In some embodiments step S-2 is performed with an alcohol as solvent. In some embodiments, the solvent is ethanol. In some embodiments steps S-1 and S-2 are performed without an intermediate purification of compound H-2.

In some embodiments, step S-3 comprises contacting the intermediate of formula H-3 with formamide to form a thienopyrimidine compound of formula H-4. In some embodiments the reaction further comprises contacting the reaction mixture with formamidine acetate.

In some embodiments, step S-4 comprises contacting the compound of formula H-4 with a reagent to convert the hydroxyl group into a leaving group LG, thereby forming a compound of formula H-5. In some embodiments LG is a halogen. In some embodiments LG is chlorine. In some embodiments LG is a sulfonate. In some embodiments the reagent used to convert the hydroxyl group into LG is phosphorus oxychloride. In some embodiments step S-4 is performed in a solvent. In some embodiments the solvent is acetonitrile. In some embodiments step S-4 is performed without additional solvent.

In some embodiments step S-5 comprises contacting a compound of formula H-5 with a reagent to convert the ester group into a carboxylic acid, thereby forming a compound of formula H-6. In some embodiments the deesterification reagent is a base. In some embodiments the base is lithium hydroxide. In some embodiments the reagent is an acid. In some embodiments the reaction is performed in aqueous solvent. In some embodiments tetrahydrofuran is employed as a cosolvent. In some embodiments the reaction mixture further comprises TEAC (tetraethylammonium chloride) as a catalyst. In some embodiments the TEAC is present in substoichiometric amounts. In some embodiments step S-5 further comprises acidifying the crude reaction to obtain the free acid.

One of skill in the art will appreciate that compounds of formulae H-1, H-2, H-3, H-4, H-5, and H-6 contain a stereocenter, and are present as an racemic mixture. One of skill in the art will also appreciate that there are many methods known in the art for the separation of enantiomers to obtain enantioenriched or enantiopure isomers of those compounds, including but not limited to chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent. In some embodiments, the enantiomers of a compound of formula H-5 are resolved by the action of lipase enzymes.

In some embodiments step S-6 comprises contacting a racemic compound of formula H-6 with a chiral agent to form a mixture of diastereomeric salts. The resulting diastereomeric mixture is then separated by suitable means to obtain a compound of formula H-7. Such suitable means for separating diastereomeric mixtures are well known to one of ordinary skill in the art and include, but are not limited to, those methods described herein. It will be appreciated that, depending upon the chiral agent used, there may be one or more basic moieties present. In certain embodiments, the chiral base has two basic moieties as with, for example, 1,2-diphenylethane-1,2-diamine. In some embodiments the chiral agent is an enantioenriched monoamine. In some embodiments the chiral agent is selected from 1-phenethylamine, aminobutanol, phenylglycinol, p-methoxybenzyl-1-phenethylamine, cinchonine, p-dimethylaminobenzyl-1-phenethylamine, quinidine, cinchonidine, quinine, ephedrine, and norephedrine. In some embodiments the chiral agent is selected from cinchonine, cinchonidine, and ephedrine. In some embodiments the chiral agent is cinchonine. In some embodiments the chiral agent is cinchonidine. In some embodiments the chiral agent is ephedrine. In some embodiments the chiral agent is (−)-ephedrine.

Accordingly, one of ordinary skill in the art would appreciate that a compound of formula H-6 may form a hemi salt with said bi-functional chiral agent. As used herein, the term "hemi salt" refers to an adduct having two molecules of a compound of formula H-6 to each molecule of chiral acid. Alternatively, the resulting salt may have a one-to-one mixture chiral acid to a compound of formula H-6. In certain embodiments, the present invention provides a compound comprises equal molar amounts of the chiral agent to an acid of formula H-6. Furthermore, one of skill in the art that following resolution of the diastereomeric mixture of salts (e.g. by fractional crystallization), an enantioenriched salt is obtained from both the crystalline fraction and from the mother liquor. Accordingly, in some embodiments, the present invention provides a compound of formula H-7 wherein said compound comprises a molecule of a compound of formula H-8 in its salt form together with one or more molecules of the chiral agent. In some embodiments, the salt compound of formula H-7 comprises one molecule of a compound of formula H-8 together with one molecule of a chiral agent. In some embodiments, the salt compound of formula H-7 is a hemi salt comprising two molecules of a compound of formula H-8 together with one molecule of a dibasic chiral agent. In some embodiments, the compound of formula H-7 is a cinchonine salt, a cinchonidine salt, or an ephedrine salt.

In some embodiments the method of chiral resolution step S-6 comprises contacting a compound of formula H-6 with a chiral agent in a solvent. In some embodiments the chiral agent is selected from cinchonine, cinchonidine, and ephedrine. In some embodiments the solvent is an alcohol. In some embodiments the solvent is isopropanol. In some embodiments the mixture is heated. In some embodiments the solution is supersaturated. In some embodiments the reaction is seeded with a crystal. In some embodiments the resulting crystal mass is recrystallized from isopropanol.

When the chiral agent is a chiral amine, the compound of formula H-7, in step S-7, is treated with a suitable acid to form the enantioenriched free acid compound H-8. Free acids according to the invention are also prepared, for example, by contacting a compound of formula H-7 with a suitable acid in the presence of a solvent suitable for free acid formation. Such suitable acids include strong inorganic acids, i.e., those that completely dissociate in water. In certain embodiments, the acid is added in an amount of at least about 1 mol. eq. and, in other embodiments, in an amount of at least about 1 mol. eq. to about 2 mol. eq. relative to the compound of formula H-7. Examples of such acids include mineral acids, sulfonic acids, and combinations thereof. In some embodiments, the suitable acid is hydrochloric acid. In some embodiments, the solvent used to extract the free acid formed is an organic solvent.

Examples of solvents suitable for use during free base formation at step S-7 include polar solvents such as alkyl alcohols, such as $C_1$ to $C_4$ alcohols (e.g. ethanol, methanol, 2-propanol), water, dioxane, or THF (tetrahydrofuran) or combinations thereof. In certain embodiments, the suitable solvent is a $C_1$ to $C_4$ alcohol such as methanol, ethanol, 2-propanol, water, or combination thereof. According to one aspect of the present invention, aqueous hydrochloric acid is used at step S-7. According to another aspect of the present invention, the free base formation at step S-7 is performed in a bi-phasic mixture of solvents whereby the compound of formula H-8, as it is formed, is extracted into an organic layer. Thus, a suitable bi-phasic mixture of solvents includes an aqueous solvent and a non-miscible organic solvent. Such non-miscible organic solvents are well known to one of ordinary skill in the art and include halogenated hydrocarbon solvents (e.g. dichloromethane and chloroform), benzene and derivatives thereof (e.g. toluene), esters (e.g. ethyl acetate and isopropyl acetate), and ethers (e.g. MTBE, THF and derivatives thereof, glyme, and diglyme) and the like. In certain embodiments, the free acid formation at step S-7 is performed in a bi-phasic mixture comprising aqueous hydrochloric acid and dichloromethane. In some embodiments, the suitable acid is water soluble such that the reaction is performed in a mixture of dichloromethane and a suitable aqueous acid, such as aqueous hydrochloric acid.

At step S-8, displacement of LG of the chiral compound H-8 affords a compound of formula H-9. In certain embodiments, step S-8 comprises contacting a compound of formula H-8 with a compound of the formula

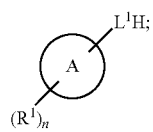

wherein
$L^1$, $R^1$, Ring A, and n are defined above and below and in classes and subclasses as described herein.

In some embodiments $L^1$ is selected from O— and —NH—, such that together with the hydrogen filling the open valence, $L^1H$ denotes an —OH or —NH$_2$ group. In some embodiments $L^1H$ is —OH. In some embodiments $L^1H$ is —NH$_2$.

In some embodiments n is 0-4. In some embodiments n is 1-4. In some embodiments n is 1.

In some embodiments $R^1$ is —NR$_2$. In some embodiments $R^1$ is dimethylamino. In some embodiments $R^1$ is morpholino. In some embodiments, Ring A is piperidine. In some embodiments Ring A is cyclohexyl.

In some embodiments step S-8 further comprises contacting the reaction mixture with a base. In some embodiments the base is sodium bis(trimethylsilyl)amide. In some embodiments the reaction further comprises a solvent. In some embodiments the solvent is THF.

In some embodiments step S-9 comprises contacting a compound of formula H-9 with a compound of formula [Ar]—NH$_2$, thereby forming a compound of formula H-10. In some embodiments step S-9 further comprises contacting the reaction mixture with a base. In some embodiments step S-9 further comprises contacting the reaction mixture with a palladium catalyst. In some embodiments [Ar] is an optionally substituted phenyl or heteroaromatic ring. In some embodiments [Ar] is an optionally substituted phenyl ring. In some embodiments [Ar] is an optionally substituted heteroaromatic ring. In some embodiments [Ar] is an optionally substituted 5-6 membered heteroaromatic ring containing 1-2 heteroatoms independently selected from nitrogen, oxygen and sulfur.

In some embodiments step S-10 comprises contacting a compound of formula H-10 with an amidating reagent system, thereby forming a compound of formula H-11. In some embodiments the amidating reagent system comprises thionyl chloride and ammonia. In some embodiments step S-10 further comprises use of a solvent. In some embodiments the solvent is methanol. In some embodiments step S-10 comprises contacting a compound of formula H-10 first with an activating reagent, and second with ammonia. In some embodiments the activating reagent is thionyl chloride.

As used herein, the term "diastereomeric salt" refers to the adduct of a chiral compound of formula H-6 with a chiral base.

As used herein, the term "enantiomeric salt" refers to the salt of the resolved chiral compound of formula H-8, wherein said compound of formula H-8 is enriched in one enantiomer. As used herein, the term "enantiomerically enriched", as used herein signifies that one enantiomer makes up at least 80% or 85% of the preparation. In certain embodiments, the term enantiomerically enriched signifies that at least 90% of the preparation is one of the enantiomers. In other embodiments, the term signifies that at least 95% of the preparation is one of the enantiomers. In other embodiments, the term signifies that at least 98% of the preparation is one of the enantiomers.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", $5^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit an IRAK protein kinase, or a mutant thereof, in a biological sample or in a patient. In certain embodiments, the amount of compound in compositions of this invention is such that is effective to measurably inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes.

Examples of kinases that are inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. L[1] et al., "IRAK-4: A novel member of the IRAK family with the properties of an IRAK-kinase," *PNAS* 2002, 99(8), 5567-5572, Flannery et al., "The interleukin-1 receptor-associated kinases: Critical regulators of innate immune signaling" Biochem Pharm 2010, 80(12), 1981-1991 incorporated by reference in its entirety.

The activity of a compound utilized in this invention as an inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204(5), 1025-1036; Lebakken et al., "A Fluorescence Lifetime Based Binding Assay to Characterize Kinase Inhibitors," *J. Biomol. Screen.* 2007, 12(6), 828-841; Maschera et al., "Overexpression of an enzymatically inactive interleukin-1-receptor-associated kinase activates nuclear factor-κB," *Biochem. J.* 1999, 339, 227-231; Song et al., "The kinase activities of interleukin-e receptor associated kinase (IRAK)-1 and 4 are redundant in the control of inflammatory cytokine expression in human cells," *Mol. Immunol.* 2009, 46, 1458-1466, each of which is herein incorporated by reference in its entirety. Detailed conditions for assaying a compound utilized in this invention as an inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1α, IL-6 and IL-8. The kinase activity of IRAK-4 has been shown to play a critical role in the TLR-mediated immune and inflammatory responses. IRAK4 is a key mediator of the innate immune response orchestrated by interleukin-1 receptor (IL-1R), interleukin-18 receptor (IL-18R), IL-33 receptor (IL-33R), and Toll-like receptors (TLRs). Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," *Medi-* cine (Baltimore), 2010, 89(6), 043-25; L¹, "IRAK4 in TLR/IL-1R signaling: Possible clinical applications," *Eur. J. Immunology* 2008, 38:614-618; Cohen et al., "Targeting protein kinases for the development of anti-inflammatory drugs," *Curr. Opin. Cell Bio.* 2009, 21:317-324; Flannery et al., "The interleukin-1 receptor-associated kinases: Critical regulators of innate immune signalling," *Biochem. Pharm.* 2010, 80(12), 1981-1991; Gottipati et al., "IRAK1: A critical signaling mediator of innate immunity," *Cellular Signaling* 2008, 20, 269-276; Kim et al., "A critical role for IRAK4 kinase activity in Toll-like receptor-mediated innate immunity," *J. Exp. Med.* 2007 204(5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282 (18), 13552-13560; Kubo-Murai et al., "IRAK-4-dependent Degradation of IRAK-1 is a Negative Feedback Signal for TLR-mediated NF-κB Activation," *J. Biochem.* 2008, 143, 295-302; Maschera et al., "Overexpression of an enzymatically inactive interleukin-1-receptor-associated kinase activates nuclear factor-κB," *Biochem. J.* 1999, 339, 227-231; Lin et al., "Helical assembly in the MyD88-IRAK4-IRAK2 complex in TLR/IL-1R signalling," *Nature* 2010, 465(17), 885-891; Suzuki et al., "IRAK-4 as the central TIR signaling mediator in innate immunity," *TRENDS in Immunol.* 2002, 23(10), 503-506; Suzuki et al., "Severe impairment of interleukin-1 and Toll-like receptor signalling in mice lacking IRAK-4," *Nature* 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), each of which is herein incorporated by reference in its entirety. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr. Opin. Cell Bio.* 2009, 21:317-324; Ku et al., "Selective predisposition to bacterial infections in IRAK-4-deficient children: IRAK-4-dependent TLRs are otherwise redundant in protective immunity," *J. Exp. Med.* 2007, 204(10), 2407-2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets*, 12(7), pp: 883-903 (2008); Gearing, A. "Targeting toll-like receptors for drug development: a summary of commercial approaches," *Immunology and Cell Biology*, 85, pp: 490-494 (2007); Dinarello, C. "IL-1: Discoveries, controversies and future directions," *European Journal of Immunology*, 40, pp: 595-653 (2010), each of which is herein incorporated by reference in its entirety. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med. Chem. Lett.* 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wng et al., "IRAK-4 Inhibitors for Inflammation," *Curr. Topics in Med. Chem.* 2009, 9, 724-737, each of which is herein incorporated by reference in its entirety.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature*, vol. 000, pp: 1-7 (2010); Lust, J. et al., "Induction of a Chronic Disease State in patients With Smoldering of Indolent Multiple Myeloma by Targeting Interleukin 1β-Induced Interleukin 6 Production and the Myeloma Proliferative Component," *Mayo Clinic Proceedings*, 84(2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of anti-inflammatory drugs," *Curr. Opin. Cell Bio.* 2009, 21:317-324) and rheumatoid arthritis (see, e.g., Geyer, M. et al., "Actual status of antiinterleukin-1 therapies in rheumatic diseases," *Current Opinion in Rheumatology*, 22, pp: 246-251 (2010)), autoinflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.*, 14, pp: 411-421 (2008)), inflammation (see, e.g., Dinarello, C. "Interleukin 1 and interleukin 18 as mediators of inflammation and the aging process," *The American Journal of Clinical Nutrition*, 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-S12 (2008); Dalbeth, N. et al., "Hyperuricaemia and gout: state of the art and future perspectives," *Annals of Rheumatic Diseases*, 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomised, single-blind pilot study," *Annals of Rheumatic Diseases*, 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases*, 68, pp: 1602-1608 (2009)), neurological disorders, metabolic syndrome (see, e.g., Troseid, M. "The role of interleukin-18 in the metabolic syndrome," *Cardiovascular Diabetology*, 9:11, pp: 1-8 (2010)), immunodeficiency disorders such as AIDS and HIV (see, e.g., Iannello, A. et al., "Role of Interleukin-18 in the Development and Pathogenesis of AIDS," *AIDS Reviews*, 11, pp: 115-125 (2009)), destructive bone disorders (see, e.g., Hennessy, E., et al., "Targeting Toll-like receptors: emerging therapeutics?" *Nature Reviews*, vol. 9, pp: 293-307 (2010)), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenstrom's Macroglobulinemia" 53rd ASH Annual Meeting; Xu, et al., "A somatic variant in MYD88 (L256P) revealed by whole genome sequencing differentiates lymphoplasmacytic lymphoma from marginal zone lymphomas" 53rd ASH Annual Meeting; Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53rd ASH Annual Meeting; Iriyama et al., "Clinical significance of genetic mutations of CD79B, CARD11, MYD88, and EZH2 genes in diffuse large B-cell lymphoma patients" 53rd ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably inhibit IRAK-1 only, IRAK-2-only, IRAK-4-only and/or IRAK1- and IRAK4 kinase activity.

Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma).

In some embodiments the proliferative disease which can be treated according to the methods of this invention is an MyD88 driven disorder. In some embodiments, the MyD88 driven disorder which can be treated according to the methods of this invention is selected from ABC DLBCL, Waldenstrom's macroglobulinemia, Hodgkin's lymphoma, primary cutaneous T-cell lymphoma and chronic lymphocytic leukemia.

In some embodiments the proliferative disease which can be treated according to the methods of this invention is an IL-1 driven disorder. In some embodiments the IL-1 driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitis, atompic dermatitis, alopecia greata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

The loss of IRAK4 function results in decreased Aβ levels in an in vivo murine model of Alzheimer's disease and was associated with diminished microgliosis and astrogliosis in aged mice. Analysis of microglia isolated from the adult mouse brain revealed an altered pattern of gene expression associated with changes in microglial phenotype that were associated with expression of IRF transcription factors that govern microglial phenotype. Further, loss of IRAK4 function also promoted amyloid clearance mechanisms, including elevated expression of insulin-degrading enzyme. Finally, blocking IRAK function restored olfactory behavior (Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience (2012) 32(43), 15112-15123.

In some embodiments the invention provides a method of treating, preventing or lessening the severity of Alzheimer's disease comprising administering to a patient in need thereof a compound of formula I or a pharmaceutically acceptable salt or composition thereof.

In some embodiments the invention provides a method of treating a disease or condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebie), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bidt, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bidt, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bidt, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a compound of formula I and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et at "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a compound of formula I and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, the present invention provides a method of treating Alzheimer's disease comprising administering to a patient in need thereof a compound of formula I and one or more additional therapeutic agents selected from donepezil (Aricept®), rivastigmine (Excelon®), galantamine (Razadyne®), tacrine (Cognex®), and memantine (Namenda®).

In another embodiment, the present invention provides a method of treating organ transplant rejection or graft vs. host disease comprising administering to a patient in need thereof a compound of formula I and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated, with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting IRAK-1, IRAK-2, and/or IRAK-4, or a mutant thereof, activity in a biological sample comprising the step of contacting said biological sample with a compound of this invention, or a composition comprising said compound. In certain embodiments, the invention relates to a method of irreversibly inhibiting IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof and blood, saliva, urine, feces, semen, tears, or other body fluids or extracts thereof.

Inhibition of protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or more of IRAK-1, IRAK-2, and/or IRAK-4, or a mutant thereof, activity in a patient comprising the step of administering to said patient a compound of the present invention, or a composition comprising said compound. According to certain embodiments, the invention relates to a method of irreversibly inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl] amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, US8138347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfuram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™ Pamidronic acid is marketed under the trade name Aredia™. Alendronic acid is marketed under the trade name Fosamax™. Ibandronic acid is marketed under the trade name Bondranat™ Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY$^{720}$. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; AngioStatin™; Endo Statin™; anthranilic acid amides; ZD4190; ZD6474; SU5416; SU6668; bevacizumab; or anti-VEGF antibodies or anti-VEGF receptor antibodies, such as rhuMAb and RHU-Fab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-Page inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY$^{19}$-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

Intermediate 1.4

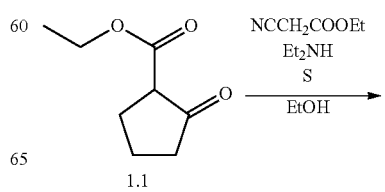

-continued

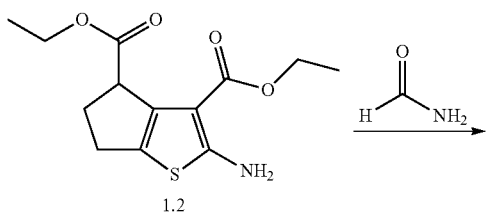

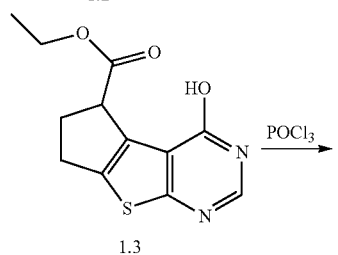

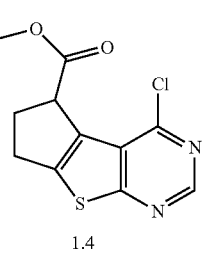

Synthesis of Compound 1.2.

Into a 10-L 4-necked round-bottom flask was placed ethyl 2-oxocyclopentane-1-carboxylate (1.1, 1000 g, 6.40 mol, 1.00 equiv), ethyl 2-cyanoacetate (861 g, 7.61 mol, 1.19 equiv), ethanol (4000 mL), diethylamine (571 g, 7.81 mol, 1.22 equiv), and sulfur (248 g, 7.75 mol, 1.21 equiv). The resulting solution was stirred overnight at room temperature and then concentrated under vacuum. The solution was diluted with 10 L of ethyl acetate and washed with 3×1 L of brine. The mixture was dried over anhydrous sodium sulfate and concentrated under vacuum. The residue was loaded onto a silica gel column and eluted with ethyl acetate/petroleum ether (1:10) to afford 800 g (44%) of 1.2 as a yellow solid.

Synthesis of Compound 1.3.

A 10-L 4-necked round-bottom flask, purged and maintained under an inert atmosphere of nitrogen, was charged with 1.2 (800 g, 2.82 mol, 1.00 equiv) and formamide (8 L). The resulting solution was stirred for 5 h at 180° C. The reaction mixture was cooled to room temperature with a water bath. The resulting solution was diluted with 10 L of water/ice. The solution was extracted with 3×5 L of ethyl acetate and the organic layers were combined. The mixture was washed with 2×5 L of brine, dried over anhydrous sodium sulfate and concentrated under vacuum. The residue was loaded onto a silica gel column and eluted with ethyl acetate/petroleum ether (1:1) to afford 350 g (47%) of ethyl 12-hydroxy-7-thia-9,11-diazatricyclo[6.4.0.0^[2,6]]dodeca-1(8),2(6),9,11-tetraene-3-carboxylate 1.3 as a light yellow solid.

Synthesis of Compound 1.4.

A 5-L 4-necked round-bottom flask, purged and maintained under an inert atmosphere of nitrogen, was charged with 1.3 (350 g, 1.32 mol, 1.00 equiv) and POCl₃ (1800 mL).

The resulting solution was stirred for 1 h at 110° C. in an oil bath. The reaction mixture was cooled to room temperature with a water bath. The mixture was concentrated under vacuum. The reaction was then quenched by the addition of 1 L of water/ice. The solution was extracted with 2×500 mL of ethyl acetate and the organic layers were combined. The mixture was washed with 1×500 mL of brine and the residue loaded onto a silica gel column and eluted with ethyl acetate/petroleum ether (1:5) to afford 260 g (69%) of intermediate 1.4 as a white solid.

Example 2

Synthesis of Intermediate 2.5. (I-11); I-3 (2.2), (I-9) (2.4), I-1 (2.1)

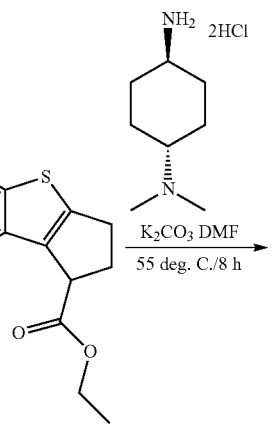

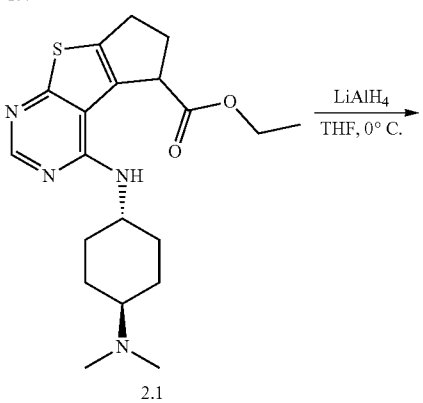

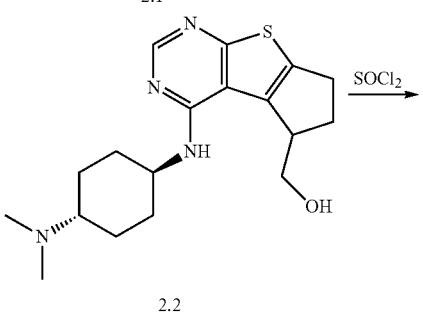

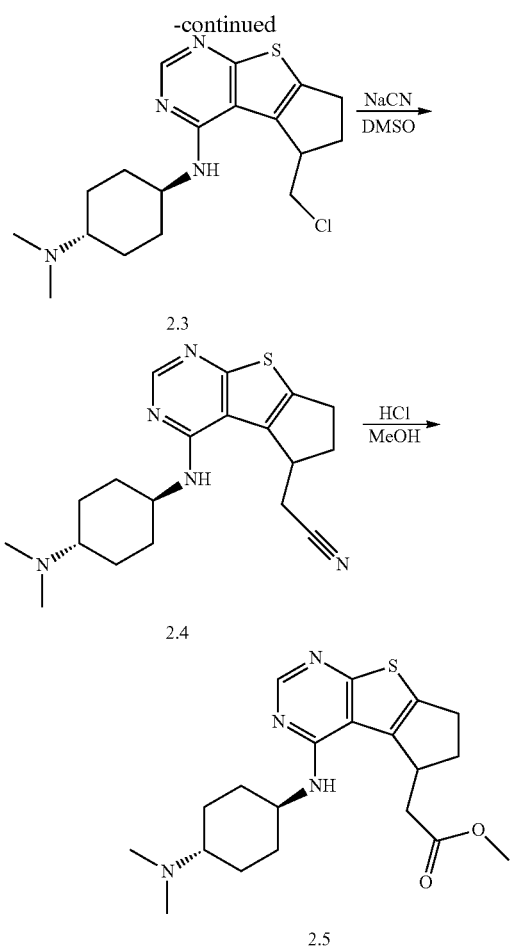

Synthesis of Compound 2.1.

A 50-mL round-bottom flask was charged with intermediate 1.4 (1.79 g, 6.20 mmol, 1.00 equiv, 98%), N,N-dimethylformamide (15 mL), 1-N,1-N-dimethylcyclohexane-1,4-diamine dihydrochloride (1.63 g, 7.58 mmol, 1.81 equiv), and potassium carbonate (3.5 g, 24.82 mmol, 4.01 equiv, 98%). The resulting solution was stirred for 8 h at 55° C. in an oil bath. The reaction's progress was monitored by TLC/LC-MS (ethyl acetate/petroleum ether=1/5). The reaction was then quenched by the addition of 50 mL of water. The resulting solution was extracted with 3×30 mL of ethyl acetate and the organic layers combined. The resulting mixture was washed with 2×20 mL of water. The mixture was dried over anhydrous sodium sulfate and concentrated under vacuum to afford 2.1 g (87%) of 2.1 as a yellow oil.

Synthesis of Compound 2.2.

To a solution of compound 2.1 (0.66 g, 1.7 mmol) in THF (30 mL) was added LiAlH$_4$ (258 mg, 6.8 mmol) in portions at 0° C. The mixture was allowed to warm to r.t. with stirring for 2 hours, and then Na$_2$SO$_4$.10H$_2$O (2.2 g, 6.8 mmol) was added. The suspension was stirred for 2 hours and filtered. The filtrate was concentrated and the residue was purified by silica gel column chromatography with MeOH/DCM (1:10) to give a white solid product (450 mg, 76%). MS: m/z 347 (M+H)$^+$.

Synthesis of Compound 2.3.

Compound 2.2 (1.9 g, 5.5 mmol, 1 equiv) was dissolved in SOCl$_2$ (30 ml). The mixture was stirred at room temperature overnight, whereupon the SOCl$_2$ was removed under vacuum. The residue was quenched by the addition of aqueous NaHCO$_3$. The mixture was extracted with CH$_2$Cl$_2$ (3×100 ml). The combined CH$_2$Cl$_2$ layers were washed with brine, dried with Na$_2$SO$_4$, filtered and concentrated. The residue was used in the next step without further purification (1.8 g, 91%). MS: m/z 365 (M+H)$^+$.

Synthesis of Compound 2.4.

NaCN (450 mg, 9 mmol, 2 equiv) was dissolved in DMSO (10 ml) at 60° C. Then compound 2.3 (1.65 g, 4.5 mmol, 1 equiv) was added. The mixture was heated to 70° C. and stirred at this temperature for 5 hours, whereupon the mixture was cooled to room temperature and aqueous NaHCO$_3$ (20 ml) was added. The mixture was extracted with CH$_2$Cl$_2$ (3×30 ml). The CH$_2$Cl$_2$ phase was washed with brine, dried with Na$_2$SO$_4$, filtered and concentrated. The residue was purified on silica gel to give the desired product (1.15 g, 74%). MS: m/z 356 (M+H)$^+$.

Synthesis of Intermediate 2.5.

SOCl$_2$ (10 ml) was added to MeOH (40 ml) under cooling with an ice bath. After the addition was complete, the mixture was stirred for 1 hour, whereupon compound 2.4 (1.1 g, 3 mmol) was added to the solution. The mixture was heated to 70° C. and stirred at this temperature for 16 hours at which point the MeOH was removed and water was added. NaHCO$_3$ was added to the mixture to adjust the pH to greater than 7. The mixture was extracted by CH$_2$Cl$_2$ (50 ml). The CH$_2$Cl$_2$ phase was washed with brine, dried with Na$_2$SO$_4$, filtered and concentrated. The residue was purified on silica gel to give the desired product (600 mg, 55%).

Example 3

Synthesis of Intermediate 3.1. (I-18 HCl)

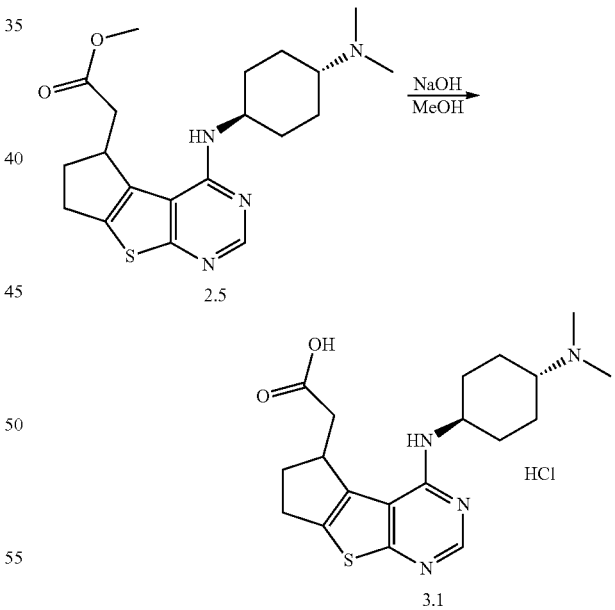

A 50-mL round-bottom flask was charged with a solution of intermediate 2.5 (500 mg, 1.29 mmol, 1.00 equiv) and sodium hydroxide (130 mg, 3.25 mmol, 2.53 equiv) in methanol (10 mL). The reaction was stirred for 5 h at 50° C. The resulting mixture was concentrated under vacuum to afford a solution that was then diluted with 20 mL of water. The resulting mixture was washed with 2×20 mL of dichloromethane in a reparatory funnel. The pH value of the aqueous layer was adjusted to 3 with 6N HCl. Concentration of the solution under vacuum afforded 0.6 g (crude) of intermediate 3.1 as a yellow solid that was used without further purification.

Example 4

Intermediate 4.1. (I-18 Free Base)

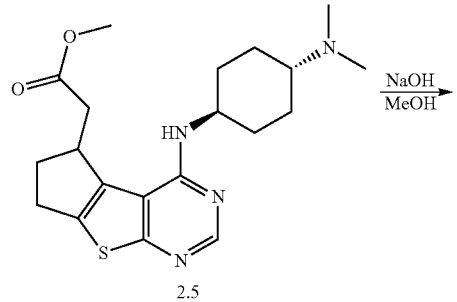

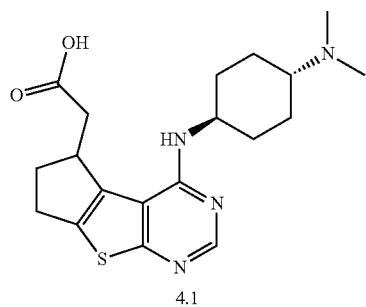

To a solution of 2.5 (1 g, 2.57 mmol) in THF (5 mL) and MeOH (5 mL) was added a solution of NaOH (1 g, 25.7 mmol) in H$_2$O (5 mL). The mixture was stirred for 15 hours at r.t. At this time the pH was adjusted to 5 with HCl (1 M) and the desired product was purified by reverse phase chromatography (Biotage) to give a white solid (500 mg, 52%). $^1$H NMR (500 MHz, D$_2$O) δ 7.958 (s, 1H), 3.755 (m, 1H), 3.479-3.468 (m, 1H), 3.197 (t, 1H), 2.861 (m, 1H), 2.748 (s, 7H), 2.503 (m, 1H), 2.190-2.009 (m, 7H), 1.584-1.420 (m, 4H). MS: m/z 347 (M+H)$^+$.

Example 5

Synthesis of (1r,4r)-N1,N1-dimethyl-N4-(5-(pyrrolidin-1-ylmethyl)-6,7-dihydro-5H-cyclopenta[4,5]thieno[2,3-d]pyrimidin-4-yl)cyclohexane-1,4-diamine (I-10)

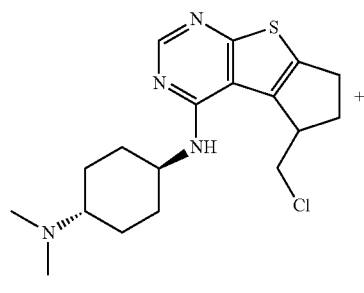

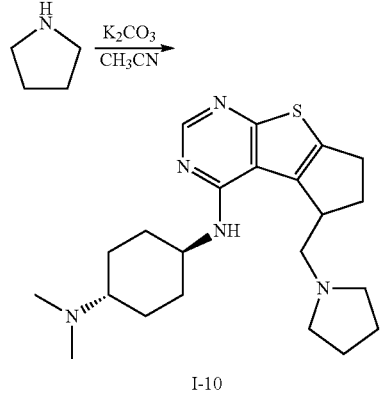

Compound 2.3 (prepared as in Example 2; 150 mg, 0.4 mmol, 1 equiv) was dissolved in CH$_3$CN. Then pyrrolidine (175 mg, 2.5 mmol, 6 equiv) and K$_2$CO$_3$ (110 mg, 0.8 mmol, 2 equiv) were added. The mixture was heated to 80° C. and stirred at this temperature for 5 hours. The CH$_3$CN was removed in vacuo. The residue was purified by preparative HPLC to give Compound I-10 (40 mg, 20%). $^1$H NMR (500 MHz, CDCl$_3$) δ 8.35 (1H, s), 8.18-8.20 (1H, d), 4.10-4.13 (1H, m), 3.40-3.41 (1H, m), 2.94-3.01 (1H, m), 2.70-2.87 (2H, m), 2.56-2.68 (6H, m), 2.31 (6H, m), 2.23-2.30 (2H, m), 2.10-2.13 (2H, m), 1.95-1.93 (2H, m), 1.74-1.83 (4H, m), 1.45-1.51 (2H, m), 1.16-1.38 (2H, m). MS: m/z 400 (M+H)$^+$.

Example 6

Synthesis of 2-(12-[[4-(dimethylamino)cyclohexyl]amino]-7-thia-9,11-diazatricyclo[6.4.0.0^[2,6]]dodeca-1(8),2(6),9,11-tetraen-3-yl)-N-ethylacetamide (I-23)

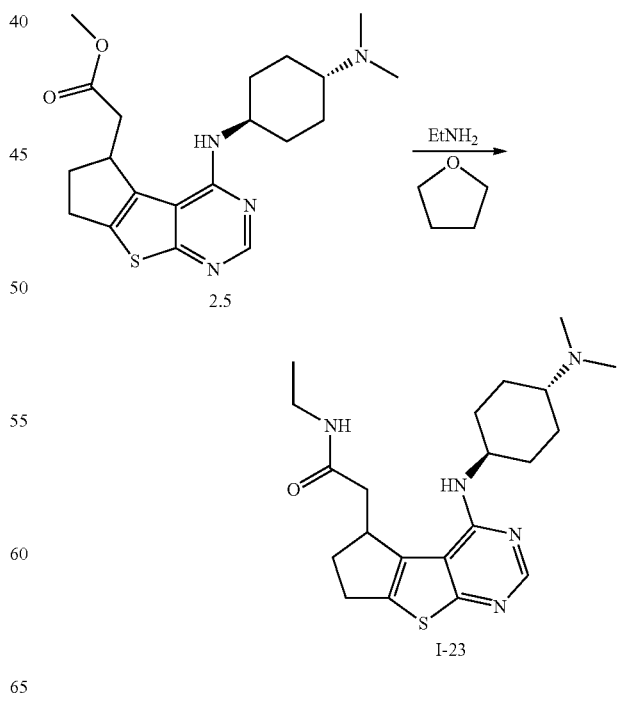

A 100-mL round-bottom flask was charged with a solution of intermediate 2.5 (220 mg, 0.57 mmol, 1.00 equiv) in tetrahydrofuran (4 mL) and ethylamine (65-70% in H₂O, 75 mL). This solution was stirred overnight at room temperature. The resulting mixture was concentrated under vacuum. The crude product (200 mg) was purified by preparative HPLC (column: Waters-1 Xbridge RP 19*150; mobile phase: 0.05% NH₄HCO₃ in H₂O (A) and CH₃CN (B); detector: 220 nm and 254 nm) to afford 62.4 mg (27%) of Compound I-23 as a white solid. ¹H NMR (400 MHz, CDCl₃) δ 8.36 (s, 1H), 5.91-5.89 (d, 1H), 5.39 (m, 1H), 3.83-3.81 (m, 1H), 3.39-3.22 (m, 3H), 3.08-2.72 (m, 2H), 2.38-2.32 (m, 9H), 2.20-2.16 (m, 3H). 1.99-1.97 (m, 2H), 1.48-1.45 (m, 4H), 1.12-1.07 (t, 3H). MS: m/z 400 (M+H)⁺.

Example 7

Synthesis of 2-(4-(((1r,4r)-4-(dimethylamino)cyclohexyl)amino)-6,7-dihydro-5H-cyclopenta[4,5]thieno[2,3-d]pyrimidin-5-yl)ethanol (I-12)

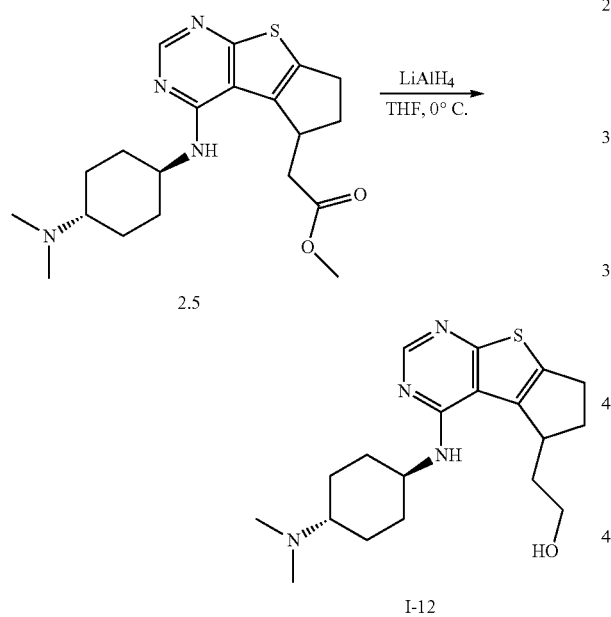

To a solution of 2.5 (0.66 g, 1.7 mmol) in THF (30 mL) was added LiAlH₄ (508 mg, 13.3 mmol) in portions at 0° C. The mixture was allowed to warm to r.t. with stirring for 2 hours. Then, Na₂SO₄·10H₂O (4.3 g, 13.3 mmol) was added and the suspension was stirred for 2 hours. The solids were filtered off and the filtrate was purified by silica gel column chromatography with MeOH/CH₂Cl₂=1:10 to give Compound I-12 as a white solid product (450 mg, 73%). ¹H NMR (500 MHz, CDCl₃) δ 8.365 (1H, s), 5.850-5.834 (1H, d), 4.169-4.138 (1H, m), 3.753-3.716 (2H, m), 3.570-3.563 (1H, t), 3.073-3.022 (1H, m), 2.920-2.869 (1H, m), 2.705-2.663 (1H, m), 2.391 (1H, m), 2.341 (6H, s), 2.274-2.145 (4H, m), 1.971-1.948 (2H, m), 1.805-1.714 (2H, m), 1.503-1.362 (4H, m). MS: m/z 347 (M+H)⁺.

Example 8

Synthesis of 2-(12-[[4-(dimethylamino)cyclohexyl]amino]-7-thia-9,11-diazatricyclo[6.4.0.0^[2,6]]dodeca-1(8),2(6),9,11-tetraen-3-yl)-N-(2-hydroxyethyl)acetamide (I-26)

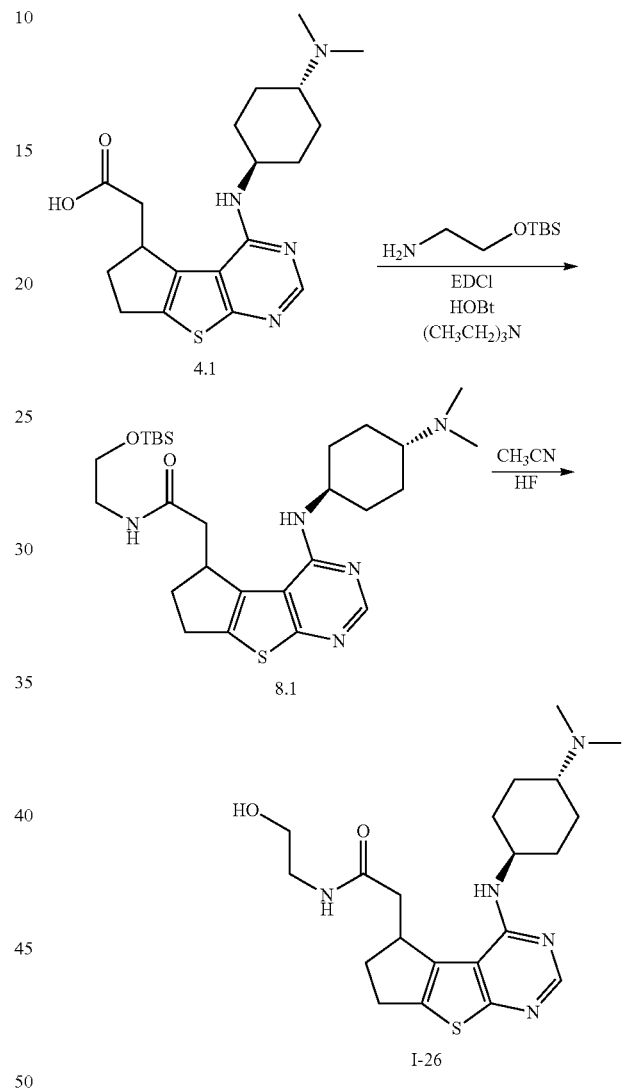

Synthesis of Compound 8.1.

A 50-mL round-bottom flask was charged with intermediate 4.1 (80 mg, 0.21 mmol, 1.00 equiv) in DMF (10 mL), HOBT (35 mg, 0.26 mmol, 1.20 equiv), EDCI (81 mg, 2.00 equiv), (2-aminoethoxy)(tert-butyl)dimethylsilane (93 mg, 0.53 mmol, 2.50 equiv) and triethylamine (65 mg, 0.64 mmol, 3.00 equiv). This solution was stirred overnight at room temperature. The resulting mixture was concentrated under vacuum to afford 80 mg (crude) of compound 8.1 as a white solid that was used without further purification.

Synthesis of Compound I-26.

A 50-mL round-bottom flask was charged with a solution of 8.1 (80 mg, 0.15 mmol, 1.00 equiv) in CH₃CN (5 mL). HF (40 wt. % in water, 0.25 mL) was added and the solution was stirred overnight at room temperature. The resulting mixture was concentrated under vacuum. The crude product was purified by preparative HPLC (column: Waters-1 Xbridge RP 19*150; mobile phase: 0.05% NH₄HCO₃ in H₂O (A), CH₃CN (B); detector: UV 220 nm and 254 nm) to afford 4.5 mg (7%) of Compound I-26 as a white solid. $^1$H NMR (400 MHz, CDCl₃) δ 8.38 (s, 1H), 5.97 (s, 1H), 5.86-5.87 (d, 1H), 4.12 (s, 1H), 3.95-3.81 (d, 1H), 3.80-3.60 (s, 2H), 3.60-3.30 (m, 2H), 3.20-3.00 (m, 1H), 3.00-2.87 (m, 1H), 2.86-2.70 (m, 1H), 2.50-2.30 (m, 1H) 2.27-2.10 (m, 3H), 1.90-2.70 (m, 1H) 1.60-1.20 (m, 4H). MS: m/z 400 (M+H)⁺.

Example 9

Synthesis of 2-(12-[[4-(dimethylamino)cyclohexyl]amino]-7-thia-9,11-diazatricyclo[6.4.0.0^[2,6]]dodeca-1(8),2(6),9,11-tetraen-3-yl)-N-(2-hydroxyethyl)acetamide (I-27)

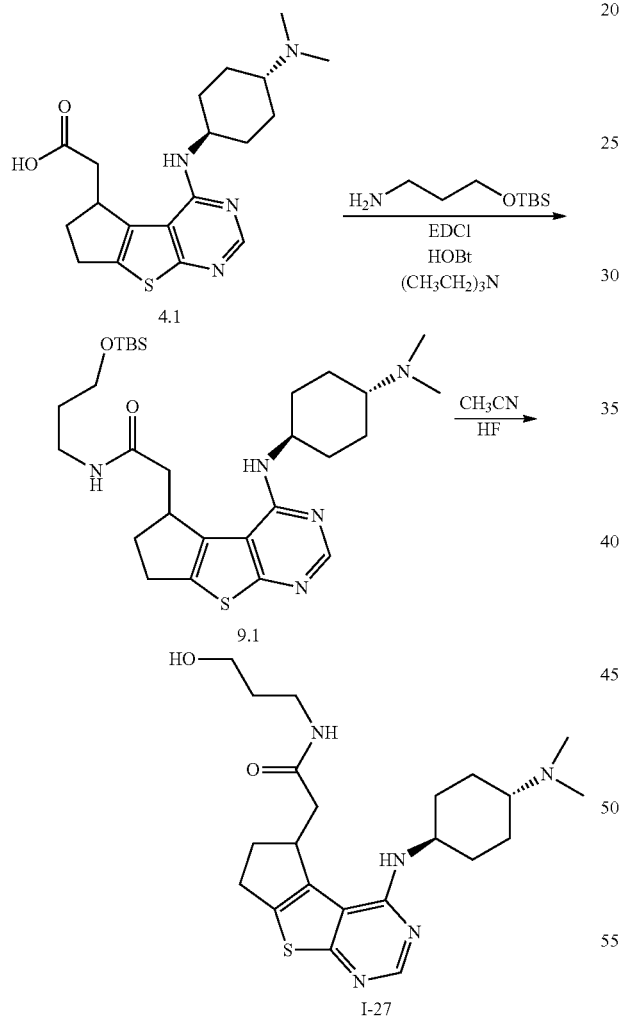

Synthesis of Compound 9.1.

A 50-mL round-bottom flask was charged with a solution of intermediate 4.1 (83 mg, 0.22 mmol, 1.00 equiv), N,N-dimethylformamide (12 mL), EDCI (83 mg, 0.43 mmol, 2.00 equiv), HOBT (35 mg, 0.26 mmol, 1.20 equiv), (3-aminopropoxy)(tert-butyl)dimethylsilane (120 mg, 0.63 mmol, 2.90 equiv), and triethylamine (65 mg, 0.64 mmol, 3.00 equiv). This solution was stirred overnight at room temperature. The resulting mixture was concentrated under vacuum to afford 100 mg (crude) of 9.1 as a white solid that was used without further purification.

Synthesis of Compound I-27.

A 50-mL round-bottom flask was charged with 9.1 (100 mg, 0.18 mmol, 1.00 equiv) in CH₃CN (5 mL). This was followed by the addition of HF (40 wt. % in water, 0.25 mL) dropwise with stirring. This solution was stirred overnight at room temperature. The resulting mixture was concentrated under vacuum to afford 11.8 mg (15%) of I-27 as a white solid. $^1$H NMR (400 MHz, CDCl₃) δ 8.40 (s, 1H), 6.10-5.90 (s, 1H), 5.90-5.80 (d, 1H), 4.20-4.00 (s, 1H), 3.95-3.81 (d, 1H), 3.70-3.55 (m, 2H), 3.55-3.45 (m, 1H), 3.45-3.30 (m, 1H), 3.30-3.00 (m, 1H), 3.00-2.85 (m, 1H), 2.85-2.70 (m, 1H) 2.50-2.30 (m, 9H), 2.39-2.15 (m, 3H) 2.16-1.90 (m, 2H), 1.90-1.60 (m, 2H), 1.58-1.40 (m, 4H). MS: m/z 434 (M+H)⁺.

Example 10

Synthesis of 2-(4-(((1r,4r)-4-(dimethylamino)cyclohexyl)amino)-6,7-dihydro-5H-cyclopenta[4,5]thieno[2,3-d]pyrimidin-5-yl)acetamide (I-13)

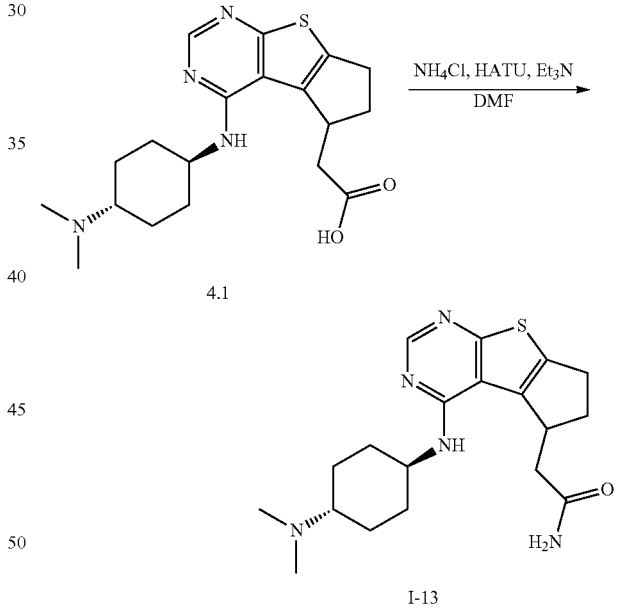

A mixture of intermediate 4.1 (200 mg, 0.5 mmol, 1 equiv), NH₄Cl (200 mg, 4 mmol, 8 equiv), TEA (500 mg, 5 mmol, 10 equiv) and HATU (380 mg, 1 mmol, 2 equiv) in DMF (3 mL) was stirred at 20° C. for 24 h. The mixture was purified by preparative HPLC to afford Compound I-13 (60 mg, 20%). $^1$H NMR (500 MHz, CDCl₃) δ 8.37 (1H, s), 5.82 (1H, m), 5.37-5.45 (2H, m), 4.10-4.13 (1H, m), 3.85-3.87 (1H, m), 3.03-3.08 (1H, m), 2.90-2.95 (1H, m), 2.77-2.81 (1H, m), 2.45-2.47 (2H, m), 2.34 (6H, s), 2.17-2.24 (4H, m), 1.98-1.99 (2H, m), 1.38-1.47 (4H, m). MS: m/z 374 (M+H)⁺.

Example 11

Synthesis of 2-(4-(((1r,4r)-4-(dimethylamino)cyclohexyl)amino)-6,7-dihydro-5H-cyclopenta[4,5]thieno[2,3-d]pyrimidin-5-yl)-1-(pyrrolidin-1-yl)ethanone (I-14)

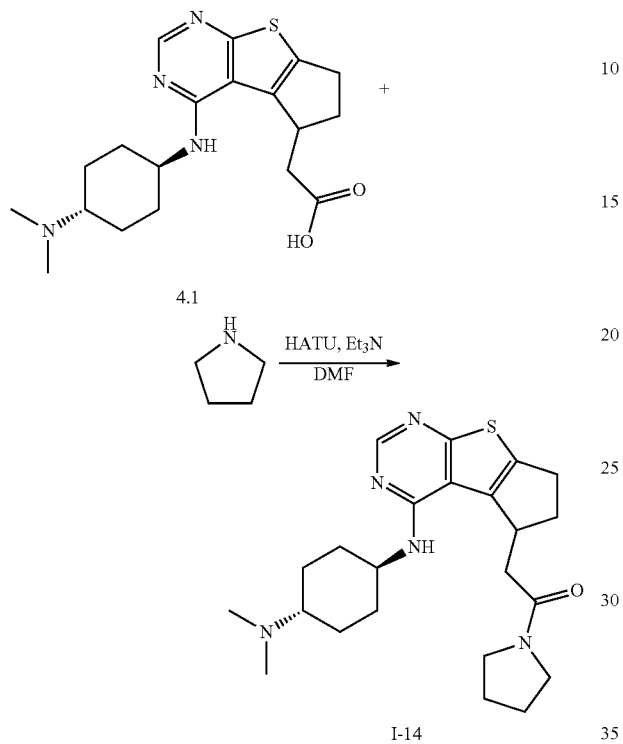

A mixture of 4.1 (200 mg, 0.5 mmol, 1 equiv), pyrrolidine (70 mg, 1 mmol, 2 equiv), TEA (150 mg, 1.5 mmol, 3 equiv) and HATU (200 mg, 0.5 mmol, 1 equiv) in DMF (3 mL) was stirred at 20° C. for 24 h. The mixture was purified by preparative HPLC to afford Compound I-14 (70 mg, 30%). $^1$H NMR (500 MHz, CDCl$_3$) δ 8.35 (1H, s), 6.26-6.28 (1H, d), 4.07-4.09 (1H, m), 3.93-3.95 (1H, m), 3.30-3.50 (3H, m), 3.04-3.09 (3H, m), 2.88-2.93 (1H, m), 2.75-2.80 (1H, m), 2.50-2.54 (1H, m), 2.31 (6H, s), 2.16-2.21 (4H, m), 1.75-1.96 (6H, m), 1.43-1.50 (4H, m). MS: m/z 428 (M+H)$^+$.

Example 12

Synthesis of 2-(4-(((1r,4S)-4-(dimethylamino)cyclohexyl)amino)-6,7-dihydro-5H-cyclopenta[4,5]thieno[2,3-d]pyrimidin-5-yl)-1-((S)-3-hydroxypyrrolidin-1-yl)ethanone (I-15)

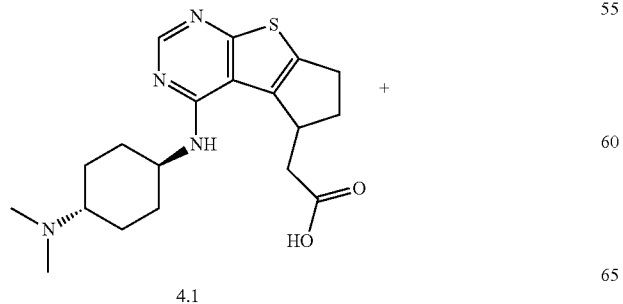

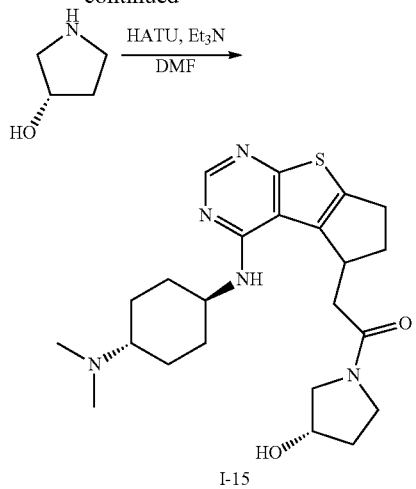

Compound I-15 was synthesized from intermediate 4.1 and (S)-pyrrolidin-3-ol in a manner consistent with Example 9 to afford Compound I-15 in 31% yield. $^1$H NMR (500 MHz, CDCl$_3$) δ 8.34 (1H, s), 6.14-6.32 (1H, m), 4.38-4.44 (1H, m), 4.02-4.13 (1H, m), 3.88-3.98 (1H, m), 3.42-3.69 (3H, m), 3.14-3.38 (1H, m), 3.05-3.12 (1H, m), 2.72-2.96 (2H, m), 2.42-2.61 (2H, m), 2.30 (7H, m), 2.16-2.23 (2H, m), 1.78-2.04 (5H, m), 1.34-1.50 (4H, m). MS: m/z 444 (M+H)$^+$.

Example 13

Synthesis of 2-(4-(((1r,4R)-4-(dimethylamino)cyclohexyl)amino)-6,7-dihydro-5H-cyclopenta[4,5]thieno[2,3-d]pyrimidin-5-yl)-1-((R)-3-hydroxypyrrolidin-1-yl)ethanone (I-16)

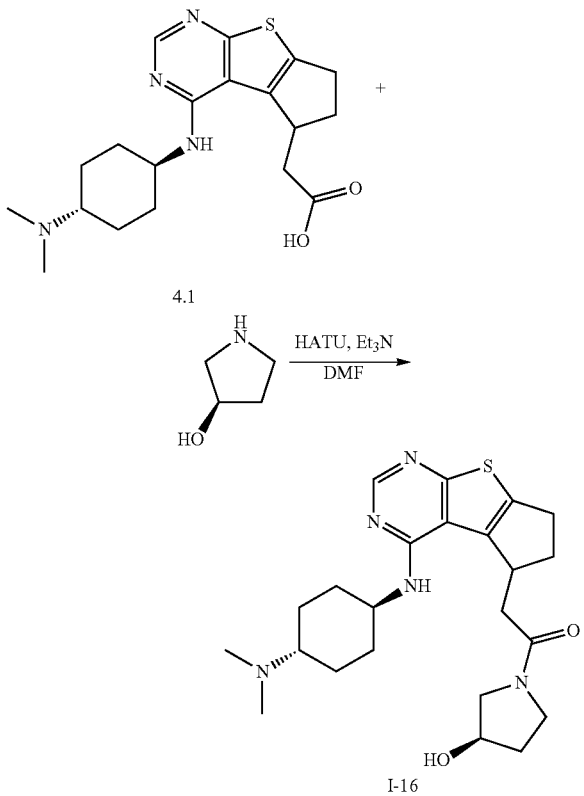

Compound I-16 was synthesized from intermediate 4.1 and (R)-pyrrolidin-3-ol in a manner consistent with Example 9 to afford Compound I-16 in 46% yield. $^1$H NMR (500 MHz, CDCl$_3$) δ 8.34 (1H, s), 6.14-6.18 (1H, m), 4.38-4.44 (1H, m), 4.02-4.13 (1H, m), 3.88-3.98 (1H, m), 2.71-3.72 (7H, m), 2.42-2.61 (2H, m), 2.29 (7H, s), 2.14-2.23 (2H, m), 1.75-2.04 (4H, m), 1.68-1.74 (1H, m), 1.34-1.50 (4H, m). MS: m/z 444 (M+H)$^+$.

Example 14

Synthesis of 2-(12-[[4-(dimethylamino)cyclohexyl]amino]-7-thia-9,11-diazatricyclo[6.4.0.0ˆ[2,6]]dodeca-1(8),2(6),9,11-tetraen-3-yl)-N-(2-hydroxyethyl)-N-methylacetamide (I-30)

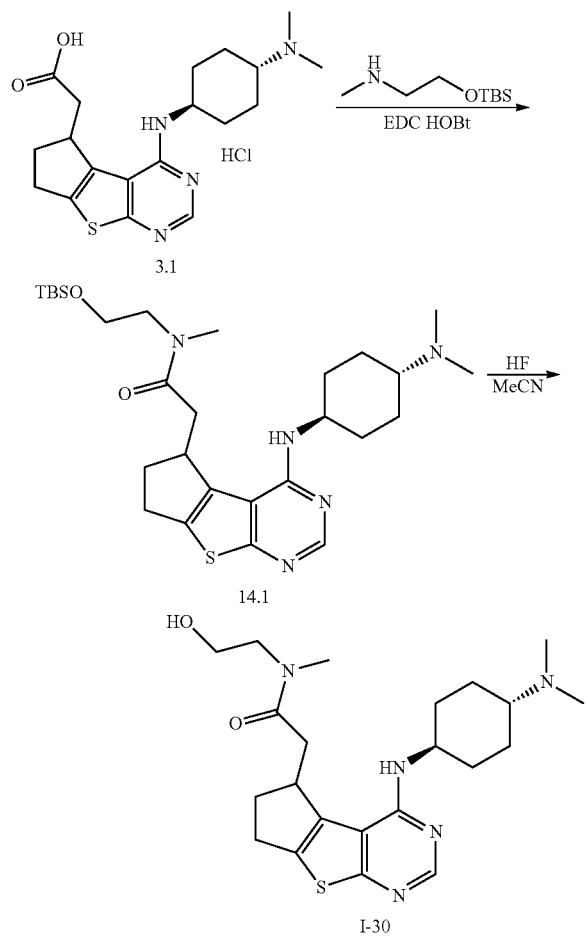

Synthesis of Compound 14.1.

A 100-mL round-bottom flask was charged with a solution of intermediate 3.1 (600 mg, 1.46 mmol, 1.00 equiv) in N,N-dimethylformamide (20 mL), 2-[(tert-butyldimethylsilyl)oxy]ethyl(methyl)amine (360 mg, 1.90 mmol, 1.30 equiv), HOBT (320 mg, 2.37 mmol, 1.62 equiv), EDC (920 mg, 4.82 mmol, 3.30 equiv), and TEA (810 mg, 8.00 mmol, 5.48 equiv). The resulting solution was stirred overnight at room temperature. The reaction was then quenched by the addition of 100 mL of water. The resulting solution was extracted with 3×50 mL of ethyl acetate and the organic layers combined. The combined organic layers were washed with 3×50 mL of brine, dried over anhydrous sodium sulfate and concentrated under vacuum. The residue was loaded onto a silica gel column with dichloromethane/methanol (elution gradient: 100:1-10:1 DCM:MeOH). Purification afforded 0.2 g (25%) of 14.1 as a yellow oil. MS: m/z 546 (M+H)$^+$.

Synthesis of Compound I-30.

A 50-mL round-bottom flask was charged with a solution of 14.1 (200 mg, 0.37 mmol, 1.00 equiv) in acetonitrile (5 mL) and hydrogen fluoride (40 wt % in water, 0.2 mL). After stirring for 5 h at room temperature, the resulting mixture was concentrated under vacuum. The crude product was purified by preparative HPLC [column: Xbridge Shield RP 18, 5 um, 19*150 mm; mobile phase: water (50 mM NH$_4$HCO$_3$) and CH$_3$CN (5.0% CH$_3$CN up to 45.0% in 8 min, hold for 2 min, ramp up to 100.0% in 1 min, then ramp down to 5.0% in 1 min); detector: UV 254 and 220 nm. 45.7 mg (29%) of I-30 were obtained as a white solid. $^1$H NMR (400 MHz, CDCl$_3$) δ 8.33 (d, 1H), 6.06-6.09 (m, 1H), 4.08 (s, 1H), 3.92-3.94 (m, 1H), 3.79-3.81 (m, 1H), 3.67-3.77 (m, 1H), 3.48-3.65 (m, 1H), 3.34-3.38 (m, 1H), 3.02-3.08 (m, 1H), 2.99 (s, 3H), 2.62-2.92 (m, 3H), 2.52-2.58 (m, 1H), 2.30 (s, 7H), 2.16-2.26 (m, 2H), 1.94 (s, 2H), 1.36-1.46 (m, 4H). MS: m/z 432 (M+H)$^+$.

Example 15

Synthesis of Intermediate 15.4

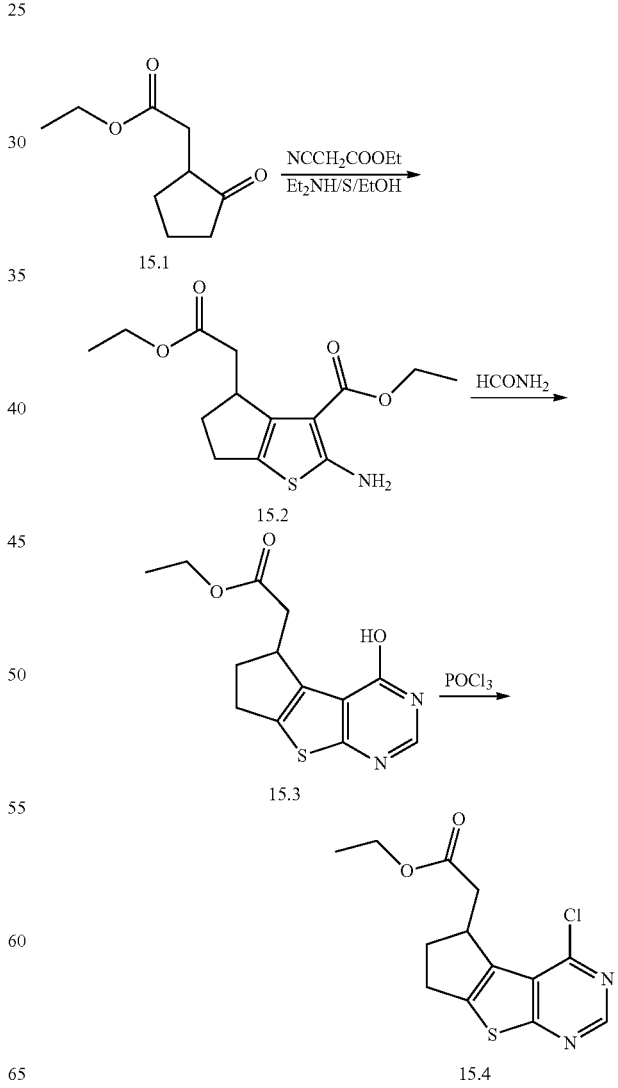

Synthesis of Compound 15.2.

Into a 10-L 4-necked round-bottom flask was placed a solution of ethyl 2-(2-oxocyclopentyl)acetate (15.1, 550 g, 3.23 mol, 1.00 equiv) in ethanol (2200 mL) at room temperature. This was followed by the addition of NCCH$_2$COOEt (440 g, 1.21 equiv), Et$_2$NH (291.5 g, 1.23 equiv) and S (126.5 g, 1.22 equiv) in portions at room temperature. The solution was stirred overnight at room temperature and then concentrated under vacuum. The resulting solution was diluted with 5000 mL of ethyl acetate and washed with 2×1000 mL of brine. The mixture was dried over anhydrous sodium sulfate and concentrated under vacuum. The residue was loaded onto a silica gel column with ethyl acetate/petroleum ether (1:10) and purified to afford 430 g (45%) of ethyl 2-amino-4-(2-ethoxy-2-oxoethyl)-4H,5H,6H-cyclopenta[b]thiophene-3-carboxylate (15.2) as an orange oil.

Synthesis of Compound 15.3.

To a 10-L 4-necked round-bottom flask, purged and maintained with an inert atmosphere of nitrogen, was added a solution of 15.2 (500 g, 1.68 mol, 1.00 equiv) in formamide (5 L) at room temperature. The resulting solution was stirred for 5 h at 180° C. in an oil bath. The reaction mixture was cooled to room temperature and then quenched by the addition of 10 L of water/ice. The resulting solution was extracted with 3×5 L of ethyl acetate and the organic layers were combined. The mixture was washed with 3×3000 mL of brine, dried over anhydrous sodium sulfate and concentrated under vacuum. The solids were collected by filtration to afford 200 g (43%) of ethyl 2-[12-hydroxy-7-thia-9,11-diazatricyclo[6.4.0.0^[2,6]]dodeca-1(8),2(6),9,11-tetraen-3-yl]acetate (15.3) as a yellow solid.

Synthesis of Intermediate 15.4.

Two 2000-mL 4-necked round-bottom flasks were charged with a solution of 15.3 (200 g, 718.58 mmol, 1.00 equiv) in POCl$_3$ (2000 mL) at room temperature. The resulting solution was stirred for 2 h at 110° C. in an oil bath. The reaction mixture was cooled to room temperature and concentrated under vacuum. The reaction was then quenched by the addition of 1000 mL of ice-water. The resulting solution was extracted with 3×500 mL of ethyl acetate and the organic layers were combined. The combined organic layers were washed with 2×500 mL of brine, dried over anhydrous sodium sulfate and concentrated under vacuum to afford 200 g (94%) of ethyl 2-[12-chloro-7-thia-9,11-diazatricyclo[6.4.0.0^[2,6]]dodeca-1(12),2(6),8,10-tetraen-3-yl]acetate (15.4) as a light yellow solid.

Example 16

Synthesis of 2-[(3S)-12-[[4-(dimethylamino)cyclohexyl]oxy]-7-thia-9,11-diazatricyclo[6.4.0.0[2,6]]dodeca-1(12),2(6),8,10-tetraen-3-yl]ethan-1-ol (I-33)

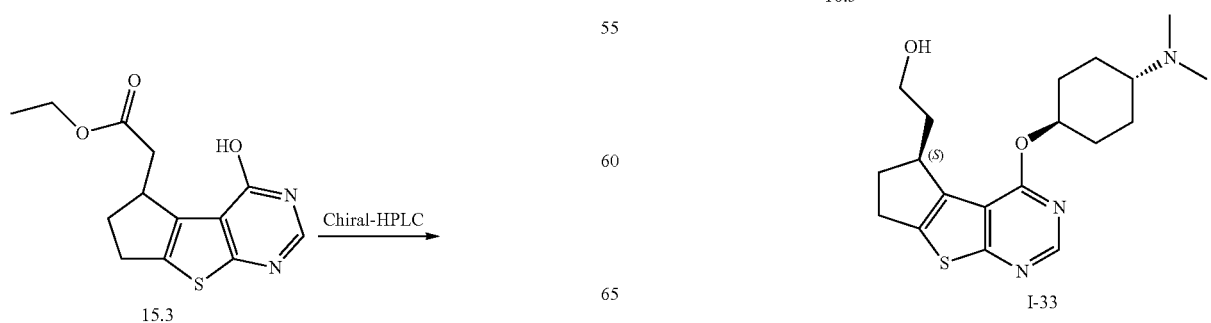

Synthesis of Compound 16.1.

The enantiomers of racemic 15.3 (4.7 g) were separated by chiral HPLC under the following conditions: column: CHIRALPAK IC, 0.46*25 cm, 5 um; mobile phase: Hex: EtOH=50:50; flow rate: 1.0 ml/min; UV detection at 254 nm. The first enantiomer to elute (16.2, $t_R$=7.76 min, 1.5 g) was obtained in 100% ee as a light yellow solid and the second enantiomer to elute (16.1, $t_R$=10.39 min, 1.4 g) was also obtained in 100% ee as a light yellow solid.

Synthesis of Compound 16.3.

To a 50-mL round-bottom flask was added ethyl 2-[(3S)-12-hydroxy-7-thia-9,11-diazatricyclo[6.4.0.0[2,6]]dodeca-1(12),2(6),8,10-tetraen-3-yl]acetate (16.2, 560 mg, 2.01 mmol, 1.00 equiv), dioxane (10 mL) and phosphoroyl trichloride (3.5 mL). The reaction was stirred for 4 h at 110° C. under nitrogen. After concentration under reduced pressure, the resulting solution was poured dropwise into saturated aqueous $NaHCO_3$ and extracted with ethyl acetate (3×50 mL). The combined organic layers were washed with brine and dried over sodium sulfate. After evaporation in vacuo, the residue was purified by column chromatography on silica gel with ethyl acetate/petroleum ether (1:7) to afford ethyl 2-[(3S)-12-chloro-7-thia-9,11-diazatricyclo[6.4.0.0[2,6]]dodeca-1(12),2(6),8,10-tetraen-3-yl]acetate (16.3, 550 mg, 92%) as a yellow oil.

Synthesis of Compound 16.4.

A solution of tert-butyl N-(4-hydroxycyclohexyl)carbamate (412 mg, 1.91 mmol, 1.10 equiv) in freshly distilled tetrahydrofuran (10 mL) was treated with sodium hydride (60% dispersion in mineral oil, 280 mg, 4.00 equiv) for 1 h at room temperature under nitrogen. To this mixture was then added a solution of 16.3 (510 mg, 1.72 mmol, 1.00 equiv) in dry tetrahydrofuran (5 mL) via syringe. After stirring overnight at room temperature, the reaction was then quenched with water and extracted with ethyl acetate (3×50 mL). The combined organic layers were washed with brine and dried over sodium sulfate. After filtration and concentration under reduced pressure, the residue was loaded onto a silica gel column with ethyl acetate/petroleum ether (1:2) and purified to afford ethyl 2-[(3S)-12-[(4-[[(tert-butoxy)carbonyl]amino]cyclohexyl)oxy]-7-thia-9,11-diazatricyclo[6.4.0.0^[2,6]]dodeca-1(12),2(6),8,10-tetraen-3-yl]acetate (16.4, 400 mg, 49%) as a yellow oil.

Synthesis of Compound 16.5.

To a 50-mL round-bottom flask containing 16.4 (180 mg, 0.38 mmol, 1.00 equiv) in distilled tetrahydrofuran (10 mL) was added $LiAlH_4$ (30 mg, 0.79 mmol, 2.00 equiv) at 0° C. under nitrogen. The resulting solution was stirred for 30 min at room temperature. The reaction was then quenched with water and extracted with ethyl acetate (3×20 mL). The combined organic layers were washed with brine and dried over anhydrous sodium sulfate and concentrated under vacuum to afford tert-butyl N-(4-[[(3S)-3-(2-hydroxyethyl)-7-thia-9,11-diazatricyclo[6.4.0.0[2,6]]dodeca-1(12),2(6),8,10-tetraen-12-yl]oxy]cyclohexyl)carbamate (16.5, 100 mg, 61%) as a yellow oil. MS: m/z 434 $(M+H)^+$.

Synthesis of Compound I-33.

To a 25-mL round-bottom flask containing a solution of 16.5 (100 mg, 0.23 mmol, 1.00 equiv) in methanol (5 mL) was added HCHO (37%, 1 mL) and HCOOH (5 mL) at room temperature under nitrogen. The resulting solution was stirred overnight at 100° C. and evaporated under reduced pressure. The crude product (80 mg) was purified by preparative HPLC(SHIMADZU) under the following conditions: column: SunFire Prep C18, 19*150 mm 5 um; mobile phase: water (0.05% $NH_4HCO_3$) and $CH_3CN$ (start at 7.0% $CH_3CN$ then ramp up to 63.0% in 13 min); UV detection at 254 and 220 nm. The product-containing fractions were collected and the solvents evaporated to afford Compound I-33 (8 mg) as a colorless oil. An ee of 100% was measured by chiral-SFC analysis. $^1H$ NMR (300 MHz, $CDCl_3$) δ 7.26 (s, 1H), 5.24 (m, 1H), 3.72 (t, 1H), 3.47 (m, 1H), 3.08 (m, 2H), 2.70 (m, 1H), 2.03-2.68 (m, 11H), 1.25-1.81 (m, 9H). MS: m/z 362 $(M+H)^+$.

Example 17

Synthesis of 2-[(3R)-12-[[4-(dimethylamino)cyclohexyl]oxy]-7-thia-9,11-diazatricyclo[6.4.0.0[2,6]]dodeca-1(12),2(6),8,10-tetraen-3-yl]ethan-1-ol (I-34)

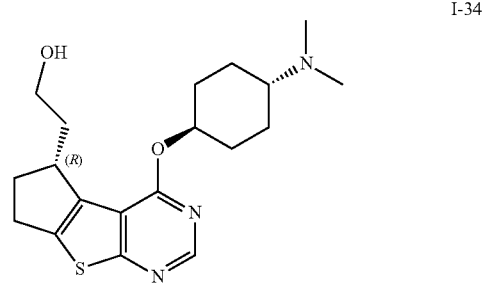

I-34

Compound I-34 was synthesized in a manner consistent with Example 16, except that 16.1 was used rather than 16.2. $^1H$ NMR (300 MHz, $CDCl_3$) δ 7.26 (s, 1H), 5.24 (m, 1H), 3.75 (t, 1H), 3.47 (m, 1H), 3.08 (m, 2H), 2.70 (m, 1H), 2.03-2.68 (m, 13H), 1.25-1.80 (m, 6H). MS: m/z 362 $(M+H)^+$.

Example 18

Intermediate 18.3

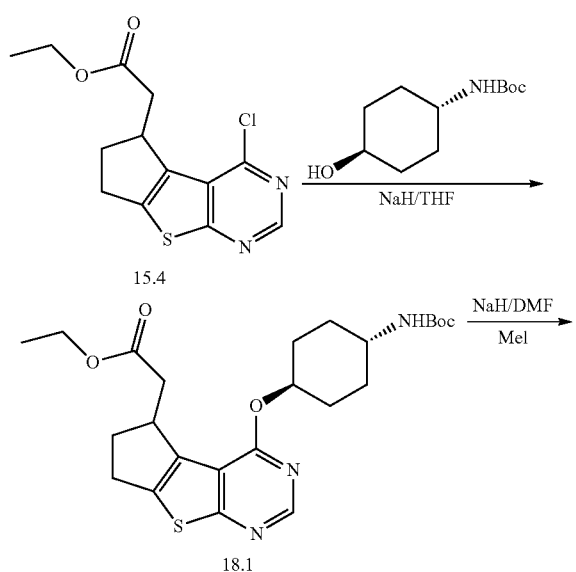

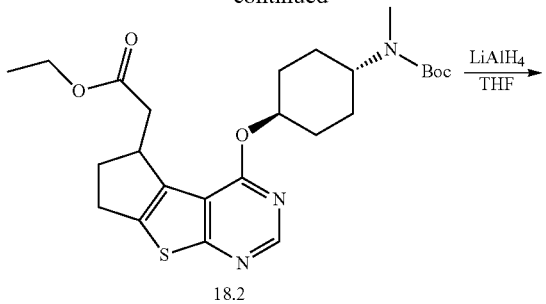

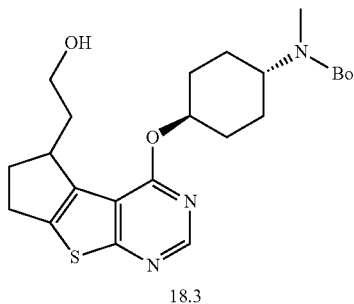

Synthesis of compound 18.1.

To a solution of tert-butyl N-(4-hydroxycyclohexyl)carbamate (710 mg, 3.30 mmol, 1.10 equiv) in 10 mL of distilled THF was added sodium hydride (60% dispersion in mineral oil, 720 mg, 18.00 mmol, 6.00 equiv) at room temperature under nitrogen. After stirring for 30 min, intermediate 15.4 (891 mg, 3.00 mmol, 1.00 equiv) in THF (10 mL) was added via syringe and the resulting solution was stirred for 12 h at room temperature. The reaction was then quenched by the addition of water and extracted with 3×50 mL of ethyl acetate. The combined organic layers were washed with brine, dried over anhydrous sodium sulfate and concentrated under vacuum. The residue was loaded onto a silica gel column with ethyl acetate/petroleum ether (1:4 to 1:2). Purification afforded 18.1 (260 mg, 18%) as a white solid.

Synthesis of Compound 18.2.

To a 50-mL round-bottom flask containing a solution of 18.1 (415 mg, 0.87 mmol, 1.00 equiv) in distilled DMF (10 mL) was added sodium hydride (60% dispersion in mineral oil, 225 mg, 6.5 mmol) at 0° C. and the reaction mixture was stirred for 30 min under nitrogen. Then MeI (1.2 g) was added via syringe and the resulting solution was stirred overnight at room temperature. The reaction was then quenched with water and extracted with 3×50 mL of ethyl acetate. The organic layers were combined, washed with brine and dried over anhydrous sodium sulfate. After concentration under reduced pressure, the residue was loaded onto a silica gel column with ethyl acetate/petroleum ether (1:5) to afford 18.2 (278 mg, 65%) as a yellow oil.

Synthesis of Compound 18.3.

LiAlH$_4$ (980 mg, 25.8 mmol) was treated with 18.2 (278 mg, 0.57 mmol, 1.00 equiv) in 20 mL of distilled THF in an ice/salt bath under nitrogen. Then the resulting solution was stirred for 2 h at room temperature and the reaction was quenched by the addition of methanol and diluted with water. The resulting solution was extracted with 100 mL of ethyl acetate and the organic layer was washed with brine and dried over anhydrous sodium sulfate. After concentration in vacuo, the desired tert-butyl N-(4-[[3-(2-hydroxyethyl)-7-thia-9,11-diazatricyclo[6.4.0.0[2,6]]dodeca-1(8),2(6),9,11-tetraen-12-yl]oxy]cyclohexyl)-N-methylcarbamate (18.3, 251 mg, 99%) was obtained as a yellow oil.

Example 19

Synthesis of 4-[[3-(2-ethoxyethyl)-7-thia-9,11-diazatricyclo[6.4.0.0[2,6]]dodeca-1(8),2(6),9,11-tetraen-12-yl]oxy]-N,N-dimethylcyclohexan-1-amine (I-31)

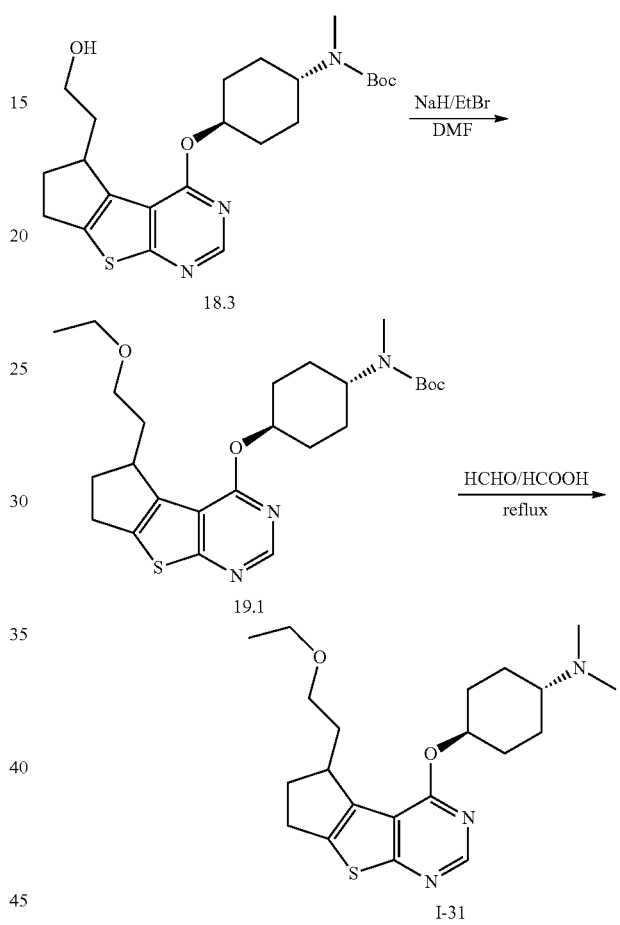

Synthesis of Compound 19.1.

To a 25-mL round-bottom flask was added a solution of intermediate 18.3 (125 mg, 0.28 mmol, 1.00 equiv) in distilled DMF (10 mL) followed by sodium hydride (60% dispersion in mineral oil, 96 mg, 2.80 mmol) at 0° C. and the reaction mixture was stirred for 30 min. Then bromoethane (305 mg, 2.80 mmol) was added and the resulting solution was stirred overnight at room temperature. The reaction was then quenched with water and extracted with 100 mL of ethyl acetate. The organic layer was washed with brine and dried over anhydrous sodium sulfate and concentrated under vacuum. The residue was loaded onto a silica gel column with EtOAc/petroleum ether (1:5). Purification afforded tert-butyl N-(4-[[3-(2-ethoxyethyl)-7-thia-9,11-diazatricyclo[6.4.0.0 [2,6]]dodeca-1(8),2(6),9,11-tetraen-12-yl]oxy]cyclohexyl)-N-methylcarbamate (19.1, 19 mg, 14%) as a colorless oil.

Synthesis of Compound I-31.

A 25-mL round-bottom flask containing 19.1 (19 mg, 0.04 mmol, 1.00 equiv), formic acid (1 mL) and formaldehyde (37%, 5 mL) was heated at 100° C. for 12 h in an oil bath under nitrogen. The mixture was concentrated under reduced pressure and the residue (45 mg) purified by preparative HPLC(SHIMADZU) under the following conditions: column: Xbridge Prep C18, 19*150 mm 5 um; mobile phase: water (0.05% NH$_4$HCO$_3$) and CH$_3$CN (5.0% CH$_3$CN up to 53.0% in 16 min); UV detection at 254 and 220 nm. The product-containing fractions were collected and evaporated under reduced pressure to afford compound I-31 (5.7 mg, 37%) as an off-white oil. $^1$H NMR (300 MHz, CDCl$_3$) δ 1.20 (m, 3H), 1.54 (m, 4H), 1.61 (m, 1H), 2.02-2.80 (m, 14H), 2.28-3.10 (m, 2H), 3.48 (m, 5H), 5.24 (m, 1H), 8.50 (s, 1H). MS: m/z 390 (M+H)$^+$.

Example 20

Synthesis of 4-[[3-(2-methoxyethyl)-7-thia-9,11-diazatricyclo[6.4.0.0[2,6]]dodeca-1(8),2(6),9,11-tetraen-12-yl]oxy]-N,N-dimethylcyclohexan-1-amine (I-32)

acetate. The organic layer was washed with brine and dried over anhydrous sodium sulfate and concentrated under vacuum. The residue was loaded onto a silica gel column with EtOAc/petroleum ether (1:5) and purified to afford 20.1 (50 mg, 61%) as a colorless oil.

Synthesis of Compound I-32.

A solution of 20.1 (50 mg, 0.11 mmol, 1.00 equiv) in formaldehyde (37%, 5 mL) and formic acid (1 mL) was stirred for 12 h at 100° C. in an oil bath under nitrogen. The mixture was concentrated under vacuum and the crude product (50 mg) was purified by preparative HPLC(SHIMADZU) under the following conditions: column: Xbridge Prep C18, 19*150 mm 5 um; mobile phase: water (0.05% NH$_4$HCO$_3$) and CH$_3$CN (5.0% CH$_3$CN up to 55.0% in 15 min); UV detection at 254 and 220 nm. The product-containing fractions were collected and evaporated under reduced pressure to afford Compound I-32 (17.1 mg, 42%) as a colorless oil. $^1$H NMR (300 MHz, CDCl$_3$) δ 1.47 (m, 4H), 1.76 (m, 1H), 1.98 (m, 2H), 2.20-2.32 (m, 11H), 2.66 (m, 1H), 2.94 (m, 1H), 3.07 (m, 1H), 3.30 (s, 3H), 3.42 (m, 3H), 5.23 (m, 1H), 8.50 (s, 1H). MS: m/z 376 (M+H)$^+$.

Example 21

Synthesis of Intermediates 21.3 and 21.4

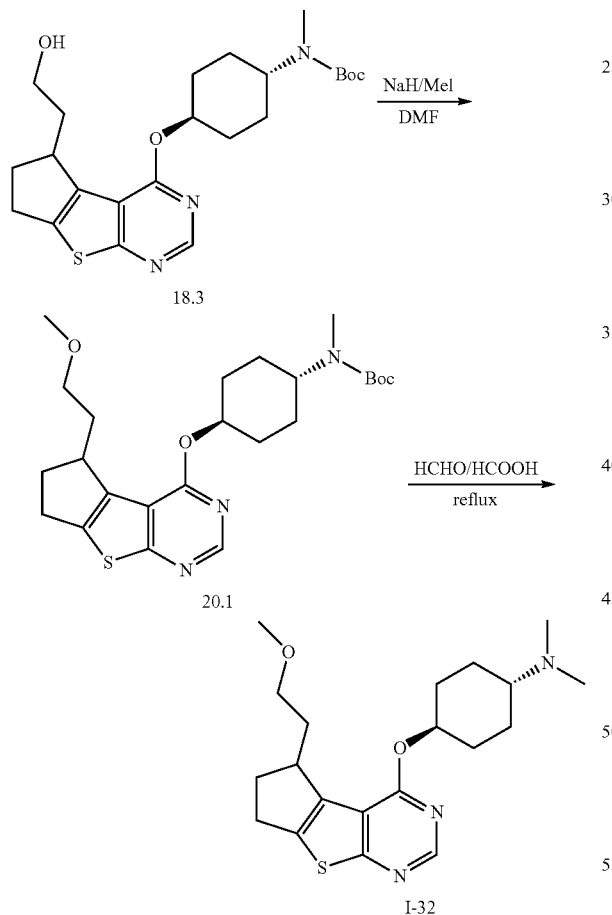

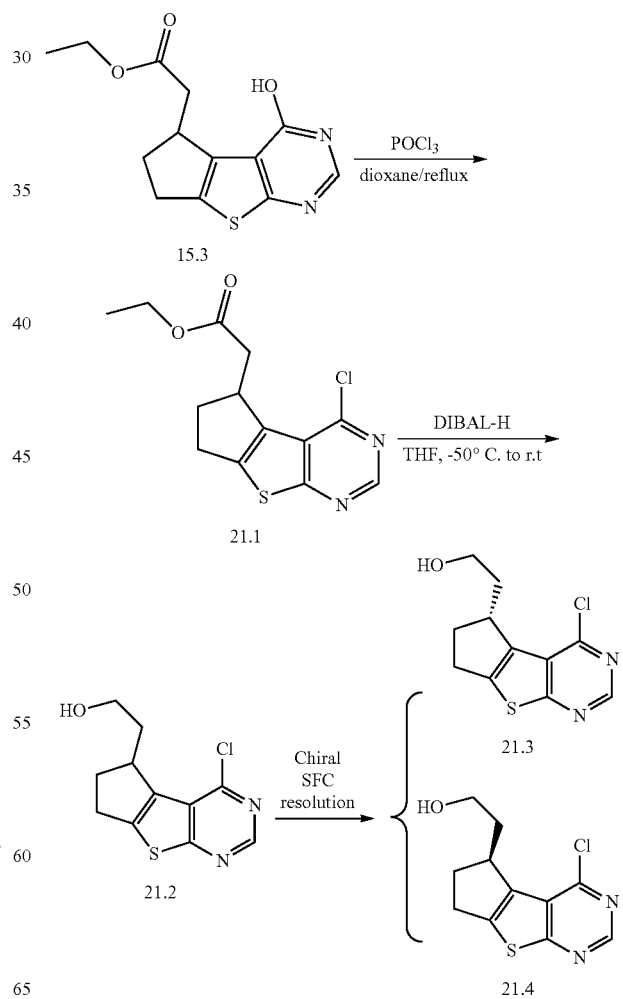

Synthesis of Compound 20.1.

To a 25-mL round-bottom flask was added a solution of intermediate 18.3 (80 mg, 0.18 mmol, 1.00 equiv) in distilled DMF (8 mL) followed by sodium hydride (60% dispersion in mineral oil, 36 mg, 0.90 mmol) at 0° C. and the reaction mixture was stirred for 30 min. Then iodomethane (255 mg, 1.80 mmol) was added and the resulting solution was stirred overnight at room temperature. The reaction was then quenched with water and extracted with 100 mL of ethyl

183

Synthesis of Compound 21.1.

A solution of 15.3 (15 g, 53.89 mmol, 1.00 equiv) and POCl₃ (100 mL) in 100 mL of dioxane was heated at reflux for 3 h under nitrogen. After concentration under reduced pressure, the resulting solution was poured dropwise into saturated aqueous NaHCO₃ and extracted with ethyl acetate (3×150 mL). The combined organic layers were washed with brine and dried over sodium sulfate. After evaporation in vacuo, the residue was purified by column chromatography on silica gel with ethyl acetate/petroleum ether (1:7) to afford 21.1 (15 g, 94%) as a light yellow oil. MS: m/z 297, 299 (M+H)⁺.

Synthesis of Compound 21.2.

To a 500-mL round-bottom flask under an atmosphere of nitrogen was added 21.1 (6 g, 20.22 mmol, 1.00 equiv) in 100 mL of distilled THF at −50° C. DIBAL-H (25% w/w in hexane, 50 mL) was added dropwise and the resulting solution was stirred for 2 h at under −30° C. under nitrogen. The reaction was quenched with saturated aqueous ammonium chloride and extracted with ethyl acetate (2×150 mL). The combined organic layers were washed with brine, dried over anhydrous sodium sulfate and concentrated under vacuum. The residue was purified by column chromatography on silica gel with EtOAc/petroleum ether (1:5 to 1:1) to afford 21.2 (5.0 g, 97%) as a yellow solid. MS: m/z 255, 257 (M+H)⁺.

Synthesis of Compounds 21.3 and 21.4.

The enantiomers of racemic 21.2 (5.0 g, 19.6 mmol) were separated by chiral-SFC under the following conditions: column: CHIRALPAK IA; 20% methanol with CO₂; flow rate: 250 mL/min; UV detection at 254 nm. The fractions corresponding to the peak with $t_R$=1.63 were collected and the methanol removed in vacuo to give enantiomerically pure (3R)-3-[2-[(tert-butyldimethylsilyl)oxy]ethyl]-12-chloro-7-thia-9,11-diazatricyclo[6.4.0.0[2,6]]dodeca-1(8),2(6),9,11-tetraene (21.3, 2.0 g) in 100% ee. Similar treatment of the fractions corresponding to the peak with $t_R$=2.69 gave enantiomerically pure (3S)-3-[2-[(tert-butyldimethylsilyl)oxy]ethyl]-12-chloro-7-thia-9,11-diazatricyclo[6.4.0.0[2,6]]dodeca-1(8),2(6),9,11-tetraene (21.4, 2.0 g) in 100% ee.

Example 22

Synthesis of Intermediate 22.4

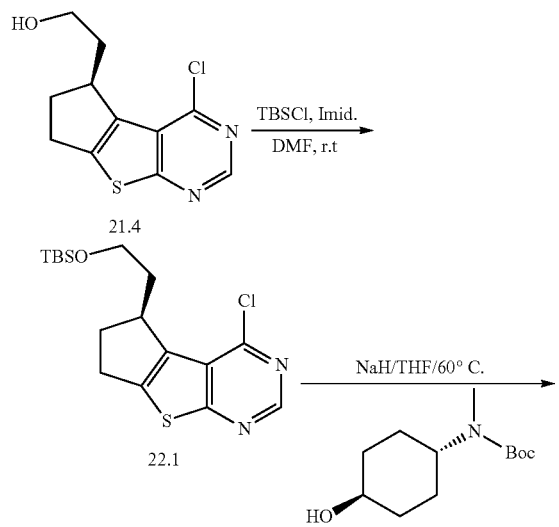

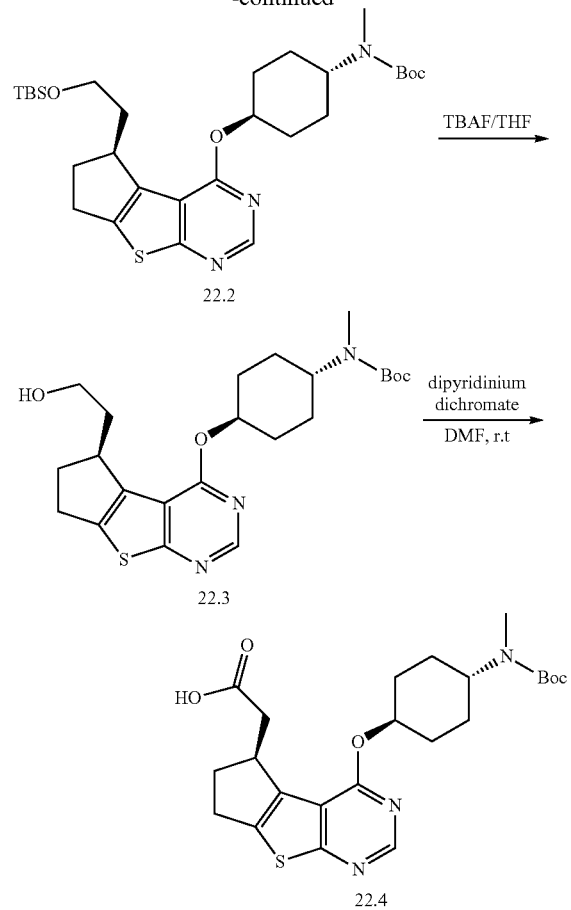

Synthesis of Compound 22.1.

Intermediate 21.4 (3.3 g, 12.95 mmol, 1.00 equiv) was treated with imidazole (1.24 g, 18.24 mmol, 1.41 equiv) and TBDMSCl (2.34 g, 15.53 mmol, 1.20 equiv) in distilled DMF (10 mL) for 2 h at room temperature under nitrogen. The reaction was then quenched with water and extracted with ethyl acetate (3×50 mL). The combined organic layers were washed with brine and dried over anhydrous sodium sulfate. After filtration and concentration under reduced pressure, the residue was loaded onto a silica gel column with ethyl acetate/petroleum ether (1:5) and purified to afford (3S)-3-[2-[(tert-butyldimethylsilyl)oxy]ethyl]-12-chloro-7-thia-9,11-diazatricyclo[6.4.0.0[2,6]]dodeca-1(8),2(6),9,11-tetraene (22.1, 4.5 g, 94%) as a yellow oil.

Synthesis of Compound 22.2.

Sodium hydride (60% dispersion in mineral oil, 1.96 g, 49.00 mmol, 4.02 equiv) was treated with tert-butyl N-(4-hydroxycyclohexyl)-N-methylcarbamate (3.92 g, 17.09 mmol, 1.40 equiv) in distilled THF (50 mL) at 0° C. for 1 h under nitrogen. Then a solution of 22.1 (4.5 g, 12.20 mmol, 1.00 equiv) in 15 mL of THF was added to the reaction mixture, which was stirred for a further 2 h at 60° C. The reaction was then quenched by the addition of 20 mL of water at 0° C. and extracted with ethyl acetate (3×100 mL). The combined organic layers were washed with brine and dried over anhydrous sodium sulfate. After filtration and concentration under reduced pressure, the residue was loaded onto a silica gel column with ethyl acetate/petroleum ether (1:5) and purified to afford tert-butyl N-(4-[[(3S)-3-[2-[(tert-butyldimethylsilyl)oxy]ethyl]-7-thia-9,11-diazatricyclo[6.4.0.0[2,6]]

dodeca-1(8),2(6),9,11-tetraen-12-yl]oxy]cyclohexyl)-N-methylcarbamate (22.2, 6.5 g, 95%) as yellow oil. MS: m/z 562 (M+H)+.

Synthesis of Compound 22.3.

A solution of 22.2 (6.5 g, 11.57 mmol, 1.00 equiv) and Bu4NF (4.5 g, 17.24 mmol, 1.49 equiv) in tetrahydrofuran (100 mL) was stirred for 2 h at room temperature. The reaction was then quenched by the addition of water and extracted with ethyl acetate (2×100 mL). The combined organic layers were washed with brine and dried over anhydrous sodium sulfate. After filtration and concentration under reduced pressure, the residue was loaded onto a silica gel column with ethyl acetate/petroleum ether (1:1) and purified to give tert-butyl N-(4-[[(3S)-3-(2-hydroxyethyl)-7-thia-9,11-diazatricyclo[6.4.0.0[2,6]]dodeca-1(8),2(6),9,11-tetraen-12-yl]oxy]cyclohexyl)-N-methylcarbamate (22.3, 5 g, 97%) as a yellow oil. MS: m/z 448 (M+H)+.

Synthesis of Intermediate 22.4.

A solution of 22.3 (1.25 g, 2.79 mmol, 1.00 equiv) and dipyridinium dichromate (4 g, 10.64 mmol, 4.00 equiv) in 10 mL of DMF was stirred for 15 h at room temperature. The reaction was then quenched with water and extracted with ethyl acetate (3×50 mL). The combined organic layers were washed with brine, dried over anhydrous sodium sulfate and concentrated under vacuum. The residue was loaded onto a silica gel column with ethyl acetate/petroleum ether (1:2 to 3:5) and purified to afford 2-[(3S)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]acetic acid (22.4, 900 mg, 70%) as a colourless oil.

Example 23

Synthesis of 2-[(3S)-12-[[4-(dimethylamino)cyclohexyl]oxy]-7-thia-9,11-diazatricyclo[6.4.0.0[2,6]]dodeca-1(8),2(6),9,11-tetraen-3-yl]-N-(5-fluoropyridin-2-yl)acetamide (I-38)

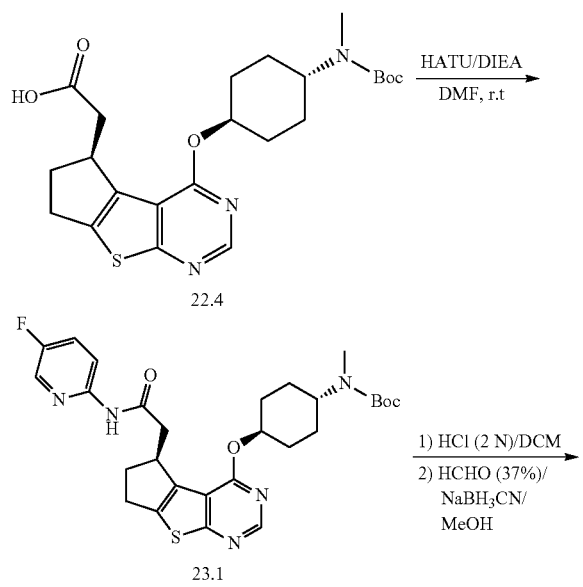

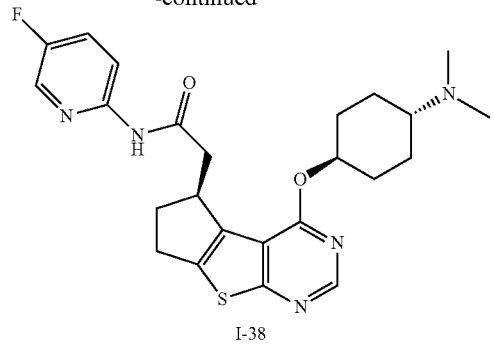

I-38

Synthesis of Compound 23.1.

To a solution of intermediate 22.4 (200 mg, 0.43 mmol, 1.00 equiv) in distilled DMF (8 mL) at room temperature under nitrogen was added 5-fluoropyridin-2-amine (55 mg, 0.49 mmol, 1.13 equiv), HATU (200 mg) and DIPEA (170 mg). The resulting solution was stirred for 2 h at room temperature and quenched with water and extracted with ethyl acetate (3×30 mL). The combined organic layers were washed with brine, dried over anhydrous sodium sulfate and concentrated under vacuum. The residue was loaded onto a silica gel column with ethyl acetate/petroleum ether (1:2 to 3:5) and purified to give tert-butyl N-(4-[[(3S)-3-[[(5-fluoropyridin-2-yl)carbamoyl]methyl]-7-thia-9,11-diazatricyclo[6.4.0.0[2,6]]dodeca-1(8),2(6),9,11-tetraen-12-yl]oxy]cyclohexyl)-N-methylcarbamate (23.1, 195 mg, 81%) as a yellow oil. MS: m/z 556 (M+H)+.

Synthesis of Compound I-38.

To a 25-mL round-bottom flask containing a solution of 23.1 (195 mg, 0.35 mmol, 1.00 equiv) in dichloromethane (15 mL) was added hydrochloric acid (12 M, 2 mL) at 0° C. under nitrogen. The resulting solution was stirred for 2 h at room temperature and concentrated under vacuum. The resulting N-(5-fluoropyridin-2-yl)-2-[(3S)-12-[[4-(methylamino)cyclohexyl]oxy]-7-thia-9,11-diazatricyclo[6.4.0.0[2,6]]dodeca-1(8),2(6),9,11-tetraen-3-yl]acetamide hydrochloride (130 mg, crude) was used in the next step directly without further purification. A solution of this material (130 mg, crude) and HCHO (37%, 1 mL) in methanol (10 mL) was stirred at room temperature for 30 min, whereupon NaBH3CN (55 mg, 0.78 mmol, 3.06 equiv) was added and the mixture stirred for an additional 2 h at room temperature. The reaction was then quenched by the addition of 20 mL of water and extracted with 3×30 mL of ethyl acetate. The combined organic layers were concentrated under vacuum. The crude product (70 mg) was purified by preparative HPLC(SHIMADZU) under the following conditions: column: Xbridge Prep C18 5 um, 19*150 mm; mobile phase: water (0.05% NH4HCO3) and CH3CN (6.0% CH3CN up to 50.0% in 25 min); UV detection at 254 and 220 nm. The fractions were collected and evaporated under reduced pressure to give the 2-[(3S)-12-[[4-(dimethylamino)cyclohexyl]oxy]-7-thia-9,11-diazatricyclo[6.4.0.0[2,6]]dodeca-1(8),2(6),9,11-tetraen-3-yl]-N-(5-fluoropyridin-2-yl)acetamide (I-38, 21.4 mg) as a white solid. 1H NMR (300 MHz, CDCl3) δ 8.49 (s, 1H), 8.20 (m, 2H), 7.63 (m, 1H), 5.28 (m, 1H), 3.93 (t, 1H), 3.33 (m, 2H), 3.03 (m, 1H), 2.82 (m, 1H), 2.77 (m, 1H), 2.55 (m, 10H), 2.03 (m, 2H), 1.55 (m, 4H). MS: m/z 470 (M+H)+.

Example 24

Synthesis of 2-[(3S)-12-[[4-(dimethylamino)cyclohexyl]oxy]-7-thia-9,11-diazatricyclo[6.4.0.0[2,6]]dodeca-1(12),2(6),8,10-tetraen-3-yl]-N-ethylacetamide (I-36)

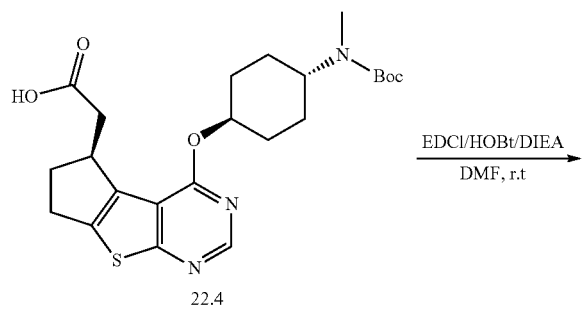

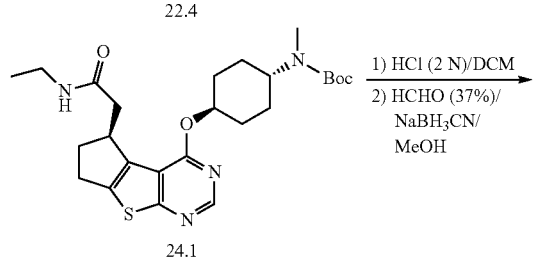

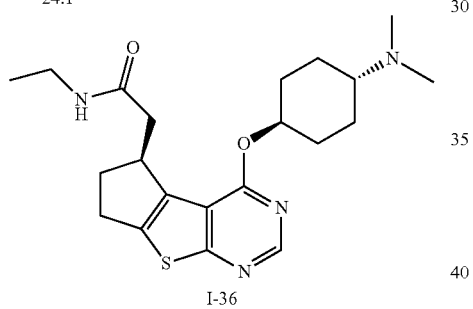

Synthesis of Compound 24.1.

A 25-mL round-bottom flask was charged with intermediate 22.4 (200 mg, 0.43 mmol, 1.00 equiv), HOBt (90 mg, 0.67 mmol, 1.54 equiv), EDCI (191 mg, 1.00 mmol, 2.31 equiv), ethanamine hydrochloride (45 mg, 0.55 mmol, 1.27 equiv), triethylamine (135 mg, 1.34 mmol, 3.08 equiv) and 10 mL of distilled DMF. The resulting solution was stirred for 4 h at room temperature under nitrogen. The reaction was then quenched with water and extracted with 3×25 mL of ethyl acetate. The combined organic layers were washed with brine and dried over anhydrous sodium sulfate. After filtration and concentration under reduced pressure, the residue was loaded onto a silica gel column with ethyl acetate/petroleum ether (1:2 to 3:5) and purified to provide the desired tert-butyl N-(4-[[(3S)-3-[(ethylcarbamoyl)methyl]-7-thia-9,11-diazatricyclo[6.4.0.0[2,6]]dodeca-1(8),2(6),9,11-tetraen-12-yl]oxy]cyclohexyl)-N-methylcarbamate (24.1, 165 mg, 78%) as a white solid. MS: m/z 470 (M+H)+.

Synthesis of Compound I-36.

To a 25-mL round-bottom flask was added 24.1 (165 mg, 0.34 mmol, 1.00 equiv) and hydrochloric acid (12 M, 2 mL) in dichloromethane (12 mL). The reaction was stirred for 2 h at room temperature. The resulting mixture was concentrated under vacuum to afford 1-(ethylamino)-2-[(3S)-12-[[4-(methylamino)cyclohexyl]oxy]-7-thia-9,11-diazatricyclo[6.4.0.0[2,6]]dodeca-1(12),2(6),8,10-tetraen-3-yl]ethan-1-ol hydrochloride (105 mg, crude) as a yellow oil that was used in the next step without further purification. To a solution of this compound (105 mg, crude) in methanol (10 mL) was added HCHO (37%, 2 mL) and the reaction was stirred for 1 h at room temperature. Then NaBH$_3$CN (50 mg, 63%) was added and the reaction stirred for another 2 h at ambient temperature. The resulting mixture was concentrated under reduced pressure and the crude product (85 mg) purified by preparative HPLC(SHIMADZU) under the following conditions: column: Xbridge Prep C18 5 um, 19*150 mm; mobile phase: water (0.05% NH$_4$HCO$_3$) and CH$_3$OH NMR (6.0% CH$_3$OH up to 50.0% in 25 min); UV detection at 254 nm. The fractions were collected and evaporated under reduced pressure to give the desired Compound I-36 (43 mg) as a white solid. An enantiomeric excess of 100% was measured by chiral HPLC analysis. $^1$H NMR (400 MHz, CD$_3$OD): δ 8.48 (s, 1H), 5.30 (m, 1H), 3.84 (m, 1H), 2.94-3.32 (m, 5H), 2.73 (m, 1H), 2.20-2.68 (m, 11H), 1.50-1.72 (m, 4H), 1.15 (t, 3H). MS: m/z 403 (M+H)+.

Example 25

Synthesis of Intermediate 25.1

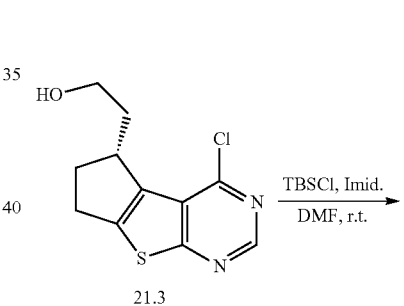

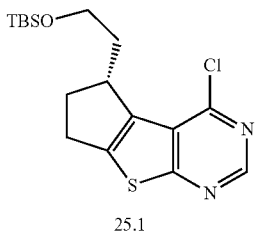

Intermediate 21.3 (1.3 g, 5.10 mmol, 1.00 equiv) was treated with imidazole (500 mg, 7.44 mmol, 1.40 equiv) and TBDMSCl (920 mg, 6.10 mmol, 1.20 equiv) in distilled DMF (10 mL) for 2 h at room temperature under nitrogen. The reaction was then quenched with water and extracted with ethyl acetate (3×50 mL). The combined organic layers were washed with brine and dried over anhydrous sodium sulfate. After filtration and concentration under reduced pressure, the residue was loaded onto a silica gel column with ethyl acetate/petroleum ether (1:5) and purified to give (3R)-3-[2-[(tert-butyldimethylsilyl)oxy]ethyl]-12-chloro-7-thia-9,11-diazatricyclo[6.4.0.0[2,6]]dodeca-1(8),2(6),9,11-tetraene (25.1, 1.8 g, 96%) as a yellow oil.

Example 26

Synthesis of Intermediate 26.3

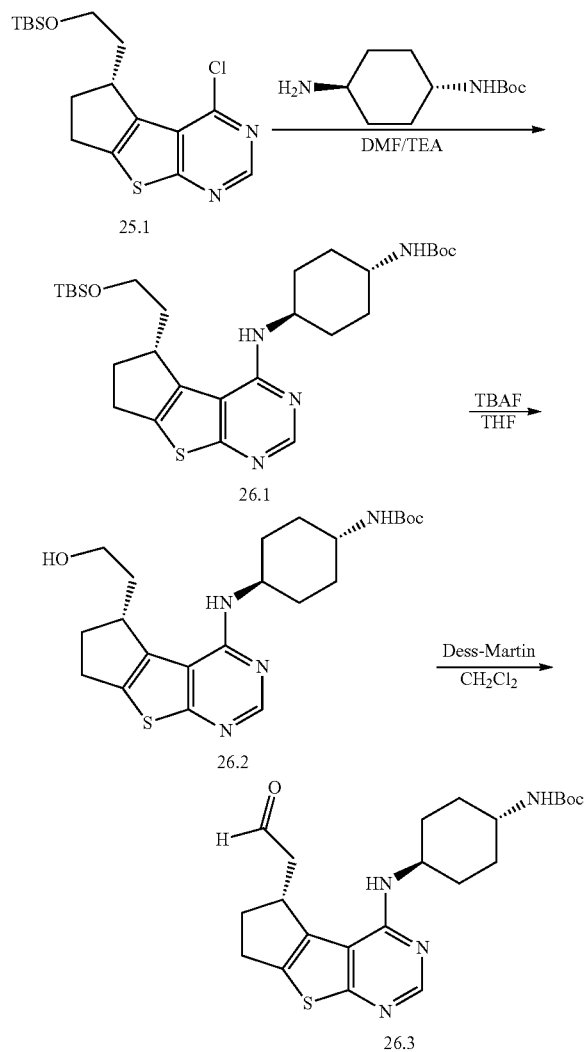

Synthesis of Compound 26.1.

To a 50-mL round-bottom flask was added a solution of 25.1 (560 mg, 1.52 mmol, 1.00 equiv) and TEA (461 mg, 3.0 equiv) in distilled DMF (10 mL) at room temperature under nitrogen. Then tert-butyl trans-N-(4-aminocyclohexyl)carbamate (1628 mg, 7.60 mmol, 4.98 equiv) was added and the resulting solution was stirred for 14 h at 50° C. The reaction was then quenched with water and extracted with 2×100 mL of ethyl acetate. The combined organic layers were dried over sodium sulfate and concentrated under vacuum to afford 26.1 (721 mg, 87%) as a colorless oil.

Synthesis of Compound 26.2.

To a solution of 26.1 (721 mg, 1.32 mmol, 1.00 equiv) in 10 mL of THF was added TBAF (476 mg, 1.82 mmol, 1.38 equiv) at room temperature. The resulting solution was stirred for 2 h at ambient temperature and then quenched by the addition of water and extracted with 2×80 mL of ethyl acetate. The combined organic layers were dried over sodium sulfate and concentrated under reduced pressure. The residue was purified by column chromatography on silica gel with ethyl acetate/petroleum ether (1:2) to give the desired tert-butyl N-(4-[[(3R)-3-(2-hydroxyethyl)-7-thia-9,11-diazatricyclo [6.4.0.0[2,6]]dodeca-1(8),2 (6),9,11-tetraen-12-yl]amino] cyclohexyl)carbamate (26.2, 542 mg, 95%) as a white solid.

Synthesis of Compound 26.3.

Compound 26.2 (542 mg, 1.25 mmol, 1.00 equiv) was treated with Dess-Martin periodinane (637 mg, 1.50 mmol, 1.20 equiv) in 20 mL of DCM at 0° C. The resulting solution was stirred for 4 h at room temperature then quenched with water and extracted with 2×50 mL of ethyl acetate. The combined organic layers were washed with brine, dried over sodium sulfate and concentrated under reduced pressure. The residue was loaded onto a silica gel column with ethyl acetate/ petroleum ether (1:2) to provide the desired tert-butyl N-(4-[[[(3R)-3-(2-oxoethyl)-7-thia-9,11-diazatricyclo[6.4.0.0[2,6]]dodeca-1(8),2(6),9,11-tetraen-12-yl]amino]cyclohexyl) carbamate 26.3 (494 mg, 92%) as a white solid.

Example 27 and Example 28

Synthesis of (R)-3-((R)-4-(((1r,4R)-4-(dimethylamino)cyclohexyl)oxy)-6,7-dihydro-5H-cyclopenta [4,5]thieno[2,3-d]pyrimidin-5-yl)-1,1,1-trifluoropropan-2-ol (I-68) and (S)-3-((R)-4-(((1r,4R)-4-(dimethylamino)cyclohexyl)oxy)-6,7-dihydro-5H-cyclopenta[4,5]thieno[2,3-d]pyrimidin-5-yl)-1,1,1-trifluoropropan-2-ol (I-70)

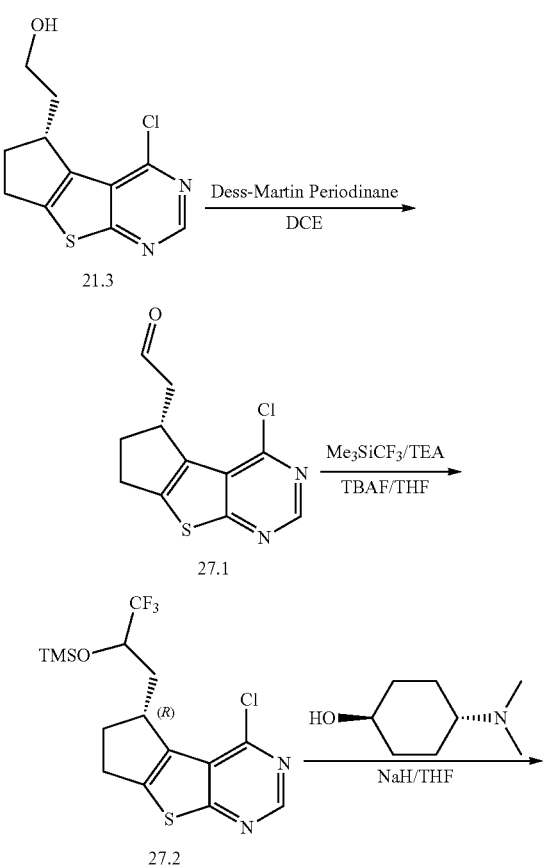

-continued

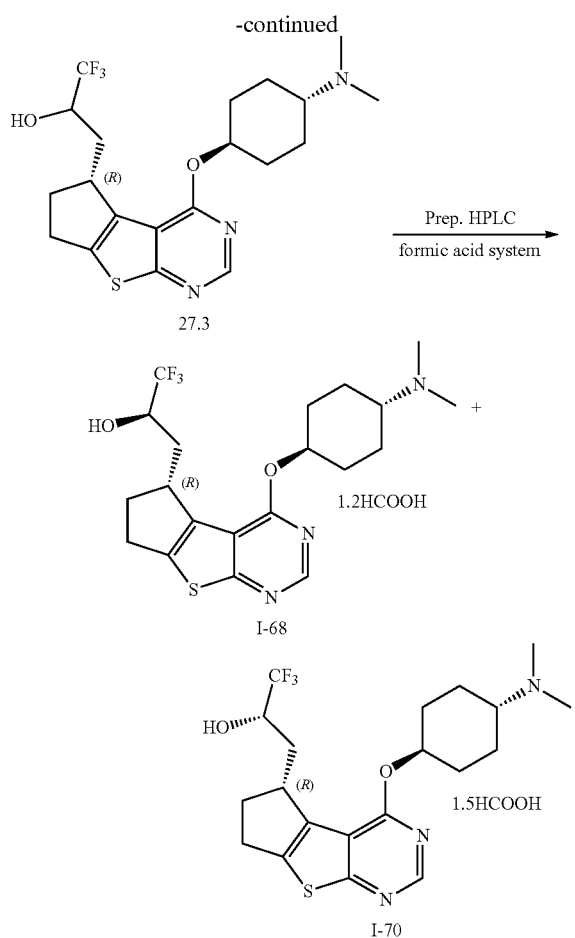

Synthesis of Compound 27.1.

A 25-mL round-bottom flask, purged and maintained with an inert atmosphere of nitrogen, was charged with a solution of 21.3 (300 mg, 1.18 mmol, 1.00 equiv) in 10 mL) in anhydrous dichloromethane (15 mL). Dess-Martin periodinane (757 mg, 1.79 mmol, 1.52 equiv) was added and the resulting solution was stirred for 2 h at 0° C. in a water/ice bath. After completion of the reaction, the reaction was then quenched by the addition of saturated aqueous sodium bicarbonate and extracted with 3×20 mL of DCM. The combined organic layers were washed with brine, dried (Na$_2$SO$_4$) and concentrated under vacuum. The residue was applied onto a silica gel column with ethyl acetate/petroleum ether (1:8) and purified to afford the compound 27.1 (267 mg, 90%) as a white solid.

Synthesis of Compound 27.2.

To a solution of 27.1 (267 mg, 1.06 mmol, 1.00 equiv) in 10 mL of distilled THF was added trimethyl(trifluoromethyl)silane (280 mg, 1.97 mmol, 1.86 equiv) and TEA (0.1 mL). The reaction was stirred at 0° C. for 30 min under nitrogen. Then TBAF (0.01 mL) was added via syringe at 0° C. and the resulting solution was stirred for 5 min. The resulting solution was diluted with 15 mL of water and extracted with of ethyl acetate (100 mL). The organic layer was washed with brine, dried over sodium sulfate and concentrated under vacuum. The residue was applied onto a silica gel column with ethyl acetate/petroleum ether (1:1) to afford 27.2 (320 mg, 77%) as a red oil.

Synthesis of Compound 27.3.

To a 100-mL 3-necked round-bottom flask containing a solution of trans-4-(dimethylamino)cyclohexan-1-ol (232 mg, 1.62 mmol, 2.00 equiv) in 10 mL of anhydrous THF was added NaH (60% dispersion in mineral oil, 128 mg, 5.33 mmol, 6.58 equiv) at 0° C. and the resulting mixture was stirred for 30 min in a water/ice bath. Then compound 27.2 (320 mg, 0.81 mmol, 1.00 equiv) was added and the resulting solution was allowed to react, with stirring, for an additional 3 h while the temperature was maintained at 55° C. in an oil bath. After completion, the reaction was quenched by the addition of 10 mL of saturated aqueous NH$_4$Cl and extracted with 3×30 mL of DCM. The organic layers were combined, dried (Na$_2$SO$_4$) and concentrated under vacuum. The residue was applied onto a silica gel column with dichloromethane/methanol/NH$_4$OH (10:1:0.1) and purified to give the product as a mixture of diastereomers (180 mg).

Synthesis of Compounds I-68 and I-70.

The diastereomers of 27.3 (180 mg) were separated by preparative HPLC(SHIMADZU) under the following conditions: column: Xbridge Prep C18 5 um, 19*150 mm; mobile phase: water (0.1% HCOOH) and MeOH (6.0% MeOH up to 53.0% in 19 min); UV detection at 254/220 nm. The product-containing fractions were collected and evaporated (to remove the water and CH$_3$OH) to give Compounds I-70 (28 mg) and I-68 (74.1 mg) as white solids.

Analytical data for I-70: $^1$H NMR (300 MHz, CD$_3$OD) δ 8.45 (s, 2H), 5.32-5.30 (m, 1H), 3.93-3.99 (m, 1H), 3.78-3.66 (m, 1H), 3.32-2.94 (m, 3H), 2.84-2.65 (m, 7H), 2.40-2.19 (m, 7H), 1.90-1.56 (m, 5H). MS: m/z 430 (M+H)$^+$.

Analytical data for I-68: $^1$H NMR (300 MHz, CD$_3$OD) δ 8.44 (s, 2H), 5.33-5.31 (m, 1H), 4.10-4.05 (m, 1H), 3.47-3.32 (m, 1H), 3.29-2.90 (m, 3H), 2.84-2.68 (m, 7H), 2.55-2.17 (m, 7H), 1.77-1.62 (m, 5H). MS: m/z 430 (M+H)$^+$.

Example 29

Synthesis of 2-((R)-4-(((1r,4R)-4-morpholinocyclohexyl)oxy)-6,7-dihydro-5H-cyclopenta[4,5]thieno[2,3-d]pyrimidin-5-yl)acetamide (I-67)

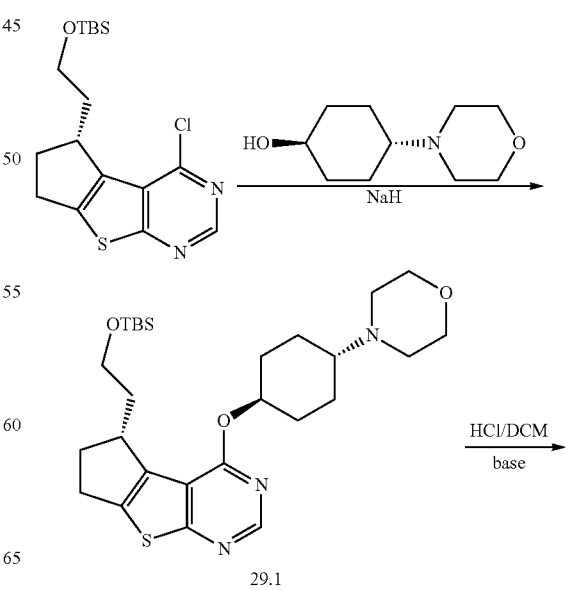

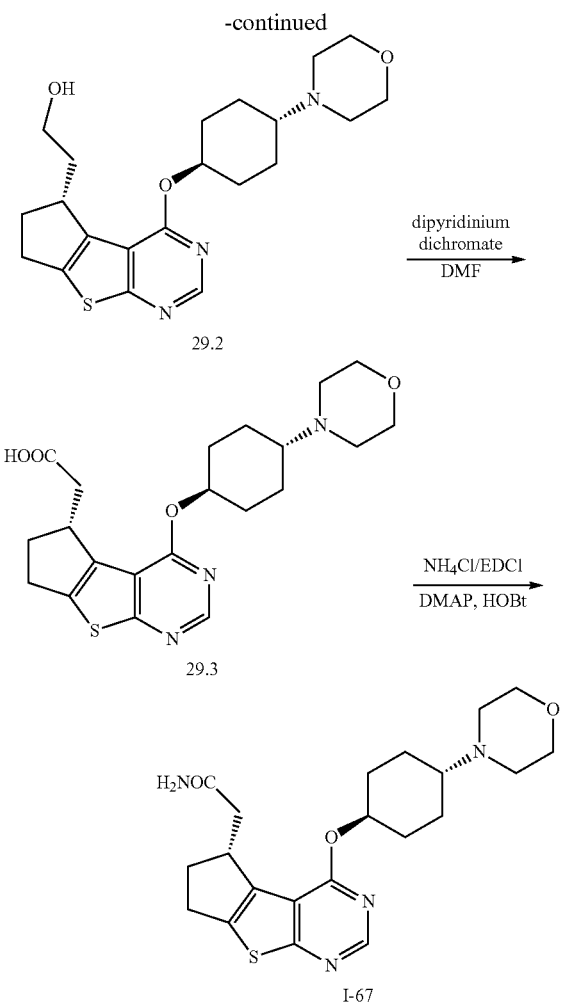

Synthesis of Compound 29.3.

Alcohol 29.2 (185 mg, 0.46 mmol, 1.00 equiv) was oxidized with dipyridinium dichromate (752 mg, 2.00 mmol, 4.36 equiv) in 50 mL of DMF for 24 h at room temperature. The resulting solution was diluted with water and extracted with 3×50 mL of mixed solutions of $CHCl_3$/iso-PrOH. The organic layers were combined, dried ($Na_2SO_4$) and concentrated under vacuum. The residue was applied onto a silica gel column with dichloromethane/methanol (5:1 to 1:1) and purified to afford 105 mg (55%) of acid 29.3 as a yellow oil.

Synthesis of Compound I-67.

A 50 mL round-bottom flask containing a solution of acid 29.3 (105 mg, 0.25 mmol, 1.00 equiv), $NH_4Cl$ (80 mg, 1.50 mmol, 6.00 equiv), EDCI (57 mg, 0.3 mmol, 1.2 equiv), 4-dimethylaminopyridine (37 mg, 0.3 mmol, 1.2 equiv) and HOBt (40 mg, 0.3 mmol, 1.2 equiv) in 5 mL of anhydrous DMF was stirred for 24 h at room temperature. The resulting solution was diluted with water and extracted with 4×50 mL of mixed solution of $CHCl_3$:iso-PrOH. The combined organic layers were concentrated under vacuum. The crude product was purified by preparative HPLC(SHIMADZU) under the following conditions: column: SunFire Prep C18, 19*150 mm 5 um; mobile phase: water (0.05% $NH_4CO_3$) and $CH_3CN$ (6.0% $CH_3CN$ up to 50.0% in 25 min); UV detection at 254/220 nm. The product-containing fractions were collected and concentrated to give Compound I-67 (22.5 mg) as a white solid. $^1$H NMR (300 MHz, $CD_3OD$) δ 8.43 (s, 1H), 5.27-5.20 (m, 1H), 3.80-3.70 (m, 5H), 3.29-3.27 (m, 1H), 3.12-2.90 (m, 2H), 2.73-2.67 (m, 5H), 2.49-2.42 (m, 1H), 2.32-2.19 (m, 4H), 2.10-2.06 (d, 2H), 1.67-1.46 (m, 4H). MS: m/z 417 $(M+H)^+$.

Example 30 and Example 31

Synthesis of (2R)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]butan-2-ol formate (I-52) and (2S)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]butan-2-ol formate (I-54)

Synthesis of Compound 29.1.

4-(Morpholin-4-yl)cyclohexan-1-ol (commercially available; 218 mg, 1.2 mmol, 1.50 equiv) was treated with NaH (60% dispersion in mineral oil, 128 mg, 3.2 mmol, 4 equiv) in freshly distilled tetrahydrofuran (15 mL) for 30 min at 0° C. in a water/ice bath under nitrogen. Then a solution of intermediate 25.1 (289 mg, 0.8 mmol, 1.00 equiv) in 5 mL of THF was added via syringe and the resulting solution was allowed to stir for an additional 3 h at 60° C. in an oil bath. The reaction was then quenched with saturated aqueous $NH_4Cl$ and extracted with 3×50 mL of ethyl acetate. The combined organic layers were washed with brine, dried ($Na_2SO_4$) and concentrated under vacuum. The residue was applied onto a silica gel column with ethyl acetate/petroleum ether (1:5-1:2) and purified to afford compound 29.1 (260 mg, 63%) as a colorless oil.

Synthesis of Compound 29.2.

To a solution of 29.1 (260 mg, 0.5 mmol, 1.0 equiv) in 10 mL of DCM was added 0.5 mL of concentrated hydrochloric acid in an ice/water bath. The resulting solution was stirred for 2 h and concentrated in vacuo. The residue was neutralized with saturated aqueous $Na_2CO_3$ and extracted with 3×50 mL of ethyl acetate. The organic layers were combined, washed with brine, dried ($Na_2SO_4$) and concentrated under reduced pressure. The residue was purified by column chromatography on silica gel with DCM/MeOH (15:1) to afford the desired alcohol 29.2 (185 mg, 91%) as a colorless oil.

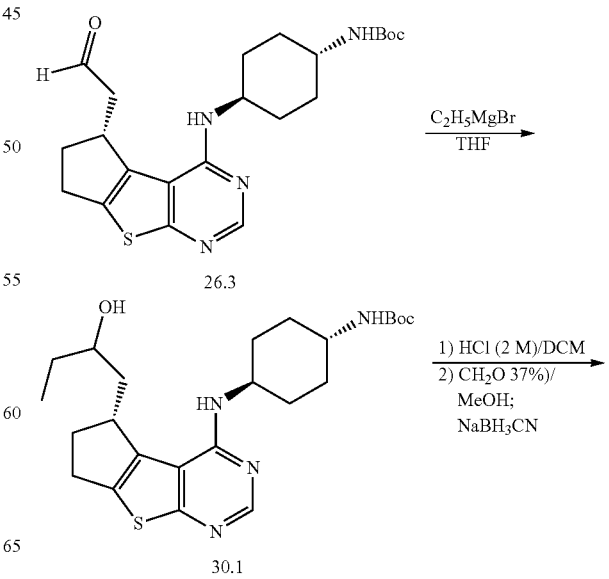

-continued

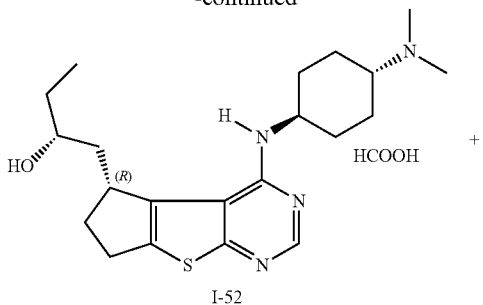

I-52

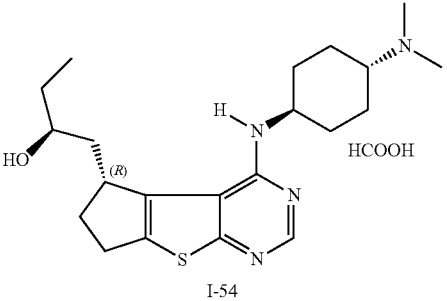

I-54

Synthesis of Compound 30.1.

To a 50-mL round-bottom flask, purged and maintained under an inert atmosphere of nitrogen, was added a solution of 26.3 (244 mg, 0.57 mmol, 1.00 equiv) in distilled THF (10 mL) at 0° C. under nitrogen. Then $C_2H_5MgBr$ (1 M in THF, 2.85 mL, 5.0 equiv) was added dropwise at 0° C. via syringe. The resulting solution was stirred for an additional 2 h at 0° C., quenched with saturated aqueous $NH_4Cl$ and extracted with 3×20 mL of ethyl acetate. The combined organic layers were washed with brine, dried over sodium sulfate and concentrated under reduced pressure. The residue was loaded onto a silica gel column with ethyl acetate/petroleum ether (1:5) and purified to give racemic tert-butyl N-(4-[[(3R)-3-(2-hydroxybutyl)-7-thia-9,11-diazatricyclo[6.4.0.0[2,6]]dodeca-1(8),2(6),9,11-tetraen-12-yl]amino]cyclohexyl)carbamate (30.1, 130 mg, 50%) as a colorless oil.

Synthesis of Compounds I-52 and I-54.

A 50-mL round-bottom flask was charged with 30.1 (130 mg, 0.28 mmol, 1.00 equiv) and dichloromethane (10 mL) and cooled to 0° C. Then hydrochloric acid (12 M, 2.0 mL) was added and the resulting solution was stirred for 3 h at room temperature. After 3 h, the mixture was concentrated under vacuum. The pH value of the solution was adjusted to 8 with saturated aqueous sodium carbonate and then the solution was extracted with 2×40 mL of ethyl acetate. The organic layers were combined and dried over sodium sulfate and concentrated under vacuum to give 1-[(3R)-12-[(4-aminocyclohexyl)amino]-7-thia-9,11-diazatricyclo[6.4.0.0[2,6]]dodeca-1(8),2(6),9,11-tetraen-3-yl]butan-2-ol (80 mg, crude) as a colorless oil. To a solution of this material (80 mg, crude) in methanol (5 mL) was added HCHO (37%, 0.8 mL). The reaction was stirred for 1 h at room temperature. Then $NaBH_3CN$ (33.9 mg, 0.54 mmol, 2.44 equiv) was added and the resulting solution was stirred for an additional 2 h at ambient temperature and concentrated under vacuum. The crude product (80 mg) was purified by preparative HPLC (SHIMADZU) under the following conditions: column: SunFire Prep C18, 19*150 mm 5 um; mobile phase: water with 0.1% HCOOH and $CH_3CN$; UV detection at 254 nm. The product-containing fractions were collected and evaporated to remove the water and $CH_3CN$ to give (2R)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]butan-2-ol formate (I-52, 8.6 mg) as a white solid and (2S)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]butan-2-ol formate (I-54, 5.9 mg) as a grey solid, respectively.

Analytical data for I-52: $^1$H NMR (300 MHz, $CD_3OD$) δ 8.55 (br s, 1H), 8.23 (s, 1H) 4.19 (m, 1H), 3.57-3.59 (m, 1H), 3.31-3.38 (m, 1H), 3.23 (m, 1H), 3.11-3.14 (m, 1H), 2.83-2.91 (m, 7H), 2.68-2.75 (m, 1H), 2.33-2.37 (m, 1H), 2.18-2.27 (m, 4H), 1.61-1.79 (m, 6H), 1.48-1.57 (m, 2H), 0.95 (t, 3H). MS: m/z 389 (M+H)$^+$.

Analytical data for I-54: $^1$H NMR (300 MHz, $CD_3OD$) δ 8.45 (br s, 1H), 8.12 (s, 1H), 4.08-4.12 (m, 1H), 3.51-3.54 (m, 2H), 3.20-3.22 (m, 1H), 2.82-2.98 (m, 1H), 2.74-2.79 (m, 6H), 2.57-2.64 (m, 1H), 2.05-2.18 (m, 5H), 1.32-1.83 (m, 8H), 0.84 (t, 3H). MS: m/z 389 (M+H)$^+$.

Example 32 and Example 33

Synthesis of (2R)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propan-2-ol formate (I-53) and (2S)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propan-2-ol formate (I-55)

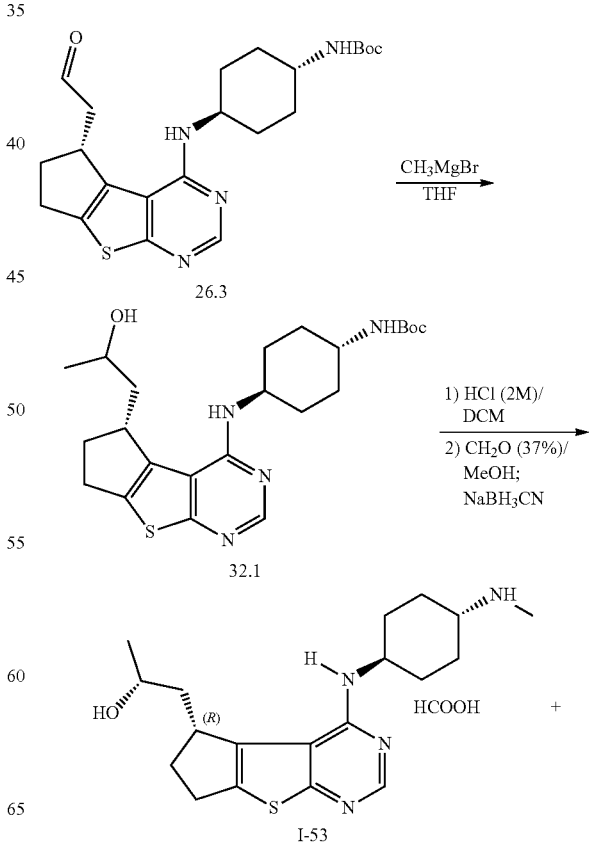

197
-continued

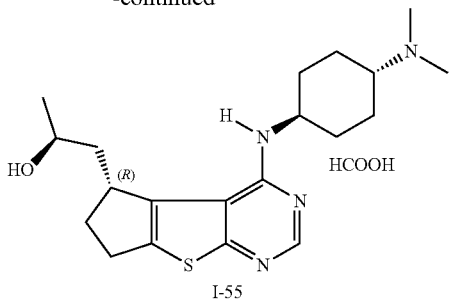

I-55

Synthesis of Compound 32.1.

To a 50-mL 3-neck round-bottom flask, purged and maintained under an atmosphere of nitrogen, was added a solution of 26.3 (250 mg, 0.58 mmol, 1.00 equiv) in freshly distilled tetrahydrofuran (10 mL) at 0° C. under nitrogen. $CH_3MgBr$ (1.0 M in THF, 2.9 mL, 5.0 equiv) was added at 0° C. via syringe. The resulting solution was stirred for 2 h at 0° C. and quenched with saturated aqueous $NH_4Cl$ and extracted with 3×30 mL of ethyl acetate. The combined organic layers were washed with brine, dried over sodium sulfate and concentrated under reduced pressure. The residue was loaded onto a silica gel column with ethyl acetate/petroleum ether (1:5) to give a mixture of the 2-hydroxy diastereomers of tert-butyl N-(4-[[(3R)-3-(2-hydroxypropyl)-7-thia-9,11-diazatricyclo[6.4.0.0[2,6]]dodeca-1(8),2(6),9,11-tetraen-12-yl]amino]cyclohexyl)carbamate (32.1, 109 mg, 42%) as a colorless oil.

Synthesis of Compounds I-53 and I-55.

To a 50-mL round-bottom flask was added 32.1 (109 mg, 0.24 mmol, 1.00 equiv) and dichloromethane (10 mL) and the solution was cooled to 0° C. Then hydrochloric acid (12 M, 2.0 mL) was added and the solution was stirred for 3 h at room temperature. The resulting mixture was concentrated under vacuum. The pH value of the solution was adjusted to 8 with saturated aqueous sodium carbonate and extracted with 2×40 mL of ethyl acetate. The organic layers were combined, dried over sodium sulfate and concentrated under vacuum to give the desired 1-[(3R)-12-[(4-aminocyclohexyl)amino]-7-thia-9,11-diazatricyclo[6.4.0.0[2,6]]dodeca-1(8),2(6),9,11-tetraen-3-yl]propan-2-ol (70 mg, crude) as a colorless oil. To a solution of this oil (70 mg, crude) in methanol (5 mL) was added HCHO (37%, 0.8 mL) and then the reaction was stirred for 1 h at room temperature. Then $NaBH_3CN$ (29.7 mg, 0.47 mmol, 2.35 equiv) was added and stirring was continued for an additional 2 h at ambient temperature, whereupon it was concentrated under vacuum. The crude product (80 mg) was purified by preparative HPLC(SHIMADZU) under the following conditions: column: SunFire Prep C18, 19*150 mm 5 um; mobile phase: water (0.05% HCOOH solution) and $CH_3CN$ (start at 6.0% $CH_3CN$ then ramp up to 50.0% over 25 min); UV detection at 254 and 220 nm. The product-containing fractions were collected and evaporated to afford Compound I-53 (12.9 mg) as a white solid and Compound I-55 (5.6 mg) as a grey solid.

Analytical data for I-53: $^1H$ NMR (300 MHz, $CD_3OD$) δ 8.54 (br s, 1H), 8.23 (s, 1H), 4.18-4.19 (m, 1H), 3.70-3.76 (m, 1H), 3.55-3.58 (m, 1H), 3.05-3.33 (m, 2H), 2.84-2.92 (m, 7H), 2.68-2.75 (m, 1H), 2.16-2.37 (m, 5H), 1.55-1.78 (m, 6H), 1.23 (t, 3H). MS: m/z 375 $(M+H)^+$.

Analytical data for I-55: $^1H$ NMR (300 MHz, $CD_3OD$) δ 8.55 (br s, 1H), 8.23 (s, 1H), 4.18-4.19 (m, 1H), 3.70-3.76 (m, 1H), 3.55-3.58 (m, 1H), 3.05-3.33 (m, 2H), 2.84-2.92 (m, 7H), 2.68-2.75 (m, 1H), 2.16-2.37 (m, 5H), 1.55-1.78 (m, 6H), 1.23 (t, 3H). MS: m/z 375 $(M+H)^+$.

198

Example 34

Synthesis of Intermediate 34.2

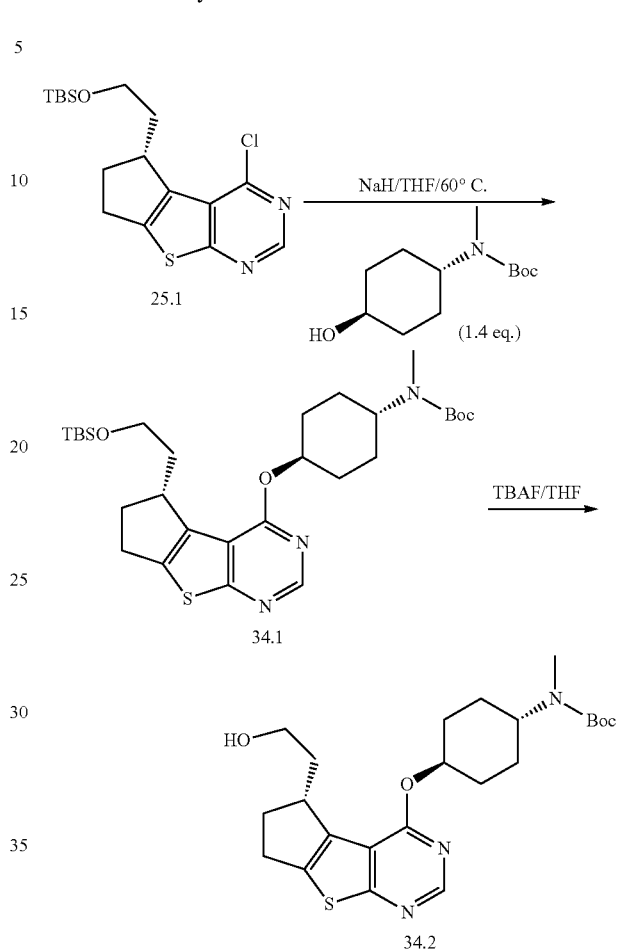

Synthesis of Compound 34.1.

Sodium hydride (60% dispersion in mineral oil, 0.9 g, 22.5 mmol, 4.60 equiv) was treated with tert-butyl N-(4-hydroxycyclohexyl)-N-methylcarbamate (1.8 g, 7.85 mmol, 1.6 equiv) in distilled THF (50 mL) at 0° C. for 1 h under nitrogen. Then a solution of 25.1 (1.8 g, 4.88 mmol, 1.00 equiv) in 15 mL of THF was added to the reaction mixture and the latter was stirred for 2 h at 60° C. The reaction was then quenched by the addition of 20 mL of water at 0° C. and extracted with ethyl acetate (3×100 mL). The combined organic layers were washed with brine and dried over anhydrous sodium sulfate. After filtration and concentration under reduced pressure, the residue was loaded onto a silica gel column with ethyl acetate/petroleum ether (1:5) and purified to afford tert-butyl N-(4-[[(3R)-3-[2-[(tert-butyldimethylsilyl)oxy]ethyl]-7-thia-9,11-diazatricyclo[6.4.0.0[2,6]]dodeca-1(8),2 (6),9,11-tetraen-12-yl]oxy]cyclohexyl)-N-methylcarbamate (34.1, 1.6 g, 58%) as a yellow oil.

Synthesis of Compound 34.2.

A solution of 34.1 (1.6 g, 2.85 mmol, 1.00 equiv) and $Bu_4NF$ (1.1 g, 1.5 equiv) in tetrahydrofuran (50 mL) was stirred for 2 h at room temperature. The reaction was then quenched by the addition of water and extracted with ethyl acetate (3×50 mL). The combined organic layers were washed with brine and dried over anhydrous sodium sulfate. After filtration and concentration under reduced pressure, the residue was loaded onto a silica gel column with ethyl acetate/petroleum ether (1:1) and purified to afford intermediate 34.2 (1.2 g, 81%) as a yellow oil. MS: m/z 448 $(M+H)^+$.

Example 35

Synthesis of Intermediate 35.1

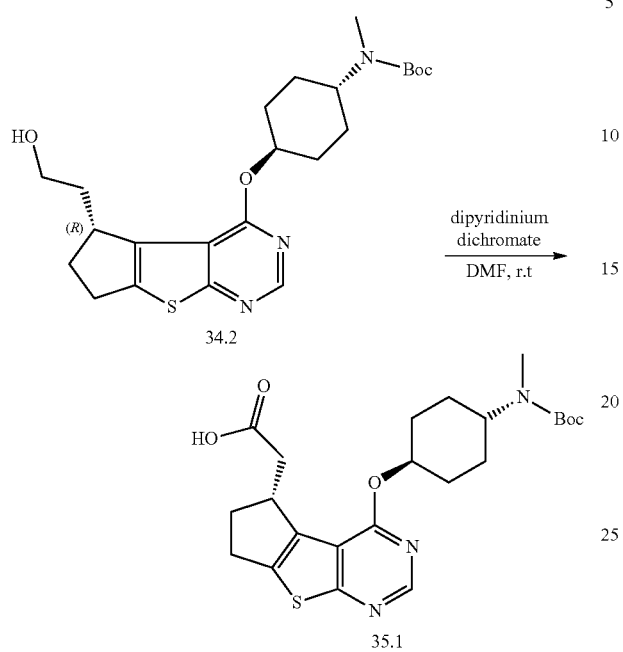

Synthesis of Intermediate 35.1.

A solution of 34.2 (1.15 g, 2.57 mmol, 1.00 equiv) and dipyridinium dichromate (4 g, 10.64 mmol, 4.14 equiv) in 10 mL of DMF was stirred for 15 h at room temperature. The reaction was then quenched with water and extracted with ethyl acetate (3×50 mL). The combined organic layers were washed with brine, dried over anhydrous sodium sulfate and concentrated under vacuum. The residue was loaded onto a silica gel column with ethyl acetate/petroleum ether (1:2 to 3:5) to afford 2-[(3R)-12-[(4-[[(tert-butoxy)carbonyl](methyl)amino]cyclohexyl)oxy]-7-thia-9,11-diazatricyclo[6.4.0.0[2,6]]-dodeca-1(8),2(6),9,11-tetraen-3-yl]acetic acid (35.1, 0.9 g, 76%) as a colourless oil.

Example 36

Synthesis of 2-[(3R)-12-[[4-(dimethylamino)cyclohexyl]oxy]-7-thia-9,11-diazatricyclo[6.4.0.0[2,6]]-dodeca-1(8),2(6),9,11-tetraen-3-yl]-N-(5-fluoropyridin-2-yl)acetamide (I-37)

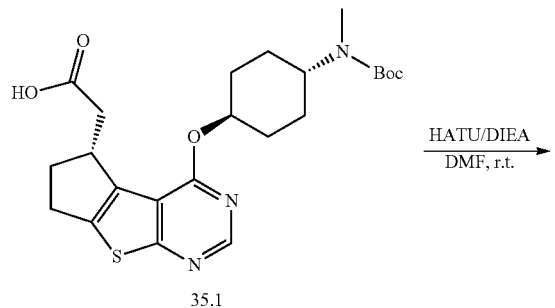

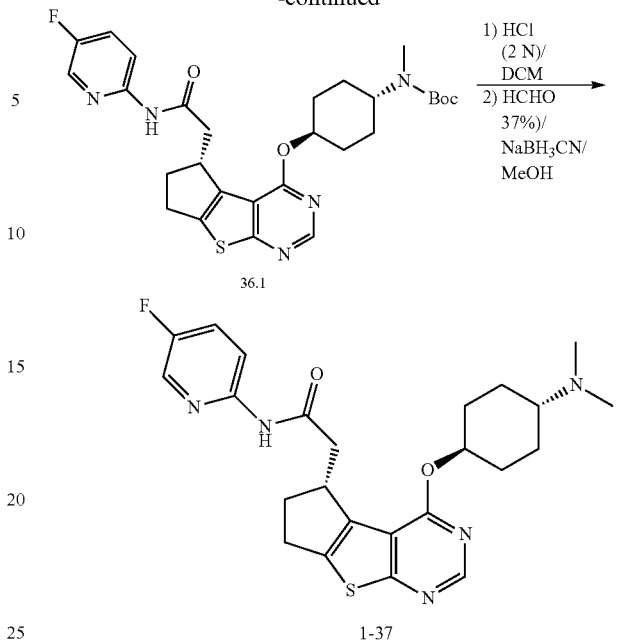

Synthesis of Compound 36.1.

A solution of 35.1 (200 mg, 0.43 mmol, 1.00 equiv), 5-fluoropyridin-2-amine (55 mg, 0.49 mmol, 1.13 equiv), HATU (200 mg) and DIPEA (170 mg) in distilled DMF (8 mL) was stirred at room temperature under nitrogen for 2 h. The reaction was then quenched with water and extracted with ethyl acetate (3×30 mL). The combined organic layers were washed with brine, dried over anhydrous sodium sulfate and concentrated under vacuum. The residue was loaded onto a silica gel column with ethyl acetate/petroleum ether (1:2 to 3:5) to give tert-butyl N-(4-[[(3R)-3-[[(5-fluoropyridin-2-yl)carbamoyl]methyl]-7-thia-9,11-diazatricyclo[6.4.0.0[2,6]] dodeca-1(8),2(6),9,11-tetraen-12-yl]oxy]cyclohexyl)-N-methylcarbamate (36.1, 200 mg, 83%) as a yellow oil. MS: m/z 556 (M+H)⁺.

Synthesis of Compound I-37.

To a 25-mL round-bottom flask containing a solution of 36.1 (200 mg, 0.36 mmol, 1.00 equiv) in dichloromethane (15 mL) was added hydrochloric acid (12 M, 2 mL) at 0° C. under nitrogen. The resulting solution was stirred for 2 h at room temperature and concentrated under vacuum to afford N-(5-fluoropyridin-2-yl)-2-[(3R)-12-[[4-(methylamino)cyclohexyl]oxy]-7-thia-9,11-diazatricyclo[6.4.0.0ˆ[2,6]]dodeca-1(8),2(6),9,11-tetraen-3-yl]acetamide hydrochloride (130 mg, crude), which was used in the next step without further purification.

A solution of this compound (130 mg, crude) and HCHO (37%, 1 mL) in methanol (10 mL) was stirred at room temperature for 30 min., whereupon NaBH₃CN (55 mg, 0.78 mmol, 3.06 equiv) was added to the mixture and stirring was continued for an additional 2 h at room temperature. The reaction was then quenched by the addition of 20 mL of water and extracted with 3×30 mL of ethyl acetate. The combined organic layers were concentrated under vacuum. The crude product (70 mg) was purified by preparative HPLC (SHIMADZU) under the following conditions: column: Xbridge Prep C18 5 um, 19*150 mm; mobile phase: water (0.05% NH₄HCO₃ solution) and CH₃CN (start at 6.0% CH₃CN then ramp up to 50.0% over 25 min); UV detection at 254 and 220 nm. The fractions were collected and evaporated under reduced pressure to give Compound I-37 (33.4 mg) as a white solid. $^1$H NMR (300 MHz, CD$_3$OD) δ 8.49 (s, 1H), 8.20 (m, 2H), 7.63 (m, 1H), 5.29 (m, 1H), 3.91 (t, 1H), 3.32 (m, 2H), 3.03 (m, 1H), 2.82 (m, 1H), 2.77 (m, 1H), 2.55 (m, 10H), 2.03 (m, 2H), 1.55 (m, 4H). MS: m/z 470 (M+H)$^+$.

Example 37

Synthesis of 2-[(3S)-12-[[4-(dimethylamino)cyclo-hexyl]oxy]-7-thia-9,11-diazatricyclo[6.4.0.0[2,6]]dodeca-1(12),2(6),8,10-tetraen-3-yl]-N-ethylacetamide (I-35)

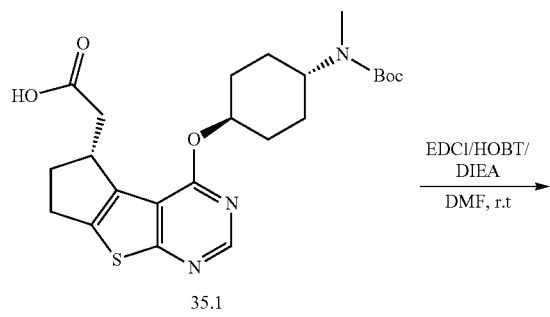

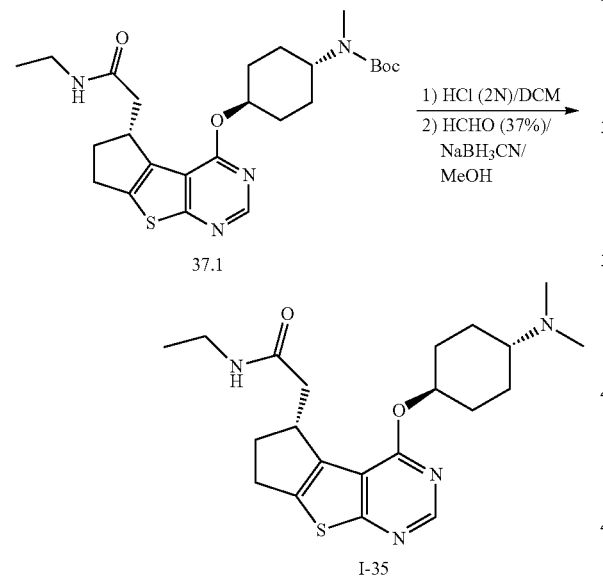

Synthesis of Compound 37.1.

To a 25-mL round-bottom flask was added intermediate 35.1 (200 mg, 0.43 mmol, 1.00 equiv), HOBt (90 mg, 0.67 mmol, 1.54 equiv), EDCI (191 mg, 1.00 mmol, 2.31 equiv), ethanamine hydrochloride (45 mg, 0.55 mmol, 1.27 equiv) and triethylamine (135 mg, 1.34 mmol, 3.08 equiv) in 10 mL of distilled DMF. The reaction was stirred for 4 h at room temperature under nitrogen. It was then quenched with water and extracted with 3×25 mL of ethyl acetate. The combined organic layers were washed with brine and dried over anhydrous sodium sulfate. After filtration and concentration under reduced pressure, the residue was loaded onto a silica gel column with ethyl acetate/petroleum ether (1:2 to 3:5) and purified to provide the desired compound 37.1 (160 mg, 76%) as a white solid. MS: m/z 489 (M+H)$^+$.

Synthesis of Compound I-35.

To a 25-mL round-bottom flask was added 37.1 (160 mg, 0.33 mmol, 1.00 equiv) and hydrochloric acid (12 M, 2 mL) in dichloromethane (12 mL). The reaction was stirred for 2 h at room temperature. The resulting mixture was concentrated under vacuum to give 1-(ethylamino)-2-[(3S)-12-[[4-(methylamino)cyclohexyl]oxy]-7-thia-9,11-diazatricyclo[6.4.0.0[2,6]]dodeca-1(12),2(6),8,10-tetraen-3-yl]ethan-1-ol hydrochloride (100 mg, crude) as yellow oil which was used in the next step without further purification. To a solution of this compound (100 mg, crude) in methanol (10 mL) was added HCHO (37%, 2 mL) and the reaction was stirred for 1 h at room temperature. Then NaBH$_3$CN (50 mg, 63%) was added and stirring continued for another 2 h at ambient temperature. The resulting mixture was concentrated under reduced pressure and the crude product (80 mg) purified by preparative HPLC(SHIMADZU) under the following conditions: column: Xbridge Prep C18 5 um, 19*150 mm; mobile phase: water (0.05% NH$_4$HCO$_3$ solution) and CH$_3$OH NMR (start at 6.0% CH$_3$OH and ramp up to 50.0% over 25 min); UV detection at 254 nm. The product-containing fractions were collected and evaporated under reduced pressure to afford Compound I-35 (12.5 mg) as a white solid. An ee of 100% was measured by chiral HPLC analysis. $^1$H NMR (400 MHz, CD$_3$OD) δ 8.48 (s, 1H), 5.30 (m, 1H), 3.82 (m, 1H), 2.98-3.33 (m, 5H), 2.73 (m, 1H), 2.20-2.68 (m, 11H), 1.50-1.72 (m, 4H), 1.15 (t, 3H). MS: m/z 403 (M+H)$^+$.

Example 38

Synthesis of Intermediate 38.2

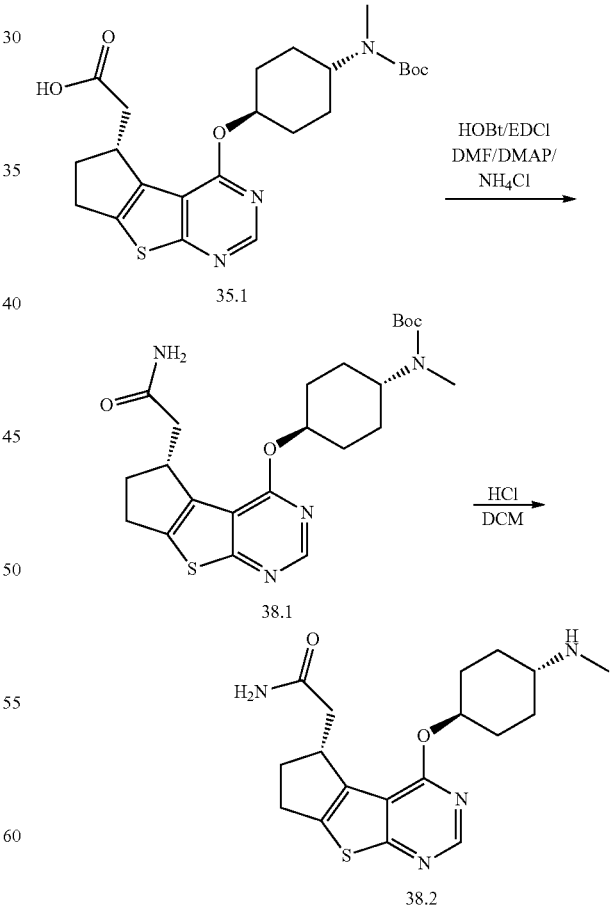

Synthesis of Compound 38.1.

To a 25-mL, round-bottom, dry flask containing a solution of 35.1 (200 mg, 0.43 mmol, 1.00 equiv) in distilled DMF (6 mL) was added EDCI (99 mg, 0.52 mmol, 1.19 equiv), HOBt (70 mg, 0.52 mmol, 1.20 equiv), 4-dimethylaminopyridine (63 mg, 0.52 mmol, 1.19 equiv) and NH$_4$Cl (68 mg, 1.28 mmol, 2.96 equiv) successively at room temperature under nitrogen. The resulting solution was stirred for 14 h at ambient temperature and quenched with 20 mL of water and extracted with 3×30 mL of ethyl acetate. The combined organic layers were washed with brine (three times) and dried over anhydrous sodium sulfate. After filtration and concentration under reduced pressure, the residue was loaded onto a silica gel column with ethyl acetate/petroleum ether (1:1) and purified to afford 38.1 (150 mg, 75%) as a white solid.

Synthesis of Intermediate 38.2.

To a solution of 38.1 (150 mg, 0.33 mmol, 1.00 equiv) in dichloromethane (10 mL) was added hydrochloric acid (12 M, 2 mL) at 0° C. and the resulting solution was stirred for 2 h at room temperature. The reaction was then quenched with saturated aqueous sodium bicarbonate and extracted with ethyl acetate (3×20 mL). The combined organic layers were washed with brine and concentrated under reduced pressure to give 2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]acetamide (100 mg, crude) as a yellow oil.

Example 39

Synthesis of 2-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]acetamide (I-43)

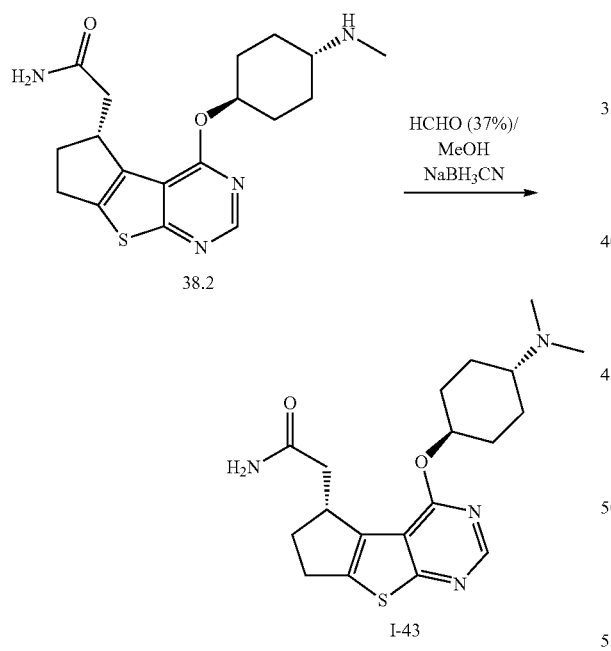

Synthesis of Compound I-43. Intermediate 38.2 (100 mg, crude) was treated with HCHO (37%, 1 mL) in methanol (8 mL) and the reaction stirred at room temperature for 30 min. Then NaBH$_3$CN (52.5 mg, 0.83 mmol, 3.00 equiv) was added and the reaction stirred for a further 2 h at ambient temperature. The solvent was removed under reduced pressure to give the product (100 mg, crude), which was purified by preparative HPLC (SHIMADZU) under the following conditions: column: Xbridge Prep C18 5 um, 19*150 mm; mobile phase: water (0.05% NH$_4$HCO$_3$ solution) and CH$_3$CN (start at 6.0% CH$_3$CN then ramp up to 50.0% over 25 min); UV detection at 254 nm. The product-containing fractions were collected and evaporated under reduced pressure to provide Compound I-43 (76.8 mg) as a white solid. $^1$H NMR (300 MHz, CDCl$_3$): δ 8.51 (s, 1H), 5.34 (m, 3H), 3.81 (m, 1H), 3.04 (m, 3H), 2.98 (m, 2H), 2.35 (m, 11H), 2.01 (m, 2H), 1.74 (m, 1H), 1.44-1.66 (m, 4H). MS: m/z 374 (M+H)$^+$.

Example 40

Synthesis of Intermediate 40.2

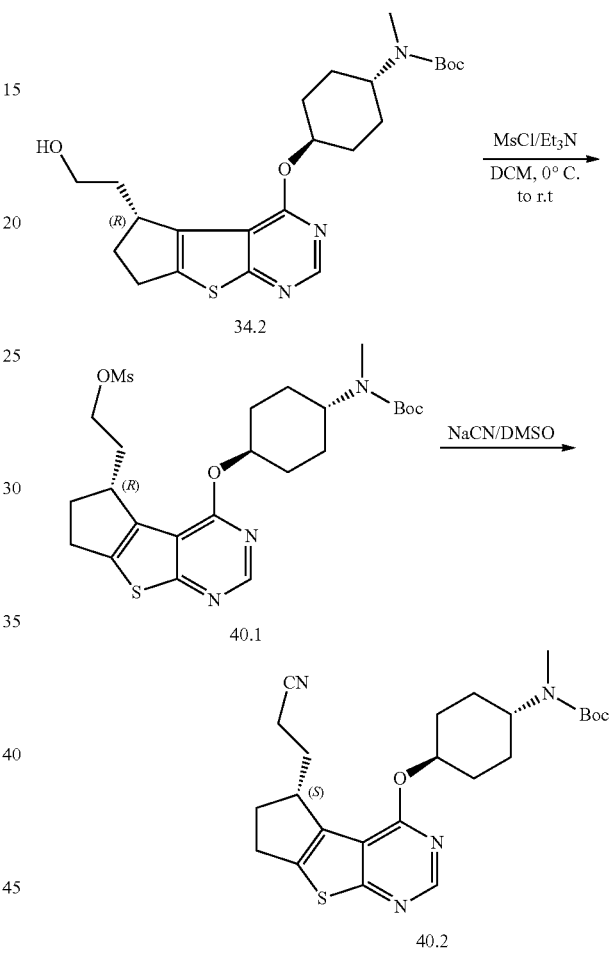

Synthesis of Compound 40.1.

A 50-mL round-bottom flask containing a solution of intermediate 34.2 (1.0 g, 2.23 mmol, 1.00 equiv) and TEA (339 mg, 3.35 mmol, 1.50 equiv) in dichloromethane (25 mL) was added methanesulfonyl chloride (306 mg, 2.67 mmol, 1.20 equiv) at 0° C. under nitrogen. The resulting solution was stirred for 2 h at room temperature and quenched by the addition of water. The reaction mixture was extracted with dichloromethane (2×40 mL). The combined organic layers were washed with brine and dried over anhydrous sodium sulfate. After filtration and concentration under reduced pressure, the residue was loaded onto a silica gel column with ethyl acetate/petroleum ether (1:2) and purified to afford compound 40.1 (1.1 g, 94%) as a yellow oil. MS: m/z 526 (M+H)$^+$.

Synthesis of compound 40.2. 40.1 (1.1 g, 2.09 mmol, 1.00 equiv) was placed in a 50 mL round-bottom flask and treated with NaCN (308 mg, 6.29 mmol, 3.00 equiv) in DMSO (15 mL) for 4 h at 80° C. under nitrogen. The reaction was then quenched with water and extracted with ethyl acetate (3×40 mL). The organic layers were combined, washed with brine and dried over anhydrous sodium sulfate. After filtration and concentration under reduced pressure, the residue was purified by column chromatography on silica gel with ethyl acetate/petroleum ether (1:3) to give the desired intermediate 40.2 (920 mg, 96%) as a yellow solid. MS: m/z 457 (M+H)$^+$.

Example 41

Synthesis of 3-[(3S)-12-[[4-(dimethylamino)cyclohexyl]oxy]-7-thia-9,11-diazatricyclo[6.4.0.0[2,6]]dodeca-1(8),2(6),9,11-tetraen-3-yl]propanenitrile (I-42)

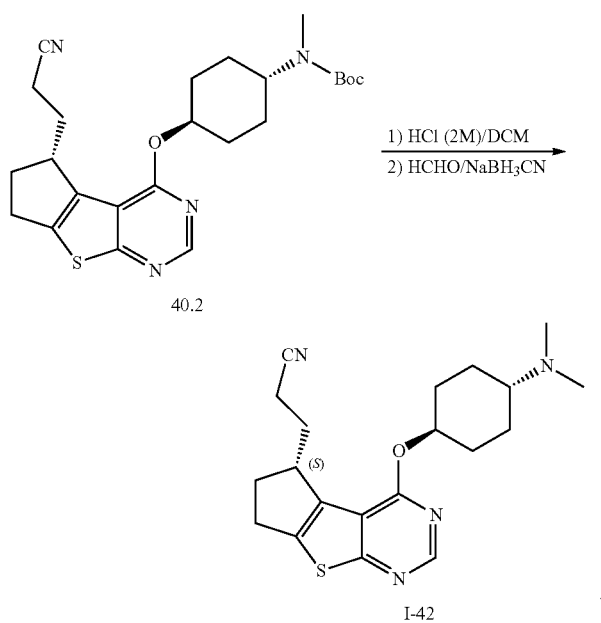

Synthesis of Compound I-42.

To a solution of intermediate 40.2 (200 mg, 0.44 mmol, 1.00 equiv) in dichloromethane (10 mL) was added hydrochloric acid (12 M, 2 mL) at 0° C. and the resulting solution was stirred for 2 h at room temperature. The reaction was then quenched with saturated aqueous sodium bicarbonate and extracted with ethyl acetate (3×20 mL). The combined organic layers were washed with brine and concentrated under reduced pressure to afford 3-[(3S)-12-[[4-(methylamino)cyclohexyl]oxy]-7-thia-9,11-diazatricyclo[6.4.0.0[2,6]]dodeca-1(8),2(6),9,11-tetraen-3-yl]propanenitrile (120 mg, crude) as a yellow oil.

A solution of this material and HCHO (37%, 1 mL) in methanol (8 mL) was stirred at room temperature for 30 min. Then NaBH$_3$CN (64 mg, 1.02 mmol, 3.02 equiv) was added and stirred for 2 h at ambient temperature. The solvent was removed under reduced pressure to give the product (100 mg, crude), which was purified by preparative HPLC (SHIMADZU) under the following conditions: column: Xbridge Prep C18 5 um, 19*150 mm; mobile phase: water (0.05% NH$_4$HCO$_3$ solution) and CH$_3$CN (start at 6.0% CH$_3$CN then ramp up to 50.0% over 25 min); UV detection at 254 nm. The product-containing fractions were collected and evaporated under reduced pressure to provide Compound I-42 (86.4 mg) as a white solid. $^1$H NMR (300 MHz, CD$_3$OD): δ 8.49 (s, 1H), 5.32 (m, 1H), 3.33 (m, 1H), 3.07 (m, 2H), 2.74 (m, 1H), 2.35-2.54 (m, 12H), 2.11 (m, 2H), 1.74 (m, 1H), 1.44-1.66 (m, 4H). MS: m/z 371 (M+H)$^+$.

Example 42

Synthesis of 3-[(3S)-12-[[4-(dimethylamino)cyclohexyl]oxy]-7-thia-9,11-diazatricyclo[6.4.0.0[2,6]]dodeca-1(8),2(6),9,11-tetraen-3-yl]propanamide (I-44)

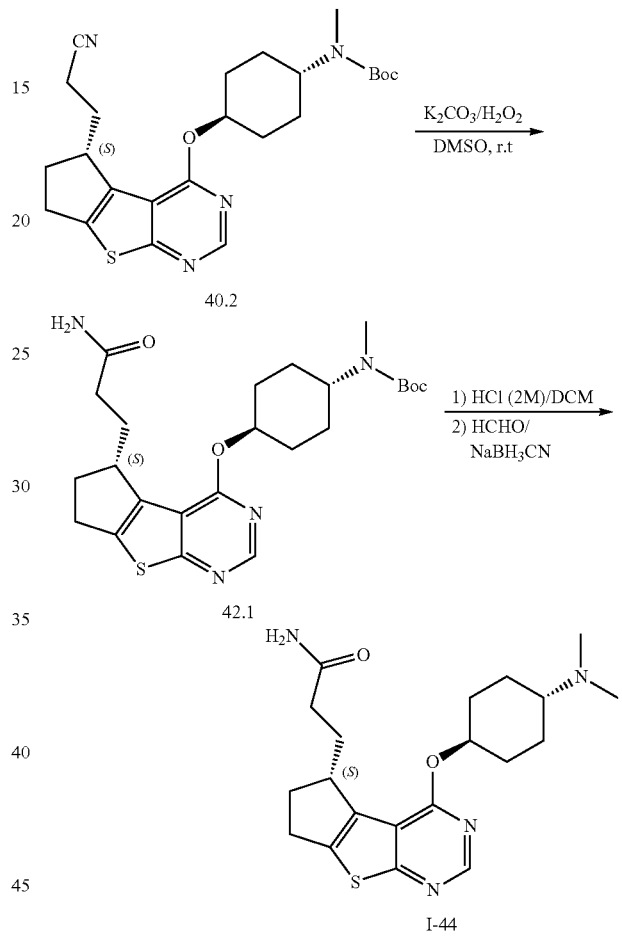

Synthesis of Compound 42.1.

To a solution of intermediate 40.2 (200 mg, 0.44 mmol, 1.00 equiv) and potassium carbonate (166 mg, 1.20 mmol, 2.75 equiv) in DMSO (10 mL) was added H$_2$O$_2$ (30%, 3 mL) at 0° C. The resulting solution was stirred for 18 h at room temperature, quenched with saturated aqueous Na$_2$SO$_3$ and extracted with ethyl acetate (3×60 mL). The combined organic layers were washed with brine, dried over anhydrous sodium sulfate and concentrated under vacuum. Compound 42.1 (110 mg, 53%) was obtained as a white solid. MS: m/z 475 (M+H)$^+$.

Synthesis of Compound I-44.

To a solution of 42.1 (110 mg, 0.23 mmol, 1.00 equiv) in dichloromethane (10 mL) was added hydrochloric acid (12 M, 2 mL) at 0° C. and the resulting solution was stirred for 2 h at room temperature. The reaction was then quenched with saturated aqueous sodium bicarbonate and extracted with ethyl acetate (3×20 mL). The combined organic layers were washed with brine and concentrated under reduced pressure to give 3-[(3S)-12-[[4-(methylamino)cyclohexyl]oxy]-7-thia-9,11-diazatricyclo[6.4.0.0[2,6]]dodeca-1(8),2(6),9,11-tetraen-3-yl]propanamide (70 mg, 81%) as a yellow oil. A solution of this material (70 mg, 0.19 mmol, 1.00 equiv) and HCHO (37%, 1 mL) in methanol (8 mL) was stirred at room temperature for 30 min. Then NaBH$_3$CN (35 mg, 0.56 mmol, 2.97 equiv) was added and stirring continued for 2 h at ambient temperature. The solvent was removed under reduced pressure to give the product (70 mg, crude), which was purified by preparative HPLC(SHIMADZU) under the following conditions: column: Xbridge Prep C18 5 um, 19*150 mm; mobile phase: water (0.05% NH$_4$HCO$_3$ solution) and CH$_3$CN (start at 6.0% CH$_3$CN then ramp up to 50.0% over 25 min); UV detection at 254 nm. The product-containing fractions were collected and evaporated under reduced pressure to afford Compound I-44 (67.5 mg) as a white solid. $^1$H NMR (300 MHz, CDCl$_3$) δ 8.46 (s, 1H), 5.78 (d, 2H), 5.22 (m, 1H), 3.44 (m, 1H), 3.02 (m, 2H), 2.67 (m, 1H), 2.33 (m, 13H), 1.90 (m, 3H), 1.44 (m, 4H). MS: m/z 389 (M+H)$^+$.

Example 43

Synthesis of Intermediate 43.1

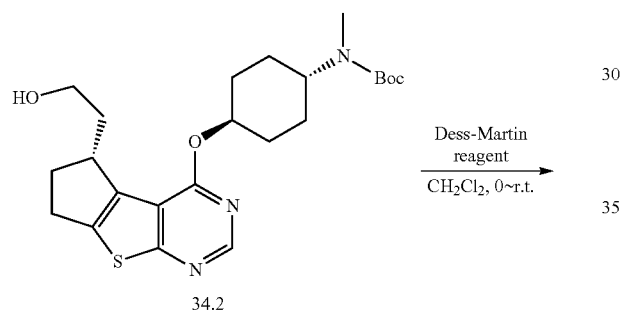

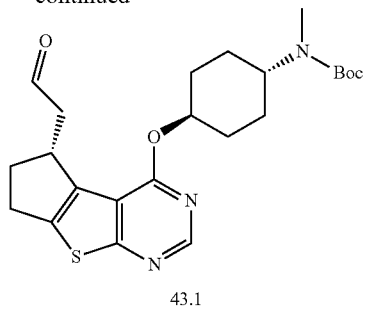

Synthesis of Compound 43.1.

To a solution of 34.2 (1.1 g, 2.46 mmol, 1.00 equiv) in dichloromethane (60 mL) was added Dess-Martin periodinane (1.1 g, 2.69 mmol, 1.10 equiv) in portions at 0° C. under nitrogen. After the addition was complete, the resulting solution was stirred for 2 h at room temperature and then diluted with ethyl acetate. The organic layer was washed with NaHCO$_3$ (aq.), brine, dried over anhydrous Na$_2$SO$_4$, and concentrated under reduced pressure. The residue was loaded onto a silica gel column with ethyl acetate/petroleum ether (1:10-1:5) and purified to afford intermediate 43.1 (0.93 g, 85%) as a light yellow oil.

Example 44

Synthesis of (2S)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propan-2-ol
(I-40)

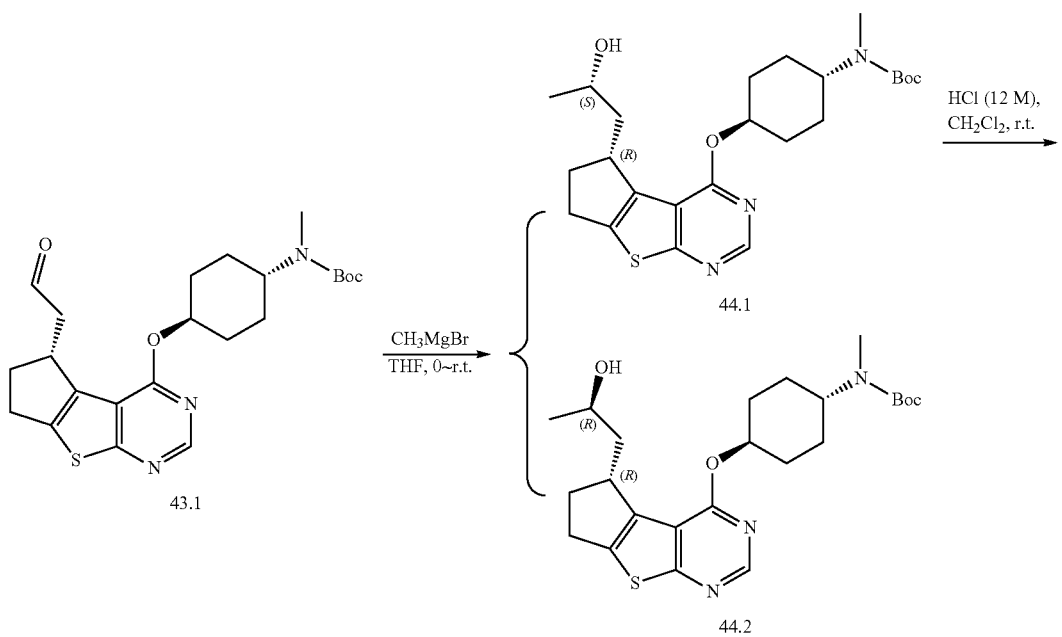

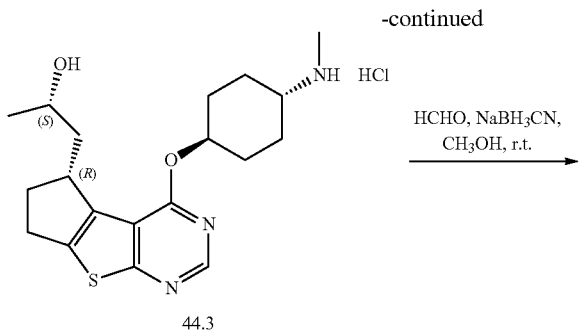
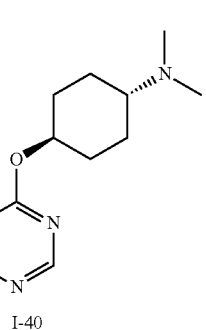

Synthesis of Compounds 44.1 and 44.2.

To a solution of 43.1 (450 mg, 1.01 mmol, 1.00 equiv) in distilled tetrahydrofuran (20 mL) was added dropwise bromo(methyl)magnesium (0.5 mL, 1.50 equiv) at 0° C. under nitrogen. The resulting solution was stirred for 2 h at room temperature, quenched with water and extracted with ethyl acetate. After drying over $Na_2SO_4$ and evaporation of the solvents under reduced pressure, the residue was loaded onto a silica gel column with ethyl acetate/petroleum ether (1:10-1:5) and the diastereomers separated to give both 44.1 (0.11 g) and 44.2 (0.16 g) as light yellow oils.

Synthesis of Compound 44.3.

To a solution of 44.1 (100 mg, 0.22 mmol, 1.00 equiv) in dichloromethane (8 mL) was added hydrochloric acid (12 M, 0.5 mL) at 0° C. under nitrogen. The resulting solution was stirred for 2 h at room temperature. After the reaction was complete, the solvent was removed by evaporation under reduced pressure to give 44.3 (70 mg, crude) as a light yellow oil which was used directly without further purification.

Synthesis of compound I-40.

To a solution of 44.3 (70 mg, 0.18 mmol, 1.00 equiv) in methanol (8 mL) was added HCHO (37%, 1.5 mL) at room temperature. The resulting solution was stirred for 1 h at ambient temperature, and then $NaBH_3CN$ (33.0 mg, 0.53 mmol, 3.00 equiv) was added. The resulting mixture was stirred overnight at room temperature. After evaporation, the crude product (80 mg) was purified by preparative HPLC (SHIMADZU) under the following conditions: column: SunFire Prep C18, 19*150 mm 5 um; mobile phase: water (0.05% $NH_4HCO_3$ solution) and $CH_3CN$ (7.0% $CH_3CN$ then ramp up to 63.0% over 14 min); UV detection at 254 and 220 nm. The product fractions were collected and evaporated under reduced pressure to afford Compound I-40 (40 mg, 61%) as a white solid. $^1$H NMR (400 MHz, $CD_3OD$): δ 8.48 (s, 1H), 5.30-5.32 (m, 1H), 3.90-3.98 (m, 1H), 3.30-3.40 (m, 1H), 3.09-3.15 (m, 1H), 2.95-3.02 (m, 1H), 2.60-2.70 (m, 1H), 2.45-2.53 (m, 1H), 2.30-2.40 (m, 9H), 2.02-2.12 (m, 3H), 1.50-1.70 (m, 5H), 1.31 (d, 3H). MS: m/z 376 (M+H)$^+$.

Example 45

Synthesis of (2R)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propan-2-ol (I-41)

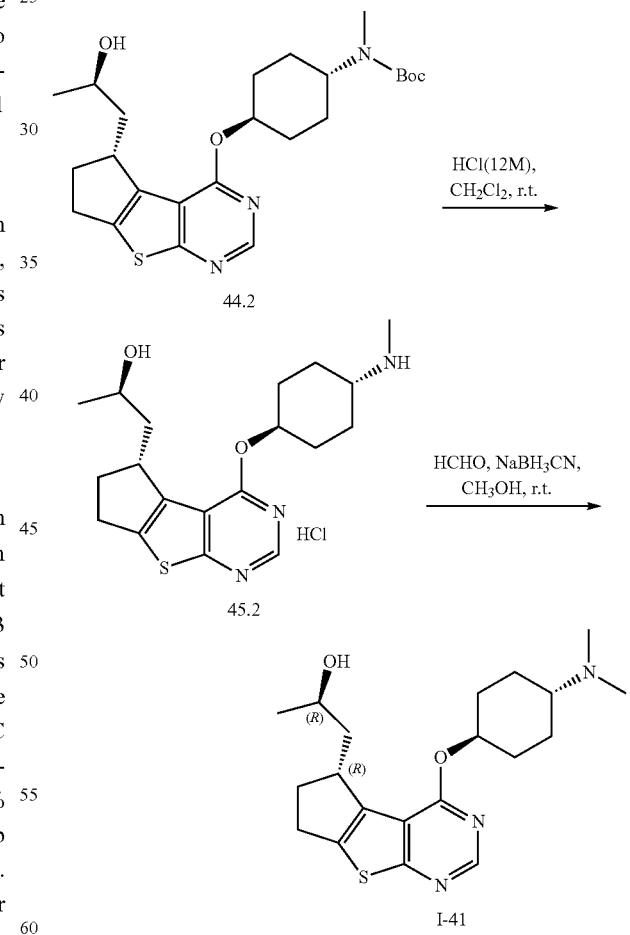

Synthesis of Compound 45.2.

To a solution of 44.2 (prepared as in Example 44; 150 mg, 0.32 mmol, 1.00 equiv) in dichloromethane (10 mL) was added hydrochloric acid (12 M, 0.8 mL) at 0° C. under nitrogen. The resulting solution was stirred for 2 h at room temperature. The solvent was removed under reduced pressure to afford compound 45.2 (110 mg, crude) as a light yellow oil which was used in the next step without further purification.

Synthesis of Compound I-41.

To a solution of 45.2 (110 mg, crude) in methanol (10 mL) was added HCHO (37%, 2.0 mL) and the reaction was stirred for 1 h at room temperature. Then NaBH$_3$CN (52.2 mg, 0.83 mmol, 3.00 equiv) was added and the resulting solution was stirred overnight at room temperature. After evaporation under reduced pressure, the crude product (100 mg) was purified by preparative HPLC (SHIMADZU) under the following conditions: column: SunFire Prep C18, 19*150 mm 5 um; mobile phase: water (0.05% NH$_4$HCO$_3$) and CH$_3$CN (7.0% CH$_3$CN then ramp up to 63.0% in 13 min); UV detection at 254 and 220 nm. The product-containing fractions were collected and evaporated to remove the solvents to afford Compound I-41 (46.3 mg, 58%) as a white solid. $^1$H NMR (300 MHz, CD$_3$OD): δ 8.48 (s, 1H), 5.20-5.30 (m, 1H), 3.85-3.95 (m, 1H), 3.50-3.60 (m, 1H), 3.05-3.15 (m, 1H), 2.90-3.00 (m, 1H), 2.60-2.70 (m, 1H), 2.25-2.40 (m, 10H), 2.15-2.25 (m, 1H), 2.00-2.14 (m, 2H), 1.63-1.68 (m, 2H), 1.40-1.52 (m, 3H), 1.21 (d, 3H). MS: m/z 376 (M+H)$^+$.

Example 46

Synthesis of 2-(((1R,4r)-4-(((R)-5-((S)-2-hydroxypropyl)-6,7-dihydro-5H-cyclopenta[4,5]thieno[2,3-d]pyrimidin-4-yl)oxy)cyclohexyl)(methyl)amino)-1-(pyrrolidin-1-yl)ethanone (I-69)

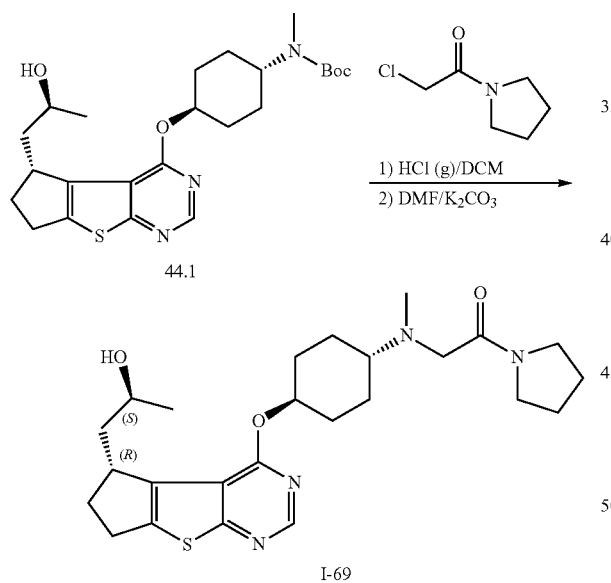

To a 50-mL round-bottom flask was added a solution of 44.1 (130 mg, 0.28 mmol, 1.0 equiv) in 5.5 mL of dichloromethane. After cooling to 0° C., hydrochloric acid (12 M, 0.5 mL) was added and the resulting solution was stirred for 3 h at room temperature. The reaction mixture was concentrated under reduced pressure to give the (2S)-1-[(3R)-12-[[4-(methylamino)cyclohexyl]oxy]-7-thia-9,11-diazatricyclo [6.4.0.0[2,6]]dodeca-1(8),2(6),9,11-tetraen-3-yl]propan-2-ol hydrochloride (80 mg, crude) as a light yellow oil. This material (80 mg, crude) was dissolved in DMF (5 mL) and potassium carbonate (240 mg) and 2-chloro-1-(pyrrolidin-1-yl)ethan-1-one (120 mg) were added at room temperature and the resulting mixture was stirred for 14 h at 25° C. After completion of the reaction, the product was extracted with DCM, washed with brine, and concentrated in vacuo. The crude product (120 mg) was purified by preparative HPLC (SHIMADZU) under the following conditions: column: SunFire Prep C18, 19*150 mm 5 um; mobile phase: water (0.1% HCOOH) and CH$_3$CN (6.0% CH$_3$CN up to 50.0% in 25 min); UV detection at 254/220 nm. The product containing fractions were collected and concentrated to afford Compound I-69 (32.8 mg) as a white solid. $^1$H NMR (400 MHz, CD$_3$OD): δ 8.45 (1H, s), 5.35-5.15 (1H, m), 3.99-3.80 (1H, m), 3.59-3.56 (3H, m), 3.43 (2H, t), 3.31-3.36 (2H, s), 3.16-3.05 (1H, m), 3.04-2.89 (1H, m), 2.62-2.67 (2H, m), 2.39-2.21 (6H, m), 2.20-2.10 (1H, m), 2.03-1.97 (4H, m), 1.92-1.85 (2H, m), 1.73-1.60 (2H, m), 1.59-1.41 (3H, m), 1.20 (3H, d). MS: m/z 473 (M+H)$^+$.

Example 47

Synthesis of racemic 2-[(3R)-12-[[4-(dimethylamino)cyclohexyl]oxy]-7-thia-9,11-diazatricyclo [6.4.0.0[2,6]]dodeca-1(8),2(6),9,11-tetraen-3-yl]-1-(1,3-oxazol-2-yl)ethan-1-ol (I-60)

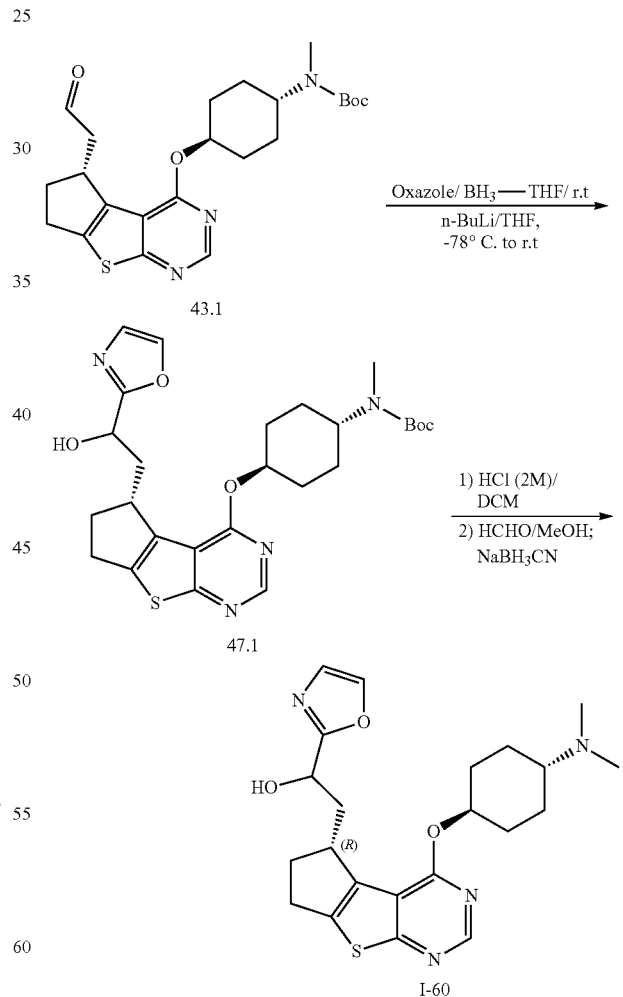

Synthesis of Compound 47.1.

To a 50-mL round-bottom flask containing 1,3-oxazole (90 mg, 1.30 mmol, 1.00 equiv) in freshly distilled THF (10 mL) was added BH$_3$-THF (1 M, 1.43 mL) dropwise at 0° C. under nitrogen. After stirring at room temperature for 1 h, the solution was cooled to −78° C. and then n-BuLi (2.5 M in hexane, 0.68 mL) was added dropwise via a syringe. Stirring was continued for an additional 1 h. A solution of intermediate 43.1 (580 mg, 1.30 mmol, 1.00 equiv) in THF (50 mL) was added at −78° C. and stirred for 2 h at −40° C. After the reaction was complete, it was quenched with 5% AcOH-EtOH and stirred for an additional 14 h at room temperature. The resulting solution was concentrated under vacuum and the residue was loaded onto a silica gel column with ethyl acetate/petroleum ether (1:1) to afford 47.1 (250 mg, 37%) as a yellow oil. MS: m/z 515 (M+H)$^+$.

Synthesis of Compound I-60.

Hydrochloric acid (12 M, 2 mL) was added to a solution of 47.1 (250 mg, 0.49 mmol, 1.00 equiv) in dichloromethane (10 mL) at 0° C. The reaction was stirred for 2 h at room temperature then quenched by the addition of 20 mL of saturated aqueous sodium bicarbonate and extracted with 2×30 mL of dichloromethane. The combined organic layers were washed with brine, dried over anhydrous sodium sulfate and concentrated under vacuum to afford 2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]-1-(1,3-oxazol-2-yl)ethan-1-ol (180 mg, crude) as a yellow oil which was used in the next reaction without further purification. To a solution of this material (180 mg, 0.43 mmol, 1.00 equiv) in 4 mL of methanol was added HCHO (30%, 1 mL) and the reaction mixture was stirred at room temperature for 30 min. NaBH$_3$CN (109 mg, 1.73 mmol, 3.98 equiv) was added to the mixture and stirring was continued for another 2 h at ambient temperature. The reaction was then quenched by the addition of H$_2$O and extracted with dichloromethane (15 mL), dried over anhydrous sodium sulfate and concentrated under vacuum. The crude product (80 mg) was purified by preparative HPLC(SHIMADZU) under the following conditions: column: SunFire Prep C18, 19*150 mm 5 um; mobile phase: water (0.05% NH$_4$HCO$_3$) and CH$_3$CN (start at 6.0% CH$_3$CN then ramp up to 55.0% over 19 min); UV detection at 254 and 220 nm. The product-containing fractions were collected and evaporated to remove the solvents under reduced pressure to afford the racemic Compound I-60 (48.2 mg, 26%) as a white solid. $^1$H NMR (400 MHz, CDCl$_3$): δ 8.511 (s, 1H), 7.58 (d, 1H), 7.07 (d, 1H), 5.24-5.28 (m, 1H), 4.90-5.00 (m, 1H), 3.7-3.8 (m, 0.5H), 3.4-3.6 (m, 0.5H), 2.95-3.12 (m, 3H), 2.59-2.74 (m, 2H), 2.23-2.37 (m, 10H), 2.00-2.09 (m, 3H), 1.47-1.61 (m, 4H). MS: m/z 429 (M+H)$^+$.

Example 48

Synthesis of 3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-2-hydroxypropanamide (I-57)

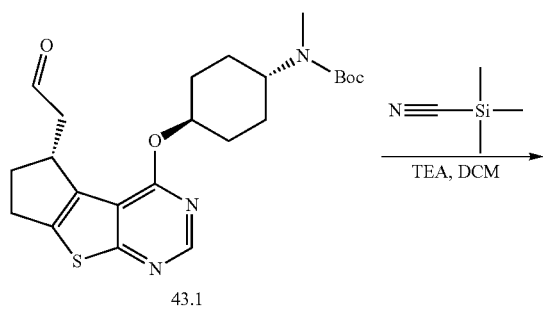

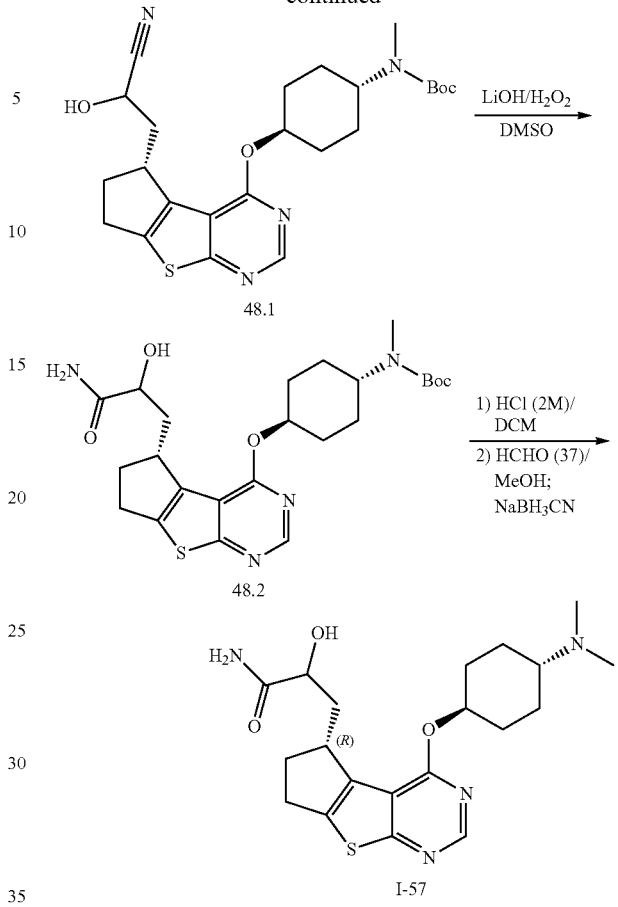

Synthesis of Compound 48.1.

A 25-mL round-bottom flask was charged with 43.1 (250 mg, 0.56 mmol, 1.00 equiv) and TEA (57 mg, 0.56 mmol, 1.00 equiv) in distilled dichloromethane (15 mL). Trimethylsilanecarbonitrile (111 mg, 1.12 mmol, 2.0 equiv) was added and the reaction was stirred for 2 h at room temperature under nitrogen. The reaction was then quenched by the addition of water and extracted with 3×20 mL of dichloromethane. The combined organic layers were washed with brine and dried over sodium sulfate. After concentration in vacuo, the residue was loaded onto a silica gel column with ethyl acetate/petroleum ether (1:3) and purified to afford compound 48.1 (200 mg, 75%) as a colorless oil. MS: m/z 473 (M+H)$^+$.

Synthesis of Compound 48.2.

A solution of 48.1 (170 mg, 0.36 mmol, 1.00 equiv), LiOH (13 mg) and H$_2$O$_2$ (30%, 0.5 mL) in methanol (4 mL) was stirred for 3 h at 0° C. The reaction was then quenched by the addition of water and extracted with 3×20 mL of ethyl acetate. The combined organic layers were washed with brine and dried over sodium sulfate. Concentration in vacuo afforded compound 48.2 (70 mg, 40%) as a white solid. MS: m/z 491 (M+H)$^+$.

Synthesis of Compound I-57.

To a 25-mL round-bottom flask was added a solution of 48.2 (70 mg, 0.14 mmol, 1.00 equiv) in dichloromethane (5 mL) at 0° C. Then hydrochloric acid (12 M, 1 mL) was added and the resulting solution was stirred for 2 h at room temperature. The reaction was then quenched by the addition of saturated aqueous sodium bicarbonate and extracted with 2×20 mL of dichloromethane. The combined organic layers was concentrated in vacuo to give the 2-hydroxy-3-[(3R)-12-[[4-(methylamino)cyclohexyl]oxy]-7-thia-9,11-diazatricyclo[6.4.0.0[2,6]]dodeca-1(8),2(6),9,11-tetraen-3yl]propanamide (50 mg, crude) as a yellow oil. This material (50 mg, crude) was dissolved in methanol (5 mL). HCHO (37%, 0.5 mL) was added and the resulting solution was stirred for 30 min at room temperature. Then NaBH$_3$CN (32 mg, 0.51 mmol, 4.0 equiv) was added and stirring was continued overnight at ambient temperature. The reaction was then quenched by the addition of H$_2$O and extracted with dichloromethane (15 mL), dried over anhydrous sodium sulfate and concentrated under vacuum. The crude product (80 mg) was purified by preparative HPLC(SHIMADZU) under the following conditions: column: SunFire Prep C18, 19*150 mm 5 um; mobile phase: water (0.05% NH$_4$HCO$_3$) and CH$_3$CN (start at 6.0% CH$_3$CN then ramp up to 55.0% over 19 min); UV detection at 254 and 220 nm. The product-containing fractions were collected and evaporated under reduced pressure to afford Compound I-57 (26.4 mg) as a white solid. $^1$H NMR (400 MHz, CDCl$_3$): δ 8.52 (s, 1H), 6.49 (d, 1H), 5.72 (d, 1H), 5.23 (m, 1H), 4.16 (m, 1H), 3.68 (m, 2H), 3.14 (m, 1H), 3.01 (m, 1H), 2.74 (m, 1H), 2.23-2.39 (m, 10H), 2.01 (m, 3H), 1.27-1.47 (m, 4H). MS: m/z 405 (M+H)$^+$.

Example 49

Synthesis of (2S)-3-[(3R)-12-[[4-(dimethylamino)cyclohexyl]oxy]-7-thia-9,11-diazatricyclo[6.4.0.0^[2,6]]dodeca-1(8),2(6),9,11-tetraen-3-yl]-2-hydroxypropanamide (I-74)

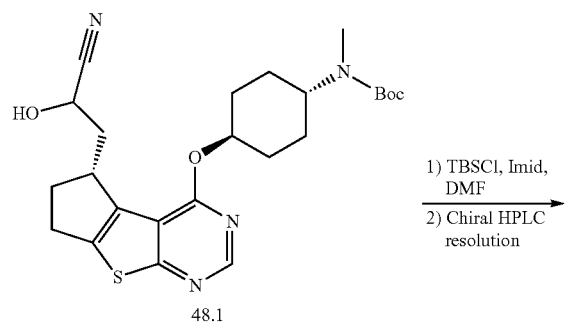

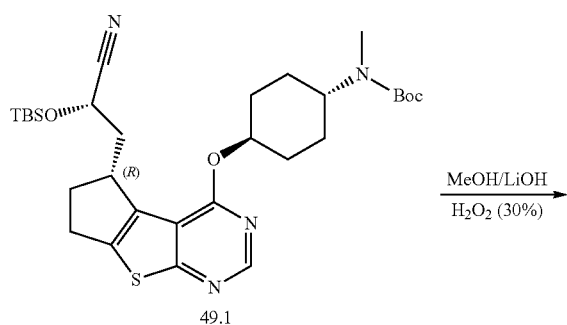

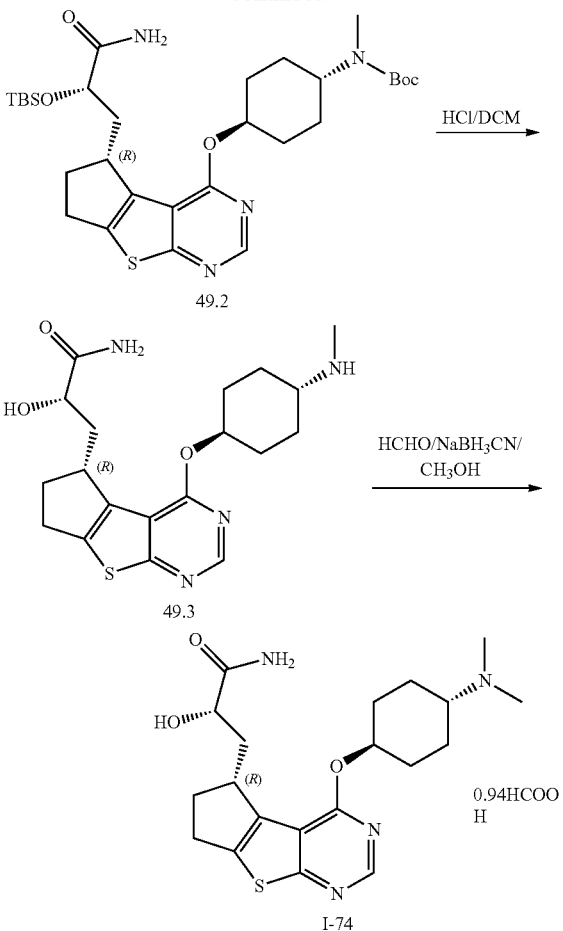

Synthesis of Compound 49.1.

Reference: For the preparation of the starting material compound 48.1, please refer to the experimental procedure for the synthesis of compound I-57. Into a 50-mL round-bottom flask, a solution of tert-butyl N-(4-[[(3R)-3-(2-cyano-2-hydroxyethyl)-7-thia-9,11-diazatricyclo[6.4.0.0[2,6]]dodeca-1(8),2(6),9,11-tetraen-12-yl]oxy]cyclohexyl)-N-methylcarbamate (1.9 g, 4.02 mmol, 1.00 equiv) in 10 mL of distilled DMF was added imidazole (544 mg, 8.00 mmol, 2.0 equiv) and tert-butyl(chloro)dimethylsilane (905 mg, 6.00 mmol, 1.49 equiv) at 0° C. under nitrogen. The resulting solution was stirred for 2 h at 20° C. After completion, the reaction was then quenched by the addition of 20 mL of water and extracted with 3×80 mL of ethyl acetate. The combined organic layers were washed with brine (three times), dried over anhydrous sodium sulfate and concentrated under vacuum. The residue was purified by column chromatography on silica gel with EtOAc/petroleum ether (1:20 to 1:5) to give 2.2 g (93%) of the desired tert-butyl N-(4-[[(3R)-3-[2-[(tert-butyldimethylsilyl)oxy]-2-cyanoethyl]-7-thia-9,11-diazatricyclo[6.4.0.0[2,6]]dodeca-1(8),2 (6),9,11-tetraen-12-yl]oxy]cyclohexyl)-N-methylcarbamate as a yellow oil. MS: m/z 587 (M+H)$^+$.

217

Synthesis of Compound 49.2.

A 50-mL round-bottom flask containing a solution of tert-butyl N-(4-[[(3R)-3-[2-[(tert-butyldimethylsilyl)oxy]-2-cyanoethyl]-7-thia-9,11-diazatricyclo[6.4.0.0[2,6]]dodeca-1(8),2(6),9,11-tetraen-12-yl]oxy]cyclohexyl)-N-methylcarbamate (2.2 g, 3.75 mmol, 1.00 equiv) in 20 mL of methanol was added LiOH (315 mg) followed by addition of $H_2O_2$ (30%, 3 mL) via syringe at 0° C. with vigorous stirring. The resulting solution was stirred for 3 h at 20° C. The reaction was then quenched by the addition of 50 mL of saturated aqueous $Na_2SO_3$ and extracted with 3×100 mL of ethyl acetate. The organic layers were combined, washed with 2×30 mL of brine, and concentrated under reduced pressure. The residue was applied onto a silica gel column with ethyl acetate/petroleum ether (1:1-2:1) to afford the desired tert-butyl N-(4-[[(3R)-3-[(2S)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)-N-methylcarbamate (0.9 g) as a white solid. MS: m/z 605 (M+H)$^+$, 627 (M+Na)$^+$.

Synthesis of Compound 49.3.

Into a 10-mL round-bottom flask was placed a solution of tert-butyl N-(4-[[(3R)-3-[(2S)-2-carbamoyl-2-hydroxyethyl]-7-thia-9,11-diazatricyclo[6.4.0.0ˆ[2,6]]dodeca-1(8),2(6),9,11-tetraen-12-yl]oxy]cyclohexyl)-N-methylcarbamate (0.9 g, 1.49 mmol, 1.00 equiv) in dichloromethane (10 mL) at 0° C. under nitrogen. Then hydrochloric acid (12 M, 2.0 mL) was added and the resulting solution was stirred for 5 h at 0° C. After completion of the reaction, the solvents were evaporated under reduced pressure. The residue was neutralized with 2 M aqueous sodium bicarbonate and extracted with 3×60 mL of dichloromethane. The organic layers were combined and washed with brine, dried over anhydrous sodium sulfate and concentrated under vacuum to give 520 mg (crude) of (2S)-2-hydroxy-3-[(3R)-12-[[4-(methylamino)cyclohexyl]oxy]-7-thia-9,11-diazatricyclo[6.4.0.0ˆ[2,6]]dodeca-1(8),2(6),9,11-tetraen-3-yl]propanamide as a yellow oil.

Synthesis of Compound I-74.

Compound 49.3 (520 mg, crude) and HCHO (37%, 608 uL, 7.5 mmol, 5.0 equiv) in methanol (8 mL) was stirred at room temperature for 30 min. and then $NaBH_3CN$ (283 mg, 4.5 mmol, 3.0 equiv) was added and the resulting solution was stirred for 12 h at room temperature. The crude product (500 mg) was purified by preparative HPLC under the following conditions (SHIMADZU): column: SunFire Prep C18, 19*150 mm 5 um; mobile phase: water with 0.05% HCOOH and $CH_3CN$ (6.0% $CH_3CN$ up to 55.0% in 19 min); UV detection at 254/220 nm. The product-containing fractions were collected and partially evaporated to remove $CH_3CN$ and water (bath temperature 25° C.) under reduced pressure. The residue was lyophilized overnight to afford the desired (2S)-3-[(3R)-12-[[4-(dimethylamino)cyclohexyl]oxy]-7-thia-9,11-diazatricyclo[6.4.0.0ˆ[2,6]]dodeca-1(8),2(6),9,11-tetraen-3-yl]-2-hydroxypropanamide formate (182 mg) as a white solid. MS: m/z 405 (M+H)$^+$. $^1$H NMR (400 MHz, $CD_3OD$): δ 8.60 (1H, brs), 8.47 (1H, s), 5.36-5.30 (1H, m), 4.15 (1H, t), 3.55 (1H, t), 3.36 (1H, m), 3.18-3.09 (1H, m), 3.08-2.94 (1H, m), 2.87 (6H, s), 2.76-2.69 (1H, m), 2.59-2.41 (3H, m), 2.40-2.32 (1H, m), 2.25-2.15 (2H, m), 1.95-1.55 (5H, m).

218

Example 50

Synthesis of (2R)-2-hydroxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanamide (I-140)

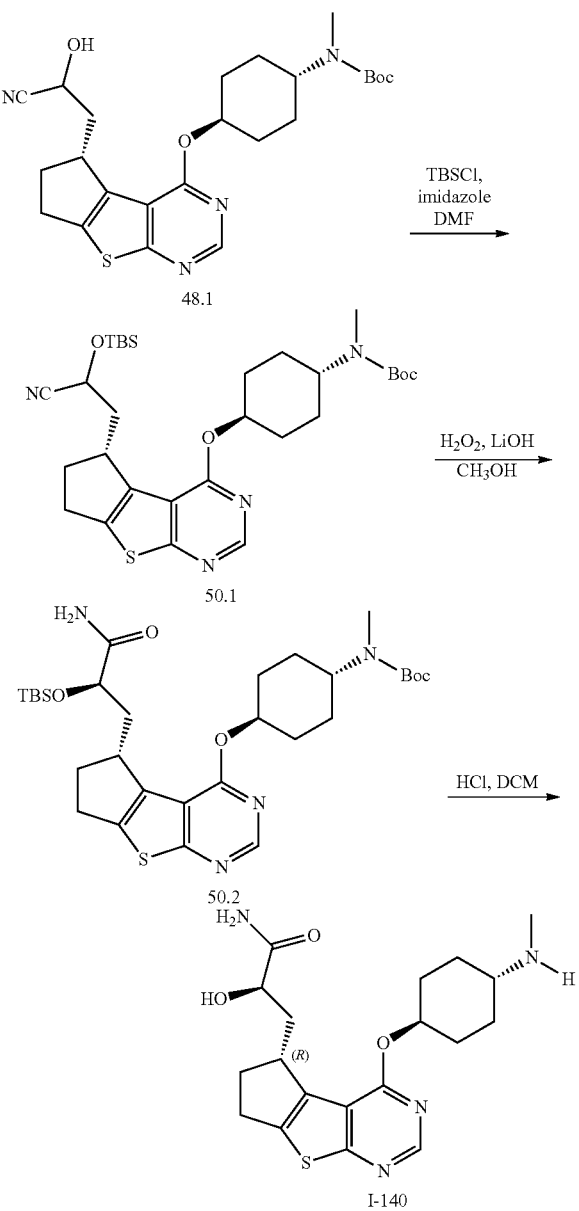

Synthesis of Compound 50.1.

A solution of tert-butyl N-(4-[[(3R)-3-(2-cyano-2-hydroxyethyl)-7-thia-9,11-diazatricyclo[6.4.0.0[2,6]]dodeca-1(8),2(6),9,11-tetraen-12-yl]oxy]cyclohexyl)-N-methylcarbamate (301 mg, 0.64 mmol, 1.00 equiv), imidazole (73 mg, 1.07 mmol, 1.69 equiv) and TBSCl (150 mg, 1.00 mmol, 1.57 equiv) in N,N-dimethylformamide (7 mL) was stirred overnight at room temperature. The resulting solution was diluted with 30 mL of water, extracted with 3×40 mL of ethyl acetate, washed with 50 mL of brine, concentrated under vacuum and purified onto a silica gel column with ethyl acetate/petroleum ether (1:3). This resulted in tert-butyl N-(4-[[(3R)-3-[2-[(tert-butyldimethylsilyl)oxy]-2-cyanoethyl]-7-thia-9,11-diazatricyclo[6.4.0.0[2,6]]dodeca-1(8),2(6),9,11-tetraen-12-yl]oxy]

cyclohexyl)-N-methylcarbamate (350 mg, 94%) as colorless oil.

Synthesis of Compound 50.2.

A 50-mL round-bottom flask containing a solution of tert-butyl N-(4-[[(3R)-3-[2-[(tert-butyldimethylsilyl)oxy]-2-cyanoethyl]-7-thia-9,11-diazatricyclo[6.4.0.0[2,6]]dodeca-1(8),2(6),9,11-tetraen-12-yl]oxy]cyclohexyl)-N-methylcarbamate (2.2 g, 3.75 mmol, 1.00 equiv) in 20 mL of methanol was added LiOH (315 mg), followed by addition of $H_2O_2$ (30%, 3 mL) via syringe at 0° C. with vigorous stirring. The resulting solution was stirred for 3 h at 20° C. The reaction was then quenched by the addition of 50 mL of saturated aqueous $Na_2SO_3$, extracted with 3×100 mL of ethyl acetate. The organic layers were combined, washed with 2×30 mL of brine, and concentrated under reduced pressure. The residue was applied onto a silica gel column with ethyl acetate/petroleum ether (1:1-2:1) to afford the desired tert-butyl N-(4-[[(3R)-3-[(2R)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)-N-methylcarbamate (0.7 g) as a white solid. MS: m/z 605 (M+H)$^+$, 627 (M+Na)$^+$.

Synthesis of Compound I-140.

Into a 10-mL round-bottom flask was placed a solution of tert-butyl N-(4-[[(3R)-3-[(2R)-2-carbamoyl-2-hydroxyethyl]-7-thia-9,11-diazatricyclo[6.4.0.0ˆ[2,6]]dodeca-1(8),2(6),9,11-tetraen-12-yl]oxy]cyclohexyl)-N-methylcarbamate (0.7 g, 1.16 mmol, 1.00 equiv) in dichloromethane (10 mL) at 0° C. under nitrogen. Then hydrochloric acid (12 M, 2.0 mL) was added and the resulting solution was stirred for 5 h at 0° C. After completion of the reaction, the solvents were evaporated under reduced pressure. The residue was neutralized with 2 M aqueous sodium bicarbonate and extracted with 3×60 mL of dichloromethane. The organic layers were combined and washed with brine, dried over anhydrous sodium sulfate and concentrated under vacuum to give 400 mg (crude) of (2R)-2-hydroxy-3-[(3R)-12-[[4-(methylamino)cyclohexyl]oxy]-7-thia-9,11-diazatricyclo[6.4.0.0ˆ[2,6]]dodeca-1(8),2(6),9,11-tetraen-3-yl]propanamide as a yellow oil. $^1$H NMR (300 MHz, CD$_3$OD): δ 8.46 (s, 1H), 5.30 (m, 1H), 4.08 (m, 1H), 3.66 (m, 1H), 3.19-3.12 (m, 1H), 3.02-2.96 (m, 1H), 2.74-2.25 (m, 9H), 2.13-2.10 (m, 2H), 1.82-1.68 (m, 3H), 1.45-1.25 (m, 2H). MS: m/z 391 (M+H)$^+$.

Example 51

Synthesis of (2R)-3-[(3R)-12-[[4-(dimethylamino)cyclohexyl]oxy]-7-thia-9,11-diazatricyclo[6.4.0.0ˆ[2,6]]dodeca-1(8),2(6),9,11-tetraen-3-yl]-2-hydroxypropanamide (I-75)

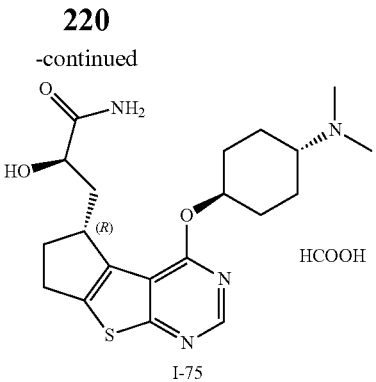

I-75

Synthesis of compound I-75.

Compound I-140 (400 mg, crude) and HCHO (37%, 486 uL, 6.0 mmol, 5.0 equiv) in methanol (8 mL) were stirred at room temperature for 30 min. then NaBH$_3$CN (221 mg, 3.5 mmol, 3.0 equiv) was added and the resulting solution was stirred for 12 h at room temperature. The crude product (400 mg) was purified by preparative HPLC under the following conditions (SHIMADZU): column: SunFire Prep C18, 19*150 mm 5 um; mobile phase: water with 0.05% HCOOH and CH$_3$CN (6.0% CH$_3$CN up to 55.0% in 19 min); UV detection at 254/220 nm. The product-containing fractions were collected and partially evaporated to remove CH$_3$CN and water (bath temperature 25° C.) under reduced pressure to afford the desired (2R)-3-[(3R)-12-[[4-(dimethylamino)cyclohexyl]oxy]-7-thia-9,11-diazatricyclo[6.4.0.0ˆ[2,6]]dodeca-1(8),2(6),9,11-tetraen-3-yl]-2-hydroxypropanamide formate (200 mg) as a white solid. MS m/z 405 (M+H)$^+$. $^1$H NMR (300 MHz, CD$_3$OD): δ 8.60 (1H, brs), 8.45 (1H, s), 5.28-5.25 (1H, m), 4.08 (1H, dd), 3.66 (1H, t), 3.30-3.20 (1H, m), 3.19-3.09 (1H, m), 3.08-2.95 (1H, m), 2.86 (6H, s), 2.78-2.62 (1H, m), 2.52-2.38 (3H, m), 2.32-2.15 (3H, m), 1.87-1.72 (5H, m).

Example 52

Synthesis of 2-[(4-[[(3R)-3-[(2R)-2-hydroxybutyl]-7-thia-9,11-diazatricyclo[6.4.0.0[2,6]]dodeca-1(8),2(6),9,11-tetraen-12-yl]oxy]cyclohexyl)(methyl)amino]-1-(pyrrolidin-1-yl)ethan-1-one (I-71)

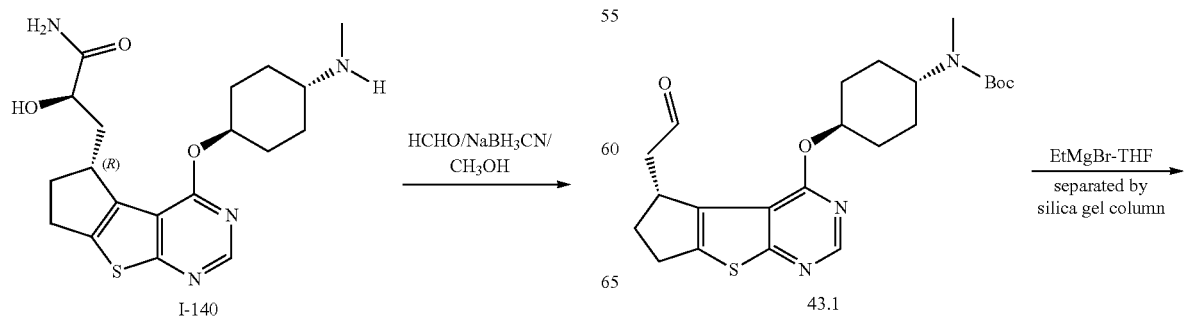

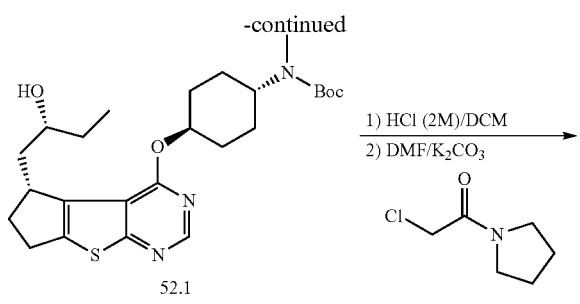

Synthesis of compounds 52.1 and 52.2.

A 50-mL round-bottom flask containing a solution of 43.1 (460 mg, 1.03 mmol, 1.00 equiv) in 20 mL of freshly distilled THF was cooled down to 0° C. under nitrogen. Then bromo(ethyl)magnesium (1 M in THF, 3.10 mL) was added dropwise via syringe and the resulting solution was stirred for 2 h at 0° C. The reaction was then quenched with saturated aqueous $NH_4Cl$ and extracted with 3×50 mL of ethyl acetate. The combined organic layers were washed with brine, dried ($Na_2SO_4$) and concentrated under reduced pressure. The residue was applied onto a silica gel column with ethyl acetate/petroleum ether (1:2) and purified to give the alcohols 52.1 (180 mg) and 52.2 (160 mg) as colorless oils.

Synthesis of Compound I-71.

A 50-mL round-bottom flask was charged with 52.1 (180 mg, 0.38 mmol, 1.00 equiv) in 5.5 mL of dichloromethane and cooled to 0° C. Then hydrochloric acid (12 M, 0.5 mL) was added and the resulting solution was stirred for 3 h at room temperature. The reaction mixture was concentrated under reduced pressure to give (2R)-1-[(3R)-12-[[4-(methylamino)cyclohexyl]oxy]-7-thia-9,11-diazatricyclo[6.4.0.0[2,6]]dodeca-1(8),2(6),9,11-tetraen-3-yl]butan-2-ol hydrochloride (100 mg, crude) as a light yellow oil. This material (100 mg, crude) was dissolved in DMF (4 mL) and potassium carbonate (220 mg) and 2-chloro-1-(pyrrolidin-1-yl)ethan-1-one (100 mg) were added at room temperature and the resulting mixture was stirred for 14 h at 25° C. After completion of the reaction, the product was extracted with DCM, washed with brine, and concentrated in vacuo. The crude product (160 mg) was purified by preparative HPLC(SHIMADZU) under the following conditions: column: SunFire Prep C18, 19*150 mm 5 um; mobile phase: water (0.1% HCOOH) and $CH_3CN$ (6.0% $CH_3CN$ up to 50.0% in 25 min); UV detection at 254/220 nm. The product-containing fractions were collected and concentrated to give the Compound I-71 (85.8 mg) as a white solid. $^1H$ NMR (400 MHz, $CD_3OD$) δ 8.47 (1H, s), 5.29 (1H, m), 3.67-3.68 (1H, m), 3.56-3.59 (2H, t), 3.43-3.47 (2H, t), 3.38-3.32 (2H, m), 3.09 (1H, m), 2.97-2.98 (1H, m), 2.64-2.68 (2H, m), 2.25-2.46 (5H, m), 1.88-1.08 (7H, m), 1.44-1.59 (6H, m), 1.04 (3H, t). MS: m/z 487 $(M+H)^+$.

Example 53

Synthesis of 2-(((1R,4r)-4-(((R)-5-((S)-2-hydroxybutyl)-6,7-dihydro-5H-cyclopenta[4,5]thieno[2,3-d]pyrimidin-4-yl)oxy)cyclohexyl)(methyl)amino)-1-(pyrrolidin-1-yl)ethanone (I-72)

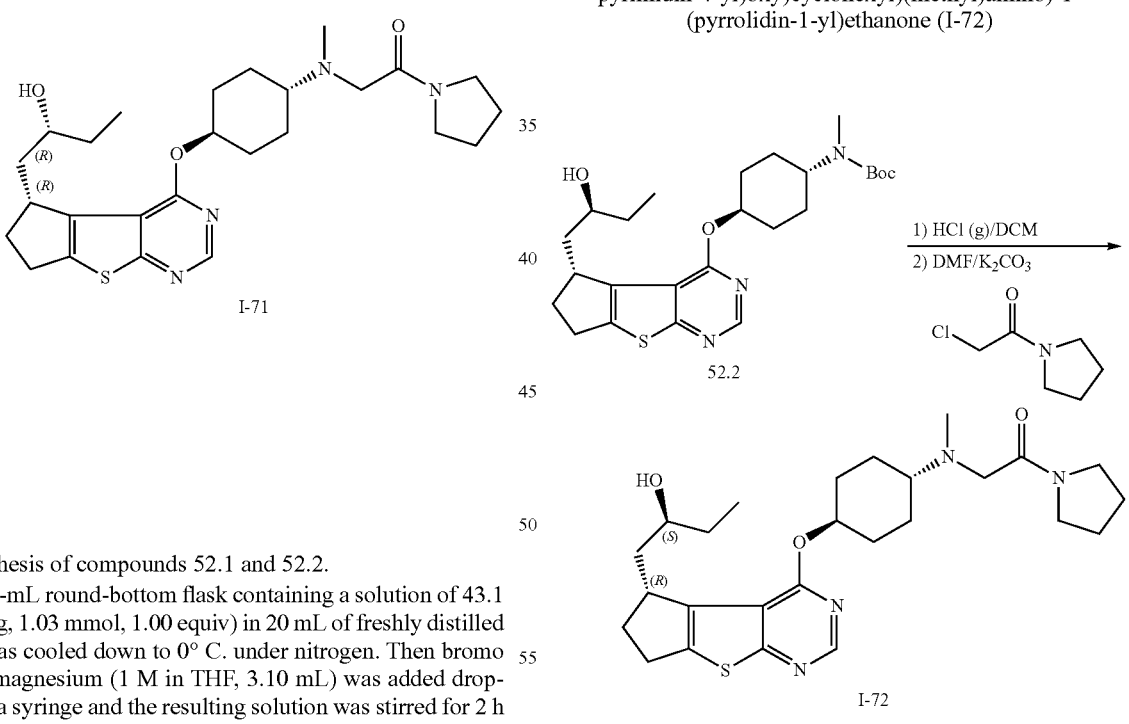

Compound I-72 was synthesized in a manner consistent with Example 46 from alcohol 52.2 (prepared as described in Example 52) and 2-chloro-1-(pyrrolidin-1-yl)ethan-1-one. Isolated a white solid in 31% yield. $^1H$ NMR (400 MHz, $CD_3OD$): δ 8.46 (1H, s), 5.40-5020 (1H, m), 3.63-3.56 (4H, m), 3.47-3.43 (2H, t), 3.35 (2H, m), 3.03 (1H, m), 2.99-2.97 (1H, m), 2.70-2.64 (2H, m), 2.37-2.30 (6H, m), 2.28-2.16 (1H, m), 2.03-1.88 (6H, m), 1.73-1.67 (2H, m), 1.53-1.45 (5H, m), 0.96 (3H, t). MS: m/z 487 $(M+H)^+$.

Example 54

Synthesis of 2-(12-[[4-(dimethylamino)cyclohexyl]oxy]-7-thia-9,11-diazatricyclo[6.4.0.0^[2,6]]dodeca-1(8),2(6),9,11-tetraen-3-yl)acetonitrile (I-22)

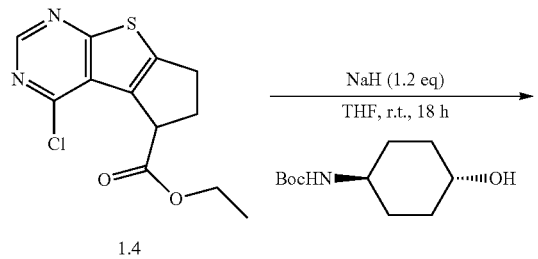

1.4

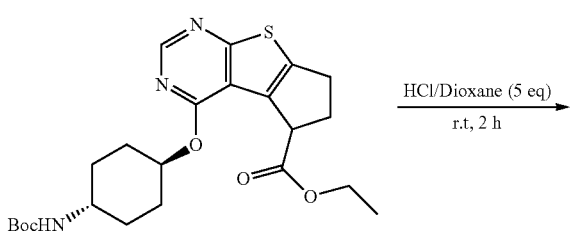

54.1

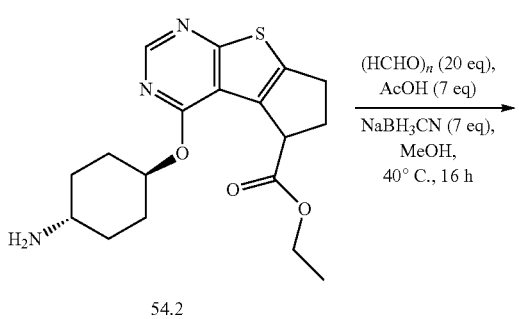

54.2

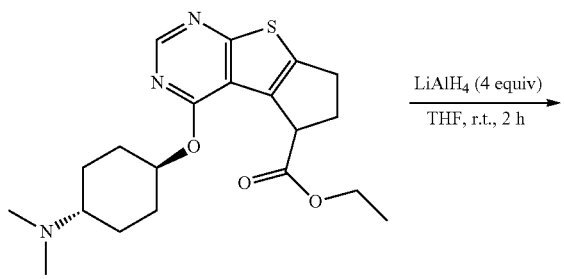

54.3

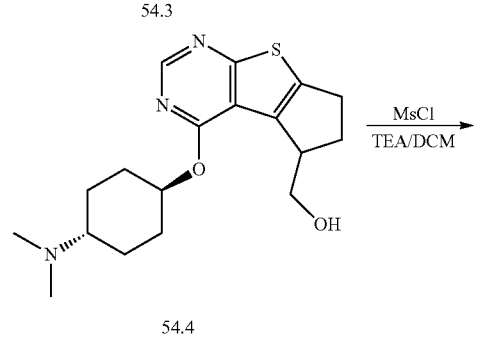

54.4

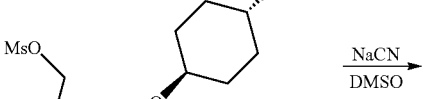

54.5

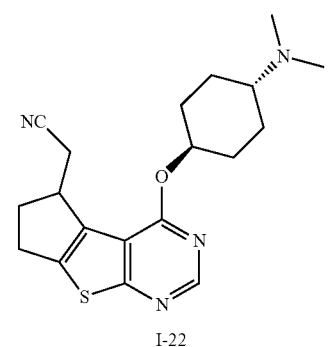

I-22

Synthesis of Compound 54.1.

To a solution of commercially-available trans-tert-butyl 4-hydroxycyclohexylcarbamate (1.83 g, 8.5 mmol) in anhydrous THF (30 mL) was added NaH (340 mg, 8.5 mmol) at 0° C. The mixture was allowed to warm to r.t. with stirring for 2 hours. Then intermediate 1.4 (2 g, 7.1 mmol) was added. The mixture was stirred for 18 hours then poured into ice water (100 mL) and extracted with EtOAc (3×80 mL). The combined organic layers were washed (brine), dried ($Na_2SO_4$), filtered and concentrated. The residue was purified by silica gel column chromatography with petroleum ether/ethyl acetate (1:1) to give a white solid product (1.72 g, 56%). MS: m/z 462 (M+H)$^+$.

Synthesis of Compound 54.2.

Compound 54.1 (1.72 g, 3.73 mmol) was added to a solution of HCl in 1,4-dioxane (18.6 mL, 18.6 mmol) at r.t. The mixture was stirred for 2 h and then concentrated under reduced pressure. Washing with petroleum ether gave a white solid product (2.2 g, 100%). MS: m/z 362 (M+H)$^+$.

Synthesis of Compound 54.3.

To a solution of 54.2 (1.3 g, 3.6 mmol) in MeOH (60 mL) was added (CHO)$_n$ (2.16 g, 72 mmol) and AcOH (1.51 g, 25.2 mmol). The suspension was heated at 40° C. with stirring for 15 hours and then concentrated. The residue was purified by silica gel column chromatography with MeOH/$CH_2Cl_2$ (1:20) to give a white solid product (1.3 g, 89%). $^1$H NMR (500 MHz, CDCl$_3$) δ 8.50 (s, 1H), 5.19-5.17 (m, 1H), 4.17-4.13 (m, 3H), 3.22-3.16 (m, 1H), 3.06-3.01 (m, 1H), 2.92-2.85 (m, 1H), 2.62-2.55 (m, 1H), 2.52-2.36 (m, 6H), 2.27 (m, 2H), 2.07-2.04 (m, 2H), 1.57-1.48 (m, 4H), 1.38-1.35 (t, 1H), 1.25-1.22 (t, 3H). MS: m/z 390 (M+H)$^+$.

Synthesis of Compound 54.4.

To a solution of 54.3 (1.3 g, 3.3 mmol) in THF (30 mL) was added LiAlH$_4$ (508 mg, 13.3 mmol) in portions at 0° C. The mixture was allowed to warm to r.t. with stirring for 2 hours, and then Na$_2$SO$_4$.10H$_2$O (4.3 g, 13.3 mmol) was added. The suspension was stirred for 2 hours and filtered. The filtrate was purified by silica gel column chromatography with MeOH/DCM (1:10) to give a white solid product (810 mg, 70%). $^1$H NMR (500 MHz, CDCl$_3$) δ 8.51 (s, 1H), 5.30-5.24 (m, 1H), 3.86-3.85 (d, 2H), 3.56-3.53 (m, 1H), 3.15-3.08 (m, 1H), 3.00-2.94 (m, 1H), 2.70-2.65 (m, 1H), 2.43-2.29 (m, 10H), 2.04-2.02 (d, 2H), 1.60-1.50 (m, 5H). MS: m/z 348 (M+H)$^+$.

Synthesis of Compound 54.5.

To a 100-mL 3-necked round-bottom flask was added a solution of 54.4 (1.3 g, 3.74 mmol, 1.00 equiv) in dichloromethane (20 mL) and TEA (570 mg, 5.63 mmol, 1.51 equiv). This was followed by the addition of methanesulfonyl chloride (520 mg, 4.54 mmol, 1.21 equiv) dropwise with stirring at 0° C. The resulting solution was stirred for 2 h at room temperature. The reaction was then quenched by the addition of 20 mL of water. The resulting solution was diluted with 100 mL of dichloromethane and washed with 3×50 mL of brine. The mixture was dried over anhydrous sodium sulfate and concentrated under vacuum to afford 1.5 g (crude) of mesylate 54.5 as a yellow oil.

Synthesis of Compound I-22.

To a 50-mL 3-necked round-bottom flask was added compound 54.5 (500 mg, 1.17 mmol, 1.00 equiv), DMSO (20 mL) and sodium carbonitrile (100 mg, 2.04 mmol, 1.74 equiv). The reaction was stirred for 3 h at 70° C., whereupon it was diluted with 100 mL of DCM. The resulting mixture was washed with 3×10 mL of saturated aqueous sodium bicarbonate and 3×20 mL of brine. The mixture was dried over anhydrous sodium sulfate and concentrated under vacuum. The residue was purified by preparative HPLC (2#-Waters 2767-2(HPLC-08)) under the following conditions: column: Xbridge Shield RP 18; mobile phase: water (50 mM ammonium bicarbonate) and acetonitrile (start at 5.0% acetonitrile then ramp up to 30.0% in 7 min, up to 100.0% in 1 min, then down to 5.0% in 1 min); detector: UV 254 and 220 nm. This procedure afforded 50 mg (11%) of Compound I-22 as a white solid. $^1$H NMR (400 MHz, CDCl$_3$) δ 8.53 (s, 1H), 5.24-5.27 (d, 1H), 3.69 (s, 1H), 3.18-3.28 (m, 1H), 3.00-3.09 (m, 1H), 2.81-2.98 (m, 2H), 2.69-2.77 (m, 1H), 2.55 (br 1H), 2.45 (s, 6H), 2.37-2.41 (m, 3H), 2.02-2.24 (m, 2H), 1.50-1.79 (q, 4H). MS: m/z 357 (M+H)$^+$.

Example 55

Synthesis of 2-(4-(((1r,4r)-4-(dimethylamino)cyclohexyl)oxy)-6,7-dihydro-5H-cyclopenta[4,5]thieno[2,3-d]pyrimidin-5-yl)ethanol (I-21)

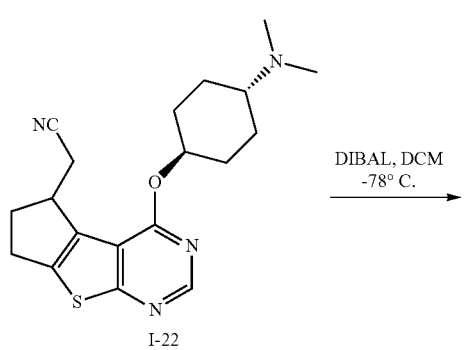

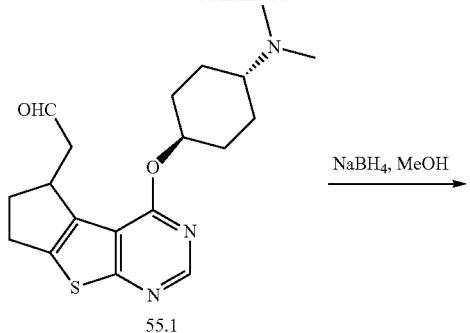

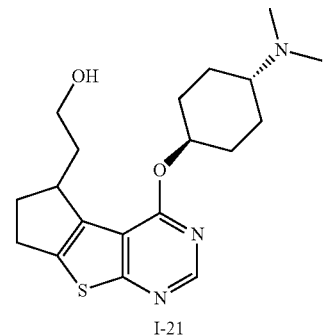

Synthesis of 55.1.

A 100-mL 3-necked round-bottom flask purged and maintained with an inert atmosphere of nitrogen was charged with a solution of I-22 (600 mg, 1.68 mmol, 1.00 equiv) in dichloromethane (60 mL). This was followed by the addition of diisobutylaluminium hydride (0.3 mL) dropwise with stirring at −78° C. The resulting solution was stirred for 30 min at −30° C. Then to this mixture was added diisobutylaluminium hydride (0.3 mL) dropwise with stirring at −78° C. The resulting solution was stirred for 30 min at −30° C. The reaction was quenched by the addition of 3 mL of water and diluted with 200 mL of dichloromethane. The resulting mixture was washed with 4×50 mL of brine. The organic layer was dried over anhydrous sodium sulfate and concentrated under vacuum to afford 0.4 g (66%) of aldehyde 55.1 as a yellow solid.

Synthesis of Compound I-21.

A 100-mL 3-necked round-bottom flask, purged and maintained with an inert atmosphere of nitrogen, was charged with aldehyde 55.1 (400 mg, 1.11 mmol, 1.00 equiv), methanol (10 mL) and sodium borohydride (100 mg, 2.72 mmol, 2.44 equiv). The resulting solution was stirred for 1 h at room temperature. The reaction was then quenched by the addition of 50 mL of water. The resulting solution was extracted with 3×50 mL of ethyl acetate and the organic layers combined. The resulting mixture was washed with 3×50 mL of brine. The mixture was dried over anhydrous sodium sulfate and concentrated under vacuum to afford 0.35 g (87%) of Compound I-21 as a yellow oil. MS: m/z 362 (M+H)$^+$.

Example 56

Synthesis of 4-(((1r,4r)-4-(dimethylamino)cyclohexyl)oxy)-6,7-dihydro-5H-cyclopenta[4,5]thieno[2,3-d]pyrimidine-5-carboxylic acid (I-8)

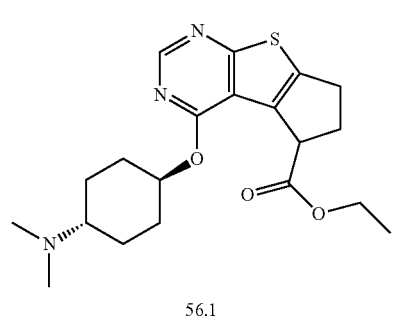

56.1

NaOH (10 eq)
THF/MeOH/H₂O
r.t. 16 h

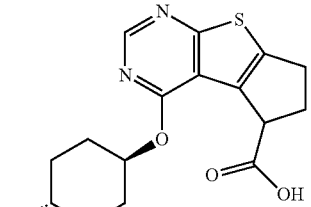

I-8

To a solution of 56.1 (1 g, 2.57 mmol) in THF (5 mL) and MeOH (5 mL) was added a solution of NaOH (1 g, 25.7 mmol) in H₂O (5 mL). The mixture was stirred for 15 hours at r.t. and then the pH was adjusted to 5 with HCl (1 M). Purification by reverse phase chromatography (Biotage) gave a white solid product (350 mg, 38%). $^1$H NMR (500 MHz, CDCl$_3$) δ 8.46 (1H, s), 5.20-5.16 (1H, m), 4.10-4.07 (1H, m), 3.23-3.17 (1H, m), 3.02-2.96 (1H, m), 2.91-2.84 (1H, m), 2.68-2.62 (1H, m), 2.55-2.29 (7H, s), 2.40-2.37 (1H, d), 2.29 (1H, s), 2.17 (1H, s), 2.09-2.07 (1H, m), 1.67-1.52 (4H, m) MS: m/z 362 (M+H)$^+$.

Example 57

Synthesis of Intermediate 57.4

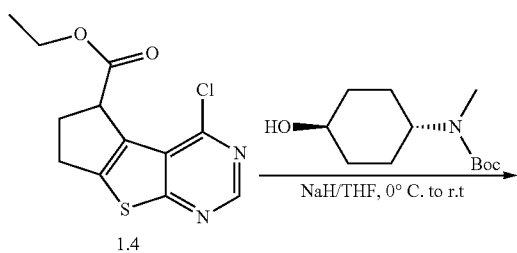

1.4

HO—[cyclohexyl]—N(Me)Boc

NaH/THF, 0° C. to r.t

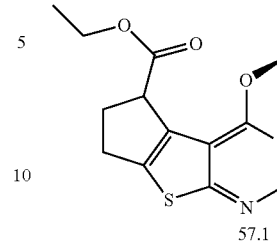

57.1

LAH
THF, 0° C. to r.t

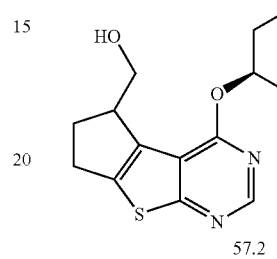

57.2

MsCl
Et₃N/DCM, 0° C.

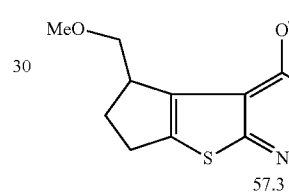

57.3

EtSH
NaH/DMF

57.4

Synthesis of Compound 57.1.

Sodium hydride (60% dispersion in mineral oil, 3.4 g, 84.16 mmol, 4.00 equiv) was added slowly to a solution of tert-butyl ((1r,4r)-4-hydroxycyclohexyl)(methyl)carbamate (commercially-available; 6.27 g, 27.34 mmol, 1.40 equiv) in distilled THF (50 ml) at 0° C. under nitrogen. The resulting mixture was stirred for 30 min at room temperature. Intermediate 1.4 (5.95 g, 21.04 mmol, 1.00 equiv) in THF (20 ml) was added dropwise to the above mixture and stirred for 4 hours at ambient temperature. The reaction was then quenched with water and extracted with ethyl acetate (3×100 mL). The organic layers were combined, dried over anhydrous sodium sulfate, and concentrated under vacuum. The residue was purified by a silica gel column with ethyl acetate/petroleum ether (1:10 to 1:3) to provide 57.1 (8.3 g, 83%) as a colorless oil.

Synthesis of Compound 57.2.

To a 500-mL round-bottom flask, purged and maintained under an inert atmosphere of nitrogen, was added a solution of 57.1 (8.3 g, 17.45 mmol, 1.00 equiv) in 200 mL of distilled THF at 0° C. under nitrogen. LAH (663 mg, 17.45 mmol, 1.00 equiv) was slowly added and then the reaction was stirred for 4 h at room temperature. The reaction was then quenched by the addition of saturated aqueous NH₄Cl and extracted with ethyl acetate (2×150 mL). The combined organic layers were washed with brine and dried over anhydrous sodium sulfate. After concentration under reduced pressure, the residue was purified with a silica gel column (eluting with ethyl acetate/petroleum ether (1:2 to 2:1)) to provide compound 57.2 (7.2 g, 95%) as a white solid.

Synthesis of Compound 57.3.

To a solution of 57.2 (3.6 g, 8.30 mmol, 1.00 equiv) and triethylamine (2.53 g, 25.00 mmol, 3.00 equiv) in dry dichloromethane (100 ml) was added methanesulfonyl chloride (1.9 g, 16.59 mmol, 1.50 equiv) dropwise at 0° C. under nitrogen. The resulting solution was stirred for an additional 2 h at room temperature. The reaction solution was diluted with dichloromethane and washed with brine (twice). The organic layer was dried and concentrated under vacuum to give the desired compound 57.3 (4.7 g, crude) as a light yellow syrup which was used in the next step without further purification.

Synthesis of Compound 57.4.

To a 100-mL 3-necked round-bottom flask purged and maintained with an inert atmosphere of nitrogen was added a solution of ethanethiol (485 mg, 7.81 mmol, 1.00 equiv) in distilled DMF (10 mL). After cooling to 0° C. under nitrogen, sodium hydride (605 dispersion in mineral oil, 312 mg, 2.00 equiv) was added and stirring continued for 30 min at room temperature. A solution of 57.3 (2.0 g, crude) in DMF (10 ml) was added via syringe and the resulting solution was stirred for 3 h at ambient temperature. The reaction was quenched with water and extracted with ethyl acetate (2×100 mL). The combined organic layers were dried over anhydrous sodium sulfate and concentrated under reduced pressure. The residue was purified by column chromatography on silica gel (using ethyl acetate/petroleum ether (1:3 to 1:1) as the eluent) to provide compound 57.4 (1.2 g) as a yellow oil.

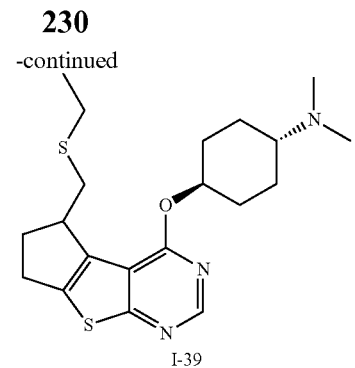

I-39

To a solution of intermediate 57.4 (400 mg, 0.84 mmol, 1.00 equiv) in 10 mL of dichloromethane was added hydrochloric acid (12 M, 2 ml) at 0° C. and the resulting solution was stirred for 2 h at room temperature. The reaction mixture was concentrated under reduced pressure. The crude product was dissolved in methanol (10 ml) and formaldehyde (37%, 2 ml) was added. After stirring for 1 h at room temperature NaBH₃CN (158 mg, 2.51 mmol, 3.00 equiv) was slowly added at 0° C. and the resulting solution was stirred overnight at room temperature. The next day, the reaction mixture was quenched with water and extracted with ethyl acetate (2×50 mL). The organic layers were combined, dried over anhydrous sodium sulfate, and concentrated under vacuum. The crude product (140 mg) was purified by preparative HPLC (Waters) under the following conditions: column: SunFire Prep C18, 19*150 mm 5 um; mobile phase: water (0.05% NH₄HCO₃ solution) and CH₃CN (30% CH₃CN then ramp up to 100.0% over 20 min); UV detection at 254 nm. The product-containing fractions were collected and concentrated under reduced pressure. The residue was lyophilized overnight to give I-39 (31.4 mg) as a white solid. ¹H NMR (400 MHz, CDCl₃) δ 8.24 (s, 1H), 8.14 (s, 1H), 8.03 (s, 1H), 7.75 (s, 1H), 7.41 (s, 1H), 7.20-7.30 (m, 2H), 7.10 (d, 2H), 7.00 (d, 2H), 4.50-4.60 (m, 1H), 3.81 (s, 2H), 3.71 (s, 2H), 3.55-3.60 (m, 2H), 3.16-3.22 (m, 2H), 2.30-2.40 (m, 2H), 2.10-2.20 (m, 2H). MS: m/z 392 (M+H)⁺.

Example 58

Synthesis of 4-([3-[(ethylsulfanyl)methyl]-7-thia-9,11-diazatricyclo[6.4.0.0[2,6]]dodeca-1(12),2(6),8,10-tetraen-12-yl]oxy)-N,N-dimethylcyclohexan-1-amine (I-39)

Example 59

Synthesis of 4-[[(3S)-3-[[(S)-ethanesulfinyl]methyl]-7-thia-9,11-diazatricyclo[6.4.0.0[2,6]]dodeca-1(12),2(6),8,10-tetraen-12-yl]oxy]-N,N-dimethylcyclohexan-1-amine (I-45) and Example 60: Synthesis of 4-[[(3S)-3-[[(R)-ethanesulfinyl]methyl]-7-thia-9,11-diazatricyclo[6.4.0.0[2,6]]dodeca-1(12),2(6),8,10-tetraen-12-yl]oxy]-N,N-dimethylcyclohexan-1-amine (I-46)

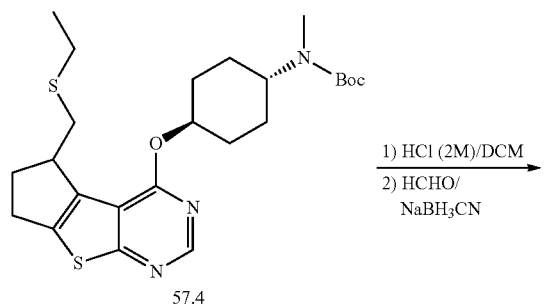

57.4

1) HCl (2M)/DCM
2) HCHO/ NaBH₃CN

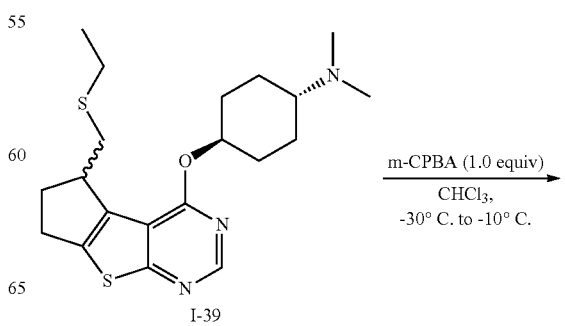

I-39 m-CPBA (1.0 equiv)
CHCl₃,
−30° C. to −10° C.

231

-continued

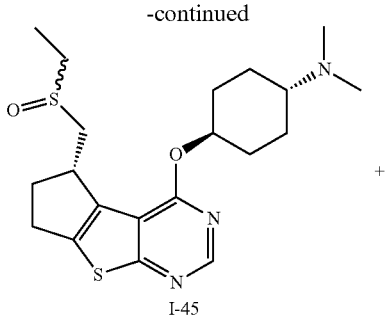

I-45

+

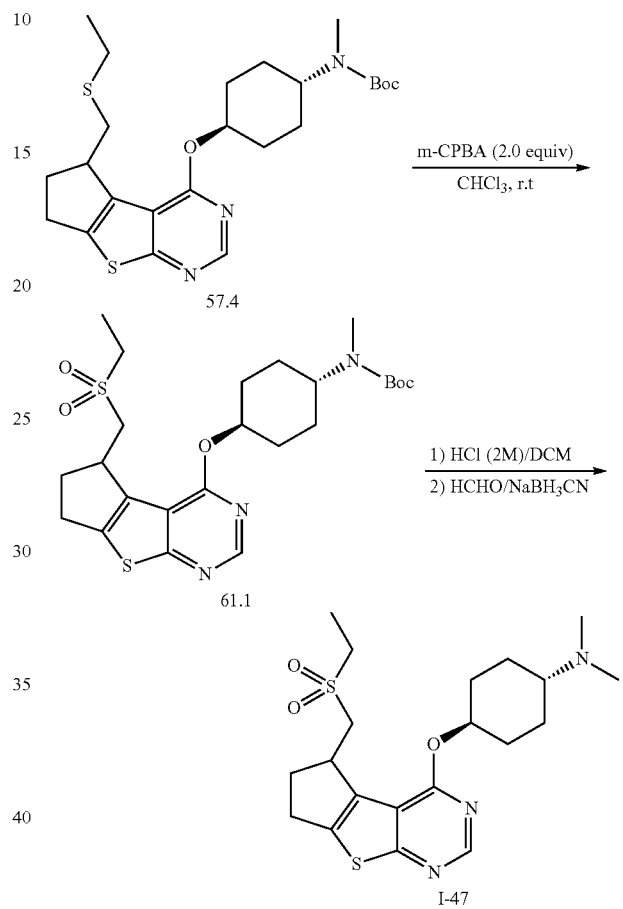

A solution of Compound I-39 (140 mg, 0.36 mmol, 1.00 equiv) in chloroform (8 ml) was cooled to −30° C. A solution of m-CPBA (62 mg, 0.36 mmol, 1.00 equiv) in chloroform (2 ml) was added dropwise under nitrogen. The resulting solution was stirred for 3 hours below −10° C. The pH value of the reaction solution was adjusted to 10 with saturated aqueous sodium bicarbonate and extracted with dichloromethane. The combined organic layers were washed with brine, dried over anhydrous sodium sulfate and concentrated under vacuum. The crude product (100 mg) was purified by preparative HPLC(SHIMADZU) under the following conditions: column: SunFire Prep C18, 19*150 mm 5 um; mobile phase: water (0.05% NH$_4$HCO$_3$) and CH$_3$CN (35% CH$_3$CN then ramp up to 100.0% over 20 min); UV detection at 254 nm. The fractions containing the first peak were collected and concentrated under reduced pressure. The residue was lyophilized overnight to give Compound I-45 (26.2 mg) as a white solid. $^1$H NMR (300 MHz, CD$_3$OD): δ 8.24 (s, 1H), 8.14 (s, 1H), 8.03 (s, 1H), 7.75 (s, 1H), 7.41 (s, 1H), 7.20-7.30 (m, 2H), 7.10 (d, 2H), 7.00 (d, 2H), 4.50-4.60 (m, 1H), 3.81 (s, 2H), 3.71 (s, 2H), 3.55-3.60 (m, 2H), 3.16-3.22 (m, 2H), 2.30-2.40 (m, 2H), 2.10-2.20 (m, 2H). MS: m/z 408 (M+H)$^+$.

Compound I-47 was obtained under the same conditions as in Example 59 by collecting the fractions that contained the second peak to elute in the purification. Evaporation of the solvent followed by lyophilization of the residue afforded I-47 (12.8 mg) as a white solid. $^1$H NMR (300 MHz, CD$_3$OD) δ 8.24 (s, 1H), 8.14 (s, 1H), 8.03 (s, 1H), 7.75 (s, 1H), 7.41 (s, 1H), 7.20-7.30 (m, 2H), 7.10 (d, 2H), 7.00 (d, 2H), 4.50-4.60 (m, 1H), 3.81 (s, 2H), 3.71 (s, 2H), 3.55-3.60 (m, 2H), 3.16-3.22 (m, 2H), 2.30-2.40 (m, 2H), 2.10-2.20 (m, 2H). MS: m/z 408 (M+H)$^+$.

232

Example 61

Synthesis of 4-([3-[(ethanesulfonyl)methyl]-7-thia-9,11-diazatricyclo[6.4.0.0[2,6]]dodeca-1(12),2(6),8,10-tetraen-12-yl]oxy)-N,N-dimethylcyclohexan-1-amine (I-47)

Synthesis of Compound 61.1.

To a solution of intermediate 57.4 (200 mg, 0.42 mmol, 1.00 equiv) in chloroform (10 ml) was added m-CPBA (145 mg, 0.84 mmol, 2.00 equiv) at 0° C. under nitrogen. The resulting solution was stirred for 3 hours at room temperature. The pH value of the solution was adjusted to 10 with saturated aqueous sodium bicarbonate and extracted with dichloromethane (2×30 mL). The combined organic layers were washed with brine, dried over anhydrous sodium sulfate and concentrated under vacuum. The residue was loaded onto a silica gel column and eluted with ethyl acetate/petroleum ether (1:10) to afford the sulfone δ1.1 (140 mg, 66%) as a white solid.

Synthesis of Compound I-47.

To a 50-mL round-bottom flask containing a solution of 61.1 (140 mg, 0.27 mmol, 1.00 equiv) in 10 mL of dichloromethane was added hydrochloric acid (12 M, 2 ml) at 0° C. and the resulting solution was stirred for 2 h at room temperature. The reaction mixture was concentrated under reduced pressure. The crude product was dissolved in methanol (10 ml) and formaldehyde (37%, 2 ml) was added. The reaction was stirred for 1 h at room temperature, then NaBH$_3$CN (158 mg, 2.51 mmol) was slowly added at 0° C. The resulting solution was stirred overnight at room temperature. The reaction mixture was quenched with water and extracted with ethyl acetate (2×50 mL). The organic layers were combined, dried over anhydrous sodium sulfate, and concentrated under vacuum. The crude product (140 mg) was purified by preparative HPLC(SHIMADZU) under the following conditions: column: SunFire Prep C18, 19*150 mm 5 um; mobile phase: water (0.05% NH$_4$HCO$_3$) and CH$_3$CN (6.0% CH$_3$CN then ramp up to 50.0% over 12 min); UV detection at 254 and 220 nm. The product-containing fractions were collected and concentrated under reduced pressure. The residue was lyophilized overnight to give Compound I-47 (41.9 mg, 36%) as a white solid. $^1$H NMR (400 MHz, CD$_3$OD): δ 8.24 (s, 1H), 8.14 (s, 1H), 8.03 (s, 1H), 7.75 (s, 1H), 7.41 (s, 1H), 7.20-7.30 (m, 2H), 7.10 (d, 2H), 7.00 (d, 2H), 4.50-4.60 (m, 1H), 3.81 (s, 2H), 3.71 (s, 2H), 3.55-3.60 (m, 2H), 3.16-3.22 (m, 2H), 2.30-2.40 (m, 2H), 2.10-2.20 (m, 2H). MS: m/z 424 (M+H)$^+$.

Example 62

Intermediate 62.1

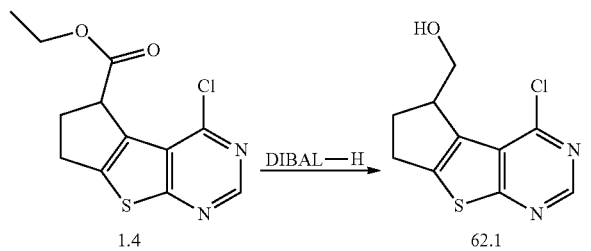

To a 5-L 4-necked round-bottom flask was added intermediate 1.4 (200 g, 707.35 mmol, 1.00 equiv) and tetrahydrofuran (2 L). This was followed by the addition of DIBAL-H (2 L) dropwise with stirring at −78° C. in 30 min. The resulting solution was stirred for 1 h at −78° C. and an additional 1 h with warming to −10° C. The reaction was then quenched by the addition of 2 L of water. The pH value of the solution was adjusted to 7 with hydrogen chloride (3 mol/L). The resulting solution was diluted with 1 L of ethyl acetate and the solids were filtered off. The resulting solution was extracted with 2×500 mL of ethyl acetate and the organic layers were combined. The combined organic layers were washed with 2×1 L of brine, dried over anhydrous sodium sulfate and concentrated under vacuum. The residue was loaded onto a silica gel column with ethyl acetate/petroleum ether (1:1) and purified to afford 120 g (70%) of intermediate 62.1 as a light yellow solid. $^1$H NMR (300 MHz, CDCl$_3$): δ 2.57-2.79 (m, 2H), 2.99-3.28 (m, 2H), 3.68-3.85 (m, 2H), 4.01-4.05 (m, 1H), 8.75 (s, 1H). MS: m/z 241 (M+H)$^+$.

Example 63

Intermediates 63.1 and 63.2

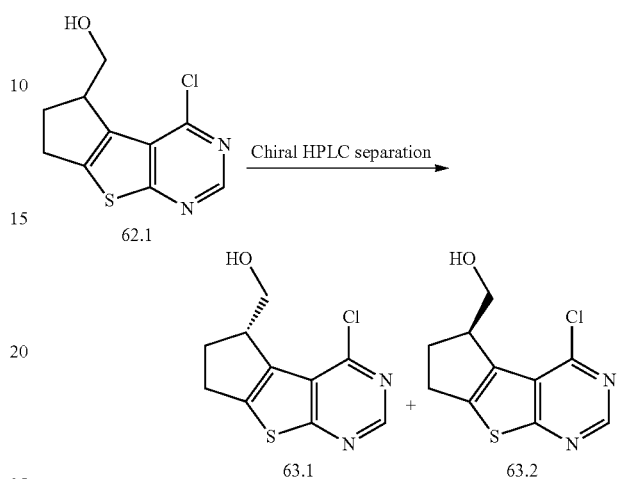

The enantiomers of racemic 62.1 (6.0 g) were separated by chiral HPLC (SHIMADZU) under the following conditions: column: Chiralpak IC, 0.46*25 cm, 5 um; mobile phase: hexane (0.1% TEA): IPA=90:10; UV detection at 254 nm. The desired [(3S)-12-chloro-7-thia-9,11-diazatricyclo [6.4.0.0^[2,6]]dodeca-1(8),2(6),9,11-tetraen-3-yl]methanol (63.1, t$_R$=15.15 min, 2.0 g) was obtained as a pale-yellow solid in 100% ee. [(3R)-12-chloro-7-thia-9,11-diazatricyclo [6.4.0.0^[2,6]]dodeca-1(8),2(6),9,11-tetraen-3-yl]methanol (63.2, t$_R$=12.22 min, 2.0 g) was also obtained in 100% ee.

Example 64

Synthesis of N,N-dimethyl-4-[[(3R)-3-[(prop-2-yn-1-yloxy)methyl]-7-thia-9,11-diazatricyclo[6.4.0.0[2,6]]dodeca-1(8),2(6),9,11-tetraen-12-yl]oxy]cyclohexan-1-amine (I-48)

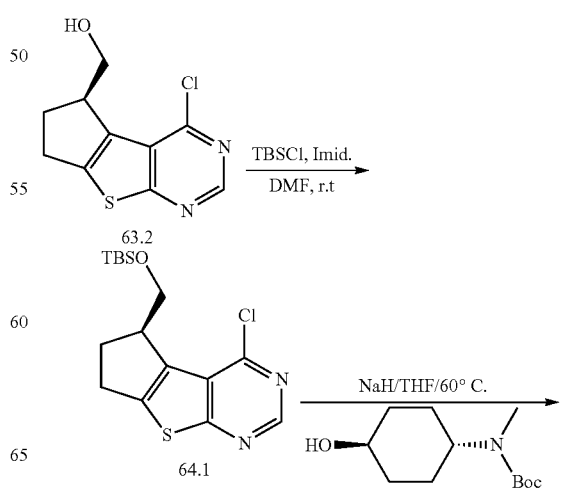

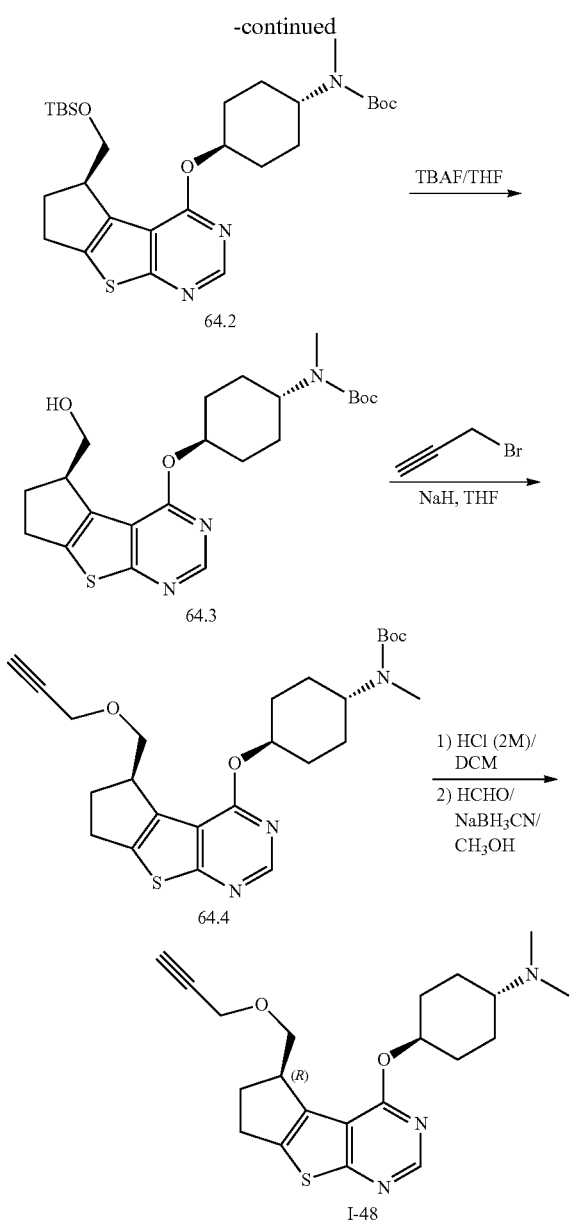

Synthesis of Compound 64.1.

A solution of intermediate 63.2 (prepared as in Example 63; 1.2 g, 4.99 mmol, 1.00 equiv), 1H-imidazole (680 mg, 9.99 mmol, 2.00 equiv) and TBDMSCl (0.87 g) in distilled DMF (20 mL) was stirred for 2 h at room temperature. The reaction was then quenched with water and extracted with ethyl acetate (3×50 mL). The combined organic layers were washed with brine, dried over sodium sulfate and concentrated under vacuum. The residue was purified by column chromatography on silica gel with EtOAc/petroleum ether (1:10 to 1:5) to afford compound 64.1 (2.0 g) as a yellow oil. MS: m/z 355 (M+H)$^+$.

Synthesis of Compound 64.2.

Sodium hydride (60% dispersion in mineral oil, 650 mg, 16.25 mmol, 3.00 equiv) was treated with tert-butyl trans-4-hydroxycyclohexyl(methyl)carbamate (1.73 g, 7.54 mmol, 1.40 equiv) in 20 mL of distilled THF at 0° C. for 1 h under nitrogen. Then a solution of 64.1 (1.908 g, 5.38 mmol, 1.00 equiv) in dry THF (10 mL) was added and the resulting solution was stirred for 2 h at 60° C. in an oil bath. After cooling to room temperature, the reaction was quenched with water and extracted with ethyl acetate (3×50 mL). The combined organic layers were washed with brine, dried over anhydrous sodium sulfate and concentrated under vacuum. The residue was loaded onto a silica gel column with ethyl acetate/petroleum ether (1:5) and purified to give compound 64.2 (1.94 g, 66%) as a yellow oil.

Synthesis of Compound 64.3.

To a 100-mL round-bottom flask was added a solution of 64.2 (1.94 g, 3.54 mmol, 1.00 equiv) in 50 mL of THF followed by TBAF (1.85 g, 7.08 mmol, 2.00 equiv) and the resulting solution was stirred for 3 h at room temperature. The solvent was evaporated under reduced pressure and the residue diluted with 100 mL of ethyl acetate and washed with brine. The organic phase was dried over anhydrous sodium sulfate and concentrated in vacuo, whereupon the residue was loaded onto a silica gel column with ethyl acetate/petroleum ether (1:4) and purified to afford the alcohol 64.3 (1.5 g, 98%) as a white solid.

Synthesis of Compound 64.4.

To a 100-mL 3-necked round-bottom flask containing a solution of 64.3 (200 mg, 0.46 mmol, 1.00 equiv) in distilled THF (20 mL) was added sodium hydride (60% dispersion in mineral oil, 73.6 mg, 1.84 mmol, 4.00 equiv) at 0° C. under nitrogen. After stirring for 30 min, 3-bromoprop-1-yne (164 mg, 1.38 mmol, 3.00 equiv) was added via syringe and the resulting solution was heated to reflux overnight in an oil bath. The reaction was then quenched with water and extracted with 3×20 mL of ethyl acetate. The combined organic layers were dried over sodium sulfate and concentrated under reduced pressure, and then the residue was loaded onto a silica gel column with ethyl acetate/petroleum ether (1:5). Purification afforded alkyne 64.4 (150 mg, 69%) as a yellow solid.

Synthesis of Compound I-48.

To a 100-mL round-bottom flask was added a solution of 64.4 (200 mg, 0.42 mmol, 1.00 equiv) in dichloromethane (10 mL). HCl (12 M, 2 mL) was added at 0° C. and the resulting mixture was stirred for 1 hour at room temperature. The solvent was removed under vacuum. The resulting residue was dissolved in MeOH (10 mL) and HCHO (37%, 1 mL) was added followed by stirring at ambient temperature for 1 h. Then NaBH$_3$CN (79 mg, 1.26 mmol, 3.00 equiv) was added and the resulting solution was stirred overnight at room temperature. The reaction's progress was monitored by LCMS. Upon completion, the mixture was concentrated in vacuo and the crude product (100 mg) was purified by preparative HPLC (Waters) under the following conditions: column: Xbridge RP18, 19*150 mm 5 um; mobile phase: water (with 20 mM NH$_4$HCO$_3$) and CH$_3$CN (10.0% CH$_3$CN then ramp up to 40.0% over 20 min, up to 95.0% over 2 min, then down to 10.0% over 2 min); UV detection at 254 and 220 nm. The product-containing fractions were collected and evaporated under reduced pressure to give Compound I-48 (12.8 mg) as a colorless oil. $^1$H NMR (300 MHz, CD$_3$OD): δ 8.49 (s, 1H), 5.26-5.29 (m, 1H), 4.12-4.16 (m, 2H), 3.95-3.98 (m, 1H), 3.58-3.64 (m, 2H), 2.82-3.4 (m, 2H), 2.81 (m, 1H), 2.42-2.65 (m, 2H), 2.31 (s, 9H), 2.06-2.09 (m, 2H), 1.47-1.70 (m, 4H). MS: m/z 386 (M+H)$^+$.

237

Example 65

Synthesis of Intermediate 65.1

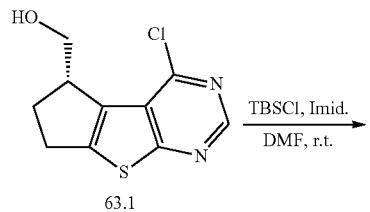

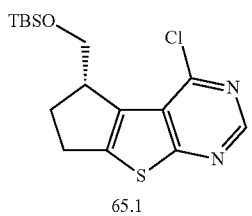

A solution of 63.1 (1.2 g, 4.99 mmol, 1.00 equiv), 1H-imidazole (680 mg, 9.99 mmol, 2.00 equiv) and TBDMSCl (0.87 g) in distilled DMF (20 mL) was stirred for 2 h at room temperature. The reaction was then quenched with water and extracted with ethyl acetate (3×50 mL). The combined organic layers were washed with brine, dried over sodium sulfate and concentrated under vacuum. The residue was purified by column chromatography on silica gel with EtOAc/petroleum ether (1:10 to 1:5) to afford 65.1 (2.0 g) as a yellow oil. MS: m/z 355 (M+H)$^+$.

Example 66

Synthesis of Intermediate 66.2

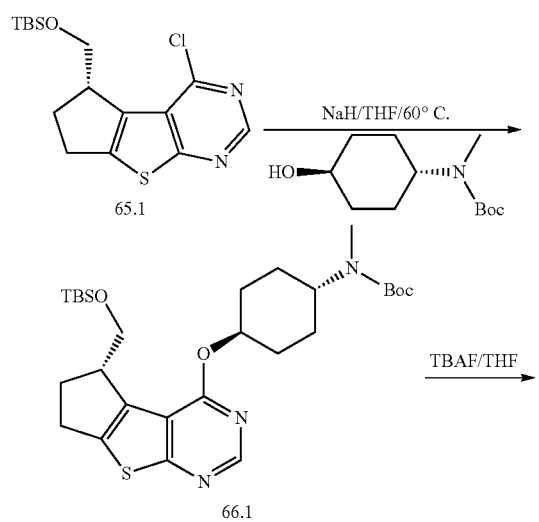

238

-continued

Synthesis of Compound 66.1.

Sodium hydride (60% dispersion in mineral oil, 1.33 g, 33.24 mmol, 4.0 equiv) was treated with tert-butyl N-(4-hydroxycyclohexyl)-N-methylcarbamate (2.66 g, 11.6 mmol, 1.40 equiv) in 50 mL of distilled THF at 0° C. under nitrogen. After stirring for 30 min, a solution of 65.1 (2.0 g, 8.31 mmol, 1.00 equiv) in dry THF (10 mL) was added dropwise and the resulting solution was stirred for 5 h at 60° C. The reaction was then quenched with saturated aqueous ammonium chloride and extracted with ethyl acetate (3×100 mL). The combined organic layers were washed with brine, dried over Na$_2$SO$_4$ and concentrated in vacuo. The residue was loaded onto a silica gel column with ethyl acetate/petroleum ether (1:10 to 1:2) and purified to afford carbamate 66.1 (2.3 g, 64%) as a yellow oil. MS: m/z 548 (M+H)$^+$.

Synthesis of Compound 66.2.

To a solution of 66.1 (1.0 g, 1.83 mmol, 1.00 equiv) in 10 mL of tetrahydrofuran was added TBAF (600 mg, 2.29 mmol, 1.26 equiv) at room temperature. The resulting solution was stirred for 4 h at ambient temperature and quenched by the addition of water. The resulting solution was extracted with ethyl acetate (3×50 mL). The organic layers were washed with brine and dried over anhydrous sodium sulfate. After concentration in vacuo, the residue was loaded onto a silica gel column with ethyl acetate/petroleum ether (1:15 to 1:1) and purified to afford intermediate 66.2 (0.7 g, 88%) as a yellow oil. MS: m/z 435 (M+H)$^+$.

Example 67

Synthesis of N,N-dimethyl-4-[[(3S)-3-[(prop-2-yn-1-yloxy)methyl]-7-thia-9,11-diazatricyclo[6.4.0.0[2,6]]dodeca-1(8),2(6),9,11-tetraen-12-yl]oxy]cyclohexan-1-amine (I-49)

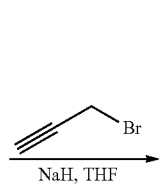

(m, 1H), 2.72 (t, J=2.4 Hz, 1H), 3.22 (m, 1H), 3.85 (m, 1H), 4.05 (m, 2H), 5.15 (m, 1H), 8.35 (s, 1H). MS: m/z 386 (M+H)$^+$.

Example 68

Synthesis of 4-[[(3S)-3-[(but-2-yn-1-yloxy)methyl]-7-thia-9,11-diazatricyclo[6.4.0.0[2,6]]dodeca-1(8),2 (6),9,11-tetraen-12-yl]oxy]-N,N-dimethylcyclohexan-1-amine (I-56)

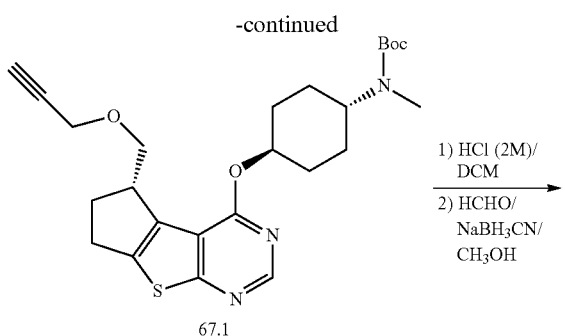

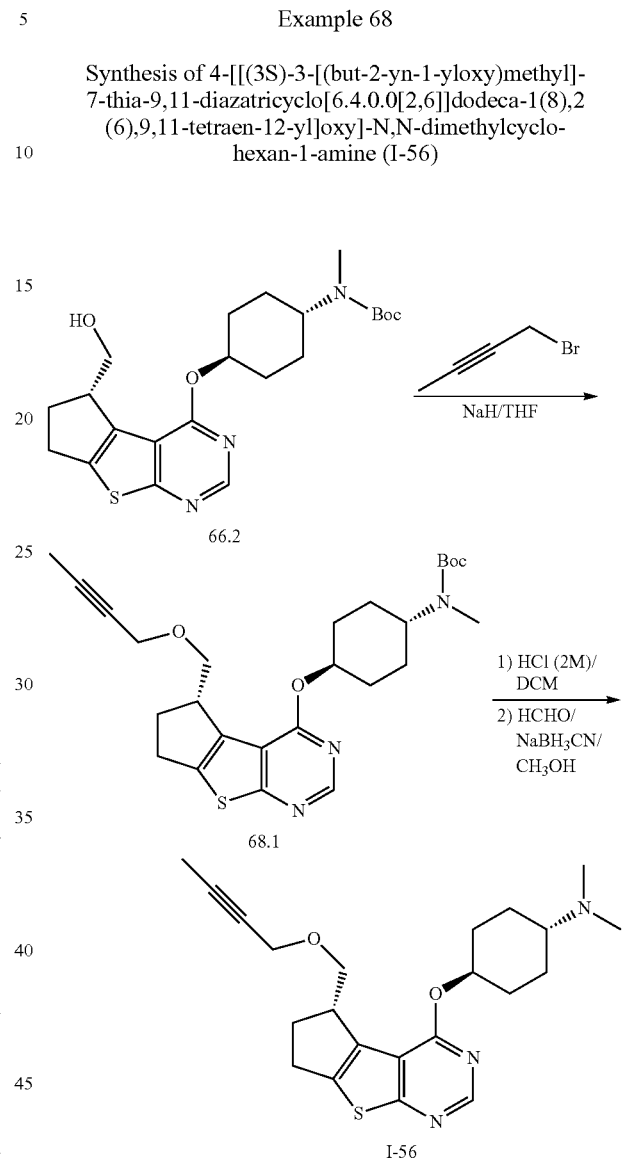

Synthesis of Compound 67.1.

To a solution of intermediate 66.2 (200 mg, 0.46 mmol, 1.00 equiv) in distilled THF (10 mL) was added sodium hydride (60% dispersion in mineral oil, 400 mg, 10.00 mmol, 21.7 equiv) at 0° C. under nitrogen. After stirring for 30 min, 3-bromoprop-1-yne (118 mg, 0.99 mmol, 2.15 equiv) was added via syringe and the reaction solution was stirred for 3 h at 60° C. in an oil bath. The reaction was then quenched with water and extracted with 3×25 mL of ethyl acetate. The combined organic layers were washed with brine and dried over anhydrous sodium sulfate. After concentration in vacuo, the residue was loaded onto a silica gel column with EtOAc/petroleum ether (1:3) and purified to afford alkyne 67.1 (210 mg, 97%) as a yellow oil. MS: m/z 472 (M+H)$^+$.

Synthesis of Compound I-49.

To a 25-mL round-bottom flask, purged and maintained with an inert atmosphere of nitrogen, was added alkyne 67.1 (200 mg, 0.42 mmol, 1.00 equiv) and 10 mL of dichloromethane. Then hydrochloric acid (12 M, 2.0 mL) was added at 0° C. and the resulting solution was stirred for 3 h at room temperature. The reaction mixture was concentrated under vacuum to give N-methyl-4-[[(3S)-3-[(prop-2-yn-1-yloxy)methyl]-7-thia-9,11-diazatricyclo[6.4.0.0[2,6]]dodeca-1(8),2(6),9,11-tetraen-12-yl]oxy]cyclohexan-1-amine hydrochloride (150 mg, crude) as a yellow oil. To a solution of this material (150 mg, crude) in 10 mL of methanol was added HCHO (37%, 1.5 mL) at room temperature and the reaction mixture was stirred for about 30 min. Then NaBH$_3$CN (80 mg, 1.26 mmol, 3 equiv) was added and the resulting solution was stirred overnight. After concentration under reduced pressure, the crude product (150 mg) was purified by preparative HPLC (Waters) under the following conditions: column: Xbridge RP18, 19*150 mm 5 um; mobile phase: water (with 20 mM NH$_4$HCO$_3$) and CH$_3$CN (10.0% CH$_3$CN then ramp up to 40.0% in 20 min, up to 95.0% in 2 min, then down to 10.0% in 2 min); UV detection at 254 and 220 nm. The product-containing fractions were collected and evaporated under reduced pressure to give Compound I-49 (50 mg) as a white solid. $^1$H NMR (300 MHz, CD$_3$OD): δ 1.48 (m, 4H), 1.95 (m, 2H), 2.25 (m, 8H), 2.42 (m, 1H), 2.50

Synthesis of Compound 68.1.

To a solution of intermediate 66.2 (200 mg, 0.46 mmol, 1.00 equiv) in 10 mL of distilled THF was added sodium hydride (60% dispersion in mineral oil, 100 mg, 2.5 mmol) at 0° C. under nitrogen. After stirring for 30 min, 1-bromobut-2-yne (132 mg, 0.99 mmol, 2.15 equiv) was added via syringe and the reaction mixture was stirred at 60° C. for 3 h. The cooled reaction mixture was then quenched with water and extracted with 3×30 mL of ethyl acetate. The organic layers were combined, washed with brine and dried over sodium sulfate. After concentration in vacuo, the residue was loaded onto a silica gel column with ethyl acetate/petroleum ether (1:5) to give the desired alkyne 67.1 (180 mg, 80%) as a yellow oil. MS: m/z 486 (M+H)$^+$.

Synthesis of Compound I-56.

Compound I-56 was prepared in a manner consistent with Example 67. 97 mg of a colorless oil were obtained. $^1$H NMR (300 MHz, CD$_3$OD): δ 1.49 (m, 4H), 1.69 (t, 3H), 1.95 (m, 2H), 2.23 (m, 9H), 2.53 (m, 2H), 2.97 (m, 2H), 3.75 (m, 1H), 3.98 (m, 1H), 5.18 (m, 2H), 8.36 (s, 1H). MS: m/z 400 (M+H)+.

Example 69

Synthesis of 4-[[(3S)-3-[[(2E)-but-2-en-1-yloxy]methyl]-7-thia-9,11-diazatricyclo[6.4.0.0[2,6]]dodeca-1 (8),2(6),9,11-tetraen-12-yl]oxy]-N,N-dimethylcyclohexan-1-amine (I-59)

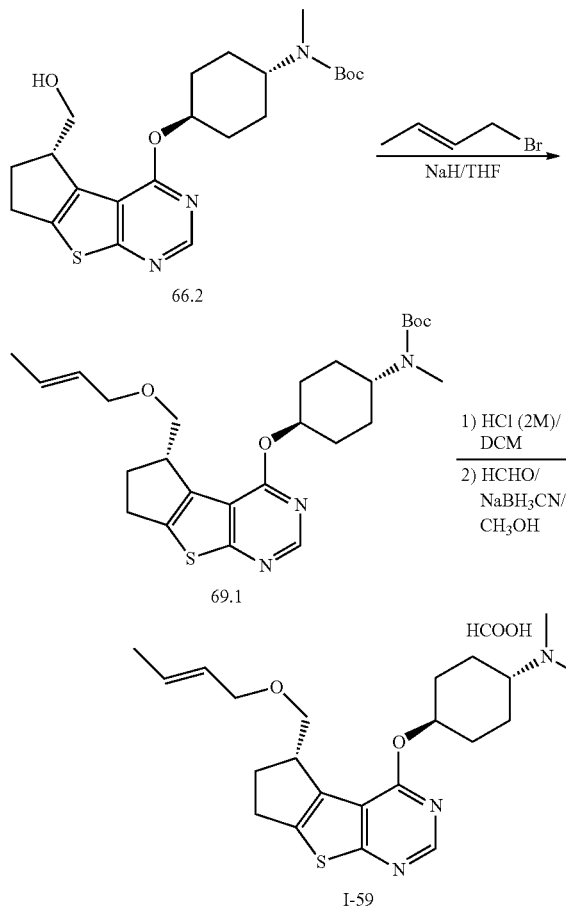

Synthesis of Compound 69.1.

To a solution of intermediate 66.2 (400 mg, 0.92 mmol, 1.00 equiv) in 10 mL of distilled THF was added sodium hydride (60% dispersion in mineral oil, 200 mg, 2.5 mmol) was added at 0° C. under nitrogen. After stirring for 30 min, (2E)-1-bromobut-2-ene (150 mg, 1.12 mmol, 1.20 equiv) was added via syringe and the reaction mixture was stirred at 60° C. for 3 h. The cooled reaction mixture was then quenched with water and extracted with 3×60 mL of ethyl acetate. The organic layers were combined, washed with brine and dried over sodium sulfate. After concentration in vacuo, the residue was loaded onto a silica gel column with ethyl acetate/petroleum ether (1:5 to 1:2) and purified to give alkene 69.1 (200 mg, 40%) as a yellow oil. MS: m/z 488 (M+H)+.

Synthesis of Compound I-59.

Compound I-59 was prepared in a manner consistent with Example 67. 50 mg of a colorless oil were obtained. 1H NMR (300 MHz, CD3OD): δ 1.52 (m, 6H), 2.08 (t, J=2.7 Hz, 2H),
2.38 (m, 3H), 2.39 (m, 1H), 2.52 (s, 6H), 2.86 (m, 1H), 3.02 (m, 2H), 3.43 (m, 2H), 3.72 (m, 2H), 3.93 (m, 1H), 5.40 (m, 1H), 5.49 (m, 1H), 5.51 (m, 1H), 8.35 (s, 1H), 8.44 (br s, 1H). MS: m/z 402 (M+H)+.

Example 70

Synthesis of (S)-1-((S)-4-(((1r,4S)-4-(dimethylamino)cyclohexyl)oxy)-6,7-dihydro-5H-cyclopenta[4,5]thieno[2,3-d]pyrimidin-5-yl)propan-1-ol (I-50)

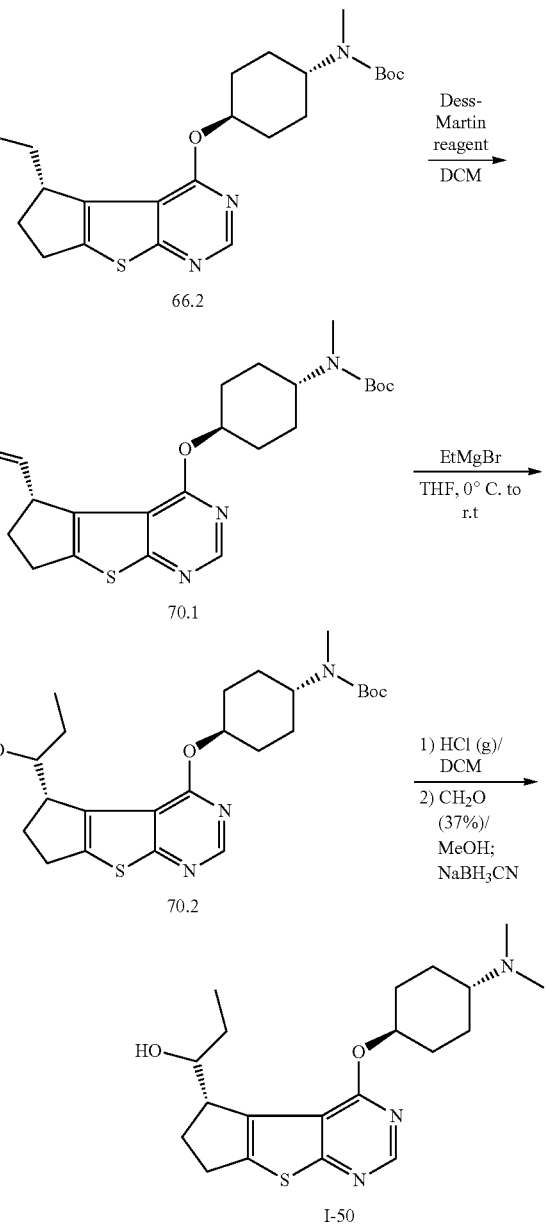

Synthesis of Compound 70.1.

To a solution of intermediate 66.2 (260.4 mg, 0.60 mmol, 1.00 equiv) in dichloromethane (10 mL) was added Dess-Martin periodinane (279.8 mg, 0.66 mmol, 1.10 equiv) at room temperature under nitrogen. The reaction mixture was stirred for 5 h at ambient temperature and diluted with DCM (30 mL), washed with brine and dried over anhydrous sodium sulfate. After concentration under reduced pressure, the aldehyde 70.1 (210 mg, 82%) was obtained as a yellow oil. MS: m/z 432 (M+H)$^+$.

Synthesis of Compound 70.2.

To a solution of 70.1 (210 mg, 0.49 mmol, 1.00 equiv) in distilled THF (10 mL) was added bromo(ethyl)magnesium (129 mg, 0.97 mmol, 1.99 equiv) at 0° C. under nitrogen. The resulting solution was stirred for 2 h at room temperature. The reaction was then quenched by the addition of H$_2$O and extracted with ethyl acetate (50 mL), dried over anhydrous sodium sulfate and concentrated under vacuum. The residue was loaded onto a silica gel column with EtOAc/petroleum ether (1:1) and purified to give alcohol 70.2 (100 mg, 45%) as a yellow oil. MS: m/z 462 (M+H)$^+$.

Synthesis of Compound I-50.

A solution of 70.2 (100 mg, 0.22 mmol, 1.00 equiv) in 5 mL of DCM was added to a solution of saturated HCl(g)/1,4-dioxane (10 mL) at room temperature. The reaction mixture was stirred at ambient temperature for 2 h. The pH value of the solution was adjusted to 10 with 2 M aqueous sodium hydroxide and extracted with dichloromethane (50 mL). The organic layer was concentrated under reduced pressure to give the desired 1-[(3S)-12-[[4-(methylamino)cyclohexyl]oxy]-7-thia-9,11-diazatricyclo[6.4.0.0[2,6]]dodeca-1(8),2(6),9,11-tetraen-3-yl]propan-1-ol (78 mg, crude) as a yellow oil. To a solution of this material (78 mg, crude) in methanol (3 mL) was added HCHO (37%, 1 mL) and the reaction was stirred for 30 min at room temperature. Then NaBH$_3$CN (42 mg, 0.67 mmol, 3.10 equiv) was added and the resulting solution was stirred overnight at ambient temperature. The reaction was then quenched by the addition of H$_2$O and extracted with dichloromethane (15 mL), dried over anhydrous sodium sulfate and concentrated under vacuum. The crude product (80 mg) was purified by preparative HPLC(SHIMADZU) under the following conditions: column: SunFire Prep C18, 19*150 mm 5 um; mobile phase: water (0.05% NH$_4$HCO$_3$) and CH$_3$CN (6.0% CH$_3$CN then ramp up to 55.0% in 19 min); UV detection at 254 and 220 nm. The product-containing fractions were collected and evaporated under reduced pressure to afford Compound I-50 (10.4 mg) as a white solid. $^1$H NMR (400 MHz, CD$_3$OD): δ 8.47 (s, 1H), 5.28-5.30 (m, 1H), 4.16-4.19 (m, 1H), 3.43-3.45 (m, 1H), 3.08-3.10 (m, 1H), 2.92-2.99 (m, 1H), 2.45-2.62 (m, 2H), 2.29-2.40 (m, 9H), 2.01-2.13 (m, 2H), 1.50-1.79 (m, 6H), 1.07 (t, 3H). MS: m/z 376 (M+H)$^+$.

Example 71

Synthesis of racemic 2-cyano-3-(12-[[4-(dimethylamino)cyclohexyl]oxy]-7-thia-9,11-diazatricyclo[6.4.0.0[2,6]]dodeca-1(12),2(6),8,10-tetraen-3-yl) propanamide (I-51)

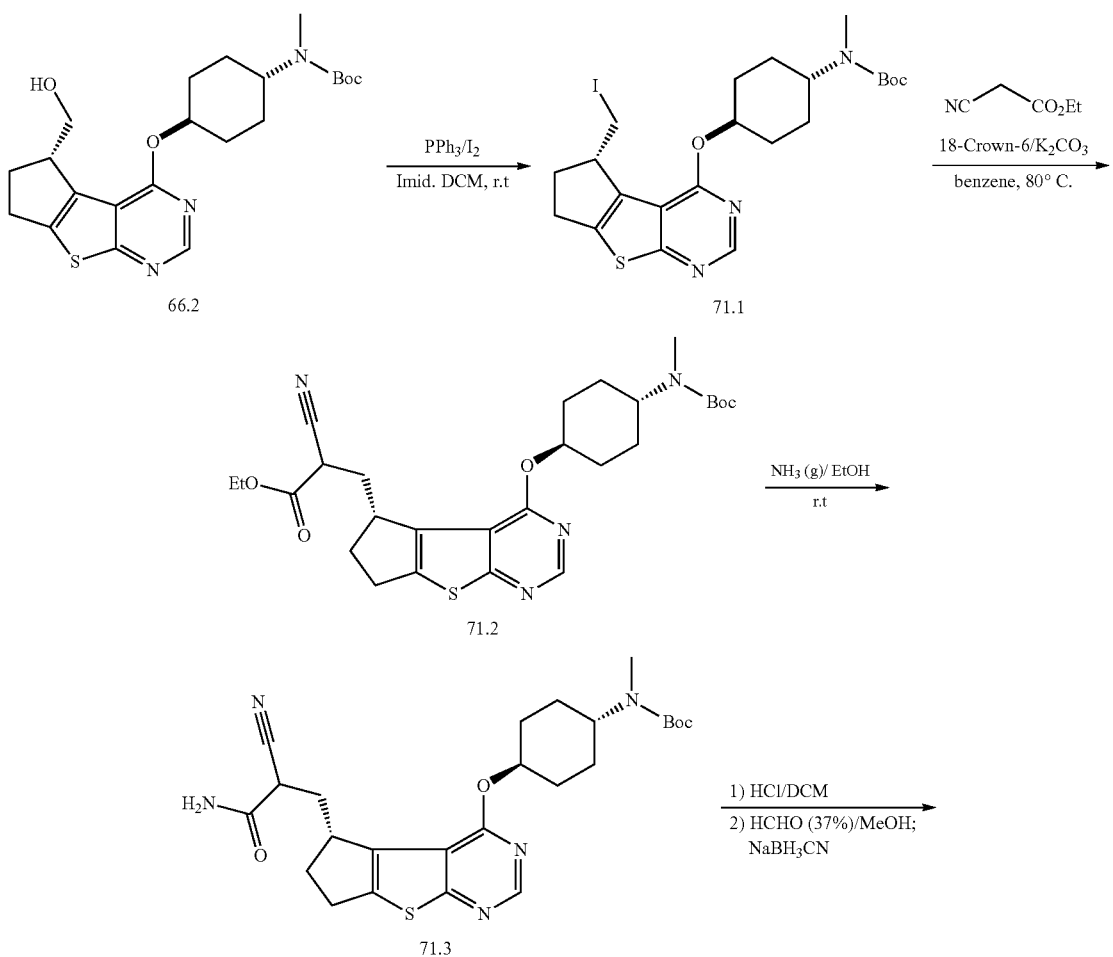

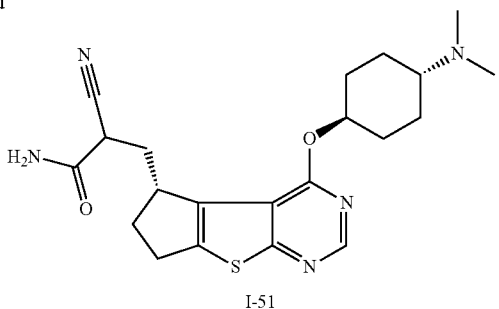

I-51

Synthesis of Compound 71.1.

To a solution of 66.2 (270 mg, 0.62 mmol, 1.00 equiv) in dichloromethane (25 mL) cooled to 0° C. was added PPh₃ (244 mg, 0.93 mmol, 1.50 equiv) and imidazole (63 mg, 0.93 mmol, 1.50 equiv) under nitrogen, followed by iodine (236 mg, 0.93 mmol, 1.50 equiv). The resulting solution was stirred overnight at room temperature and diluted with dichloromethane (100 mL), then washed with saturated aqueous sodium sulfite and brine. The dichloromethane layer was dried over anhydrous sodium sulfate. After filtration and concentration, the residue was purified using a silica gel column (eluting with EtOAc/petroleum ether (1:6-1:3)) to provide the desired iodide 71.1 (270 mg, 80%) as a light yellow foam. MS: m/z 544 (M+H)⁺.

Synthesis of Compound 71.2.

A mixture of 71.1 (270 mg, 0.50 mmol, 1.00 equiv), 18-crown-6 (159 mg, 0.60 mmol, 1.20 equiv), potassium carbonate (117 mg, 0.85 mmol, 1.70 equiv) and ethyl 2-cyanoacetate (565 mg, 5.00 mmol, 10.00 equiv) in benzene (25 mL) was stirred overnight at 80° C. under nitrogen. After concentration under reduced pressure, the residue was purified using a silica gel column (eluting with EtOAc/petroleum ether (1:4 to 1:1)) to provide 71.2 (230 mg, 88%) as a yellow oil. MS: m/z 529 (M+H)⁺.

Synthesis of Compound 71.3.

NH₃ (gas) was bubbled through 10 mL of ethanol at 0° C. for 30 min. Then a solution of 71.2 (230 mg, 0.44 mmol, 1.00 equiv) in ethanol was added and the reaction was stirred overnight at room temperature. Upon completion of the reaction, the solvents were evaporated under reduced pressure to give 71.3 (210 mg, 97%) as a yellow solid which was used directly without further purification. MS: m/z 500 (M+H)⁺.

Synthesis of Compound I-51.

A solution of 71.3 (210 mg, 0.42 mmol, 1.00 equiv) in dichloromethane (10 mL) was cooled to 0° C., hydrochloric acid (12 M, 0.3 mL) was added and the resulting solution was stirred for 1 h at room temperature. The solvent was removed under vacuum to provide 180 mg (crude) of 2-cyano-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanamide hydrochloride. This solid was dissolved in methanol (20 mL) and formaldehyde (37%, 0.5 mL) was added. After stirring for 20 min. NaBH₃CN (100 mg, 1.59 mmol) was added and stirring was continued for 1 h at room temperature. The reaction mixture was diluted with EtOAc (150 mL) and washed with saturated aqueous Na₂CO₃ and brine (100 mL). The organic layer was dried over anhydrous Na₂SO₄. After filtration and concentration, the residue was purified by preparative HPLC (Waters) under the following conditions: column: Xbridge RP18, 19*150 mm 5 um; mobile phase: water (with 20 mM NH₄HCO₃) and CH₃CN (10.0% CH₃CN and ramp up to 40.0% in 20 min, up to 95.0% in 2 min, then down to 10.0% in 2 min); UV detection at 254 and 220 nm. After concentration and lyophilization in vacuo, the desired racemic Compound I-51 (35 mg) was obtained as a white solid. ¹H NMR (300 MHz, CD₃OD): δ 7.48 (s, 1H); 5.36-5.28 (m, 1H); 3.62-3.54 (m, 1H); 3.18-3.06 (m, 2H); 2.79-2.72 (m, 2H); 2.68-2.28 (m, 11H); 2.17-2.06 (m, 2H); 1.90-1.72 (m, 3H); 1.56-1.47 (m, 2H). MS: m/z 414 (M+H)⁺.

Example 72

Synthesis of 4-(((1s,4s)-4-(dimethylamino)cyclohexyl)amino)-6,7-dihydro-5H-cyclopenta[4,5]thieno[2,3-d]pyrimidine-5-carboxylic acid (I-5)

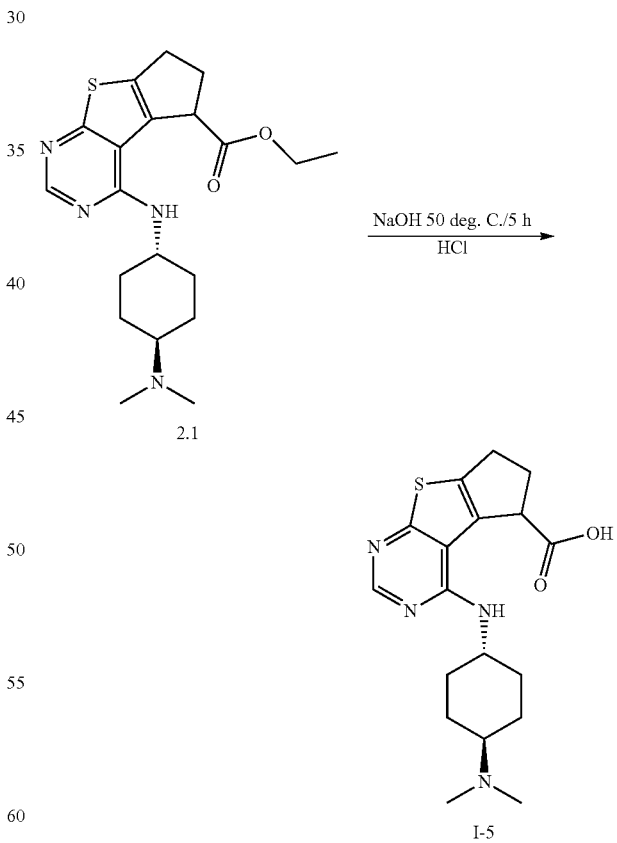

A 50-mL round-bottom flask was charged with 2.1 (2 g, 5.04 mmol, 1.00 equiv, 98%) in methanol (15 mL) and sodium hydroxide (310 mg, 7.59 mmol, 1.51 equiv). The resulting solution was stirred for 5 hours at 50° C. in an oil bath. The resulting mixture was concentrated under vacuum.

The residue was dissolved in 20 mL of sodium hydroxide (aq., 10%). The resulting solution was extracted with 3×20 mL of ethyl acetate and the aqueous layers combined. The pH value of the aqueous layer was adjusted to 3 with hydrogen chloride (aq., 10%). The resulting mixture was concentrated under vacuum to afford 4.5 g (74%) Compound I-5 as a yellow solid.

Example 73

Synthesis of 12-[[4-(dimethylamino)cyclohexyl]amino]-N-(2-hydroxyethyl)-N-methyl-7-thia-9,11-diazatricyclo[6.4.0.0^[2,6]]dodeca-1(12),2(6),8,10-tetraene-3-carboxamide (I-29)

anhydrous sodium sulfate and concentrated under vacuum to afford 3 g (24%) of amine 73.2 as a green liquid.

Synthesis of Compound 73.3.

A 20-mL round-bottom flask was charged with a solution of I-5 (600 mg, 0.50 mmol, 1.00 equiv, 30%) in N,N-dimethylformamide (5 mL), 2-[(tert-butyldimethylsilyl)oxy]ethyl (methyl)amine (100 mg, 0.53 mmol, 1.06 equiv), EDCI (260 mg, 1.33 mmol, 2.66 equiv, 98%), HOBt (90 mg, 0.65 mmol, 1.31 equiv, 98%), and triethylamine (130 mg, 1.26 mmol, 2.52 equiv, 98%). The resulting solution was stirred for 2 h at room temperature. The reaction was then quenched by the addition of 20 mL of water. The resulting solution was extracted with 4×20 mL of ethyl acetate and the organic layers combined. The combined organic layers were washed with 2×20 mL of water. The mixture was dried over anhydrous sodium sulfate and concentrated under vacuum. The residue

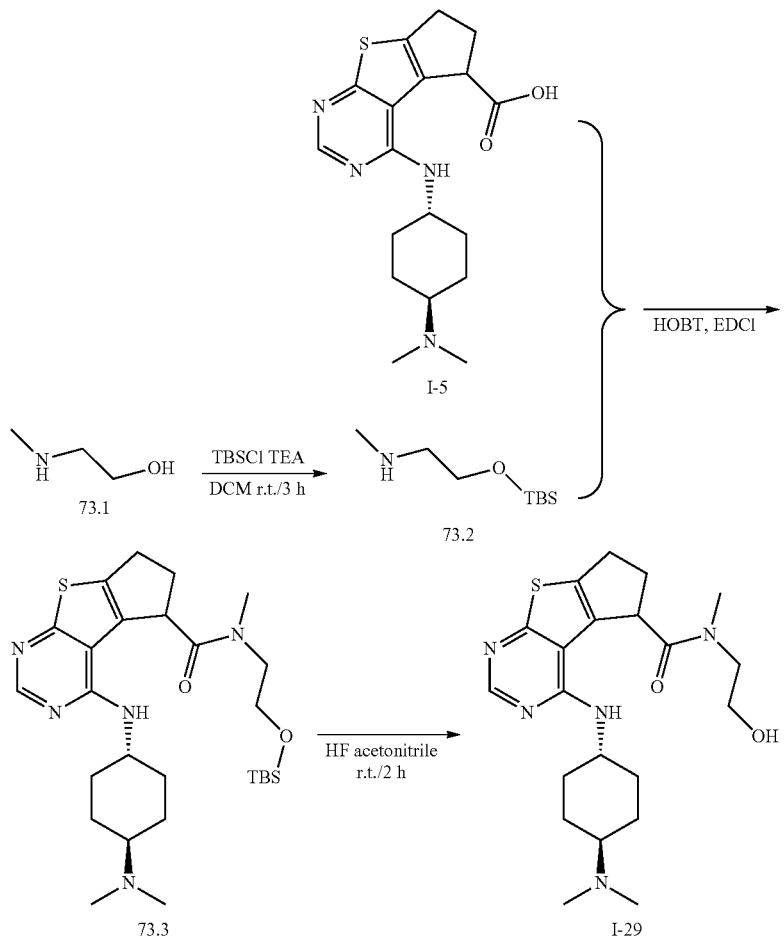

Synthesis of Compound 73.2.

A 100-mL 3-necked round-bottom flask was charged with 2-(methylamino)ethan-1-ol (5 g, 65.24 mmol, 1.00 equiv, 98%) in dichloromethane (80 mL) and TEA (21 g, 203.76 mmol, 3.12 equiv, 98%). This was followed by the addition of tert-butyl(chloro)dimethylsilane (15 g, 97.53 mmol, 1.49 equiv) at 0° C. The resulting solution was stirred for 3 h at room temperature. The reaction was then quenched by the addition of 200 mL of water and ice mixture. The resulting solution was extracted with 3×100 mL of dichloromethane and the organic layers combined. The resulting mixture was washed with 2×50 mL of water. The mixture was dried over was loaded onto a silica gel column with dichloromethane/methanol (5:1) and purified to afford 180 mg (68%) of amide 73.3 as a yellow oil.

Synthesis of Compound I-29.

A 10-mL round-bottom flask was charged with a solution of 73.3 (600 mg, 1.11 mmol, 1.00 equiv, 98%) in acetonitrile (5 mL) and HF (40 wt % in water, 0.25 mL). The resulting solution was stirred for 2 h at room temperature. The reaction was then quenched by the addition of 2 mL of saturated aqueous sodium carbonate. The resulting mixture was concentrated under vacuum and purified by flash preparative HPLC to afford 63.4 mg (13%) of Compound I-29 as a white solid. $^1$H NMR (300 MHz, CDCl$_3$): δ 8.33 (s, 1H), 5.58-5.70 (m, 1H), 3.98-3.80 (m, 1H), 4.00-4.01 (d, J=3 Hz, 1H), 3.72-3.89 (m, 2H), 3.08-3.58 (m, 2H), 2.87-3.31 (m, 3H), 2.44-2.56 (m, 1H), 2.24-2.31 (d, J=21 Hz, 6H), 2.16-2.19 (d, J=9 Hz, 2H), 1.91 (s, 2H), 1.74 (s, 4H), 1.36-1.44 (m, 2H), 1.15-1.25 (m, 2H). MS: m/z 418 (M+H)$^+$.

Example 74

Synthesis of 12-[[4-(dimethylamino)cyclohexyl]amino]-N-(2-hydroxyethyl)-7-thia-9,11-diazatricyclo[6.4.0.0^[2,6]]dodeca-1(12),2(6),8,10-tetraene-3-carboxamide (I-17)

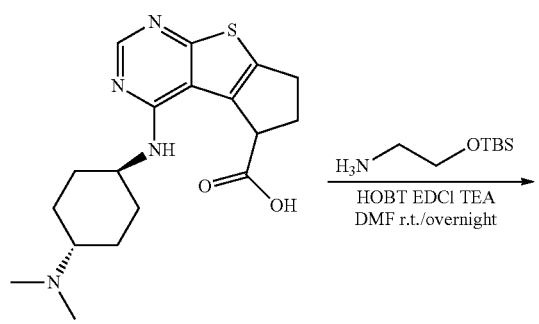

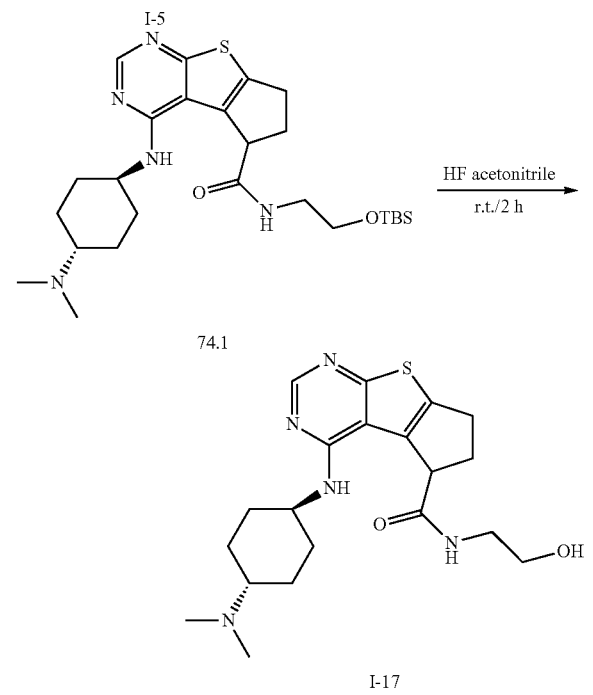

Synthesis of Compound 74.1.

A 10-mL round-bottom flask was charged with a solution of I-5 (600 mg, 0.50 mmol, 1.00 equiv, 30%) in N,N-dimethylformamide (7 mL), (2-aminoethoxy)(tert-butyl)dimethylsilane (100 mg, 0.57 mmol, 1.14 equiv), EDCI (260 mg, 1.33 mmol, 2.67 equiv, 98%), HOBt (90 mg, 0.65 mmol, 1.31 equiv, 98%), and triethylamine (130 mg, 1.26 mmol, 2.53 equiv, 98%). The resulting solution was stirred for 9 h at room temperature. The reaction was then quenched by the addition of 30 mL of water. The resulting solution was extracted with 3×30 mL of ethyl acetate and the organic layers combined. The resulting mixture was washed with 2×20 mL of water. The mixture was dried over anhydrous sodium sulfate and concentrated under vacuum to afford 105 mg (41%) of 74.1 as a yellow oil.

Synthesis of Compound I-17.

A 10-mL round-bottom flask was charged with compound 74.1 (105 mg, 0.20 mmol, 1.00 equiv, 98%), acetonitrile (5 mL), and hydrogen fluoride (40 wt % in water, 0.25 mL). The resulting solution was stirred for 2 h at room temperature. The reaction was then quenched by the addition of 0.5 mL of saturated sodium carbonate aqueous. The resulting mixture was concentrated under vacuum. The residue was dissolved in 5 mL of DMF and purified by flash preparative HPLC to give 52.6 mg (65%) of Compound I-17 as a white solid. $^1$H NMR (400 MHz, CDCl$_3$): δ 8.38 (s, 1H), 7.02 (s, 1H), 6.34 (s, 1H), 4.17-4.20 (d, 1H), 4.07-4.09 (m, 1H), 3.72-3.74 (d, 2H), 3.50-3.53 (t, 1H), 3.38-3.42 (m, 1H), 3.22-3.28 (m, 1H), 3.06-3.12 (m, 1H), 2.91-2.94 (t, 1H), 2.64-2.70 (t, 1H), 2.51 (s, 4H), 2.24-2.29 (t, 2H), 2.02-2.15 (m, 2H), 1.37-1.66 (m, 6H), 1.28-1.34 (t, 2H). MS: m/z 404 (M+H)$^+$.

Example 75

Synthesis of 12-[[4-(dimethylamino)cyclohexyl]amino]-Nyridin-3-ylmethyl)-7-thia-9,11-diazatricyclo[6.4.0.0^[2,6]]dodeca-1 (12),2(6),8,10-tetraene-3-carboxamide (I-25)

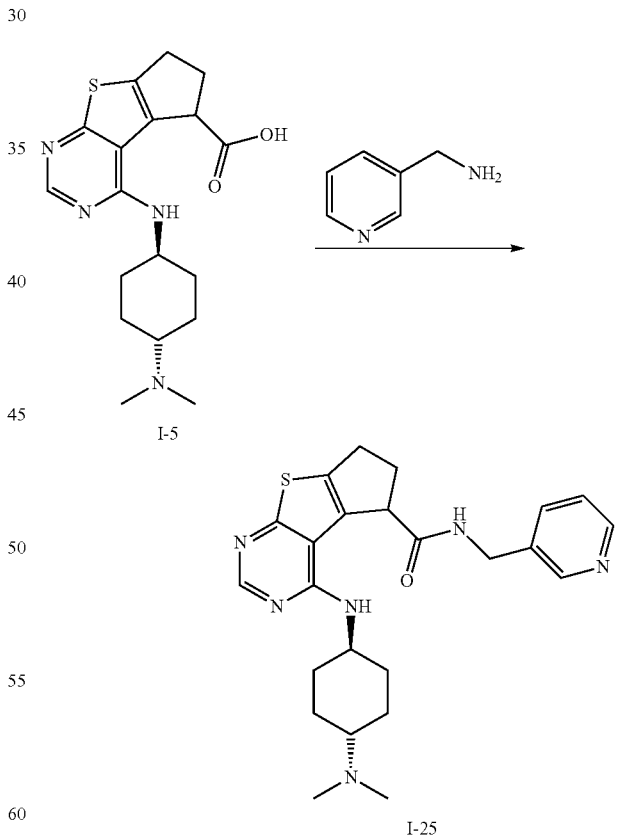

A 10-mL round-bottom flask was charged with 1-5 (700 mg, 0.58 mmol, 1.00 equiv, 30%), N,N-dimethylformamide (5 mL), pyridin-3-ylmethanamine (75.6 mg, 0.69 mmol, 1.18 equiv), EDCI (335 mg, 1.72 mmol, 2.95 equiv, 98%), HOBt (119 mg, 0.86 mmol, 1.48 equiv, 98%), and TEA (177 mg, 1.72 mmol, 2.95 equiv, 98%). The resulting solution was stirred overnight at room temperature. The reaction was then quenched by the addition of 20 mL of water. The resulting solution was extracted with 3×20 mL of ethyl acetate and the organic layers combined. The resulting mixture was washed with 2×20 mL of water. The mixture was dried over anhydrous sodium sulfate and concentrated under vacuum. The residue was purified by flash preparative HPLC to give 5.2 mg (2%) of Compound I-25 as an off-white solid. $^1$H NMR (300 MHz, CDCl$_3$): δ 8.52 (s, 1H), 8.48 (s, 1H), 8.36 (s, 1H), 7.46-7.48 (d, J=6, 1H), 7.21-7.26 (t, J=3, 1H), 6.97 (s, 1H), 6.11 (s, 1H), 4.50-4.57 (m, 1H), 4.33-4.39 (m, 1H), 4.20-4.23 (d, J=9, 1H), 4.04-4.07 (t, J=3, 1H), 2.98-3.17 (m, 2H), 2.88-2.95 (m, 2H), 2.57-2.64 (t, J=6, 6H), 2.33 (s, 1H), 2.17-2.21 (d, J=12, 3H), 1.45-1.57 (m, 1H), 1.25-1.40 (m, 4H). MS: m/z 451 (M+H)$^+$.

Example 76

12-[[4-(dimethylamino)cyclohexyl]amino]-N-(3-hydroxypropyl)-7-thia-9,11-diazatricyclo[6.4.0.0^[2,6]]dodeca-1(12),2(6),8,10-tetraene-3-carboxamide (I-28)

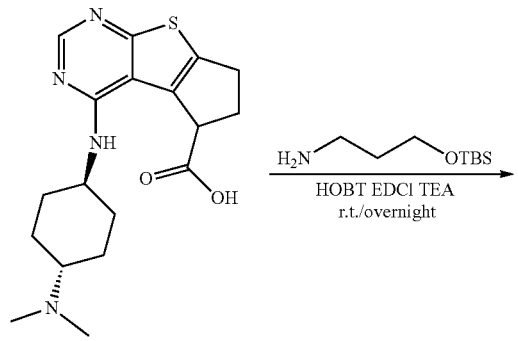

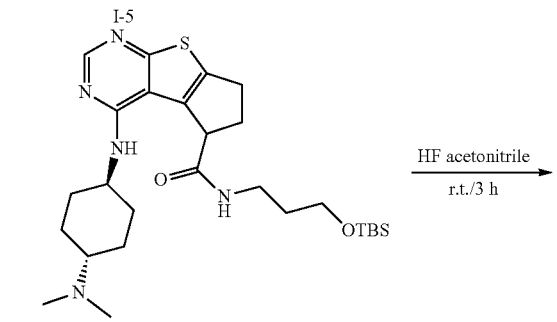

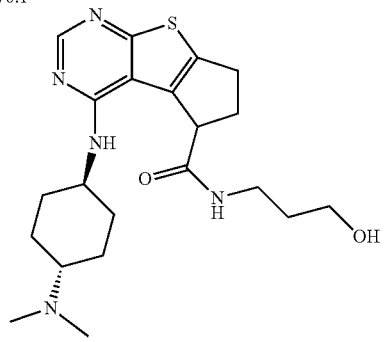

Synthesis of Compound 76.1.

A 10-mL round-bottom flask was charged with a solution of intermediate 1-5 (1 g, 0.83 mmol, 1.00 equiv, 30%) in N,N-dimethylformamide (7 mL), (3-aminopropoxy)(tert-butyl)dimethylsilane (190 mg, 0.98 mmol, 1.18 equiv), EDCI (478 mg, 2.45 mmol, 2.95 equiv, 98%), HOBt (169 mg, 1.23 mmol, 1.47 equiv, 98%), and TEA (253 mg, 2.45 mmol, 2.95 equiv, 98%). The resulting solution was stirred overnight at room temperature. The reaction was then quenched by the addition of 30 mL of water. The resulting solution was extracted with 3×30 mL of ethyl acetate and the organic layers combined. The resulting mixture was washed with 2×20 mL of water. The mixture was dried over anhydrous sodium sulfate and concentrated under vacuum to afford 200 mg (45%) of amide 76.1 as a yellow green oil.

Synthesis of Compound I-28.

A 10-mL round-bottom flask was charged with a solution of amide 76.1 (200 mg, 0.30 mmol, 1.00 equiv, 80%) in acetonitrile (5 mL) and HF (40 wt % in water, 0.25 mL). The resulting solution was stirred for 3 h at room temperature. The reaction was then quenched by the addition of 2 mL of saturated aqueous sodium carbonate. The resulting mixture was concentrated under vacuum. The residue was purified by flash preparative HPLC to give 12.8 mg (10%) of Compound I-28 as a light yellow solid. $^1$H NMR (400 MHz, CDCl$_3$): δ 8.37 (s, 1H), 7.17 (s, 1H), 6.53 (s, 1H), 4.14-4.16 (d, 1H), 4.06-4.10 (m, 1H), 3.67-3.70 (t, 2H), 3.67-3.68 (d, 1H), 3.41-3.46 (m, 1H), 3.15-3.22 (m, 1H), 3.04-3.10 (m, 1H), 2.85-2.91 (m, 1H), 2.61-2.66 (m, 1H), 2.44-2.53 (d, 6H), 2.29-2.44 (d, 2H), 2.04-2.26 (d, 2H), 1.72 (s, 2H), 1.42-1.58 (m, 4H), 1.26 (s, 2H). MS: m/z 418 (M+H)$^+$.

Example 77

Synthesis of N-benzyl-12-[[4-(dimethylamino)cyclohexyl]amino]-7-thia-9,11-diazatricyclo[6.4.0.0^[2,6]]dodeca-1(12),2(6),8,10-tetraene-3-carboxamide (I-24)

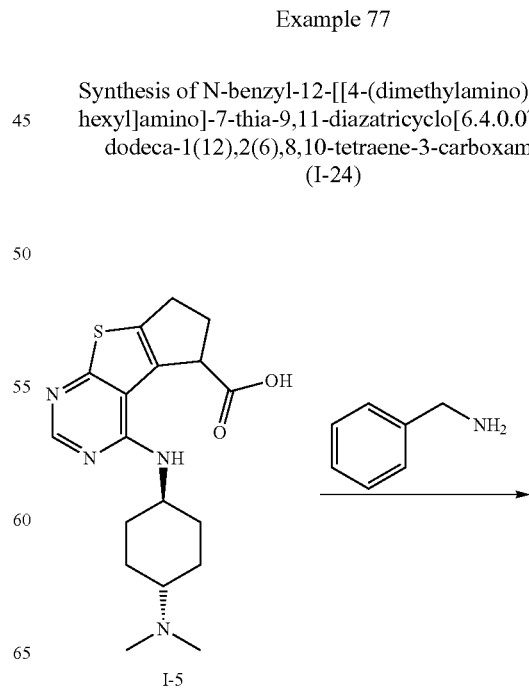

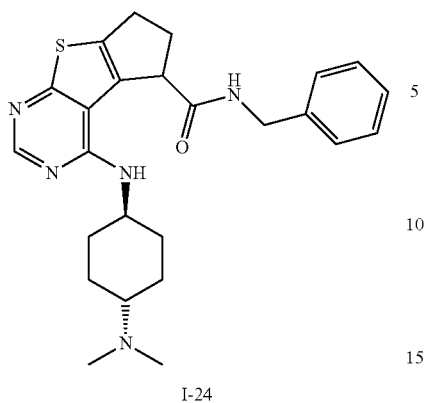

I-24

A 10-mL round-bottom flask was charged with 1-5 (700 mg, 0.58 mmol, 1.00 equiv, 30%) in N,N-dimethylformamide (5 mL), phenylmethanamine (75.1 mg, 0.69 mmol, 1.18 equiv), EDCI (335 mg, 1.72 mmol, 2.95 equiv, 98%), HOBt (119 mg, 0.86 mmol, 1.48 equiv, 98%), TEA (177 mg, 1.72 mmol, 2.95 equiv, 98%). The resulting solution was stirred overnight at room temperature. The reaction was then quenched by the addition of 20 mL of water. The resulting solution was extracted with 3×15 mL of ethyl acetate and the organic layers combined. The resulting mixture was washed with 2×15 mL of water. The resulting mixture was dried and concentrated under vacuum. The residue was purified by flash preparative HPLC to give 40 mg (15%) of Compound I-24 as a white solid. $^1$H NMR (300 MHz, CDCl$_3$) δ 8.38 (1H, s), 7.11-7.13 (1H, d, J=6 Hz), 5.85 (1H, s), 4.45-4.50 (1H, m), 4.34-4.39 (1H, t, J=6 Hz), 4.18-4.22 (1H, d, J=12 Hz), 4.01-4.04 (1H, d, J=9 Hz), 3.08-3.16 (2H, m), 2.88-2.96 (1H, m), 2.60-2.65 (1H, m), 2.37-2.58 (6H, m), 2.24-2.37 (1H, m), 2.14-2.22 (1H, m), 2.06-2.14 (2H, t, J=12 Hz), 1.36-1.48 (1H, m), 1.22-1.29 (5H, m). MS: m/z 450 (M+H)$^+$.

Example 78

Synthesis of ethyl 4-(((1r,4r)-4-aminocyclohexyl)amino)-6,7-dihydro-5H-cyclopenta[4,5]thieno[2,3-d]pyrimidine-5-carboxylate (1-2)

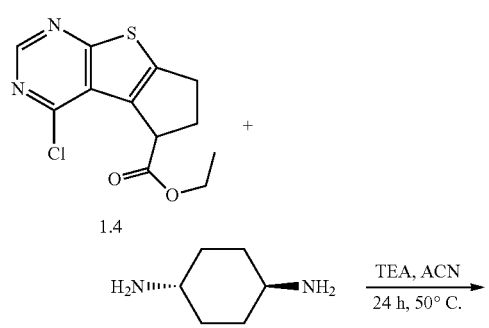

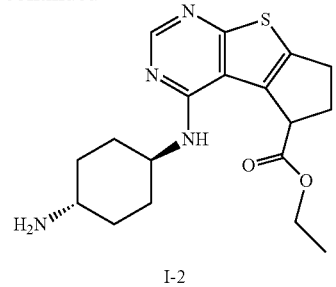

I-2

A mixture of intermediate 1.4 (2.8 g, 10 mmol, 1 equiv), TEA (5 g, 50 mmol, 5 equiv) and (1r,4r)-cyclohexane-1,4-diamine (5.7 g, 50 mmol, 5 equiv) in CH$_3$CN (30 mL) was heated at 45° C. for 24 h. The solvent was removed under vacuum and the residue was purified by column chromatography to afford 3 g (83%) of 1-2. $^1$H NMR (500 MHz, CDCl$_3$) δ 8.36 (1H, s), 6.59 (1H, d), 4.23-4.09 (4H, m), 3.25-3.22 (1H, m), 3.00-2.87 (2H, m), 2.80-2.78 (1H, m), 2.65-2.61 (1H, m), 2.22-1.87 (6H, m), 1.44 (4H, m), 1.34 (3H, t). MS: m/z 361 (M+H)$^+$.

Example 79

Synthesis of Intermediate 79.4

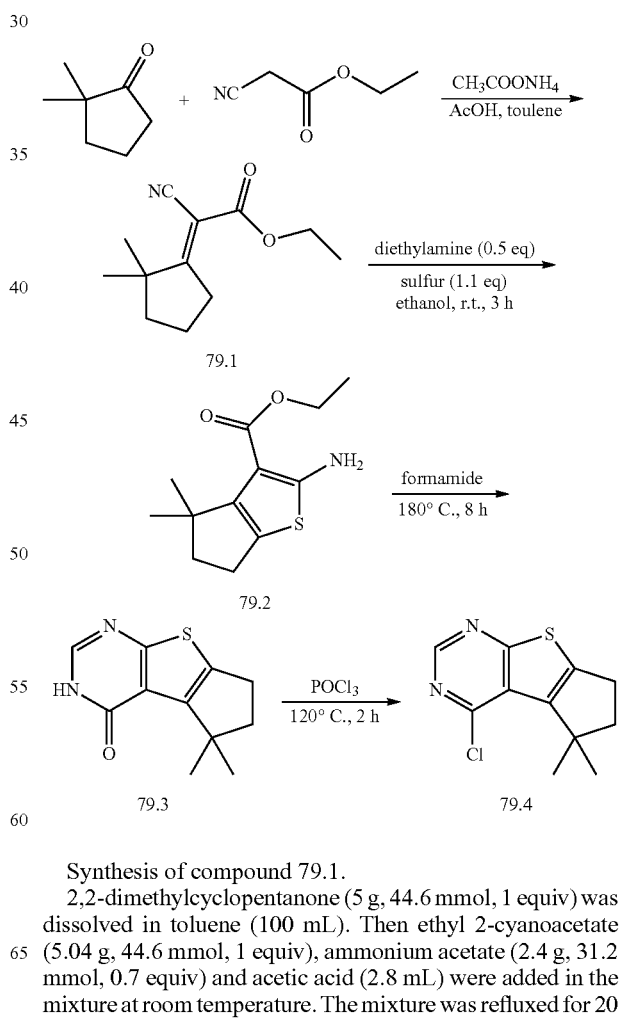

Synthesis of compound 79.1.

2,2-dimethylcyclopentanone (5 g, 44.6 mmol, 1 equiv) was dissolved in toluene (100 mL). Then ethyl 2-cyanoacetate (5.04 g, 44.6 mmol, 1 equiv), ammonium acetate (2.4 g, 31.2 mmol, 0.7 equiv) and acetic acid (2.8 mL) were added in the mixture at room temperature. The mixture was refluxed for 20 hours. 10% NaCl solution (100 mL) was added. The organic layer was washed with water (50 mL) and brine (50 mL), dried with sodium sulfate and filtered. The organic layer was concentrated and the residue was purified by column chromatography to give 79.1 (2.47 g, 32%) as a colorless oil. MS: m/z 208 (M+H)$^+$.

Synthesis of Compound 79.2.

Diethylamine (433 mg, 5.93 mmol, 0.5 equiv) was slowly added to a solution of 79.1 (2.47 g, 11.87 mmol, 1 equiv) and sulfur (418 mg, 13.06 mmol, 1.1 equiv) in ethanol (120 mL) at 50° C. The reaction was stirred for 2 hours at 50° C. The mixture was filtered and the filtrate concentrated. The residue was purified by column chromatography (hexane:ethyl acetate=20:1) to give 79.2 (2.34 g, 83%) as a yellow solid. MS: m/z 240 (M+H)$^+$.

Synthesis of Compound 79.3. 79.2

(2.3 g, 9.9 mmol, 1 equiv) was dissolved in formamide (12 mL). The reaction was stirred for 1 hour at 180° C. Then water (50 mL) was added and the product extracted with ethyl acetate (50 mL×3). The combined organic layers were washed with water (100 mL×2) and brine (100 mL), dried with sodium sulfate and filtered. The organic layer was concentrated and the residue purified by column chromatography (hexane:ethyl acetate=6:5) to give the desired product (1.57 g, 75%) as a yellow solid. MS: m/z 221 (M+H)$^+$.

Synthesis of Compound 79.4. 79.3

(1.5 g, 6.8 mmol, 1 equiv) was dissolved in phosphoryl trichloride (40 mL). The reaction was stirred for 2 hours at 120° C., whereupon it was slowly added to water (150 mL) and extracted with ethyl acetate (60 mL×3). The combined organic layers were washed with brine (100 mL) and dried with sodium sulfate. The organic layer was concentrated and the residue purified by column chromatography (hexane: ethyl acetate=20:1). The desired product (1.3 g, 83%) was obtained as a yellow solid. MS: m/z 239 (M+H)$^+$.

Example 80

Synthesis of (1r,4r)-N1-(5,5-dimethyl-6,7-dihydro-5H-cyclopenta[4,5]thieno[2,3-d]pyrimidin-4-yl)-N4,N4-dimethylcyclohexane-1,4-diamine (1-6)

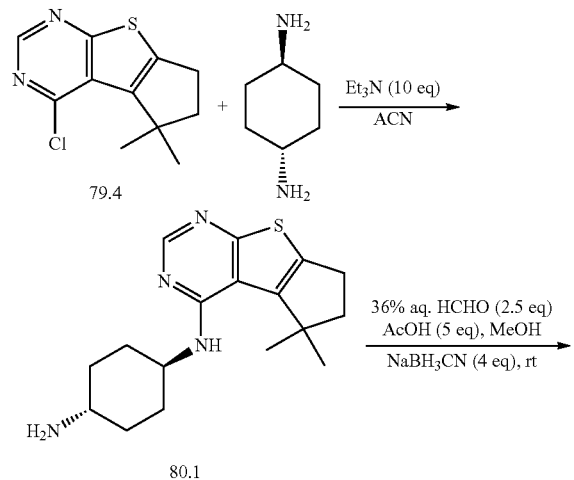

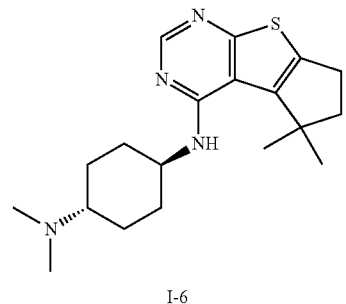

I-6

Synthesis of Compound 80.1.

Intermediate 79.4 (238 mg, 1 mmol, 1 equiv) and trans-1,4-diaminocyclohexane (1.1 g, 10 mmol, 10 equiv) were dissolved in acetonitrile (15 mL). Then triethylamine (1 g, 10 mmol, 10 equiv) was added to the mixture. The reaction was stirred for 20 hours at 50° C. It was then concentrated and the residue was purified by reverse phase chromatography on a Biotage instrument. The desired product (154 mg, 48%) was obtained as a yellow solid. MS: m/z 317 (M+H)$^+$.

Synthesis of Compound I-6.

80.1 (140 mg, 0.44 mmol, 1 equiv) was dissolved in methanol (5 mL). 36% aq. formaldehyde (92 mg, 1.1 mmol, 2.5 equiv) and acetic acid (133 mg, 2.2 mmol, 5 equiv) were added to the solution. The mixture was stirred for 10 minutes at room temperature, and then sodium cyanoborohydride (377 mg, 1.77 mmol, 4 equiv) was added to the mixture. The reaction was stirred for 20 hours at room temperature. It was then added to water (50 mL) slowly, and extracted with ethyl acetate (50 mL×3). The organic layer was washed with brine (100 mL), and dried with sodium sulfate. The organic layer was concentrated and purified by preparative HPLC. The desired product I-6 (31 mg, 20%) was obtained as a white solid. $^1$H NMR: (400 MHz, CDCl$_3$) δ 8.36 (s, 1H), 5.04 (d, 1H), 4.17-2.24 (m, 1H), 3.22 (t, 1H), 2.97 (t, 2H), 2.78 (m, 6H), 2.40 (d, 2H), 2.33-2.37 (m, 4H), 1.73 (dd, 2H), 1.44 (s, 6H), 1.25-1.42 (m, 2H). MS: m/z 345 (M+H)$^+$.

Example 81

Synthesis of (1r,4r)-4-1((5,5-dimethyl-6,7-dihydro-5H-cyclopenta[4,5]thieno[2,3-d]pyrimidin-4-yl)oxy)-N,N-dimethylcyclohexanamine (1-7)

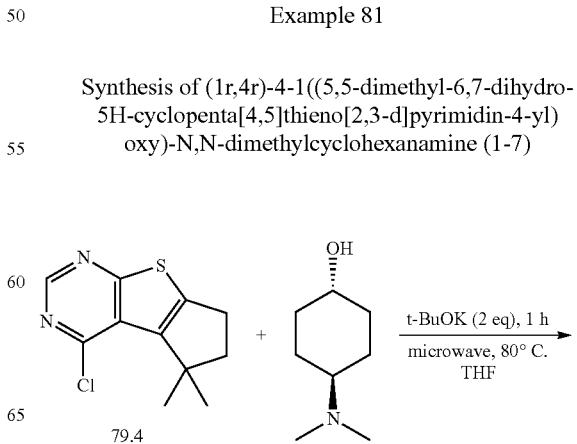

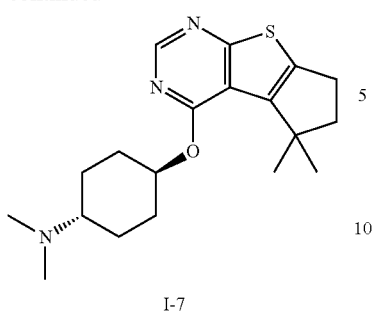

I-7

To a suspension of (1r,4r)-4-(dimethylamino)cyclohexanol (600 mg, 4.2 mmol, 1 equiv) in THF (10 mL) was added compound 79.4 (250 mg, 1.05 mmol) and t-BuOK (235 mg, 2.1 mmol). The suspension was heated to 80° C. in a sealed tube for 1 h in a microwave. The suspension was poured into water (10 mL) and then extracted by EtOAc (10 mL×3). The residue was purified by preparative HPLC to give a white solid product (30 mg, 10%). $^1$H NMR: (500 MHz, CDCl$_3$) δ 8.52 (1H, s), 8.47 (1H, 2), 5.31-5.29 (1H, m), 3.04-2.99 (3H, m), 2.63 (6H, s), 2.44 (2H, s), 2.33-2.30 (2H, t), 2.22 (2H, s), 1.68-1.64 (4H, m), 1.38 (6H, s). MS: m/z 346 (M+H)$^+$.

Example 82

N-(2-amino-2-oxoethyl)-2-(R)-4-(((1r,4R)-4-(dimethylamino)cyclohexyl)oxy)-6,7-dihydro-5H-cyclopenta[4,5]thieno[2,3-d]pyrimidin-5-yl)acetamide (I-58)

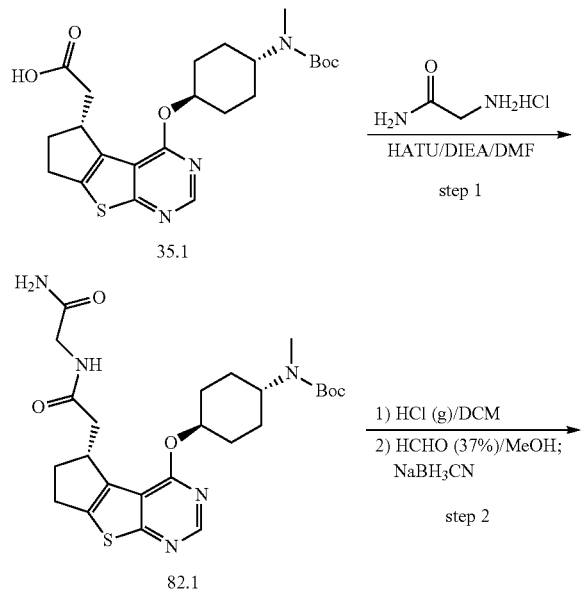

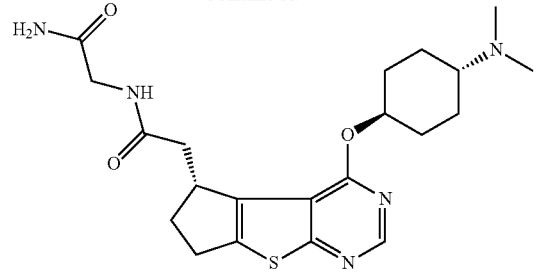

Synthesis of Compound 82.1.

Into a 50-mL round-bottom flask, a solution of 2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]acetic acid (270 mg, 0.58 mmol, 1.00 equiv) in 30 mL of distilled DMF was added HATU (331 mg, 0.87 mmol, 1.50 equiv), DIEA (375 mg, 2.90 mmol, 5.00 equiv) and 2-aminoacetamide hydrochloride (128 mg, 1.16 mmol, 2.00 equiv) subsequently at room temperature under nitrogen. The resulting solution was stirred for 1 h at room temperature. After completion, the reaction was diluted with EtOAc, washed with brine, dried over anhydrous sodium sulfate. After filtration and concentration in vacuo, the residue was purified by a silica gel column with DCM/MeOH (30:1-10:1) to provide 280 mg (92%) of tert-butyl N-(4-[[(3R)-3-[[(carbamoylmethyl)carbamoyl]methyl]-7-thia-9,11-diazatricyclo[6.4.0.0[2,6]]dodeca-1(8),2(6),9,11-tetraen-12-yl]oxy]cyclohexyl)-N-methylcarbamate as a yellow solid. MS: m/z 518 (M+H)$^+$.

Synthesis of Compound I-58.

HCl (gas) was introduced into DCM (50 mL) at 0° C. for 30 min with stirring. Then a solution of tert-butyl N-(4-[[(3R)-3-[[(carbamoylmethyl)carbamoyl]methyl]-7-thia-9,11-diazatricyclo[6.4.0.0[2,6]]dodeca-1(8),2(6),9,11-tetraen-12-yl]oxy]cyclohexyl)-N-methylcarbamate (140 mg, 0.27 mmol, 1.00 equiv) in 5 mL of DCM was added and the resulting solution was stirred overnight at room temperature. The solvent was removed under vacuum to provide 120 mg of N-(carbamoylmethyl)-2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]acetamide hydrochloride as a yellow solid. The solid was dissolved in methanol (10 mL) and HCHO (37%, 0.5 mL) and acetic acid (0.5 mL) were added at room temperature. After stirring for 20 min at room temperature, NaBH$_3$CN (100 mg) was added and the resulting mixture was stirred for 1 h at ambient temperature. After concentration in vacuo, the residue was purified by preparative HPLC under the following conditions (Waters): column: X-briage C18, 19*150 mm 5 um; mobile phase: CH$_3$CN and water with 20 mM NH$_4$HCO$_3$ (10.0% CH$_3$CN up to 50.0% in 10 min, up to 95% in 2 min, down to 10.0% in 2 min); flow rate: 20 mL/min; UV detection at 254/220 nm. The product-containing fractions were collected and partially evaporated to remove water and CH$_3$CN under reduced pressure. The residue was lyophilized overnight to give the desired N-(2-amino-2-oxoethyl)-2-((R)-4-(((1r,4R)-4-(dimethylamino)cyclohexyl)oxy)-6,7-dihydro-5H-cyclopenta[4,5]thieno[2,3-d]pyrimidin-5-yl)acetamide (154.3 mg, 71%) as a white solid. MS: m/z 432 [M+H]$^+$, 454 [M+Na]$^+$; $^1$H NMR (400 MHz, CD$_3$OD): δ 8.47 (1H, s), 5.28-5.23 (1H, m), 3.89 (2H, s), 3.86-3.77 (1H, m), 3.15-2.99 (3H, m), 2.74-2.68 (1H, m), 2.44-2.34 (11H, m), 2.06-2.04 (2H, m), 1.73-1.58 (2H, m), 1.57-1.43 (2H, m).

Example 83

Synthesis of Intermediate 83.5
(2-amino-N-methylacetamide hydrochloride)

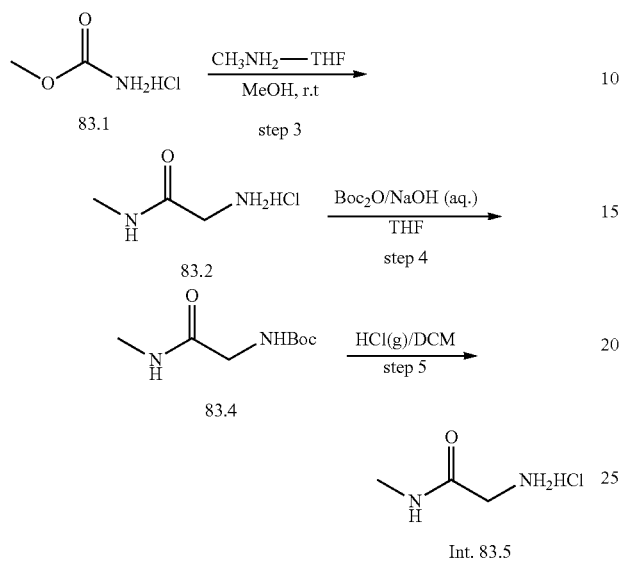

Synthesis of Compound 83.2.

Into a 250-mL round-bottom flask, a solution of methyl 2-aminoacetate hydrochloride (2.0 g, 15.93 mmol, 1.00 equiv) in 100 mL of anhydrous methanol was added $CH_3NH_2$ (2 M in THF, 35.7 mL) and the resulting solution was stirred for 48 h at room temperature under nitrogen. After completion of the reaction, the resulting mixture was concentrated under reduced pressure to afford 2-amino-N-methylacetamide hydrochloride (2.5 g, crude) as a colorless oil containing large amounts of methylamine.

Synthesis of Compound 83.3.

Into a 50-mL round-bottom flask, a solution of 2-amino-N-methylacetamide hydrochloride (1.2 g, crude) and 4 M aqueous sodium hydroxide (3 mL) in 10 mL of THF was added $Boc_2O$ (900 mg) at 0° C. and the resulting solution was stirred for 2 h at room temperature. The resulting solution was diluted with 20 mL of water and extracted with 3×50 mL of ethyl acetate. The combined organic layers were washed with brine, dried over anhydrous sodium sulfate and concentrated under vacuum. The residue was applied onto a silica gel column with ethyl acetate/petroleum ether (1:20 to 1:10) to afford the desired tert-butyl N—[(methylcarbamoyl)methyl]carbamate (0.3 g, 31%) as a colorless oil. $^1H$ NMR (300 MHz, $CDCl_3$) δ 6.51 (br s, 1H), 5.43 (br s, 1H), 3.78 (d, 2H), 2.87-2.81 (d, 3H), 1.44 (s, 9H).

Synthesis of Intermediate 83.5.

A solution of tert-butyl N-[(methylcarbamoyl)methyl]carbamate (300 mg, 1.59 mmol, 1.00 equiv) in DCM (5 mL) was added hydrochloric acid (1.2 mL) and stirred for 4 h at room temperature. The resulting mixture was concentrated under vacuum to afford the corresponding 2-amino-N-methylacetamide hydrochloride (185 mg) as a colorless oil. MS: m/z 89 $(M+H)^+$. $^1H$ NMR (300 MHz, $CDCl_3$): δ 8.45 (br s, 1H), 8.19 (s, 3H), 3.50 (d, 2H), 2.65 (d, 3H).

Example 84

2-[2-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]acetamido]-N-methylacetamide
(I-61)

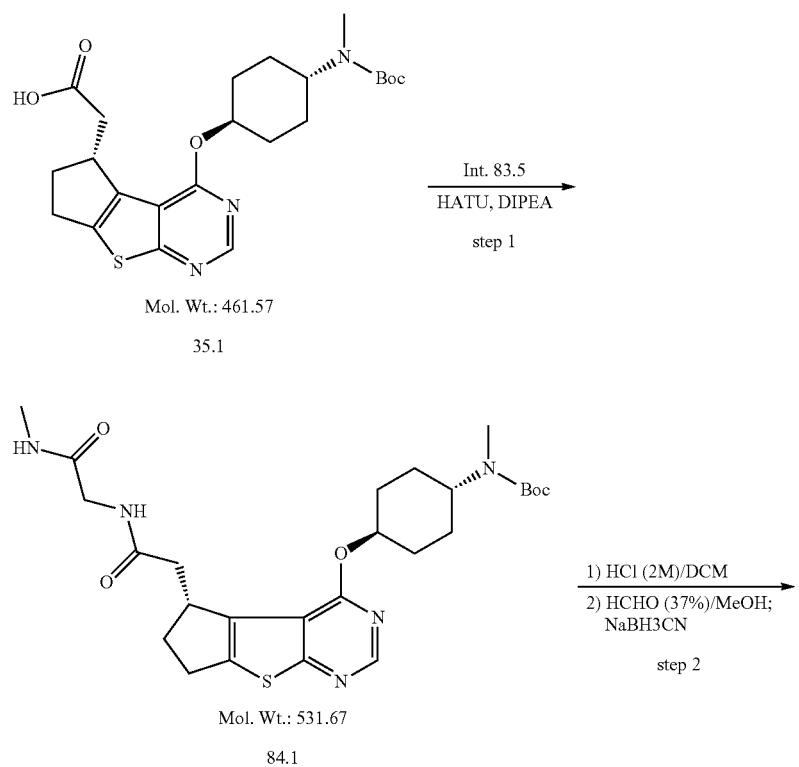

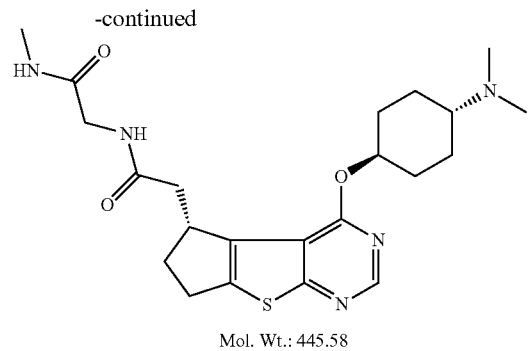

Mol. Wt.: 445.58
I-61

Synthesis of Compound 84.1. Note:

For the preparation of the starting material compound 35.1, please see Example 35. A solution of 2-[(3R)-12-[(4-[[tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]acetic acid (150 mg, 0.32 mmol, 1.00 equiv), HATU (183 mg, 0.48 mmol, 1.48 equiv), DIPEA (165 mg) and 2-amino-N-methylacetamide hydrochloride (intermediate 83.5, 120 mg, 0.96 mmol, 3.0 equiv) in 10 mL of anhydrous DMF was stirred for 24 h at room temperature under nitrogen. After completion of the reaction, the resulting solution was diluted with water and extracted with 3×40 mL of ethyl acetate. The organic layers were combined, washed with brine, dried ($Na_2SO_4$) and concentrated under vacuum. The residue was applied onto a silica gel column with dichloromethane/methanol (30:1) to afford tert-butyl N-methyl-N-(4-[[(3R)-3-([[(methylcarbamoyl)methyl]carbamoyl]methyl)-7-thia-9,11-diazatricyclo[6.4.0.0[2,6]]dodeca-1(8),2(6),9,11-tetraen-12-yl]oxy]cyclohexyl)carbamate (130 mg, 75%) as a yellow oil. MS: m/z 532 $[M+H]^+$.

Synthesis of Compound I-61.

A solution of tert-butyl N-methyl-N-(4-[[(3R)-3-([[(methylcarbamoyl)methyl]carbamoyl]methyl)-7-thia-9,11-diazatricyclo[6.4.0.0[2,6]]dodeca-1(8),2(6),9,11-tetraen-12-yl]oxy]cyclohexyl)carbamate (130 mg, 0.24 mmol, 1.00 equiv) in 5.5 mL of dichloromethane was added concentrated hydrochloric acid (0.5 mL) at 0° C. under nitrogen. The resulting solution was stirred for 2 h at 0° C. in a water/ice bath and concentrated under reduced pressure to afford N-methyl-2-[2-[(3R)-12-[[4-(methylamino)cyclohexyl]oxy]-7-thia-9,11-diazatricyclo[6.4.0.0[2,6]]dodeca-1(8),2 (6),9,11-tetraen-3-yl]acetamido]acetamide hydrochloride (105 mg, crude) as a yellow oil. MS: m/z 432 $[M+H]^+$.

A solution of N-methyl-2-[2-[(3R)-12-[[4-(methylamino)cyclohexyl]oxy]-7-thia-9,11-diazatricyclo[6.4.0.0[2,6]]dodeca-1(8),2 (6),9,11-tetraen-3-yl]acetamido]acetamide hydrochloride (105 mg, 0.22 mmol, 1.00 equiv) in 5 mL of methanol was added formaldehyde (37%, 1.0 mL) at room temperature under nitrogen for 1 h. Then sodium cyanoborohydride (59 mg, 0.97 mmol, 4.32 equiv) was added and stirred overnight at ambient temperature. The solvent was removed under reduced pressure and the crude product (100 mg, crude) was purified by preparative HPLC under the following conditions (SHIMADZU): column: SunFire Prep C18, 19*150 mm 5 um; mobile phase: water with 0.05% $NH_4CO_3$ and $CH_3CN$ (6.0% $CH_3CN$ up to 50.0% in 25 min); UV detection at 254/220 nm. The product containing fractions were collected and evaporated to remove the water and $CH_3CN$ to give 2-[2-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]acetamido]-N-methylacetamide (40 mg) as a white solid. MS: m/z 446 $[M+H]^+$. $^1$H NMR (300 MHz, $CD_3OD$) δ 8.37 (s, 1H), 5.20-5.12 (m, 1H), 3.74-3.68 (m, 3H), 3.20-2.84 (m, 3H), 2.65-2.47 (m, 4H), 2.36-2.17 (m, 11H), 1.95 (d, 2H), 1.59-1.51 (m, 4H).

Example 85

(2R)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propan-2-ol (I-53) and Example (2S)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propan-2-ol (I-55)

Alcohol stereochemistry unconfirmed

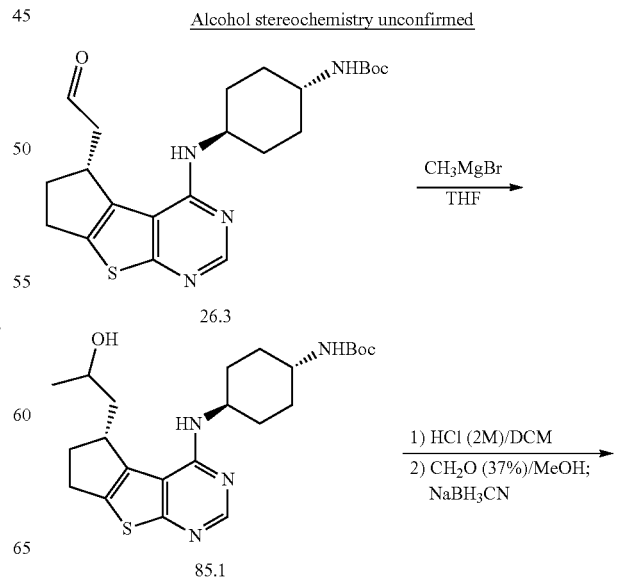

-continued

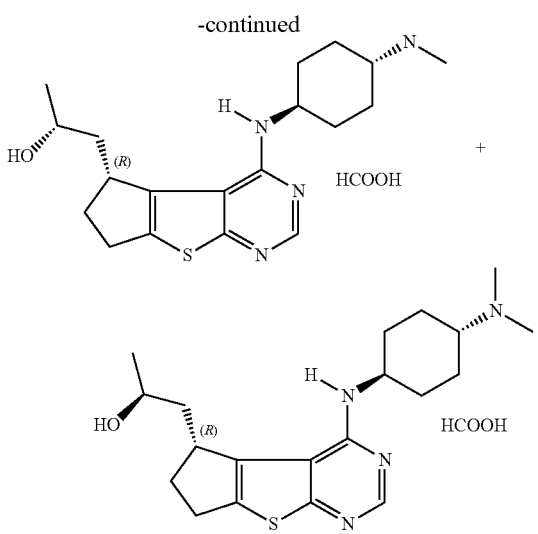

Synthesis of Compound 85.1. Note:

For the preparation of the starting material compound 26.3, see Example 26. Into a 50-mL 3-necked round-bottom flask, purged and maintained with an inert atmosphere of nitrogen, was placed a solution of tert-butyl N-(4-[[(3R)-3-(2-oxoethyl)-7-thia-9,11-diazatricyclo[6.4.0.0[2,6]]dodeca-1(8),2(6),9,11-tetraen-12-yl]amino]cyclohexyl)carbamate (250 mg, 0.58 mmol, 1.00 equiv) in freshly distilled tetrahydrofuran (10 mL) at 0° C. under nitrogen. The CH₃MgBr (1.0 M in THF, 2.9 mL, 5.0 equiv) was added at 0° C. via syringe. The resulting solution was stirred for 2 h at 0° C. and quenched with saturated aqueous NH₄Cl and extracted with 3×30 mL of ethyl acetate. The combined organic layers were washed with brine and dried over sodium sulfate and concentrated under reduced pressure. The residue was applied onto a silica gel column with ethyl acetate/petroleum ether (1:5) to give the desired racemic tert-butyl N-(4-[[(3R)-3-(2-hydroxypropyl)-7-thia-9,11-diazatricyclo[6.4.0.0[2,6]]dodeca-1(8),2(6),9,11-tetraen-12-yl]amino]cyclohexyl)carbamate (109 mg, 42%) as a colorless oil.

Synthesis of Compound I-53 and Compound I-55.

Into a 50-mL round-bottom flask containing tert-butyl N-(4-[[(3R)-3-(2-hydroxypropyl)-7-thia-9,11-diazatricyclo[6.4.0.0[2,6]]dodeca-1(8),2(6),9,11-tetraen-12-yl]amino]cyclohexyl)carbamate (109 mg, 0.24 mmol, 1.00 equiv) in dichloromethane (10 mL) at 0° C. Then hydrochloric acid (12 M, 2.0 mL) was added and the resulting solution was stirred for 3 h at room temperature. The resulting mixture was concentrated under vacuum. The pH value of the solution was adjusted to 8 with saturated aqueous sodium carbonate and extracted with 2×40 mL of ethyl acetate. The organic layers were combined and dried over sodium sulfate and concentrated under vacuum to give the desired 1-[(3R)-12-[(4-amino cyclohexyl)amino]-7-thia-9,11-diazatricyclo[6.4.0.0[2,6]]dodeca-1(8),2(6),9,11-tetraen-3-yl]propan-2-ol (70 mg, crude) as a colorless oil.

To a solution of 1-[(3R)-12-[(4-amino cyclohexyl)oxy]-7-thia-9,11-diazatricyclo[6.4.0.0[2,6]]dodeca-1(8),2(6),9,11-tetraen-3-yl]propan-2-ol (70 mg, crude) in methanol (5 mL) was added HCHO (37%, 0.8 mL) and stirred for 1 h at room temperature. Then NaBH₃CN (29.7 mg, 0.47 mmol, 2.35 equiv) was added and the resulting solution was stirred for additional 2 h at ambient temperature and concentrated under vacuum. The crude product (80 mg) was purified by preparative HPLC under the following conditions (SHIMADZU):

column: SunFire Prep C18, 19*150 mm 5 um; mobile phase: water with 0.05% HCOOH and CH₃CN (6.0% CH₃CN up to 50.0% in 25 min); UV detection at 254/220 nm. The product containing fractions were collected and evaporated to remove the water and CH₃CN to give (2R)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propan-2-ol formate (12.9 mg) as a white solid and (2S)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propan-2-ol formate (5.6 mg) as a grey solid, respectively.

Example 85 (I-53)

MS: (ES, m/z): 375 (M+H)⁺. ¹H NMR (300 MHz, CD₃OD) δ 8.54 (1H, br s), 8.23 (1H, s), 4.18-4.19 (1H, m), 3.70-3.76 (1H, m), 3.55-3.58 (1H, m), 3.05-3.33 (2H, m), 2.84-2.92 (7H, m), 2.68-2.75 (1H, m), 2.16-2.37 (5H, m), 1.55-1.78 (6H, m), 1.23 (3H, t).

Example 86 (I-55)

MS (ES): m/z 375 (M+H)⁺. ¹H NMR (300 MHz, CD₃OD) δ 8.55 (1H, br s), 8.23 (1H, s), 4.18-4.19 (1H, m), 3.70-3.76 (1H, m), 3.55-3.58 (1H, m), 3.05-3.33 (2H, m), 2.84-2.92 (7H, m), 2.68-2.75 (1H, m), 2.16-2.37 (5H, m), 1.55-1.78 (6H, m), 1.23 (3H, t).

Example 87

N,N-dimethyl-4-[[(3S)-3-[2-(1,3-oxazol-2-yl)ethyl]-7-thia-9,11-diazatricyclo[6.4.0.0[2,6]]dodeca-1(8),2(6),9,11-tetraen-12-yl]oxy]cyclohexan-1-amine.
(I-63)

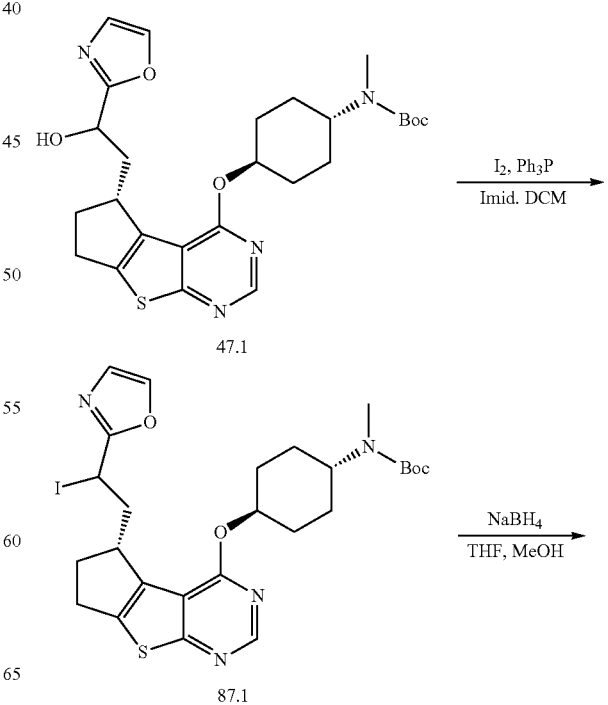

-continued

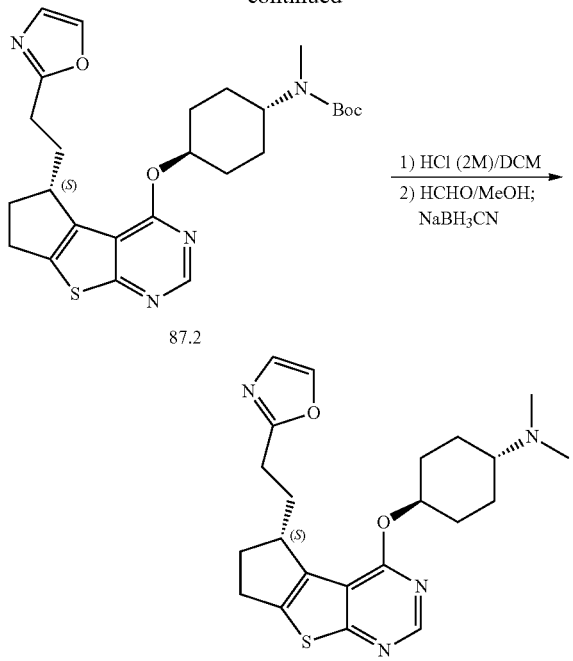

Synthesis of Compound 87.1. Note:

For the preparation of the starting material compound 47.1, see Example 47. A solution of iodine (244 mg), Ph₃P (252 mg) and imidazole (143 mg, 2.10 mmol, 3.49 equiv) in dry dichloromethane (20 mL) was stirred at 0° C. for 30 min under nitrogen. Then a solution of tert-butyl N-(4-[[(3R)-3-[2-hydroxy-2-(1,3-oxazol-2-yl)ethyl]-7-thia-9,11-diazatricyclo[6.4.0.0[2,6]]dodeca-1(8),2(6),9,11-tetraen-12-yl]oxy]cyclohexyl)-N-methylcarbamate (310 mg, 0.60 mmol, 1.00 equiv) was added dropwise to the reaction mixture and the resulting solution was stirred for 2.5 h at room temperature. The reaction was then quenched with saturated aqueous NaHSO₃ and extracted with 2×30 mL of dichloromethane. The organic layers were combined and washed with brine, dried over anhydrous sodium sulfate. After concentrated in vacuo, the residue was applied onto a silica gel column with ethyl acetate/petroleum ether (1:1) to give tert-butyl N-(4-[[(3R)-3-[2-iodo-2-(1,3-oxazol-2-yl)ethyl]-7-thia-9,11-diazatricyclo[6.4.0.0[2,6]]dodeca-1(8),2(6),9,11-tetraen-12-yl]oxy]cyclohexyl)-N-methylcarbamate (230 mg, 61%) as a yellow solid. MS (ES): m/z 625 (M+H)⁺.

Synthesis of Compound 87.2.

A 25-mL round-bottom flask containing a solution of tert-butyl N-(4-[[(3R)-3-[2-iodo-2-(1,3-oxazol-2-yl)ethyl]-7-thia-9,11-diazatricyclo[6.4.0.0[2,6]]dodeca-1(8),2(6),9,11-tetraen-12-yl]oxy]cyclohexyl)-N-methylcarbamate (150 mg, 0.24 mmol, 1.00 equiv) in a mixed methanol (5 mL) and tetrahydrofuran (5 mL) was added NaBH₄ (40 mg, 1.08 mmol, 4.50 equiv) at 0° C. The resulting solution was stirred for 4 h at 0° C. and concentrated under reduced pressure. The residue was diluted with EtOAc and washed with brine, dried over sodium sulfate and concentrated under vacuum. The residue was applied onto a silica gel column with ethyl acetate/petroleum ether (1:10 to 1:22) to afford the desired tert-butyl N-methyl-N-(4-[[(3S)-3-[2-(1,3-oxazol-2-yl)ethyl]-7-thia-9,11-diazatricyclo[6.4.0.0[2,6]]dodeca-1(8),2(6),9,11-tetraen-12-yl]oxy]cyclohexyl)carbamate (110 mg, 92%) as a yellow solid. MS (ES, m/z): 499 (M+H)⁺.

Synthesis of Compound I-63.

To a solution of tert-butyl N-methyl-N-(4-[[(3S)-3-[2-(1,3-oxazol-2-yl)ethyl]-7-thia-9,11-diazatricyclo[6.4.0.0[2,6]]dodeca-1(8),2(6),9,11-tetraen-12-yl]oxy]cyclohexyl)carbamate (110 mg, 0.22 mmol, 1.00 equiv) in dichloromethane (5 mL) was added hydrogen chloride (12 M, 1 mL) at 0° C. and the resulting mixture was stirred at room temperature for 2 h. The reaction mixture was concentrated under reduced pressure and the residue was neutralized with sodium hydroxide and extracted with 2×30 mL of dichloromethane. The combine organic layers were concentrated in vacuo to give N-methyl-4-[[(3S)-3-[2-(1,3-oxazol-2-yl)ethyl]-7-thia-9,11-diazatricyclo[6.4.0.0[2,6]]dodeca-1(8),2(6),9,11-tetraen-12-yl]oxy]cyclohexan-1-amine (80 mg, crude) as a yellow oil.

To the crude product (80 mg) in methanol (5 mL) was added HCHO (37%, 0.8 mL) and the reaction solution was stirred at room temperature for 30 min. NaBH₃CN (50 mg) was added and the resulting solution was stirred for 12 h at ambient temperature. The crude product (70 mg) was purified by preparative HPLC under the following conditions (SHIMADZU): column: SunFire Prep C18, 19*150 mm 5 um; mobile phase: water with 0.05% NH₄HCO₃ and CH₃CN (7.0% CH₃CN up to 63.0% in 14 min); UV detection at 254/220 nm. The product fractions was collected and evaporated under reduced pressure to remove the solvents to give N,N-dimethyl-4-[[(3S)-3-[2-(1,3-oxazol-2-yl)ethyl]-7-thia-9,11-diazatricyclo[6.4.0.0[2,6]]dodeca-1(8),2(6),9,11-tetraen-12-yl]oxy]cyclohexan-1-amine (39 mg) as an off-white semi-solid. MS (ES, m/z): 413 (M+H)⁺. ¹H NMR (300 MHz, CD₃OD): δ 8.41 (1H, s), 7.70 (1H, s), 6.96 (1H, s), 5.22 (1H, m), 3.42 (1H, m), 3.05 (2H, m), 2.77 (3H, m), 2.37 (11H, m), 2.05 (3H, m), 1.55 (4H, m).

Example 88

(S)-1-((R)-4-(((1r,4R)-4-morpholinocyclohexyl)oxy)-6,7-dihydro-5H-cyclopenta[4,5]thieno[2,3-d]pyrimidin-5-yl)butan-2-ol (I-64) and Example 89: (R)-1-((R)-4-(((1r,4R)-4-morpholinocyclohexyl)oxy)-6,7-dihydro-5H-cyclopenta[4,5]thieno[2,3-d]pyrimidin-5-yl)butan-2-ol. (I-65)

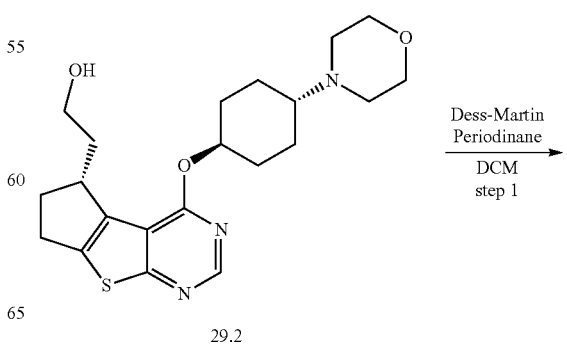

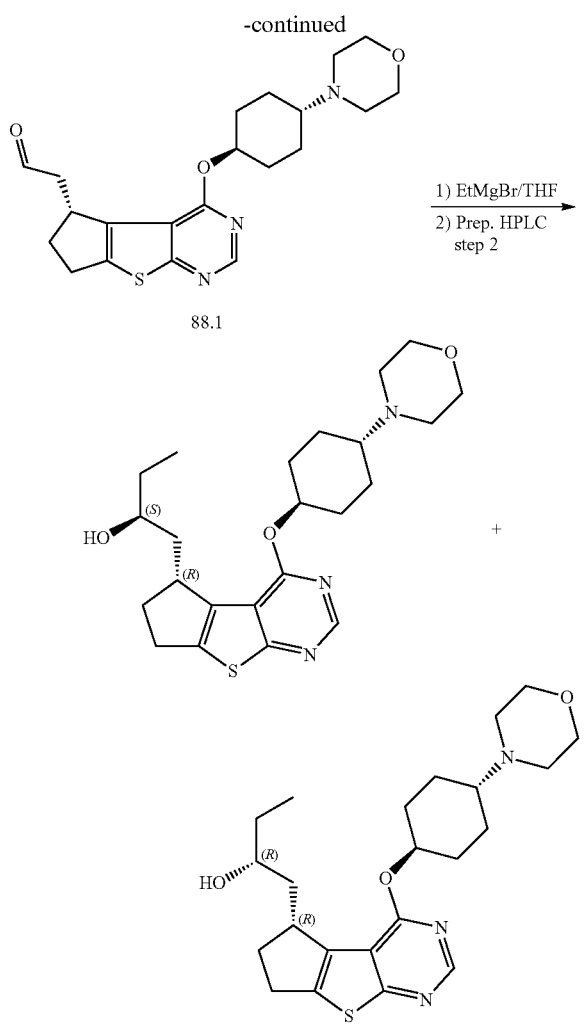

rated aqueous NH₄Cl and extracted with 3×50 mL of DCM/ i-PrOH (3:1). The combined organic layers was dried over anhydrous sodium sulfate and concentrated under vacuum. The crude product (150 mg) was purified by preparative HPLC under the following conditions (SHIMADZU): column: SunFire Prep C18, 19*150 mm 5 um; mobile phase: water with 0.05% NH₄CO₃ and CH₃CN (6.0% CH₃CN up to 54.0% in 25 min); UV detection at 254/220 nm to afford (S)-1-((R)-4-(((1r,4R)-4-morpholinocyclohexyl)oxy)-6,7-dihydro-5H-cyclopenta[4,5]thieno[2,3-d]pyrimidin-5-yl)butan-2-ol (11.8 mg) and (R)-1-((R)-4-(((1r,4R)-4-morpholinocyclohexyl)oxy)-6,7-dihydro-5H-cyclopenta[4,5]thieno [2,3-d]pyrimidin-5-yl)butan-2-ol (23.9 mg) as white solids.

Example 88 (I-64)

MS: 432 (M+H)⁺. ¹H NMR (300 MHz, CDCl₃) δ 8.47 (s, 2H), 5.24-5.20 (m, 1H), 3.75-3.58 (m, 5H), 3.06-2.93 (m, 2H), 2.70-2.61 (m, 4H), 2.28-1.98 (m, 3H), 1.59-1.41 (m, 10H), 1.28-1.23 (m, 2H), 0.95-0.85 (m, 3H).

Example 89 (I-65)

MS: 432 (M+H)⁺. ¹H NMR (300 MHz, CDCl₃) δ 8.47 (s, 2H), 5.25 (m, 1H), 3.71-3.39 (m, 6H), 3.04-2.90 (m, 2H), 2.67-2.55 (m, 5H), 2.34-2.22 (m, 4H), 2.01-1.81 (m, 3H), 1.64-1.39 (m, 7H), 0.94-0.92 (m, 3H).

Example 90

2-[(3R)-12-[[4-(morpholin-4-yl)cyclohexyl]oxy]-7-thia-9,11-diazatricyclo[6.4.0.0[2,6]]dodeca-1(12),2 (6),8,10-tetraen-3-yl]ethan-1-ol. (I-66)

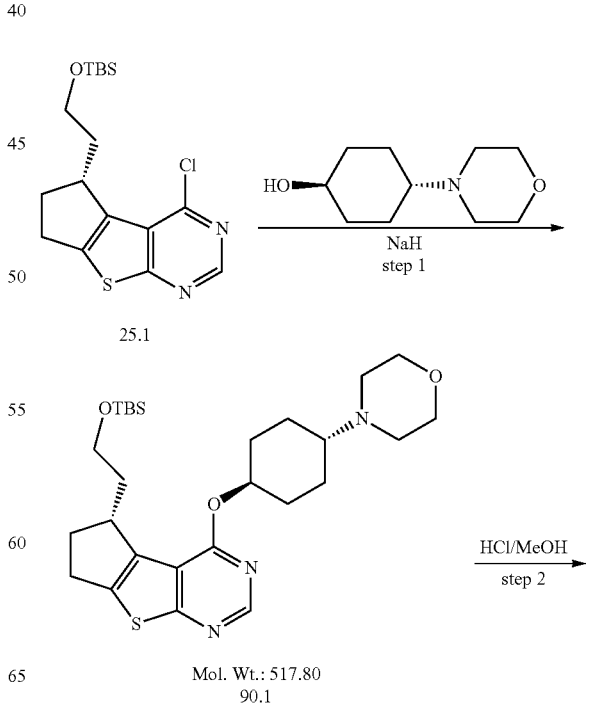

Synthesis of Compound 88.1. Note:

For the preparation of the starting material compound 29.2, please see Example 29. A solution of 2-[(3R)-12-[[4-(morpholin-4-yl)cyclohexyl]oxy]-7-thia-9,11-diazatricyclo [6.4.0.0[2,6]]dodeca-1(8),2(6),9,11-tetraen-3-yl]ethan-1-ol (190 mg, 0.47 mmol, 1.00 equiv) in 10 mL of dichloromethane was added Dess-Martin periodinane at 0° C. in a water/ice bath under nitrogen. The resulting mixture was stirred for 2 h at room temperature. After completion of the reaction, the mixture was then diluted with saturated aqueous sodium bicarbonate and extracted with 3×30 mL of ethyl acetate. The combined organic layers were dried over sodium sulfate and concentrated under vacuum. The residue was applied onto a silica gel column with ethyl acetate/petroleum ether (1:5 to 1:1) to afford 2-[(3R)-12-[[4-(morpholin-4-yl) cyclohexyl]oxy]-7-thia-9,11-diazatricyclo[6.4.0.0[2,6]] dodeca-1(8),2(6),9,11-tetraen-3-yl]acetaldehyde (130 mg, 69%) as a colorless oil. MS (ES): m/z 402 [M+H]⁺.

Synthesis of Compound I-64 and Compound I-65.

A solution of [(3R)-12-[[4-(morpholin-4-yl)cyclohexyl] oxy]-7-thia-9,11-diazatricyclo[6.4.0.0[2,6]]dodeca-1(8),2 (6),9,11-tetraen-3-yl]acetaldehyde (130 mg, 0.32 mmol, 1.00 equiv) in 5 mL of anhydrous THF was added bromo(ethyl) magnesium (1 M in THF, 0.62 mL, 2.0 equiv) dropwise at 0° C. under nitrogen. The resulting solution was stirred for 4 h at room temperature and then quenched by the addition of satu-

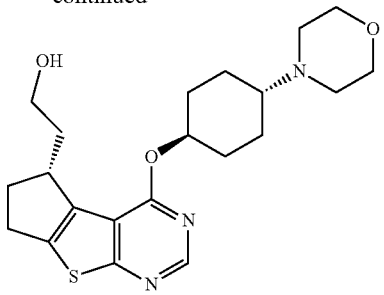

Synthesis of Compound 90.1. Note:

For the preparation of the starting material compound 25.1, see Example 25. Sodium hydride (60% dispersion in mineral oil, 130 mg, 3.25 mmol, 4.00 equiv) was treated with trans-4-(morpholin-4-yl)cyclohexan-1-ol (192 mg, 1.04 mmol, 1.27 equiv) in freshly distilled THF (15 mL) at 0° C. under nitrogen. After stirring for 30 min at room temperature, then (3R)-3-[2-[(tert-butyldimethylsilyl)oxy]ethyl]-12-chloro-7-thia-9,11-diazatricyclo[6.4.0.0[2,6]]dodeca-1(12),2(6),8,10-tetraene (300 mg, 0.81 mmol, 1.00 equiv) was added and the resulting solution was allowed to react, with stirring, for an additional 2 hr at room temperature. The reaction was then quenched with saturated aqueous NH₄Cl, extracted with 3×20 mL of ethyl acetate. The combined organic layers were washed with brine, dried over sodium sulfate and concentrated under vacuum. The residue was applied onto a silica gel column with ethyl acetate/petroleum ether (1:8) to provide (3R)-3-[2-[(tert-butyldimethylsilyl)oxy]ethyl]-12-[[4-(morpholin-4-yl)cyclohexyl]oxy]-7-thia-9,11-diazatricyclo[6.4.0.0[2,6]]dodeca-1(12),2(6),8,10-tetraene (378 mg, 90%) as a yellow oil. MS (ES): m/z 518 [M+H]⁺.

Synthesis of Compound I-66.

To (3R)-3-[2-[(tert-butyldimethylsilyl)oxy]ethyl]-12-[[4-(morpholin-4-yl)cyclohexyl]oxy]-7-thia-9,11-diazatricyclo[6.4.0.0[2,6]]dodeca-1(12),2(6),8,10-tetraene (230 mg, 0.44 mmol, 1.00 equiv) dissolved in methanol (10 mL) was added hydrochloric acid (12 M, 0.5 mL) slowly at 0° C. The resulting solution was stirred for 2 hr at room temperature and then quenched with saturated aqueous sodium bicarbonate, extracted with 3×50 mL of ethyl acetate. The combined organic layers were concentrated under vacuum. The crude product (200 mg) was purified by preparative HPLC under the following conditions (SHIMADZU): column: SunFire Prep C18, 19*150 mm 5 um; mobile phase: water with 0.05% NH₄HCO₃ and CH₃CN (25% CH₃CN up to 100% in 15 min); flow rate: 20 mL/min; UV detection at 254/220 nm. The product-containing fractions were collected and partially evaporated to remove water and CH₃CN under reduced pressure. The residue was lyophilized overnight to give 2-[(3R)-12-[[4-(morpholin-4-yl)cyclohexyl]oxy]-7-thia-9,11-diazatricyclo[6.4.0.0[2,6]]dodeca-1(12),2(6),8,10-tetraen-3-yl]ethan-1-ol (94 mg) as a white solid. MS (ES): m/z 404 [M+H]⁺. ¹H NMR (400 MHz, CD₃OD): δ 8.48 (1H, s), 5.29 (1H, m) 3.76 (4H, m), 3.66 (3H, m), 3.10-2.95 (2H, m), 2.72 (5H, m), 2.69 (1H, s), 2.41 (3H, m), 2.36 (1H, m), 2.15 (2H, m), 1.73-1.54 (5H, m).

Example 91

2-[(3R)-12-[[4-(methylamino)cyclohexyl]oxy]-7-thia-9,11-diazatricyclo[6.4.0.0^[2,6]]dodeca-1(8),2(6),9,11-tetraen-3-yl]acetamide (I-79)

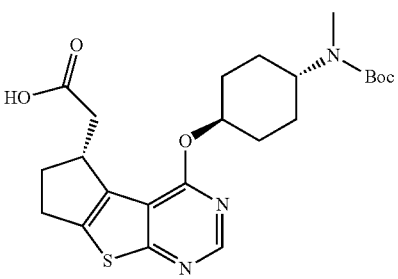

Mol. Wt.: 461.57
35.1

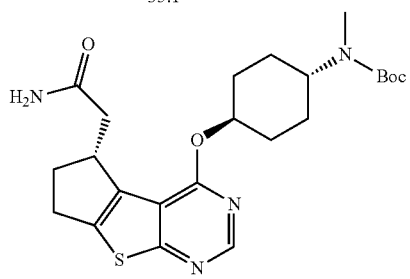

Mol. Wt.: 460.59
91.1

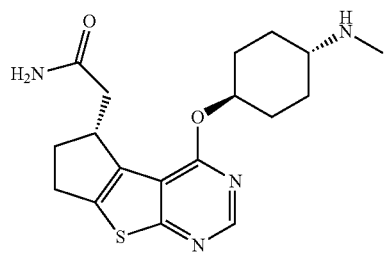

Mol. Wt.: 360.47

Synthesis of Compound 91.1. Note:

For the preparation of the starting material 35.1, please see Example 35. Into a 50-mL round-bottom flask containing a solution of 2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]acetic acid (220 mg, 0.48 mmol, 1.00 equiv) in 4 mL of distilled DMF was added HOBT (96.6 mg), 4-dimethylaminopyridine (86.6 mg), EDCI (136.7 mg) and NH₄Cl (153.18 mg, 2.86 mmol, 6.01 equiv) successively at room temperature under nitrogen. The resulting solution was stirred for 14 hr at 25° C. and diluted with water, extracted with 3×50 mL of ethyl acetate. The combined organic layers was washed with brine, dried over sodium sulfate and concentrated under vacuum. The residue was applied onto a silica gel column with ethyl acetate/petroleum ether (2:1) to give tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]cyclohexyl)-N-methylcarbamate (176 mg, 80%) as a colorless oil. MS (ES): m/z 461 [M+H]⁺.

Synthesis of Compound I-79.

Into a 50-mL round-bottom flask placed a solution of tert-butyl N-(4-[[(3R)-3-(carbamoylmethyl)-7-thia-9,11-diazatricyclo[6.4.0.0^[2,6]]dodeca-1(8),2(6),9,11-tetraen-12-yl]oxy]cyclohexyl)-N-methylcarbamate (170 mg, 0.37 mmol, 1.00 equiv) in dichloromethane (4 mL) was added hydrochloric acid (12 M, 0.5 mL) at 0° C. and the resulting solution was stirred for 4 hr at 25° C. The reaction was then quenched with saturated aqueous sodium bicarbonate, extracted with 3×50 mL of DCM. The organic layers were combined and concentrated under vacuum. The crude product (150 mg) was purified by preparative HPLC under the following conditions (SHIMADZU): column: SunFire Prep C18, 19*150 mm 5 um; mobile phase: water with 100 mM $NH_4HCO_3$ and $CH_3CN$ (6.0% $CH_3CN$ up to 60% in 20 min); flow rate: 20 mL/min; UV detection at 254/220 nm. The product-containing fractions were collected and partially evaporated to remove water and $CH_3CN$ under reduced pressure. The residue was lyophilized overnight to give the desired 2-[(3R)-12-[[4-(methylamino)cyclohexyl]oxy]-7-thia-9,11-diazatricyclo[6.4.0.0^[2,6]]dodeca-1(8),2(6),9,11-tetraen-3-yl]acetamide (83 mg, 62%) as a white solid. MS (ES): m/z 361 [M+H]$^+$. $^1$H NMR (300 MHz, $CD_3OD$): δ 8.43 (1H, s), 5.28 (1H, m), 3.76 (1H, m), 3.00-3.28 (1H, m), 2.97-2.99 (2H, m), 2.66-2.73 (1H, m), 2.42-2.49 (1H, m), 2.36 (3H, s), 2.29-2.18 (4H, m), 2.00-2.03 (2H, m), 1.65-1.57 (2H-m), 1.26-1.35 (2H, m).

Example 92

2-[(3R)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]acetamide (I-73)

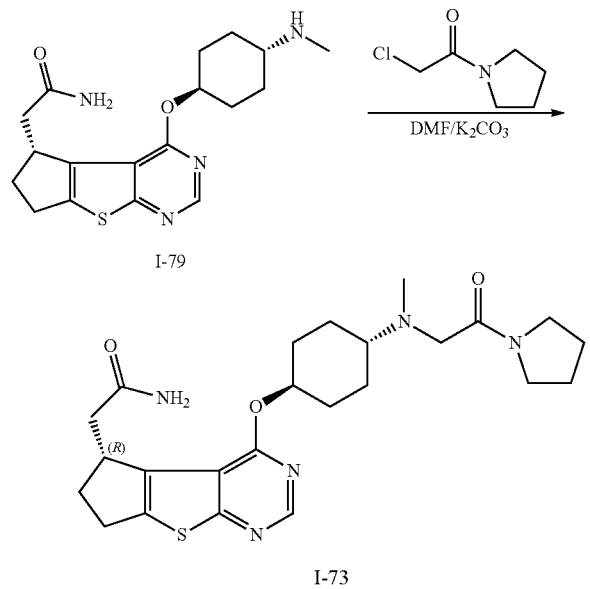

Synthesis of Compound I-73:

A solution of 2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]acetamide (90 mg, 0.25 mmol, 1.00 equiv) in 8 mL of DMF was added 2-chloro-1-(pyrrolidin-1-yl)ethan-1-one (55 mg, 0.37 mmol, 1.50 equiv) and potassium carbonate (69 mg, 0.50 mmol, 2.00 equiv) and the resulting solution was stirred overnight at room temperature. The reaction was quenched with water and extracted with DCM. The organic phase was washed with brine, dried over anhydrous sodium sulfate and concentrated under vacuum. The crude product (80 mg) was purified by preparative HPLC under the following conditions (SHIMADZU): column: SunFire Prep C18, 19*150 mm 5 um; mobile phase: water with 0.05% $NH_4HCO_3$ and $CH_3CN$ (6.0% $CH_3CN$ up to 50.0% in 16 min); flow rate: 20 mL/min; UV detection at 254/220 nm. The product-containing fractions were collected and partially evaporated to remove water and $CH_3CN$ under reduced pressure. The residue was lyophilized overnight to give the desired 2-[(3R)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]acetamide (50 mg) as a white solid. LCMS (ES): m/z 472 [M+H]$^+$. $^1$H NMR (300 MHz, $CD_3OD$): δ 8.43 (1H, s), 5.25-5.20 (1H, m), 3.85-3.69 (1H, m), 3.52 (2H, t), 3.42 (2H, t), 3.37 (2H, s), 3.15-2.85 (2H, m), 2.73-2.58 (2H, m), 2.29-2.18 (7H, m), 1.96-1.79 (6H, m), 1.67-1.47 (4H, m).

Example 93

2-[[(3S)-12-[[4-(dimethylamino)cyclohexyl]oxy]-7-thia-9,11-diazatricyclo[6.4.0.0[2,6]]dodeca-1(8),2(6),9,11-tetraen-3-yl]methoxy]acetamide (I-76)

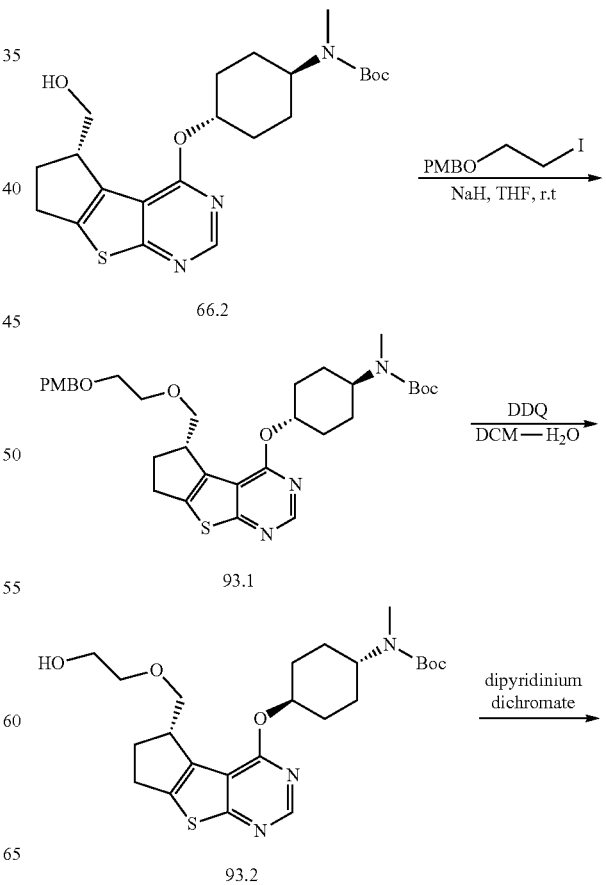

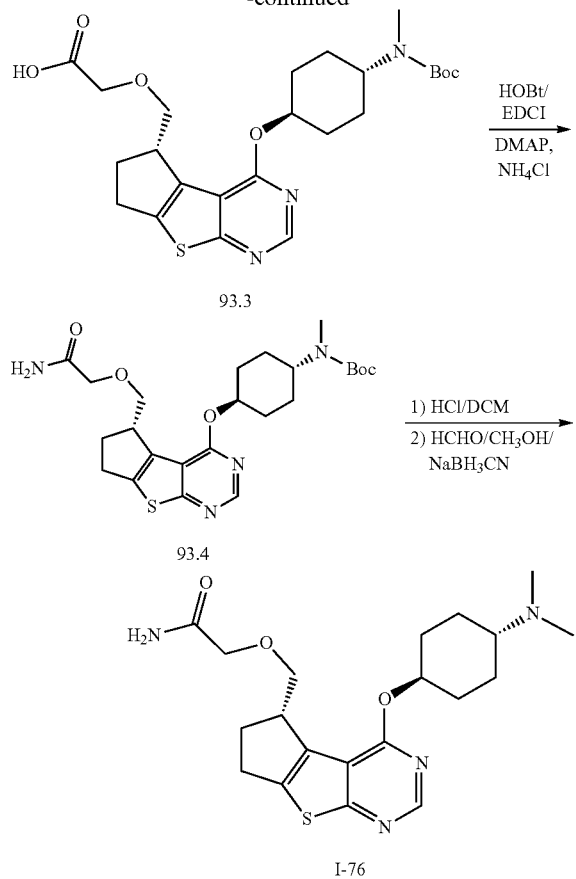

Synthesis of Compound 93.1.

To a 50-mL round-bottom flask containing a solution of tert-butyl N-(4-[[(3S)-3-(hydroxymethyl)-7-thia-9,11-diazatricyclo[6.4.0.0[2,6]]dodeca-1(8),2(6),9,11-tetraen-12-yl]oxy]cyclohexyl)-N-methylcarbamate (940 mg, 2.17 mmol, 1.00 equiv) in freshly distilled DMF (6 mL) was added sodium hydride (60% dispersion in mineral oil, 347.3 mg) slowly at 0° C. under nitrogen. After the addition, the reaction mixture was stirred at room temperature for 30 min. Then 1-[(2-iodoethoxy)methyl]-4-methoxybenzene (2.535 g, 8.68 mmol, 4.00 equiv) was added to the mixture and stirred for 14 hrs at ambient temperature. The reaction was quenched slowly with saturated aqueous NH$_4$Cl and extracted with 3×100 mL of ethyl acetate. The combined organic layers were washed with brine, dried over sodium sulfate and concentrated in vacuo. The residue was applied onto a silica gel column with ethyl acetate/petroleum ether (1:5) to give tert-butyl N-(4-[[(3S)-3-([2-[(4-methoxyphenyl)methoxy]ethoxy]methyl)-7-thia-9,11-diazatricyclo[6.4.0.0[2,6]]dodeca-1(8),2(6),9,11-tetraen-12-yl]oxy]cyclohexyl)-N-methylcarbamate (700 mg, 54%) as a colorless oil. MS: m/z 598 (M+H)$^+$.

Synthesis of Compound 93.2.

A solution of tert-butyl N-(4-[[(3S)-3-([2-[(4-methoxyphenyl)methoxy]ethoxy]methyl)-7-thia-9,11-diazatricyclo[6.4.0.0˚[2,6]]dodeca-1(8),2(6),9,11-tetraen-12-yl]oxy]cyclohexyl)-N-methylcarbamate (700 mg, 1.17 mmol, 1.00 equiv) in dichloromethane (10 mL)/water (0.5 mL) was added DDQ (399 mg, 1.76 mmol, 1.50 equiv) and the resulting solution was stirred for 14 hrs at 25° C. under nitrogen. The resulting solution was diluted with water and extracted with 3×100 mL of ethyl acetate. The organic layers were combined, washed with brine, dried over sodium sulfate and concentrated in vacuo. The residue was applied onto a silica gel column with ethyl acetate/petroleum ether (1:1) to give tert-butyl N-(4-[[(3S)-3-[(3-hydroxypropoxy)methyl]-7-thia-9,11-diazatricyclo[6.4.0.0[2,6]]dodeca-1(8),2(6),9,11-tetraen-12-yl]oxy]cyclohexyl)-N-methylcarbamate (370 mg, 64%) as a colorless oil. MS: m/z 478 (M+H)$^+$.

Synthesis of Compound 93.3.

A 50-mL round-bottom flask was charged with a solution of tert-butyl N-(4-[[(3S)-3-[(3-hydroxypropoxy)methyl]-7-thia-9,11-diazatricyclo[6.4.0.0[2,6]]dodeca-1(8),2(6),9,11-tetraen-12-yl]oxy]cyclohexyl)-N-methylcarbamate (370 mg, 0.75 mmol, 1.00 equiv) in 5 mL of DMF and PDC (1.656 g, 4.40 mmol, 5.85 equiv) was added at room temperature. The resulting solution was stirred for 14 hrs at 25° C. After completion, the resulting solution was extracted with 3×50 mL of ethyl acetate. The combined organic layers were washed with brine, dried over sodium sulfate and concentrated in vacuo. The residue was applied onto a silica gel column with ethyl acetate/petroleum ether (1:2) to give 3-[[(3S)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]methoxy]propanoic acid (190 mg, 50%) as a colorless oil. MS: m/z 492 (M+H)$^+$.

Synthesis of Compound 93.4.

To a 50-mL round-bottom flask purged and maintained with an inert atmosphere of nitrogen was added a solution of 2-[[(3S)-12-[(4-[[(tert-butoxy)carbonyl](methyl)amino]cyclohexyl)oxy]-7-thia-9,11-diazatricyclo[6.4.0.0[2,6]]dodeca-1(12),2(6),8,10-tetraen-3-yl]methoxy]acetic acid (120 mg, 0.24 mmol, 1.00 equiv), HOBT (49 mg, 0.36 mmol, 1.49 equiv), EDCI (70 mg, 0.37 mmol, 1.50 equiv), 4-dimethylaminopyridine (44 mg, 0.36 mmol, 1.48 equiv) and NH$_4$Cl (76 mg, 1.42 mmol, 5.82 equiv) in distilled DMF (5 mL) at room temperature under nitrogen. The resulting solution was stirred for 14 hrs at ambient temperature, quenched with water and extracted with 3×50 mL of ethyl acetate. The combined organic layers were washed with brine, dried over sodium sulfate and concentrated under vacuum. The residue was applied onto a silica gel column with ethyl acetate/petroleum ether (2:1) to afford the desired tert-butyl N-(4-[[(3S)-3-[(carbamoylmethoxy)methyl]-7-thia-9,11-diazatricyclo[6.4.0.0[2,6]]dodeca-1(12),2(6),8,10-tetraen-12-yl]oxy]cyclohexyl)-N-methylcarbamate (75 mg, 63%) as a colorless oil. MS: m/z 491 (M+H)$^+$.

Synthesis of Compound I-76.

A solution of tert-butyl N-(4-[[(3S)-3-[(carbamoylmethoxy)methyl]-7-thia-9,11-diazatricyclo[6.4.0.0[2,6]]dodeca-1(8),2(6),9,11-tetraen-12-yl]oxy]cyclohexyl)-N-methylcarbamate (115 mg, 0.23 mmol, 1.00 equiv) in dichloromethane (4 mL) cooled down to 0° C. was added hydrochloric acid (12 M, 0.5 mL). The resulting solution was stirred for 1 h at 0° C. and concentrated in vacuo to give 2-[[(3S)-12-[[4-(methylamino)cyclohexyl]oxy]-7-thia-9,11-diazatricyclo[6.4.0.0[2,6]]dodeca-1(8),2(6),9,11-tetraen-3-yl]methoxy]acetamide hydrochloride (100 mg, crude) as a light yellow solid. The crude hydrochloride (100 mg) dissolved in methanol (3 mL) was added HCHO (37%, 0.5 mL) and stirred for 1 h at 0° C. Then NaBH$_3$CN (44.35 mg, 0.71 mmol) was added and the resulting solution was stirred for 2 h at room temperature. The reaction mixture was diluted with water, extracted with 3×20 mL of chloroform/i-PrOH. The combined organic layers were concentrated under vacuum. The crude product (80 mg) was purified by preparative HPLC under the following conditions (SHIMADZU): column: SunFire Prep C18, 19*150 mm 5 um; mobile phase: water with 0.05% NH$_4$HCO$_3$ and CH$_3$CN (6.0% CH$_3$CN up to 53.0% in 13 min); flow rate: 20 mL/min; UV detection at 254/220 nm. The product-containing fractions were collected and partially evaporated to remove water and CH$_3$CN under reduced pressure. The residue was lyophilized overnight to give the desired 2-[[(3S)-12-[[4-(dimethylamino)cyclohexyl]oxy]-7-thia-9,11-diazatricyclo[6.4.0.0[2,6]]dodeca-1(8),2(6),9,11-tetraen-3-yl]methoxy]acetamide (35 mg) as a white solid. MS (ES): m/z 405 [M+H]$^+$. $^1$H NMR (300 MHz, CD$_3$OD): δ 8.44 (1H, s), 5.28-5.21 (1H, m), 3.94-3.88 (3H, m), 3.61-3.56 (2H, m), 3.14-2.97 (2H, m), 2.67-2.54 (2H, m), 2.42-2.31 (10H, m), 2.02 (2H, d), 1.62-1.43 (4H, m).

Example 94

(2R)-3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-2-methoxypropanamide (I-77)

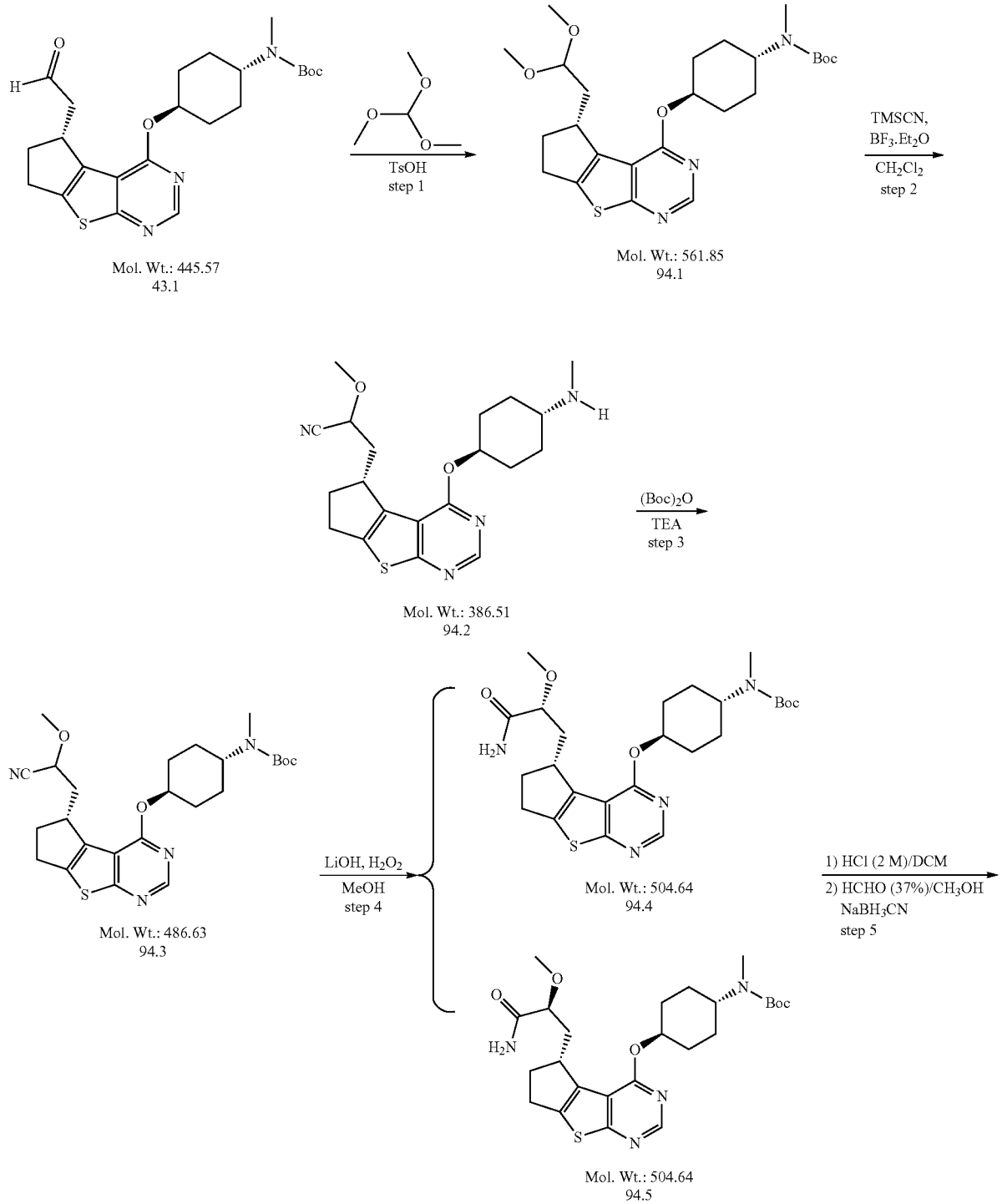

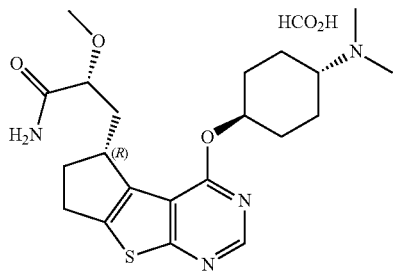

Mol. Wt.: 418.55

Synthesis of Compound 94.1. Note:

For the preparation of the starting material compound 43.1, see Example 43. Into a 50-mL round-bottom flask containing a solution of tert-butyl N-methyl-N-(4-[[(3R)-3-(2-oxoethyl)-7-thia-9,11-diazatricyclo[6.4.0.0[2,6]]dodeca-1(8),2 (6),9,11-tetraen-12-yl]oxy]cyclohexyl)carbamate (460 mg, 1.03 mmol, 1.00 equiv) in methanol (15 mL) was added trimethoxymethane (548 mg, 5.16 mmol, 5.00 equiv) and 4-methylbenzene-1-sulfonic acid (18 mg, 0.10 mmol, 0.10 equiv) at room temperature under nitrogen. The reaction mixture was stirred for 4 hr at ambient temperature. After completion, the reaction was quenched with saturated aqueous $NaHCO_3$ and extracted with 3×50 mL of ethyl acetate. The combined organic layers were washed with brine, dried over anhydrous sodium sulfate and concentrated under vacuum. The residue was purified on a silica gel column with ethyl acetate/petroleum ether (1:8) to afford the desired tert-butyl N-(4-[[(3R)-3-(2,2-dimethoxyethyl)-7-thia-9,11-diazatricyclo[6.4.0.0[2,6]]dodeca-1(8),2(6),9,11-tetraen-12-yl]oxy]cyclohexyl)-N-methylcarbamate (470 mg, 93%) as a colorless oil. LC-MS (ES): m/z 562 [M+H]+.

Synthesis of Compound 94.2.

Into a 100-mL 3-necked round-bottom flask was placed a solution of tert-butyl N-(4-[[(3R)-3-(2,2-dimethoxyethyl)-7-thia-9,11-diazatricyclo[6.4.0.0[2,6]]dodeca-1(8),2(6),9,11-tetraen-12-yl]oxy]cyclohexyl)-N-methylcarbamate (470 mg, 0.96 mmol, 1.00 equiv) in distilled DCM (15 mL). TMSCN (474 mg) and $BF_3.Et_2O$ (15 mg) were added via syringe under nitrogen at 0° C. The resulting solution was stirred for 3 hr in a water/ice bath. After completion, the reaction was quenched with saturated aqueous $NaHCO_3$ and extracted with 3×50 mL of ethyl acetate. The combined organic layers were washed with brine, dried over anhydrous sodium sulfate and concentrated under vacuum to afford the desired 2-methoxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl] propanenitrile (400 mg, crude) as a yellow oil. MS (ES): m/z 387 [M+H]+.

Synthesis of Compound 94.3.

Into a 50-mL round-bottom flask, a solution of 2-methoxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanenitrile (400 mg, 1.03 mmol, 1.00 equiv) in dichloromethane (20 mL) was added di-tert-butyl dicarbonate (500 mg, 2.29 mmol, 2.21 equiv) and TEA (1.0 mL) and the resulting mixture was stirred for 3 hr at room temperature. After completion, the resulting solution was diluted with 20 mL of water and extracted with 3×50 mL of dichloromethane. The combined organic layers were washed with brine, dried over anhydrous sodium sulfate and concentrated under vacuum. The residue was purified on a silica gel column with ethyl acetate/petroleum ether (1:5) to afford the corresponding tert-butyl N-(4-[[(3R)-3-(2-cyano-2-methoxyethyl)-7-thia-9,11-diazatricyclo[6.4.0.0[2,6]]dodeca-1(8),2(6),9,11-tetraen-12-yl]oxy]cyclohexyl)-N-methylcarbamate (360 mg, 71%) as a colorless oil. MS (ES): m/z 487 [M+H]+.

Synthesis of Compound 94.4.

A solution of tert-butyl N-(4-[[(3R)-3-(2-cyano-2-methoxyethyl)-7-thia-9,11-diazatricyclo[6.4.0.0[2,6]]dodeca-1(8),2(6),9,11-tetraen-12-yl]oxy]cyclohexyl)-N-methylcarbamate (360 mg, 0.74 mmol, 1.00 equiv) in methanol (10 mL) was added $H_2O_2$ (30%, 1 mL) and LiOH (36 mg, 1.50 mmol, 2.03 equiv) in a water/ice bath and the resulting mixture was stirred for 2 h. After completion, the reaction was quenched with saturated aqueous $NaHSO_3$ and extracted with 3×50 mL of ethyl acetate. The combined organic layers were washed with brine, dried over anhydrous sodium sulfate and concentrated under vacuum. The residue was purified by preparative TLC (eluent with EtOAc/petroleum ether 1:1) to afford tert-butyl N-(4-[[(3R)-3-[(2S)-2-carbamoyl-2-methoxyethyl]-7-thia-9,11-diazatricyclo[6.4.0.0[2,6]]dodeca-1(8),2(6),9,11-tetraen-12-yl]oxy]cyclohexyl)-N-methylcarbamate (100 mg) as a colorless oil and tert-butyl N-(4-[[(3R)-3-[(2R)-2-carbamoyl-2-methoxyethyl]-7-thia-9,11-diazatricyclo [6.4.0.0[2,6]]dodeca-1(8),2(6),9,11-tetraen-12-yl]oxy]cyclohexyl)-N-methylcarbamate (140 mg) as a colorless oil, respectively. MS (ES): m/z 505 [M+H]+.

Synthesis of Compound I-77

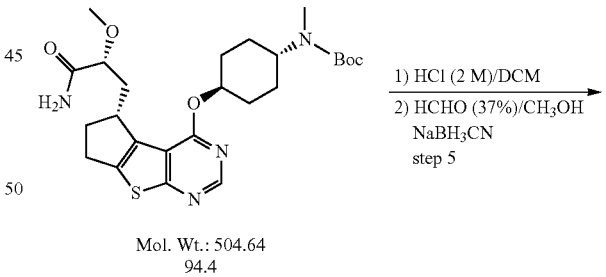

Mol. Wt.: 504.64
94.4

1) HCl (2 M)/DCM
2) HCHO (37%)/$CH_3OH$
NaBH$_3$CN
step 5

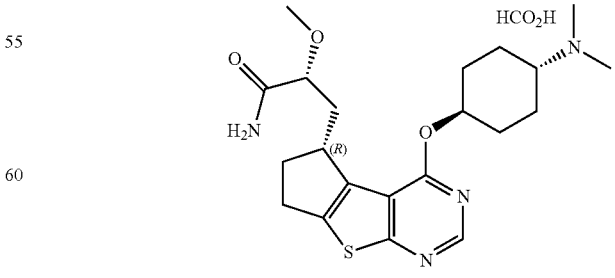

Mol. Wt.: 418.55

Into a 25-mL round-bottom flask, a solution of tert-butyl N-(4-[[(3R)-3-[(2R)-2-carbamoyl-2-methoxyethyl]-7-thia-9,11-diazatricyclo[6.4.0.0[2,6]]dodeca-1(8),2(6),9,11-tetraen-12-yl]oxy]cyclohexyl)-N-methylcarbamate (140 mg, 0.28 mmol, 1.00 equiv) in dichloromethane (10 mL) was added hydrochloric acid (2 M, 1.0 mL) at 0° C. and the resulting mixture was stirred at room temperature for 5 h. After completion, the resulting mixture was concentrated under vacuum to afford (2R)-2-methoxy-3-[(3R)-12-[[4-(methylamino)cyclohexyl]oxy]-7-thia-9,11-diazatricyclo [6.4.0.0[2,6]]dodeca-1 (8),2 (6),9,11-tetraen-3-yl]propanamide hydrochloride (110 mg) as a light yellow solid. The residue hydrochloride (110 mg) was dissolved in 5 mL of methanol, HCHO (37%, 0.5 mL) was added and the solution stirred for 30 min at room temperature. Then NaBH$_3$CN (65 mg) was added and the resulting solution was allowed to react, with stirring, for an additional 2 hr at ambient temperature. After completion, the resulting solution was diluted with 20 mL of water, extracted with 3×50 mL of DCM and concentrated under vacuum. The crude product (100 mg) was purified by preparative HPLC under the following conditions (SHIMADZU): column: SunFire Prep C18, 19*150 mm 5 um; mobile phase: water with 0.1% HCOOH and CH$_3$CN (6.0% CH$_3$CN up to 75% in 20 min); flow rate: 20 mL/min; UV detection at 254/220 nm. The product-containing fractions were collected and partially evaporated to remove water and CH$_3$CN under reduced pressure. The residue was lyophilized overnight to give the desired (2R)-3-[(3R)-12-[[4-(dimethylamino)cyclohexyl]oxy]7-thia-9,11-diazatricyclo [6.4.0.0[2,6]]dodeca-1(8),2(6),9,11-tetraen-3-yl]-2-methoxypropanamide formate (47.5 mg, 45%) as an off-white solid. MS (ES): m/z 419 [M−HCOOH+H]$^+$. $^1$H NMR (300 MHz, CD$_3$OD): δ 8.44 (m, 2H), 5.28 (s, 1H), 3.59-3.52 (m, 2H), 3.34-3.27 (m, 4H), 3.08-2.82 (m, 8H), 2.65-2.62 (m, 1H), 2.45-2.18 (m, 6H), 1.85-1.82 (m, 5H).

Example 95

(2S)-3-[(3R)-12-[[4-(dimethylamino)cyclohexyl] oxy]-7-thia-9,11-diazatricyclo[6.4.0.0[2,6]]dodeca-1 (8),2(6),9,11-tetraen-3-yl]-2-methoxypropanamide (I-78)

Synthesis of Compound I-78. Note:

For the preparation of the starting material compound 94.5, please see Example 94. A 25-mL round-bottom flask was charged with a solution of tert-butyl N-(4-[[(3R)-3-[(2S)-2-carbamoyl-2-methoxyethyl]-7-thia-9,11-diazatricyclo [6.4.0.0[2,6]]dodeca-1(8),2(6),9,11-tetraen-12-yl]oxy]cyclohexyl)-N-methylcarbamate (100 mg, 0.20 mmol, 1.00 equiv) in dichloromethane (10 mL). Hydrochloric acid (2 M, 0.8 mL) was added at 0° C. and the resulting mixture was stirred at room temperature for 5 h. After completion, the resulting mixture was concentrated under vacuum to afford (2S)-2-methoxy-3-[(3R)-12-[[4-(methylamino)cyclohexyl] oxy]-7-thia-9,11-diazatricyclo[6.4.0.0[2,6]]dodeca-1(8),2 (6),9,11-tetraen-3-yl]propanamide hydrochloride (90 mg) as a light yellow solid. The residue hydrochloride (90 mg) dissolved in 5 mL of methanol was added HCHO (37%, 0.5 mL) and stirred for 30 min at room temperature. Then NaBH$_3$CN (50 mg) was added and the resulting solution was allowed to react, with stirring, for an additional 2 hr at ambient temperature. After completion, the resulting solution was diluted with 20 mL of water, extracted with 3×50 mL of DCM and concentrated under vacuum. The crude product (90 mg) was purified by preparative HPLC under the following conditions (SHIMADZU): column: SunFire Prep C18, 19*150 mm 5 um; mobile phase: water with 0.1% HCOOH and CH$_3$CN (6.0% CH$_3$CN up to 75% in 20 min); flow rate: 20 mL/min; UV detection at 254/220 nm. The product-containing fractions were collected and partially evaporated to remove water and CH$_3$CN under reduced pressure. The residue was lyophilized overnight to give the desired (2S)-3-[(3R)-12-[[4-(dimethylamino)cyclohexyl]oxy]-7-thia-9,11-diazatricyclo [6.4.0.0[2,6]]dodeca-1(8),2(6),9,11-tetraen-3-yl]-2-methoxypropanamide (31.3 mg, 40%) as an off-white semi-solid. MS (ES): m/z 419 [M-1.2HCOOH+H]$^+$. $^1$H NMR (300 MHz, CD$_3$OD): δ 8.44 (m, 2H), 5.30-5.27 (s, 1H), 3.67-3.63 (m, 1H), 3.46-3.27 (m, 5H), 3.08-2.84 (m, 8H), 2.72-2.66 (m, 1H), 2.48-2.17 (m, 6H), 1.83-1.28 (m, 5H).

Example 96

(2S)-2-methoxy-3-[(3R)-12-[[4-(methylamino)cyclohexyl]oxy]-7-thia-9,11-diazatricyclo[6.4.0.0[2,6]] dodeca-1(8),2(6),9,11-tetraen-3-yl]propanenitrile (I-80) and Example 97: (2R)-2-methoxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanenitrile (I-81)

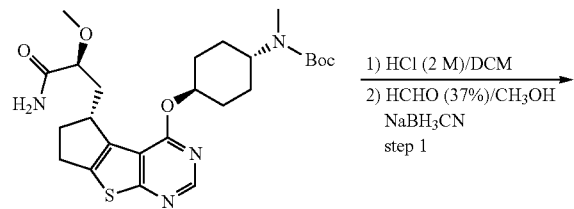

Mol. Wt.: 504.64
94.5

1) HCl (2 M)/DCM
2) HCHO (37%)/CH$_3$OH
   NaBH$_3$CN
step 1

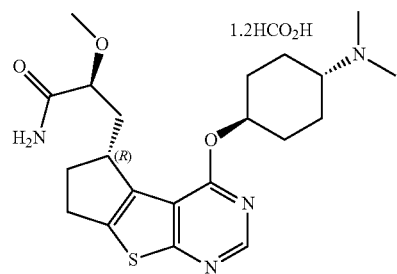

Mol. Wt.: 418.55

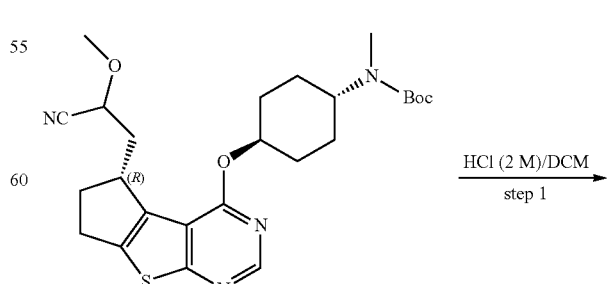

HCl (2 M)/DCM
step 1

94.3

281
-continued

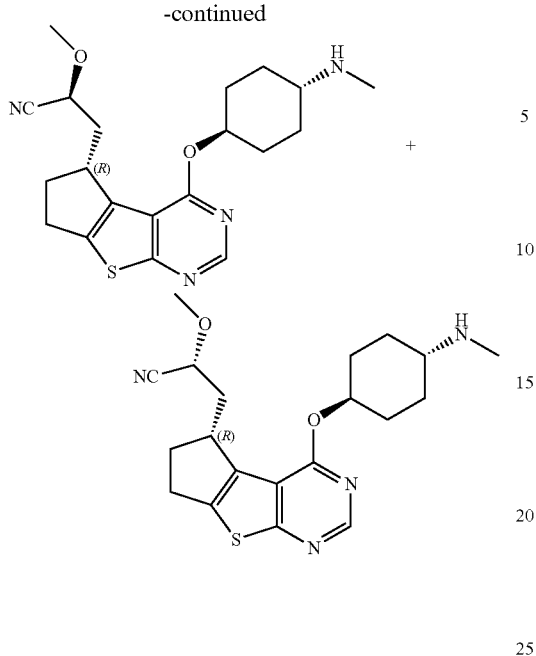

Into a 50-mL round-bottom flask, a solution of tert-butyl N-(4-[[(3R)-3-(2-cyano-2-methoxyethyl)-7-thia-9,11-diazatricyclo[6.4.0.0[2,6]]dodeca-1(8),2(6),9,11-tetraen-12-yl]oxy]cyclohexyl)-N-methylcarbamate (100 mg, 0.21 mmol, 1.00 equiv) in dichloromethane (10 mL) was added hydrochloric acid (12 M, 0.5 mL) in a water/ice bath and stirred for 4 h. After completion and concentration in vacuo, the residue was neutralised with saturated aqueous sodium bicarbonate, extracted with 3×50 mL of DCM. The combined organic layers were concentrated under vacuum and the crude product (80 mg) was purified by preparative HPLC under the following conditions: (SHIMADZU): column: Xbridge Prep C18 5 um, 19*150 mm; mobile phase: water with 0.05% $NH_4HCO_3$ and $CH_3CN$ (6.0% $CH_3CN$ up to 56.0% in 15 min); flow rate: 20 mL/min; UV detection at 254/220 nm. The product-containing fractions were collected and partially evaporated to remove water and $CH_3CN$ under reduced pressure. The residue was lyophilized overnight to give the corresponding (2S)-2-methoxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanenitrile (12.5 mg) as a off-white semi-solid and (2R)-2-methoxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanenitrile (3.5 mg) as a light yellow semi-solid, respectively.

Example 96 (I-80)

MS (ES): m/z 387 [M+H]⁺. ¹H NMR (300 MHz, $CD_3OD$): δ 8.44 (m, 1H), 5.32 (m, 1H), 3.44-3.09 (m, 6H), 2.57-2.23 (m, 11H), 2.12-1.90 (m, 1H), 1.72-1.63 (m, 3H), 1.33-1.25 (m, 5H), 0.95 (m, 1H).

Example 97 (I-81)

MS (ES): m/z 387 [M+H]⁺. ¹H NMR (300 MHz, $CD_3OD$): δ 8.44 (m, 1H), 5.30 (m, 1H), 4.83-4.25 (m, 1H), 3.63-3.27

282

(m, 5H), 3.06-2.95 (m, 2H), 2.65-2.26 (m, 11H), 2.13-1.90 (m, 4H), 1.69-1.25 (m, 4H).

Example 98

Synthesis of (R)-1-(R)-4-(((1r,4R)-4-morpholinocyclohexyl)oxy)-6,7-dihydro-5H-cyclopenta[4,5]thieno[2,3-d]pyrimidin-5-yl)propan-2-ol (I-82) and
Example 99: Synthesis of (S)-1-(R)-4-(((1r,4R)-4-morpholinocyclohexyl)oxy)-6,7-dihydro-5H-cyclopenta[4,5]thieno[2,3-d]pyrimidin-5-yl)propan-2-ol (I-83)

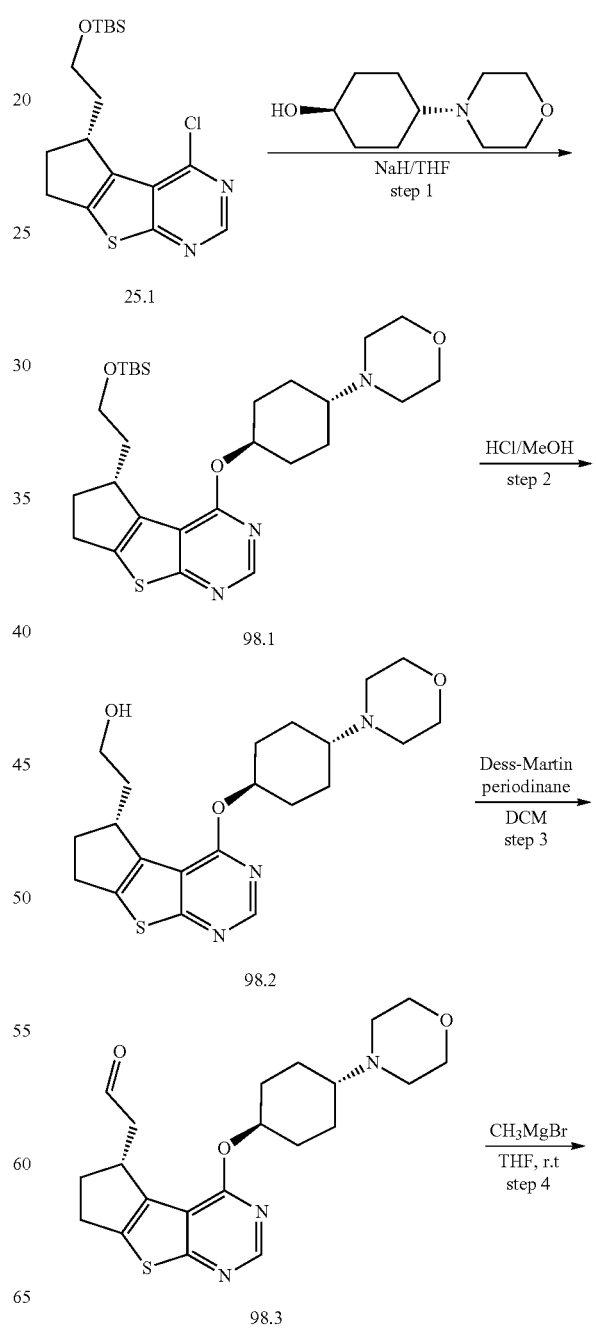

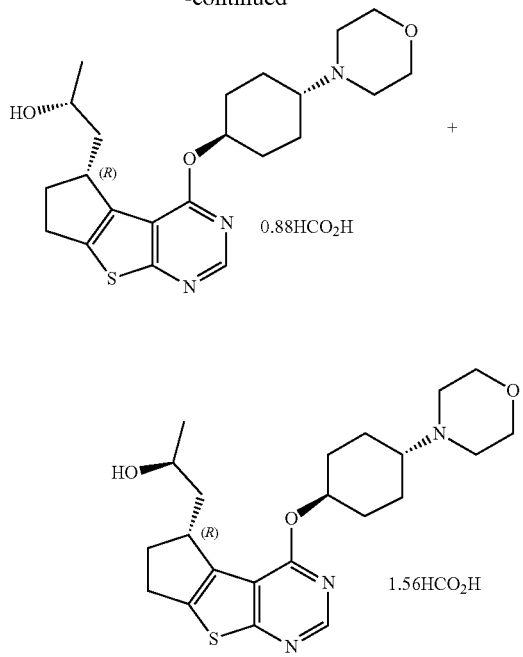

Synthesis of Compound 98.1. Note:

For the preparation of the starting material 25.1, see Example 25. Into a 100-mL round-bottom flask purged and maintained with an inert atmosphere of nitrogen, a solution of trans-4-(morpholin-4-yl)cyclohexan-1-ol (528 mg, 2.85 mmol, 1.50 equiv) in freshly distilled THF (30 mL) was added sodium hydride (304 mg, 7.60 mmol, 4.01 equiv, 60% dispersion in mineral oil) portionwise at 0° C. under nitrogen. The resulting mixture was stirred for 30 min in a water/ice bath. Then a solution of (3R)-3-[2-[(tert-butyldimethylsilyl)oxy]ethyl]-12-chloro-7-thia-9,11-diazatricyclo[6.4.0.0[2,6]]dodeca-1(8),2(6),9,11-tetraene (700 mg, 1.90 mmol, 1.00 equiv) in 5 mL of THF was added via syringe and the resulting solution was allowed to react, with stirring, for an additional 4 hr at 55° C. in an oil bath. After completion, the reaction was quenched by the addition of 20 mL of saturated aqueous NH$_4$Cl and extracted with 3×80 mL of ethyl acetate. The combined organic layers were washed with brine, dried over sodium sulfate and concentrated under vacuum. The residue was purified on a silica gel column with ethyl acetate/petroleum ether (1:5 to 1:0) to afford the desired (3R)-3-[2-[(tert-butyldimethylsilyl)oxy]ethyl]-12-[[4-(morpholin-4-yl)cyclohexyl]oxy]-7-thia-9,11-diazatricyclo[6.4.0.0[2,6]]dodeca-1(8),2(6),9,11-tetraene (850 mg, 87%) as a colorless oil. MS (ES): m/z 518 [M+H]$^+$.

Synthesis of Compound 98.2.

To a solution of (3R)-3-[2-[(tert-butyldimethylsilyl)oxy]ethyl]-12-[[4-(morpholin-4-yl)cyclohexyl]oxy]-7-thia-9,11-diazatricyclo[6.4.0.0[2,6]]dodeca-1(8),2(6),9,11-tetraene (850 mg, 1.64 mmol, 1.00 equiv) in methanol (20 mL) was added hydrochloric acid (2 M, 1.0 mL) and the resulting mixture was stirred for 1 hr at 0° C. in a water/ice bath. After completion, the reaction was quenched with sodium bicarbonate (sat.) and extracted with 3×80 mL of ethyl acetate. The combined organic layers were washed with brine, dried over sodium sulfate and concentrated under vacuum. The residue was purified on a silica gel column with chloroform/methanol (15:1) to afford 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]ethan-1-ol (600 mg, 91%) as a colorless oil. MS (ES): m/z 404 [M+H]$^+$.

Synthesis of Compound 98.3.

A 50-mL round-bottom flask, purged and maintained with an inert atmosphere of nitrogen, was charged with a dichloromethane (15 mL) solution of 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]ethan-1-ol (200 mg, 0.50 mmol, 1.00 equiv). Dess-Martin periodinane (318 mg, 0.75 mmol, 1.51 equiv) was added and the resulting mixture was stirred for 2 hr at 0° C. in a water/ice bath. After completion, the reaction was quenched with sodium bicarbonate (sat.) and extracted with 3×60 mL of EtOAc. The combined organic layers were washed with brine, dried over sodium sulfate and concentrated under vacuum. The residue was purified on a silica gel column with ethyl acetate/petroleum ether (1:1) to afford the corresponding 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]acetaldehyde (150 mg, 75%) as a colorless oil. MS (ES): m/z 402 [M+H]$^+$.

Synthesis of I-82 and I-83.

A solution of 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]acetaldehyde (150 mg, 0.37 mmol, 1.00 equiv) in 20 mL of distilled THF was cooled down to 0° C. under nitrogen. A solution of bromo(methyl)magnesium (1 M in hexane, 0.74 mL, 2.00 equiv) was added slowly via syringe and stirred for 3 hr in a water/ice bath. After completion, the reaction was quenched with NH$_4$Cl (sat.), extracted with 3×80 mL of ethyl acetate. The combined organic layers were concentrated under vacuum, the residue (200 mg) was purified by preparative HPLC under the following conditions (SHIMADZU): column: SunFire Prep C18, 19*150 mm 5 um; mobile phase: water with 100 mM NH$_4$HCO$_3$ and CH$_3$CN (6.0% CH$_3$CN up to 60% in 20 min); flow rate: 20 mL/min; UV detection at 254/220 nm. The product-containing fractions were collected and partially evaporated to remove water and CH$_3$CN under reduced pressure. The residue was lyophilized overnight to give the desired product (R)-1-((R)-4-(((1r,4R)-4-morpholinocyclohexyl)oxy)-6,7-dihydro-5H-cyclopenta[4,5]thieno[2,3-d]pyrimidin-5-yl)propan-2-ol (32 mg) as a white solid and (S)-1-((R)-4-(((1r,4R)-4-morpholinocyclohexyl)oxy)-6,7-dihydro-5H-cyclopenta[4,5]thieno[2,3-d]pyrimidin-5-yl)propan-2-ol (55.5 mg) as a white solid.

Example 98 (I-82)

MS (ES): m/z 418 [M-0.88HCOOH+H]$^+$. $^1$H NMR (300 MHz, CD$_3$OD): δ 8.44 (s, 2H), 5.29-5.27 (m, 1H), 3.91-3.79 (m, 5H), 3.29-3.27 (m, 1H), 3.09-2.85 (m, 7H), 2.66-2.58 (m, 1H), 2.3.9-1.90 (m, 6H), 1.64-1.50 (m, 5H), 1.27-1.25 (m, 3H).

Example 99 (I-83)

MS (ES): m/z 418 [M-1.56HCOOH+H]$^+$. $^1$H NMR (300 MHz, CD$_3$OD): δ 8.42 (s, 2H), 5.29-5.26 (m, 1H), 3.90-3.83 (m, 5H), 3.56-3.51 (m, 1H), 3.32-3.27 (m, 1H), 3.04-2.88 (m, 7H), 2.68-2.61 (m, 1H), 2.40-2.90 (m, 6H), 1.75-1.15 (m, 8H).

Example 100

Synthesis of 3-((S)-4-(((1r,4S)-4-morpholinocyclohexyl)oxy)-6,7-dihydro-5H-cyclopenta[4,5]thieno[2,3-d]pyrimidin-5-yl)propanamide (I-84)

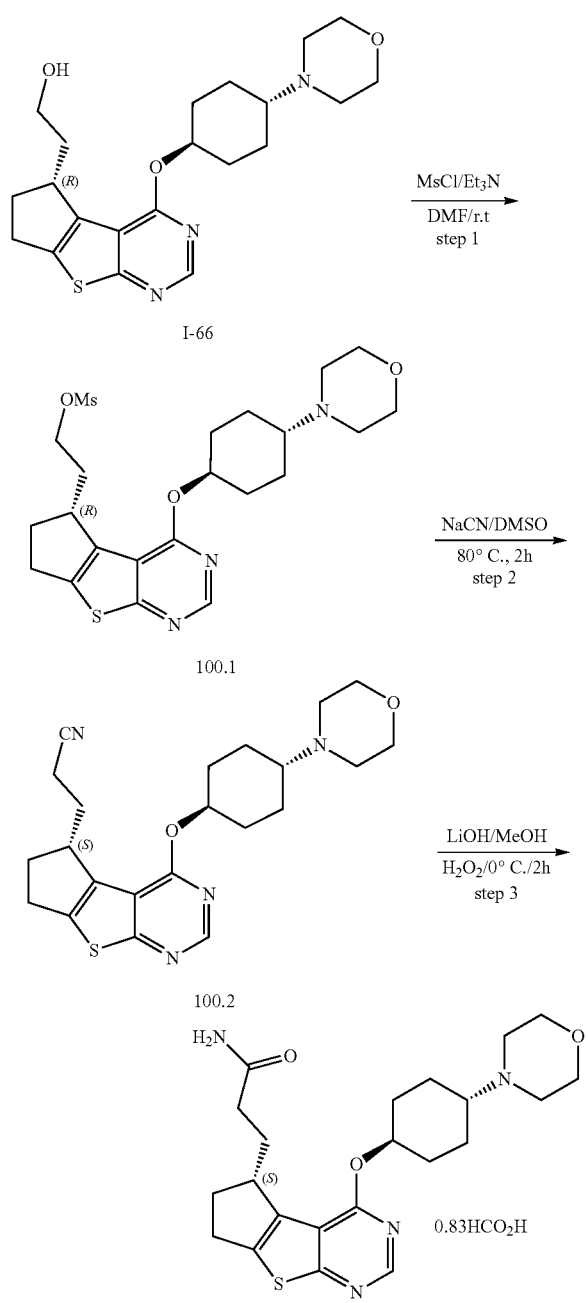

Synthesis of Compound 100.1.

To a solution of 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]ethan-1-ol (202 mg, 0.50 mmol, 1.00 equiv) in N,N-dimethylformamide (5 mL) was added MsCl (86 mg, 0.75 mmol, 1.50 equiv) and triethylamine (153 mg, 1.51 mmol, 3.00 equiv) at 0° C. under nitrogen. The resulting solution was stirred for 2 h at room temperature and diluted with DCM (80 mL), washed with brine, dried over anhydrous sodium sulfate and concentrated under vacuum to give the desired 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]ethyl methanesulfonate (230 mg, 95%) as a white solid. MS (ES): m/z 482 [M+H]$^+$.

Synthesis of Compound 100.2.

Into a 50-mL round-bottom flask, purged and maintained with an inert atmosphere of nitrogen, was placed a solution of 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]ethyl methanesulfonate (230 mg, 0.48 mmol, 1.00 equiv) in DMSO (5 mL) at room temperature. Then NaCN (141 mg, 2.88 mmol, 6.00 equiv) and 4-dimethylaminopyridine (5.86 mg, 0.05 mmol, 0.10 equiv) were added and the resulting solution was stirred for 2 h at 80° C. After cooling down to room temperature, the reaction was quenched with brine, extracted with DCM. The organic phase was dried over anhydrous sodium sulfate and concentrated under vacuum. The residue was purified by column chromatography on silica gel with EtOAc/petroleum ether (1:10 to 1:2) to afford the desired 3-[(3S)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanenitrile (170 mg, 86%) as a white solid. LCMS (ES): m/z 413 [M+H]$^+$.

Synthesis of I-84.

A solution of 3-[(3S)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanenitrile (170 mg, 0.41 mmol, 1.00 equiv) in methanol (5 mL) was added LiOH.H$_2$O (53 mg, 1.26 mmol, 3.00 equiv) at 0° C. Then H$_2$O$_2$ (30%, 0.5 mL) was added via syringe at 0° C. The resulting solution was stirred for 2 h and quenched with saturated aqueous Na$_2$SO$_3$, extracted with 3×30 mL of dichloromethane. The combined organic layers were washed with brine, dried over anhydrous sodium sulfate and concentrated under vacuum. The residue was purified by preparative HPLC under the following conditions (SHIMADZU): column: SunFire Prep C18, 19*150 mm 5 um; mobile phase: water with 0.05% NH$_4$HCO$_3$ and CH$_3$CN (25% CH$_3$CN up to 100% in 25 min); flow rate: 20 mL/min; UV detection at 254/220 nm. The product-containing fractions were collected and partially evaporated to remove water and CH$_3$CN under reduced pressure. The residue was lyophilized overnight to give product 3-((S)-4-(((1r,4S)-4-morpholino cyclohexyl)oxy)-6,7-dihydro-5H-cyclopenta[4,5]thieno[2,3-d]pyrimidin-5-yl)propanamide formate (92.6 mg, 47%) as a white solid. MS (ES): m/z 431 [M-0.83HCOOH+H]$^+$. $^1$H NMR (400 MHz, CD$_3$OD) δ 8.48 (1H, s), 8.38 (1H, s), 5.33-5.25 (1H, m), 3.85 (4H, t), 3.50-3.41 (1H, m), 3.15-3.09 (1H, m), 3.08-2.95 (5H, m), 2.93-2.85 (1H, m), 2.75-2.65 (1H, m), 2.50-2.35 (2H, m), 2.30-2.15 (6H, m), 1.95-1.82 (1H, m), 1.80-1.55 (4H, m).

Example 101

The preparation of the Intermediate 101.5

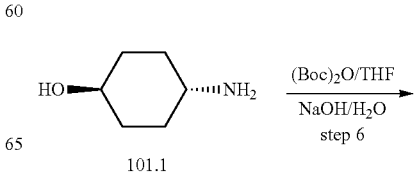

-continued

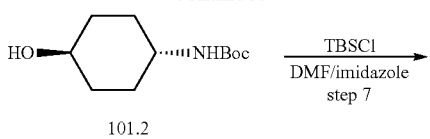
101.2

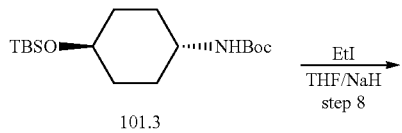
101.3

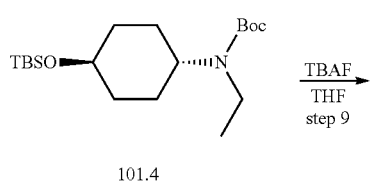
101.4

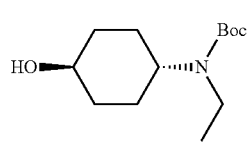
Int. 101.5

Example 102

Synthesis of 2-((R)-4-(((1r,4R)-4-(ethylamino)cyclohexyl)oxy)-6,7-dihydro-5H-cyclopenta[4,5]thieno[2,3-d]pyrimidin-5-yl)acetamide. (I-85)

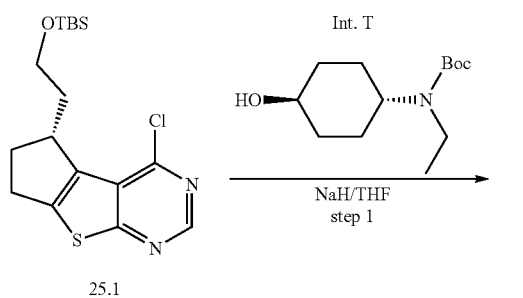
25.1

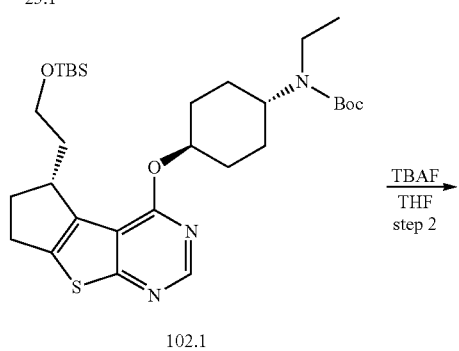
102.1

-continued

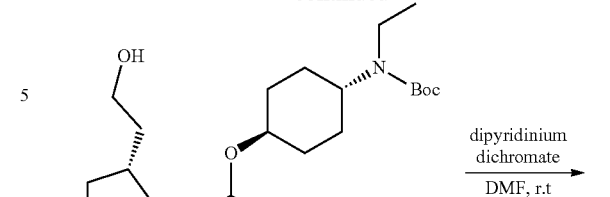
102.2

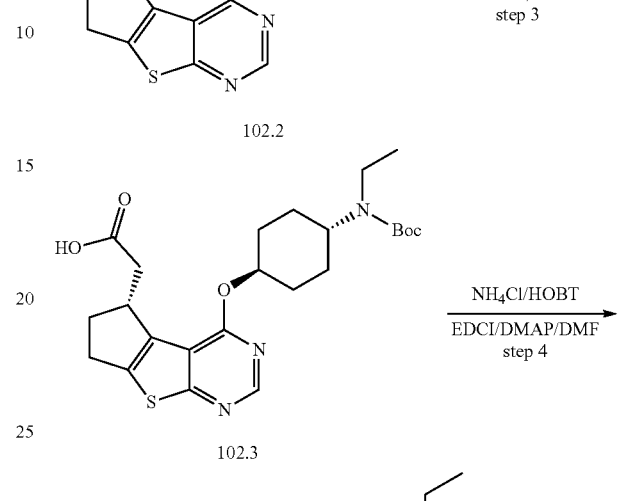

Synthesis of Compound 102.1. Note:

For the preparation of the starting material compound 25.1, please refer to the experimental procedure for the synthesis of compound Example 25. To a solution of tert-butyl N-ethyl-N-(4-hydroxycyclohexyl)carbamate (intermediate 101.5, 322.68 mg, 1.33 mmol, 1.22 equiv) in distilled tetrahydrofuran (10 mL) was added sodium hydride (151.76 mg) slowly at 0° C. and the reaction mixture was stirred at room temperature for 30 min. Then (3R)-3-[2-[(tert-butyldimethylsilyl)oxy]ethyl]-12-chloro-7-thia-9,11-diazatricyclo[6.4.0.0[2,6]]dodeca-1(8),2(6),9,11-tetraene (400 mg, 1.08 mmol, 1.00 equiv) in THF (5 mL) was added to the mixture via syringe and the resulting solution was stirred for 3 hr at ambient temperature. The reaction was then quenched by the addition of 40 mL of saturated aqueous NH₄Cl and extracted with 3×80 mL of ethyl acetate. The combined organic layers were combined, washed with brine, dried over sodium sulfate and concentrated under vacuum. The residue was applied onto a silica gel column with ethyl acetate/petroleum ether (1:5) to afford tert-butyl N-(4-[[(3R)-3-[2-[(tert-butyldimethylsilyl)oxy]ethyl]-7-thia-9,11-diazatricyclo[6.4.0.0[2,6]]dodeca-1(8),2(6),9,11-tetraen-12-yl]oxy]cyclohexyl)-N-ethylcarbamate (570 mg, 91%) as a colorless oil. MS (ES): m/z 576 [M+H]$^+$.

Synthesis of Compound 102.2.

Into a 50-mL round-bottom flask containing a solution of tert-butyl N-(4-[[(3R)-3-[2-[(tert-butyldimethylsilyl)oxy]ethyl]-7-thia-9,11-diazatricyclo[6.4.0.0[2,6]]dodeca-1(8),2(6),9,11-tetraen-12-yl]oxy]cyclohexyl)-N-ethylcarbamate (570 mg, 0.99 mmol, 1.00 equiv) in THF (6 mL) was added TBAF (522 mg, 2.00 mmol, 2.02 equiv) and the resulting solution was stirred for 2 hrs at 25° C. The reaction mixture was concentrated under vacuum. The residue was applied onto a silica gel column with ethyl acetate/petroleum ether (1:2) to provide the desired tert-butyl N-ethyl-N-(4-[[(3R)-3-(2-hydroxyethyl)-7-thia-9,11-diazatricyclo[6.4.0.0[2,6]]dodeca-1(8),2(6),9,11-tetraen-12-yl]oxy]cyclohexyl)carbamate (450 mg, 98%) as a colorless oil. MS (ES): m/z 462 [M+H]$^+$.

Synthesis of Compound 102.3.

A solution of tert-butyl N-ethyl-N-(4-[[(3R)-3-(2-hydroxyethyl)-7-thia-9,11-diazatricyclo[6.4.0.0[2,6]]dodeca-1(8),2(6),9,11-tetraen-12-yl]oxy]cyclohexyl)carbamate (450 mg, 0.97 mmol, 1.00 equiv) and PDC (1791 mg, 4.76 mmol, 4.88 equiv) in 5 mL of DMF was stirred for 14 hrs at 25° C. After completion, the resulting solution was diluted with water and extracted with 3×50 mL of ethyl acetate. The combined organic layers were washed with 3×20 mL of brine, dried over sodium sulfate and concentrated under vacuum. The residue was applied onto a silica gel column with ethyl acetate/petroleum ether (2:1) to give 310 mg (67%) of 2-[(3R)-12-[(4-[[(tert-butoxy)carbonyl](ethyl)amino]cyclohexyl)oxy]-7-thia-9,11-diazatricyclo[6.4.0.0[2,6]]dodeca-1(8),2(6),9,11-tetraen-3-yl]acetic acid as a colorless oil. MS (ES): m/z 476 [M+H]$^+$.

Synthesis of Compound 102.4.

A 50-mL round-bottom flask was charged with a solution of 2-[(3R)-12-[(4-[[(tert-butoxy)carbonyl](ethyl)amino]cyclohexyl)oxy]-7-thia-9,11-diazatricyclo[6.4.0.0[2,6]]dodeca-1(8),2(6),9,11-tetraen-3-yl]acetic acid (310 mg, 0.65 mmol, 1.00 equiv), HOBt (132 mg), EDCI (186.9 mg), 4-dimethylaminopyridine (118 mg) and NH$_4$Cl (209 mg, 3.91 mmol, 5.99 equiv) in distilled DMF (6 mL). The solution was stirred for 14 hrs at 25° C. under nitrogen. The resulting solution was diluted with water and extracted with 3×50 mL of ethyl acetate. The combined organic layers were washed with 3×20 mL of brine, dried over sodium and concentrated under vacuum. The residue was applied onto a silica gel column with ethyl acetate/petroleum ether (2:1) to afford tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]cyclohexyl)-N-ethylcarbamate (230 mg, 74%) as a colorless oil. MS (ES): m/z 475 [M+H]$^+$.

Synthesis of Compound I-85.

To a solution of tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]cyclohexyl)-N-ethylcarbamate (230 mg, 0.48 mmol, 1.00 equiv) in dichloromethane (4 mL) was added hydrochloric acid (12 M, 0.5 mL) at 0° C. and the resulting solution was stirred for 3 hr at 0° C. The resulting mixture was concentrated under vacuum. The crude product (180 mg) was purified by preparative HPLC under the following conditions (SHIMADZU): column: SunFire Prep C18, 19*150 mm 5 um; mobile phase: water with 100 mM NH$_4$HCO$_3$ and CH$_3$CN (6.0% CH$_3$CN up to 60% in 20 min); flow rate: 20 mL/min; UV detection at 254/220 nm. The product-containing fractions were collected and partially evaporated to remove water and CH$_3$CN under reduced pressure. The residue was lyophilized overnight to give the desired 2-[(3R)-12-[[4-(ethylamino)cyclohexyl]oxy]-7-thia-9,11-diazatricyclo[6.4.0.0[2,6]]dodeca-1(8),2(6),9,11-tetraen-3-yl]acetamide (114.4 mg, 63%) as a white solid. MS (ES): m/z 375 [M+H]$^+$. $^1$H-NMR (300 MHz, CD$_3$OD): δ 8.47 (1H, s), 5.29 (1H, m), 4.82 (1H, m), 3.07-3.10 (1H, m), 2.93-2.99 (2H, m), 2.58-2.73 (4H, m), 2.23-2.23 (4H, m), 2.03-2.18 (2H, m), 1.66 (2H, m), 1.40-1.30 (2H, m), 1.03-1.18 (3H, t).

Example 103

Synthesis of 2-cyano-3-((R)-4-(((1r,4R)-4-morpholinocyclohexyl)oxy)-6,7-dihydro-5H-cyclopenta[4,5]thieno[2,3-d]pyrimidin-5-yl)propanamide (I-86)

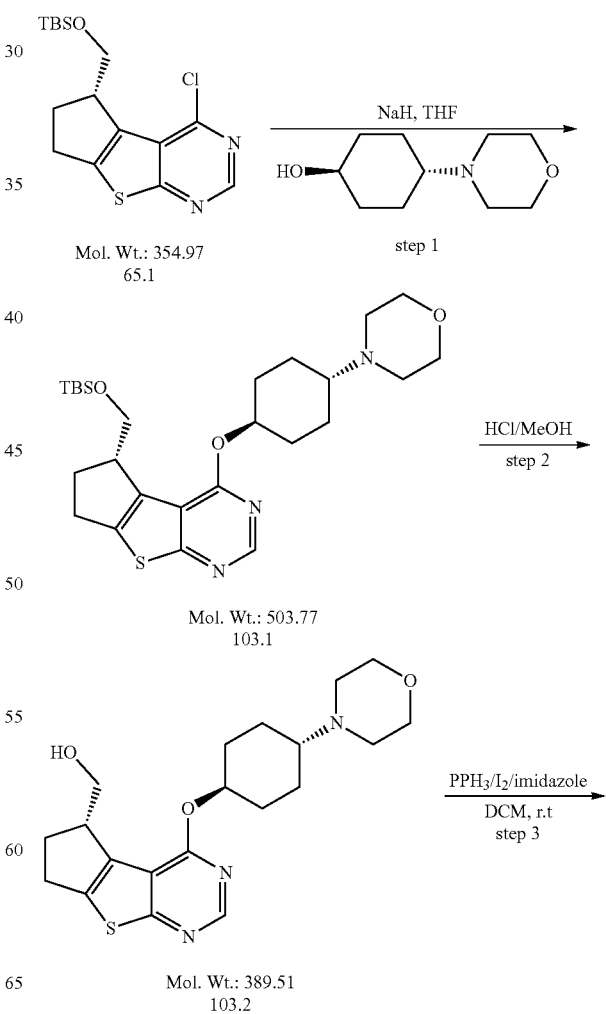

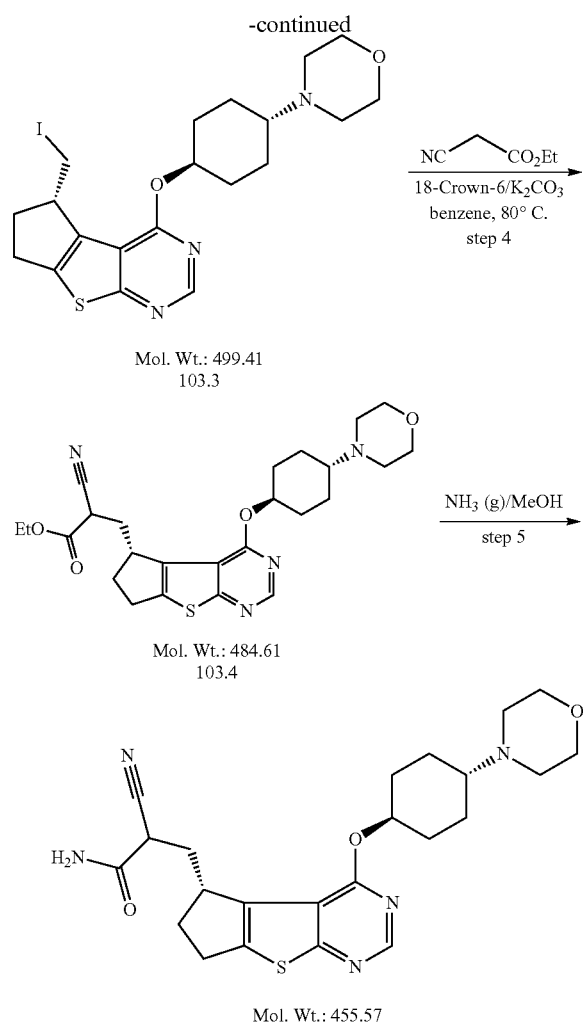

Synthesis of Compound 103.1. Note:

For the preparation of the starting material compound 65.1, please refer to the experimental procedure for Example 65. To a solution of trans-4-(morpholin-4-yl)cyclohexan-1-ol (277 mg, 1.50 mmol, 1.50 equiv) in distilled THF (20 mL) was added sodium hydride (605 dispersion in mineral oil, 200 mg, 5.00 mmol, 5.00 equiv) slowly at 0° C. under nitrogen. After stirring for 30 min at room temperature, a solution of 3-[[(tert-butyldimethylsilyl)oxy]methyl]-12-chloro-7-thia-9,11-diazatricyclo[6.4.0.0[2,6]]dodeca-1(12),2(6),8,10-tetraene (355 mg, 1.00 mmol, 1.00 equiv) in 5 mL of THF was added dropwise and the resulting solution was stirred for 6 h at ambient temperature. The reaction was quenched with NH$_4$Cl (sat.), extracted with EtOAc (3×80 mL). The combined organic layers were washed with brine, dried over anhydrous sodium sulfate. After filtration and concentration in vacuo, the residue was purified by a silica gel column with EtOAc/petroleum ether (1:1-3:1) to provide 350 mg (69%) of the title 3-[[(tert-butyldimethylsilyl)oxy]methyl]-12-[[4-(morpholin-4-yl)cyclohexyl]oxy]-7-thia-9,11-diazatricyclo[6.4.0.0 [2,6]]dodeca-1(12),2(6),8,10-tetraene as a light yellow oil. MS: (ES, m/z): 504 [M+H]$^+$.

Synthesis of Compound 103.2.

To a solution of 3-[[(tert-butyldimethylsilyl)oxy]methyl]-12-[[4-(morpholin-4-yl)cyclohexyl]oxy]-7-thia-9,11-diaza-tricyclo[6.4.0.0[2,6]]dodeca-1(12),2(6),8,10-tetraene (350 mg, 0.69 mmol, 1.00 equiv) in methanol (30 mL) was added hydrochloric acid (3 M in water, 1 mL) was added at 0° C. and the resulting solution was stirred for 1 h at room temperature. The reaction was quenched with NaHCO$_3$/brine and extracted with EtOAc ((3×80 mL). The organic layers were combined and dried over anhydrous sodium sulfate. After filtration and concentration in vacuo, the residue was purified by a silica gel column with DCM/MeOH (30:1-10:1) to provide 260 mg (96%) of (12-[[4-(morpholin-4-yl)cyclohexyl]oxy]-7-thia-9,11-diazatricyclo[6.4.0.0[2,6]]dodeca-1(12),2 (6),8,10-tetraen-3-yl)methanol as a light yellow semi-solid. MS (ES): m/z 390 [M+H]$^+$.

Synthesis of Compound 103.3.

A 20-mL round-bottom flask purged and maintained with an inert atmosphere of nitrogen was charged with a solution of (12-[[4-(morpholin-4-yl)cyclohexyl]oxy]-7-thia-9,11-diazatricyclo[6.4.0.0[2,6]]dodeca-1(12),2(6),8,10-tetraen-3-yl)methanol (260 mg, 0.67 mmol, 1.00 equiv) in DCM (20 mL). Imidazole (91 mg, 1.34 mmol, 2.00 equiv) and PPh$_3$ (264 mg, 1.01 mmol, 1.50 equiv) were added successively, followed by the addition of I$_2$ (255 mg, 1.00 mmol, 1.50 equiv) at room temperature. The resulting solution was stirred overnight at ambient temperature and diluted with DCM and washed with Na$_2$SO$_3$ (sat.) and brine. The organic layer was dried over anhydrous sodium sulfate. After filtration and concentration under reduced pressure, the residue was purified by a silica gel column with EtOAc/petroleum ether (1:1-3:1) to provide the desired 3-(iodomethyl)-12-[[4-(morpholin-4-yl) cyclohexyl]oxy]-7-thia-9,11-diazatricyclo[6.4.0.0[2,6]] dodeca-1(12),2(6),8,10-tetraene (287 mg, 86%) as a light yellow solid. MS (ES): m/z 500 [M+H]$^+$.

Synthesis of Compound 103.4.

A mixture of (3S)-3-(iodomethyl)-12-[[4-(morpholin-4-yl)cyclohexyl]oxy]-7-thia-9,11-diazatricyclo[6.4.0.0[2,6]] dodeca-1(12),2(6),8,10-tetraene (287 mg, 0.57 mmol, 1.00 equiv), 18-Crown-6 (190 mg, 0.72 mmol, 1.25 equiv), potassium carbonate (141 mg, 1.02 mmol, 1.78 equiv) and ethyl 2-cyanoacetate (678 mg, 5.99 mmol, 10.43 equiv) in benzene (20 mL) was stirred overnight at 80° C. under nitrogen. After cooling to room temperature, the solvent was removed under vacuum and the residue was purified by a silica gel column with DCM/MeOH (30:1-10:1) to provide 230 mg (83%) of ethyl 2-cyano-3-[(3R)-12-[[4-(morpholin-4-yl)cyclohexyl] oxy]-7-thia-9,11-diazatricyclo[6.4.0.0[2,6]]dodeca-1(12),2 (6),8,10-tetraen-3-yl]propanoate as a light yellow solid. MS (ES): m/z 485 [M+H]$^+$.

Synthesis of compound I-86.

NH$_3$ (gas) was introduced into ethanol (60 mL) at 0° C. with stirring for 1 h. Ethyl 2-cyano-3-[(3R)-12-[[4-(morpholin-4-yl)cyclohexyl]oxy]-7-thia-9,11-diazatricyclo[6.4.0.0 [2,6]]dodeca-1(12),2(6),8,10-tetraen-3-yl]propanoate (230 mg, 0.47 mmol, 1.00 equiv) was added and the resulting solution was stirred overnight at room temperature. After concentration in vacuo, the residue was purified by preparative HPLC under the following conditions (Waters): column: Xbridge Prep C18, 19*150 mm 5 um; mobile phase: water with 100 mM NH$_4$HCO$_3$ and CH$_3$CN (20.0% CH$_3$CN up to 63.0% in 12 min); flow rate: 20 mL/min; UV detection at 254/220 nm. The product-containing fractions were collected and partially evaporated to remove water and CH$_3$CN under reduced pressure. The residue was lyophilized overnight to give the desired 2-cyano-3-((R)-4-(((1r,4R)-4-morpholinocyclohexyl)oxy)-6,7-dihydro-5H-cyclopenta[4,5]thieno [2,3-d]pyrimidin-5-yl)propanamide (154.3 mg, 71%) as a white solid. MS (ES): m/z 456 [M+H]$^+$. $^1$H NMR (400 MHz, CD$_3$OD): δ 8.48 (1H, s), 5.36-5.29 (1H, m), 3.73 (4H, t), 3.62-3.59 (1H, m), 3.39-3.33 (1H, m), 3.25-3.02 (2H, m), 2.82-2.59 (6H, m), 2.48-2.23 (4H, m), 2.18-2.06 (2H, m), 1.91-1.72 (3H, m), 1.55-1.43 (2H, m).

Example 104

Synthesis of 2-hydroxy-3-((R)-4-(((1r,4R)-4-morpholinocyclohexyl)oxy)-6,7-dihydro-5H-cyclopenta[4,5]thieno[2,3-d]pyrimidin-5-yl)propanamide (I-87)

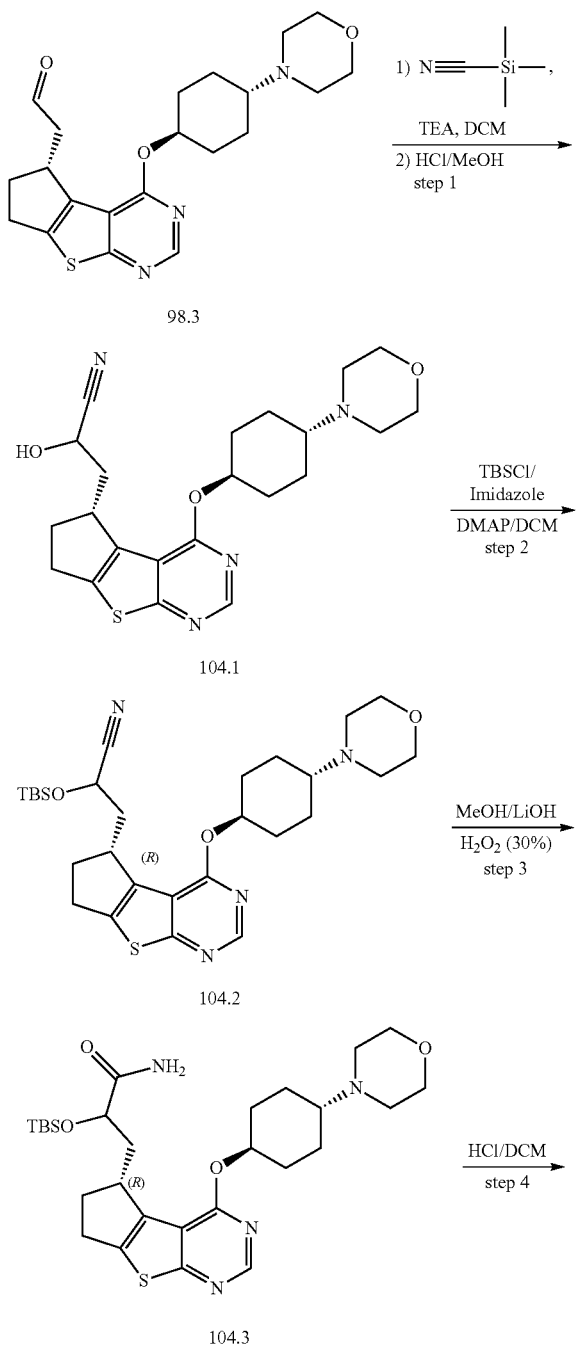

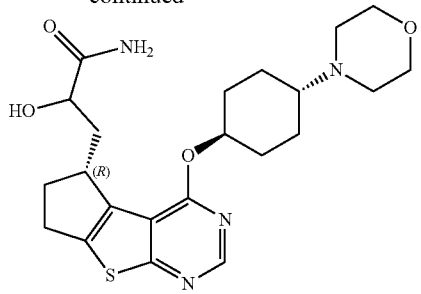

Synthesis of Compound 104.1. Note:

The starting material compound 98.3, please see Example 98. A solution of 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]acetaldehyde (450 mg, 1.12 mmol, 1.00 equiv) in 10 mL of DCM was added trimethylsilanecarbonitrile (333 mg, 3.36 mmol, 3.00 equiv) and TEA (61 mg, 0.60 mmol, 0.54 equiv) at 0° C. under nitrogen. The resulting solution was stirred for 2 h in a water/ice bath. After completion, the resulting solution was diluted with water and extracted with 3×50 mL of DCM. The combined organic layers were concentrated under reduced pressure. The desired 3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]-2-[(trimethylsilyl)oxy]propanenitrile (500 mg, with major removal of TMS compound) was obtained as a yellow oil which was used directly in the next step. The mixture (500 mg, crude) was dissolved in 10 mL of methanol and hydrochloric acid (2 M, 0.5 mL) was added with cooling by a water/ice bath. The solution was stirred for 2 h. After completion, the reaction was quenched by the addition of 20 mL of saturated sodium bicarbonate (aq.), extracted with 3×50 mL of ethyl acetate. The combined organic layers were dried over anhydrous sodium sulfate. After filtration and concentration under reduced pressure, the residue was purified on a silica gel column with dichloromethane/methanol (30:1) to afford the resulting 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]ethan-1-ol (370 mg) as a colorless oil. MS (ES): m/z 429 [M+H]$^+$.

Synthesis of Compound 104.2.

A 100-mL round-bottom flask was charged with a solution of 2-hydroxy-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanenitrile (290 mg, 0.68 mmol, 1.00 equiv) in dichloromethane (10 mL). TBSCl (153 mg, 1.02 mmol, 1.51 equiv), imidazole (92 mg, 1.35 mmol, 2.00 equiv) and 4-dimethylaminopyridine (17 mg, 0.14 mmol, 0.21 equiv) were added successively at 0° C. under nitrogen. The resulting mixture was stirred overnight at room temperature. After completion, the resulting solution was diluted with water, extracted with 3×30 mL of dichloromethane, dried over sodium sulfate and concentrated under vacuum. The residue was purified by column chromatography on silica gel with ethyl acetate/petroleum ether (1:1) to afford the desired 2-[(tert-butyldimethylsilyl)oxy]-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanenitrile (350 mg, 95%) as a yellow oil. MS (ES): m/z 543 [M+H]$^+$.

Synthesis of Compound 104.3.

To a solution of 2-[(tert-butyldimethylsilyl)oxy]-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]

propanenitrile (300 mg, 0.55 mmol, 1.00 equiv) in methanol (20 mL) was added LiOH.H₂O (47 mg, 1.12 mmol, 3.55 equiv) and H₂O₂ (30%, 0.8 mL). The solution was stirred for 2 hr in a water/ice bath. After completion, the reaction was quenched by the addition of 30 mL of saturated aqueous Na₂SO₃ and extracted with 3×50 mL of ethyl acetate. The combined organic layers were dried over anhydrous sodium sulfate. After filtration and concentration under reduced pressure, purification by column chromatography on silica gel with dichloromethane/methanol (20:1) afforded the 2-[(tert-butyldimethylsilyl)oxy]-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanamide (197 mg, 64%) as a colorless oil. MS (ES): m/z 561 [M+H]⁺.

Synthesis of Example I-87.

A 100-mL round-bottom flask was charged with a solution of 2-[(tert-butyldimethylsilyl)oxy]-3-[(3R)-12-[[4-(morpholin-4-yl)cyclohexyl]oxy]-7-thia-9,11-diazatricyclo[6.4.0.0[2,6]]dodeca-1(8),2 (6),9,11-tetraen-3-yl]propanamide (197 mg, 0.35 mmol, 1.00 equiv) in methanol (10 mL). Hydrochloric acid (2 M, 0.8 mL) was added and stirring continued for 2 hr in a water/ice bath. After completion, the reaction was quenched with saturated aqueous sodium bicarbonate and extracted with 3×30 mL of DCM. The organic phase was dried over sodium sulfate and concentrated under vacuum. The residue was purified by preparative TLC (DCM/MeOH: 10/1) to afford the 2-hydroxy-3-[(3R)-12-[[4-(morpholin-4-yl)cyclohexyl]oxy]-7-thia-9,11-diazatricyclo[6.4.0.0[2,6]]dodeca-1(8),2 (6),9,11-tetraen-3-yl]propanamide (124 mg, 79%) as a white solid. MS (ES): m/z 447 [M+H]⁺. ¹H NMR (400 MHz, CDCl₃): δ 8.46 (s, 1H), 5.28-5.25 (m, 1H), 4.17-4.06 (m, 51H), 3.74-3.72 (m, 5H), 3.37-2.98 (m, 2H), 2.72-2.28 (m, 10H), 2.11-2.08 (m, 2H), 1.79-1.46 (m, 5H).

Example 105 and Example 106

Syntheses of (1R)-2-(R)-4-(((1r,4R)-4-(dimethylamino)cyclohexyl)oxy)-6,7-dihydro-5H-cyclopenta[4,5]thieno[2,3-d]pyrimidin-5-yl)-1-(tetrahydrofuran-2-yl)ethanol (I-88) and (1S)-2-(R)-4-(((1r,4R)-4-(dimethylamino)cyclohexyl)oxy)-6,7-dihydro-5H-cyclopenta[4,5]thieno[2,3-d]pyrimidin-5-yl)-1-(tetrahydrofuran-2-yl)ethanol (I-89)

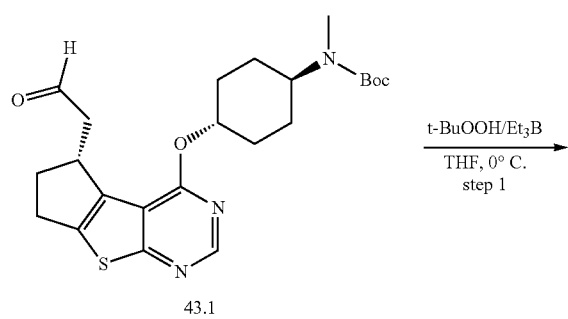

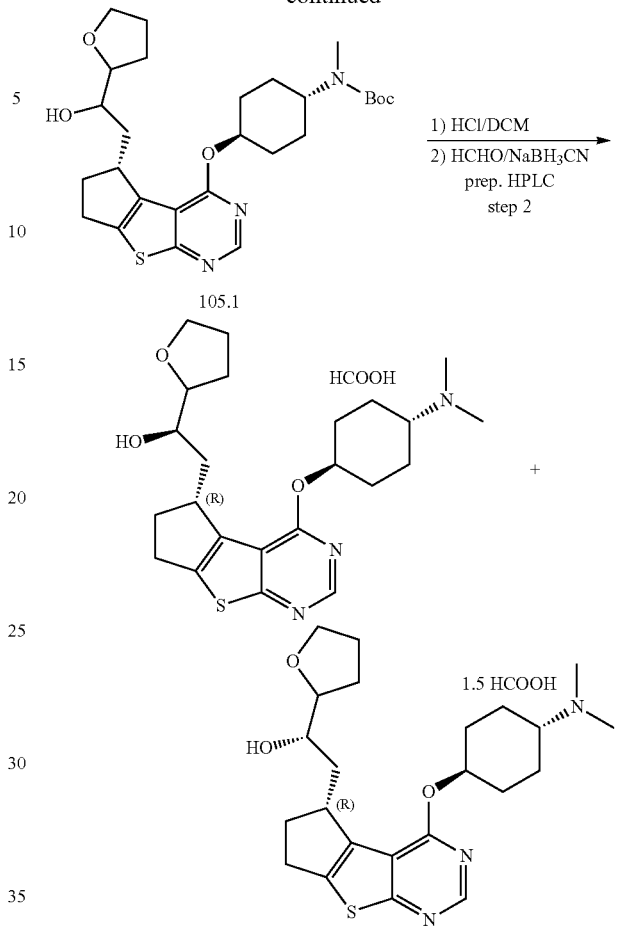

Synthesis of Compound 105.1.

For the preparation of the starting material compound 43.1, please refer to Example 43. A 50-mL three necked round-bottom flask, purged and maintained with an inert atmosphere of nitrogen, was charged with a solution of tert-butyl N-methyl-N-(4-[[(3R)-3-(2-oxoethyl)-7-thia-9,11-diazatricyclo[6.4.0.0[2,6]]dodeca-1(12),2(6),8,10-tetraen-12-yl]oxy]cyclohexyl)carbamate (500 mg, 1.12 mmol, 1.00 equiv) in 10 mL of distilled THF. Et₃B (11.2 mL, 1N) was added slowly at 0° C. over 20 min. Then t-BuOOH (1.225 mL) was added dropwise to the mixture at the same temperature. After being stirred for 10 min, the mixture was allowed to warmed to room temperature and stirring was continued for an additional period during which the reaction proceeded to completion (Caution: Triethylborane, a liquid pyrophoric toward oxygen, should be handled so as to avoid exposure to air. The addition of tert-butyl hydroperoxide to trialkylboranes may lead to highly exothermic reactions and gas evolution. We encountered no violent reaction with the present procedures, but special care is advised.) The reaction mixture was treated with 28% NH₄OH and extracted with CH₂Cl₂. (A 28% NH₄OH solution allows the removal of unidentified polar materials possibly derived from Et₃B. Removal of polar byproducts in the crude mixture, detectable on an iodine/silica gel TLC plate, may otherwise be difficult. The crude mixture must thus be washed with 28% NH₄OH for adequate purification.) The extracts were washed with saturated aqueous NaHSO₃ and dried over anhydrous sodium sulfate and concentrated under vacuum. The residue was applied onto a silica gel column with ethyl acetate/petroleum ether (1:5) to provide tert-butyl N-(4-[[(3R)-3-[(2S)-2-hydroxy-2-[(2S)-oxolan-2-yl]ethyl]-7-thia-9,11-diazatricyclo[6.4.0.0[2,6]]

dodeca-1(12),2(6),8,10-tetraen-12-yl]oxy]cyclohexyl)-N-methylcarbamate (230 mg, 40%) as a colorless oil. MS (ES): m/z 518 [M+H]+.

Syntheses of Compound I-88 and Compound I-89.

Into a 50-mL round-bottom flask containing tert-butyl N-(4-[[(3R)-3-[(2S)-2-hydroxy-2-[(2s)-oxolan-2-yl]ethyl]-7-thia-9,11-diazatricyclo[6.4.0.0^[2,6]]dodeca-1(12),2(6),8,10-tetraen-12-yl]oxy]cyclohexyl)-N-methylcarbamate (230 mg, 0.44 mmol, 1.00 equiv) in dichloromethane (10 mL) at 0° C. was added hydrochloric acid (12 M, 2.0 mL) and the resulting solution was stirred for 3 h at room temperature. The resulting mixture was concentrated under vacuum to give the corresponding hydrochloride (220 mg, crude) which was used directly in the next step. A solution of hydrochloride (220 mg, crude) in methanol (8 mL) was added HCHO (37%, 1.0 mL) and stirred for 1 h at room temperature. Then NaBH₃CN (68 mg, 1.08 mmol, 3.0 equiv) was added and the resulting solution was stirred for additional 2 h at ambient temperature and concentrated under vacuum. The crude product (200 mg) was purified by preparative HPLC under the following conditions (SHIMADZU): column: SunFire Prep C18, 19*150 mm 5 um; mobile phase: water with 0.1% HCOOH and CH₃CN (30% CH₃CN up to 60% in 20 min); flow rate: 20 mL/min; UV detection at 254 nm. The product-containing fractions were collected and partially evaporated to remove the water and CH₃CN under reduced pressure and the residue was lyophilized overnight to give (1R)-2-((R)-4-(((1r,4R)-4-(dimethylamino)cyclohexyl)oxy)-6,7-dihydro-5H-cyclopenta[4,5]thieno[2,3-d]pyrimidin-5-yl)-1-(tetrahydro furan-2-yl)ethanol (17.6 mg) as an off-white semi-solid and (1S)-2-((R)-4-(((1r,4R)-4-(dimethylamino)cyclohexyl)oxy)-6,7-dihydro-5H-cyclopenta[4,5]thieno[2,3-d]pyrimidin-5-yl)-1-(tetrahydro furan-2-yl)ethanol (10.5 mg) as an off-white semi-solid, respectively.

Example 105 (I-88)

MS (ES): m/z 432 [M–HCOOH+H]+. ¹H NMR (400 MHz, CD₃OD): δ 8.48 (2H, br s), 5.35 (1H, s) 3.88 (4H, m), 3.13 (3H, m), 2.99 (6H, m), 2.84 (1H, m), 2.71-2.66 (3H, m), 2.45 (3H, m), 1.95-1.90 (9H, m), 1.61 (1H, m).

Example 106 (I-89)

MS (ES): m/z 432 [M-1.5HCOOH+H]+. ¹H NMR (400 MHz, CD₃OD) δ 8.48 (2.5H, br s), 5.35 (1H, s) 3.88-3.75 (5H, m), 3.13 (2H, m), 2.99 (6H, m), 2.84 (1H, m), 2.21-2.40 (6H, m), 1.78-1.95 (8H, m), 1.46 (1H, t).

Example 107

Synthesis of 2-(((1R,4r)-4-(((R)-5-(2-hydroxyethyl)-6,7-dihydro-5H-cyclopenta[4,5]thieno[2,3-d]pyrimidin-4-yl)oxy)cyclohexyl)(methyl)amino)-1-(pyrrolidin-1-yl)ethanone. (I-90)

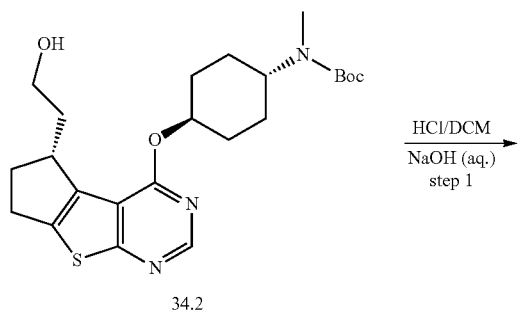

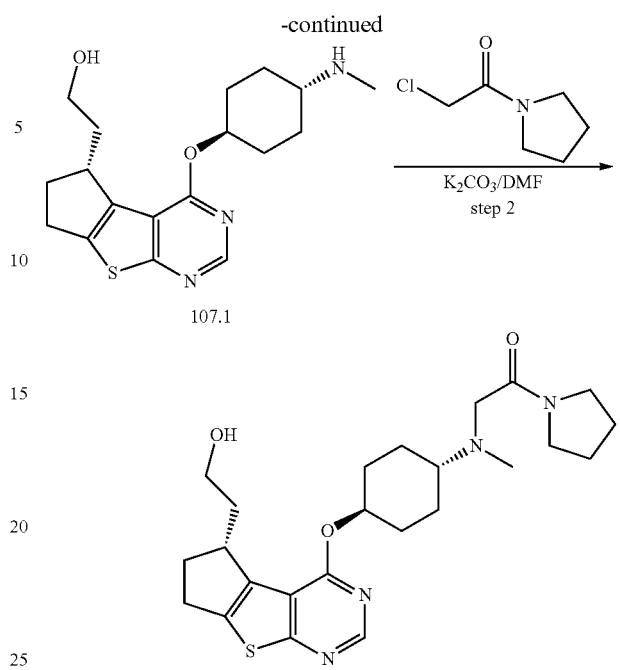

Synthesis of Compound 107.1. Note:

For the preparation of the starting material compound 34.2, please refer to the experimental procedure for the synthesis of compound Example 34. A 50-mL round-bottom flask, purged and maintained with an inert atmosphere of nitrogen, was charged with a solution of tert-butyl N-(4-[[(3R)-3-(2-hydroxyethyl)-7-thia-9,11-diazatricyclo[6.4.0.0[2,6]]dodeca-1(8),2(6),9,11-tetraen-12-yl]oxy]cyclohexyl)-N-methylcarbamate (197 mg, 0.44 mmol, 1.00 equiv) in dichloromethane (15 mL). Hydrochloric acid (conc., 0.5 mL) was added at 0° C. and the resulting solution was stirred for 2 h at room temperature. The pH value of the solution was adjusted to 10 with aqueous sodium bicarbonate (sat.) and extracted with dichloromethane. The organic layer was washed with brine, dried over anhydrous sodium sulfate and concentrated under vacuum to give 2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]ethan-1-ol (118 mg, 77%) as a yellow solid. MS (ES): m/z 348[M+H]+.

Synthesis of Compound I-90.

To a solution of 2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]ethan-1-ol (120 mg, 0.35 mmol, 1.00 equiv) in distilled DMF (5 mL) was added 2-chloro-1-(pyrrolidin-1-yl)ethan-1-one (75 mg, 0.51 mmol, 1.50 equiv) and potassium carbonate (26 mg, 0.19 mmol, 2.00 equiv) at room temperature. The resulting solution was stirred overnight at room temperature. The reaction mixture was diluted with DCM (100 mL), washed with brine, dried over anhydrous sodium sulfate and concentrated under vacuum. The residue was applied onto a silica gel column with methanol/DCM (1:10) to afford the desired 2-[(4-[[(3R)-3-(2-hydroxyethyl)-7-thia-9,11-diazatricyclo[6.4.0.0[2,6]]dodeca-1(8),2(6),9,11-tetraen-12-yl]oxy]cyclohexyl)(methyl)amino]-1-(pyrrolidin-1-yl)ethan-1-one (130 mg, 82%) as a white solid. MS (ES): m/z 459 [M+H]+. ¹H NMR (400 MHz, CD₃OD): δ 8.47 (1H, s), 5.32-5.20 (1H, m), 3.66 (2H, t), 3.58 (2H, t), 3.50-3.41 (3H, m), 3.37 (2H, s), 3.15-3.05 (1H, m), 3.00-2.92 (1H, m), 2.75-2.60 (2H, m), 2.37 (3H, s), 2.33-2.15 (4H, m), 2.03-1.88 (6H, m), 1.71-1.54 (4H, m).

Example 108

Intermediate 108.12

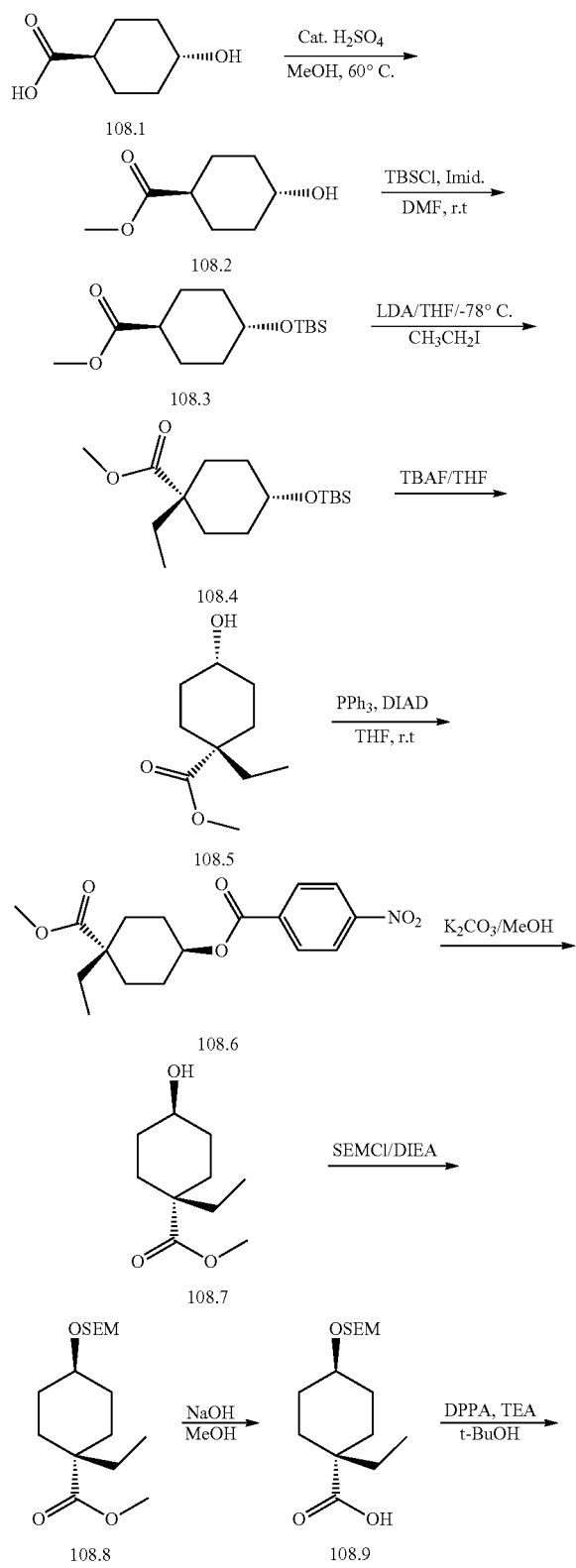

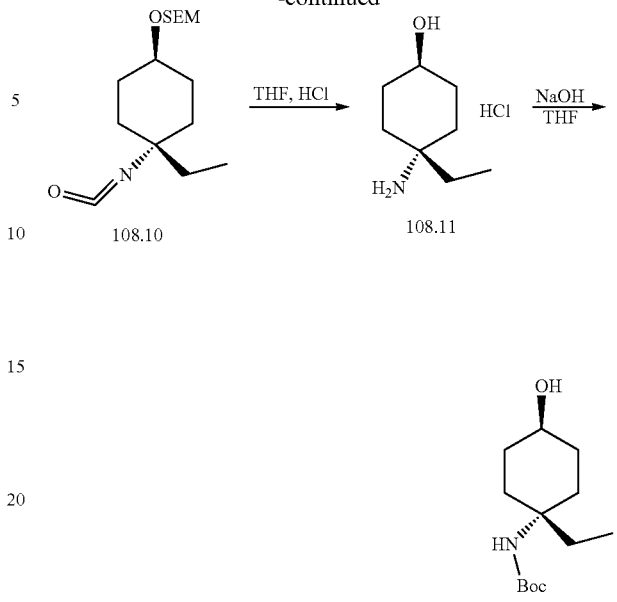

Synthesis of Compound 108.2.

A 250-mL round-bottom flask, purged and maintained with an inert atmosphere of nitrogen, was charged with 4-hydroxycyclohexane-1-carboxylic acid (15.7 g, 108.90 mmol, 1.00 equiv) in methanol (90 mL). Sulfuric acid (0.8 mL) was added to the mixture slowly. The resulting solution was stirred for 10 hr at 60° C. The reaction was then quenched by the addition of 200 mL of sodium bicarbonate (sat.). The resulting solution was extracted with 3×200 mL of ethyl acetate and the organic layers combined and dried over anhydrous sodium sulfate and concentrated under reduced pressure. The resulting trans-methyl 4-hydroxycyclohexane-1-carboxylate (16.6 g, 96%) was obtained as a light yellow oil.

Synthesis of Compound 108.3.

A 500-mL round-bottom flask, purged and maintained with an inert atmosphere of nitrogen, was charged with a solution of methyl trans-4-hydroxycyclohexane-1-carboxylate (16.6 g, 104.93 mmol, 1.00 equiv) and imidazole (14.28 g, 180.53 mmol, 1.72 equiv) in distilled DMF (25 mL). Tert-butyl(chloro)dimethylsilane (28.3 g, 187.76 mmol, 1.79 equiv) was added slowly and the resulting solution was stirred for 14 hrs at room temperature. After completion, the reaction was then quenched with water and extracted with 3×200 mL of ethyl acetate. The combined organic layers were washed with water, brine and dried over sodium sulfate. After concentration under reduced pressure, the residue was applied onto a silica gel column with ethyl acetate/petroleum ether (10:1) to give the desired methyl trans-4-[(tert-butyldimethylsilyl)oxy]cyclohexane-1-carboxylate (27.4 g, 96%) as a colorless oil.

Synthesis of Compound 108.4.

A 500-mL round-bottom flask containing a solution of diisopropylamine (10 g, 99.01 mmol, 3.00 equiv) in freshly distilled THF (100 mL) was cooled down to –78° C. under nitrogen. Then n-BuLi (2.5 M in hexane, 39.6 mL) was added dropwise and the resulting solution was stirred at –78° C. for 1 h. A solution of methyl trans-4-[(tert-butyldimethylsilyl)oxy]cyclohexane-1-carboxylate (9 g, 33.03 mmol, 1.00 equiv) in THF (20 mL) was added via syringe and the reaction mixture was held at −78° C. for another 1 h. Iodoethane (25.74 g, 165.04 mmol, 5.00 equiv) was added to the mixture and stirred for additional 2 h at −78° C. Then the reaction temperature was raised to room temperature in 1 h with stirring. The reaction was then quenched with saturated aqueous NH$_4$Cl and extracted with 3×100 mL of ethyl acetate. The combined organic layers were washed with brine, dried over sodium sulfate and concentrated under vacuum. The residue was applied onto a silica gel column with ethyl acetate/petroleum ether (1:15) to give the major methyl cis-4-[(tert-butyldimethylsilyl)oxy]-1-ethylcyclohexane-1-carboxylate (8.2 g, 83%) as a yellow oil. The desired cis-compound was confirmed by $^1$H NMR spectroscopy.

Synthesis of Compound 108.5.

To a 500-mL round-bottom flask containing a solution of methyl cis-4-[(tert-butyldimethylsilyl)oxy]-1-ethylcyclohexane-1-carboxylate (8.2 g, 27.29 mmol, 1.00 equiv) in 150 mL of THF was added TBAF·3H$_2$O (12.9 g, 40.95 mmol, 1.50 equiv) and the resulting solution was stirred for 4 hrs at 30° C. The resulting mixture was concentrated under vacuum and the residue was applied onto a silica gel column with ethyl acetate/petroleum ether (1:2) to give methyl cis-1-ethyl-4-hydroxycyclohexane-1-carboxylate (4.5 g, 89%) as a yellow oil.

Synthesis of Compound 108.6.

A solution of methyl cis-1-ethyl-4-hydroxycyclohexane-1-carboxylate (3.5 g, 18.79 mmol, 1.00 equiv) in 100 mL of THF was added 4-nitrobenzoic acid (6.3 g, 37.70 mmol, 2.01 equiv), PPh$_3$ (9.85 g, 37.55 mmol, 2.00 equiv) and DIAD (7.6 g, 37.58 mmol, 2.00 equiv) successively at room temperature under N$_2$. The resulting solution was stirred for 48 hrs at ambient temperature. After completion, the reaction was quenched with water and extracted with EtOAc (3×100 mL). The combined organic layers were dried over sodium sulfate and concentrated under vacuum. The residue was applied onto a silica gel column with ethyl acetate/petroleum ether (1:15) to give the desired trans-4-ethyl-4-(methoxycarbonyl)cyclohexyl 4-nitrobenzoate (2.3 g, 36%) as a white solid. $^1$H NMR (300 MHz, CDCl$_3$): δ 8.32 (2H, d), 8.21 (2H, d), 5.28-5.20 (1H, M), 3.72 (3H, s), 2.10-2.04 (2H, m), 1.98-1.90 (2H, m), 1.84-1.73 (2H, m), 1.68-1.56 (5H, m), 0.88 (3H, t).

Synthesis of Compound 108.7.

To a 50-mL round-bottom flask containing a solution of 4-ethyl-4-(methoxycarbonyl)cyclohexyl 4-nitrobenzoate (2.3 g, 6.86 mmol, 1.00 equiv) in a mixture of methanol (15 mL) and water (3 mL) was added potassium carbonate (2.84 g, 20.55 mmol, 3.00 equiv) and the resulting solution was stirred for 2 hr at 40° C. The resulting solution was quenched with water and extracted with 3×50 mL of ethyl acetate. The combined organic layers were washed with brine and dried over anhydrous sodium sulfate and concentrated under vacuum. The residue was purified by column chromatography on silica gel with ethyl acetate/petroleum ether (1:18) to afford the corresponding trans-methyl 1-ethyl-4-hydroxycyclohexane-1-carboxylate (1.2 g, 94%) as a white solid. $^1$H NMR (300 MHz, CDCl$_3$): δ 3.89-3.85 (1H, m), 3.69 (3H, s), 1.95-1.79 (2H, m), 1.72-1.54 (8H, m), 0.80 (3H, t).

Synthesis of Compound 108.8.

To a solution of trans-methyl 1-ethyl-4-hydroxycyclohexane-1-carboxylate (1.0 g, 5.37 mmol, 1.00 equiv) and DIEA (2.08 g, 16.09 mmol, 3.00 equiv) in dichloromethane (20 mL) was added SEMCl (1.79 g) slowly at room temperature. The resulting solution was stirred for 14 hr at ambient temperature. The reaction was then quenched with water and extracted with 3×40 mL of ethyl acetate. The combined organic layers were washed with brine, dried over sodium sulfate and concentrated under vacuum. The residue was applied onto a silica gel column with ethyl acetate/petroleum ether (1:10) to provide trans-methyl 1-ethyl-4-[[2-(trimethylsilyl)ethoxy]methoxy]cyclohexane-1-carboxylate (1.5 g, 88%) as a colorless oil. $^1$H NMR (300 MHz, CD$_3$OD): δ 4.65 (2H, s), 3.71-3.58 (6, H, m), 1.86-1.82 (2H, m), 1.68-1.49 (8H, m), 0.90 (2H, t), 0.78 (3H, t).

Synthesis of Compound 108.9.

A solution of trans-methyl 1-ethyl-4-[[2-(trimethylsilyl)ethoxy]methoxy]cyclohexane-1-carboxylate (1.5 g, 4.74 mmol, 1.00 equiv) in a mixed methanol (20 mL)/water (5 mL) was added sodium hydroxide (948 mg, 23.70 mmol, 5.00 equiv) and the resulting solution was stirred for 14 hr at 75° C. After cooling down to r.t, the pH value of the mixture was adjusted to 4 with 2 M aqueous hydrochloric acid and extracted with 3×50 mL of ethyl acetate. The combined organic layers were washed with brine, dried over anhydrous sodium sulfate and concentrated under vacuum. The desired trans-1-ethyl-4-[[2-(trimethylsilyl)ethoxy]methoxy]cyclohexane-1-carboxylic acid (1.3 g, 91%) was obtained as a yellow oil. $^1$H NMR (300 MHz, CD$_3$OD): δ 4.69 (2H, s), 3.80-3.70 (1H, m), 3.67 (2H, t), 1.87-1.82 (2H, m), 1.75-1.54 (8H, m), 0.95 (2H, t), 0.92 (3H, t).

Synthesis of Compound 108.10.

A solution of 1-ethyl-4-[[2-(trimethylsilyl)ethoxy]methoxy]cyclohexane-1-carboxylic acid (1.24 g, 4.10 mmol, 1.00 equiv), DPPA (2.03 g, 7.38 mmol, 1.80 equiv) and TEA (1.24 g, 12.25 mmol, 2.99 equiv) in 2-methylpropan-2-ol (30 mL) was stirred for 14 hr at reflux under nitrogen. The reaction mixture was quenched with water, extracted with 3×50 mL of EtOAc. The organic layers were combined, washed with brine, dried over sodium sulfate and concentrated under vacuum. The residue was applied onto a silica gel column with ethyl acetate/petroleum ether (1:6) to give (2-[[(4-ethyl-4-isocyanatocyclohexyl)oxy]methoxy]ethyl)trimethylsilane (0.9 g, 73%) as colorless oil. $^1$H NMR (400 MHz, CD$_3$OD): δ 4.70 (2H, s), 3.89-3.80 (1H, m), 3.67 (2H, t), 1.80-1.73 (6H, m), 1.65-1.58 (4H, m), 1.00 (3H, t), 0.94 (2H, t).

Synthesis of Compound 108.11.

Into a 25-mL round-bottom flask contained a solution of (2-[[(4-ethyl-4-isocyanatocyclohexyl)oxy]methoxy]ethyl), trimethylsilane (840 mg, 2.80 mmol, 1.00 equiv) in tetrahydrofuran (10 mL) was added hydrochloric acid (5 M, 2 mL) slowly and the resulting solution was stirred for 14 hrs at 30° C. The resulting mixture was concentrated under vacuum to provide the desired 4-amino-4-ethylcyclohexan-1-ol hydrochloride (410 mg, crude) as a white solid.

Synthesis of Intermediate 108.12.

A solution of 4-amino-4-ethylcyclohexan-1-ol hydrochloride (380 mg, 2.11 mmol, 1.00 equiv) and sodium hydroxide (127 mg, 1.13 mmol, 0.54 equiv) in a mixture of THF (30 mL)/water (5 mL) was added (Boc)$_2$O (462 mg, 2.12 mmol, 1.00 equiv) at 0° C. The resulting solution was stirred for 3 hr at room temperature and diluted with water, extracted with 3×50 mL of ethyl acetate. The organic layers were combined, washed with brine, dried over anhydrous sodium sulfate and concentrated under vacuum. The residue was purified by column chromatography on silica gel with ethyl acetate/petroleum ether (1:6) to give the desired trans-tert-butyl N-(1-ethyl-4-hydroxycyclohexyl)carbamate (450 mg, 87%) as a colorless oil. $^1$H NMR (300 MHz, CD$_3$OD): δ 3.80-3.72 (1H, m), 1.69-1.61 (8H, m), 1.50-1.32 (11H, m), 0.78 (3H, t).

Example 109

Synthesis of 2-((R)-4-(((1r,4R)-4-(dimethylamino)-4-ethylcyclohexyl)oxy)-6,7-dihydro-5H-cyclopenta[4,5]thieno[2,3-d]pyrimidin-5-yl)ethanol (I-91)

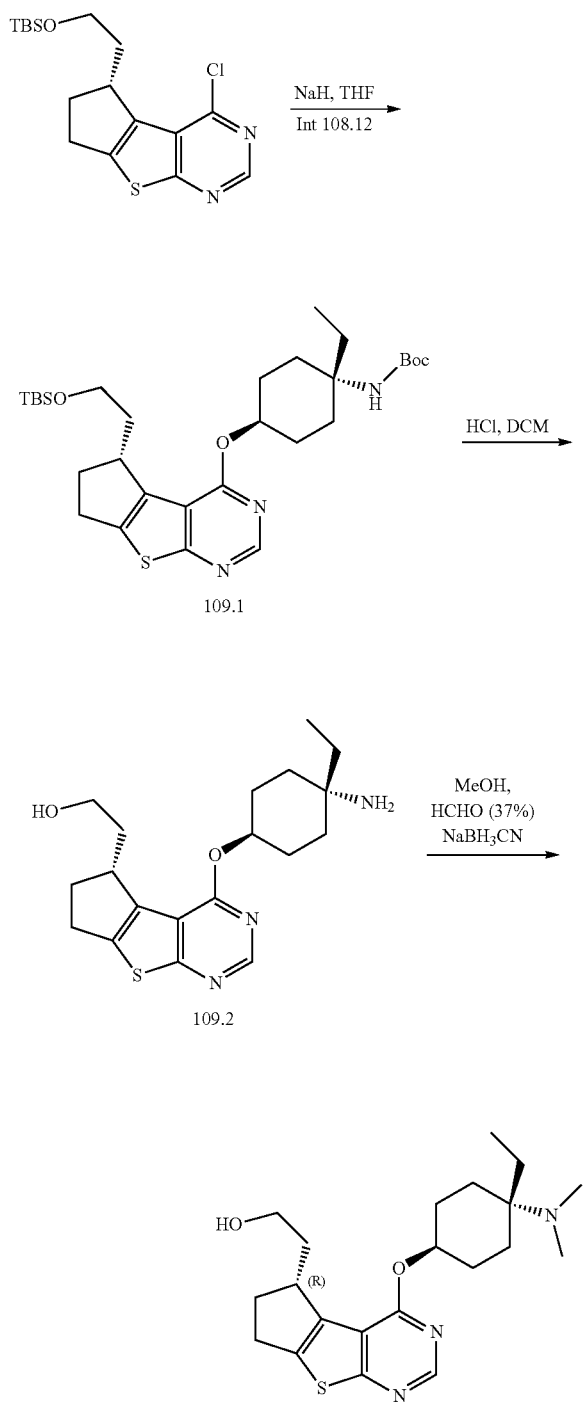

Synthesis of Compound 109.1.

Sodium hydride (60% dispersion in mineral oil, 283 mg, 7.08 mmol, 3.65 equiv) was treated with tert-butyl N-(1-ethyl-4-hydroxycyclohexyl)carbamate (430 mg, 1.77 mmol, 0.91 equiv) in 50 mL of distilled THF at room temperature for 30 mins. Then a solution of (3R)-3-[2-[(tert-butyldimethylsilyl)oxy]ethyl]-12-chloro-7-thia-9,11-diazatricyclo[6.4.0.0[2,6]]dodeca-1(8),2(6),9,11-tetraene (25.1, 716 mg, 1.94 mmol, 1.00 equiv) in THF (5 mL) was added dropwise and the resulting solution was stirred for 14 hr at 18° C. The reaction was then quenched with saturated aqueous NH$_4$Cl and extracted with 3×50 mL of ethyl acetate. The combined organic layers were washed with brine, dried over sodium sulfate and concentrated in vacuo. The residue was applied onto a silica gel column with ethyl acetate/petroleum ether (1:5) to afford the corresponding tert-butyl N-(4-[[(3R)-3-[2-[(tert-butyldimethylsilyl)oxy]ethyl]-7-thia-9,11-diazatricyclo[6.4.0.0[2,6]]dodeca-1(8),2(6),9,11-tetraen-12-yl]oxy]-1-ethylcyclohexyl)carbamate (480 mg, 43%) as a colorless oil. MS: 576 [M+H]$^+$.

Synthesis of Compound 109.2.

Into a 25-mL round-bottom flask contained a solution of tert-butyl N-(4-[[(3R)-3-[2-[(tert-butyldimethylsilyl)oxy]ethyl]-7-thia-9,11-diazatricyclo[6.4.0.0[2,6]]dodeca-1(8),2(6),9,11-tetraen-12-yl]oxy]-1-ethylcyclohexyl)carbamate (240 mg, 0.42 mmol, 1.00 equiv) in dichloromethane (10 mL) was added hydrochloric acid (5 M, 1 mL) and the resulting solution was stirred for 5 hr at RT. The reaction was then quenched saturated aqueous sodium bicarbonate, extracted with 3×40 mL of dichloromethane. The combined organic layers were washed with brine, dried over anhydrous sodium sulfate and concentrated under vacuum to give 120 mg (80%) of 2-[(3R)-12-[(4-amino-4-ethylcyclohexyl)oxy]-7-thia-9,11-diazatricyclo[6.4.0.0[2,6]]dodeca-1(8),2(6),9,11-tetraen-3-yl]ethan-1-ol as a yellow oil. MS: 362 [M+H]$^+$.

Synthesis of Compound I-91.

Into a 10-mL round-bottom flask placed a solution of 2-[(3R)-12-[(4-amino-4-ethylcyclohexyl)oxy]-7-thia-9,11-diazatricyclo[6.4.0.0[2,6]]dodeca-1(8),2(6),9,11-tetraen-3-yl]ethan-1-ol (120 mg, 0.33 mmol, 1.00 equiv) in 5 mL of methanol was added HCHO (37%, 1 mL) and the reaction was stirred at room temperature for 30 min. Then NaBH$_3$CN (83 mg, 1.32 mmol, 3.97 equiv) was added to the reaction mixture and stirred for 8 hr at room temperature. After completion, the reaction mixture was diluted with water and extracted with DCM. After concentration in vacuo, The crude product (120 mg) was purified by preparative HPLC under the following conditions (SHIMADZU): column: SunFire Prep C18, 19*150 mm 5 um; mobile phase: water with 50 mM NH$_4$HCO$_3$ and CH$_3$CN (6.0% CH$_3$CN up to 52.0% in 14 min); flow rate: 20 mL/min; UV detection at 254/220 nm. The product-containing fractions were collected and partially evaporated to remove water and CH$_3$CN under reduced pressure. The residue was lyophilized overnight to give the desired 2-[(3R)-12-[[4-(dimethylamino)-4-ethylcyclohexyl]oxy]-7-thia-9,11-diazatricyclo[6.4.0.0[2,6]]dodeca-1(8),2(6),9,11-tetraen-3-yl]ethan-1-ol (41.4 mg) as a white semi-solid. MS (ES): m/z 390 [M+H]$^+$. $^1$H NMR (400 MHz, CD$_3$OD): δ 8.47 (s, 1H), 5.44-5.46 (m, 1H), 3.64-3.69 (m, 2H), 3.32-3.33 (m, 1H), 3.10-3.12 (m, 1H), 2.99-3.02 (m, 1H), 2.68 (m, 1H), 2.09-2.39 (m, 10H), 1.61-1.86 (m, 9H), 0.93-0.96 (t, 3H).

Example 110

(S)-2-hydroxy-3-((R)-4-(((1r,4R)-4-morpholinocyclohexyl)oxy)-6,7-dihydro-5H-cyclopenta[4,5]thieno[2,3-d]pyrimidin-5-yl)propanamide (I-92) and Example 111: (R)-2-hydroxy-3-((R)-4-(((1r,4R)-4-morpholinocyclohexyl)oxy)-6,7-dihydro-5H-cyclopenta[4,5]thieno[2,3-d]pyrimidin-5-yl)propanamide (I-93)

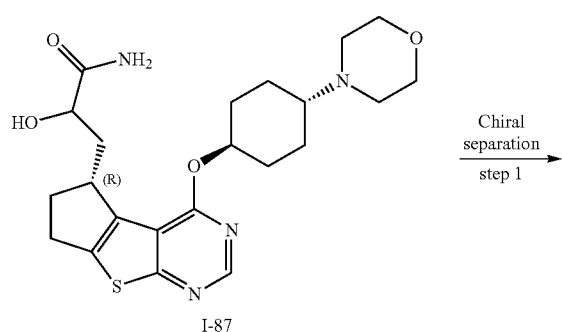

I-87

Chiral separation step 1

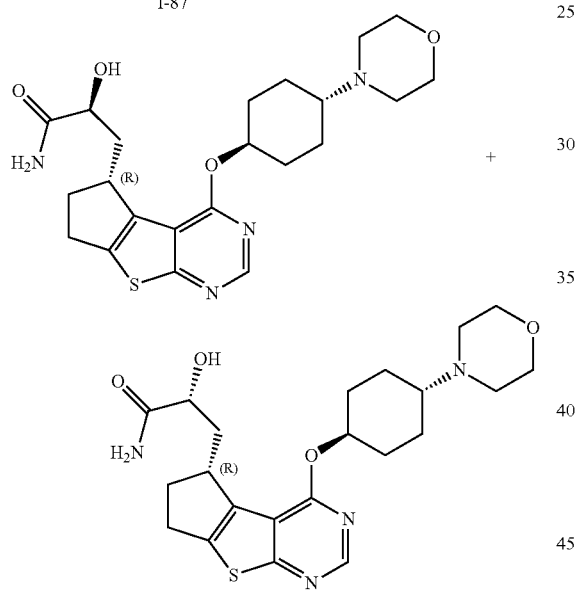

Note:

The starting material Compound I-87, please see Example 104. The racemic I-87 (1.6 g, 96.5% purity) was separated by chiral HPLC under the following conditions (Gilson Gx281): column: Chiralpak AD-H, 2*25 cm Chiral-P(AD-H); Mobile Phase: phase A: hexanes (0.1% DEA) (HPLC grade), phase B: IPA (HPLC grade), gradient: 30% B in 9 min; flow rate: 20 mL/min; UV detection at 220/254 nm; The former fractions (tR=4.75 min) were collected and evaporated under reduced pressure and lyophilized overnight to afford the (R)-2-hydroxy-3-((R)-4-(((1r,4R)-4-morpholinocyclohexyl)oxy)-6,7-dihydro-5H-cyclopenta[4,5]thieno[2,3-d]pyrimidin-5-yl) propanamide I-93 (520 mg) with 100% ee as a white solid. And the latter fractions (tR=5.82 min) were handled as former fractions to give the desired (S)-2-hydroxy-3-((R)-4-(((1r,4R)-4-morpholino cyclohexyl)oxy)-6,7-dihydro-5H-cyclopenta[4,5]thieno[2,3-d]pyrimidin-5-yl)propanamide I-92 (510 mg) with 99.6% ee as a white solid. The ee values of the two isomers were determined by chiral HPLC under the following conditions (SHIMADZU-SPD-20A): column: Chiralpak AD-H, 0.46*25 cm, 5 um (DAICEL); Mobile phase: Hex (0.1% TEA): IPA=85:15; UV detection at 254 nm. Flow rate: 1.0 mL/min. tR (I-93)=7.939 min and tR (I-92)=11.918 min.

Example 110 (I-92)

MS (ES): m/z 447 [M+H]$^+$. $^1$H NMR (400 MHz, CDCl$_3$): δ 8.46 (s, 1H), 5.32-5.22 (m, 1H), 4.15 (t, 1H), 3.73 (t, 4H), 3.59 (td, 1H), 3.19-3.08 (m, 1H), 3.02-2.92 (m, 1H), 2.78-2.70 (m, 1H), 2.69-2.60 (m, 4H), 2.58-2.20 (m, 5H), 2.10 (d, 2H), 1.75-1.63 (m, 3H), 1.53-1.40 (m, 2H).

Example 111 (I-93)

MS (ES, m/z) 447 [M+H]$^+$. $^1$H NMR (400 MHz, CD$_3$CD+CDCl$_3$): δ 8.47 (s, 1H), 5.32-5.22 (m, 1H), 4.08 (dd, 1H), 4.89-4.62 (m, 5H), 3.20-3.10 (m, 1H), 3.05-2.95 (m, 1H), 2.75-2.55 (m, 5H), 2.44-2.38 (m, 2H), 2.34-2.28 (m, 3H), 2.10 (d, 2H), 1.82-1.62 (m, 3H), 1.58-1.40 (m, 2H).

Example 112

Synthesis of 3-((S)-4-(((1r,4S)-4-(methyl(2-oxo-2-(pyrrolidin-1-yl)ethyl)amino)cyclohexyl)oxy)-6,7-dihydro-5H-cyclopenta[4,5]thieno[2,3-d]pyrimidin-5-yl)propanamide (I-94)

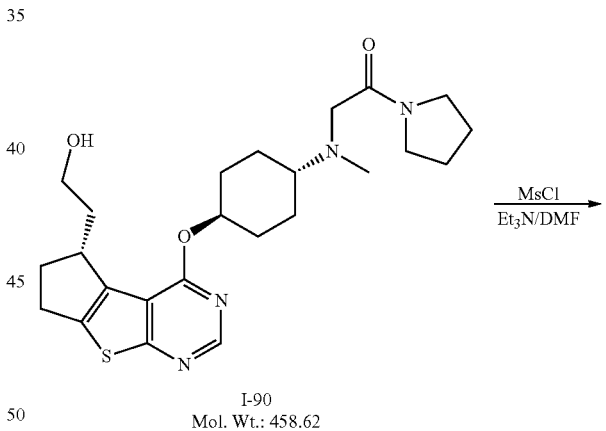

I-90
Mol. Wt.: 458.62

MsCl
Et$_3$N/DMF

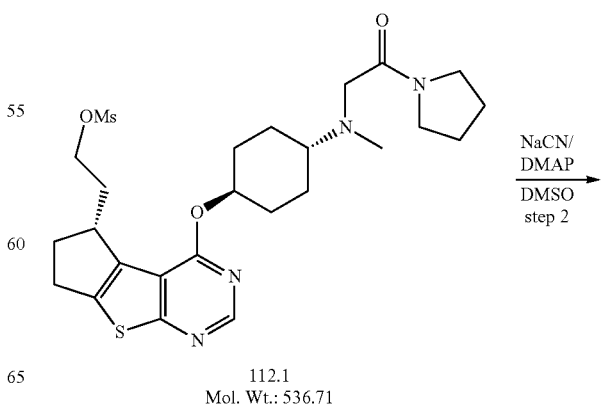

112.1
Mol. Wt.: 536.71

NaCN/
DMAP
DMSO
step 2

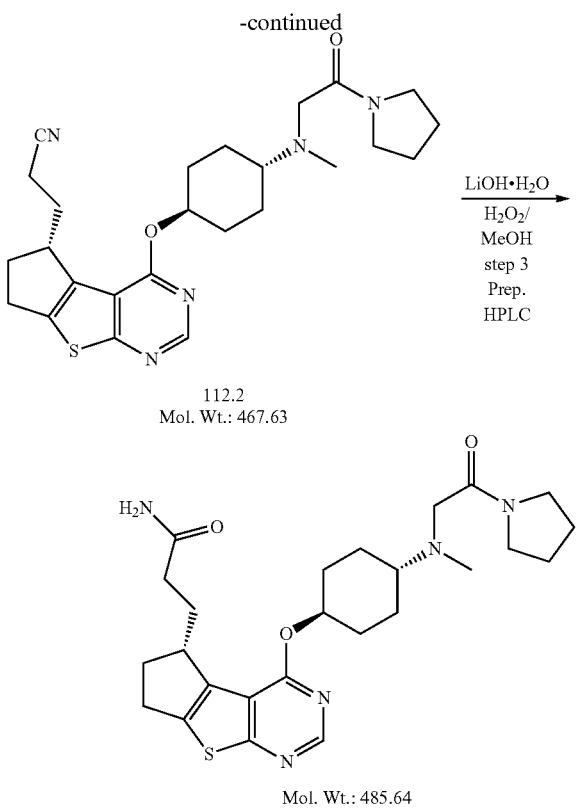

Synthesis of Compound 112.1. Note:

For the preparation of the starting material Compound I-90, please refer to Example 107. A 25-mL round-bottom flask, purged and maintained with an inert atmosphere of nitrogen, was charged with a solution of 2-[(4-[[(3R)-3-(2-hydroxyethyl)-7-thia-9,11-diazatricyclo[6.4.0.0[2,6]]dodeca-1(8),2(6),9,11-tetraen-12-yl]oxy]cyclohexyl)(methyl)amino]-1-(pyrrolidin-1-yl)ethan-1-one (100 mg, 0.22 mmol, 1.00 equiv) in 5 mL of distilled DMF. MsCl (38 mg, 0.33 mmol, 1.50 equiv) and triethylamine (66.7 mg, 0.66 mmol, 3.00 equiv) were added at 0° C. The resulting solution was stirred overnight at room temperature. The reaction was then quenched with water, extracted with DCM. The organic phase was washed with brine, dried over anhydrous sodium sulfate and concentrated under vacuum. The residue was purified by column chromatography on silica gel with DCM/MeOH (20:1 to 10:1) to give 2-[(3R)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]ethyl methanesulfonate (107 mg) as a white solid. MS (ES): m/z 537 [M+H]$^+$.

Synthesis of Compound 112.2.

To a solution of 2-[(3R)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]ethyl methanesulfonate (107 mg, 0.20 mmol, 1.00 equiv) in DMSO (5 mL) were added NaCN (58.8 mg, 1.20 mmol, 6.00 equiv) and 4-dimethylaminopyridine (2.4 mg, 0.02 mmol, 0.10 equiv) at room temperature. The resulting solution was stirred for 2 h at 80° C. After cooling to room temperature, the reaction was then quenched by the addition of aqueous FeSO$_4$ solution and extracted with DCM. The organic phase was washed with brine, dried over anhydrous sodium sulfate and concentrated under vacuum. The residue was applied onto a silica gel column with DCM/MeOH (10:1) to give the desired 3-[(3S)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]propanenitrile (80 mg, 86%) as a yellow solid. MS (ES): m/z 468 [M+H]$^+$.

Synthesis of Compound I-94.

A 25-mL round-bottom flask, purged and maintained with an inert atmosphere of nitrogen, was charged with a solution of 3-[(3S)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]propanenitrile (80 mg, 0.17 mmol, 1.00 equiv) in methanol (5 mL) and cooled to 0° C. Then LiOH.H$_2$O (22 mg, 0.52 mmol, 3.00 equiv) and H$_2$O$_2$ (30%, 0.3 mL) were added at 0° C. and the resulting solution was stirred for 2 h at the same temperature. The reaction was quenched by the addition of saturated aqueous Na$_2$SO$_3$ and extracted DCM. The organic phase was washed with brine, dried over anhydrous sodium sulfate and concentrated under vacuum. The residue was purified by preparative HPLC under the following conditions (SHIMADZU): column: SunFire Prep C18, 19*150 mm 5 um; mobile phase: water with 0.05% NH$_4$HCO$_3$ and CH$_3$CN (6.0% CH$_3$CN up to 50.0% in 16 min); flow rate: 20 mL/min; UV detection at 254/220 nm. The product-containing fractions were collected and partially evaporated to remove water and CH$_3$CN under reduced pressure. The residue was lyophilized overnight to give the desired 3-[(3S)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]propanamide (82.5 mg) as a white solid. MS (ES): m/z 486 [M+H]$^+$; $^1$H NMR (400 MHz, CD$_3$OD): δ 8.47 (1H, s), 5.32-5.22 (1H, m), 3.58 (2H, t), 3.45 (2H, t), 3.35 (2H, s), 3.20-3.09 (1H, m), 3.03-2.95 (1H, m), 2.73-2.65 (2H, m), 2.37 (3H, s), 2.33-2.19 (5H, m), 2.03-1.88 (6H, m), 1.66 (2H, m), 1.69-1.52 (4H, m).

Example 113

Synthesis of 2-[(3R)-12-[[4-(dimethylamino)-4-ethylcyclohexyl]oxy]-7-thia-9,11-diazatricyclo[6.4.0.0[2,6]]dodeca-1(8),2(6),9,11-tetraen-3-yl]acetamide (I-95)

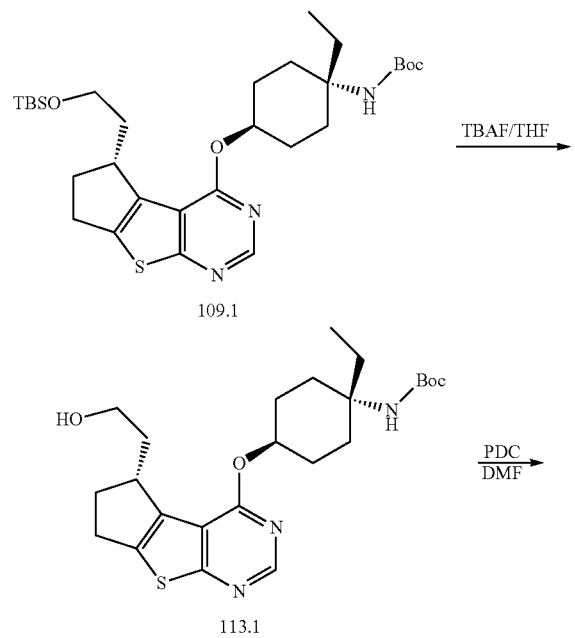

-continued

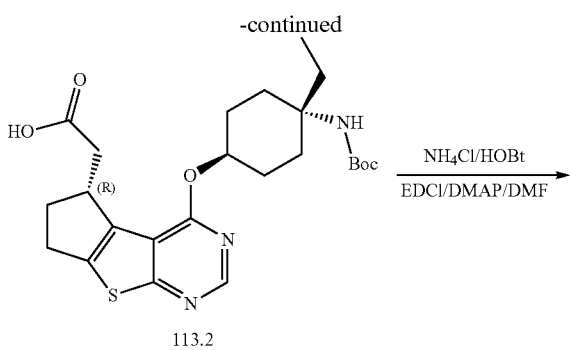

113.2

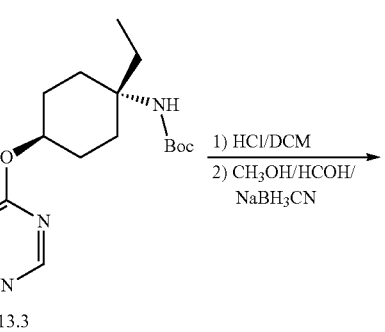

113.3

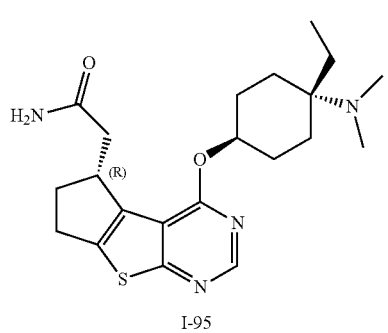

I-95

Synthesis of Compound 113.1.

To a 25-mL round-bottom flask containing a solution of tert-butyl N-(4-[[(3R)-3-[2-[(tert-butyldimethylsilyl)oxy]ethyl]-7-thia-9,11-diazatricyclo[6.4.0.0[2,6]]dodeca-1(8),2 (6),9,11-tetraen-12-yl]oxy]-1-ethylcyclohexyl)carbamate (240 mg, 0.42 mmol, 1.00 equiv) in 10 mL of THF was added TBAF·3H$_2$O (264 mg, 0.84 mmol, 2.01 equiv) at room temperature. The resulting solution was stirred for 3 h at this temperature and concentrated under reduced pressure. The residue was applied onto a silica gel column with ethyl acetate/petroleum ether (1:1) to give 180 mg (94%) of the desired tert-butyl N-(1-ethyl-4-[[(3R)-3-(2-hydroxyethyl)-7-thia-9,11-diazatricyclo[6.4.0.0[2,6]]dodeca-1(8),2 (6),9,11-tetraen-12-yl]oxy]cyclohexyl)carbamate as a colorless oil. MS: m/z 462 (M+H)$^+$.

Synthesis of Compound 113.2.

To a 50-mL round-bottom flask containing a solution of tert-butyl N-(1-ethyl-4-[[(3R)-3-(2-hydroxyethyl)-7-thia-9,11-diazatricyclo[6.4.0.0[2,6]]dodeca-1(8),2(6),9,11-tetraen-12-yl]oxy]cyclohexyl)carbamate (180 mg, 0.39 mmol, 1.00 equiv) in N,N-dimethylformamide (5 mL) was added PDC (716 mg, 1.90 mmol, 4.88 equiv) and the resulting solution was stirred for 14 hrs at 25° C. The reaction was then quenched by the addition of 20 mL of water and extracted with 3×50 mL of ethyl acetate. The combined organic layers were washed with brine, dried over sodium sulfate and concentrated under vacuum. The residue was applied onto a silica gel column with ethyl acetate/petroleum ether (1:1) to give the desired 2-[(3R)-12-[(4-[[(tert-butoxy)carbonyl]amino]-4-ethylcyclohexyl)oxy]-7-thia-9,11-diazatricyclo[6.4.0.0[2,6]]dodeca-1(8),2 (6),9,11-tetraen-3-yl]acetic acid (100 mg, 54%) as a colorless oil. MS (ES): m/z 476 [M+H]$^+$.

Synthesis of Compound 113.3.

To a solution of 2-[(3R)-12-[(4-[[(tert-butoxy)carbonyl]amino]-4-ethylcyclohexyl)oxy]-7-thia-9,11-diazatricyclo[6.4.0.0[2,6]]dodeca-1(8),2(6),9,11-tetraen-3-yl]acetic acid (100 mg, 0.21 mmol, 1.00 equiv) in 5 mL of distilled DMF was added HOBt (42.6 mg), EDCI (60 mg), 4-dimethylaminopyridine (38.2 mg) and NH$_4$Cl (56 mg, 1.05 mmol, 4.98 equiv) successively and the resulting solution was stirred for 14 hr at 25° C. under nitrogen. The reaction was then quenched with water and extracted with 3×50 mL of ethyl acetate. The organic layers were combined, washed with brine, dried over sodium sulfate and concentrated under vacuum. The residue was applied onto a silica gel column with ethyl acetate/petroleum ether (2:1) to give tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]-1-ethylcyclohexyl)carbamate (60 mg, 60%) as colorless oil. MS (ES): m/z 476 [M+H]$^+$.

Synthesis of Compound I-95.

To a 50-mL round-bottom flask containing a solution of tert-butyl N-(4-[[(3R)-3-(carbamoylmethyl)-7-thia-9,11-diazatricyclo[6.4.0.0[2,6]]dodeca-1(8),2 (6),9,11-tetraen-12-yl]oxy]-1-ethylcyclohexyl)carbamate (60 mg, 0.13 mmol, 1.00 equiv) in dichloromethane (4 mL) was added hydrochloric acid (8 M, 0.5 mL) at 0° C. The resulting solution was stirred for 1 hr at the same temperature. The reaction mixture was concentrated in vacuo to give the 2-[(3R)-12-[(4-amino-4-ethylcyclohexyl)oxy]-7-thia-9,11-diazatricyclo[6.4.0.0[2,6]]dodeca-1(8),2 (6),9,11-tetraen-3-yl]acetamide hydrochloride (50 mg, crude) as a white solid. The solid (50 mg, crude) was dissolved in 5 mL of methanol, HCHO (37%, 0.5 mL) was added and the solution was stirred at room temperature for 30 min. NaBH$_3$CN (22 mg) was added to the mixture and stirred overnight. The reaction was then quenched by the addition of 30 mL of water, extracted with 3×40 mL of chloroform/isopropanol. The combined organic layers were concentrated under vacuum. The crude product (50 mg) was purified by preparative HPLC under the following conditions (SHIMADZU): column: SunFire Prep C18, 19*150 mm 5 um; mobile phase: water with 50 mM NH$_4$HCO$_3$ and CH$_3$CN (6.0% CH$_3$CN up to 52.0% in 14 min); flow rate: 20 mL/min; UV detection at 254/220 nm. The product-containing fractions were collected and partially evaporated to remove water and CH$_3$CN under reduced pressure. The residue was lyophilized overnight to give the desired 2-[(3R)-12-[[4-(dimethylamino)-4-ethylcyclohexyl]oxy]-7-thia-9,11-diazatricyclo[6.4.0.0[2,6]]dodeca-1(8),2(6),9,11-tetraen-3-yl]acetamide (25.1 mg) as a white solid. MS (ES): m/z 403 [M+H]$^+$. $^1$H NMR (300 MHz, CD$_3$OD): 8.47 (1H, s), 5.29 (1H, m), 3.85-3.89 (1H, m), 2.9-3.20 (3H, m), 2.70-2.88 (1H, m), 2.22-2.46 (8H, m), 2.06-2.17 (2H, m), 1.65-1.93 (8H, m), 0.98-1.07 (3H, m).

Example 114

Synthesis of (R)-2-(R)-4-(((1r,4R)-4-(dimethylamino)cyclohexyl)oxy)-6,7-dihydro-5H-cyclopenta[4,5]thieno[2,3-d]pyrimidin-5-yl)-1-(1H-pyrazol-3-yl)ethanol (I-98) and Example 115: Synthesis of (S)-2-(R)-4-(((1r,4R)-4-(dimethylamino)cyclohexyl)oxy)-6,7-dihydro-5H-cyclopenta[4,5]thieno[2,3-d]pyrimidin-5-yl)-1-(1H-pyrazol-3-yl)ethanol (I-96)

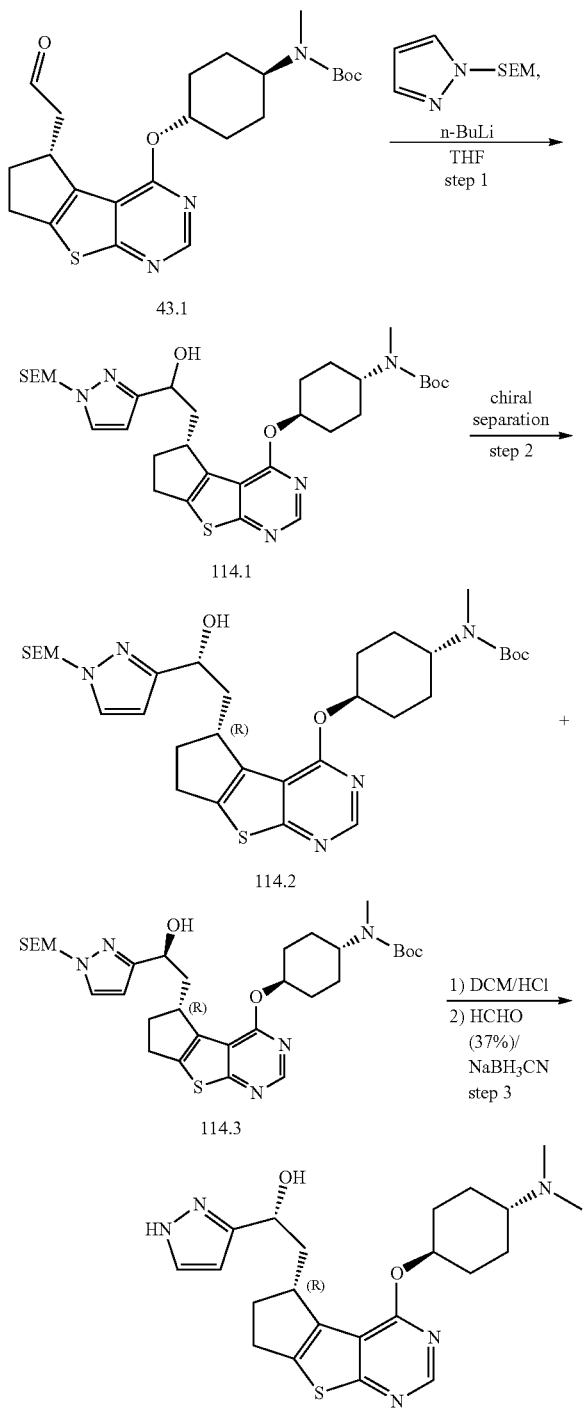

Synthesis of Compound 114.1. Note:

For the preparation of the starting material compound 43.1, please refer to Example 43. Into a 50-mL round-bottom flask purged and maintained with an inert atmosphere of nitrogen, 1-[[2-(trimethylsilyl)ethoxy]methyl]-1H-pyrazole (245 mg, 1.24 mmol, 1.20 equiv) in 20 mL of distilled THF was cooled down to −78° C. in liquid $N_2$/ethanol bath. n-BuLi (2.5 M in hexane, 0.536 mL) was added dropwise with stirring, which was continued for 1 h. Then a solution of tert-butyl N-methyl-N-(4-[[(3R)-3-(2-oxoethyl)-7-thia-9,11-diazatricyclo[6.4.0.0[2,6]]dodeca-1(8),2(6),9,11-tetraen-12-yl]oxy]cyclohexyl)carbamate (460 mg, 1.03 mmol, 1.00 equiv) in tetrahydrofuran (10 mL) was added dropwise −78° C. via syringe and the resulting mixture was stirred for 3 h at the same temperature. The reaction was quenched with saturated aqueous $NH_4Cl$ and extracted with 3×50 mL of ethyl acetate. The combined organic layers were washed with brine, dried over sodium sulfate and concentrated in vacuo. The residue was applied onto a silica gel column with ethyl acetate/petroleum ether (1:1) to give the desired product 114.1 (500 mg, 75%) as a white solid. The ratio of the isomers (27:73) was determined by chiral HPLC under the following conditions: CHIRALPAK AD-H, 0.46*25 cm, 5 um; mobile phase: hex: EtOH=90:10; flow rate: 1 mL/min; UV detection at 220/254 nm. MS (ES): m/z 644 [M+H]⁺.

Synthesis of Compound 114.2 and 114.3.

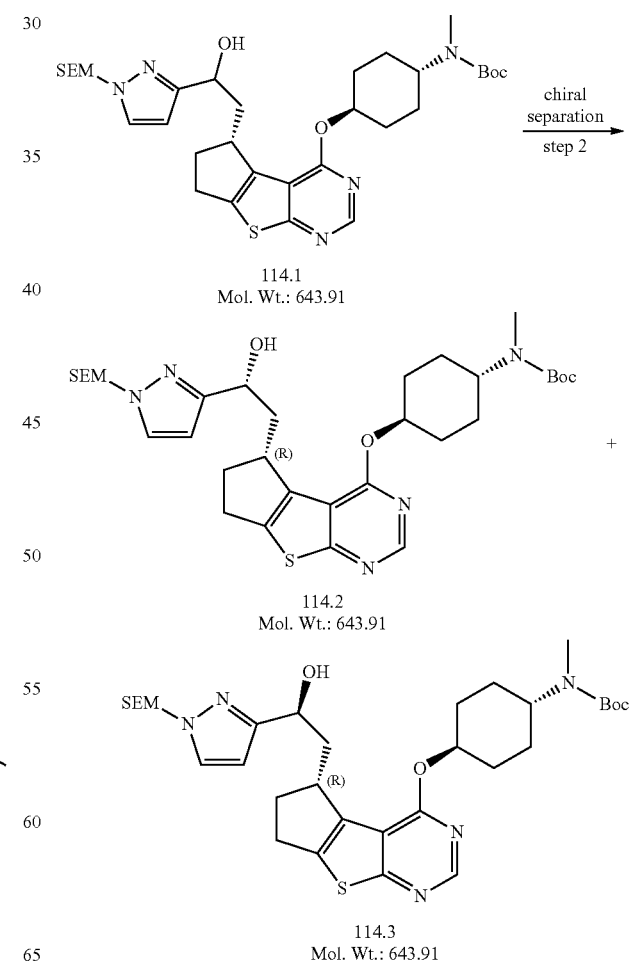

The racemate 114.1 (500 mg) was separated by chiral HPLC under the following conditions (Gilson Gx 281): column: Chiralpak AD-H, 2*25 cm; mobile phase, hexane (HPLC grade):EtOH(HPLC grade)=90:10; flow rate: 20 mL/min; UV detection at 220/254 nm. The former fractions were collected and evaporated under reduced pressure to give tert-butyl N-(4-[[(3R)-3-[(2R)-2-hydroxy-2-(1-[[2-(trimethylsilyl)ethoxy]methyl]-1H-pyrazol-3-yl)ethyl]-7-thia-9,11-diazatricyclo[6.4.0.0[2,6]]dodeca-1(8),2(6),9,11-tetraen-12-yl]oxy]cyclohexyl)-N-methylcarbamate (70 mg) as a white solid with 99% ee and the latter fractions were concentrated to provide the desired tert-butyl N-(4-[[(3R)-3-[(2S)-2-hydroxy-2-(1-[[2-(trimethylsilyl)ethoxy]methyl]-1H-pyrazol-3-yl)ethyl]-7-thia-9,11-diazatricyclo[6.4.0.0[2,6]]dodeca-1(8),2(6),9,11-tetraen-12-yl]oxy]cyclohexyl)-N-methylcarbamate (180 mg) as a white solid with 99.7% ee. The ee values of the isomers were determined by chiral HPLC under the following conditions: CHIRALPAK IA, 0.46*25 cm, 5 um; mobile phase: Hex:IPA=90:10; flow rate: 1 mL/min; UV detection at 220/254 nm.

Synthesis of Compound I-98.

A solution of tert-butyl N-(4-[[(3R)-3-[(2R)-2-hydroxy-2-(1-[[2-(trimethylsilyl)ethoxy]methyl]-1H-pyrazol-3-yl)ethyl]-7-thia-9,11-diazatricyclo[6.4.0.0[2,6]]dodeca-1(8),2(6),9,11-tetraen-12-yl]oxy]cyclohexyl)-N-methylcarbamate (70 mg, 0.11 mmol, 1.00 equiv) in dichloromethane (10 mL) was added hydrochloric acid (2 M, 1 mL) with stirring at 0° C. The resulting solution was stirred for 24 h at room temperature and concentrated under vacuum to give 60 mg of the crude (1R)-2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]-1-(1H-pyrazol-3-yl)ethan-1-ol hydrochloride as a yellow solid. The crude hydrochloride in 5 mL of methanol was added HCHO (37%, 0.5 mL) and the reaction solution was stirred at room temperature for 30 min. The NaBH₃CN (18 mg, 0.30 mmol, 3.10 equiv) was added to the mixture and the resulting solution was stirred for 4 h at ambient temperature. After concentration in vacuo, the crude product was purified by preparative HPLC under the following conditions (Waters): column: X-briage C18, 19*150 mm 5 um; mobile phase, CH₃CN and water with 20 mM NH₄HCO₃ (10.0% CH₃CN up to 50.0% in 10 min, up to 95% in 2 min, down to 10.0% in 2 min); flow rate: 20 mL/min; UV detection at 254/220 nm. The product-containing fractions were collected and partially evaporated to remove water and CH₃CN under reduced pressure. The residue was lyophilized overnight to give the desired (1R)-2-[(3R)-12-[[4-(dimethylamino)cyclohexyl]oxy]-7-thia-9,11-diazatricyclo[6.4.0.0[2,6]]dodeca-1(12),2(6),8,10-tetraen-3-yl]-1-(1H-pyrazol-3-yl)ethan-1-ol (26 mg) as a white solid. MS (ES): m/z 428 [M+H]⁺. ¹H NMR (400 MHz, CD₃OD): δ 8.46 (s, 1H), 7.50 (s, 1H), 6.27 (s, 1H), 5.25-5.29 (m, 1H), 3.67-3.71 (m, 1H), 3.01-3.15 (m, 1H), 2.97-3.00 (m, 1H), 2.57-2.65 (m, 3H), 2.46 (s, 6H), 2.30-2.34 (m, 3H), 2.08-2.10 (m, 2H), 1.90-1.92 (m, 1H), 1.85-1.89 (m, 2H), 1.53-1.59 (m, 2H), 1.30-1.37 (m, 1H). Synthesis of Compound I-96. To a solution of tert-butyl N-(4-[[(3R)-3-[(2S)-2-hydroxy-2-(1-[[2-(trimethylsilyl)ethoxy]methyl]-1H-pyrazol-3-yl)ethyl]-7-thia-9,11-diazatricyclo[6.4.0.0[2,6]]dodeca-1(8),2(6),9,11-tetraen-12-yl]oxy]cyclohexyl)-N-methylcarbamate (180 mg, 0.28 mmol, 1.00 equiv) in dichloromethane (10 mL) was added hydrochloric acid (12 M, 1 mL) with stirring at 0° C. The resulting solution was stirred for 24 h at room temperature and concentrated under vacuum to give 160 mg of the crude (1S)-2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]-1-(1H-pyrazol-3-yl)ethan-1-ol hydrochloride as a yellow solid. The crude hydrochloride in 5 mL of methanol was added HCHO (37%, 0.5 mL) and the reaction solution was stirred at room temperature for 30 min. The NaBH₃CN (46 mg, 0.73 mmol, 3.0 equiv) was added to the mixture and the resulting solution was stirred for 4 h at ambient temperature. After concentration in vacuo, the crude product was purified by preparative HPLC under the following conditions (Waters): column: X-briage C18, 19*150 mm 5 um; mobile phase, CH₃CN and water with 20 mM NH₄HCO₃ (10.0% CH₃CN up to 50.0% in 10 min, up to 95% in 2 min, down to 10.0% in 2 min); flow rate: 20 mL/min; UV detection at 254/220 nm. The product-containing fractions were collected and partially evaporated to remove water and CH₃CN under reduced pressure. The residue was lyophilized overnight to give the desired (1S)-2-[(3R)-12-[[4-(dimethylamino)cyclohexyl]oxy]-7-thia-9,11-diazatricyclo[6.4.0.0[2,6]]dodeca-1(12),2(6),8,10-tetraen-3-yl]-1-(1H-pyrazol-3-yl)ethan-1-ol (65.9 mg) as a white solid. MS (ES): m/z 428 [M+H]⁺. ¹H NMR (400 MHz, CD₃OD): δ 8.45 (s, 1H), 7.65 (s, 1H), 6.35 (s, 1H), 5.23-5.25 (m, 1H), 4.92-4.95 (m, 1H), 3.36-3.38 (m, 1H), 3.10-3.15 (m, 1H), 2.93-2.98 (m, 1H), 2.71-2.74 (m, 1H), 2.51-2.52 (m, 2H), 2.48 (s, 6H), 2.15-2.17 (m, 2H), 1.89-2.03 (m, 3H), 1.44-1.49 (m, 4H).

Example 116

Synthesis of 2-hydroxy-3-((R)-4-(((1r,4R)-4-morpholinocyclohexyl)amino)-6,7-dihydro-5H-cyclopenta[4,5]thieno[2,3-d]pyrimidin-5-yl)propanamide (I-118)

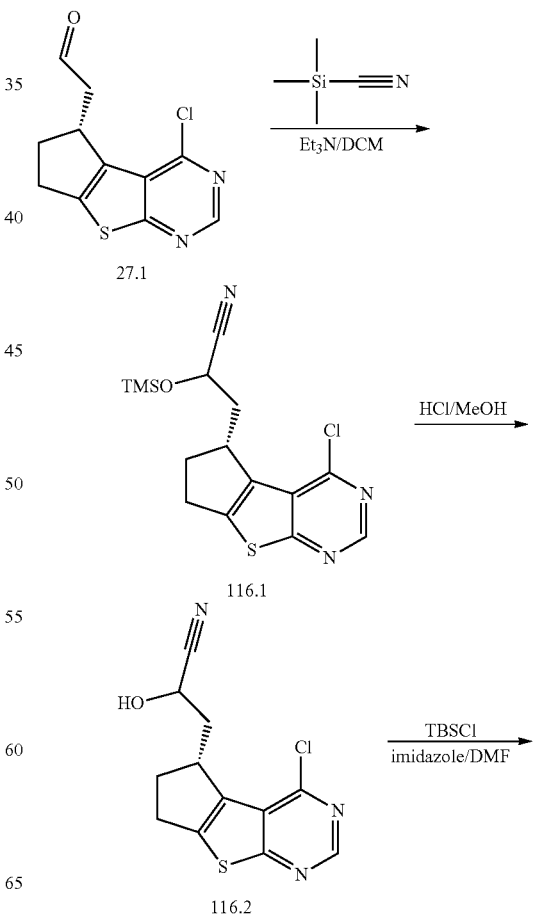

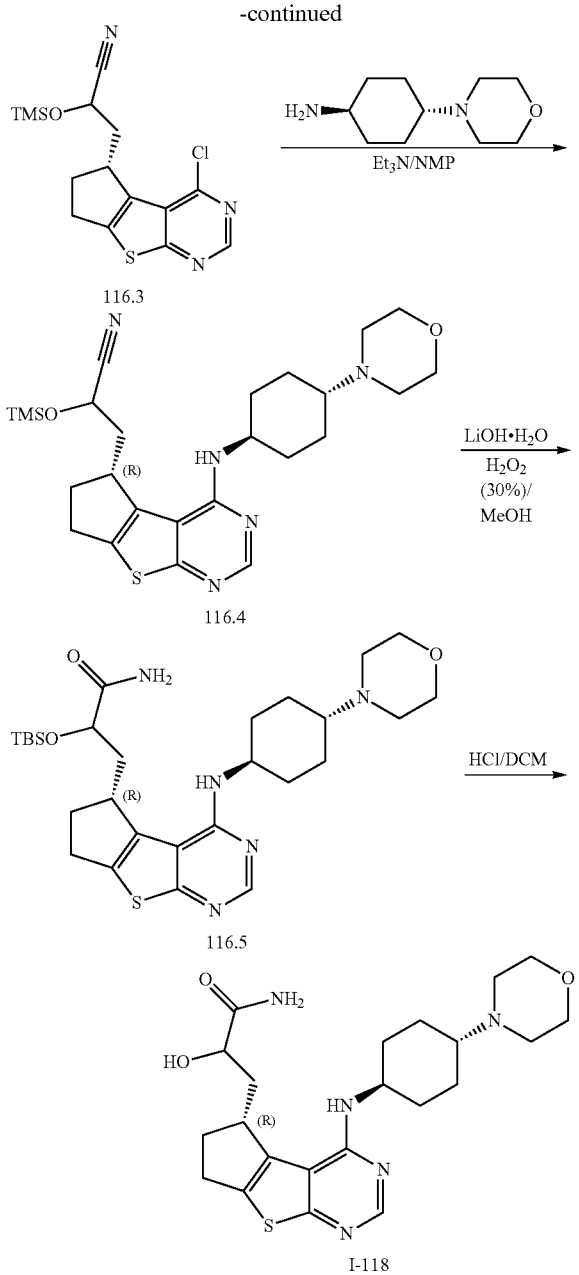

[(trimethylsilyl)oxy]propanenitrile (240 mg, 0.68 mmol, 1.00 equiv) in methanol (5 mL) was added 1 mL of concentrated hydrochloric acid at 0° C. After stirring for 1 h at room temperature, the pH value of the solution was adjusted to 10 with saturated aqueous sodium bicarbonate, diluted with DCM, washed with brine, dried over anhydrous sodium sulfate and concentrated under vacuum to give 170 mg (89%) of 3-[(3R)-12-chloro-7-thia-9,11-diazatricyclo[6.4.0.0ˆ[2,6]]dodeca-1(12),2(6),8,10-tetraen-3-yl]-2-hydroxypropanenitrile as a white solid. MS: m/z 280 (M+H)⁺.

Synthesis of Compound 116.3.

To a solution of 3-[(3R)-12-chloro-7-thia-9,11-diazatricyclo[6.4.0.0ˆ[2,6]]dodeca-1(12),2(6),8,10-tetraen-3-yl]-2-hydroxypropanenitrile (170 mg, 0.61 mmol, 1.00 equiv) in 5 mL of distilled DMF was added tert-butyl(chloro)dimethylsilane (138 mg, 0.92 mmol, 1.50 equiv) and imidazole (124 mg, 1.82 mmol, 3.00 equiv) at room temperature under nitrogen. The resulting solution was stirred for 2 h at ambient temperature and diluted with DCM (30 mL), washed with brine, dried over anhydrous sodium sulfate and concentrated under vacuum to give 236 mg (99%) of 2-[(tert-butyldimethylsilyl)oxy]-3-[(3R)-12-chloro-7-thia-9,11-diazatricyclo[6.4.0.0[2,6]]dodeca-1(12),2(6),8,10-tetraen-3-yl]propanenitrile as a white solid. MS: m/z 395 (M+H)⁺.

Synthesis of Compound 116.4.

To a solution of 2-[(tert-butyldimethylsilyl)oxy]-3-[(3R)-12-chloro-7-thia-9,11-diazatricyclo[6.4.0.0ˆ[2,6]]dodeca-1(12),2(6),8,10-tetraen-3-yl]propanenitrile (150 mg, 0.38 mmol, 1.00 equiv) in NMP (1 mL) was added triethylamine (310 mg, 3.06 mmol, 8.00 equiv) and 4-(morpholin-4-yl)cyclohexan-1-amine (560 mg, 3.04 mmol, 8.00 equiv) at room temperature. The resulting solution was stirred overnight at 75° C. under nitrogen. After cooling to room temperature, the resulting solution was diluted with DCM (30 mL), washed with brine, dried over anhydrous sodium sulfate and concentrated under vacuum. The residue was applied onto a silica gel column with dichloromethane/methanol (20:1) to give 185 mg (90%) of 2-[(tert-butyldimethylsilyl)oxy]-3-[(3R)-12-[[4-(morpholin-4-yl)cyclohexyl]amino]-7-thia-9,11-diazatricyclo[6.4.0.0[2,6]]dodeca-1(12),2(6),8,10-tetraen-3-yl]propanenitrile as a white solid. MS: m/z 542 (M+H)⁺.

Synthesis of Compound 116.5.

To a solution of 2-[(tert-butyldimethylsilyl)oxy]-3-[(3R)-12-[[4-(morpholin-4-yl)cyclohexyl]amino]-7-thia-9,11-diazatricyclo[6.4.0.0[2,6]]dodeca-1(12),2(6),8,10-tetraen-3-yl]propanenitrile (180 mg, 0.33 mmol, 1.00 equiv) in methanol (5 mL) was added LiOH.H₂O (40 mg, 0.95 mmol, 3.00 equiv) and 0.5 mL of H₂O₂ (30%) at 0° C. The resulting solution was stirred for 1 h at 0° C. and then quenched with saturated aqueous Na₂SO₃, diluted with DCM (30 mL), washed with brine, dried over anhydrous sodium sulfate and concentrated under vacuum. The residue was applied onto a silica gel column with dichloromethane/methanol (20:1) to give 130 mg (70%) of 2-[(tert-butyldimethylsilyl)oxy]-3-[(3R)-12-[[4-(morpholin-4-yl)cyclohexyl]amino]-7-thia-9,11-diazatricyclo[6.4.0.0[2,6]]dodeca-1(12),2(6),8,10-tetraen-3-yl]propanamide as a white solid. MS: m/z 560 (M+H)⁺.

Synthesis of compound I-118.

To a solution of 2-[(tert-butyldimethylsilyl)oxy]-3-[(3R)-12-[[4-(morpholin-4-yl)cyclohexyl]amino]-7-thia-9,11-diazatricyclo[6.4.0.0[2,6]]dodeca-1(12),2(6),8,10-tetraen-3-yl]propanamide (200 mg, 0.36 mmol, 1.00 equiv) in methanol (5 mL) was added hydrochloric acid (0.5 mL) and stirred for 2 h at room temperature. After completion of the reaction, the pH value of the mixture was adjusted to 10 with Synthesis of Compound 116.1.

To a solution of compound 27.1 (140 mg, 0.55 mmol, 1.00 equiv) in dichloromethane (5 mL) was added trimethylsilanecarbonitrile (168 mg, 1.69 mmol, 3.00 equiv) and triethylamine (28 mg, 0.28 mmol, 0.50 equiv) at 0° C. under nitrogen. The resulting solution was stirred for 1 h at 0° C. until the starting aldehyde disappeared. The resulting mixture was diluted with DCM, washed with saturated aqueous sodium bicarbonate, dried over anhydrous sodium sulfate and concentrated under vacuum. The residue was applied onto a silica gel column with ethyl acetate/petroleum ether (1:10) to provide 155 mg of 3-[(3R)-12-chloro-7-thia-9,11-diazatricyclo[6.4.0.0[2,6]]dodeca-1(12),2(6),8,10-tetraen-3-yl]-2-[(trimethylsilyl)oxy]propanenitrile (contains de-TMS alcohol 116.2) as a white solid. MS: m/z 352 (M+H)⁺.

Synthesis of Compound 116.2.

To a solution of 3-[(3R)-12-chloro-7-thia-9,11-diazatricyclo[6.4.0.0ˆ[2,6]]dodeca-1(12),2(6),8,10-tetraen-3-yl]-2- saturated aqueous sodium bicarbonate, diluted with DCM (30 mL), washed with brine, dried over anhydrous sodium sulfate and concentrated under vacuum. The residue was applied onto a silica gel column with dichloromethane/methanol (20:1) to give 140 mg (88%) of Compound I-118 as a white solid. MS: m/z 446 (M+H)$^+$.

Example 117

Synthesis of (S)-2-hydroxy-3-((R)-4-(((1r,4R)-4-morpholinocyclohexyl)amino)-6,7-dihydro-5H-cyclopenta[4,5]thieno[2,3-d]pyrimidin-5-yl)propanamide (I-120) and (R)-2-hydroxy-3-((R)-4-(((1r,4R)-4-morpholinocyclohexyl)amino)-6,7-dihydro-5H-cyclopenta[4,5]thieno[2,3-d]pyrimidin-5-yl)propanamide (I-121)

100% ee as a white solid. The ee value ($t_R$=26.363 min) was determined under the following conditions (SHIMADZU): column: Chiralpak IC, 0.46*25 cm, 5 um; mobile phase: hexanes (0.1% TEA): EtOH=75:25; UV detection at 254 nm. Flow rate: 1.0 mL/min. MS: m/z 446 (M+H)$^+$. $^1$H NMR (400 MHz, CD$_3$OD): δ 8.23 (s, 1H), 4.21-4.11 (M, 1H), 4.10 (t, 1H), 3.80-3.60 (m, 5H), 3.20-3.05 (m, 1H), 3.01-2.85 (m, 1H), 2.74-2.65 (m, 5H), 2.45-2.23 (m, 2H), 2.25-1.95 (m, 6H), 1.78-1.43 (m, 4H). The fractions containing Compound I-121 were collected and evaporated under reduced pressure and lyophilized overnight to afford the compound I-121 (83 mg) with 99.6% ee as a white solid. The ee value (tR=31.755 min) was determined by the same conditions. MS: m/z 445 (M+H)$^+$. $^1$H NMR (400 MHz, CD$_3$OD): δ 8.24 (s, 1H), 4.19-4.14 (M, 1H), 4.12 (dd, 1H), 3.75-3.73 (m, 4H), 3.65-3.57 (m, 1H), 3.17-3.09 (m, 1H), 2.99-2.92 (m, 1H), 2.76-2.66 (m, 5H), 2.51-2.37 (m, 2H), 2.22-2.07 (m, 4H), 2.00-1.92 (m, 1H), 1.80-1.72 (m, 1H), 1.68-1.43 (m, 4H).

Example 118

Synthesis of Intermediate 118.7

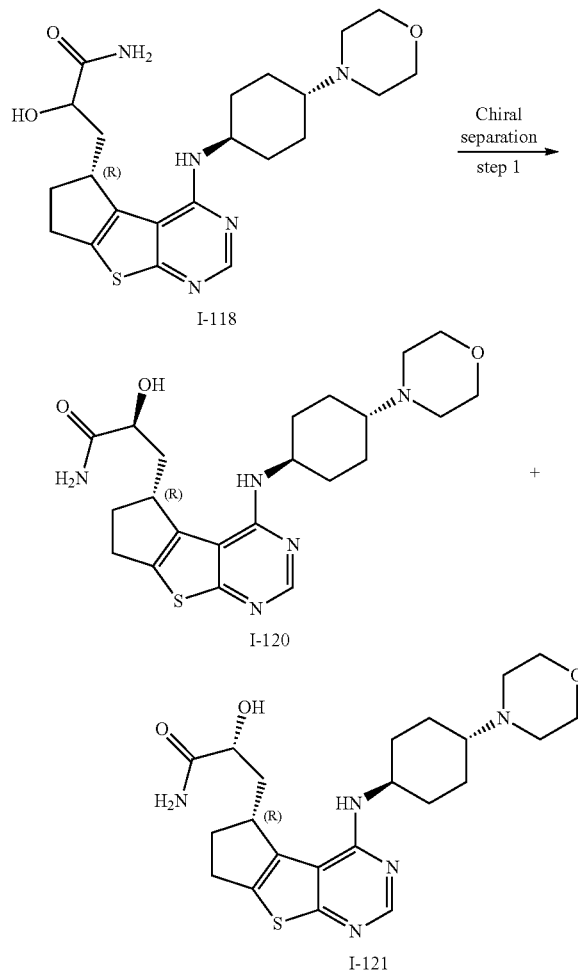

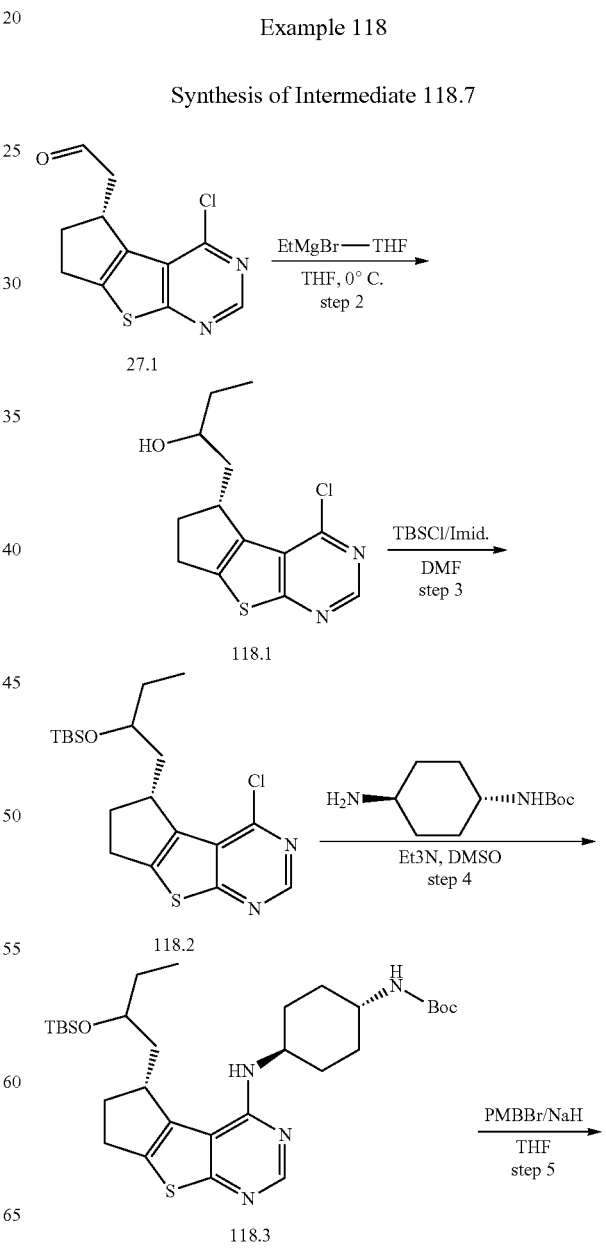

Synthesis of compounds I-120 and I-121.

The enantiomers of racemic Compound I-118 (250 mg) were separated by preparative chiral HPLC under the following conditions (Gilson Gx281): column: Chiralpak IC, 2*25 cm, 5 um; mobile phase: phase A: hexanes (0.2% TEA, HPLC grade), phase B: EtOH (0.2% TEA, HPLC grade), gradient: 20% B in 30 min; flow rate: 17 mL/min; UV detection at 220/254 nm. The fractions containing Compound I-120 were collected and evaporated under reduced pressure and lyophilized overnight to afford Compound I-120 (113 mg) with

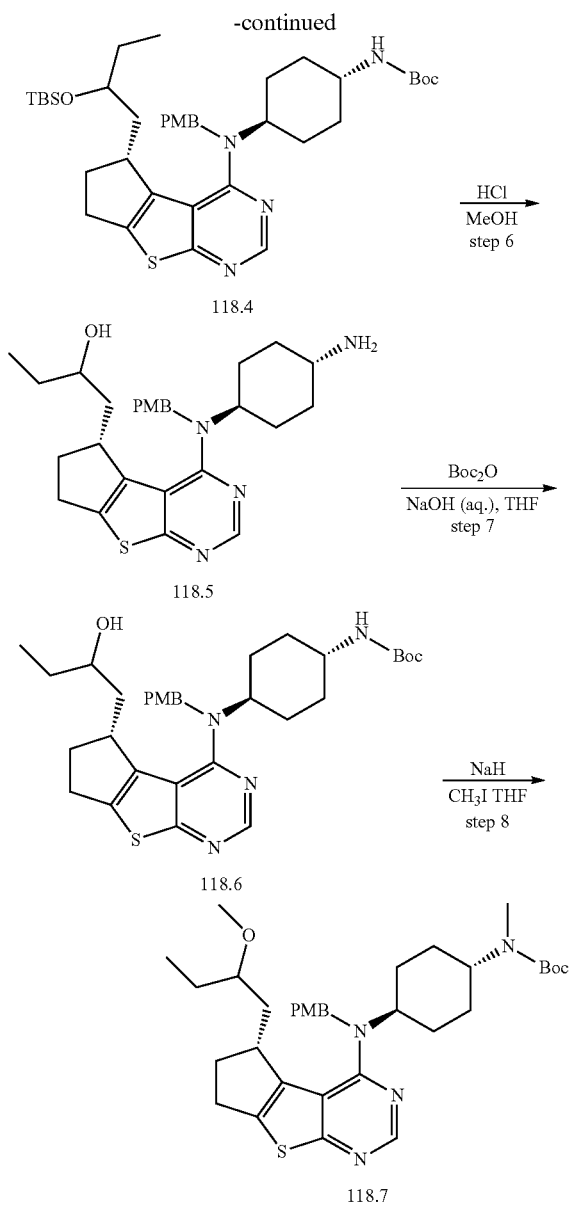

Synthesis of Compound 118.1.

A solution of 2-[(3R)-12-chloro-7-thia-9,11-diazatricyclo[6.4.0.0[2,6]]dodeca-1(8),2(6),9,11-tetraen-3-yl]acetaldehyde (450 mg, 1.78 mmol, 1.00 equiv) in tetrahydrofuran (10 mL) was stirred at 0° C. Then EtMgBr (3.4 mL, 1 N in THF) was added at −10° C. The resulting solution was stirred for 3 h at −10° C. The reaction was then quenched by the addition of 10 mL of water. The resulting solution was extracted with 3×60 mL of ethyl acetate and the organic layers combined and concentrated under vacuum. The residue was applied onto a silica gel column with ethyl acetate/petroleum ether (1:5). This resulted in 450 mg (89%) of 1-[(3R)-12-chloro-7-thia-9,11-diazatricyclo[6.4.0.0[2,6]]dodeca-1(8),2(6),9,11-tetraen-3-yl]butan-2-ol as a colorless oil.

Synthesis of Compound 118.2.

A solution of 1-[(3R)-12-chloro-7-thia-9,11-diazatricyclo[6.4.0.0[2,6]]dodeca-1(8),2(6),9,11-tetraen-3-yl]butan-2-ol (450 mg, 1.59 mmol, 1.00 equiv), imidazole (195 mg, 2.86 mmol, 1.80 equiv) and TBSCl (357 mg, 2.38 mmol, 1.50 equiv) in N,N-dimethylformamide (7 mL) was stirred at room temperature for 4 h. The reaction was then quenched by the addition of 10 mL of water. The resulting solution was extracted with 3×60 mL of ethyl acetate and the organic layers combined. The resulting mixture was washed with 3×40 mL of water. The solvent was removed. The residue was applied onto a silica gel column and eluted with PE/EA (10:1). This resulted in 480 mg (76%) of (3R)-3-[2-[(tert-butyldimethylsilyl)oxy]butyl]-12-chloro-7-thia-9,11-diazatricyclo[6.4.0.0[2,6]]dodeca-1(8),2(6),9,11-tetraene as a colorless oil.

Synthesis of Compound 118.3.

A solution of (3R)-3-[2-[(tert-butyldimethylsilyl)oxy]butyl]-12-chloro-7-thia-9,11-diazatricyclo[6.4.0.0[2,6]]dodeca-1(8),2(6),9,11-tetraene (480 mg, 1.21 mmol, 1.00 equiv), triethylamine (350 mg, 3.46 mmol, 2.86 equiv) and tert-butyl N-(4-aminocyclohexyl)carbamate (760 mg, 3.55 mmol, 2.93 equiv) in DMSO (5 mL) was stirred overnight at 60° C. The reaction was then quenched by the addition of 15 mL of water. The resulting solution was extracted with 3×70 mL of ethyl acetate and the organic layers combined. The resulting mixture was washed with 3×40 mL of water. The resulting mixture was concentrated under vacuum. The residue was applied onto a silica gel column with ethyl acetate/petroleum ether (1:5). This resulted in 800 mg (crude) of tert-butyl N-(4-[[(3R)-3-[2-[(tert-butyldimethylsilyl)oxy]butyl]-7-thia-9,11-diazatricyclo[6.4.0.0[2,6]]dodeca-1(8),2(6),9,11-tetraen-12-yl]amino]cyclohexyl)carbamate as a white solid. MS: m/z 575 (M+H)+.

Synthesis of Compound 118.4.

A solution of tert-butyl-N-(4-[[(3R)-3-[2-[(tert-butyldimethylsilyl)oxy]butyl]-7-thia-9,11-diazatricyclo[6.4.0.0[2,6]]dodeca-1(8),2(6),9,11-tetraen-12-yl]amino]cyclohexyl)carbamate (800 mg, 1.39 mmol, 1.00 equiv) in tetrahydrofuran (20 mL) was stirred at 0° C. This was followed by the addition of sodium hydride (134 mg, 3.35 mmol, 2.41 equiv) at 0° C. The resulting solution was stirred for 30 min at 0° C. To this was added PMBBr (1.397 g, 6.95 mmol, 4.99 equiv). The resulting solution was allowed to react, with stirring, overnight at 50° C. The reaction was then quenched by the addition of 20 mL of water. The resulting solution was extracted with 3×80 mL of ethyl acetate and the organic layers combined and concentrated under vacuum. The residue was applied onto a silica gel column with dichloromethane/methanol (20:1). This resulted in 650 mg (67%) of tert-butyl N-(4-[[(3R)-3-[2-[(tert-butyldimethylsilyl)oxy]butyl]-7-thia-9,11-diazatricyclo[6.4.0.0[2,6]]dodeca-1(8),2(6),9,11-tetraen-12-yl][(4-methoxyphenyl)methyl]amino]cyclohexyl)carbamate as a yellow solid. MS: m/z 695 (M+H)+.

Synthesis of Compound 118.5.

A solution of tert-butyl N-(4-[[(3R)-3-[2-[(tert-butyldimethylsilyl)oxy]butyl]-7-thia-9,11-diazatricyclo[6.4.0.0[2,6]]dodeca-1(12),2 (6), 8,10-tetraen-12-yl][(4-methoxyphenyl)methyl]amino]cyclohexyl)carbamate (480 mg, 0.69 mmol, 1.00 equiv) in methanol (8 mL) was stirred at room temperature and hydrogen chloride (5 N) (3 mL) was added to the mixture. The resulting solution was stirred for 5 h at room temperature. The reaction was then quenched by the addition of 20 mL of sodium bicarbonate (sat.). The resulting solution was extracted with 3×50 mL of ethyl acetate and the organic layers combined and concentrated under vacuum. This resulted in 300 mg (90%) of 1-[(3R)-12-[(4-aminocyclohexyl)[(4-methoxyphenyl)methyl]amino]-7-thia-9,11-diazatricyclo[6.4.0.0[2,6]]dodeca-1(12),2(6),8,10-tetraen-3-yl]butan-2-ol as a white solid.

Synthesis of Compound 118.6.

A solution of 1-[(3R)-12-[(4-amino cyclohexyl)amino]-7-thia-9,11-diazatricyclo[6.4.0.0[2,6]]dodeca-1(8),2 (6),9,11-tetraen-3-yl]butan-2-ol (250 mg, 0.69 mmol, 1.00 equiv) and Boc₂O (215 mg, 0.99 mmol, 1.42 equiv) in tetrahydrofuran (15 mL) was stirred at room temperature and then a solution of sodium hydroxide (39 mg, 0.97 mmol, 1.41 equiv) in water (3.5 mL) was added to the mixture. The resulting solution was stirred for 3 h at room temperature. The reaction was then quenched by the addition of 10 mL of NH₄Cl(aq.). The resulting solution was extracted with 4×30 mL of ethyl acetate and the organic layers combined and concentrated under vacuum. The residue was applied onto a silica gel column with DCM/MeOH (10/1). This resulted in 110 mg (34%) of tert-butyl N-(4-[[(3R)-3-(2-hydroxybutyl)-7-thia-9,11-diazatricyclo[6.4.0.0[2,6]]dodeca-1(8),2 (6),9,11-tetraen-12-yl]amino]cyclohexyl)carbamate as a yellow solid.

Synthesis of Compound 118.7.

A solution of tert-butyl N-(4-[[(3R)-3-(2-hydroxybutyl)-7-thia-9,11-diazatricyclo[6.4.0.0[2,6]]dodeca-1(12),2(6),8,10-tetraen-12-yl][(4-methoxyphenyl)methyl]amino]cyclohexyl)carbamate (200 mg, 0.34 mmol, 1.00 equiv) in tetrahydrofuran (26 mg, 0.36 mmol, 1.05 equiv) was stirred at 0° C., sodium hydride (69 mg, 2.88 mmol, 8.35 equiv) was added to the mixture, the reaction was stirred for 30 min. Then iodomethane (122 mg) was added too. The resulting solution was stirred for 3 h at 0° C. The reaction was then quenched by the addition of 50 mL of water. The resulting solution was extracted with 3×50 mL of ethyl acetate and the organic layers combined and concentrated under vacuum. The residue was applied onto a silica gel column with dichloromethane/methanol (10/1). This resulted in 200 mg (98%) of tert-butyl N-(4-[[(3R)-3-(2-methoxybutyl)-7-thia-9,11-diazatricyclo[6.4.0.0[2,6]]dodeca-1(12),2(6),8,10-tetraen-12-yl][(4-methoxyphenyl)methyl]amino]cyclohexyl)carbamate as a yellow solid.

Example 119

Synthesis of (1r,4R)—N-1-((R)-5-(R)-2-methoxybutyl)-6,7-dihydro-5H-cyclopenta[4,5]thieno[2,3-d]pyrimidin-4-yl)-N4,N4-dimethylcyclohexane-1,4-diamine (I-147) and (1r,4R)—N-1-((R)-5-((S)-2-methoxybutyl)-6,7-dihydro-5H-cyclopenta[4,5]thieno[2,3-d]pyrimidin-4-yl)-N4,N4-dimethylcyclohexane-1,4-diamine (1-148)

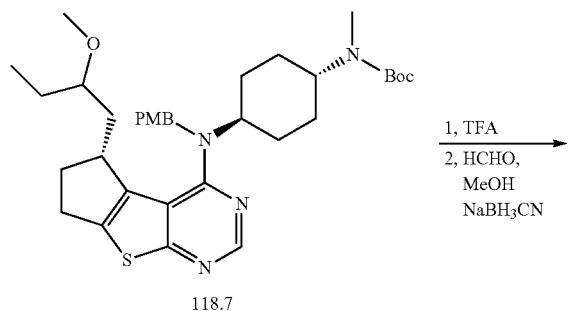

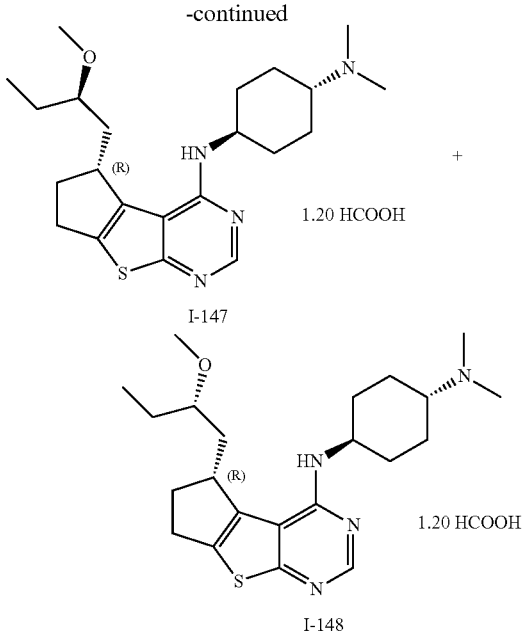

Synthesis of Compound I-147 and I-148.

A solution of tert-butyl N-(4-[[(3R)-3-(2-methoxybutyl)-7-thia-9,11-diazatricyclo[6.4.0.0[2,6]]dodeca-1(8),2(6),9,11-tetraen-12-yl][(4-methoxyphenyl)methyl]amino]cyclohexyl)carbamate (200 mg, 0.34 mmol, 1.00 equiv) in trifluoroacetic acid (5 mL) was heated to reflux for 2 hr. The resulting mixture was concentrated under vacuum. This resulted in 120 mg (crude) of 1-N-[(3R)-3-(2-methoxybutyl)-7-thia-9,11-diazatricyclo[6.4.0.0[2,6]]dodeca-1(8),2(6),9,11-tetraen-12-yl]cyclohexane-1,4-diamine as a colorless oil. It was not purified for the next reaction.

A solution of 1-N-[(3R)-3-(2-methoxybutyl)-7-thia-9,11-diazatricyclo[6.4.0.0[2,6]]dodeca-1(12),2(6),8,10-tetraen-12-yl]cyclohexane-1,4-diamine (120 mg, 0.33 mmol, 1.00 equiv) and HCHO (37%) (1.0 mL) in MeOH (6 mL). The resulting solution was stirred for 0.5 h at room temperature. Then NaBH₃CN (66.0 mg, 1.05 mmol, 3.17 equiv) was added. The resulting solution was allowed to react, with stirring, for an additional 3 h at room temperature. The crude product (70 mg) was purified by preparative HPLC under the following conditions (1#-Pre-HPLC-001(SHIMADZU)): column: Xbridge Prep C18 5 um, 19*150 mm; mobile phase: water with 0.05% NH₄HCO₃ and CH₃CN (6.0% CH₃CN up to 50.0% in 25 min); Detector, 254/220 nm. This resulted in 11.2 mg of Compound I-147 as a yellow solid and 17.7 mg of Compound I-148.

Analytical data for I-147: MS: m/z 403 (M−1.2HCOOH+ H)⁺. ¹H NMR (400 Hz, CD₃OD): δ 8.48 (2H, br s), 4.19 (1H, m), 3.50 (1H, m), 3.33 (3H, m), 3.11 (1H, m), 2.91 (7H, m), 2.72 (1H, m), 2.35 (2H, m), 2.28 (2H, m), 1.95 (1H, m), 1.70-1.89 (7H, m), 0.94 (3H, t).

Analytical data for I-148: MS: m/z 403 (M−1.29HCOOH+ H)⁺. ¹H NMR (400 Hz, CD₃OD): δ 8.48 (2.28H, br s), 4.19 (1H, m) 3.50 (1H, m), 3.33 (3H, m), 3.11 (1H, m), 2.91 (7H, m), 2.72 (1H, m), 2.27 (5H, m), 1.62-1.96 (8H, m), 0.94 (3H, t).

Example 120

Synthesis of Intermediate 120.5

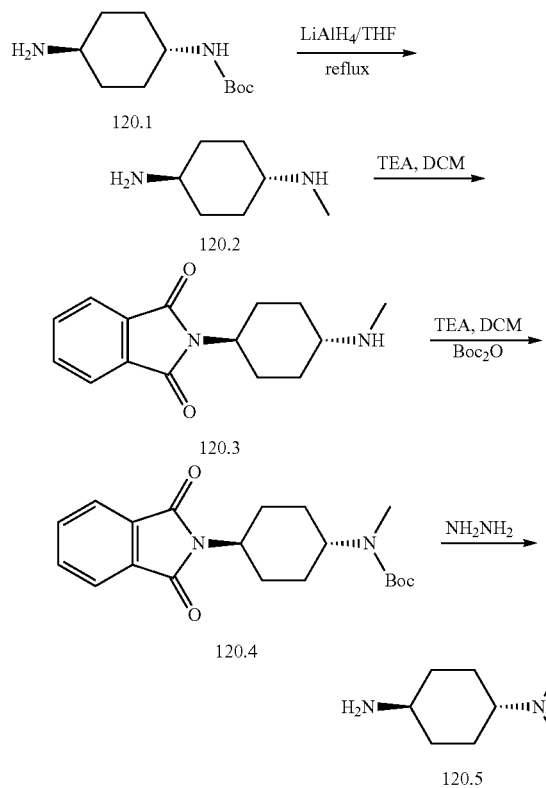

Synthesis of Compound 120.2.

Into a 500-mL round-bottom flask (1 atm) purged and maintained with an inert atmosphere of nitrogen, was placed a suspension of LiAlH$_4$ (3.8 g) in tetrahydrofuran (150 mL). This was followed by the addition of a solution of tert-butyl N-(4-aminocyclohexyl)carbamate (4.28 g, 19.97 mmol, 1.00 equiv) in tetrahydrofuran (50 mL) dropwise with stirring. The resulting solution was stirred for 4 hr at 80° C. The reaction was then quenched by the addition of Na$_2$SO$_4$.10H$_2$O. The solids were filtered out. The filtrate was concentrated under vacuum. This resulted in 2.3 g (90%) of 1-N-methylcyclohexane-1,4-diamine as a yellow solid.

Synthesis of Compound 120.3.

Into a 50-mL round-bottom flask was placed a solution of ethyl 1,3-dioxo-2,3-dihydro-1H-isoindole-2-carboxylate (1.55 g, 7.07 mmol, 0.91 equiv), 1-N-methylcyclohexane-1,4-diamine (1 g, 7.80 mmol, 1.00 equiv) and TEA (1.58 g, 15.61 mmol, 2.00 equiv) in dichloromethane (25 mL). The resulting solution was stirred for 14 hr at room temperature. The reaction was then quenched by the addition of 20 mL of water. The resulting solution was extracted with 3×30 mL of dichloromethane and the organic layers combined. The resulting mixture was washed with 2×20 mL of sodium chloride (sat.). The mixture was dried over anhydrous sodium sulfate and concentrated under vacuum. This resulted in 1.6 g (79%) of 2-[4-(methylamino)cyclohexyl]-2,3-dihydro-1H-isoindole-1,3-dione as a yellow oil.

Synthesis of Compound 120.4.

Into a 50-mL round-bottom flask was placed a solution of 2-[4-(methylamino)cyclohexyl]-2,3-dihydro-1H-isoindole-1,3-dione (1.6 g, 6.19 mmol, 1.00 equiv) and TEA (1.25 g, 12.35 mmol, 1.99 equiv) in dichloromethane (20 mL). This was followed by the addition of di-tert-butyl dicarbonate (1.62 g, 7.42 mmol, 1.20 equiv) in portions. The resulting solution was stirred for 4 hr at room temperature. The reaction was then quenched by the addition of 30 mL of water. The resulting solution was extracted with 3×30 mL of dichloromethane and the organic layers combined. The resulting mixture was washed with 2×20 mL of sodium chloride (sat.). The residue was applied onto a silica gel column with ethyl acetate/petroleum ether (1:5). The collected fractions were combined and concentrated under vacuum. This resulted in 1.8 g (81%) of tert-butyl N-[4-(1,3-dioxo-2,3-dihydro-1H-isoindol-2-yl)cyclohexyl]-N-methylcarbamate as a white solid.

Synthesis of Compound 120.5.

Into a 100-mL round-bottom flask was placed a solution of tert-butyl N-[4-(1,3-dioxo-2,3-dihydro-1H-isoindol-2-yl)cyclohexyl]-N-methylcarbamate (1.8 g, 5.02 mmol, 1.00 equiv) and hydrazine hydrate (2 mL) in ethanol (40 mL). The resulting solution was stirred for 4 hr at 50° C. The solids were filtered out. The resulting mixture was concentrated under vacuum. This resulted in 600 mg (52%) of tert-butyl N-(4-aminocyclohexyl)-N-methylcarbamate as a yellow solid.

Example 121

Synthesis of 2-(((1R,4r)-4-(((R)-5-(2-hydroxyethyl)-6,7-dihydro-5H-cyclopenta[4,5]thieno[2,3-d]pyrimidin-4-yl)amino)cyclohexyl)(methyl)amino)-1-(pyrrolidin-1-yl)ethanone (I-116)

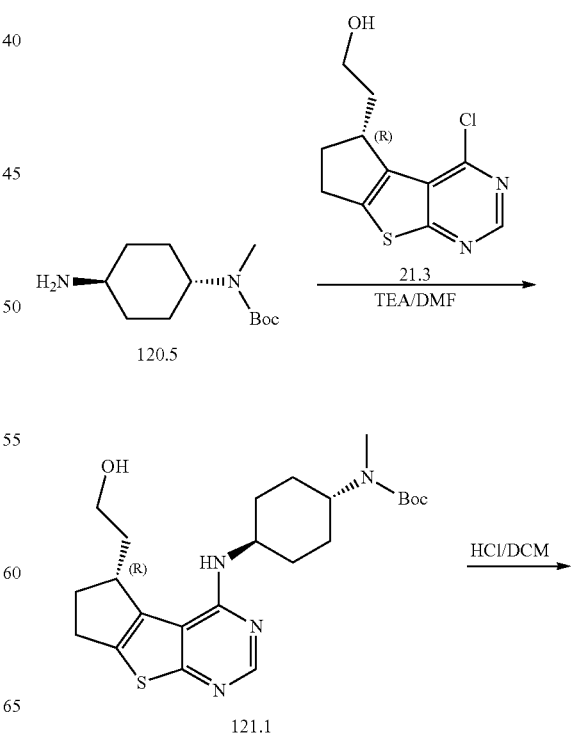

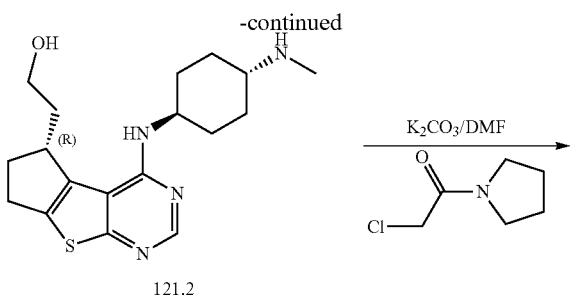

Synthesis of Compound 121.1.

Into a 25-mL round-bottom flask was placed a solution of tert-butyl N-(4-aminocyclohexyl)-N-methylcarbamate (430 mg, 1.88 mmol, 4.00 equiv), 2-[(3R)-12-chloro-7-thia-9,11-diazatricyclo[6.4.0.0[2,6]]dodeca-1(12),2(6),8,10-tetraen-3-yl]ethan-1-ol (120 mg, 0.47 mmol, 1.00 equiv) and TEA (143 mg, 1.41 mmol, 3.00 equiv) in N,N-dimethylformamide (8 mL). The resulting solution was stirred for 60 hr at 45° C. The reaction was then quenched by the addition of 20 mL of water. The resulting solution was extracted with 3×20 mL of ethyl acetate and the organic layers combined. The resulting mixture was washed with 2×20 mL of sodium chloride (sat.). The residue was applied onto a silica gel column with ethyl acetate (100%). The collected fractions were combined and concentrated under vacuum. This resulted in 120 mg (57%) of tert-butyl N-(4-[[(3R)-3-(2-hydroxyethyl)-7-thia-9,11-diazatricyclo[6.4.0.0[2,6]]dodeca-1(12),2(6),8,10-tetraen-12-yl]amino]cyclohexyl)-N-methylcarbamate as a yellow oil.

Synthesis of Compound 121.2.

Into a 50-mL round-bottom flask was placed a solution of tert-butyl N-(4-[[(3R)-3-(2-hydroxyethyl)-7-thia-9,11-diazatricyclo[6.4.0.0[2,6]]dodeca-1(12),2(6),8,10-tetraen-12-yl]amino]cyclohexyl)-N-methylcarbamate (120 mg, 0.27 mmol, 1.00 equiv) in dichloromethane (10 mL). This was followed by the addition of hydrogen chloride (conc.) (1 mL) dropwise with stirring. The resulting solution was stirred for 4 h at room temperature. The reaction was then quenched by the addition of 30 mL of sodium bicarbonate (sat.). The resulting solution was extracted with 3×20 mL of dichloromethane and the organic layers combined. The resulting mixture was washed with 2×20 mL of sodium chloride (sat.). The mixture was dried over anhydrous sodium sulfate and concentrated under vacuum. This resulted in 85 mg (91%) of 2-[(3R)-12-[[4-(methylamino)cyclohexyl]amino]-7-thia-9,11-diazatricyclo[6.4.0.0[2,6]]dodeca-1(12),2(6),8,10-tetraen-3-yl]ethan-1-ol as a yellow oil.

Synthesis of Compound I-116.

Into a 50-mL round-bottom flask (1 atm) purged and maintained with an inert atmosphere of nitrogen was placed a solution of 2-chloro-1-(pyrrolidin-1-yl)ethan-1-one (144 mg, 0.98 mmol, 3.98 equiv), 2-[(3R)-12-[[4-(methylamino)cyclohexyl]amino]-7-thia-9,11-diazatricyclo[6.4.0.0[2,6]]dodeca-1(12),2(6),8,10-tetraen-3-yl]ethan-1-ol (85 mg, 0.25 mmol, 1.00 equiv) and potassium carbonate (101 mg, 0.73 mmol, 3.00 equiv) in N,N-dimethylformamide (10 mL). The resulting solution was stirred for 14 hr at room temperature. The reaction was then quenched by the addition of 20 mL of water. The resulting solution was extracted with 3×20 mL of dichloromethane and the organic layers combined. The mixture was concentrated. The crude product (150 mg) was purified by flash preparative HPLC under the following conditions (IntelFlash-2): column: C18 silica gel; mobile phase: methanol:$H_2O$:$NH_4HCO_3$=1:1:0.05 increasing to methanol:$H_2O$:$NH_4HCO_3$=3:1:0.05 within 15 min; detector: 254 nm. 110 mg product was obtained. The product (110 mg) was repurified by preparative HPLC under the following conditions (1#-Pre-HPLC-016(Waters)): column: SunFire Prep C18, 19*150 mm 5 um; mobile phase: water with 50 mL $NH_4CO_3$ and $CH_3CN$ (5.0% $CH_3CN$ up to 43.0% in 11 min, up to 95.0% in 2 min, down to 5.0% in 2 min); detector: 254/220 nm. This resulted in 80.5 mg (72%) of 2-[(4-[[(3R)-3-(2-hydroxyethyl)-7-thia-9,11-diazatricyclo[6.4.0.0[2,6]]dodeca-1(12),2(6),8,10-tetraen-12-yl]amino]cyclohexyl)(methyl)amino]-1-(pyrrolidin-1-yl)ethan-1-one as a white solid. $^1$H NMR (300 MHz, $CD_3OD$): δ 8.25 (s, 1H), 4.11 (m, 1H), 3.62-3.69 (m, 5H), 3.55-3.59 (m, 2H), 3.42-3.47 (m, 2H), 3.09-3.12 (m, 1H), 2.93 (m, 1H), 2.69-2.749 (m, 2H), 2.37 (s, 3H), 2.11-2.32 (m, 3H), 1.87-2.01 (m, 6H), 1.72 (m, 2H), 1.50 (t, 3H).

Example 122

Synthesis of 3-((S)-4-(((1r,4S)-4-(methyl(2-oxo-2-(pyrrolidin-1-yl)ethyl)amino)cyclohexyl)amino)-6,7-dihydro-5H-cyclopenta[4,5]thieno[2,3-d]pyrimidin-5-yl)propanamide (I-127)

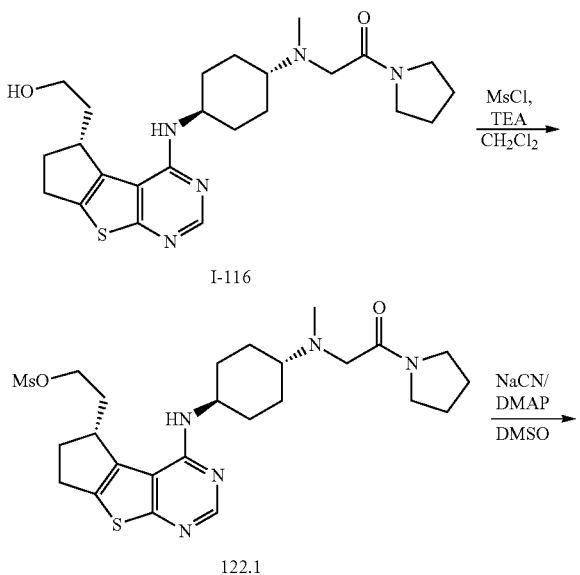

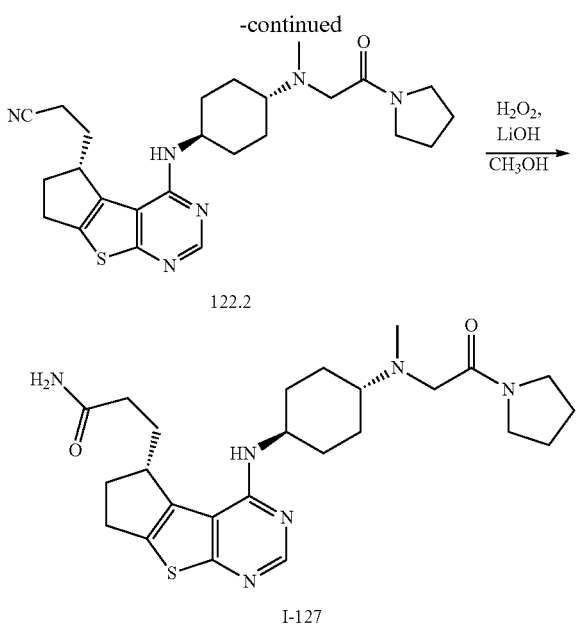

122.2

I-127

Synthesis of Compound 122.1.

Into a 50-mL round-bottom flask was placed a solution of 2-[(4-[[(3R)-3-(2-hydroxyethyl)-7-thia-9,11-diazatricyclo[6.4.0.0[2,6]]dodeca-1(8),2(6),9,11-tetraen-12-yl]oxy]cyclohexyl)(methyl)amino]-1-(pyrrolidin-1-yl)ethan-1-one (80 mg, 0.17 mmol, 1.00 equiv), TEA (53 mg, 0.52 mmol, 3.00 equiv) and MsCl (40 mg) in dichloromethane (10 mL). The reaction was stirred overnight at room temperature. The resulting solution was diluted with 20 mL of water. The resulting solution was extracted with 3×30 mL of ethyl acetate and the organic layers combined and dried over anhydrous sodium sulfate and concentrated under vacuum. This resulted in 2-[(3R)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]ethyl methanesulfonate (91 mg, 97%) as a yellow oil.

Synthesis of Compound 122.2.

Into a 50-mL round-bottom flask was placed a solution of 2-[(3R)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]ethyl methanesulfonate (91 mg, 0.17 mmol, 1.00 equiv), 4-dimethylaminopyridine (11 mg, 0.09 mmol, 0.53 equiv) and NaCN (50 mg, 1.02 mmol, 6.02 equiv) in DMSO (10 mL). The solution was stirred for 5 h at 60° C. The resulting solution was diluted with 30 mL of saturated sodium bicarbonate. The resulting solution was extracted with 3×30 mL of ethyl acetate and the organic layers combined and dried over anhydrous sodium sulfate and concentrated under vacuum. The residue was purified by preparative TLC (DCM/MeOH=10:1). This resulted in 3-[(3S)-12-[(4-[methyl[2-oxo-2-(pyrrolidin-1-yl)ethyl]amino]cyclohexyl)oxy]-7-thia-9,11-diazatricyclo[6.4.0.0[2,6]]dodeca-1(8),2(6),9,11-tetraen-3-yl]propanenitrile (75 mg, 95%) as a colorless oil.

Synthesis of Compound I-127.

Into a 50-mL round-bottom flask was placed a solution of 3-[(3S)-12-[(4-[methyl[2-oxo-2-(pyrrolidin-1-yl)ethyl]amino]cyclohexyl)amino]-7-thia-9,11-diazatricyclo[6.4.0.0[2,6]]dodeca-1(8),2(6),9,11-tetraen-3-yl]propanenitrile (75 mg, 0.16 mmol, 1.00 equiv), LiOH.H$_2$O (5 mg, 0.12 mmol, 0.74 equiv) and H$_2$O$_2$(30%) (0.3 mL) in methanol (10 mL). The reaction was stirred for 2 h at 0° C. in a water/ice bath. The reaction was then quenched by the addition of 20 mL of saturated Na$_2$SO$_3$. The resulting solution was extracted with 3×30 mL of ethyl acetate and the organic layers combined and concentrated under vacuum. The crude product (70 mg) was purified by preparative HPLC under the following conditions (1#-Pre-HPLC-016(Waters)): column: SunFire Prep C18, 19*150 mm 5 um; mobile phase: water with 50 mL NH$_4$CO$_3$ and CH$_3$CN (5.0% CH$_3$CN up to 46.0% in 10 min, up to 95.0% in 2 min, down to 5.0% in 2 min); detector: 254/220 nm. The product was freeze-dried. This resulted in 3-[(3S)-12-[(4-[methyl[2-oxo-2-(pyrrolidin-1-yl)ethyl]amino]cyclohexyl)amino]-7-thia-9,11-diazatricyclo[6.4.0.0[2,6]]dodeca-1(8),2(6),9,11-tetraen-3-yl]propanamide (10.6 mg, 14%) as a white solid. MS: m/z 485 (M+H)$^+$. $^1$H NMR (400 MHz, CD$_3$OD): δ 8.23 (s, 1H), 4.89-4.27 (m, 1H), 3.59-3.33 (m, 7H), 3.08-2.94 (m, 2H), 2.69-2.61 (m, 2H), 2.75-2.17 (m, 6H), 2.10-1.47 (m, 14H).

Example 123

Synthesis of Intermediate 123.2

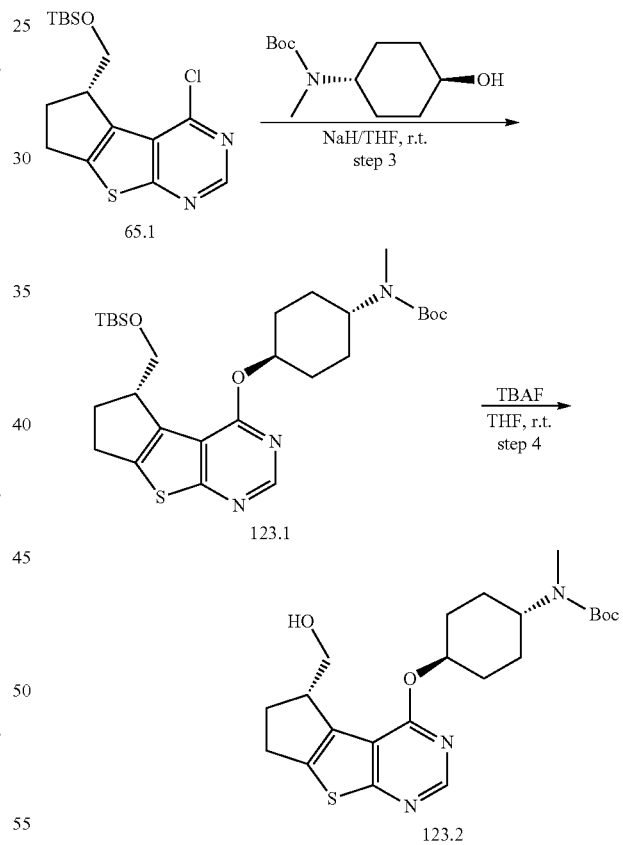

Synthesis of Compound 123.1.

Sodium hydride (60% dispersion in mineral oil, 240 mg, 6.00 mmol, 3.00 equiv) was treated with tert-butyl N-(4-hydroxycyclohexyl)-N-methylcarbamate (642 mg, 2.80 mmol, 1.40 equiv) in freshly distilled tetrahydrofuran (14 mL) at 0° C. under nitrogen for 30 min. To this mixture was added a solution of (3S)-3-[[(tert-butyldimethylsilyl)oxy]methyl]-12-chloro-7-thia-9,11-diazatricyclo[6.4.0.0[2,6]]dodeca-1(8),2(6),9,11-tetraene (710 mg, 2.00 mmol, 1.00 equiv) in 5 mL of THF via syringe and the resulting solution was stirred overnight at room temperature. After completion, the reaction was quenched with saturated aqueous NH₄Cl and extracted with ethyl acetate. The combined organic layers were washed with brine, dried over anhydrous sodium sulfate and concentrated under vacuum. The residue was applied onto a silica gel column with dichloromethane/methanol (8:1) to give the desired tert-butyl N-(4-[[(3S)-3-[[(tert-butyldimethylsilyl)oxy]methyl]-7-thia-9,11-diazatricyclo[6.4.0.0[2,6]]dodeca-1(8),2(6),9,11-tetraen-12-yl]oxy]cyclohexyl)-N-methylcarbamate (963 mg, 88%) as light yellow oil. MS: m/z 548 (M+H)⁺.

Synthesis of Compound 123.2.

A solution of tert-butyl N-(4-[[(3S)-3-[[(tert-butyldimethylsilyl)oxy]methyl]-7-thia-9,11-diazatricyclo[6.4.0.0[2,6]]dodeca-1(8),2(6),9,11-tetraen-12-yl]oxy]cyclohexyl)-N-methylcarbamate (963 mg, 1.76 mmol, 1.00 equiv) in 5 mL of THF was added TBAF (919 mg, 3.51 mmol, 2.00 equiv) at room temperature. The resulting solution was stirred overnight at 25° C. and diluted with water, extracted with 3×50 mL of ethyl acetate. The combined organic layers were washed with brine, dried over anhydrous sodium sulfate and concentrated under vacuum. The residue was applied onto a silica gel column with ethyl acetate/petroleum ether (1:1) to afford the tert-butyl N-(4-[[(3S)-3-(hydroxymethyl)-7-thia-9,11-diazatricyclo[6.4.0.0[2,6]]dodeca-1(8),2(6),9,11-tetraen-12-yl]oxy]cyclohexyl)-N-methylcarbamate (691 mg, 91%) as a white solid. MS: m/z 434 (M+H)⁺.

Example 124

Synthesis of Intermediate 124.3

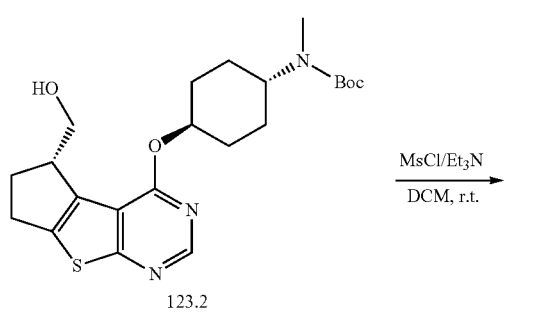

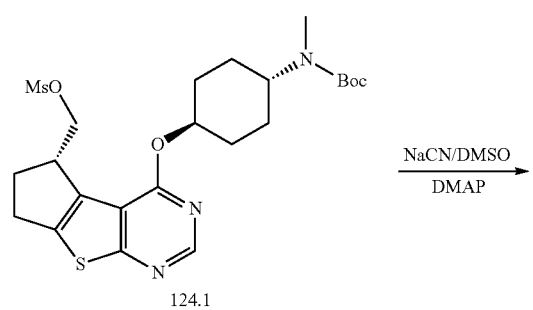

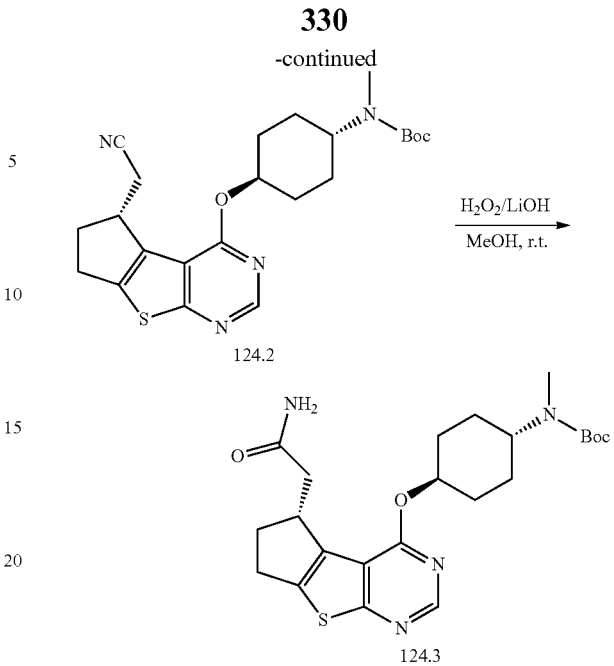

Synthesis of Compound 124.1.

A solution of tert-butyl N-(4-[[(3S)-3-(hydroxymethyl)-7-thia-9,11-diazatricyclo[6.4.0.0[2,6]]dodeca-1(8),2 (6),9,11-tetraen-12-yl]oxy]cyclohexyl)-N-methylcarbamate (691 mg, 1.59 mmol, 1.00 equiv) in 4 mL of DCM was added MsCl (366 mg, 3.18 mmol, 2.00 equiv) and triethylamine (643 mg, 6.35 mmol, 4.00 equiv) at 0° C. under nitrogen. The resulting solution was stirred for 2 h at room temperature and quenched with water. The resulting solution was extracted with 3×30 mL of DCM. The combined organic layers were washed with brine, dried over anhydrous sodium sulfate and concentrated under vacuum afford tert-butyl N-(4-[[(3S)-3-[(methanesulfonyloxy)methyl]-7-thia-9,11-diazatricyclo[6.4.0.0[2,6]]dodeca-1(8),2 (6),9,11-tetraen-12-yl]oxy]cyclohexyl)-N-methylcarbamate (900 mg, crude) as a red oil. MS: m/z 512 (M+H)⁺.

Synthesis of Compound 124.2.

Into a 50-mL round-bottom flask purged and maintained with an inert atmosphere of nitrogen, was placed tert-butyl N-(4-[[(3S)-3-[(methanesulfonyloxy)methyl]-7-thia-9,11-diazatricyclo[6.4.0.0[2,6]]dodeca-1(8),2 (6),9,11-tetraen-12-yl]oxy]cyclohexyl)-N-methylcarbamate (900 mg, 1.76 mmol, 1.00 equiv) in 6 mL of DMSO at room temperature. NaCN (600 mg, 12.24 mmol, 6.96 equiv) and 4-dimethylaminopyridine (100 mg, 0.82 mmol, 0.47 equiv) were added and the resulting solution was stirred for 2 h at 80° C. After cooling to room temperature, the reaction was quenched with water and extracted with 3×50 mL of ethyl acetate. The combined organic layers were washed with brine, dried over anhydrous sodium sulfate and concentrated under vacuum. The residue was applied onto a silica gel column with ethyl acetate/petroleum ether (1:4) to provide tert-butyl N-(4-[[(3R)-3-(cyanomethyl)-7-thia-9,11-diazatricyclo[6.4.0.0[2,6]]dodeca-1(8),2 (6),9,11-tetraen-12-yl]oxy]cyclohexyl)-N-methylcarbamate (709 mg, 91%) as a white solid. MS: m/z 443 (M+H)⁺.

Synthesis of Compound 124.3.

A solution of tert-butyl N-(4-[[(3R)-3-(cyanomethyl)-7-thia-9,11-diazatricyclo[6.4.0.0[2,6]]dodeca-1(8),2(6),9,11-tetraen-12-yl]oxy]cyclohexyl)-N-methylcarbamate (709 mg, 1.60 mmol, 1.00 equiv) in 6 mL of MeOH was added LiOH.H2O (135 mg, 3.21 mmol, 2.01 equiv) and $H_2O_2$ (30%, 1 mL) at 0° C. The resulting solution was stirred for 2 h at room temperature and quenched with saturated aqueous $NaHSO_3$ solution and extracted with 3×50 mL of ethyl acetate. The combined extracts were washed with brine, dried over anhydrous sodium sulfate and concentrated under vacuum. The residue was applied onto a silica gel column with ethyl acetate/petroleum ether (1:4) to give tert-butyl N-(4-[[(3R)-3-(carbamoylmethyl)-7-thia-9,11-diazatricyclo [6.4.0.0[2,6]]dodeca-1(8),2(6),9,11-tetraen-12-yl]oxy]cyclohexyl)-N-methylcarbamate (524 mg, 71%) as a white solid. MS: m/z 461 [M+H]+.

Example 125

2-((R)-4-(((1r,4R)-4-(methyl(2-(pyridin-2-yl)ethyl)amino)cyclohexyl)oxy)-6,7-dihydro-5H-cyclopenta[4,5]thieno[2,3-d]pyrimidin-5-yl)acetamide (I-128)

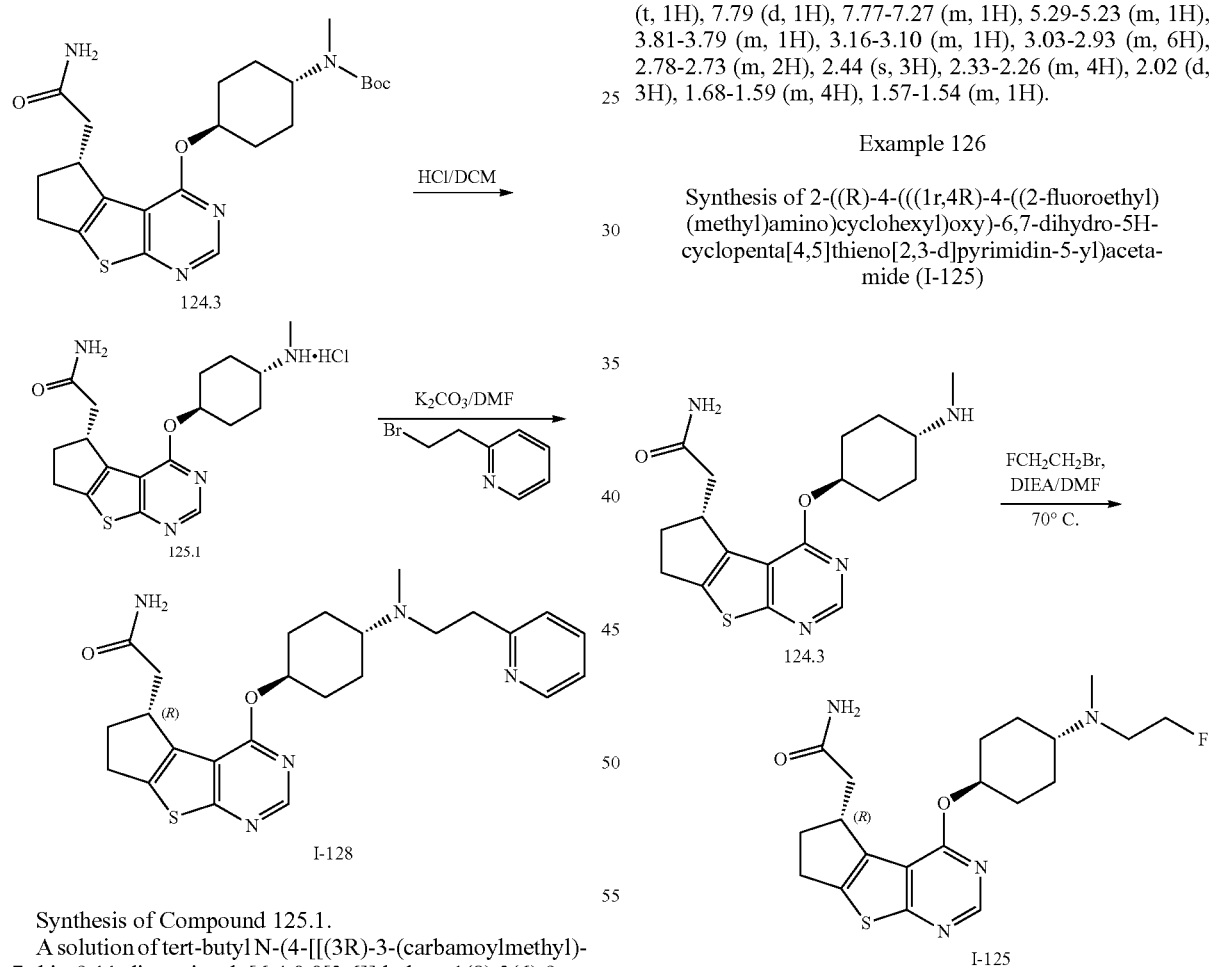

Synthesis of Compound 125.1.

A solution of tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]cyclohexyl)-N-methylcarbamate (524 mg, 1.14 mmol, 1.00 equiv) in DCM (6 mL) was added 6 M aqueous hydrochloric acid (1 mL) at 0° C. and the resulting solution was stirred for 2 h at room temperature. After concentrated under reduced pressure, the desired 2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]acetamide hydrochloride (451 mg, crude) was obtained as a light yellow solid.

Synthesis of Compound I-128.

The hydrochloride (111 mg, 0.29 mmol, 1.00 equiv) in 4 mL of distilled DMF was added DIEA (119 mg, 0.92 mmol, 3.13 equiv) and 2-(2-bromoethyl)pyridine (57 mg, 0.31 mmol, 1.04 equiv) at room temperature. The resulting solution was stirred overnight at 100° C. in an oil bath. The resulting mixture was diluted with water and extracted with DCM and concentrated under vacuum. The crude product (110 mg) was purified by preparative HPLC under the following conditions (Waters): column: Xbridge Prep C18, 5 um, 19*50 mm; mobile phase: water with 0.05% NH4HCO3 and CH3CN (10% CH3CN up to 25% in 10 min, up to 95% in 1.5 min, down to 10% in 1.5 min); UV detection at 254/220 nm. The product-containing fractions were collected and partially evaporated under reduced pressure to remove $CH_3CN$ and water. The residue was lyophilized overnight to give the desired 2-[(1R)-8-[(4-[methyl[2-(pyridin-2-yl)ethyl]amino]cyclohexyl)oxy]-1H,2H,3H,4H-cyclopenta[α]inden-1-yl]acetamide (16.3 mg) as a light yellow solid. MS: m/z 466 (M+H)+. $^1$H NMR (400 MHz, $CD_3OD$): δ 8.48 (d, 2H), 7.80 (t, 1H), 7.79 (d, 1H), 7.77-7.27 (m, 1H), 5.29-5.23 (m, 1H), 3.81-3.79 (m, 1H), 3.16-3.10 (m, 1H), 3.03-2.93 (m, 6H), 2.78-2.73 (m, 2H), 2.44 (s, 3H), 2.33-2.26 (m, 4H), 2.02 (d, 3H), 1.68-1.59 (m, 4H), 1.57-1.54 (m, 1H).

Example 126

Synthesis of 2-((R)-4-(((1r,4R)-4-((2-fluoroethyl)(methyl)amino)cyclohexyl)oxy)-6,7-dihydro-5H-cyclopenta[4,5]thieno[2,3-d]pyrimidin-5-yl)acetamide (I-125)

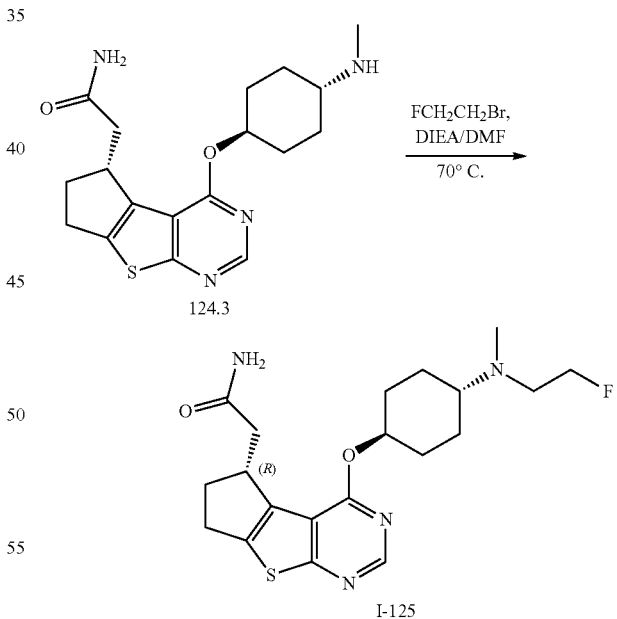

Synthesis of Compound I-125.

To a solution of 2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]acetamide (90 mg, 0.25 mmol, 1.00 equiv) in DMF (4 mL) was added 1-bromo-2-fluoroethane (317.5 mg, 2.50 mmol, 10.00 equiv) and DIEA (195 mg, 1.51 mmol, 6.00 equiv). The resulting solution was stirred overnight at 70° C. The mixture was diluted with DCM (40 mL), washed with brine (40 mL), dried over sodium sulfate and concentrated under vacuum. The crude product (70 mg) was purified by preparative HPLC under the following conditions (Waters): column: SunFire Prep C18, 19*150 mm 5 um; mobile phase: water with $NH_4CO_3$ and $CH_3CN$ (6.0% $CH_3CN$ up to 46.0% in 10 min, up to 95.0% in 2 min down to 6.0% in 2 min); flow rate: 20 mL/min; UV detection at 254/220 nm. The product-containing fractions were collected and evaporated partially to remove water and $CH_3CN$ under reduced pressure. The residue was lyophilized overnight to give (60 mg) of the corresponding product 2-[(3R)-12-([4-[(2-fluoroethyl)(methyl)amino]cyclohexyl]oxy)-7-thia-9,11-diazatricyclo[6.4.0.0[2,6]]dodeca-1(8),2(6),9,11-tetraen-3-yl]acetamide as a white solid. MS: m/z 407 (M+H)$^+$. $^1$H NMR (400 MHz, $CD_3OD$): δ 8.48 (s, 1H), 5.25-5.30 (m, 1H), 4.62 (t, 1H, J=4.8 Hz), 4.50 (t, 1H, J=4.8 Hz), 3.78-3.83 (m, 1H), 3.11-3.18 (m, 1H), 2.97-3.01 (m, 2H), 2.91 (t, 1H, J=4.8 Hz), 2.85 (t, 1H, J=4.8 Hz), 2.59-2.83 (m, 2H), 2.41 (s, 3H), 2.21-2.40 (m, 4H), 1.98-2.01 (m, 2H), 1.53-1.68 (m, 4H).

Example 127

Synthesis of 2,2-difluoro-3-((R)-4-(((1r,4R)-4-morpholinocyclohexyl)oxy)-6,7-dihydro-5H-cyclopenta[4,5]thieno[2,3-d]pyrimidin-5-yl)propanamide (I-142)

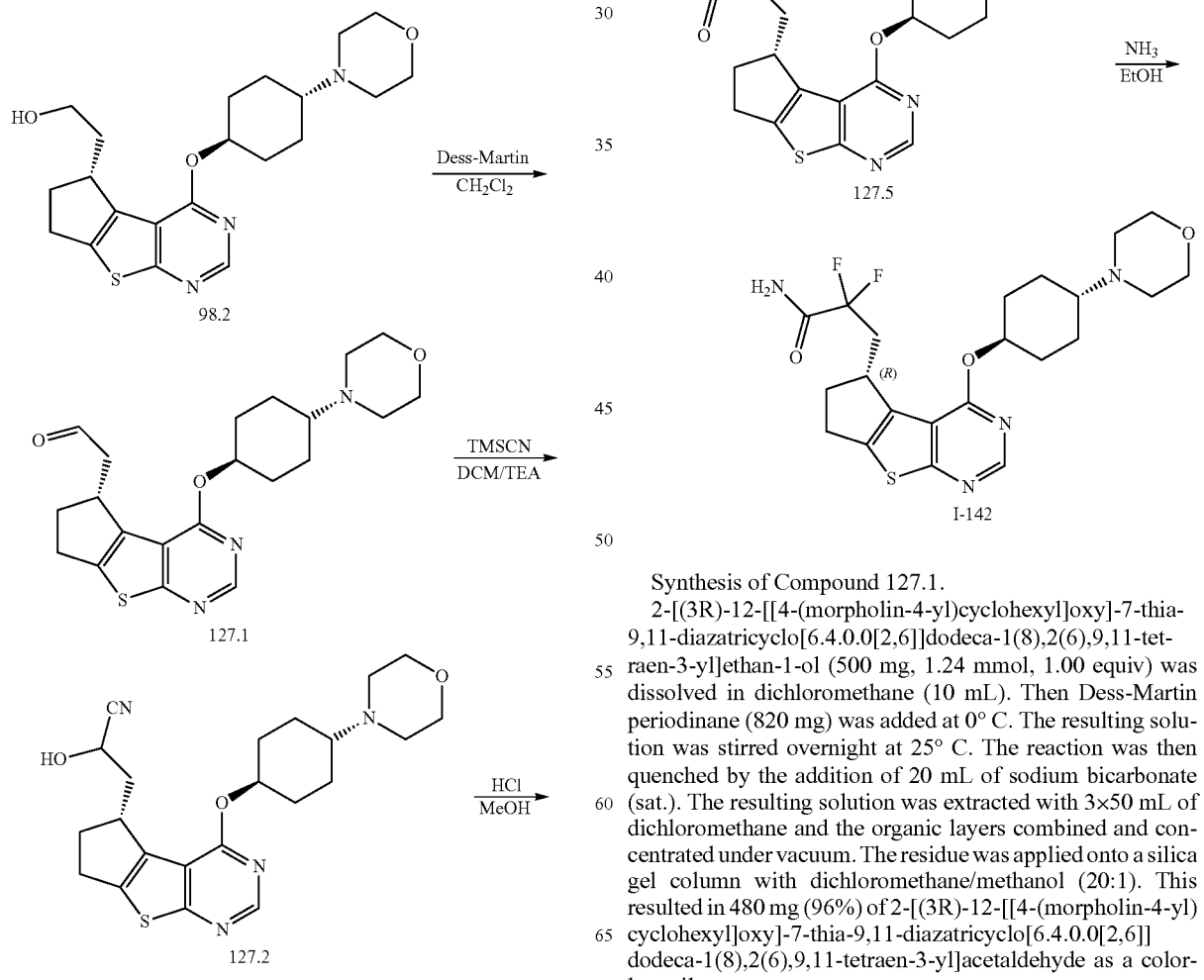

Synthesis of Compound 127.1.

2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]ethan-1-ol (500 mg, 1.24 mmol, 1.00 equiv) was dissolved in dichloromethane (10 mL). Then Dess-Martin periodinane (820 mg) was added at 0° C. The resulting solution was stirred overnight at 25° C. The reaction was then quenched by the addition of 20 mL of sodium bicarbonate (sat.). The resulting solution was extracted with 3×50 mL of dichloromethane and the organic layers combined and concentrated under vacuum. The residue was applied onto a silica gel column with dichloromethane/methanol (20:1). This resulted in 480 mg (96%) of 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]acetaldehyde as a colorless oil.

335

Synthesis of Compound 127.2.

A solution of 2-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]acetaldehyde (480 mg, 1.20 mmol, 1.00 equiv), TEA (60 mg, 0.59 mmol, 0.50 equiv) and TMSCN (355 mg, 3.59 mmol, 3.00 equiv) in dichloromethane (10 mL) was prepared and stirred for 2 h at 25° C. The reaction was then quenched by the addition of 20 mL of water. The resulting solution was extracted with 3×50 mL of ethyl acetate and the organic layers combined. The resulting mixture was washed with 3×20 mL of brine. The mixture was dried over anhydrous sodium sulfate and concentrated under vacuum. This resulted in 450 mg (crude) of 2-hydroxy-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanenitrile as a colorless oil.

Synthesis of Compound 127.3.

A solution of 2-hydroxy-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanenitrile (400 mg, 0.93 mmol, 1.00 equiv) and hydrogen chloride (12 N) (0.6 mL) in methanol (10 mL) was prepared and stirred overnight at room temperature. The reaction was then quenched by the addition of 20 mL of sodium bicarbonate (sat.). The resulting solution was extracted with 3×50 mL of ethyl acetate and the organic layers combined and concentrated under vacuum. The residue was applied onto a silica gel column with dichloromethane/methanol (20:1). This resulted in 230 mg (53%) of methyl 2-hydroxy-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanoate as a colorless oil.

Synthesis of Compound 127.4.

A solution of ethyl 2-hydroxy-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanoate (230 mg, 0.50 mmol, 1.00 equiv) and Dess-Martin periodinane (317 mg) in dichloromethane (10 mL) was prepared. The resulting solution was stirred for 3 h at 25° C. The reaction was then quenched by the addition of 20 mL of sodium bicarbonate (sat.). The resulting solution was extracted with 3×50 mL of dichloromethane and the organic layers combined and concentrated under vacuum. The residue was applied onto a silica gel column with dichloromethane/methanol (30:1). This resulted in 180 mg (79%) of methyl 3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]-2-oxopropanoate as a colorless oil.

Synthesis of Compound 127.5.

A solution of methyl 3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]-2-oxopropanoate (150 mg, 0.33 mmol, 1.00 equiv), DAST (150 mg, 0.93 mmol, 2.85 equiv) in dichloromethane (10 mL) was prepared and stirred overnight at 25° C. The reaction was then quenched by the addition of 20 mL of sodium bicarbonate (sat.). The resulting solution was extracted with 3×50 mL of ethyl acetate and the organic layers combined and concentrated under vacuum. The residue was applied onto a silica gel column with dichloromethane/methanol (40:1). This resulted in 120 mg (76%) of methyl 2,2-difluoro-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanoate as a colorless oil.

Synthesis of Compound I-142.

A 50-mL sealed tube was charged with ethanol (20 mL) and NH₃(g) (30 mL) was introduced at 0° C. This was followed by the addition of methyl 2,2-difluoro-3-[(3R)-12-[[4-(morpholin-4-yl)cyclohexyl]oxy]-7-thia-9,11-diazatricyclo

336

[6.4.0.0[2,6]]dodeca-1(8),2(6),9,11-tetraen-3-yl]propanoate (120 mg, 0.25 mmol, 1.00 equiv). The resulting solution was stirred overnight at 25° C. The resulting mixture was concentrated under vacuum. The crude product (100 mg) was purified by preparative HPLC under the following conditions (1#-Pre-HPLC-016(Waters)): column: SunFire Prep C18, 19*150 mm 5 um; mobile phase: water with 50 mL NH₄CO₃ and CH₃CN (5.0% CH₃CN up to 45.0% in 11 min, up to 95.0% in 2 min, down to 5.0% in 2 min); detector: 254/220 nm. This resulted in 31.9 mg (27%) of 2,2-difluoro-3-[(3R)-12-[[4-(morpholin-4-yl)cyclohexyl]oxy]-7-thia-9,11-diazatricyclo[6.4.0.0[2,6]]dodeca-1(8),2(6),9,11-tetraen-3-yl]propanamide as a white solid. MS: m/z 467 (M+H)⁺. ¹H NMR (300 MHz, CD₃OD: δ 8.474 (1H, s), 5.226-5.333 (1H, m), 3.70-3.73 (5H, m), 2.728-3.172 (4H, m), 2.62-2.65 (4H, m), 2.07-2.49 (7H, m), 1.63-1.75 (2H, m), 1.41-1.53 (2H, m).

Example 128

Synthesis of (S)-3-((R)-4-(((1r,4R)-4-aminocyclohexyl)oxy)-6,7-dihydro-5H-cyclopenta[4,5]thieno[2,3-d]pyrimidin-5-yl)-2-hydroxypropanamide (I-135) and (R)-3-((R)-4-(((1r,4R)-4-aminocyclohexyl)oxy)-6,7-dihydro-5H-cyclopenta[4,5]thieno[2,3-d]pyrimidin-5-yl)-2-hydroxypropanamide (I-138)

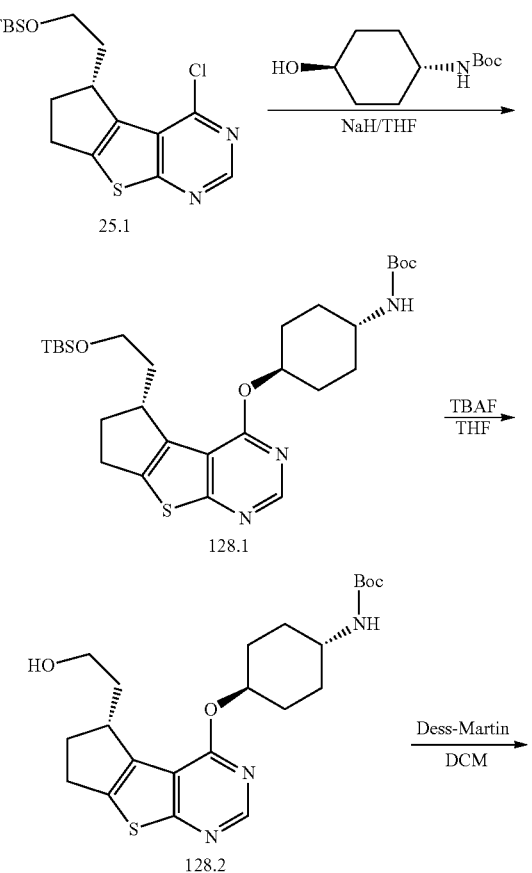

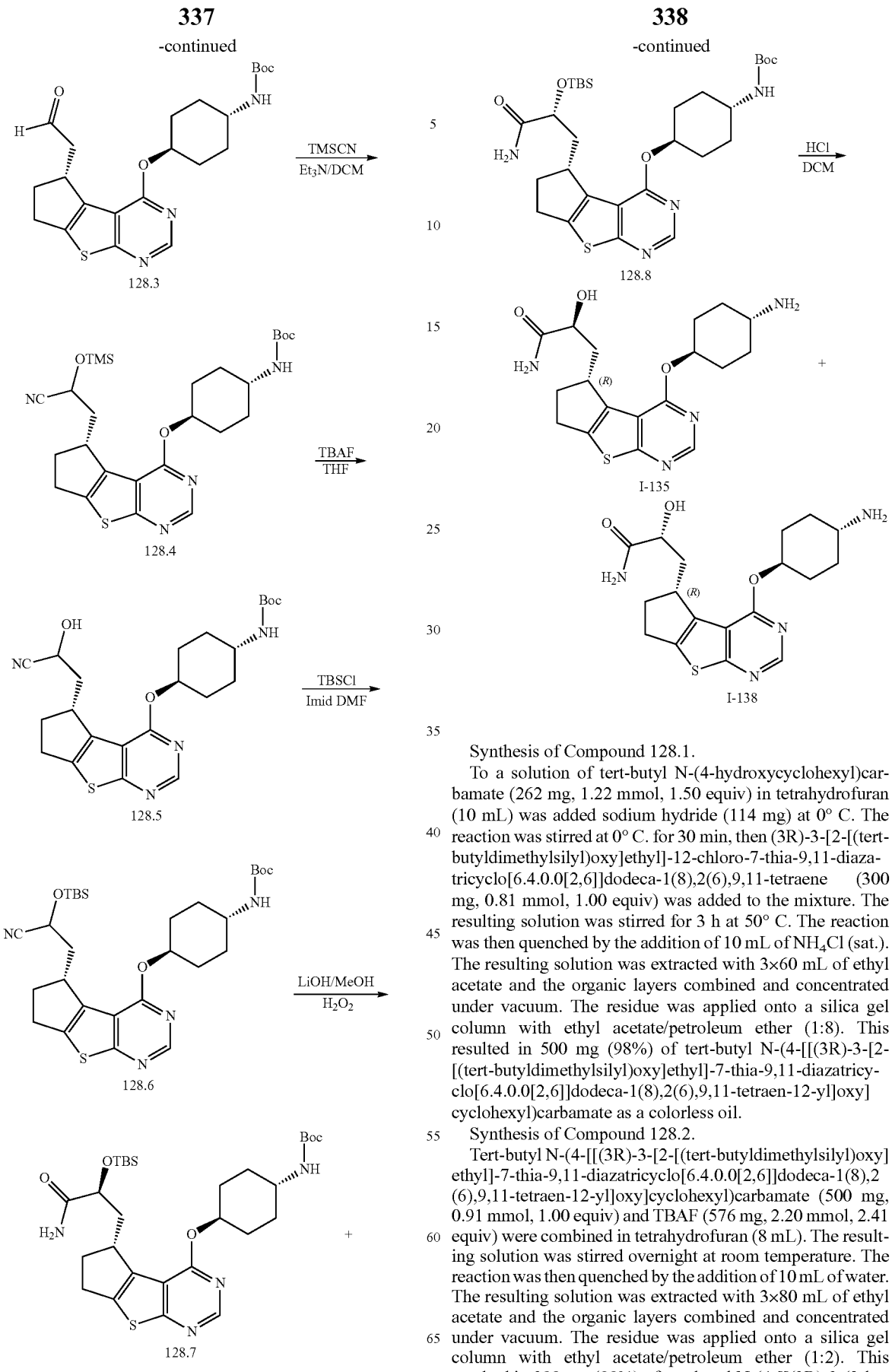

Synthesis of Compound 128.1.

To a solution of tert-butyl N-(4-hydroxycyclohexyl)carbamate (262 mg, 1.22 mmol, 1.50 equiv) in tetrahydrofuran (10 mL) was added sodium hydride (114 mg) at 0° C. The reaction was stirred at 0° C. for 30 min, then (3R)-3-[2-[(tert-butyldimethylsilyl)oxy]ethyl]-12-chloro-7-thia-9,11-diazatricyclo[6.4.0.0[2,6]]dodeca-1(8),2(6),9,11-tetraene (300 mg, 0.81 mmol, 1.00 equiv) was added to the mixture. The resulting solution was stirred for 3 h at 50° C. The reaction was then quenched by the addition of 10 mL of NH$_4$Cl (sat.). The resulting solution was extracted with 3×60 mL of ethyl acetate and the organic layers combined and concentrated under vacuum. The residue was applied onto a silica gel column with ethyl acetate/petroleum ether (1:8). This resulted in 500 mg (98%) of tert-butyl N-(4-[[(3R)-3-[2-[(tert-butyldimethylsilyl)oxy]ethyl]-7-thia-9,11-diazatricyclo[6.4.0.0[2,6]]dodeca-1(8),2(6),9,11-tetraen-12-yl]oxy] cyclohexyl)carbamate as a colorless oil.

Synthesis of Compound 128.2.

Tert-butyl N-(4-[[(3R)-3-[2-[(tert-butyldimethylsilyl)oxy] ethyl]-7-thia-9,11-diazatricyclo[6.4.0.0[2,6]]dodeca-1(8),2 (6),9,11-tetraen-12-yl]oxy]cyclohexyl)carbamate (500 mg, 0.91 mmol, 1.00 equiv) and TBAF (576 mg, 2.20 mmol, 2.41 equiv) were combined in tetrahydrofuran (8 mL). The resulting solution was stirred overnight at room temperature. The reaction was then quenched by the addition of 10 mL of water. The resulting solution was extracted with 3×80 mL of ethyl acetate and the organic layers combined and concentrated under vacuum. The residue was applied onto a silica gel column with ethyl acetate/petroleum ether (1:2). This resulted in 390 mg (99%) of tert-butyl N-(4-[[(3R)-3-(2-hydroxyethyl)-7-thia-9,11-diazatricyclo[6.4.0.0[2,6]]dodeca-1(8),2 (6),9,11-tetraen-12-yl]oxy]cyclohexyl)carbamate as a white solid.

Synthesis of Compound 128.3.

Tert-butyl N-(4-[[(3R)-3-(2-hydroxyethyl)-7-thia-9,11-diazatricyclo[6.4.0.0[2,6]]dodeca-1(8),2(6),9,11-tetraen-12-yl]oxy]cyclohexyl)carbamate (390 mg, 0.90 mmol, 1.00 equiv) and Dess-Martin periodinane (571 mg, 1.35 mmol, 1.50 equiv) were combined in dichloromethane (8 mL). The resulting solution was stirred for 3 h at 0° C. The reaction was then quenched by the addition of 15 mL of sodium bicarbonate (sat.). The resulting solution was extracted with 3×80 mL of ethyl acetate and the organic layers combined and concentrated under vacuum. The residue was applied onto a silica gel column with ethyl acetate/petroleum ether (1:3). This resulted in 300 mg (77%) of tert-butyl N-(4-[[(3R)-3-(2-oxoethyl)-7-thia-9,11-diazatricyclo[6.4.0.0[2,6]]dodeca-1(8),2(6),9,11-tetraen-12-yl]oxy]cyclohexyl)carbamate as a white solid.

Synthesis of Compound 128.4.

Tert-butyl N-(4-[[(3R)-3-(2-oxoethyl)-7-thia-9,11-diazatricyclo[6.4.0.0[2,6]]dodeca-1(8),2(6),9,11-tetraen-12-yl]oxy]cyclohexyl)carbamate (300 mg, 0.70 mmol, 1.00 equiv), triethylamine (35 mg, 0.35 mmol, 0.50 equiv) and TMSCN (206 mg) were combined in dichloromethane (8 mL). The resulting solution was stirred for 3 h at 0° C. The reaction was then quenched by the addition of 10 mL of $NH_4Cl$ (sat.). The resulting solution was extracted with 3×80 mL of ethyl acetate and the organic layers combined and concentrated under vacuum. The residue was applied onto a silica gel column with ethyl acetate/petroleum ether (1/5). This resulted in 330 mg (89%) of tert-butyl N-(4-[[(3R)-3-[2-cyano-2-[(trimethylsilyl)oxy]ethyl]-7-thia-9,11-diazatricyclo[6.4.0.0[2,6]]dodeca-1(8),2(6),9,11-tetraen-12-yl]oxy]cyclohexyl)carbamate as a white solid.

Synthesis of Compound 128.5.

Tert-butyl N-(4-[[(3R)-3-[2-cyano-2-[(trimethylsilyl)oxy]ethyl]-7-thia-9,11-diazatricyclo[6.4.0.0[2,6]]dodeca-1(8),2(6),9,11-tetraen-12-yl]oxy]cyclohexyl)carbamate (320 mg, 0.60 mmol, 1.00 equiv) and TBAF (286 mg, 1.09 mmol, 1.81 equiv) were combined in tetrahydrofuran (8 mL). The resulting solution was stirred for 3 h at room temperature. The reaction was then quenched by the addition of 10 mL of water. The resulting solution was extracted with 3×50 mL of ethyl acetate and the organic layers combined and concentrated under vacuum. The residue was applied onto a silica gel column with ethyl acetate/petroleum ether (1/2). This resulted in 215 mg (78%) of tert-butyl N-(4-[[(3R)-3-(2-cyano-2-hydroxyethyl)-7-thia-9,11-diazatricyclo[6.4.0.0[2,6]]dodeca-1(8),2(6),9,11-tetraen-12-yl]oxy]cyclohexyl)carbamate as a white solid.

Synthesis of Compound 128.6.

Tert-butyl N-(4-[[(3R)-3-(2-cyano-2-hydroxyethyl)-7-thia-9,11-diazatricyclo[6.4.0.0[2,6]]dodeca-1(8),2(6),9,11-tetraen-12-yl]oxy]cyclohexyl)carbamate (210 mg, 0.46 mmol, 1.00 equiv), imidazole (62 mg, 0.91 mmol, 1.99 equiv) and TBSCl (103 mg) were combined in N,N-dimethylformamide (5 mL). The resulting solution was stirred for 3 h at room temperature. The reaction was then quenched by the addition of 20 mL of water. The resulting solution was extracted with 3×60 mL of ethyl acetate and the organic layers combined. The resulting mixture was washed with 3×40 mL of water. The resulting mixture was concentrated under vacuum. The residue was applied onto a silica gel column with ethyl acetate/petroleum ether (1/5). This resulted in 280 mg (98%) of tert-butyl N-(4-[[(3R)-3-[2-[(tert-butyldimethylsilyl)oxy]-2-cyano ethyl]-7-thia-9,11-diazatricyclo[6.4.0.0[2,6]]dodeca-1(8),2(6),9,11-tetraen-12-yl]oxy]cyclohexyl)carbamate as colorless oil.

Synthesis of Compounds 128.7 and 128.8.

Tert-butyl N-(4-[[(3R)-3-[2-[(tert-butyldimethylsilyl)oxy]-2-cyanoethyl]-7-thia-9,11-diazatricyclo[6.4.0.0[2,6]]dodeca-1(8),2(6),9,11-tetraen-12-yl]oxy]cyclohexyl)carbamate (250 mg, 0.44 mmol, 1.00 equiv), LiOH (54 mg, 2.25 mmol, 5.17 equiv) and $H_2O_2$ (0.5 mL) were combined in methanol (8 mL). The resulting solution was stirred for 4 h at 0° C. The reaction was then quenched by the addition of 20 mL of $Na_2SO_3$ (sat.). The resulting solution was extracted with 3×40 mL of ethyl acetate and the organic layers combined and concentrated under vacuum. The residue was applied onto a silica gel column with ethyl acetate/petroleum ether (1.2/1). This resulted in 80 mg (31%) of tert-butyl N-(4-[[(3R)-3-[(2S)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)carbamate as a white solid and 70 mg (27%) of tert-butyl N-(4-[[(3R)-3-[(2R)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl) carbamate as a white solid.

Synthesis of Compound I-135.

A solution of tert-butyl N-(4-[[(3R)-3-[(2S)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)carbamate (80 mg, 0.14 mmol, 1.00 equiv), dichloromethane (5 mL) and hydrogen chloride (conc.) (0.3 mL) was prepared. After stirring for 3 h at room temperature, the reaction was then quenched by the addition of 10 mL of sodium bicarbonate (aq.). The resulting mixture was concentrated under vacuum. The crude product (80 mg) was purified by preparative HPLC under the following conditions (1#-Pre-HPLC-015(Waters)): column: Xbridge Prep C18, 5 um, 19*50 mm; mobile phase: water with 50 mmol NH4HCO3 and CH3CN (10% CH3CN up to 27% in 10 min, up to 95% in 1.5 min, down to 10% in 1.5 min); detector: 254/220 nm. 30.9 mg product was obtained. This resulted in 30.9 mg (61%) of (2S)-3-[(3R)-12-[(4-amino cyclohexyl)oxy]-7-thia-9,11-diazatricyclo[6.4.0.0[2,6]]dodeca-1(8),2(6),9,11-tetraen-3-yl]-2-hydroxypropanamide as a white solid. MS: m/z 377 (M+H)$^+$. $^1$H NMR (400 Hz, $CD_3OD$): δ 8.47 (1H, br s), 5.33 (1H, m) 4.15 (1H, m), 3.50 (1H, m), 3.12 (2H, m), 3.00 (1H, m), 2.98 (1H, m), 2.88-2.53 (3H, m), 2.47-2.20 (4H, m), 1.87-1.66 (5H, m), 1.42 (2H, m).

Synthesis of Compound I-138.

A solution of tert-butyl N-(4-[[(3R)-3-[(2R)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)carbamate (70 mg, 0.12 mmol, 1.00 equiv), hydrogen chloride (conc.) (0.3 mL) in dichloromethane (5 mL). The resulting solution was stirred for 3 h at room temperature. The reaction was then quenched by the addition of 10 mL of sodium bicarbonate (aq.). The resulting mixture was concentrated under vacuum. The crude product (100 mg) was purified by preparative HPLC under the following conditions (1#-Pre-HPLC-015(Waters)): column: Xbridge Prep C18, 5 um, 19*50 mm; mobile phase: water with 50 mmol $NH_4HCO_3$ and $CH_3CN$ (5% $CH_3CN$ up to 28% in 10 min, up to 95% in 1.5 min, down to 5% in 1.5 min); detector: 254/220 nm. 32 mg product was obtained. This resulted in 32 mg (72%) of (2R)-3-[(3R)-12-[(4-aminocyclohexyl)oxy]-7-thia-9,11-diazatricyclo[6.4.0.0[2,6]]dodeca-1(8),2(6),9,11-tetraen-3-yl]-2-hydroxypropanamide as a white solid. MS: m/z 377 (M+H)$^+$. $^1$H NMR (300 MHz, $CD_3OD$): δ 8.46 (1H, br s), 5.33 (1H, m), 4.15 (1H, m), 3.60 (1H, m), 3.16 (1H, m), 3.00-2.90 (2H, m), 2.87 (1H, m), 2.88-2.53 (3H, m), 2.45-2.24 (4H, m), 1.87-1.66 (5H, m), 1.42 (2H, m).

Example 129
Synthesis of (2S)-3-[(3R)-12-[[4-(ethylamino)cyclohexyl]oxy]-7-thia-9,11-diazatricyclo[6.4.0.0[2,6]]dodeca-1(8),2(6),9,11-tetraen-3-yl]-2-hydroxypropanamide (I-136)
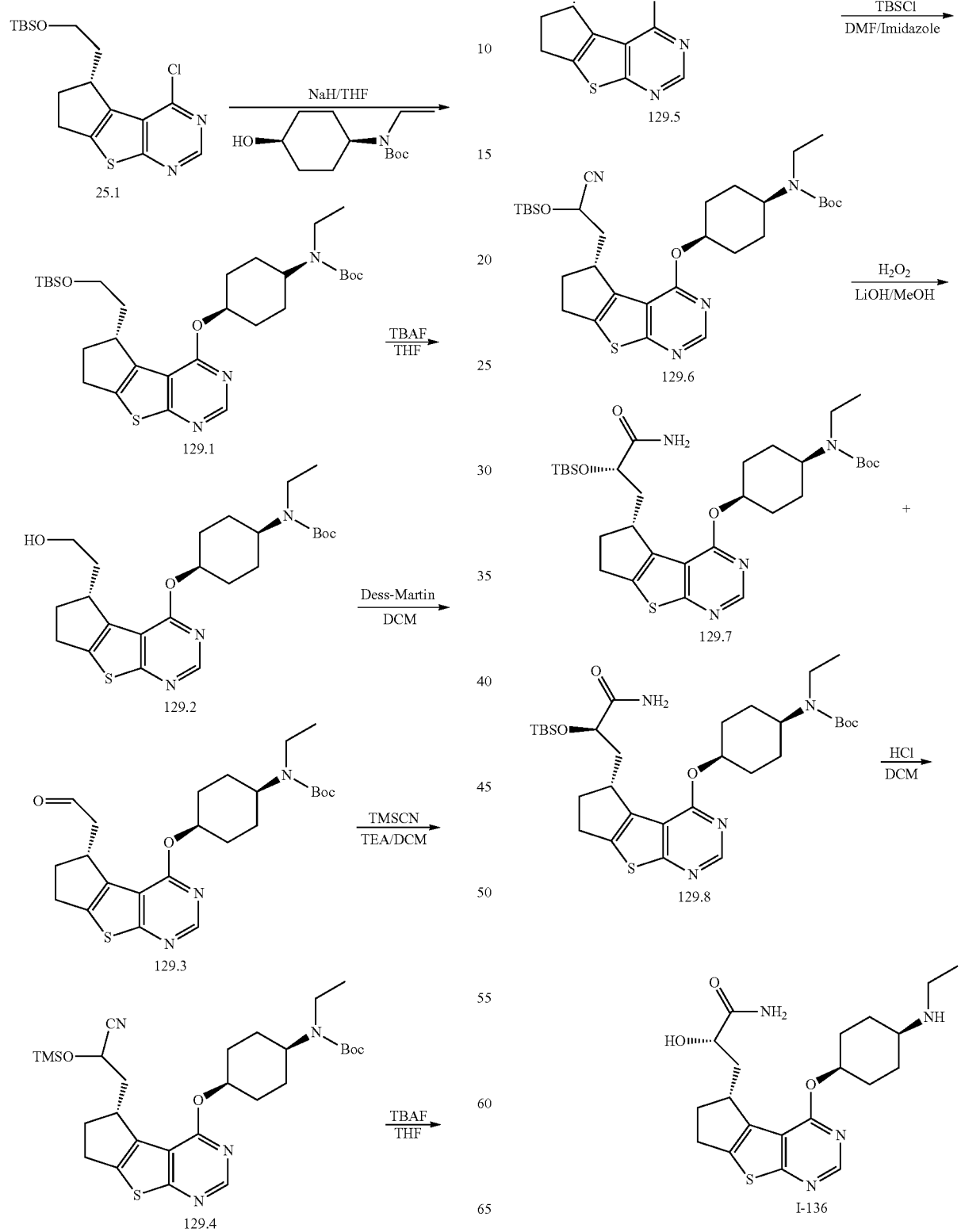

Synthesis of Compound 129.1.

Into a 100-mL round-bottom flask was placed a solution of tert-butyl N-ethyl-N-(4-hydroxycyclohexyl)carbamate (811 mg, 3.33 mmol, 2.05 equiv) in tetrahydrofuran (6 mL). Then sodium hydride (472 mg, 11.80 mmol, 7.26 equiv, 60%) was added to the mixture. The resulting solution was stirred for 0.5 h at 0° C. Then (3R)-3-[2-[(tert-butyldimethylsilyl)oxy] ethyl]-12-chloro-7-thia-9,11-diazatricyclo[6.4.0.0[2,6]] dodeca-1(8),2(6),9,11tetraene (600 mg, 1.63 mmol, 1.00 equiv) was added. The resulting solution was allowed to react, with stirring, for an additional 2.5 h at room temperature. The reaction was then quenched by the addition of 29 mL of NH$_4$Cl (sat.). The resulting solution was extracted with 3×50 mL of ethyl acetate and the organic layers combined and concentrated under vacuum. The residue was applied onto a silica gel column with ethyl acetate/petroleum ether (1:8). This resulted in 680 mg (73%) of tert-butyl N-(4-[[(3R)-3-[2-[(tert-butyldimethylsilyl)oxy]ethyl]-7-thia-9,11-diazatricyclo[6.4.0.0[2,6]]dodeca-1(8),2(6),9,11-tetraen-12-yl]oxy] cyclohexyl)-N-ethylcarbamate as colorless oil.

Synthesis of Compound 129.2.

Into a 100-mL round-bottom flask was placed a solution of tert-butyl N-(4-[[(3R)-3-[2-[(tert-butyldimethylsilyl)oxy] ethyl]-7-thia-9,11-diazatricyclo[6.4.0.0[2,6]]dodeca-1(8),2 (6),9,11-tetraen-12-yl]oxy]cyclohexyl)-N-ethylcarbamate (680 mg, 1.18 mmol, 1.00 equiv) and TBAF.3H2O (747 mg, 2.36 mmol, 2.00 equiv) in tetrahydrofuran (10 mL). The resulting solution was stirred for 2 h at 25° C. The resulting mixture was concentrated under vacuum. The residue was applied onto a silica gel column with ethyl acetate/petroleum ether (1:1). This resulted in 500 mg (92%) of tert-butyl N-ethyl-N-(4-[[(3R)-3-(2-hydroxyethyl)-7-thia-9,11-diazatricyclo[6.4.0.0[2,6]]dodeca-1(8),2(6),9,11-tetraen-12-yl] oxy]cyclohexyl)carbamate as a colorless oil.

Synthesis of Compound 129.3.

Into a 100-mL round-bottom flask was placed a solution of tert-butyl N-ethyl-N-(4-[[(3R)-3-(2-hydroxyethyl)-7-thia-9, 11-diazatricyclo[6.4.0.0[2,6]]dodeca-1(8),2(6),9,11-tetraen-12-yl]oxy]cyclohexyl)carbamate (500 mg, 1.08 mmol, 1.00 equiv) and Dess-Martin periodinane (689 mg, 1.62 mmol, 1.50 equiv) in dichloromethane (10 mL). The resulting solution was stirred for 2 h at 25° C. The reaction was then quenched by the addition of 30 mL of water. The resulting solution was extracted with 3×50 mL of dichloromethane and the organic layers combined and concentrated under vacuum. The residue was applied onto a silica gel column with ethyl acetate/petroleum ether (1:3). This resulted in 480 mg (96%) of tert-butyl N-ethyl-N-(4-[[(3R)-3-(2-oxoethyl)-7-thia-9, 11-diazatricyclo[6.4.0.0[2,6]]dodeca-1(8),2(6),9,11-tetraen-12-yl]oxy]cyclohexyl) carbamate as colorless oil.

Synthesis of Compound 129.4.

Into a 100-mL round-bottom flask was placed a solution of tert-butyl N-ethyl-N-(4-[[(3R)-3-(2-oxoethyl)-7-thia-9,11-diazatricyclo[6.4.0.0[2,6]]dodeca-1(8),2(6),9,11-tetraen-12-yl]oxy]cyclohexyl)carbamate (480 mg, 1.04 mmol, 1.00 equiv), TEA (50.6 mg, 0.50 mmol, 0.48 equiv) and TMSCN (297 mg, 3.00 mmol, 2.87 equiv) in dichloromethane (6 mL). The resulting solution was stirred for 1 h at 0° C. The resulting mixture was concentrated under vacuum. This resulted in 580 mg (crude) of tert-butyl N-(4-[[(3R)-3-[2-cyano-2-[(trimethylsilyl)oxy]ethyl]-7-thia-9,11-diazatricyclo[6.4.0.0[2,6]] dodeca-1(8),2(6),9,11-tetraen-12-yl]oxy]cyclohexyl)-N-ethylcarbamate as a colorless oil.

Synthesis of Compound 129.5.

Into a 50-mL round-bottom flask was placed a solution of tert-butyl N-(4-[[(3R)-3-[2-cyano-2-[(trimethylsilyl)oxy] ethyl]-7-thia-9,11-diazatricyclo[6.4.0.0[2,6]]dodeca-1(8),2 (6),9,11-tetraen-12-yl]oxy]cyclohexyl)-N-ethylcarbamate (580 mg, 1.04 mmol, 1.00 equiv) and TBA-3H$_2$O (656 mg, 2.08 mmol, 2.00 equiv) in tetrahydrofuran (6 mL). The resulting solution was stirred for 1 h at room temperature. The resulting mixture was concentrated under vacuum. The residue was applied onto a silica gel column with ethyl acetate/ petroleum ether (1:1). This resulted in 500 mg (99%) of tert-butyl N-(4-[[(3R)-3-(2-cyano-2-hydroxyethyl)-7-thia-9, 11-diazatricyclo[6.4.0.0[2,6]]dodeca-1(8),2(6),9,11-tetraen-12-yl]oxy]cyclohexyl)-N-ethylcarbamate as colorless oil.

Synthesis of Compound 129.6.

Into a 50-mL round-bottom flask, was placed a solution of tert-butyl N-(4-[[(3R)-3-(2-cyano-2-hydroxyethyl)-7-thia-9, 11-diazatricyclo[6.4.0.0[2,6]]dodeca-1(8),2(6),9,11-tetraen-12-yl]oxy]cyclohexyl)-N-ethylcarbamate (500 mg, 1.03 mmol, 1.00 equiv), imidazole (139 mg, 2.04 mmol, 1.99 equiv) and TBSCl (231 mg, 1.54 mmol, 1.50 equiv) in N,N-dimethylformamide (3 mL). The resulting solution was stirred for 1 h at room temperature. The reaction was then quenched by the addition of 20 mL of water. The resulting solution was extracted with 3×50 mL of ethyl acetate and the organic layers combined. The resulting mixture was washed with 3×30 mL of brine. The resulting mixture was concentrated under vacuum. The residue was applied onto a silica gel column with ethyl acetate/petroleum ether (1:10). This resulted in 590 mg (96%) of tert-butyl N-(4-[[(3R)-3-[2-[(tert-butyldimethylsilyl)oxy]-2-cyano ethyl]-7-thia-9,11-diazatricyclo[6.4.0.0[2,6]]dodeca-1(8),2(6),9,11-tetraen-12-yl]oxy]cyclohexyl)-N-ethylcarbamate as colorless oil.

Synthesis of Compounds 129.7 and 129.8.

Into a 50-mL round-bottom flask was placed a solution of tert-butyl N-(4-[[(3R)-3-[2-[(tert-butyldimethylsilyl)oxy]-2-cyanoethyl]-7-thia-9,11-diazatricyclo[6.4.0.0[2,6]]dodeca-1 (8),2(6),9,11-tetraen-12-yl]oxy]cyclohexyl)-N-ethylcarbamate (490 mg, 0.82 mmol, 1.00 equiv), LiOH.H$_2$O (66.9 mg, 1.59 mmol, 1.96 equiv) and H$_2$O$_2$ (30%) (0.5 mL) in methanol (4 mL). The resulting solution was stirred for 1 h at 0° C. The reaction was then quenched by the addition of 20 mL of Na$_2$SO$_3$ (sat.). The resulting solution was extracted with 3×50 mL of ethyl acetate and the organic layers combined and concentrated under vacuum. The residue was applied onto a silica gel column with ethyl acetate/petroleum ether (1:2.5). This resulted in 200 mg (79%) of tert-butyl,N-(4-[[(3R)-3-[(2R)-2-[(tert-butyldimethylsilyl)oxy]-2-carbamoylethyl]-7-thia-9,11-diazatricyclo[6.4.0.0[2,6]] dodeca-1(8),2(6),9,11-tetraen-12-yl]oxy]cyclohexyl)-N-ethylcarbamate as a colorless oil and 160 mg (63%) of tert-butyl ((1R,4r)-4-(((R)-5-((S)-3-amino-2-((tert-butyldimethylsilyl)oxy)-3-oxopropyl)-6,7-dihydro-SH-cyclopenta[4,5]thieno[2,3-d]pyrimidin-4-yl)oxy) cyclohexyl)(ethyl)carbamate as a colorless oil.

Synthesis of Compound I-136.

Into a 50-mL round-bottom flask was placed a solution of tert-butyl N-(4-[[(3R)-3-[(2S)-2-[(tert-butyldimethylsilyl) oxy]-2-carbamoylethyl]-7-thia-9,11-diazatricyclo[6.4.0.0[2, 6]]dodeca-1(8),2(6),9,11-tetraen-12-yl]oxy]cyclohexyl)-N-ethylcarbamate (160 mg, 0.26 mmol, 1.00 equiv) and hydrogen chloride (conc.) (0.3 mL) in dichloromethane (3 mL). The resulting solution was stirred for 1 h at 0° C. The resulting mixture was concentrated under vacuum. The crude product (200 mg) was purified by preparative HPLC under the following conditions (1#-Pre-HPLC-015(Waters)): column: Xbridge Prep C18, 5 um, 19*50 mm; mobile phase: water with 50 mmol NH₄HCO₃ and CH₃CN (10% CH₃CN up to 25% in 10 min, up to 95% in 1.5 min, down to 10% in 1.5 min); detector: 254/220 nm. 47.3 mg product was obtained. This resulted in 47.3 mg (45%) of (2S)-3-[(3R)-12-[[4-(ethylamino)cyclohexyl]oxy]-7-thia-9,11-diazatricyclo[6.4.0.0 [2,6]]dodeca-1(8),2(6),9,11-tetraen-3-yl]-2-hydroxypropanamide as a white solid. MS: m/z 405 (M+H)⁺. ¹H NMR (300 MHz, CD₃OD): δ 8.474 (1H, s), 5.24-5.26 (1H, m), 4.08-4.12 (1H, d), 3.53 (1H, m), 3.04-3.28 (1H, m), 2.92-2.95 (1H, m), 2.50-2.71 (4H, m), 2.40-2.47 (2H, m), 2.15-2.23 (2H, m), 1.98-2.07 (2H, m), 1.61-1.96 (3H, m), 1.26-1.34 (2H, m).

Example 130

Synthesis of (2R)-3-[(3R)-12-[[4-(ethylamino)cyclohexyl]oxy]-7-thia-9,11-diazatricyclo[6.4.0.0[2,6]]dodeca-1 (8),2(6),9,11-tetraen-3-yl]-2-hydroxypropanamide (I-139)

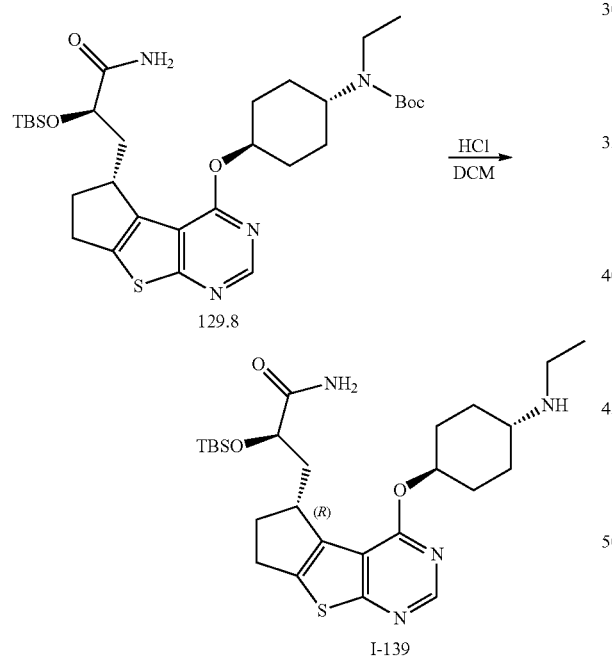

Synthesis of Compound I-139.

A solution of tert-butyl N-(4-[[(3R)-3-[(2R)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)-N-ethylcarbamate (200 mg, 0.32 mmol, 1.00 equiv), hydrogen chloride(conc.) (0.3 mL) in dichloromethane (3 mL). The resulting solution was stirred for 1 h at 0° C. The resulting mixture was concentrated under vacuum. The crude product (200 mg) was purified by preparative HPLC under the following conditions (1#-Pre-HPLC-016(Waters)): column: SunFire Prep C18, 19*150 mm 5 um; mobile phase: water WITH 50 mL NH₄CO₃ and CH₃CN (5.0% CH₃CN up to 44.5.0% in 10 min, up to 95.0% in 2 min, down to 5.0% in 2 min); detector: 254/220 nm. 57.4 mg product was obtained. This resulted in 57.4 mg (44%) of (2R)-3-[(3R)-12-[[4-(ethylamino)cyclohexyl]oxy]-7-thia-9,11-diazatricyclo[6.4.0.0[2,6]]dodeca-1(8),2(6),9,11-tetraen-3-yl]-2-hydroxypropanamide as a white solid. MS: m/z 405 (M+H)⁺. ¹H-NMR (300 MHz, CD₃OD): δ 8.474 (1H, s), 5.25-5.22 (1H, m), 4.00-4.03 (1H, t), 3.61 (1H, m), 3.07-3.10 (1H, m), 2.94-2.98 (1H, m), 2.52-2.68 (4H, m), 2.18-2.39 (2H, m), 1.64-1.71 (3H, m), 1.26-1.34 (2H, m), 1.08-1.13 (3H, d).

Example 131

Synthesis of Intermediate 131.1

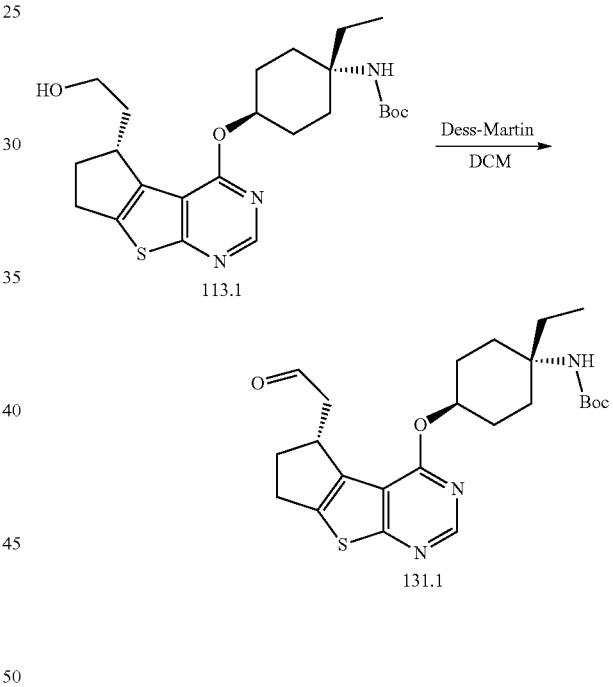

Synthesis of Intermediate 131.1.

A solution of tert-butyl N-(1-ethyl-4-[[(3R)-3-(2-hydroxyethyl)-7-thia-9,11-diazatricyclo[6.4.0.0[2,6]]dodeca-1(8),2 (6),9,11-tetraen-12-yl]oxy]cyclohexyl)carbamate (1.1 g, 2.38 mmol, 1.00 equiv) in dichloromethane (10 mL) was stirred at 0° C., then Dess-Martin (1.5 g) was added at 0° C. The resulting solution was stirred for 2 h at 25° C. The reaction was then quenched by the addition of 10 mL of sodium bicarbonate (aq.), extracted with 3×80 mL of dichloromethane and the organic layers combined and concentrated under vacuum. The residue was applied onto a silica gel column with ethyl acetate/petroleum ether (1:3). This resulted in 1.0 g (91%) of tert-butyl N-(1-ethyl-4-[[(3R)-3-(2-oxoethyl)-7-thia-9,11-diazatricyclo[6.4.0.0[2,6]]dodeca-1(8),2(6),9,11-tetraen-12-yl]oxy]cyclohexyl)carbamate as a colorless oil.

Example 132

Synthesis of (2R)-1-[(3R)-12-[[4-(dimethylamino)-4-ethylcyclohexyl]oxy]-7-thia-9,11-diazatricyclo[6.4.0.0[2,6]]dodeca-1(8),2(6),9,11-tetraen-3-yl]butan-2-ol (I-101)

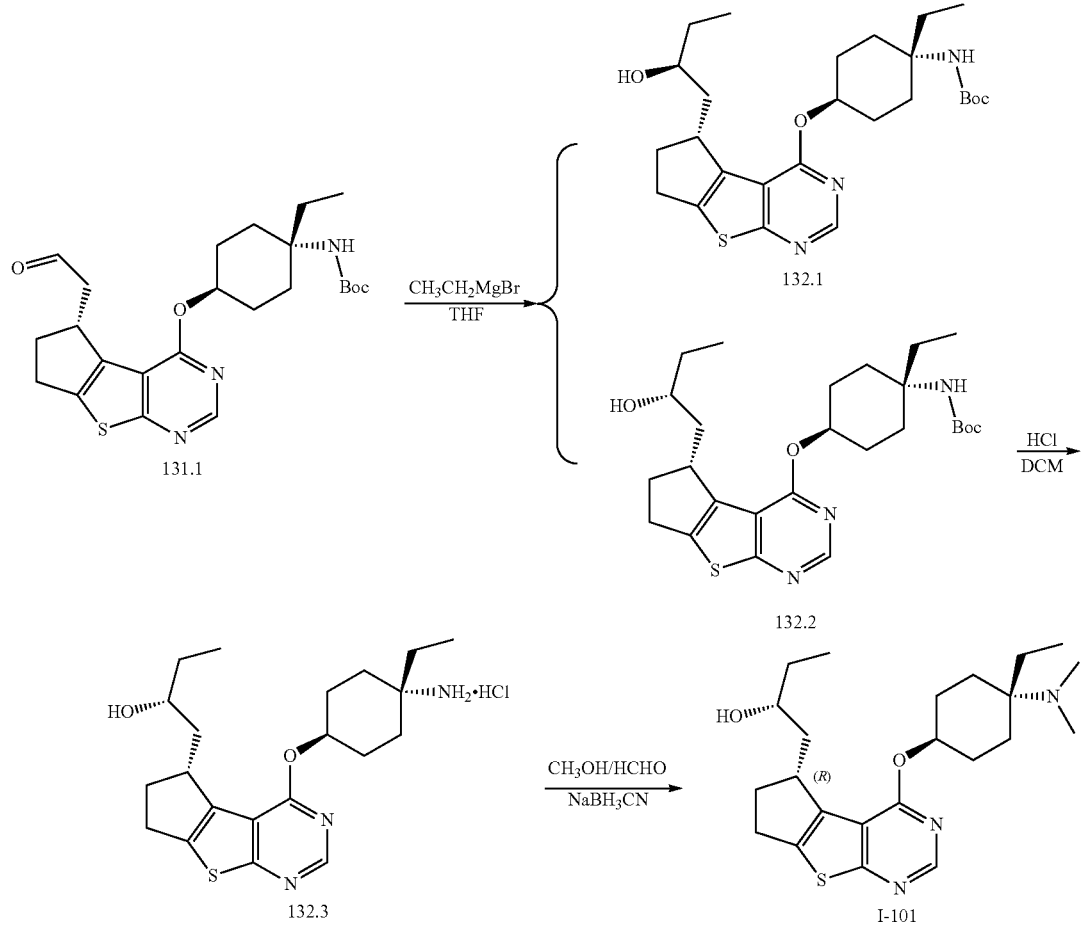

Synthesis of Compounds 132.1 and 132.2.

A solution of tert-butyl N-(1-ethyl-4-[[(3R)-3-(2-oxopropyl)-7-thia-9,11-diazatricyclo[6.4.0.0[2,6]]dodeca-1(8),2(6),9,11-tetraen-12-yl]oxy]cyclohexyl)carbamate (330 mg, 0.70 mmol, 1.00 equiv) in tetrahydrofuran (10 mL) was stirred at 0° C. This was followed by the addition of C₂H₅MgBr (0.479 mL) dropwise with stirring at 0° C. The resulting solution was stirred for 2 h at 0° C. The reaction was then quenched by the addition of 20 mL of NH₄Cl (aq.) and then extracted with 3×40 mL of ethyl acetate and the organic layers combined and concentrated under vacuum. The residue was applied onto a silica gel column with ethyl acetate/petroleum ether (1:4.5). This resulted in 120 mg (35%) of tert-butyl N-(1-ethyl-4-[[(3R)-3-[(2R)-2-hydroxybutyl]-7-thia-9,11-diazatricyclo[6.4.0.0[2,6]]dodeca-1(8),2(6),9,11-tetraen-12-yl]oxy]cyclohexyl)carbamate as a colorless oil and 70 mg (21%) of tert-butyl N-(1-ethyl-4-[[(3R)-3-[(2S)-2-hydroxybutyl]-7-thia-9,11-diazatricyclo[6.4.0.0[2,6]]dodeca-1(8),2(6),9,11-tetraen-12-yl]oxy]cyclohexyl)carbamate as a colorless oil.

Synthesis of Compound 132.3.

A solution of tert-butyl N-(1-ethyl-4-[[(3R)-3-[(2R)-2-hydroxybutyl]-7-thia-9,11-diazatricyclo[6.4.0.0[2,6]]dodeca-1(8),2(6),9,11-tetraen-12-yl]oxy]cyclohexyl)carbamate (120 mg, 0.25 mmol, 1.00 equiv) in dichloromethane (10 mL) was stirred at 0° C. And then hydrogen chloride (0.5 mL) was added. The resulting solution was stirred for 1 h at 0° C. The resulting mixture was concentrated under vacuum. This resulted in 90 mg (crude) of (2R)-1-[(3R)-12-[(4-amino-4-ethylcyclohexyl)oxy]-7-thia-9,11-diazatricyclo[6.4.0.0[2,6]]dodeca-1(8),2(6),9,11-tetraen-3-yl]butan-2-ol hydrochloride as colorless oil.

Synthesis of Compound I-101.

A solution of (2R)-1-[(3R)-12-[(4-amino-4-ethylcyclohexyl)oxy]-7-thia-9,11-diazatricyclo[6.4.0.0[2,6]]dodeca-1(8),2(6),9,11-tetraen-3-yl]butan-2-ol hydrochloride (90 mg, 0.21 mmol, 1.00 equiv) and HCHO (0.8 mL)(37%) in methanol (6 mL) was stirred at room temperature for 0.5 h. Then NaBH₃CN (72.88 mg, 1.16 mmol, 5.49 equiv) was added. The resulting solution was allowed to react, with stirring, for an additional 2 h at room temperature. The reaction was then quenched by the addition of 20 mL of water and then extracted with 3×50 mL of chloroform/iso-propanol(3/1) and the organic layers combined and concentrated under vacuum. The crude product (98 mg) was purified by preparative HPLC under the following conditions (Waters): column: column: SunFire Prep C18, 19*150 mm 5 um; mobile phase: water with 50 mL NH4CO3 and CH3CN (5.0% CH3CN up to 44.0% in 12 min, up to 95.0% in 2 min, down to 5.0% in 2 min); Detector, 254/220 nm. This resulted in 34.6 mg (39%) of (2R)-1-[(3R)-12-[[4-(dimethylamino)-4-ethylcyclohexyl]

oxy]-7-thia-9,11-diazatricyclo[6.4.0.0[2,6]]dodeca-1(8),2(6),9,11-tetraen-3-yl]butan-2-ol as an off-white solid. MS: 418 (M+H)⁺. ¹H NMR (300 MHz, CD₃OD): δ 8.47 (1H, s), 5.33-5.42 (1H, m), 3.68 (1H, m), 3.42-3.45 (1H, m), 3.00-3.14 (1H, m), 2.92-2.98 (1H, m), 2.70-2.73 (1H, m),2.50-2.67 (1H, m), 2.31-2.45 (1H, m), 2.06-2.11 (3H, m), 1.41-1.82 (11H, m), 0.91-1.05 (6H, m).

Example 133

Synthesis of (2S)-1-[(3R)-12-[(4-amino-4-ethylcyclohexyl)oxy]-7-thia-9,11-diazatricyclo[6.4.0.0[2,6]]dodeca-1(8),2(6),9,11-tetraen-3-yl]but-3-en-2-ol (I-126)

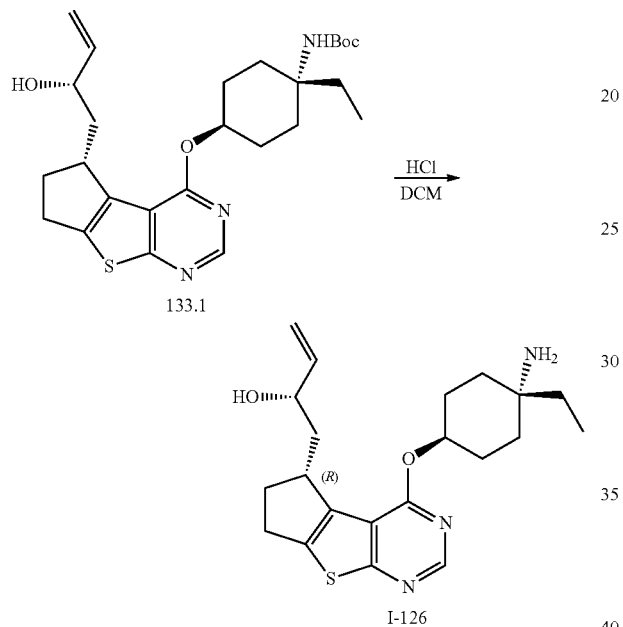

A 50-mL round-bottom flask was charged with a solution of tert-butyl N-(1-ethyl-4-[[(3R)-3-[(2S)-2-hydroxybut-3-en-1-yl]-7-thia-9,11-diazatricyclo[6.4.0.0[2,6]]dodeca-1(8),2(6),9,11-tetraen-12-yl]oxy]cyclohexyl)carbamate (35 mg, 0.07 mmol, 1.00 equiv; prepared in a manner analogous to compounds 132.1 and 132.2 in Example 132) and hydrogen chloride (conc.) (0.2 mL) in dichloromethane (10 mL). After stirring for 1 h at 0° C. in an water/ice bath, the reaction was then quenched by the addition of 20 mL of saturated sodium bicarbonate. The resulting solution was extracted with 4×30 mL of ethyl acetate and the organic layers combined and concentrated under vacuum. The crude product (30 mg) was purified by preparative HPLC under the following conditions (1#-Pre-HPLC-016(Waters)): column: SunFire Prep C18, 19*150 mm 5 um; mobile phase: water with 50 mL NH₄CO₃ and CH₃CN (5.0% CH₃CN up to 44.0% in 10 min, up to 95.0% in 2 min, down to 5.0% in 2 min); detector: 254/220 nm. The product was freeze-dried. This resulted in (2S)-1-[(3R)-12-[(4-amino-4-ethylcyclohexyl)oxy]-7-thia-9,11-diazatricyclo[6.4.0.0[2,6]]dodeca-1(8),2(6),9,11-tetraen-3-yl]but-3-en-2-ol (14.6 mg, 52%) as a white solid. ¹H NMR (400 MHz, CD₃OD): δ: 8.48 (s, 1H), 5.97-5.93 (m, 1H), 5.45-5.43 (m, 1H), 5.29 (d, J=8, 1H), 5.17 (d, J=8, 1H), 4.24-4.26 (m, 1H), 3.39-3.32 (m, 1H), 3.13-2.99 (m 2H), 2.66-2.47 (m, 2H), 2.20-2.16 (m, 3H), 1.93-1.55 (m, 9H), 0.99 (s, 3H). MS: m/z 388 (M+H)⁺.

Example 134

Synthesis of (R)-1-((R)-4-(((1r,4R)-4-(dimethylamino)-4-ethylcyclohexyl)oxy)-6,7-dihydro-5H-cyclopenta[4,5]thieno[2,3-d]pyrimidin-5-yl)but-3-en-2-ol (I-124)

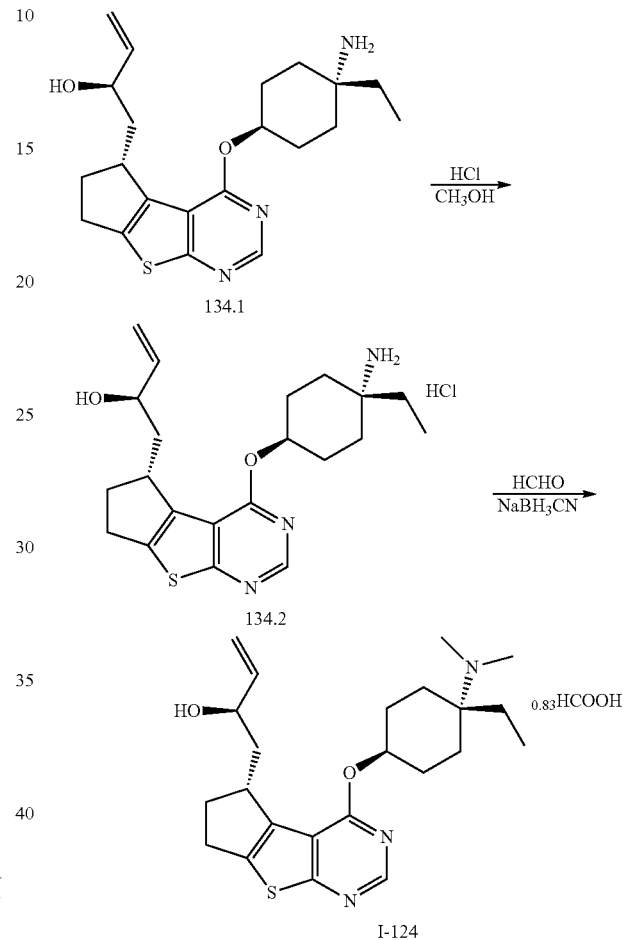

Synthesis of Compound 134.2.

A 100-mL round-bottom flask was charged with a solution of tert-butyl N-(1-ethyl-4-[[(3R)-3-[(2R)-2-hydroxybut-3-en-1-yl]-7-thia-9,11-diazatricyclo[6.4.0.0[2,6]]dodeca-1(8),2(6),9,11-tetraen-12-yl]oxy]cyclohexyl)carbamate (60 mg, 0.12 mmol, 1.00 equiv; prepared in a manner analogous to compounds 132.1 and 132.2 in Example 132) and hydrogen chloride (conc.) (0.3 mL) in methanol (10 mL). After stirring for 2 h at 0° C. in a water/ice bath. The resulting mixture was concentrated under vacuum. This resulted in (2R)-1-[(3R)-12-[(4-amino-4-ethylcyclohexyl)oxy]-7-thia-9,11-diazatricyclo[6.4.0.0[2,6]]dodeca-1(8),2(6),9,11-tetraen-3-yl]but-3-en-2-ol hydrochloride (30 mg, crude) as colorless oil.

Synthesis of Compound I-124.

A 50-mL round-bottom flask was charged with a solution of (2R)-1-[(3R)-12-[(4-amino-4-ethylcyclohexyl)oxy]-7-thia-9,11-diazatricyclo[6.4.0.0[2,6]]dodeca-1(8),2(6),9,11-tetraen-3-yl]but-3-en-2-ol hydrochloride (30 mg, 0.07 mmol, 1.00 equiv) and HCHO (0.5 mL) in methanol (10 mL). After stirring for 0.5 h at room temperature, NaBH₃CN (10 mg, 0.16 mmol, 2.25 equiv) was added. The resulting solution was allowed to react, with stirring, for an additional 4 h at room temperature. The resulting solution was diluted with 20 mL of water. The resulting solution was extracted with 3×30 mL of ethyl acetate and the organic layers combined and concentrated under vacuum. The crude product (30 mg) was purified by preparative HPLC under the following conditions (1#-Pre-HPLC-016(Waters)): column: SunFire Prep C18, 19*150 mm 5 um; mobile phase: water with 50 mL HCOOH and CH₃CN (5.0% CH₃CN up to 43.0% in 11 min, up to 95.0% in 2 min, down to 5.0% in 2 min); detector: 254/220 nm. Compound I-124 (5.3 mg, 16%) was obtained as a yellow solid. $^1$H NMR (400 MHz, CD₃OD): δ 8.50 (br, 1H), 8.45 (s, 1H), 5.90-5.86 (m, 1H), 5.45-5.44 (m, 1H), 5.24 (d, J=13 Hz, 1H), 5.02 (d, J=8 Hz, 1H), 4.24-4.21 (m, 1H), 3.68 (m, 1H), 3.33-3.00 (m, 2H), 2.84-2.71 (m, 1H), 2.34-1.92 (m, 13H), 1.05 (m, 3H).

LCMS: m/z 416 (M-0.83HCOOH+H)⁺.

Example 135

2-((R)-4-(((1r,4R)-4-(dimethylamino)cyclohexyl)oxy)-6,7-dihydro-5H-cyclopenta[4,5]thieno[2,3-d]pyrimidin-5-yl)-N—((R)-2-hydroxypropyl)acetamide (I-141)

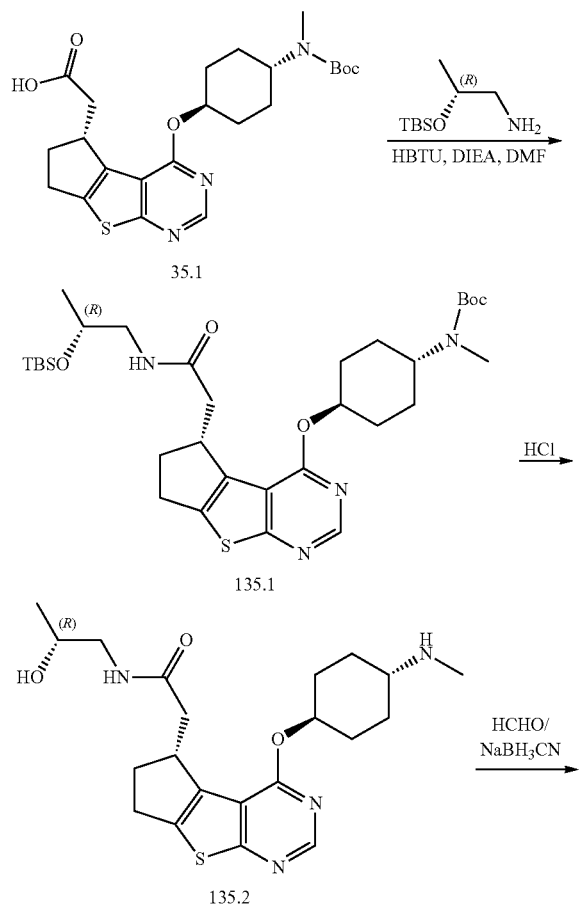

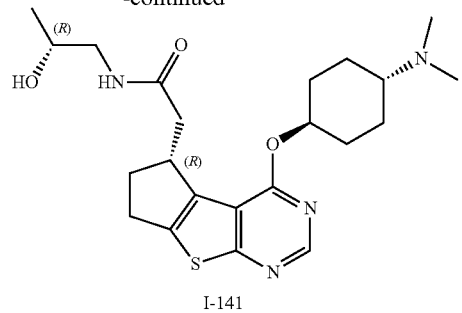

Synthesis of Compound 135.1.

To a solution of 2-[(3R)-12-[(4-[[(tert-butoxy)carbonyl](methyl)amino]cyclohexyl)oxy]-7-thia-9,11-diazatricyclo[6.4.0.0[2,6]]dodeca-1(12),2(6),8,10-tetraen-3-yl]acetic acid (500 mg, 1.08 mmol, 1.00 equiv) and [(2S)-1-aminopropan-2-yl]oxy(tert-butyl)dimethylsilane (250 mg, 1.32 mmol, 1.22 equiv) in N,N-dimethylformamide (30 mL) were added DIEA (500 mg, 3.87 mmol, 3.57 equiv) and HBTU (2.1 g, 5.54 mmol, 5.11 equiv). The resulting solution was stirred for 5 h at room temperature. The residue was dissolved in 50 mL of H₂O. The resulting solution was extracted with 5×40 mL of dichloromethane and the organic layers combined and dried over anhydrous sodium sulfate. The solids were filtered off. The resulting mixture was concentrated under vacuum. The residue was applied onto a silica gel column and eluted with EtOAc/PE (1/1). This resulted in 480 mg (70%) of tert-butyl N-(4-[[(3R)-3-([[(2R)-2-[(tert-butyldimethylsilyl)oxy]propyl]carbamoyl]methyl)-7-thia-9,11-diazatricyclo[6.4.0.0[2,6]]dodeca-1(12),2(6),8,10-tetraen-12-yl]oxy]cyclohexyl)-N-methylcarbamate.

Synthesis of Compound 135.2.

To a solution of tert-butyl N-(4-[[(3R)-3-([[(2R)-2-[(tert-butyldimethylsilyl)oxy]propyl]carbamoyl]methyl)-7-thia-9,11-diazatricyclo[6.4.0.0[2,6]]dodeca-1(12),2(6),8,10-tetraen-12-yl]oxy]cyclohexyl)-N-methylcarbamate (300 mg, 0.47 mmol, 1.00 equiv) in dichloromethane (3 mL) was added hydrogen chloride (conc.) (2 mL). The resulting solution was stirred for 2 h at room temperature. The pH value of the solution was adjusted to 7-8 with sodium carbonate (sat.). The resulting solution was extracted with 5×30 mL of ethyl acetate and the organic layers combined and dried over sodium sulfate and concentrated under vacuum. This resulted in 150 mg (76%) of N-[(2R)-2-hydroxypropyl]-2-[(3R)-12-[[4-(methylamino)cyclohexyl]oxy]-7-thia-9,11-diazatricyclo[6.4.0.0[2,6]]dodeca-1(12),2(6),8,10-tetraen-3-yl]acetamide as a yellow oil.

Synthesis of Compound I-141.

To a solution of N-[(2R)-2-hydroxypropyl]-2-[(3R)-12-[[4-(methylamino)cyclohexyl]oxy]-7-thia-9,11-diazatricyclo[6.4.0.0[2,6]]dodeca-1(12),2(6),8,10-tetraen-3-yl]acetamide (130 mg, 0.31 mmol, 1.00 equiv) in methanol (5 mL) was added HCHO (37%) (1 mL). The resulting solution was stirred for 20 min at room temperature. Then NaBH3CN (100 mg, 1.59 mmol, 5.12 equiv) was added. The resulting solution was allowed to react, with stirring, for an additional 3 h at room temperature. The reaction was then quenched by the addition of 1 mL of water. The resulting mixture was concentrated under vacuum. The crude product (120 mg) was purified by preparative HPLC under the following conditions: column: SunFire Prep C18, 19*150 mm 5 um; mobile phase: water with 50 mL NH₄CO₃ and CH₃CN (5.0% CH₃CN up to 43.0% in 12 min, up to 95.0% in 2 min, down to 5.0% in 2 min); detector: 254/220 nm. This resulted in 21 mg (16%) of 2-[(3R)-12-[[4-(dimethylamino)cyclohexyl]oxy]-7-thia-9,11-diazatricyclo[6.4.0.0[2,6]]dodeca-1(12),2(6),8,10-tetraen-3-yl]-N-[(2R)-2-hydroxypropyl]acetamide as a white solid. MS: m/z 433 (M+H)$^+$. $^1$H NMR (300 MHz, CD$_3$OD): δ 1.20 (3H, d), 1.41-1.75 (4H, m), 2.14 (2H, d), 2.21-2.41 (10H, m), 2.40 (1H, m), 2.67 (1H, m), 2.90-3.10 (2H, m), 3.2 (2H, m), 3.3 (1H, m), 3.82 (2H, m), 5.27 (1H, m), 8.47 (1H, s).

Example 136

Synthesis of 2-((R)-4-(((1r,4R)-4-((2-methoxyethyl)(methyl)amino)cyclohexyl)oxy)-6,7-dihydro-5H-cyclopenta[4,5]thieno[2,3-d]pyrimidin-5-yl)acetamide (I-130)

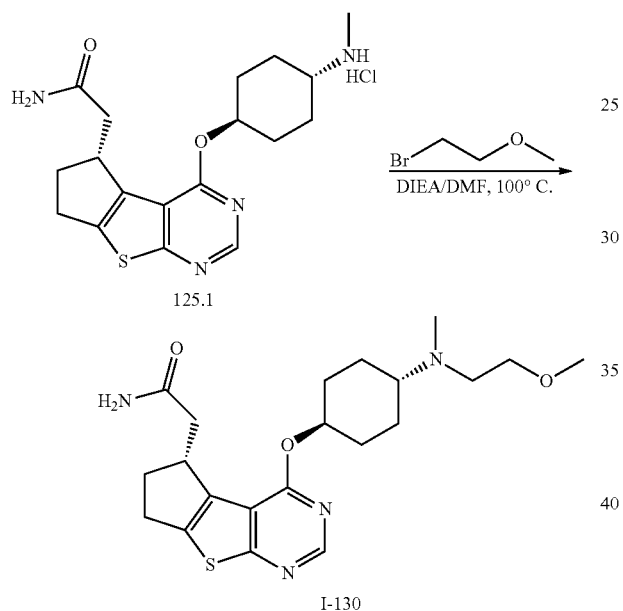

Synthesis of Compound I-130.

To a solution of 125.1 (100 mg, 0.25 mmol, 1.00 equiv) in N,N-dimethylformamide (4 mL) was added 1-bromo-2-methoxyethane (1 mL) and DIEA (97 mg, 0.75 mmol, 3.00 equiv) at room temperature under nitrogen. The resulting solution was stirred overnight at 100° C. in an oil bath. After completion, the reaction was cooled down to room temperature and diluted with 50 mL of ethyl acetate. The organic layer was washed with water and brine, dried over sodium sulfate and concentrated under vacuum. The crude product (100 mg) was purified by preparative HPLC under the following conditions (Waters): column: Xbridge Prep C18, 5 um, 19*50 mm; mobile phase: water with 50 mmol NH$_4$HCO$_3$ and CH$_3$CN (10% CH$_3$CN up to 36% in 10 min, up to 95% in 2.5 min, down to 10% in 2.5 min); flow rate: 20 mL/min; UV detection at 254/220 nm. The product-containing fractions were collected and partially evaporated to remove water and CH$_3$CN under reduced pressure. The residue was lyophilized overnight to give the desired product (30 mg) as a white solid.

MS: m/z 419 (M+H)$^+$. $^1$H NMR (400 MHz, CD$_3$OD): δ 8.45 (s, 1H), 5.25-4.85 (m, 1H), 3.79-3.73 (m, 1H), 3.51-3.47 (t, 2H), 3.32 (s, 3H), 3.12-3.05 (m, 1H), 2.99-2.91 (m, 2H), 2.77-2.60 (m, 4H), 2.33-2.18 (m, 7H), 1.98-1.94 (d, 2H), 1.64-1.44 (m, 4H).

Example 137

Synthesis of 2-((R)-4-(((1r,4R)-4-(methyl(oxetan-3-yl)amino)cyclohexyl)oxy)-6,7-dihydro-5H-cyclopenta[4,5]thieno[2,3-d]pyrimidin-5-yl)acetamide (I-129)

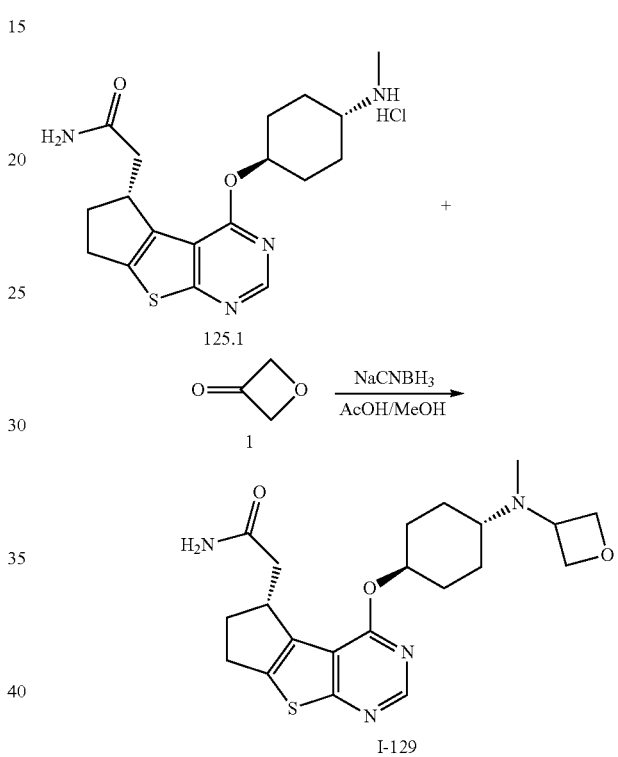

To a solution of 2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]acetamide hydrochloride (100 mg, 0.25 mmol, 1.00 equiv) in methanol (5 mL) was added oxetan-3-one (1 mL), NaCNBH$_3$ (44 mg, 0.75 mmol, 3.00 equiv) and AcOH (0.2 mL) in water/ice bath. The resulting solution was stirred for 2 h at room temperature. After completion, the resulting mixture was concentrated under vacuum. The crude product (100 mg) was purified by preparative HPLC under the following conditions (Waters): column: Xbridge Prep C18, 5 um, 19*50 mm; mobile phase: water with 0.05% NH$_4$HCO$_3$ and CH$_3$CN (10% CH$_3$CN up to 35% in 11 min, up to 95% in 2.5 min, down to 10% in 2.5 min); flow rate: 20 mL/min; UV detection at 254/220 nm. The product-containing fractions were collected and partially evaporated to remove water and CH$_3$CN under reduced pressure. The residue was lyophilized overnight to give the desired product (74 mg) as a white solid. MS: m/z 417 (M+H)$^+$. $^1$H NMR (400 MHz, CD$_3$OD): δ 8.48 (s, 1H), 5.28-5.21 (m, 1H), 4.69-4.67 (d, 4H), 4.08-4.01 (m, 1H), 3.82-3.80 (m, 1H), 3.18-3.10 (m, 1H), 3.04-2.97 (m, 2H), 2.77-2.70 (m, 1H), 2.53-2.47 (m, 1H), 2.32-2.30 (m, 3H), 2.29-2.25 (m, 4H), 1.88-1.84 (d, 2H), 1.66-1.31 (m, 4H).

Example 138

Synthesis of 4-[[(3R)-3-[(2R)-2-methoxybutyl]-7-thia-9,11-diazatricyclo[6.4.0.0[2,6]]dodeca-1(8),2(6),9,11-tetraen-12-yl]oxy]-N,N-dimethylcyclohexan-1-amine (I-117)

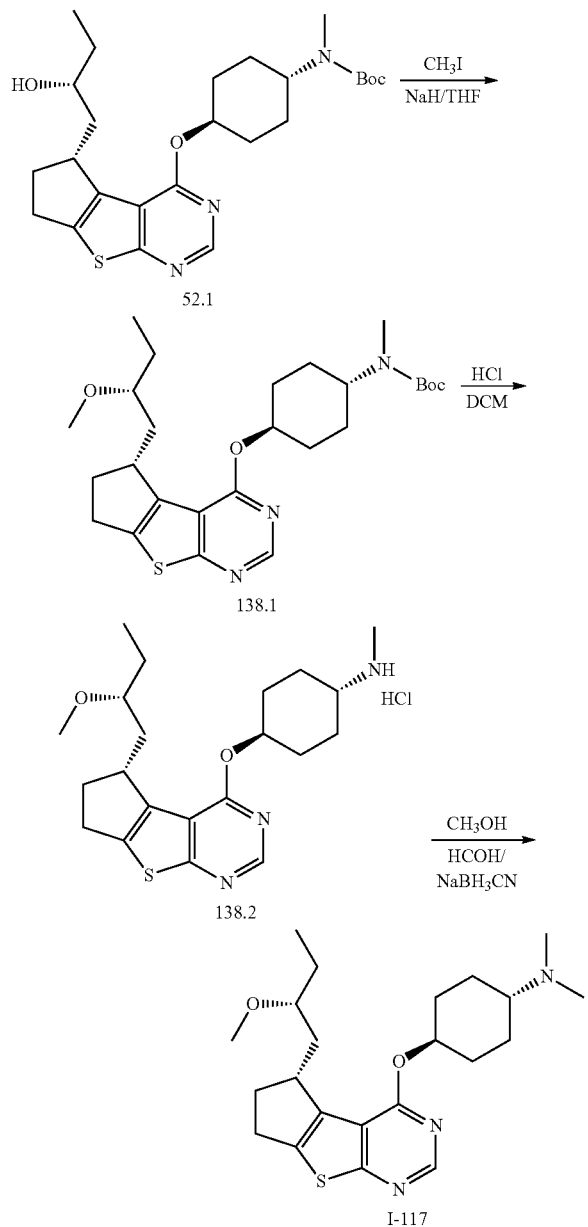

Synthesis of Compound 138.1.

A solution of compound 52.1 (250 mg, 0.53 mmol, 1.00 equiv) in tetrahydrofuran (10 mL) was stirred at 0° C. Then sodium hydride (105 mg) was added at 0° C. After stirring for 30 min, CH$_3$I (112 mg, 0.79 mmol, 1.50 equiv) was added. The resulting solution was stirred for 2 h at 25° C. The reaction was then quenched by the addition of 20 mL of NH$_4$Cl (aq.). The resulting solution was extracted with 3×50 mL of ethyl acetate and the organic layers combined and concentrated under vacuum. The residue was applied onto a silica gel column with ethyl acetate/petroleum ether (1:5). This resulted in 200 mg (78%) of tert-butyl N-(4-[[(3R)-3-[(2R)-2-methoxybutyl]-7-thia-9,11-diazatricyclo[6.4.0.0[2,6]]dodeca-1(8),2(6),9,11-tetraen-12-yl]oxy]cyclohexyl)-N-methylcarbamate as a colorless oil.

Synthesis of Compound 138.2.

A solution of tert-butyl N-(4-[[(3R)-3-[(2R)-2-methoxybutyl]-7-thia-9,11-diazatricyclo[6.4.0.0[2,6]]dodeca-1(8),2(6),9,11-tetraen-12-yl]oxy]cyclohexyl)-N-methylcarbamate (200 mg, 0.41 mmol, 1.00 equiv) in dichloromethane (10 mL) was stirred at room temperature. This was followed by the addition of hydrogen chloride (0.8 mL) dropwise with stirring at 0° C. The resulting solution was stirred for 1 h at 0° C. The resulting mixture was concentrated under vacuum. This resulted in 120 mg (crude) of 4-[[(3R)-3-[(2R)-2-methoxybutyl]-7-thia-9,11-diazatricyclo[6.4.0.0[2,6]]dodeca-1(8),2(6),9,11-tetraen-12-yl]oxy]-N-methylcyclohexan-1-amine hydrochloride as a colorless oil.

Synthesis of Compound I-117.

A solution of 4-[[(3R)-3-[(2R)-2-methoxybutyl]-7-thia-9,11-diazatricyclo[6.4.0.0[2,6]]dodeca-1(8),2(6),9,11-tetraen-12-yl]oxy]-N-methylcyclohexan-1-amine hydrochloride (120 mg, 0.28 mmol, 1.00 equiv) and HCHO (0.8 mL in methanol (6 mL) was stirred at room temperature. The resulting solution was stirred for 0.5 h at room temperature. Then NaBH$_3$CN (97.02 mg, 1.54 mmol, 5.48 equiv) was added. The resulting solution was allowed to react, with stirring, for an additional 2 h at room temperature. The reaction was then quenched by the addition of 10 mL of water. The resulting solution was extracted with 3×50 mL of chloroform/iso-propanol (3/1) and the organic layers combined and concentrated under vacuum. The crude product (100 mg) was purified by preparative HPLC under the following conditions (1#-Pre-HPLC-016(Waters)): column: SunFire Prep C18, 19*150 mm 5 um; mobile phase: water with 50 mL HCOOH and CH$_3$CN (5.0% CH$_3$CN up to 45.0% in 11 min, up to 95.0% in 2 min, down to 5.0% in 2 min); Detector, UV 254/220 nm. This resulted in 34.2 mg (30%) of Compound I-117 as a colorless oil. $^1$H NMR (CD$_3$OD, 300 MHz): δ 8.47 (1H, s), 5.26-5.27 (1H, m), 3.31-3.35 (1H, m), 3.26-3.30 (4H, m), 3.08-3.11 (1H, m), 2.95-3.00 (1H, m), 2.64 (1H, m), 2.20-2.42 (10H, m), 1.97-2.08 (3H, m), 1.47-1.75 (7H, m), 0.96-1.01 (3H, t). MS: m/z 404 (M+H)$^+$.

Example 139

Synthesis of (1R,4r)-4-(((R)-5-((S)-2-methoxybutyl)-6,7-dihydro-5H-cyclopenta[4,5]thieno[2,3-d]pyrimidin-4-yl)oxy)-N,N-dimethylcyclohexanamine (I-119)

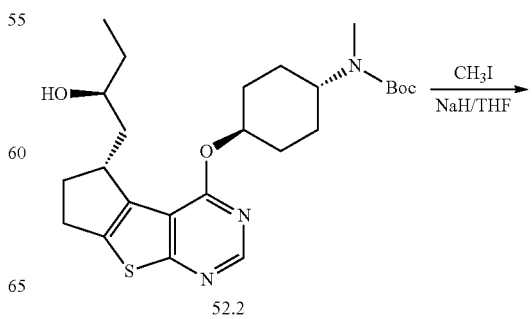

357
-continued

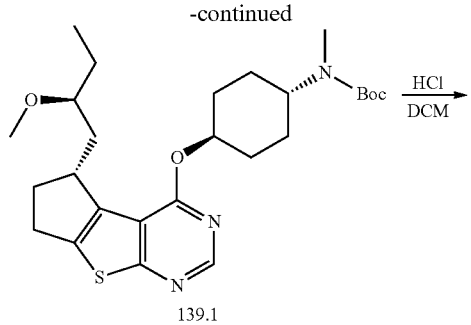
139.1

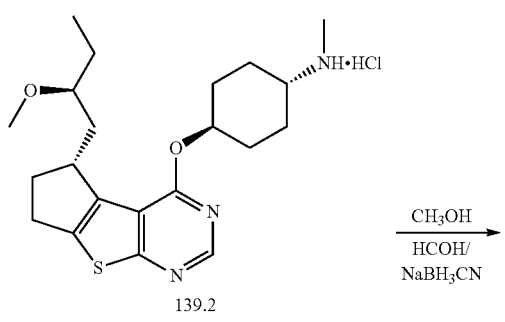
139.2

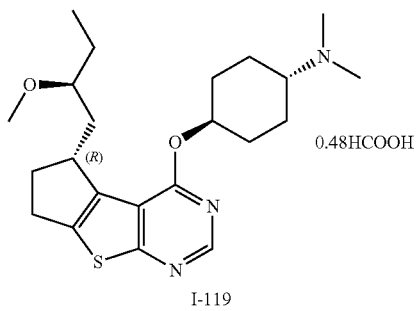
I-119

Compound I-119 was prepared in a manner consistent with I-117 except that starting material 52.2 was used rather than 52.1. Isolated a light yellow oil. MS: m/z 404 (M-0.48HCOOH+H)$^+$. $^1$H NMR (CD$_3$OD, 300 MH): δ 8.47 (1H, s), 5.26-5.27 (1H, m), 3.58 (1H, m), 3.31-3.37 (3H, d), 3.22-3.25 (1H, m), 3.05-3.09 (1H, m), 2.91-3.01 (2H, m), 2.63-2.72 (7H, m), 2.31-2.38 (3H, m), 2.11-2.19 (3H, m), 1.60-1.74 (4H, m), 1.42-1.57 (3H, m), 0.87-0.92 (3H, t).

358
Example 140

Synthesis of (S)-3-((R)-4-(((1r,4R)-4-(dimethylamino)cyclohexyl)oxy)-6,7-dihydro-5H-cyclopenta[4,5]thieno[2,3-d]pyrimidin-5-yl)-2-hydroxy-N-(hydroxymethyl)propanamide (I-100)

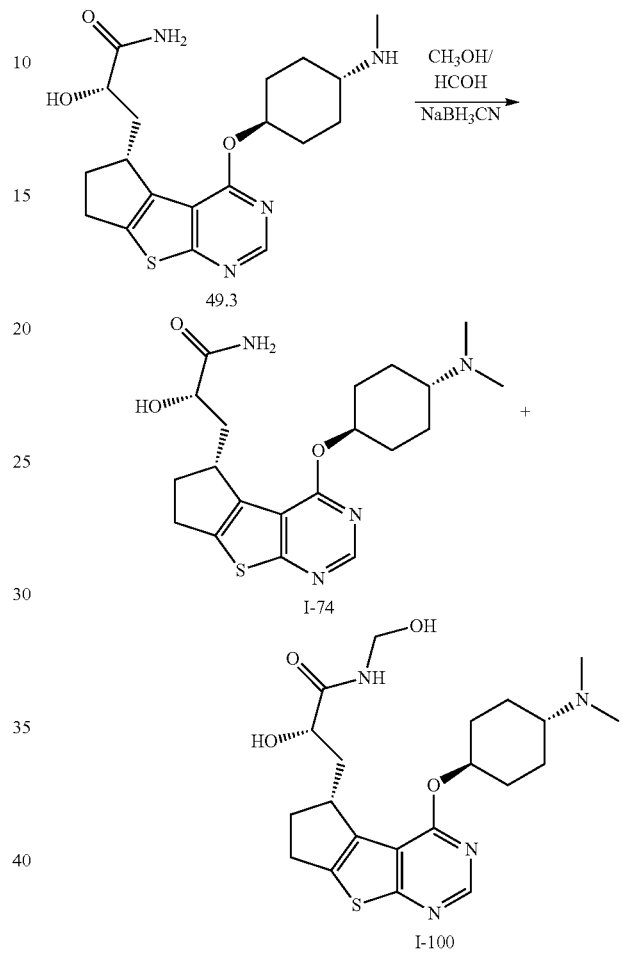

A solution of (2S)-2-hydroxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanamide (400 mg, 1.02 mmol, 1.00 equiv) and HCOH (37%) (0.8 mL) in methanol (5 mL) was stirred at room temperature for 30 min, then NaBH$_3$CN (323 mg, 5.14 mmol, 5.02 equiv) was added. The resulting solution was stirred for 2 h at 25° C. The reaction was then quenched by the addition of water. The resulting solution was extracted with 3×20 mL of chloroform/iso-propanol (3/1) and the organic layers combined and concentrated under vacuum. The crude product (80 mg) was purified by preparative HPLC under the following conditions (1#-Pre-HPLC-001(SHIMADZU)): column: SunFire Prep C18, 19*150 mm 5 um; mobile phase: water with 0.05% HCOOH and CH$_3$CN (6.0% CH$_3$CN up to 56.0% in 13 min); Detector, 254/220 nm. This resulted in 67.5 mg (16%) of I-74 as an off-white solid and 55.4 mg (12%) of I-100. MS: m/z 435 (M+H)$^+$. $^1$H NMR (400 MHz, CD$_3$OD): δ 8.474 (1H, s), 5.226-5.333 (1H, m), 4.10-4.20 (1H, d), 3.70-3.77 (1H, m), 3.10-3.20 (1H, m), 2.90-3.05 (1H, m), 2.69-2.88 (1H, m), 2.45-2.60 (3H, m), 2.20-2.40 (8H, m), 2.00-2.15 (2H, m), 1.66-1.91 (3H, m), 1.45-1.55 (2H, m).

Example 141

Synthesis of (2S)-2-hydroxy-3-[(3R)-12-[(4-[methyl[2-oxo-2-(pyrrolidin-1-yl)ethyl]amino]cyclohexyl)oxy]-7-thia-9,11-diazatricyclo[6.4.0.0^[2,6]]dodeca-1(8),2(6),9,11-tetraen-3-yl]propanamide (I-149)

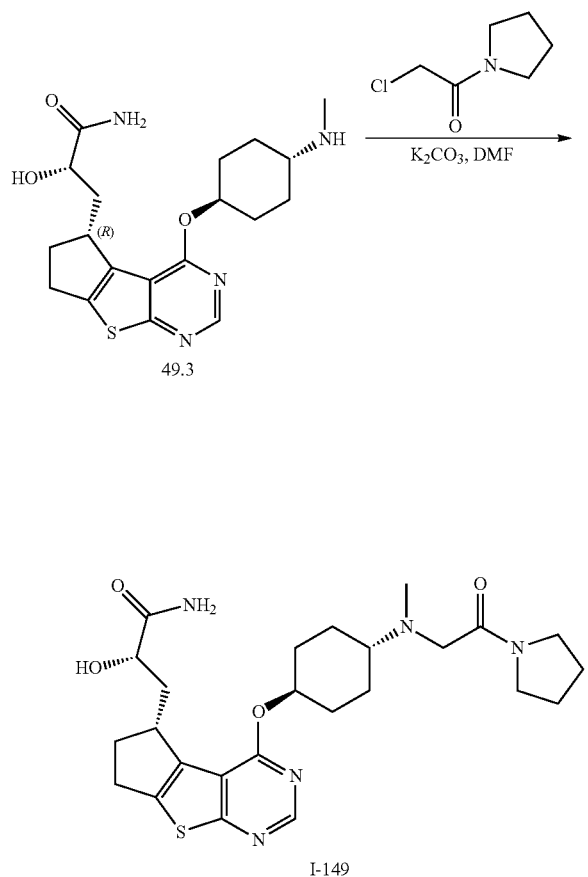

Into a 50-mL round-bottom flask, a solution of (2S)-2-hydroxy-3-[(3R)-12-[[4-(methylamino)cyclohexyl]oxy]-7-thia-9,11-diazatricyclo[6.4.0.0^[2,6]]dodeca-1(8),2(6),9,11-tetraen-3-yl]propanamide hydrochloride (110 mg, 0.26 mmol, 1.00 equiv), potassium carbonate (179 mg, 1.30 mmol, 5.03 equiv) and 2-chloro-1-(pyrrolidin-1-yl)ethan-1-one (152 mg, 1.03 mmol, 4.00 equiv) in N,N-dimethylformamide (6 mL) was stirred overnight at room temperature. The resulting solution was diluted with 20 mL of water. The resulting solution was extracted with 4×20 mL of ethyl acetate and the organic layers combined and concentrated under vacuum. The crude product was purified by flash preparative HPLC under the following conditions (IntelFlash-1): column: silica gel; mobile phase; Detector, UV 254 nm. This resulted in (2S)-2-hydroxy-3-[(3R)-12-[(4-[methyl[2-oxo-2-(pyrrolidin-1-yl)ethyl]amino]cyclohexyl)oxy]-7-thia-9,11-diazatricyclo[6.4.0.0^[2,6]]dodeca-1(8),2(6),9,11-tetraen-3-yl]propanamide (63.8 mg, 49%) as a white solid. $^1$H NMR (400 MHz, CD$_3$OD): δ 8.47 (s, 1H), 5.28 (m, 1H), 4.17-4.14 (m, 1H), 3.59-3.32 (m, 7H), 3.15-2.98 (m, 2H), 2.76-2.70 (m, 2H), 2.52-2.33 (m, 7H), 2.04-1.89 (m, 6H), 1.74-1.53 (m, 5H). MS: m/z 502 (M+H)$^+$.

Example 142

Synthesis of 3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-2,2-difluoropropanamide (I-144)

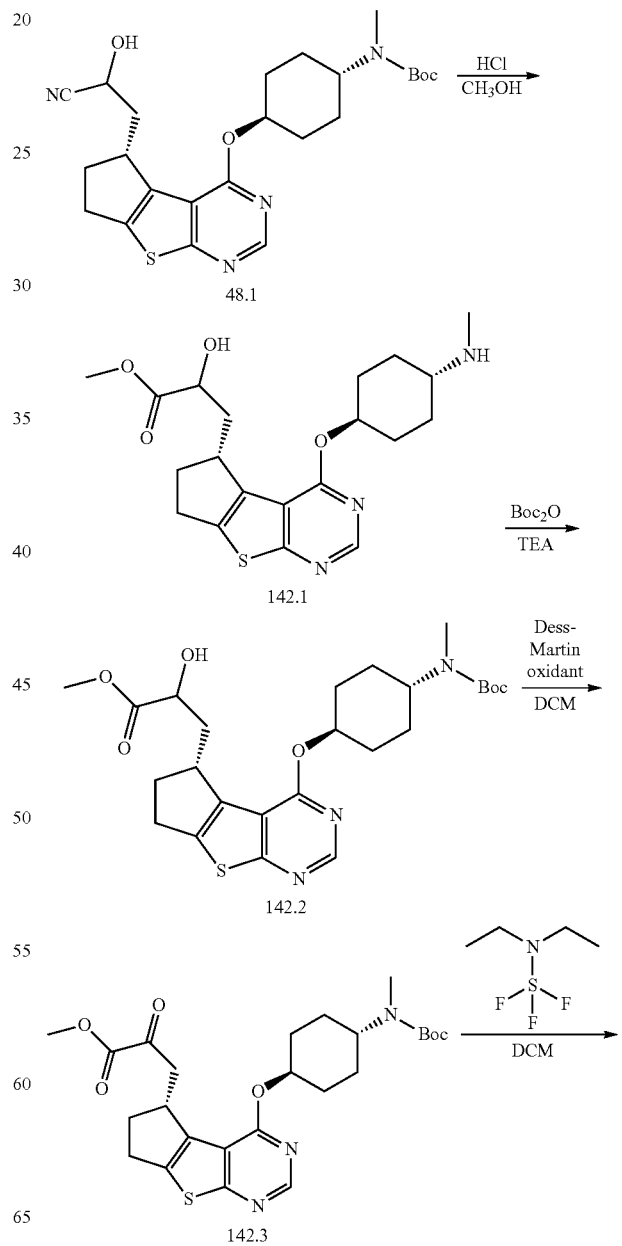

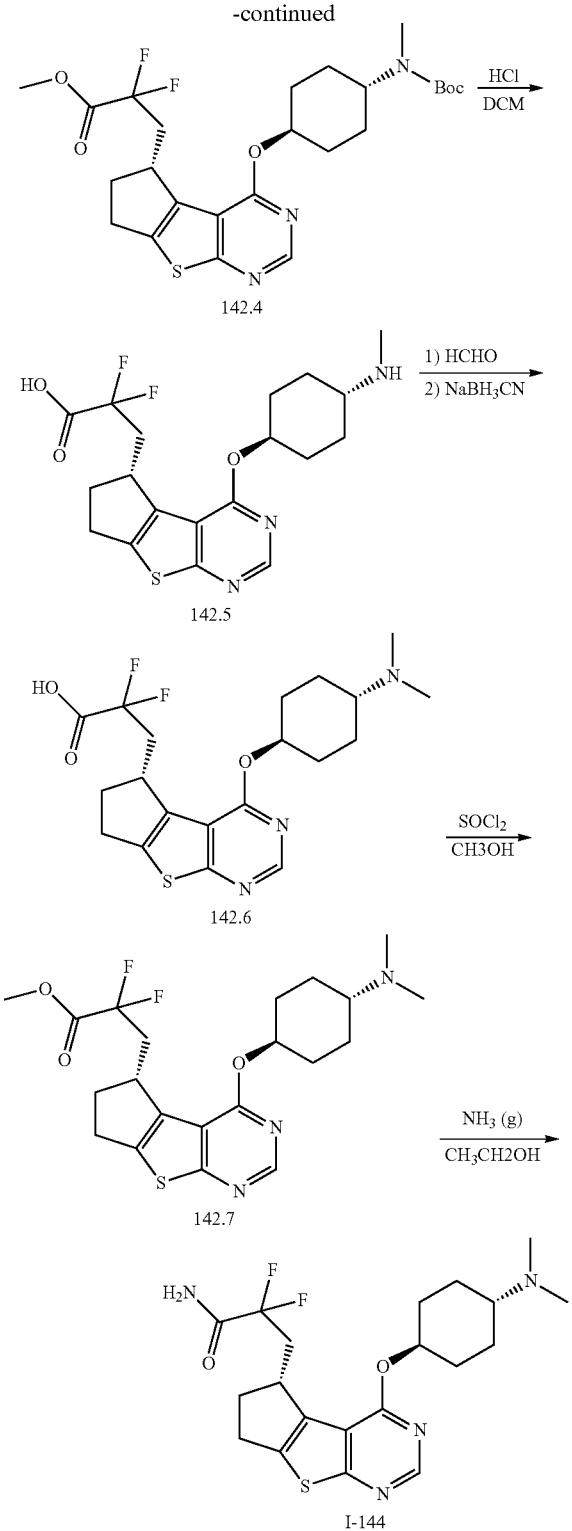

chloride (conc.) (2.9 mL) in methanol (7 mL) was stirred for 8 h at 50° C. The reaction was diluted with 50 mL water, and then quenched by the addition of 10 mL of sodium carbonate (sat.). The resulting solution was extracted with 3×30 mL of ethyl acetate, dried over anhydrous sodium sulfate and concentrated under vacuum. This resulted in methyl 2-hydroxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanoate (375 mg, crude) as a yellow oil.

Synthesis of Compound 142.2.

A solution of methyl 2-hydroxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanoate (375 mg, 0.92 mmol, 1.00 equiv), TEA (0.5 mL) and di-tert-butyl dicarbonate (303 mg, 1.39 mmol, 1.50 equiv) in dichloromethane (20 mL) was stirred overnight at room temperature. The resulting solution was diluted with 30 mL of water. The resulting solution was extracted with 3×30 mL of ethyl acetate and the organic layers combined and concentrated under vacuum. The residue was purified onto a silica gel column with ethyl acetate/petroleum ether (1:3). This resulted in methyl 3-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]-2-hydroxypropanoate (275 mg, 59%) as a colorless oil.

Synthesis of Compound 142.3.

A solution of methyl 3-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]-2-hydroxypropanoate (275 mg, 0.54 mmol, 1.00 equiv) and Dess-Martin oxidant (230 mg, 0.54 mmol, 1.00 equiv) in dichloromethane (15 mL) was stirred for 2 h at room temperature. The reaction was then quenched by the addition of 20 mL of saturated sodium bicarbonate, extracted with 3×30 mL of ethyl and concentrated under vacuum. The residue was applied onto a silica gel column with ethyl acetate/petroleum ether (1:4). This resulted in methyl 3-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]-2-oxopropanoate (205 mg, 75%) as a colorless oil.

Synthesis of Compound 142.4.

A solution of methyl 3-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]-2-oxopropanoate (170 mg, 0.34 mmol, 1.00 equiv) and diethyl (trifluoro-4-sulfanyl)amine (163 mg, 1.01 mmol, 3.00 equiv) in dichloromethane (8 mL) was stirred for 2 days at 25° C. The reaction was then quenched by the addition of 20 mL of saturated sodium bicarbonate, extracted with 3×30 mL of ethyl acetate, concentrated under vacuum and applied onto a silica gel column with ethyl acetate/petroleum ether (1:4). This resulted in methyl 3-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2 (6),9,11-tetraen-3-yl]-2,2-difluoropropanoate (180 mg) as a colorless oil.

Synthesis of Compound 142.5.

A solution of methyl 3-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]-2,2-difluoropropanoate (170 mg, 0.32 mmol, 1.00 equiv) and Synthesis of Compound 142.1.

A solution of tert-butyl N-(4-[[(3R)-3-(2-cyano-2-hydroxyethyl)-7-thia-9,11-diazatricyclo[6.4.0.0[2,6]]dodeca-1(8),2(6),9,11-tetraen-12-yl]oxy]cyclohexyl)-N-methylcarbamate (445 mg, 0.94 mmol, 1.00 equiv) and hydrogen hydrogen chloride (conc.) (10 mL) in dichloromethane (0.3 mL) was stirred for 2 h at 0° C. in a water/ice bath. The resulting mixture was concentrated under vacuum. This resulted in 2,2-difluoro-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanoic acid hydrochloride (130 mg, crude) as a yellow oil.

Synthesis of Compound 142.6.

A solution of 2,2-difluoro-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanoic acid hydrochloride (130 mg, 0.29 mmol, 1.00 equiv) and HCHO (37%) (0.15 mL) in methanol (10 mL) was stirred for 30 min at room temperature. NaBH₃CN (80 mg, 1.27 mmol, 4.38 equiv) was added. The resulting solution was allowed to react, with stirring, for an additional 4 h at room temperature. The resulting solution was diluted with 20 mL of water, extracted with 3×30 mL of ethyl acetate, dried over anhydrous sodium sulfate and concentrated under vacuum. This resulted in 3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-2,2-difluoropropanoic acid (105 mg, 85%) as a yellow oil.

Synthesis of Compound 142.7.

A solution of 3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-2,2-difluoropropanoic acid (130 mg, 0.31 mmol, 1.00 equiv) was dissolved in methanol (15 mL). Sulfuroyl dichloride (72 mg, 0.61 mmol, 1.98 equiv) was added dropwise. The resulting solution was stirred overnight at 30° C. The reaction was then quenched by the addition of 20 mL of saturated sodium bicarbonate, extracted with chloroform, dried over anhydrous sodium sulfate and concentrated under vacuum. This resulted in methyl 3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-2,2-difluoropropanoate (103 mg, crude) as a yellow oil.

Synthesis of Compound I-144.

A solution of NH₃ (g) was transferred into ethanol (20 mL) over 30 min. This was followed by the addition of methyl 3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-2,2-difluoropropanoate (103 mg, 0.23 mmol, 1.00 equiv). The resulting solution was stirred overnight at room temperature. The resulting mixture was concentrated under vacuum. The crude product (100 mg) was purified by preparative HPLC under the following conditions (1#-Pre-HPLC-016(Waters)): column: XBridge Prep C18 OBD column: 5 um, 19*150 mm; mobile phase: water (50 mM NH₄HCO₃) and CH₃CN (14.0% CH₃CN up to 33.0% in 12 min, up to 95.0% in 1 min, down to 14.0% in 2 min); Detector, UV 254/220 nm. The product was freeze-dried. This resulted in 3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-2,2-difluoropropanamide (41.3 mg, 42%) as a white solid. ¹H NMR (300 MHz, CD₃OD): δ 8.51 (s, 1H), 5.30-5.23 (m, 1H), 3.66-3.51 (m, 1H), 3.32-2.70 (m, 4H), 2.51-2.01 (m, 13H), 1.74-1.44 (m, 4H). MS: m/z 425 (M+H)⁺.

Example 143

Synthesis of 2-[(3R)-12-[(4-[methyl[2-oxo-2-(pyrrolidin-1-yl)ethyl]amino]cyclohexyl)amino]-7-thia-9,11-diazatricyclo[6.4.0.0[2,6]]dodeca-1(8),2(6),9,11-tetraen-3-yl]acetamide (I-123)

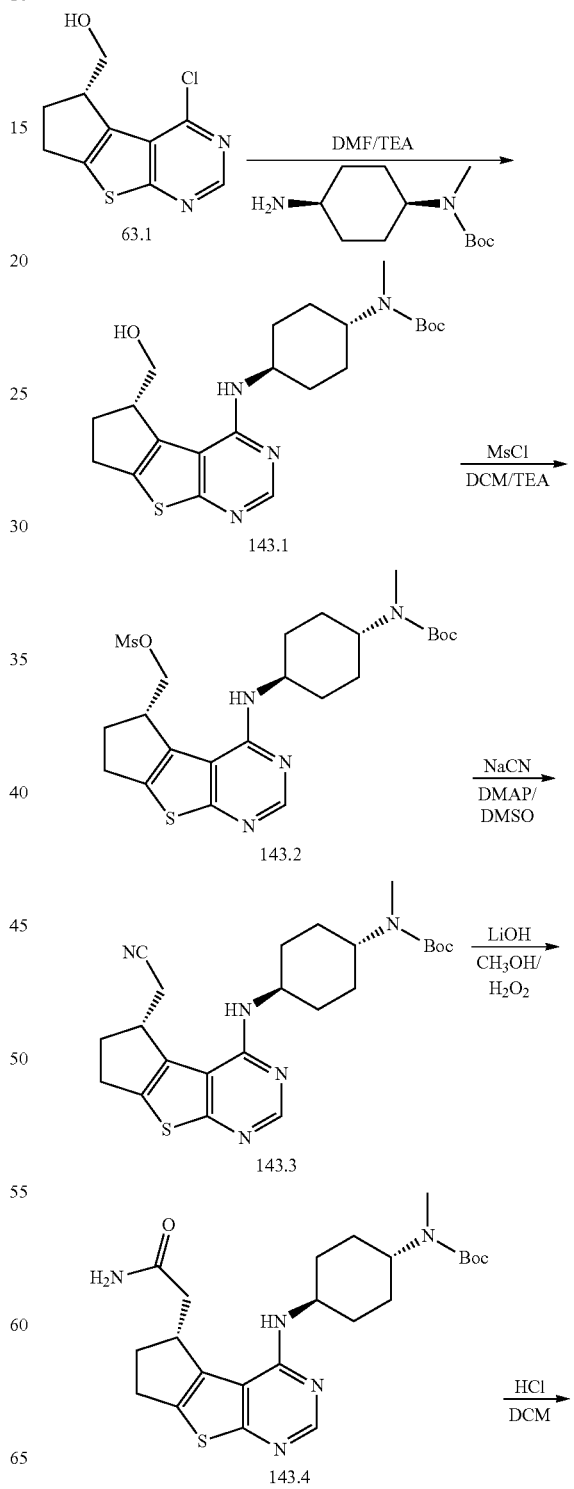

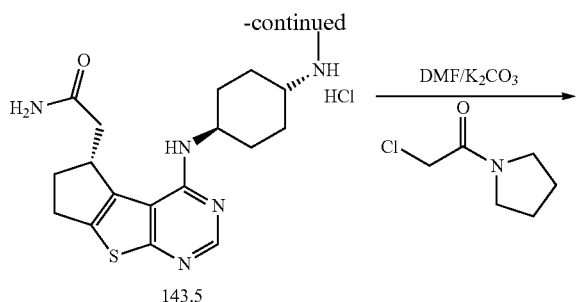

Synthesis of Compound 143.1.

[(3S)-12-chloro-7-thia-9,11-diazatricyclo[6.4.0.0[2,6]]dodeca-1(8),2(6),9,11-tetraen-3-yl]methanol (315 mg, 1.31 mmol, 1.00 equiv), TEA (530 mg) and tert-butyl N-(4-aminocyclohexyl)-N-methylcarbamate (450 mg, 1.97 mmol, 1.51 equiv) were combined in N,N-dimethylformamide (5 mL). The resulting solution was stirred for 48 h at 25° C. The reaction was then quenched by the addition of 20 mL of water. The resulting solution was extracted with 3×100 mL of ethyl acetate and the organic layers combined and concentrated under vacuum. The residue was applied onto a silica gel column with ethyl acetate/petroleum ether (1:2). This resulted in 400 mg (70%) of tert-butyl N-(4-[[(3S)-3-(hydroxymethyl)-7-thia-9,11-diazatricyclo[6.4.0.0[2,6]]dodeca-1(8),2(6),9,11-tetraen-12-yl]oxy]cyclohexyl)-N-methylcarbamate as a colorless oil.

Synthesis of Compound 143.2.

Tert-butyl N-(4-[[(3S)-3-(hydroxymethyl)-7-thia-9,11-diazatricyclo[6.4.0.0[2,6]]dodeca-1(8),2(6),9,11-tetraen-12-yl]oxy]cyclohexyl)-N-methylcarbamate (400 mg, 0.92 mmol, 1.00 equiv), TEA (374 mg) and MsCl (212.8 mg) were combined in dichloromethane (10 mL). The resulting solution was stirred for 1 h at 25° C. The reaction was then quenched by the addition of 30 mL of water. The resulting solution was extracted with 3×80 mL of ethyl acetate and the organic layers combined. The resulting mixture was washed with 3×30 mL of brine. The mixture was dried over anhydrous sodium sulfate and concentrated under vacuum. This resulted in 500 mg (crude) of tert-butyl N-(4-[[(3S)-3-[(methanesulfonyloxy)methyl]-7-thia-9,11-diazatricyclo[6.4.0.0[2,6]]dodeca-1(8),2(6),9,11-tetraen-12-yl]oxy]cyclohexyl)-N-methylcarbamate as a yellow oil.

Synthesis of Compound 143.3.

Tert-butyl N-(4-[[(3S)-3-[(methanesulfonyloxy)methyl]-7-thia-9,11-diazatricyclo[6.4.0.0[2,6]]dodeca-1(8),2(6),9,11-tetraen-12-yl]amino]cyclohexyl)-N-methylcarbamate (500 mg, 0.98 mmol, 1.00 equiv), 4-dimethylaminopyridine (11.9 mg, 0.15 mmol, 0.16 equiv) and NaCN (400 mg, 8.16 mmol, 8.34 equiv) were combined in DMSO (6 mL). The resulting solution was stirred for 3 h at 80° C. The reaction was then quenched by the addition of 20 mL of sodium bicarbonate (aq.). The resulting solution was extracted with 3×60 mL of ethyl acetate and the organic layers combined and concentrated under vacuum. The residue was applied onto a silica gel column with ethyl acetate/petroleum ether (1:1). This resulted in 300 mg (69%) of tert-butyl N-(4-[[(3R)-3-(cyanomethyl)-7-thia-9,11-diazatricyclo[6.4.0.0[2,6]]dodeca-1(8),2(6),9,11-tetraen-12-yl]amino]cyclohexyl)-N-methylcarbamate as a colorless oil.

Synthesis of Compound 143.4.

A solution of tert-butyl N-(4-[[(3R)-3-(cyanomethyl)-7-thia-9,11-diazatricyclo[6.4.0.0[2,6]]dodeca-1(8),2(6),9,11-tetraen-12-yl]amino]cyclohexyl)-N-methylcarbamate (300 mg, 0.68 mmol, 1.00 equiv), LiOH.H$_2$O (35.67 mg, 0.87 mmol, 1.28 equiv) in methanol (5 mL) was stirred at room temperature. This was followed by the addition of H$_2$O$_2$ (0.8 mL) dropwise with stirring at 0° C. The resulting solution was stirred for 2 h at 0° C. The reaction was then quenched by the addition of 20 mL of Na$_2$SO$_3$ (aq.). The resulting solution was extracted with 3×50 mL of ethyl acetate and the organic layers combined and concentrated under vacuum. The residue was applied onto a silica gel column with ethyl acetate/petroleum ether (1:1). This resulted in 130 mg (42%) of tert-butyl N-(4-[[(3R)-3-(carbamoylmethyl)-7-thia-9,11-diazatricyclo[6.4.0.0[2,6]]dodeca-1(8),2(6),9,11-tetraen-12-yl]amino]cyclohexyl)-N-methylcarbamate as a white solid.

Synthesis of Compound 143.5.

A solution of tert-butyl N-(4-[[(3R)-3-(carbamoylmethyl)-7-thia-9,11-diazatricyclo[6.4.0.0[2,6]]dodeca-1(8),2(6),9,11-tetraen-12-yl]amino]cyclohexyl)-N-methylcarbamate (130 mg, 0.28 mmol, 1.00 equiv) in dichloromethane (10 mL) was stirred at room temperature. This was followed by the addition of hydrogen chloride (0.8 mL) dropwise with stirring at 0° C. The resulting solution was stirred for 1 h at 0° C. The resulting mixture was concentrated under vacuum. This resulted in 100 mg (crude) of 2-[(3R)-12-[[4-(methylamino)cyclohexyl]amino]-7-thia-9,11-diazatricyclo[6.4.0.0[2,6]]dodeca-1(8),2(6),9,11-tetraen-3-yl]acetamide hydrochloride as a colorless oil.

Synthesis of Compound I-123.

A solution of 2-[(3R)-12-[[4-(methylamino)cyclohexyl]amino]-7-thia-9,11-diazatricyclo[6.4.0.0[2,6]]dodeca-1(8),2(6),9,11-tetraen-3-yl]acetamide hydrochloride (100 mg, 0.25 mmol, 1.00 equiv), potassium carbonate (62.4 mg, 0.45 mmol, 1.79 equiv) and 2-chloro-1-(pyrrolidin-1-yl)ethan-1-one (234.5 mg, 1.59 mmol, 6.29 equiv) in N,N-dimethylformamide (3 mL). The resulting solution was stirred for 14 h at 25° C. The reaction was then quenched by the addition of 10 mL of water. The resulting solution was extracted with 3×50 mL of chloroform/iso-propanol (3:1) and the organic layers combined and concentrated under vacuum. The crude product (70 mg) was purified by preparative HPLC under the following conditions (1#-Pre-HPLC-016(Waters)): column: SunFire Prep C18, 19*150 mm 5 um; mobile phase: water WITH 50 mL NH$_4$CO$_3$ and CH$_3$CN (6.0% CH$_3$CN up to 46.0% in 10 min, up to 95.0% in 2 min, down to 6.0% in 2 min); detector: 254/220 nm. 24.2 mg product was obtained. This resulted in 24.2 mg (20%) of 2-[(3R)-12-[(4-[methyl[2-oxo-2-(pyrrolidin-1-yl)ethyl]amino]cyclohexyl)amino]-7-thia-9,11-diazatricyclo[6.4.0.0[2,6]]dodeca-1(8),2(6),9,11-tetraen-3-yl]acetamide as a white solid. MS: m/z 471 (M+H)$^+$. $^1$H NMR (CD$_3$OD, 300 MHz): δ 8.47 (1H, s), 40.9-4.14 (1H, m), 3.81-3.88 (1H, m), 3.55-3.59 (2H, t), 3.42-3.47 (2H, t), 3.31-3.37 (2H, d), 3.06-3.14 (1H, m), 2.89-2.97 (1H, m), 2.64-2.79 (2H, m), 2.43-2.45 (5H, m), 2.31-2.38 (1H, m), 2.26-2.29 (2H, m), 1.87-2.16 (6H, m), 1.47-1.59 (4H, m).

Example 145

Synthesis of 2-[(3R)-12-(piperidin-4-ylmethoxy)-7-thia-9,11-diazatricyclo[6.4.0.0[2,6]]dodeca-1(12),2(6),8,10-tetraen-3-yl]acetamide (I-143)

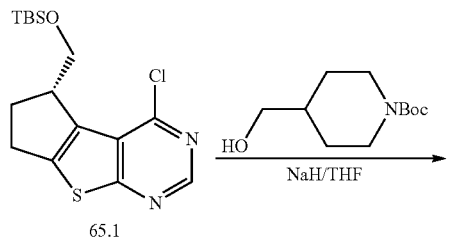

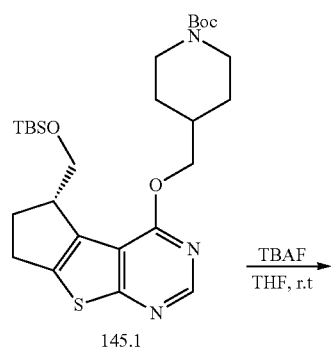

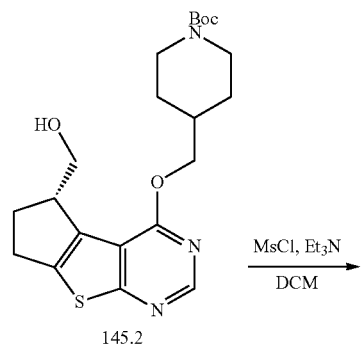

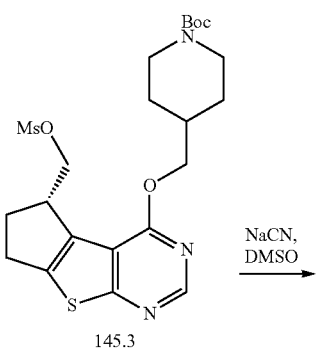

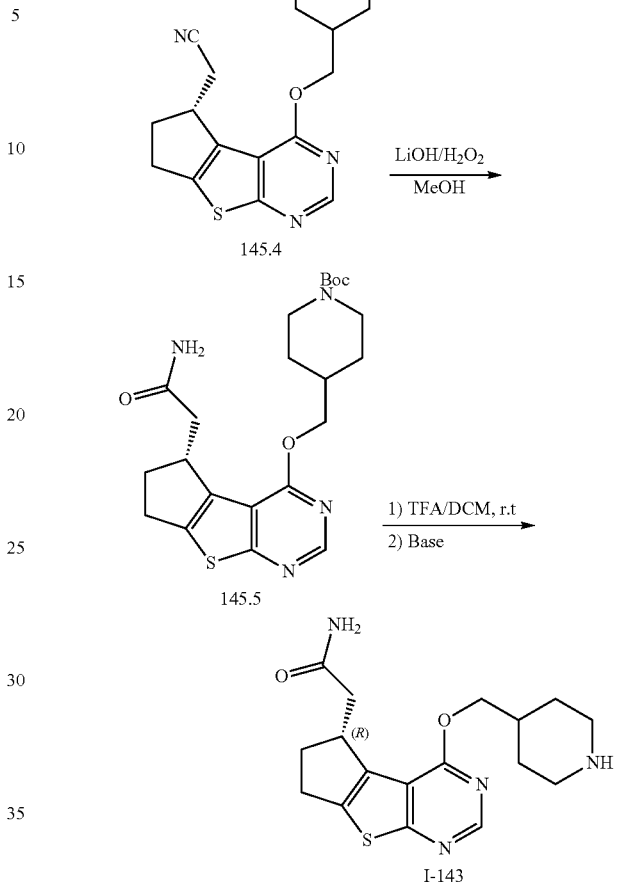

Synthesis of Compound 145.1.

To a solution of tert-butyl 4-(hydroxymethyl)piperidine-1-carboxylate (319 mg, 1.48 mmol, 1.50 equiv) in tetrahydrofuran (10 mL) was added sodium hydride (79 mg, 1.98 mmol, 2.00 equiv, 60%). The resulting solution was stirred for 0.5 h at 60° C. in an oil bath. Then (3S)-3-[[(tert-butyldimethylsilyl)oxy]methyl]-12-chloro-7-thia-9,11-diazatricyclo[6.4.0.0[2,6]]dodeca-1(8),2(6),9,11-tetraene (350 mg, 0.99 mmol, 1.00 equiv) was added. The resulting solution was allowed to react, with stirring, for an additional 1 h while the temperature was maintained at reflux in an oil bath. The reaction was then quenched by the addition of 10 mL of ethanol. The resulting mixture was concentrated under vacuum. The residue was applied onto a silica gel column with ethyl acetate/petroleum ether (1:10). This resulted in 450 mg (85%) of tert-butyl 4-([[(3S)-3-[[(tert-butyldimethylsilyl)oxy]methyl]-7-thia-9,11-diazatricyclo[6.4.0.0[2,6]]dodeca-1(8),2(6),9,11-tetraen-12-yl]oxy]methyl)piperidine-1-carboxylate as a colorless oil.

Synthesis of Compound 145.2.

To a solution of tert-butyl 4-([[[(3S)-3-[[(tert-butyldimethylsilyl)oxy]methyl]-7-thia-9,11-diazatricyclo[6.4.0.0[2,6]]dodeca-1(12),2(6),8,10-tetraen-12-yl]oxy]methyl)piperidine-1-carboxylate (437 mg, 0.82 mmol, 1.00 equiv) in tetrahydrofuran (20 mL) was added TBAF (427 mg, 1.64 mmol, 2.00 equiv). The resulting solution was stirred for 2 h at room temperature. The resulting solution was diluted with 100 mL of ethyl acetate. The resulting mixture was washed with 3×30 mL of brine. The mixture was dried over anhydrous sodium sulfate and concentrated under vacuum. This resulted in 320 mg (93%) of tert-butyl 4-([[(3S)-3-(hydroxymethyl)-7-thia-9,11-diazatricyclo[6.4.0.0[2,6]]dodeca-1(12),2(6),8,10-tetraen-12-yl]oxy]methyl)piperidine-1-carboxylate as a colorless oil.

Synthesis of Compound 145.3.

To a solution of tert-butyl 4-([[(3S)-3-(hydroxymethyl)-7-thia-9,11-diazatricyclo[6.4.0.0[2,6]]dodeca-1(8),2(6),9,11-tetraen-12-yl]oxy]methyl)piperidine-1-carboxylate (300 mg, 0.72 mmol, 1.00 equiv) and triethylamine (287 mg, 2.84 mmol, 4.00 equiv) in dichloromethane (20 mL) was added dropwise methanesulfonyl chloride (163 mg, 1.42 mmol, 2.00 equiv). The resulting solution was stirred for 1 h at room temperature. The reaction was then quenched by the addition of 20 mL of water. The resulting solution was extracted with 3×30 mL of dichloromethane and the organic layers combined and dried over anhydrous sodium sulfate and concentrated under vacuum. This resulted in 360 mg (crude) of tert-butyl 4-([[(3S)-3-[(methanesulfonyloxy)methyl]-7-thia-9,11-diazatricyclo[6.4.0.0[2,6]]dodeca-1(8),2(6),9,11-tetraen-12-yl]oxy]methyl)piperidine-1-carboxylate as a yellow oil.

Synthesis of Compound 145.4.

To a solution of tert-butyl 4-([[(3S)-3-[(methanesulfonyloxy)methyl]-7-thia-9,11-diazatricyclo[6.4.0.0[2,6]]dodeca-1(8),2(6),9,11-tetraen-12-yl]oxy]methyl)piperidine-1-carboxylate (390 mg, 0.78 mmol, 1.00 equiv) and 4-dimethylaminopyridine (10 mg, 0.08 mmol, 0.10 equiv) in DMSO (10 mL) was added sodium carbonitrile (390 mg, 7.96 mmol, 10.00 equiv). The resulting solution was stirred for 1 h at 65° C. in an oil bath. The reaction was then quenched by the addition of 20 ml of sodium bicarbonate solution. The resulting solution was extracted with 3×50 mL of ethyl acetate and the organic layers combined. The resulting mixture was washed with 3×20 mL of brine. The solid was dried in an oven under reduced pressure. The residue was applied onto a silica gel column with ethyl acetate:PE (1:5). This resulted in 300 mg (89%) of tert-butyl 4-([[(3R)-3-(cyanomethyl)-7-thia-9,11-diazatricyclo[6.4.0.0[2,6]]dodeca-1(8),2(6),9,11-tetraen-12-yl]oxy]methyl)piperidine-1-carboxylate as a white solid.

Synthesis of Compound 145.5.

To a solution of tert-butyl 4-([[(3R)-3-(cyanomethyl)-7-thia-9,11-diazatricyclo[6.4.0.0[2,6]]dodeca-1(8),2(6),9,11-tetraen-12-yl]oxy]methyl)piperidine-1-carboxylate (290 mg, 0.68 mmol, 1.00 equiv) in methanol (20 mL) were added LiOH·H$_2$O (114 mg, 2.71 mmol, 4.01 equiv). This was followed by the addition of H$_2$O$_2$ (30%) (114 mg, 4.00 equiv) dropwise with stirring at 0° C. The resulting solution was stirred for 4 h at room temperature. The resulting solution was diluted with 50 mL of ethyl acetate. The resulting mixture was washed with 3×20 mL of brine. The mixture was dried over sodium sulfate and concentrated under vacuum. This resulted in 220 mg (73%) of tert-butyl 4-([[(3R)-3-(carbamoylmethyl)-7-thia-9,11-diazatricyclo[6.4.0.0[2,6]]dodeca-1(8),2(6),9,11-tetraen-12-yl]oxy]methyl)piperidine-1-carboxylate as a white solid.

Synthesis of Compound I-143.

To a solution of tert-butyl 4-([[(3R)-3-(carbamoylmethyl)-7-thia-9,11-diazatricyclo[6.4.0.0[2,6]]dodeca-1(12),2(6),8,10-tetraen-12-yl]oxy]methyl)piperidine-1-carboxylate (200 mg, 0.45 mmol, 1.00 equiv) in dichloromethane (15 mL) was added hydrogen chloride (12 N) (0.5 mL). The resulting solution was stirred for 1 h at room temperature. The resulting mixture was concentrated under vacuum. The crude product (200 mg) was purified by preparative HPLC under the following conditions (1#-Pre-HPLC-016(Waters)): column: SunFire Prep C18, 19*150 mm 5 um; mobile phase: water with 50 mL NH$_4$CO$_3$ and CH$_3$CN (5.0% CH$_3$CN up to 42.0% in 10 min, up to 95.0% in 2 min, down to 5.0% in 2 min); detector: 254/220 nm. This resulted in 33.6 mg (22%) of 2-[(3R)-12-(piperidin-4-ylmethoxy)-7-thia-9,11-diazatricyclo[6.4.0.0[2,6]]dodeca-1(12),2(6),8,10-tetraen-3-yl]acetamide as a white solid. $^1$H NMR (400 MHz, CD$_3$OD): δ 1.44-1.59 (m, 2H), 1.86-1.97 (m, 2H), 2.11 (s, 1H), 2.21-2.36 (m, 2H), 2.69-2.78 (m, 3H), 2.91-3.09 (m, 2H), 3.12-3.33 (m, 3H), 3.47-3.90 (m, 1H), 4.37-4.90 (m, 2H), 8.49 (s, 1H).

Example 146

Synthetic of Intermediate 146.5

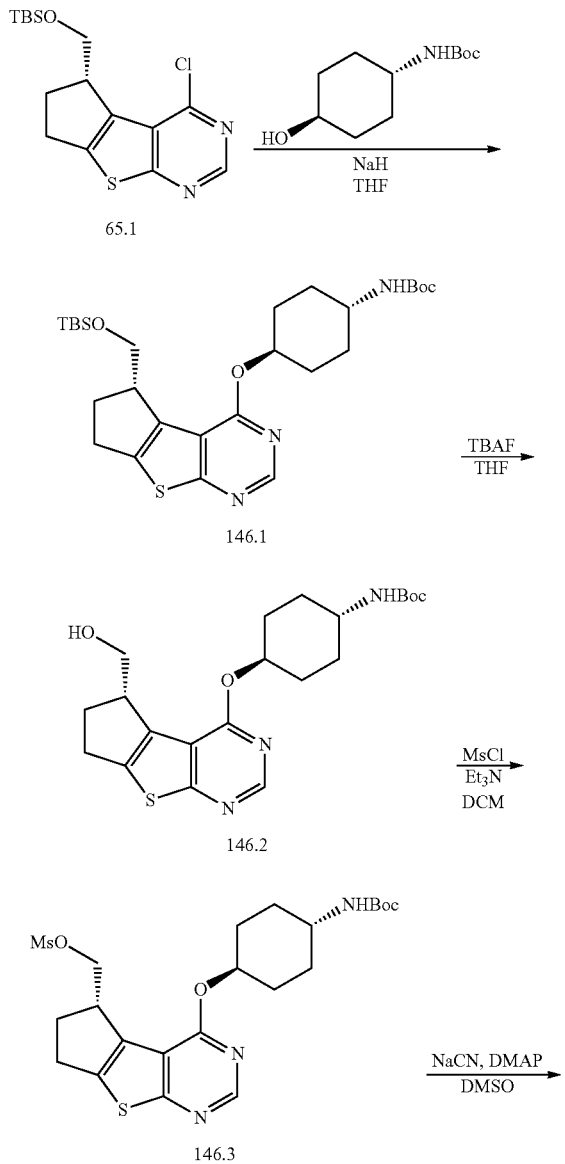

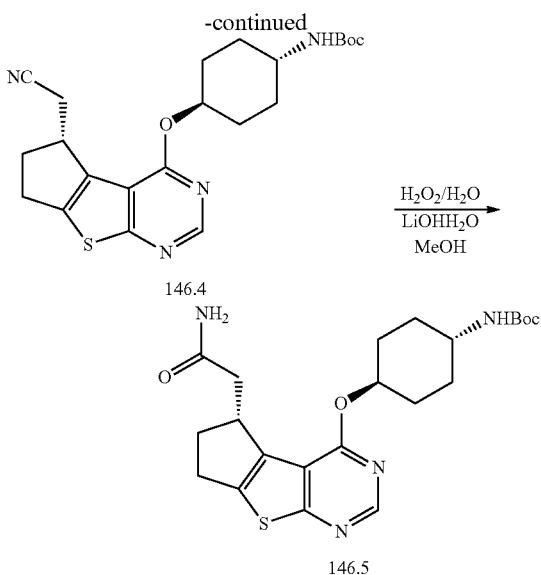

Synthesis of Compound 146.1.

To a solution of tert-butyl N-(4-hydroxycyclohexyl)carbamate (860 mg, 3.99 mmol, 2.00 equiv) in tetrahydrofuran (25 mL) was added sodium hydride (240 mg, 6.00 mmol, 3.00 equiv, 60%). The resulting mixture was stirred for 30 minutes at 60° C. (3S)-3-[[(tert-butyldimethylsilyl)oxy]methyl]-12-chloro-7-thia-9,11-diazatricyclo[6.4.0.0[2,6]]dodeca-1(12),2(6),8,10-tetraene (700 mg, 1.97 mmol, 1.00 equiv) was added to this solution. Stirring was continued for 4 h at 60° C. The reaction was then quenched by the addition of 10 mL of water. The resulting solution was extracted with 3×50 mL of ethyl acetate and the organic layers combined and dried over anhydrous sodium sulfate and concentrated under vacuum. The residue was applied onto a silica gel column with ethyl acetate/petroleum ether (1:4). This resulted in 0.35 g (33%) of tert-butyl N-(4-[[(3S)-3-[[(tert-butyldimethylsilyl)oxy]methyl]-7-thia-9,11-diazatricyclo[6.4.0.0ˆ[2,6]]dodeca-1(12),2(6),8,10-tetraen-12-yl]oxy]cyclohexyl)carbamate as a light yellow solid.

Synthesis of Compound 146.2.

To a solution of tert-butyl N-(4-[[(3S)-3-[[(tert-butyldimethylsilyl)oxy]methyl]-7-thia-9,11-diazatricyclo[6.4.0.0[2,6]]dodeca-1(12),2(6),8,10-tetraen-12-yl]oxy]cyclohexyl)carbamate (400 mg, 0.75 mmol, 1.00 equiv) in tetrahydrofuran (20 mL) was added TBAF (392 mg, 1.50 mmol, 2.00 equiv). The resulting solution was stirred for 2 h at room temperature and concentrated under vacuum. The residue was applied onto a silica gel column with ethyl acetate/petroleum ether (1:3). This resulted in 230 mg (73%) of tert-butyl N-(4-[[(3S)-3-(hydroxymethyl)-7-thia-9,11-diazatricyclo[6.4.0.0[2,6]]dodeca-1(12),2(6),8,10-tetraen-12-yl]oxy]cyclohexyl)carbamate as a white solid.

Synthesis of Compound 146.3.

To a solution of tert-butyl N-(4-[[(3S)-3-(hydroxymethyl)-7-thia-9,11-diazatricyclo[6.4.0.0[2,6]]dodeca-1(12),2(6),8,10-tetraen-12-yl]oxy]cyclohexyl) carbamate (230 mg, 0.55 mmol, 1.00 equiv) and triethylamine (167 mg, 1.65 mmol, 3.00 equiv) in dichloromethane (20 mL) was added methanesulfonyl chloride (126 mg, 1.10 mmol, 2.00 equiv). The resulting solution was stirred for 2 h at room temperature. The resulting mixture was washed with 2×20 mL of brine. The mixture was dried over anhydrous sodium sulfate and concentrated under vacuum. This resulted in 240 mg (88%) of tert-butyl N-(4-[[(3S)-3-[(methanesulfonyloxy)methyl]-7-thia-9,11-diazatricyclo[6.4.0.0[2,6]]dodeca-1(12),2(6),8,10-tetraen-12-yl]oxy]cyclohexyl)carbamate as a yellow oil.

Synthesis of Compound 146.4.

To a solution of tert-butyl N-(4-[[(3S)-3-[(methanesulfonyloxy)methyl]-7-thia-9,11-diazatricyclo[6.4.0.0[2,6]]dodeca-1(8),2(6),9,11-tetraen-12-yl]oxy]cyclohexyl)carbamate (220 mg, 0.44 mmol, 1.00 equiv) and 4-dimethylaminopyridine (10 mg, 0.08 mmol, 0.19 equiv) in DMSO (10 mL) was added sodium carbonitrile (220 mg, 4.49 mmol, 10.00 equiv). The resulting solution was stirred for 2 h at 60° C. The resulting solution was diluted with 50 mL of ethyl acetate. The resulting mixture was washed with 20 mL of sodium bicarbonate solution. The resulting mixture was washed with 3×20 mL of brine. The mixture was dried over anhydrous sodium sulfate and concentrated under vacuum. This resulted in 180 mg (crude) of tert-butyl N-(4-[[(3R)-3-(cyanomethyl)-7-thia-9,11-diazatricyclo[6.4.0.0[2,6]]dodeca-1(8),2(6),9,11-tetraen-12-yl]oxy]cyclohexyl)carbamate as a yellow solid.

Synthesis of Intermediate 146.5.

To a solution of tert-butyl N-(4-[[(3R)-3-(cyanomethyl)-7-thia-9,11-diazatricyclo[6.4.0.0[2,6]]dodeca-1(8),2(6),9,11-tetraen-12-yl]oxy]cyclohexyl)carbamate (160 mg, 0.37 mmol, 1.00 equiv) and LiOH.H$_2$O (80 mg, 1.90 mmol, 5.00 equiv) in methanol (15 mL) was added H$_2$O$_2$/H$_2$O (1.0 mL). The resulting solution was stirred for 2 h at room temperature. The resulting solution was extracted with 3×50 mL of chloroform and the organic layers combined and dried over anhydrous sodium sulfate and concentrated under vacuum. This resulted in 132 mg (79%) of tert-butyl N-(4-[[(3R)-3-(carbamoylmethyl)-7-thia-9,11-diazatricyclo[6.4.0.0ˆ[2,6]]dodeca-1(8),2(6),9,11-tetraen-12-yl]oxy]cyclohexyl)carbamate as a white solid.

Example 147

Synthesis of 2-[(3R)-12-[(4-aminocyclohexyl)oxy]-7-thia-9,11-diazatricyclo[6.4.0.0[2,6]]dodeca-1(12),2(6),8,10-tetraen-3-yl]acetamide (I-150)

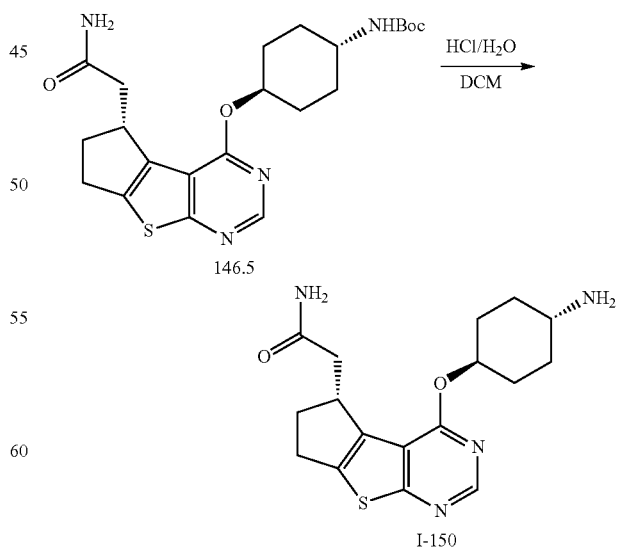

To a solution of tert-butyl N-(4-[[(3R)-3-(carbamoylmethyl)-7-thia-9,11-diazatricyclo[6.4.0.0[2,6]]dodeca-1(12),2

(6),8,10-tetraen-12-yl]oxy]cyclohexyl)carbamate (120 mg, 0.27 mmol, 1.00 equiv) in dichloromethane (15 mL) was added hydrochloric acid (conc.) (0.2 mL). The resulting solution was stirred for 1 h at room temperature. The pH value of the solution was adjusted to pH>8 with saturated sodium bicarbonate solution. The solids were collected by filtration and then washed with water and methanol. This afforded 33.2 mg (36%) of 2-[(3R)-12-[(4-aminocyclohexyl)oxy]-7-thia-9,11-diazatricyclo[6.4.0.0[2,6]]dodeca-1(12),2(6),8,10-tetraen-3-yl]acetamide as a white solid. $^1$H NMR (300 MHz, $CD_3OD$, ppm): δ 1.32-1.46 (m, 2H), 1.61-1.70 (m, 2H), 1.98-2.03 (m, 2H), 2.17-2.30 (m, 4H), 2.62-2.74 (m, 1H), 2.82-3.20 (m, 4H), 2.72-3.80 (m, 1H), 5.23-5.31 (m, 1H), 8.42 (s, 1H).

Example 148

Synthesis of 2-[(3R)-12-([4-[(oxetan-3-yl)amino] cyclohexyl]oxy)-7-thia-9,11-diazatricyclo[6.4.0.0[2,6]]dodeca-1(8),2(6),9,11-tetraen-3-yl]acetamide (I-132)

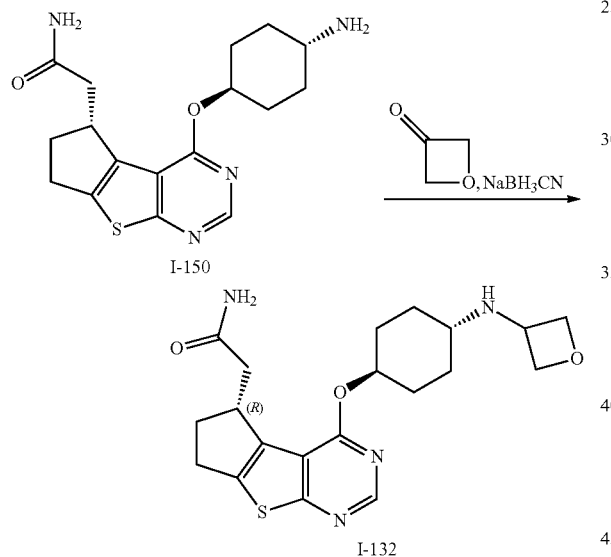

A solution of tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]cyclohexyl)carbamate (400 mg, 0.90 mmol, 1.00 equiv) in DCM (10 mL) was added concentrated hydrochloric acid (0.5 mL) at 0° C. The resulting solution was stirred for 2 h at room temperature. The pH value of the solution was adjusted to 10 with saturated aqueous sodium bicarbonate, extracted with dichloromethane (50 mL), dried over anhydrous sodium sulfate and concentrated under vacuum. The residue was dissolved in 5 mL of MeOH (5 mL), oxetan-3-one (288 mg, 4.00 mmol, 10.00 equiv) was added and the reaction was stirred for around 30 min. Then NaBH$_3$CN (76 mg, 1.21 mmol, 3.00 equiv) was added and the resulting solution was stirred overnight at 35° C. The reaction was then quenched by the addition of cooled brine, extracted with DCM (50 mL), dried over anhydrous sodium sulfate and concentrated under vacuum. The crude product (110 mg) was purified by preparative HPLC under the following conditions (Waters): column: SunFire Prep C18, 19*150 mm 5 um; mobile phase: water with NH$_4$HCO$_3$ and CH$_3$CN (5.0% CH$_3$CN up to 45.0% in 12 min, up to 95.0% in 2 min, down to 5.0% in 2 min); UV detection at 254/220 nm. Flow rate: 20 mL/min. The desired 2-[(3R)-12-([4-[(oxetan-3-yl)amino] cyclohexyl]oxy)-7-thia-9,11-diazatricyclo[6.4.0.0[2,6]] dodeca-1(8),2(6),9,11-tetraen-3-yl]acetamide (90 mg) was obtained as a white solid. MS: m/z 403 (M+H)$^+$. $^1$H NMR (300 MHz, CDCl$_3$): δ 8.51 (s, 1H), 5.24-5.35 (m, 3H), 4.85 (t, 2H, J=6.9 Hz), 4.46 (t, 2H, J=6.9 Hz), 4.06-4.11 (m, 1H), 3.80-3.85 (m, 1H), 2.95-3.21 (m, 3H), 2.78-2.86 (m, 1H), 2.55-2.71 (m, 1H), 2.21-2.33 (m, 4H), 1.91-1.99 (m, 2H), 1.57-1.74 (m, 4H), 1.29-1.43 (m, 4H).

Example 149

Synthesis of 2-[(3R)-12-([4-[bis(2-methoxyethyl) amino]cyclohexyl]oxy)-7-thia-9,11-diazatricyclo [6.4.0.0[2,6]]dodeca-1(12),2(6),8,10-tetraen-3-yl] acetamide (I-134)

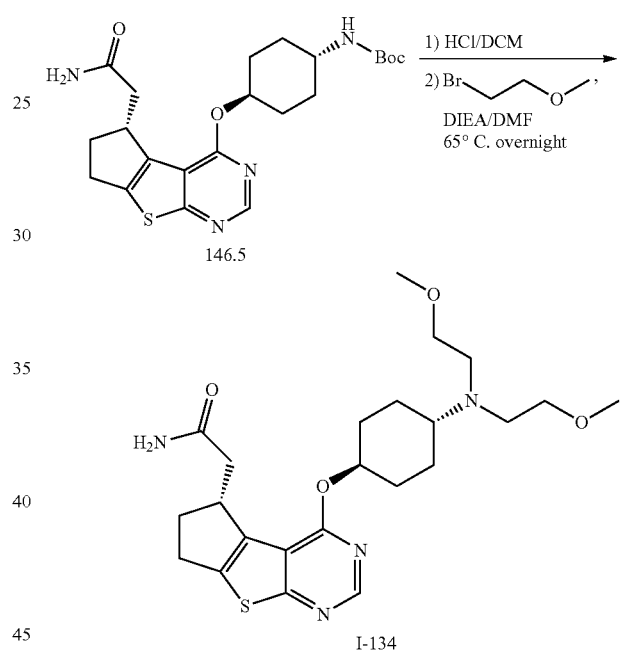

To a solution of intermediate 146.5 (200 mg, 0.45 mmol, 1.00 equiv) in DCM (10 mL) was added hydrogen chloride (conc., 0.5 mL) at 0° C. The resulting solution was stirred for 2 h at room temperature. The pH value of the solution was adjusted to 10 with saturated aqueous sodium bicarbonate, extracted with DCM (40 mL), dried over anhydrous sodium sulfate and evaporated to give the crude product. The product was dissolved in DMF (5 mL) and DIEA (333 mg, 2.58 mmol, 6.00 equiv) and 1-bromo-2-methoxyethane (598 mg, 4.30 mmol, 10.00 equiv) were added. The resulting solution was stirred overnight at 65° C. The mixture was diluted with DCM (50 mL), washed with brine (50 mL), dried over anhydrous sodium sulfate and concentrated under vacuum. The crude product (100 mg) was purified by preparative HPLC under the following conditions (Waters): column: SunFire Prep C18, 19*150 mm 5 um; mobile phase: water with NH$_4$HCO$_3$ and CH$_3$CN (5.0% CH$_3$CN up to 43.0% in 10 min, up to 95.0% in 2 min, down to 5.0% in 2 min); flow rate: 20 mL/min; UV detection at 254/220 nm. The desired 2-[(3R)-12-([4-[bis(2-methoxyethyl)amino]cyclohexyl]oxy)-7-thia- 9,11-diazatricyclo[6.4.0.0[2,6]]dodeca-1(12),2(6),8,10-tetraen-3-yl]acetamide (65.7 mg) was obtained at a white solid. MS: m/z 463 (M+H)+. 1H NMR (300 MHz, CDCl3): δ 8.51 (s, 1H), 5.32-5.21 (m, 3H), 3.91-3.83 (m, 1H), 3.52-3.45 (m, 7H), 3.38 (s, 3H), 3.19-2.98 (m, 3H), 2.89-2.61 (m, 5H), 2.39-2.25 (m, 4H), 1.98-1.89 (m, 2H), 1.69-1.45 (m, 5H).

Example 150

Synthesis of 2-[(3R)-12-([4-[(2-methoxyethyl)amino]cyclohexyl]oxy)-7-thia-9,11-diazatricyclo[6.4.0.0[2,6]]dodeca-1(12),2(6),8,10-tetraen-3-yl]acetamide (I-133)

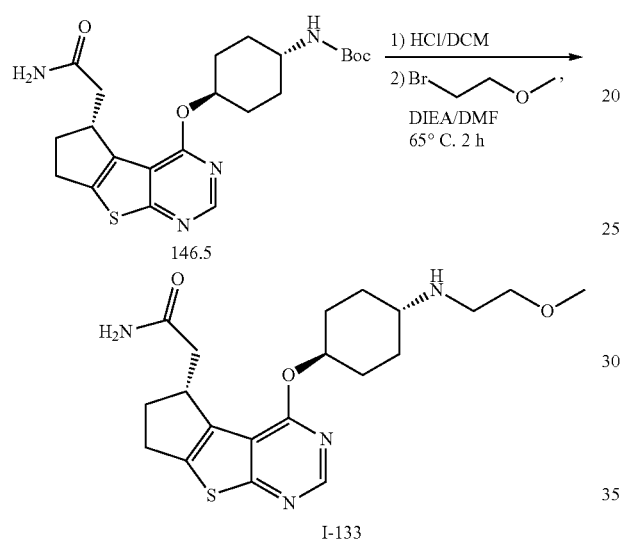

To a solution of tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]cyclohexyl)carbamate (200 mg, 0.45 mmol, 1.00 equiv) in DCM (10 mL) was added hydrogen chloride (conc., 0.5 mL) at 0° C. The resulting solution was stirred for 2 h at room temperature. The pH value of the solution was adjusted to 10 with saturated aqueous sodium bicarbonate, extracted with DCM (40 mL), dried over anhydrous sodium sulfate and evaporated under reduced pressure. The crude product was dissolved in DMF (5 mL) and DIEA (333 mg, 2.58 mmol, 6.00 equiv) and 1-bromo-2-methoxyethane (598 mg, 4.30 mmol, 10.00 equiv) were added. Stirring was continued for 2 h at 65° C. The mixture was diluted with DCM (50 mL), washed with brine (50 mL), dried over anhydrous sodium sulfate and concentrated under vacuum. The crude product (100 mg) was purified by preparative HPLC under the following conditions (Waters): column: SunFire Prep C18, 19*150 mm 5 um; mobile phase: water with NH4HCO3 and CH3CN (5.0% CH3CN up to 43.0% in 10 min, up to 95.0% in 2 min, down to 5.0% in 2 min); flow rate: 20 mL/min; UV detection at 254/220 nm. The product-containing fractions were collected and partially evaporated under reduced pressure to give the desired 2-[(3R)-12-([4-[(2-methoxyethyl)amino]cyclohexyl]oxy)-7-thia-9,11-diazatricyclo[6.4.0.0[2,6]]dodeca-1(12),2(6),8,10-tetraen-3-yl]acetamide (50 mg) as a white solid. MS: m/z 405 (M+H)+. 1H NMR (300 MHz, CDCl3): δ 8.52 (s, 1H), 5.32-5.23 (m, 2H), 3.91-3.83 (m, 1H), 3.52 (t, 2H, J=5.1 Hz), 3.38 (s, 3H), 3.19-2.98 (m, 3H), 2.91-2.71 (m, 3H), 2.69-2.55 (m, 1H), 2.39-2.21 (m, 4H), 2.11-2.01 (m, 2H), 1.72-1.23 (m, 4H).

Example 151

Synthesis of Intermediate 151.7

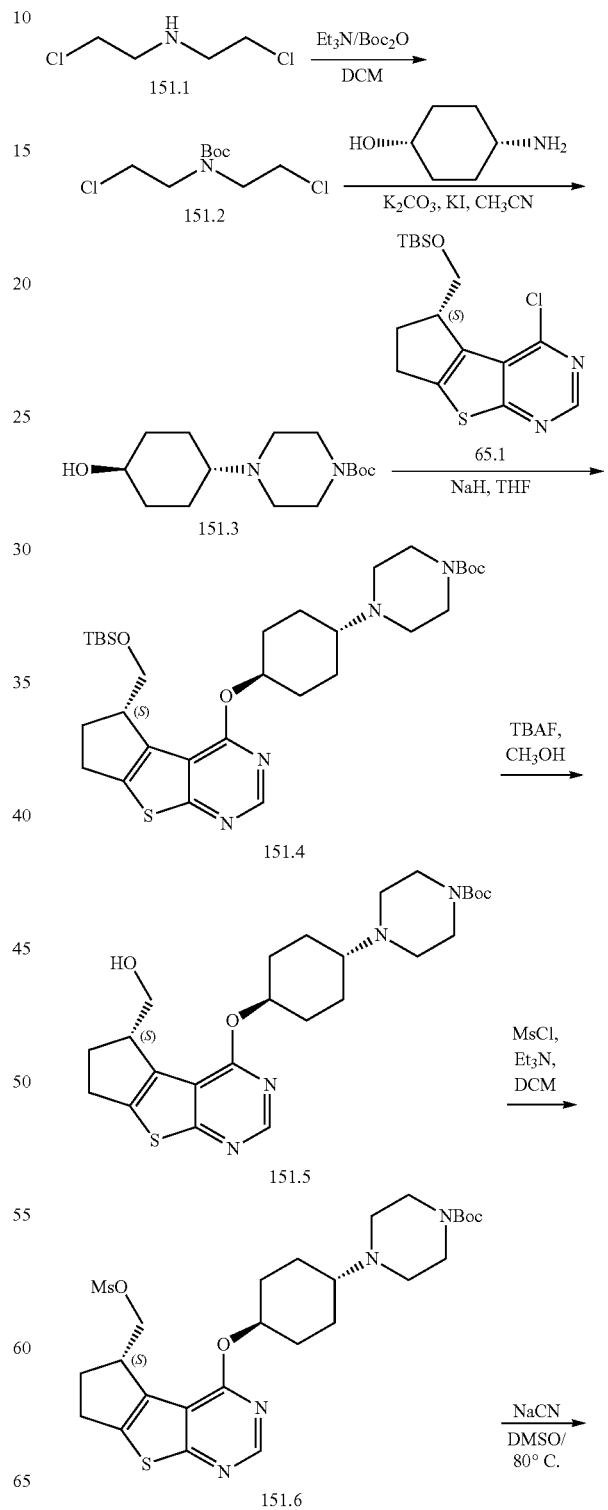

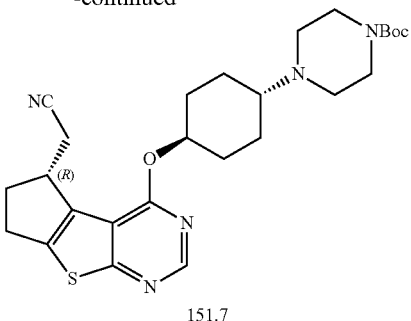

151.7

Synthesis of Compound 151.2.

To a solution of bis(2-chloroethyl)amine (20 g, 112.05 mmol, 1.00 equiv) and triethylamine (17 mL) in dichloromethane (250 mL) was added di-tert-butyl dicarbonate (26.9 g, 123.25 mmol, 1.10 equiv). The resulting solution was stirred for 30 min at 0° C. in a water/ice bath. The resulting mixture was washed with 2×200 mL of H₂O. The mixture was dried over anhydrous magnesium sulfate. The solids were filtered out. The resulting mixture was concentrated under vacuum. This resulted in 34.6 g (crude) of tert-butyl N,N-bis(2-chloroethyl)carbamate as an off-white oil.

Synthesis of Compound 151.3.

Into a 500-mL round-bottom flask was placed tert-butyl 2-chloroethyl N-(2-chloroethyl)carbamate (24 g, 98.70 mmol, 1.00 equiv), 4-aminocyclohexan-1-ol (12 g, 104.19 mmol, 1.06 equiv), KI (20 g), potassium carbonate (41 g, 296.65 mmol, 3.01 equiv) and CH₃CN (200 mL). The resulting solution was heated to reflux for 3 hr. The solids were filtered out. The resulting mixture was concentrated under vacuum. The residue was applied onto a silica gel column with dichloromethane/methanol (7:1). This resulted in 5.5 g (20%) of 1-tert-butyl-6-(4-hydroxycyclohexyl)-1[3],3,6-oxadiazocan-2-one as a yellow oil.

Synthesis of Compound 151.4.

To a solution of tert-butyl 4-(4-hydroxycyclohexyl)piperazine-1-carboxylate (700 mg, 2.46 mmol, 1.94 equiv) in tetrahydrofuran (15 mL) was added sodium hydride (600 mg, 15.00 mmol, 11.83 equiv). The resulting solution was stirred for 0.5 h at 0° C. Then 65.1 (450 mg, 1.27 mmol, 1.00 equiv) was added. The resulting solution was allowed to react with stirring for an additional 3 h while the temperature was maintained at reflux. The reaction was then quenched by the addition of 30 mL of water. The resulting solution was extracted with 3×30 mL of dichloromethane and the organic layers combined and dried over anhydrous sodium sulfate. The solids were filtered out. The resulting mixture was concentrated under vacuum. This resulted in 400 mg (52%) of tert-butyl 4-(4-[[(3S)-3-[[(tert-butyldimethylsilyl)oxy]methyl]-7-thia-9,11-diazatricyclo[6.4.0.0[2,6]]dodeca-1(12),2(6),8,10-tetraen-12-yl]oxy]cyclohexyl)piperazine-1-carboxylate as a yellow oil.

Synthesis of Compound 151.5.

To a solution of tert-butyl 4-(4-[[(3S)-3-[[(tert-butyldimethylsilyl)oxy]methyl]-7-thia-9,11-diazatricyclo[6.4.0.0[2,6]]dodeca-1(12),2(6),8,10-tetraen-12-yl]oxy]cyclohexyl)piperazine-1-carboxylate (400 mg, 0.66 mmol, 1.00 equiv) in methanol (10 mL) was added TBAF (1 g, 3.82 mmol, 5.76 equiv). The resulting solution was stirred for 2 h at 0° C. The reaction was then quenched by the addition of 30 mL of water. The resulting solution was extracted with 3×30 mL of dichloromethane and the organic layers combined and dried over anhydrous sodium sulfate. The solids were filtered out. The resulting mixture was concentrated under vacuum. This resulted in 300 mg (93%) of tert-butyl 4-(4-[[(3S)-3-(hydroxymethyl)-7-thia-9,11-diazatricyclo[6.4.0.0[2,6]]dodeca-1(12),2(6),8,10-tetraen-12-yl]oxy]cyclohexyl)piperazine-1-carboxylate as a yellow oil.

Synthesis of Compound 151.6.

To a solution of tert-butyl 4-(4-[[(3S)-3-(hydroxymethyl)-7-thia-9,11-diazatricyclo[6.4.0.0[2,6]]dodeca-1(12),2(6),8,10-tetraen-12-yl]oxy]cyclohexyl)piperazine-1-carboxylate (300 mg, 0.61 mmol, 1.00 equiv) and triethylamine (190 mg, 1.88 mmol, 3.06 equiv) in dichloromethane (10 mL) was added MsCl (140 mg, 1.22 mmol, 1.98 equiv). The resulting solution was stirred for 1 h at room temperature. The resulting mixture was washed with 30 mL of H₂O. The mixture was dried over anhydrous sodium sulfate. The solids were filtered out. The resulting mixture was concentrated under vacuum. This resulted in 300 mg (86%) of tert-butyl 4-(4-[[(3S)-3-[(methanesulfonyloxy)methyl]-7-thia-9,11-diazatricyclo[6.4.0.0[2,6]]dodeca-1(12),2(6),8,10-tetraen-12-yl]oxy]cyclohexyl)piperazine-1-carboxylate as a yellow oil.

Synthesis of Intermediate 151.7.

To a solution of tert-butyl 4-(4-[[(3S)-3-[(methanesulfonyloxy)methyl]-7-thia-9,11-diazatricyclo[6.4.0.0[2,6]]dodeca-1(12),2(6),8,10-tetraen-12-yl]oxy]cyclohexyl)piperazine-1-carboxylate (300 mg, 0.53 mmol, 1.00 equiv) in DMSO (10 mL) was added NaCN (160 mg, 3.20 mmol, 6.05 equiv) and 4-dimethylaminopyridine (3 mg, 0.02 mmol, 0.05 equiv). The resulting solution was stirred for 2 h at 80° C. The reaction was then quenched by the addition of 30 mL of sodium bicarbonate (sat.). The resulting solution was extracted with 3×30 mL of dichloromethane and the organic layers combined and dried over anhydrous sodium sulfate. The solids were filtered out. The resulting mixture was concentrated under vacuum. This resulted in 260 mg (crude) of tert-butyl 4-(4-[[(3R)-3-(cyanomethyl)-7-thia-9,11-diazatricyclo[6.4.0.0[2,6]]dodeca-1(12),2(6),8,10-tetraen-12-yl]oxy]cyclohexyl)piperazine-1-carboxylate as a yellow oil.

Example 152

Synthesis of 2-[(3R)-12-[[4-(piperazin-1-yl)cyclohexyl]oxy]-7-thia-9,11-diazatricyclo[6.4.0.0[2,6]]dodeca-1(12),2(6),8,10-tetraen-3-yl]acetamide (I-131)

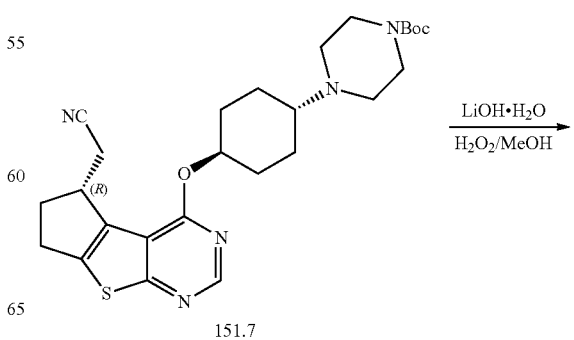

151.7

379
-continued

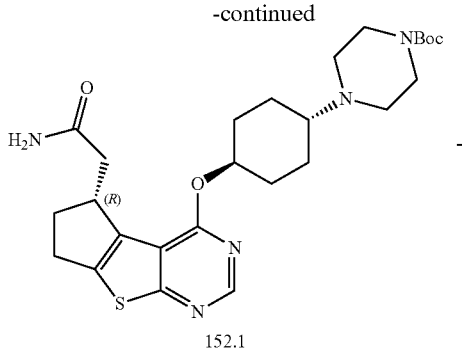
152.1

↓ TFA

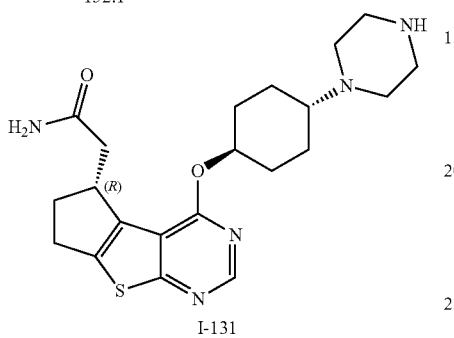
I-131

Synthesis of Compound 152.1.

To a solution of tert-butyl-4-(4-[[(3R)-3-(cyanomethyl)-7-thia-9,11-diazatricyclo[6.4.0.0[2,6]]dodeca-1(12),2(6),8,10-tetraen-12-yl]oxy]cyclohexyl)piperazine-1-carboxylate (260 mg, 0.52 mmol, 1.00 equiv) in methanol (15 mL) were added LiOH.H$_2$O (150 mg, 3.57 mmol, 6.84 equiv), H$_2$O$_2$ (30%) (0.8 mL). The resulting solution was stirred for 4 h at 0° C. The reaction was then quenched by the addition of 10 mL of Na$_2$SO$_3$ (aq.). The resulting solution was extracted with 3×30 mL of dichloromethane and the organic layers combined and concentrated under vacuum. This resulted in 120 mg (45%) of tert-butyl 4-(4-[[(3R)-3-(carbamoylmethyl)-7-thia-9,11-diazatricyclo[6.4.0.0[2,6]]dodeca-1(12),2(6),8,10-tetraen-12-yl]oxy]cyclohexyl)piperazine-1-carboxylate as a yellow oil.

Synthesis of Compound I-131.

To a solution of tert-butyl 4-(4-[[(3R)-3-(carbamoylmethyl)-7-thia-9,11-diazatricyclo[6.4.0.0[2,6]]dodeca-1(12),2(6),8,10-tetraen-12-yl]oxy]cyclohexyl)piperazine-1-carboxylate (120 mg, 0.23 mmol, 1.00 equiv) in dichloromethane (4 mL) was added trifluoroacetic acid (2 mL). The resulting solution was stirred for 2 h at room temperature. The resulting mixture was concentrated under vacuum. The crude product (110 mg) was purified by preparative HPLC under the following conditions: column: SunFire Prep C18, 19*150 mm 5 um; mobile phase: water with 50 mL NH$_4$CO$_3$ and CH$_3$CN (15.0% CH$_3$CN up to 36.0% in 13 min, up to 95.0% in 2 min, down to 15.0% in 2 min); detector: 254/220 nm. This resulted in 64.7 mg (67%) of 2-[(3R)-12-[[4-(piperazin-1-yl)cyclohexyl]oxy]-7-thia-9,11-diazatricyclo[6.4.0.0[2,6]]dodeca-1(12),2(6),8,10-tetraen-3-yl]acetamide as a white solid. MS: m/z 416 (M+H)$^+$. $^1$H NMR (300 MHz, CD$_3$OD): δ 1.46-1.86 (4H, m), 2.03-2.24 (2H, m) 2.29-2.44 (5H, m), 2.69-2.77 (5H, m), 2.96-3.01 (6H, m), 3.01-3.10 (1H, m), 3.59-3.79 (1H, m), 5.00-5.26 (1H, m), 8.47 (1H, s).

380

Example 153

Synthesis of Intermediate 153.7

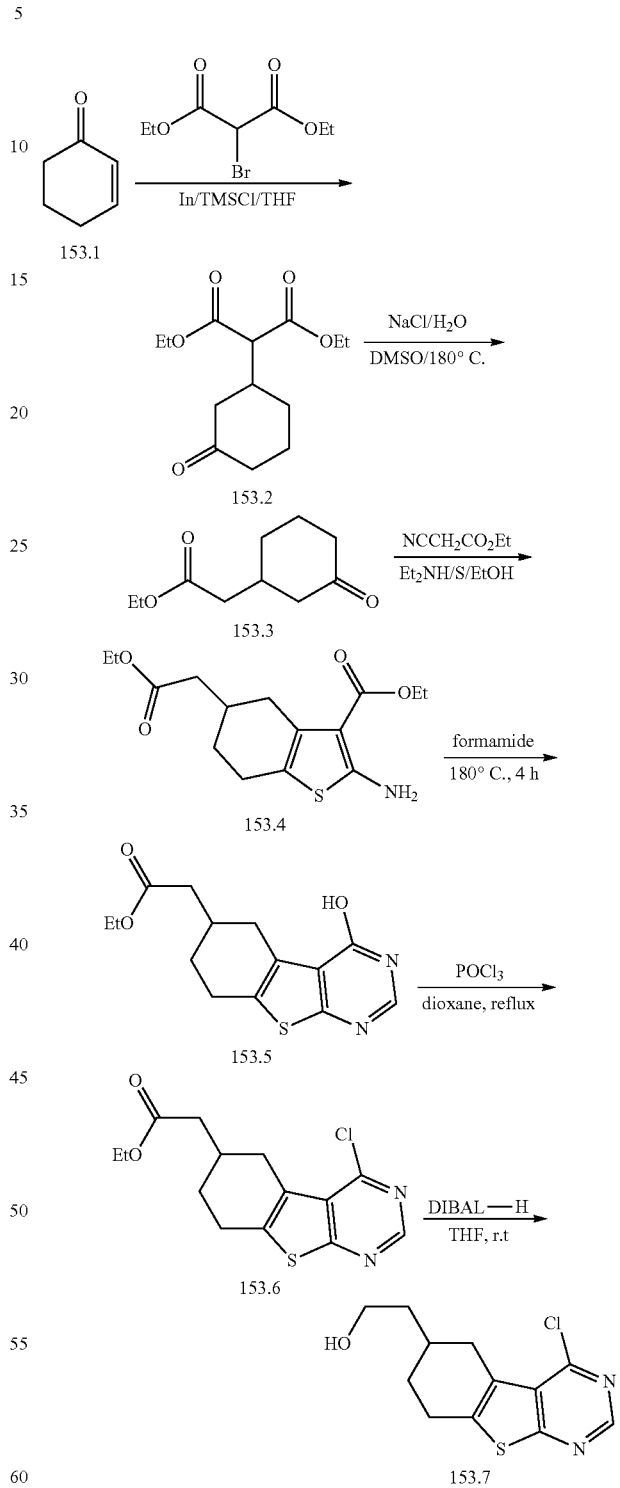

Synthesis of Compound 153.2.

Into a 1 L round-bottom flask was placed a solution of cyclohex-2-en-1-one (15.00 g, 156.04 mmol, 1.00 equiv) in anhydrous THF (300 mL). 1,3-diethyl 2-bromopropanedioate (56.00 g, 234.25 mmol, 1.50 equiv), In powder (18.00 g, 1.00 equiv) and TMSCl (87.00 g, 800.81 mmol, 5.00 equiv) were added under nitrogen. The resulting solution was stirred for 30 min at room temperature and quenched by the addition of 200 mL of saturated aqueous sodium carbonate, extracted with 3×300 mL of ethyl acetate. The combined organic layers were washed with brine, dried over anhydrous sodium sulfate and concentrated under vacuum. The residue was applied onto a silica gel column with ethyl acetate/petroleum ether (1:5) to give 1,3-diethyl 2-(3-oxocyclohexyl)propanedioate (28.50 g, 71%) as a yellow oil.

Synthesis of Compound 153.3.

A solution of 1,3-diethyl 2-(3-oxocyclohexyl)propanedioate (28.50 g, 111.20 mmol, 1.00 equiv) and sodium chloride (7.02 g, 1.10 equiv) in a mixture of water (4 mL) and DMSO (80 mL) was heated for 24 h at 180° C. in an oil bath. After cooling to r.t, the reaction was diluted with water and extracted with 3×300 mL of ethyl acetate. The organic layers were combined, washed with water and brine, dried over anhydrous sodium sulfate and concentrated under vacuum to give the desired ethyl 2-(3-oxocyclohexyl)acetate (22.7 g, crude) as a yellow oil.

Synthesis of Compound 153.4.

A 500-mL round-bottom flask was charged with a solution of ethyl 2-(3-oxocyclohexyl)acetate (22.70 g, crude), ethyl 2-cyanoacetate (16.30 g, 144.10 mmol, 1.20 equiv), S (4.70 g, 1.20 equiv) and Et$_2$NH (10.50 g, 1.20 equiv) in 200 mL of ethanol. The reaction was stirred overnight at room temperature. The solvent was removed under reduced pressure. The residue was applied onto a silica gel column with ethyl acetate/petroleum ether (1:5) to give ethyl 2-amino-5-(2-ethoxy-2-oxoethyl)-4,5,6,7-tetrahydro-1-benzothiophene-3-carboxylate (20.68 g) as yellow oil. MS: m/z 312 (M+H)$^+$.

Synthesis of Compound 153.5.

A solution of ethyl 2-amino-5-(2-ethoxy-2-oxoethyl)-4,5,6,7-tetrahydro-1-benzothiophene-3-carboxylate (20.68 g, 66.41 mmol, 1.00 equiv) in 100 mL of formamide was stirred overnight at 180° C. in an oil bath. After the starting material disappeared, the reaction was cooled to room temperature, quenched with water and extracted with 3×200 mL of ethyl acetate. The combined organic layers were washed with brine, dried over anhydrous sodium sulfate and concentrated under vacuum. The residue was applied onto a silica gel column with ethyl acetate/petroleum ether (1:2) to afford the corresponding ethyl 2-[3-hydroxy-8-thia-4,6-diazatricyclo[7.4.0.0[2,7]]trideca-1(9),2(7),3,5-tetraen-12-yl]acetate (10.10 g, 52%) as yellow oil. MS: m/z 293 (M+H)$^+$.

Synthesis of Compound 153.6.

A 250-mL round-bottom flask was charged with a solution of ethyl 2-[3-hydroxy-8-thia-4,6-diazatricyclo[7.4.0.0[2,7]]trideca-1(9),2(7),3,5-tetraen-12-yl]acetate (10.10 g, 34.55 mmol, 1.00 equiv) in POCl$_3$ (80 g, 521.75 mmol, 15.00 equiv) was stirred for 1 h at 90° C. in an oil bath under nitrogen. The resulting mixture was concentrated under vacuum. The residue was added dropwise to a cooled saturated aqueous sodium bicarbonate and extracted with 3×200 mL of ethyl acetate. The combined organic layers were washed with brine, dried over anhydrous sodium sulfate and concentrated under vacuum. The residue was applied onto a silica gel column with ethyl acetate/petroleum ether (1:5) to give the ethyl 2-[3-chloro-8-thia-4,6-diazatricyclo[7.4.0.0[2,7]]trideca-1(9),2(7),3,5-tetraen-12-yl]acetate (6.67 g, 62%) as a yellow solid. MS: m/z 311, 313 (M+H)$^+$.

Synthesis of Intermediate 153.7.

A solution of ethyl 2-[3-chloro-8-thia-4,6-diazatricyclo[7.4.0.0[2,7]]trideca-1(9),2(7),3,5-tetraen-12-yl]acetate (2.88 g, 9.27 mmol, 1.00 equiv) in 25 mL of distilled THF was added DIBAL-H (25% in hexane, 10.56 g, 2.00 equiv) dropwise at −30° C. under nitrogen. The resulting solution was stirred for 2 h at this temperature and quenched with saturated aqueous NH$_4$Cl, extracted with 3×100 mL of ethyl acetate. The organic layers were combined, washed with brine, dried over anhydrous sodium sulfate and concentrated under vacuum. The residue was applied onto a silica gel column with ethyl acetate/petroleum ether (1:1) to afford 2.20 g (88%) of the desired 2-[3-chloro-8-thia-4,6-diazatricyclo[7.4.0.0[2,7]]trideca-1(9),2(7),3,5-tetraen-12-yl]ethan-1-ol as a light yellow solid. MS: m/z 269, 270 [M+H]$^+$.

Example 154

Synthesis of 2-[(12S)-3-[[4-(dimethylamino)cyclohexyl]oxy]-8-thia-4,6-diazatricyclo[7.4.0.0[2,7]]trideca-1(9),2(7),3,5-tetraen-12-yl]acetamide (I-112)

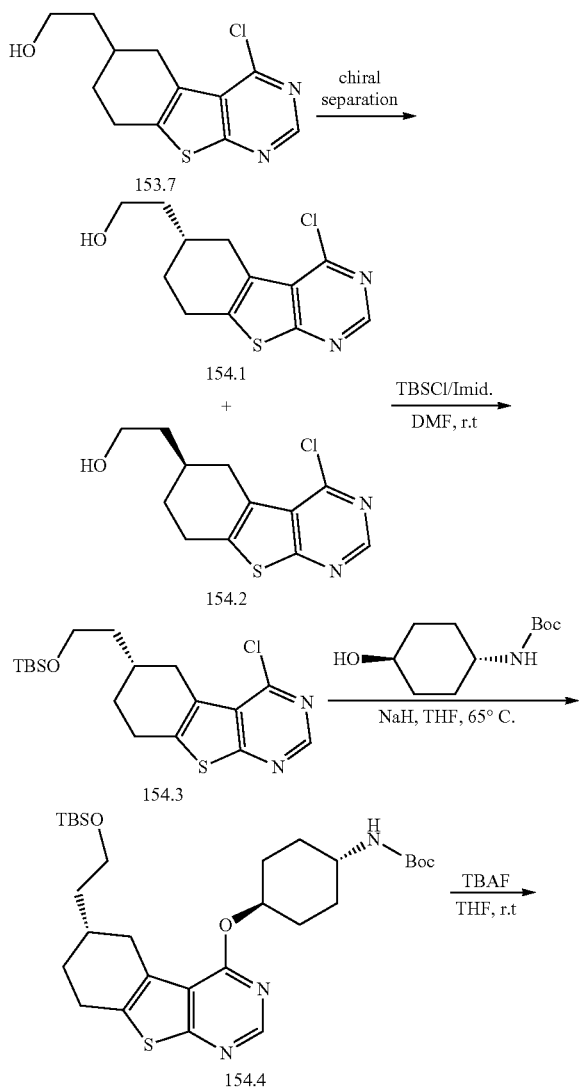

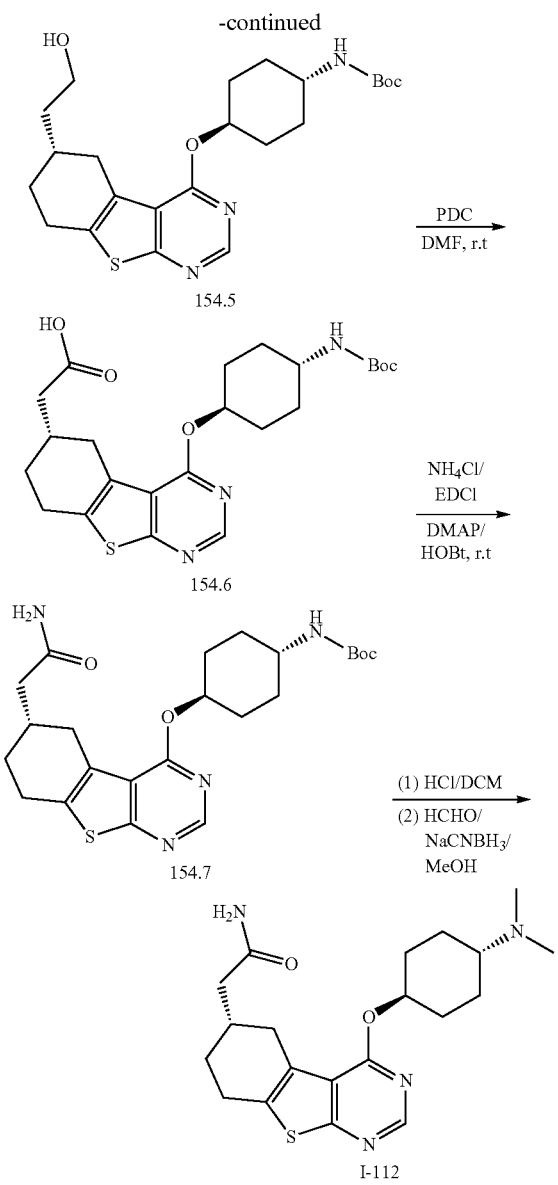

Purification of compound 154.1. The racemic 2-[3-chloro-8-thia-4,6-diazatricyclo[7.4.0.0[2,7]]trideca-1(9),2(7),3,5-tetraen-12-yl]ethan-1-ol (2.20 g, 8.19 mmol, 1.00 equiv) was resolute by chiral preparative SFC under the following conditions: column: Chiralpak IA, 2*25 cm, 5 um; mobile phase, $CO_2$ (80%), methanol (domestic, 20%); flow rate: 40 g/min; UV detection at 254 nm. The fractions of the first peak to elute ($t_R$=9.28 min) were collected and evaporated under reduced pressure to give the desired 2-[(12S)-3-chloro-8-thia-4,6-diazatricyclo[7.4.0.0[2,7]]trideca-1(9),2(7),3,5-tetraen-12-yl]ethan-1-ol (compound 154.1, stereochemistry unconfirmed, 660 mg) as an off-white solid with 100% ee. The fractions of the second peak to elute ($t_R$=10.53 min) were concentrated to give 2-[(12R)-3-chloro-8-thia-4,6-diazatricyclo[7.4.0.0[2,7]]trideca-1(9),2(7),3,5-tetraen-12-yl]ethan-1-ol (compound 154.2, stereochemistry unconfirmed, 790 mg) as an off-white solid with 98.5% ee.

Synthesis of Compound 154.3.

To a solution of 2-[(12S)-3-chloro-8-thia-4,6-diazatricyclo[7.4.0.0[2,7]]trideca-1(9),2(7),3,5-tetraen-12-yl]ethan-1-ol (300 mg, 1.12 mmol, 1.00 equiv) in 5 mL of distilled DMF was added TBSCl (252 mg, 1.50 equiv) and imidazole (137 mg, 2.01 mmol, 1.80 equiv) at room temperature under nitrogen. The resulting solution was stirred for 1 h at ambient temperature and then quenched with water, extracted with 3×50 mL of ethyl acetate. The combined organic layers were washed with brine, dried over anhydrous sodium sulfate and concentrated under reduced pressure. The residue was applied onto a silica gel column with ethyl acetate/petroleum ether (1:5) to provide (12S)-12-[2-[(tert-butyldimethylsilyl)oxy]ethyl]-3-chloro-8-thia-4,6-diazatricyclo[7.4.0.0[2,7]]trideca-1(9),2(7),3,5-tetraene (420 mg, 98%) as a light yellow solid. MS: m/z 384, 386 (M+H)$^+$.

Synthesis of Compound 154.4.

A solution of tert-butyl N-(4-hydroxycyclohexyl)carbamate (181 mg, 0.84 mmol, 1.40 equiv) in 8 mL of distilled THF was added sodium hydride (60% dispersion in mineral oil, 72 mg, 1.80 mmol, 3.00 equiv) at 0° C. and stirred for another 30 min under nitrogen. Then (12S)-12-[2-[(tert-butyldimethylsilyl)oxy]ethyl]-3-chloro-8-thia-4,6-diazatricyclo[7.4.0.0[2,7]]trideca-1(9),2(7),3,5-tetraene (230 mg, 0.60 mmol, 1.00 equiv) was added and stirred overnight at room temperature. The reaction was then quenched with saturated aqueous $NH_4Cl$, extracted with 3×50 mL of ethyl acetate. The combined organic layers were washed with brine, dried over anhydrous sodium sulfate and concentrated under vacuum. The residue was applied onto a silica gel column with ethyl acetate/petroleum ether (1:4) to give 240 mg (71%) of tert-butyl N-(4-[[(12S)-12-[2-[(tert-butyldimethylsilyl)oxy]ethyl]-8-thia-4,6-diazatricyclo[7.4.0.0[2,7]]trideca-1(9),2(7),3,5-tetraen-3-yl]oxy]cyclohexyl)carbamate as a yellow oil. MS: m/z 562 [M+H]$^+$.

Synthesis of Compound 154.5.

To a solution of tert-butyl N-(4-[[(12S)-12-[2-[(tert-butyldimethylsilyl)oxy]ethyl]-8-thia-4,6-diazatricyclo[7.4.0.0[2,7]]trideca-1(9),2(7),3,5-tetraen-3-yl]oxy]cyclohexyl)carbamate (240 mg, 0.43 mmol, 1.00 equiv) in 4 mL of THF was added TBAF (223 mg, 0.85 mmol, 2.00 equiv) and the resulting solution was stirred overnight at 25° C. in an oil bath. The reaction was then quenched with water and extracted with 3×50 mL of ethyl acetate. The combined organic layers were washed with brine, dried over anhydrous sodium sulfate and concentrated under vacuum. The residue was applied onto a silica gel column with ethyl acetate/petroleum ether (1:2) to provide tert-butyl N-(4-[[(12S)-12-(2-hydroxyethyl)-8-thia-4,6-diazatricyclo[7.4.0.0[2,7]]trideca-1(9),2(7),3,5-tetraen-3-yl]oxy]cyclohexyl)carbamate (172 mg, 90%) as yellow oil. MS: m/z 448 (M+H)$^+$.

Synthesis of Compound 154.6.

To a solution of tert-butyl N-(4-[[(12S)-12-(2-hydroxyethyl)-8-thia-4,6-diazatricyclo[7.4.0.0[2,7]]trideca-1(9),2(7),3,5-tetraen-3-yl]oxy]cyclohexyl)carbamate (172 mg, 0.38 mmol, 1.00 equiv) in 4 mL of DMF was added PDC (847 mg, 2.25 mmol, 6.00 equiv) and the resulting solution was stirred overnight at room temperature. The reaction was then quenched by the addition of water and extracted with 4×50 mL of chloroform/isopropanol (3:1). The combined organic layers were washed with brine, dried over anhydrous sodium sulfate and concentrated under vacuum. The residue was applied onto a silica gel column with ethyl acetate/petroleum ether (1:1) to provide 2-[(12S)-3-[(4-[[(tert-butoxy)carbonyl]amino]cyclohexyl)oxy]-8-thia-4,6-diazatricyclo[7.4.0.0[2,7]]trideca-1(9),2(7),3,5-tetraen-12-yl]acetic acid (148 mg, 83%) as an off-white solid. MS: m/z 462 (M+H)$^+$.

Synthesis of Compound 154.7.

To a solution of 2-[(12S)-3-[(4-[[(tert-butoxy)carbonyl]amino]cyclohexyl)oxy]-8-thia-4,6-diazatricyclo[7.4.0.0[2,7]]trideca-1(9),2(7),3,5-tetraen-12-yl]acetic acid (148 mg, 0.32 mmol, 1.00 equiv) in 6 mL of distilled DMF was added NH4Cl (103 mg, 1.93 mmol, 6.00 equiv), EDCI (92 mg, 0.48 mmol, 1.50 equiv), 4-dimethylaminopyridine (58 mg, 0.47 mmol, 1.50 equiv) and HOBt (65 mg, 0.48 mmol, 1.50 equiv) successively and the resulting solution was stirred overnight at room temperature. The reaction was then quenched with water and extracted with 3×50 mL of ethyl acetate. The organic layers were combined, washed with brine, dried over anhydrous sodium sulfate and concentrated under vacuum. The residue was applied onto a silica gel column with ethyl acetate/petroleum ether (2:1) to give 80 mg (54%) of the desired tert-butyl N-(4-[[(12S)-12-(carbamoylmethyl)-8-thia-4,6-diazatricyclo[7.4.0.0[2,7]]trideca-1(9),2(7),3,5-tetraen-3-yl]oxy]cyclohexyl)carbamate as a white solid. MS: m/z 460 (M+H)+.

Synthesis of Compound I-112.

Into a 50-mL round-bottom flask purged and maintained with an inert atmosphere of nitrogen, was placed tert-butyl N-(4-[[(12S)-12-(carbamoylmethyl)-8-thia-4,6-diazatricyclo[7.4.0.0[2,7]]trideca-1(9),2(7),3,5-tetraen-3-yl]oxy]cyclohexyl)carbamate (80 mg, 0.17 mmol, 1.00 equiv) in dichloromethane (5 mL) at 0° C. Then hydrochloric acid (6 M, 0.5 mL) was added and the resulting solution was stirred overnight at room temperature. The resulting mixture was concentrated under vacuum to give 86 mg (crude) of 2-[(12S)-3-[(4-aminocyclohexyl)oxy]-8-thia-4,6-diazatricyclo[7.4.0.0[2,7]]trideca-1(9),2(7),3,5-tetraen-12-yl]acetamide hydrochloride as a yellow solid. The crude hydrochloride dissolved in 5 mL of methanol was added HCHO (37%, 1 mL) and AcOH (0.5 mL). After stirring for 30 min, NaCNBH3 (34 mg, 0.54 mmol, 2.50 equiv) was added and the resulting mixture was stirred overnight at room temperature. The resulting mixture was concentrated under vacuum. The crude product (80 mg) was purified by preparative HPLC under the following conditions (Waters): column: X bridge Prep C18 5 um, 19*150 mm; mobile phase: water with 0.05% NH4HCO3 and CH3CN (5.0% CH3CN up to 41.0% in 9 min, up to 95.0% in 2 min, down to 5.0% in 2 min); flow rate: 20 mL/min; UV detection at 220/254 nm. This resulted in 21.5 mg (26%) of 2-[(12S)-3-[[4-(dimethylamino)cyclohexyl]oxy]-8-thia-4,6-diazatricyclo[7.4.0.0[2,7]]trideca-1(9),2(7),3,5-tetraen-12-yl]acetamide as a white solid. MS: m/z 389 (M+H)+. 1H NMR (400 MHz, CDCl3): δ 8.51 (s, 1H), 5.47-5.40 (d, 2H), 5.25-5.19 (m, 1H), 3.31-3.25 (m, 1H), 2.92-2.90 (m, 2H), 2.61-2.55 (m, 1H), 2.41-2.29 (m, 11H), 2.20-2.15 (m, 1H), 2.13-2.00 (m, 2H), 1.69-1.56 (m, 6H).

Example 155

Synthesis of 2-((R)-4-(((1r,4R)-4-morpholinocyclohexyl)oxy)-5,6,7,8-tetrahydrobenzo[4,5]thieno[2,3-d]pyrimidin-6-yl)ethanol (I-145)

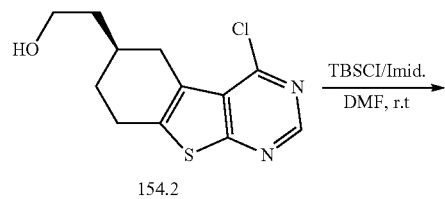

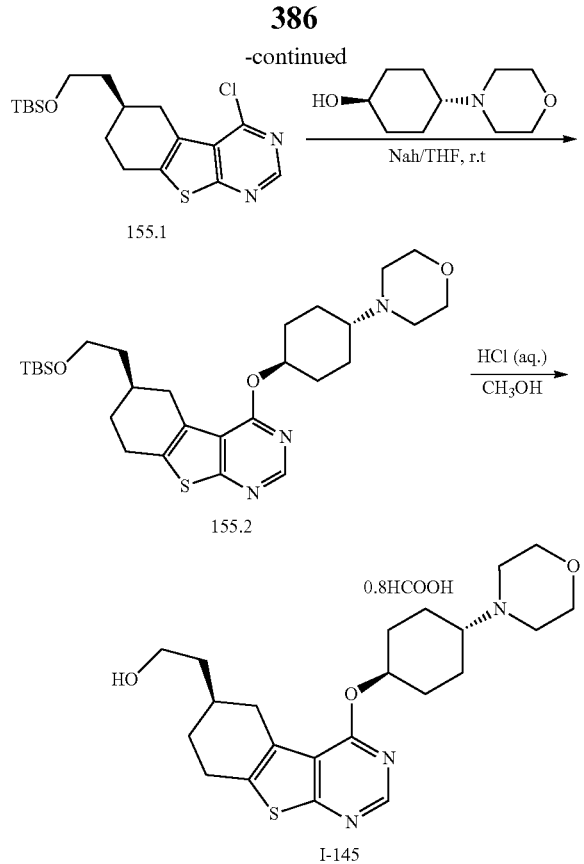

Synthesis of Compound 155.1.

A solution of 2-[(12R)-3-chloro-8-thia-4,6-diazatricyclo[7.4.0.0[2,7]]trideca-1(9),2(7),3,5-tetraen-12-yl]ethan-1-ol (300 mg, 1.12 mmol, 1.00 equiv) in 5 mL of distilled DMF was added TBSCl (252 mg, 1.50 equiv) and imidazole (137 mg, 2.01 mmol, 1.80 equiv) at room temperature under nitrogen. The resulting solution was stirred for 1 h at ambient temperature and then quenched water, extracted with 3×50 mL of ethyl acetate. The combined organic layers were washed with brine, dried over anhydrous sodium sulfate and concentrated under reduced pressure. The residue was applied onto a silica gel column with ethyl acetate/petroleum ether (1:5) to provide (12R)-12-[2-[(tert-butyldimethylsilyl)oxy]ethyl]-3-chloro-8-thia-4,6-diazatricyclo[7.4.0.0[2,7]]trideca-1(9),2(7),3,5-tetraene (420 mg, 98%) as a light yellow solid. LC-MS (ES, m/z): 384, 386 [M+H]+.

Synthesis of Compound 155.2.

A solution of trans-4-(morpholin-4-yl)cyclohexan-1-ol (135 mg, 0.73 mmol, 1.40 equiv) in 6 mL of distilled THF was added sodium hydride (60% dispersion in mineral oil, 83 mg, 2.08 mmol, 4.00 equiv) at 0° C. under nitrogen. Then (12R)-12-[2-[(tert-butyldimethylsilyl)oxy]ethyl]-3-chloro-8-thia-4,6-diazatricyclo[7.4.0.0[2,7]]trideca-1(9),2(7),3,5-tetraene (200 mg, 0.52 mmol, 1.00 equiv) was added and the resulting solution was stirred for 1 h at 70° C. in an oil bath. After cooling to r.t, the reaction was quenched with water and extracted with 3×50 mL of ethyl acetate. The organic layers were combined, washed with brine, dried over anhydrous sodium sulfate and concentrated under vacuum. The residue was applied onto a silica gel column with dichloromethane/methanol (10:1). This resulted in 200 mg (72%) of (12R)-12-[2-[(tert-butyldimethylsilyl)oxy]ethyl]-3-[[4-(morpholin-4-yl)cyclohexyl]oxy]-8-thia-4,6-diazatricyclo[7.4.0.0[2,7]]trideca-1(9),2(7),3,5-tetraene as a white solid. MS: m/z 532 (M+H)+.

Synthesis of Compound I-145.

To a 50-mL round-bottom flask containing (12R)-12-[2-[(tert-butyldimethylsilyl)oxy]ethyl]-3-[[4-(morpholin-4-yl)cyclohexyl]oxy]-8-thia-4,6-diazatricyclo[7.4.0.0[2,7]]trideca-1(9),2(7),3,5-tetraene (157 mg, 0.30 mmol, 1.00 equiv) in methanol (4 mL) was added 6 M aqueous hydrochloric acid (0.9 mL) at 0° C. and the resulting solution was stirred for 2 h at room temperature. The resulting mixture was concentrated under vacuum. After basification, the crude product (160 mg) was purified by preparative HPLC under the following conditions (Waters): column: SunFire Prep C18, 19*150 mm 5 um; mobile phase: water with 0.05% HCOOH and CH$_3$CN (5.0% CH$_3$CN up to 40.0% in 11 min, up to 95.0% in 2 min, down to 5.0% in 2 min); flow rate: 20 mL/min; UV detection at 254/220 nm. This resulted in 53.4 mg (40%) of Compound I-145 as a white solid. MS: m/z 418 (M-0.8HCOOH+H)$^+$. $^1$H NMR: (300 MHz, CDCl$_3$) δ 8.50 (s, 1H), 8.36 (s, 1H), 6.18-5.61 (m, 1H), 5.23-5.19 (m, 1H), 3.89-3.80 (m, 6H), 3.23-3.13 (m, 1H), 2.88 (s, 1H), 2.77-2.66 (m, 1H), 2.52-2.43 (m, 1H), 2.48-2.35 (m, 2H), 2.12-1.81 (m, 4H), 1.78-1.42 (m, 7H).

Example 156

Synthesis of 2-[(12R)-3-[[4-(dimethylamino)cyclohexyl]oxy]-8-thia-4,6-diazatricyclo[7.4.0.0[2,7]]trideca-1 (9),2(7),3,5-tetraen-12-yl]acetamide (I-113)

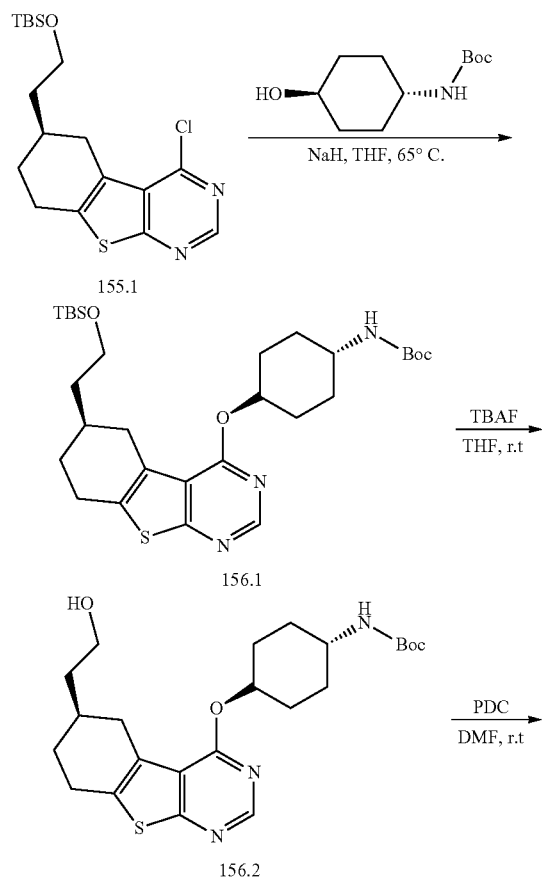

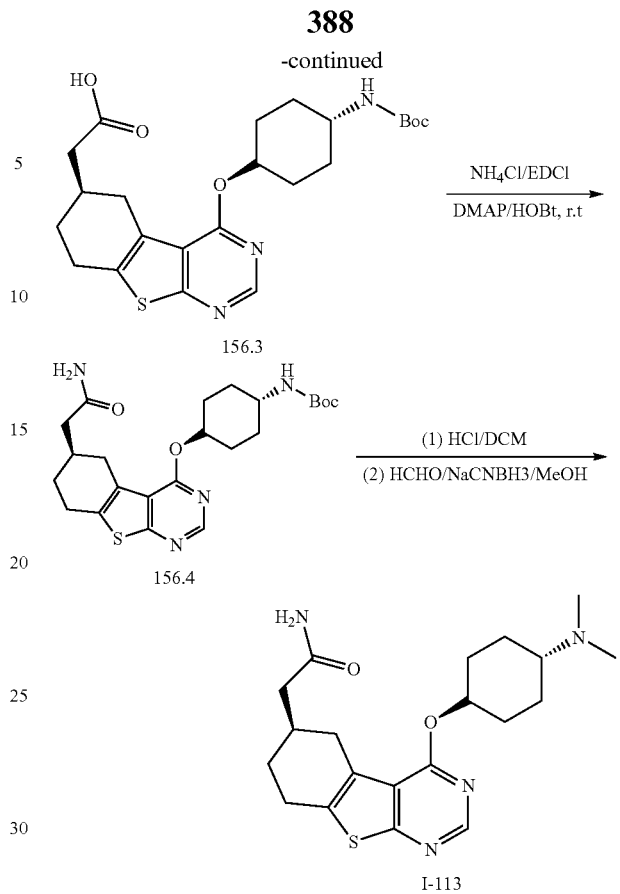

Synthesis of Compound 156.1.

Sodium hydride (60% dispersion in mineral oil, 62 mg, 1.55 mmol, 30.00 equiv) was treated with tert-butyl trans-N-(4-hydroxycyclohexyl)carbamate (157 mg, 0.73 mmol, 1.40 equiv) in 8 mL of freshly distilled THF for 30 min in a water/ice bath under nitrogen. Then a solution of (12R)-12-[2-[(tert-butyldimethylsilyl)oxy]ethyl]-3-chloro-8-thia-4,6-diazatricyclo[7.4.0.0[2,7]]trideca-1(9),2(7),3,5-tetraene (200 mg, 0.52 mmol, 1.00 equiv) in 5 mL of THF was added via syringe and the mixture was stirred at room temperature overnight. The reaction was quenched with saturated aqueous NH$_4$Cl and extracted with 3×50 mL of ethyl acetate. The combined organic layers were washed with brine, dried over anhydrous sodium sulfate and concentrated under reduced pressure. The residue was applied onto a silica gel column with ethyl acetate/petroleum ether (1:4) to give tert-butyl N-(4-[[(12R)-12-[2-[(tert-butyldimethylsilyl)oxy]ethyl]-8-thia-4,6-diazatricyclo[7.4.0.0[2,7]]trideca-1(9),2(7),3,5-tetraen-3-yl]oxy]cyclohexyl)carbamate (200 mg, 68%) as a yellow oil.

Synthesis of Compound 156.2.

To a solution of tert-butyl N-(4-[[(12R)-12-[2-[(tert-butyldimethylsilyl)oxy]ethyl]-8-thia-4,6-diazatricyclo[7.4.0.0[2,7]]trideca-1(9),2 (7),3,5-tetraen-3-yl]oxy]cyclohexyl)carbamate (200 mg, 0.36 mmol, 1.00 equiv) in 6 mL of THF was added TBAF (186 mg, 0.71 mmol, 2.00 equiv) at room temperature and the resulting solution was stirred overnight at ambient temperature. The reaction was then quenched with water, extracted with 3×30 mL of ethyl acetate. The combined organic layers were washed with brine, dried over anhydrous sodium sulfate and concentrated under vacuum. Purification by column chromatography on silica gel with ethyl acetate/petroleum ether (1:2) afford 129 mg (81%) of the desired tert-butyl N-(4-[[(12R)-12-(2-hydroxyethyl)-8-thia-4,6-diazatricyclo[7.4.0.0[2,7]]trideca-1(9),2(7),3,5-tetraen-3-yl]oxy]cyclohexyl)carbamate as a yellow oil.

Synthesis of Compound 156.3.

To a 50-mL round-bottom flask purged and maintained with an inert atmosphere of nitrogen was added tert-butyl N-(4-[[(12R)-12-(2-hydroxyethyl)-8-thia-4,6-diazatricyclo[7.4.0.0[2,7]]trideca-1(9),2(7),3,5-tetraen-3-yl]oxy]cyclohexyl)carbamate (129 mg, 0.29 mmol, 1.00 equiv) in 4 mL of DMF. Then PDC (639 mg, 1.70 mmol, 6.00 equiv) was added and the resulting solution was stirred overnight at room temperature. The reaction was then quenched with water and extracted with 4×40 mL of CHCl₃/isopropanol (3:1). The combined organic layers were washed with brine, dried over anhydrous sodium sulfate and concentrated under vacuum. The residue was applied onto a silica gel column with ethyl acetate/petroleum ether (1:1) to provide 2-[(12R)-3-[(4-[[(tert-butoxy)carbonyl]amino]cyclohexyl)oxy]-8-thia-4,6-diazatricyclo[7.4.0.0[2,7]]trideca-1(9),2(7),3,5-tetraen-12-yl]acetic acid (98 mg, 74%) as an off-white solid.

Synthesis of Compound 156.4.

To a 50-mL round-bottom flask purged and maintained with an inert atmosphere of nitrogen and containing a solution of 2-[(12R)-3-[(4-[[(tert-butoxy)carbonyl]amino]cyclohexyl)oxy]-8-thia-4,6-diazatricyclo[7.4.0.0[2,7]]trideca-1-(9),2(7),3,5-tetraen-12-yl]acetic acid (98 mg, 0.21 mmol, 1.00 equiv) in 4 mL of DMF was added NH₄Cl (68 mg, 1.27 mmol, 6.00 equiv), EDCI (61 mg, 0.32 mmol, 1.50 equiv), 4-dimethylaminopyridine (39 mg, 0.32 mmol, 1.50 equiv) and HOBt (43 mg, 0.32 mmol, 1.50 equiv) successively. The resulting solution was stirred overnight at room temperature and quenched with water and extracted with 3×50 mL of ethyl acetate. The combined organic layers were washed with brine, dried over anhydrous sodium sulfate and concentrated under vacuum. The residue was applied onto a silica gel column with ethyl acetate/petroleum ether (2:1) to give tert-butyl N-(4-[[(12R)-12-(carbamoylmethyl)-8-thia-4,6-diazatricyclo[7.4.0.0[2,7]]trideca-1(9),2(7),3,5-tetraen-3-yl]oxy]cyclohexyl)carbamate (72 mg, 74%) as a white solid.

Synthesis of Compound I-113.

A solution of tert-butyl N-(4-[[(12R)-12-(carbamoylmethyl)-8-thia-4,6-diazatricyclo[7.4.0.0[2,7]]trideca-1(9),2(7),3,5-tetraen-3-yl]oxy]cyclohexyl)carbamate (72 mg, 0.16 mmol, 1.00 equiv) in 5 mL of dichloromethane (5 mL) was added 6 M aqueous hydrochloric acid (0.5 mL) at 0° C. and the resulting solution was stirred overnight at room temperature. The resulting mixture was concentrated under vacuum to give 62 mg (crude) of 2-[(12R)-3-[(4-aminocyclohexyl)oxy]-8-thia-4,6-diazatricyclo[7.4.0.0[2,7]]trideca-1(9),2(7),3,5-tetraen-12-yl]acetamide hydrochloride as a yellow solid. The crude hydrochloride in 4 mL of MeOH was added HCHO (37%, 1 mL) and 0.5 mL of HOAc at room temperature. Then NaCNBH₃ (31 mg, 0.49 mmol, 2.54 equiv) was added and the resulting solution was stirred for 4 h at ambient temperature. The resulting mixture was filtered through a thin silica column and further purified by preparative HPLC under the following conditions (Waters): column: Xbridge Prep C18 5 um, 19*150 mm; mobile phase: water with 0.05% NH₄HCO₃ and CH₃CN (5.0% CH₃CN up to 41.0% in 9 min, up to 95.0% in 2 min, down to 5.0% in 2 min); flow rate: 20 mL/min; UV detection at 220/254 nm. The product-containing fractions were collected and evaporated under reduced pressure to give the desired 2-[(12R)-3-[[4-(dimethylamino)cyclohexyl]oxy]-8-thia-4,6-diazatricyclo[7.4.0.0[2,7]]trideca-1(9),2(7),3,5-tetraen-12-yl]acetamide (13.8 mg) as a white solid. MS: 389 (M+H)⁺. ¹H NMR (300 MHz, CDCl₃): δ 8.51 (s, 1H), 5.46-5.40 (m, 1H), 5.24-5.21 (m, 1H), 3.30-3.24 (m, 1H), 2.91 (m, 2H), 2.62-2.59 (m, 1H), 2.56-2.32 (m, 11H), 2.15-2.11 (m, 1H), 2.02-2.00 (m, 3H), 1.74-1.49 (m, 6H).

Example 157

Synthesis of N-[(2R)-2-hydroxypropyl]-2-[(3R)-12-[[4-(methylamino)cyclohexyl]oxy]-7-thia-9,11-diazatricyclo[6.4.0.0[2,6]]dodeca-1(12),2(6),8,10-tetraen-3-yl]acetamide (I-151)

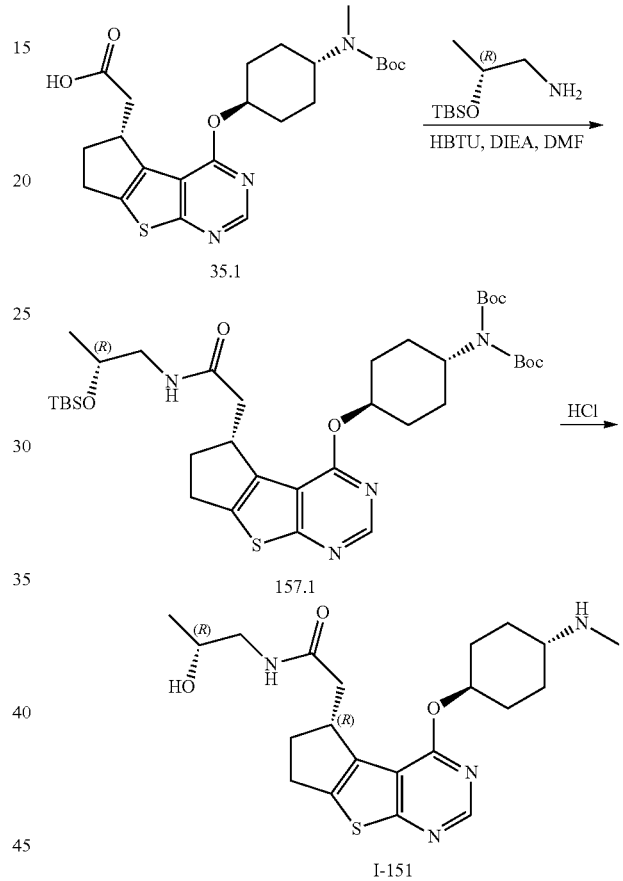

Synthesis of Compound 157.1.

To a solution of 2-[(3R)-12-[(4-[[(tert-butoxy)carbonyl](methyl)amino]cyclohexyl)oxy]-7-thia-9,11-diazatricyclo[6.4.0.0[2,6]]dodeca-1(12),2(6),8,10-tetraen-3-yl]acetic acid (500 mg, 1.08 mmol, 1.00 equiv) and [(2S)-1-aminopropan-2-yl]oxy(tert-butyl)dimethylsilane (250 mg, 1.32 mmol, 1.22 equiv) in N,N-dimethylformamide (30 mL) were added DIEA (500 mg, 3.87 mmol, 3.57 equiv) and HBTU (2.1 g, 5.54 mmol, 5.11 equiv). The resulting solution was stirred for 5 h at room temperature. The residue was dissolved in 50 mL of H₂O. The resulting solution was extracted with 5×40 mL of dichloromethane and the organic layers combined and dried over anhydrous sodium sulfate. After evaporation, the residue was applied onto a silica gel column and eluted with EA/PE (1/1). This resulted in 480 mg (70%) of tert-butyl N-(4-[[(3R)-3-([[(2R)-2-[(tert-butyldimethylsilyl)oxy]propyl]carbamoyl]methyl)-7-thia-9,11-diazatricyclo[6.4.0.0[2,6]]dodeca-1(12),2(6),8,10-tetraen-12-yl]oxy]cyclohexyl)-N-methylcarbamate as a yellow solid.

Synthesis of Compound I-151.

To a solution of tert-butyl N-(4-[[(3R)-3-([[(2R)-2-[(tert-butyldimethylsilyl)oxy]propyl]carbamoyl]methyl)-7-thia-9,11-diazatricyclo[6.4.0.0[2,6]]dodeca-1(12),2(6),8,10-tetraen-12-yl]oxy]cyclohexyl)-N-methylcarbamate (60 mg, 0.09 mmol, 1.00 equiv) in dichloromethane (2 mL) was added hydrogen chloride (6 N) (1 mL). The resulting solution was stirred for 1 h at room temperature. The resulting mixture was concentrated under vacuum. The crude product (50 mg) was purified by preparative HPLC under the following conditions: column: SunFire Prep C18, 19*150 mm 5 um; mobile phase: water with 50 mL $NH_4CO_3$ and $CH_3CN$ (5.0% $CH_3CN$ up to 43.0% in 12 min, up to 95.0% in 2 min, down to 5.0% in 2 min); detector: 254/220 nm. This resulted in 22 mg (55%) of N-[(2R)-2-hydroxypropyl]-2-[(3R)-12-[[4-(methylamino)cyclohexyl]oxy]-7-thia-9,11-diazatricyclo[6.4.0.0[2,6]]dodeca-1(12),2(6),8,10-tetraen-3-yl]acetamide as a white solid.

MS: m/z 419 (M+H)$^+$. $^1$H NMR (300 MHz, $CD_3OD$): δ 1.20 (3H, d), 1.41-1.61 (2H, m), 1.61-1.75 (2H, m), 2.15 (2H, d), 2.21-2.40 (4H, m), 2.61 (3H, s), 2.67-2.81 (2H, m), 2.90-3.10 (2H, m), 3.10-3.21 (2H, m), 3.3 (1H, m), 3.82 (2H, m), 5.27 (1H, m), 8.48 (1H, s).

Example 158

Synthesis of 2-[(3R)-12-[[4-(4-benzylpiperazin-1-yl)cyclohexyl]oxy]-7-thia-9,11-diazatricyclo[6.4.0.0[2,6]]dodeca-1(12),2(6),8,10-tetraen-3-yl]acetamide (I-122)

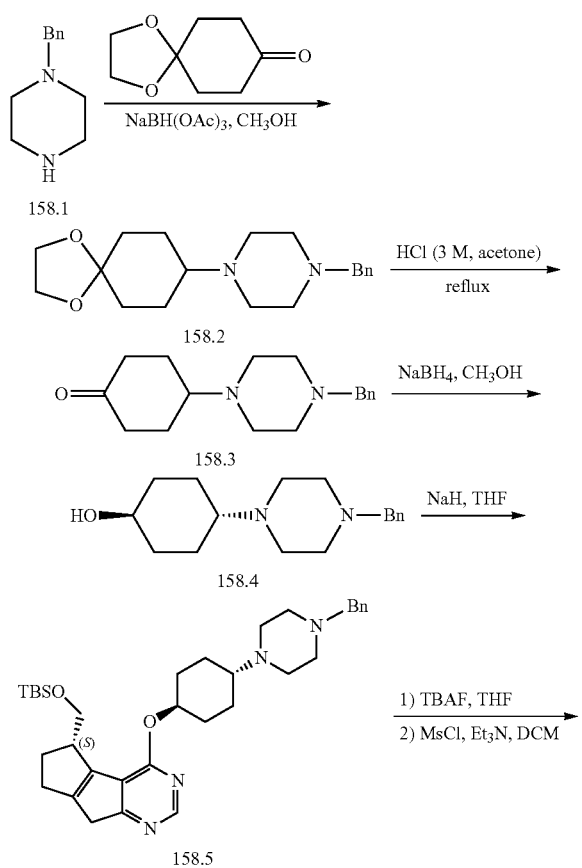

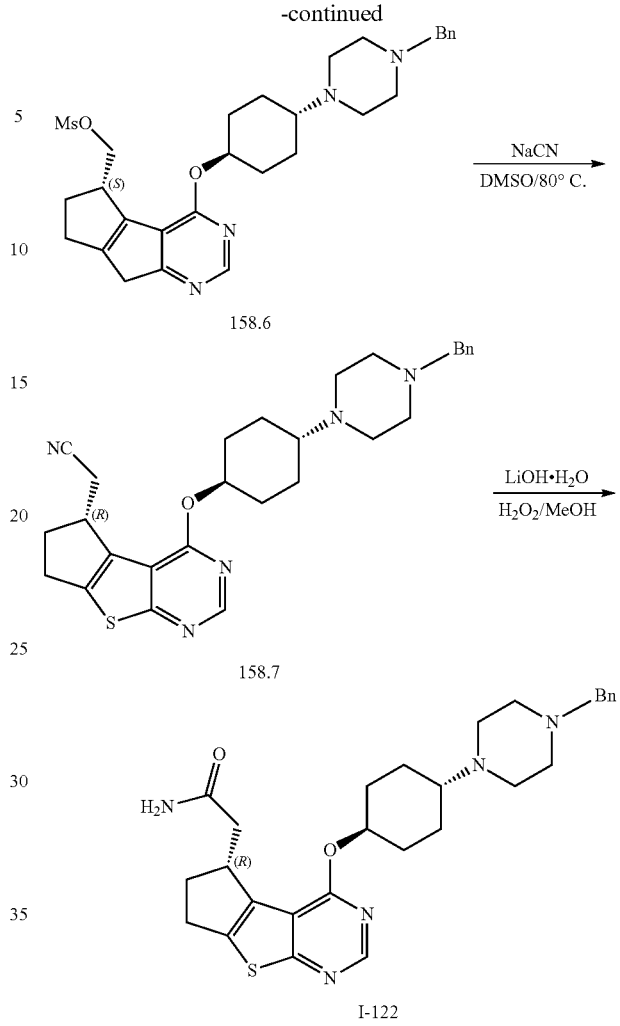

Synthesis of Compound 158.2.

To a solution of 1,4-dioxaspiro[4.5]decan-8-one (11 g, 70.43 mmol, 1.24 equiv) and acetic acid (3 mL) in DCE (100 mL) was added 1-benzylpiperazine (10 g, 56.73 mmol, 1.00 equiv). The resulting solution was stirred for 30 min at 0° C., and then to the above solution was added NaBH(OAc)$_3$ (20 g). The resulting solution was stirred overnight at room temperature. The reaction was then quenched by the addition of 60 mL of NaOH (10%). The resulting solution was extracted with 5×50 mL of dichloromethane and the organic layers combined. The mixture was dried over anhydrous sodium sulfate. The solids were filtered out. The resulting mixture was concentrated under vacuum. This resulted in 16 g (89%) of 1-benzyl-4-[1,4-dioxaspiro[4.5]decan-8-yl]piperazine as a white solid.

Synthesis of Compound 158.3.

To a solution of 1-benzyl-4-[1,4-dioxaspiro[4.5]decan-8-yl]piperazine (8.9 g, 28.13 mmol, 1.00 equiv) in acetone (150 mL) was added (3 mol/L) hydrogen chloride (350 mL). The resulting solution was stirred overnight at 70° C. in an oil bath. Acetone was removed under vacuum. The pH was adjust to the value of 9-10 with $K_2CO_3$ (aq.). The resulting solution was extracted with 3×200 mL of dichloromethane and the organic layers combined. The resulting mixture was washed with 200 mL of saturated sodium chloride solution. The mixture was dried over anhydrous sodium sulfate and concentrated under vacuum. This resulted in 7.6 g (crude) of 4-(4-benzylpiperazin-1-yl)cyclohexan-1-one as an off-white solid.

Synthesis of Compound 158.4.

To a solution of 4-(4-benzylpiperazin-1-yl)cyclohexan-1-one (10 g, 36.71 mmol, 1.00 equiv) in tetrahydrofuran (150 mL) was added LAH (3 g, 79.05 mmol, 2.15 equiv). The resulting solution was stirred for 2 h at 70° C. The reaction was then quenched by the addition of 5 mL of water. The resulting mixture was concentrated under vacuum. The residue was applied onto a silica gel column with dichloromethane/methanol (10:1). This resulted in 6 g (60%) of 4-(4-benzylpiperazin-1-yl)cyclohexan-1-ol as a white solid.

Synthesis of Compound 158.5.

To a solution of 4-(4-benzylpiperazin-1-yl)cyclohexan-1-ol (1160 mg, 4.23 mmol, 3.00 equiv) in tetrahydrofuran (50 mL) was added sodium hydride (170 mg, 4.25 mmol, 3.02 equiv, 60%). The reaction mixture was stirred for 30 min, and then to the above solution was added (3S)-3-[[(tert-butyldimethylsilyl)oxy]methyl]-12-chloro-7-thia-9,11-diazatricyclo[6.4.0.0[2,6]]dodeca-1(12),2(6),8,10-tetraene (500 mg, 1.41 mmol, 1.00 equiv). Stirring was continued at 55° C. overnight. The reaction was then quenched by the addition of 50 mL of water. The resulting solution was extracted with 5×50 mL of dichloromethane and the organic layers combined and dried over anhydrous magnesium sulfate. After evaporation, the residue was applied onto a silica gel column with ethyl acetate/petroleum ether (1:1). This resulted in 420 mg (50%) of (3S)-12-[[4-(4-benzylpiperazin-1-yl)cyclohexyl]oxy]-3-[[(tert-butyldimethylsilyl)oxy]methyl]-7-thia-9,11-diazatricyclo[6.4.0.0[2,6]]dodeca-1(12),2(6),8,10-tetraene as a yellow oil.

Synthesis of Compound 158.6.

To a solution of (3S)-12-[[4-(4-benzylpiperazin-1-yl)cyclohexyl]oxy]-3-[[(tert-butyldimethylsilyl)oxy]methyl]-7-thia-9,11-diazatricyclo[6.4.0.0[2,6]]dodeca-1(12),2(6),8,10-tetraene (420 mg, 0.71 mmol, 1.00 equiv) in tetrahydrofuran (15 mL) was added TBAF (570 mg, 2.18 mmol, 3.08 equiv). The resulting solution was stirred for 3 h at 25° C. After concentration under vacuum, dichloromethane (15 mL), triethylamine (0.1 mL) and MsCl (0.1 mL) were added to the residue. The resulting solution was stirred for 2 h at 25° C. The reaction was then quenched by the addition of 50 mL of water. The resulting solution was extracted with 4×50 mL of dichloromethane and the organic layers combined and dried over anhydrous magnesium sulfate. The solids were filtered out. The resulting mixture was concentrated under vacuum. This resulted in 350 mg (89%) of [(3S)-12-[[4-(4-benzylpiperazin-1-yl)cyclohexyl]oxy]-7-thia-9,11-diazatricyclo[6.4.0.0[2,6]]dodeca-1(12),2(6),8,10-tetraen-3-yl]methyl methanesulfonate as a yellow oil.

Synthesis of Compound 158.7.

To a solution of [(3S)-12-[[4-(4-benzylpiperazin-1-yl)cyclohexyl]oxy]-7-thia-9,11-diazatricyclo[6.4.0.0[2,6]]dodeca-1(12),2(6),8,10-tetraen-3-yl]methyl methanesulfonate (360 mg, 0.65 mmol, 1.00 equiv) in DMSO (10 mL) was added NaCN (160 mg). The resulting solution was stirred for 2 h at 80° C. in an oil bath. The reaction was then quenched by the addition of 100 mL of sodium bicarbonate (sat.). The resulting solution was extracted with 6×50 mL of dichloromethane and the organic layers combined. The mixture was dried over anhydrous magnesium sulfate. The resulting mixture was concentrated under vacuum. This resulted in 270 mg (86%) of 2-[(3R)-12-[[4-(4-benzylpiperazin-1-yl)cyclohexyl]oxy]-7-thia-9,11-diazatricyclo[6.4.0.0[2,6]]dodeca-1(12),2(6),8,10-tetraen-3-yl]acetonitrile as a yellow solid.

Synthesis of Compound I-122.

To a solution of 2-[(3R)-12-[[4-(4-benzylpiperazin-1-yl)cyclohexyl]oxy]-7-thia-9,11-diazatricyclo[6.4.0.0[2,6]]dodeca-1(12),2(6),8,10-tetraen-3-yl]acetonitrile (270 mg, 0.55 mmol, 1.00 equiv) in methanol (25 mL) were added LiOH.H$_2$O (70 mg) and H$_2$O$_2$ (30%) (1.2 mL). The resulting solution was stirred for 4 h at 0° C. in a water/ice bath. The reaction was then quenched by the addition of 100 mL of Na$_2$SO$_3$ (sat.). The resulting solution was extracted with 6×50 mL of dichloromethane and the organic layers combined. After evaporation, the residue was purified by silica gel column with dichloromethane/methanol (4:1). This resulted in 90 mg (32%) of Compound I-122 as a white solid.

$^1$H NMR (300 MHz, CD$_3$OD): δ 1.40-1.70 (m, 4H), 2.00-2.10 (m, 2H), 2.20-2.40 (m, 6H), 2.55-2.80 (m, 8H), 2.95-3.05 (m, 2H), 3.10-3.20 (m, 1H), 3.56 (s, 2H), 3.70-3.85 (m, 1H), 5.20-5.35 (m, 1H), 7.20-7.50 (m, 5H), 8.48 (s, 1H).

Example 159

Synthesis of 2-((R)-4-(((1r,4R)-4-(3-oxopiperazin-1-yl)cyclohexyl)oxy)-6,7-dihydro-5H-cyclopenta[4,5]thieno[2,3-d]pyrimidin-5-yl)acetamide (I-158) and Example 160: Synthesis of 2-((R)-4-(((1s,4S)-4-(3-oxopiperazin-1-yl)cyclohexyl)oxy)-6,7-dihydro-5H-cyclopenta[4,5]thieno[2,3-d]pyrimidin-5-yl)acetamide (I-157)

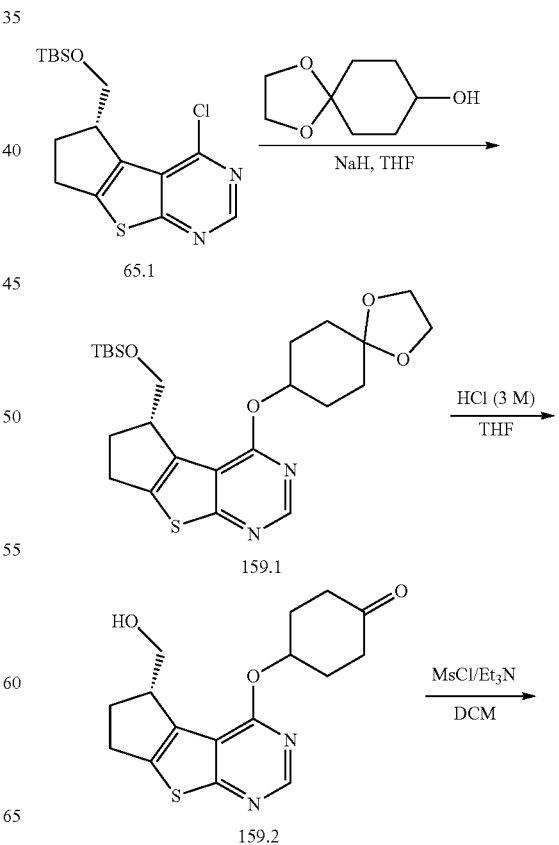

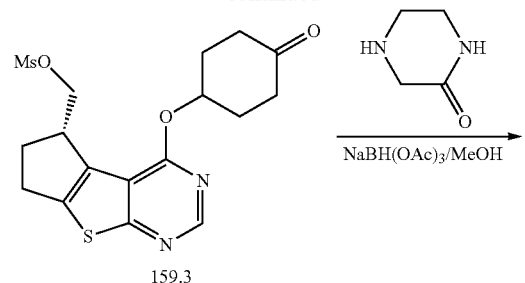

159.3

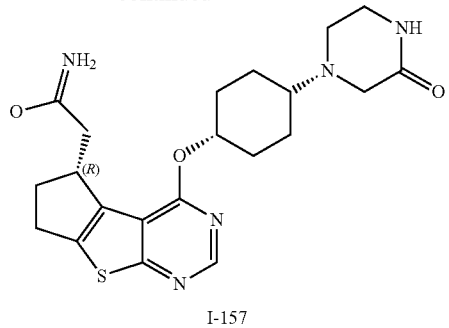

I-157

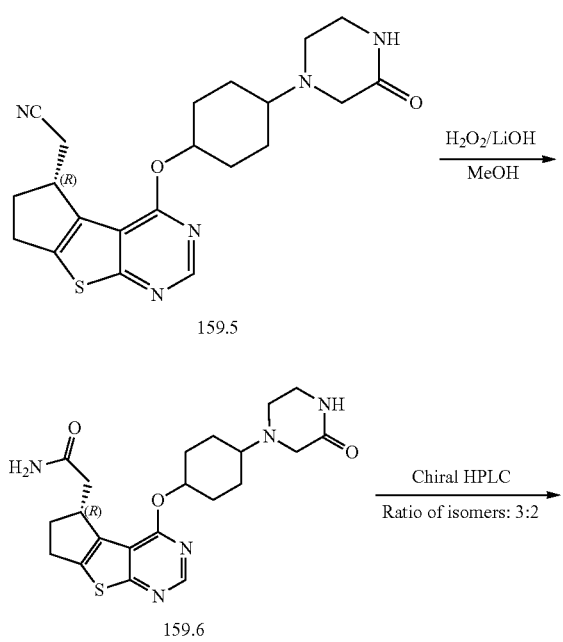

159.4

159.5

159.6

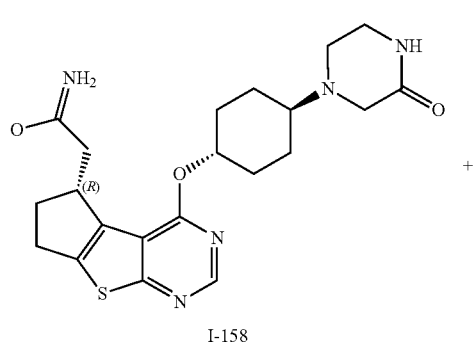

I-158

+

Synthesis of Compound 159.1.

To a solution of 1,4-dioxaspiro[4.5]decan-8-ol (379 mg, 2.40 mmol, 1.20 equiv) in freshly distilled THF (10 mL) was added sodium hydride (60% dispersion in mineral oil, 320 mg, 8.00 mmol, 4.00 equiv) in ice/water bath and stirred for 30 min under nitrogen. A solution of (3S)-3-[[(tert-butyldimethylsilyl)oxy]methyl]-12-chloro-7-thia-9,11-diazatricyclo [6.4.0.0[2,6]]dodeca-1(8),2(6),9,11-tetraene (710 mg, 2.00 mmol, 1.00 equiv) in 10 mL of anhydrous THF was added dropwise and the resulting solution was stirred for 3 h at 60° C. After cooling, the mixture was then quenched with water, extracted with EtOAc (100 mL), dried over anhydrous sodium sulfate. The solvents were evaporated under reduced pressure to obtain (3S)-3-[[(tert-butyldimethylsilyl)oxy]methyl]-12-[1,4-dioxaspiro[4.5]decan-8-yloxy]-7-thia-9,11-diazatricyclo[6.4.0.0[2,6]]dodeca-1(8),2(6),9,11-tetraene (840 mg, 88%) as a yellow oil.

Synthesis of Compound 159.2.

To a solution of (3S)-3-[[(tert-butyldimethylsilyl)oxy]methyl]-12-[1,4-dioxaspiro[4.5]decan-8-yloxy]-7-thia-9,11-diazatricyclo[6.4.0.0[2,6]]dodeca-1(8),2(6),9,11-tetraene (840 mg, 1.76 mmol, 1.00 equiv) in THF (20 mL) was added hydrochloric acid (3 M, 10 mL) at 0° C. and stirred overnight at room temperature. The pH value of the solution was adjusted to 10 with sodium bicarbonate (sat.), extracted with dichloromethane (100 mL), dried over anhydrous sodium sulfate and concentrated under vacuum. The residue was applied on a silica gel column and eluted with EtOAc/petroleum ether (1:1) to give 450 mg (80%) of 4-[[(3S)-3-(hydroxymethyl)-7-thia-9,11-diazatricyclo[6.4.0.0[2,6]] dodeca-1(8),2(6),9,11-tetraen-12-yl]oxy]cyclohexan-1-one as a yellow oil.

Synthesis of Compound 159.3.

To a solution of 4-[[(3S)-3-(hydroxymethyl)-7-thia-9,11-diazatricyclo[6.4.0.0[2,6]]dodeca-1(8),2(6),9,11-tetraen-12-yl]oxy]cyclohexan-1-one (450 mg, 1.41 mmol, 1.00 equiv) in DCM (10 mL) was added methanesulfonyl chloride (242 mg, 2.11 mmol, 1.50 equiv) and triethylamine (430 mg, 4.25 mmol, 3.00 equiv) via syringe under nitrogen. The resulting solution was stirred for 2 h at room temperature. The resulting mixture was diluted with 50 mL of DCM, washed with brine, dried over anhydrous sodium sulfate and evaporated to give 500 mg (89%) of [(3S)-12-[(4-oxocyclohexyl)oxy]-7-thia-9,11-diazatricyclo[6.4.0.0[2,6]]dodeca-1(8),2(6),9,11-tetraen-3-yl]methyl methanesulfonate as a yellow oil.

Synthesis of Compound 159.4.

To a solution of [(3S)-12-[(4-oxocyclohexyl)oxy]-7-thia-9,11-diazatricyclo[6.4.0.0[2,6]]dodeca-1(8),2(6),9,11-tetraen-3-yl]methyl methanesulfonate (500 mg, 1.26 mmol, 1.00 equiv) in methanol (10 mL) was added piperazin-2-one (126 mg, 1.26 mmol, 1.00 equiv) and acetic acid (1 mL). The solution was stirred for 1 h and then acetyl ethaneperoxoate sodioboranyl acetate (534 mg, 2.52 mmol, 2.00 equiv) was added. Stirring was continued for 2 h at 0° C. The mixture was then quenched with saturated aqueous sodium bicarbonate, extracted with DCM (60 mL), dried over anhydrous sodium sulfate and concentrated under vacuum. The desired [(3S)-12-[[4-(3-oxopiperazin-1-yl)cyclohexyl]oxy]-7-thia-9,11-diazatricyclo[6.4.0.0[2,6]]dodeca-1(8),2(6),9,11-tetraen-3-yl]methyl methanesulfonate (450 mg, 74%) was obtained as a yellow solid.

Synthesis of Compound 159.5.

To a solution of [(3S)-12-[[4-(3-oxopiperazin-1-yl)cyclohexyl]oxy]-7-thia-9,11-diazatricyclo[6.4.0.0[2,6]]dodeca-1(8),2(6),9,11-tetraen-3-yl]methyl methanesulfonate (450 mg, 0.94 mmol, 1.00 equiv) in DMSO (10 mL) was added NaCN (276 mg, 5.63 mmol, 6.00 equiv) and DMAP (11 mg, 0.094 mmol, 0.10 equiv) at room temperature. The resulting solution was stirred for 2 h at 80° C. After cooling to r.t, the resulting solution was diluted with DCM (100 mL), washed with brine, dried over anhydrous sodium sulfate and concentrated under vacuum. The residue was purified by column chromatography on silica gel with DCM/MeOH (10:1) to afford 330 mg (86%) of 2-[(3R)-12-[[4-(3-oxopiperazin-1-yl)cyclohexyl]oxy]-7-thia-9,11-diazatricyclo[6.4.0.0[2,6]]dodeca-1(8),2(6),9,11-tetraen-3-yl]acetonitrile as a yellow solid.

Synthesis of Compound 159.6.

To a solution of 2-[(3R)-12-[[4-(3-oxopiperazin-1-yl)cyclohexyl]oxy]-7-thia-9,11-diazatricyclo[6.4.0.0[2,6]]dodeca-1(12),2(6),8,10-tetraen-3-yl]acetonitrile (330 mg, 0.80 mmol, 1.00 equiv) in methanol (10 mL) was added LiOH.H$_2$O (101 mg, 2.40 mmol, 3.00 equiv) and H$_2$O$_2$ (30%, 0.5 mL) at 0° C. The resulting solution was stirred for 2 h at room temperature and quenched with Na$_2$SO$_3$ (aq.), extracted with DCM (80 mL), dried over anhydrous sodium sulfate and concentrated under vacuum. The residue was applied onto a silica gel column with dichloromethane/methanol (10:1) to give 50 mg (15%) of 2-[(3R)-12-[[4-(3-oxopiperazin-1-yl)cyclohexyl]oxy]-7-thia-9,11-diazatricyclo[6.4.0.0[2,6]]dodeca-1(12),2(6),8,10-tetraen-3-yl]acetamide as a white solid. [Note: The product was found to decompose during column purification].

Synthesis of Compounds I-158 and I-157.

The racemic 2-[(3R)-12-[[4-(3-oxopiperazin-1-yl)cyclohexyl]oxy]-7-thia-9,11-diazatricyclo[6.4.0.0[2,6]]dodeca-1(12),2(6),8,10-tetraen-3-yl]acetamide (50 mg) was resolved by preparative chiral HPLC under the following conditions (Gilson): column: Venusil Chiral OD-H21.1*25 cm, 5 um Chiral-P(OD); mobile phase: Hex (0.2% TEA):EtOH (0.2% TEA); flow rate: 20 mL/min; UV detection at 254/220 nm. The product-containing fractions were collected and partially evaporated to remove hexane and EtOH under reduced pressure. The residues were lyophilized overnight to give the desired products I-158 (28 mg) and I-157 (18 mg) as white solids.

Example 159

MS: m/z 430 (M+H)$^+$. $^1$H NMR (300 MHz, CD$_3$OD): δ 8.48 (s, 1H), 5.61-5.57 (m, 1H), 3.91-3.79 (m, 1H), 3.31 (s, 2H), 3.21-2.71 (m, 7H), 2.66-2.52 (m, 1H), 2.39-2.18 (m, 4H), 1.89-1.61 (m, 7H).

Example 160

MS: m/z 430 (M+H)$^+$. $^1$H NMR (300 MHz, CD$_3$OD): δ 8.47 (s, 1H), 5.33-5.26 (m, 1H), 3.89-3.75 (m, 1H), 3.31-2.98 (m, 6H), 2.95-2.71 (m, 3H), 2.61-2.45 (m, 1H), 2.39-2.21 (m, 4H), 2.10-2.01 (m, 2H), 1.78-1.41 (m, 5H).

Example 161

Synthesis of Intermediate 161.12

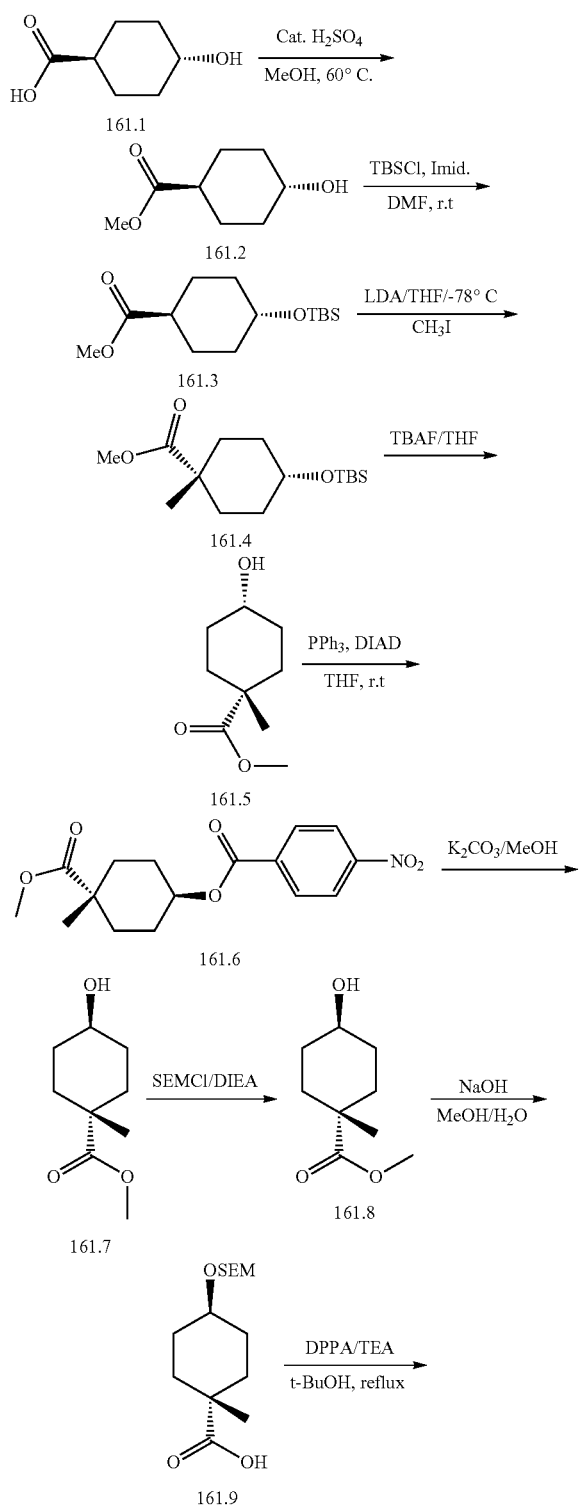

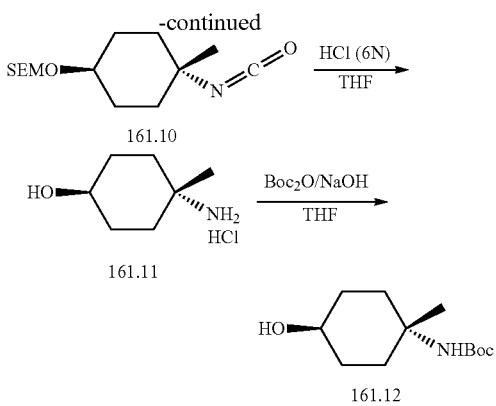

Synthesis of Compound 161.2.

To a solution of 4-hydroxycyclohexane-1-carboxylic acid (13 g, 90.17 mmol, 1.00 equiv) in methanol (100 mL) was added sulfuric acid (0.8 mL) and the resulting solution was stirred for 5 h at 60° C. After cooling, the reaction mixture was concentrated under reduced pressure and the residue was diluted with saturated aqueous sodium bicarbonate and extracted with 3×200 mL of ethyl acetate. The combined organic layers were washed with brine, dried over anhydrous sodium sulfate and concentrated under vacuum. This resulted in 14 g (crude) of methyl 4-hydroxycyclohexane-1-carboxylate as a colorless oil.

Synthesis of Compound 161.3.

A 500-mL round-bottom flask purged and maintained with an inert atmosphere of nitrogen was charged with a solution of methyl 4-hydroxycyclohexane-1-carboxylate (14.0 g, 88.50 mmol, 1.00 equiv) in anhydrous N,N-dimethylformamide (20 mL) at 0° C. Then tert-butyl(chloro)dimethylsilane (23.9 g, 158.57 mmol, 1.79 equiv) and imidazole (12.05 g) were added and the resulting solution was stirred overnight at room temperature. The reaction was then quenched by the addition of 100 mL of water and extracted with 3×150 mL of ethyl acetate. The combined organic layers were washed with brine, dried over anhydrous sodium sulfate and concentrated under vacuum. The residue was applied onto a silica gel column with ethyl acetate/petroleum ether (1/10) to give 4-[(tert-butyldimethylsilyl)oxy]cyclohexane-1-carboxylate (24.0 g, 95%) as a colorless oil.

Synthesis of Compound 161.4.

To a solution of anhydrous DIPA (26.7 g, 263.86 mmol, 3.00 equiv) in freshly distilled THF (500 mL) was added n-BuLi (2.5 M in hexane, 110 mL) dropwise with stirring at −78° C. under nitrogen. After the addition, the resulting solution was stirred for 0.5 h at −78° C. To this was added dropwise a solution of methyl 4-[(tert-butyldimethylsilyl)oxy]cyclohexane-1-carboxylate (24 g, 88.09 mmol, 1.00 equiv) in 50 mL of THF and the resulting solution was allowed to react for an additional 1 h at −78° C. To the mixture was added CH₃I (62.64 g, 441.31 mmol, 5.01 equiv) dropwise with stirring at this low temperature. Stirring was continued for 1 h. The reaction was quenched with water and extracted with 3×150 mL of ethyl acetate. The combined organic layers were washed with brine, dried over anhydrous sodium sulfate and concentrated under vacuum. The residue was applied onto a silica gel column with ethyl acetate/petroleum ether (1/10) to provide the desired methyl 4-[(tert-butyldimethylsilyl)oxy]-1-methylcyclohexane-1-carboxylate (22.0 g, 87%) as a colorless oil.

Synthesis of Compound 161.5.

To a solution of methyl 4-[(tert-butyldimethylsilyl)oxy]-1-methylcyclohexane-1-carboxylate (10.0 g, 34.91 mmol, 1.00 equiv) in 100 mL of tetrahydrofuran was added TBAF-3H₂O (16.5 g, 52.30 mmol, 1.50 equiv) at room temperature and stirred for 5 h. Then the reaction was quenched with water, extracted with 3×100 mL of ethyl acetate. The organic layers were combined, washed with brine, dried over sodium sulfate and concentrated under vacuum. The residue was applied onto a silica gel column with ethyl acetate/petroleum ether (1/2) to give 5.8 g (96%) of methyl 4-hydroxy-1-methylcyclohexane-1-carboxylate as a light yellow oil.

Synthesis of Compound 161.6.

To a solution of methyl 4-hydroxy-1-methylcyclohexane-1-carboxylate (5.8 g, 33.68 mmol, 1.00 equiv) and 4-nitrobenzoic acid (11.26 g, 67.38 mmol, 2.00 equiv) in 80 mL of anhydrous THF was added PPh₃ (17.67 g, 67.37 mmol, 2.00 equiv) at room temperature. Then DIAD (13.62 g, 67.36 mmol, 2.00 equiv) was added dropwise and the resulting solution was stirred for 2 h at room temperature. The reaction was quenched water, extracted with 3×150 mL of ethyl acetate. The combined organic layers were dried over sodium sulfate and concentrated under vacuum. The residue was applied onto a silica gel column with ethyl acetate/petroleum ether (1/50) to give 4-(methoxycarbonyl)-4-methylcyclohexyl 4-nitrobenzoate (5.5 g, 51%) as a white solid.

Synthesis of Compound 161.7.

Into a 250-mL round-bottom flask containing a solution of 4-(methoxycarbonyl)-4-methylcyclohexyl 4-nitrobenzoate (4.5 g, 14.00 mmol, 1.00 equiv) in methanol/water (30 mL/6 mL) was added potassium carbonate (5.8 g, 41.97 mmol, 3.00 equiv) and the resulting solution was stirred overnight at 50° C. The reaction was quenched by the addition of NH₄Cl (aq.) and extracted with 3×100 mL of ethyl acetate. The organic phase was washed with brine, dried over sodium sulfate and concentrated under vacuum. The residue was applied onto a silica gel column with ethyl acetate/petroleum ether (1/2) to afford the desired methyl 4-hydroxy-1-methylcyclohexane-1-carboxylate (2.2 g, 91%) as a colorless oil.

Synthesis of Compound 161.8.

To a solution of methyl 4-hydroxy-1-methylcyclohexane-1-carboxylate (2.1 g, 12.19 mmol, 1.00 equiv) in 20 mL of dichloromethane was added DIEA (4.74 g, 36.68 mmol, 3.01 equiv) and SEMCl (4.08 g, 24.47 mmol, 2.00 equiv) at 0° C. under nitrogen. The resulting solution was stirred for 2 h at room temperature and quenched with water. The resulting solution was extracted with 3×100 mL of ethyl acetate. The organic layers were washed with brine, dried over sodium sulfate and concentrated under reduced pressure. The residue was applied onto a silica gel column with ethyl acetate/petroleum ether (1/20) to give the desired methyl 1-methyl-4-[[2-(trimethylsilyl)ethoxy]methoxy]cyclohexane-1-carboxylate (3.6 g, 98%) as a colorless oil.

Synthesis of Compound 161.9.

To a 250-mL round-bottom flask containing a solution of methyl 1-methyl-4-[[2-(trimethylsilyl)ethoxy]methoxy]cyclohexane-1-carboxylate (3.6 g, 11.90 mmol, 1.00 equiv) in a mixed methanol/water (25 mL/4 mL) was added sodium hydroxide (2.38 g, 59.50 mmol, 5.00 equiv) and the resulting solution was heated to reflux overnight. After cooling, the pH value of the solution was adjusted to 4 with hydrochloric acid (2.0 M), extracted with 3×100 mL of ethyl acetate. The combined organic layers were washed with brine, dried over sodium sulfate and concentrated under reduced pressure. The desired 1-methyl-4-[[2-(trimethylsilyl)ethoxy]methoxy]cyclohexane-1-carboxylic acid (3.12 g, 91%) was obtained as a light yellow oil which was used in the next step without further purification.

401

Synthesis of Compound 161.10.

To a solution of 1-methyl-4-[[2-(trimethylsilyl)ethoxy]methoxy]cyclohexane-1-carboxylic acid (3.1 g, 10.75 mmol, 1.00 equiv) in tert-butanol (40 mL) was added DPPA (5.33 g, 19.37 mmol, 1.80 equiv) and TEA (3.28 g, 32.41 mmol, 3.02 equiv) at room temperature. The resulting solution was heated to reflux overnight and cooled down to room temperature. The reaction was quenched with water and extracted with 3×100 mL of ethyl acetate. The combined organic layers were washed with brine, dried over sodium sulfate and concentrated under reduced pressure. The residue was applied onto a silica gel column with ethyl acetate/petroleum ether (1/100) to give (2-[[(4-isocyanato-4-methylcyclohexyl)oxy]methoxy]ethyl)trimethylsilane (1.5 g, 49%) as a colorless oil.

Synthesis of Compound 161.11.

To a solution of (2-[[(4-isocyanato-4-methylcyclohexyl)oxy]methoxy]ethyl)trimethylsilane (1.5 g, 5.25 mmol, 1.00 equiv) in THF (30 mL) was added hydrochloric acid (6 N, 3.0 mL) and the resulting solution was stirred for 2 h at room temperature. Upon completion, the resulting mixture was concentrated under vacuum to give trans-4-amino-4-methylcyclohexanol hydrochloride (1.0 g, crude) as a white solid.

Synthesis of Intermediate 161.12.

To a solution of 4-amino-4-methylcyclohexan-1-ol hydrochloride (1.0 g, 6.04 mmol, 1.00 equiv) in THF/water (20 mL/5 mL) was added 2M aqueous sodium hydroxide until the pH was 9-10 at 0° C. Then Boc₂O (1.57 g, 7.19 mmol, 1.19 equiv) was added and the resulting solution was stirred for 4 h at room temperature. The reaction was diluted with water and extracted with 3×80 mL of ethyl acetate. The combined organic layers were washed with brine, dried over sodium sulfate and concentrated under reduced pressure. The residue was applied onto a silica gel column with ethyl acetate/petroleum ether (1/1) to give the desired tert-butyl N-(4-hydroxy-1-methylcyclohexyl)carbamate (720 mg, 52%) as a white solid.

Example 162

Synthesis of Intermediate 162.4

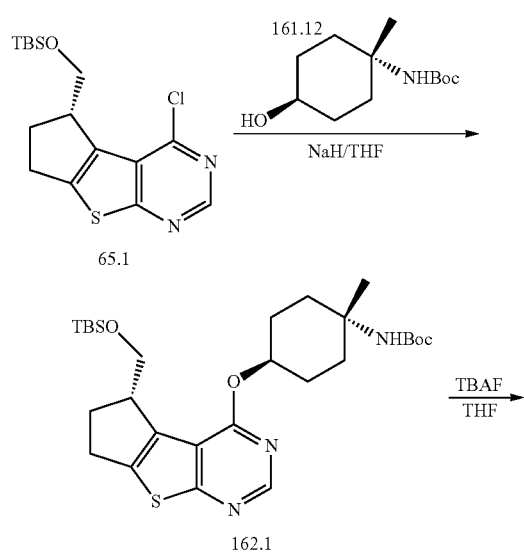

402

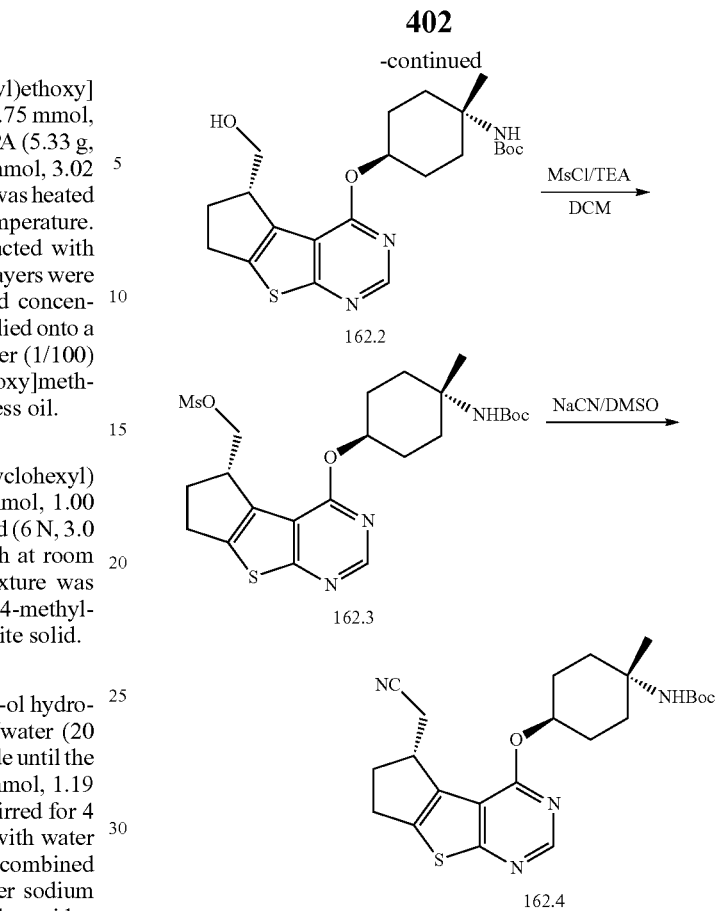

Synthesis of Compound 162.1.

To a solution of tert-butyl N-(4-hydroxy-1-methylcyclohexyl)carbamate (700 mg, 3.05 mmol, 1.00 equiv) in anhydrous THF (10 mL) was added sodium hydride (60% dispersion in mineral oil, 600 mg, 15.00 mmol, 4.91 equiv) at 0° C. under nitrogen. The resulting solution was stirred for 0.5 h at room temperature. To this was added (3S)-3-[[(tert-butyldimethylsilyl)oxy]methyl]-12-chloro-7-thia-9,11-diazatricyclo[6.4.0.0[2,6]]dodeca-1(8),2(6),9,11-tetraene (1.18 g, 3.32 mmol, 1.09 equiv) and stirring was continued for 5 h at 30° C. The reaction was then quenched by the addition of 30 mL of NH₄Cl (aq.) and extracted with 3×80 mL of ethyl acetate. The organic phase was dried over sodium sulfate and concentrated under vacuum. The residue was applied onto a silica gel column with ethyl acetate/petroleum ether (1/15) to yield 1.20 g (72%) of tert-butyl N-(4-[[(3S)-3-[[(tert-butyldimethylsilyl)oxy]methyl]-7-thia-9,11-diazatricyclo[6.4.0.0[2,6]]dodeca-1(8),2(6),9,11-tetraen-12-yl]oxy]-1-methylcyclohexyl)carbamate as a light yellow solid.

Synthesis of Compound 162.2.

To a solution of tert-butyl N-(4-[[(3S)-3-[[(tert-butyldimethylsilyl)oxy]methyl]-7-thia-9,11-diazatricyclo[6.4.0.0[2,6]]dodeca-1(8),2(6),9,11-tetraen-12-yl]oxy]-1-methylcyclohexyl)carbamate (1.20 g, 2.19 mmol, 1.00 equiv) in tetrahydrofuran (15 mL) was added TBAF-3H₂O (1.09 g, 3.45 mmol, 1.58 equiv) at 0° C. and the resulting solution was stirred for 3 h at room temperature. The reaction was quenched with water and extracted with 3×100 mL of ethyl acetate. The organic layers were washed with brine, dried over sodium sulfate and concentrated under vacuum. Purification by column chromatography on silica gel with ethyl acetate/petroleum ether (1:20 to 1:5) afforded tert-butyl N-(4-

[[(3S)-3-(hydroxymethyl)-7-thia-9,11-diazatricyclo[6.4.0.0 [2,6]]dodeca-1(8),2(6),9,11-tetraen-12-yl]oxy]-1-methylcyclohexyl)carbamate (900 mg, 95%) as a colorless oil.

Synthesis of Compound 162.3.

To a solution of tert-butyl N-(4-[[(3S)-3-(hydroxymethyl)-7-thia-9,11-diazatricyclo[6.4.0.0[2,6]]dodeca-1(8),2(6),9,11-tetraen-12-yl]oxy]-1-methylcyclohexyl)carbamate (1.0 g, 2.31 mmol, 1.00 equiv) in dichloromethane (20 mL) was added MsCl (632 mg, 5.54 mmol, 2.40 equiv) and triethylamine (839 mg, 8.29 mmol, 3.59 equiv) at 0° C. The resulting solution was stirred for 1 h at room temperature and quenched with water. The resulting solution was extracted with 3×50 mL of DCM and the organic layers were combined, dried over sodium sulfate and concentrated under vacuum. The residue was applied onto a silica gel column with ethyl acetate/petroleum ether (1/3) to yield 1.07 g (91%) of tert-butyl N-(4-[[(3S)-3-[(methanesulfonyloxy)methyl]-7-thia-9,11-diazatricyclo[6.4.0.0[2,6]]dodeca-1(8),2(6),9,11-tetraen-12-yl] oxy]-1-methylcyclohexyl)carbamate as a light yellow oil.

Synthesis of Intermediate 162.4

To a 50-mL round-bottom flask containing a solution of tert-butyl N-(4-[[(3S)-3-[(methanesulfonyloxy)methyl]-7-thia-9,11-diazatricyclo[6.4.0.0[2,6]]dodeca-1(8),2(6),9,11-tetraen-12-yl]oxy]-1-methylcyclohexyl)carbamate (1.0 g, 1.95 mmol, 1.00 equiv) in DMSO (12 mL) was added NaCN (479 mg, 9.78 mmol, 5.00 equiv) and 4-dimethylaminopyridine (30 mg, 0.25 mmol, 0.13 equiv) and the solution was stirred for 2.5 h at 80° C. After cooling, the reaction was then quenched by the addition of water, extracted with 3×100 mL of ethyl acetate. The organic layers were combined, washed with brine, dried over sodium sulfate and concentrated under vacuum. The residue was applied onto a silica gel column with ethyl acetate/petroleum ether (1/2) to give the desired tert-butyl N-(4-[[(3R)-3-(cyanomethyl)-7-thia-9,11-diazatricyclo[6.4.0.0[2,6]]dodeca-1(8),2(6),9,11-tetraen-12-yl] oxy]-1-methylcyclohexyl)carbamate (830 mg, 96%) as a white solid.

Example 163

Synthesis of 2-[(3R)-12-[(4-amino-4-methylcyclohexyl)oxy]-7-thia-9,11-diazatricyclo[6.4.0.0[2,6]] dodeca-1(8),2(6),9,11-tetraen-3-yl]acetamide (I-161)

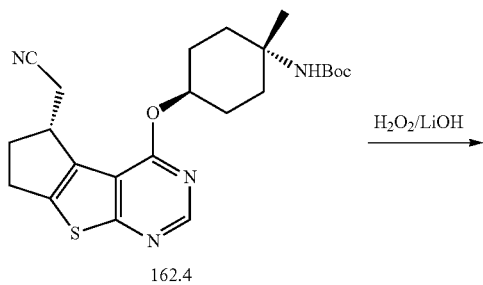

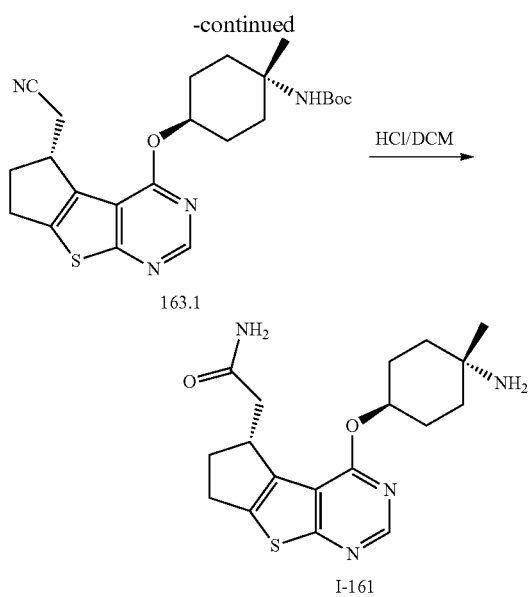

Synthesis of Compound 163.1.

A 50-mL round-bottom flask purged and maintained with an inert atmosphere of nitrogen was charged with tert-butyl N-(4-[[(3R)-3-(cyanomethyl)-7-thia-9,11-diazatricyclo [6.4.0.0[2,6]]dodeca-1(8),2(6),9,11-tetraen-12-yl]oxy]-1-methylcyclohexyl)carbamate (600 mg, 1.36 mmol, 1.00 equiv) in methanol (8.0 mL). Then LiOH.H$_2$O (171 mg, 4.08 mmol, 3.00 equiv) and H$_2$O$_2$ (30%, 1.0 mL) were added at 0° C. and the resulting solution was stirred overnight at this temperature. The reaction was then quenched by the addition of 40 mL of NaHSO$_3$ (aq.) and extracted with 3×60 mL of ethyl acetate. The combined organic layers were washed with brine, dried over sodium sulfate and concentrated under vacuum. The residue was applied onto a silica gel column with ethyl acetate/petroleum ether (1/1) to afford tert-butyl N-(4-[[(3R)-3-(carbamoylmethyl)-7-thia-9,11-diazatricyclo [6.4.0.0[2,6]]dodeca-1(8),2(6),9,11-tetraen-12-yl]oxy]-1-methylcyclohexyl)carbamate (450 mg, 72%) as a white solid.

Synthesis of Compound I-161.

A solution of tert-butyl N-(4-[[(3R)-3-(carbamoylmethyl)-7-thia-9,11-diazatricyclo[6.4.0.0[2,6]]dodeca-1(8),2 (6),9,11-tetraen-12-yl]oxy]-1-methylcyclohexyl)carbamate (100 mg, 0.22 mmol, 1.00 equiv) in dichloromethane (5.0 mL) was added hydrochloric acid (6 N, 0.3 mL) at 0° C. The resulting solution was stirred for 2 h at room temperature and concentrated under vacuum. The crude product (90 mg) was purified by preparative HPLC under the following conditions (Waters): column: XBridge Prep C18 OBD column: 5 um, 19*150 mm, mobile phase: water with 0.05% NH4HCO3 and CH3CN (5% CH3CN up to 16% in 2 min, hold 16% in 11 min, up to 95% in 2 min, down to 5% in 2 min); flow rate: 20 mL/min; UV detection at 254 & 220 nm. This resulted in 28.4 mg (36%) of 2-[(3R)-12-[(4-amino-4-methylcyclohexyl) oxy]-7-thia-9,11-diazatricyclo[6.4.0.0[2,6]]dodeca-1(8),2 (6),9,11-tetraen-3-yl]acetamide as a white solid. MS: m/z 361 (M+H)$^+$.

$^1$H NMR (300 MHz, CD$_3$OD): δ 8.48 (1H, s), 5.44 (1H, m), 3.80 (1H, m), 3.28 (1H, m), 2.96 (2H, m), 2.71 (1H, m), 2.26 (2H, m), 2.09 (2H, m), 1.79-1.91 (4H, m), 1.55 (2H, m), 1.22 (3H, s).

Example 164

Synthesis of 2-[(3R)-12-[[4-(dimethylamino)-4-methylcyclohexyl]oxy]-7-thia-9,11-diazatricyclo[6.4.0.0[2,6]]dodeca-1(8),2(6),9,11-tetraen-3-yl]acetamide (I-155)

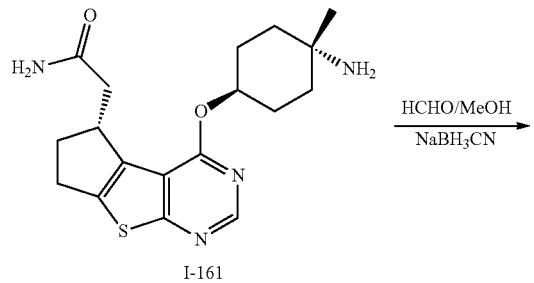

Example 165

Synthesis of 2-[(3R)-12-[[4-methyl-4-(methylamino)cyclohexyl]oxy]-7-thia-9,11-diazatricyclo[6.4.0.0[2,6]]dodeca-1(8),2(6),9,11-tetraen-3-yl]acetamide (I-156)

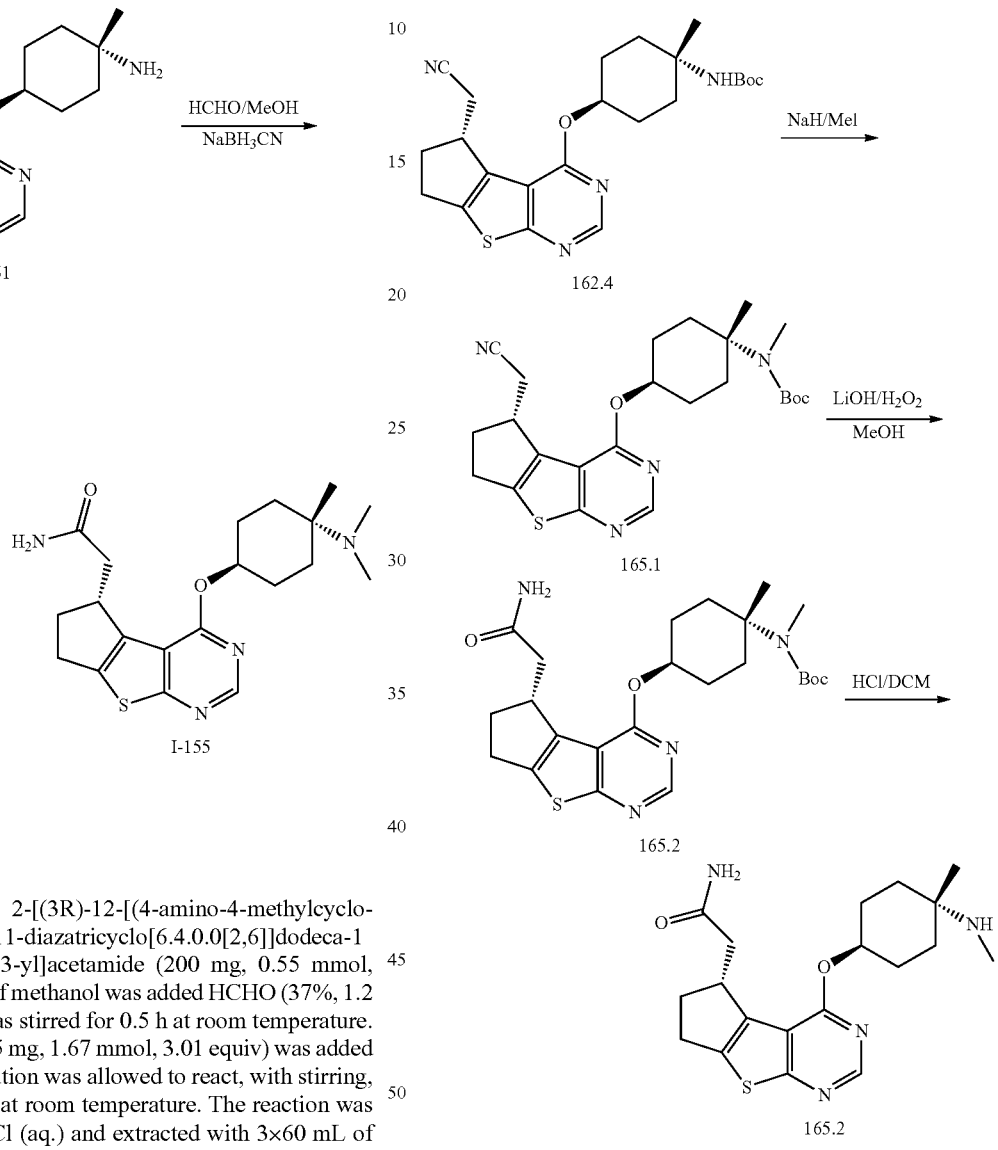

To a solution of 2-[(3R)-12-[(4-amino-4-methylcyclohexyl)oxy]-7-thia-9,11-diazatricyclo[6.4.0.0[2,6]]dodeca-1(8),2(6),9,11-tetraen-3-yl]acetamide (200 mg, 0.55 mmol, 1.00 equiv) in 8 mL of methanol was added HCHO (37%, 1.2 mL). The solution was stirred for 0.5 h at room temperature. Then NaBH₃CN (105 mg, 1.67 mmol, 3.01 equiv) was added and the resulting solution was allowed to react, with stirring, for an additional 1 h at room temperature. The reaction was quenched with NH₄Cl (aq.) and extracted with 3×60 mL of DCM. The combined organic layers were concentrated under vacuum. The crude product (150 mg) was purified by preparative HPLC under the following conditions (Waters): column: XBridge Prep C18 OBD column: 5 um, 19*150 mm; mobile phase: water with 0.05% NH₄HCO₃ and CH₃CN (5% CH₃CN up to 47% in 13 min, up to 95% in 2 min, down to 5% in 2 min); flow rate: 20 mL/min; UV detection at 254 & 220 nm. This resulted in 39.8 mg of 2-[(3R)-12-[[4-(dimethylamino)-4-methylcyclohexyl]oxy]-7-thia-9,11-diazatricyclo[6.4.0.0[2,6]]dodeca-1(8),2(6),9,11-tetraen-3-yl]acetamide as a white solid. MS: m/z 389 (M+H)⁺. ¹H NMR (300 MHz, CD₃OD): δ 8.49 (1H, s), 5.41 (1H, m), 3.80 (1H, m), 3.19 (1H, m), 3.04 (1H, m), 2.98 (1H, m), 2.85 (6H, s), 2.76 (1H, m), 2.31 (4H, m), 2.14 (2H, m), 1.96 (4H, m), 1.47 (3H, s).

Synthesis of 165.1.

To a 50-mL round-bottom flask containing a solution of tert-butyl N-(4-[[(3R)-3-(cyanomethyl)-7-thia-9,11-diazatricyclo[6.4.0.0[2,6]]dodeca-1(8),2(6),9,11-tetraen-12-yl]oxy]-1-methylcyclohexyl)carbamate (100 mg, 0.23 mmol, 1.00 equiv) in distilled DMF (3 mL) was added sodium hydride (60% dispersion in mineral oil 37 mg, 0.93 mmol, 4.09 equiv) at 0° C. The resulting solution was stirred for 0.5 h at this temperature. Then CH₃I (321 mg, 2.26 mmol, 1.00 equiv) was added and the resulting solution was allowed to react, with stirring, for an additional 2 h at 30° C. The reaction was then quenched with saturated aqueous NH₄Cl and extracted with 3×30 mL of ethyl acetate. The combined organic layers were washed with brine, dried over sodium sulfate and concentrated under vacuum. The residue was applied onto a silica gel column with ethyl acetate/petroleum ether (1:2) to give tert-butyl N-(4-[[(3R)-3-(cyanomethyl)-7-thia-9,11-diazatricyclo[6.4.0.0[2,6]]dodeca-1(8),2(6),9,11-tetraen-12-yl]oxy]-1-methylcyclohexyl)-N-methylcarbamate (80 mg, 78%) as a white solid.

Synthesis of 165.2

To a solution of tert-butyl N-(4-[[(3R)-3-(cyanomethyl)-7-thia-9,11-diazatricyclo[6.4.0.0[2,6]]dodeca-1(8),2(6),9,11-tetraen-12-yl]oxy]-1-methylcyclohexyl)-N-methylcarbamate (100 mg, 0.2 mmol, 1.00 equiv) in 10 mL of methanol was added LiOH.H$_2$O (30 mg, 0.7 mmol, 3.26 equiv) and H$_2$O$_2$ (30%, 0.8 mL) and stirred for 4 h at 0° C. The reaction was then quenched with saturated aqueous NaHSO$_3$, extracted with 3×50 mL of ethyl acetate. The combined organic layers were washed with brine, dried over sodium sulfate and concentrated under vacuum. The residue was purified by column chromatography on silica gel with EtOAc/PE (1:2) to give the desired tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]-1-methylcyclohexyl)-N-methylcarbamate (85 mg) as a light yellow oil.

Synthesis of Compound I-156.

To a 50-mL round-bottom flask containing a solution of tert-butyl N-(4-[[(3R)-3-(carbamoylmethyl)-7-thia-9,11-diazatricyclo[6.4.0.0[2,6]]dodeca-1(8),2(6),9,11-tetraen-12-yl]oxy]-1-methylcyclohexyl)-N-methylcarbamate (85 mg, 0.18 mmol, 1.00 equiv) in dichloromethane (5 mL) was added hydrochloric acid (6 M, 0.1 mL) at 0° C. The resulting solution was stirred for 2 h at room temperature and concentrated under vacuum. The crude product (70 mg) was purified by preparative HPLC under the following conditions (Waters): column: XBridge Prep C18 OBD column: 5 um, 19*150 mm; mobile phase: water with 0.05% NH$_4$HCO$_3$ and CH$_3$CN (10% CH$_3$CN up to 30% in 10 min, up to 95% in 2 min, down to 10% in 2 min); flow rate: 20 mL/min; UV detection at 254 & 220 nm. This resulted in 46.9 mg (70%) of 2-[(3R)-12-[[4-methyl-4-(methylamino)cyclohexyl]oxy]-7-thia-9,11-diazatricyclo[6.4.0.0[2,6]]dodeca-1(8),2(6),9,11-tetraen-3-yl]acetamide as a white solid. MS: m/z 375 (M+H)$^+$. $^1$H NMR (300 MHz, CD$_3$OD): δ 8.47 (1H, s), 5.44 (1H, m), 3.84 (1H, m), 3.14 (1H, m), 3.02 (1H, m), 2.79 (1H, m), 2.25-2.35 (5H, m), 2.10 (2H, m), 1.75-1.90 (4H, m), 1.63 (2H, m), 1.19 (3H, s).

Example 166

Synthesis of 2-[(3R)-12-[(4-[2-oxa-6-azaspiro[3.3]heptan-6-yl]cyclohexyl)oxy]-7-thia-9,11-diazatricyclo[6.4.0.0[2,6]]dodeca-1(8),2(6),9,11-tetraen-3-yl]acetamide (I-152)

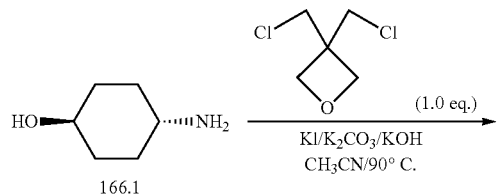

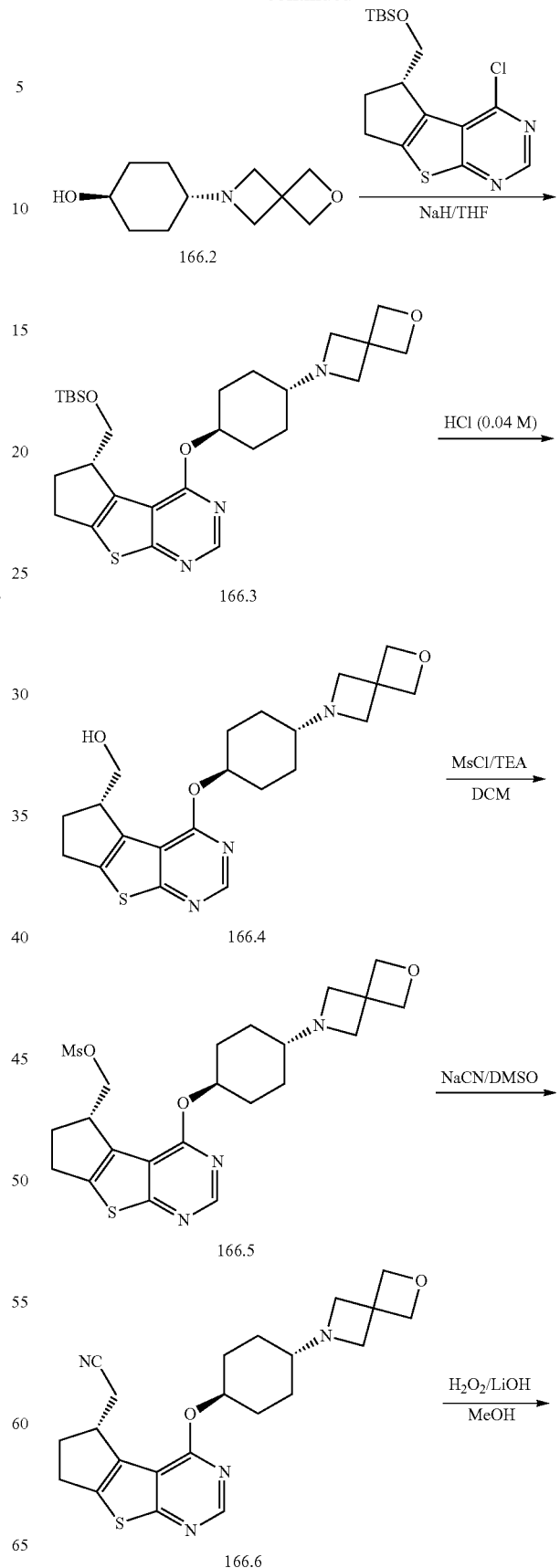

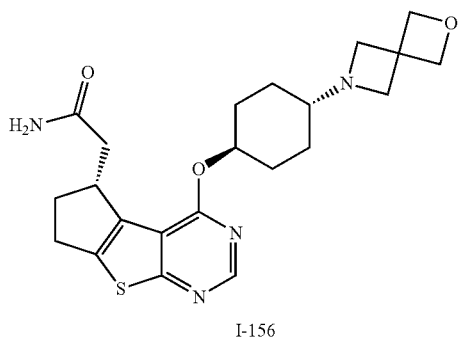 [SMILES: NC(=O)C[C@H]1CCc2sc3ncnc(O[C@H]4CC[C@H](N5CC6(COC6)C5)CC4)c3c21]

I-156

Synthesis of Compound 166.2.

To a solution of 4-aminocyclohexan-1-ol (690 mg, 5.99 mmol, 1.00 equiv), 3,3-bis(chloromethyl)oxetane (1.395 g, 9.00 mmol, 1.50 equiv) in acetonitrile (25 mL) was added potassium carbonate (3.0 g, 21.71 mmol, 3.62 equiv), KI (250 mg, 1.49 mmol, 0.25 equiv) and potassium hydroxide (672 mg, 11.98 mmol, 2.00 equiv) at room temperature and the resulting mixture was stirred overnight at 90° C. in an oil bath. The solids were filtered out and the filtrate was concentrated under vacuum. The residue was applied onto a silica gel column with dichloromethane/methanol (30:1 to 10:1) to give the desired 4-[2-oxa-6-azaspiro[3.3]heptan-6-yl]cyclohexan-1-ol (370 mg, 31%) as an off-white solid.

Synthesis of Compound 166.3.

To a solution of 4-[2-oxa-6-azaspiro[3.3]heptan-6-yl]cyclohexan-1-ol (250 mg, 1.27 mmol, 1.19 equiv) in 15 mL of freshly distilled THF was added sodium hydride (60% dispersion in mineral oil, 169.9 mg, 4.25 mmol, 4.00 equiv) in portions at 0° C. under nitrogen. The resulting solution was stirred for 0.5 h at this temperature. Then (3S)-3-[[(tert-butyldimethylsilyl)oxy]methyl]-12-chloro-7-thia-9,11-diazatricyclo[6.4.0.0[2,6]]dodeca-1(12),2(6),8,10-tetraene (377 mg, 1.06 mmol, 1.00 equiv) was added and the resulting solution was allowed to react, with stirring, for an additional 2 h at ambient temperature. After completion of the reaction, the reaction mixture was quenched by the addition of 20 mL of saturated aqueous NH$_4$Cl and extracted with 3×50 mL of ethyl acetate. The combined organic layers were washed with brine, dried over sodium sulfate and concentrated under vacuum. The residue was applied onto a silica gel column with ethyl acetate to give the desired (3S)-3-[[(tert-butyldimethylsilyl)oxy]methyl]-12-[(4-[2-oxa-6-azaspiro[3.3]heptan-6-yl]cyclohexyl)oxy]-7-thia-9,11-diazatricyclo[6.4.0.0[2,6]]dodeca-1(12),2(6),8,10-tetraene (0.5 g, 91%) as a colorless oil.

Synthesis of Compound 166.4.

To a solution of (3S)-3-[[(tert-butyldimethylsilyl)oxy]methyl]-12-[(4-[2-oxa-6-azaspiro[3.3]heptan-6-yl]cyclohexyl)oxy]-7-thia-9,11-diazatricyclo[6.4.0.0[2,6]]dodeca-1(12),2(6),8,10-tetraene (360 mg, 0.70 mmol, 1.00 equiv) in methanol (65 mL) was added 0.04 M aqueous hydrochloric acid (13 mL) at 0° C. The resulting solution was stirred for 4 h at 0° C. and then quenched with saturated aqueous sodium bicarbonate. The resulting solution was extracted with 3×50 mL of ethyl acetate. The combined organic layers were washed with brine, dried over anhydrous sodium sulfate and concentrated under vacuum. The solvents were evaporated under reduced pressure to yield 250 mg (crude) of the desired [(3S)-12-[(4-[2-oxa-6-azaspiro[3.3]heptan-6-yl]cyclohexyl)oxy]-7-thia-9,11-diazatricyclo[6.4.0.0[2,6]]dodeca-1(12),2(6),8,10-tetraen-3-yl]methanol as a colorless oil.

Synthesis of Compound 166.5.

To a solution of [(3S)-12-[(4-[2-oxa-6-azaspiro[3.3]heptan-6-yl]cyclohexyl)oxy]-7-thia-9,11-diazatricyclo[6.4.0.0[2,6]]dodeca-1(12),2(6),8,10-tetraen-3-yl]methanol (250 mg, 0.62 mmol, 1.00 equiv) and TEA (188 mg, 1.86 mmol, 2.99 equiv) in dichloromethane (10 mL) was added MsCl (142 mg, 1.25 mmol, 2.00 equiv) and the resulting mixture was stirred for 1 h at 25° C. under nitrogen. After completion, the reaction was quenched with water and extracted with 3×50 mL of ethyl acetate. The organic layers were combined, washed with brine and dried over anhydrous sodium sulfate. The solvents were concentrated under reduced pressure vacuum to afford [(3S)-12-[(4-[2-oxa-6-azaspiro[3.3]heptan-6-yl]cyclohexyl)oxy]-7-thia-9,11-diazatricyclo[6.4.0.0[2,6]]dodeca-1(12),2(6),8,10-tetraen-3-yl]methyl methanesulfonate (250 mg, crude) as a yellow oil.

Synthesis of Compound 166.6.

A solution of [(3S)-12-[(4-[2-oxa-6-azaspiro[3.3]heptan-6-yl]cyclohexyl)oxy]-7-thia-9,11-diazatricyclo[6.4.0.0[2,6]]dodeca-1(12),2(6),8,10-tetraen-3-yl]methyl methanesulfonate (250 mg, 0.52 mmol, 1.00 equiv) and NaCN (153 mg, 3.12 mmol, 5.99 equiv) in DMSO (10 mL) was stirred for 3 h at 60° C. After cooling, the reaction was quenched by the addition of 30 mL of saturated aqueous sodium bicarbonate and extracted with 3×50 mL of ethyl acetate. The combined organic layers combined were washed with brine, dried over anhydrous sodium sulfate and concentrated under vacuum. The residue was applied onto a silica gel column with dichloromethane/methanol (10:1) to give 2-[(3R)-12-[(4-[2-oxa-6-azaspiro[3.3]heptan-6-yl]cyclohexyl)oxy]-7-thia-9,11-diazatricyclo[6.4.0.0[2,6]]dodeca-1(12),2(6),8,10-tetraen-3-yl]acetonitrile (140 mg, 65%) as a colorless oil.

Synthesis of Compound I-156.

A solution of 2-[(3R)-12-[(4-[2-oxa-6-azaspiro[3.3]heptan-6-yl]cyclohexyl)oxy]-7-thia-9,11-diazatricyclo[6.4.0.0[2,6]]dodeca-1(8),2(6),9,11-tetraen-3-yl]acetonitrile (140 mg, 0.34 mmol, 1.00 equiv) in methanol (5 mL) was cooled to 0° C. This was followed by the addition of LiOH.H$_2$O (28 mg, 0.67 mmol, 2.00 equiv) and H$_2$O$_2$ (30%, 0.5 mL) at 0° C. under nitrogen. The resulting solution was stirred for 2 h at this temperature. The reaction was quenched with saturated aqueous Na$_2$SO$_3$ and extracted with 3×50 mL of ethyl acetate. The combined organic layers were concentrated under vacuum. The crude product (100 mg) was purified by preparative HPLC under the following conditions (Waters): column: XBridge Shield RP18 OBD column: 5 um, 19*150 mm; mobile phase: water with 0.05% NH$_4$HCO$_3$ and CH$_3$CN (10% CH$_3$CN up to 30% in 10 min, up to 95% in 2 min, down to 10% in 2 min); flow rate: 20 mL/min; UV detection at 254/220 nm. This afforded 43 mg (29%) of 2-[(3R)-12-[(4-[2-oxa-6-azaspiro[3.3]heptan-6-yl]cyclohexyl)oxy]-7-thia-9,11-diazatricyclo[6.4.0.0[2,6]]dodeca-1(8),2(6),9,11-tetraen-3-yl]acetamide as a white solid. MS: m/z 429 (M+H)$^+$. $^1$H NMR (300 MHz, CD$_3$OD): δ 8.45 (1H, s), 5.26-5.31 (1H, m), 4.75-4.87 (4H, s), 3.80-3.83 (1H, m), 3.45 (4H, m), 2.95-3.33 (3H, m), 2.71-2.77 (1H, m), 2.15-2.29 (5H, m), 1.90-1.95 (2H, m), 1.56-1.65 (2H, m), 1.18-1.27 (2H, m).

Example 167

Synthesis of Intermediates 167.3 and 167.4

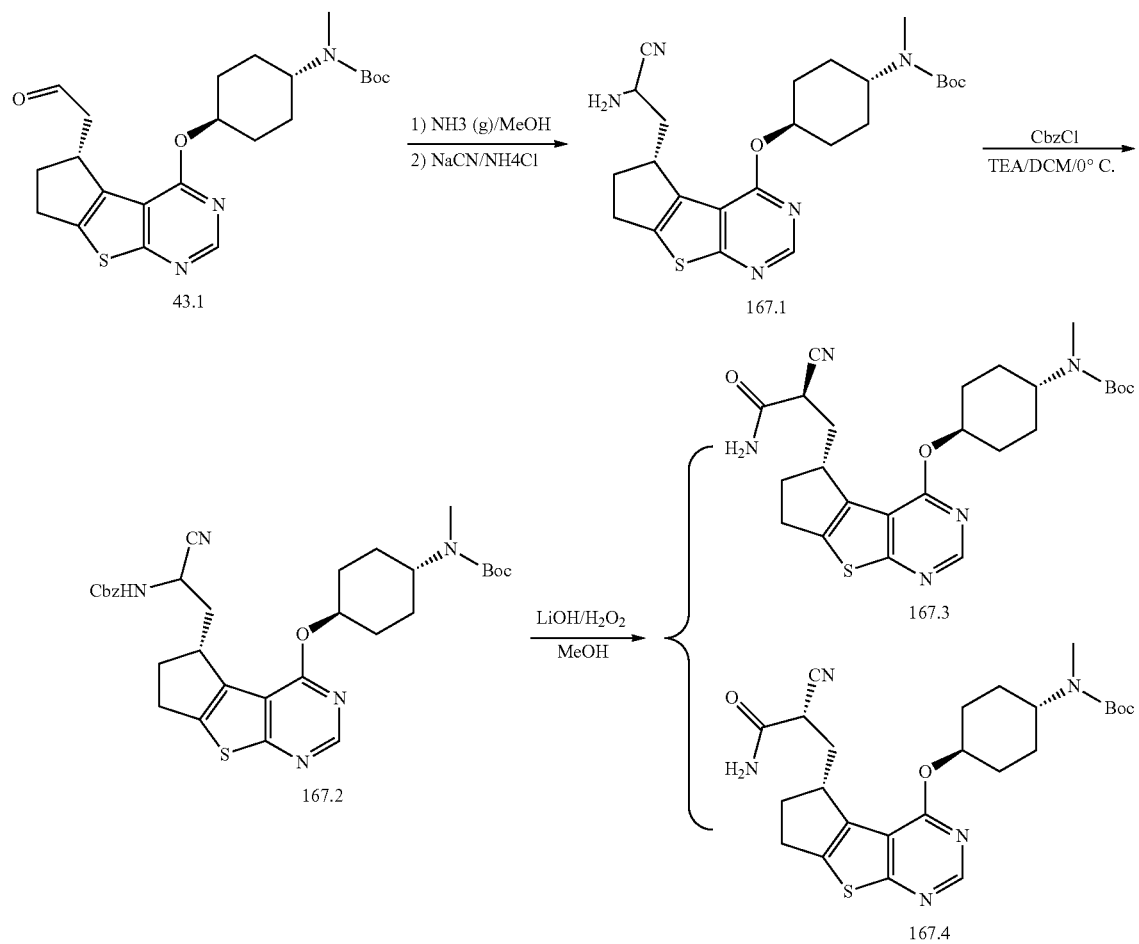

Synthesis of Compound 167.1.

Ammonia gas was introduced in 50 mL of CH$_3$OH at 5° C. for 15 min. To the above solution was added tert-butyl N-methyl-N-(4-[[(3R)-3-(2-oxoethyl)-7-thia-9,11-diazatricyclo[6.4.0.0[2,6]]dodeca-1(8),2(6),9,11-tetraen-12-yl]oxy]cyclohexyl)carbamate (700 mg, 1.57 mmol, 1.00 equiv), NaCN (93.1 mg, 1.90 mmol, 1.20 equiv) and NH$_4$Cl (92.5 mg, 1.73 mmol, 1.10 equiv) successively. The resulting mixture was stirred for 16 h at room temperature and concentrated under reduced pressure. The residue was applied onto a silica gel column with dichloromethane/methanol (1:30) to afford tert-butyl N-(4-[[(3R)-3-(2-amino-2-cyanoethyl)-7-thia-9,11-diazatricyclo[6.4.0.0[2,6]]dodeca-1(8),2(6),9,11-tetraen-12-yl]oxy]cyclohexyl)-N-methylcarbamate (600 mg, 81%) as a yellow oil.

Synthesis of Compound 167.2.

To a solution of tert-butyl N-(4-[[(3R)-3-(2-amino-2-cyanoethyl)-7-thia-9,11-diazatricyclo[6.4.0.0[2,6]]dodeca-1(8),2 (6),9,11-tetraen-12-yl]oxy]cyclohexyl)-N-methylcarbamate (800 mg, 1.70 mmol, 1.00 equiv) and triethylamine (340 mg, 3.36 mmol, 2.00 equiv) in dichloromethane (50 mL) was added dropwise a solution of benzyl chloroformate (320 mg, 1.88 mmol, 1.10 equiv) in 10 mL of DCM at 0° C. The resulting solution was stirred for 30 min at this temperature and then quenched with water. The resulting solution was extracted with 3×50 mL of ethyl acetate and the combined organic layers were washed with brine, dried over sodium sulfate and concentrated under vacuum. The residue was applied onto a silica gel column with ethyl acetate/petroleum ether (1:10-1:5) to give benzyl N-[2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2 (6),9,11-tetraen-3-yl]-1-cyano ethyl]carbamate (0.5 g, 49%) as a white solid.

Synthesis of Intermediates 167.3 and 167.4.

To a 50-mL round-bottom flask containing a solution of benzyl N-[2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2 (6),9,11-tetraen-3-yl]-1-cyano ethyl]carbamate (450 mg, 0.74 mmol, 1.00 equiv) in methanol (20 mL) was added LiOH.H$_2$O (94 mg, 2.24 mmol, 3.00 equiv) and H$_2$O$_2$ (30%, 2 mL) at 0° C. The resulting solution was stirred for 2 h at 0° C. and quenched with saturated aqueous Na$_2$SO$_3$ and extracted with 3×50 mL of ethyl acetate. The combined organic layers were washed with brine, dried over sodium sulfate and concentrated in vacuo. The residue was applied onto a silica gel column with ethyl acetate/petroleum ether (1:5-1:3) to afford the corresponding benzyl N-[(1S)-2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2 (6),9,11-tetraen-3-yl]-1-carbamoylethyl]carbamate (167.3, 230 mg) as a white solid and benzyl N-[(1R)-2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]-1-carbamoylethyl]carbamate (167.4, 90 mg) as a white solid.

Example 168

Synthesis of (2S)-2-amino-3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propanamide (I-160)

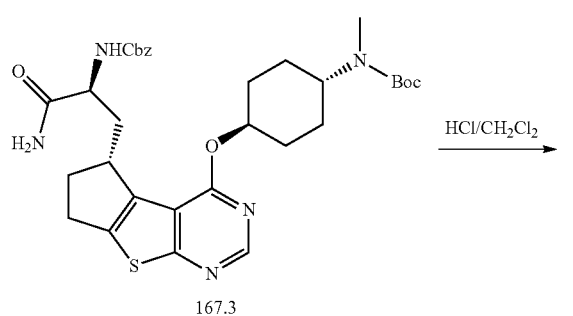

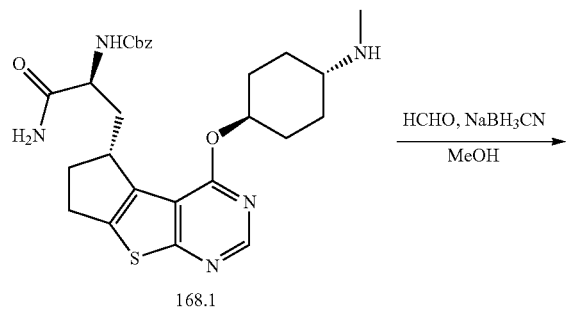

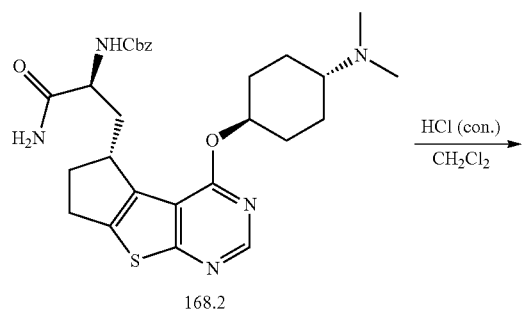

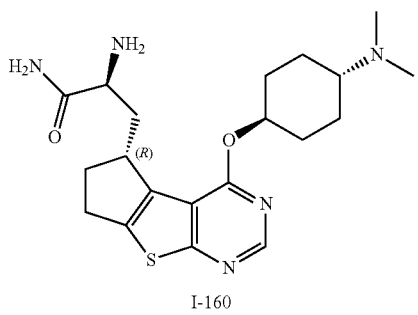

Synthesis of Compound 168.1.

To a solution of benzyl N-[(1S)-2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2 (6),9,11-tetraen-3-yl]-1-carbamoylethyl]carbamate (120 mg, 0.19 mmol, 1.00 equiv) in dichloromethane (5 mL) was added hydrochloric acid (12 M, 1 mL) at 0° C. The resulting solution was stirred for 1 h at this temperature and concentrated under vacuum. This resulted in 100 mg (crude) of benzyl N-[(1S)-1-carbamoyl-2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]ethyl]carbamate hydrochloride as a yellow solid.

Synthesis of Compound 168.2.

A solution of benzyl N-[(1S)-1-carbamoyl-2-[(3R)-12-[[4-(methylamino)cyclohexyl]oxy]-7-thia-9,11-diazatricyclo[6.4.0.0[2,6]]dodeca-1(8),2(6),9,11-tetraen-3-yl]ethyl]carbamate hydrochloride (100 mg, 0.18 mmol, 1.00 equiv) in methanol (10 mL) was added HCHO (37%, 2 mL) and stirred for 0.5 h at room temperature. This was followed by the addition of NaBH$_3$CN (33.6 mg, 0.53 mmol, 2.99 equiv) at 0° C. and the resulting solution was allowed to react, with stirring, for an additional 2 h at room temperature. The reaction was then quenched by the addition of 20 mL of water and extracted with 3×50 mL of dichloromethane and the combined organic layers were dried over sodium sulfate and concentrated in vacuo. The residue was applied onto a silica gel column with CH$_2$Cl$_2$: CH$_3$OH (10:1) to provide benzyl N-[(1S)-1-carbamoyl-2-[(3R)-12-[[4-(dimethylamino)cyclohexyl]oxy]7-thia-9,11-diazatricyclo[6.4.0.0[2,6]]dodeca-1(8),2(6),9,11-tetraen-3-yl]ethyl]carbamate (50 mg, 52%) as a white solid.

Synthesis of Compound I-160.

To a solution of benzyl N-[(1S)-1-carbamoyl-2-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]ethyl]carbamate (40 mg, 0.07 mmol, 1.00 equiv) in dichloromethane (2 mL) was added hydrochloric acid (conc., 1 mL) and the resulting solution was stirred for 5 h at 30° C. The resulting mixture was concentrated under vacuum and the crude product was purified by preparative HPLC under the following conditions (Waters): column: XBridge Prep C18 OBD column: 5 um, 19*150 mm; Mobile phase: water with 0.03% NH$_3$.H$_2$O and CH$_3$CN (13.0% CH$_3$CN up to 30.0% in 10 min, up to 100.0% in 2 min, down to 13.0% in 2 min); flow rate: 20 mL/min; UV detection at 254/220 nm. The product-containing fractions were collected and concentrated to remove CH$_3$CN and water under reduced pressure. The residue was lyophilized overnight to give (2S)-2-amino-3-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]propanamide (11.2 mg, 37%) as a white solid. MS: m/z 404 (M+H)$^+$. $^1$H NMR (300 MHz, CD$_3$OD): δ 1.40-1.50 (m, 4H), 1.68-1.75 (m, 2H), 2.00-2.10 (m, 2H), 2.12-2.18 (m, 1H), 2.25-2.35 (m, 2H), 2.33 (s, 6H), 2.50-2.60 (m, 1H), 2.65-2.75 (m, 1H), 2.90-2.95 (m, 1H), 3.00-3.15 (m, 1H), 3.35-3.48 (m, 2H), 5.20-5.30 (m, 1H), 8.42 (s, 1H).

Example 169

Synthesis of (5R)-5-[[(3R)-12-[[4-(methylamino)cyclohexyl]oxy]-7-thia-9,11-diazatricyclo[6.4.0.0[2,6]]dodeca-1(8),2(6),9,11-tetraen-3-yl]methyl]imidazolidine-2,4-dione (I-159)

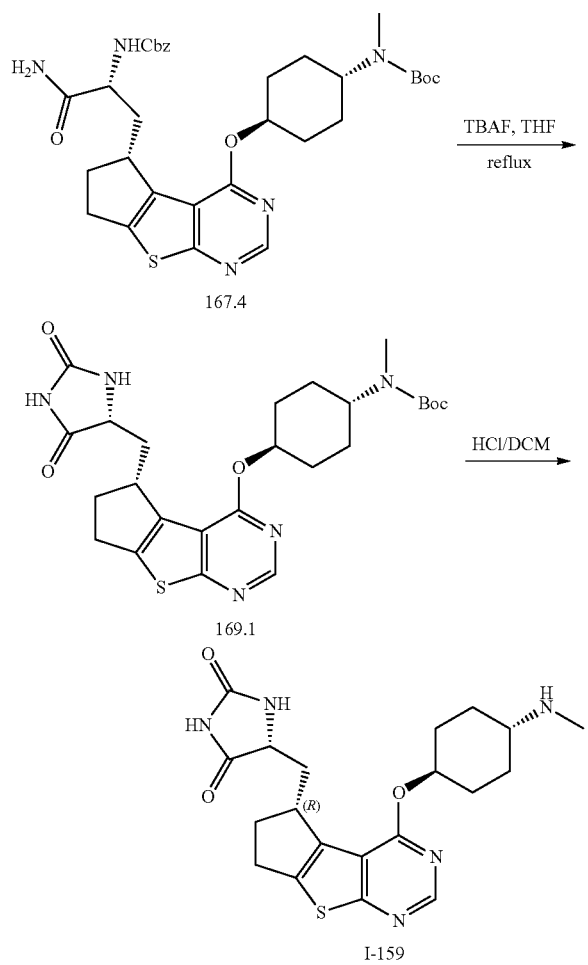

Synthesis of Compound 169.1.

To a solution of benzyl N-[(1R)-2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]-1-carbamoylethyl]carbamate (80 mg, 0.15 mmol, 1.00 equiv) in 20 mL of THF was added TBAF hydrate (134 mg, 0.51 mmol, 4.00 equiv) at room temperature. The resulting solution was stirred for 4 h at 70° C. under nitrogen. After cooling down to room temperature, the resulting solution was diluted with 50 mL of ethyl acetate and washed with $H_2O$ and brine. The organic layer was dried over anhydrous sodium sulfate and concentrated under vacuum. The residue was applied onto a silica gel column with ethyl acetate/petroleum ether (1:10) to yield 60 mg (94%) of tert-butyl N-(4-[[(3R)-3-[[(4R)-2,5-dioxoimidazolidin-4-yl]methyl]-7-thia-9,11-diazatricyclo[6.4.0.0[2,6]]dodeca-1(8),2(6),9,11-tetraen-12-yl]oxy]cyclohexyl)-N-methylcarbamate as a white solid.

Synthesis of Compound I-159.

To a solution of tert-butyl N-(4-[[(3R)-3-[[(4R)-2,5-dioxoimidazolidin-4-yl]methyl]-7-thia-9,11-diazatricyclo[6.4.0.0[2,6]]dodeca-1(8),2(6),9,11-tetraen-12-yl]oxy]cyclohexyl)-N-methylcarbamate (45 mg, 0.09 mmol, 1.00 equiv) in dichloromethane (3 mL) was added hydrogen chloride (conc., 0.5 mL) at 0° C. under nitrogen. The resulting solution was stirred for 2 h at room temperature and evaporated under reduced pressure. The crude product (45 mg) was purified by preparative HPLC under the following conditions (Waters): column: XBridge Shield RP18 OBD column: 5 um, 19*150 mm; mobile phase: water with 0.03% $NH_3.H_2O$ and $CH_3CN$ (16% $CH_3CN$ up to 22% in 11 min, up to 100% in 2 min, down to 16% in 2 min); UV detection at 254 and 220 nm. The product-containing fractions were collected and concentrated to remove $CH_3CN$ and water under reduced pressure. The residue was lyophilized overnight to give (5R)-5-[[(3R)-12-[[4-(methylamino)cyclohexyl]oxy]-7-thia-9,11-diazatricyclo[6.4.0.0[2,6]]dodeca-1(8),2(6),9,11-tetraen-3-yl]methyl]imidazolidine-2,4-dione (16.5 mg) as a white solid. MS: m/z 416 (M+H)$^+$. $^1$H NMR (300 MHz, $CD_3OD$): δ 1.20-1.40 (m, 2H), 1.50-1.65 (m, 2H), 1.72-1.95 (m, 1H), 2.00-2.37 (m, 6H), 2.45 (s, 3H), 2.56-2.68 (m, 2H), 2.98-3.05 (m, 1H), 3.08-3.15 (m, 1H), 3.50 (t, 1H, J=1.5 Hz), 4.19 (dd, 2H, J=11.7, 2.7 Hz), 5.20-5.30 (m, 1H), 8.42 (s, 1H).

Example 170

Synthesis of Intermediates 170.1 and 170.2

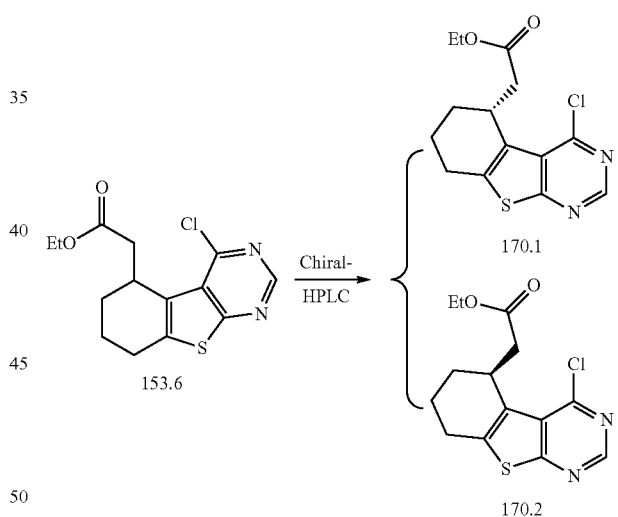

The enantiomers of racemic ethyl 2-[3-chloro-8-thia-4,6-diazatricyclo[7.4.0.0[2,7]]trideca-1(9),2(7),3,5-tetraen-13-yl]acetate (1.4 g, 4.50 mmol, 1.00 equiv) in MeOH (10 mL) were separated by preparative chiral HPLC under the following conditions: column: Chiralpak IC 0.46*25 cm, 5 um; mobile phase, Hex (0.1% TEA): EtOH=70:30; UV detection at 254 nm. The product-containing fractions were collected and evaporated to remove solvents under reduced pressure to give 520 mg (37%) of ethyl 2-[(13R)-3-chloro-8-thia-4,6-diazatricyclo[7.4.0.0[2,7]]trideca-1(9),2(7),3,5-tetraen-13-yl]acetate 170.1 (first peak) as a white solid and 520 mg (37%) of ethyl 2-[(13S)-3-chloro-8-thia-4,6-diazatricyclo[7.4.0.0[2,7]]trideca-1(9),2(7),3,5-tetraen-13-yl]acetate 170.2 (second peak) as a white solid, respectively.

Example 171

Synthesis of 3-((S)-4-(((1r,4S)-4-aminocyclohexyl)oxy)-5,6,7,8-tetrahydrobenzo[4,5]thieno[2,3-d]pyrimidin-5-yl)propanamide (I-154)

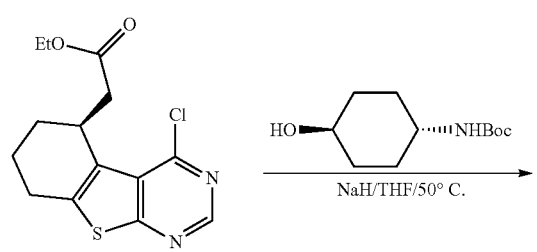

170.2

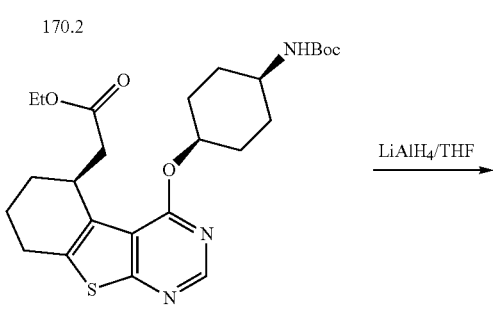

171.1

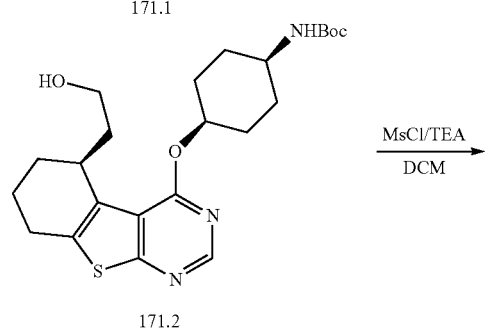

171.2

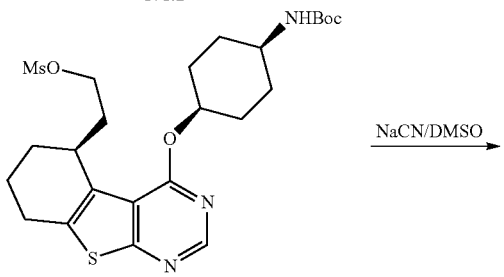

171.3

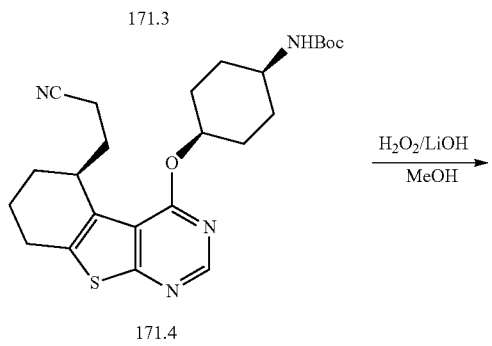

171.4

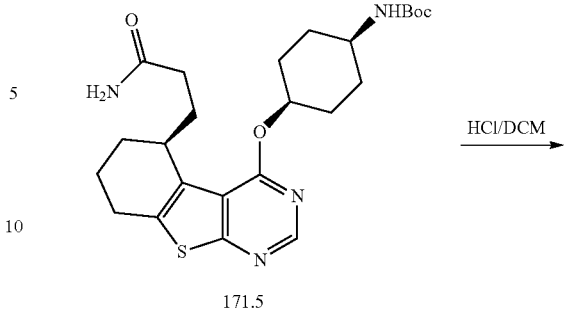

171.5

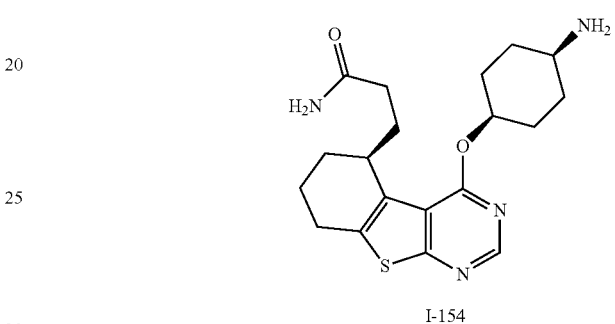

I-154

Synthesis of Compound 171.1.

NaH (60% dispersion in mineral oil, 438 mg, 10.95 mmol, 4.00 equiv) was treated with tert-butyl N-(4-hydroxycyclohexyl)carbamate (710 mg, 3.30 mmol, 1.20 equiv) in freshly distilled THF at 50° C. for 30 min under nitrogen. Then a solution of ethyl 2-[(13S)-3-chloro-8-thia-4,6-diazatricyclo[7.4.0.0[2,7]]trideca-1(9),2(7),3,5-tetraen-13-yl]acetate (850 mg, 2.73 mmol, 1.00 equiv) in THF (10 mL) was added via syringe and stirred for 2 h at 60° C. After cooling, the reaction was quenched with brine, extracted with ethyl acetate (80 mL), dried over anhydrous sodium sulfate and concentrated under vacuum. The residue was applied onto a silica gel column with ethyl acetate/petroleum ether (1:5) to give 800 mg (60%) of ethyl 2-[(13S)-3-[(4-[[(tert-butoxy)carbonyl]amino]cyclohexyl)oxy]-8-thia-4,6-diazatricyclo[7.4.0.0[2,7]]trideca-1(9),2(7),3,5-tetraen-13-yl]acetate as a colorless oil.

Synthesis of Compound 171.2.

To a solution of ethyl 2-[(13S)-3-[(4-[[(tert-butoxy)carbonyl]amino]cyclohexyl)oxy]-8-thia-4,6-diazatricyclo[7.4.0.0[2,7]]trideca-1(9),2(7),3,5-tetraen-13-yl]acetate (800 mg, 1.63 mmol, 1.00 equiv) in THF (30 mL) in an ice/water bath under nitrogen was added LiAlH$_4$ (121.2 mg, 3.20 mmol, 2.00 equiv). The resulting solution was stirred for 2 h at room temperature and quenched with water, extracted with ethyl acetate (80 mL), dried over anhydrous sodium sulfate and concentrated under vacuum. The residue was applied onto a silica gel column with ethyl acetate/petroleum ether (1:1) to give 490 mg (67%) of tert-butyl N-(4-[[(13S)-13-(2-hydroxyethyl)-8-thia-4,6-diazatricyclo[7.4.0.0[2,7]]trideca-1(9),2(7),3,5-tetraen-3-yl]oxy]cyclohexyl)carbamate as a colorless oil.

Synthesis of Compound 171.3.

To a solution of tert-butyl N-(4-[[(13S)-13-(2-hydroxyethyl)-8-thia-4,6-diazatricyclo[7.4.0.0[2,7]]trideca-1(9),2(7),3,5-tetraen-3-yl]oxy]cyclohexyl)carbamate (490 mg, 1.09 mmol, 1.00 equiv) in DCM (20 mL) was added triethylamine (201 mg, 1.99 mmol, 1.80 equiv) and methanesulfonyl chloride (189 mg, 1.65 mmol, 1.50 equiv) at 0° C. The resulting solution was stirred for 2 h at room temperature and then washed with brine, dried over anhydrous sodium sulfate and concentrated under vacuum. The residue was applied onto a silica gel column with ethyl acetate/petroleum ether (1:3) to provide 530 mg of tert-butyl N-(4-[[(13S)-13-[2-(methanesulfonyloxy)ethyl]-8-thia-4,6-diazatricyclo[7.4.0.0[2,7]]trideca-1(9),2(7),3,5-tetraen-3-yl]oxy]cyclohexyl)carbamate as a white solid.

Synthesis of Compound 171.4.

To a solution of tert-butyl N-(4-[[(13S)-13-[2-(methanesulfonyloxy)ethyl]-8-thia-4,6-diazatricyclo[7.4.0.0[2,7]]trideca-1(9),2(7),3,5-tetraen-3-yl]oxy]cyclohexyl)carbamate (525 mg, 1.00 mmol, 1.00 equiv) in DMSO (20 mL) was added NaCN (294 mg, 6.00 mmol, 6.00 equiv) and the resulting solution was stirred for 2 h at 70° C. under nitrogen. After cooling, the mixture was diluted with DCM (80 mL), washed with brine, dried over anhydrous sodium sulfate and concentrated under vacuum. The residue was applied onto a silica gel column with ethyl acetate/petroleum ether (1:3) to yield 380 mg (83%) of tert-butyl N-(4-[[(13S)-13-(2-cyanoethyl)-8-thia-4,6-diazatricyclo[7.4.0.0[2,7]]trideca-1(9),2(7),3,5-tetraen-3-yl]oxy]cyclohexyl)carbamate as a white solid.

Synthesis of Compound 171.5.

To a solution of tert-butyl N-(4-[[(13S)-13-(2-cyanoethyl)-8-thia-4,6-diazatricyclo[7.4.0.0[2,7]]trideca-1(9),2(7),3,5-tetraen-3-yl]oxy]cyclohexyl)carbamate (300 mg, 0.66 mmol, 1.00 equiv) in methanol (15 mL) was added LiOH.H$_2$O (82 mg, 1.95 mmol, 3.00 equiv) and H$_2$O$_2$ (30%, 0.5 mL) at 0° C. and the resulting solution was stirred for 2 h at 30° C. The reaction was quenched with saturated aqueous sodium sulfite, extracted with DCM (30 mL), washed with brine, dried over anhydrous sodium sulfate and concentrated under vacuum. The residue was applied onto a silica gel column with dichloromethane/methanol (20:1) to give 240 mg (77%) of tert-butyl N-(4-[[(13S)-13-(2-carbamoylethyl)-8-thia-4,6-diazatricyclo[7.4.0.0[2,7]]trideca-1(9),2(7),3,5-tetraen-3-yl]oxy]cyclohexyl)carbamate as a white solid.

Synthesis of Compound I-154.

To a solution of tert-butyl N-(4-[[(13S)-13-(2-carbamoylethyl)-8-thia-4,6-diazatricyclo[7.4.0.0[2,7]]trideca-1(9),2(7),3,5-tetraen-3-yl]oxy]cyclohexyl)carbamate (240 mg, 0.51 mmol, 1.00 equiv) in dichloromethane (20 mL) was added hydrogen chloride (12M) (0.5 mL). The resulting solution was stirred for 2 h at room temperature. The pH value of the solution was adjusted to 10 with sodium bicarbonate (aq) (20 mL), extracted with dichloromethane (30 mL), dried over anhydrous sodium sulfate and concentrated under vacuum. The residue was applied onto a silica gel column with dichloromethane/methanol (2:1) to give 130 mg (69%) of the desired product I-154 as a white solid. MS: m/z 375 (M+H)$^+$.

$^1$H NMR (300 MHz, CD$_3$OD): δ 8.46 (s, 1H), 5.35-5.27 (m, 1H), 3.19-3.16 (m, 1H), 2.98-2.75 (m, 3H), 2.61-2.42 (m, 1H), 2.39-2.15 (m, 3H), 2.14-1.87 (m, 6H), 1.86-1.65 (m, 4H), 1.45-1.32 (m, 2H).

Example 172

Synthesis of 3-((R)-4-(((1r,4R)-4-aminocyclohexyl)oxy)-5,6,7,8-tetrahydrobenzo[4,5]thieno[2,3-d]pyrimidin-5-yl)propanamide (I-153)

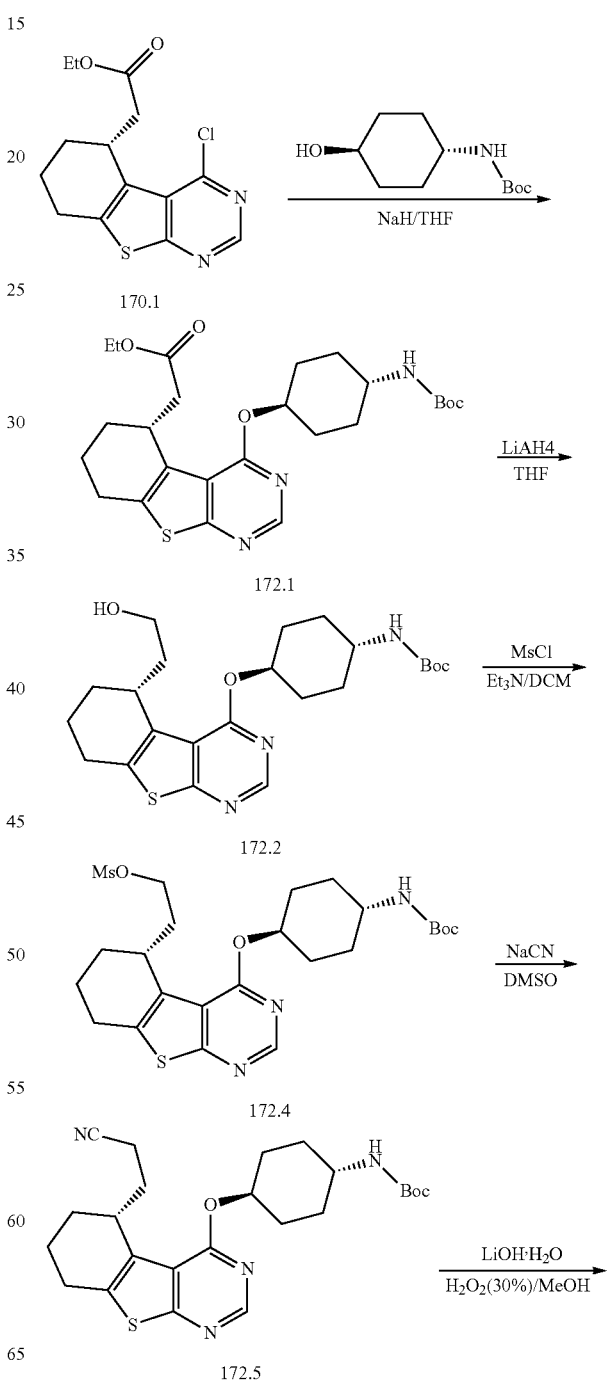

421

-continued

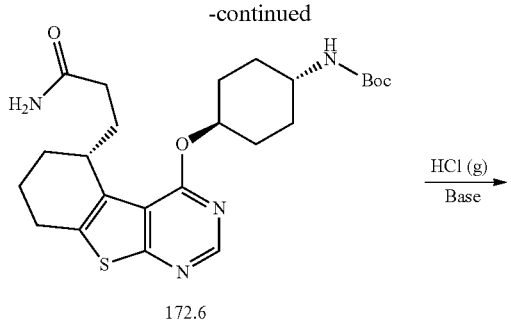

172.6

HCl (g) / Base →

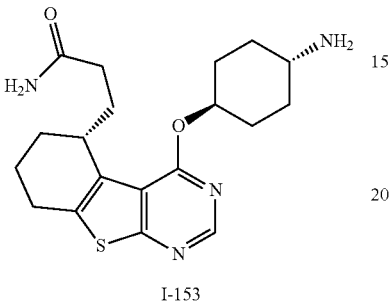

I-153

Compound I-153 was synthesized in a manner consistent with Example 171, except that intermediate 170.1 was used rather than 170.2. MS: m/z 375 (M+H)+. 1H NMR (300 MHz, CD3OD): δ 8.47 (s, 1H), 5.38-5.29 (m, 1H), 3.25-3.17 (m, 2H), 2.98-2.78 (m, 2H), 2.61-2.20 (m, 4H), 2.19-2.08 (m, 3H), 2.05-1.95 (m, 3H), 1.93-1.75 (m, 4H), 1.74-1.57 (m, 2H).

Example 173

Synthesis of 3-((R)-4-(((1r,4R)-4-(methylamino)cyclohexyl)oxy)-5,6,7,8-tetrahydrobenzo[4,5]thieno[2,3-d]pyrimidin-5-yl)propanamide (I-162)

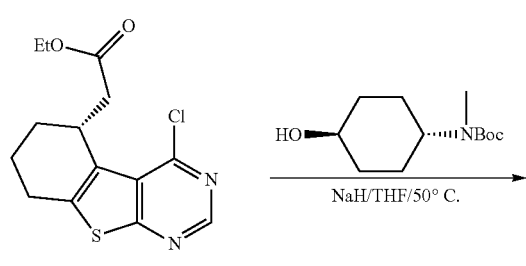

170.1

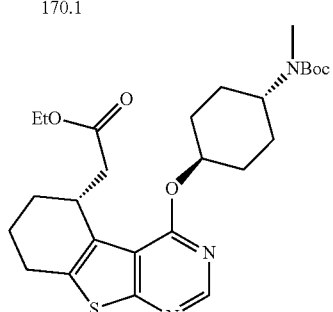

LiAlH4/THF →

173.1

422

-continued

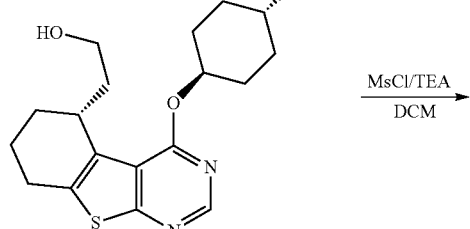

173.2

MsCl/TEA / DCM →

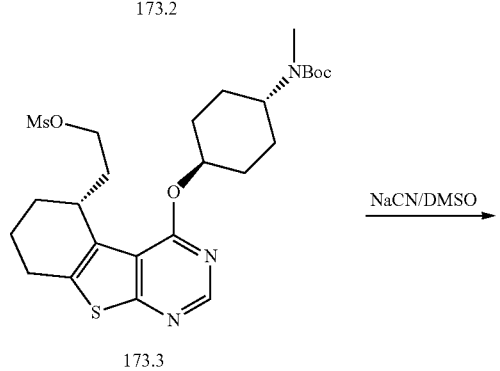

173.3

NaCN/DMSO →

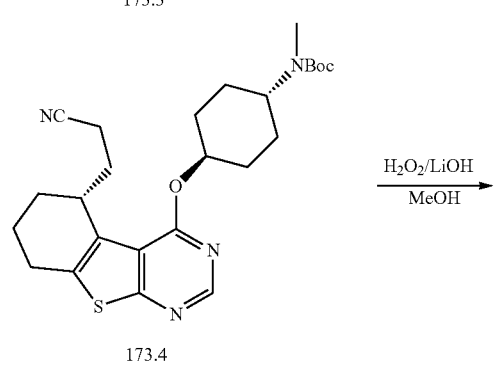

173.4

H2O2/LiOH / MeOH →

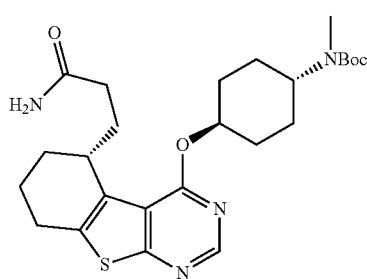

173.5

HCl/DCM →

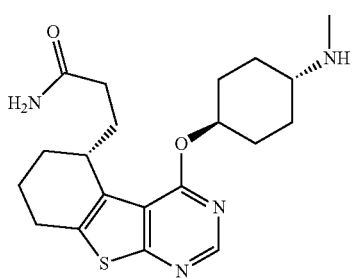

I-162

Compound I-162 was prepared in a manner consistent with Example 171 except that tert-butyl N-(4-hydroxycyclohexyl)-N-methylcarbamate was used rather than tert-butyl N-(4-hydroxycyclohexyl)carbamate. MS: m/z 389 (M+H)+. 1H NMR (300 MHz, CD3OD): δ 8.46 (s, 1H), 5.37-5.27 (m, 1H), 3.25-3.17 (m, 1H), 2.98-2.78 (m, 2H), 2.61-2.46 (m, 2H), 2.45 (s, 3H), 2.44-2.20 (m, 3H), 2.18-1.90 (m, 6H), 1.93-1.75 (m, 4H), 1.74-1.57 (m, 2H).

Example 174

Synthesis of 3-((R)-4-(((1r,4R)-4-(dimethylamino)cyclohexyl)oxy)-5,6,7,8-tetrahydrobenzo[4,5]thieno[2,3-d]pyrimidin-5-yl)propanamide (I-163)

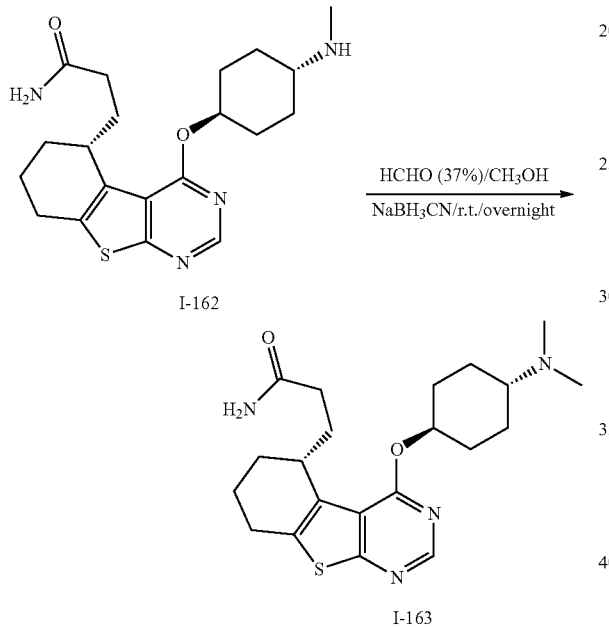

To a solution of 3-[(13R)-3-[[4-(methylamino)cyclohexyl]oxy]-8-thia-4,6-diazatricyclo[7.4.0.0[2,7]]trideca-1(9),2(7),3,5-tetraen-13-yl]propanamide (100 mg, 0.26 mmol, 1.00 equiv) in MeOH (15 mL) was added HCHO (37%, 1 mL) and stirred for 1 h at room temperature. Then NaBH3CN (49 mg, 0.78 mmol, 3.00 equiv) was added and the resulting solution was stirred overnight at room temperature. The mixture was then quenched with water, extracted with dichloromethane (3×30 mL), dried over anhydrous sodium sulfate and concentrated under vacuum. The residue (150 mg) was purified by preparative HPLC under the following conditions (SHI-MADZU): column: SunFire Prep C18, 19*150 mm 5 um; mobile phase: water with 0.1% NH4HCO3 and CH3CN (6.0% CH3CN up to 60% in 20 min); flow rate: 20 mL/min; UV detection at 254/220 nm. The product-containing fractions were collected and partially evaporated to remove water and CH3CN under reduced pressure. The residue was lyophilized overnight to give the desired product (63.2 mg) as a white solid. MS: m/z 403 (M+H)+. 1H NMR (300 MHz, CD3OD): δ 8.46 (s, 1H), 5.32-5.26 (m, 1H), 3.25-3.17 (m, 1H), 2.98-2.78 (m, 2H), 2.61-2.46 (m, 2H), 2.45 (s, 6H), 2.44-2.24 (m, 3H), 2.18-1.90 (m, 6H), 1.93-1.65 (m, 4H), 1.74-1.47 (m, 2H).

Example 175

Synthesis of Intermediate 175.3

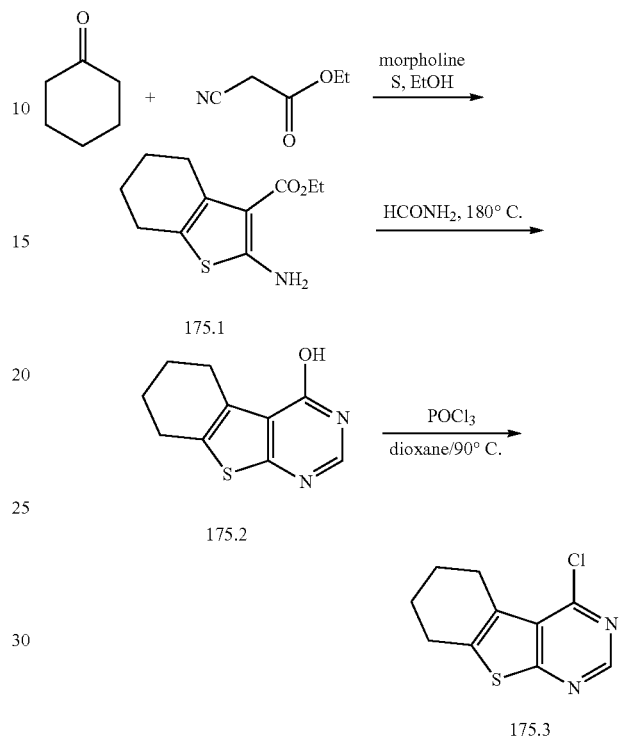

Synthesis of Compound 175.1.

To a mixture of cyclohexanone (49 g, 0.5 mol, 1.0 equiv), ethyl 2-cyanoacetate (56 g, 0.5 mol, 1.0 equiv) and sulphur (16 g, 0.5 mol, 1.0 equiv) in 150 mL of ethanol was added morpholine (44 g, 0.5 mol, 1.0 equiv). The mixture was stirred for 8 h at room temperature. The reaction mixture was diluted with water and the precipitate was collected by filtration and recrystallized from ethanol to afford compound 175.1 as a yellow solid (62 g, 55%).

Synthesis of Compound 175.2.

A solution of compound 175.1 (35 g, 0.16 mol) in 150 mL of formamide was heated at 180° C. for 4 h. Upon cooling, the mixture was poured into 200 mL of water and filtered. The solid was collected and recrystallized from ethanol to afford compound 175.2 as a yellow solid (25 g, 75%). 1H NMR (400 MHz, DMSO-d6): δ 1.75-1.82 (m, 4H), 2.72-2.75 (m, 2H), 2.85-2.88 (m, 2H), 8.00 (s, 1H), 12.31 (br s, 1H). MS: m/z 207.0 (M+H)+.

Synthesis of Compound 175.3.

To a 100-mL round-bottom flask containing a solution of 175.2 (450 mg, 2.2 mmol, 1.00 equiv) in 1,4-dioxane (30 mL) was added POCl3 (5.1 g, 34.09 mmol, 15.25 equiv) at room temperature under nitrogen. The resulting solution was stirred for 4 h at 90° C. and concentrated under reduced pressure. The residue was diluted with EtOAc and poured into 50 mL of cooled saturated aqueous NaHCO3 and extracted with 3×80 mL of dichloromethane. The combined organic layers were washed with brine, dried over anhydrous sodium sulfate and concentrated under vacuum. The residue was applied onto a silica gel column with ethyl acetate/petroleum ether (1:7) to give 3-chloro-8-thia-4,6-diazatricyclo[7.4.0.0^[2,7]]trideca-1(9),2,4,6-tetraene (360 mg, 73%) as a yellow solid.

Example 176

Synthesis of Intermediate 176.8

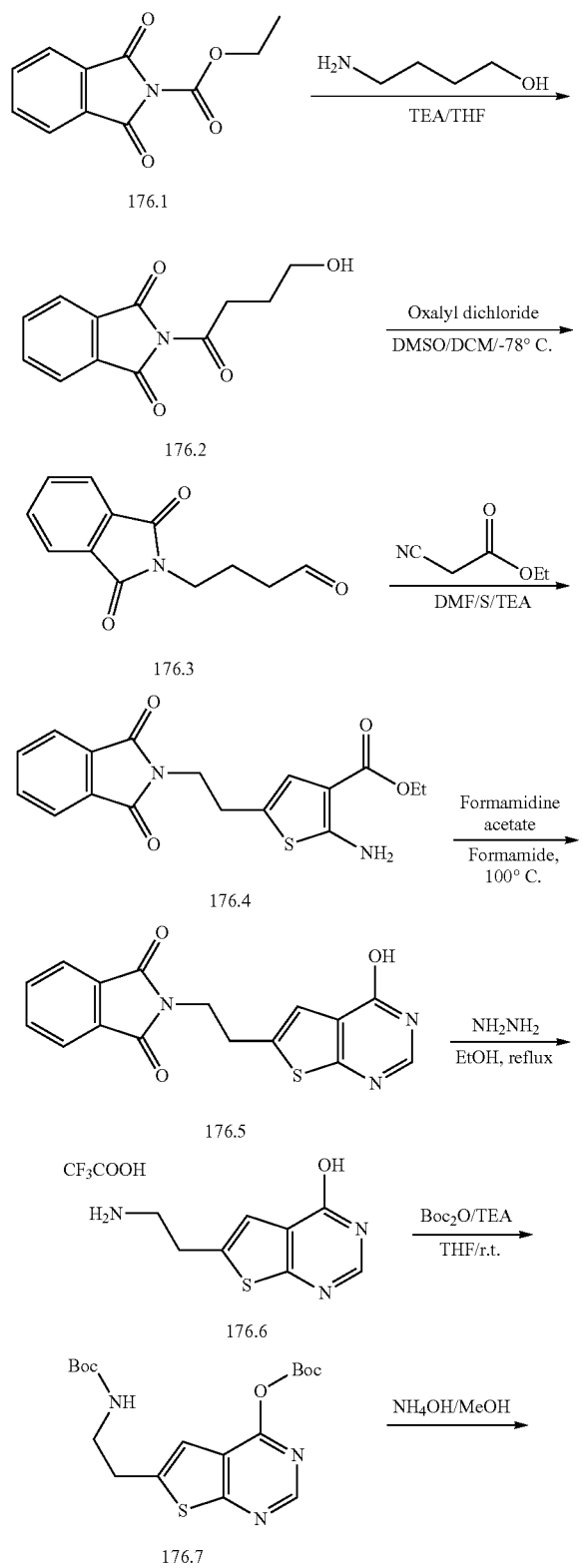

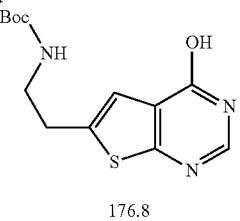

Synthesis of Compound 176.2.

A solution of 4-aminobutan-1-ol (18 g, 201.94 mmol, 1.00 equiv), ethyl 1,3-dioxo-2,3-dihydro-1H-isoindole-2-carboxylate (44.5 g, 203.02 mmol, 1.01 equiv) and TEA (28 g, 276.71 mmol, 1.37 equiv) in 500 mL of THF was heated to reflux overnight. The reaction mixture was cooled to room temperature, quenched with water and extracted with ethyl acetate. The combined organic layers were washed with brine and dried over sodium sulfate. The solids were filtered out and the filtrate was concentrated under vacuum. The residue was applied onto a silica gel column with PE/EtOAc (10:1 to 1:1) to give 30 g (68%) of 2-(4-hydroxybutyl)-2,3-dihydro-1H-isoindole-1,3-dione as a white solid. MS (ES): m/z 220 (M+H)$^+$.

Synthesis of Compound 176.3.

To a 250-mL round-bottom flask, purged and maintained with an inert atmosphere of nitrogen, was added a solution of oxalic dichloride (2.52 g, 19.85 mmol, 1.98 equiv) in 40 mL of anhydrous dichloromethane. This solution was cooled to −78° C. under nitrogen. A solution of DMSO (1.56 g, 19.97 mmol, 1.99 equiv) in dichloromethane (10 mL) was added dropwise with stirring at −78° C. and the resulting solution was stirred for 20 min at −78° C. A solution of 2-(4-hydroxybutyl)-2,3-dihydro-1H-isoindole-1,3-dione (2.2 g, 10.03 mmol, 1.00 equiv) in 20 mL of dichloromethane was added dropwise with stirring. Stirring was continued for 20 min at −78° C., and then TEA (8.1 g, 80.20 mmol, 7.99 equiv) was added via syringe at the same temperature. The resulting solution was allowed to react, with stirring, for an additional 60 min at 0° C. After completion, the resulting mixture was diluted with 1 M aqueous hydrochloric acid, extracted with DCM, washed with 3×100 mL of brine, dried over sodium sulfate and concentrated under vacuum. The residue was purified by a silica gel column with ethyl acetate/petroleum ether (1:1) to provide the desired 4-(1,3-dioxo-2,3-dihydro-1H-isoindol-2-yl)butanal (1.9 g, 87%) as a white solid. MS (ES): m/z 218 (M+H)$^+$.

Synthesis of Compound 176.4.

A mixture of 4-(1,3-dioxo-2,3-dihydro-1H-isoindol-2-yl)butanal (2.2 g, 10.13 mmol, 1.00 equiv), TEA (2 g, 19.76 mmol, 1.95 equiv), S (340 mg, 10.61 mmol, 1.05 equiv) and ethyl 2-cyanoacetate (1.2 g, 10.61 mmol, 1.05 equiv) in 50 mL of ethanol was stirred for 20 hours at 65° C. under nitrogen. The reaction mixture was cooled to room temperature and concentrated in vacuo. The residue was diluted with EtOAc, washed with brine, dried over anhydrous sodium sulfate and concentrated under vacuum. The residue was applied onto a silica gel column with ethyl acetate/petroleum ether (1:1) to afford 2.4 g (69%) of ethyl 2-amino-5-[2-(1,3-dioxo-2,3-dihydro-1H-isoindol-2-yl)ethyl]thiophene-3-carboxylate as an off-white solid. MS (ES): m/z 345 (M+H)$^+$.

427

Synthesis of Compound 176.5.

To a 250-mL round-bottom flask, purged and maintained with an inert atmosphere of nitrogen, was added a solution of ethyl 2-amino-5-[2-(1,3-dioxo-2,3-dihydro-1H-isoindol-2-yl)ethyl]thiophene-3-carboxylate (3.4 g, 9.87 mmol, 1.00 equiv) and formamidine acetate (1.5 g, 14.41 mmol, 1.46 equiv) dissolved in 50 mL of N,N-dimethylformamide. This solution was heated at 100° C. for 12 hrs. The reaction was cooled to room temperature and quenched with water. The resulting mixture was extracted with 3×100 mL of ethyl acetate and the combined organic layers were washed with brine, dried over sodium sulfate and concentrated under vacuum. The residue was applied onto a silica gel column with ethyl acetate/petroleum ether (1:1) to yield 1.76 g (55%) of 2-(2-[4-hydroxythieno[2,3-d]pyrimidin-6-yl]ethyl)-2,3-dihydro-1H-isoindole-1,3-dione as an off-white solid. MS (ES): m/z 326 (M+H)$^+$.

Synthesis of Compound 176.6.

To a 250-mL round-bottom flask, purged and maintained with an inert atmosphere of nitrogen, was added a solution of ethyl 2-amino-5-[2-(1,3-dioxo-2,3-dihydro-1H-isoindol-2-yl)ethyl]thiophene-3-carboxylate (3.4 g, 9.87 mmol, 1.00 equiv) and formamidine acetate (1.5 g, 14.41 mmol, 1.46 equiv) dissolved in 50 mL of N,N-dimethylformamide. This solution was heated at 100° C. for 12 hrs. The reaction was cooled to room temperature and quenched with water. The resulting mixture was extracted with 3×100 mL of ethyl acetate and the combined organic layers were washed with brine, dried over sodium sulfate and concentrated under vacuum. The residue was applied onto a silica gel column with ethyl acetate/petroleum ether (1:1) to yield 1.76 g (55%) of 2-(2-[4-hydroxythieno[2,3-d]pyrimidin-6-yl]ethyl)-2,3-dihydro-1H-isoindole-1,3-dione as an off-white solid. MS (ES): m/z 326 (M+H)$^+$.

Synthesis of Compound 176.7.

To a solution of 6-(2-aminoethyl)thieno[2,3-d]pyrimidin-4-ol (2.0 g, 10.24 mmol, 1.00 equiv) and TEA (5 g, 49.41 mmol, 4.82 equiv) in 50 mL of THF was added Boc$_2$O (7.0 g, 32.07 mmol, 3.13 equiv), in portions, at 0° C. under nitrogen. The resulting solution was warmed up to room temperature and stirred for 12 h at 40° C. TLC analysis indicated that the amine was consumed completely and the resulting mixture was concentrated under vacuum. The residue was diluted with 50 mL of ethyl acetate, washed with brine, dried over Na$_2$SO$_4$ and concentrated under reduced pressure. The residue was applied onto a silica gel column with ethyl acetate/petroleum ether (1:4) to give 3.6 g (89%) of 6-(2-[[(tert-butoxy)carbonyl]amino]ethyl)thieno[2,3-d]pyrimidin-4-yl tert-butyl carbonate as a white solid. MS (ES): m/z 396 (M+H)$^+$.

Synthesis of Intermediate 176.8.

To a 25-mL round-bottom flask containing a solution of 6-(2-[[(tert-butoxy)carbonyl]amino]ethyl)thieno[2,3-d]pyrimidin-4-yl tert-butyl carbonate (370 mg, 0.94 mmol, 1.00 equiv) in 10 mL of methanol was added NH$_4$OH (2.1 mL) at room temperature and the resulting solution was stirred for 2 hours under N$_2$. After completion, the resulting mixture was concentrated under vacuum and the residue was applied onto a silica gel column with ethyl acetate/petroleum ether (1:1) to afford 252 mg (91%) of the desired tert-butyl N-(2-[4-hydroxythieno[2,3-d]pyrimidin-6-yl]ethyl)carbamate as a white solid. MS (ES): m/z 296 (M+H)$^+$.

428

Example 177

Synthesis of Intermediate 177.1

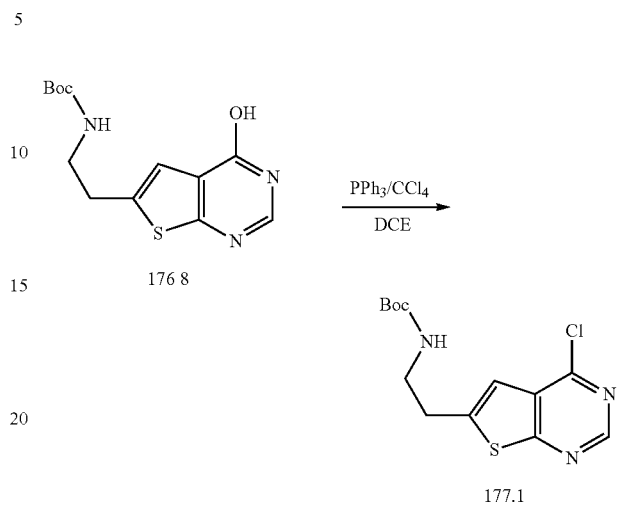

To a solution of tert-butyl N-(2-[4-hydroxythieno[2,3-d]pyrimidin-6-yl]ethyl)carbamate (2.3 g, 7.79 mmol, 1.00 equiv) in DCE (300 mL) was added PPh$_3$ (4.1 g, 15.63 mmol, 2.00 equiv). The solution was stirred for 1 h at room temperature under nitrogen. Then CCl$_4$ (3.6 g, 23.38 mmol, 3.00 equiv) was added and the resulting solution was stirred at 72° C. overnight. After cooling, the resulting mixture was concentrated under vacuum. The residue was applied onto a silica gel column with ethyl acetate/petroleum ether (1:5 to 1:3) to give tert-butyl N-(2-[4-chlorothieno[2,3-d]pyrimidin-6-yl]ethyl)carbamate (1.0 g) as a light yellow solid. MS (ES): m/z 314 and 316 (M+H)$^+$.

Example 178

Synthesis of Intermediate 178.3

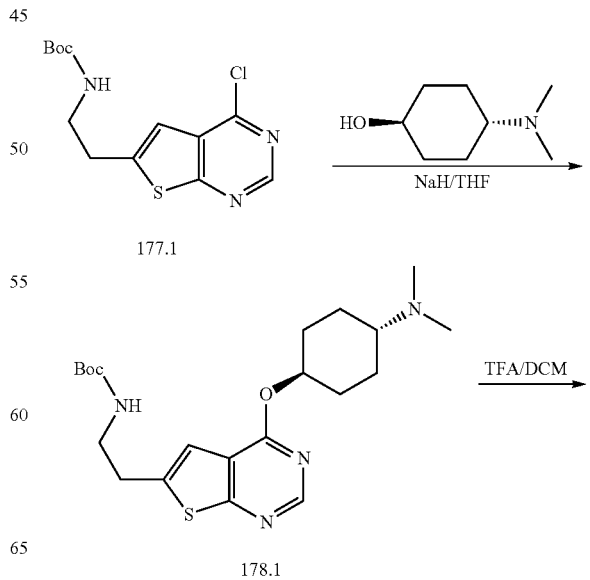

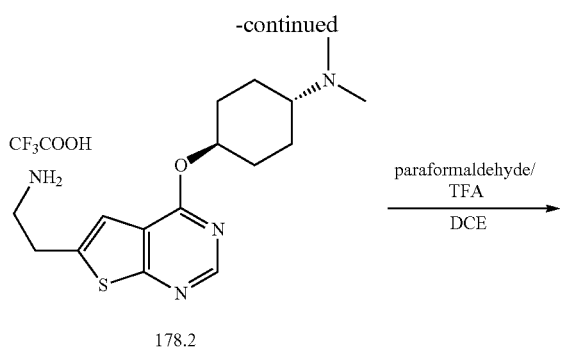

178.2

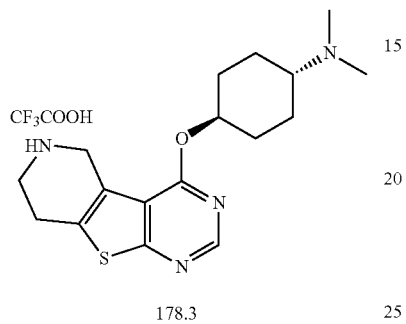

178.3

Synthesis of Compound 178.1.

Sodium hydride (80 mg, 2.00 mmol, 4.83 equiv, 60% dispersion in mineral oil) was treated with trans-4-(dimethylamino)cyclohexan-1-ol (80 mg, 0.56 mmol, 1.35 equiv) in 10 mL of distilled THF for 30 min at 0° C. under nitrogen. Then a solution of tert-butyl N-(2-[4-chlorothieno[2,3-d]pyrimidin-6-yl]ethyl)carbamate (130 mg, 0.41 mmol, 1.00 equiv) in 3 mL of THF was added and stirred at room temperature for 12 hours. After cooling to 0° C., the reaction was quenched with water and extracted with 3×30 mL of ethyl acetate. The organic layers were combined, washed with brine, dried over anhydrous sodium sulfate and concentrated under vacuum. The residue was applied onto a silica gel column with dichloromethane/methanol (4:1) to give 140 mg (80%) of tert-butyl N-[2-(4-[[4-(dimethylamino)cyclohexyl]oxy]thieno[2,3-d]pyrimidin-6-yl)ethyl]carbamate as a white solid. MS (ES): m/z 421 (M+H)$^+$.

Synthesis of Compound 178.2.

To a solution of tert-butyl N-[2-(4-[[4-(dimethylamino)cyclohexyl]oxy]thieno[2,3-d]pyrimidin-6-yl)ethyl]carbamate (140 mg, 0.33 mmol, 1.00 equiv) in 5 mL of DCM was added $CF_3COOH$ (0.5 mL) at room temperature. The resulting solution was stirred for 5 h at ambient temperature and then concentrated under vacuum to give the desired 4-[[6-(2-aminoethyl)thieno[2,3-d]pyrimidin-4-yl]oxy]-N,N-dimethylcyclohexan-1-amine trifluoroacetate (100 mg) as a yellow oil which was used directly without further purification. MS (ES): m/z 321 (M+H)$^+$.

Synthesis of Intermediate 178.3.

To a 25-mL round-bottom flask (1 atm), purged and maintained with an inert atmosphere of nitrogen, was placed 4-[[6-(2-aminoethyl)thieno[2,3-d]pyrimidin-4-yl]oxy]-N,N-dimethylcyclohexan-1-amine (100 mg, 0.31 mmol, 1.00 equiv) in 25 mL of 1,2-dichloroethane. Then paraformaldehyde (80 mg, 2.67 mmol, 8.55 equiv) and $CF_3COOH$ (0.5 mL) were added simultaneously at 0° C. and the resulting mixture was heated to 45° C. and stirred for 12 h. The reaction mixture was cooled to room temperature with a water bath and concentrated under reduced pressure. The crude product was purified by preparative HPLC under the following conditions (Waters): Column: Xbridge Prep C18, 5 μm, 19*50 mm; mobile phase: water with 0.01% TFA and $CH_3CN$ (10% $CH_3CN$ up to 35% in 11 min, up to 95% in 1.5 min, down to 10% in 1.5 min); flow rate: 20 mL/min; UV detection at 254/220 nm. This resulted in 40 mg (39%) of N,N-dimethyl-4-[8-thia-4,6,12-triazatricyclo[7.4.0.0-[2,7]]trideca-1(9),2(7),3,5-tetraen-3-yloxy]cyclohexan-1-amine trifluoroacetate as a light yellow solid. MS (ES): m/z 333 (M+H)$^+$.

Example 179

Synthesis of 1-(13-[[4-(dimethylamino)cyclohexyl]oxy]-8-thia-4-azatricyclo[7.4.0.0-[2,7]]trideca-1(13),2(7),9,11-tetraen-4-yl)ethan-1-one (I-167)

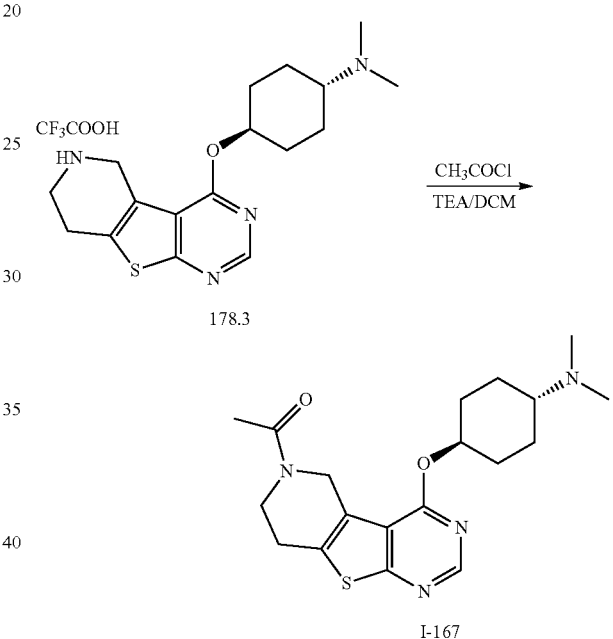

To a solution of N,N-dimethyl-4-[8-thia-4-azatricyclo[7,4,0,0-[2,7]]trideca-1(13),2(7),9,11-tetraen-13-yloxy]cyclohexan-1-amine trifluoroacetate (43 mg) and TEA (50 mg, 0.49 mmol, 3.80 equiv) in 10 mL of dichloromethane at 0° C. was added acetyl chloride (20 mg, 0.25 mmol, 1.96 equiv) at 0° C. The resulting solution was stirred for 2 hours at this temperature under nitrogen. The reaction was then quenched with $CH_3OH$ and concentrated under vacuum. The crude product was purified by preparative HPLC under the following conditions (Waters): Column: Xbridge Prep C18, 5 μm, 19*50 mm; mobile phase: water with 0.05% $NH_4HCO_3$ and $CH_3CN$ (10% $CH_3CN$ up to 35% in 11 min, up to 95% in 1.5 min, down to 10% in 1.5 min); flow rate: 20 mL/min; UV detection at 254/220 nm. This resulted in 12.6 mg (26%) of 1-(13-[[4-(dimethylamino)cyclohexyl]oxy]-8-thia-4-azatricyclo[7.4.0.0-[2,7]]trideca-1(13),2(7),9,11-tetraen-4-yl)ethan-1-one as a white solid. MS (ES): m/z 375 (M+H)$^+$. $^1$H NMR (400 MHz, $CD_3OD$): δ 1.30-1.65 (m, 4H), 1.94 (d, 2H), 2.13 (s, 3H), 2.20-2.32 (m, 9H), 2.81, 2.91 (t, t, 2H, J=5.7 Hz), 3.77, 3.84 (t, t, 2H, J=5.7 Hz), 5.02-5.18 (m, 1H), 8.38, 8.39 (s, s, 1H).

Example 180

Synthesis of 4-([12-methanesulfonyl-8-thia-4,6,12-triazatricyclo[7.4.0.0-[2,7]]trideca-1(9),2(7),3,5-tetraen-3-yl]oxy)-N,N-dimethylcyclohexan-1-amine (I-168)

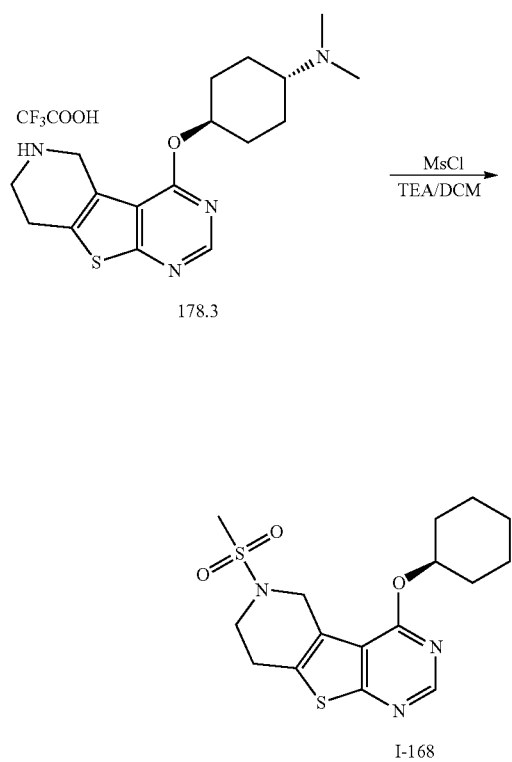

Example 181

Synthesis of 3-[[4-(dimethylamino)cyclohexyl]oxy]-N-methyl-8-thia-4,6,12-triazatricyclo[7.4.0.0[2,7]]trideca-1(9),2(7),3,5-tetraene-12-carboxamide (I-169)

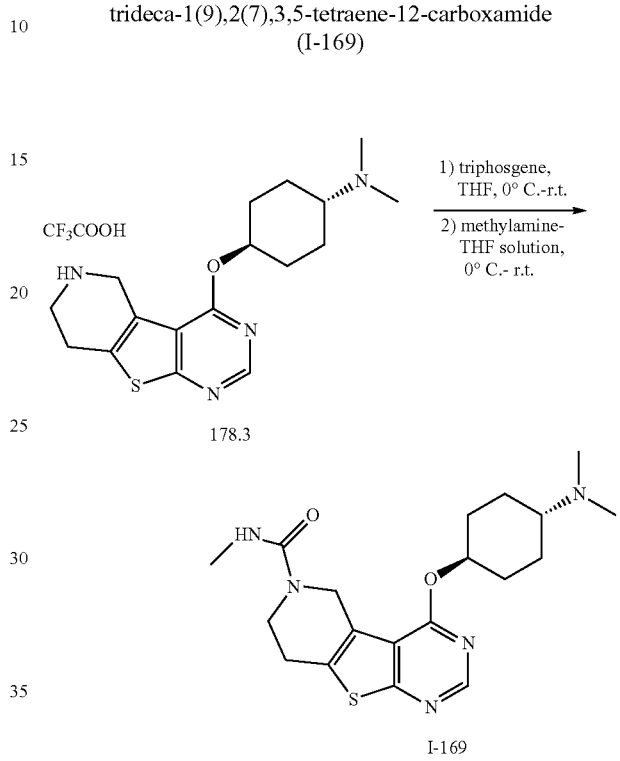

To a solution of N,N-dimethyl-4-[8-thia-4,6,12-triazatricyclo[7.4.0.0-[2,7]]trideca-1(9),2(7),3,5-tetraen-3-yloxy]cyclohexan-1-amine trifluoroacetate (30 mg, 0.09 mmol, 1.00 equiv) in 5 mL of anhydrous dichloromethane was added TEA (40 mg, 0.40 mmol, 4.38 equiv) and MsCl (14 mg, 0.12 mmol, 1.36 equiv) at 0° C. under nitrogen. The resulting solution was stirred for 2 h at room temperature. The reaction mixture was concentrated under vacuum and the residue was purified by preparative HPLC under the following conditions (Waters): Column: XBridge Prep C18 OBD Column, 5 μm, 19*150 mm; mobile phase: water with 0.05% NH$_4$HCO$_3$ and CH$_3$CN (16% CH$_3$CN increasing to 23% in 10 min, up to 100% in 2 min, down to 16% in 2 min); flow rate: 20 mL/min; UV Detection at 254/220 nm. This resulted in 8.0 mg (22%) of 4-([12-methanesulfonyl-8-thia-4,6,12-triazatricyclo[7.4.0.0-[2,7]]trideca-1(9),2(7),3,5-tetraen-3-yl]oxy)-N,N-dimethylcyclohexan-1-amine as a white solid. MS (ES): m/z 411 (M+H)$^+$; $^1$H NMR (300 MHz, CD$_3$OD): δ 1.59-1.71 (m, 4H), 2.05-2.10 (d, 2H, J=15 Hz), 2.34-2.50 (m, 9H), 2.98 (s, 3H), 3.08 (t, 2H, J=5.7 Hz), 3.06 (t, 2H, J=5.7 Hz), 4.67 (t, 2H, J=1.8 Hz), 5.26 (m, 1H), 8.53 (s, 1H).

To a 3-necked round-bottom flask containing a solution of N,N-dimethyl-4-[8-thia-4,6,12-triazatricyclo[7.4.0.0[2,7]]trideca-1(9),2(7),3,5-tetraen-3-yloxy]cyclohexan-1-amine trifluoroacetate (300 mg, 1.00 equiv, 30% purity) in THF (50 mL) was added triethylamine (0.4 mL). The solution was stirred at 0° C. for 10 min under nitrogen. Then triphosgene (300 mg, 1.0 mmol) in 10 mL of DCM was added via syringe at 0° C. and stirred for 2 h at room temperature. Then methanamine-THF (2 M, 1.8 mL) was added at 0° C. and the resulting solution was stirred overnight at room temperature. The reaction was quenched by the addition of methanol and concentrated under vacuum. The residue was pre-purified by a silica gel column with DCM/MeOH (30:1-10:1) to give the crude product, which was purified by preparative HPLC under the following conditions (Waters): Column: XBridge Shield RP18 OBD Column, 5 μm, 19*150 mm; mobile phase, water with 0.05% NH$_4$HCO$_3$ and CH$_3$CN (9% CH$_3$CN up to 21% in 12 min, up to 95% in 2 min, down to 9% in 2 min); flow rate: 20 mL/min; UV detection at 254/220 nm. After concentration in vacuo and lyophilization overnight, the corresponding 3-[[4-(dimethylamino)cyclohexyl]oxy]-N-methyl-8-thia-4,6,12-triazatricyclo[7.4.0.0[2,7]]trideca-1(9),2(7),3,5-tetraene-12-carboxamide (30 mg) was obtained as a white solid. MS (ES): m/z 390 (M+H)$^+$ and 412 (M+Na)$^+$. $^1$H NMR (300 MHz, CD$_3$OD): δ 8.50 (1H, s), 5.30-5.21 (1H, m), 4.78 (2H, s), 3.75 (2H, t), 2.95 (2H, t), 2.78 (3H, s), 2.50-2.30 (9H, m), 2.07 (2H, d), 1.8-1.62 (2H, m), 1.60-1.50 (2H, m).

Example 182

Synthesis of 2-cyclopropyl-1-(3-[[4-(dimethylamino)cyclohexyl]oxy]-8-thia-4,6,12-triazatricyclo[7.4.0.0^[2,7]]trideca-1(9),2(7),3,5-tetraen-12-yl)ethan-1-one (I-170)

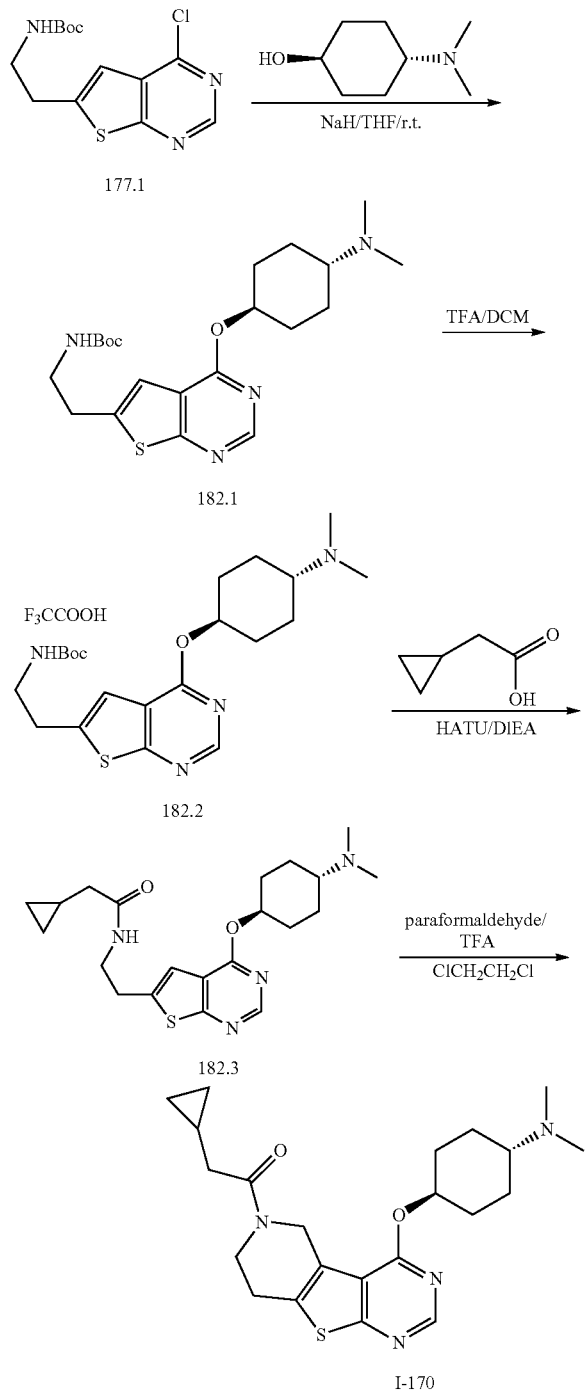

Synthesis of Compound 182.1.

To a solution of tert-butyl N-(2-[4-chlorothieno[2,3-d]pyrimidin-6-yl]ethyl)carbamate (100 mg, 0.32 mmol, 1.00 equiv) in freshly distilled THF (20 mL) was added sodium hydride (64 mg, 1.6 mmol, 5.0 equiv, 60% dispersion in mineral oil) at 0° C. under nitrogen. After stirring for 30 min at room temperature, a solution of 4-(dimethylamino)cyclohexan-1-ol (50 mg, 0.35 mmol, 1.06 equiv) was added and stirred overnight at room temperature. The reaction was then quenched by the addition of brine and extracted with EtOAc. The organic layers was combined and dried over anhydrous sodium sulfate. After filtration and concentration, the residue was applied onto a silica gel column with DCM/MeOH (50:1-30:1) to provide 70 mg (52%) of tert-butyl N-[2-(4-[[4-(dimethylamino)cyclohexyl]oxy]thieno[2,3-d]pyrimidin-6-yl)ethyl]carbamate as a light yellow solid. MS (ES): m/z 421 (M+H)$^+$.

Synthesis of Compound 182.2.

To a solution of tert-butyl 2-(4-((1r,4r)-4-(dimethylamino)cyclohexyloxy)thieno[2,3-d]pyrimidin-6-yl)ethylcarbamate (70 mg, 0.17 mmol, 1.0 equiv) in DCM (20 mL) was added trifluoroacetic acid (1 mL) and stirred overnight at room temperature. After concentration under vacuum, we obtained 70 mg of (1r,4r)-4-(6-(2-aminoethyl)thieno[2,3-d]pyrimidin-4-yloxy)-N,N-dimethylcyclohexanamine trifluoroacetate as a light yellow oil and used it directly without further purification. MS (ES): m/z 321 (M+H)$^+$.

Synthesis of Compound 182.3.

To a solution of 2-cyclopropylacetic acid (51 mg, 0.51 mmol, 3.0 equiv) in dry DMF (20 mL) was added DIEA (110 mg, 0.85 mmol, 5.0 equiv) followed by HATU (194 mg, 0.51 mmol, 3.0 equiv) at 0° C. The resulting solution was stirred for 10 min at room temperature. Then (1r,4r)-4-(6-(2-aminoethyl)thieno[2,3-d]pyrimidin-4-yloxy)-N,N-dimethylcyclohexanamine trifluoroacetate (70 mg, 0.17 mmol, 1.0 equiv) in DMF was added and stirred for 3 h at room temperature. The reaction was then quenched by the addition of brine and extracted with EtOAC. The organic layer was extracted with water thrice. The water layer was collected and concentrated under vacuum and the residue was dissolved in THF and stirred for 30 min. After filtration and concentration, the residue was purified by flash preparative HPLC under the following conditions: Column: C18 silica gel; mobile phase: water then ramp up CH$_3$CN to 80% within 30 min; detector: UV 254 nm. After removed the eluting solvent, we obtained 40 mg (58%) of 2-cyclopropyl-N-[2-(4-[[4-(dimethylamino)cyclohexyl]oxy]thieno[2,3-d]pyrimidin-6-yl)ethyl]acetamide as a yellow solid. MS (ES): m/z 403 (M+H)$^+$.

Synthesis of Compound I-170.

To a solution of 2-cyclopropyl-N-(2-(4-41r,4r)-4-(dimethylamino)cyclohexyloxy)thieno[2,3-d]pyrimidin-6-yl)ethyl)acetamide (40 mg, 1.0 mmol, 1.0 equiv) in DCE (40 mL) was added paraformaldehyde (40 mg, 1.3 mmol, 13.0 equiv) followed by trifluoroacetic acid (0.6 mL). The resulting solution was stirred overnight at room temperature. After concentration under vacuum, the residue was purified by preparative HPLC under the following conditions (1#-Pre-HPLC-016(Waters)): Column: XBridge Shield RP18 OBD 5 μm, 19*150 mm; mobile phase: water (50 mM NH$_4$HCO$_3$) and CH$_3$CN (5% CH$_3$CN up to 30% in 13 min, up to 95% in 2 min, down to 5% in 2 min); detector: UV 254, 220 nm. After concentration and re-lyophilization, we obtained 10.2 mg( ) of 2-cyclopropyl-1-(3[[4-(dimethylamino)cyclohexyl]oxy]-8-thia-4,6,12-triazatricyclo[7.4.0.0^[2,7]]trideca-1(9),2(7),3,5-tetraen-12-1)ethan-1-one as an off-white solid. MS (ES): m/z 415 (M+H)$^+$, 437 (M+Na)$^+$; $^1$H NMR (300 MHz, CD$_3$OD): δ 8.52 (1H, s), 5.28 (1H, m), 4.92 (2H, s), 3.95 (2H, dt), 3.04-2.94 (2H, m), 2.69-2.54 (1H, m), 2.52-2.43 (8H, m), 2.42-2.33 (2H, m), 2.12-2.08 (2H, m), 1.78-1.47 (4H, m), 1.10-1.02 (1H, m), 0.59-0.54 (2H, m), 0.27-0.21 (2H, m).

Example 183

Synthesis of 1-(3-[[4-(morpholin-4-yl)cyclohexyl]oxy]-8-thia-4,6,12-triazatricyclo[7.4.0.0[2,7]]trideca-1(9),2(7),3,5-tetraen-12-yl)ethan-1-one (I-171)

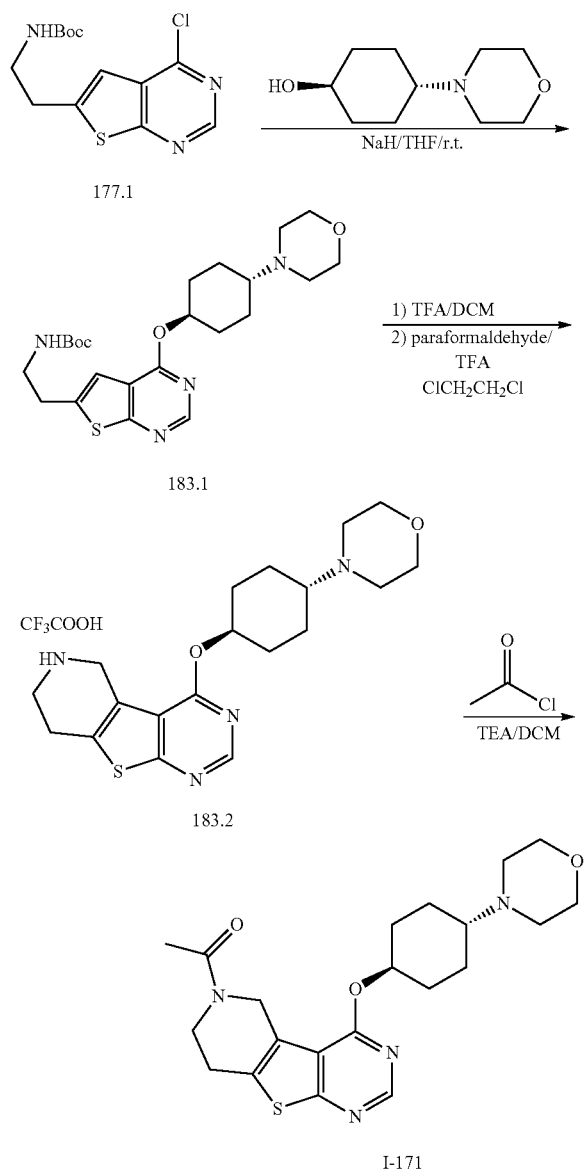

Synthesis of Compound 183.1.

To a solution of 4-(morpholin-4-yl)cyclohexan-1-ol (143 mg, 0.77 mmol, 1.10 equiv) in THF (20 mL) was added sodium hydride (140 mg, 3.50 mmol, 5.00 equiv, 60% dispersion in mineral oil) at 0° C. The solution was stirred for 30 min at room temperature under nitrogen. Then tert-butyl N-(2-[4-chlorothieno[2,3-d]pyrimidin-6-yl]ethyl)carbamate (220 mg, 0.70 mmol, 1.00 equiv) in 5 mL of THF was added via syringe and the resulting solution was stirred overnight at room temperature. The reaction was then quenched by the addition of brine and extracted with EtOAc. The organic layers were combined and dried over anhydrous sodium sulfate. After filtration and concentration in vacuo, the residue was purified by a silica gel column with DCM/MeOH (30:1-10:1) to provide 127 mg (39%) of tert-butyl N-[2-(4-[[4-(morpholin-4-yl)cyclohexyl]oxy]thieno[2,3-d]pyrimidin-6-yl)ethyl]carbamate as a white solid. MS (ES): m/z 463 (M+H)$^+$.

Synthesis of Compound 183.2.

To a solution of tert-butyl N-[2-(4-[[4-(morpholin-4-yl)cyclohexyl]oxy]thieno[2,3-d]pyrimidin-6-yl)ethyl]carbamate (150 mg, 0.32 mmol, 1.00 equiv) in DCM/H$_2$O (10/0.5 mL) was added trifluoroacetic acid (0.8 mL) at 0° C. and stirred overnight at room temperature. After concentration under vacuum, the residue was dissolved in DCE (30 mL) and paraformaldehyde (180 mg) and trifluoroacetic acid (1 mL) were added. The resulting solution was stirred overnight at 45° C. under nitrogen. After concentration under vacuum, the residue was purified by preparative HPLC under the following conditions: Column: XBridge Shield RP18 OBD, 5 µm, 19*150 mm; mobile phase: water (with 0.5% TFA) and CH$_3$CN (0% CH$_3$CN up to 21% in 12 min, up to 95% in 2 min, down to 0% in 2 min); flow rate: 20 mL/min; UV detection at 254/220 nm. After concentration under vacuum, the desired 3-[[4-(morpholin-4-yl)cyclohexyl]oxy]-8-thia-4,6,12-triazatricyclo[7.4.0.0[2,7]]trideca-1(9),2(7),3,5-tetraene trifluoroacetate (100 mg, crude) was obtained as a light yellow solid. MS (ES): m/z 375 (M+H)$^+$.

Synthesis of Compound I-171.

To a solution of 3-[[4-(morpholin-4-yl)cyclohexyl]oxy]-8-thia-4,6,12-triazatricyclo[7.4.0.0[2,7]]trideca-1(9),2 (7),3,5-tetraene trifluoroacetate (100 mg, crude) in DCM (20 mL) was added TEA (108 mg, 1.07 mmol). The solution was stirred for 10 min at 0° C. under nitrogen. Then acetyl chloride (41.9 mg, 0.53 mmol) was added to the reaction solution at this temperature and the resulting solution was stirred for 1.5 h at room temperature. The reaction was then quenched by the addition of ethanol and concentrated under vacuum. The crude product was purified by preparative HPLC under the following conditions (Waters): Column: Xbridge Prep C18, 5 µm, 19*50 mm; mobile phase: water with 0.05% NH$_4$HCO$_3$ and CH$_3$CN (10% CH$_3$CN up to 35% in 11 min, up to 95% in 1.5 min, down to 10% in 1.5 min); detector: UV 254/220 nm. After concentration in vacuo and lyophilization overnight, the corresponding 1-(3-[[4-(morpholin-4-yl)cyclohexyl]oxy]-8-thia-4,6,12-triazatricyclo[7.4.0.0[2,7]]trideca-1(9),2(7),3,5-tetraen-12-yl)ethan-1-one (22.1 mg) was obtained as a white solid. MS (ES): m/z 417 (M+H)$^+$ and 429 (M+Na)$^+$. $^1$H NMR (300 MHz, CD$_3$OD): δ 8.54 (1H, s), 5.33-5.23 (1H, m), 4.91 (2H, s), 3.97, 3.90 (2H, t, t), 3.76-3.69 (4H, m), 3.05, 2.95 (2H, t, t), 2.67-2.58 (4H, t), 2.34-2.25 (3H, m), 2.25, 2.23 (3H, s, s), 2.10 (2H, d), 1.74-1.45 (4H, m).

Example 184

Synthesis of Intermediate 184.4

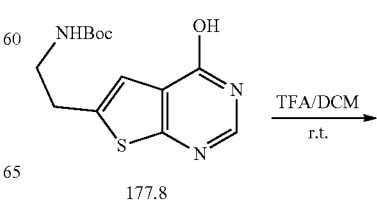

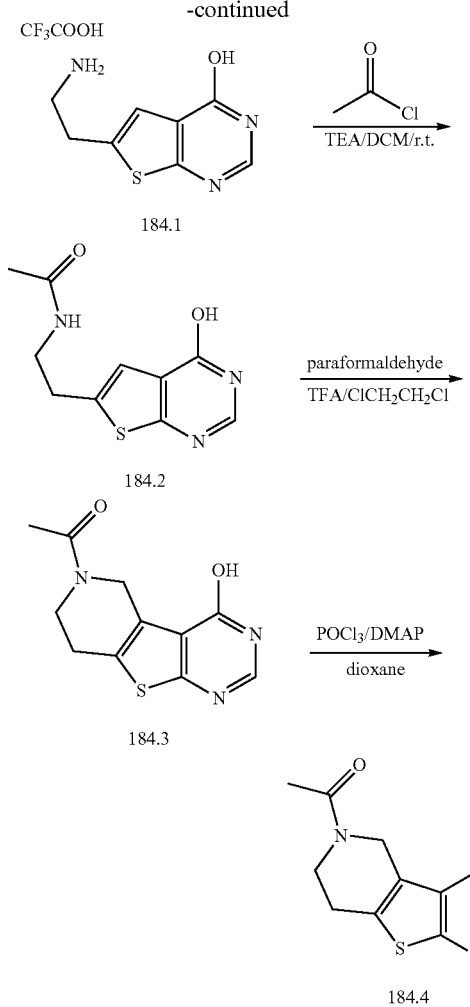

mL of 1,2-dichloroethane at 0° C. was added CF₃COOH (6 mL). The solution was stirred for 12 h at room temperature. The resulting mixture was concentrated under vacuum. The residue was applied onto a silica gel column with dichloromethane/methanol (10:1) to afford the desired 1-[3-hydroxy-8-thia-4,6,12-triazatricyclo[7.4.0.0-[2,7]]trideca-1(9),2,4,6-tetraen-12-yl]ethan-1-one (200 mg, 63%) as a light yellow solid. MS (ES): m/z 250 (M+H)⁺.

Synthesis of 184.4.

To a solution of 1-[3-hydroxy-8-thia-4,6,12-triazatricyclo[7.4.0.0-[2,7]]trideca-1(9),2(7),3,5-tetraen-12-yl]ethan-1-one (250 mg, 1.00 mmol, 1.00 equiv) in 25 mL of anhydrous 1,4-dioxane was added POCl₃ (1.53 g, 9.98 mmol, 9.95 equiv) and 4-dimethylaminopyridine (1.22 g, 9.99 mmol, 9.96 equiv) simultaneously at room temperature under nitrogen. The resulting solution was heated to 100° C. for 2 h. After completion, the reaction mixture was cooled to room temperature and concentrated under vacuum. The residue was diluted with EtOAc, poured into cooled saturated aqueous sodium bicarbonate and extracted with ethyl acetate. The combined organic layers were washed with brine, dried over sodium sulfate and concentrated under vacuum. The residue was applied onto a silica gel column with ethyl acetate/petroleum ether (1:4) to give the corresponding 1-13-chloro-8-thia-4,6,12-triazatricyclo[7.4.0.0-[2,7]]trideca-1(9),2(7),3,5-tetraen-12-yl)ethan-1-one (160 mg, 60%) as a yellow solid. MS (ES): m/z 268 and 270 (M+H)⁺.

Example 185

Synthesis of 1-(3-[[4-(morpholin-4-yl)cyclohexyl]amino]-8-thia-4,6,12-triazatricyclo[7.4.0.0-[2,7]]trideca-1(9),2(7),3,5-tetraen-12-yl)ethan-1-one (I-172)

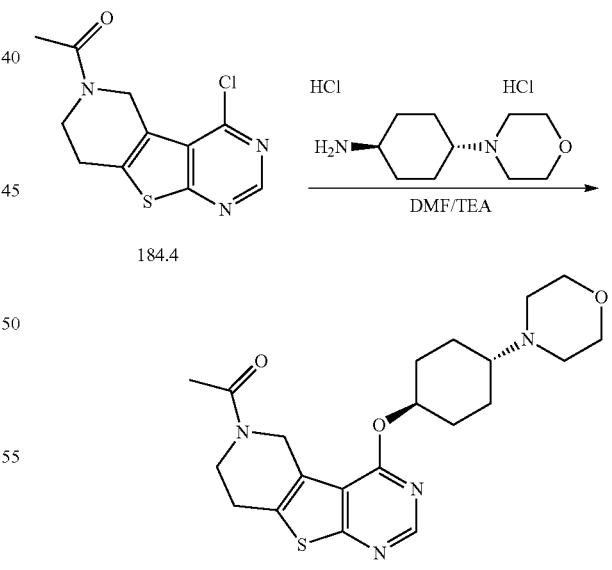

Synthesis of Compound 184.1.

A solution of tert-butyl N-(2-[4-hydroxythieno[2,3-d]pyrimidin-6-yl]ethyl)carbamate (600 mg, 2.03 mmol, 1.00 equiv) in 25 mL of dichloromethane at 0° C. was added 4 mL of CF₃COOH and the resulting solution was stirred for 6 hours at room temperature. The resulting mixture was concentrated under vacuum to give 6-(2-aminoethyl)thieno[2,3-d]pyrimidin-4-ol trifluoroacetate (570 mg, 91%) as a yellow oil which was used directly in the next step without further purification. MS (ES): m/z 196 (M+H)⁺.

Synthesis of Compound 184.2.

To a 25-mL round-bottom flask (1 atm) purged and maintained with an inert atmosphere of nitrogen was added a solution of 6-(2-aminoethyl)thieno[2,3-d]pyrimidin-4-ol (570 mg, 2.92 mmol, 1.00 equiv) in 10 mL of dichloromethane. TEA (1.2 g, 11.86 mmol, 4.06 equiv) and acetyl chloride (460 mg, 5.86 mmol) were added at 0° C. under nitrogen. The resulting solution was stirred for 2 h at room temperature and concentrated under vacuum. The residue was applied onto a silica gel column with dichloromethane/methanol (10:1) to give 400 mg (crude) of the desired N-(2-[4-hydroxythieno[2,3-d]pyrimidin-6-yl]ethyl)acetamide as a white solid. MS (ES): m/z 238 (M+H)⁺.

Synthesis of Compound 184.3.

To a solution of N-(2-[4-hydroxythieno[2,3-d]pyrimidin-6-yl]ethyl)acetamide (300 mg, 1.26 mmol, 1.00 equiv) and paraformaldehyde (300 mg, 10.00 mmol, 7.91 equiv) in 50

To a solution of 1-[3-chloro-8-thia-4,6,12-triazatricyclo[7.4.0.0-[2,7]]trideca-1(9),2(7),3,5-tetraen-12-yl]ethan-1-one (100 mg, 0.37 mmol, 1.00 equiv) and trans-4-(morpholin-4-yl)cyclohexan-1-amine dihydrochloride (412 mg, 1.61 mol, 4.32 equiv) in 10 mL of N,N-dimethylformamide was added TEA (200 mg, 1.98 mmol, 5.29 equiv) and the resulting solution was stirred for 12 h at 50° C. under nitrogen. After concentration in vacuo, the crude product was purified by preparative HPLC under the following conditions (Waters): Column: Xbridge Prep C18, 5 μm, 19*50 mm; mobile phase: water with 0.05% NH$_4$HCO$_3$ and CH$_3$CN (10% CH$_3$CN up to 35% in 11 min, up to 95% in 1.5 min, down to 10% in 1.5 min); detector: UV 254/220 nm. The product-containing fractions were collected and partially evaporated under reduced pressure and lyophilized overnight to give 76.9 mg (50%) of 1-(3-[[4-(morpholin-4-yl)cyclohexyl]amino]-8-thia-4,6,12-triazatricyclo[7.4.0.0-[2,7]]trideca-1(9),2(7),3,5-tetraen-12-yl)ethan-1-one as a white solid. MS (ES): m/z 416 (M+H)$^+$.
$^1$H NMR (300 MHz, CD$_3$OD): δ 1.40-1.60 (m, 4H), 2.08 (d, 2H), 2.20-2.45 (m, 6H), 2.60-2.70 (m, 4H), 2.92, 3.02 (t, t, 2H), 3.70-3.80 (m, 4H), 3.89, 3.95 (t, t, 2H), 4.05-4.22 (m, 1H), 4.96, 5.00 (s, s, 2H), 8.29, 8.30 (s, s, 1H).

Example 186

Synthesis of 1-(3-[[4-(dimethylamino)cyclohexyl]amino]-8-thia-4,6,12-triazatricyclo[7.4.0.0-[2,7]]trideca-1(9),2(7),5-trien-12-yl)ethan-1-one (I-173)

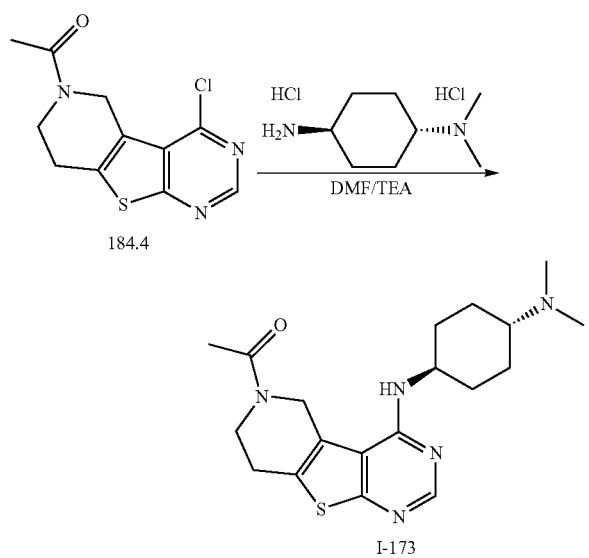

A 25-mL round-bottom flask (1.0 atm) purged and maintained with an inert atmosphere of nitrogen was charged with a solution of 1-[3-chloro-8-thia-4,6,12-triazatricyclo[7.4.0.0-[2,7]]trideca-1(9),2(7),3,5-tetraen-12-yl]ethan-1-one (37 mg, 0.14 mmol, 1.00 equiv) and trans-dimethylcyclohexane-1,4-diamine (37 mg, 0.26 mmol, 1.88 equiv) in 5 mL of DMF. TEA (0.2 mL) was added at room temperature. The resulting solution was heated to 50° C. for 12 hours. After concentration in vacuo, the crude product was purified by preparative HPLC under the following conditions (Waters): Column: Xbridge Prep C18, 5 μm, 19*50 mm; mobile phase: water with 0.05% NH$_4$HCO$_3$ and CH$_3$CN (10% CH$_3$CN up to 35% in 11 min, up to 95% in 1.5 min, down to 10% in 1.5 min); detector: UV 254/220 nm. The product-containing fractions were collected and partially evaporated under reduced pressure and lyophilized overnight to give 1-(3-[[4-(dimethylamino)cyclohexyl]amino]-8-thia-4,6,12-triazatricyclo[7.4.0.0-[2,7]]trideca-1(9),2(7),5-trien-12-yl)ethan-1-one (76.9 mg, 50%) as a white solid. MS (ES): m/z 374 (M+H)$^+$;
$^1$H NMR (300 MHz, CD$_3$OD): δ 1.40-1.60 (m, 4H), 1.85-1.95 (m, 2H), 2.05-2.20 (m, 5H), 2.22-2.40 (m, 7H), 2.81, 2.91 (t, t, 2H), 3.78, 3.83 (t, t, 2H), 3.98-4.18 (m, 1H), 4.84, 4.88 (s, s, 2H), 8.18 (s, 1H).

Example 187

Synthesis of 2-[(12S)-3-[[4-(dimethylamino)cyclohexyl]oxy]-8-thia-4,6-diazatricyclo[7.4.0.0[2,7]]trideca-1(9),2(7),3,5-tetraen-12-yl]ethan-1-ol formate (I-111)

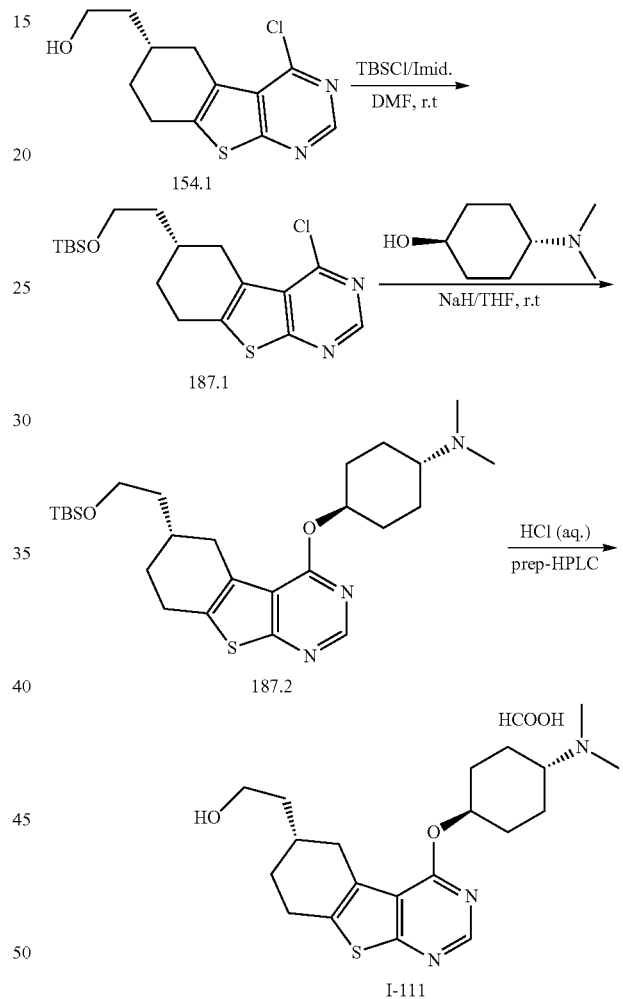

Synthesis of Compound 187.1.

To a solution of 2-[(12S)-3-chloro-8-thia-4,6-diazatricyclo[7.4.0.0[2,7]]trideca-1(9),2 (7),3,5-tetraen-12-yl]ethan-1-ol (300 mg, 1.12 mmol, 1.00 equiv) in 5 mL of distilled DMF was added TBSCl (252 mg, 1.50 equiv) and imidazole (137 mg, 2.01 mmol, 1.80 equiv) at room temperature under nitrogen. The resulting solution was stirred for 1 h at ambient temperature, quenched with water and extracted with 3×50 mL of ethyl acetate. The combined organic layers were washed with brine, dried over anhydrous sodium sulfate and concentrated under reduced pressure. The residue was applied onto a silica gel column with ethyl acetate/petroleum ether (1:5) to provide (12S)-12-[2-[(tert-butyldimethylsilyl)oxy]ethyl]-3-chloro-8-thia-4,6-diazatricyclo[7.4.0.0[2,7]]

trideca-1(9),2(7),3,5-tetraene (420 mg, 98%) as a light yellow solid. MS (ES): m/z 384, 386 (M+H)+.

Synthesis of Compound 187.2.

NaH (60% dispersion in mineral oil, 63 mg, 3.00 equiv) was treated with trans-4-(dimethylamino)cyclohexan-1-ol (104 mg, 0.73 mmol, 1.40 equiv) in distilled tetrahydrofuran (8 mL) at room temperature under nitrogen. After stirring for min, (12S)-12-[2-[(tert-butyldimethylsilyl)oxy]ethyl]-3-chloro-8-thia-4,6-diazatricyclo[7.4.0.0[2,7]]trideca-1(9),2(7),3,5-tetraene (200 mg, 0.52 mmol, 1.00 equiv) was added and the resulting solution was stirred overnight at room temperature for 8 h. The reaction was then quenched with saturated aqueous NH4Cl and extracted with 3×50 mL of ethyl acetate. The organic layers were combined, washed with brine, dried over anhydrous sodium sulfate and concentrated under vacuum. The residue was applied onto a silica gel column with dichloromethane/methanol (4:1) to afford 4-[[(12S)-12-[2-[(tert-butyldimethylsilyl)oxy]ethyl]-8-thia-4,6-diazatricyclo[7.4.0.0[2,7]]trideca-1(9),2(7),3,5-tetraen-3-yl]oxy]-N,N-dimethylcyclohexan-1-amine (110 mg, 43%) as a light yellow solid. MS (ES): m/z 490 (M+H)+.

Synthesis of Compound I-111.

To a solution of 4-[[(12S)-12-[2-[(tert-butyldimethylsilyl)oxy]ethyl]-8-thia-4,6-diazatricyclo[7.4.0.0[2,7]]trideca-1(9),2(7),3,5-tetraen-3-yl]oxy]-N,N-dimethylcyclohexan-1-amine (110 mg, 0.22 mmol, 1.00 equiv) in methanol (5 mL) was added hydrochloric acid (12 M, 0.5 mL) at 0° C. The resulting solution was stirred for 1 h at room temperature. The solvent was removed in vacuo and the crude product (80 mg) was purified by preparative HPLC under the following conditions (SHIMADZU): Column: SunFire Prep C18, 19*150 mm, 5 μm; mobile phase: water (with 0.1% HCOOH) and CH3CN (6.0% CH3CN up to 53.0% in 16 min); flow rate: 20 mL/min; UV detection at 254/220 nm. The product-containing fractions were collected and partially evaporated under reduced pressure to remove water and CH3CN. The residue was lyophilized overnight to give the 2-[(12S)-3-[[4-(dimethylamino)cyclohexyl]oxy]-8-thia-4,6-diazatricyclo[7.4.0.0[2,7]]trideca-1(9),2(7),3,5-tetraen-12-yl]ethan-1-ol formate (46 mg, 55%) as an off-white semi-solid. MS (ES): m/z 376 (M+H)+. 1H NMR (300 MHz, CDCl3): δ 8.49 (d, 2H), 5.22 (s, 1H), 3.82 (t, 2H), 3.16 (m, 2H), 2.88 (s, 2H), 2.66 (s, 6H), 2.48 (t, 3H), 2.19 (s, 2H), 2.05 (d, 2H), 1.70 (m, 7H).

Example 188

Synthesis of 2-[3-[[4-(dimethylamino)cyclohexyl]oxy]-8-thia-4,6-diazatricyclo[7.4.0.0[2,7]]trideca-1(9),2(7),3,5-tetraen-12-yl]ethan-1-ol formate (I-108)

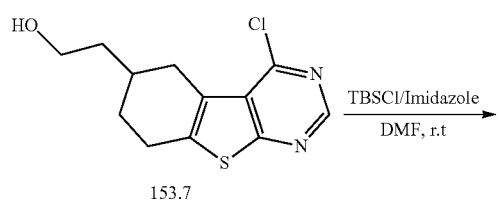

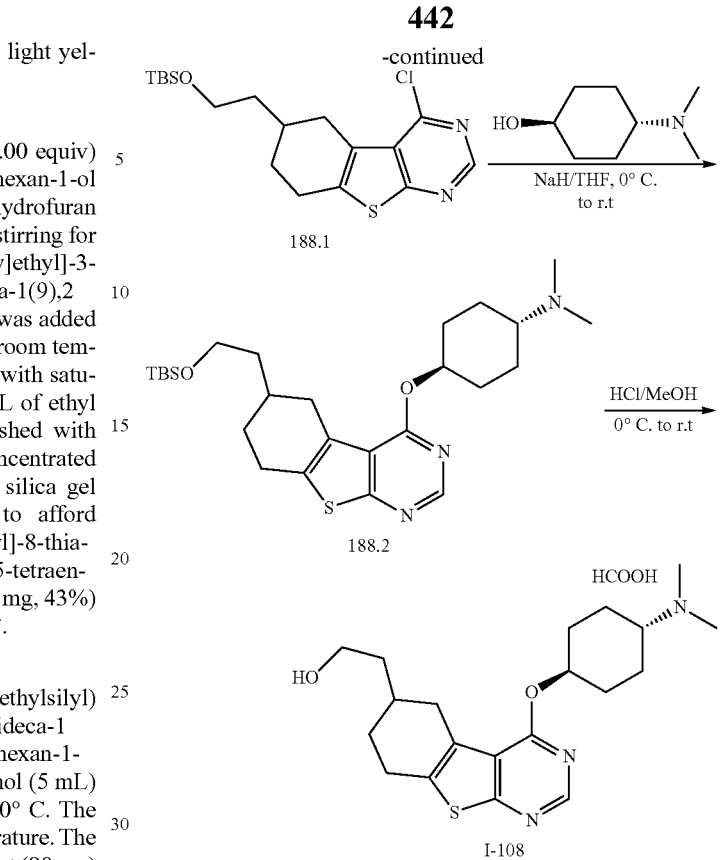

Compound I-108 was prepared in a manner consistent with Example 186, except that compound 153.7 was used rather than 154.1. A white semi-solid was obtained (44% overall yield). MS (ES): m/z 376 (M−HCOOH+H)+. 1H NMR (400 MHz, CDCl3): δ 8.52 (s, 1H) 8.46 (d, 1H) 6.93 (m, 2H) 5.20 (d, 1H) 3.81 (t, 2H) 3.20 (dd, 2H) 2.86 (m, 2H) 2.65 (s, 6H) 2.46 (m, 3H) 2.18 (s, 2H) 2.04 (d, 2H) 1.65 (m, 7H).

Example 189

Synthesis of 2-[(12R)-3-[[4-(dimethylamino)cyclohexyl]oxy]-8-thia-4,6-diazatricyclo[7.4.0.0[2,7]]trideca-1(9),2(7),3,5-tetraen-12-yl]ethan-1-ol formate (1-110)

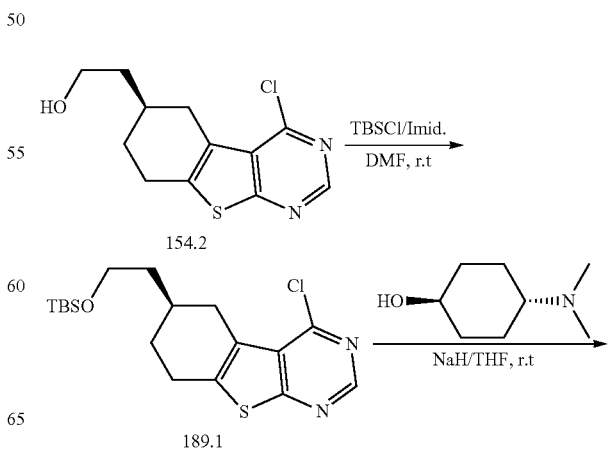

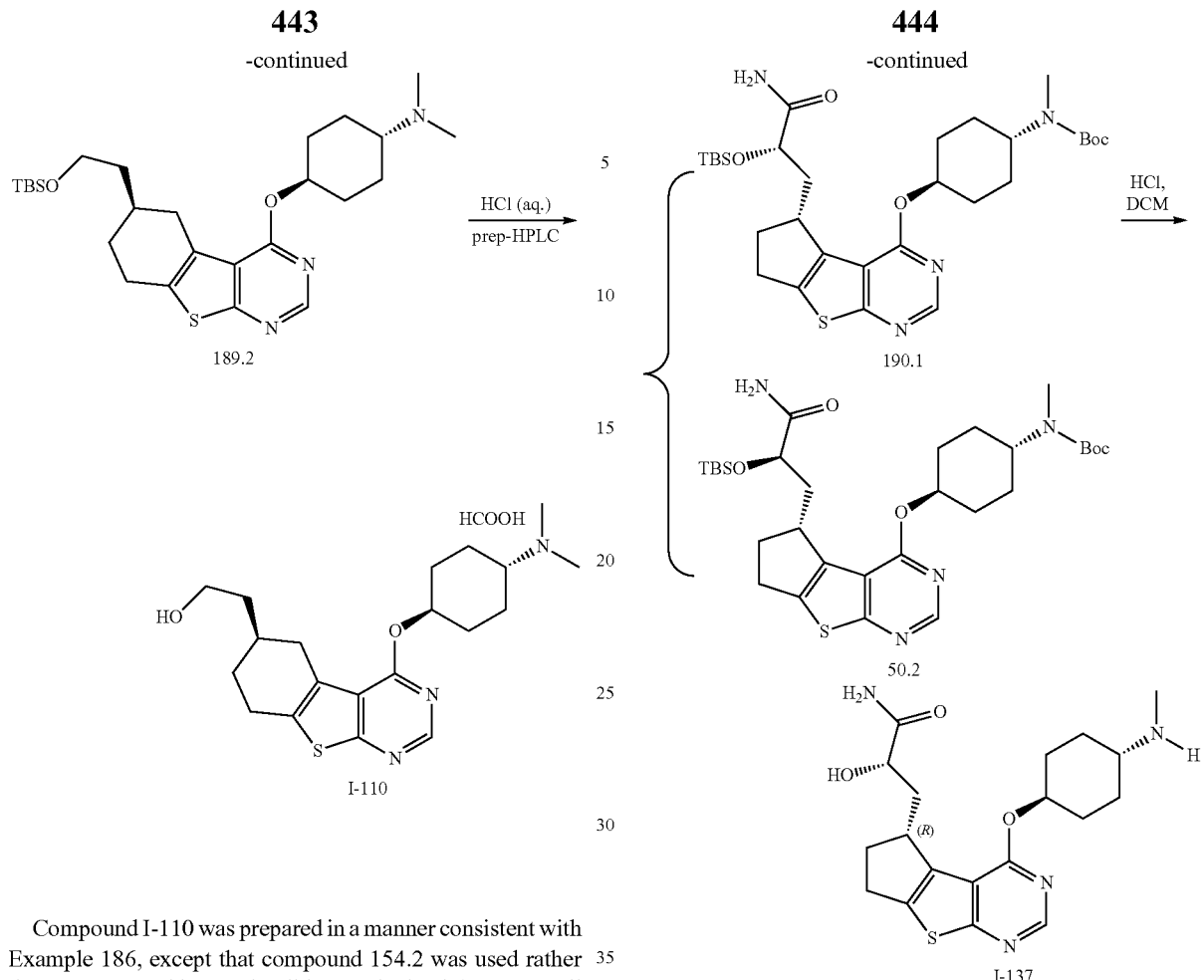

Compound I-110 was prepared in a manner consistent with Example 186, except that compound 154.2 was used rather than 154.1. A white semi-solid was obtained (23% overall yield). MS (ES): m/z 376 (M−HCOOH+H)$^+$. $^1$H NMR (300 MHz, CDCl$_3$): δ 8.49 (d, 2H,) 5.22 (s, 1H), 3.83 (t, 2H), 3.15 (dd, 2H), 2.88 (s, 2H), 2.65 (s, 6H), 2.48 (t, 3H), 2.07 (t, 4H), 1.70 (m, 7H).

Example 190

Synthesis of (2S)-2-hydroxy-3-[(3R)-12-[[4-(methylamino)cyclohexyl]oxy]-7-thia-9,11-diazatricyclo [6.4.0.0[2,6]]dodeca-1(8),2(6),9,11-tetraen-3-yl]propanamide (I-137)

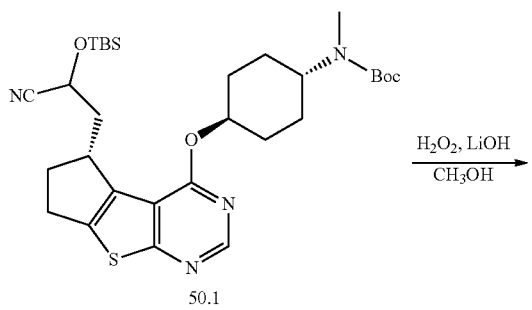

Synthesis of Compound 190.1.

A solution of tert-butyl N-(4-[[(3R)-3-[2-[(tert-butyldimethylsilyl)oxy]-2-cyanoethyl]-7-thia-9,11-diazatricyclo [6.4.0.0[2,6]]dodeca-1(8),2(6),9,11-tetraen-12-yl]oxy]cyclohexyl)-N-methylcarbamate (420 mg, 0.72 mmol, 1.00 equiv), LiOH.H$_2$O (60 mg, 1.43 mmol, 2.00 equiv) and H$_2$O$_2$ (30%) (0.5 mL) in methanol (20 mL) was stirred for 2 h at 0° C. in a water/ice bath. The reaction was then quenched by the addition of 30 mL of saturated Na$_2$SO$_3$. The resulting solution was extracted with 3×40 mL of ethyl acetate, concentrated under vacuum and purified by preparative TLC (PE/EA=1:1). This resulted in tert-butyl N-(4-[[(3R)-3-[(2S)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)-N-methylcarbamate (190.1, 180 mg) as a colorless oil and tert-butyl N-(4-[[(3R)-3-[(2R)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)-N-methylcarbamate (50.2, 160 mg) as a colorless oil.

Synthesis of Compound I-137.

A solution of tert-butyl N-(4-[[(3R)-3-[(2S)-2-[(tert-butyldimethylsilyl)oxy]-2-carbamoylethyl]-7-thia-9,11-diazatricyclo[6.4.0.0[2,6]]dodeca-1(8),2(6),9,11-tetraen-12-yl]oxy]cyclohexyl)-N-methylcarbamate (160 mg, 0.26 mmol, 1.00 equiv) and hydrogen chloride (conc.) (0.3 mL) in dichloromethane (10 mL) was stirred for 2 h at 0° C. in a water/ice bath. The pH value of the solution was adjusted to 8 with NH$_4$OH. The resulting mixture was concentrated under vacuum. The crude product (150 mg) was purified by preparative HPLC under the following conditions (1#-Pre-HPLC-015(Waters)): Column, Xbridge C18, 19*150 mm, 5 μm; mobile phase: water (50 mM NH$_4$HCO$_3$) and CH$_3$CN (10% CH$_3$CN up to 21% in 15 min, up to 95% in 1.5 min, down to 10% in 1.5 min); UV detection at 254/220 nm. The product was freeze-dried to afford (2S)-2-hydroxy-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanamide (48.3 mg, 47%) as a white solid. $^1$H NMR (400 MHz, CD$_3$OD): δ 8.46 (s, 1H), 5.30 (m, 1H), 4.16 (m, 1H), 3.59 (m, 1H), 3.16-2.94 (m, 2H), 2.77-2.68 (m, 1H), 2.58-2.52 (m, 6H), 2.48-2.10 (m, 4H), 1.75-1.72 (m, 3H), 1.66-1.34 (m, 2H). MS: m/z=391 (M+H)$^+$.

Example 191

Synthesis of (2S)-2-amino-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanamide (I-146)

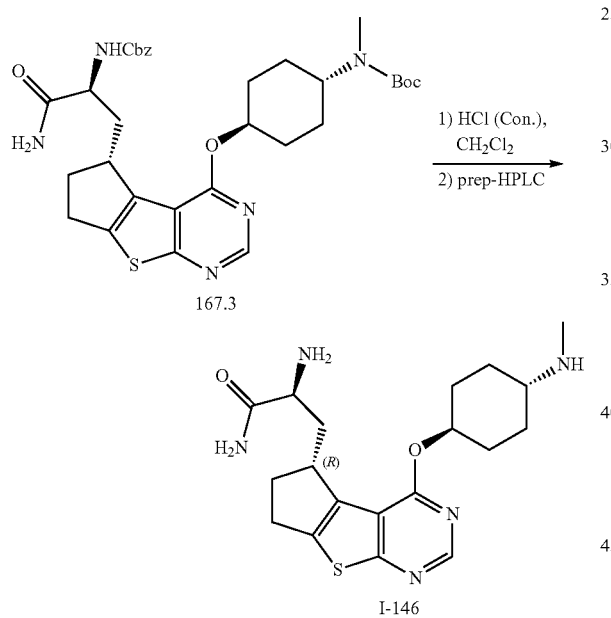

To a solution of benzyl N-[(1S)-2-[(3R)-12-[(4-[[(tert-butoxy)carbonyl](methyl)amino]cyclohexyl)oxy]-7-thia-9,11-diazatricyclo[6.4.0.0[2,6]]dodeca-1(8),2(6),9,11-tetraen-3-yl]-1-carbamoylethyl]carbamate (70 mg, 0.11 mmol, 1.00 equiv) in dichloromethane (5 mL) was added hydrogen chloride (12 M, 2 mL). The resulting solution was stirred for 5 h at 30° C. and then concentrated under vacuum. The crude product (70 mg) was purified by preparative HPLC under the following conditions: Column: SunFire Prep C18, 19*150 mm, 5 μm; mobile phase: water (with 50 mL NH$_4$HCO$_3$) and CH$_3$CN (5.0% CH$_3$CN up to 43.0% in 12 min, up to 95.0% in 2 min, down to 5.0% in 2 min); UV detection at 254/220 nm. This resulted in 28 mg (64%) of (2S)-2-amino-3-[(3R)-12-[[4-(methylamino)cyclohexyl]oxy]-7-thia-9,11-diazatricyclo[6.4.0.0[2,6]]dodeca-1(8),2(6),9,11-tetraen-3-yl]propanamide as a white solid. MS (ES): m/z 390 (M+H)$^+$. $^1$H NMR (300 MHz, CD$_3$OD): δ 1.39-1.55 (m, 3H), 1.72-1.85 (m, 2H), 2.17-2.28 (m, 3H), 2.29-2.39 (m, 3H), 2.56 (s, 3H), 2.63-2.72 (m, 1H), 2.81-3.97 (m, 2H), 3.05-3.15 (m, 1H), 3.35-3.45 (m, 2H), 5.20-5.35 (m, 1H), 8.42 (s, 1H).

Example 192

Synthesis of (1S)-2-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-1-(1,3-oxazol-2-yl)ethan-1-ol (I-62)

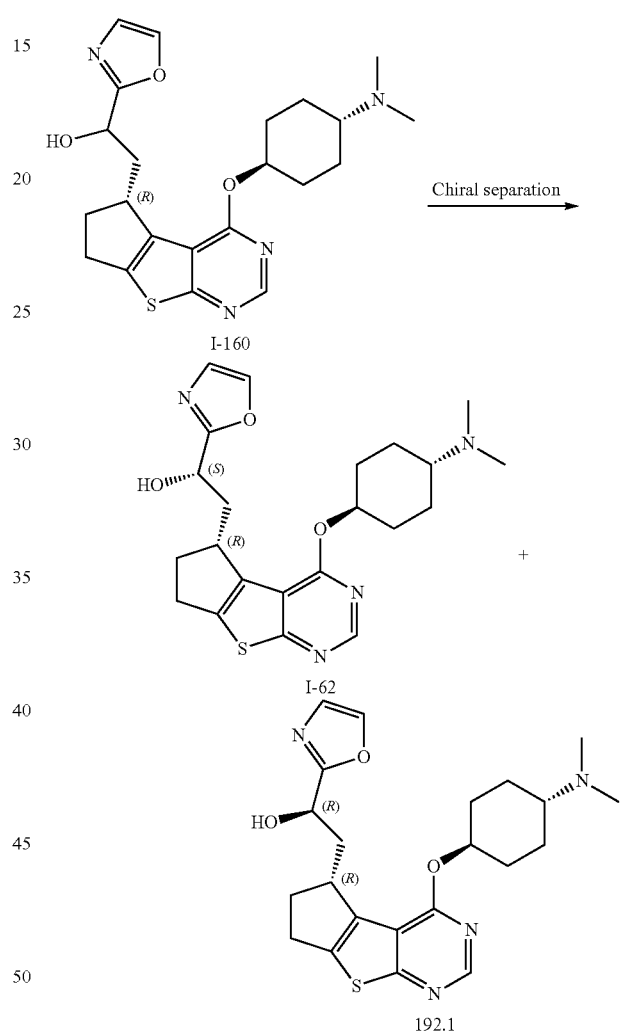

2-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]-1-(1,3-oxazol-2-yl)ethan-1-ol (45 mg, 0.11 mmol, 1.00 equiv) was purified by chiral preparative HPLC under the following conditions: Column: CHIRALPAK IC; mobile phase: hexanes (0.1% TEA):EtOH=70:30; UV detection at 254 nm. This resulted in 31.6 mg (70%) of 192.1 as a white solid and 12.7 mg (28%) of Compound I-62 as a white solid. Analytical data for I-62: MS: 429 (M+H)$^+$. $^1$H NMR (300 MHz, CDCl$_3$): δ 8.49 (s, 1H), 7.64 (s, 1H), 7.28 (s, 1H), 5.22-5.27 (m, 1H), 4.97 (t, 1H), 3.10-3.12 (m, 1H), 2.94-3.09 (m, 2H), 2.62-2.72 (m, 2H), 2.21-2.37 (m, 10H), 1.95-2.03 (m, 3H), 1.40-1.58 (m, 4H).

Example 193

Synthesis of 2-[(4-[[(3R)-3-[(2R)-2-hydroxypropyl]-7-thia-9,11-diazatricyclo[6.4.0.0[2,6]]dodeca-1(8),2(6),9,11-tetraen-12-yl]oxy]cyclohexyl)(methyl)amino]-1-(pyrrolidin-1-yl)ethan-1-one (I-109)

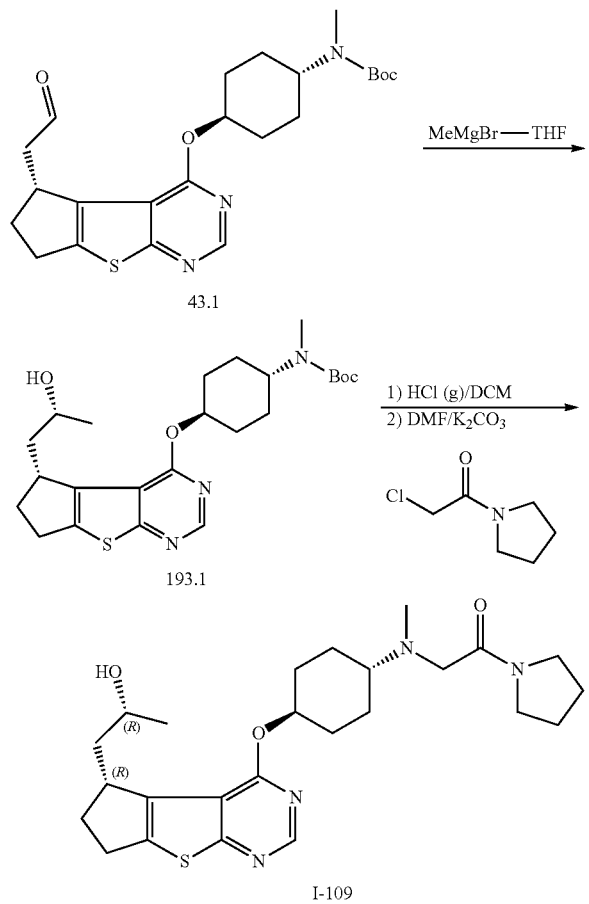

Synthesis of Compound 193.1.

A 50-mL round-bottom flask containing a solution of tert-butyl N-methyl-N-(4-[[(3R)-3-(2-oxoethyl)-7-thia-9,11-diazatricyclo[6.4.0.0[2,6]]dodeca-1(8),2(6),9,11-tetraen-12-yl]oxy]cyclohexyl)carbamate (500 mg, 1.12 mmol, 1.00 equiv) in anhydrous THF (20 mL) was cooled down to 0° C. under nitrogen. Then $CH_3MgBr$ (1 M in THF, 3.36 mL) was added dropwise via syringe and the resulting solution was stirred for 2 h at 0° C. The reaction was then quenched with saturated aqueous $NH_4Cl$ and extracted with 3×50 mL of ethyl acetate. The combined organic layers were washed with brine, dried ($Na_2SO_4$) and concentrated under reduced pressure. The residue was applied onto a silica gel column with ethyl acetate/petroleum ether (1:2) to give the desired tert-butyl N-(4-[[(3R)-3-[(2R)-2-hydroxypropyl]-7-thia-9,11-diazatricyclo[6.4.0.0[2,6]]dodeca-1(8),2 (6),9,11-tetraen-12-yl]oxy]cyclohexyl)-N-methylcarbamate (192.1, 170 mg, 33%) as a colorless oil and tert-butyl N-(4-[[(3R)-3-[(2S)-2-hydroxypropyl]-7-thia-9,11-diazatricyclo[6.4.0.0[2,6]]dodeca-1(8),2(6),9,11-tetraen-12-yl]oxy]cyclohexyl)-N-methylcarbamate (130 mg, 25%) as a colorless oil, respectively.

Synthesis of Compound I-109.

A 50-mL round-bottom flask was charged with a solution of tert-butyl N-(4-[[(3R)-3-[(2R)-2-hydroxypropyl]-7-thia-9,11-diazatricyclo[6.4.0.0[2,6]]dodeca-1(8),2(6),9,11-tetraen-12-yl]oxy]cyclohexyl)-N-methylcarbamate (170 mg, 0.38 mmol, 1.0 equiv) in 5.5 mL of dichloromethane cooled to 0° C. Then hydrochloric acid (12 M, 0.5 mL) was added and the resulting solution was stirred for 3 h at room temperature. The reaction mixture was concentrated under reduced pressure to give (2R)-1-[(3R)-12-[[4-(methylamino)cyclohexyl]oxy]-7-thia-9,11-diazatricyclo[6.4.0.0[2,6]]dodeca-1(8),2 (6),9,11-tetraen-3-yl]propan-2-ol hydrochloride (130 mg, crude) as a light yellow oil. The resulting hydrochloride (130 mg, crude) was dissolved in DMF (5 mL). Potassium carbonate (359 mg) and 2-chloro-1-(pyrrolidin-1-yl)ethan-1-one (125 mg) were added at room temperature and the resulting mixture was stirred for 14 h at 25° C. After completion of the reaction, the product was extracted with DCM, washed with brine and concentrated in vacuo. The crude product (160 mg) was purified by preparative HPLC under the following conditions (SHIMADZU): Column: SunFire Prep C18, 19*150 mm, 5 μm; mobile phase: water (with 0.1% HCOOH) and $CH_3CN$ (6.0% $CH_3CN$ up to 50.0% in 25 min); UV detection at 254/220 nm. The product containing fractions were collected and evaporated to remove the water and $CH_3CN$ to give 2-[(4-[[(3R)-3-[(2R)-2-hydroxypropyl]-7-thia-9,11-diazatricyclo[6.4.0.0[2,6]]dodeca-1(8),2(6),9,11-tetraen-12-yl]oxy]cyclohexyl)(methyl)amino]-1-(pyrrolidin-1-yl)ethan-1-one (52.7 mg) as a white solid. MS (ES): m/z 473 (M+H)$^+$. $^1$H NMR (400 MHz, $CD_3OD$): δ 8.46 (1H, s), 5.32-5.18 (1H, m), 3.94-3.92 (1H, m), 3.57 (2H, t), 3.45 (2H, t), 3.36 (3H, m), 3.08-3.10 (1H, m), 2.96-2.98 (1H, m), 2.67-2.62 (2H, m), 2.41-2.29 (6H, m), 2.070-1.97 (5H, m), 1.95-1.87 (2H, m), 1.64-1.52 (5H, m), 1.30 (3H, d).

Example 194

Synthesis of 2-[(3R)-12-[[4-(dimethylamino)cyclohexyl]amino]-7-thia-9,11-diazatricyclo[6.4.0.0[2,6]]dodeca-1(12),2(6),8,10-tetraen-3-yl]acetamide (I-99)

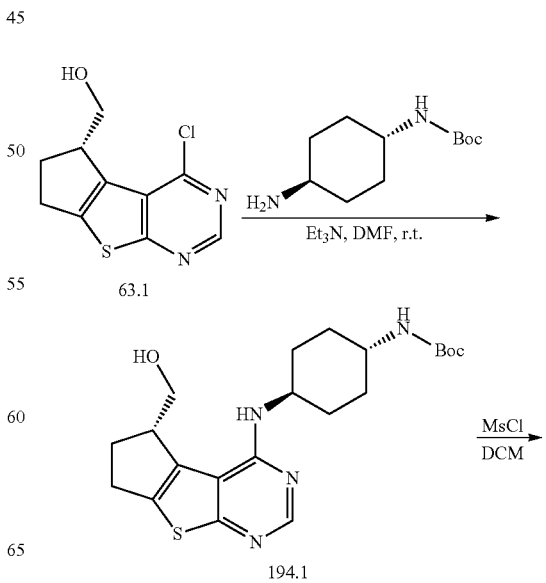

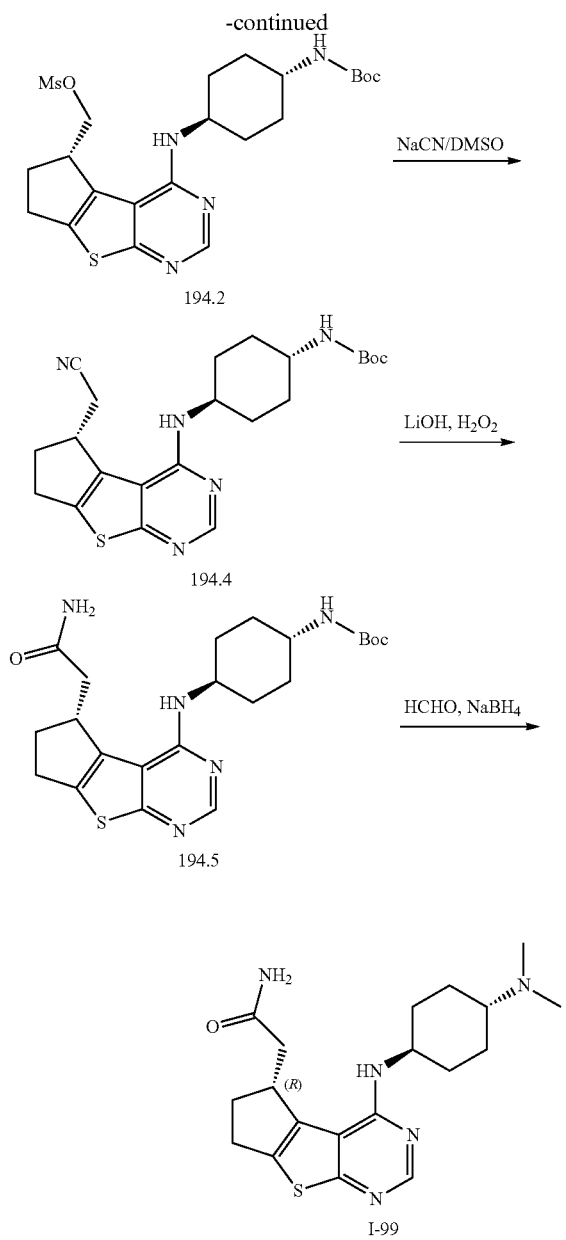

Synthesis of Compound 194.1.

To a solution of [(3S)-12-chloro-7-thia-9,11-diazatricyclo[6.4.0.0[2,6]]dodeca-1(8),2(6),9,11-tetraen-3-yl]methanol (300 mg, 1.25 mmol, 1.00 equiv) and tert-butyl N-(4-aminocyclohexyl)carbamate (801 mg, 3.74 mmol, 3.00 equiv) in N,N-dimethylformamide (10 mL) was added triethylamine (1.7 mL, 10.00 equiv). The resulting solution was stirred overnight at 50° C. The reaction was then quenched by the addition of 50 mL of water. The resulting solution was extracted with 2×50 mL of ethyl acetate and the organic layers combined and concentrated under vacuum. The residue was applied onto a silica gel column with ethyl acetate/petroleum ether (1:10-1:5). This resulted in 400 mg (77%) of tert-butyl N-(4-[[(3S)-3-(hydroxymethyl)-7-thia-9,11-di azatricyclo[6.4.0.0[2,6]]dodeca-1(12),2(6),8,10-tetraen-12-yl]amino]cyclohexyl)carbamate as a light yellow solid.

Synthesis of Compound 194.2.

To a solution of tert-butyl N-(4-[[(3S)-3-(hydroxymethyl)-7-thia-9,11-diazatricyclo[6.4.0.0[2,6]]dodeca-1(12),2(6),8,10-tetraen-12-yl]amino]cyclohexyl)carbamate (400 mg, 0.96 mmol, 1.00 equiv) and triethylamine (0.27 mL, 2.00 equiv) in dichloromethane (20 mL) was added dropwise MsCl (164 mg, 1.43 mmol, 1.50 equiv). The resulting solution was stirred for 2 h at room temperature. The reaction was then quenched by the addition of 50 mL of water. The resulting solution was extracted with 2×40 mL of ethyl acetate and the organic layers combined and concentrated under vacuum. The residue was applied onto a silica gel column with ethyl acetate/petroleum ether (1:10). Purification afforded 379 mg (80%) of tert-butyl N-(4-[[(3S)-3-[(methanesulfonyloxy)methyl]-7-thia-9,11-diazatricyclo[6.4.0.0[2,6]]dodeca-1(12),2(6),8,10-tetraen-12-yl]amino]cyclohexyl)carbamate as a light yellow oil.

Synthesis of Compound 194.3.

To a solution of tert-butyl N-(4-[[(3S)-3-[(methanesulfonyloxy)methyl]-7-thia-9,11-diazatricyclo[6.4.0.0[2,6]]dodeca-1(12),2(6),8,10-tetraen-12-yl]amino]cyclohexyl)carbamate (379 mg, 0.76 mmol, 1.00 equiv) in DMSO (8 mL) was added NaCN (112.2 mg, 2.29 mmol, 5.00 equiv). The resulting solution was stirred for 5 h at 80° C. The reaction was then quenched by the addition of 50 mL of water. The resulting solution was extracted with 2×40 mL of ethyl acetate and the organic layers combined and concentrated under vacuum. The residue was applied onto a silica gel column with ethyl acetate/petroleum ether (1:10). This resulted in 260 mg (80%) of tert-butyl N-(4-[[(3R)-3-(cyanomethyl)-7-thia-9,11-diazatricyclo[6.4.0.0[2,6]]dodeca-1(12),2(6),8,10-tetraen-12-yl]amino]cyclohexyl)carbamate as a yellow oil.

Synthesis of Compound 194.4.

To a solution of tert-butyl N-(4-[[(3R)-3-(cyanomethyl)-7-thia-9,11-diazatricyclo[6.4.0.0[2,6]]dodeca-1(12),2(6),8,10-tetraen-12-yl]amino]cyclohexyl)carbamate (260 mg, 0.61 mmol, 1.00 equiv) and LiOH.H$_2$O (76.6 mg, 1.82 mmol, 3.00 equiv) in methanol (10 mL) was added H$_2$O$_2$ (37%, 1 mL). The resulting solution was stirred for 3 h at room temperature. The reaction was then quenched by the addition of 50 mL of Na$_2$SO$_3$ (aq.). The resulting solution was extracted with 3×40 mL of ethyl acetate and the organic layers combined and concentrated under vacuum. The residue was applied onto a silica gel column with dichloromethane/methanol (30:1). This resulted in 187 mg (69%) of tert-buty N-(4-[[(3R)-3-(carbamoylmethyl)-7-thia-9,11-diazatricyclo[6.4.0.0[2,6]]dodeca-1(12),2(6),8,10-tetraen-12-yl]amino]cyclohexyl)carbamate as a light yellow solid.

Synthesis of Compound I-99.

To a solution of tert-butyl N-(4-[[(3R)-3-(carbamoylmethyl)-7-thia-9,11-diazatricyclo[6.4.0.0[2,6]]dodeca-1(12),2(6),8,10-tetraen-12-yl]amino]cyclohexyl)carbamate (187 mg, 0.42 mmol, 1.00 equiv) in dichloromethane (5 mL) was added hydrogen chloride (12 M, 1 mL). The resulting solution was stirred for 2 h at room temperature. After evaporation, the residue was dissolved in CH$_3$OH (10 mL) and HCHO (1.5 mL) was added. The resulting solution was stirred for 1 h at room temperature. To the above solution was added NaBH$_3$CN (79 mg, 1.26 mmol, 3.00 equiv). The resulting solution was allowed to react, with stirring, overnight at room temperature. The reaction was then quenched by the addition of 10 mL of water. The resulting solution was extracted with 2×50 mL of dichloromethane and the organic layers combined. The crude product (100 mg) was purified by preparative HPLC under the following conditions: Column: Xbridge Prep C18, 5 μm, 19*150 mm; mobile phase, water (with 50 mL $NH_4CO_3$) and $CH_3CN$ (10.0% $CH_3CN$ up to 32.0% in 10 min, up to 95.0% in 1 min, down to 10.0% in 2 min); UV detection at 254 nm. This procedure afforded 50 mg (32%) of 2-[(3R)-12-[[4-(dimethylamino)cyclohexyl]amino]-7-thia-9,11-diazatricyclo[6.4.0.0[2,6]]dodeca-1(12),2(6),8,10-tetraen-3-yl]acetamide as a white solid. MS (ES): m/z 374 (M+H)$^+$. $^1$H NMR (300 MHz, $CD_3OD$): δ 1.35-1.60 (m, 4H), 1.95-2.04 (m, 2H), 2.09-2.10 (m, 2H), 2.28-2.38 (m, 7H), 2.40-2.45 (m, 3H), 2.68-2.80 (m, 1H), 2.89-2.30 (m, 1H), 3.05-3.15 (m, 1H), 4.05-4.15 (m, 1H), 3.87 (dd, J=14.1, 6.3 Hz, 1H), 8.23 (s, 1H).

Example 195

Synthesis of (2S)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]butan-2-ol (I-107) and Example 196: Synthesis of (2R)-1-[(3R)-12-[[4-(dimethylamino)cyclohexyl]oxy]-7-thia-9,11-diazatricyclo[6.4.0.0[2,6]]dodeca-1(8),2(6),9,11-tetraen-3-yl]butan-2-ol (I-106)

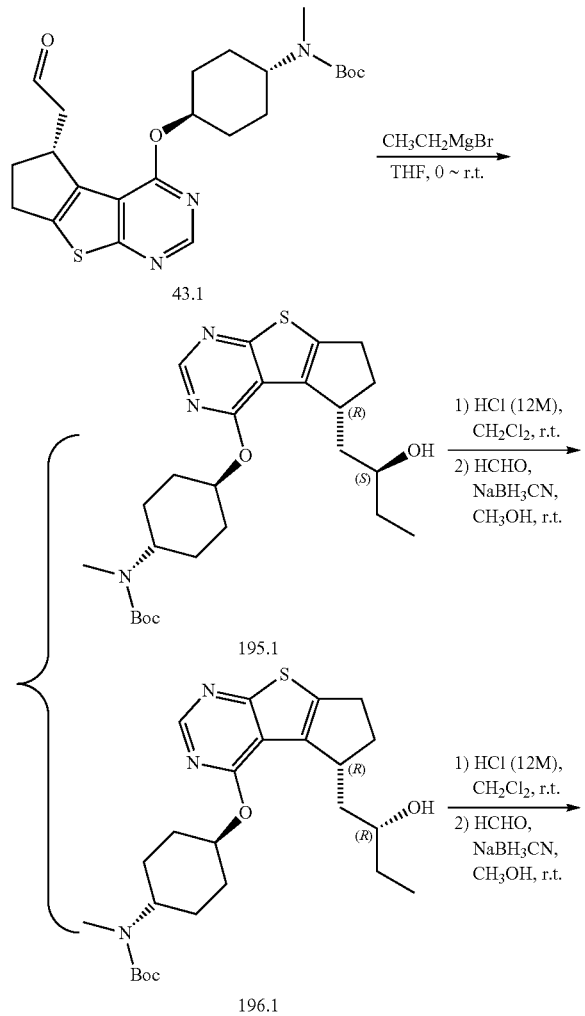

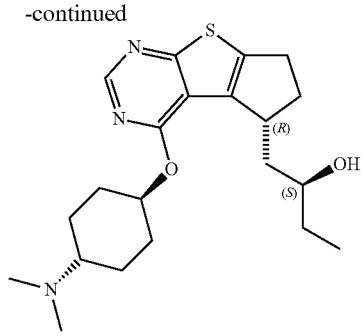

I-107

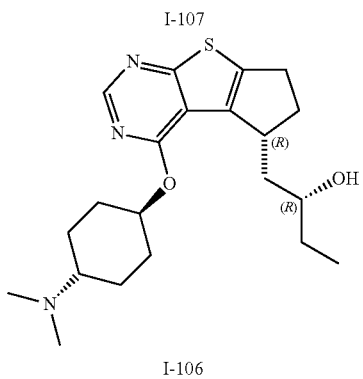

I-106

Synthesis of Compounds 195.1 and 196.1.

To a solution of tert-butyl N-methyl-N-(4-[[(3R)-3-(2-oxoethyl)-7-thia-9,11-diazatricyclo[6.4.0.0[2,6]]dodeca-1(8),2(6),9,11-tetraen-12-yl]oxy]cyclohexyl)carbamate (370 mg, 0.83 mmol, 1.00 equiv) in freshly distilled THF (15 mL) was added dropwise bromo(ethyl)magnesium (0.46 mL, 1.25 mmol, 1.50 equiv) at 0° C. under nitrogen. The resulting solution was stirred for 2 h at r.t and quenched by the addition of $H_2O$. The mixture was extracted with ethyl acetate, dried over anhydrous sodium sulfate and evaporated in vacuo. The residue was applied onto a silica gel column with ethyl acetate/petroleum ether (1:10-1:5) to give 0.11 g (56%) of tert-butyl N-(4-[[(3R)-3-[(2S)-2-hydroxybutyl]-7-thia-9,11-diazatricyclo[6.4.0.0[2,6]]dodeca-1(8),2(6),9,11-tetraen-12-yl]oxy]cyclohexyl)-N-methylcarbamate (195.1) as a light yellow oil and 0.16 g (81%) of tert-butyl N-(4-[[(3R)-3-[(2R)-2-hydroxybutyl]-7-thia-9,11-diazatricyclo[6.4.0.0[2,6]]dodeca-1(8),2(6),9,11-tetraen-12-yl]oxy]cyclohexyl)-N-methylcarbamate (196.1) as a light yellow oil.

Synthesis of Compound I-107.

To a solution of tert-butyl N-(4-[[(3R)-3-[(2S)-2-hydroxybutyl]-7-thia-9,11-diazatricyclo[6.4.0.0[2,6]]dodeca-1(8),2(6),9,11-tetraen-12-yl]oxy]cyclohexyl)-N-methylcarbamate (110 mg, 0.23 mmol, 1.00 equiv) in dichloromethane (7 mL) was added hydrochloric acid (12 M, 0.5 mL) at 0° C. The resulting solution was stirred for 2 h at room temperature. The solvent was removed under reduced pressure to give (2S)-1-[(3R)-12-[[4-(methylamino)cyclohexyl]oxy]-7-thia-9,11-diazatricyclo[6.4.0.0[2,6]]dodeca-1(8),2(6),9,11-tetraen-3-yl]butan-2-ol hydrochloride (90 mg, crude), which was used in the next step directly without further purification. The hydrochloride salt thus obtained (90 mg) was dissolved in methanol (8 mL). Then HCHO (37%, 1 mL) was added and the mixture was stirred at room temperature for 1 h. This was followed by the addition of $NaBH_3CN$ (41 mg, 0.65 mmol, 2.99 equiv). The resulting solution was stirred overnight at room temperature and quenched by the addition of water. The mixture was extracted with 3×10 mL of dichloromethane and the organic layers combined and concentrated under vacuum. The crude product (80 mg) was purified by preparative HPLC under the following conditions (Waters): Column: SunFire Prep C18, 19*150 mm, 5 μm; mobile phase: water (with 0.05% NH$_4$HCO$_3$) and CH$_3$CN (7.0% CH$_3$CN up to 60.0% in 14 min); flow rate: 20 mL/min; UV detection at 254/220 nm. The product-containing fractions were collected and partially evaporated to remove water and CH$_3$CN under reduced pressure. The residue was lyophilized overnight to give the corresponding 48.4 mg (57%) of (2S)-1-[(3R)-12-[[4-(dimethylamino)cyclohexyl]oxy]-7-thia-9,11-diazatricyclo[6.4.0.0 [2,6]]dodeca-1(8),2(6),9,11-tetraen-3-yl]butan-2-ol as a light yellow semi-solid. MS (ES): m/z 390 (M+H)$^+$. $^1$H NMR (400 MHz, CD$_3$OD): δ 8.46 (1H, s), 5.26-5.31 (1H, m), 3.61-3.63 (2H, m), 3.05-3.15 (1H, m), 2.95-3.00 (1H, m), 2.60-2.71 (1H, m), 2.25-2.50 (10H, m), 2.10-2.20 (1H, m), 2.00-2.08 (2H, m), 1.65-1.75 (2H, m), 1.40-1.52 (5H, m), 0.97 (3H, t).

Synthesis of Compound I-106.

Compound I-106 was prepared in a manner consistent with I-107, except that compound 196.1 was used rather than 195.1. 66.1 mg (58%) of I-106 were obtained as a light yellow semi-solid. MS (ES): m/z 390 (M+H)$^+$. $^1$H NMR (400 MHz, CD$_3$OD): δ 8.48 (1H, s), 5.23-5.35 (1H, m), 3.60-3.70 (1H, m), 3.35-3.40 (1H, m), 3.10-3.15 (1H, m), 2.90-3.00 (1H, m), 2.60-2.70 (1H, m), 2.30-2.50 (10H, m), 2.00-2.15 (3H, m), 1.30-1.75 (7H, m), 1.05 (3H, t).

Example 197

Synthesis of (2S)-1-[(3R)-12-[[4-(dimethylamino)-4-ethylcyclohexyl]oxy]-7-thia-9,11-diazatricyclo[6.4.0.0[2,6]]dodeca-1(8),2(6),9,11-tetraen-3-yl]butan-2-ol (I-104)

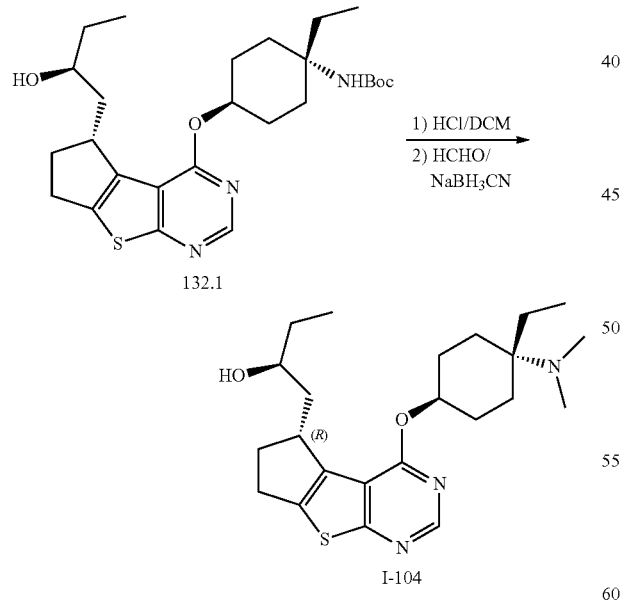

Compound I-104 was prepared in a manner consistent with Compound I-101, except that compound 132.1 was used rather than 132.2. I-104 was obtained as an off-white solid (13.6 mg, 5.4% overall yield). MS (ES): m/z 418 (M+H)$^+$. $^1$H NMR (300 MHz, CD$_3$OD): δ 8.474 (1H, s), 333-5.42 (1H, m), 3.48-3.68 (2H, m), 3.00-3.14 (1H, m), 2.92-2.98 (1H, m), 2.70-2.73 (1H, m), 2.31-2.55 (6H, m), 2.06-2.11 (3H, m), 1.60-2.00 (8H, m), 1.26-1.58 (4H, m), 0.91-1.07 (6H, m).

Example 198

Synthesis of 2-[(3R)-12-[[4-(morpholin-4-yl)cyclohexyl]amino]-7-thia-9,11-diazatricyclo[6.4.0.0ˆ[2,6]]dodeca-1(12),2(6),8,10-tetraen-3-yl]acetamide (I-97)

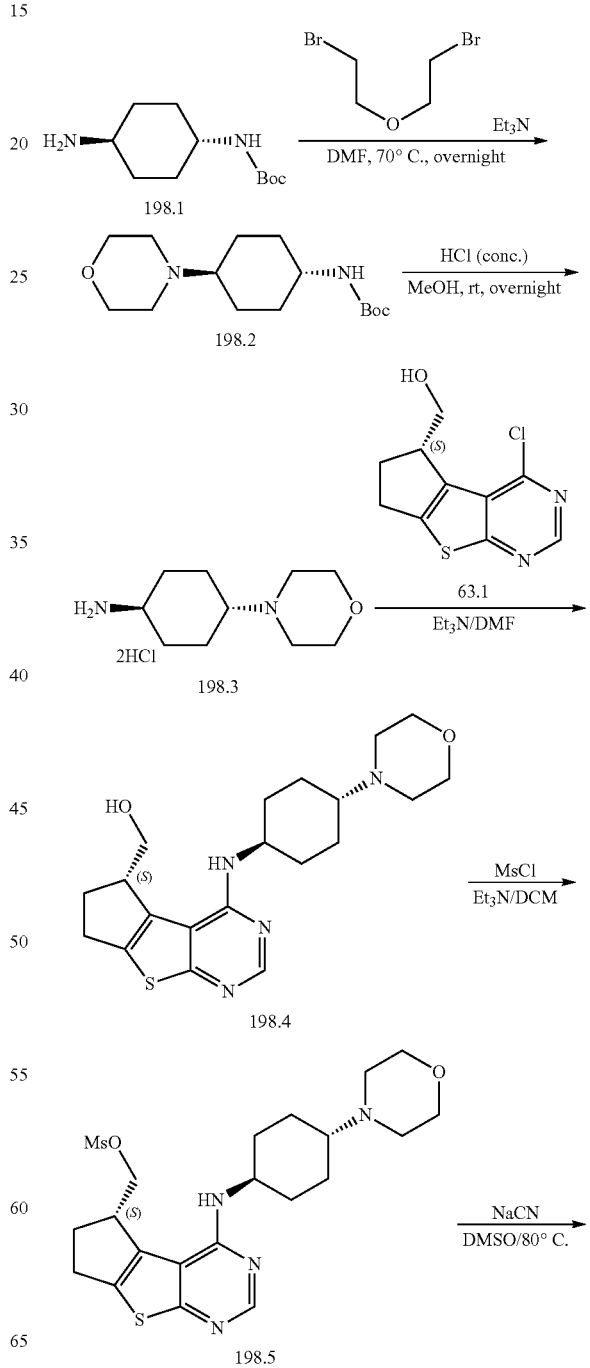

198.6

I-97

Synthesis of Compound 198.2.

To a solution of tert-butyl N-(4-aminocyclohexyl)carbamate (1.07 g, 4.99 mmol, 1.00 equiv) in DMF (10 mL) was added triethylamine (1.26 g, 12.48 mmol, 2.50 equiv) and 1-bromo-2-(2-bromoethoxy)ethane (1.4 g, 6.04 mmol, 1.20 equiv). The resulting solution was stirred overnight at 70° C. The resulting solution was diluted with ethyl acetate (100 mL), washed with brine (100 mL), dried over anhydrous sodium sulfate and concentrated under vacuum to give 1.2 g (crude) of tert-butyl N-[4-(morpholin-4-yl)cyclohexyl]carbamate as a light yellow solid. MS (ES): m/z 285 (M+H)$^+$.

Synthesis of Compound 198.3.

To a solution of tert-butyl N-[4-(morpholin-4-yl)cyclohexyl]carbamate (1.0 g, 3.52 mmol, 1.00 equiv) in methanol (5 mL) was added concentrated hydrochloric acid (1.5 mL) at 0° C. The resulting solution was stirred overnight at room temperature. To this mixture was slowly added ether (50 mL). The precipitates were collected by filtration and dried in an oven to give 4-(morpholin-4-yl)cyclohexan-1-amine dihydrochloride (500 mg, 55%) as a white solid.

Synthesis of Compound 198.4.

To a 100 mL round-bottom flask containing a solution of [(3S)-12-chloro-7-thia-9,11-diazatricyclo[6.4.0.0[2,6]]dodeca-1(12),2(6),8,10-tetraen-3-yl]methanol (100 mg, 0.42 mmol, 1.00 equiv) in anhydrous DMF (8 mL) was added triethylamine (372 mg, 3.68 mmol, 9.00 equiv) and 4-(morpholin-4-yl)cyclohexan-1-amine hydrochloride (214 mg, 0.83 mmol, 2.00 equiv) at room temperature. The resulting solution was stirred overnight at 80° C. After cooling, the resulting solution was diluted with DCM (50 mL), washed with brine, dried over anhydrous sodium sulfate and concentrated under vacuum to obtain 130 mg (81%) of [(3S)-12-[[4-(morpholin-4-yl)cyclohexyl]amino]-7-thia-9,11-diazatricyclo[6.4.0.0[2,6]]dodeca-1(12),2(6),8,10-tetraen-3-yl]methanol as a yellow oil. MS (ES): m/z 389 (M+H)$^+$.

Synthesis of Compound 198.5.

To a solution of [(3S)-12-[[4-(morpholin-4-yl)cyclohexyl]amino]-7-thia-9,1'-diazatricyclo[6.4.0.0[2,6]]dodeca-1(12),2(6),8,10-tetraen-3-yl]methanol (130 mg, 0.33 mmol, 1.00 equiv) in dichloromethane (5 mL) was added MsCl (57 mg, 0.50 mmol, 1.50 equiv) and triethylamine (100 mg, 0.99 mmol, 3.00 equiv) at 0° C. The resulting solution was stirred for 2 h at room temperature and diluted with DCM (30 mL). the organic layer was washed with brine, dried over anhydrous sodium sulfate and concentrated under vacuum to obtain 140 mg (90%) of [(3S)-12-[[4-(morpholin-4-yl)cyclohexyl]amino]-7-thia-9,1'-diazatricyclo[6.4.0.0[2,6]]dodeca-1(12),2(6),8,10-tetraen-3-yl]methyl methanesulfonate as a yellow oil. MS (ES): m/z 467 (M+H)$^+$.

Synthesis of Compound 198.6.

To a solution of [(3S)-12-[[4-(morpholin-4-yl)cyclohexyl]amino]-7-thia-9,1'-diazatricyclo[6.4.0.0[2,6]]dodeca-1(12),2(6),8,10-tetraen-3-yl]methyl methanesulfonate (140 mg, 0.30 mmol, 1.00 equiv) in DMSO (5 mL) was added NaCN (88 mg, 1.80 mmol, 6.00 equiv) at room temperature. The resulting solution was stirred for 2 h at 80° C. After cooling, the resulting solution was diluted with DCM (30 mL), washed with brine, dried over anhydrous sodium sulfate and concentrated under vacuum to give 2-[(3R)-12-[[4-(morpholin-4-yl)cyclohexyl]amino]-7-thia-9,11-diazatricyclo[6.4.0.0[2,6]]dodeca-1(12),2(6),8,10-tetraen-3-yl]acetonitrile (90 mg, 84%) as a yellow oil. MS (ES): m/z 398 (M+H)$^+$.

Synthesis of Compound I-97.

To a solution of 2-[(3R)-12-[[4-(morpholin-4-yl)cyclohexyl]amino]-7-thia-9,11-diazatricyclo[6.4.0.0ˆ[2,6]]dodeca-1(12),2(6),8,10-tetraen-3-yl]acetonitrile (120 mg, 0.30 mmol, 1.00 equiv) in methanol (8 mL) was added LiOR.H$_2$O (37.8 mg, 0.90 mmol, 3.00 equiv) and H$_2$O$_2$ (30%, 0.5 mL) in an ice-water bath. The resulting solution was stirred for 2 h at room temperature and diluted with DCM (30 mL), washed with brine, dried over anhydrous sodium sulfate and concentrated under vacuum. The residue was applied onto a silica gel column with DCM/MeOH (20:1) to give 100 mg (80%) of 2-[(3R)-12-[[4-(morpholin-4-yl)cyclohexyl]amino]-7-thia-9,11-diazatricyclo[6.4.0.0ˆ[2,6]]dodeca-1(12),2(6),8,10-tetraen-3-yl]acetamide as a white solid. MS (ES): m/z 416 (M+H)$^+$. $^1$H NMR (400 MHz, CD$_3$OD): δ 8.23 (s, 1H), 4.11-4.20 (m, 1H), 3.82-3.89 (m, 1H), 3.72 (s, 4H), 3.09-3.17 (m, 1H), 2.93-2.99 (m, 1H), 2.70-2.82 (m, 1H), 2.65 (s, 4H), 2.47 (s, 2H), 2.27-2.35 (m, 2H), 2.11-2.19 (m, 2H), 2.05-2.10 (m, 2H), 1.40-1.67 (m, 4H).

Example 199

Synthesis of (2R)-1-[(3R)-12-[[4-(dimethylamino)-4-ethylcyclohexyl]oxy]-7-thia-9,11-diazatricyclo[6.4.0.0[2,6]]dodeca-1 (12),2(6),8,10-tetraen-3-yl]propan-2-ol (I-102)

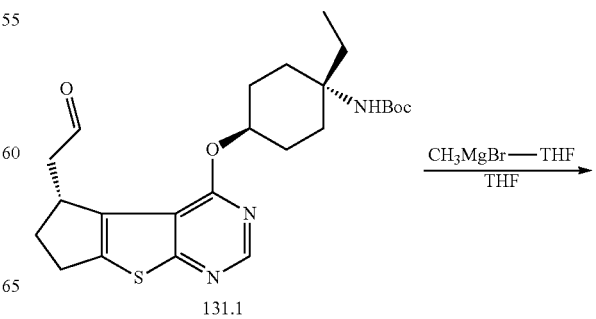

131.1

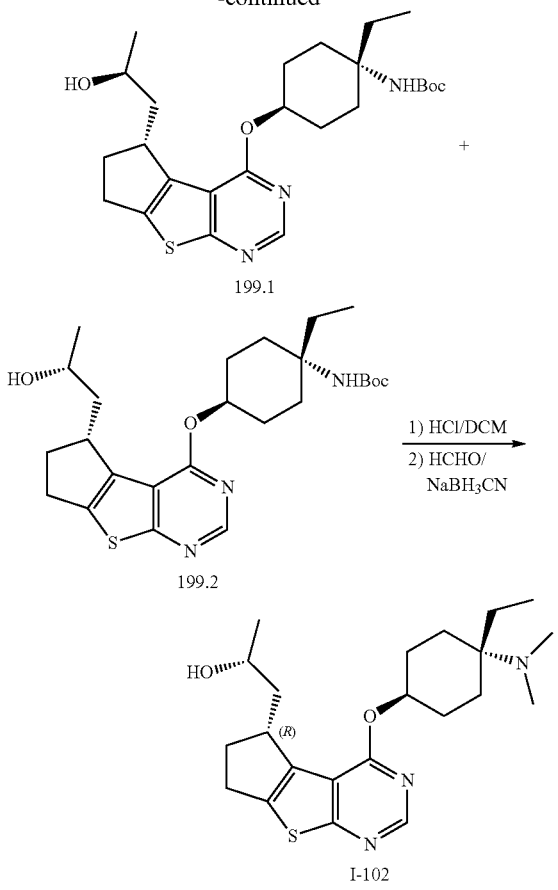

Synthesis of Compound 199.1 and 199.2.

Into a 100-mL round-bottom flask, purged and maintained under an inert atmosphere of nitrogen, was placed a solution of tert-butyl N-(1-ethyl-4-[[(3R)-3-(2-oxoethyl)-7-thia-9,11-diazatricyclo[6.4.0.0[2,6]]dodeca-1(12),2(6),8,10-tetraen-12-yl]oxy]cyclohexyl)carbamate (330 mg, 0.72 mmol, 1.00 equiv) in 10 mL of distilled tetrahydrofuran. This solution was cooled to 0° C. Then CH₃MgBr-THF (1 M, 1.5 mL) was added dropwise via syringe. The resulting solution was stirred for 2 h at this temperature. The reaction was then quenched by the addition of 10 mL of NH₄Cl (aq.) and extracted with 3×50 mL of ethyl acetate. The combined organic layers were washed with brine, dried over sodium sulfate and concentrated under vacuum. The residue was applied onto a silica gel column with ethyl acetate/petroleum ether (1:5) to give 160 mg (47%) of tert-butyl N-(1-ethyl-4-[[(3R)-3-[(2R)-2-hydroxypropyl]-7-thia-9,11-diazatricyclo[6.4.0.0[2,6]]dodeca-1(12),2(6),8,10-tetraen-12-yl]oxy]cyclohexyl)carbamate 199.2 as a white solid and 70 mg (20%) of tert-butyl N-(1-ethyl-4-[[(3R)-3-[(2S)-2-hydroxypropyl]-7-thia-9,11-diazatricyclo[6.4.0.0[2,6]]dodeca-1(12),2(6),8,10-tetraen-12-yl]oxy]cyclohexyl)carbamate 199.1 as a white solid.

Synthesis of Compound I-102.

A 50-mL round-bottom flask, purged and maintained with an inert atmosphere of nitrogen, was charged with a solution of tert-butyl N-(1-ethyl-4-[[(3R)-3-[(2R)-2-hydroxypropyl]-7-thia-9,11-diazatricyclo[6.4.0.0[2,6]]dodeca-1(12),2(6),8,10-tetraen-12-yl]oxy]cyclohexyl)carbamate (160 mg, 0.34 mmol, 1.00 equiv) in dichloromethane (6 mL) at 0° C. Then hydrochloric acid (conc., 0.5 mL) was added at this temperature and stirred for 2 h at room temperature. The reaction solution was concentrated under vacuum to give 150 mg (crude) of (2R)-1-[(3R)-12-[(4-amino-4-ethylcyclohexyl)oxy]-7-thia-9,11-diazatricyclo[6.4.0.0[2,6]]dodeca-1(12),2(6),8,10-tetraen-3-yl]propan-2-ol hydrochloride as a white solid.

This solid (150 mg, crude) was dissolved in methanol (6 mL) and HCHO (37%, 1.0 mL) was added at room temperature. After stirring for 30 min, NaBH₃CN (61.8 mg, 0.98 mmol, 3.21 equiv) was added and the resulting mixture was stirred for 5 h at room temperature. The solution was then diluted with 10 mL of water, extracted with 3×50 mL of CHCl₃/i-PrOH (3/1) and the combined organic layers were concentrated under vacuum. The crude product (100 mg) was purified by preparative HPLC under the following conditions (Waters): Column: SunFire Prep C18, 19*150 mm, 5 μm; mobile phase, water (with 0.05% NH₄HCO₃) and CH₃CN (5.0% CH₃CN up to 45.0% in 10 min, up to 95.0% in 2 min, down to 5.0% in 2 min); flow rate: 20 mL/min; UV detection at 254/220 nm. This resulted in 46.4 mg (38%) of (2R)-1-[(3R)-12-[[4-(dimethylamino)-4-ethylcyclohexyl]oxy]-7-thia-9,11-diazatricyclo[6.4.0.0[2,6]]dodeca-1(12),2(6),8,10-tetraen-3-yl]propan-2-ol as an off-white semi-solid. MS (ES): m/z 404 (M+H)⁺. ¹H NMR (300 MHz, CD₃OD): δ 8.48 (1H, s), 5.41 (1H, m), 3.95 (1H, m), 3.33 (1H, m), 3.08 (1H, m), 2.97 (1H, m), 2.64 (1H, m), 2.49 (1H, m), 2.32 (6H, m), 2.18 (1H, m), 2.06 (2H, m), 1.60-1.85 (9H, m), 1.30 (3H, d), 0.95 (2H, m).

Example 200

Synthesis of (2S)-1-[(3R)-12-[[4-(dimethylamino)-4-ethylcyclohexyl]oxy]-7-thia-9,11-diazatricyclo[6.4.0.0[2,6]]dodeca-1(12),2(6),8,10-tetraen-3-yl]propan-2-ol (I-103)

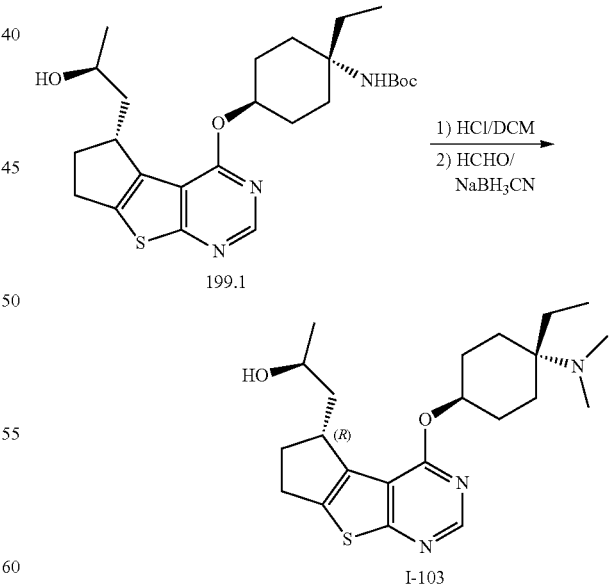

Into a 50-mL round-bottom flask containing a solution of tert-butyl N-(1-ethyl-4-[[(3R)-3-[(2S)-2-hydroxypropyl]-7-thia-9,11-diazatricyclo[6.4.0.0[2,6]]dodeca-1(12),2(6),8,10-tetraen-12-yl]oxy]cyclohexyl)carbamate (70 mg, 0.15 mmol, 1.00 equiv) in dichloromethane (3 mL) was added 12 M hydrochloric acid (0.3 mL) at 0° C. The resulting solution was stirred for 2 h at room temperature and concentrated under vacuum to give 60 mg (crude) of (2S)-1-[(3R)-12-[(4-amino-4-ethylcyclohexyl)oxy]-7-thia-9,11-diazatricyclo[6.4.0.0[2,6]]dodeca-1(12),2(6),8,10-tetraen-3-yl]propan-2-ol hydrochloride as a white solid.

This solid (60 mg, crude) was dissolved in 3 mL of methanol. HCHO (37%, 0.5 mL) was added followed by stirring for 30 min at room temperature. Then NaBH₃CN (27 mg, 0.43 mmol, 3.54 equiv) was added and stirring was continued for 5 h at ambient temperature. The resulting solution was diluted with 10 mL of water, extracted with 3×30 mL of trichloromethane/i-PrOH (3/1) and the combined organic layers were concentrated under vacuum. The crude product (50 mg) was purified by preparative HPLC under the following conditions (Waters): Column: SunFire Prep C18, 19*150 mm, 5 μm; mobile phase: water (with 0.05% $NH_4HCO_3$) and $CH_3CN$ (5.0% $CH_3CN$ up to 45.0% in 10 min, up to 95.0% in 2 min, down to 5.0% in 2 min); flow rate: 20 mL/min; UV detection at 254/220 nm. This procedure resulted in 11.3 mg (23%) of (2S)-1-[(3R)-12-[[4-(dimethylamino)-4-ethylcyclohexyl]oxy]-7-thia-9,11-diazatricyclo[6.4.0.0[2,6]]dodeca-1(12),2(6),8,10-tetraen-3-yl]propan-2-ol as a white solid. MS (ES): m/z 404 (M+H)⁺. ¹H NMR (300 MHz, $CD_3OD$): 8.48 (1H, s), 5.41 (1H, m), 3.95 (1H, m), 3.33 (1H, m), 3.08 (1H, m), 2.97 (1H, m), 2.64 (1H, m), 2.49 (1H, m), 2.32 (6H, m), 2.18 (1H, m), 2.06 (2H, m), 1.60-1.85 (9H, m), 1.30 (3H, d), 0.95 (2H, m).

Example 201

Synthesis of ((R)-4-(((1r,4R)-4-(dimethylamino)cyclohexyl)oxy)-6,7-dihydro-5H-cyclopenta[4,5]thieno[2,3-d]pyrimidin-5-yl)methanol (I-19) and ((S)-4-(((1r,4S)-4-(dimethylamino)cyclohexyl)oxy)-6,7-dihydro-5H-cyclopenta[4,5]thieno[2,3-d]pyrimidin-5-yl)methanol (I-20), and Separation of Chiral Compounds

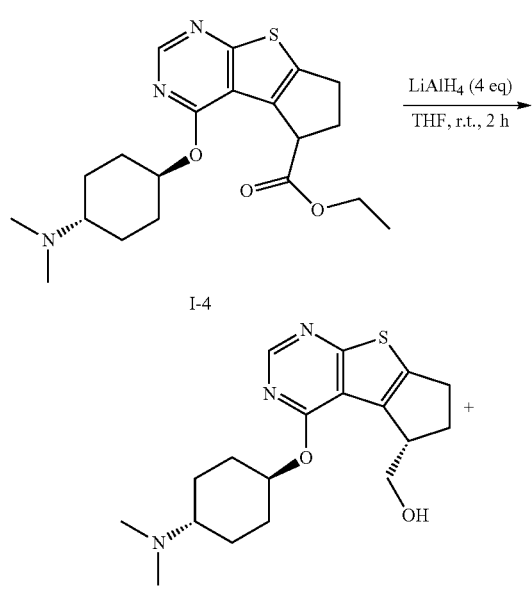

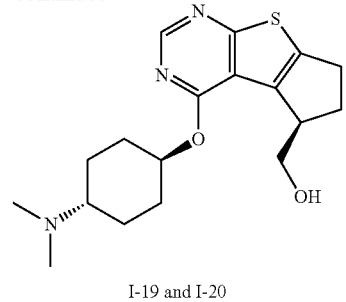

I-19 and I-20

To a solution of 1-4 (1.3 g, 3.3 mmol) in THF (30 mL) was added LiAlH₄ (508 mg, 13.3 mmol) in portions at 0° C. The mixture was allowed to warm to r.t. with stirring for 2 hours, and then $Na_2SO_4 \cdot 10H_2O$ (4.3 g, 13.3 mmol) was added. The suspension was stirred for 2 hours and then filtrated and the filtrate was purified by silica gel column chromatography with MeOH/DCM=1:10 to give a white solid product (810 mg, 70%). The product (550 mg) was resolved by Chiral-HPLC using the following conditions: Instrument: Thar SFC Prep 80 (Thar Technologies, Waters); Column: ChiralPak AD-H, 50 mm I.D.×250 mm Length, 5 μm (Daicel Chemical Industries Co., Ltd); Column Temperature: 35; Mobile Phase: $CO_2$/MeOH/DEA=70/30/0.1; Flow rate: 80 g/min; Back Pressure: 100 Bar; Wavelength: 214 nm; Cycle time: 7.0 min; Injection Volume: 1.0 mL; Feed solution: 550 mg dissolved in 14 mL MeOH. The solvent was concentrated under vacuum to obtain 150 mg I-19 and 150 mg I-20.

Example 202

Synthesis of (12S)-3-[[(1r,4r)-4-(morpholin-4-yl)cyclohexyl]oxy]-8-thia-4,6-diazatricyclo[7.4.0.0[2,7]]trideca-1 (9),2(7),3,5-tetraene-12-carboxylic acid (I-234)

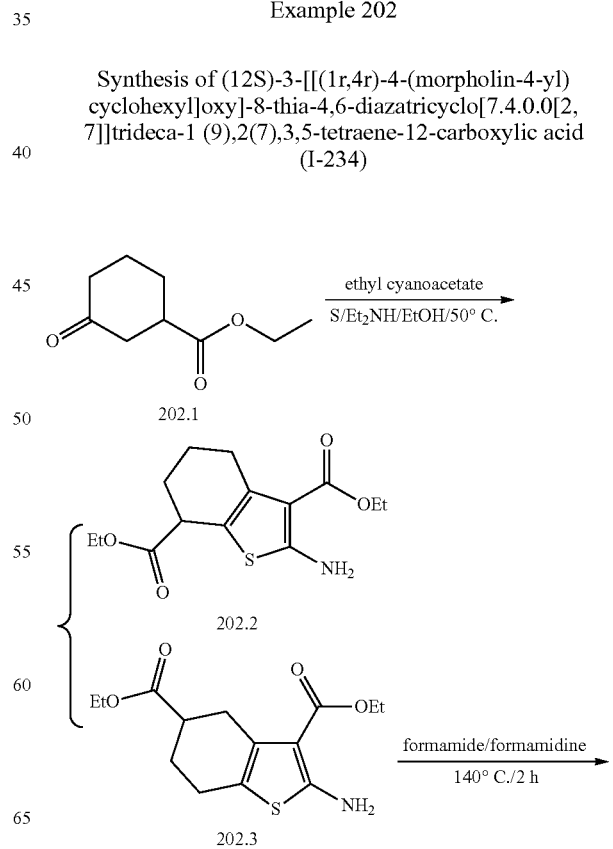

-continued

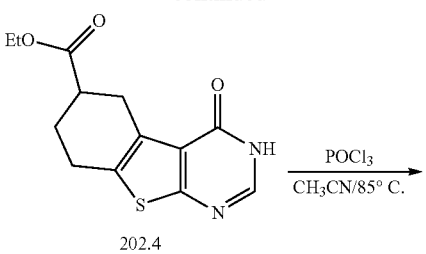
202.4

POCl₃ / CH₃CN/85° C.

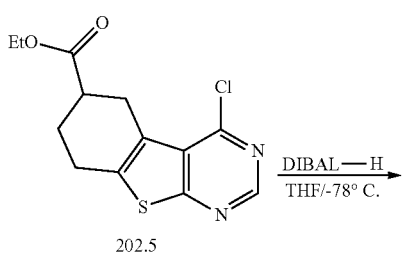
202.5

DIBAL—H / THF/-78° C.

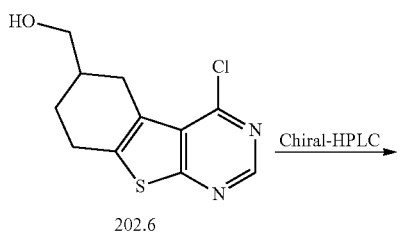
202.6

Chiral-HPLC

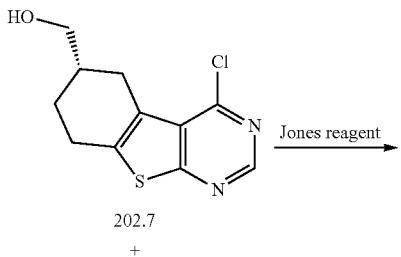
202.7
+
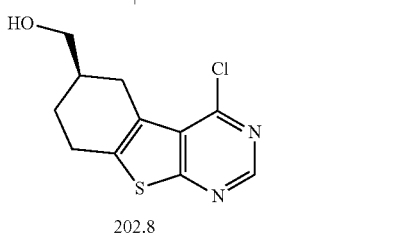
202.8

Jones reagent

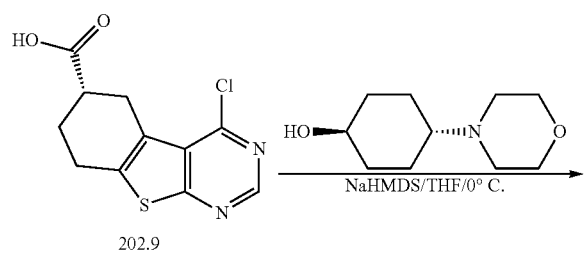
202.9

NaHMDS/THF/0° C.

-continued

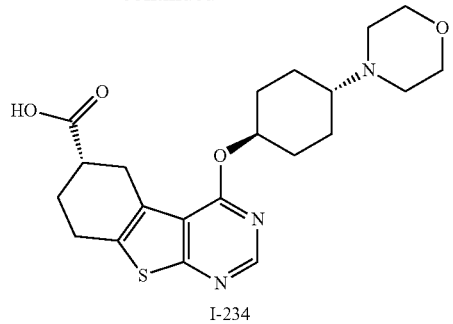
I-234

Synthesis of Compound 202.6.

Compound 202.6 was prepared from 202.1 in a manner analogous to the synthesis of 153.7 from 153.3. Isolated 954 mg of a colorless oil in 61% overall yield.

Synthesis of Compound 202.7.

The enantiomers of 202.6 (1.25 g) were separated by preparative chiral HPLC under the following conditions: Column: Chiralpak IC, 2*25 cm, 5 μm; mobile phase: hexane and EtOH (85:15); flow rate: 20 mL/min; UV detection at 254/220 μm. The desired isomer-containing fractions were collected and evaporated to remove solvent under reduced pressure to give 448 mg of 202.8 (tR=14.68 min) and 404 mg of 202.7 (tR=16.12 min) respectively. The ee was found to be 98.7% ee for 202.7 (tR=7.71 min) and 100% ee for 202.8 (tR=9.59 min) as determined by analytical chiral HPLC under the following conditions: Column: Lux Cellulose-4, 0.46*15 cm, 5 μm, 4.6*250 mm, 5 μm; mobile phase: Hex:IPA=80:20; flow rate: 1 mL/min; UV detection at 254 μm.

Analytical data for 202.7: MS (ES): m/z 255 (M+H)+. 1H-NMR (300 MHz, CDCl₃): δ 8.75 (1H, s), 3.81-3.69 (2H, m), 3.38 (1H, dd, J=16.8, 5.1 Hz), 3.05-2.82 (2H, m), 2.78-2.64 (1H, m), 2.20-2.07 (2H, m), 1.69-1.61 (1H, m).

Analytical data for 202.8: MS (ES): m/z 255 (M+H)+. 1H-NMR (300 MHz, CDCl₃): δ 8.75 (1H, s), 3.81-3.69 (2H, m), 3.38 (1H, dd, J=16.8, 5.1 Hz), 3.05-2.82 (2H, m), 2.78-2.64 (1H, m), 2.20-2.07 (2H, m), 1.69-1.61 (1H, m).

Synthesis of Compound 202.9.

To a solution of 202.7 (253 mg, 0.99 mmol, 1.00 equiv) in acetone (10 mL) was added dropwise Jones reagent (2 mL) at 0° C. The resulting mixture was stirred for 20 min at this temperature, quenched with aqueous saturated NaHSO₃ and extracted with EtOAc (2×100 mL). The combined organic layers were washed with brine, dried over anhydrous sodium sulfate and concentrated under vacuum to yield 247 mg (93%) of 201.9 as a white solid.

Synthesis of Compound I-234.

Into a 50-mL 3-necked round-bottom flask purged and maintained with an inert atmosphere of nitrogen, was placed a solution of 4-(morpholin-4-yl)cyclohexan-1-ol (111 mg, 0.60 mmol, 1.20 equiv) in 5 mL of distilled THF at 0° C. This was followed by the addition of NaHMDS (0.75 mL, 2 M in THF) dropwise via a syringe and stirring for 30 min. To a solution of 202.9 (135 mg, 0.50 mmol, 1.00 equiv) in 2 mL of THF was added and the resulting solution was stirred for 2 h at 0° C. The reaction was then quenched by the addition of 5 mL of water and the pH value of the solution was adjusted to 5 with 1 M hydrochloric acid and extracted with 5×10 mL of chloroform/i-PrOH (3:1). The combined organic layers were dried over anhydrous sodium sulfate and concentrated under vacuum to give the resultant I-234 (200 mg, crude) as a white solid. MS (ES): m/z 418 (M+H)+. ¹H-NMR (400 MHz, CDCl₃): δ 8.48 (1H, s), 5.25-5.12 (1H, m), 3.87 (4H, brs), 3.30 (1H, dd), 3.08-2.74 (9H, m), 2.45-2.25 (3H, m), 2.19-1.88 (3H, m), 1.80-1.50 (4H, m).

Example 203

Synthesis of (12S)-3-[[4-(morpholin-4-yl)cyclohexyl]oxy]-8-thia-4,6-diazatricyclo[7.4.0.0[2,7]]trideca-1(9),2(7),3,5-tetraene-12-carboxamide (I-220)

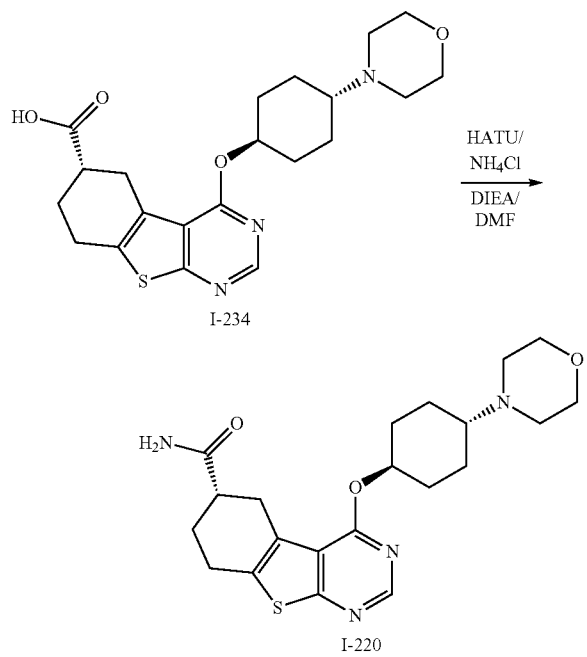

Synthesis of Compound I-220.

Compound I-220 was prepared from I-234 (Example 202) in a manner consistent with the synthesis of I-13 from 4.1. Isolated 79.6 mg of a white solid in 38% yield. MS (ES): m/z 417 (M+H)+. $^1$H NMR (300 MHz, CD$_3$OD): δ 8.45 (1H, s), 5.30-5.22 (1H, m), 3.74-3.71 (4H, t), 3.33-3.26 (1H, m), 3.09-2.97 (3H, m), 2.87-2.70 (1H, m), 2.65-2.62 (4H, t), 2.45-2.30 (3H, m), 2.23-2.18 (1H, m), 2.11-2.07 (2H, m), 2.07-1.91 (1H, m), 1.64-1.44 (4H, m).

Example 204

Synthesis of 2-[(3S)-12-[[4-(dimethylamino)cyclohexyl]oxy]-10-[(1-methyl-1H-pyrazol-4-yl)amino]-7-thia-9,11-diazatricyclo[6.4.0.0[2,6]]dodeca-1(8),2(6),9,11-tetraen-3-yl]acetamide (I-224)

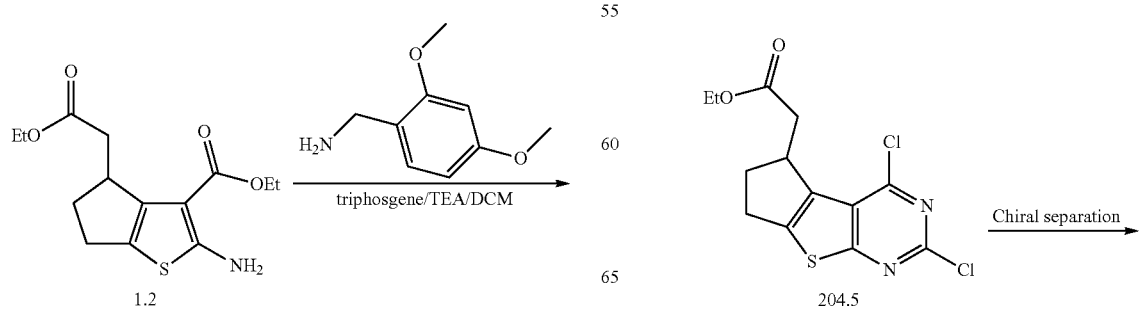

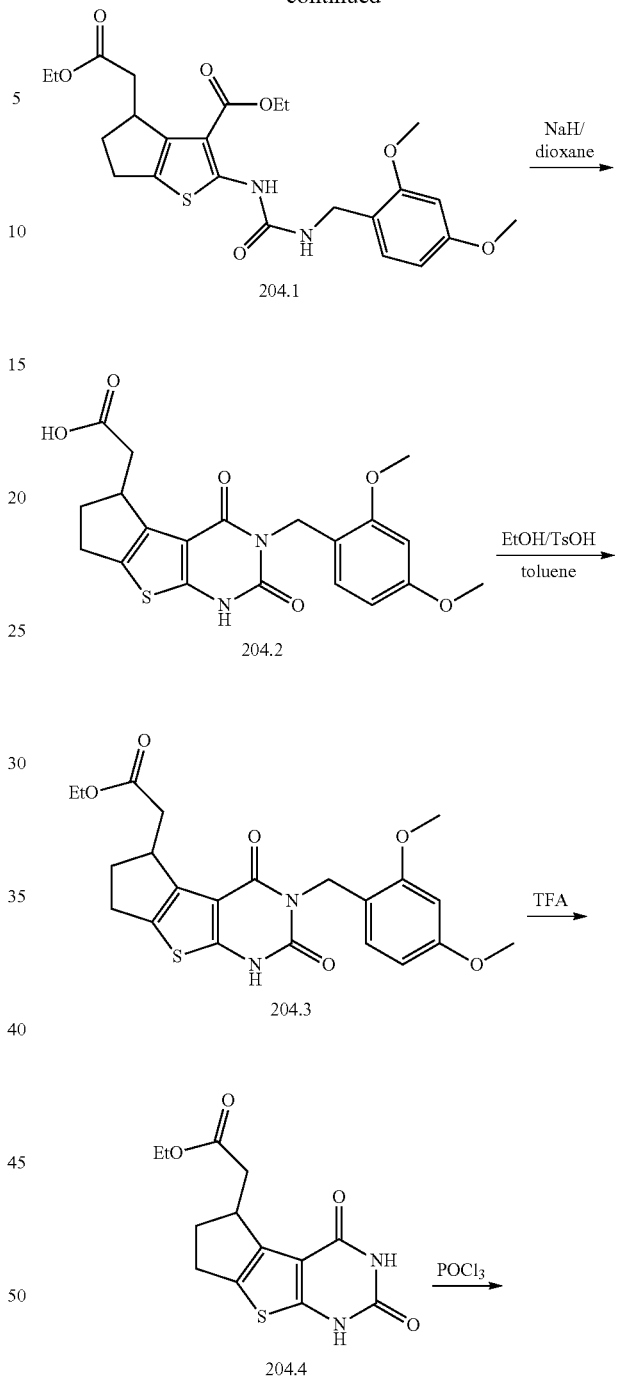

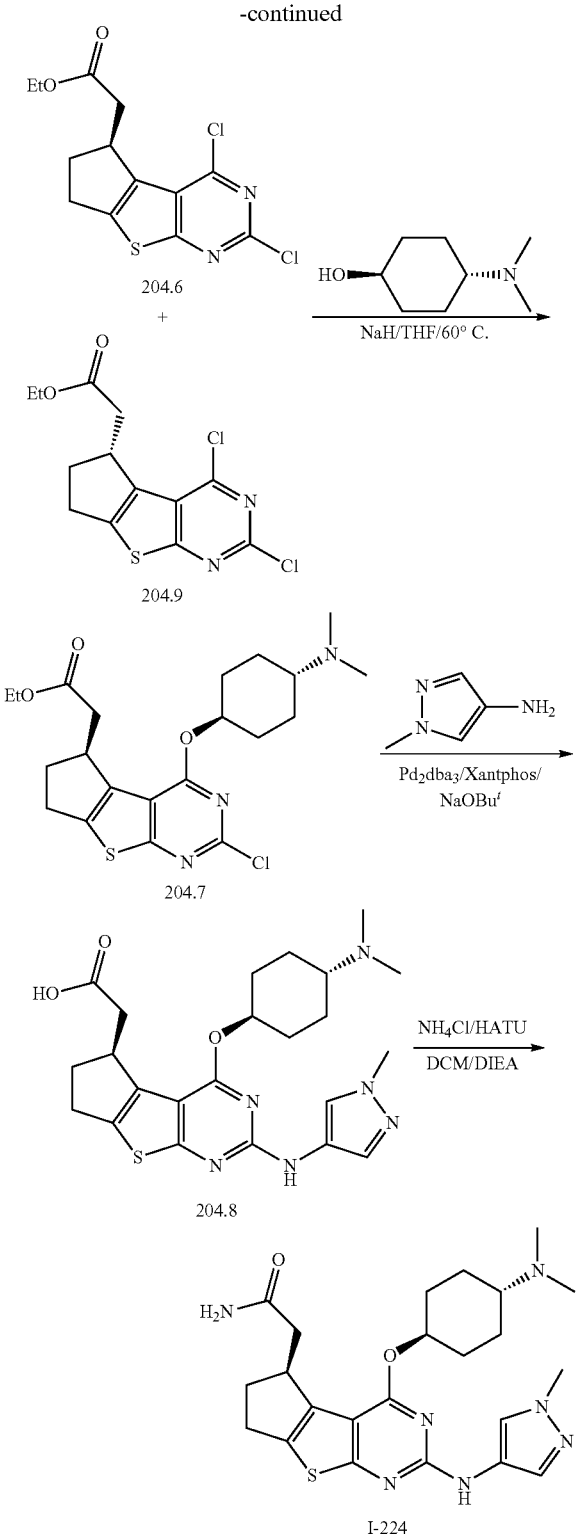

Synthesis of Compound 204.1.

To a solution of triphosgene (2.205 g, 7.43 mmol, 1.0 equiv) in 80 mL of anhydrous DCM was added a solution of 1.2 (4.455 g, 14.98 mmol, 2.00 equiv) in DCM (20 mL) dropwise with stirring at 0° C., followed by addition of TEA (3.8 g, 37.43 mmol, 5.0 equiv) via syringe under nitrogen. The resulting solution was stirred for 1 h at room temperature. To the mixture was added (2,4-dimethoxyphenyl)methanamine (5.01 g, 29.96 mmol, 4.00 equiv) and the resulting solution was allowed to react, with stirring, for an additional 1 h at ambient temperature. The solids were filtered out, washed with 2×100 mL of DCM and the filtrate was concentrated under vacuum. The residue was applied onto a silica gel column with ethyl acetate/petroleum ether (1:5) to give 204.1 (4.5 g, 61%) as a yellow solid.

Synthesis of Compound 204.2.

Sodium hydride (2.2 g, 55.00 mmol, 3.00 equiv, 60%) was treated with 204.1 (9.0 g, 18.35 mmol, 1.00 equiv) in 100 mL of dioxane overnight at 100° C. under nitrogen. After cooling, the reaction was then quenched with water and the pH value of the solution was adjusted to 4 with 4 M hydrochloric acid. The solids were collected by filtration and dried in an oven (45° C.) to yield 6.2 g (81%) of 204.2 as an off-white solid.

Synthesis of Compound 204.3.

To a solution of 204.2 (6.0 g, 14.41 mmol, 1.00 equiv), ethanol (10 mL) and 4-methylbenzene-1-sulfonic acid (800 mg, 4.65 mmol, 0.32 equiv) in toluene (110 mL) was stirred overnight at 120° C. After cooling, the reaction was quenched with aqueous saturated sodium bicarbonate and extracted with 2×200 mL of ethyl acetate. The combined organic layers were dried over sodium sulfate and concentrated under vacuum. The residue was applied onto a silica gel column with ethyl acetate/petroleum ether (1/2) to give 204.3 (6.0 g, 94%) as a yellow solid.

Synthesis of Compound 204.4.

To a solution of 204.3 (6.0 g, 13.4 mmol, 1.00 equiv) in 50 mL of trifluoroacetic acid was stirred for 4.5 h at 50° C. in an oil bath under nitrogen. After completion of the reaction, the resulting mixture was concentrated under vacuum to give 204.4 (4.5 g, crude) as a white solid.

Synthesis of Compound 204.5.

Into a 250-mL round-bottom flask was placed 204.4 (4.0 g, 13.59 mmol, 1.00 equiv) in POCl$_3$ (70 mL) under nitrogen and the resulting mixture was stirred overnight at 105° C. in an oil bath. The resulting mixture was concentrated under vacuum and the residue was diluted with 150 mL of EtOAc. The pH value of the solution was adjusted to 7-8 with saturated sodium bicarbonate and extracted with 2×150 mL of ethyl acetate. The organic layers were washed with brine, dried over anhydrous sodium sulfate and concentrated under vacuum. The residue was applied onto a silica gel column with ethyl acetate/petroleum ether (1:10) to give the desired 204.5 (1.95 g, 43%) as a light yellow solid.

Synthesis of Compound 204.6.

The enantiomers of 204.5 (2.3 g) were separated by chiral-SFC under the following conditions: Column: Phenomenex Lux 5 u Cellulose-3, 5*25 cm, 5 μm; mobile phase: 75% CO$_2$ and 25% MeOH (0.01 DEA); flow rate: 200 g/min; UV detection at 220 μm. The first fraction to elute (tR=3.5 min) were collected and evaporated to remove solvent under reduced pressure to give 900 mg of 204.6. The second fraction to elute (tR=4.25 min) was collected and evaporated to remove solvent under reduced pressure to give 900 mg of compound 204.9. The ee of 204.6 (98.5%) and of 204.9 were determined by analytical chiral SFC under the following conditions: Column: phenomenex Lux 5 u Cellulose-3, 4.6*250 mm, 5 μm; mobile phase: 90% CO$_2$ and 10% MeOH (0.01 DEA); flow rate: 4 mL/min; UV detection at 254 μm.

Synthesis of Compound 204.7.

Compound 204.7 was prepared from 204.6 in a manner analogous to the synthesis of compound 16.4. Isolated 0.55 g of a light yellow oil in 46% yield.

Synthesis of Compound 204.8.

A mixture of 204.7 (275 mg, 0.625 mmol, 1.00 equiv), 1-methyl-1H-pyrazol-4-amine (152 mg, 1.56 mmol, 2.50 equiv), Pd$_2$dba$_3$ (28.6 mg, 0.03 mmol, 0.05 equiv), Xantphos (36.2 mg, 0.065 mmol, 0.10 equiv), NaOBu$^t$ (145 mg, 1.5 mmol, 2.5 equiv) in 30 mL of 1,4-dioxane was degassed three times with nitrogen. The resulting mixture was stirred for 4 h at 100° C. The reaction mixture was concentrated under vacuum and the residue was diluted with water. The pH value was adjusted to 5 with 1 M hydrochloric acid and extracted with 5×50 mL of chloroform/iso-propanol (3:1). The combined organic layers were dried over sodium sulfate and concentrated under vacuum. Purification by chromatography on silica gel column with DCM/MeOH (10:1 to 2:1) gave 204.8 (180 mg, 62%) as a grey solid.

Synthesis of Compound I-224.

Compound I-224 was prepared from 204.8 in a manner analogous to the synthesis of Compound I-13. Isolated 35.9 mg of a white solid in 20% yield. MS (ES): m/z 470 (M+H)$^+$. $^1$H NMR (300 MHz, CD$_3$OD): δ 7.89 (1H, br s), 7.59 (1H, s), 5.19 (1H, m), 3.89 (3H, s), 3.66 (1H, m), 2.83-2.99 (4H, m), 2.70 (7H, m), 2.43 (2H, m), 2.14-2.39 (4H, m), 1.76-1.94 (4H, m).

Example 205

Synthesis of 2-[(3R)-12-[[4-(morpholin-4-yl)cyclo-hexyl]oxy](4,4,5,5-d4)-7-thia-9,11-diazatricyclo[6.4.0.0[2,6]]dodeca-1(8),2(6),9,11-tetraen-3-yl]ac-etamide-d$_4$ (I-188)

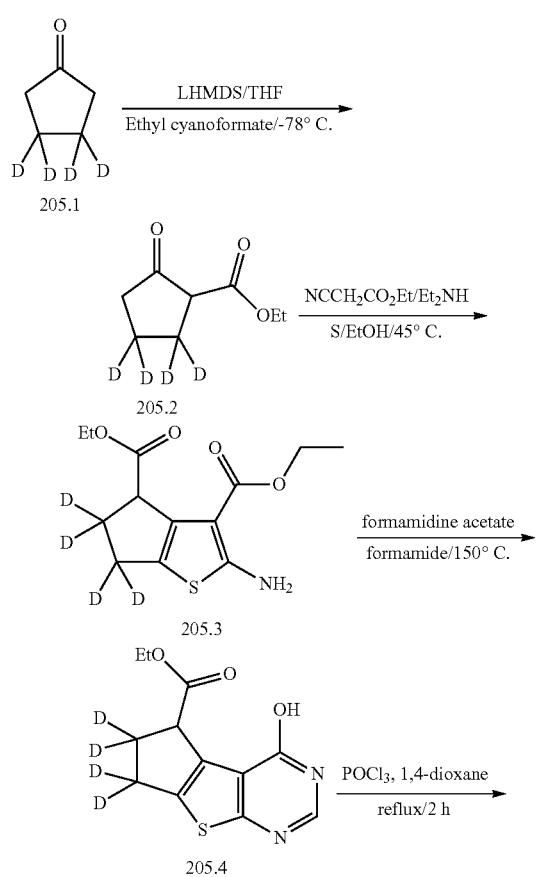

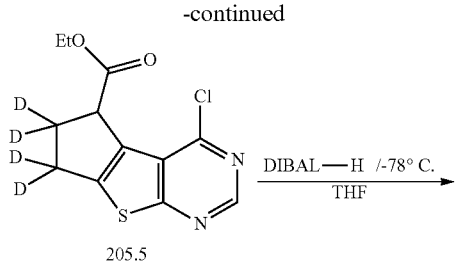

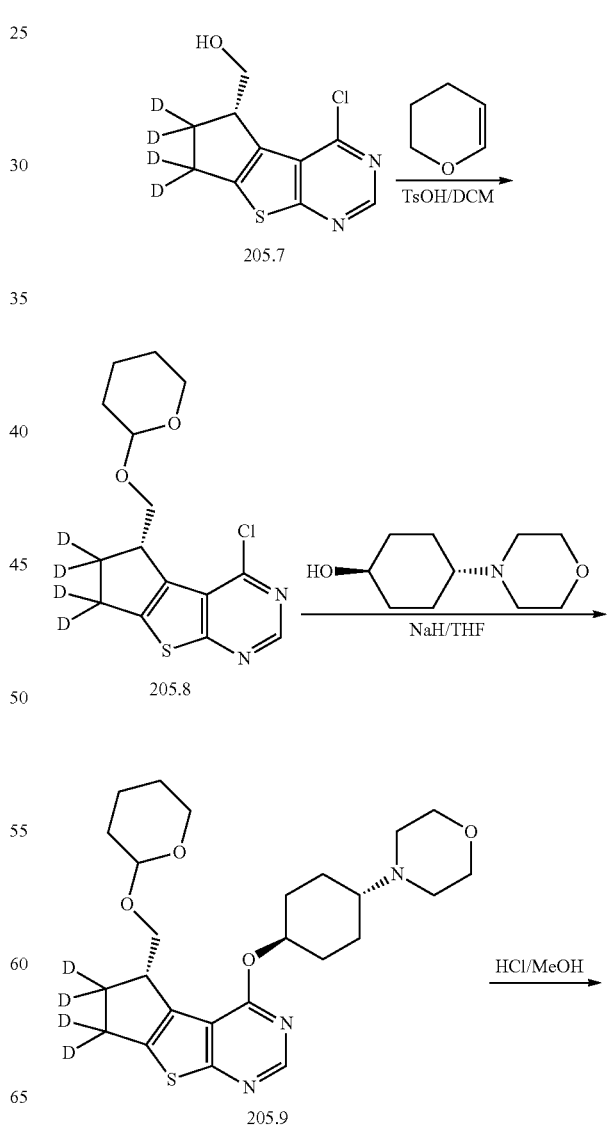

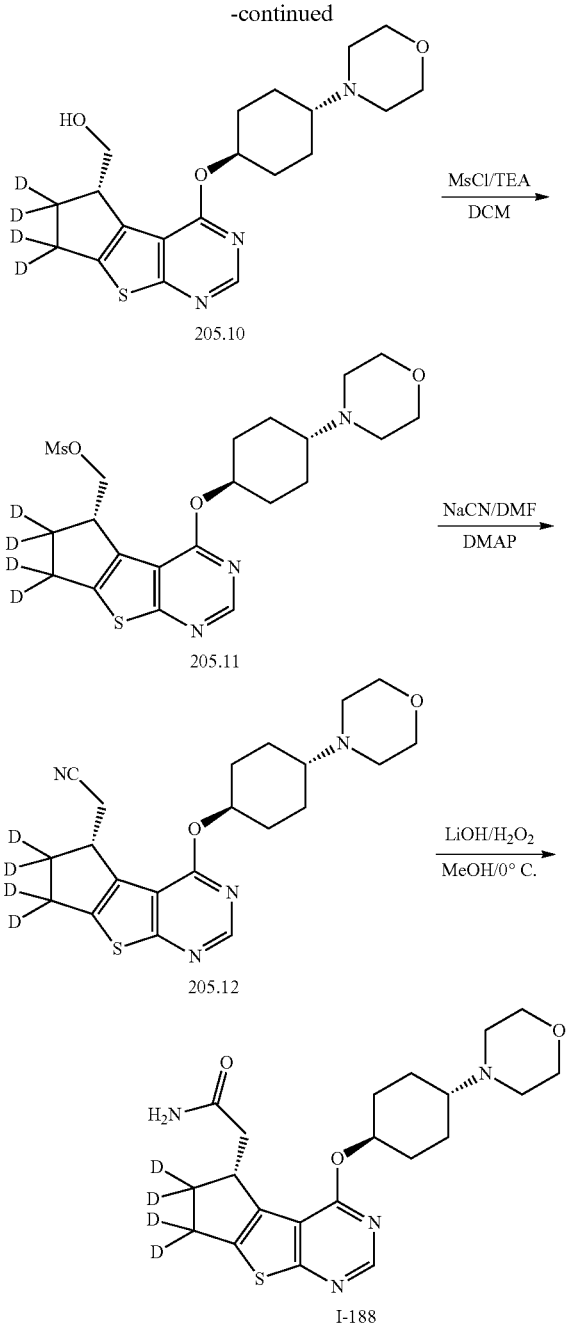

Synthesis of Compound 205.2.

To a solution of (3,3,4,4-4)cyclopentan-1-one (3.0 g, 34.0 mmol, 1.00 equiv) in 15 mL of distilled THF was added dropwise 2 M LiHMDS in THF (20.5 mL, 1.20 equiv) at −78° C. under nitrogen. After addition, the resulting solution was stirred for 1 h at −20° C. Then ethyl cyanoformate (3.7 g, 37.4 mmol, 1.10 equiv) was added at −78° C. and the resulting solution was allowed to react, with stirring, for an additional 30 min at −78° C. The reaction was quenched with saturated NH$_4$Cl solution and extracted with 2×100 mL of ethyl acetate. The combined organic layers were washed with brine, dried over sodium sulfate and concentrated under vacuum. The residue was applied onto a silica gel column with ethyl acetate/petroleum ether (1:20-1:10) to give 3.5 g (64%) of 205.2.

Synthesis of Compound 205.3.

To a solution of 205.2 (3.5 g, 21.85 mmol, 1.00 equiv) in ethanol (100 mL) was added S (784 mg, 1.10 equiv), ethyl 2-cyanoacetate (2.7 g, 24.03 mmol, 1.10 equiv) and Et$_2$NH (3.19 g, 43.7 mmol, 2.00 equiv) subsequently under nitrogen. The resulting mixture was stirred for 5 h at 45° C. and cooled to room temperature and quenched by the addition of 50 mL of water. After extraction with 3×100 mL of ethyl acetate, the combined organic layers were washed with brine and dried over sodium sulfate and concentrated under vacuum. The residue was applied onto a silica gel column with ethyl acetate/petroleum ether (1:10-1:5) to give 205.3 (3.2 g, 51%) as a yellow solid.

Synthesis of Compound 205.4.

To a solution of 205.3 (3.2 g, 11.1 mmol, 1.00 equiv) in formamide (10 mL) was added formamidine acetate (2.4 g) and the resulting mixture was stirred for 5 h at 150° C. under nitrogen. After cooling to room temperature, the reaction was quenched with water and extracted with 3×100 mL of ethyl acetate. The organic layers were combined, washed with brine, dried over sodium sulfate and concentrated under vacuum. The residue was applied onto a silica gel column with ethyl acetate/petroleum ether (1:10-1:5) to provide 1.6 g (54%) of 205.4 as a yellow solid.

Synthesis of Compound 205.5.

Into a 100-mL round-bottom flask containing a solution of 205.4 (1.6 g, 6.0 mmol, 1.00 equiv) in 20 mL of 1,4-dioxane was added POCl$_3$ (10 mL) under nitrogen. The resulting solution was stirred for 3 h at reflux. After cooling down to room temperature the excess of POCl$_3$ was removed under reduced pressure and the residue was dissolved in 50 mL of EtOAc and poured into water/ice. The resulting solution was neutralized with saturated sodium bicarbonate solution and extracted with 3×80 mL of ethyl acetate. The combined organic layers was dried over sodium sulfate and concentrated under vacuum. The residue was applied onto a silica gel column with ethyl acetate/petroleum ether (1:10) to give 205.5 (950 mg, 55%) as a yellow solid.

Synthesis of Compound 205.6.

To a 100-mL 3-necked round-bottom flask was added a mixture of 205.5 (900 mg, 3.14 mmol, 1.00 equiv) in 20 mL of freshly distilled THF followed by DIBAL-H (895 mg, 6.30 mmol, 2.00 equiv) at −78° C. under nitrogen. The resulting solution was stirred for 2 h at −78° C., quenched by the addition of aqueous saturated NH$_4$Cl and extracted with 3×100 mL of ethyl acetate. The organic layers were combined, washed with brine, dried over sodium sulfate and concentrated under vacuum. The residue was applied onto a silica gel column with ethyl acetate/petroleum ether (1:1) to afford 205.6 (720 mg, 94%) as a colorless oil.

Synthesis of Compound 205.7.

The enantiomers of 205.6 (720 mg) were resolved by preparative SFC under the following conditions: Column: Chiralpak AD-H, 2*25 cm; mobile phase: CO$_2$ (60%) and methanol (40%); flow rate: 40 g/min; UV detection at 254/220 nm. The product-containing fractions were collected and evaporated to remove methanol to afford 205.7 (tR=10 min, 320 mg, 89%) as a colorless oil. A 100% ee value (tR=3.2 min) was measured by analytical SFC under the following conditions: Column: CHIRALPAK AD-H, 4.6*150 mm, 5 μm Chiral-A(AD-H); mobile phase: CO$_2$ (60%), methanol (40%); flow rate: 4 mL/min; UV detection at 220 nm.

Synthesis of Compound 205.8.

To a solution of 205.7 (160 mg, 0.65 mmol, 1.00 equiv) in anhydrous DCM (10 mL) was added 3,4-dihydro-2H-pyran (110 mg, 1.31 mmol, 2.00 equiv) and TsOH (56 mg, 0.33 mmol, 0.50 equiv). The solution was stirred for 30 min at 0°

C. under nitrogen. The resulting solution was diluted with water and extracted with dichloromethane and the organic layers were combined, washed with brine, dried over Na₂SO₄ and concentrated under vacuum. The residue was applied onto a silica gel column with ethyl acetate/petroleum ether (1:5) to give the desired 205.8 (170 mg, 79%) as a colorless oil.

Synthesis of Compound 205.9.

Sodium hydride (104 mg, 2.60 mmol, 5.03 equiv, 60% dispersion in mineral oil) was treated with trans-4-(morpholin-4-yl)cyclohexan-1-ol (143 mg, 0.77 mmol, 1.49 equiv) in 25 mL of distilled THF for 30 min at 0° C. under nitrogen. Then 205.8 (170 mg, 0.52 mmol, 1.00 equiv) in 5 mL of THF was added via syringe and the resulting solution was allowed to react, with stirring, for an additional 3 h while the temperature was maintained at 55° C. in an oil bath. The reaction was then quenched by the addition of NH₄Cl (aq.) and extracted with ethyl acetate. The organic layers were combined, washed with brine, dried over Na₂SO₄ and concentrated under vacuum. The residue was applied onto a silica gel column with dichloromethane/methanol (30:1) to afford 205.9 (110 mg, 45%) as a colorless oil.

Synthesis of Compound 205.10.

To a solution of 205.9 (120 mg, 0.25 mmol, 1.00 equiv) and conc. hydrochloric acid (0.5 mL) in methanol (15 mL) was stirred for 30 min at 0° C. in a water/ice bath. The reaction was then quenched by the addition of sodium bicarbonate (sat.) and extracted with 4×50 mL of DCM. The combined organic layers were dried over sodium sulfate and concentrated under vacuum. The residue was applied onto a silica gel column with dichloromethane/methanol (25:1) to provide the 205.10 (85 mg, 86%) as a colorless oil.

Synthesis of Compound 205.11.

To a solution of 205.10 (120 mg, 0.25 mmol, 1.00 equiv) and conc. hydrochloric acid (0.5 mL) in methanol (15 mL) was stirred for 30 min at 0° C. in a water/ice bath. The reaction was then quenched by the addition of sodium bicarbonate (sat.) and extracted with 4×50 mL of DCM. The combined organic layers were dried over sodium sulfate and concentrated under vacuum. The residue was applied onto a silica gel column with dichloromethane/methanol (25:1) to provide 205.11 (85 mg, 86%) as a colorless oil.

Synthesis of Compound 205.12.

To a solution of 205.11 (95 mg, 0.20 mmol, 1.00 equiv), NaCN (99 mg, 2.02 mmol, 10.03 equiv) and 4-dimethylaminopyridine (5 mg, 0.04 mmol, 0.20 equiv) in DMSO (5 mL) was stirred for 35 h at 60° C. in an oil bath. The resulting solution was diluted with 50 mL of water and extracted with 3×60 mL of DCM. The combined organic layers were washed with brine, dried over sodium sulfate and concentrated under vacuum. The residue was applied onto a silica gel column with dichloromethane/methanol (30:1) to afford 205.12 (80 mg, 99%) as a colorless oil.

Synthesis of Compound I-188.

To a solution of 205.12 (80 mg, 0.20 mmol, 1.00 equiv), LiOH.H₂O (17 mg, 0.40 mmol, 2.04 equiv) and H₂O₂ (0.5 mL, 30%) in methanol (10 mL) was stirred for 3 h at 0° C. The reaction was then quenched by the addition of saturated Na₂SO₃ and extracted with 3×50 mL of DCM. The organic layers were combined and concentrated under vacuum. The residue was purified by preparative TLC with dichloromethane/methanol (30:1) to give Compound I-188 (48.9 mg, 59%) as a white solid. MS (ES): m/z 421 (M+H)⁺. ¹H NMR (400 MHz, CD₃OD): δ 8.49 (s, 1H), 5.33-5.25 (m, 1H), 3.82-3.72 (m, 5H), 3.03-2.99 (m, 1H), 2.67-2.63 (m, 4H), 2.41-2.27 (m, 4H), 2.12-2.09 (m, 2H), 1.71-1.47 (m, 4H).

Example 206

Synthesis of 12-[[4-(morpholin-4-yl)cyclohexyl]oxy]-7-thia-4,9,11-triazatricyclo[6.4.0.0[2,6]]dodeca-1(12),2(6),8,10-tetraene (I-192)

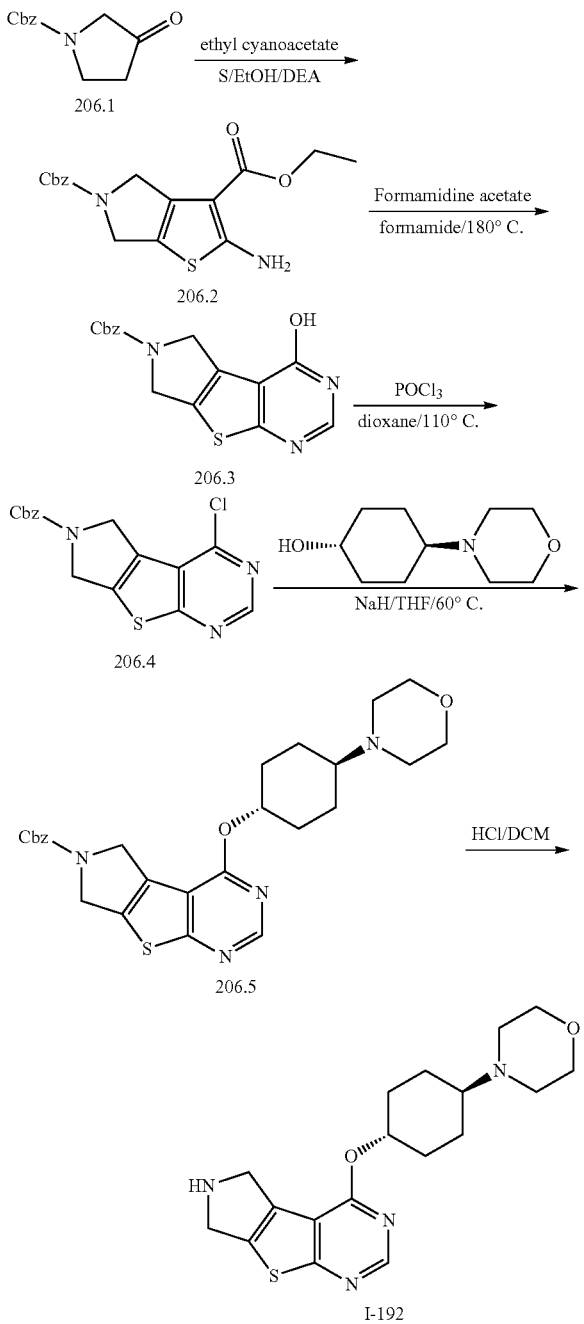

Synthesis of Compound 206.2.

To a solution of benzyl 3-oxopyrrolidine-1-carboxylate (4.5 g, 20.53 mmol, 1.00 equiv), ethyl 2-cyanoacetate (2.773 g, 24.51 mmol, 1.19 equiv), S (780 mg, 24.38 mmol, 1.19 equiv) and diethylamine (1.791 g, 24.53 mmol, 1.20 equiv) in ethanol (40 mL) was stirred for 5 h at 50° C. The solids were collected by filtration and dried in an oven at 45° C. to give the desired 206.2 (1.7 g, 24%) as a yellow solid.

Synthesis of Compound 206.3.

A mixture of 206.2 (1.5 g, 4.33 mmol, 1.00 equiv) and formamidine acetate (4.582 g, 43.23 mmol, 9.98 equiv) in 50 mL of formamide was stirred for 3 h at 180° C. under nitrogen. The reaction was then quenched by the addition of water and extracted with 3×100 mL of ethyl acetate. The organic layers were combined, washed with brine, dried over sodium sulfate and concentrated under vacuum. The residue was applied onto a silica gel column with dichloromethane/methanol (15:1) to provide 206.3 (1.2 g, 85%) as a white solid.

Synthesis of Compound 206.4.

To a solution of 206.3 (1.9 g, 5.80 mmol, 1.00 equiv) and POCl$_3$ (8.89 g, 57.98 mmol, 10.0 equiv) in 1,4-dioxane (50 mL) was stirred for 3 h at 110° C. under nitrogen. The resulting mixture was concentrated under vacuum and the residue was dissolved in EtOAc (100 mL) and poured into a cooled saturated sodium bicarbonate and extracted with 3×80 mL of ethyl acetate. The organic layers were combined, washed with brine, dried over sodium sulfate and concentrated in vacuo. The residue was applied onto a silica gel column with ethyl acetate/petroleum ether (1:1) to yield 206.4 (1.5 g, 75%) as a white solid.

Synthesis of Compound 206.5.

Sodium hydride (60%, 416 mg, 17.33 mmol, 6.66 equiv) was treated with trans-4-(morpholin-4-yl)cyclohexan-1-ol (577 mg, 3.11 mmol, 1.20 equiv) in distilled THF (10 mL) at room temperature for 40 min under nitrogen. 206.4 (900 mg, 2.60 mmol, 1.00 equiv) was added and the resulting solution was stirred for 4 h at 70° C. and cooled and quenched by the addition of NH$_4$Cl (sat.) and extracted with 3×50 mL of ethyl acetate. The organic layers were combined, washed with brine, dried over sodium sulfate and concentrated in vacuo. The residue was applied onto a silica gel column with dichloromethane/methanol (15:1) to furnish 206.5 (900 mg, 70%) as colorless oil.

Synthesis of Compound I-192.

To a solution of 206.5 (200 mg, 0.40 mmol, 1.00 equiv) in 10 mL of DCM was added hydrochloric acid (12 M, 1 mL) followed by stirring for 8 h at 25° C. The pH value of the solution was adjusted to 8 with ammonia and the resulting mixture was concentrated under vacuum. The crude product (100 mg) was purified by preparative HPLC under the following conditions (Waters): Column: SunFire Prep C18 19*150 mm 5 µm; mobile phase: water with 0.05% NH$_4$HCO$_3$ and CH$_3$CN (50% CH$_3$CN up to 85% in 10 min); flow rate: 20 mL/min; UV detection at 254 nm. This resulted in Compound I-192 (7.6 mg, 5%) as a yellow solid. MS (ES): m/z 361 (M+H)$^+$. $^1$H NMR (400 MHz, CD$_3$OD): δ 8.58 (s, 1H), 5.31-5.21 (m, 1H), 4.45-4.42 (m, 4H), 3.77-3.74 (m, 4H), 2.72-2.70 (m, 4H), 2.48-2.33 (m, 3H), 2.13-2.10 (m, 2H), 1.67-1.50 (m, 4H).

Example 207

Synthesis of 4-N-[12,12-dimethyl-11-oxa-8-thia-4,6-diazatricyclo[7.4.0.0[2,7]]trideca-1(9),2(7),3,5-tetraen-3-yl]-1-N,1-N-dimethylcyclohexane-1,4-diamine (I-194)

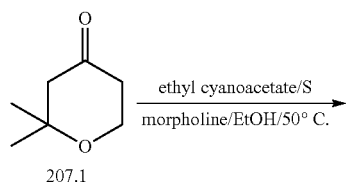

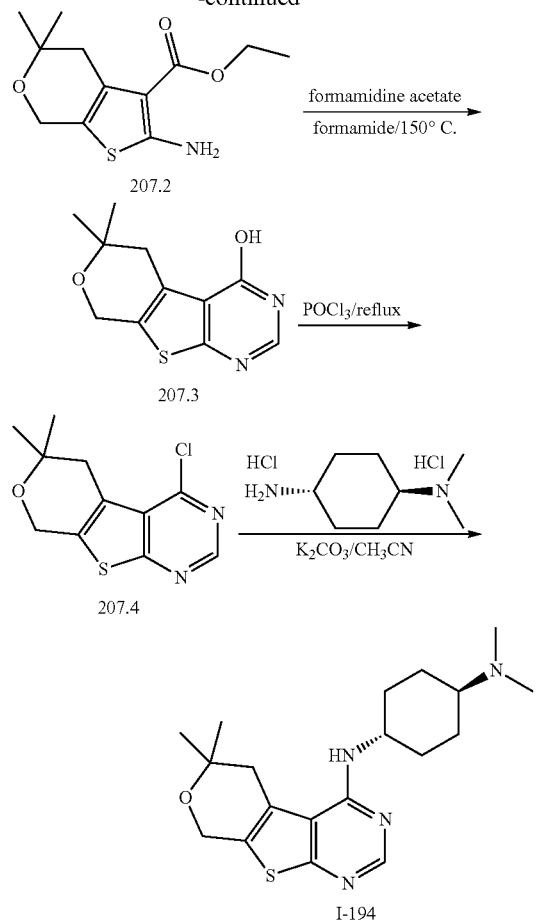

Synthesis of Compound 207.2.

To a solution of 2,2-dimethyloxane (2.5 g, 19.5 mmol, 1.00 equiv), ethyl 2-cyanoacetate (2.43 g, 21.45 mmol, 1.1 equiv) and morpholine (2.55 g, 29.25 mmol, 1.5 equiv) in 80 mL of ethanol was added S (0.69 g, 21.45 mmol, 1.1 equiv) at room temperature. The resulting mixture was stirred overnight at 50° C. in an oil bath under nitrogen. After completion, the resulting mixture was concentrated under vacuum and the residue was diluted with water and extracted with 3×80 mL of ethyl acetate. The organic layers were combined, washed with brine, dried over sodium sulfate and concentrated under vacuum. The residue was applied onto a silica gel column with ethyl acetate/petroleum ether (1:5) to give the desired 207.2 (4.5 g, 90%) as a light yellow solid.

Synthesis of Compound 207.3.

Into a 50-mL round-bottom flask was placed 207.2 (2.2 g, 8.62 mmol, 1.00 equiv) and formamidine acetate (8.6 g, 82.69 mmol, 9.60 equiv) in 20 mL of formamide at room temperature. The resulting solution was stirred for 3 h at 140° C. in an oil bath under nitrogen. The resulting solution was quenched with water and extracted with ethyl acetate. The organic layers were washed with brine, dried over sodium sulfate and concentrated in vacuo to give 1.8 g (78%) of 207.3 as a white solid.

Synthesis of Compound 207.4. 207.3 (1.8 g, 7.62 mmol, 1.00 equiv) in POCl$_3$ (20 mL) was stirred for 2 h at 110° C. in an oil bath under nitrogen. After completion, the reaction mixture was concentrated in vacuo and the residue was diluted with EtOAc and poured into 100 g of water/ice. The solution was neutralized with saturated sodium bicarbonate and extracted with 2×80 mL of ethyl acetate. The combined organic layers were dried over sodium sulfate and concentrated under vacuum. Purification by chromatography on silica gel column with EtOAc/PE (1:30 to 1:10) to afford the 1.3 g (67%) of 207.4 as a light yellow solid.

Synthesis of Compound I-194.

A mixture of 207.4 (196.8 mg, 0.77 mmol, 1.00 equiv), potassium carbonate (533 mg, 5.04 equiv) and 1-N,1-N-dimethylcyclohexane-1,4-diamine dihydrochloride (423.6 mg, 1.97 mmol, 2.57 equiv) in CH$_3$CN (15 mL) was heated overnight at 70° C. under nitrogen. The resulting mixture was concentrated under vacuum and the residue was diluted with water and extracted with 4×40 mL of DCM. The combined organic layers were dried over sodium sulfate and concentrated under vacuum. The residue was applied onto a silica gel column with dichloromethane/methanol (15:1) to afford the desired I-194 (138.7 mg, 50%) as an off-white solid. MS (ES): m/z 361 (M+H)$^+$. $^1$H-NMR (300 MHz, CD$_3$OD): δ 8.26 (1H, s), 4.83 (2H, t), 2.96 (2H, s), 2.65-2.55 (1H, m), 2.40 (6H, s), 2.25-2.16 (2H, m), 2.09-1.98 (2H, m), 1.55-1.45 (4H, m), 1.36 (6H, s).

Example 208

Synthesis of 12,12-dimethyl-3-[[4-(morpholin-4-yl)cyclohexyl]oxy]-11-oxa-8-thia-4,6-diazatricyclo[7.4.0.0[2,7]]trideca-1 (9),2(7),3,5-tetraene (I-193)

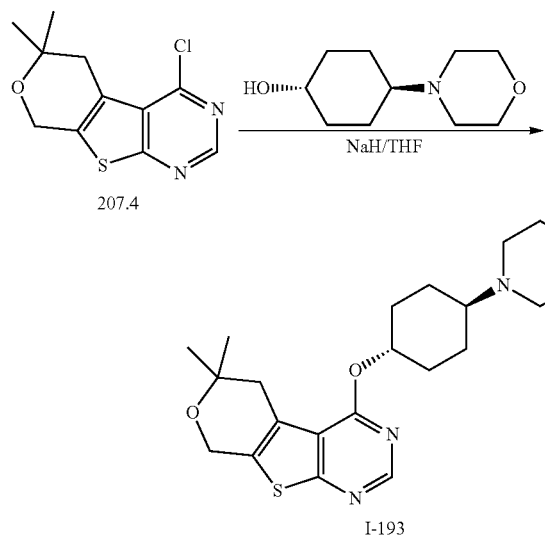

Sodium hydride (118.1 mg, 2.95 mmol, 5.01 equiv, 60%) was treated with trans-4-(morpholin-4-yl)cyclohexan-1-ol (218.7 mg, 1.18 mmol, 2.00 equiv) in 10 mL of distilled THF for 30 min under nitrogen. 207.4 (150.2 mg, 0.59 mmol, 1.00 equiv) was added and the resulting solution was stirred for 3 h at 55° C. After cooled down to rt, the reaction was then quenched by the addition of NH$_4$Cl (aq.) and extracted with 3×60 mL of DCM. The combined organic layers were dried over sodium sulfate and concentrated under vacuum. The residue was applied onto a silica gel column with dichloromethane/methanol (20:1) to provide the desired 158.1 mg (66%) of I-193 as an off-white solid. MS (ES): m/z 404 (M+H)$^+$. $^1$H-NMR (300 MHz, CD$_3$OD): δ 8.49 (1H, s), 5.35-5.15 (1H, m), 3.72 (4H, t), 2.93 (2H, s), 2.63 (4H, t), 2.45-2.25 (3H, m), 2.15-2.02 (2H, m), 1.69-1.40 (4H, m), 1.34 (6H, s).

Example 209

Synthesis of 4-methyl-12-[[4-(morpholin-4-yl)cyclohexyl]oxy]-7-thia-4,9,11-triazatricyclo[6.4.0.0[2,6]]dodeca-1(12),2(6),8,10-tetraene (I-196)

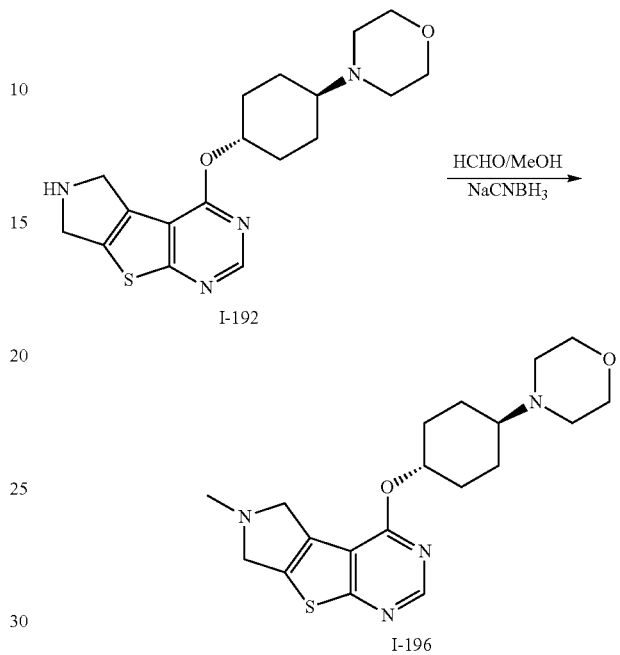

A solution of I-192 (Example 207; 200 mg, 0.55 mmol, 1.00 equiv), HCHO (37%, 0.2 mL) and NaBH$_3$CN (104.9 mg, 1.67 mmol, 3.01 equiv) in methanol (5 mL) was stirred for 2 h at 25° C. The crude product (100 mg) was purified by preparative HPLC under the following conditions (Waters): Column: SunFire Prep C18 19*150 mm 5 μm; mobile phase: water with 0.05 NH$_4$HCO$_3$ and CH$_3$CN (50% CH$_3$CN up to 85% in 10 min); flow rate: 20 mL/min; UV detection at 254 nm. This resulted in I-196 (4.7 mg, 2%) as a white solid. MS (ES): m/z 375 (M+H)$^+$. $^1$H NMR (400 MHz, d$_6$-DMSO): δ 8.53 (s, 1H), 5.30-5.23 (m, 1H), 4.15-4.12 (m, 4H), 3.94-3.72 (m, 4H), 2.65 (s, 3H), 2.64-2.63 (m, 4H), 2.41-2.34 (m, 3H), 2.11-2.08 (m, 2H), 1.65-1.53 (m, 4H).

Example 210

Synthesis of 1-(12-[[4-(morpholin-4-yl)cyclohexyl]oxy]-7-thia-4,9,11-triazatricyclo[6.4.0.0[2,6]]dodeca-1(12),2(6),8,10-tetraen-4-yl)ethan-1-one (I-198)

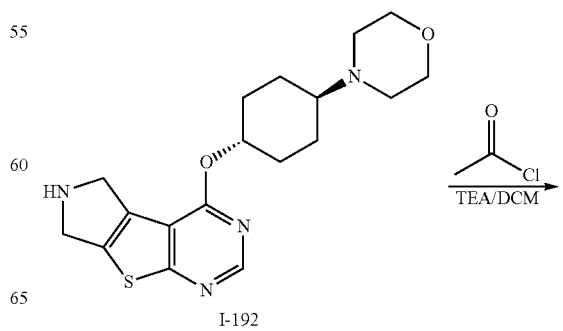

-continued

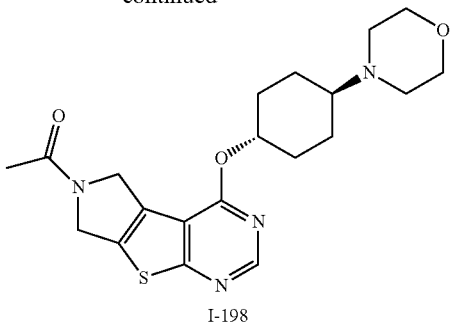

I-198

A solution of I-192 (Example 207; 150 mg, 0.42 mmol, 1.00 equiv), TEA (84.3 mg, 0.83 mmol, 2.00 equiv) and acetyl chloride (65 mg, 0.83 mmol, 1.99 equiv) in dichloromethane (5 mL) was stirred for 0.5 h room temperature. The resulting mixture was concentrated under vacuum. The crude product (100 mg) was purified by preparative HPLC under the following conditions (Waters): Column: Xbridge Prep C18 5 μm, 19*150 mm; mobile phase: water with 0.05% NH$_4$HCO$_3$ and CH$_3$CN (10.0% CH$_3$CN up to 30.0% in 10 min, up to 100.0% in 5 min, down to 10.0% in 1 min); flow rate: 20 mL/min; UV detection at 254 nm. This resulted in I-198 (28.8 mg, 17%) as a white solid. MS (ES): m/z 403 (M+H)$^+$. $^1$H NMR (300 MHz, CD$_3$OD): δ 8.56 (s, 1H), 5.32-5.24 (m, 1H), 5.00-4.92 (m, 2H), 4.85-4.80 (m, 2H), 3.74-2.71 (m, 4H), 2.65-2.62 (m, 4H), 2.41-2.07 (m, 8H), 1.75-1.45 (m, 4H).

Example 211

Synthesis of methyl 12-[[4-(morpholin-4-yl)cyclohexyl]oxy]-7-thia-4,9,11-triazatricyclo[6.4.0.0[2,6]]dodeca-1(12),2(6),8,10-tetraene-4-carboxylate (I-199)

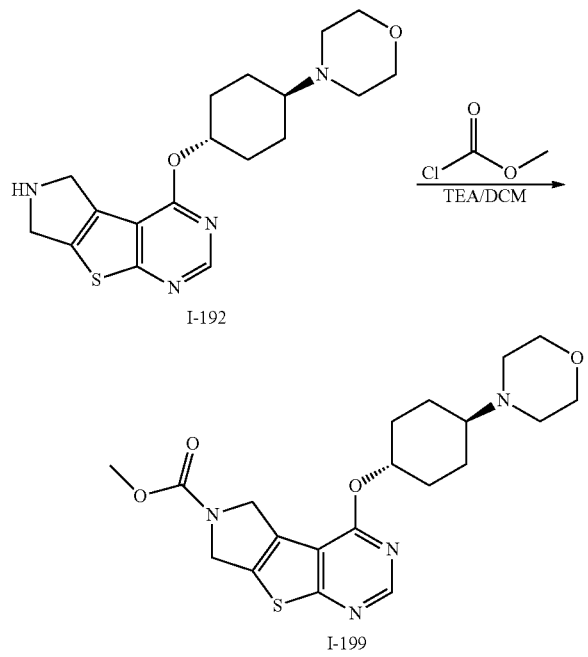

Compound I-199 was prepared from I-192 in a manner analogous to the synthesis of Compound I-198. Isolated a white oil in 4% yield. MS (ES): m/z 419 (M+H)$^+$. $^1$H NMR (300 MHz, CDCl$_3$): δ 8.56 (s, 1H), 5.12-5.23 (m, 1H), 4.82-4.77 (m, 4H), 3.82-3.49 (m, 7H), 2.60 (s, 4H), 2.28-2.01 (m, 5H), 1.61-1.36 (m, 4H).

Example 212

Synthesis of N-methyl-12-[[4-(morpholin-4-yl)cyclohexyl]oxy]-7-thia-4,9,11-triazatricyclo[6.4.0.0[2,6]]dodeca-1(8),9,11-triene-4-carboxamide (I-200)

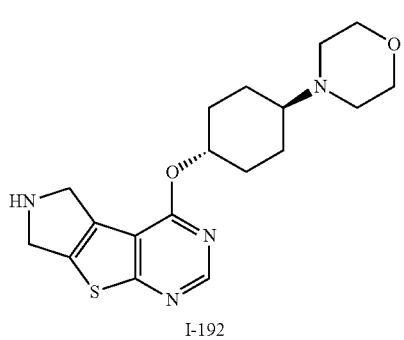

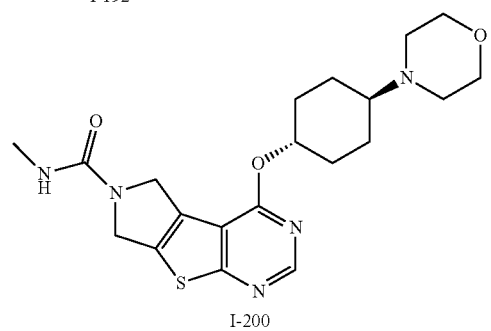

A solution of I-192 (100 mg, 0.28 mmol, 1.00 equiv) in 3 mL of DCM was added to a solution of triphosgene (40.8 mg, 0.14 mmol, 0.50 equiv) in DCM (7 mL) dropwise under nitrogen at 0° C. After 0.5 h, TEA (84 mg, 0.83 mmol, 3.01 equiv) and CH$_3$NH$_2$-THF (0.5 mL) were added and the resulting solution was stirred for 1.5 h at room temperature. The resulting mixture was concentrated under vacuum. The crude product (100 mg) was purified by preparative HPLC under the following conditions (Waters): Column: SunFire Prep C18, 19*150 mm 5 μm; mobile phase: water with 0.05% NH$_4$HCO$_3$ and CH$_3$CN (10.0% CH$_3$CN up to 30.0% in 10 min, up to 100.0% in 2 min, down to 10.0% in 1 min); flow rate: 20 mL/min; UV detection at 254 nm. This resulted in I-200 (21 mg, 18%) as a white solid. MS (ES): m/z 418 (M+H)$^+$. $^1$H NMR (300 MHz, CDCl$_3$): δ 8.56 (s, 1H), 5.32-5.24 (m, 1H), 4.77 (d, J=6.3 Hz, 4H), 4.32-4.21 (m, 1H), 3.93-3.79 (m, 4H), 2.93 (d, J=4.5 Hz, 3H), 2.79-2.50 (m, 4H), 2.40-1.89 (m, 5H), 1.71-1.58 (m, 2H).

Example 213

Synthesis of 3-[[4-(morpholin-4-yl)cyclohexyl]amino]-8-thia-4,6-diazatricyclo[7.4.0.0[2,7]]trideca-1(9),2,4,6-tetraene-12-carboxamide (I-203)

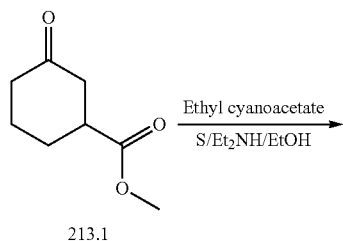

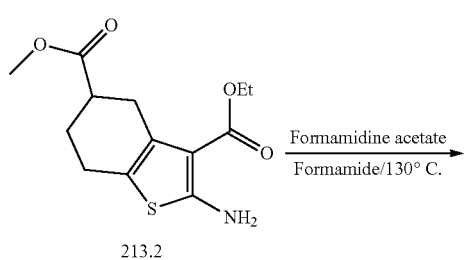

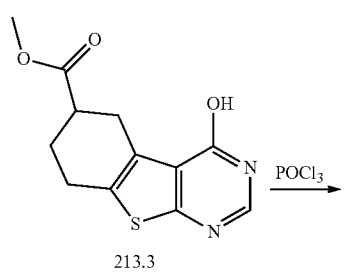

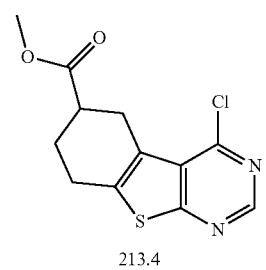

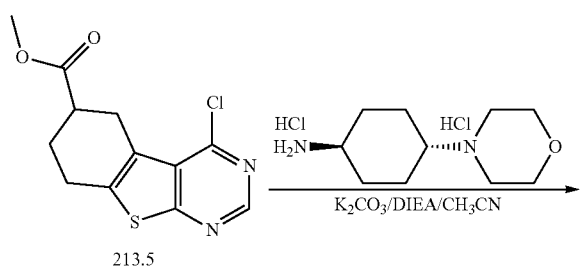

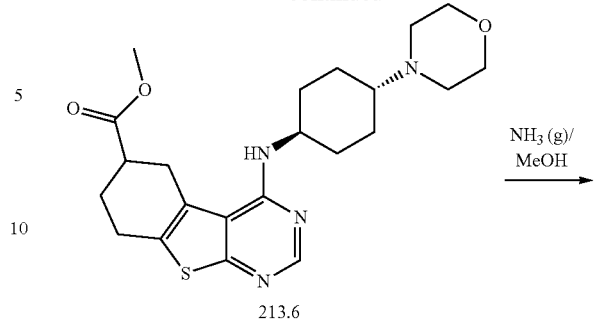

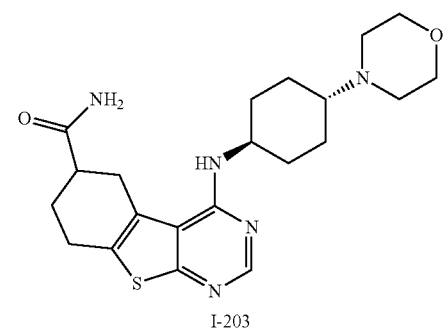 [SMILES: NC(=O)C1CCc2sc3ncnc(N[C@H]4CC[C@H](N5CCOCC5)CC4)c3c2C1]

Synthesis of Compound 213.5.

Compound 213.5 was prepared from methyl 3-oxocyclohexane-1-carboxylate in a manner analogous to the synthesis of 207.4. Isolated 1.38 g of a white solid in 8% overall yield. MS (ES): m/z 283 and 285 (M+H)+.

Synthesis of Compound 213.6.

Into a 50-mL round-bottom flask containing a mixture of 213.5 (200 mg, 0.71 mmol, 1.00 equiv), trans-4-(morpholin-4-yl)cyclohexan-1-amine dihydricholoride (269 mg, 1.05 mmol, 1.49 equiv), potassium carbonate (290 mg, 2.10 mmol, 2.97 equiv) in $CH_3CN$ (20 mL) was stirred for 14 h at 80° C. under nitrogen. The reaction was then quenched by the addition of 20 mL of water and extracted with 3×80 mL of DCM. The combined organic layers were washed with brine, dried over anhydrous sodium sulfate and concentrated under vacuum. The residue was applied onto a silica gel column with dichloromethane/methanol (15:1) to give 250 mg (82%) of 213.6 as a white solid.

Synthesis of Compound I-203.

$NH_3$ (g) was introduced to methanol (35 mL) at 0° C. for 1 hr. Then 213.6 (250 mg, 0.58 mmol, 1.00 equiv) was added and the resulting solution was stirred for 14 h at room temperature. The resulting mixture was concentrated under vacuum and the residue was applied onto a silica gel column with dichloromethane/methanol (8:1) to give the desired Compound I-203 (170 mg, 70%) as a white solid. MS (ES): m/z 416 (M+H)+. $^1$H-NMR (300 MHz, $CD_3OD$): δ 8.25 (s, 1H), 4.15 (m, 1H), 3.75 (m, 4H), 3.15 (m, 2H), 2.92-2.61 (m, 7H), 2.39-1.82 (m, 7H), 1.62-1.47 (m, 4H).

Example 214

2-(12-[[4-(dimethylamino)cyclohexyl]oxy]-10-(phenylamino)-7-thia-9,11-diazatricyclo[6.4.0.0^[2,6]]dodeca-1(12),2(6),8,10-tetraen-3-yl)acetamide
(I-204)

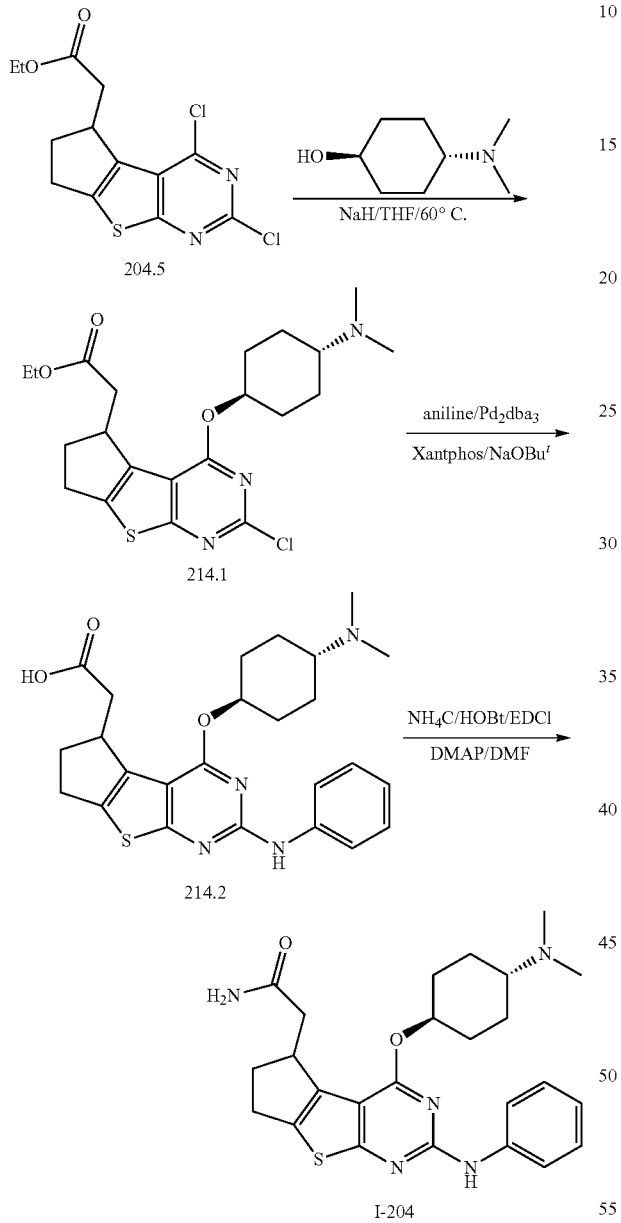

Synthesis of Compound 214.1.

NaH (60% dispersion in mineral oil, 543.4 mg, 22.64 mmol, 5.00 equiv) was treated with trans-4-(dimethylamino)cyclohexan-1-ol (428 mg, 2.99 mmol, 1.10 equiv) in freshly distilled THF (10 mL) at room temperature for 1 h under nitrogen. To a solution of 204.5 (900 mg, 2.72 mmol, 1.00 equiv) in 10 mL of THF was added via syringe and the resulting solution was stirred for 3 h at 60° C. After completion of the reaction, the reaction was cooled to room temperature and quenched with saturated NH$_4$Cl and extracted with 3×100 mL of DCM. The organic layers were washed with brine, dried over anhydrous sodium sulfate and concentrated under vacuum. The residue was applied onto a silica gel column with dichloromethane/methanol (50:1 to 30:1) to give the desired 214.1 (0.55 g, 46%) as a light yellow oil.

Synthesis of Compound 214.2.

To a 50 mL of dry round-bottom flask containing a solution of 214.1 (270 mg, 0.62 mmol, 1.00 equiv) in 15 mL of dioxane was added Pd$_2$ dba$_3$ (31.9 mg, 0.03 mmol, 0.05 equiv), Xantphos (35.6 mg, 0.06 mmol, 0.10 equiv), t-BuONa (142.9 mg, 1.49 mmol, 2.41 equiv) and aniline (142.9 mg, 1.54 mmol, 2.49 equiv) sequentially at room temperature. Then the reaction mixture was degassed three times with nitrogen and stirred for 4 h at 100° C. The solids were filtered out by filtration and the filtrate was neutralized with 1 M hydrochloric acid and extracted with 3×50 mL of CHCl$_3$/isopropanol (3:1). The organic layers were dried over sodium sulfate and concentrated under vacuum to yield 214.2 (190 mg, crude) as a white solid.

Synthesis of Compound I-204.

Into a 50-mL round-bottom flask was placed a mixture of 214.2 (104 mg), NH$_4$Cl (53 mg, 0.99 mmol, 4.58 equiv), HOBt (45 mg, 0.33 mmol, 1.54 equiv), EDCI (87 mg, 0.45 mmol, 2.10 equiv) and 4-dimethylaminopyridine (29 mg, 0.24 mmol, 1.10 equiv) in DMF (6 mL) under nitrogen. The resulting solution was stirred overnight at room temperature. The reaction was quenched with water and extracted with DCM and concentrated in vacuo. The residue was purified by preparative HPLC under the following conditions (Waters): Column: XBridge Shield RP18 OBD 5 μm, 19*150 mm; mobile phase: water with 0.01% NH$_4$HCO$_3$ and CH$_3$CN (Gradient B % 20%-24%, run time 10 min); flow rate: 15 ml/min; UV detection at 254 nm. This resulted in 4.6 mg (5%) of I-204 as a solid. MS (ES): m/z 466 (M+H)$^+$. $^1$H-NMR (300 MHz, CD$_3$OD+CDCl$_3$): δ 7.65 (2H, d), 7.43-7.31 (2H, m), 7.15-6.99 (1H, m), 5.25-5.05 (1H, m), 3.79-3.68 (1H, m), 3.08-2.82 (3H, m), 2.79-2.65 (1H, m), 2.61-2.31 (9H, m), 2.28-2.02 (4H, m), 1.75-1.39 (4H, m).

Example 215

Synthesis of [(12S)-3-[[4-(morpholin-4-yl)cyclohexyl]amino]-8-thia-4,6-diazatricyclo[7.4.0.0[2,7]]-trideca-2,4,6-trien-12-yl]methanol (I-210)

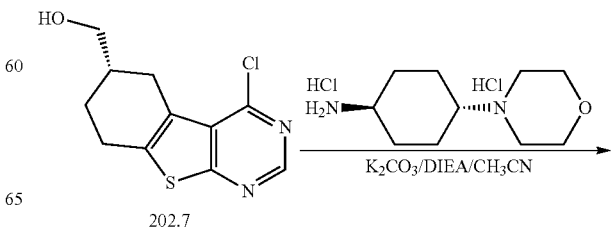

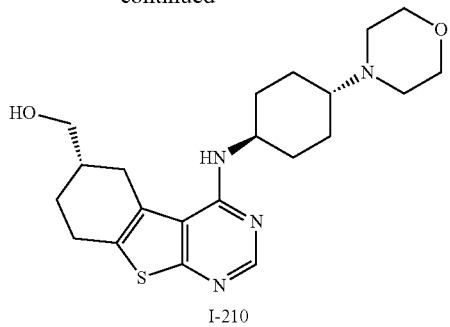

I-210

A mixture of 202.7 (50 mg, 0.20 mmol, 1.00 equiv), trans-4-(morpholin-4-yl)cyclohexan-1-amine dihydrochloride (109 mg, 0.59 mmol, 3.00 equiv), DIEA (51 mg, 0.39 mmol, 2.01 equiv) and potassium carbonate (136 mg, 0.98 mmol, 5.01 equiv) in 25 mL of CH$_3$CN (25 mL) was stirred for 60 h at 80° C. under nitrogen. The reaction was then quenched by the addition of 30 mL of water and extracted with 3×60 mL of chloroform/iso-propanol (3:1). The combined organic layers were concentrated under vacuum. The crude product (80 mg) was purified by preparative HPLC under the following conditions (Waters): Column: SunFire Prep C18, 19*150 mm 5 μm; mobile phase: water with 0.05% NH$_4$HCO$_3$ and CH$_3$CN (10.0% CH$_3$CN up to 30.0% in 9 min, up to 100.0% in 2 min, down to 10.0% in 1 min); flow rate: 20 mL/min; UV detection at 220/254 nm. This resulted in 20.1 mg (25%) of I-201 as a white solid. MS (ES): m/z 403 (M+H)$^+$. $^1$H NMR (300 MHz, CDCl$_3$): δ 8.35 (1H, s), 5.13-5.11 (1H, d), 4.12-4.10 (1H, m), 3.73-3.68 (6H, s), 3.06-3.00 (1H, d), 2.87 (2H, s), 2.70-2.58 (5H, t), 2.30-2.27 (3H, d), 2.10-1.96 (4H, m), 1.67-1.25 (5H, m).

Example 216

Synthesis of [(12R)-3-[[4-(morpholin-4-yl)cyclo-hexyl]amino]-8-thia-4,6-diazatricyclo[7.4.0.0[2,7]]trideca-1(9),2,4,6-tetraen-12-yl]methanol (I-211)

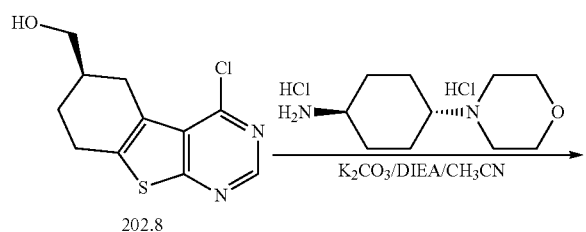

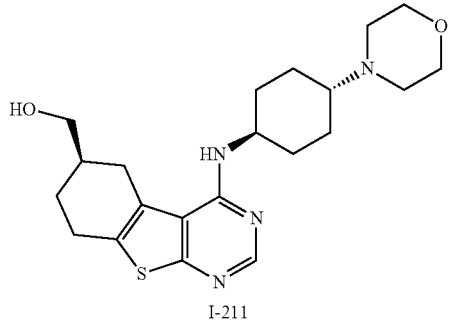

I-211

Compound I-211 was prepared from 202.8 in a manner analogous to the synthesis of Compound I-210 from 202.7. Isolated 19.3 mg of a white solid in 24% yield. MS (ES): m/z 403 (M+H)$^+$. $^1$H NMR (400 MHz, CDCl$_3$): δ 8.38 (1H, s), 5.15-5.14 (1H, d), 4.17-4.14 (1H, m), 3.85-3.81 (4H, s), 3.79-3.71 (2H, m), 3.09-3.04 (1H, m), 2.90-2.86 (2H, s), 2.75-2.69 (5H, m), 2.65-2.34 (1H, s), 2.33-2.30 (2H, m), 2.14-2.07 (4H, m), 1.66-1.62 (5H, m).

Example 217

Synthesis of 3-[(3R)-12-[[4-(morpholin-4-yl)cyclo-hexyl]oxy]-7-thia-9,11-diazatricyclo[6.4.0.0[2,6]]dodeca-1(8),2(6),9,11-tetraen-3-yl]-2-oxopropana-mide (I-213)

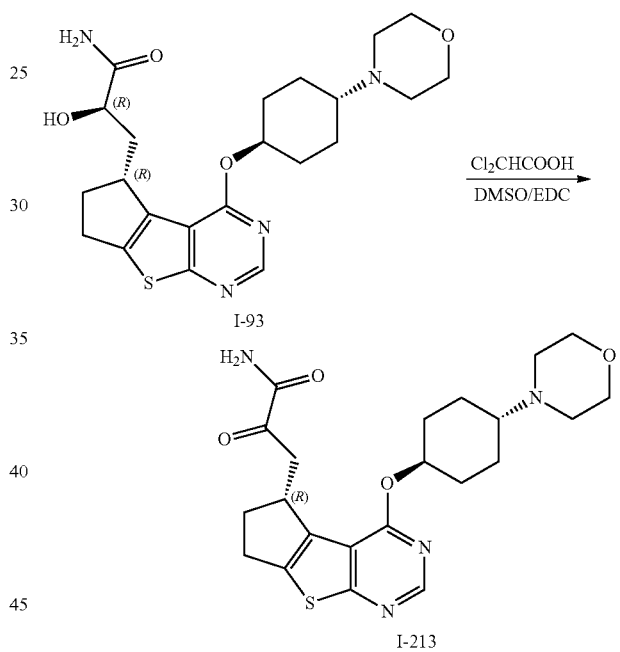

Into a 500-mL round-bottom flask was placed a solution of I-93 (8.5 g, 19.03 mmol, 1.00 equiv) in DMSO (300 mL) followed by EDC (36.48 g, 10.00 equiv). This was followed by the addition of 2,2-dichloroacetic acid (9.8 g, 76.00 mmol, 4.00 equiv) dropwise with stirring at 0° C. The resulting solution was stirred for 3 h at room temperature. The reaction was then quenched by the addition of 120 mL of sodium bicarbonate (sat., aq.). The resulting solution was extracted with 4×200 mL of ethyl acetate and the organic layers combined. The resulting mixture was washed with 5×300 mL of brine. The mixture was dried over anhydrous sodium sulfate and concentrated under vacuum. The residue was applied onto a silica gel column with dichloromethane/methanol (30:1) to give 7.8 g (92%) of I-213 as a white solid. MS (ES): m/z 445 (M+H)$^+$. $^1$H NMR (300 MHz, CDCl$_3$): δ 8.50 (1H, s), 6.82 (1H, s), 5.44 (1H, s), 5.23-5.20 (1H, m), 3.81-3.62 (6H, m), 3.20-2.93 (3H, m), 2.86-2.76 (1H, m), 2.60 (4H, s), 2.30-2.28 (3H, m), 2.15-1.98 (3H, m), 1.55-1.42 (4H, m).

Example 218

Synthesis of 2-[(3R)-12-[[4-(piperidin-1-yl)cyclohexyl]oxy]-7-thia-9,11-diazatricyclo[6.4.0.0[2,6]]dodeca-1(8),2(6),9,11-tetraen-3-yl]acetamide (I-214)

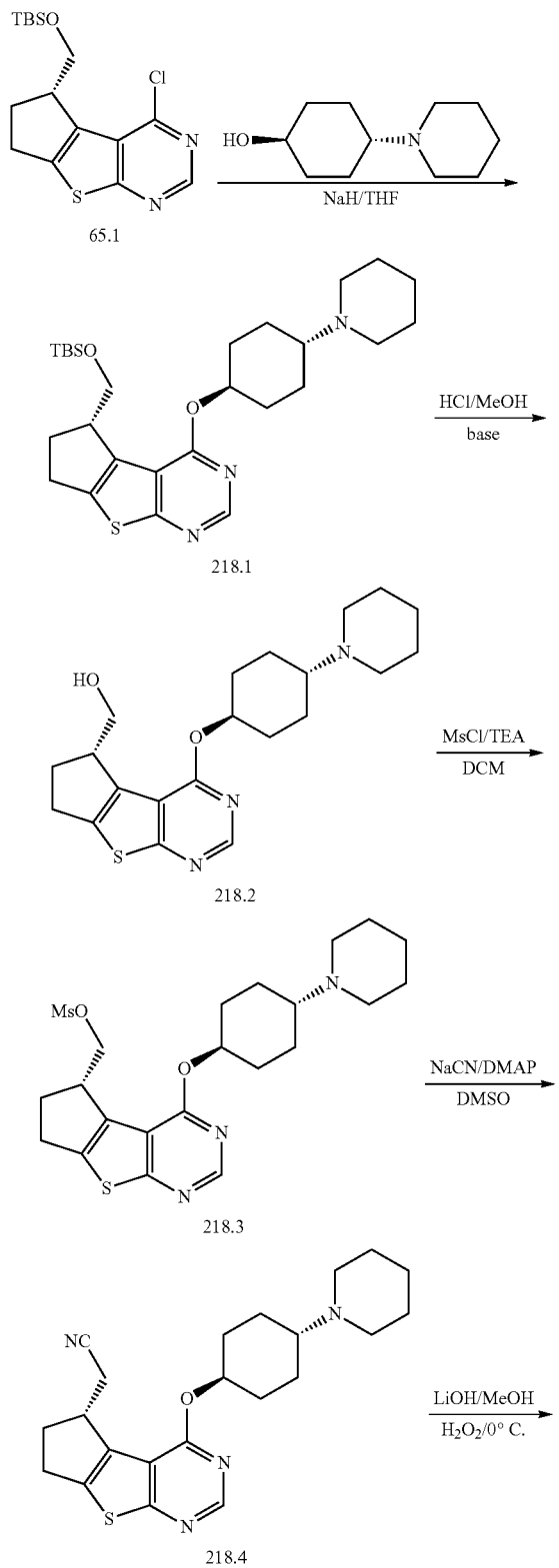

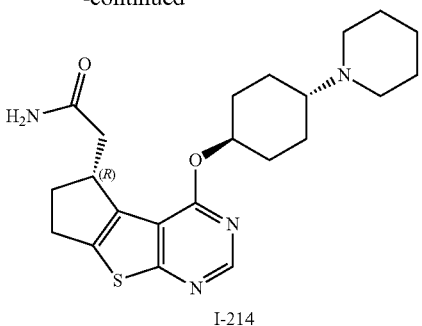

I-214

Synthesis of Compound 218.1.

Sodium hydride (60%, 140 mg, 3.50 mmol, 5.00 equiv) was treated with trans-4-(piperidin-1-yl)cyclohexan-1-ol (258 mg, 1.41 mmol, 2.00 equiv) in distilled tetrahydrofuran (10 mL) under nitrogen for 1 h. Then a solution of 65.1 (250 mg, 0.70 mmol, 1.00 equiv) in tetrahydrofuran (5 mL) was added and stirred for 2 h at room temperature. The reaction was then quenched by the addition of 20 mL of water and extracted with 3×100 mL of ethyl acetate. The combined organic layers were dried over anhydrous sodium sulfate and concentrated under vacuum. The residue was applied onto a silica gel column with dichloromethane/methanol (100:1) to give 300 mg (85%) of 218.1 as a white solid.

Synthesis of Compound 218.2.

Into a 100-mL round-bottom flask was placed a solution of 219.1 (300 mg, 0.60 mmol, 1.00 equiv) in methanol (20 mL) followed by cooling to 0° C. Then 12 M hydrochloric acid (1 mL) was added and the resulting solution was stirred for 2 h at room temperature. The resulting mixture was concentrated under vacuum, diluted with DCM, neutralized with saturated sodium bicarbonate, washed with brine. The organic phase was dried over sodium sulfate and concentrated in vacuo to give the desired 218.2 (250 mg, crude) as a yellow oil.

Synthesis of Compound 218.3.

To a solution of 218.2 (170 mg, 0.44 mmol, 1.00 equiv) in DCM (20 mL) was added methanesulfonyl chloride (94 mg, 0.82 mmol, 2.00 equiv) and TEA (127 mg, 1.26 mmol, 3.00 equiv) at 0° C. The resulting solution was stirred for 2 h at room temperature and diluted with 100 mL of DCM, washed with brine, dried over anhydrous sodium sulfate and concentrated under vacuum to afford 250 mg (crude) of 218.3 as a yellow oil.

Synthesis of Compound 218.4.

Into a 25-mL round-bottom flask containing a solution of 218.3 (200 mg, 0.43 mmol, 1.00 equiv) in DMSO (10 mL) was added sodiumcarbonitrile (105 mg, 2.14 mmol, 5.00 equiv). The resulting solution was stirred for 2 h at 100° C. in an oil bath. After cooling, the reaction was then quenched by the addition of 50 mL of water and extracted with 3×100 mL of dichloromethane, washed with brine, dried over anhydrous sodium sulfate and concentrated under vacuum to provide 120 mg (crude) of 218.4 as a yellow oil.

Synthesis of Compound I-214.

To a solution of 218.4 (120 mg, 0.30 mmol, 1.00 equiv) in MeOH (5 mL) was added LiOH.H$_2$O (25.2 mg, 0.60 mmol, 2.00 equiv) followed by cooling in an ice/water bath. Then hydrogen peroxide (1 mL) was added slowly and the resulting solution was stirred for 1 h at this temperature. The reaction was then quenched with saturated NaHSO$_3$ and extracted with 3×50 mL of dichloromethane. The combined organic layers were dried over anhydrous sodium sulfate and concentrated under vacuum. The crude product (100 mg) was purified by preparative HPLC under the following conditions ((Waters): Column: SunFire Prep C18, 19*150 mm 5 μm; mobile phase: water with 0.05% NH$_4$HCO$_3$ and CH$_3$CN (40% CH$_3$CN up to 70% in 10 min); flow rate: 20 mL/min; UV detection at 254 nm. This resulted in 22 mg (18%) of I-214 as a white solid. MS (ES): m/z 415 (M+H)$^+$. $^1$H NMR (400 MHz, CD$_3$OD): δ 8.49 (s, 1H), 5.29-5.24 (m, 1H), 3.81 (m, 1H), 3.33-3.25 (m, 1H), 3.03-2.98 (m, 2H), 2.85-2.68 (m, 5H), 2.53 (m, 1H), 2.33-2.25 (m, 4H), 2.09-2.06 (m, 2H), 1.68-1.31 (m, 10H).

Example 219

Synthesis of [(12R)-3-[[4-(morpholin-4-yl)cyclohexyl]oxy]-8-thia-4,6-diazatricyclo[7.4.0.0[2,7]]trideca-1(9),2(7),3,5-tetraen-12-yl]methanol (I-215)

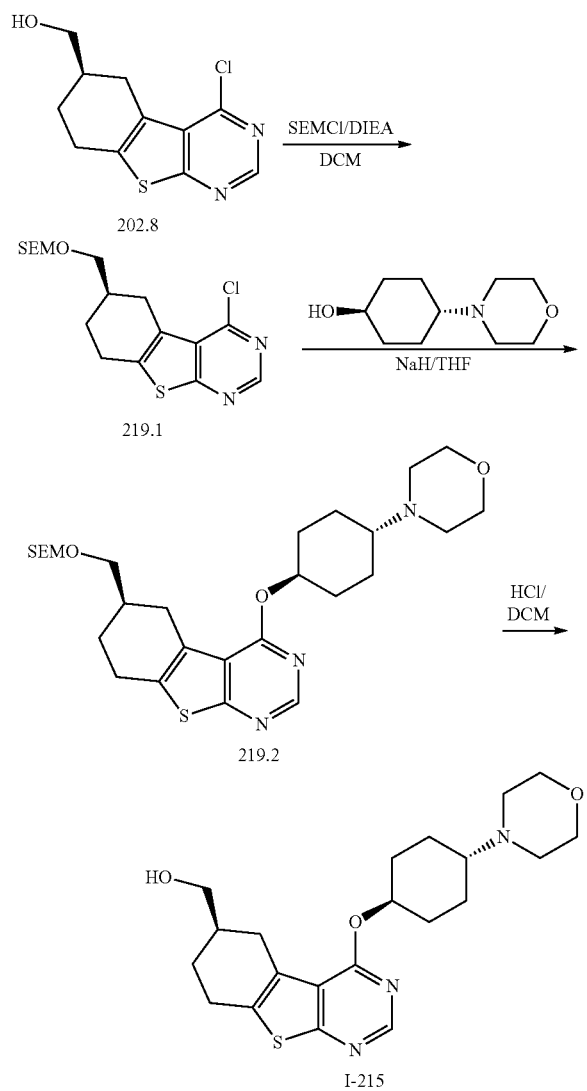

Synthesis of Compound 219.1.

To a solution of 202.8 (100 mg, 0.39 mmol, 1.00 equiv) in dichloromethane (15 mL) was added DIEA (0.2 mL, 3.00 equiv) and SEMCl (131 mg, 2.00 equiv) at 0° C. under nitrogen. The resulting solution was stirred for 2 h at room temperature and then concentrated under vacuum. The residue was diluted with water and extracted with EtOAc, washed with 1M aqueous HCl and brine, dried over sodium sulfate and evaporated under reduced pressure. The residue was applied onto a silica gel column with ethyl acetate/petroleum ether (1:20) to give 100 mg (66%) of 219.1 as a white solid.

Synthesis of Compound 219.2.

Sodium hydride (60%, 52 mg, 1.30 mmol, 5.00 equiv) was treated with trans-4-(morpholin-4-yl)cyclohexan-1-ol (96 mg, 0.52 mmol, 2.00 equiv) in 3 mL of distilled THF at 0° C. for 1 h under nitrogen. A solution of 219.1 (100 mg, 0.26 mmol, 1.00 equiv) in tetrahydrofuran (2 mL) was added at 45° C. via syringe. The resulting solution was stirred for 4 h at this temperature. After cooling, the reaction was then quenched by the addition of 10 mL of water. The pH value of the solution was adjusted to 6 with 1 M aqueous hydrochloric acid followed by extraction with 3×50 mL of dichloromethane. The organic layers were combined and concentrated under vacuum to give 90 mg (crude) of 219.2 as a white solid.

Synthesis of Compound I-215.

To a solution of 219.2 (90 mg, 0.17 mmol, 1.00 equiv) in methanol (5 mL) was added 12 M hydrochloric acid (0.2 mL) at 0° C. The resulting solution was stirred for 2 h at room temperature. The resulting solution was concentrated in vacuo and the residue was diluted with DCM, washed with saturated aqueous sodium bicarbonate and brine, dried over sodium sulfate and evaporated under reduced pressure. Purification by chromatography on silica gel with DCM/MeOH (1:50 to 1:30) yielded 19.7 mg of I-215 as a white solid. MS (ES): m/z 404 (M+H)$^+$. $^1$H-NMR (400 MHz, CDCl$_3$): δ 8.50 (s, 1H), 5.29-5.18 (m, 1H), 3.95-3.64 (m, 6H), 3.20 (dd, 1H), 2.98-2.80 (m, 2H), 2.78-2.45 (m, 5H), 2.38-2.25 (m, 3H), 2.18-1.95 (m, 4H), 1.45-1.25 (m, 5H).

Example 220

Synthesis of [(12S)-3-[[4-(morpholin-4-yl)cyclohexyl]oxy]-8-thia-4,6-diazatricyclo[7.4.0.0[2,7]]trideca-1(9),2(7),3,5-tetraen-12-yl]methanol (I-216)

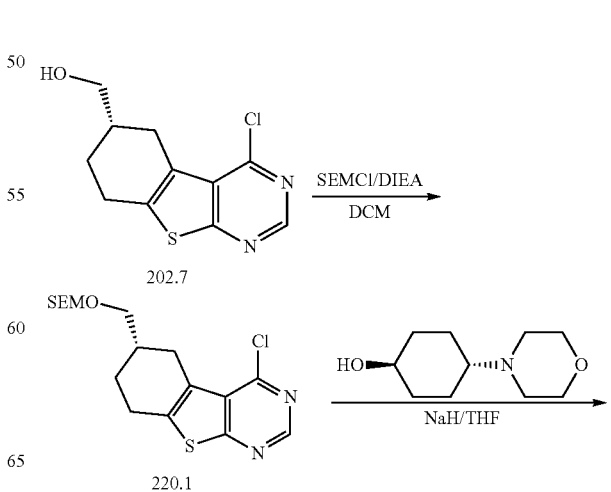

-continued

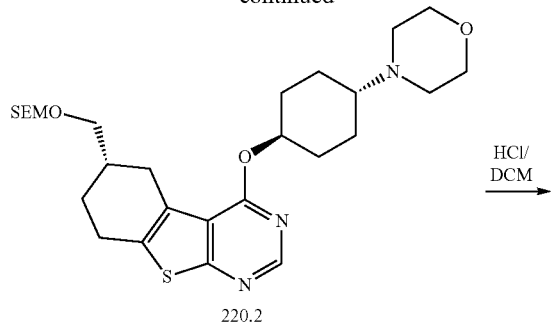

220.2

HCl/
DCM
→

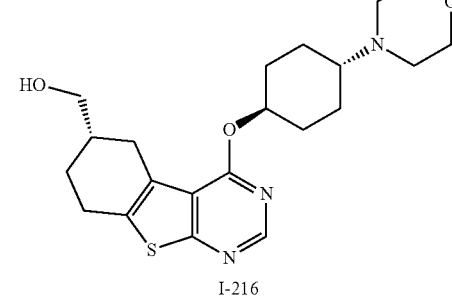

I-216

Compound I-216 was prepared from 202.7 in a manner analogous to the synthesis of Compound I-215 from 202.8. Isolated 24.3 mg of a white solid in 15% overall yield from 202.7. MS (ES): m/z 404 (M+H)$^+$. $^1$H-NMR (300 MHz, CDCl$_3$): δ 8.49 (s, 1H), 5.30-5.15 (m, 1H), 3.78-3.64 (m, 6H), 3.18 (dd, 1H), 2.98-2.78 (m, 2H), 2.75-2.50 (m, 5H), 2.48-2.20 (m, 3H), 2.16-1.95 (m, 4H), 1.92-1.62 (m, 5H).

Example 221

Synthesis of 2-(3-[[4-(dimethylamino)cyclohexyl]oxy]-11-oxa-8-thia-4,6-diazatricyclo[7.4.0.0[2,7]]-trideca-1(9),2(7),3,5-tetraen-12-yl)acetamide (I-221)

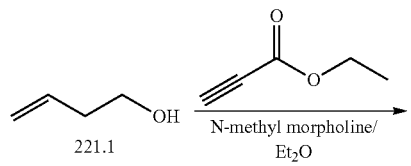

221.1

N-methyl morpholine/
Et$_2$O
→

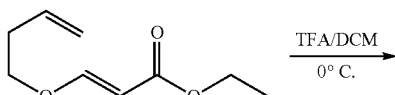

221.2

TFA/DCM
0° C.
→

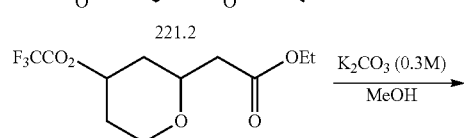

221.3

K$_2$CO$_3$ (0.3M)
MeOH
→

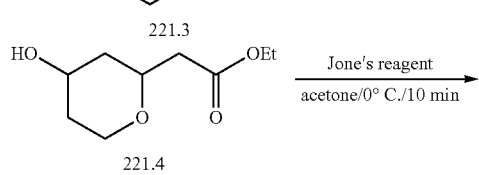

221.4

Jone's reagent
acetone/0° C./10 min
→

-continued

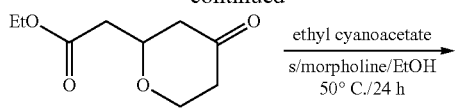

221.5 ethyl cyanoacetate
s/morpholine/EtOH
50° C./24 h
→

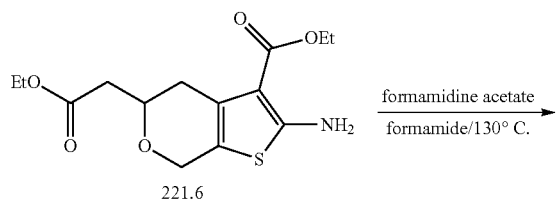

221.6 formamidine acetate
formamide/130° C.
→

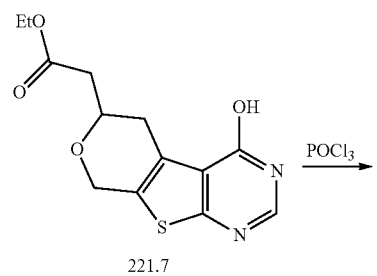

221.7

POCl$_3$
→

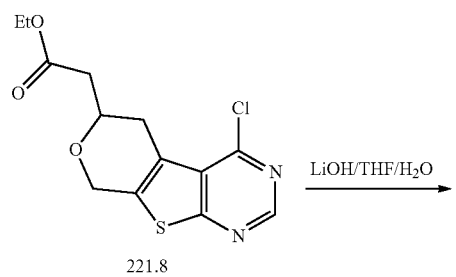

221.8

LiOH/THF/H$_2$O
→

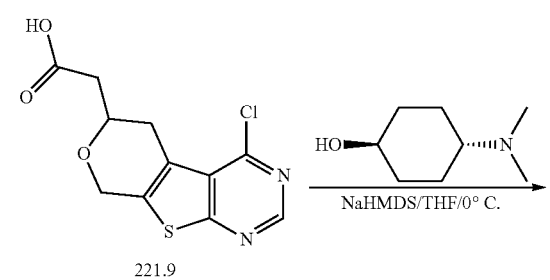

221.9

NaHMDS/THF/0° C.
→

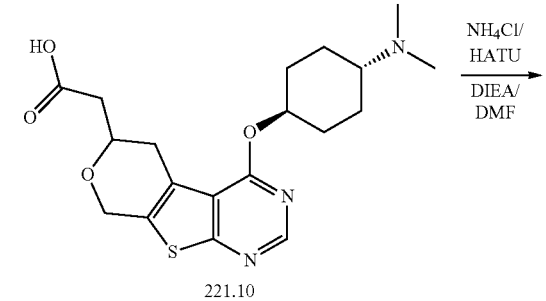

221.10

NH$_4$Cl/
HATU
DIEA/
DMF
→

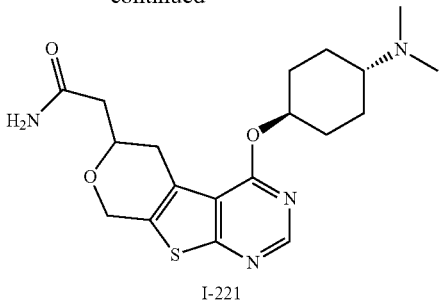

I-221

Synthesis of Compound 221.2.

To a solution of ethyl prop-2-ynoate (6.2 g, 63.20 mmol, 1.07 equiv) in 80 mL of dry ether was added 4-methylmorpholine (6.3 g, 62.29 mmol, 1.06 equiv), pent-4-en-1-ol (4.25 g, 58.94 mmol, 1.00 equiv) successively. The resulting solution was stirred overnight at room temperature under nitrogen. The resulting mixture was poured into 150 mL of 0.5 M aqueous HOAc and extracted with 2×150 mL of ethyl acetate. The combined organic layers were dried over sodium sulfate and concentrated under vacuum. The residue was applied onto a silica gel column with ethyl acetate/petroleum ether (1:30 to 1:10) to afford 9.6 g (96%) of 221.2 as a colorless oil.

Synthesis of Compound 221.3.

To a solution of 221.2 (9.8 g, 57.58 mmol, 1.00 equiv) in 150 mL of dry DCM at 0° C. was added TFA (25 mL) dropwise over 30 min. The resulting solution was stirred for 2 h at 0° C. After completion, the reaction mixture was concentrated in vacuo and diluted with 200 mL of EtOAc, washed with a cold 1 M NaHCO$_3$ solution. The organic layer was washed with brine, dried over anhydrous sodium sulfate and concentrated under vacuum to afford 14.1 g (crude) of 221.3 as a yellow oil which was used for the next step without further purification.

Synthesis of Compound 221.4.

To a solution of 221.3 (14.1 g, crude) in 80 mL of methanol (80 mL) was added potassium carbonate (0.3M, 200 mL) and the resulting solution was stirred for 30 min at 25° C. The pH value of the solution was adjusted to 7 with AcOH. The resulting solution was extracted with 3×100 mL of dichloromethane. The organic layers were washed with brine, dried over anhydrous magnesium sulfate and concentrated under vacuum to provide 8.2 g (crude) of 221.4 as a colorless viscous liquid.

Synthesis of Compound 221.5.

To a solution of 221.4 (8.2 g, 43.57 mmol, 1.00 equiv) in acetone (160 mL) at 0° C. was added dropwise Jones reagent (20 mL) and the resulting mixture was stirred for approx. 10 min. The reaction was then quenched by the addition of saturated aqueous NaHSO$_3$ and extracted with 2×100 mL of ethyl acetate. The combined organic layers were washed with brine, dried over anhydrous sodium sulfate and concentrated under vacuum to provide 7.2 g (crude) of 221.5 as a light yellow oil.

Synthesis of Compound 221.6.

Into a 250-mL round-bottom flask containing a solution of 221.5 (7.2 g, 38.67 mmol, 1.00 equiv) in dry ethanol (85 mL) was added S (1.2 g, 37.50 mmol, 0.97 equiv), ethyl 2-cyanoacetate (4.8 g, 42.43 mmol, 1.10 equiv) and morpholine (3.4 g, 39.03 mmol, 1.01 equiv) sequentially at room temperature. The resulting solution was stirred overnight at 50° C. in an oil bath under nitrogen. The resulting mixture was concentrated under vacuum and the residue was diluted with 100 mL of water and extracted with 2×150 mL of ethyl acetate. The organic layers were combined, washed with brine, dried over sodium sulfate and concentrated under vacuum. The residue was applied onto a silica gel column with ethyl acetate/petroleum ether (1:9) to give 11.5 g (95%) of 221.6 as a yellow oil.

Synthesis of Compound 221.7.

To a solution of 221.6 (500 mg, 1.60 mmol, 1.00 equiv) in 15 mL of formamide (15 mL) was added formamidine acetate (830 mg, 7.97 mmol, 5.00 equiv) and the resulting mixture was stirred 5 h at 140° C. in an oil bath under nitrogen. After cooling, the resulting mixture was diluted with water and extracted with 3×60 mL of ethyl acetate. The combined organic layers were washed with brine, dried over sodium sulfate and concentrated under reduced pressure. The residue was applied onto a silica gel column with ethyl acetate/petroleum ether (2:1) to give 283 mg (60%) of 221.7 as a white solid.

Synthesis of Compound 221.8.

To a solution of 221.7 (1.3 g, 4.42 mmol, 1.00 equiv) in 15 mL of dry 1,4-dioxane was added POCl$_3$ (5 mL) at room temperature under nitrogen. The resulting solution was stirred for 1 h at 100° C. in an oil bath. The resulting mixture was concentrated under vacuum and the residue was diluted with EtOAc (150 mL), neutralized with saturated aqueous sodium bicarbonate, washed with brine, dried over sodium sulfate and concentrated under reduced pressure. The residue was applied onto a silica gel column with ethyl acetate/petroleum ether (1:10) to provide 1 g (72%) of 221.8 as a white solid.

Synthesis of Compound 221.9.

To a solution of 221.8 (500 mg, 1.6 mmol, 1.0 equiv) in a mixture of THF/water (6/6 mL) was added LiOH.H$_2$O (202 mg, 4.8 mmol, 3.0 equiv) at 0° C. The resultant solution was stirred at room temperature for 3 h. The contents of the flask were transferred to a separatory funnel, made acidic with 1M HCl and then extracted with ethyl acetate (2×100 ml). Combined the organics and washed 1× with brine before drying over sodium sulfate, filtering and concentrating in vacuo. This afforded 342 mg (crude) of compound 221.9 as a yellow solid that was used as is in the next reaction.

Synthesis of Compound 221.10.

To a solution of compound 221.9 (100 mg, 0.35 mmol, 1.0 equiv) and trans-4-(dimethylamino)cyclohexanol (60 mg, 0.42 mmol, 1.2 equiv) in 3 mL of freshly distilled THF at 0° C. was added NaHMDS (2 M in THF, 0.5 mL, 1.05 mmol, 3.0 equiv) via syringe under nitrogen. The resultant solution was stirred at this temperature for 30 min and then diluted with water. The resultant solution was acidified to pH 4-5 with 1M HCl solution and extracted with CHCl$_3$/iso-propanol (V/V=3/1), dried over sodium sulfate and concentrated in vacuo. The residue was purified by reverse-phase chromatography (water and CH$_3$CN as eluent) to give 30 mg (90% purity) of the desired compound 221.10 as a yellow oil.

Synthesis of Compound I-221.

To a solution of 221.10 (25 mg, 0.06 mmol, 1.00 equiv) in N,N-dimethylformamide (10 mL) was added NH$_4$Cl (3.8 mg, 0.07 mmol, 1.20 equiv), HATU (27 mg, 0.07 mmol, 1.20 equiv) and DIEA (15 mg, 0.12 mmol, 2.00 equiv) successively at room temperature under nitrogen. The resulting solution was stirred overnight at ambient temperature, quenched with water and extracted with 4×20 mL of dichloromethane. The combined organic layers were washed with brine, dried over anhydrous sodium sulfate and concentrated under vacuum. The crude product (40 mg) was purified by preparative HPLC under the following conditions (Waters): Column: SunFire Prep C18, 19*150 mm 5 µm; mobile phase: water with 0.05% NH$_4$HCO$_3$ and CH$_3$CN (10.0% CH$_3$CN up to 36.0% in 10 min, up to 100.0% in 2 min, down to 10.0% in 1 min); flow rate: 20 mL/min; UV detection at 220/254 nm. This resulted in 9.6 mg (38%) of I-221 as a white solid. MS (ES): m/z 391 (M+H)+. 1H NMR (300 MHz, CD3OD): δ 8.38 (1H, s), 5.17-5.10 (1H, m), 4.86-4.78 (2H, m), 4.08-4.02 (1H, m), 3.21 (1H, dd), 2.72-2.62 (1H, m), 2.57-2.48 (2H, m), 2.39-2.30 (1H, m), 2.30-2.20 (8H, m), 1.97-1.93 (2H, d), 1.57-1.38 (4H, m).

Example 222

Synthesis of 2-[(3R)-12-[[4-(pyrrolidin-1-yl)cyclohexyl]oxy]-7-thia-9,11-diazatricyclo[6.4.0.0[2,6]]dodeca-1(8),2(6),9,11-tetraen-3-yl]acetamide (I-105)

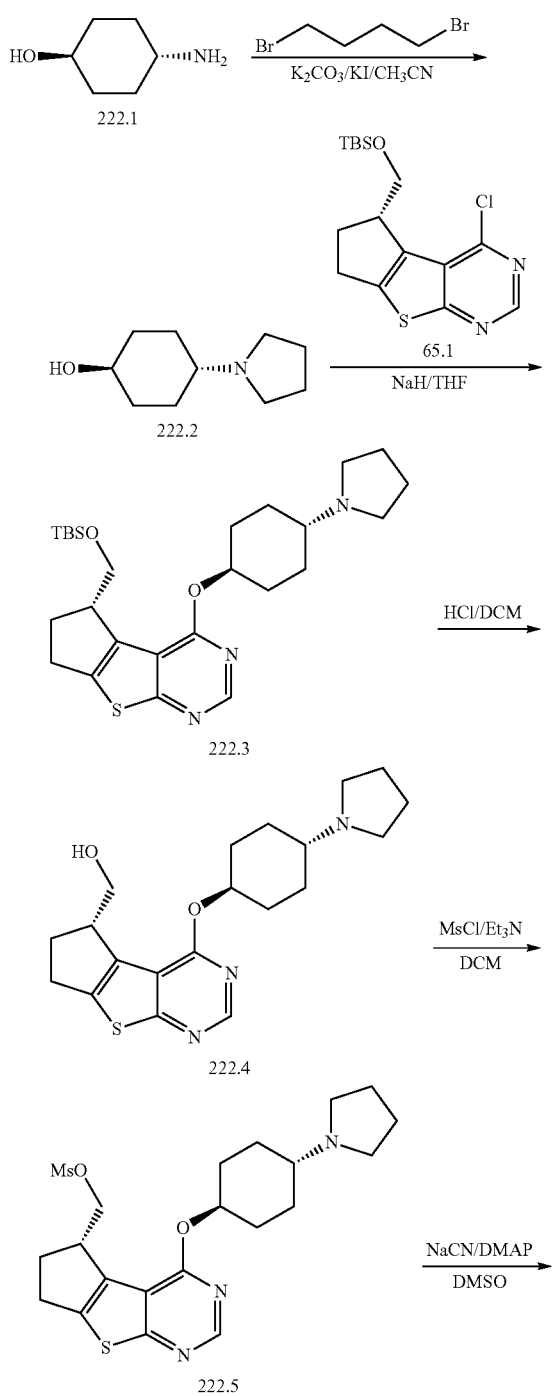

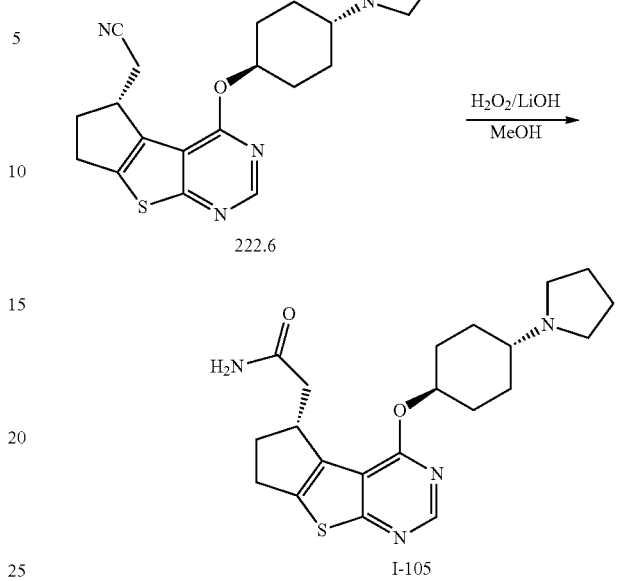

Synthesis of Compound 222.2.

Into a 50-mL round-bottom flask purged and maintained with an inert atmosphere of nitrogen was placed a mixture of trans-4-aminocyclohexan-1-ol (1.0 g, 8.7 mmol, 1.00 equiv), KI (1.87 g), potassium carbonate (0.3 g, 2.2 mmol, 0.25 equiv) and 1,4-dibromobutane (1.93 g, 8.9 mmol, 1.03 equiv) in CH3CN (30 mL). The resulting solution was heated to reflux for 2 hr and filtered to remove the solids. The filtrate was concentrated in vacuo and the residue was diluted with water and extracted with 3×50 mL of ethyl acetate. The combined organic layers were dried over sodium sulfate and concentrated under vacuum. The residue was applied onto a silica gel column with dichloromethane/methanol (10/1) to give in 1.4 g (95%) of 222.2 as a yellow solid.

Synthesis of Compound 222.3.

Sodium hydride (108 mg, 4.50 mmol, 4.0 equiv, 60% dispersion in mineral oil) was treated with 222.2 (290 mg, 1.71 mmol, 1.52 equiv) in distilled tetrahydrofuran (10 mL) for 30 min at room temperature under nitrogen. This was followed by the addition of 65.1 (400 mg, 1.13 mmol, 1.00 equiv) and the resulting solution was allowed to react, with stirring, for an additional 1 h at 40° C. The reaction was then quenched with saturated aqueous NH4Cl and extracted with 4×30 mL of ethyl acetate. The organic layers were combined, dried over sodium sulfate and concentrated under vacuum. The residue was applied onto a silica gel column with dichloromethane/methanol (30:1) to give the desired 222.3 (440 mg, 80%) as a yellow oil.

Synthesis of Compound 222.4.

To a solution of 222.3 (440 mg, 0.90 mmol, 1.00 equiv) in 10 mL of dichloromethane was added hydrochloric acid (conc., 0.5 mL) at 0° C. and the resulting solution was stirred for 4 h at this temperature. The reaction was then quenched by the addition of 15 mL of sodium bicarbonate and extracted with 3×50 mL of trichloromethane/1-PrOH (3:1). The combined organic layers were dried over sodium sulfate and concentrated under vacuum. The residue was applied onto a silica gel column with dichloromethane/methanol (10:1) to give 250 mg (74%) of 222.4 as yellow oil.

Synthesis of Compound 222.5.

Into a 50-mL round-bottom flask, purged and maintained with an inert atmosphere of argon, was placed a solution of 222.4 (250 mg, 0.67 mmol, 1.00 equiv) in dichloromethane (8 mL) was added MsCl (152 mg, 1.33 mmol, 1.99 equiv) and triethylamine (230 mg, 2.27 mmol, 3.40 equiv) at 0° C. under nitrogen. The resulting solution was stirred for 4 h at room temperature and diluted with water and extracted with 3×50 mL of trichloromethane/i-PrOH (3:1). The organic layers were dried over sodium sulfate and concentrated under vacuum to give 222.5 (200 mg, crude) as a yellow solid.

Synthesis of Compound 222.6.

To a solution of 222.5 (200 mg, 0.44 mmol, 1.00 equiv) in 5 mL of DMSO was added NaCN (103 mg, 2.10 mmol, 4.85 equiv) and 4-dimethylaminopyridine (10 mg, 0.08 mmol, 0.18 equiv) at room temperature. The resulting solution was stirred for 5 h at 80° C. After cooling, the reaction was quenched with sodium bicarbonate (aq.) and extracted with 4×50 mL of ethyl acetate and the organic layers were combined, dried over sodium sulfate and concentrated under vacuum. 222.6 (160 mg, 94%) was obtained as a yellow solid.

Synthesis of Compound I-105.

To a solution of 222.6 (160 mg, 0.42 mmol, 1.00 equiv) in methanol (5 mL) was added LiOH.H$_2$O (49 mg, 1.17 mmol, 2.79 equiv) and H$_2$O$_2$ (30%, 0.4 mL) at 0° C. The resulting solution was stirred for 5 h at this temperature and quenched with Na$_2$SO$_3$ (aq.) and extracted with 3×50 mL of ethyl acetate. The organic layers were combined, washed with brine, dried over sodium sulfate and concentrated under vacuum. The crude product (150 mg) was purified by preparative HPLC under the following conditions (Waters): Column: SunFire Prep C18, 19*150 mm 5 μm; mobile phase: water with 0.05% NH$_4$CO$_3$ and CH$_3$CN (5.0% CH$_3$CN up to 42.0% in 9 min, up to 95.0% in 2 min, down to 5.0% in 2 min); flow rate: 20 mL/min; UV detection at 254/220 nm. After evaporating the solvents and lyophilizing overnight, the desired I-105 (116 mg, 69%) was obtained as a white solid. MS (ES): m/z 401 (M+H)$^+$. $^1$H-NMR (400 MHz, CD$_3$OD): δ 8.47 (1H, s), 5.31 (1H, m), 4.80 (1H, m), 3.14 (1H, m), 3.02 (2H, m), 2.70 (5H, m), 2.15-2.33 (7H, m), 1.84 (4H, s), 1.68 (2H, m), 1.63 (2H, m).

Example 223

Synthesis of propyl 3-[[4-(dimethylamino)cyclohexyl]oxy]-8-thia-4,6,12-triazatricyclo[7.4.0.0[2,7]]trideca-1(9),2(7),3,5-tetraene-12-carboxylate (I-184)

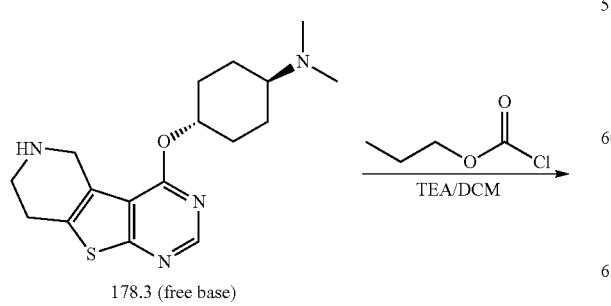

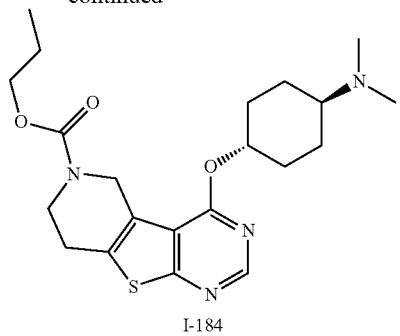

Compound I-184 was prepared from 178.3 (free base) in a manner analogous to the synthesis of Compound I-167. Isolated 11 mg of a white solid in 15% yield. MS (ES): m/z 419 (M+H)$^+$. $^1$H NMR (400 MHz, CDCl$_3$): δ 8.55 (1H, br s), 5.30-5.15 (1H, m), 4.84 (2H, s), 4.14 (2H, t), 3.86 (2H, brs), 2.95 (2H, brs), 2.65-2.25 (9H, m), 2.12-2.05 (2H, m), 1.72 (2H, sextet), 1.58-45 (4H, m), 1.03 (3H, t).

Example 224

Synthesis of 2-(3-[[4-(morpholin-4-yl)cyclohexyl]amino]-8-thia-4,6,12-triazatricyclo[7.4.0.0[2,7]]trideca-1(9),2(7),3,5-tetraene-12-sulfonyl)ethan-1-ol (I-185)

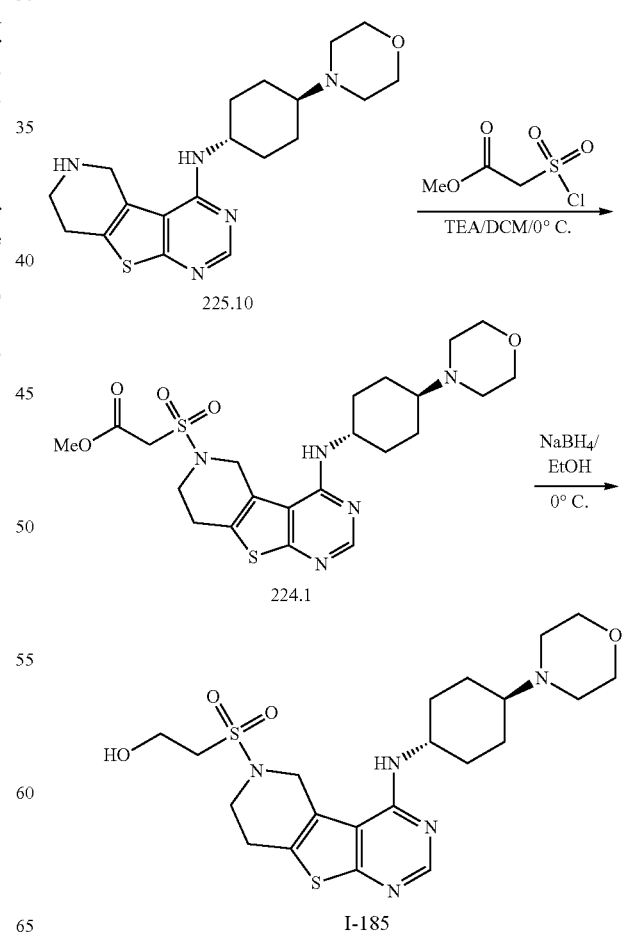

Synthesis of Compound 224.1.

To a solution of 225.10 (100 mg, 0.27 mmol, 1.00 equiv) in 10 mL of anhydrous DCM was added methyl 2-(chlorosulfonyl)acetate (70 mg, 0.405 mmol, 1.50 equiv) at 0° C., followed by addition of TEA (82 mg, 0.81 mmol, 3.0 equiv) via syringe under nitrogen. The resulting solution was stirred for 2 h at this temperature and quenched with water and extracted with DCM, dried over sodium sulfate and concentrated in vacuo. The residue was purified with a silica gel column: eluting with DCM/MeOH (50:1 to 30:1), to give the desired compound 224.1 (100 mg, 90% purity) as a light yellow solid.

Synthesis of Compound I-185.

To a solution of 224.1 (50 mg, 0.10 mmol, 1.00 equiv) in 8 mL of ethanol was added NaBH$_4$ (50 mg, 1.32 mmol, 13.47 equiv) at 0° C. The resulting solution was stirred for 4 h at room temperature and quenched by the addition of water and extracted with DCM and concentrated under vacuum. The crude product (60 mg) was purified by preparative HPLC under the following conditions (Waters): Column: SunFire Prep C18, 19*150 mm 5 µm; mobile phase: water with 0.05% NH$_4$HCO$_3$ and CH$_3$CN (15.0% CH$_3$CN up to 45.0% in 12 min, up to 100.0% in 2 min, down to 15.0% in 1 min); flow rate: 20 mL/min; UV detection at 220/254 nm. This resulted in 5.7 mg (12%) of Compound I-185 as a white solid. MS (ES): m/z 482 (M+H)$^+$. $^1$H-NMR (400 MHz, DMSO): δ 1.23 (m, 4H), 1.82 (m, 2H), 1.97 (m, 2H), 2.08 (m, 1H), 2.50 (m, 4H), 2.95 (s, 2H), 3.44 (m, 2H), 3.58 (m, 6H), 3.79 (t, J=7.6 Hz, 2H), 4.11 (m, 1H), 4.71 (s, 2H), 5.07 (t, J=7.2 Hz, 1H), 5.93 (m, 1H), 8.33 (s, 1H).

Example 225

Synthesis of 12-(ethanesulfonyl)-N-[4-(morpholin-4-yl)cyclohexyl]-8-thia-4,6,12-triazatricyclo[7.4.0.0[2,7]]trideca-1 (9),2(7),3,5-tetraen-3-amine (I-181)

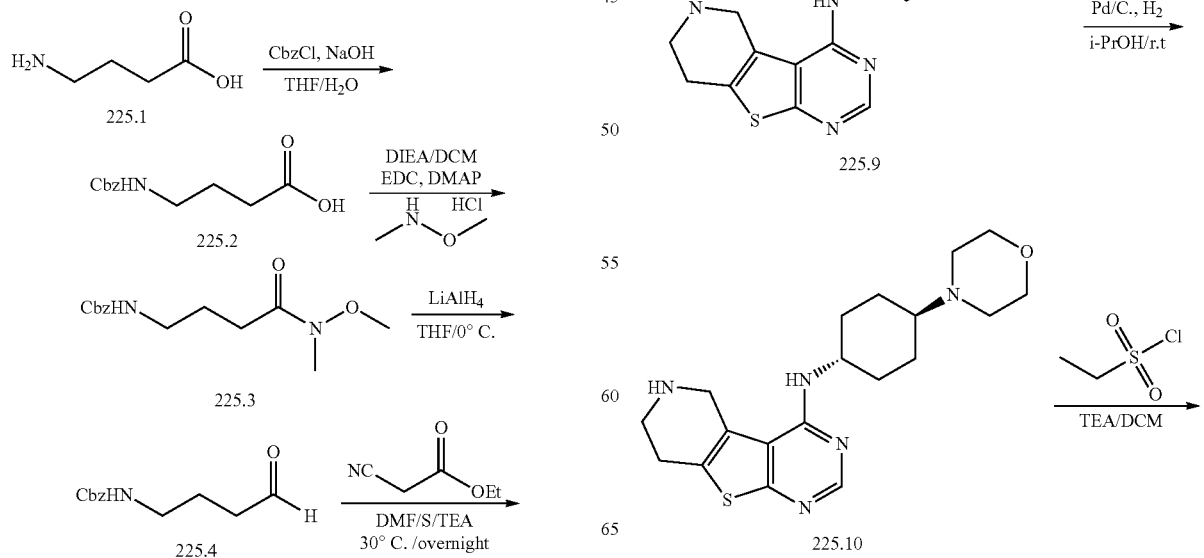

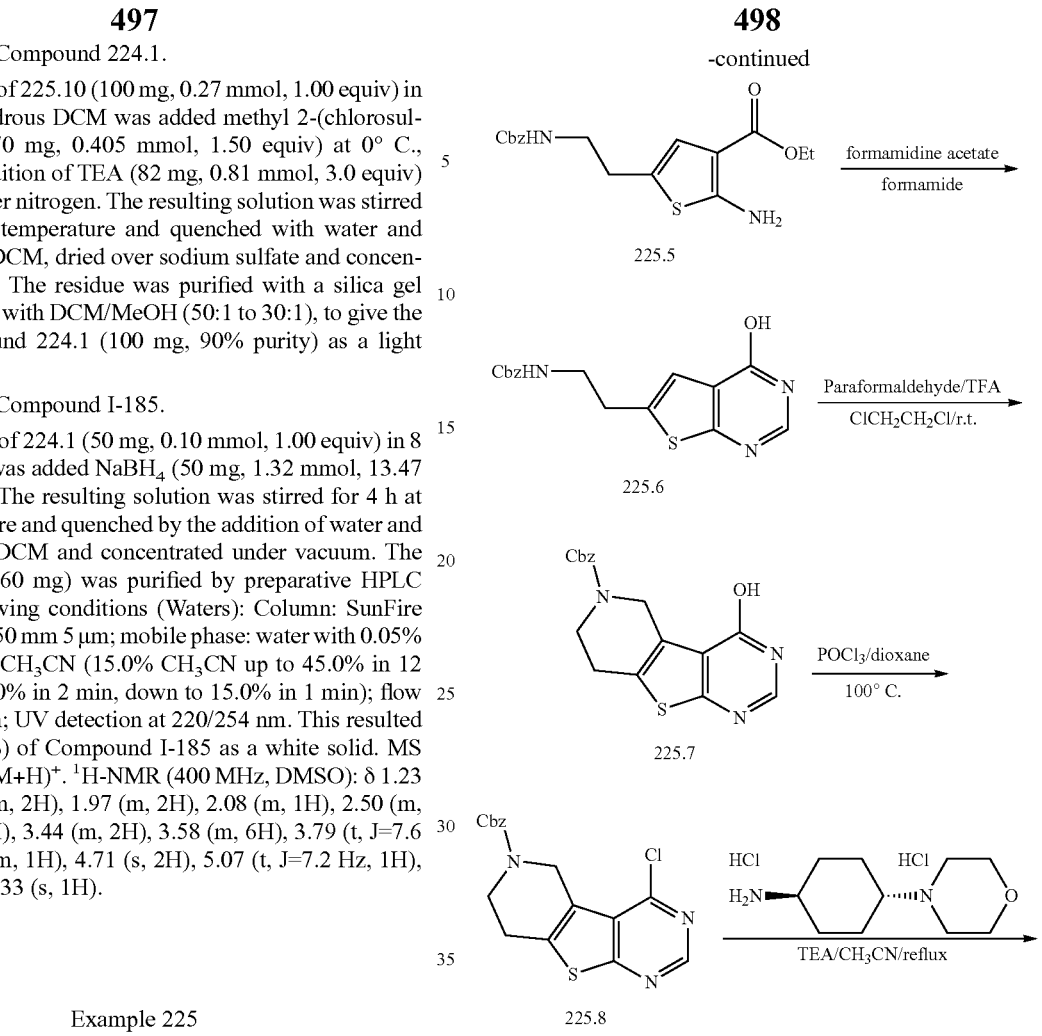

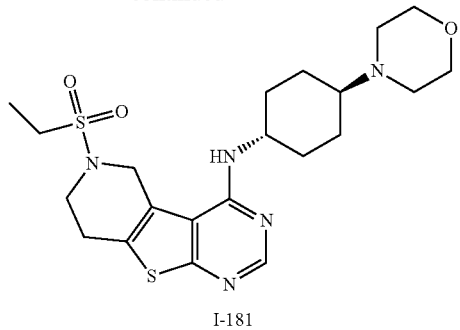

I-181

Synthesis of Compound 225.2.

A mixture of 4-aminobutanoic acid (10.3 g, 100 mmol, 1.00 equiv) and 4.2 g (1.05 eq) of sodium hydroxide in THF/H$_2$O (200/250 mL) was added dropwise benzyl chloroformate (17.1 g, 100 mmol, 1.00 equiv) in THF (100 mL) at 0° C. with the additional of a solution of sodium hydroxide (4.0 g) in water (150 mL) at the same time. Then the resulting solution was stirred overnight at room temperature. The pH value of the solution was adjusted to 5 with 2 M aqueous hydrochloric acid followed by extraction with ethyl acetate. The organic layers were dried over anhydrous sodium sulfate and concentrated in vacuo, the residue was applied onto a silica gel column with ethyl acetate/petroleum ether (1:1 to 1:0) to provide 19.6 g (83%) of 225.2 as a white solid.

Synthesis of Compound 225.3.

A solution of 225.2 (23.7 g, 99.89 mmol, 1.00 equiv), 4-dimethylaminopyridine (13.4 g, 109.68 mmol, 1.11 equiv), DIEA (25.8 g, 199.69 mmol, 2.01 equiv), EDCI (21.1 g, 110.07 mmol, 1.10 equiv) and methoxy(methyl)amine hydrochloride (10.7 g, 109.74 mmol, 1.10 equiv) in DCM (800 mL) was stirred 48 h at room temperature under nitrogen. The reaction was quenched with water and extracted with DCM. The organic layers were washed with 1 M aqueous HCl and brine and then dried over sodium sulfate. After filtration and concentration in vacuo, the residue was purified by a silica gel column with EtOAc/petroleum ether (1:1 to 100% EtOAc) to provide 25 g (89%) of 225.3 as a colorless oil.

Synthesis of Compound 225.4.

To a solution of 225.3 (2.8 g, 10.0 mmol, 1.00 equiv) in THF (150 mL) was added LiAlH$_4$ (760 mg, 20.0 mmol, 2.00 equiv) slowly at 0° C. The resulting mixture was stirred for 1.5 h at 0° C. under nitrogen. The reaction was quenched with Na$_2$SO$_4$.10H$_2$O and filtered. The solids were washed with THF (three times) and the filtrates were dried over anhydrous sodium sulfate. After filtration, the solvent was removed to provide 2.2 g of 225.4 as a colorless oil which was used directly in the next step.

Synthesis of Compound 225.5.

To a solution of 225.4 (500 mg, 2.26 mmol, 1.00 equiv), ethyl 2-cyanoacetate (306 mg, 2.71 mmol, 1.20 equiv) and S (87 mg, 2.72 mmol, 1.20 equiv) in ethanol (10 mL) was added Et$_2$NH (198 mg, 2.71 mmol, 1.20 equiv) at room temperature under nitrogen. The resulting mixture was stirred overnight at ambient temperature. The reaction was then quenched by the addition of 20 mL of saturated aqueous NH$_4$Cl, followed by extraction with 3×80 mL of ethyl acetate. The combined organic layers were washed with brine, dried over sodium sulfate and concentrated under vacuum. The residue was applied onto a silica gel column with ethyl acetate/petroleum ether (1/5) to give 225.5 (0.3 g, 38%) as a yellow oil.

Synthesis of Compound 225.6.

A solution of 225.5 (5.2 g, 14.92 mmol, 1.00 equiv) and iminoformamide acetate (5.2 g, 49.95 mmol, 3.35 equiv) in formamide (200 mL) was stirred for 2 h at 130° C. and then heated to 160° C. for 2 h under nitrogen. After cooling to room temperature, the reaction was quenched with brine and extracted with ethyl acetate. The organic layers were washed with brine and dried over anhydrous sodium sulfate. After filtration and concentration in vacuo, the residue was purified by a silica gel column with EtOAc/petroleum ether (1:1 to 100% EA) to afford 2.6 g (53%) of 225.6 as a white solid.

Synthesis of Compound 225.7.

To a mixture of 225.6 (2.0 g, 6.07 mmol, 1.00 equiv) and paraformaldehyde (2.0 g, 66.67 mmol, 10.98 equiv) in 50 mL of DCE was added F$_3$CCOOH (4.0 mL) followed by stirring overnight at room temperature under nitrogen. After concentration under vacuum, the residue was applied onto a silica gel column with EtOAc/petroleum ether (1:1-2:1) to afford 1.7 g (81%) of 225.7 as a light yellow solid.

Synthesis of Compound 225.8.

To a solution of 225.7 (1.02 g, 2.99 mmol, 1.00 equiv) in dioxane (50 mL) was added POCl$_3$ (2.3 g, 15.00 mmol, 5.02 equiv) and the resulting mixture was stirred for 3 h at 100° C. After cooling and concentration in vacuo, the reaction mixture was quenched with water/ice and the pH value of the solution was adjusted to 7 with saturated aqueous sodium bicarbonate. After extraction with ethyl acetate, the organic layer was washed with brine and dried over anhydrous sodium sulfate. After filtration and concentration in vacuo, the residue was applied onto a silica gel column with EtOAc/petroleum ether (1:5-1:3) to provide 660 mg (61%) of 225.8 as a light yellow solid.

Synthesis of Compound 225.9.

A mixture of 225.8 (194 mg, 0.54 mmol, 1.00 equiv), trans-4-(morpholin-4-yl)cyclohexan-1-amine dihydrochloride (357 mg, 1.39 mmol, 3.00 equiv), potassium carbonate (745.2 mg, 5.39 mmol, 10.00 equiv) and triethylamine (163.7 mg, 1.62 mmol, 3.00 equiv) in CH$_3$CN (50 mL) was stirred for 48 h at 80° C. under nitrogen. After concentration under vacuum, the residue was applied onto a silica gel column with DCM/MeOH (30:1-15:1) to provide 169.4 mg (62%) of 225.9 as a semi-solid.

Synthesis of Compound 225.10.

A mixture of 225.9 (150 mg, 0.24 mmol, 1.00 equiv) and Pd/C (10%, 60 mg) was stirred for 48 h at 40° C. under H$_2$. After completion, the solids were filtered out and the filtrate was concentrated under vacuum to provide 100 mg (crude) of 225.10 as a white solid.

Synthesis of Compound I-181.

To a solution of 225.10 (100 mg, 0.27 mmol, 1.00 equiv) in DCE (20 mL) was added TEA (0.4 mL) and ethanesulfonyl chloride (0.2 mL) at 0° C. followed by stirring for 2 h. The reaction was then quenched by the addition of methanol and then concentrated under vacuum. The residue was purified by preparative HPLC under the following conditions: Column: SunFire Prep C18, 19*150 mm 5 µm; mobile phase: water with 0.05% NH$_4$HCO$_3$ and CH$_3$CN (5% CH$_3$CN up to 20% in 7 min, up to 25% in 52 min, hold at 25% for 2 min, up to 95% in 2 min, down to 5% in 2 min); flow rate: 20 mL/min; UV detection at 254/220 nm. The product-containing fractions were collected and evaporated under reduced pressure to remove the solvents. Overnight lyophilization afforded the desired I-181 (26.5 mg) as a light yellow solid. LC-MS: (ES, m/z): 466 (M+H)$^+$. $^1$H-NMR (400 MHz, CD$_3$OD): δ 8.30 (1H, s), 4.79 (2H, s), 4.21-4.13 (1H, m), 3.75-3.69 (6H, m), 3.26-3.19 (2H, dd), 3.07-3.00 (2H, m), 2.71-2.63 (4H, m), 2.42-2.33 (1H, m), 2.28-2.19 (2H, m), 2.13-2.07 (2H, m), 2.58-2.42 (4H, m), 1.37 (3H, t).

Example 226

Synthesis of 12-methanesulfonyl-3-[[4-(morpholin-4-yl)cyclohexyl]oxy]-8-thia-4,6,12-triazatricyclo[7.4.0.0[2,7]]trideca-1(9),2(7),3,5-tetraene (I-187)

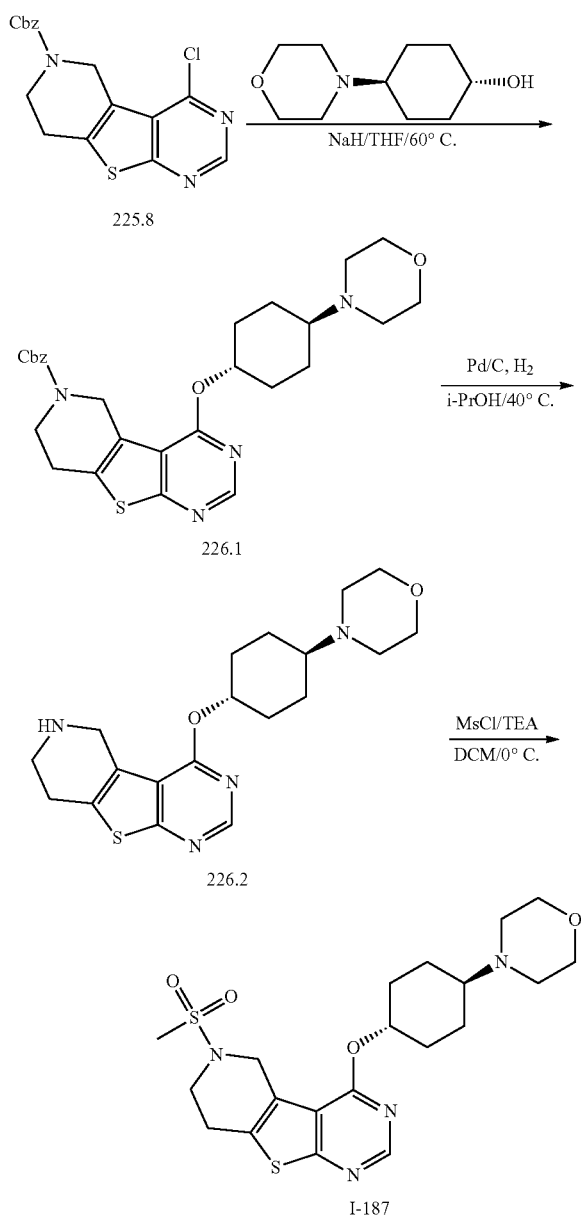

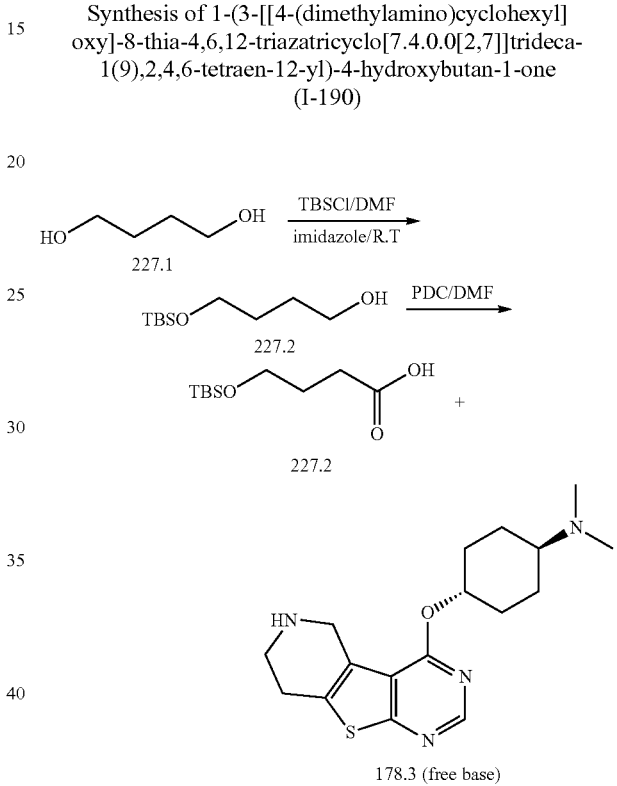

Synthesis of Compound 226.1.

Sodium hydride (60%, 74 mg, 1.85 mmol, 5.00 equiv) was treated with trans-4-morpholinocyclohexanol (104 mg, 0.56 mmol, 1.50 equiv) in 8 mL of distilled THF for 30 min at room temperature under nitrogen. Then a solution of 225.8 (133 mg, 0.37 mmol, 1.00 equiv) in 5 mL of THF was added via syringe and the resulting solution was stirred for 2 h at 70° C. After cooling, the reaction was then quenched with saturated aqueous NH$_4$Cl and extracted with 3×50 mL of DCM. The organic layers were combined, washed with brine, dried over sodium sulfate and concentrated under vacuum. The residue was applied onto a silica gel column with dichloromethane/methanol (10/1) to provide 122 mg (65%) of the desired product 226.1 as a white solid.

Synthesis of Compound I-187.

Compound I-187 was prepared from 226.1 in a manner analogous to the synthesis of I-181 from 225.9. Isolated a white solid in 6% overall yield from 226.1. MS 453 (M+H)$^+$. $^1$H-NMR (400 MHz, CD$_3$OD): δ 8.54 (s, 1H), 5.32-5.25 (m, 1H), 4.68 (s, 2H), 3.74 (t, 4H), 3.69 (t, 2H), 3.14 (t, 2H), 2.97 (s, 3H), 2.65 (t, 4H), 2.45-2.30 (m, 3H), 2.10 (d, 2H), 1.72-1.62 (m, 2H), 1.60-1.45 (m, 2H).

Example 227

Synthesis of 1-(3-[[4-(dimethylamino)cyclohexyl]oxy]-8-thia-4,6,12-triazatricyclo[7.4.0.0[2,7]]trideca-1(9),2,4,6-tetraen-12-yl)-4-hydroxybutan-1-one (I-190)

Synthesis of Compound 227.2.

To a solution of butane-1,4-diol (4.5 g, 50.0 mmol, 1.00 equiv) in 15 mL of dry DMF was added imidazole (6.8 g, 100.0 mmol, 2.00 equiv) followed by the addition of a solution of TBSCl (7.55 g, 50.00 mmol, 1.00 equiv) in DMF (5 mL) dropwise with stirring at 0° C. under nitrogen. The resulting solution was stirred for 3 h at room temperature, quenched with water and extracted with 3×100 mL of ethyl acetate. The combined organic layers were washed with brine, dried over sodium sulfate and concentrated under vacuum. The residue was applied onto a silica gel column with ethyl acetate/petroleum ether (1/5) to give 2.2 g (22%) of 227.2 as a colorless oil.

Synthesis of Compound 227.3.

To a solution of 227.2 (2.2 g, 10.76 mmol, 1.00 equiv) in 20 mL of dry DMF was added PDC (20 g, 53.16 mmol, 4.94 equiv) at room temperature. The resulting mixture was stirred overnight at ambient temperature and quenched by the addition of 100 mL of water and extracted with 3×200 mL of ethyl acetate. The combined organic layers were washed with water, brine and dried over sodium sulfate and concentrated under vacuum. The residue was applied onto a silica gel column with ethyl acetate/petroleum ether (1/5-1/1) to afford the desired 227.3 (700 mg, 30%) as a light yellow oil.

Synthesis of Compound 227.4.

Into a 50-mL round-bottom flask containing a solution of 178.3 (free base; 100 mg, 0.30 mmol, 1.00 equiv) in dry 5 mL of DMF was added 227.3 (78 mg, 0.36 mmol, 1.19 equiv), HATU (114 mg, 0.30 mmol, 1.00 equiv) and DIEA (80 mg, 0.62 mmol, 2.06 equiv) sequentially at room temperature under nitrogen. The resulting solution was stirred overnight at ambient temperature, quenched with saturated aqueous NH$_4$Cl and extracted with 3×30 mL of DCM. The combined organic layers were washed with brine, dried over sodium sulfate and concentrated under vacuum. The residue was applied onto a silica gel column with dichloromethane/methanol (10/1) to provide 80 mg (50%) of 227.4 as a white solid.

Synthesis of Compound I-190.

To a solution of 227.4 (60 mg, 0.11 mmol, 1.00 equiv) in methanol (5 mL) was added hydrochloric acid (conc., 0.1 mL) at 0° C. followed by stirring for 5 h at room temperature. The resulting mixture was concentrated under vacuum and the crude product (60 mg) was purified by preparative HPLC under the following conditions (Waters): Column: XBridge Shield RP18 OBD Column: 5 μm, 19*150 mm; mobile phase: water with 0.1% NH$_4$HCO$_3$ and acetonitrile (10% to 36% in 10 min); flow rate: 15 ml/min; UV detection at 254 nm. This resulted in 4.5 mg of I-190 as a white solid. MS (ES): m/z 419 (M+H)$^+$. $^1$H-NMR (300 MHz, CD$_3$OD): δ 8.51 (1H, s), 5.35-5.15 (1H, m), 4.97 (2H, t), 3.94 (2H, tt), 3.62 (2H, t), 3.03, 2.94 (2H, tt), 2.88-2.75 (1H, m), 2.62-2.49 (8H, m), 2.50-2.30 (2H, m), 2.13 (2H, m), 1.85 (2H, quintet), 1.75-1.50 (4H, m).

Example 228

Synthesis of 1-[3-[(4-aminocyclohexyl)oxy]-8-thia-4,6,12-triazatricyclo[7.4.0.0[2,7]]trideca-1 (9),2,4,6-tetraen-12-yl]ethan-1-one (I-197)

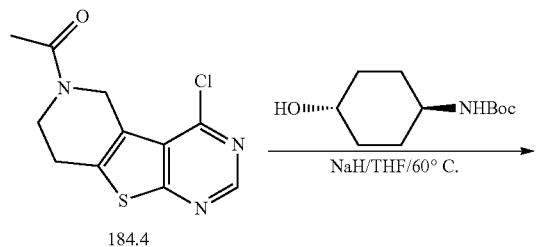

184.4

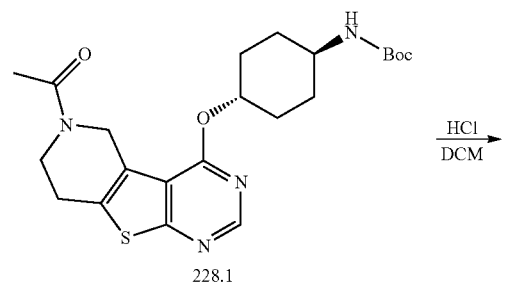

228.1

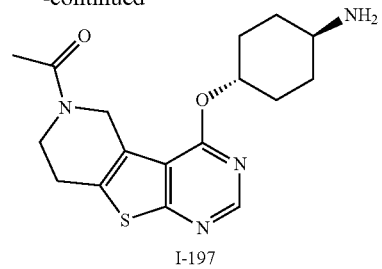

I-197

Synthesis of Compound 228.1.

Sodium hydride (60%, 74 mg, 1.85 mmol, 5.00 equiv) was treated with tert-butyl N-(4-hydroxycyclohexyl)carbamate (120 mg, 0.56 mmol, 1.50 equiv) in 5 mL of distilled THF for 30 min at room temperature under nitrogen. Then a solution of 184.4 (100 mg, 0.37 mmol, 1.00 equiv) in 5 mL of THF was added via syringe and the resulting solution was stirred for 2 h at 70° C. After cooling, the reaction was then quenched with saturated aqueous NH$_4$Cl and extracted with 3×50 mL of DCM. The organic layers were combined, washed with brine, dried over sodium sulfate and concentrated under vacuum. The residue was applied onto a silica gel column with dichloromethane/methanol (10/1) to provide 120 mg (72%) of 228.1 as a white solid.

Synthesis of Compound I-197.

To a solution of 228.1 (50 mg, 0.11 mmol, 1.00 equiv) in 5 mL of DCM was added hydrochloric acid (conc., 0.1 mL) at 0° C. and the resulting solution was stirred for 4 h at room temperature. After completion, the resulting mixture was concentrated under vacuum and the crude product (50 mg) was purified by preparative HPLC under the following conditions (Waters): Column: XBridge Shield RP18 OBD Column: 5 μm, 19*150 mm; mobile phase: water with 0.1% NH$_4$HCO$_3$ and acetonitrile (20% up to 24% in 10 min); flow rate: 15 mL/min; UV detection at 254 nm. This resulted in 18.1 mg (47%) of I-197 as a white solid. MS (ES): m/z 347 (M+H)$^+$. $^1$H-NMR (400 MHz, CD$_3$OD): δ 8.54 (1H, s), 5.40-5.22 (1H, m), 4.92 (2H, s), 3.98, 3.91 (2H, tt), 3.09-3.02 (1H, m), 2.95-2.92 (2H, m), 2.48-2.30 (5H, m), 2.06 (2H, d), 1.80-1.60 (2H, m), 1.55-1.40 (2H, m).

Example 229

Synthesis of 1-(3-[[4-(methylamino)cyclohexyl] oxy]-8-thia-4,6,12-triazatricyclo[7.4.0.0[2,7]] trideca-1 (9),2,4,6-tetraen-12-yl)ethan-1-one (I-202)

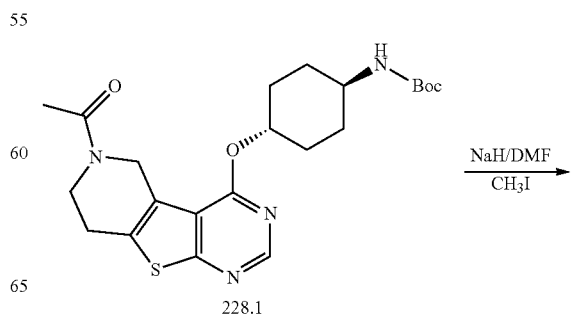

228.1

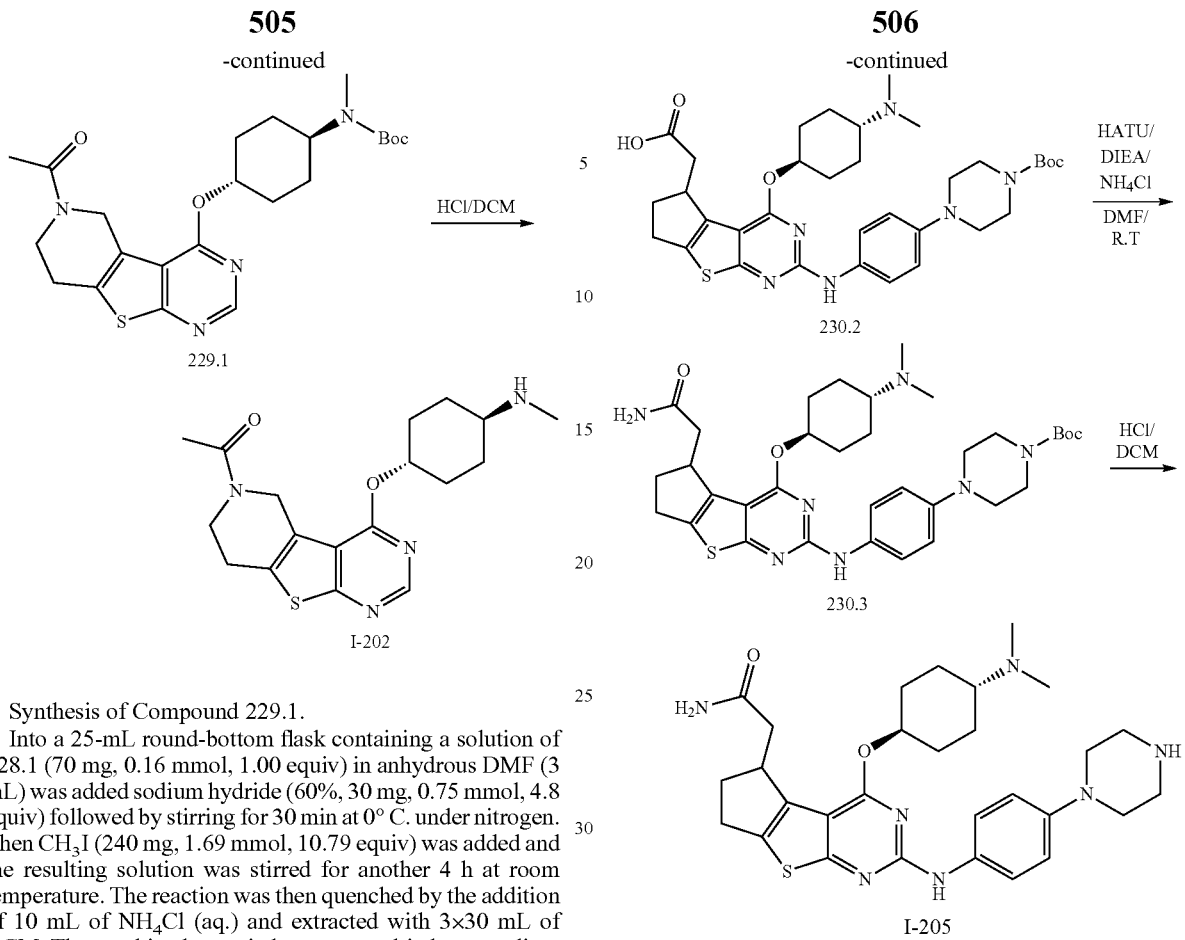

Synthesis of Compound 229.1.

Into a 25-mL round-bottom flask containing a solution of 228.1 (70 mg, 0.16 mmol, 1.00 equiv) in anhydrous DMF (3 mL) was added sodium hydride (60%, 30 mg, 0.75 mmol, 4.8 equiv) followed by stirring for 30 min at 0° C. under nitrogen. Then $CH_3I$ (240 mg, 1.69 mmol, 10.79 equiv) was added and the resulting solution was stirred for another 4 h at room temperature. The reaction was then quenched by the addition of 10 mL of $NH_4Cl$ (aq.) and extracted with 3×30 mL of DCM. The combined organic layers were dried over sodium sulfate and concentrated under vacuum. The residue was applied onto a silica gel column with dichloromethane/methanol (20/1) to yield 50 mg (69%) of 229.1 as a white solid.

Synthesis of Compound I-202.

Compound I-202 was prepared from 229.1 in a manner analogous to the synthesis of Compound I-197. Isolated 6.6 mg of a white solid in 17% yield. MS (ES): m/z 361 (M+H)$^+$. $^1$H-NMR (300 MHz, $CD_3OD$): δ 8.47 (1H, s), 5.26-5.10 (1H, m), 4.94 (2H, s), 3.86, 3.80 (2H, tt), 2.91-2.80 (3H, m), 2.66, 2.64 (3H, ss), 2.40-2.22 (2H, m), 2.18-2.05 (5H, m), 1.75-1.55 (2H, m), 1.52-1.48 (2H, m).

Example 230

Synthesis of 2-(12-[[4-(dimethylamino)cyclohexyl]oxy]-10-[[4-(piperazin-1-yl)phenyl]amino]-7-thia-9,11-diazatricyclo[6.4.0.0[2,6]]dodeca-1(12),2(6),8,10-tetraen-3-yl)acetamide (I-205)

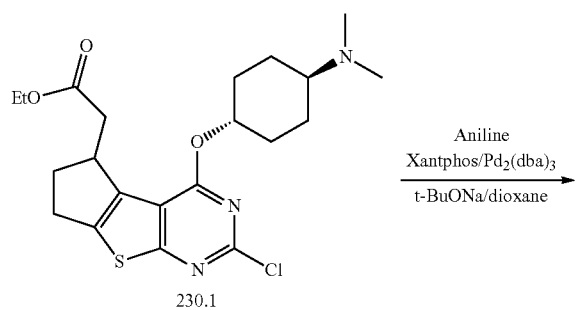

Synthesis of Compound 230.2.

To a 100 mL of dry round-bottom flask containing a solution of 230.1 (prepared using the same route as for 204.7 but omitting the chiral separation; 200 mg, 0.46 mmol, 1.00 equiv) in 15 mL of dioxane was added $Pd_2$ $dba_3$ (25 mg, 0.023 mmol, 0.05 equiv), Xantphos (27 mg, 0.046 mmol, 0.10 equiv), t-BuONa (110 mg, 1.15 mmol, 2.50 equiv) and aniline (192 mg, 0.69 mmol, 1.50 equiv) sequentially at room temperature. Then the reaction mixture was degassed three times with nitrogen and stirred for 4 h at 100° C. The solids were filtered out and the filtrate was neutralized with 1 M hydrochloric acid and extracted with 4×50 mL of $CHCl_3$/iso-propanol (3:1). The combined organic layers were dried over sodium sulfate and concentrated in vacuo. The residue was purified by chromatography on silica gel with DCM/MeOH (20:1 to 10:1) to yield 100 mg of desired 230.2 as a white solid.

Synthesis of Compound 230.3.

To a solution of 230.2 (100 mg, 0.15 mmol, 1.00 equiv) in dry DMF (5 mL) was added HATU (70 mg, 0.18 mmol, 1.20 equiv), DIEA (25 mg, 0.19 mmol, 1.26 equiv) and $NH_4Cl$ (25 mg, 0.47 mmol, 3.04 equiv) followed by stirring overnight at room temperature under nitrogen. The reaction was then quenched by the addition of 20 mL of water and extracted with 5×50 mL of DCM. The combined organic layers were dried over anhydrous sodium sulfate and concentrated under vacuum. The residue was applied onto a silica gel column with DCM/MeOH (20:1 to 10:1) to give 70 mg of 230.3 as an off-white solid.

Synthesis of Compound I-205.

To a solution of 230.3 (20 mg, 0.03 mmol, 1.00 equiv) in DCM (5 mL) was added hydrochloric acid (37%, 0.2 0.2 mL)

at 0° C. The resulting solution was stirred for 1 h at room temperature and concentrated under vacuum. The crude product (20 mg) was purified by preparative HPLC under the following conditions (Waters): Column: XBridge Shield RP18 OBD 5 µm, 19*150 mm; mobile phase: water with 0.01% NH$_4$HCO$_3$ and CH$_3$CN (20%-24%, run time 10 min); flow rate: 20 mL/min; UV detection at 254 nm. This resulted in 10.2 mg (60%) of Compound I-205 as a white solid. MS (ES): m/z 550 (M+H)$^+$. $^1$H-NMR (300 MHz, CD$_3$OD): δ 7.57 (2H, J=8.1 Hz, d), 7.00 (2H, J=8.1 Hz, d), 5.25-5.08 (1H, m), 3.78-3.65 (1H, m), 3.20-2.80 (11H, m), 2.75-2.65 (1H, m), 2.48-2.25 (9H, m), 2.24-2.02 (4H, m), 1.75-1.45 (4H, m).

Example 231

Synthesis of (12R)-3-[[4-(morpholin-4-yl)cyclohexyl]amino]-8-thia-4,6-diazatricyclo[7.4.0.0[2,7]]trideca-1(9),2(7),3,5-tetraene-12-carboxamide (I-208) and Example 232: Synthesis of (12S)-3-[[4-(morpholin-4-yl)cyclohexyl]amino]-8-thia-4,6-diazatricyclo[7.4.0.0[2,7]]trideca-1(9),2(7),3,5-tetraene-12-carboxamide (I-207)

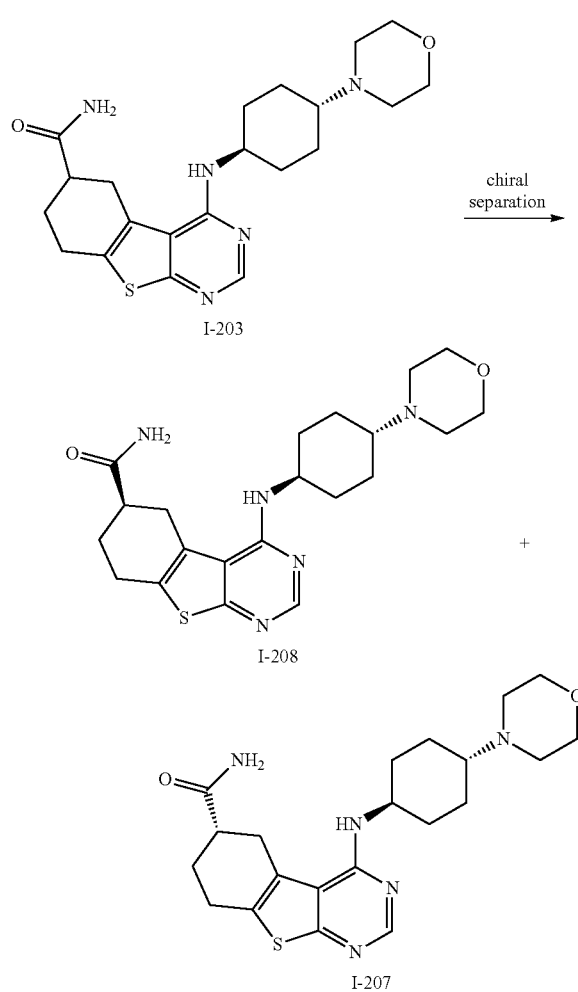

The enantiomers of racemic I-203 (50 mg, 0.12 mmol, 1.00 equiv) were separated by chiral preparative HPLC under the following conditions (Gilson Gx 281): Column: CHIRAL-PAK AD-H SFC, 5*25 cm, 5 µm; mobile phase: hexanes and IPA (30.0% IPA); flow rate: 20 mL/min; UV detection at 254/220 nm. The product-containing fractions were collected and evaporated in vacuo to give 10.8 mg (tR=5 min 20 s) of I-208 as a white solid and 9.8 mg (tR=5 min 25 s) of I-207 as a white solid, respectively.

Analytical data for I-208: MS (ES): m/z 416 (M+H)$^+$. $^1$H-NMR (400 MHz, CD$_3$OD): δ 8.24 (s, 1H), 4.19-4.06 (m, 1H), 3.76-3.74 (m, 4H), 3.16-3.10 (m, 2H), 2.98-2.94 (m, 2H), 2.80-2.69 (m, 1H), 2.68-2.65 (m, 4H), 2.45-2.38 (m, 1H), 2.25-2.20 (m, 3H), 2.10-2.08 (m, 2H), 1.99-1.90 (m, 1H), 1.64-1.55 (m, 5H).

Analytical data for I-207: MS (ES): m/z 416 (M+H)$^+$. $^1$H-NMR (400 MHz, CD$_3$OD): δ 8.24 (s, 1H), 4.16-4.08 (m, 1H), 3.76-3.74 (m, 4H), 3.16-3.10 (m, 2H), 2.98-2.94 (m, 2H), 2.80-2.69 (m, 5H), 2.45-2.38 (m, 1H), 2.25-2.20 (m, 3H), 2.10-2.08 (m, 2H), 1.99-1.90 (m, 1H), 1.64-1.55 (m, 5H).

Example 233

Synthesis of 2-(3-[[4-(dimethylamino)cyclohexyl]oxy]-8-thia-4,6,12-triazatricyclo[7.4.0.0[2,7]]trideca-1(9),2,4,6-tetraene-12-sulfonyl)ethan-1-ol (I-209)

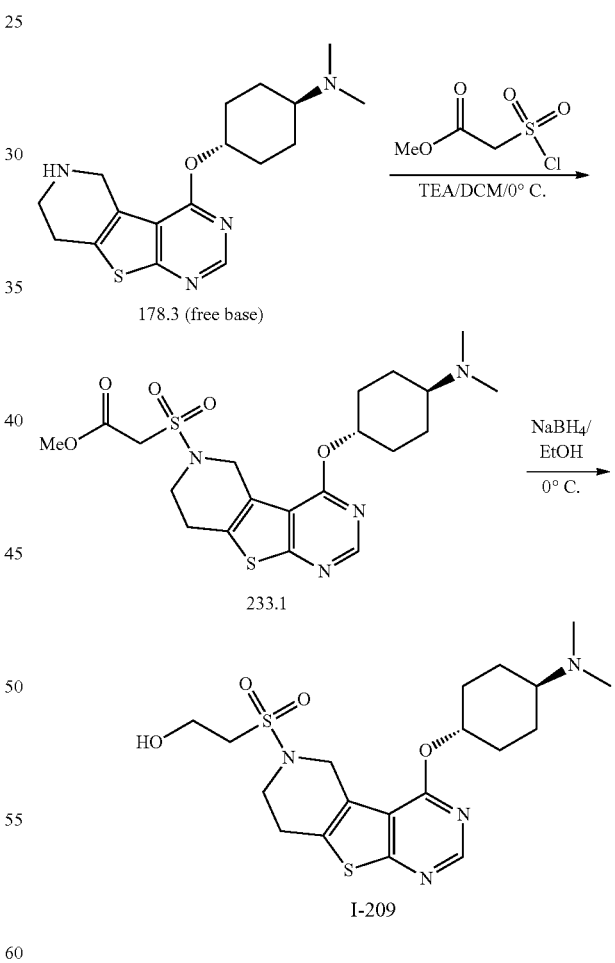

Compound I-209 was prepared from 178.3 (free base) in a manner analogous to the synthesis of Compound I-185 from 224.10. Isolated 12.4 mg of a white solid in 19% yield from 178.3. MS (ES): m/z 441 (M+H)$^+$. $^1$H NMR (300 MHz, CD$_3$OD): δ 8.47 (s, 1H), 5.35-5.15 (m, 1H), 4.72 (s, 2H), 3.98 (brs, 2H), 3.73 (br s, 2H), 3.06 (br s, 2H), 2.50-2.22 (m, 9H), 2.08 (d, 2H), 1.85-1.42 (m, 4H).

Example 234

Synthesis of 2-(12-[[4-(dimethylamino)cyclohexyl]oxy]-10-[(1-methyl-1H-pyrazol-4-yl)amino]-7-thia-9,11-diazatricyclo[6.4.0.0[2,6]]dodeca-1(8),2(6),9,11-tetraen-3-yl)acetamide (I-212)

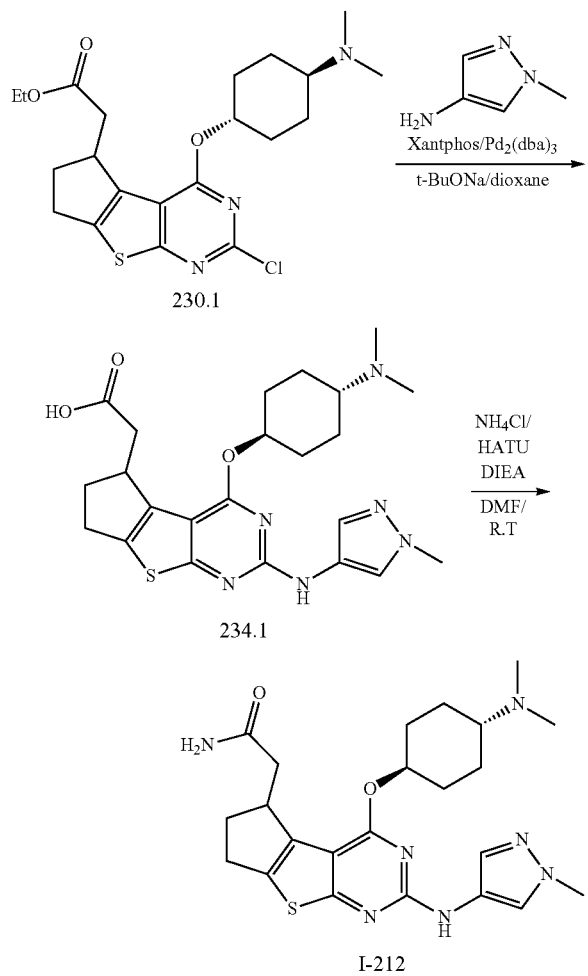

Compound I-212 was prepared from 230.1 in a manner analogous to the synthesis of compound 230.3. Isolated 10.6 mg of a white solid in 10% overall yield. MS (ES): m/z 470 (M+H)$^+$. $^1$H-NMR (300 MHz, CD$_3$OD): δ 7.90 (1H, s), 7.56 (1H, s), 5.21-5.08 (1H, m), 3.88 (3H, s), 3.75-3.60 (1H, m), 3.05-2.95 (3H, m), 2.95-2.78 (1H, m), 2.75-2.55 (1H, m), 2.54-2.30 (9H, m), 2.25-2.20 (4H, m), 1.75-1.45 (4H, m).

Example 235

(12R)-3-[[4-(morpholin-4-yl)cyclohexyl]oxy]-8-thia-4,6-diazatricyclo[7.4.0.0[2,7]]trideca-1(9),2(7),3,5-tetraene-12-carboxamide (I-240)

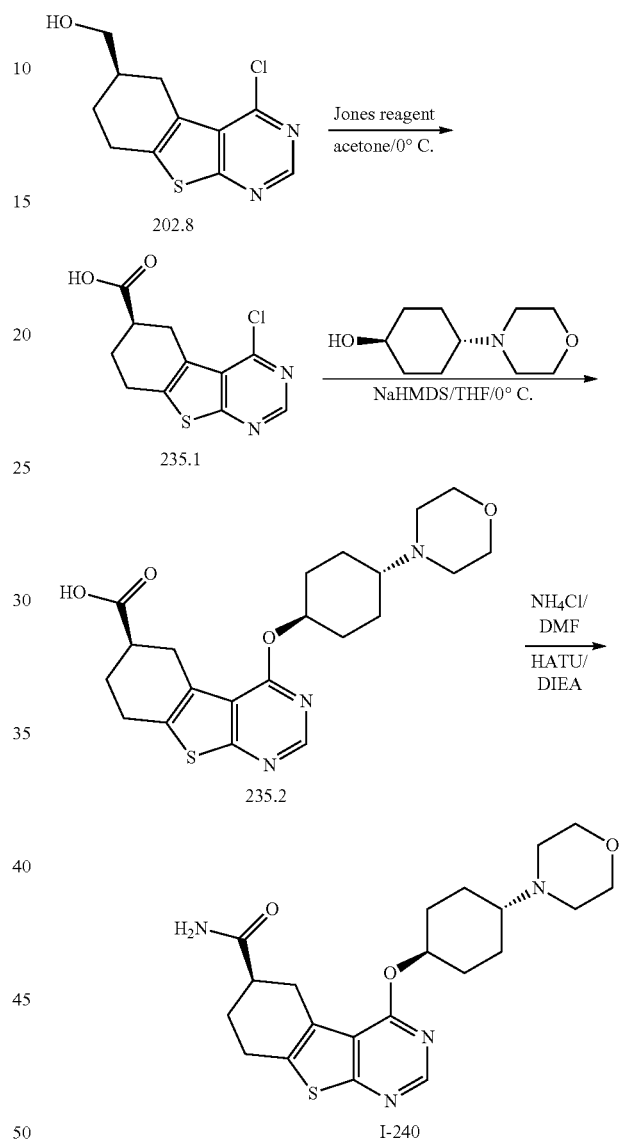

Compound I-240 was prepared from 202.8 in a manner analogous to the synthesis of Compound I-234 from 202.7. Isolated 84.3 mg of a white solid in 19% overall yield from 202.8. MS (ES): m/z 417 (M+H)$^+$. $^1$H-NMR (300 MHz, CD$_3$OD): δ 8.47 (1H, s), 5.30-5.24 (1H, m), 3.74-3.71 (4H, t, J=4.5 Hz), 3.27-3.25 (1H, d, J=6.0 Hz), 3.09-2.95 (3H, m), 2.78-2.70 (1H, m), 2.70-2.63 (4H, m), 2.38-2.30 (3H, m), 2.23-2.11 (1H, m), 2.11-2.07 (2H, d, J=12.0 Hz), 2.02-1.93 (1H, m), 1.68-1.44 (4H, m).

Example 236
Synthesis of (S)-2-hydroxy-3-((R)-4-(((1r,4R)-4-(pyrrolidin-1-yl)cyclohexyl)oxy)-6,7-dihydro-5H-cyclopenta[4,5]thieno[2,3-d]pyrimidin-5-yl)propanamide (I-226) and Example 237: Synthesis of (R)-2-hydroxy-3-((R)-4-(((1r,4R)-4-(pyrrolidin-1-yl)cyclohexyl)oxy)-6,7-dihydro-5H-cyclopenta[4,5]thieno[2,3-d]pyrimidin-5-yl)propanamide (I-228)
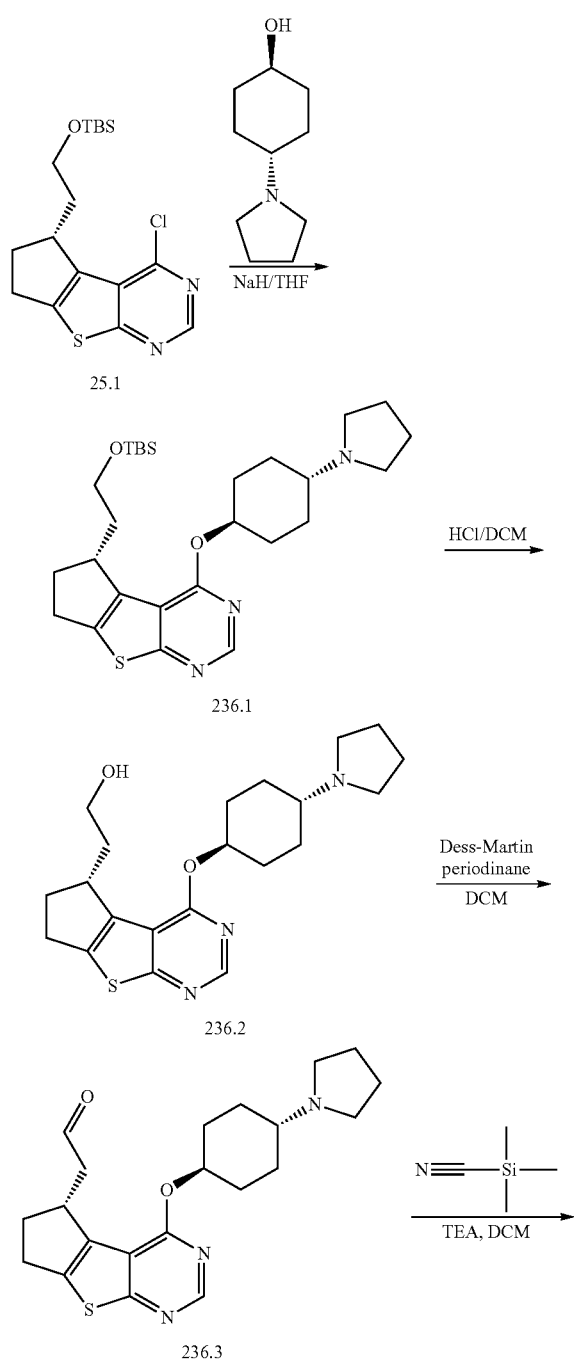
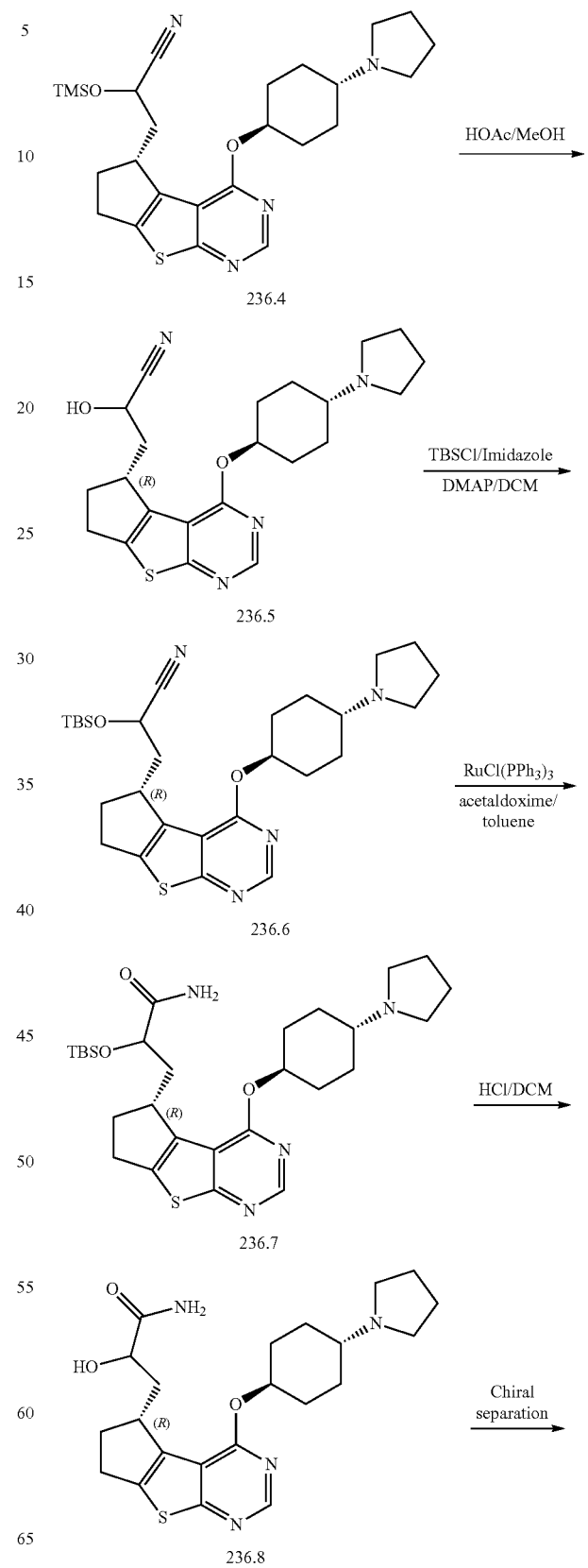

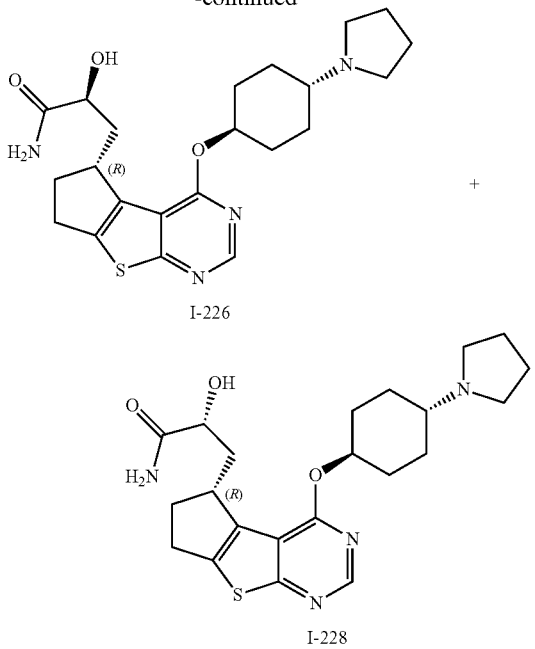

I-226

I-228

Synthesis of Compound 236.3.

Compound 236.3 was prepared from 25.1 in a manner analogous to compound 98.3. Isolated 0.45 g of a white solid in 22% overall yield from 25.1.

Synthesis of Compound 236.4.

Into a 100 mL round-bottom flask containing a solution of 236.3 (450 mg, 1.17 mmol, 1.00 equiv) in dichloromethane (20 mL) was added trimethylsilanecarbonitrile (360 mg, 3.63 mmol, 3.00 equiv) and TEA (60 mg, 0.59 mmol, 0.50 equiv) and the resulting solution was stirred for 2 h at room temperature under nitrogen. The resulting solution was quenched with water and extracted with 3×50 mL of dichloromethane. The combined organic layers were concentrated under vacuum to give 0.52 g (crude) of 236.4 as a yellow oil.

Synthesis of Compound 236.5.

To a solution of 236.4 (520 mg, 1.07 mmol, 1.00 equiv) in 20 mL of MeOH was added acetic acid (1.0 mL) at 0° C. and the resulting solution was stirred for 1 h at room temperature. The pH value of the solution was adjusted to 8 with saturated aqueous sodium bicarbonate and extracted with 3×50 mL of dichloromethane. The combined organic layers were dried over sodium sulfate and concentrated under vacuum. The residue was applied onto a silica gel column with dichloromethane/methanol (8/1). This resulted in 0.37 g (84%) of 236.5 as a white solid.

Synthesis of Compound 236.6.

Into a 50-mL round-bottom flask containing a solution of 236.5 (370 mg, 0.90 mmol, 1.00 equiv) in dichloromethane (20 mL) was added TBSCl (0.41 g, 3.00 equiv), imidazole (0.24 g, 4.00 equiv) and 4-dimethylaminopyridine (24 mg) sequentially at room temperature. The resulting solution was stirred overnight at ambient temperature and quenched with water and extracted with 3×50 mL of dichloromethane. The organic layers were combined, dried over sodium sulfate and concentrated under reduced pressure. The residue was purified by silica gel column with DCM/MeOH (30:1 to 10:1) to provide 0.33 g (70%) of 236.6 as a yellow oil.

Synthesis of Compound 236.7.

Tris(triphenylphosphine)rhodium(I) chloride (18.0 mg, 0.019 mmol) was added to a stirred solution of 236.6 (330 mg, 0.63 mmol) and acetaldoxime (0.23 mL, 3.60 mmol) in toluene (5.0 mL) and the reaction mixture heated at reflux overnight. Then tris(triphenylphosphine)rhodium(I) chloride (4.6 mg, 0.005 mmol) and acetaldoxime (62 µL, 1.0 mmol) were again added and heating continued for 2 h. After completion, the mixture was concentrated, diluted with ethyl acetate, and the organic layer washed with water, brine, dried, and concentrated in vacuo. The residue was purified by chromatography on silica gel eluting with a gradient of 0-10% MeOH in DCM to give the desired product 236.7 (250 mg) as a light yellow foam.

Synthesis of Compound 236.8.

Into a 100-mL round-bottom flask, a solution of material 236.7 (250 mg, 0.46 mmol, 1.00 equiv) in methanol (10 mL) was added hydrochloric acid (2 M, 0.8 mL) and stirred for 2 hr in a water/ice bath. After completion, the reaction was quenched with saturated aqueous sodium bicarbonate and extracted with 3×30 mL of DCM. The organic phase was dried over sodium sulfate and concentrated under vacuum. The residue was purified by preparative TLC (DCM/MeOH: 10/1) to afford the desired product 236.8 (150 mg, 76%) as a white solid.

Synthesis of Compound I-226 and I-228.

The enantiomers of racemic alcohol 236.8 (150 mg, 96% purity) were separated by chiral HPLC under the following conditions (Gilson G×281): Column: Chiralpak IA, 2*25 cm, 5 µm; mobile Phase: Phase A: hexanes (0.1% IPA) (HPLC grade), Phase B: EtOH(HPLC grade), gradient: 20% B in 7.6 min; flow rate: 20 mL/min; UV detection at 220/254 nm. The fractions of the first enantiomer to elute were collected and evaporated under reduced pressure and lyophilized overnight to afford I-226 (36.2 mg) with 100% ee as a white solid. The fractions of the second enantiomer to elute were concentrated to give I-228 (40.0 mg) with 94.2% ee, which was resubjected to the chiral HPLC conditions to give 30 mg with 98.4% ee as a white solid. The ee values of the two isomers were determined by chiral HPLC under the following conditions (SHIMADZU-PDA): Column: Chiralpak IA-3, 0.46*15 cm, 3 µm; mobile phase: hexanes (0.2% IPA): EtOH=80:20; flow rate: 1.0 mL/min; UV detection at 254 nm.

Analytical data for Compound I-226: MS (ES): m/z 431 (M+H)$^+$. $^1$H-NMR (300 MHz, CD$_3$OD): δ 8.45 (s, 1H), 5.31-5.24 (m, 1H), 4.06 (dd, J=10.8, 2.4 Hz, 1H), 3.72-3.61 (m, 1H), 3.22-3.08 (m, 1H), 3.05-2.89 (m, 1H), 2.80-2.60 (m, 5H), 2.50-2.09 (m, 7H), 1.95-1.62 (m, 7H), 1.56-1.40 (m, 2H).

Analytical data for Compound I-228: MS (ES): m/z 431 (M+H)$^+$. $^1$H-NMR (300 MHz, CD$_3$OD): δ 8.46 (s, 1H), 5.38-5.20 (m, 1H), 4.14 (dd, J=7.5, 5.7 Hz, 1H), 3.60-3.50 (m, 1H), 3.15-3.06 (m, 1H), 3.04-2.92 (m, 4H), 2.78-2.60 (m, 2H), 2.55-2.41 (m, 2H), 2.40-2.15 (m, 4H), 1.94 (brs, 4H), 1.85-1.45 (m, 5H).

Example 238

Synthesis of 1-(3-[[4-(dimethylamino)cyclohexyl]oxy]-8-thia-4,6,12-triazatricyclo[7.4.0.0[2,7]]trideca-1(9),2,4,6-tetraen-12-yl)-3-hydroxypropan-1-one (I-195)

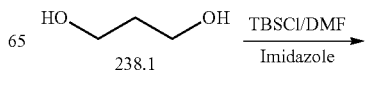

238.1 TBSCl/DMF Imidazole

515

-continued

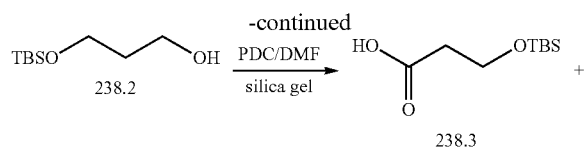

516

Example 239

Synthesis of 3-[[4-(dimethylamino)cyclohexyl]oxy]-8-thia-4,6,12-triazatricyclo[7.4.0.0[2,7]]trideca-1(9),2,4,6-tetraene-12-carboxamide (I-201)

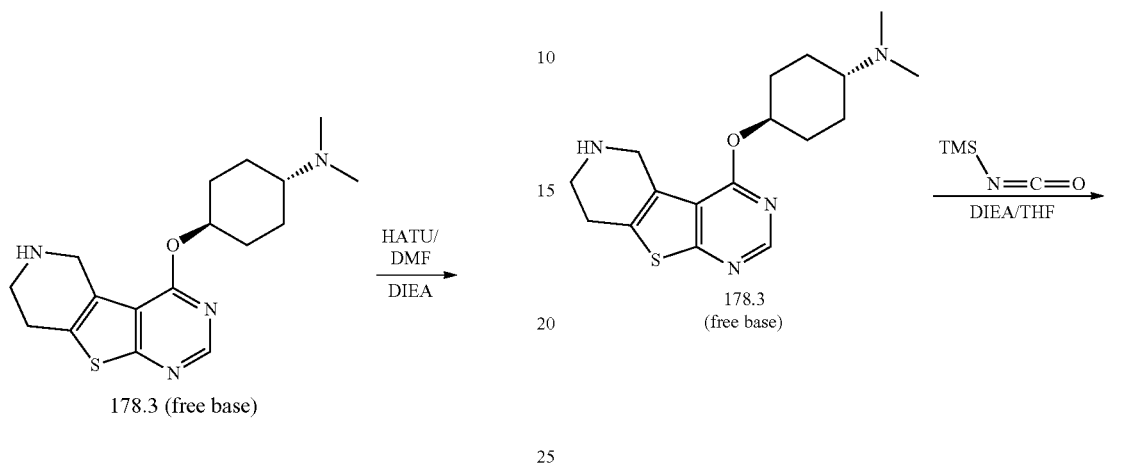

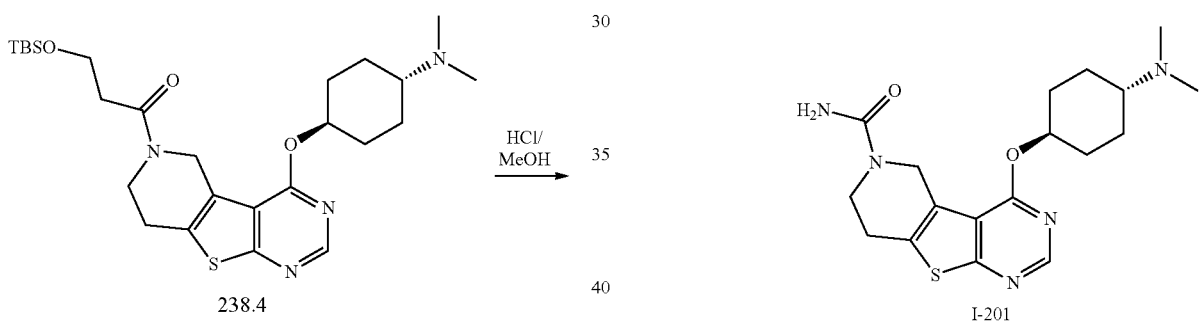

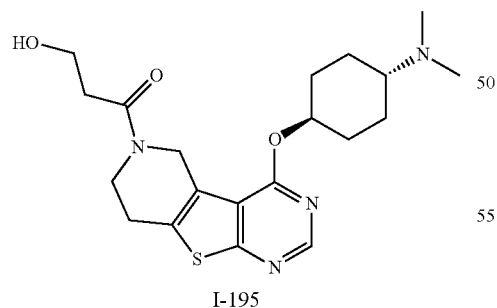

Compound I-195 was prepared from 238.1 and 178.3 (free base) in a manner consistent with the synthesis of Compound I-190. Isolated 49.1 mg of a white solid in 20% overall yield from 178.3. MS (ES): m/z 405 (M+H)+. 1H-NMR (300 MHz, CD3OD): δ 8.52 (1H, s), 5.32-5.18 (1H, m), 4.94 (2H, s), 4.02-3.80 (4H, m), 3.05, 2.96 (2H, tt), 2.80-2.70 (2H, m), 2.50-2.25 (9H, m), 2.07 (2H, d), 1.73-1.42 (4H, m).

A solution of 178.3 (free base) (100 mg, 0.30 mmol, 1.00 equiv) in 8 mL of distilled THF was added isocyanatotrimethylsilane (35 mg, 0.30 mmol, 1.01 equiv), followed by addition of DIEA (77.4 mg, 0.60 mmol, 2.0 equiv) at room temperature under nitrogen. The resulting solution was stirred overnight at this temperature and concentrated under vacuum. The crude product (120 mg) was purified by preparative HPLC under the following conditions (Waters): Column: XBridge Shield RP18 OBD 5 μm, 19*150 mm; mobile phase, water with 0.01% NH4HCO3 and acetonitrile (15%-35% in 10 min); flow rate: 15 ml/min; UV detection at 254 nm. This resulted in 22.8 mg (20%) of Compound I-201 as a white solid. MS (ES): m/z 376 (M+H)+. 1H NMR (300 MHz, CD3OD): δ 8.52 (1H, s), 5.31-5.18 (1H, m), 4.81 (3H, m), 3.79 (1H, t), 2.98 (2H, brs), 2.45-2.25 (9H, m), 2.07 (2H, d), 1.78-1.60 (2H, m), 1.58-1.38 (2H, m).

Example 240

Synthesis of propyl 3-[[4-(morpholin-4-yl)cyclohexyl]amino]-8-thia-4,6,12-triazatricyclo[7.4.0.0[2,7]]trideca-1(9),2(7),3,5-tetraene-12-carboxylate (I-186)

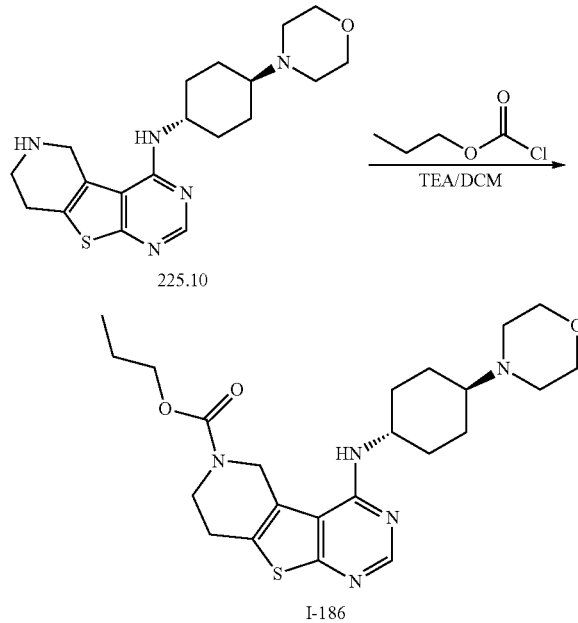

Compound I-186 was prepared from 225.10 in a manner consistent with the synthesis of Compound I-181, substituting propyl chloroformate for ethanesulfonyl chloride. Isolated 14.5 mg of a white solid in 22% yield. MS (ES): m/z 460 (M+H)$^+$. $^1$H-NMR (400 MHz, CD$_3$OD): δ 8.32 (1H, s), 4.22-4.08 (3H, m), 3.90-3.80 (2H, m), 3.75-3.72 (4H, m), 2.98 (2H, t), 2.68-2.62 (4H, m), 2.45-2.32 (1H, m), 2.28-2.16 (2H, m), 2.15-2.05 (2H, m), 1.75 (2H, sextet), 1.58-1.39 (4H, m), 1.01 (3H, t).

Example 241

Synthesis of 1-((R)-4-(((1r,4R)-4-morpholinocyclohexyl)oxy)-5,6,7,8-tetrahydrobenzo[4,5]thieno[2,3-d]pyrimidin-6-yl)butan-2-ol (I-183)

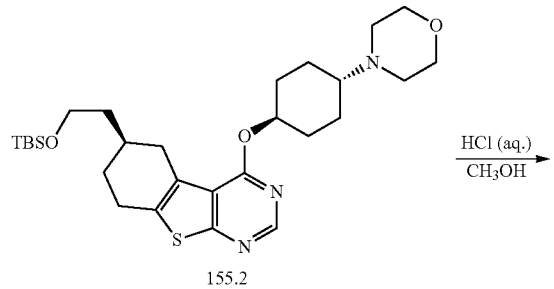

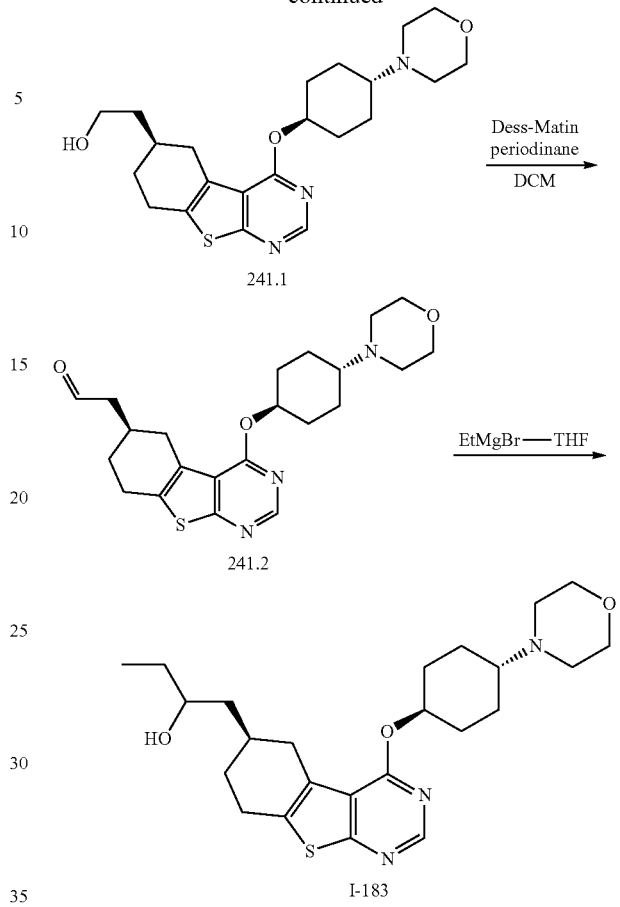

Synthesis of Compound 241.1.

To a solution of 155.2 (1.86 g, 3.50 mmol, 1.00 equiv) in methanol (50 mL) was added hydrochloric acid (12 M, 1.5 mL) followed by stirring for 2 h at room temperature. After evaporation of the solvent, the pH value of the solution was adjusted to 8 with saturated aqueous sodium bicarbonate and extracted with DCM. The combined organic layers were washed with brine, dried over anhydrous sodium sulfate and concentrated under reduced pressure. The residue was applied onto a silica gel column with dichloromethane/methanol (20:1-10:1) to give compound 241.1 (1.33 g, 91%) as a white solid.

Synthesis of Compound 241.2.

To a solution of 241.1 (700 mg, 1.68 mmol, 1.00 equiv) in dry dichloromethane (50 mL) was added Dess-Martin periodinane (1.8 g, 4.24 mmol, 2.50 equiv) portionwise followed by stirring for 6 hours at room temperature under N$_2$. The reaction was then quenched with saturated aqueous sodium bicarbonate and extracted with DCM. The organic layers were combined, washed with brine, dried over sodium sulfate and concentrated under vacuum. The residue was applied onto a silica gel column with DCM/MeOH (20:1) to give compound 241.2 (540 mg, 78%) as a yellow solid.

Synthesis of Compound I-183.

To a solution of 241.2 (250 mg, 0.60 mmol, 1.00 equiv) in distilled THF (5 mL) cooled to 0° C. was added EtMgBr-THF (1 M, 4 mL) via syringe under N$_2$. The resulting solution was stirred for 5 h at room temperature. After completion, the reaction was quenched with saturated aqueous NH$_4$Cl and extracted with 3×60 mL of ethyl acetate and the organic layers combined. The organic layer was washed with brine, dried over anhydrous sodium sulfate and concentrated under vacuum. The residue was applied onto a silica gel column with dichloromethane/methanol (20:1). The crude product (150 mg) was purified by preparative HPLC under the following conditions (Waters): Column: SunFire Prep C18, 19*150 mm 5 μm; mobile phase: water with 0.05% $NH_4CO_3$ and $CH_3CN$ (5.0% $CH_3CN$ up to 45.0% in 10 min, up to 95.0% in 2 min, down to 5.0% in 2 min); flow rate: 20 mL/min; UV detection at 254/220 nm. The product-containing fractions were collected and partially evaporated to remove water and $CH_3CN$ under reduced pressure. The residue was lyophilized overnight to give the desired product I-183 (80 mg) as a yellow solid. MS (ES, m/z) 446 (M+H)$^+$. $^1$H NMR (300 MHz, CD$_3$OD): δ 8.44 (s, 1H), 5.28-5.22 (m, 1H), 3.74-3.67 (m, 5H), 3.25-3.19 (m, 1H), 3.08-2.77 (m, 2H), 2.64-2.52 (m, 4H), 2.49-2.21 (m, 4H), 2.16-1.94 (m, 4H), 1.67-1.58 (m, 10H), 0.99 (t, 3H).

Example 242

Synthesis of 1-((R)-4-(((1r,4R)-4-morpholinocyclohexyl)oxy)-5,6,7,8-tetrahydrobenzo[4,5]thieno[2,3-d]pyrimidin-6-yl)propan-2-ol (I-182)

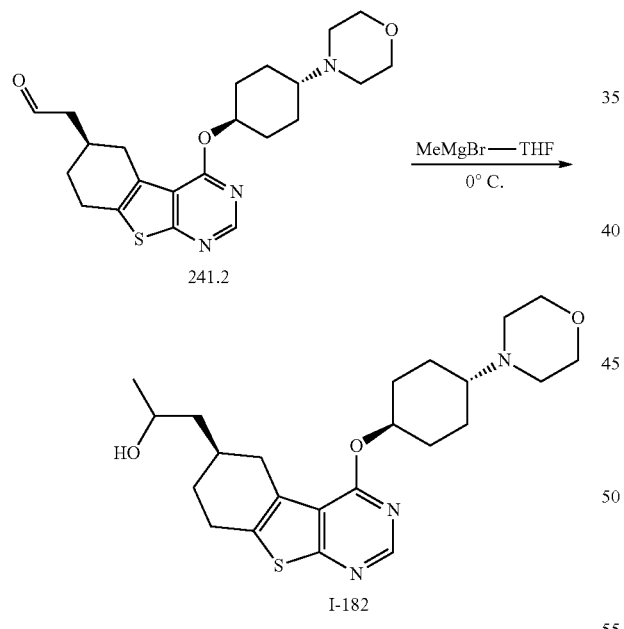

Compound I-182 was prepared from 241.2 in a manner analogous to the synthesis of Compound I-183 from 241.2, substituting MeMgBr for EtMgBr. Isolated 58.8 mg of a white solid in 19% yield. MS (ES, m/z) 432 (M+H)$^+$. $^1$H NMR (300 MHz, CD$_3$OD): δ 8.44 (s, 1H), 5.28-5.18 (m, 1H), 3.98-3.91 (m, 1H), 3.74-3.71 (m, 4H), 2.99-2.90 (m, 2H), 2.65-2.62 (m, 4H), 2.50-2.41 (m, 4H), 2.20-1.90 (m, 4H), 1.89-1.53 (m, 8H), 1.26-1.19 (d, 3H).

Example 243

Synthesis of 2-[(3R)-12-[[4-(dimethylamino)cyclohexyl]oxy]-10-[(1-methyl-1H-pyrazol-4-yl)amino]-7-thia-9,11-diazatricyclo[6.4.0.0[2,6]]dodeca-1(8),2(6),9,11-tetraen-3-yl]acetamide (I-222)

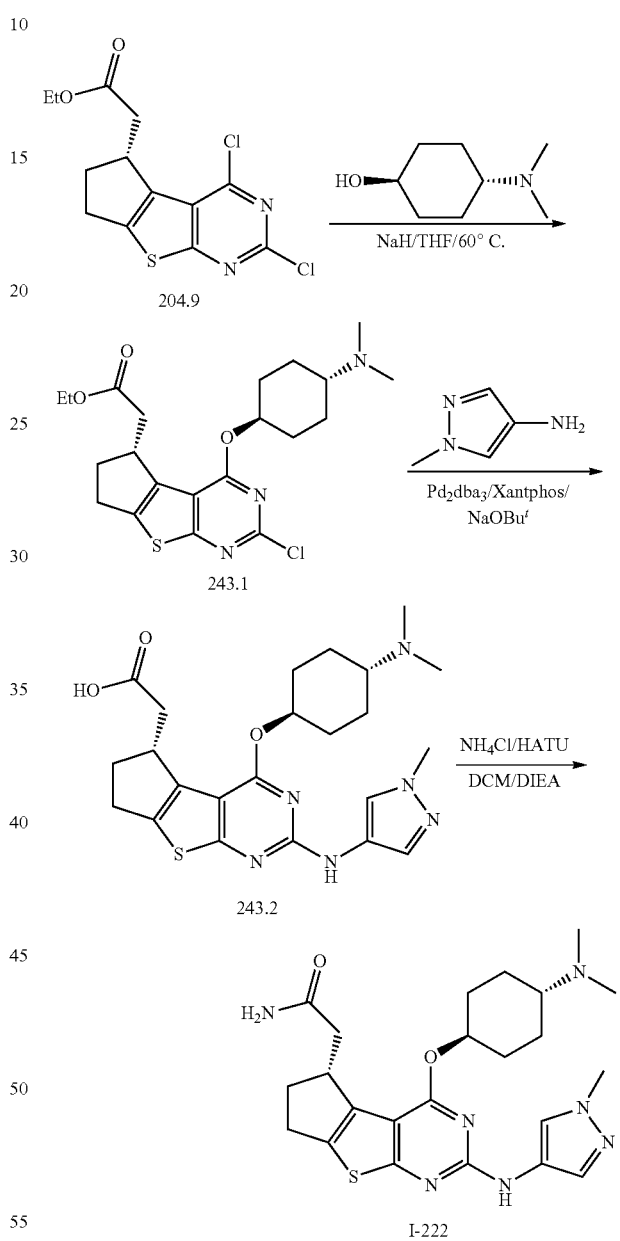

Compound I-222 was prepared from 204.9 in a manner analogous to the synthesis of Compound I-224. Isolated 62.2 mg of a white solid in 5% overall yield from 204.9. MS (ES): m/z 470 (M+H)$^+$. $^1$H-NMR (300 MHz, CD$_3$OD): δ 7.90 (1H, br s), 7.56 (1H, s), 5.22-5.12 (1H, m), 3.92 (3H, s), 3.78-3.62 (1H, m), 3.08-2.80 (3H, m), 2.75-2.50 (2H, m), 2.44 (6H, s), 2.41-2.26 (2H, m), 2.25-2.05 (4H, m), 1.70-1.46 (4H, m).

Example 244

Synthesis of 2-[(3R)-12-[[4-(4,4-difluoropiperidin-1-yl)cyclohexyl]oxy]-7-thia-9,11-diazatricyclo[6.4.0.0 [2,6]]dodeca-1(8),2(6),9,11-tetraen-3-yl]acetamide (I-229)

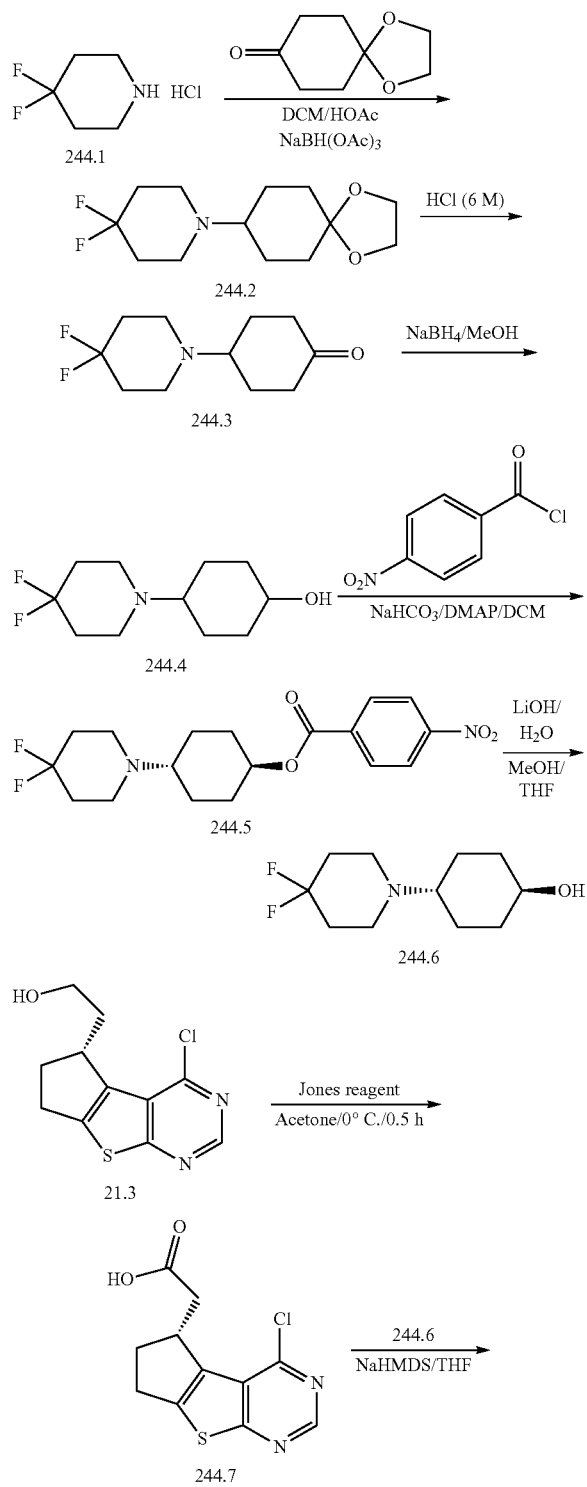

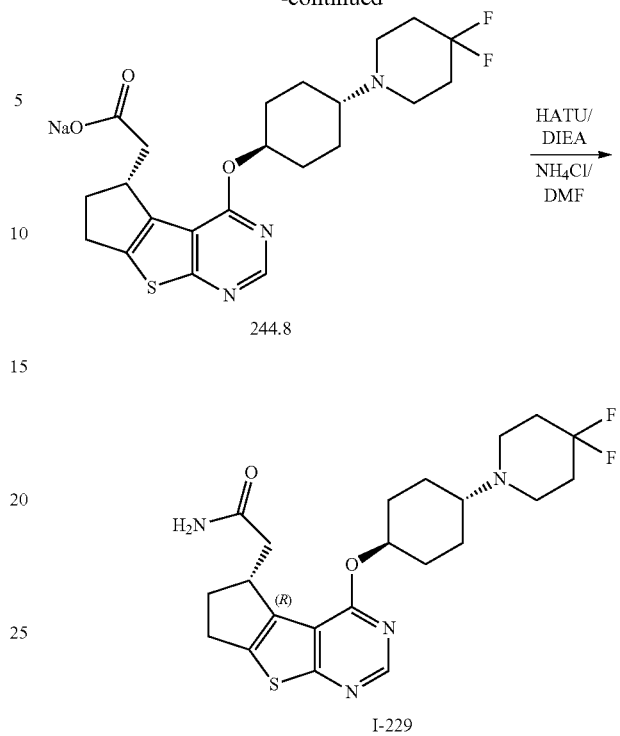

Synthesis of Compound 244.2.

To a solution of 4,4-difluoropiperidine hydrochloride (1.58 g, 10.0 mmol, 1.00 equiv) in dichloromethane (75 mL) was added 1,4-dioxaspiro[4.5]decan-8-one (1.56 g, 10.0 mmol, 1.0 equiv), acetic acid (0.5 mL, 2.00 equiv) and NaBH(OAc)$_3$ (4.24 g, 20 mmol, 2.0 equiv) at room temperature under nitrogen. The resulting solution was stirred for 24 h at ambient temperature. The pH value of the solution was adjusted to 12 with 1 M aqueous NaOH solution and extracted with 3×50 mL of dichloromethane. The combined organic layers were washed with brine, dried over sodium sulfate and concentrated in vacuo. The residue was applied onto a silica gel column with DCM/MeOH (80:1 to 50:1) to give the desired 244.2 (2.0 g) as a white solid.

Synthesis of Compound 244.3.

A mixture of 244.2 (200 mg, 0.77 mmol, 1.00 equiv) and hydrochloric acid (4 M, 6 mL) in 30 mL of THF was stirred for 24 h at 60° C. The resulting mixture was concentrated under vacuum. The pH value of the solution was adjusted to 8 with saturated aqueous sodium bicarbonate and extracted with 5×50 mL of dichloromethane. The organic layers were combined, dried over sodium sulfate and concentrated under vacuum to yield 150 mg (90%) of 244.3 as a light yellow oil.

Synthesis of Compound 244.4.

To a solution of 244.3 (100 mg, 0.46 mmol, 1.00 equiv) in methanol (10 mL) was added NaBH$_4$ (53 mg, 1.40 mmol, 3.00 equiv) and the resulting solution was stirred for 3 h at room temperature. The reaction was quenched with saturated aqueous NH$_4$Cl and extracted with 4×50 mL of dichloromethane. The combined organic layers were washed with brine, dried over anhydrous sodium sulfate and concentrated under vacuum to give 80 mg (79%) of 244.4 as a white solid.

Synthesis of Compound 244.5.

Into a 100-mL round-bottom flask containing a solution of 244.4 (100 mg, 0.46 mmol, 1.00 equiv) in dry dichloromethane (20 mL) was added 4-nitrobenzoyl chloride (170 mg, 0.92 mmol, 2.00 equiv), followed by addition of sodium bicarbonate (115 mg, 1.37 mmol, 3.00 equiv) and 4-dimethylaminopyridine (5 mg, 0.04 mmol, 0.10 equiv) at room temperature. The resulting mixture was stirred 4 h at ambient temperature. After completion, the resulting mixture was diluted with water and extracted with DCM, dried and concentrated under reduced pressure. The residue was purified by chromatography on silica gel with DCM/MeOH (50:1 to 30:1) to afford the corresponding 244.5 (120 mg) as a light yellow solid.

Synthesis of Compound 244.6.

The pure compound 244.5 (368 mg, 1.0 mmol, 1.0 equiv) in a mixture of MeOH/THF/water (4 mL/4 mL/2 mL) was added LiOH.H$_2$O (126 mg, 3.0 mmol, 3.0 equiv) at room temperature and stirred for 1 h. After evaporation in vacuo, the residue was diluted with water and acidified with 1 M hydrochloric acid to pH 6 and extracted with DCM, washed with brine and dried, concentrated under reduced pressure to give 244.6 (200 mg) as a light yellow solid.

Synthesis of Compound 244.7.

A solution of 21.3 (19.0 g, 74.59 mmol, 1.00 equiv) in acetone (500 mL) cooled at 0° C. was added dropwise Jones reagent with stirring until the alcohol was consumed completely. The resulting solution was diluted with water, washed with saturated aqueous NaHSO$_3$ and extracted with 3×800 mL of EtOAC. The combined organic layers were washed with brine, dried over sodium sulfate and concentrated under reduced pressure to give 18.0 g (crude) of 244.7 as a yellow solid. MS (ES): m/z 269 and 271 (M+H)$^+$.

Synthesis of Compound 244.8.

Into a 100-mL 3-necked round-bottom flask, purged and maintained with an inert atmosphere of nitrogen, was placed a solution of 244.6 (250 mg, 1.14 mmol, 1.20 equiv) in distilled THF (10 mL) cooled to 0° C. under nitrogen. This was followed by the addition of NaHMDS (0.25 mL, 2 M in THF) dropwise with stirring at this temperature. A solution of 244.7 (120 mg, 0.45 mmol, 1.00 equiv) in 5 mL of THF was added and the resulting solution was stirred for 2 h at 0° C. The formed solids were collected by filtration and washed with THF then MTBE, followed by drying under high vacuum to give 150 mg (crude) of 244.8 as a red solid.

Synthesis of Compound I-229.

To a solution of 244.8 (200 mg, crude) in distilled DMF (10 mL) was added HATU (98 mg, 0.26 mmol, 1.20 equiv), NH$_4$Cl (29 mg, 0.54 mmol, 1.20 equiv) and DIEA (109 mg, 0.84 mmol, 2.00 equiv) successively at room temperature under nitrogen. The resulting mixture was stirred for 4 h at this temperature, diluted with water and extracted with DCM. After concentration of the organic layers in vacuo. The crude product (100 mg) was purified by preparative HPLC under the following conditions (Waters): Column: Xbridge Prep C18 5 μm, 19*150 mm; mobile phase: water with 0.05% NH$_3$HCO$_3$ and CH$_3$CN (35% CH$_3$CN up to 65% in 10 min); flow rate: 20 mL/min; UV detection at 254 nm. The product-containing fractions were collected and evaporated under reduced pressure and lyophilized overnight to afford 56 mg of I-229 as a white solid. MS (ES): m/z 451 (M+H)$^+$. $^1$H-NMR (300 MHz, CD$_3$OD): δ 8.37 (s, 1H), 5.22-5.08 (m, 1H), 3.77-3.65 (m, 1H), 3.09-2.84 (m, 3H), 2.72-2.62 (m, 5H), 2.52-2.45 (m, 1H), 2.32-2.13 (m, 4H), 1.90-1.81 (m, 6H), 1.60-1.45 (m, 4H).

Example 245

Synthesis of (R)-2-hydroxy-3-((R)-4-(((1r,4R)-4-(piperidin-1-yl)cyclohexyl)oxy)-6,7-dihydro-5H-cyclopenta[4,5]thieno[2,3-d]pyrimidin-5-yl)propanamide (I-218) and Example 246: Synthesis of (S)-2-hydroxy-3-((R)-4-(((1r,4R)-4-(piperidin-1-yl)cyclohexyl)oxy)-6,7-dihydro-5H-cyclopenta[4,5]thieno[2,3-d]pyrimidin-5-yl)propanamide (I-217)

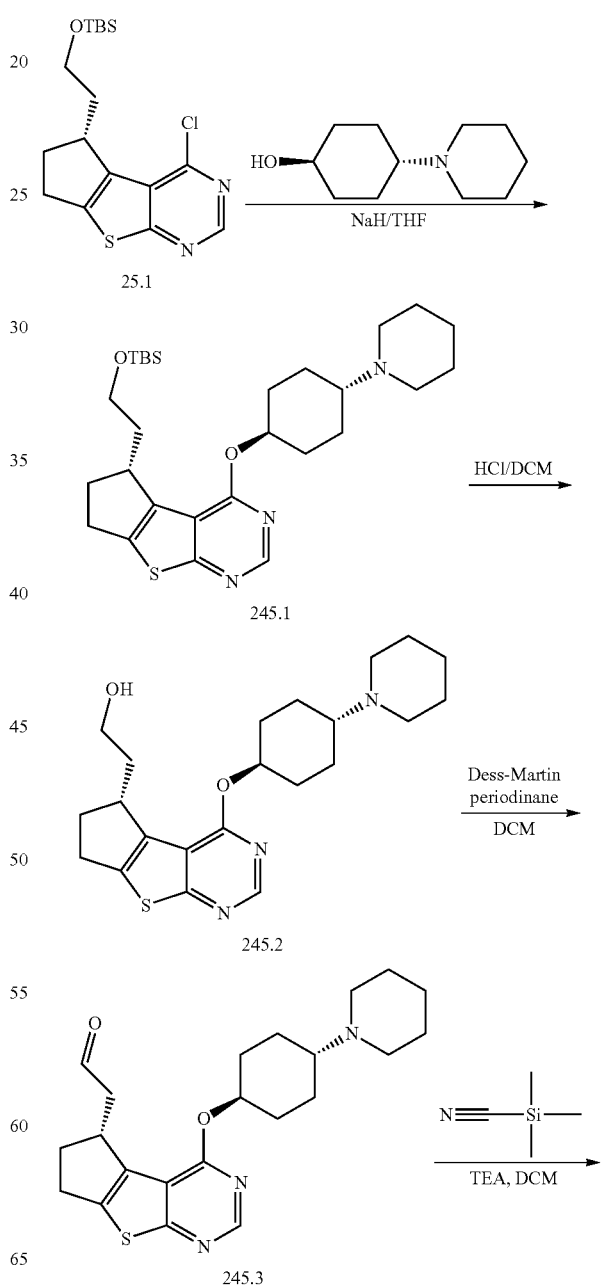

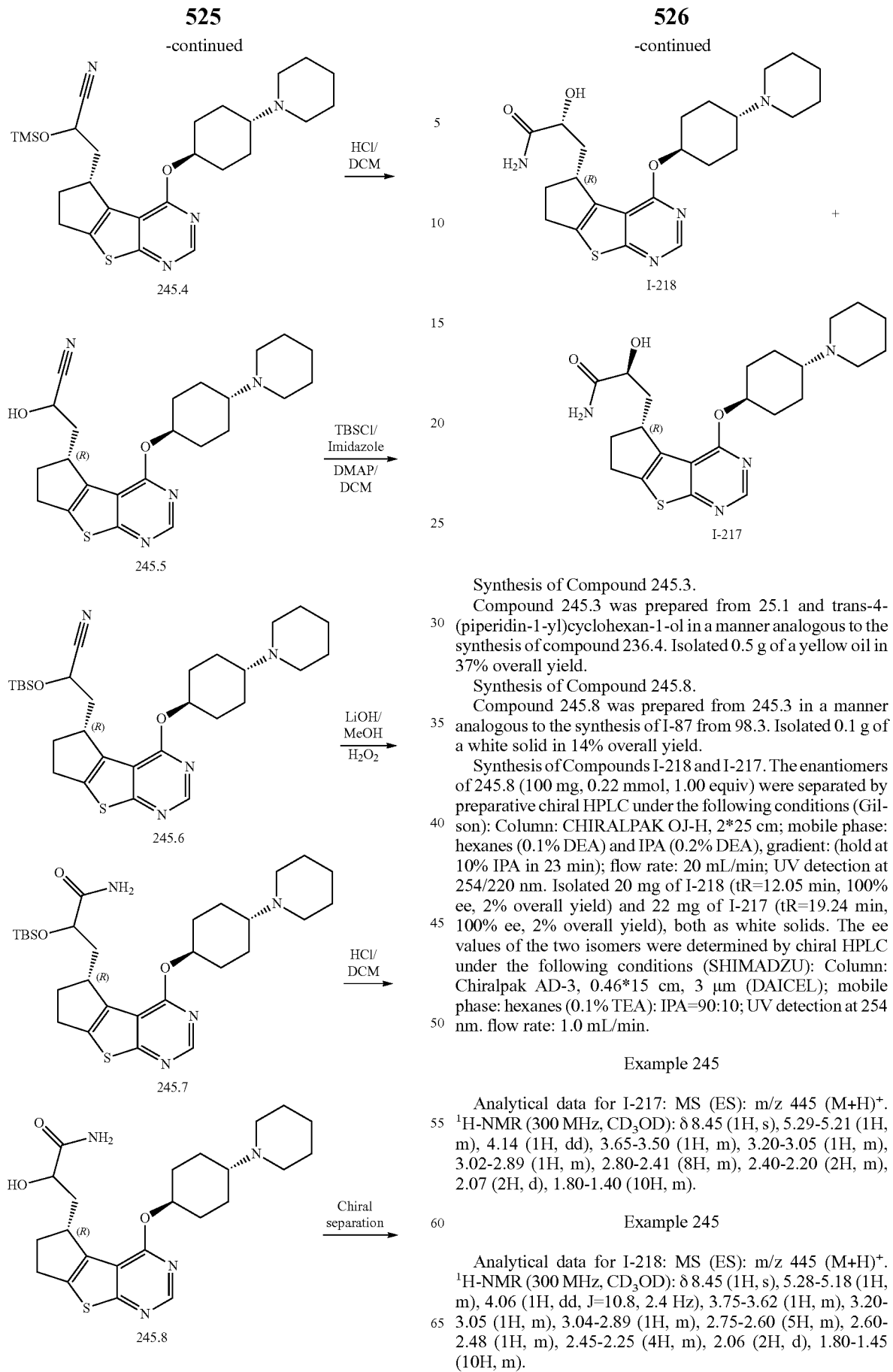

Synthesis of Compound 245.3.

Compound 245.3 was prepared from 25.1 and trans-4-(piperidin-1-yl)cyclohexan-1-ol in a manner analogous to the synthesis of compound 236.4. Isolated 0.5 g of a yellow oil in 37% overall yield.

Synthesis of Compound 245.8.

Compound 245.8 was prepared from 245.3 in a manner analogous to the synthesis of I-87 from 98.3. Isolated 0.1 g of a white solid in 14% overall yield.

Synthesis of Compounds I-218 and I-217. The enantiomers of 245.8 (100 mg, 0.22 mmol, 1.00 equiv) were separated by preparative chiral HPLC under the following conditions (Gilson): Column: CHIRALPAK OJ-H, 2*25 cm; mobile phase: hexanes (0.1% DEA) and IPA (0.2% DEA), gradient: (hold at 10% IPA in 23 min); flow rate: 20 mL/min; UV detection at 254/220 nm. Isolated 20 mg of I-218 (tR=12.05 min, 100% ee, 2% overall yield) and 22 mg of I-217 (tR=19.24 min, 100% ee, 2% overall yield), both as white solids. The ee values of the two isomers were determined by chiral HPLC under the following conditions (SHIMADZU): Column: Chiralpak AD-3, 0.46*15 cm, 3 μm (DAICEL); mobile phase: hexanes (0.1% TEA): IPA=90:10; UV detection at 254 nm. flow rate: 1.0 mL/min.

Example 245

Analytical data for I-217: MS (ES): m/z 445 (M+H)$^+$. $^1$H-NMR (300 MHz, CD$_3$OD): δ 8.45 (1H, s), 5.29-5.21 (1H, m), 4.14 (1H, dd), 3.65-3.50 (1H, m), 3.20-3.05 (1H, m), 3.02-2.89 (1H, m), 2.80-2.41 (8H, m), 2.40-2.20 (2H, m), 2.07 (2H, d), 1.80-1.40 (10H, m).

Example 245

Analytical data for I-218: MS (ES): m/z 445 (M+H)$^+$. $^1$H-NMR (300 MHz, CD$_3$OD): δ 8.45 (1H, s), 5.28-5.18 (1H, m), 4.06 (1H, dd, J=10.8, 2.4 Hz), 3.75-3.62 (1H, m), 3.20-3.05 (1H, m), 3.04-2.89 (1H, m), 2.75-2.60 (5H, m), 2.60-2.48 (1H, m), 2.45-2.25 (4H, m), 2.06 (2H, d), 1.80-1.45 (10H, m).

Example 247

Synthesis of (12S)-3-[[4-(dimethylamino)cyclohexyl]oxy]-8-thia-4,6-diazatricyclo[7.4.0.0[2,7]]trideca-1(9),2(7),3,5-tetraene-12-carboxamide (I-233)

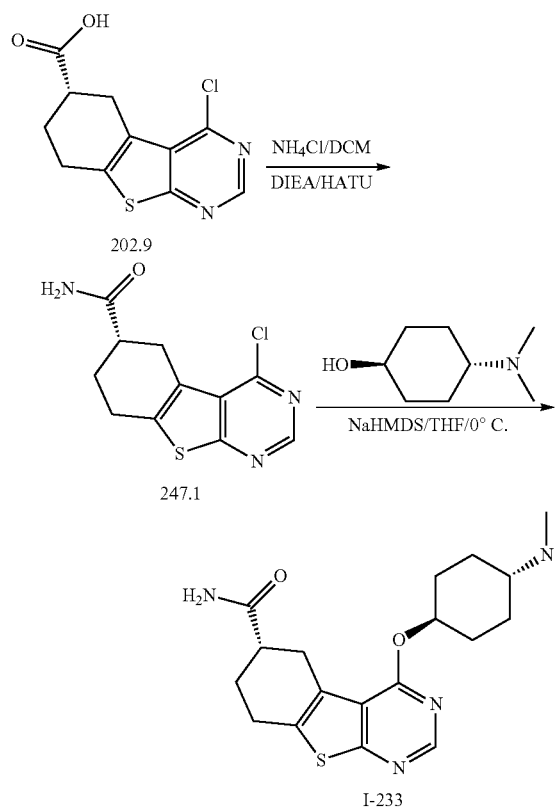

Synthesis of Compound 247.1.

To a solution of 202.9 (134 mg, 0.50 mmol, 1.00 equiv) in anhydrous DCM was added $NH_4Cl$ (160 mg, 3.0 mmol, 3.0 equiv), HATU (228 mg, 0.6 mmol, 1.2 equiv) and DIEA (129 mg, 1.0 mmol, 2.0 equiv) at room temperature under nitrogen. The resulting solution was stirred for 1 h at room temperature and diluted with water and extracted with DCM. The combined organic layers were washed with brine, dried and concentrated under vacuum. The residue was purified by silica gel column with DCM/MeOH (80:1 to 50:1) to give the desired 247.1 (120 mg, 90%) as a light yellow solid.

Synthesis of Compound I-233.

To a solution of 247.1 (75 mg, 0.20 mmol, 1.00 equiv) and trans-4-(dimethylamino)cyclohexanol (32 mg, 0.22 mmol, 1.1 equiv) in 5 mL of distilled THF was added NaHMDS (2 M in THF, 0.66 mmol, 0.33 mL) dropwise at 0° C. under nitrogen. The resulting solution was stirred for 30 min at this temperature and quenched with water and extracted with 4×50 mL of dichloromethane. The combined organic layers were concentrated under vacuum. The crude product (70 mg) was purified by preparative HPLC under the following conditions (Waters): Column: XBridge Shield RP18 OBD 5 μm, 19*150 mm; mobile phase: water with 0.01% $NH_4HCO_3$ and acetonitrile (10%-35% in 10 min); flow rate: 15 ml/min; UV detection at 254 nm. This resulted in 8.5 mg of I-233 as a white solid. MS (ES): m/z 375 (M+H)+. $^1$H-NMR (300 MHz, $CDCl_3$): δ 8.49 (1H, s), 5.66-5.58 (1H, m), 5.48-5.41 (1H, m), 5.25-5.21 (1H, m), 3.33-3.25 (1H, m), 3.15-2.91 (3H, m), 2.89-2.63 (2H, m), 2.55 (6H, s), 2.46-2.36 (2H, m), 2.26-2.10 (3H, m), 2.10-1.98 (1H, m), 1.61-1.60 (4H, m).

Example 248

Synthesis of (12S)-3-[[4-(4,4-difluoropiperidin-1-yl)cyclohexyl]oxy]-8-thia-4,6-diazatricyclo[7.4.0.0[2,7]]trideca-1(9),2(7),3,5-tetraene-12-carboxamide (I-236)

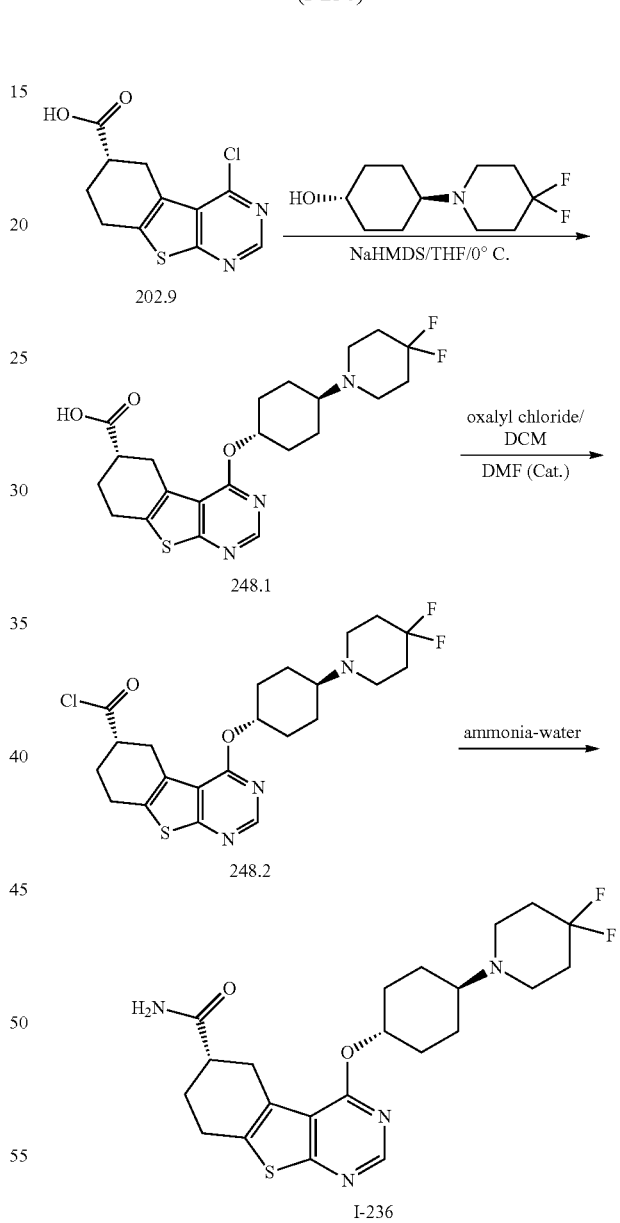

Synthesis of Compound 248.1.

To a solution of trans-4-(4,4-difluoropiperidin-1-yl)cyclohexan-1-ol (60 mg, 0.27 mmol, 1.11 equiv) in distilled THF (5 mL) was added NaHMDS (2 M in THF, 0.37 mL, 3.00 equiv) dropwise with stirring at 0° C. under nitrogen. To this was added a solution of 202.9 (66 mg, 0.25 mmol, 1.00 equiv) in 2 mL of THF via syringe at this temperature. The resulting solution was stirred for 5 min at 0° C. The reaction was then quenched with water and the pH value of the solution was adjusted to ~5.0 with 1 M hydrochloric acid and extracted with 4×20 mL of dichloromethane. The combined organic layers were dried over sodium sulfate and concentrated under vacuum to give 100 mg (crude) of 252.1 as a light yellow solid.

Synthesis of Compound 248.2.

To a solution of 248.1 (100 mg, crude) in 5 mL of DCM was added oxalic dichloride (250 mg, 5.00 equiv) dropwise at 0° C., followed by addition of DMF (1 drop) under nitrogen. The resulting solution was stirred for 1 h at room temperature and concentrated under reduced pressure to give 110 mg (crude) of 248.2 as a light yellow solid.

Synthesis of Compound I-236.

To a solution of 248.2 (110 mg, crude) in 5 mL of DCM was added dropwise 30 mL of ammonia solution. The solution was extracted with 4×50 mL of dichloromethane and the organic layers combined and dried over anhydrous sodium sulfate and concentrated under vacuum. The crude product (60 mg) was purified by preparative HPLC under the following conditions (Waters): Column: XBridge Shield RP18 OBD 5 μm, 19*150 mm; mobile phase: water with 0.01% $NH_4HCO_3$ and acetonitrile (10%-33% in 12 min); flow rate: 15 ml/min; UV detection at 254 nm. This resulted in 9.2 mg of I-236 as a white solid. MS (ES): m/z 451 (M+H)$^+$. $^1$H-NMR (300 MHz, CD$_3$OD): δ 8.47 (1H, s), 5.35-5.15 (1H, m), 3.27-3.25 (1H, d, J=6.0 Hz), 3.05-2.97 (3H, m), 2.89-2.60 (6H, m), 2.33-2.22 (2H, m), 2.20 (1H, d), 2.19-1.85 (7H, m), 1.75-1.57 (4H, m).

Example 249

Synthesis of 2-[(3R)-10-(phenylamino)-12-[[(1r,4r)-4-(dimethylamino)cyclohexyl]oxy]-7-thia-9,11-diazatricyclo[6.4.0.0[2,6]]dodeca-1(8),2(6),9,11-tetraen-3-yl]acetamide (I-232)

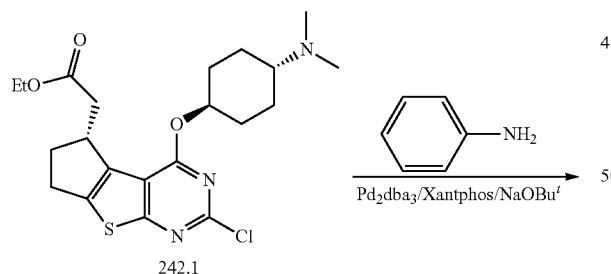

242.1

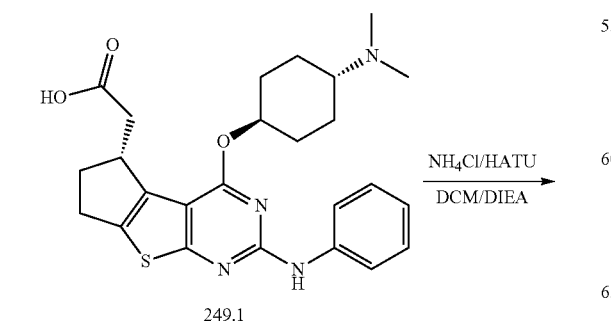

249.1

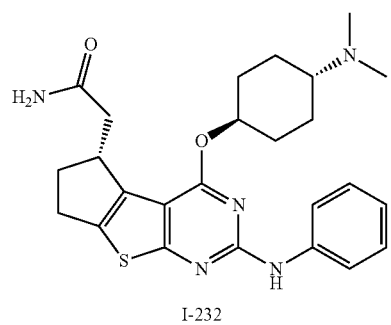

I-232

Compound I-232 was prepared from 242.1 in a manner analogous to the synthesis of Compound I-222. Isolated 27.8 mg of a white solid in 13% overall yield from 242.1. MS (ES): m/z 466 (M+H)$^+$. $^1$H-NMR (400 MHz, CD$_3$OD): δ 7.70 (2H, d), 7.32 (2H, t), 7.00 (1H, t), 5.18-5.05 (1H, m), 3.65-3.50 (1H, m), 2.95-2.85 (2H, m), 2.82-2.71 (2H, m), 2.60-2.46 (7H, s), 2.38-2.28 (2H, m), 2.15-1.98 (4H, m), 1.62-1.40 (4H, m).

Example 250

Synthesis of 2-[(3R)-12-([4-[(3R)-3-methylmorpholin-4-yl]cyclohexyl]oxy)-7-thia-9,11-diazatricyclo[6.4.0.0[2,6]]dodeca-1(8),2(6),9,11-tetraen-3-yl]acetamide (I-227)

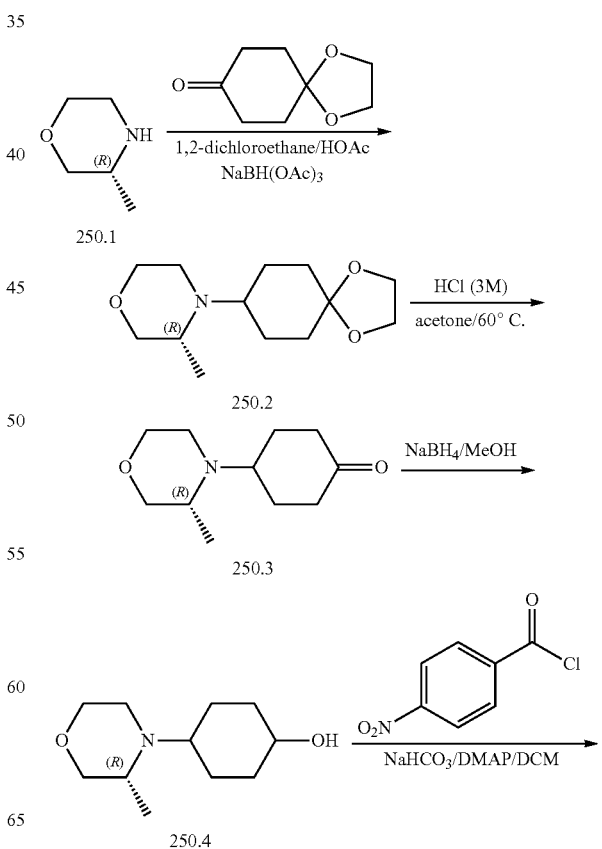

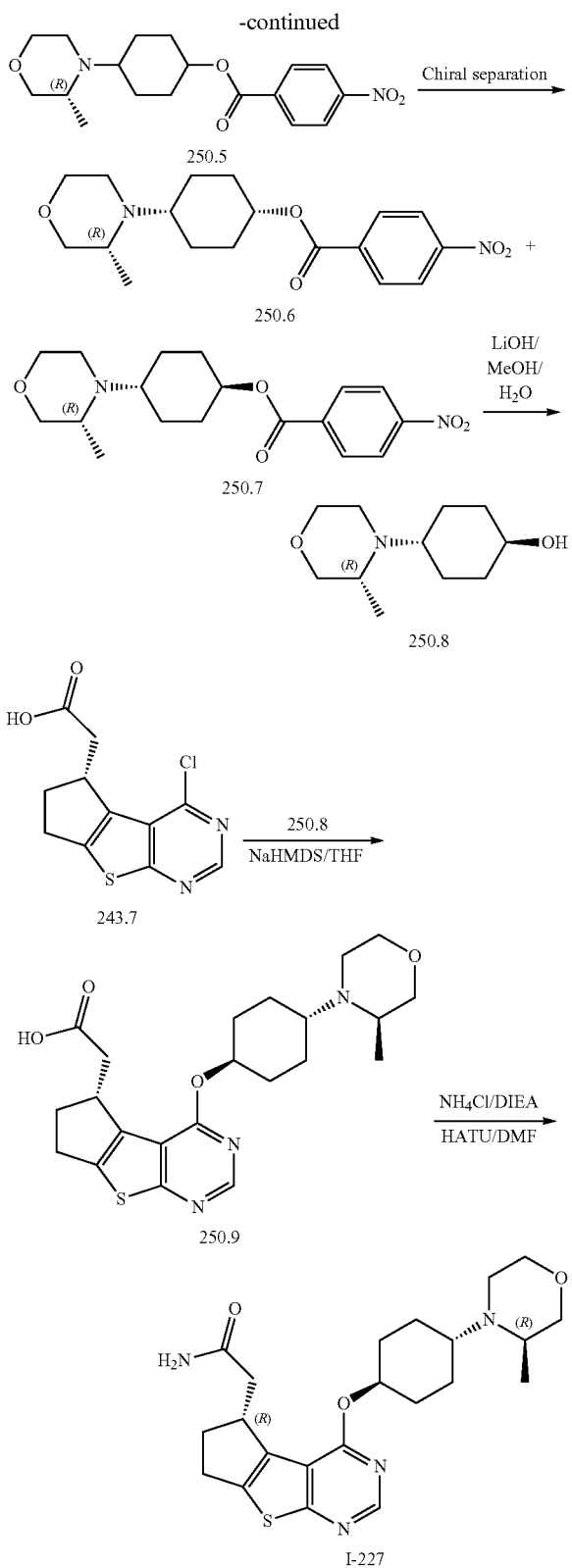

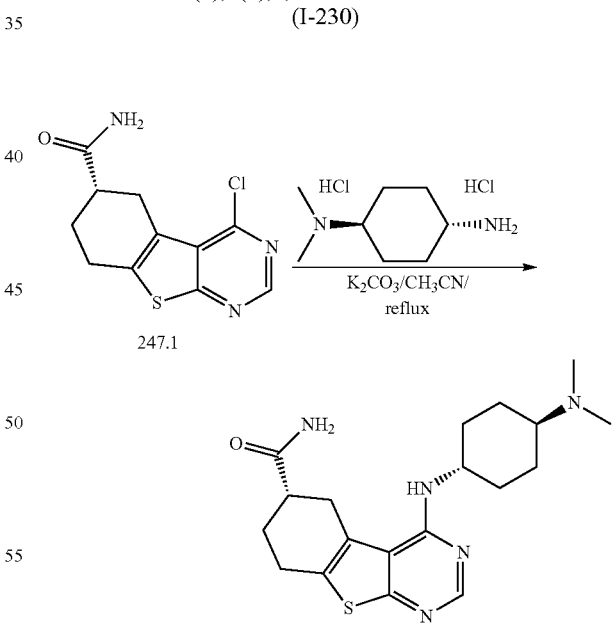

Synthesis of Compound 250.5.

Compound 250.5 was prepared from (R)-3-methylmorpholine in a manner analogous to the synthesis of 243.5 from 4,4-difluoropiperidine hydrochloride. Isolated 350 mg of a light yellow solid in 22% overall yield.

Synthesis of Compound 250.7.

The enantiomers of racemate 250.5 (350 mg) were separated by chiral preparative HPLC under the following conditions (Gilson Gx 281): Column: Chiralpak IC, 2*25 cm, 5 μm; mobile phase: hexane: EtOH=50:50; flow rate: 20 mL/min; UV detection at 254/220 nm. The second peak fractions were collected and evaporated under reduced to give 200 mg of 250.7 with 99.7% ee as a light yellow solid. The ee value was determined by chiral HPLC under the following conditions: Column: Lux Cellulose-4, 0.46*15 cm, 5 μm; mobile phase: hexanes (0.1% TEA):EtOH=70:30; flow rate: 1.0 mL/min; UV detection at 254 nm. $^1$H NMR (300 MHz, CDCl$_3$): δ 8.27 (d, 2H), 8.19 (d, 2H), 4.98-4.82 (m, 1H), 3.92-3.50 (m, 3H), 3.40-3.15 (m, 1H), 2.95-2.40 (m, 3H), 2.21 (br s, 2H), 1.98-1.75 (m, 2H), 1.68-1.30 (m, 5H), 0.95 (br s, 3H).

Synthesis of Compound 250.8.

Compound 250.8 was prepared from 250.7 in a manner analogous to the synthesis of 244.6. Isolated 110 mg (96%) of a light yellow solid.

Synthesis of Compound I-227.

Compound I-227 was prepared from 244.7 and 250.8 in a manner analogous to the synthesis of Compound I-229. MS (ES): m/z 431 (M+H)$^+$. $^1$H-NMR (400 MHz, CD$_3$OD): δ 8.49 (1H, s), 5.32-5.18 (1H, m), 3.88-3.76 (2H, m), 3.72-3.58 (2H, m), 3.30-3.28 (1H, m), 3.20-3.02 (1H, m), 3.02-2.65 (6H, m), 2.62-2.50 (1H, m), 2.40-2.19 (4H, m), 2.05-1.92 (1H, m), 1.90-1.40 (5H, m), 1.04 (3 h, d).

Example 251

Synthesis of (12S)-3-[[4-(dimethylamino)cyclohexyl]amino]-8-thia-4,6-diazatricyclo[7.4.0.0[2,7]]trideca-1 (9),2(7),3,5-tetraene-12-carboxamide (I-230)

A solution of 247.1 (50 mg, 0.19 mmol, 1.00 equiv) and trans-1-N,1-N-dimethylcyclohexane-1,4-diamine dihydrochloride (80 mg, 0.37 mmol, 2.00 equiv) in CH$_3$CN (10 mL) was added potassium carbonate (79 mg, 0.57 mmol, 3.0 equiv) and the resulting solution was stirred overnight at 80° C. in an oil bath. The solids were filtered out and washed with DCM. The filtrate was concentrated under vacuum. The crude product (50 mg) was purified by preparative HPLC under the following conditions (Waters): Column: XBridge Shield RP18 OBD 5 μm, 19*150 mm; mobile phase, water with 0.05% NH₄HCO₃ and CH₃CN (20% CH₃CN up to 40% in 10 min); flow rate: 15 mL/min; UV detection at 254 nm. This resulted in 21.5 mg (31%) of I-230 as a white solid. MS (ES): m/z 374 (M+H)⁺. ¹H NMR (300 MHz, d₆-DMSO): δ 8.26 (s, 1H), 7.45 (s, 1H), 6.97 (s, 1H), 5.98-5.96 (d, 2H), 4.05-4.01 (m, 1H), 3.08-3.06 (m, 2H), 2.85-2.82 (m, 2H), 5.59-2.51 (m, 1H), 2.17-2.13 (m, 6H), 2.05-2.03 (m, 3H), 1.84-1.76 (m, 3H), 1.49-1.26 (m, 4H).

Example 252

Synthesis of (12S)-3-[[(1r,4r)-4-(morpholin-4-yl)cyclohexyl]oxy]-8-thia-4,6-diazatricyclo[7.4.0.0[2,7]]trideca-1 (9),2(7),3,5-tetraene-12-carboxylic acid (I-234)

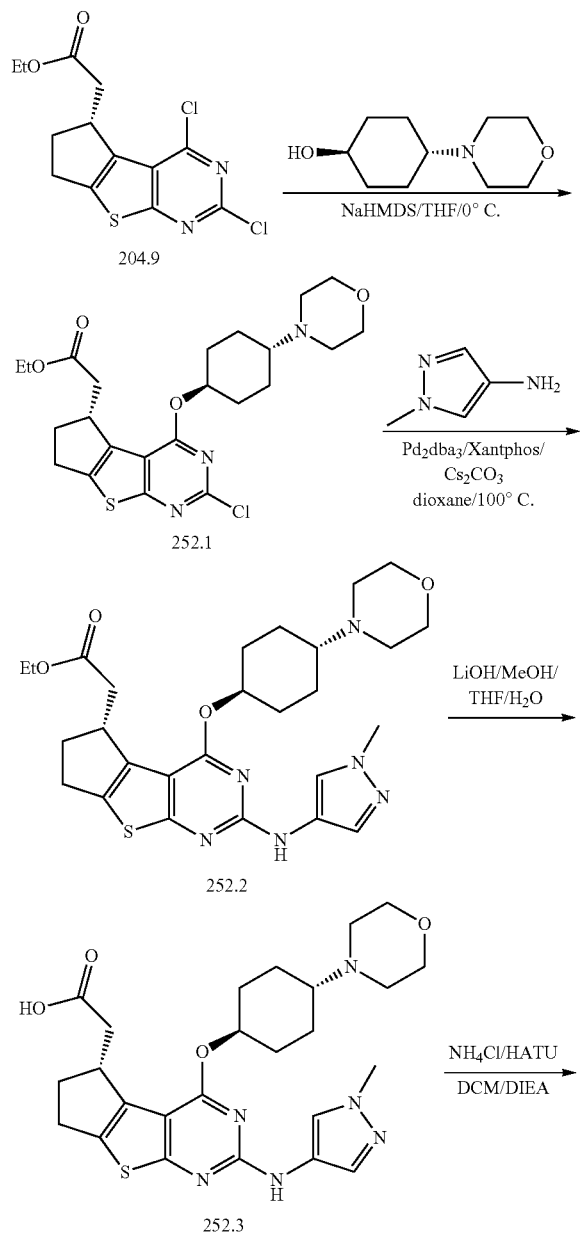

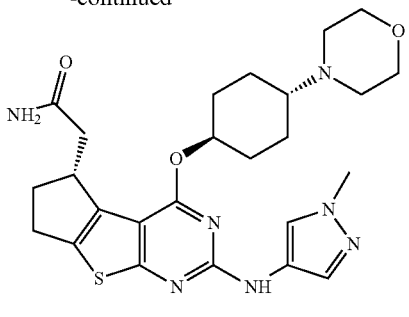

I-234

Synthesis of Compound 252.1.

A solution of trans-4-morpholinocyclohexanol (122.3 mg, 0.66 mmol, 1.1 equiv) in 5 mL of distilled THF was added NaHMDS (2 M in THF, 0.33 mL, 1.1 equiv) dropwise via a syringe at 0° C. under nitrogen. Then 204.9 (200 mg, 0.6 mmol, 1.0 equiv) in 3 mL of THF was added at this temperature and stirred for 30 min. After the reaction was complete, the reaction mixture was diluted with saturated aqueous NH₄Cl and extracted with DCM, washed with brine, dried and concentrated in vacuo. The residue was purified by chromatography on silica gel with DCM/MeOH/NH₄OH (80:1:0.01 to 50:1:0.01) to give the desired product 252.1 (140 mg) as a light yellow oil.

Synthesis of Compound 252.2.

A mixture of compound 252.1 (140 mg, 0.292 mmol, 1.00 equiv), 1-methyl-1H-pyrazol-4-amine (42.5 mg, 0.437 mmol, 1.5 equiv), Pd₂dba₃ (14.3 mg, 0.015 mmol, 0.05 equiv), Xantphos (18.1 mg, 0.030 mmol, 0.10 equiv), Cs₂CO₃ (286 mg, 0.876 mmol, 3.0 equiv) in 8 mL of dioxane was degassed three times with nitrogen. The resulting mixture was stirred for 2 h at 100° C. The reaction mixture was concentrated under vacuum and the residue was diluted with water and extracted with DCM. The combined organic layers were washed with brine, dried and concentrated in vacuo. Purification by chromatography on silica gel with DCM/MeOH/NH₄OH (80:1 to 30:1:0.01) to give the desired 252.2 (130 mg, 90% purity) as a yellow semi-solid.

Synthesis of Compound 252.3.

To the compound 252.2 (130 mg, 90% purity) dissolved in a mixture of THF/MeOH/water (3:3:1.5 mL) was added LiOH·H₂O (40 mg) at room temperature followed by stirring for 4 h at this temperature. The resulting solution was concentrated under reduced pressure. The residue was diluted with 3 mL of water, acidified with 1 M hydrochloric acid to pH 5 and extracted with CHCl₃/IPA (v/v: 3:1) four times. The combined organic layers were dried and evaporated in vacuo to give 100 mg crude of 252.3 as a yellow solid.

Synthesis of Compound I-234.

A mixture of 252.3 (60 mg, 0.12 mmol, 1.00 equiv) in distilled DMF (5 mL) was added NH₄Cl (19.08 mg, 0.36 mmol, 3.08 equiv), HATU (54.7 mg, 0.14 mmol, 1.23 equiv) and DIEA (33.4 mg, 0.26 mmol, 2.21 equiv) and stirred for 3 h at room temperature under nitrogen. The resulting solution was diluted with 5 mL of H₂O and extracted with 3×20 mL of

Example 253

Synthesis of 3-[[4-(dimethylamino)cyclohexyl]oxy]-8-thia-4,6,12-triazatricyclo[7.4.0.0[2,7]]trideca-1(9),2(7),3,5-tetraene-12-sulfonamide (I-238)

DCM and concentrated under vacuum. The crude product (56 mg) was purified by preparative HPLC under the following conditions (Waters): Column: XBridge Shield RP18 OBD 5 μm, 19*150 mm; mobile phase, water with 0.01% NH$_4$HCO$_3$ and acetonitrile (10%-35% in 10 min); flow rate: 15 ml/min; UV detection at 254 nm. This resulted in 12.5 mg (21%) of product I-234 as a white solid. MS (ES): m/z 512 (M+H)$^+$. $^1$H-NMR (400 MHz, CD$_3$OD): δ 8.90 (s, 1H), 7.57 (s, 1H), 5.22-5.10 (m, 1H), 3.90 (s, 3H), 3.75-3.50 (m, 5H), 3.02-2.95 (m, 2H), 2.90-2.80 (m, 1H), 2.70-2.58 (m, 5H), 2.50-2.41 (m, 3H), 2.25-2.08 (m, 5H), 1.70-1.56 (m, 2H), 1.54-1.38 (m, 2H).

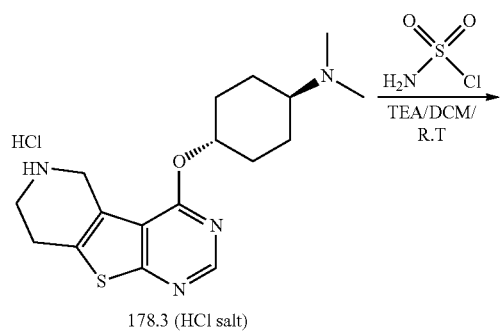

178.3 (HCl salt)

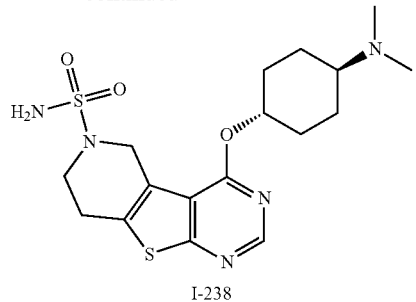

I-238

Into a 50-mL round-bottom flask was placed a solution of 178.3 (HCl salt) (50 mg, ~75 purity) in anhydrous DCM (5 mL) cooled to 0° C. Then sulfamoyl chloride (26 mg, 0.23 mmol, 1.50 equiv) was added, followed by addition of TEA (45 mg, 0.44 mmol, 2.96 equiv) and the resulting solution was stirred for 2 h at this temperature under nitrogen. The resulting mixture was concentrated under vacuum. The crude product (60 mg) was purified by preparative HPLC under the following conditions (Waters): Column: XBridge Shield RP18 OBD 5 μm, 19*150 mm; mobile phase: water with 0.01% NH$_4$HCO$_3$ and acetonitrile (gradient: 20%-24% CH$_3$CN in 10 min); flow rate: 15 ml/min; UV detection at 254 nm. This resulted in 10.7 mg (17%) of I-238 as a white solid. MS (ES): m/z 412 (M+H)$^+$. $^1$H-NMR (300 MHz, CD$_3$OD): δ 8.47 (1H, s), 5.26-5.15 (1H, m), 4.51 (2H, s), 3.52 (2H, t), 3.03 (2H, t), 2.43-2.25 (9H, m), 2.03 (2H, d), 1.67-1.45 (4H, m).

Example 254

Synthesis of 12-methyl-3-[[(1r,4r)-4-(morpholin-4-yl)cyclohexyl]oxy]-8-thia-4,6-diazatricyclo[7.4.0.0[2,7]]trideca-1(9),2,4,6-tetraene-12-carboxamide (I-237)

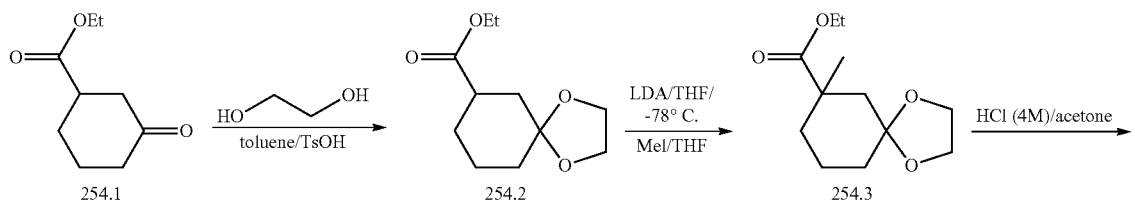

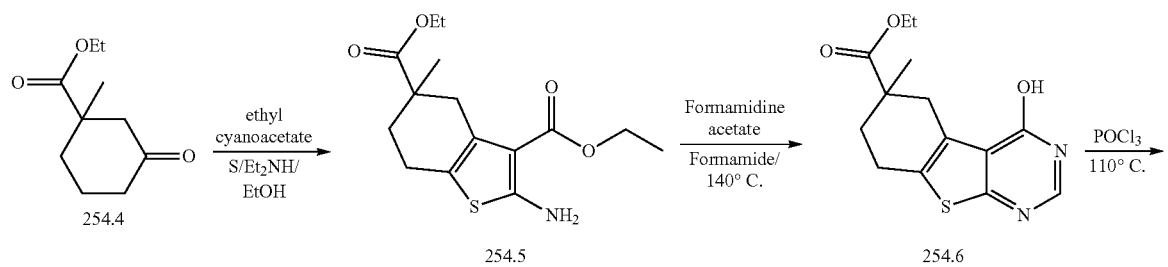

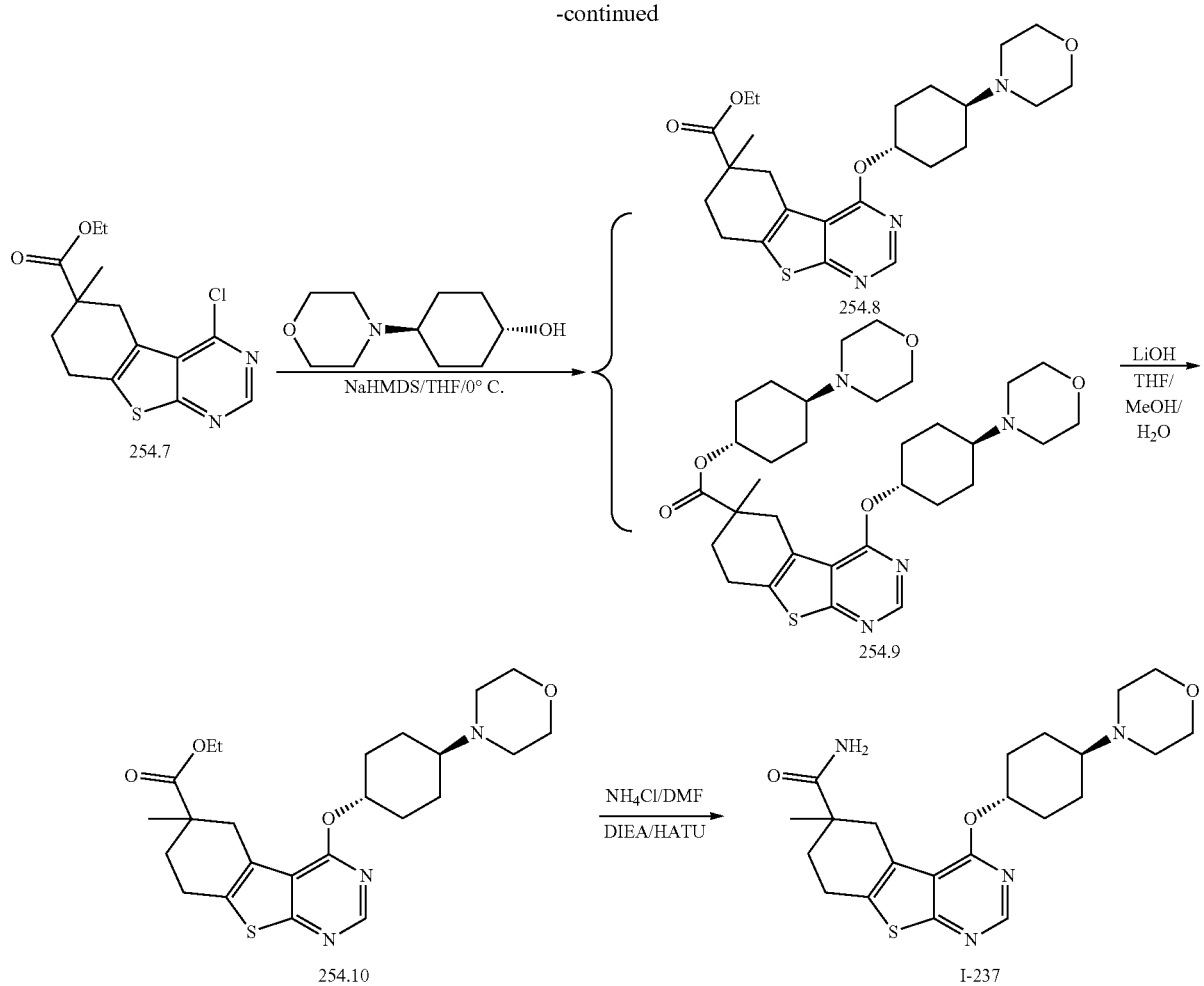

Synthesis of Compound 254.2.

To a solution of ethyl 3-oxocyclohexane-1-carboxylate (2.0 g, 11.75 mmol, 1.00 equiv) and ethane-1,2-diol (875 mg, 14.10 mmol, 1.20 equiv) in toluene (30 mL) was added TsOH (0.2 g) and the resulting solution was stirred for 12 h at 110° C. in an oil bath. After cooling, the reaction was then quenched with water and extracted with 3×60 mL of ethyl acetate. The combined organic layers were washed with brine, dried over anhydrous sodium sulfate and evaporated in vacuo. The residue was applied onto a silica gel column with ethyl acetate/petroleum ether (1:30) to give 1.7 g (68%) of 254.2 as a light yellow oil.

Synthesis of Compound 254.3.

To a solution of 254.2 (1.7 g, 7.93 mmol, 1.00 equiv) in distilled THF (30 mL) cooled to −78° C. was added newly prepared LDA (1.02 g, 9.52 mmol, 1.20 equiv) under nitrogen via syringe. After stirring for 30 min, $CH_3I$ (3.92 g, 27.62 mmol, 3.50 equiv) was added and the resulting solution was stirred for 2 h at −40° C. The reaction was then quenched with water and extracted with 3×60 mL of ethyl acetate. The organic layers were combined, washed with brine and dried over anhydrous sodium sulfate and concentrated under vacuum. The residue was applied onto a silica gel column with ethyl acetate/petroleum ether (1:30) to yield 1.7 g (94%) of 254.3 as a light yellow oil.

Synthesis of Compound 254.4.

Into a 100-mL round-bottom flask containing a solution of 254.3 (1.7 g, 7.45 mmol, 1.00 equiv) in acetone (30 mL) was added hydrochloric acid (4 M, 5 mL) and the resulting solution was stirred for 4 h at 70° C. in an oil bath. After cooling to room temperature, the reaction was then quenched with saturated aqueous sodium bicarbonate and extracted with 3×60 mL of ethyl acetate. The combined organic layers were washed with brine, dried over anhydrous sodium sulfate and concentrated under vacuum. The residue was applied onto a silica gel column with ethyl acetate/petroleum ether (1:15) to afford 1.0 g (73%) of 254.4 as a light yellow oil.

Synthesis of Compound 254.7.

Compound 254.7 was prepared from 254.4 in a manner analogous to the synthesis of 207.4. Isolated 180 mg of a light yellow liquid in 38% overall yield.

Synthesis of Compound 254.8.

trans-4-(Morpholin-4-yl)cyclohexan-1-ol (76 mg, 0.41 mmol, 1.20 equiv) was treated with NaHMDS (0.25 mL, 1.50 equiv) in 6 mL of distilled THF for 20 min at 0° C. under nitrogen. Then a solution of 254.7 (100 mg, 0.32 mmol, 1.00 equiv) in dry THF (3 mL) was added via syringe. After stirring for 1 h at this temperature, the reaction was then quenched with water and extracted with 3×20 mL of ethyl acetate. The combined organic layers were dried over anhydrous sodium sulfate and concentrated under vacuum. The residue was applied onto a silica gel column with ethyl acetate/petroleum ether (1:10) to give 45 mg (30%) of 254.8 as a white solid. 76 mg of by-product 254.9 were also obtained as a white solid.

Synthesis of 254.10.

A solution of 254.8 (40 mg, 0.09 mmol, 1.00 equiv) in methanol/THF/water (3/3/3 mL) was added LiOH (8.4 mg, 0.35 mmol, 4.00 equiv) and the resulting solution was stirred overnight at room temperature. The resulting solution was diluted with 10 mL of water, acidified with 1 M hydrochloric acid and extracted with 3×20 mL of ethyl acetate. The organic layers were combined and dried over anhydrous sodium sulfate and concentrated under vacuum to give 30 mg (crude) of 254.10 as a white solid.

Synthesis of Compound I-237.

Compound I-237 was prepared from 254.10 in a manner analogous to the synthesis of I-13. Isolated 12 mg of a white solid in 57% yield. MS (ES): m/z 431 (M+H)$^+$. 1H-NMR: (300 MHz, CD$_3$OD): δ 8.47 (s, 1H), 5.32-5.15 (m, 1H), 3.80-3.68 (m, 4H), 3.50 (d, 1H), 3.02-2.89 (m, 2H), 2.82 (d, 1H), 2.71-2.69 (m, 4H), 2.49-2.18 (m, 4H), 2.10 (d, 2H), 1.98-1.85 (m, 1H), 1.75-1.40 (m, 4H), 1.31 (s, 3H).

Example 255

Synthesis of 2-(3-[[4-(dimethylamino)cyclohexyl]oxy]-11-oxa-8-thia-4,6-diazatricyclo[7.4.0.0[2,7]]trideca-1(9),2,4,6-tetraen-12-yl)ethan-1-ol (I-219)

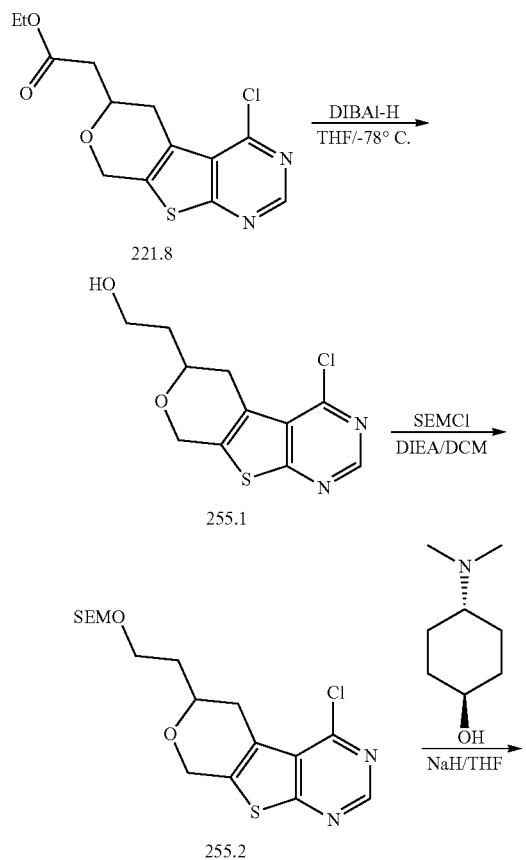

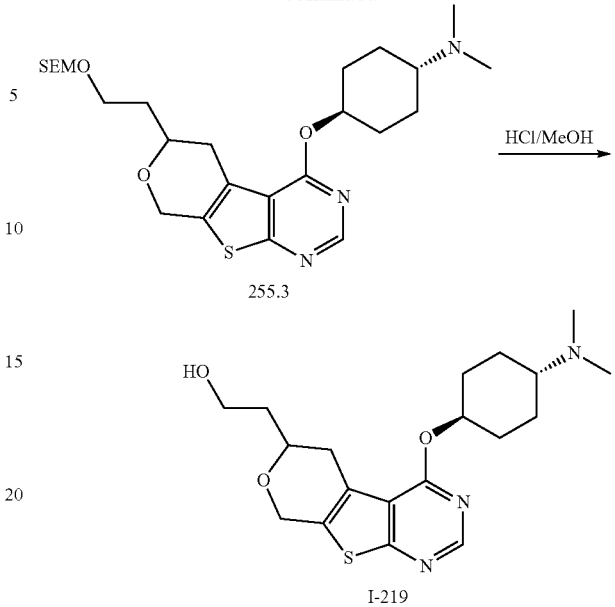

Synthesis of Compound 255.1.

A solution of 221.8 (260 mg, 0.83 mmol, 1.00 equiv) in distilled THF (10 mL) cooled down to −78° C. was added DIBAL-H (25% in hexane, 2.0 g, 3.52 mmol, 4.24 equiv) dropwise under nitrogen. The resulting solution was warmed up to −30° C. and stirred for 2 h. TLC analysis of the reaction indicated the starting 1 consumed completely. The reaction was then quenched with water and extracted with 3×50 mL of ethyl acetate. The combined organic layers were dried over sodium sulfate and concentrated under vacuum. The residue was applied onto a silica gel column with ethyl acetate/petroleum ether (1/4) to afford 190 mg (84%) of 255.1 as a white solid.

Synthesis of Compound 255.2.

To a solution of 255.1 (190 mg, 0.70 mmol, 1.00 equiv) in dichloromethane (5 mL) was added SEMCl (140 mg, 0.84 mmol, 1.32 equiv) and DIEA (180 mg, 1.39 mmol, 1.98 equiv) at 0° C. The resulting solution was stirred for 2.5 h at room temperature and quenched by the addition of saturated aqueous NH$_4$Cl and extracted with 3×50 mL of ethyl acetate. The combined organic layers were dried and concentrated under vacuum. The residue was applied onto a silica gel column with ethyl acetate/petroleum ether (1/10) to give 250 mg (89%) of the desired 255.2 as a colorless oil.

Synthesis of Compound 255.3.

Sodium hydride (60%, 100 mg, 2.50 mmol, 5.0 equiv) was treated with trans-4-(dimethylamino)cyclohexan-1-ol (143 mg, 1.00 mmol, 2.00 equiv) in distilled THF (8 mL) at 0° C. under nitrogen. Then 255.2 (200 mg, 0.50 mmol, 1.00 equiv) was added and the resulting solution was stirred for another 1 h at 60° C. After cooling, the reaction was then quenched with saturated aqueous NH$_4$Cl and extracted with 3×60 mL of ethyl acetate. The organic layers were combined, dried and concentrated under vacuum. The residue was applied onto a silica gel column with ethyl acetate/petroleum ether (1/5) to provide 190 mg (75%) of the desired 255.3 as a white solid.

Synthesis of Compound I-219.

A solution of 255.3 (190 mg, 0.37 mmol, 1.00 equiv) in methanol (6 mL) was added hydrochloric acid (37%, 0.5 mL) at 0° C. The resulting solution was stirred for 3 h at room temperature. After concentration under vacuum, the reaction mixture was acidified by 1 M hydrochloric acid and extracted with DCM and evaporated in vacuo. The crude product (190 mg) was purified by preparative HPLC under the following conditions (Waters): Column: XBridge Shield RP18 OBD 5 μm, 19*150 mm; mobile phase: water with 0.01% NH₄HCO₃ and acetonitrile (10%-33% CH₃CN in 10 min); flow rate: 15 ml/min; UV detection at 254 nm. This resulted in 21.7 mg (15%) of I-219 as a white solid. MS (ES): m/z 378 (M+H)⁺. 1H-NMR (300 MHz, CD₃OD): δ 8.50 (1H, s), 5.35-5.15 (1H, m), 4.92 (2H, s), 3.95-3.86 (1H, m), 3.82-3.72 (2H, m), 3.10 (1H, d), 2.80-2.70 (1H, m), 2.70-2.58 (1H, m), 2.47 (6H, s), 2.36 (2H, d), 2.10 (d, 2H), 1.98-1.82 (2H, m), 1.72-1.50 (4H, m).

Example 256

Synthesis of 2-((R)-4-(((1r,4R)-4-(dimethylamino) cyclohexyl)oxy)-2-((4-(4-methylpiperazin-1-yl)phenyl)amino)-6,7-dihydro-5H-cyclopenta[4,5]thieno[2, 3-d]pyrimidin-5-yl)acetamide (I-231)

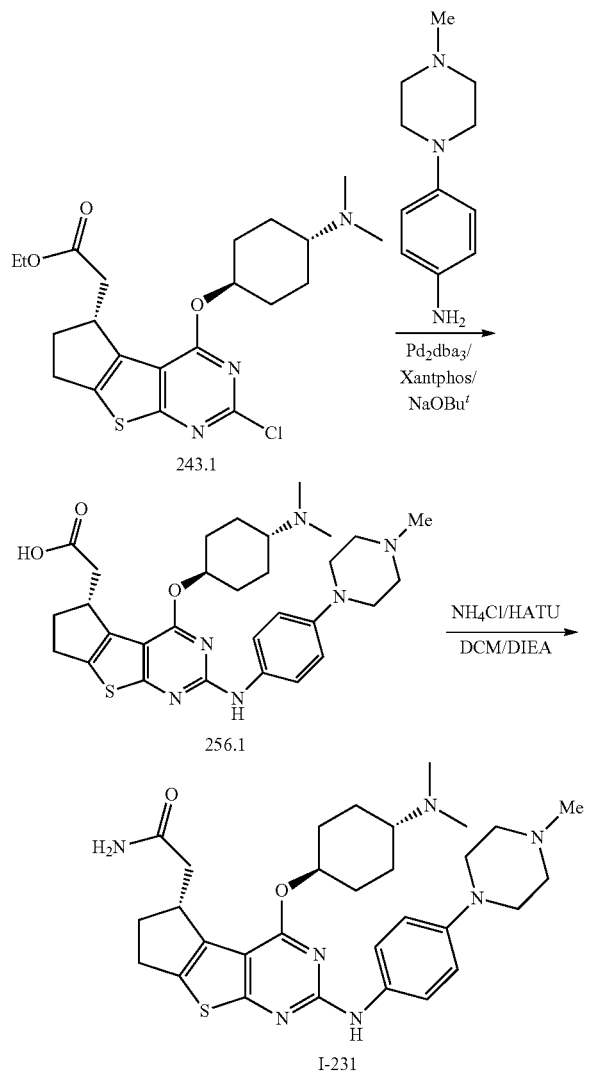

Compound I-231 was prepared from 242.1 in a manner analogous to the synthesis of Compound I-222, substituting 4-(4-methylpiperazin-1-yl)aniline for 1-methyl-1H-pyrazol-4-amine. Isolated 5.4 mg of an off-white solid in 0.4% overall yield from 242.1. MS (ES): m/z 564 (M+H)⁺. ¹H-NMR (300 MHz, CD₃OD): δ 8.40 (2.3H, brs), 7.58 (2H, d), 7.00 (2H, d), 5.25-5.08 (1H, m), 3.75-3.65 (1H, m), 3.10-2.82 (16H, m), 2.75-2.60 (5H, m), 2.52-2.48 (2H, m), 2.30-2.12 (5H, m), 1.80-1.60 (4H, m).

Example 257

Synthesis of 2-(4-(((1r,4r)-4-(dimethylamino)cyclo-hexyl)oxy)-2-((4-(4-methylpiperazin-1-yl)phenyl) amino)-6,7-dihydro-5H-cyclopenta[4,5]thieno[2,3-d] pyrimidin-5-yl)acetamide (I-206)

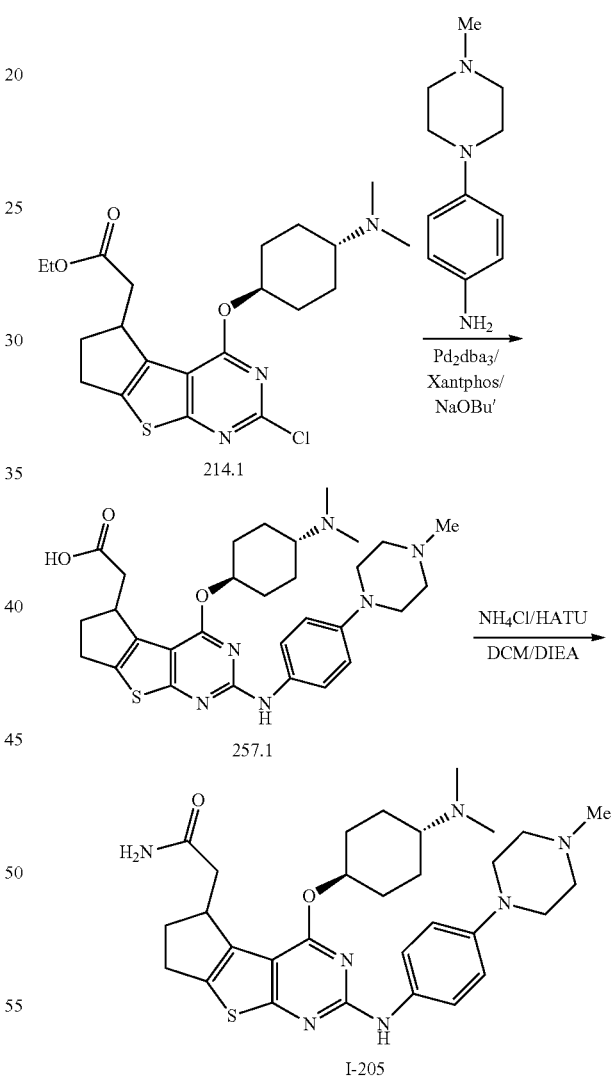

Compound I-205 was prepared from 214.1 and 4-(4-methylpiperazin-1-yl)aniline in a manner analogous to the synthesis of Compound I-231. Isolated 12.1 mg of an off-white solid in 8% overall yield from 214.1. MS (ES): m/z 564 (M+H)⁺. ¹H NMR (300 MHz, CD₃OD): δ 7.47 (2H, d), 7.60 (2H, m), 6.90 (2H, d), 5.18-5.02 (1H, m), 3.70-3.45 (3H, m), 3.13-3.09 (4H, m), 3.05-2.70 (3H, m), 2.65-2.42 (6H, m), 2.37 (6H, s), 2.30-1.98 (9H, m), 1.65-1.30 (4H, m).

Example 258

Synthesis of 4-(((1r,4r)-4-morpholinocyclohexyl)amino)-6,8-dihydro-5H-pyrano[4',3':4,5]thieno[2,3-d]pyrimidine-6-carboxamide (I-241)

reduced pressure, the residue was washed with 1 M HCl solution and extracted with EtOAc, dried over sodium sulfate and the solvents evaporated. The residue was purified by silica gel column with EtOAc/PE (1:30 to 1:10) to give 3.4 g (73%) of the desired 258.2 as a light yellow oil.

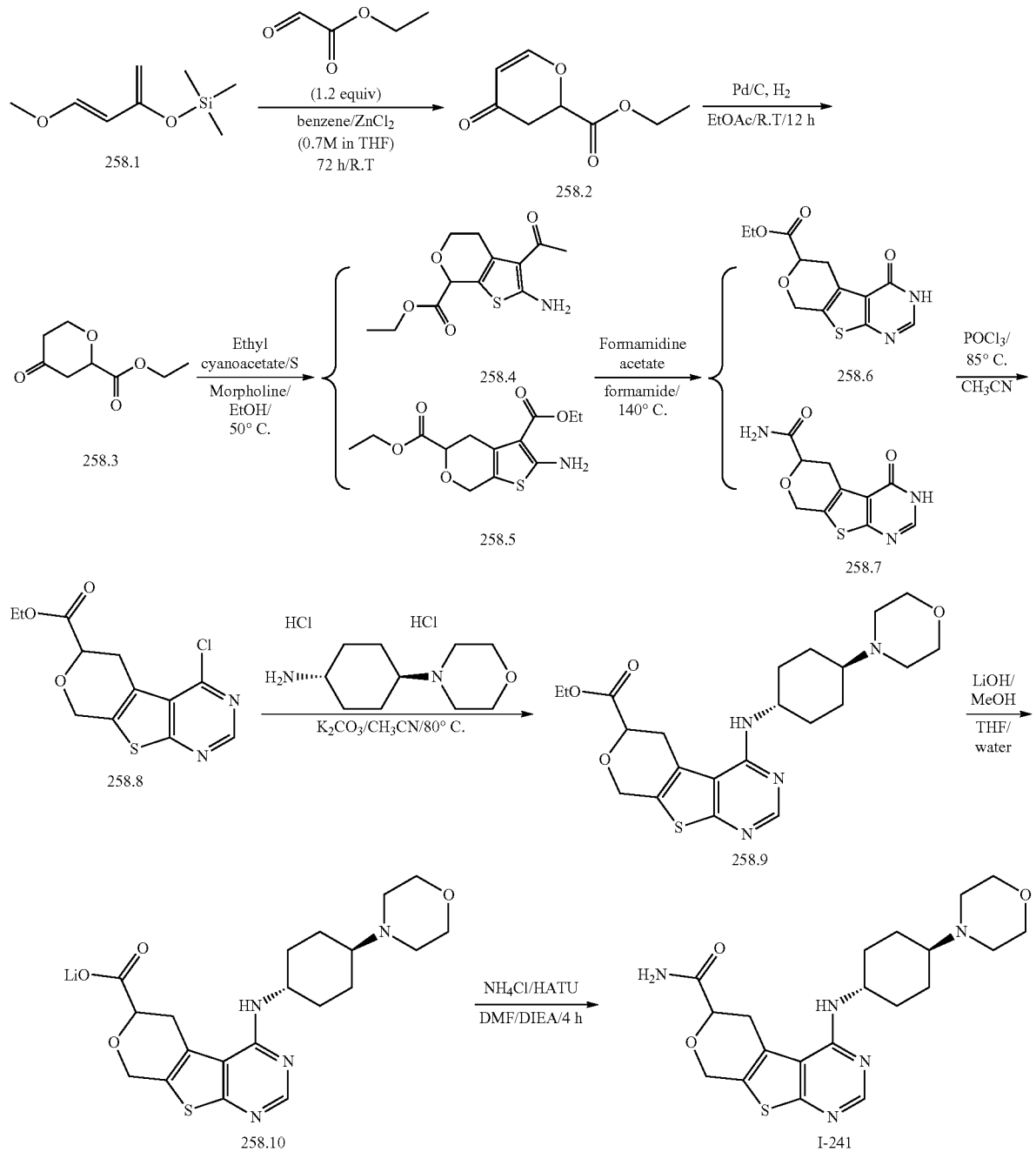

Synthesis of Compound 258.2.

To a solution of 258.1 (5.0 g, 27.28 mmol, 1.00 equiv, 94%) in freshly distilled benzene (30 mL) was added ethyl 2-oxoacetate (6.13 g, 30.0 mmol, 1.1 equiv), followed by additional 0.7 M ZnCl$_2$-THF (16.40 mmol, 23.40 mL, 0.60 equiv) at 0° C. under nitrogen. The resulting solution was stirred for 72 h at room temperature. After the starting diene was consumed completely, the reaction solution was concentrated under Synthesis of Compound 258.3.

Into a 100-mL round-bottom flask containing a solution of 258.2 (2.0 g, 11.75 mmol, 1.00 equiv) in ethyl acetate (50 mL) was added palladium on activated carbon (10%, 200 mg) under nitrogen at room temperature. Then H$_2$ (g) was introduced in and degassed three times. The resulting solution was stirred for 12 h at ambient temperature. The solids were filtered out by filtration and washed with EtOAc (3×). The filtrate was concentrated under reduced pressure and the residue was purified by silica gel column with EtOAc/PE (1:20) to give the desired 258.3 (1.62 g, 80%) as a light yellow oil.

Synthesis of Compound 258.5.

To a solution of 258.3 (1.62 g, 9.4 mmol, 1.00 equiv) in ethanol (60 mL) was added S (361 mg, 11.28 mmol, 1.20 equiv), ethyl 2-isocyanoacetate (1.28 g, 11.28 mmol, 1.20 equiv), morpholine (1.23 g, 14.1 mmol, 1.50 equiv) sequentially under nitrogen. The resulting mixture was stirred for 4 h at 50° C. in an oil bath. The resulting mixture was evaporated in vacuo, diluted with water and extracted with 3×80 mL of ethyl acetate. The combined organic layers were washed with brine, dried over anhydrous sodium sulfate and concentrated under vacuum. The residue was applied onto a silica gel column with ethyl acetate/petroleum ether (1:30 to 1:15) to give 258.5 (1.3 g, 46%) as a light yellow solid. The regioisomer 258.4 is a by-product of the reaction.

Synthesis of Compound 258.6.

A solution of 258.5 (800 mg, 2.67 mmol, 1.00 equiv) and formamidine acetate (2.78 g, 26.7 mmol, 10.0 equiv) in formamide (20 mL) was heated for 2 h at 140° C. in an oil bath under nitrogen. The resulting solution was cooled and diluted with water and extracted with 3×50 mL of ethyl acetate. The combined organic layers were washed with brine, dried over anhydrous sodium sulfate and concentrated under vacuum. The residue was applied onto a silica gel column with dichloromethane/methanol (100/1) to give 130 mg of 258.6 as a white solid. The aqueous phase was extracted with 4×50 mL of $CHCl_3$/IPA (v/v: 3:1), dried and concentrated under reduced pressure to afford around 400 mg of amide 258.7 as a brown solid.

Synthesis of Compound 258.8.

A mixture of 258.6 (130 mg, 0.46 mmol, 1.00 equiv) in dry $CH_3CN$ (10 mL) was added $POCl_3$ (355 mg, 2.32 mmol, 5.00 equiv) at room temperature and the resulting mixture was stirred for 3 h at 85° C. in an oil bath. The reaction mixture was concentrated to remove the excess of $POCl_3$ and diluted with EtOAc. The mixture was poured into a cooled saturated aqueous sodium dicarbonate and extracted with 3×50 mL of ethyl acetate. The combined organic layers were dried and concentrated under reduced pressure. The residue was applied onto a silica gel column with ethyl acetate/petroleum ether (1:20) to give 90 mg (65%) of 258.8 as a white solid.

Synthesis of Compound 258.9.

Into a 50-mL round-bottom flask was placed a mixture of 258.8 (90 mg, 0.30 mmol, 1.00 equiv) and trans-4-(morpholin-4-yl)cyclohexan-1-amine dihydrochloride (92.6 mg, 0.36 mmol, 1.20 equiv) at room temperature. Then potassium carbonate (124 mg, 0.90 mmol, 3.00 equiv) was added and the resulting mixture was stirred for 12 h at 78° C. in an oil bath under nitrogen. After cooling, the resulting solution was diluted with water and extracted with 3×50 mL of ethyl acetate. The organic layers were combined, dried over anhydrous sodium sulfate and concentrated under vacuum. The residue was applied onto a silica gel column with dichloromethane/methanol (1/10) to give 100 mg (74%) of 258.9 as a white solid.

Synthesis of Compound 258.10.

To a solution of 258.9 (100 mg, 0.224 mmol, 1.0 equiv) in a mixture of THF/MeOH/water (4/4/2 mL) was added LiOH. 120 (38 mg, 0.896 mmol, 4.0 equiv) at room temperature. The resulting solution was stirred at ambient temperature for 4 h and concentrated under reduced pressure to give around 100 mg of 258.10 as a light yellow solid.

Synthesis of Compound I-241.

The compound 258.10 (100 mg, crude) in 6 mL of distilled DMF was added $NH_4Cl$ (20 mg, 0.372 mmol), HATU (128 mg, 0.336 mmol) and DIEA (48 mg, 0.372 mmol) successively at room temperature and stirred for 4 h under nitrogen. After completion, the reaction mixture was diluted with water and extracted with DCM, dried over sodium sulfate and concentrated in vacuo. The residue was purified via a silica gel column with DCM/MeOH (50:1 to 30:1) to give the desired product I-241 (45 mg) as a white solid. MS (ES): m/z 418 $(M+H)^+$. $^1H$ NMR (300 MHz, $d_6$-DMSO): δ 8.29 (1H, s), 7.40 (s, 2H), 6.10 (d, 1H), 4.90 (dd, 2H), 4.16 (dd, 1H), 4.10-3.90 (m, 1H), 3.56 (brs, 4H), 3.25-3.05 (m, 2H), 249 (brs, 4H), 2.30-2.12 (m, 1H), 2.00 (d, 2H), 1.86 (d, 2H), 1.55-1.20 (m, 4H).

Example 259

IRAK-4 Assay

Assay Materials

| Material | Vendor | Catalog number |
| --- | --- | --- |
| HEPES | Amresco | 0511 |
| Brij-35 | Sigma | B4184-100mL |
| Coating Reagent #3 | Caliper | |
| EDTA | Sigma | E5134-1KG |
| ATP | Sigma | A7699-1G |
| $MgCl_2$ | Sigma | 63068-250G |
| $MnCl_2$ | Sigma | M8054-100G |
| Peptide 8 | GL bioscience | 112396 |
| IRAK4 | CARNA Bioscience | 09-145 |
| 384-well plate | Corning | 3573 |

A 1× kinase base buffer was prepared from 50 mM HEPES, pH 7.5 and 0.0015% Brij-35. A stop buffer was prepared from 100 mM HEPES, pH 7.5, 0.015% Brij-35, 0.2% Coating Reagent #3, and 50 mM EDTA.

Test compound was diluted to 50× of the final desired highest inhibitor concentration in reaction by 100% DMSO. 100 μl of this compound dilution was transferred to a well in a 96-well plate. For example, if desired highest inhibitor concentration in IC50 determination is 100 μM, then prepare 5000 μM of compound DMSO solution in this step.

Test compound was serially diluted by transferring 30 μl to 60 μl of 100% DMSO in the next well and so forth for a total of 10 concentrations. 100 μl of 100% DMSO was added to two empty wells for no compound control and no enzyme control in the same 96-well plate.

A new 96-well plate was marked as intermediate plate. 5 μl of compound serial dilution was transferred from source plate to the corresponding wells of the intermediate plate. 45 μl of 1× kinase base buffer (KB buffer) was added to each well of the intermediate plate. The intermediate plate was placed for 10 min on a shaker.

5 μl of each well was transferred from the 96-well intermediate plate to a 384-well plate in duplicates. For example, A1 of the 96-well plate is transferred to A1 and A2 of the 384-well plate. A2 of the 96-well plate is transferred to A3 and A4 of the 384-well plate, and so on.

IRAK4 and DTT in 1× kinase base buffer was added. The 2.5× enzyme mix contained 8.8 nM IRAK4 and 5 mM DTT.

Peptide 8, ATP, $MgCl_2$ and $MnCl_2$ were added in the 1× kinase base buffer. The 2.5× peptide mix contained 3.75 μM peptide 8, 92.5 μM ATP, 12.5 mM $MgCl_2$ and 2.5 mM $MnCl_2$.

Assay plate already contained 5 μl of compound in 10% DMSO. Added 10 μl of 2.5× enzyme solution to each well of the 384-well assay plate, except no enzyme control wells. The final concentration of IRAK4 in reaction was 3.5 nM. Added 10 µl of 1× kinase base buffer to no enzyme control wells in the assay plate. Incubated at room temperature for 10 min.

Added 10 µl of 2.5× peptide solution to each well of the 384-well assay plate. The final concentration of Peptide 8 and ATP was 1.5 µM and 37 µM, respectively. Incubated at 28° C. for 40 minutes. Added 25 µl of stop buffer to stop reaction. Collected data on Caliper.

Copied conversion % data from Caliper program. Converted conversion % values to percent inhibition values. Percent inhibition=(max-conversion %)/(max-min)*100, where "max" means the conversion % of DMSO control and "min" means the conversion % of no enzyme control.

Tables 3A, 3B and 3C show the activity of selected compounds of this invention in the IRAK-4 activity inhibition assay. The compound numbers correspond to the compound numbers in Table 1. Compounds having an activity designated as "A" provided an $IC_{50} \leq 5$ µM; compounds having an activity designated as "B" provided an $IC_{50}$ of 5-20 µM; compounds having an activity designated as "C" provided an $IC_{50}$ of 20-50 µM; and compounds having an activity designated as "D" provided an $IC_{50} \geq 50$ µM. "NA" stands for "not assayed."

TABLE 3A

IRAK-4 Activity Inhibition Data

| Cpd # | IRAK-4 | Cpd # | IRAK-4 | Cpd # | IRAK-4 | Cpd # | IRAK-4 |
|---|---|---|---|---|---|---|---|
| I-1 | B | I-21 | A | I-41 | A | I-61 | A |
| I-2 | C | I-22 | B | I-42 | A | I-62 | A |
| I-3 | A | I-23 | B | I-43 | A | I-63 | A |
| I-4 | C | I-24 | C | I-44 | A | I-64 | A |
| I-5 | B | I-25 | C | I-45 | A | I-65 | A |
| I-6 | B | I-26 | B | I-46 | A | I-66 | A |
| I-7 | A | I-27 | B | I-47 | A | I-67 | A |
| I-8 | D | I-28 | C | I-48 | A | I-68 | A |
| I-9 | A | I-29 | D | I-49 | A | I-69 | A |
| I-10 | C | I-30 | C | I-50 | B | I-70 | A |
| I-11 | B | I-31 | B | I-51 | A | I-71 | A |
| I-12 | A | I-32 | A | I-52 | A | I-72 | A |
| I-13 | A | I-33 | A | I-53 | A | I-73 | A |
| I-14 | D | I-34 | A | I-54 | A | I-74 | A |
| I-15 | D | I-35 | A | I-55 | A | I-75 | A |
| I-16 | D | I-36 | D | I-56 | A | I-76 | A |
| I-17 | A | I-37 | A | I-57 | A | I-77 | A |
| I-18 | B | I-38 | C | I-58 | A | I-78 | A |
| I-19 | A | I-39 | A | I-59 | A | I-79 | A |
| I-20 | A | I-40 | A | I-60 | A | I-80 | A |

TABLE 3B

IRAK-4 Activity Inhibition Data Continued

| Cpd # | IRAK-4 | Cpd # | IRAK-4 | Cpd # | IRAK-4 | Cpd # | IRAK-4 |
|---|---|---|---|---|---|---|---|
| I-81 | B | I-101 | A | I-121 | A | I-141 | B |
| I-82 | A | I-102 | A | I-122 | A | I-142 | A |
| I-83 | A | I-103 | B | I-123 | A | I-143 | B |
| I-84 | A | I-104 | B | I-124 | B | I-144 | A |
| I-85 | A | I-105 | A | I-125 | A | I-145 | A |
| I-86 | A | I-106 | A | I-126 | A | I-146 | A |
| I-87 | A | I-107 | A | I-127 | B | I-147 | A |
| I-88 | A | I-108 | A | I-128 | A | I-148 | A |
| I-89 | A | I-109 | A | I-129 | A | I-149 | A |
| I-90 | A | I-110 | A | I-130 | A | I-150 | A |
| I-91 | A | I-111 | A | I-131 | A | I-151 | B |
| I-92 | A | I-112 | A | I-132 | A | I-152 | A |
| I-93 | A | I-113 | A | I-133 | A | I-153 | A |
| I-94 | A | I-114 | NA | I-134 | A | I-154 | B |
| I-95 | A | I-115 | NA | I-135 | A | I-155 | A |
| I-96 | A | I-116 | A | I-136 | A | I-156 | A |
| I-97 | A | I-117 | A | I-137 | A | I-157 | A |
| I-98 | A | I-118 | A | I-138 | A | I-158 | C |
| I-99 | A | I-119 | A | I-139 | A | I-159 | A |
| I-100 | A | I-120 | A | I-140 | A | I-160 | A |

TABLE 3C

IRAK-4 Activity Inhibition Data Continued

| Cpd # | IRAK-4 | Cpd # | IRAK-4 | Cpd # | IRAK-4 | Cpd # | IRAK-4 |
|---|---|---|---|---|---|---|---|
| I-161 | B | I-182 | A | I-204 | A | I-226 | A |
| I-162 | A | I-183 | A | I-205 | A | I-227 | A |
| I-163 | A | I-184 | A | I-206 | A | I-228 | A |
| I-164 | NA | I-185 | A | I-207 | A | I-229 | A |
| I-165 | NA | I-186 | A | I-208 | A | I-230 | A |
| I-166 | NA | I-187 | A | I-209 | A | I-231 | A |
| I-167 | A | I-188 | A | I-210 | A | I-232 | A |
| I-168 | A | I-190 | C | I-211 | A | I-233 | A |
| I-169 | A | I-192 | A | I-212 | A | I-234 | A |
| I-170 | B | I-193 | A | I-213 | A | I-235 | A |
| I-171 | B | I-194 | A | I-214 | A | I-236 | A |
| I-172 | B | I-195 | B | I-215 | A | I-237 | A |
| I-173 | B | I-196 | B | I-216 | A | I-238 | A |
| I-174 | NA | I-197 | B | I-217 | A | | |
| I-175 | NA | I-198 | C | I-218 | A | | |
| I-176 | NA | I-199 | C | I-219 | A | | |
| I-177 | NA | I-200 | A | I-220 | A | | |
| I-178 | NA | I-201 | A | I-221 | A | | |
| I-179 | NA | I-202 | B | I-222 | A | | |
| I-181 | B | I-203 | A | I-224 | A | | |

Provided compounds were also assayed as inhibitors of IRAK-1. In certain embodiments, a provided compound inhibits IRAK-1 with an $IC_{50} \leq 5$ µM. In some embodiments, a provided compound inhibits IRAK-1 with an $IC_{50}$ of 5-20 µM. In other embodiments, a provided compound inhibits IRAK-1 with an $IC_{50}$ of 20-50 µM.

Provided compounds were also assayed in a panel of 334 kinases and were found to be highly selective for IRAK4. Provided compounds were also assayed for inhibition of IL-1-induced IRAK1 degradation in MRC5 cells, LPS- and R848 (TLR-7 agonist)-induced cytokine expression in human whole blood, and found to be potent inhibitors in those assays.

Provided compounds were also assayed to determine their $K_i$ versus IRAK-4 using a Reaction Biology radioactive kinase assay. Certain compounds of the invention were found to have $K_i$ values ranging from about 1 nM to about 100 nM.

Example 260

Cytokine Production Assay

Provided compounds were also assayed in an LPS (Lipopolysacharide) or R848 (TLR-7 agonist) induced cytokine (TNFα and IL8) production assay in THP-1 cells, human peripheral blood mononuclear cells (hPBMC), and whole blood. The exemplary protocol for this assay in THP-1 cells was as follows below.

THP-1 cells from ATCC (TIB-202) were cultured in RPMI Medium 1640 (Invitrogen, Cat No. A10491-01), 10% fetal bovine serum (Invitrogen, Cat No. 10099141, Lot No. 8172882) containing 100 U/mL Penicillin, 100 µg/mL streptomycin (Invitrogen, Cat No. 15140-122), and 50 uM 2-Mercaptoethanol (Invitrogen, Cat No. 21985023). LPS-EK ultra pure (Invivogen, Cat No. tlrl-peklps) was used to induce IL8 and TNFα production, that was detected in the cell culture supernatant by IL8 HTRF kit (Cisbio, Cat No. 621L8PEB) and TNFα HTRF kit (Cisbio, Cat No. 62TNFPEB), as per manufacturer instructions. Cells were cultured in 96 well assay plates at 100,000 cells per well, and compounds diluted in final 0.3% DMSO were pre-incubated with cells for 1 hour prior to stimulation with 300 ng/mL LPS. Cytokine production in cell supernatant was measured at 5 hours for TNFα and IL8 production, and for 16 hours for IL8 production and assessment of cell viability.

Table 4 shows the activity of selected compounds of this invention in the TNFα and IL8 production assay. The compound numbers correspond to the compound numbers in Table 1. Compounds having an activity designated as "A" provided an $IC_{50} \leq 0.5$ μM; compounds having an activity designated as "B" provided an $IC_{50}$ of 0.5-1.0 μM; compounds having an activity designated as "C" provided an $IC_{50}$ of 1.0-5.0 μM; and compounds having an activity designated as "D" provided an $IC_{50} \geq 5$ μM. "NA" stands for "not assayed."

TABLE 4

TNF and IL8 Production Assay

| Cpd # | TNFα | IL8 |
|---|---|---|
| I-34 | C | C |
| I-40 | C | C |
| I-42 | A | A |
| I-43 | B | B |
| I-44 | B | C |
| I-51 | B | B |
| I-57 | A | A |
| I-65 | B | C |
| I-67 | B | A |
| I-68 | B | A |
| I-71 | B | C |
| I-73 | C | C |
| I-77 | C | B |
| I-79 | C | B |
| I-83 | B | NA |
| I-85 | B | B |
| I-86 | C | NA |
| I-87 | A | A |
| I-88 | C | C |
| I-90 | C | NA |
| I-92 | A | A |
| I-93 | C | C |
| I-94 | D | NA |
| I-100 | C | C |
| I-105 | B | A |
| I-106 | B | B |
| I-108 | C | NA |
| I-109 | B | NA |
| I-110 | B | A |
| I-120 | A | A |
| I-128 | C | B |
| I-135 | B | B |
| I-136 | B | A |
| I-137 | B | B |
| I-142 | A | A |
| I-144 | A | A |
| I-149 | C | C |
| I-168 | D | D |
| I-188 | B | A |
| I-194 | D | C |
| I-204 | B | C |
| I-206 | NA | D |
| I-207 | C | C |
| I-214 | A | A |
| I-215 | B | C |
| I-217 | A | A |
| I-220 | A | A |
| I-222 | D | D |
| I-224 | A | A |
| I-228 | A | A |

TABLE 4-continued

TNF and IL8 Production Assay

| Cpd # | TNFα | IL8 |
|---|---|---|
| I-229 | A | B |
| I-230 | D | D |
| I-231 | C | D |
| I-233 | A | A |
| I-235 | A | A |

Example 261

In Vivo LPS-Induced Model of Cytokine Production

Compounds of the present invention were also evaluated in rats in an in vivo efficacy model for inhibiting LPS-mediated cytokine production. An exemplary protocol for this assay in follows.

Drug to be tested was formulated in 10% HP-β-CD in saline for i.p. injection. Male Wistar rats (180-220 g) were divided into 8 groups; every group except naive group had 10 rats at random as follows, and the rats in all group (group A to H) were fasted overnight.

| Group | number | treatment | Measurement |
|---|---|---|---|
| A) Naive | 5 | Vehicle I.P. + 30 min later PBS i.v. + 1 h later blood + 1 h later blood | Rat TNF-α |
| B) Model | 10 | Vehicle I.P. + 30 min later LPS i.v. + 1 h later blood + 1 h later blood | Rat TNF-α |
| C) dexamethasone | 10 | 5 mg/kg dexamethasone I.P. + 30 min later LPS i.v. + 1 h later blood + 1 h later blood | Rat TNF-α |
| D) 1 mg/kg drug | 10 | 1 mg/kg drug I.P. + 30 min later LPS i.v. + 1 h later blood + 1 h later blood | Rat TNF-α |
| E) 3 mg/kg drug | 10 | 3 mg/kg drug I.P. + 30 min later LPS i.v. + 1 h later blood + 1 h later blood | Rat TNF-α |
| F) 10 mg/kg drug | 10 | 10 mg/kg drug I.P. + 30 min later LPS i.v. + 1 h later blood + 1 h later blood | Rat TNF-α |
| G) 30 mg/kg drug | 10 | 30 mg/kg drug I.P. + 30 min later LPS i.v. + 1 h later blood + 1 h later blood | Rat TNF-α |
| H) 100 mg/kg drug | 10 | 100 mg/kg drug I.P. + 30 min later LPS i.v. + 1 h later blood + 1 h later blood | Rat TNF-α |

Vehicle or drug were dosed i.p. 30 min prior to LPS/PBS challenge. LPS or PBS was injected intravenously through the tail vein as indicated. 1-2 mL of blood were collected at 1 h and 2 h post LPS challenge by retro-orbital puncture by using 5 mL tube coated with heparin saline (5 Uml/1). Collected plasma and freezed it at −80° C. until TNF-α is analyzed by ELISA. LC/MS bioanalysis for drug exposure was performed for a total of 150 samples for each assay.

Example 262

In Vitro LPS/R848/CpG-Induced Cytokine Production Assays in hPBMC or Whole Blood Compounds of the present invention were also studied in in vitro LPS/R848/CpG-induced cytokine production assays. Exemplary protocols follow.

Whole Blood (LPS): 13 mL of whole blood solution was prepared by combining whole blood in no serum medium with a ratio of 1:1. Cells were seeded in a 96-well plate with 130 ul/well of the cell suspension according to the plate map. 9 ul of 30 mM compound solution was added into the wells in the assigned rows, then serial solutions with 4× dilutions were made. That is, add 9 uL of 100% DMSO into each of the rest wells and take 3 uL of compound solution from the one-step higher concentration solution and mix well with the DMSO. For the second compound master plate, 196 uL of the growth medium (no serum media) were added into each of the wells and 4 uL of the compound solution from the first compound master plate was added and mixed with the media. Cells were treated for 0.5 h by adding 20 uL of the compound and the control solutions prepared in the second master plate to each well according to the plate map. Cells were stimulated with a) 0.1 ug/mL of LPS overnight for whole blood assay; b) 0.01 ug/mL of LPS overnight for PBMC assay. Plates were sealed with sealing films and the plates were centrifuged at 3000 rpm at 4 degrees C. for 5 min. The supernatants were transferred, and 100 ul of working Capture antibody solution was added to each well. The plates were sealed and incubated overnight at RT. IL-6, IFN-α or TNF-α detection antibody labeled with biotin: Added 100 uL of the Detection Antibody solution to each well. Covered the plate and incubated for 2 h at RT. Added 100 uL of Streptavidin-HRP solution to each well. Covered the plate and incubate for 20 min at RT in dark. Added 100 uL of Substrate Solution to each well. Incubated for 20 min at RT in dark. Added 50 uL of Stop Solution to each well. Gently tapped the plate to ensure thorough mixing. Determined the optical density of each well immediately, using a microplate reader set to 450 nm and also read at 540 nm or 570 nm for correction if wavelength correction is not available.

For R848-induced or CpG-induced assays, the same procedure as above was followed except that 1 uM R848 for 20 h for TNF-α production, and for 5 hr for INF-α production in whole blood; 1 uM R848 for 5 h for PBMC cytokine production; or 0.5 uM or 0.1 uM CpG or 1 ng/mL IL-1-β overnight for PBMC cytokine production were used as indicated in Table 5, instead of LPS. Data from the whole blood and hPBMC cytokine production assays is shown in Tables 5a and 5b.

TABLE 5b

Results of in vitro cytokine production assays continued

| Cells | Stimulant | Conc. | Cytokine | Test Compound | | | |
|---|---|---|---|---|---|---|---|
| | | | | 1-220 | 1-224 | 1-233 | 1-235 |
| Whole Blood | LPS | 0.1 ug/mL | TNF-α | D | D | D | D |
| | R848 | 1 uM | TNF-α | D | D | D | D |
| | | | IFN-α | D | D | D | D |

Certain compounds of the invention inhibit ~50% of the LPS induced TNF production in vivo, at average drug concentrations greater than 2 uM and higher.

Example 263

In Vitro Inhibition of Tumor Cell Proliferation Assays

Compounds of the present invention were also studied in in vitro tumor cell proliferation inhibition assays. Exemplary protocols were taken from Ngo et al. "Oncogenically active MYD88 mutations in human lymphoma" Nature (2011) vol. 470, 115-121, the entirety of which is incorporated herein by reference. The exemplary assay protocols follow.

Cell lines were cultured in RPMI 1640 medium supplemented with penicillin/streptomycin and 10% fetal bovine serum or, for the OCI series of cell lines, Iscove's medium with 20% fresh human plasma. Cells were maintained in a humidified, 5% CO2 incubator at 37 uC. All cell lines were engineered to express an ecotropic retroviral receptor and the bacterial tetracycline repressor.

DLBCL cell lines (GCB DLBCL: HT, OCI-LY8, OCI-LY19; ABC DLBCL: HLY1, HBL[1], TMD8, OCI-LY3, OCI-LY10, U2932, SUDHL[2], DLBCL2) were plated in duplicate at a density of 50,000 cells per well in 96-well plates along with DMSO as negative control, or different concentrations of each compound of the invention. Cell viability at 1, 2 and 3 days after drug treatment was assayed by adding 3-(4,5-dimethylthiazol-2-yl)-5-(3-carboxymethoxyphenyl)-2-(4-sulphophenyl)-2H-tetrazolium and an electron coupling reagent (phenazine methosulphate; Promega), incubated for TABLE 5a Results of in vitro cytokine production assays

| Cells | Stimulant | Conc. | Cytokine | Test Compound | | | | | |
|---|---|---|---|---|---|---|---|---|---|
| | | | | I-67 | I-92 | I-73 | I-85 | I-105 | I-79 |
| Whole Blood | LPS | 0.1 ug/mL | TNF-α | | C | D | D | D | D |
| | | | IL-6 | A | A | ND | ND | ND | D |
| | R848 | 1 uM | TNF-α | C | C | ND | ND | ND | ND |
| | | | IFN-α | D | C | ND | ND | ND | ND |
| hPBMC | LPS | 0.01 ug/mL | TNF-α | B | A | ND | ND | ND | D |
| | | | IL-6 | A | A | ND | ND | ND | D |
| | R848 | 1 uM | TNF-α | C | A | ND | ND | ND | ND |
| | CpG | 0.5 uM | TNF-α | B | A | ND | ND | ND | ND |
| | | 0.1 uM | IFN-α | C | B | ND | ND | ND | ND |
| | IL-1β | 1 ng/mL | IL-6 | B | A | ND | ND | ND | ND |

Compounds having an activity designated as "A" provided an $IC_{50} \leq 0.25$ μM;
compounds having an activity designated as "B" provided an $IC_{50}$ of 0.25-0.5 μM;
compounds having an activity designated as "C" provided an $IC_{50}$ of 0.5-1.0 μM;
and compounds having an activity designated as "D" provided an $IC_{50} \geq 1.0$ μM.

3 h and measured by the amount of 490 nm absorbance using a 96-well plate reader. The presented data were derived from 3 days of drug treatment. The assay was performed twice. Results of the cell proliferation assay are shown in FIGS. 1A, 1B, 2, 3, 4, and 5.

Example 264

In Vitro Inhibition of NFκB Activity in ABC DLBCL Cells

Compounds of the present invention were also assayed for their ability to inhibit NFκB activity. The protocol of Ngo, et al. (supra) was followed. HBL[1] cells retrovirally expressing MYD88-GFP constructs were transduced with lentiviral particles containing a NF-kB firefly luciferase reporter construct by following the manufacturer's instructions (SA Biosciences). Firefly luciferase activity was measured using the Dual-Luciferase Reporter Assay System (Promega) following the manufacturer's instructions. Luminescence from equivalent amounts of lysate was read in triplicate on a Microtiter Plate Luminometer (Dyn-Ex Technologies). All readings were normalized to the mean fluorescence intensity of MYD88-GFP expression for each MYD88 mutant as determined by FACS analysis on a FACScalibur flow cytometer (Becton Dickinson). Results of the NFκB activity inhibition assay are depicted in FIG. 6.

Example 265

Inhibition of IκBα Phosphorylation & Degradation in ABC DLBCL Cells

Compounds of the present invention were also assayed to determine their ability to inhibit phosphorylation and degradation of IκBα. An exemplary procedure follows. ABC DLBCL (HBL1) cells were treated with 10 uM compounds of the invention for 3 hours, and cell lysates were separated by gel electrophoresis, then subjected to Western blotting on nitrocellulose to determine the degree of phosphorylation of IκBα. Result of this assay are depicted in FIG. 7.

Example 266

Sensitization of ABC DLBCL and GCB DLBCL Cells to IRAK Anti-Proliferative Effects Following BTK Knockdown Compounds of the present invention were also assayed to determine their ability to synergistically inhibit cell proliferation in BTK knockdown cells. ABC DLBCL (HBL[1], TMD8, OCI-Ly10) and GCB DLBCL (OCI-Ly19, BJAB) cell lines were subjected to a BTK shRNA knockdown per the procedure of Ngo, et al. (supra). Following selection of transformed cells induction and regrowth, each cell line was then treated with a 5 uM concentration of a compound of the invention. The percentage of viable GFP+ cells was plotted against the number of days post-shRNA induction to determine the degree of synergistic effect of BTK knockdown and IRAK inhibition present in each cell line. The results of the BTK knockdown experiments are depicted in FIGS. 8, 9, and 10.

Example 267

In Vivo Murine IMQ-Induced Psoriasis Model

Compounds of the present invention were also evaluated in mice in an in vivo efficacy model for inhibiting Imiquimod-induced psoriasis. An exemplary protocol for this assay follows.

Psoriasis was induced in Balb/c mice by application of imiquimod (IMQ). Dosing began on day 0 following IMQ application, with the mice receiving an intraperitoneal injection of either I-67 or I-92 twice a day at the doses indicated in FIG. 11. The animals were scored for clinical symptoms on day 1, and days 5 to 10.

IRAK4 inhibitors are efficacious in the Balb/c mouse model of IMQ-induced psoriasis. Results of the study are presented in FIG. 11, in which the degree of skin scaling is shown in photographs of representative mice. IRAK4 inhibition helps to resolve psoriatic skin with an efficaciousness comparable to dexamethasone ('Dex' in FIG. 11). FIG. 12 presents the averages of clinical scores for days 5, 8 and 10.

Example 268

In Vivo Murine Air Pouch Model of Human Gout

Compounds of the present invention were also evaluated in mice in an in vivo efficacy model for inhibiting monosodium urate (MSU) induced model of gout. An exemplary protocol for this assay follows.

A sterile air pouch was created in Balb/c mice. I-67 was administered orally to the mice twice a day for six days at doses of either 10, 30 or 100 mg/kg. Following the last dose the mice were anesthetized and the air pouch was injected with a suspension of monosodium urate (MSU) to induce the inflammatory response. Four hours after the injection the air pouch exudate was collected and the number of white blood cells was measured.

An IRAK4 inhibitor is efficacious in the Balb/c mouse model of MSU-induced gout. Results of the study are presented in FIG. 13, which shows the distribution of white blood cell counts for mice dosed with I-67 as described above.

Example 269

In Vivo Murine Collagen-Induced Arthritis Model

Compounds of the present invention were also evaluated in mice in an in vivo efficacy model for inhibiting IRAK4-mediated arthritis. An exemplary protocol for this assay follows.

Male DBA mice were immunized with collagen on day 0 and day 21 and randomly enrolled into groups upon onset of disease. The groups consisted of a naïve control group, a vehicle control group, a group injected intraperitoneally with dexamethasone at 0.1 mg/kg twice a day, a group injected intraperitoneally with I-92 at 30 mg/kg twice a day, a group injected intraperitoneally with I-67 at 30 mg/kg twice a day and two groups dosed orally with I-67 at 30 mg/kg, one once day and the other twice a day. Eight mice were enrolled per group with the exception of the naïve control group, which contained four mice. Day 1 was designated as the first treatment day, and mice were evaluated daily for clinical scores until day 11. The mice were weighed on alternating days.

IRAK4 inhibitors are efficacious in the DBA mouse model of collagen-induced arthritis. Results of the study are presented in FIG. 14A-B. FIG. 14A presents the average clinical scores of the groups dosed intraperitoneally. The left panels show the average clinical scores for each group of mice up to day 11. The middle panels show the average clinical scores calculated as the area under the curve, and % inhibition relative to the vehicle is indicated in the bar graph. The right panels show the average body weight changes from day 1 to day 11. The clinical scores indicate that I-67 and I-92 are efficacious compared to the vehicle. The vehicle is an aqueous solution containing 10% HPβCD. FIG. 14B presents the average clinical scores of the groups dosed orally with I-67. I-67 dosed orally twice a day was found to be efficacious compared to the vehicle. The vehicle is 0.5% methylcellulose in saline solution, and the dexamethasone and naïve control groups are the same as in A. All groups shown are part of the same study.

Example 270

MyD88-L265P-Induced Phosphorylation Assay

Compounds of the present invention were also evaluated in HBL[1] cells for inhibition of MyD88-L265P-IRAK4-association-mediated phosphorylation of IRAK1, and downstream signaling to TAK1, iκbα and p38. A western blot indicating the degree of phosphorylation of IRAK1, TAK1, iκbα and p38 in the absence and presence of I-67 and I-92 was obtained using the method described in Staudt et al. "Exploiting Synthetic Lethality for the Therapy of ABC Diffuse Large B Cell Lymphoma," Cancer Cell 2012, 21: 723-737

Results of the study are presented in FIG. 15. IRAK4 inhibitors abrogate MyD88-L265P-induced IRAK1, TAK1, iκbα and p38 phosphorylation.

Example 271

NF-κβ Activity Inhibition Assay

Compounds of the present invention were also evaluated in ABC DLBCL cell lines for inhibition of NF-ηβ activity. An NF-κβ-responsive luciferase reporter assay was used following the method described and disclosed in Staudt et al. (2012) and in Ngo et al. "Oncogenically active MYD88 mutations in human lymphoma," Nature 2011, 470 (7332): 115-9, each of which is herein incorporated by reference in its entirety. ABC DLBCL and GCB DLBCL cell lines were created with an NF-ηβ transcriptional reporter by transduction with lentiviral particles containing an inducible NF-κβ-responsive luciferase reporter construct following the method of Staudt et al. (2012) and Ngo et al. (2011). The readout of the results was measured as luciferase activity.

Results of the study are presented in FIG. 16. IRAK4 inhibitors suppress NF-κβ activity in Myd88L265P mut HBL1, TMD8, OCI-Ly3, OCI-Ly10 and to a lesser extent Myd88WT U2932 ABC DLBCL cell lines. There was little to no effect of IRAK4 inhibition on GCB DLBCL cell lines.

Example 272

Cytokine Secretion Assay

Compounds of the present invention were also evaluated in ABC DLBCL cell lines for inhibition of pro-inflammatory cytokine secretion. IL-6- and IL-10-responsive ELISA assays were used following the method described and disclosed in Ngo et al. (2011). Cells transduced with inducible shRNAs were placed in medium containing doxycycline and the concentrations of IL-6 and IL-10 were measured by ELISA, following the method of Ngo et al. (2011). Alternatively, unmanipulated lymphoma cells were placed into fresh media with the addition of I-67 or I-92 and assessed for cytokines as above.

Results of the study are presented in FIG. 17. IRAK4 inhibitors suppress secretion of IL-6 HBL[1], OCI-Ly3 and TMD8 ABC DLBCL cell lines; and IL-10 in HBL[1], OCI-Ly10 and TMD8 ABC DLBCL cell lines.

Example 273

In Vivo Murine Tumor Model of Human ABC DLBCL Lymphoma

Compounds of the present invention were also evaluated in a xenograft tumor model of human ABC DLBCL lymphoma first described and disclosed in Staudt et al. (2012). The tumor was established by subcutaneous injection of OCI-Ly10 cells into immunodeficient (NOD/SCID) mice. Therapy was started with I-92 once tumors reached 200 mm[3]. Tumor growth was monitored by measuring tumor size in two orthogonal directions. The tumor volume was calculated by using the formula (½)(long dimension)×(short dimension).

Results of the in vivo murine tumor model study are presented in FIGS. 18A-B. Compound I-92 reduces ABC lymphoma growth in the xenograft tumor model and is well tolerated by the animals.

Example 274

Cell Viability Assay

Compounds of the present invention were also evaluated in a cell viability assay. ABC DLBCL cell lines were treated with ibrutinib, I-67, I-92 or a combination of ibrutinib with either I-67 or I-92 according to the method reported in Staudt et al. (2012).

Results of the cell viability assay are presented in FIG. 19. Synergistic killing of ABC DLBCL cells was observed with ibrutinib and IRAK4 inhibitors (I-67 or I-92), by targeting B cell receptor and Myd88-mediated signaling.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula XIV:

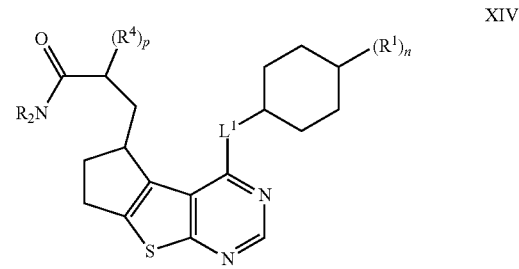

or a pharmaceutically acceptable salt thereof, wherein:
n is 1-2;
each $R^1$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur; or halogen, —CN, —NO₂, —OR, —CH₂OR, —SR, —N(R)₂, —S(O)₂R, —S(O)₂N(R)₂, —S(O)R, —C(O)R, —C(O)OR, —C(O)N(R)₂, —C(O)N(R)—OR, —N(R)C(O)R, —N(R)C(O)N(R)₂, Cy, or —N(R)S(O)₂R; or $R^1$ is selected from one of the following formulas:

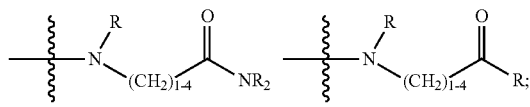

or two R¹ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

p is 0-2;

$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—; and each R⁴ is independently halogen, —CN, —NO₂, —OR, —SR, —N(R)₂, —S(O)₂R, —S(O)₂N(R)₂, —S(O)R, —C(O)R, —C(O)OR, —C(O)N(R)₂, —N(R)C(O)R, —N(R)C(O)N(R)₂, —C(O)N(R)OR, —N(R)C(O)OR, —N(R)S(O)₂N(R)₂, —N(R)S(O)₂R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur.

2. The compound of claim 1, wherein R⁴ is —OH or F, or pharmaceutically acceptable salt thereof.

3. A compound of formula XIX:

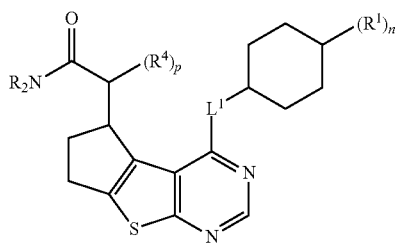

or a pharmaceutically acceptable salt thereof, wherein:

n is 1-2;

each R¹ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur; or halogen, —CN, —NO₂, —OR, —CH₂OR, —SR, —N(R)₂, —S(O)₂R, —S(O)₂N(R)₂, —S(O)R, —C(O)R, —C(O)OR, —C(O)N(R)₂, —C(O)N(R)—OR, —N(R)C(O)OR, —N(R)C(O)N(R)₂, Cy, or —N(R)S(O)₂R; or R¹ is selected from one of the following formulas:

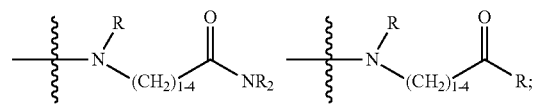

or two R¹ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

p is 0-2;

$L^1$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—; and each R⁴ is independently halogen, —CN, —NO₂, —OR, —SR, —N(R)₂, —S(O)₂R, —S(O)₂N(R)₂, —S(O)R, —C(O)R, —C(O)OR, —C(O)N(R)₂, —N(R)C(O)R, —N(R)C(O)N(R)₂, —C(O)N(R)OR, —N(R)C(O)OR, —N(R)S(O)₂N(R)₂, —N(R)S(O)₂R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur.

4. A compound of formula XXV:

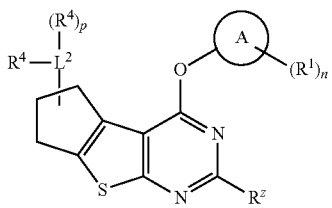

XXV or a pharmaceutically acceptable salt thereof, wherein:

Ring A is a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

n is 1-4;

each $R^1$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur; or halogen, —CN, —NO$_2$, —OR, —CH$_2$OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, Cy, or —N(R)S(O)$_2$R; or $R^1$ is selected from one of the following formulas:

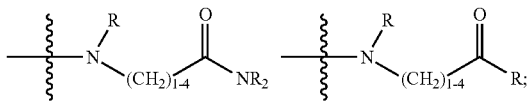

or two $R^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

p is 0-2;

$R^z$ is —R, —CN, —NO$_2$, halogen, —C(O)N(R)$_2$, —C(O)OR, —C(O)R, —N(R)C(O)OR, —N(R)C(O)N(R)$_2$, —OR, or —S(O)$_2$N(R)$_2$;

$L^2$ is a covalent bond or a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; and each $R^4$ is independently halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —N(R)C(O)R, —N(R)C(O)N(R)$_2$, —C(O)N(R)OR, —N(R)C(O)OR, —N(R)S(O)$_2$N(R)$_2$, —N(R)S(O)$_2$R, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur;

wherein said compound is not:

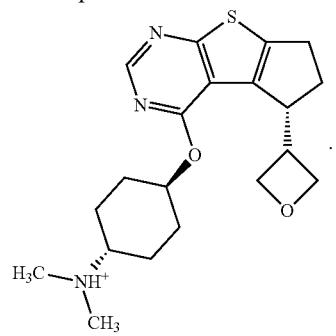

5. The compound of claim 4 of formula XXVI:

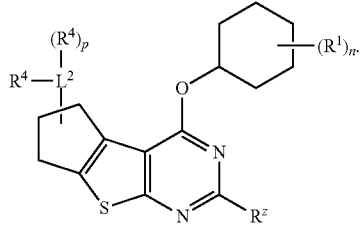

XXVI

6. The compound of claim 4 wherein n is 1, and $R^1$ is —N(R)$_2$ or Cy, or pharmaceutically acceptable salt thereof.

7. The compound of claim 4, wherein n is 1 and $R^1$ is morpholino, or pharmaceutically acceptable salt thereof.

8. The compound of claim 4, wherein n is 1 and $R^1$ is —N(CH$_3$)$_2$, or pharmaceutically acceptable salt thereof.

9. A compound of formula I:

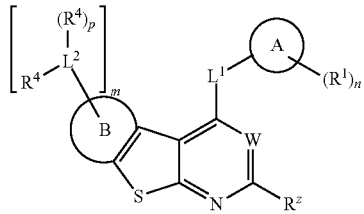

I or a pharmaceutically acceptable salt thereof, wherein:

n is 1;

Ring A is a 1,4-trans-substituted cyclohexyl ring;

each $R^1$ is independently an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur; or halogen, —CN, —NO$_2$, —OR, —CH$_2$OR, —SR, —N(R)$_2$, —S(O)$_2$R, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, Cy, or —N(R)S(O)$_2$R; or R$^1$ is selected from one of the following formulas:

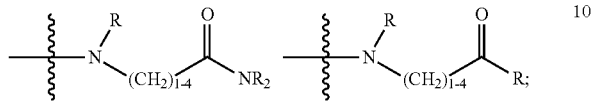

or two R$^1$ groups are taken together with their intervening atoms to form an optionally substituted 4-7 membered fused, spiro-fused, or bridged bicyclic ring having 0-2 heteroatoms independently selected from nitrogen, oxygen, or sulfur;

each Cy is an optionally substituted ring selected from a 3-7 membered saturated or partially unsaturated carbocyclic ring or a 4-7 membered saturated or partially unsaturated heterocyclic ring having 1-3 heteroatoms independently selected from nitrogen, oxygen, or sulfur;

each R is independently hydrogen, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

Ring B is a cyclopento- or cyclohexo-fused ring;
m is 1-2;
p is 0-2;
W is N;
R$^z$ is —R, —CN, —NO$_2$, halogen, —C(O)N(R)$_2$, —C(O)OR, —C(O)R, —N(R)C(O)OR, —N(R)C(O)N(R)$_2$, —OR, or —S(O)$_2$N(R)$_2$;
L$^1$ is —O—;
each L$^2$ is independently a covalent bond or a C$_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;
each R$^4$ is independently halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —N(R)C(O)R, —N(R)C(O)N(R)$_2$, —C(O)N(R)OR, —N(R)C(O)OR, —N(R)S(O)$_2$N(R)$_2$, —N(R)S(O)$_2$R, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two -L$^2$(R$^4$)$_p$—R$^4$ groups are taken together with their intervening atoms to form an optionally substituted 4-7 membered fused, spiro-fused, or bridged bicyclic ring having 0-2 heteroatoms independently selected from nitrogen, oxygen, or sulfur;

wherein said compound is not selected from the group consisting of:

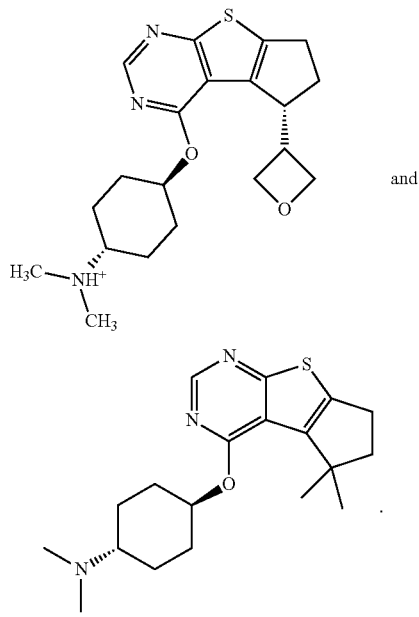

and

10. A compound selected from the following:

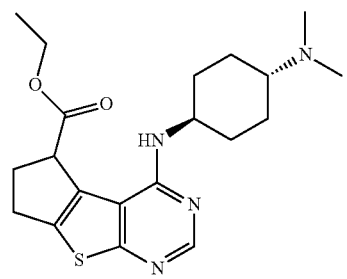

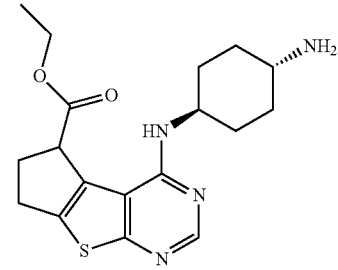

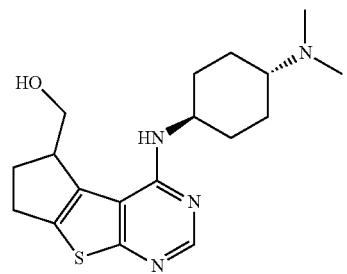

563
-continued
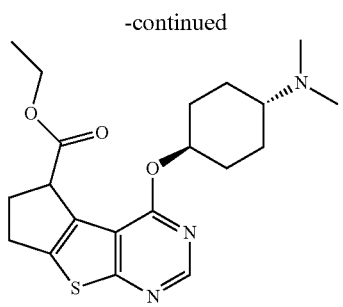
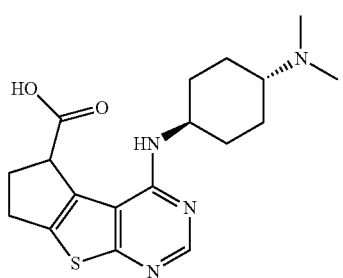
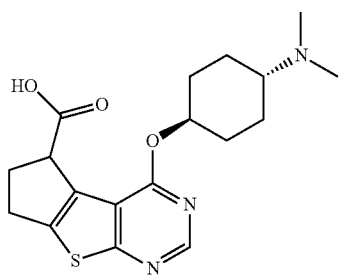
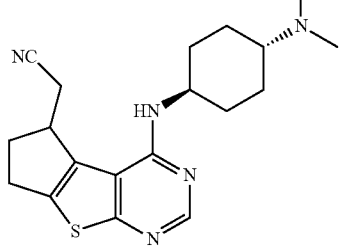
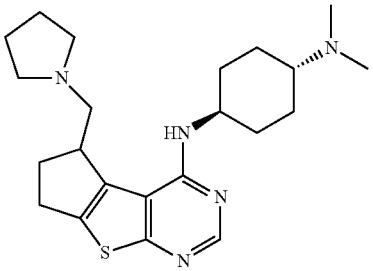
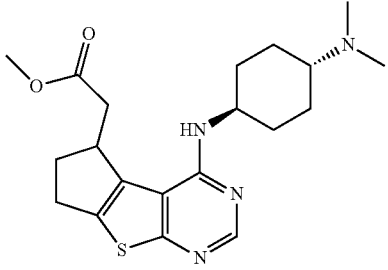
564
-continued
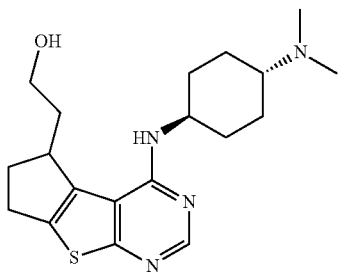
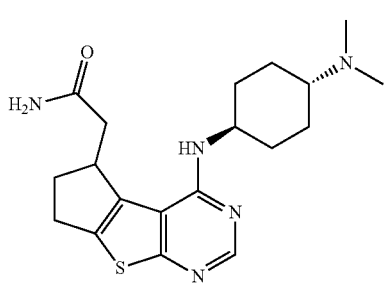
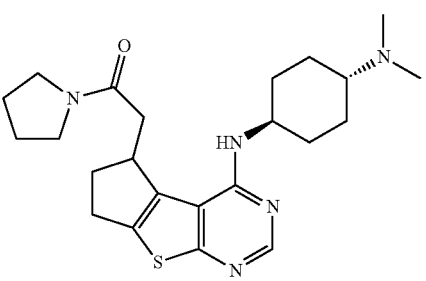
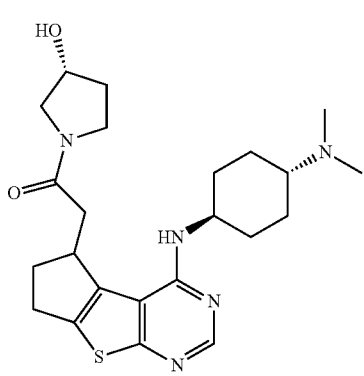
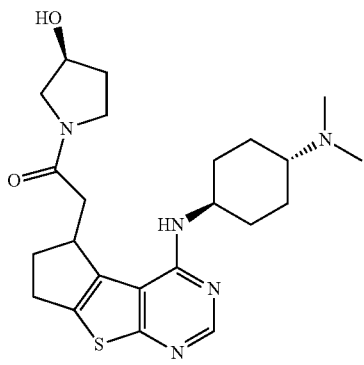

565
-continued
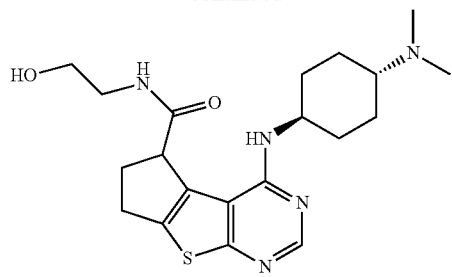
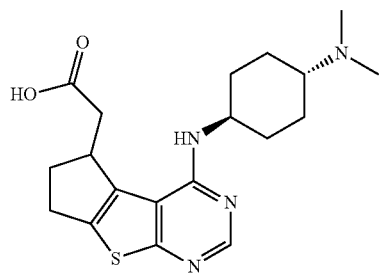
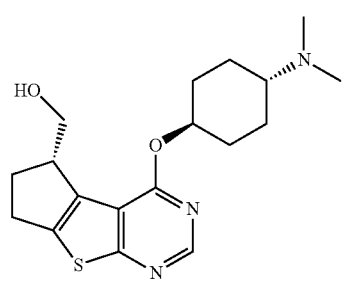
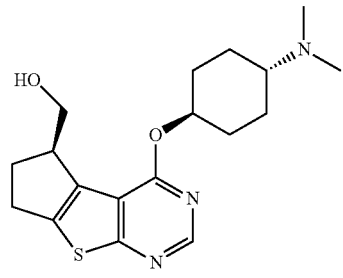
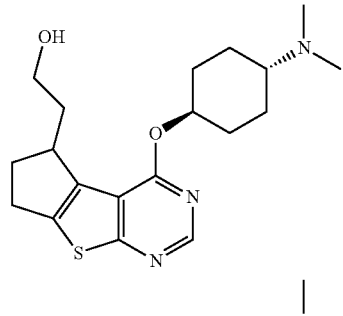
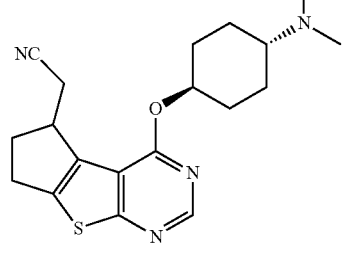
566
-continued
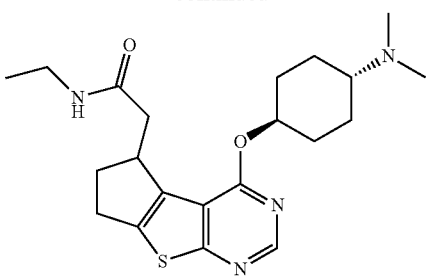
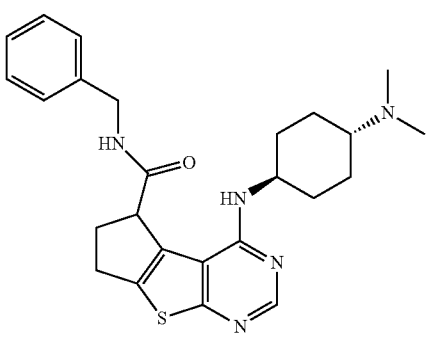
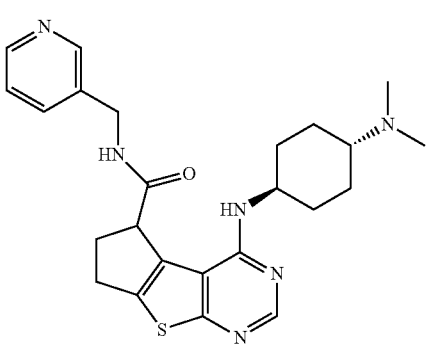
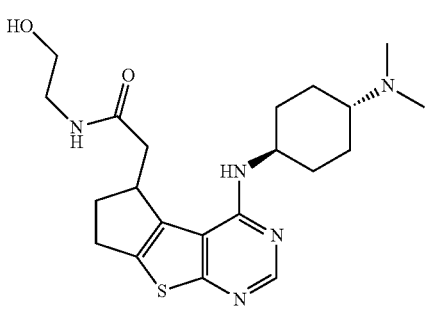
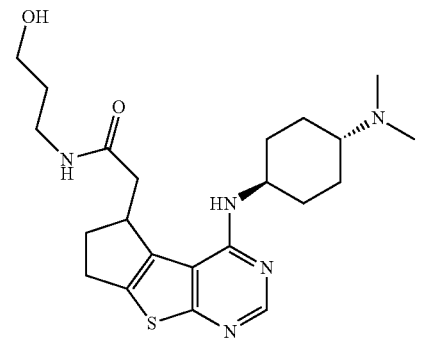

567
-continued
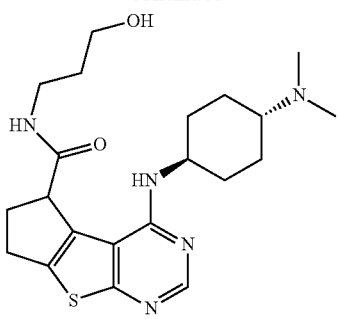
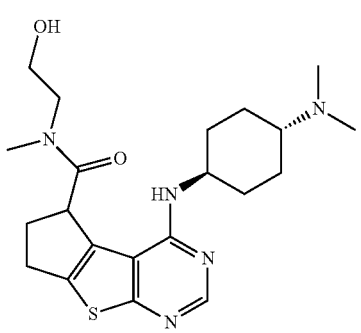
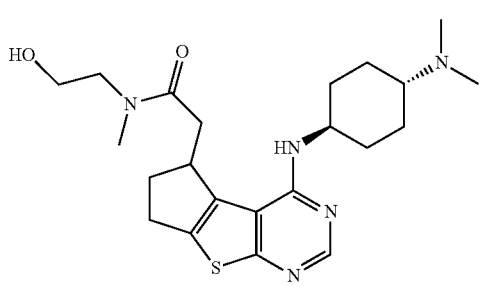
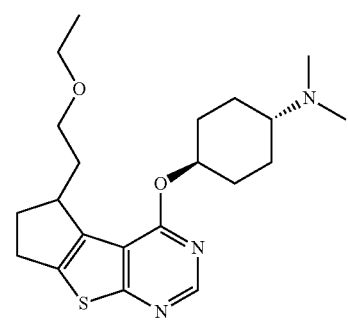
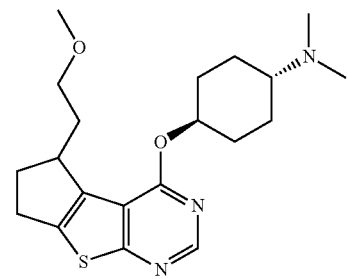
568
-continued
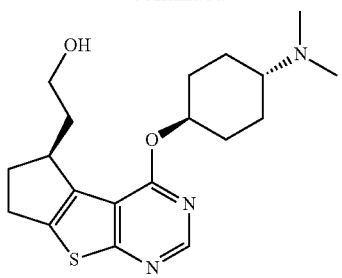
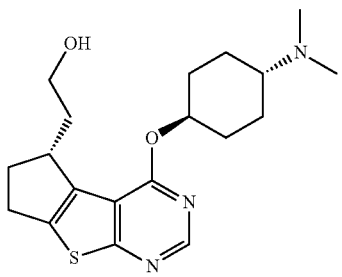
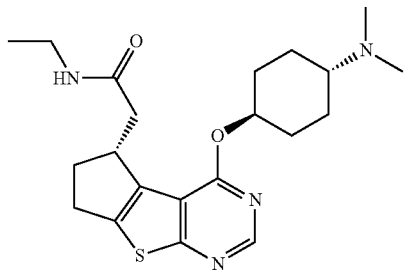
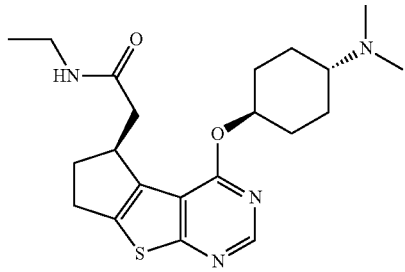
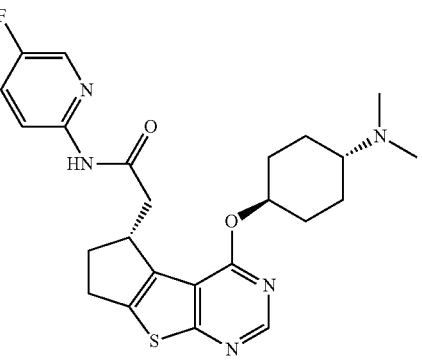

569
-continued
570
-continued
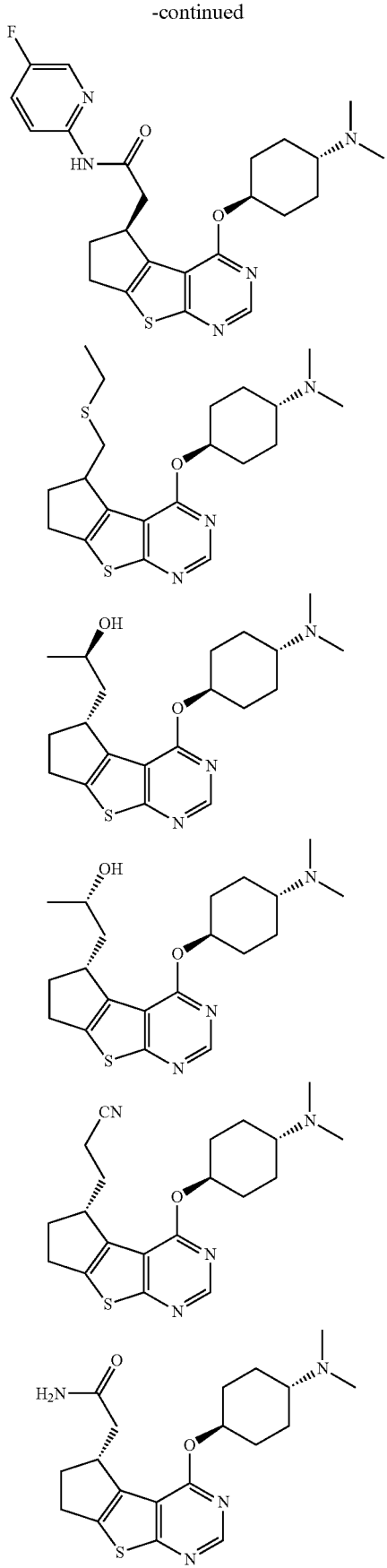
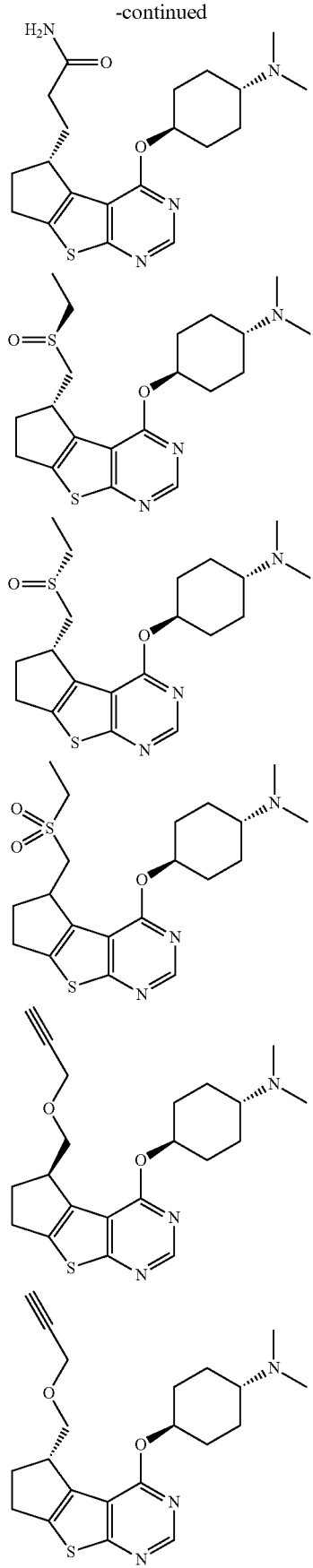

571
-continued
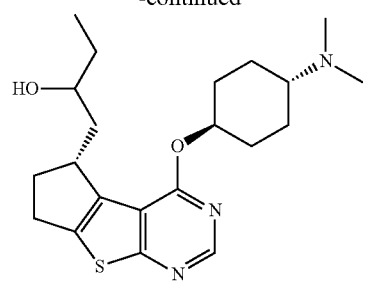
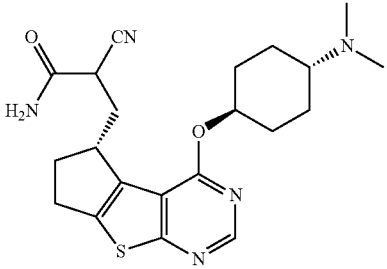
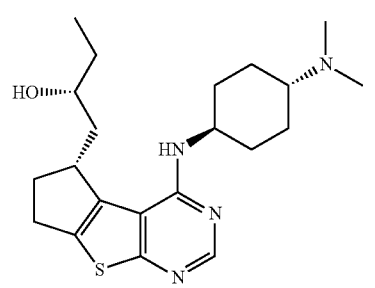
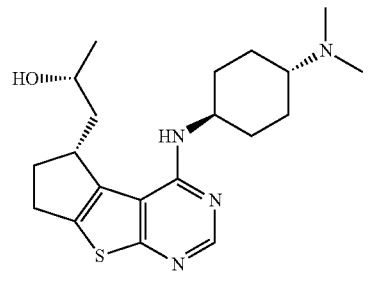
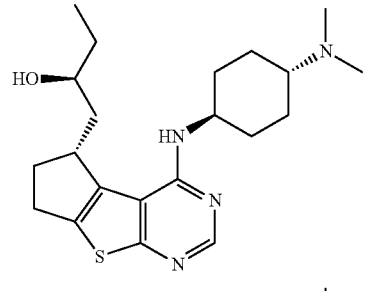
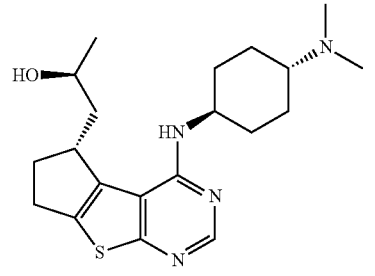
572
-continued
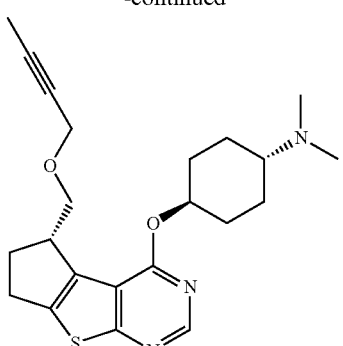
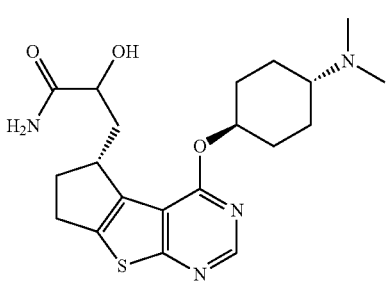
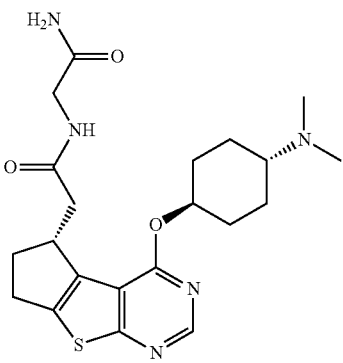
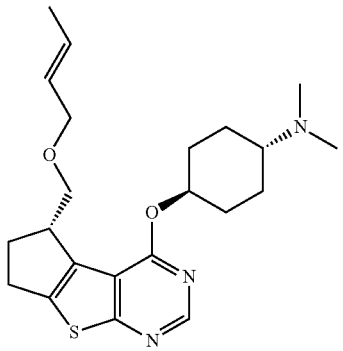
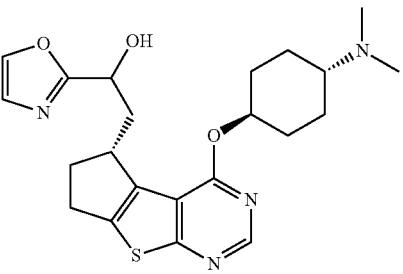

573
-continued
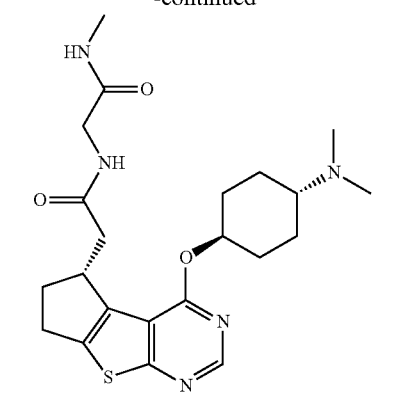
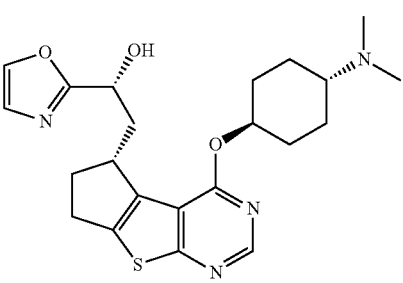
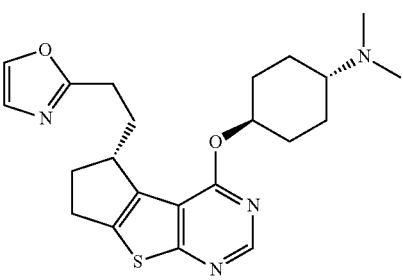
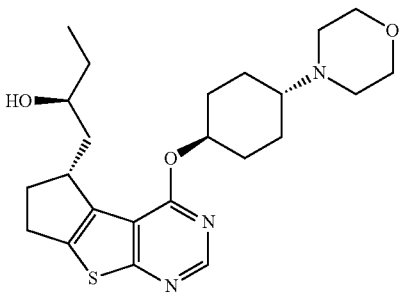
574
-continued
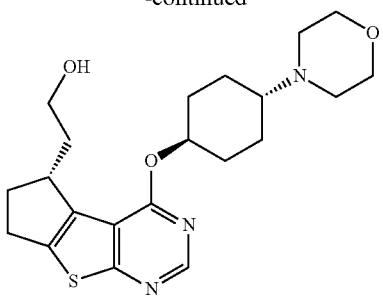
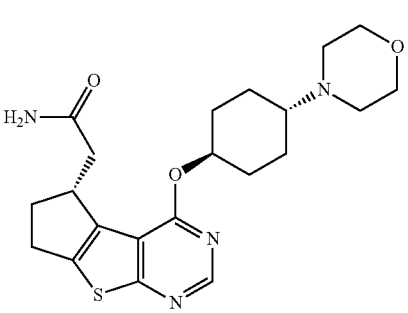
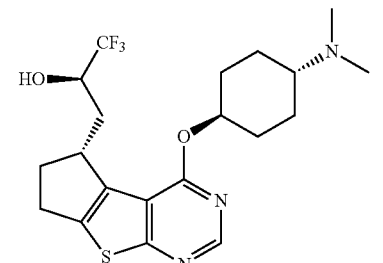
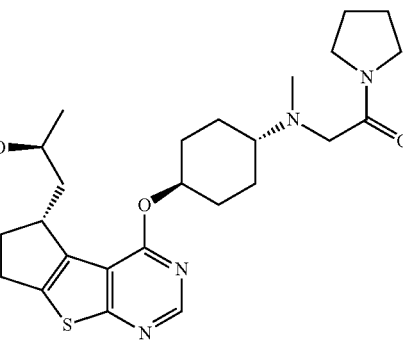
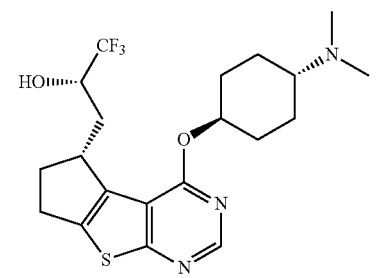

575
-continued
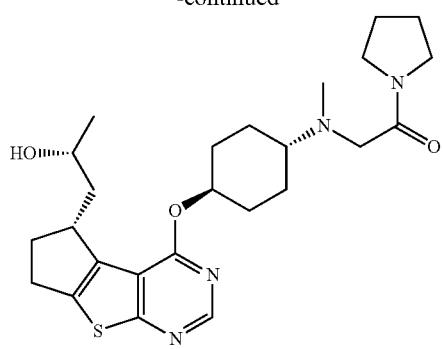
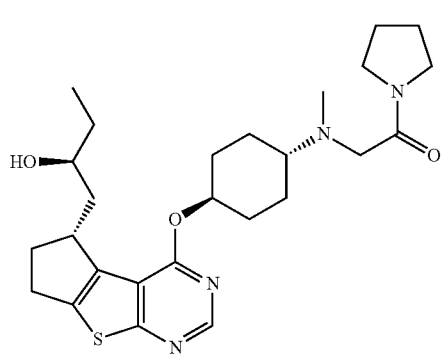
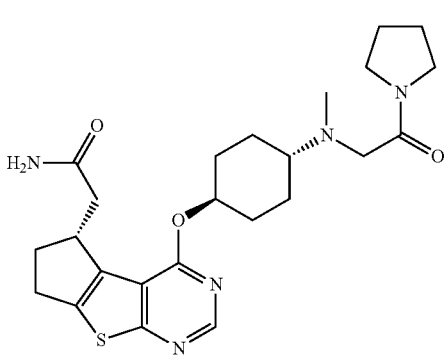
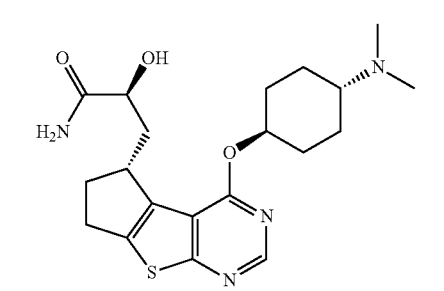
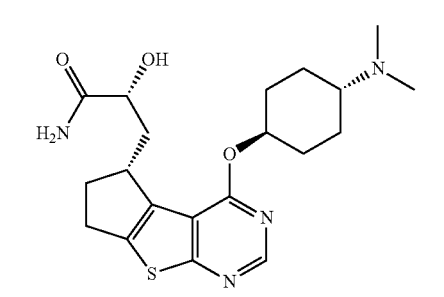
576
-continued
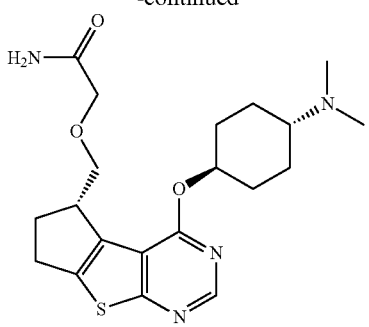
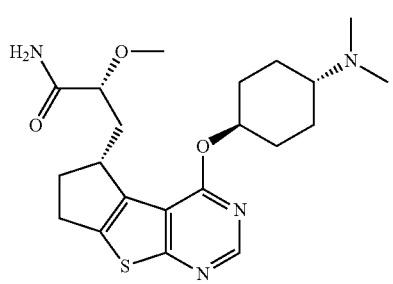
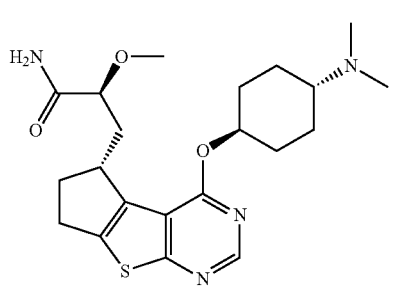
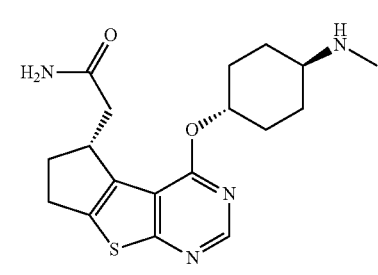
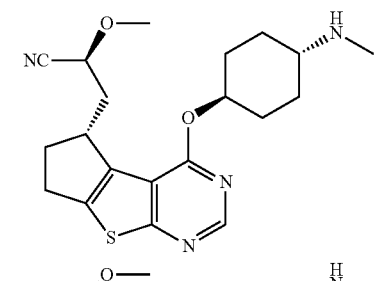
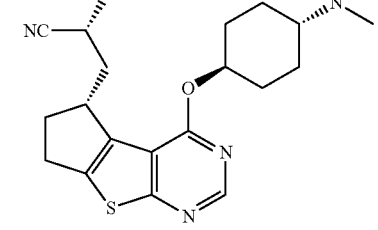

577
-continued
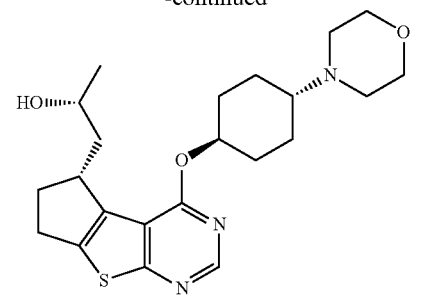
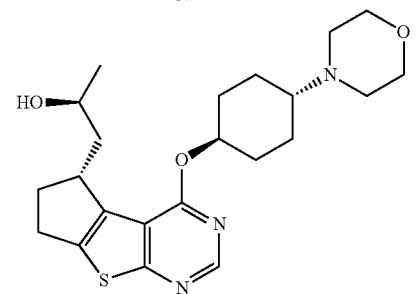
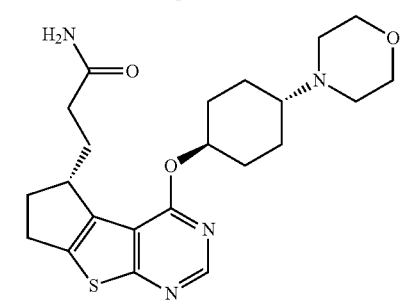
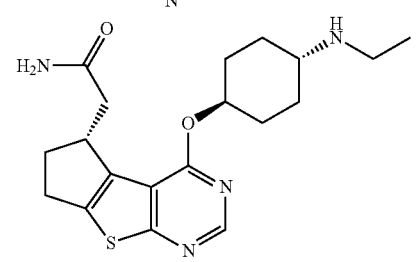
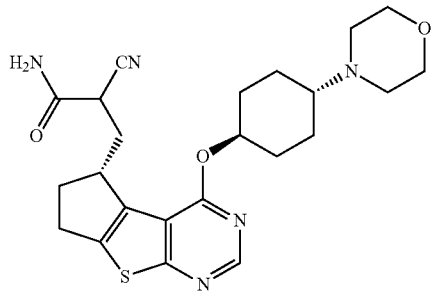
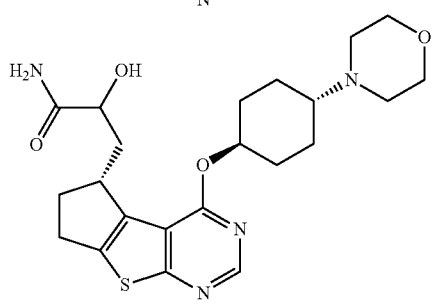
578
-continued
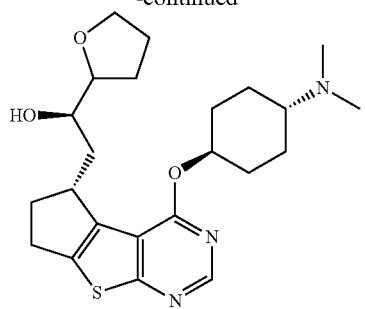
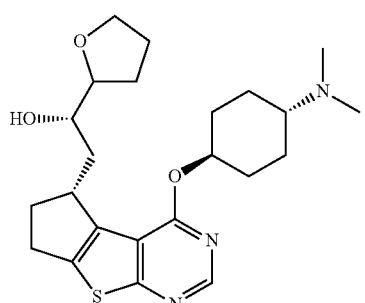
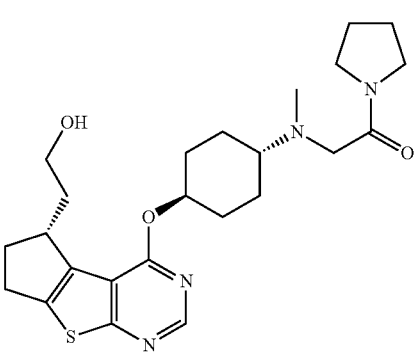
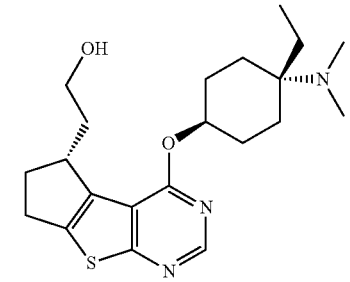
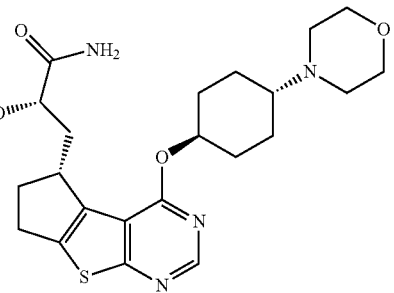

579
-continued
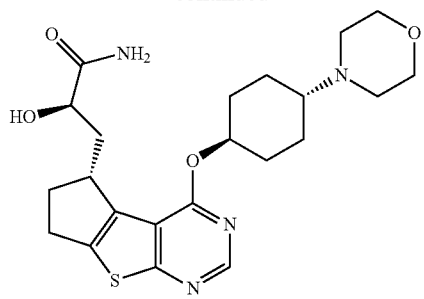
580
-continued
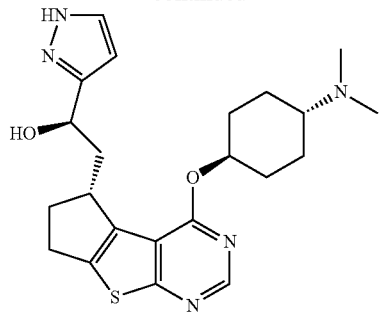
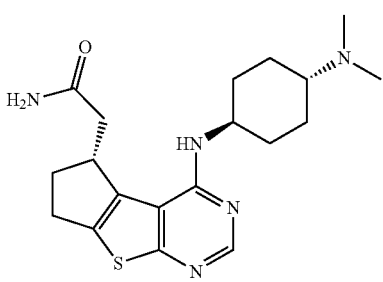
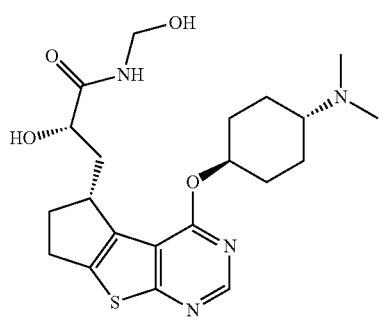
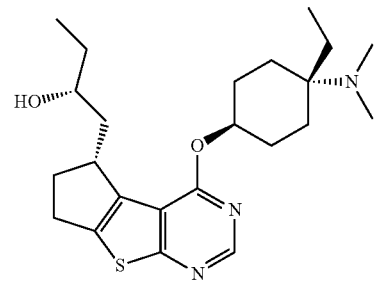
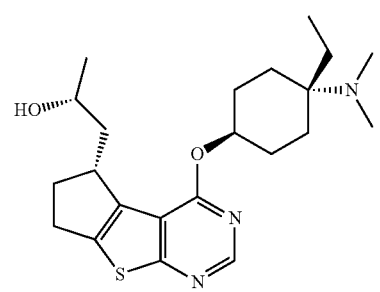

581
-continued
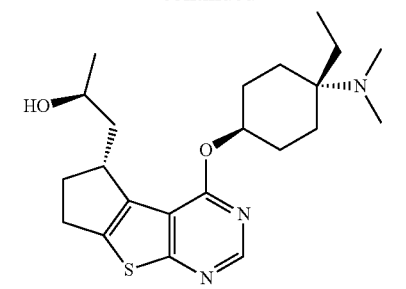
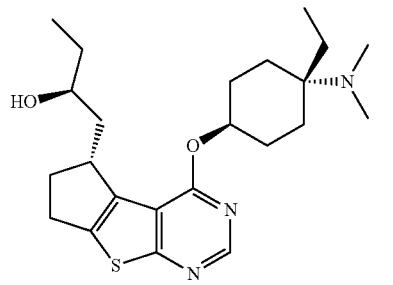
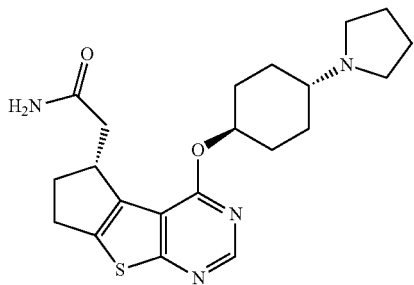
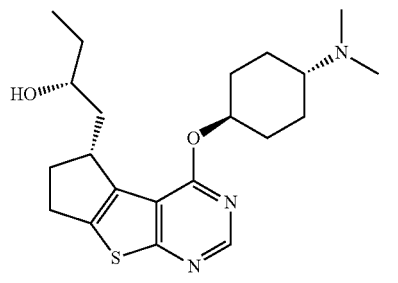
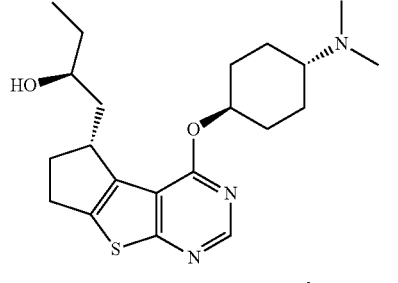
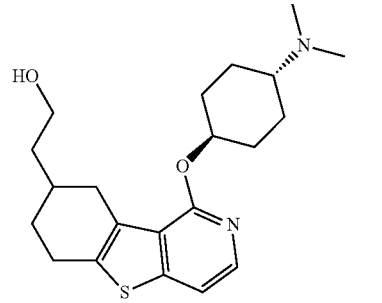
582
-continued
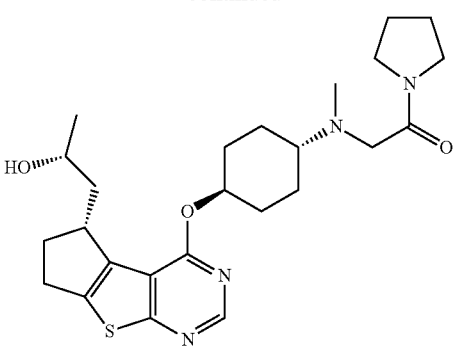
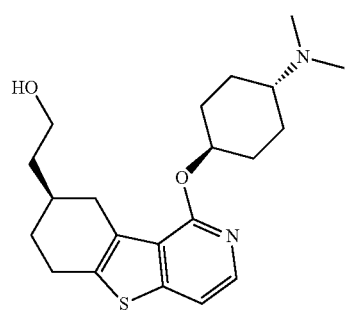
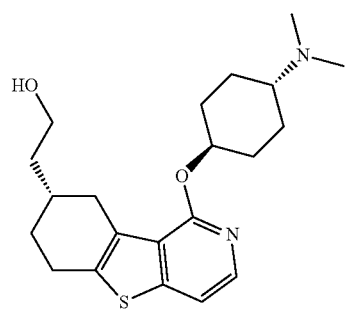
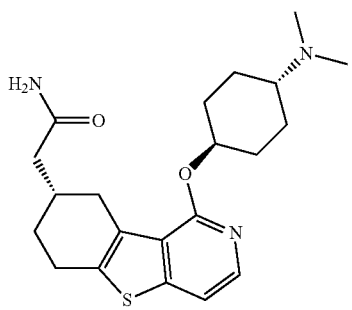
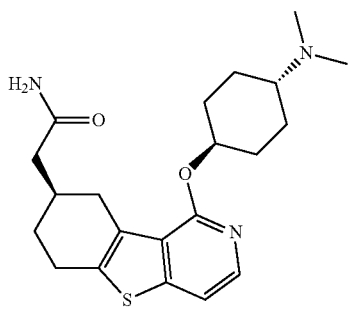

583
-continued
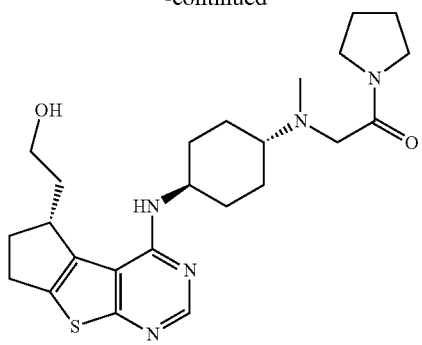
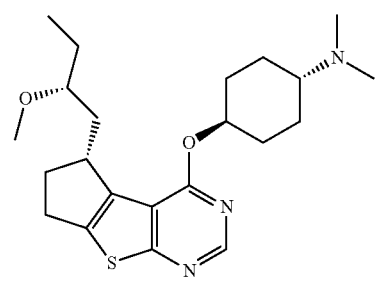
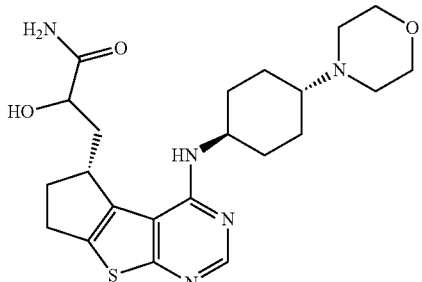
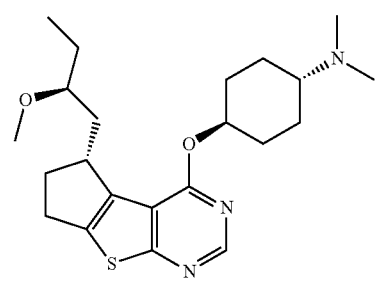
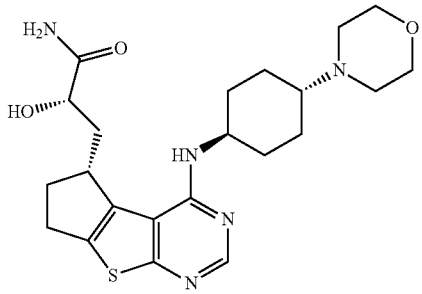
584
-continued
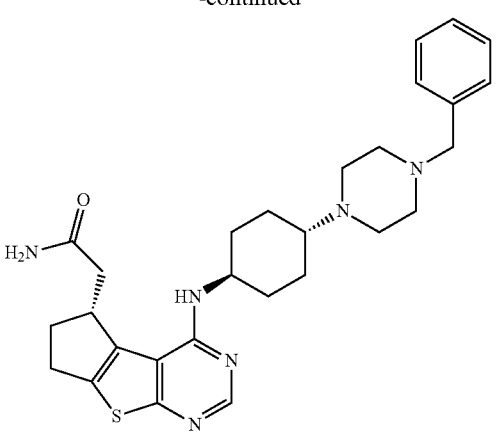
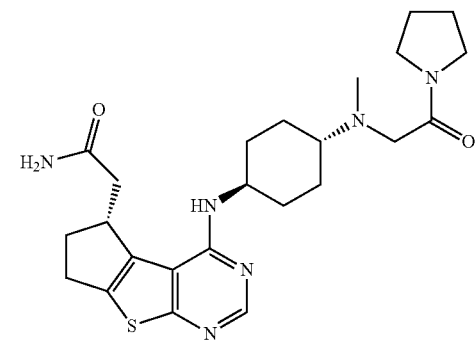
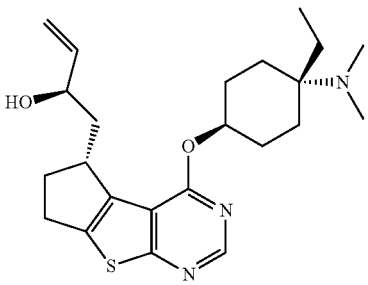
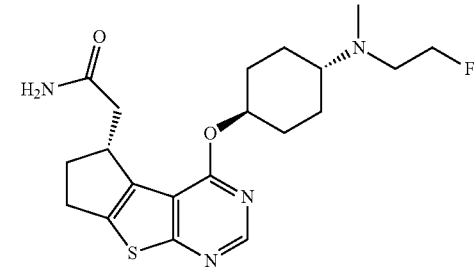
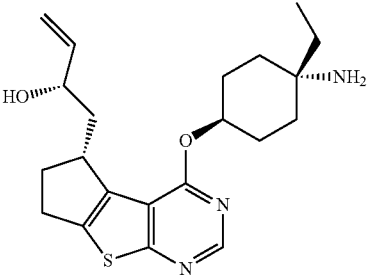

585
-continued
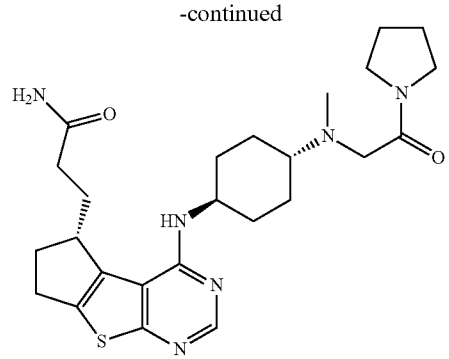
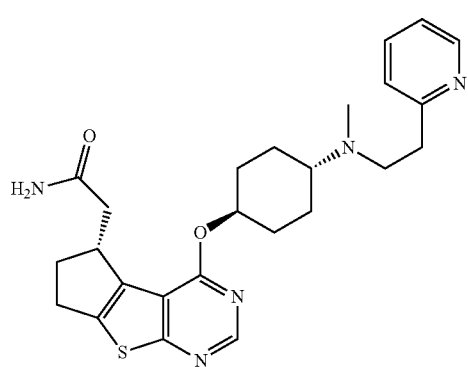
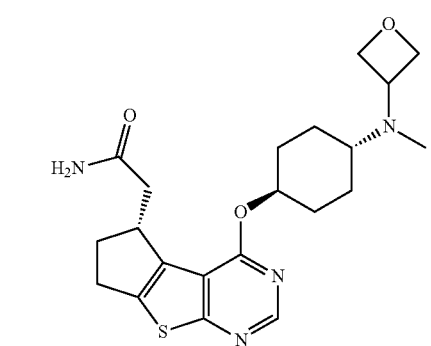
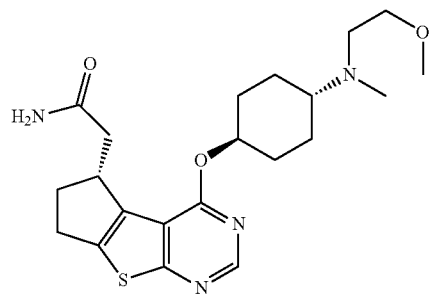
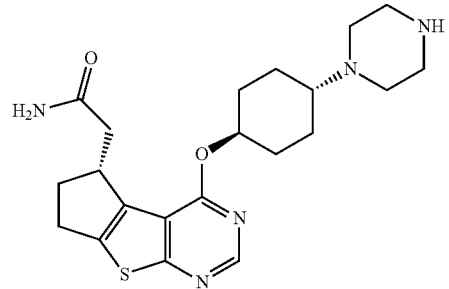
586
-continued
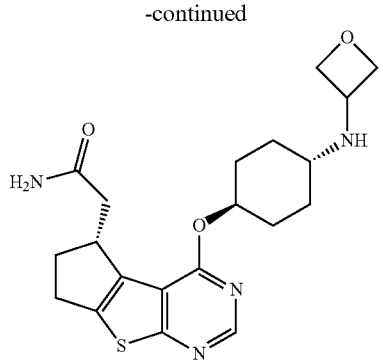
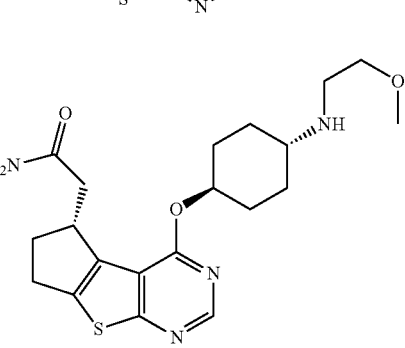
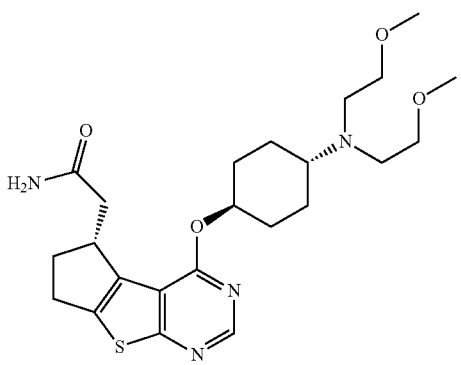
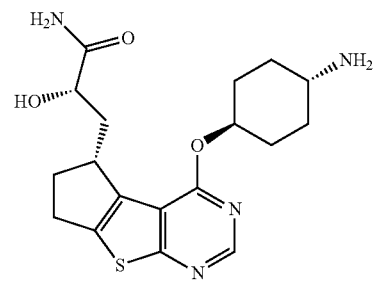
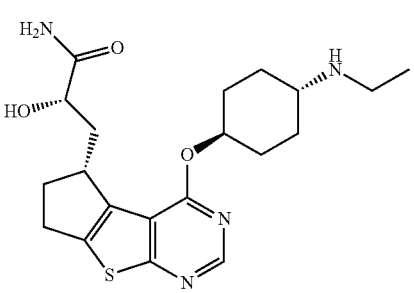

587
-continued
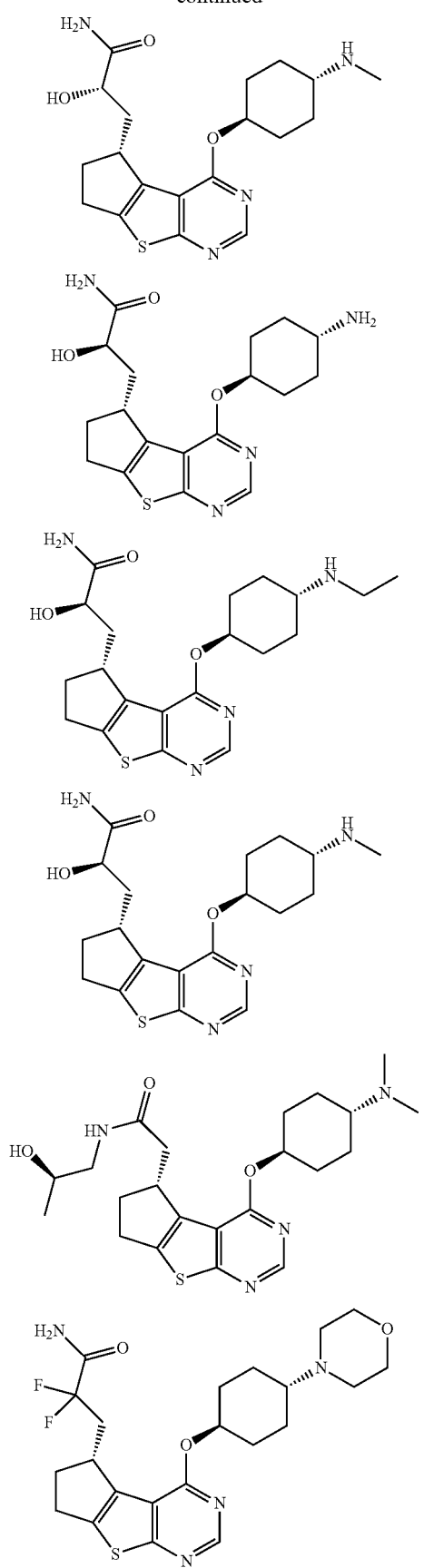
588
-continued
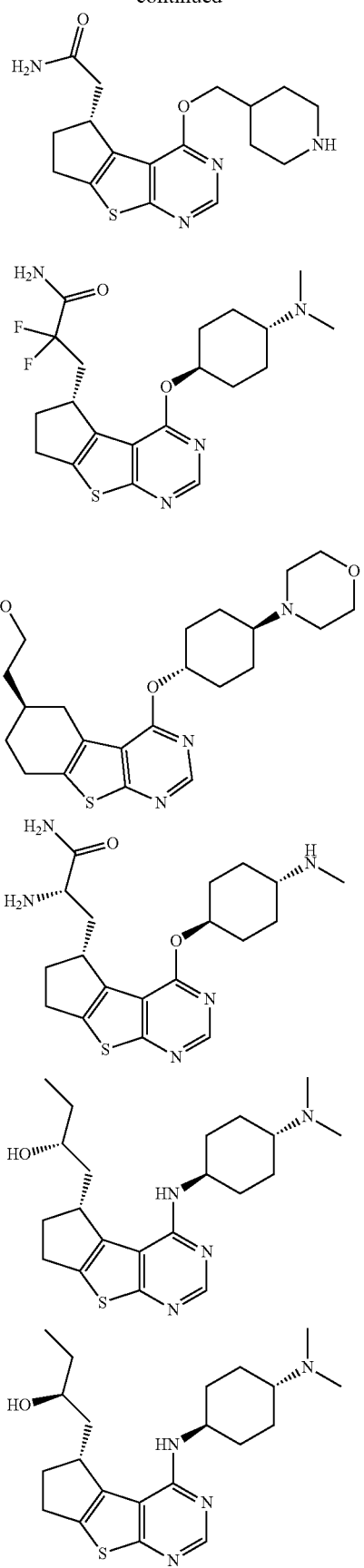

589
-continued
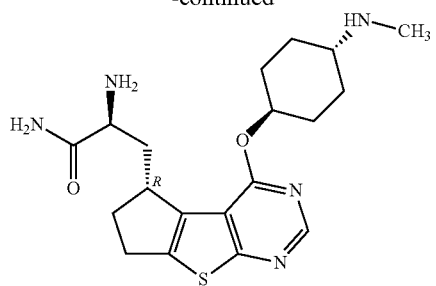
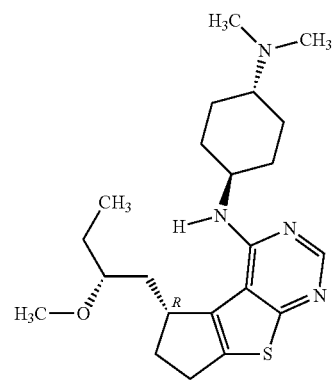
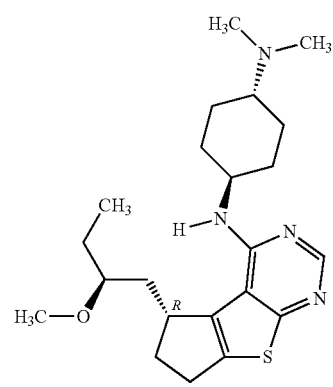
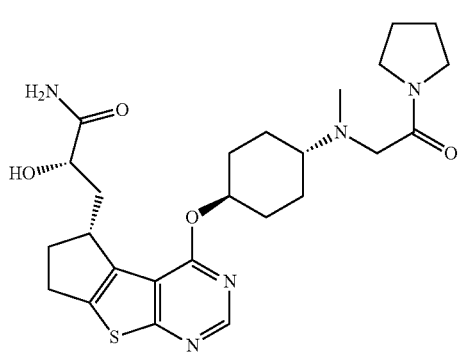
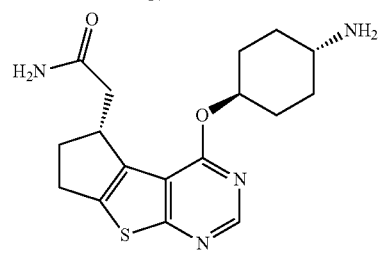
590
-continued
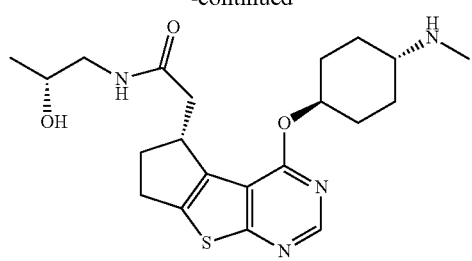
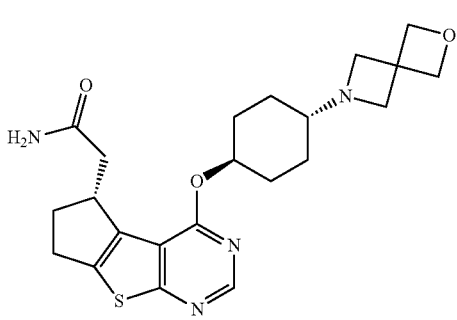
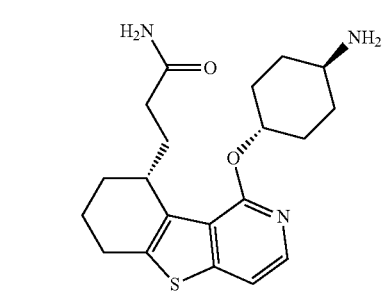
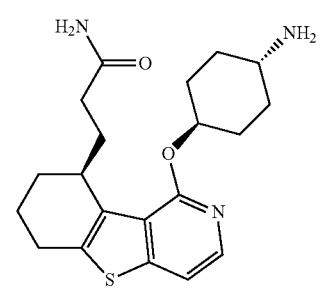
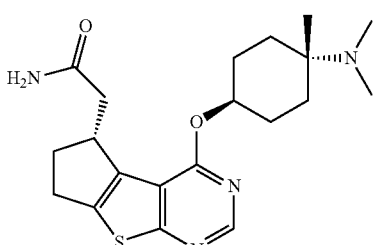
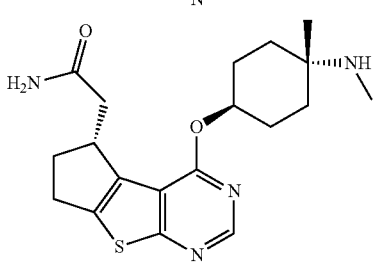

591
-continued
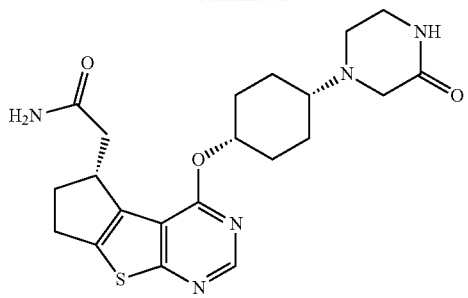
592
-continued
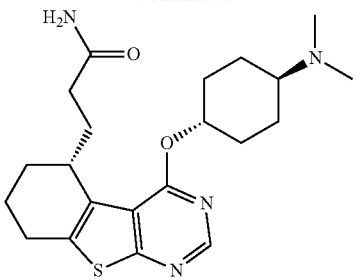
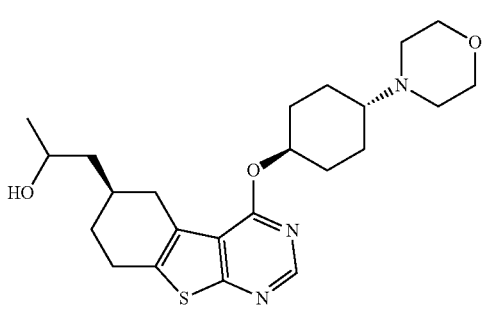
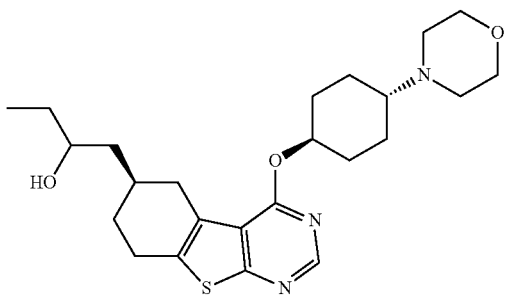
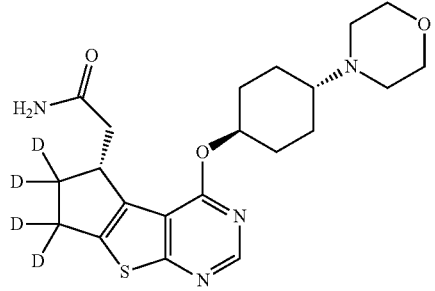
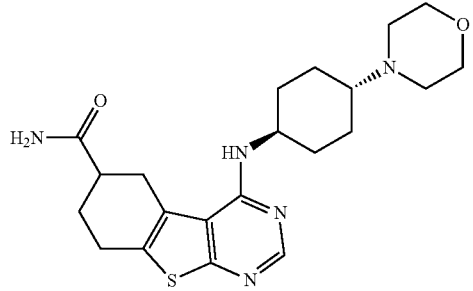

593
-continued
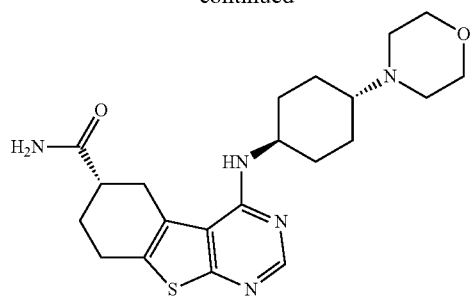
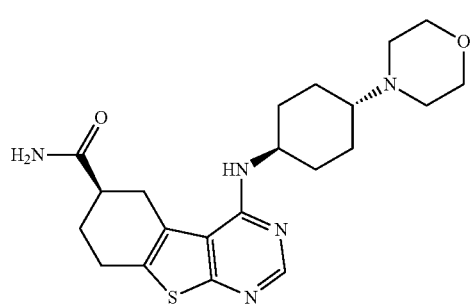
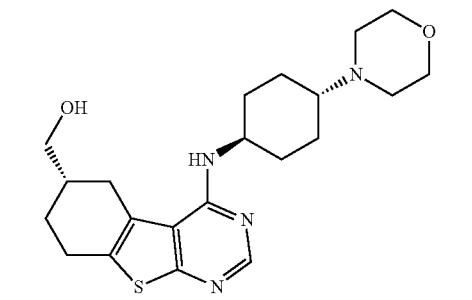
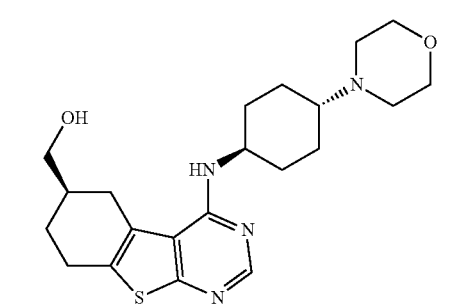
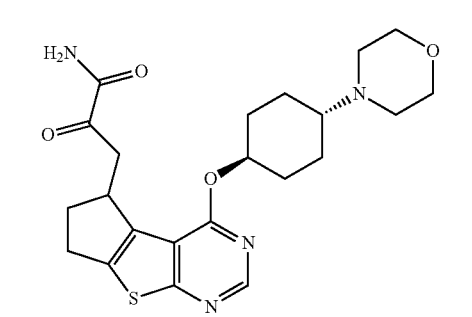
594
-continued
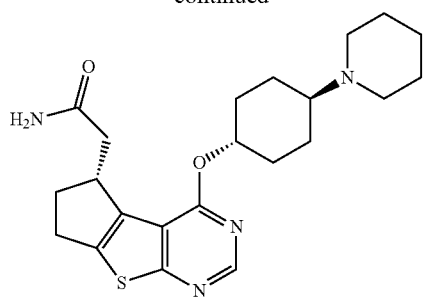
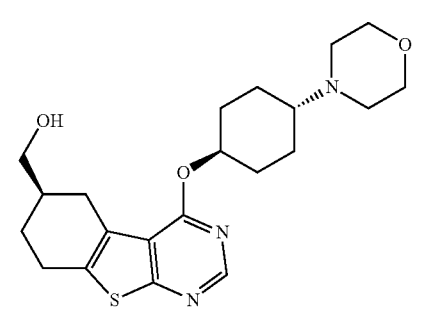
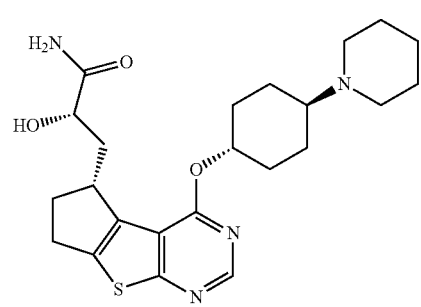
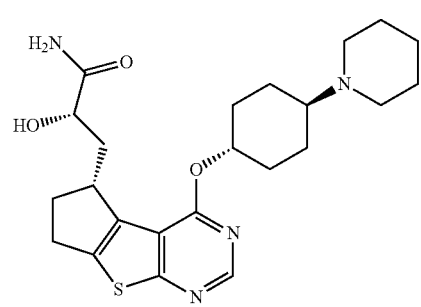
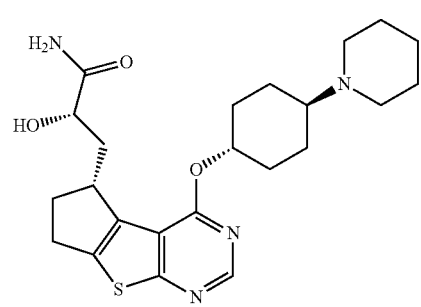

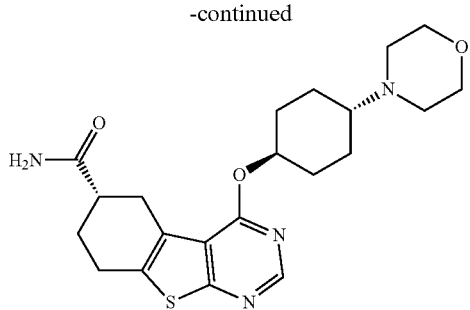
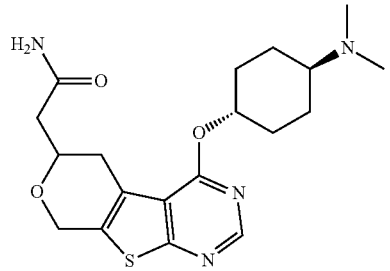
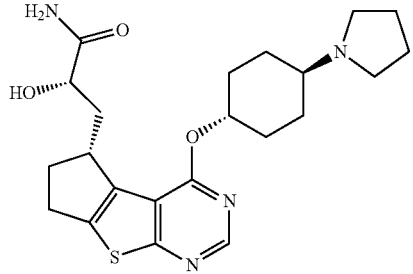
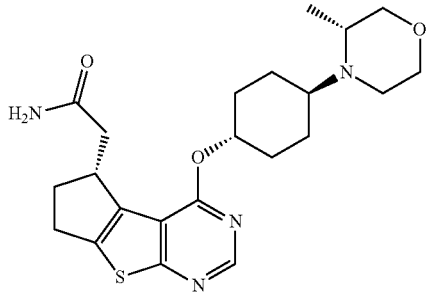
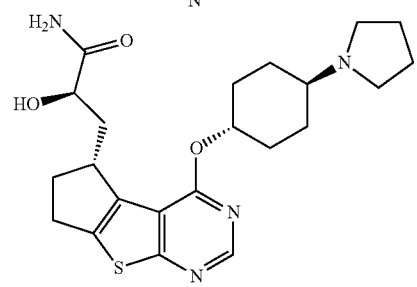
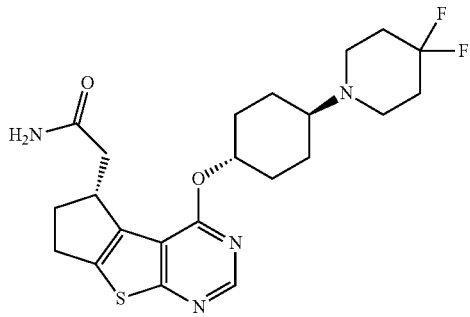
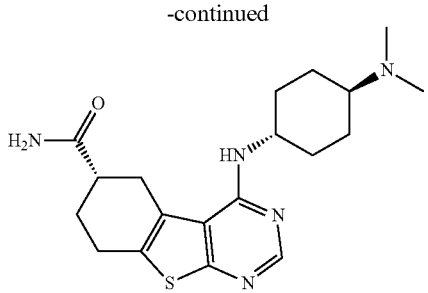
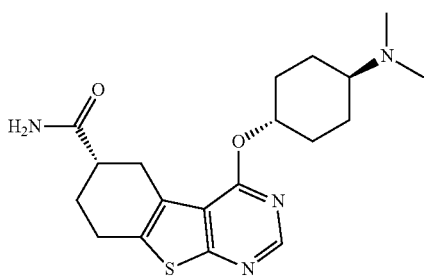
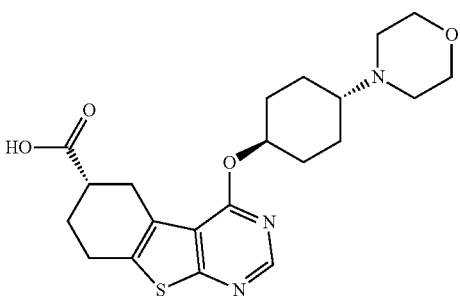
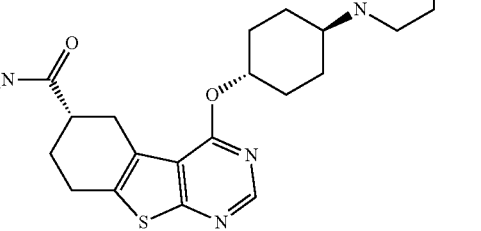
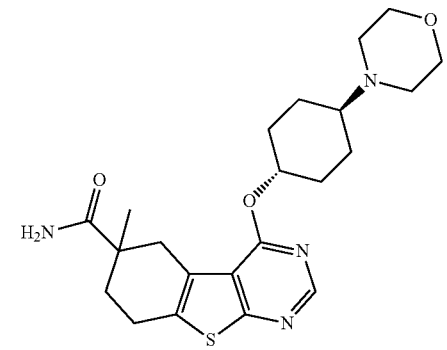

597
-continued
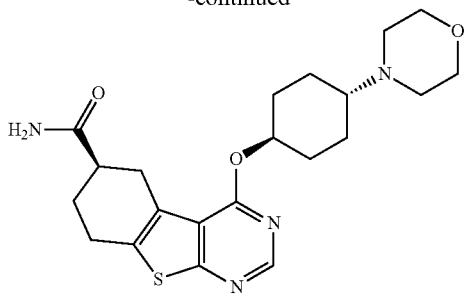
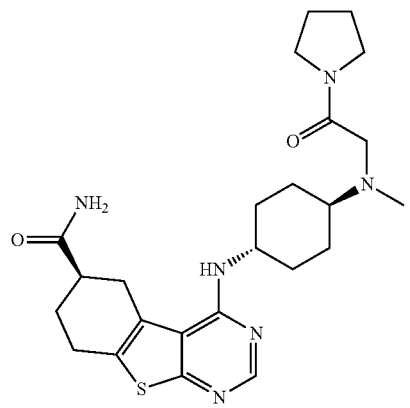
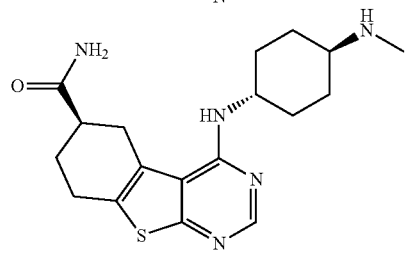
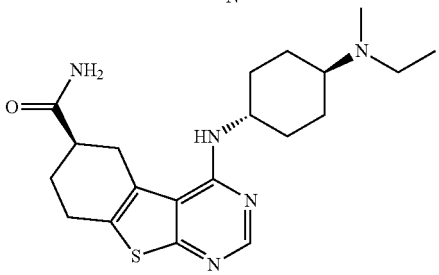
598
-continued
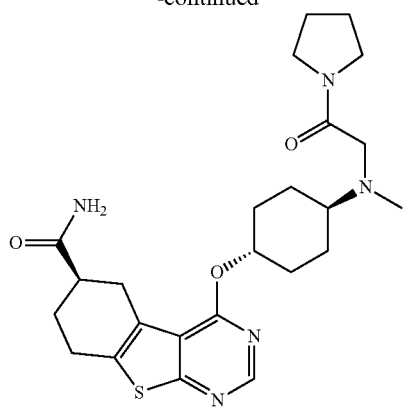
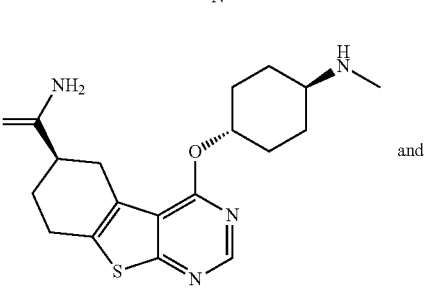
and
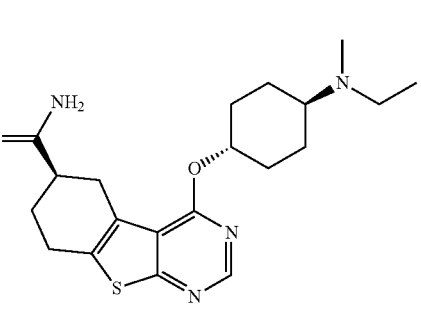
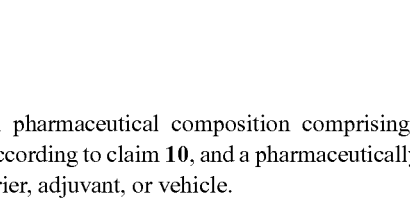
11. A pharmaceutical composition comprising a compound according to claim 10, and a pharmaceutically acceptable carrier, adjuvant, or vehicle.
* * * * *